(12) United States Patent
Turner, Jr. et al.

(10) Patent No.: US 10,968,211 B2
(45) Date of Patent: Apr. 6, 2021

(54) HEPATITIS B CORE PROTEIN MODULATORS

(71) Applicants: Assembly Biosciences, Inc., San Francisco, CA (US); INDIANA UNIVERSITY RESEARCH AND TECHNOLOGY CORPORATION, Indianapolis, IN (US)

(72) Inventors: William W. Turner, Jr., Bloomington, IN (US); Lee D. Arnold, Bloomington, IN (US); Hans Maag, Kleires Wiesental (DE); Leping Li, Carmel, IN (US); Mark G. Bures, Carmel, IN (US); Simon Nicolas Haydar, Carmel, IN (US); Samson Francis, Indianapolis, IN (US)

(73) Assignees: Assembly Biosciences, Inc., South San Francisco, CA (US); INDIANA UNIVERSITY RESEARCH AND TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 16/426,727

(22) Filed: May 30, 2019

(65) Prior Publication Data
US 2020/0131168 A1 Apr. 30, 2020

Related U.S. Application Data

(63) Continuation of application No. 15/760,284, filed as application No. PCT/US2016/051934 on Sep. 15, 2016, now Pat. No. 10,377,748.

(60) Provisional application No. 62/218,815, filed on Sep. 15, 2015.

(51) Int. Cl.
| | | |
|---|---|---|
| C07D 417/12 | (2006.01) | |
| C07D 403/12 | (2006.01) | |
| A61K 45/06 | (2006.01) | |
| C07D 401/12 | (2006.01) | |
| C07D 413/12 | (2006.01) | |
| C07D 417/14 | (2006.01) | |
| C07D 453/02 | (2006.01) | |
| C07D 471/04 | (2006.01) | |
| A61P 31/20 | (2006.01) | |
| C07D 243/38 | (2006.01) | |
| C07D 267/20 | (2006.01) | |
| C07D 281/16 | (2006.01) | |

(52) U.S. Cl.
CPC .......... *C07D 417/12* (2013.01); *A61K 45/06* (2013.01); *A61P 31/20* (2018.01); *C07D 243/38* (2013.01); *C07D 267/20* (2013.01); *C07D 281/16* (2013.01); *C07D 401/12* (2013.01); *C07D 403/12* (2013.01); *C07D 413/12* (2013.01); *C07D 417/14* (2013.01); *C07D 453/02* (2013.01); *C07D 471/04* (2013.01)

(58) Field of Classification Search
CPC .. C07D 417/12; C07D 243/38; C07D 267/20; C07D 281/16; C07D 453/02; C07D 471/04; C07D 403/12; C07D 401/12; C07D 413/12; C07D 417/14; A61P 31/20
See application file for complete search history.

(56) References Cited

U.S. PATENT DOCUMENTS

| | | | |
|---|---|---|---|
| 5,512,563 | A | 4/1996 | Albright et al. |
| 8,618,090 | B2 | 12/2013 | Desai et al. |
| 9,399,619 | B2 | 7/2016 | Guo et al. |
| 9,873,684 | B2 | 1/2018 | Kahraman et al. |
| 10,377,748 | B2 | 8/2019 | Turner et al. |
| 10,392,379 | B2 | 8/2019 | Turner et al. |
| 2007/0105819 | A1 | 5/2007 | Olsson et al. |
| 2015/0368261 | A1 | 12/2015 | Demin et al. |
| 2017/0107185 | A1 | 4/2017 | Grammneos et al. |
| 2017/0267685 | A1 | 9/2017 | D'Agostino et al. |
| 2018/0265484 | A1 | 9/2018 | Turner et al. |

FOREIGN PATENT DOCUMENTS

| | | |
|---|---|---|
| CL | 2015002706 A1 | 4/2016 |
| CL | 2015003456 A1 | 7/2016 |
| CL | 20105002628 | 8/2016 |
| CL | 2016003175 A1 | 8/2017 |
| CN | 103889953 B | 6/2016 |
| CN | 106413402 A | 2/2017 |
| GB | 1480553 A | 7/1977 |
| JP | 58225074 | 12/1983 |
| WO | WO-92/19277 A1 | 11/1992 |
| WO | WO-2005/072741 A1 | 8/2005 |
| WO | WO-2007/105819 A1 | 9/2007 |
| WO | WO-2008/036139 A3 | 12/2008 |
| WO | WO-2008/118141 A3 | 12/2008 |
| WO | WO-2010/011537 A1 | 1/2010 |
| WO | WO-2012/045194 A1 | 4/2012 |
| WO | WO-2013/006394 A1 | 1/2013 |

(Continued)

OTHER PUBLICATIONS

Supplemental European Search Report issued by the European Patent Office (Munich), dated Apr. 11, 2018, for related Application No. EP 15761201; 21 pages.

(Continued)

*Primary Examiner* — Alicia L Otton
(74) *Attorney, Agent, or Firm* — Goodwin Procter LLP

(57) ABSTRACT

The present disclosure provides, in part, compounds having allosteric effector properties against Hepatitis B virus Cp. Also provided herein are methods of treating viral infections, such as hepatitis B, comprising administering to a patient in need thereof a disclosed compound.

12 Claims, No Drawings
Specification includes a Sequence Listing.

(56) References Cited

FOREIGN PATENT DOCUMENTS

| WO | WO-2015/017412 A1 | 2/2015 |
|---|---|---|
| WO | WO-2015/138895 A1 | 9/2015 |
| WO | WO-2017/048954 A1 | 3/2017 |
| WO | WO-2017/048962 A1 | 3/2017 |

OTHER PUBLICATIONS

Supplemental Partial European Search Report issued by the European Patent Office (Munich), dated Nov. 23, 2017, for related Application No. EP 15761201; 14 pages.
Takeda, M., et al., "Synthesis of Dibenzo [b,e] [1,4] Diazepine Derivatives as Anti-depressants," Yakugaku Zahhi, vol. 89, No. 2, (1969), 6 pages.
National Center for Biotechnology Information, PubChem Compound Database; CID-4152425, XP-002779931, modified Apr. 7, 2017, created Sep. 13, 2005; 3 pages.
National Center for Biotechnology Information, PubChem Compound Database; CID-46260649, XP-002779932, modified Apr. 7, 2017, created Jul. 21, 2010; 3 pages.
National Center for Biotechnology Information, PubChem Compound Database; CID-4163919, XP-002779933, modified Apr. 7, 2018, created Sep. 13, 2005; 3 pages.
National Center for Biotechnology Information, PubChem Compound Database; CID-4167865, XP-002779934, modified Apr. 7, 2018, created Sep. 13, 2005; 3 pages.
National Center for Biotechnology Information, PubChem Compound Database; CID-4338109, XP-002779935, modified Apr. 7, 2018, created Sep. 14, 2005; 3 pages.
National Center for Biotechnology Information, PubChem Compound Database; CID-4163918, XP-002779936, modified Apr. 7, 2018, created Sep. 13, 2005; 3 pages.
National Center for Biotechnology Information, PubChem Compound Database; CID-3576843, XP-002779937, modified Apr. 7, 2018, created Sep. 9, 2005; 3 pages.
National Center for Biotechnology Information, PubChem Compound Database; CID-4577044, XP-002779938, modified Apr. 7, 2018, created Sep. 15, 2005; 3 pages.
National Center for Biotechnology Information, PubChem Compound Database; CID-4097179, XP-002779940, modified Apr. 7, 2018, created Sep. 13, 2005; 3 pages.
National Center for Biotechnology Information, PubChem Compound Database; CID-23797169, XP-002779941, modified Apr. 7, 2018, created Feb. 20, 2008; 3 pages.
National Center for Biotechnology Information, PubChem Compound Database; CID-53384785, XP-002779942, modified Apr. 7, 2018, created Oct. 13, 2011; 3 pages.
National Center for Biotechnology Information, PubChem Compound Database; CID-20885138, XP-002775927, modified 20187-11-18, created Dec. 5, 2007; 3 pages.
National Center for Biotechnology Information, PubChem Compound Database; CID-20885146, XP-002775928, modified Nov. 18, 2017, created Dec. 5, 2007; 3 pages.
National Center for Biotechnology Information, PubChem Compound Database; CID-20885149, XP-002775929, modified Nov. 18, 2017, created Dec. 5, 2007; 3 pages.
National Center for Biotechnology Information, PubChem Compound Database; CID-20885150, XP-002775930, modified Nov. 18, 2017, created Dec. 5, 2007; 3 pages.
National Center for Biotechnology Information, PubChem Compound Database; CID-20885171, XP-002775931, modified Nov. 18, 2017, created Dec. 5, 2007; 3 pages.
Letter Exam Report from the Australian Patent Office, dated May 6, 2018, for Australian Application No. 2015229174; 6 pages.
Office Action issued by the Belize Intellectual Property Office, dated May 18, 2018, for Belize Patent Application No. 887.16; 2 pages.

English translation of the First Official Action issued by the Mexican Patent Office for Mexican Patent Application No. MX/a/2016/011800, Jul. 4, 2018; 3 pages.
Letter dated Jun. 27, 2018 regarding Examination Report issued by the National Office of Industrial Property for Dominican Republic Patent Application No. P2016-0233; 2 pages.
Letter Exam Report issued by The Patent Office of the People's Republic of China (translated in English language), dated Jun. 29, 2018, for Chinese Application No. 201580024580.0; (3 pages).
Letter Exam Report issued by the Chilean Patent Office, dated Jun. 12, 2018, for Chilean Application No. 2269-2016; 15 pages.
National Center for Biotechnology Information, PubChem Compound Database; CID-23734106, XP-002779939, modified Apr. 7, 2018, created Feb. 20, 2008; 3 pages.
Hall, Pamela R., et al., "Small molecule inhibitors of hantavirus infection,"Bioorganic & Medicinal Chemistry Letters, vol. 20, (2010), pp. 7085-7091.
Xiao, et al., "Discovery, Optimization, and Characterization of Novel D2 Dopamine Receptor Selective Antagonists," Journal of Medicinal Chemistry, Mar. 25, 2014, vol. 57, pp. 3450-3463.
International Preliminary Report on Patentability issued by The International Bureau of WIPO, dated Sep. 13, 2016, for International Application No. PCT/US2015/020444; 6 pages.
International Search Report and Written Opinion issued by the ISA/US, Commissioner for Patents, dated Jul. 6, 2015, for International Application No. PCT/US2015/020444; 10 pages.
National Center for Biotechnology Information. PubChem Compound Database; CID=20885151; available at https://pubchem.ncbi.nlm.nih.gov/compound/20885151 (accessed Sep. 13, 2016; deposit date Dec. 5, 2007); 10 pages.
National Center for Biotechnology Information. PubChem Compound Database; CID=4 || 9 |71, available at https://pubchem.ncbi.nlm.nih.gov/compound/4119171 (accessed Sep. 13, 2016; deposit date Sep. 3, 2005); 12 pages.
National Center for Biotechnology Information. PubChem Compound Database; CID=4167865, https://pubchem.ncbi.nlm.nih.gov/compound/4167865 (accessed Sep. 13, 2016; deposit date Sep. 13, 2005); 12 pages.
International Preliminary Report on Patentability dated Mar. 20, 2018, for International Application No. PCT/US2016/051934 (6 pages).
International Search Report and Written Opinion dated Dec. 29, 2016 for International Application No. PCT/US16/51934.
International Preliminary Report on Patentability dated Dec. 29, 2016, for International Application No. PCT/US2016/051949.
International Search Report and Written Opinion dated Dec. 29, 2016 for International Application No. PCT/US16/51949.
International Preliminary Report on Patentability dated Oct. 28, 2016, for International Application No. PCT/US2016/051940.
International Search Report and Written Opinion dated Oct. 28, 2016 for International Application No. PCT/US16/51949.
National Center for Biotechnology Information, PubChem Compound Database; CID-201327, create date: Aug. 9, 2005; 3 pages.
Supplementary European Search Report issued for EP16847298, dated Jan. 28, 2019 (6 pages).
Notice of Reasons for Rejection issued for Japanese Patent Application No. 2016-557019, dated Oct. 30, 2018 (6 pages).
Official Office Action issued in Eurasian application No. 201890731, dated Oct. 31, 2018.
Office Action issued by the Belize Intellectual Property Office, dated Nov. 21, 2018, for Belize Patent Application No. 925.18 (3 pages).
Extended European Search Report issued in EP16847298.3, dated Jan. 2, 2019.
STN Registry Database Entry for CAS RN688762_67_6—Jun. 3, 2004, Accessed Aug. 8, 2019.
Ito et al. in Cancer Science 94(1), 3-8 (2003).
European Search Report and Search Opinion Received for EP Application No. 16847295.9, dated Apr. 15, 2019, 6 pages.
European Search Report and Search Opinion Received for EP Application No. 16847298.3, dated Feb. 1, 2019, 7 pages.
European Search Report and Search Opinion Received for EP Application No. 16847305.6, dated Mar. 26, 2019, 8 pages.

```
                        SEQUENCE LISTING

<160> NUMBER OF SEQ ID NOS: 3

<210> SEQ ID NO 1
<211> LENGTH: 19
<212> TYPE: DNA
<213> ORGANISM: Artificial Sequence
<220> FEATURE:
<223> OTHER INFORMATION: PCR Primer

<400> SEQUENCE: 1
ctgtgccttg ggtggcttt                                          19

<210> SEQ ID NO 2
<211> LENGTH: 24
<212> TYPE: DNA
<213> ORGANISM: Artificial Sequence
<220> FEATURE:
<223> OTHER INFORMATION: PCR Primer

<400> SEQUENCE: 2
aaggaaagaa gtcagaaggc aaaa                                    24

<210> SEQ ID NO 3
<211> LENGTH: 34
<212> TYPE: DNA
<213> ORGANISM: Artificial Sequence
<220> FEATURE:
<223> OTHER INFORMATION: PCR Probe

<400> SEQUENCE: 3
agctccaaat tctttataag ggtcgatgtc catg                         34
```

HEPATITIS B CORE PROTEIN MODULATORS

CROSS REFERENCE TO RELATED APPLICATIONS

This application is a continuation application under 35 U.S.C. § 120 of U.S. patent application Ser. No. 15/760,284 filed Mar. 15, 2018, which is a U.S. National Phase Application under 35 U.S.C. § 371 of International Application PCT/US2016/051934, filed Sep. 15, 2016, which claims priority to U.S. Provisional Application No. 62/218,815, filed Sep. 15, 2015, each of which is hereby incorporated by reference in its entirety.

BACKGROUND

Hepatitis B (HBV) causes viral Hepatitis that can further lead to chronic liver disease and increase the risk of liver cirrhosis and liver cancer (hepatocellular carcinoma). Worldwide, about 2 billion people have been infected with HBV, around 360 million people are chronically infected, and every year HBV infection causes more than one half million deaths (2009; WHO, 2009). HBV can be spread by body fluids: from mother to child, by sex, and via blood products. Children born to HBV-positive mothers may also be infected, unless vaccinated at birth.

The virus particle is composed of a lipid enveloped studded with surface protein (HBsAg) that surrounds the viral core. The core is composed of a protein shell, or capsid, built of 120 core protein (Cp) dimers, which in turn contains the relaxed circular DNA (rcDNA) viral genome as well as viral and host proteins. In an infected cell, the genome is found as a covalently closed circular DNA (cccDNA) in the host cell nucleus. The cccDNA is the template for viral RNAs and thus viral proteins. In the cytoplasm, Cp assembles around a complex of full-length viral RNA (the so-called pregenomic RNA or pgRNA and viral polymerase (P). After assembly, P reverse transcribes the pgRNA to rcDNA within the confines of the capsid to generate the DNA-filled viral core. For convenience, we divide the assembly process at the point of capsid assembly and pgRNA-packaging. Steps preceding this event are "upstream"; steps following RNA-packaging are "downstream".

At present, chronic HBV is primarily treated with nucleos(t)ide analogs (e.g. entecavir) that suppress the virus while the patient remains on treatment but do not eliminate the infection, even after many years of treatment. Once a patient starts taking nucleotide analogs most must continue taking them or risk the possibility of a life threatening immune response to viral rebound. Further, nucleos(t)ide therapy may lead to the emergence of antiviral drug resistance (Deres and Rubsamen-Waigmann, 1999; Tennant et al., 1998; Zhang et al., 2003) and—in rare patients—adverse events have been reported (Ayoub and Keeffe, 2011).

The only FDA approved alternative to nucleos(t)ide analogs is treatment with interferon α or pegylated interferon α. Unfortunately, the adverse event incidence and profile of interferon α can result in poor tolerability, and many patients are unable to complete therapy. Moreover, only a small percentage of patients are considered appropriate for interferon therapy, as only a small subset of patients are likely to have a sustained clinical response to a course of interferon therapy. As a result, interferon based therapies are used in only a small percentage of all diagnosed patients who elect for treatment.

Thus, current HBV treatments can range from palliative to watchful waiting. Nucleos(t)ide analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

Provided herein are compounds that can have properties such as those described below, where the compounds in some embodiments may be represented by:

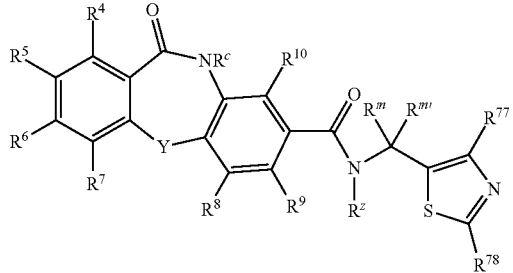

wherein
$R^4$, $R^5$, $R^6$, $R^7$, $R^8$, $R^9$, $R^{10}$, $R^c$, $R^m$, $R^{m'}$, $R^{77}$, $R^{78}$, $R^Z$ and Y are defined herein. Also provided herein are methods of treating viral infections, such as hepatitis B, comprising administering to patient a disclosed compound.

For example, the present disclosure is directed in part to compounds having allosteric effector properties against Hepatitis B virus Cp, a protein found as a dimer, a multimer, and as the protein shell of the HBV core. Without being bound by theory, disclosed compounds may ultimately target multimerization of viral core proteins, which is central to HBV infection, where the core protein multimerizes into shell, or capsid, and/or disclosed compounds may for example, ultimately target interaction of viral core proteins with other macromolecules, such as host or viral nucleic acid, host proteins, or other viral proteins. For example, disclosed compounds may be considered in some embodiments CpAM—core protein allosteric modifiers. CpAM interaction with core protein can allosterically favor an assembly-active form of Cp dimer and lead to viral capsid assembly at an inappropriate time or place or lead to non-standard intersubunit interactions, all resulting in defective capsids. CpAMs may additionally or alternatively affect steps of "upstream" of capsid assembly by altering the concentrations or nature of Cp available as dimer as compared to capsid or other multimeric forms. Disclosed compounds or CpAMs may, in some embodiments, noticeably affect functions upstream of viral assembly such as modulation of cccDNA transcription, RNA stability and/or protein-protein interactions.

DETAILED DESCRIPTION

The features and other details of the disclosure will now be more particularly described. Before further description of the present invention, certain terms employed in the specification, examples and appended claims are collected here. These definitions should be read in light of the remainder of the disclosure and as understood by a person of skill in the

Definitions

As intended herein, the terms "a" and "an" include singular as well as plural references unless the context clearly dictates otherwise. For example, the term "an assembly effector" can include one or more such effectors.

The term "alkyl" as used herein refers to a saturated straight or branched hydrocarbon. Exemplary alkyl groups include, but are not limited to, straight or branched hydrocarbons of 1-6, 1-4, or 1-3 carbon atoms, referred to herein as $C_{1-6}$alkyl, $C_{1-4}$alkyl, and $C_{1-3}$alkyl, respectively. Exemplary alkyl groups include, but are not limited to, methyl, ethyl, propyl, isopropyl, 2-methyl-1-butyl, 3-methyl-2-butyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkenyl" as used herein refers to an unsaturated straight or branched hydrocarbon having at least one carbon-carbon double bond. Exemplary alkenyl groups include, but are not limited to, a straight or branched group of 2-6 or 3-4 carbon atoms, referred to herein as $C_{2-6}$alkenyl, and $C_{3-4}$alkenyl, respectively. Exemplary alkenyl groups include, but are not limited to, vinyl, allyl, butenyl, pentenyl, etc.

The term "alkoxy" as used herein refers to a straight or branched alkyl group attached to oxygen (alkyl-O—). Exemplary alkoxy groups include, but are not limited to, alkoxy groups of 1-6 or 2-6 carbon atoms, referred to herein as $C_{1-6}$alkoxy, and $C_{2-6}$alkoxy, respectively. Exemplary alkoxy groups include, but are not limited to methoxy, ethoxy, isopropoxy, etc.

The term "alkynyl" as used herein refers to an unsaturated straight or branched hydrocarbon having at least one carbon-carbon triple bond. Exemplary alkynyl groups include, but are not limited to, straight or branched groups of 2-6, or 3-6 carbon atoms, referred to herein as $C_{2-6}$alkynyl, and $C_{3-6}$alkynyl, respectively. Exemplary alkynyl groups include, but are not limited to, ethynyl, propynyl, butynyl, pentynyl, hexynyl, methylpropynyl, etc.

The terms "cycloalkyl" or a "carbocyclic group" as used herein refers to a saturated or partially unsaturated hydrocarbon group of, for example, 3-6, or 4-6 carbons, referred to herein as $C_{3-6}$cycloalkyl or $C_{4-6}$cycloalkyl, respectively. Exemplary cycloalkyl groups include, but are not limited to, cyclohexyl, cyclopentyl, cyclopentenyl, cyclobutyl or cyclopropyl.

The terms "halo" or "halogen" as used herein refer to F, Cl, Br, or I.

The terms "heteroaryl" or "heteroaromatic group" as used herein refers to a monocyclic aromatic 5-6 membered ring system containing one or more heteroatoms, for example one to three heteroatoms, such as nitrogen, oxygen, and sulfur. Where possible, said heteroaryl ring may be linked to the adjacent radical though carbon or nitrogen. Examples of heteroaryl rings include but are not limited to furan, thiophene, pyrrole, thiazole, oxazole, isothiazole, isoxazole, imidazole, pyrazole, triazole, pyridine or pyrimidine etc.

The terms "heterocyclyl" or "heterocyclic group" are art-recognized and refer to saturated or partially unsaturated 4-7 membered ring structures, whose ring structures include one to three heteroatoms, such as nitrogen, oxygen, and sulfur. Where possible, heterocyclyl rings may be linked to the adjacent radical through carbon or nitrogen. Examples of heterocyclyl groups include, but are not limited to, pyrrolidine, piperidine, morpholine, thiomorpholine, piperazine, oxetane, azetidine, tetrahydrofuran or dihydrofuran etc.

The terms "hydroxy" and "hydroxyl" as used herein refers to the radical OH.

"Treatment" as used herein includes the alleviation, prevention, reversal, amelioration or control of a pathology, disease, disorder, process, condition or event, including viral infection. In this context, the term "treatment" is further to be understood as embracing the use of a drug to inhibit, block, reverse, restrict or control progression of viral infection.

As used herein, the term "pharmaceutical composition" refers to compositions of matter comprising at least one pharmaceutical compound and optionally a pharmaceutically acceptable carrier.

As used herein, the term "pharmaceutical compound" or "drug" refers to a free compound, its therapeutically suitable salts, solvates such as hydrates, specific crystal forms of the compound or its salts, or therapeutically suitable prodrugs of the compound.

Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, and general safety and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The compounds of the disclosure may contain one or more chiral centers and, therefore, exist as stereoisomers. The term "stereoisomers" when used herein consist of all enantiomers or diastereomers. These compounds may be designated by the symbols "(+)," "(−)," "R" or "S," depending on the configuration of substituents around the stereogenic carbon atom, but the skilled artisan will recognize that a structure may denote a chiral center implicitly. The present invention encompasses various stereoisomers of these compounds and mixtures thereof. Mixtures of enantiomers or diastereomers may be designated "(±)" in nomenclature, but the skilled artisan will recognize that a structure may denote a chiral center implicitly.

The compounds of the disclosure may contain one or more double bonds and, therefore, exist as geometric isomers resulting from the arrangement of substituents around a carbon-carbon double bond. The symbol denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond.

Compounds of the disclosure may contain a carbocyclic or heterocyclic ring and therefore, exist as geometric isomers resulting from the arrangement of substituents around the ring. The arrangement of substituents around a carbocyclic or heterocyclic ring are designated as being in the "Z" or "E" configuration wherein the terms "Z" and "E" are used in accordance with IUPAC standards. Unless otherwise specified, structures depicting carbocyclic or heterocyclic rings encompass both "Z" and "E" isomers. Substituents around a carbocyclic or heterocyclic rings may also be referred to as "cis" or "trans", where the term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

Individual enantiomers and diastereomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution using stereoselective chemical or enzymatic reagents. Racemic mixtures can also be resolved into their component enantiomers by well-known methods, such as chiral-phase liquid chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations, and may involve the use of chiral auxiliaries. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a single polymorph. In another embodiment, the compound is a mixture of polymorphs. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the examples herein by substituting an isotopically labeled reagent for a non-isotopically labeled reagent.

The term "therapeutically suitable salt," refers to salts or zwitterions of pharmaceutical compounds which are water or oil-soluble or dispersible, suitable for treatment of disorders and effective for their intended use. The salts may be prepared, for instance, during the final isolation and purification of the compounds or separately by reacting an amino group of the compounds with a suitable acid. For example, a compound may be dissolved in a suitable solvent, such as but not limited to methanol and water, and treated with at least one equivalent of an acid, for instance hydrochloric acid. The resulting salt may precipitate out and be isolated by filtration and dried under reduced pressure. Alternatively, the solvent and excess acid may be removed under reduced pressure to provide the salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric, and the like. The amino groups of a compound may also be quaternized with alkyl chlorides, bromides, and iodides such as methyl, ethyl, propyl, isopropyl, butyl, lauryl, myristyl, stearyl, and the like.

Basic addition salts may be prepared, for instance, during the final isolation and purification of pharmaceutical compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts may be derived, for example, from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like.

The term "therapeutically suitable prodrug," refers to those prodrugs or zwitterions which are suitable for use in contact with the tissues of subjects and are effective for their intended use. The term "prodrug" refers to compounds that are transformed in vivo to a pharmaceutical compound, for example, by hydrolysis in blood. The term "prodrug," refers to compounds that contain, but are not limited to, substituents known as "therapeutically suitable esters." The term "therapeutically suitable ester," refers to alkoxycarbonyl groups appended to the parent molecule on an available carbon atom. More specifically, a "therapeutically suitable ester," refers to alkoxycarbonyl groups appended to the parent molecule on one or more available aryl, cycloalkyl and/or heterocycle groups. Compounds containing therapeutically suitable esters are an example, but are not intended to limit the scope of compounds considered to be prodrugs. Examples of prodrug ester groups include pivaloyloxymethyl, acetoxymethyl, phthalidyl, indanyl and methoxymethyl, as well as other such groups known in the art. Other examples of prodrug ester groups are found in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The terms "pharmaceutically effective amount" and "effective amount", as used herein, refer to an amount of a pharmaceutical formulation that will elicit the desired therapeutic effect or response when administered in accordance with the desired treatment regimen. US2011/0144086 describes the use of some diabenzothiazepine molecules (DBTs) as anti-malarial "inhibitors of the plasmodial surface anion channel." However, no study of DBT molecules as anti-virals has yet been reported.

In an embodiment, provided herein are compounds represented by:

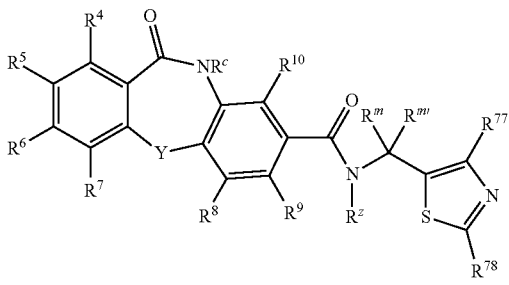

wherein

Y is selected from the group consisting of $S(O)_y$, C=O, $C(R^{11})_2$, $NR_Y$ and O wherein y is 0, 1, or 2;

$R^{11}$, for each occurrence, is selected from the group consisting of H, halogen, and $C_{1-6}$alkyl (optionally substituted with one, two, or three halogens);

$R_Y$ is selected from the group consisting of H, methyl, ethyl, propyl, propenyl, butyl, phenyl and benzyl, wherein $R_Y$ when not H may be optionally substituted by hydroxyl;

$R^Z$ is selected from the group consisting of H, methyl, ethyl, propyl, phenyl and benzyl;

$R^{m'}$ and $R^m$ are each independently selected from the group consisting of H, $C_{1-6}$alkyl (optionally substituted by one, two or three substituents each independently selected from halogen and hydroxyl), and $C_{2-6}$alkenyl (optionally substituted by one, two or three substituents each independently selected from halogen and hydroxyl);

$R^c$ is selected from the group consisting of H, $C_{1-6}$alkyl and $C_{2-6}$alkenyl;

$R^{77}$ is selected from the group consisting of H, halogen, cyano, and $C_{1-6}$alkyl;

$R^{78}$ is selected from the group consisting of H, halogen, cyano, $C_{1-6}$alkyl, carboxy, —C(O)—O—$C_{1-6}$alkyl; $C_{3-6}$cycloalkyl, —NR'R"; phenyl (optionally substituted with one, two, three or four substituents each independently selected from the group consisting of $R^{73}$); benzyl (optionally substituted with one or more substituents each independently selected from the group consisting of $R^{73}$), 4-7 membered heterocycle (optionally substituted with one or more substituents each independently selected from the group consisting of $R^{73}$); 4-6 membered monocyclic heteroaryl (optionally substituted with one or more substituents each independently selected from the group consisting of $R^{73}$); 9-10 membered bicyclic heteroaryl (optionally substituted with one or more substituents each independently selected from the group consisting of $R^{73}$), $X^2$—$R^{79}$, and $X^2$—$C_{1-6}$alkylene-$R^{79}$;

$X^2$ is selected from the group consisting of $S(O)_w$ (wherein w is 0, 1, or 2), O, —C(O)— and NR';

$R^{79}$ is selected from the group consisting of H, hydroxyl, halogen, $C_{1-6}$alkyl, —C(O)—O—$C_{1-6}$alkyl, heterocycle (optionally substituted by one or more substituents selected from the group consisting of halogen, NR'R', —C(O)—O—$C_{1-6}$alkyl, carboxy and $C_{1-6}$alkyl), —C(O)—NR'R", —C(=NH)—NR'R", heteroaryl, phenyl (optionally substituted by one or more substituents selected from the group consisting of halogen, NR'R', —C(O)—O—$C_{1-6}$alkyl, carboxy, $C_{1-6}$alkoxy, and $C_{1-6}$alkyl), $C_{2-6}$alkenyl, $C_{2-6}$alkynyl, $C_{1-6}$alkoxy, carboxy, NR'R", —C(O)—$C_{1-6}$alkyl, $C_{3-6}$cycloalkyl, —NR'—C(O)—$C_{1-6}$alkyl, NR'—C(O)—O—$C_{1-6}$ alkyl, —S(O)$_w$—$C_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2));

$R^{73}$ is selected from the group consisting of H, halogen, hydroxyl, nitro, cyano, carboxy, oxo, $C_{1-6}$alkyl, —C(O)—O—$C_{1-6}$alkyl, heterocycle (optionally substituted by one or more substituents selected from the group consisting of halogen, hydroxyl, oxo, NR'R', —C(O)—O—$C_{1-6}$alkyl, carboxy and $C_{1-6}$alkyl), —C(O)—NR'—$C_{1-6}$alkyl, —C(=NH)—NR'R", heteroaryl, phenyl, $C_{2-6}$alkenyl, $C_{2-6}$alkynyl, $C_{1-6}$alkoxy, carboxy, oxo, NR'R", —C(O)—$C_{1-6}$ alkyl, —$C_{3-6}$cycloalkyl, NR'—C(O)—$C_{1-6}$alkyl, NR'—C(O)—O—$C_{1-6}$alkyl, —S(O)$_w$—$C_{1-6}$alkyl (where w is 0, 1 or 2), —S(O)$_w$—NR'R" (where w is 1, 2 or 3), —NR'—S(O)$_w$—$C_{1-6}$alkyl (where w is 0, 1 or 2), C(O)—NR'—$C_{1-6}$alkyl, C(O)—$C_{1-3}$alkylene-NR'—C(O)—O—$C_{1-6}$ alkyl, $X^2$—$R^{79}$; and $X^2$—$C_{1-6}$alkylene-$R^{79}$;

R' is selected, independently for each occurrence, from H, methyl, ethyl, cyclopropyl, cyclobutyl, and propyl;

R" is selected, independently for each occurrence, from H, methyl, ethyl, propyl, (optionally substituted by hydroxyl), butyl (optionally substituted by hydroxyl), —C(O)-methyl and —C(O)-ethyl, or R' and R" taken together with the nitrogen to which they are attached may form a 4-7 membered heterocycle optionally substituted by one, two or more substituents selected from the group consisting of halogen, hydroxyl, $NH_2$, —C(O)—O—$C_{1-3}$ alkyl, —C(O)—$C_{1-3}$alkyl, carboxy, oxo, and $C_{1-3}$alkyl;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{1-6}$alkoxy, $C_{2-6}$alkynyl, $C_{2-6}$ alkenyl, halogen, hydroxyl, nitro, cyano, and NR'R";

wherein for each occurrence, $C_{1-6}$alkyl, $C_{2-6}$alkenyl or $C_{2-6}$alkynyl may be optionally substituted with one, two, three or more substituents selected from the group consisting of halogen, hydroxyl, nitro, cyano, carboxy, $C_{3-6}$cycloalkyl, $C_{2-4}$alkenyl, $C_{2-4}$alkynyl, $C_{1-3}$alkoxy, NR'R", —NR'—S(O)$_w$—$C_{1-2}$alkyl (where w is 0, 1 or 2), NR'—C(O)—$C_{1-3}$ alkyl, NR'—C(O)—O—$C_{1-3}$alkyl, and S(O)$_w$—NR'R"

(where w is 0, 1 or 2); $C_{1-6}$alkoxy may be optionally substituted with one, two, three or more substituents selected from the group consisting of halogen, hydroxyl, nitro, cyano, carboxy, NR'R", —NR'—S(O)$_w$—C$_{1-2}$alkyl (where w is 0, 1 or 2), and S(O)$_w$—NR'R" (where w is 0, 1 or 2); $C_{1-6}$alkylene may be optionally substituted by a substituent selected from the group consisting of $C_{3-6}$cycloalkyl, hydroxyl, cyano, and halogen;

and pharmaceutically acceptable salts and N-oxides thereof.

In some embodiments, Y may be selected from the group consisting of S(O)$_y$, C=O, C(R$^{11}$)$_2$, and O For example, Y may be S(O)$_y$.

In an embodiment, y may be 1 or 2. In another embodiment, y may be 0. In a further embodiment, y may be 1. In another other embodiment, y may be 2.

For example, in some embodiments Y may be C=O. In some embodiments, Y may be NH.

For example, in some embodiments R$^{78}$ may be selected from the group consisting of $C_{1-6}$ alkyl substituted with one, two, or three substituents each independently selected from the group consisting of halogen, hydroxyl, and cyano; phenyl substituted with one, two, three or four substituents each independently selected from the group consisting of R$^{73}$; and X$^2$—C$_{1-6}$alkylene-R$^{79}$.

For example, in some embodiments R$^{78}$ may be selected from the group consisting of CF$_3$, cyano, and phenyl substituted with one, two, three or four substituents each independently selected from the group consisting of R$^{73}$.

For example, in some embodiments R$^{78}$ may be selected from the group consisting of phenyl substituted with one, two, three or four substituents each independently selected from the group consisting of R$^{73}$; benzyl (optionally substituted with one or more substituents each independently selected from the group consisting of R$^{73}$), pyridinyl (optionally substituted with one or more substituents each independently selected from the group consisting of R$^{73}$), pyrimidinyl (optionally substituted with one or more substituents each independently selected from the group consisting of R$^{73}$), benzoimidazole (optionally substituted with one or more substituents each independently selected from the group consisting of R$^{73}$), quinolinyl (optionally substituted with one or more substituents each independently selected from the group consisting of R$^{73}$, thiazolyl, and pyrazolyl (optionally substituted with one or more substituents each independently selected from the group consisting of R$^{73}$).

For example, in some embodiments R$^{78}$ may be —NR'R", wherein R' and R" taken together with the nitrogen to which they are attached may form a 4-7 membered heterocycle optionally substituted by one, two or more substituents selected from the group consisting of halogen, hydroxyl, NH$_2$, —C(O)—O—C$_{1-3}$alkyl, —C(O)—C$_{1-3}$alkyl, carboxy, oxo, and C$_{1-3}$alkyl.

In one embodiment, R$^{77}$ may be H. In some embodiments, R$^7$ may be H or halogen.

In another embodiment, R$^{19}$ may be H, halogen or methyl.

In certain embodiments, R$^{m'}$ and R$^m$ may be each H. In other embodiments, R$^Z$ may be H.

For example, in some embodiments each of R$^4$, R$^5$, R$^6$, R$^7$, R$^8$, R$^9$, and R$^{10}$ may be H.

Also provided herein are compounds represented by:

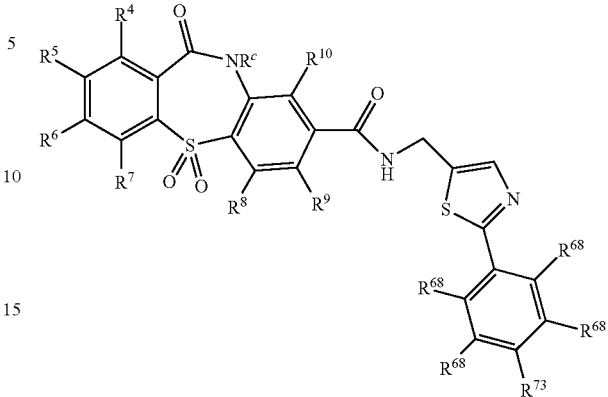

wherein
R$^{73}$ is selected from the group consisting of heterocycle (optionally substituted by one or more substituents selected from the group consisting of halogen, hydroxyl, oxo, NR'R', —C(O)—O—C$_{1-6}$alkyl, carboxy and C$_{1-6}$alkyl), —C(O)—NR'—C$_{1-6}$alkyl, —C(=NH)—NR'R", heteroaryl (optionally substituted by one or more substituents selected from the group consisting of halogen, hydroxyl, NR'R', —C(O)—O—C$_{1-6}$alkyl, carboxy and C$_{1-6}$alkyl), phenyl (optionally substituted by one or more substituents selected from the group consisting of halogen, hydroxyl, oxo, NR'R', —C(O)—O—C$_{1-6}$alkyl, carboxy and C$_{1-6}$alkyl), C$_{2-6}$alkenyl, C$_{2-6}$alkynyl, C$_{1-6}$alkoxy, carboxy, —C(O)—C$_{1-6}$alkyl, —C$_{3-6}$cycloalkyl, NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 0, 1 or 2), —NR'—S(O)$_w$—C$_{1-6}$alkyl (where w is 0, 1 or 2), C(O)—NR'—C$_{1-6}$alkyl, C(O)—C$_{1-3}$alkylene-NR'—C(O)—O—C$_{1-6}$alkyl, X$^2$—R$^{79}$; and X$^2$—C$_{1-6}$alkylene-R$^{79}$;

R$^{68}$ is independently selected for each occurrence from the group consisting of H, halogen, hydroxyl, C$_{1-6}$alkyl and C$_{1-6}$alkoxy;

X$^2$ is selected from the group consisting of S(O)$_w$ (wherein w is 0, 1, or 2), O, —C(O)— and NR';

R$^{79}$ is selected from the group consisting of H, hydroxyl, halogen, C$_{1-6}$alkyl, —C(O)—O—C$_{1-6}$alkyl, heterocycle (optionally substituted by one or more substituents selected from the group consisting of halogen, NR'R', —C(O)—O—C$_{1-6}$alkyl, carboxy and C$_{1-6}$alkyl), —C(O)—NR'R", —C(=NH)—NR'R", heteroaryl, phenyl (optionally substituted by one or more substituents selected from the group consisting of halogen, NR'R', —C(O)—O—C$_{1-6}$alkyl, carboxy, C$_{1-6}$alkoxy, and C$_{1-6}$alkyl), C$_{2-6}$alkenyl, C$_{2-6}$alkynyl, C$_{1-6}$alkoxy, carboxy, NR'R", —C(O)—C$_{1-6}$alkyl, C$_{3-6}$cycloalkyl, —NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 0, 1 or 2), and —NR'—S(O)$_w$—C$_{1-6}$alkyl (where w is 0, 1 or 2));

R' is selected, independently for each occurrence, from H, methyl, ethyl, cyclopropyl, cyclobutyl, and propyl;

R" is selected, independently for each occurrence, from H, methyl, ethyl, propyl, (optionally substituted by hydroxyl), butyl (optionally substituted by hydroxyl), —C(O)-methyl and —C(O)-ethyl, or R' and R" taken together with the nitrogen to which they are attached may form a 4-7 membered heterocycle optionally substituted by one, two or more substituents selected from the group consisting of halogen, hydroxyl, NH$_2$, —C(O)—O—C$_{1-3}$alkyl, —C(O)—C$_{1-3}$alkyl, carboxy, oxo, and C$_{1-3}$alkyl;

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{1-6}$alkoxy, $C_{2-6}$alkynyl, $C_{2-6}$ alkenyl, halogen, hydroxyl, nitro, cyano, and NR'R";

wherein for each occurrence, $C_{1-6}$alkyl, $C_{2-6}$alkenyl or $C_{2-6}$alkynyl may be optionally substituted with one, two, three or more substituents selected from the group consisting of halogen, hydroxyl, nitro, cyano, carboxy, $C_{3-6}$cycloalkyl, $C_{2-4}$alkenyl, $C_{2-4}$alkynyl, $C_{1-3}$alkoxy, NR'R", —NR'—S(O)$_w$—C$_{1-2}$alkyl (where w is 0, 1 or 2), NR'—C(O)—C$_{1-3}$alkyl, NR'—C(O)—O—C$_{1-3}$alkyl, and S(O)$_w$—NR'R" (where w is 0, 1 or 2); $C_{1-6}$alkoxy may be optionally substituted with one, two, three or more substituents selected from the group consisting of halogen, hydroxyl, nitro, cyano, carboxy, $C_{1-3}$alkyl, NR'R", —NR'—S(O)$_w$—C$_{1-2}$alkyl (where w is 0, 1 or 2), and S(O)$_w$—NR'R" (where w is 0, 1 or 2); $C_{1-6}$alkylene may be optionally substituted by a substituent selected from the group consisting of $C_{3-6}$cycloalkyl, hydroxyl, cyano, and halogen;

and pharmaceutically acceptable salts and N-oxides thereof.

Also provided herein are compounds represented by:

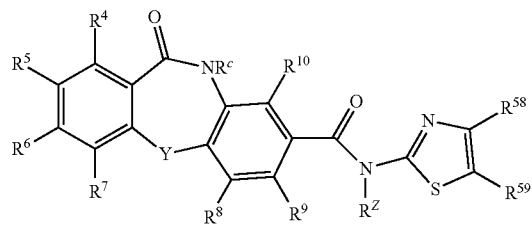

wherein

Y is selected from the group consisting of S(O)$_y$, C=O, C(R$^{11}$)$_2$, NR$_Y$ and O wherein y is 0, 1, or 2;

R$_Y$ is selected from the group consisting of H, methyl, ethyl, propyl, propenyl, butyl, phenyl and benzyl;

R$^Z$ is selected from the group consisting of H, methyl, ethyl, propyl, phenyl and benzyl;

R$^c$ is selected from the group consisting of H, $C_{1-6}$alkyl and $C_{2-6}$alkenyl;

X$^2$ is selected from the group consisting of S(O)$_w$ (wherein w is 0, 1, or 2), O, —C(O)— and NR';

R$^{58}$ and R$^{59}$ are each independently selected from the group consisting of H, halogen, hydroxyl, nitro, cyano, carboxy, $C_{1-6}$alkyl, $C_{2-6}$alkenyl, $C_{2-6}$alkynyl, $C_{1-6}$alkoxy, NR'R", —C(O)—$C_{1-6}$alkyl, —C(O)—$C_{1-6}$alkoxy, phenyl, heteroaryl, $C_{3-6}$cycloalkyl, —S(O)$_w$—C$_{1-6}$alkyl (where w is 0, 1 or 2), —S(O)$_w$—NR'R" (where w is 0, 1 or 2), and —NR'—S(O)$_w$—$C_{1-6}$alkyl (where w is 0, 1 or 2); or form a phenyl, heterocyclic or heteroaryl ring (optionally substituted by one, two, or three substituents selected from the group consisting of hydrogen, $C_{1-6}$alkyl, $C_{2-6}$alkynyl, $C_{2-6}$alkenyl, halogen, hydroxyl, nitro, cyano, and NR'R") and fused to the ring to which they are attached;

R' is selected, independently for each occurrence, from H, methyl, ethyl, cyclopropyl, cyclobutyl, and propyl;

R" is selected, independently for each occurrence, from H, methyl, ethyl, propyl (optionally substituted by hydroxyl), butyl (optionally substituted by hydroxyl), C(O)-methyl and C(O)-ethyl, or R' and R" taken together with the nitrogen to which they are attached may form a 4-6 membered heterocycle optionally substituted by one or more substituents selected from the group consisting of halogen, NH$_2$, —C(O)—O—$C_{1-6}$alkyl, —C(O)—$C_{1-6}$alkyl, carboxy and $C_{1-6}$alkyl;

R$^{11}$, for each occurrence, is selected from the group consisting of H, halogen, and $C_{1-6}$alkyl (optionally substituted with one, two, or three halogens);

each of moieties $R^4$, $R^5$, $R^6$, $R^7$, $R^8$, $R^9$, and $R^{10}$ is independently selected for each occurrence from the group consisting of hydrogen, $C_{1-6}$alkyl, $C_{2-6}$alkynyl, $C_{2-6}$alkenyl, halogen, hydroxyl, nitro, cyano, and NR'R";

wherein for each occurrence, $C_{1-6}$alkyl, $C_{2-6}$alkenyl or $C_{2-6}$alkynyl may be optionally substituted with one, two, three or more substituents selected from the group consisting of halogen, hydroxyl, nitro, cyano, carboxy, $C_{3-6}$cycloalkyl, $C_{2-4}$alkenyl, $C_{2-4}$alkynyl, $C_{1-3}$alkoxy, NR'R", —NR'—S(O)$_w$—C$_{1-2}$alkyl (where w is 0, 1 or 2), NR'—C(O)—C$_{1-3}$alkyl, NR'—C(O)—O—C$_{1-3}$alkyl, —NR'—S(O)$_w$, and S(O)$_w$—NR'R"; $C_{1-6}$alkoxy may be optionally substituted with one, two, three or more substituents selected from the group consisting of halogen, hydroxyl, nitro, cyano, carboxy, $C_{1-3}$alkyl, NR'R", $C_{1-2}$alkyl (where w is 0, 1 or 2), and S(O)$_w$—NR'R" (where w is 0, 1 or 2); $C_{1-6}$alkylene may be optionally substituted by a substituent selected from the group consisting of $C_{3-6}$cycloalkyl, hydroxyl, cyano, and halogen;

and pharmaceutically acceptable salts and N-oxides thereof.

For example, in some embodiments, Y may be selected from the group consisting of S(O)$_y$, C=O, C(R$^{11}$)$_2$, NR$_Y$ and O wherein y is 0, 1, or 2.

For example, the present disclosure also provides, in part, a compound selected from the group consisting a compound described in the Examples below and pharmaceutically acceptable salts thereof. In an embodiment, the present disclosure provides a pharmaceutically acceptable composition comprising a disclosed compound, and a pharmaceutically acceptable excipient.

For example, the present disclosure also provides, in part, a compound selected from the group consisting of (S)-11-oxo-N-((2-(4-(2-(pyrrolidin-2-yl)ethoxy)phenyl)thiazol-5-yl)methyl)-10,11-dihydrodibenzo[b,f][1,4]thiazepine-8-carboxamide 5,5-dioxide; (S)—N-((2-(4-(2-(1-methylpyrrolidin-2-yl)ethoxy)phenyl)thiazol-5-yl)methyl)-11-oxo-10,11-dihydrodibenzo[b,f][1,4]thiazepine-8-carboxamide 5,5-dioxide; (R)—N-((2-(4-((1 methylpyrrolidin-3-yl)methoxy)phenyl)thiazol-5-yl) methyl)-11-oxo-10,11-dihydrodibenzo[b,f][1,4]thiazepine-8-carboxamide 5,5-dioxide; N-((2-(4-(2-hydroxypropan-2-yl)-1H-pyrazol-1-yl)thiazol-5-yl)methyl)-11-oxo-10,11-dihydrodibenzo[b,f][1,4]thiazepine-8-carboxamide 5,5-dioxide; (E)-N-((2-(4-(3-hydroxyprop-1-en-1-yl)-1H-pyrazol-1-yl)thiazol-5-yl)methyl)-11-oxo-10,11-dihydrodibenzo[b,f][1,4]thiazepine-8-carboxamide 5,5-dioxide; N-((2-(4-(3-(dimethylamino)propyl)-1H-pyrazol-1-yl)thiazol-5-yl)methyl)-11-oxo-10,11-dihydrodibenzo[b,f][1,4]thiazepine-8-carboxamide 5,5-dioxide; N-((2-(4-(3-hydroxypropyl)-1H-pyrazol-1-yl)thiazol-5-yl)methyl)-11-oxo-10,11-dihydrodibenzo[b,f][1,4]thiazepine-8-carboxamide 5,5-dioxide; 11-oxo-N-((2-(4-(4-(piperidin-1-yl)but-1-yn-1-yl)phenyl)thiazol-5-yl)methyl)-10,11-dihydrodibenzo[b,f][1,4]thiazepine-8-carboxamide 5,5-dioxide; N-((2-(4-(4-(diethylamino)but-1-yn-1-yl)phenyl)thiazol-5-yl)methyl)-11-oxo-10,11-dihydrodibenzo[b,f][1,4]thiazepine-8-carboxamide 5,5-dioxide; 11-oxo-N-((2-(5-(3-(piperidin-1-yl)propoxy)pyridin-2-yl)thiazol-5-yl) methyl)-10,11-dihydrodibenzo[b,f][1,4]thiazepine-8-carboxamide 5,5-dioxide; N-((2-(5-(3-morpholinopropoxy) pyridin-2-yl)thiazol-5-yl)methyl)-11-oxo-10,11- dihydrodibenzo[b,f][1,4]thiazepine-8-carboxamide 5,5-dioxide; N-((2-(5-(3-(diethylamino)propoxy)pyridin-2-yl)thiazol-5-yl)methyl)-11-oxo-10,11-dihydrodibenzo[b,f][1,4]thiazepine-8-carboxamide 5,5-dioxide; 11-oxo-N-((2-(5-(4-(piperidin-1-yl)butyl)pyridin-2-yl)thiazol-5-yl)methyl)-10,11-dihydrodibenzo[b,f][1,4]thiazepine-8-carboxamide 5,5-dioxide; N-((2-(5-(4-morpholinobutyl)pyridin-2-yl)thiazol-5-yl)methyl)-11-oxo-10,11-dihydrodibenzo[b,f][1,4]thiazepine-8-carboxamide 5,5-dioxide; N-((2-(5-(4-(diethylamino)butyl)pyridin-2-yl)thiazol-5-yl)methyl)-11-oxo-10,11-dihydrodibenzo[b,f][1,4]thiazepine-8-carboxamide 5,5-dioxide; (R)-4-(3-(4-(5-((5,5-dioxido-11-oxo-10,11-dihydrodibenzo[b,f][1,4]thiazepine-8-carboxamido)methyl)thiazol-2-yl)phenoxy)propyl)morpholine-3-carboxylic acid; (S)-4-(3-(4-(5-((5,5-dioxido-11-oxo-10,11-dihydrodibenzo[b,f][1,4]thiazepine-8-carboxamido)methyl)thiazol-2-yl)phenoxy)propyl)morpholine-3-carboxylic acid; (S)—N-((2-(4-(3-(3-methylmorpholino)propoxy)phenyl)thiazol-5-yl)methyl)-11-oxo-10,11-dihydrodibenzo[b,f][1,4]thiazepine-8-carboxamide 5,5-dioxide; (R)—N-((2-(4-(3-(3-methylmorpholino)propoxy)phenyl)thiazol-5-yl)methyl)-11-oxo-10,11-dihydrodibenzo[b,f][1,4]thiazepine-8-carboxamide 5,5-dioxide; (R)—N-((2-(4-(3-(2-methylmorpholino)propoxy)phenyl)thiazol-5-yl)methyl)-11-oxo-10,11-dihydrodibenzo[b,f][1,4]thiazepine-8-carboxamide 5,5-dioxide; (S)—N-((2-(4-(3-(2-methylmorpholino)propoxy)phenyl)thiazol-5-yl)methyl)-11-oxo-10,11-dihydrodibenzo[b,f][1,4]thiazepine-8-carboxamide 5,5-dioxide; N-((2-(4-(3-(dimethylamino)propoxy)cyclohexyl)thiazol-5-yl)methyl)-11-oxo-10,11-dihydrodibenzo[b,f][1,4]thiazepine-8-carboxamide 5,5-dioxide; N-((2-(4-(3-((2R,6R)-2,6-dimethylmorpholino)propoxy)phenyl)thiazol-5-yl)methyl)-11-oxo-10,11-dihydrodibenzo[b,f][1,4]thiazepine-8-carboxamide 5,5-dioxide; N-((2-(4-(3-((2S,6S)-2,6-dimethylmorpholino)propoxy)phenyl)thiazol-5-yl)methyl)-11-oxo-10,11-dihydrodibenzo[b,f][1,4]thiazepine-8-carboxamide 5,5-dioxide; N-((2-(4-(3-((2R,6S)-2,6-dimethylmorpholino)propoxy)phenyl)thiazol-5-yl)methyl)-11-oxo-10,11-dihydrodibenzo[b,f][1,4]thiazepine-8-carboxamide 5,5-dioxide; N-((2-(5-(3-hydroxypropoxy)pyridin-2-yl)thiazol-5-yl)methyl)-11-oxo-10,11-dihydrodibenzo[b,f][1,4]thiazepine-8-carboxamide 5,5-dioxide; N-((2-(4-(3-(cyclobutyl(methyl)amino)propoxy)phenyl)thiazol-5-yl)methyl)-11-oxo-10,11-dihydrodibenzo[b,f][1,4]thiazepine-8-carboxamide 5,5-dioxide; 11-oxo-N-((2-(4-(3-(pyrrolidin-1-yl)propoxy)phenyl)thiazol-5-yl)methyl)-10,11-dihydrodibenzo[b,f][1,4]thiazepine-8-carboxamide 5,5-dioxide; methyl (3-(4-(5-((5,5-dioxido-11-oxo-10,11-dihydrodibenzo[b,f][1,4]thiazepine-8-carboxamido)methyl)thiazol-2-yl)phenoxy)propyl)-D-prolinate; (3-(4-(5-((5,5-dioxido-11-oxo-10,11-dihydrodibenzo[b,f][1,4]thiazepine-8-carboxamido)methyl)thiazol-2-yl)phenoxy)propyl)-D-proline; ethyl (3-(4-(5-((5,5-dioxido-11-oxo-10,11-dihydrodibenzo[b,f][1,4]thiazepine-8-carboxamido)methyl)thiazol-2-yl)phenoxy)propyl)-L-prolinate; isopropyl (3-(4-(5-((5,5-dioxido-11-oxo-10,11-dihydrodibenzo[b,f][1,4]thiazepine-8-carboxamido)methyl)thiazol-2-yl)phenoxy)propyl)-L-prolinate; methyl (S)-4-(3-(4-(5-((5,5-dioxido-11-oxo-10,11-dihydrodibenzo[b,f][1,4]thiazepine-8-carboxamido)methyl)thiazol-2-yl)phenoxy)propyl)morpholine-3-carboxylate; methyl (3-(4-(5-((5,5-dioxido-11-oxo-10,11-dihydrodibenzo[b,f][1,4]thiazepine-8-carboxamido)methyl)thiazol-2-yl)phenoxy)propyl)-L-alaninate; (3-(4-(5-((5,5-dioxido-11-oxo-10,11-dihydrodibenzo[b,f][1,4]thiazepine-8-carboxamido)methyl)thiazol-2-yl)phenoxy)propyl)-L-alanine; methyl N-(3-(4-(5-((5,5-dioxido-11-oxo-10,11-dihydrodibenzo[b,f][1,4]thiazepine-8-carboxamido)methyl)thiazol-2-yl)phenoxy)propyl)-N-methyl-L-alaninate; N-(3-(4-(5-((5,5-dioxido-11-oxo-10,11-dihydrodibenzo[b,f][1,4]thiazepine-8-carboxamido)methyl)thiazol-2-yl)phenoxy)propyl)-N-methyl-L-alanine; methyl (3-(4-(5-((5,5-dioxido-11-oxo-10,11-dihydrodibenzo[b,f][1,4]thiazepine-8-carboxamido)methyl)thiazol-2-yl)phenoxy)propyl)-L-valinate; (3-(4-(5-((5,5-dioxido-11-oxo-10,11-dihydrodibenzo[b,f][1,4]thiazepine-8-carboxamido)methyl)thiazol-2-yl)phenoxy)propyl)-L-valine; methyl (2-(4-(5-((5,5-dioxido-11-oxo-10,11-dihydrodibenzo[b,f][1,4]thiazepine-8-carboxamido)methyl)thiazol-2-yl)phenoxy)ethyl)-L-prolinate; (2-(4-(5-((5,5-dioxido-11-oxo-10,11-dihydrodibenzo[b,f][1,4]thiazepine-8-carboxamido)methyl)thiazol-2-yl)phenoxy)ethyl)-L-proline; methyl (4-(4-(5-((5,5-dioxido-11-oxo-10,11-dihydrodibenzo[b,f][1,4]thiazepine-8-carboxamido)methyl)thiazol-2-yl)phenyl)but-3-yn-1-yl)-L-prolinate; (4-(4-(5-((5,5-dioxido-11-oxo-10,11-dihydrodibenzo[b,f][1,4]thiazepine-8-carboxamido)methyl)thiazol-2-yl)phenyl)but-3-yn-1-yl)-L-proline; N-((2-(4-cyano-1H-pyrazol-1-yl)thiazol-5-yl)methyl)-11-oxo-10,11-dihydrodibenzo[b,f][1,4]thiazepine-8-carboxamide 5,5-dioxide; N-((2-(4-((1-ethylpiperidin-4-yl)oxy)phenyl)thiazol-5-yl)methyl)-11-oxo-10,11-dihydrodibenzo[b,f][1,4]thiazepine-8-carboxamide 5,5-dioxide; N-((2-(4-(3-morpholinopropyl)phenyl)thiazol-5-yl)methyl)-11-oxo-10,11-dihydrodibenzo[b,f][1,4]thiazepine-8-carboxamide 5,5-dioxide; methyl (3-(4-(5-((9-methyl-5,5-dioxido-11-oxo-10,11-dihydrodibenzo[b,f][1,4]thiazepine-8-carboxamido)methyl)thiazol-2-yl)phenoxy)propyl)-L-prolinate; (3-(4-(5-((9-methyl-5,5-dioxido-11-oxo-10,11-dihydrodibenzo[b,f][1,4]thiazepine-8-carboxamido)methyl)thiazol-2-yl)phenoxy)propyl)-L-proline; N-((2-(4-cyano-1H-pyrazol-1-yl)thiazol-5-yl)methyl)-9-methyl-11-oxo-10,11-dihydrodibenzo[b,f][1,4]thiazepine-8-carboxamide 5,5-dioxide; 9-methyl-N-((2-(4-(2-morpholinoethoxy)phenyl)thiazol-5-yl)methyl)-11-oxo-10,11-dihydrodibenzo[b,f][1,4]thiazepine-8-carboxamide 5,5-dioxide; 9-methyl-11-oxo-N-((2-(4-(piperidin-4-yloxy)phenyl)thiazol-5-yl)methyl)-10,11-dihydrodibenzo[b,f][1,4]thiazepine-8-carboxamide 5,5-dioxide; N-((2-(4-((1-ethylpiperidin-4-yl)oxy)phenyl)thiazol-5-yl)methyl)-9-methyl-1-oxo-10,11-dihydrodibenzo[b,f][1,4]thiazepine-8-carboxamide 5,5-dioxide; (S)—N-((2-(4-(3-(2-(hydroxymethyl)pyrrolidin-1-yl)propoxy)phenyl)thiazol-5-yl)methyl)-9-methyl-11-oxo-10,11-dihydrodibenzo[b,f][1,4]thiazepine-8-carboxamide 5,5-dioxide; (S)—N-((2-(4-(3-(2-(methoxymethyl)pyrrolidin-1-yl)propoxy)phenyl)thiazol-5-yl)methyl)-9-methyl-11-oxo-10,11-dihydrodibenzo[b,f][1,4]thiazepine-8-carboxamide 5,5-dioxide; (S)—N-((2-(4-(3-(2-cyanopyrrolidin-11-yl)propoxy)phenyl)thiazol-5-yl)methyl)-9-methyl-11-oxo-10,11-dihydrodibenzo[b,f][1,4]thiazepine-8-carboxamide 5,5-dioxide; (S)—N-((2-(4-(3-(2-(1H-tetrazol-5-yl)pyrrolidin-1-yl)propoxy)phenyl)thiazol-5-yl)methyl)-9-methyl-11-oxo-10,11-dihydrodibenzo[b,f][1,4]thiazepine-8-carboxamide 5,5-dioxide; 9-methyl-N-((2-(4-(4-morpholinobut-1-yn-1-yl)phenyl)thiazol-5-yl)methyl)-11-oxo-10,11-dihydrodibenzo[b,f][1,4]thiazepine-8-carboxamide 5,5-dioxide; 9-methyl-N-((2-(4-(4-morpholinobutyl)phenyl)thiazol-5-yl)methyl)-11-oxo-10,11-dihydrodibenzo[b,f][1,4]thiazepine-8-carboxamide 5,5-dioxide; N-((2-(4,4-difluoropiperidin-1-yl)thiazol-5-yl)methyl)-9-methyl-11-oxo-10,11-dihydrodibenzo[b,f][1,4]thiazepine-8-carboxamide 5,5-dioxide; N-((2-(4-methoxypiperidin-1-yl)thiazol-5-yl)methyl)-9-methyl-11-oxo-10,11-dihydrodibenzo[b,f][1,4]thiazepine-8- carboxamide 5,5-dioxide; 9-methyl-N-((2-(4-(3-morpholinopropyl)phenyl)thiazol-5-yl)methyl)-11-oxo-10,11-dihydrodibenzo[b,f][1,4]thiazepine-8-carboxamide 5,5-dioxide; N-((2-(4-((1-isopropylpiperidin-4-yl)oxy)phenyl)thiazol-5-yl)methyl)-9-methyl-11-oxo-10,11-dihydrodibenzo[b,f][1,4]thiazepine-8-carboxamide 5,5-dioxide; N-((2-(4-((1-(2-hydroxy-2-methylpropyl)piperidin-4-yl)oxy)phenyl)thiazol-5-yl)methyl)-9-methyl-11-oxo-10,11-dihydrodibenzo[b,f][1,4]thiazepine-8-carboxamide 5,5-dioxide; N-((2-(4-((1-ethylazetidin-3-yl)oxy)phenyl)thiazol-5-yl)methyl)-9-methyl-11-oxo-10,11-dihydrodibenzo[b,f][1,4]thiazepine-8-carboxamide 5,5-dioxide; N-((2-(4-((1-isopropylazetidin-3-yl)oxy)phenyl)thiazol-5-yl)methyl)-9-methyl-11-oxo-10,11-dihydrodibenzo[b,f][1,4]thiazepine-8-carboxamide 5,5-dioxide; N-((2-(4-((3-(dimethylamino)azetidin-1-yl)methyl)phenyl)thiazol-5-yl)methyl)-9-methyl-11-oxo-10,11-dihydrodibenzo[b,f][1,4]thiazepine-8-carboxamide 5,5-dioxide; N-((2-(4-((3-(diethylamino)azetidin-1-yl)methyl)phenyl)thiazol-5-yl)methyl)-9-methyl-11-oxo-10,11-dihydrodibenzo[b,f][1,4]thiazepine-8-carboxamide 5,5-dioxide; N-(2-(4-([1,3'-biazetidin]-1'-ylmethyl)phenyl)thiazol-5-yl)methyl)-9-methyl-11-oxo-10,11-dihydrodibenzo[b,f][1,4]thiazepine-8-carboxamide 5,5-dioxide; N-((2-(4-(azetidin-1-ylmethyl)phenyl)thiazol-5-yl)methyl)-9-methyl-11-oxo-10,11-dihydrodibenzo[b,f][1,4]thiazepine-8-carboxamide 5,5-dioxide; methyl (4-(5-((9-methyl-5,5-dioxido-11-oxo-10,11-dihydrodibenzo[b,f][1,4]thiazepine-8-carboxamido)methyl)thiazol-2-yl)benzyl)-L-prolinate; (4-(5-((9-methyl-5,5-dioxido-11-oxo-10,11-dihydrodibenzo[b,f][1,4]thiazepine-8-carboxamido)methyl)thiazol-2-yl)benzyl)-L-proline; methyl (S)-4,4-difluoro-1-(4-(5-((9-methyl-5,5-dioxido-11 1-oxo-10,11-dihydrodibenzo[b,f][1,4]thiazepine-8-carboxamido)methyl)thiazol-2-yl)benzyl)pyrrolidine-2-carboxylate; (S)-4,4-difluoro-1-(4-(5-((9-methyl-5,5-dioxido-1-oxo-10,11-dihydrodibenzo[b,f][1,4]thiazepine-8-carboxamido)methyl)thiazol-2-yl)benzyl)pyrrolidine-2-carboxylic acid; methyl (S)-4-(4-(5-((9-methyl-5,5-dioxido-1 1-oxo-10,11-dihydrodibenzo[b,f][1,4]thiazepine-8-carboxamido)methyl)thiazol-2-yl)benzyl)morpholine-3-carboxylate; (S)-4-(4-(5-((9-methyl-5,5-dioxido-11-oxo-10,11-dihydrodibenzo[b,f][1,4]thiazepine-8-carboxamido)methyl)thiazol-2-yl)benzyl)morpholine-3-carboxylic acid; N-([2,2'-bithiazol]-5-ylmethyl)-9-methyl-11-oxo-10,11-dihydrodibenzo[b,f][1,4]thiazepine-8-carboxamide 5,5-dioxide; N-([2,4'-bithiazol]-5-ylmethyl)-9-methyl-1-oxo-10,11-dihydrodibenzo[b,f][1,4]thiazepine-8-carboxamide 5,5-dioxide; N-((2-(4-(3-morpholinopropyl)phenyl)thiazol-5-yl)methyl)-11-oxo-10,11-dihydrodibenzo[b,f][1,4]oxazepine-8-carboxamide; 9-methyl-11-oxo-N-((2-(4-(3-(piperidin-1-yl)propoxy)phenyl)thiazol-5-yl)methyl)-10,11-dihydrodibenzo[b,f][1,4]oxazepine-8-carboxamide; 9-methyl-N-((2-(4-(3-morpholinopropoxy)phenyl)thiazol-5-yl)methyl)-11-oxo-10,11-dihydrodibenzo[b,f][1,4]oxazepine-8-carboxamide; N-((2-(4-(3-(diethylamino)propoxy)phenyl)thiazol-5-yl)methyl)-9-methyl-11-oxo-10,11-dihydrodibenzo[b,f][1,4]oxazepine-8-carboxamide; 9-methyl-N-((2-(4-(3-morpholinopropyl)phenyl)thiazol-5-yl)methyl)-11-oxo-10,11-dihydrodibenzo[b,f][1,4]oxazepine-8-carboxamide; 9-methyl-N-((2-(4-(2-morpholinoethoxy)phenyl)thiazol-5-yl)methyl)-11-oxo-10,11-dihydrodibenzo[b,f][1,4]oxazepine-8-carboxamide; N-((2-(4-((1-ethylpiperidin-4-yl)oxy)phenyl)thiazol-5-yl)methyl)-9-methyl-11-oxo-10,11-dihydrodibenzo[b,f][1,4]oxazepine-8-carboxamide; N-((2-(4-((1-isopropylpiperidin-4-yl)oxy)phenyl)thiazol-5-yl)methyl)-9-methyl-1-oxo-10,11-dihydrodibenzo[b,f][1,4]oxazepine-8-carboxamide; N-((2-(4-((1-(2-hydroxy-2-methylpropyl)piperidin-4-yl)oxy)phenyl)thiazol-5-yl)methyl)-9-methyl-11-oxo-10,11-dihydrodibenzo[b,f][1,4]oxazepine-8-carboxamide; N-((2-(4-((1-ethylazetidin-3-yl)oxy)phenyl)thiazol-5-yl)methyl)-9-methyl-11-oxo-10,11-dihydrodibenzo[b,f][1,4]oxazepine-8-carboxamide; N-((2-(4-((1-isopropylazetidin-3-yl)oxy)phenyl)thiazol-5-yl)methyl)-9-methyl-11-oxo-10,11-dihydrodibenzo[b,f][1,4]oxazepine-8-carboxamide; N-((2-(4-((3-(dimethylamino)azetidin-1-yl)methyl)phenyl)thiazol-5-yl)methyl)-9-methyl-11-oxo-10,11-dihydrodibenzo[b,f][1,4]oxazepine-8-carboxamide; methyl (4-(5-((9-methyl-11-oxo-10,11-dihydrodibenzo[b,f][1,4]oxazepine-8-carboxamido)methyl)thiazol-2-yl)benzyl)-L-prolinate; (4-(5-((9-methyl-11-oxo-10,11-dihydrodibenzo[b,f][1,4]oxazepine-8-carboxamido)methyl)thiazol-2-yl)benzyl)-L-proline; methyl (S)-4,4-difluoro-1-(4-(5-((9-methyl-11-oxo-10,11-dihydrodibenzo[b,f][1,4]oxazepine-8-carboxamido)methyl)thiazol-2-yl)benzyl)pyrrolidine-2-carboxylate; (S)-4,4-difluoro-1-(4-(5-((9-methyl-11-oxo-10,11-dihydrodibenzo[b,f][1,4]oxazepine-8-carboxamido)methyl)thiazol-2-yl)benzyl)pyrrolidine-2-carboxylic acid; N-([2,2'-bithiazol]-5-ylmethyl)-9-methyl-11-oxo-10,11-dihydrodibenzo[b,f][1,4]oxazepine-8-carboxamide; N-((2-(5-fluoropyridin-2-yl)thiazol-5-yl)methyl)-9-methyl-11-oxo-10,11-dihydrodibenzo[b,f][1,4]oxazepine-8-carboxamide; N-((2-(5-cyanopyridin-2-yl)thiazol-5-yl)methyl)-9-methyl-11-oxo-10,11-dihydrodibenzo[b,f][1,4]oxazepine-8-carboxamide; 11-oxo-N-((2-(4-(3-(piperidin-1-yl)propyl)-1H-pyrazol-1-yl)thiazol-5-yl)methyl)-10,11-dihydrodibenzo[b,f][1,4]thiazepine-8-carboxamide 5,5-dioxide; 9-methyl-11-oxo-N-((2-(4-(3-(piperidin-1-yl)propyl)-1H-pyrazol-1-yl)thiazol-5-yl)methyl)-10,11-dihydrodibenzo[b,f][1,4]thiazepine-8-carboxamide 5,5-dioxide; N-((2-(4-(3-(azetidin-1-yl)propyl)-1H-pyrazol-1-yl)thiazol-5-yl)methyl)-9-methyl-11-oxo-10,11-dihydrodibenzo[b,f][1,4]thiazepine-8-carboxamide 5,5-dioxide; N-((2-(4-(4-(azetidin-1-yl)but-1-yn-1-yl)phenyl)thiazol-5-yl)methyl)-9-methyl-11-oxo-10,11-dihydrodibenzo[b,f][1,4]thiazepine-8-carboxamide 5,5-dioxide; N-((2-(4-(4-(azetidin-1-yl)butyl)phenyl)thiazol-5-yl)methyl)-9-methyl-11-oxo-10,11-dihydrodibenzo[b,f][1,4]thiazepine-8-carboxamide 5,5-dioxide; 9-methyl-N-((2-(4-(3-morpholinopropyl)phenyl)thiazol-5-yl)methyl)-11-oxo-10,11-dihydrodibenzo[b,f][1,4]thiazepine-8-carboxamide 5,5-dioxide; (S)—N-((2-(4-(3-(2-cyanopyrrolidin-1-yl)propyl)phenyl)thiazol-5-yl)methyl)-9-methyl-11-oxo-10,11-dihydrodibenzo[b,f][1,4]thiazepine-8-carboxamide 5,5-dioxide; N-((2-(4-(3-(azetidin-1-yl)propyl)phenyl)thiazol-5-yl)methyl)-9-methyl-11-oxo-10,11-dihydrodibenzo[b,f][1,4]thiazepine-8-carboxamide 5,5-dioxide; 9-methyl-11-oxo-N-((2-(4-(3-(piperidin-1-yl)propyl)phenyl)thiazol-5-yl)methyl)-10,11-dihydrodibenzo[b,f][1,4]thiazepine-8-carboxamide 5,5-dioxide; 2-(5-((9-methyl-5,5-dioxido-11-oxo-10,11-dihydrodibenzo[b,f][1,4]thiazepine-8-carboxamido)methyl)thiazol-2-yl)pyridine 1-oxide; 9-chloro-N-((2-(5-cyanopyridin-2-yl)thiazol-5-yl)methyl)-11-oxo-10,11-dihydrodibenzo[b,f][1,4]oxazepine-8-carboxamide; 6-(5-((9-methyl-5,5-dioxido-11-oxo-10,11-dihydrodibenzo[b,f][1,4]thiazepine-8-carboxamido)methyl)thiazol-2-yl) picolinic acid; methyl (S)-4,4-difluoro-1-(4-(5-((9-methyl-5,5-dioxido-11-oxo-10,11-dihydrodibenzo[b,f][1,4]thiazepine-8-carboxamido)methyl)thiazol-2-yl)benzyl)pyrrolidine-2-carboxylate; 2-methyl-2-(5-((9-methyl-5,5-dioxido-11-oxo-10,11-dihydrodibenzo[b,f][1,4]thiazepine-8-carboxamido)methyl)thiazol-2-yl)propanoic acid; (S)-4,4-difluoro-1-(4-(5-((9-methyl-5,5-dioxido-11-oxo-10,11-dihydrodibenzo[b,f][1,4]thiazepine-8-carboxamido)methyl)

thiazol-2-yl)benzyl)pyrrolidine-2-carboxylic acid; and pharmaceutically acceptable salts thereof. In an embodiment, the present disclosure provides a pharmaceutically acceptable composition comprising a disclosed compound, and a pharmaceutically acceptable excipient.

In a further aspect, a method for treating a hepatitis B infection in a patient in need thereof is provided, comprising administering to a subject or patient an effective amount of a disclosed compound, and/or administering a first disclosed compound and optionally, and additional, different disclosed compound(s). In another embodiment, a method for treating a hepatitis B infection in a patient in need thereof is provided, comprising administering to a subject or patient a therapeutically effective amount of a pharmaceutical composition comprising a disclosed compound, or two or more disclosed compounds.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 1000 μg/kg body weight. In some cases, the administration dose of the compound may be less than 400 μg/kg body weight. In other cases, the administration dose may be less than 200 μg/kg body weight. In yet other cases, the administration dose may be in the range between about 0.1 to about 100 μg/kg body weight. The dose may be conveniently administered once daily, or in divided doses up to, for example, four times a day or in sustained release form.

A compound may be administered by any conventional route, in particular: enterally, topically, orally, nasally, e.g. in the form of tablets or capsules, via suppositories, or parenterally, e.g. in the form of injectable solutions or suspensions, for intravenous, intra-muscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). Tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A disclosed compound may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and/or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

In some cases, a disclosed compound may be administered as part of a combination therapy in conjunction with one or more antivirals. Example antivirals include nucleoside analogs, interferon α, and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate (HAP-1). For example, provided herein is a method of treating patient suffering from hepatitis B comprising administering to a subject a first amount of a disclosed compound and a second amount of an antiviral, or other anti HBV agent, for example a second amount of a second compound selected from the group consisting of: another HBV caspid assembly promoter (such as certain compounds disclosed herein or for example, GLS4, BAY 41-4109, AT-130, DVR-23 (e.g., as depicted below),

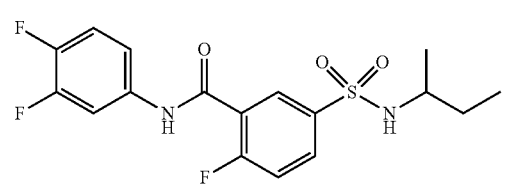

DVR-23

NVR 3-778, NVR1221 (by code); and N890 (as depicted below):

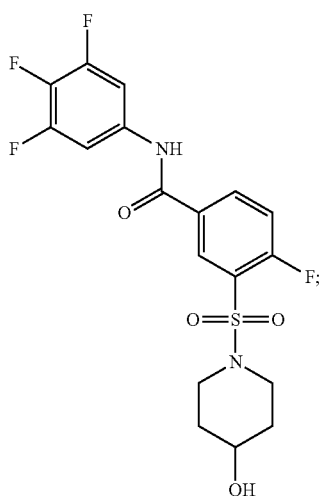 [SMILES: O=C(Nc1cc(F)c(F)c(F)c1)c1ccc(F)c(S(=O)(=O)N2CCC(O)CC2)c1]

other CpAMs such as those disclosed in the following patent applications hereby incorporated by reference: WO2014037480, WO2014184328, WO2013006394, WO2014089296, WO2014106019, WO2013102655, WO2014184350, WO2014184365, WO2014161888, WO2014131847, WO2014033176, WO2014033167, and WO2014033170; Nucleoside analogs interfering with viral polymerase, such as entecavir (Baraclude), Lamivudine, (Epivir-HBV), Telbivudine (Tyzeka, Sebivo), Adefovir dipivoxil (Hepsera), Tenofovir (Viread), Tenofovir alafenamide fumarate (TAF), prodrugs of tenofovir (e.g. AGX-1009), L-FMAU (Clevudine), LB80380 (Besifovir) and:

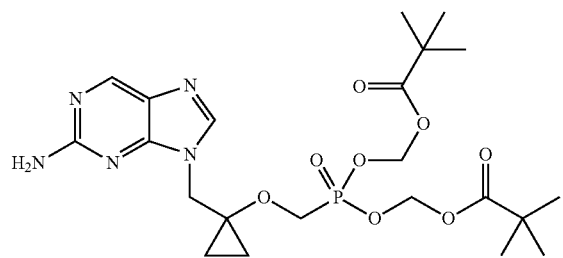

viral entry inhibitors such as Myrcludex B and related lipopeptide derivatives; HBsAg secretion inhibitors such as REP 9AC' and related nucleic acid-based amphipathic polymers, HBF-0529 (PBHBV-001), PBHBV-2-15 as depicted below:

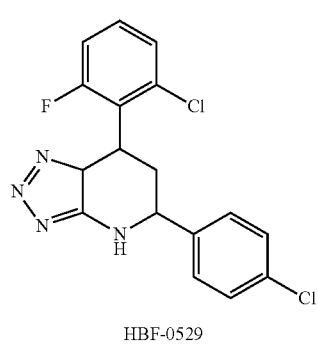

HBF-0529

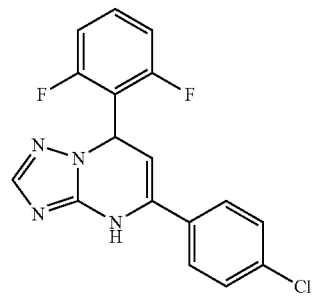

PBHBV-2-15 and BM601 as depicted below:

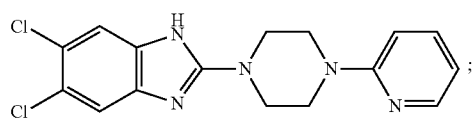 [SMILES: Clc1cc2nc(N3CCN(c4ccccn4)CC3)[nH]c2cc1Cl]

disruptors of nucleocapsid formation or integrity such as NZ-4/W28F:

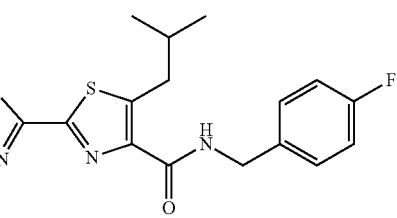

cccDNA formation inhibitors: such as BSBI-25, CCC-0346, CCC-0975 (as depicted below):

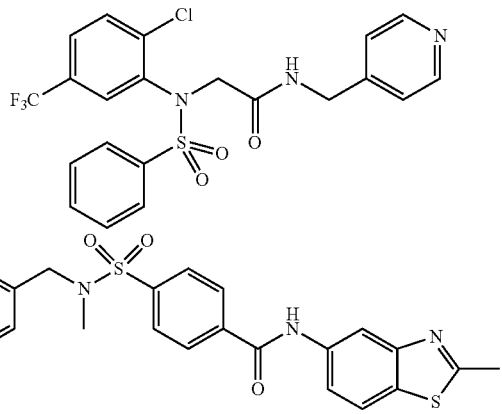

HBc directed transbodies such as those described in Wang Y, et al, Transbody against hepatitis B virus core protein inhibits hepatitis B virus replication in vitro, Int. Immunopharmacol (2014), located at //dx.doi.org/10.1016/j.intimp.2015.01.028; antiviral core protein mutant (such as Cp183-V124W and related mutations as described in WO/2013/010069, WO2014/074906 each incorporated by reference); inhibitors of HBx-interactions such as RNAi, antisense and nucleic acid based polymers targeting HBV RNA; e.g., RNAi (for example ALN-HBV, ARC-520, TKM-HBV, ddRNAi), antisense (ISIS-HBV), or nucleic acid based polymer: (REP 2139-Ca); immunostimulants such as Interferon alpha 2a (Roferon), Intron A (interferon alpha 2b), Pegasys (peginterferon alpha 2a), Pegylated IFN 2b, IFN lambda 1a and PEG IFN lambda 1a, Wellferon, Roferon, Infergen, lymphotoxin beta agonists such as CBE11 and BS1); Non-Interferon Immune enhancers such as Thymosin alpha-1 (Zadaxin) and Interleukin-7 (CYT107); TLR-7/9 agonists such as GS-9620, CYT003, Resiquimod; Cyclophilin Inhibitors such as NVP018; OCB-030; SCY-635; Alisporivir; NIM811 and related cyclosporine analogs; vaccines such as GS-4774, TG1050, Core antigen vaccine; SMAC mimetics such as birinapant and other IAP-antagonists; Epigenetic modulators such as KMT inhibitors (EZH1/2, G9a, SETD7, Suv39 inhibitors), PRMT inhibitors, HDAC inhibitors, SIRT agonists, HAT inhibitors, WD antagonists (e.g. OICR-9429), PARP inhibitors, APE inhibitors, DNMT inhibitors, LSD1 inhibitors, JMJD HDM inhibitors, and Bromodomain antagonists; kinase inhibitors such as TKB1 antagonists, PLK1 inhibitors, SRPK inhibitors, CDK2 inhibitors, ATM & ATR kinase inhibitors; STING Agonists; Ribavirin; N-acetyl cysteine; NOV-205 (BAM205); Nitazoxanide (Alinia), Tizoxanide; SB 9200 Small Molecule Nucleic Acid Hybrid (SMNH); DV-601; Arbidol; FXR agonists (such as GW 4064 and Fexaramin); antibodies, therapeutic proteins, gene therapy, and biologics directed against viral components or interacting host proteins.

In some embodiments, the disclosure provides a method of treating a hepatitis B infection in a patient in need thereof, comprising administering a first compound selected from any one of the disclosed compounds, and one or more other HBV agents each selected from the group consisting of HBV capsid assembly promoters, HBF viral polymerase interfering nucleosides, viral entry inhibitors, HBsAg secretion inhibitors, disruptors of nucleocapsid formation, cccDNA formation inhibitors, antiviral core protein mutant, HBc directed transbodies, RNAi targeting HBV RNA, immunostimulants, TLR-7/9 agonists, cyclophilin inhibitors, HBV vaccines, SMAC mimetics, epigenetic modulators, kinase inhibitors, and STING agonists. In some embodiments, the disclosure provides a method of treating a hepatitis B infection in a patient in need thereof, comprising administering an amount of a disclosed compound, and administering another HBV capsid assembly promoter.

In some embodiments, the first and second amounts together comprise a pharmaceutically effective amount. The first amount, the second amount, or both may be the same, more, or less than effective amounts of each compound administered as monotherapies. Therapeutically effective amounts of a disclosed compound and antiviral may be co-administered to the subject, i.e., administered to the subject simultaneously or separately, in any given order and by the same or different routes of administration. In some instances, it may be advantageous to initiate administration of a disclosed compound first, for example one or more days or weeks prior to initiation of administration of the antiviral. Moreover, additional drugs may be given in conjunction with the above combination therapy.

In another embodiment, a disclosed compound may be conjugated (e.g., covalently bound directly or through molecular linker to a free carbon, nitrogen (e.g. an amino group), or oxygen (e.g. an active ester) of a disclosed compound), with a detection moiety, e.g. a fluorophore moiety (such a moiety may for example re-emit a certain light frequency upon binding to a virus and/or upon photon excitation. Contemplated fluorophores include AlexaFluor® 488 (Invitrogen) and BODIPY FL (Invitrogen), as well as fluorescein, rhodamine, cyanine, indocarbocyanine, anthraquinones, fluorescent proteins, aminocoumarin, methoxycoumarin, hydroxycoumarin, Cy2, Cy3, and the like. Such disclosed compounds conjugated to a detection moiety may be used in e.g. a method for detecting HBV or biological pathways of HBV infection, e.g., in vitro or in vivo; and/or methods of assessing new compounds for biological activity.

EXAMPLES

The compounds described herein can be prepared in a number of ways based on the teachings contained herein and synthetic procedures known in the art. In the description of the synthetic methods described below, it is to be understood that all proposed reaction conditions, including choice of solvent, reaction atmosphere, reaction temperature, duration of the experiment and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials. At least some of the compounds identified as "intermediates" herein are contemplated as compounds of the invention.

Example 1: Synthesis of Compounds

Synthesis of 11-oxo-10, 11-dihydrodibenzo [b, f] [1, 4] thiazepine-8-carboxylic acid (6): A Common Intermediate

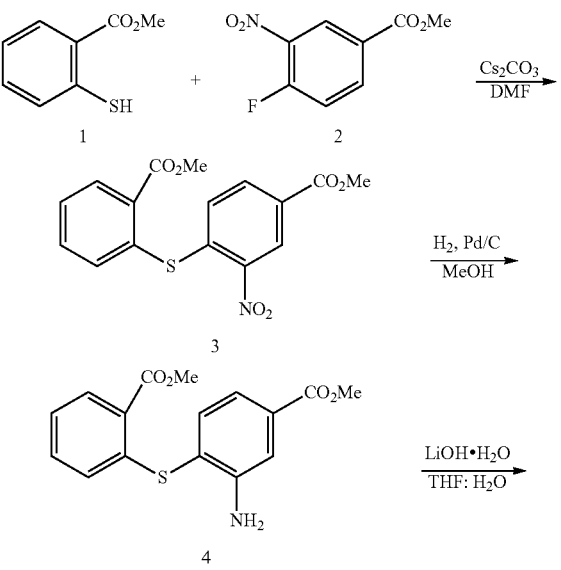

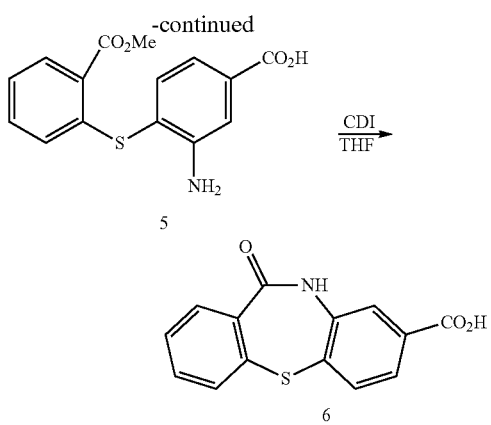

Synthesis of methyl 4-((2-(methoxycarbonyl) phenyl) thio)-3-nitrobenzoate (3)

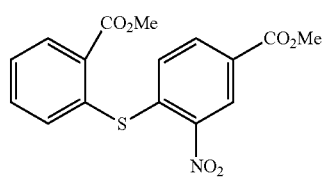

To a stirring solution of methyl 4-fluoro-3-nitrobenzoate 2 (30 g, 150.67 mmol) in DMF (300 mL) under inert atmosphere were added cesium carbonate (58.76 g, 180.8 mmol) and methyl 2-mercaptobenzoate 1 (22.6 mL, 165.47 mmol) at RT; heated to 55-60° C. and stirred for 2 h. The reaction was monitored by TLC; after completion of the reaction, the reaction mixture was diluted with water (1500 mL) and the precipitated solid was filtered to obtain the crude. The crude was washed with water (500 mL), hexane (200 mL) and dried in vacuo to afford compound 3 (48.8 g, 93%) as yellow solid. TLC: 20% EtOAc/hexanes ($R_f$: 0.4); $^1$H NMR (CDCl$_3$, 400 MHz): δ 8.85 (s, 1H), 7.99-7.92 (m, 2H), 7.66-7.56 (m, 3H), 6.93 (d, J=8.6 Hz, 1H), 3.94 (s, 3H), 3.79 (s, 3H).

Synthesis of methyl 3-amino-4-((2-(methoxycarbonyl) phenyl) thio) benzoate (4)

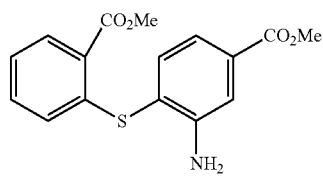

To a stirring solution of compound 3 (48 g, 138.32 mmol) in MeOH (1000 mL) under inert atmosphere was added 10% Pd/C (20 g, wet) at RT under hydrogen atmosphere in an autoclave (100 psi pressure) and stirred for 24 h. The reaction was monitored by TLC; after completion of the reaction, the reaction mixture was filtered through celite, washed with 50% MeOH/CH$_2$Cl$_2$ (500 mL). The filtrate was removed in vacuo to obtain the crude which as triturated with diethyl ether (200 mL), washed with hexane (200 mL) and dried in vacuo to afford compound 4 (40 g, 91%) as yellow solid. TLC: 10% EtOAc/hexanes ($R_f$: 0.3); $^1$H NMR (DMSO-d$_6$, 400 MHz): δ 7.95 (dd, J=7.8, 1.4 Hz, 1H), 7.48-7.35 (m, 3H), 7.23 (td, J=7.5, 1.1 Hz, 1H), 7.15 (dd, J=8.0, 1.8 Hz, 1H), 6.66 (dd, J=8.2, 0.8 Hz, 1H), 5.67 (br s, 2H), 3.88 (s, 3H), 3.84 (s, 3H).

Synthesis of 3-amino-4-((2-carboxyphenyl) thio) benzoic acid (5)

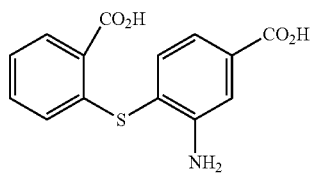

To a stirring solution of compound 4 (40 g, 126.18 mmol) in THF:H$_2$O (5:1, 400 mL) was added lithium hydroxide monohydrate (26 g, 619.0 mmol) at 0° C.; warmed to RT and stirred for 48 h. The reaction was monitored by TLC; after completion of the reaction, the volatiles were removed in vacuo. The pH of the residue was acidified with 2 N HCl to ~2. The precipitated solid was filtered and dried in vacuo to afford compound 5 (34.6 g, 95%) as an off-white solid. TLC: 30% EtOAc/hexanes ($R_f$: 0.1); $^1$H NMR (DMSO-d$_6$, 500 MHz): δ 13.00 (br s, 2H), 7.93 (dd, J=7.7, 1.0 Hz, 1H), 7.42 (s, 1H), 7.40-7.31 (m, 2H), 7.18 (t, J=7.4 Hz, 1H), 7.13 (dd, J=8.0, 1.6 Hz, 1H), 6.61 (d, J=7.8 Hz, 1H), 5.55 (br s, 2H).

Synthesis of 11-oxo-10, 11-dihydrodibenzo [b, f] [1, 4] thiazepine-8-carboxylic acid (6)

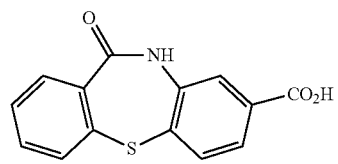

To a stirring solution of compound 5 (31 g, 107.26 mmol) in THF (600 mL) under inert atmosphere was added CDI (86.88 g, 536.29 mmol) at 0° C.; warmed to RT and stirred for 16 h. The reaction was monitored by TLC; after completion of the reaction, the reaction mixture was acidified with 2 N HCl to pH~4. The obtained solid was filtered and further dried by using toluene (2×200 mL) to afford compound 6 (26 g, 90%) as white solid. TLC: 10% MeOH/CH$_2$Cl$_2$ ($R_f$: 0.3); $^1$H NMR (DMSO-d$_6$, 400 MHz): δ 13.22 (br s, 1H), 10.81 (s, 1H), 7.78 (s, 1H), 7.72-7.64 (m, 3H), 7.57-7.44 (m, 3H).

Synthesis of 7-methyl-11-oxo-10, 11-dihydrodibenzo [b, f] [1, 4] thiazepine-8-carboxylic acid (13): A Common Intermediate

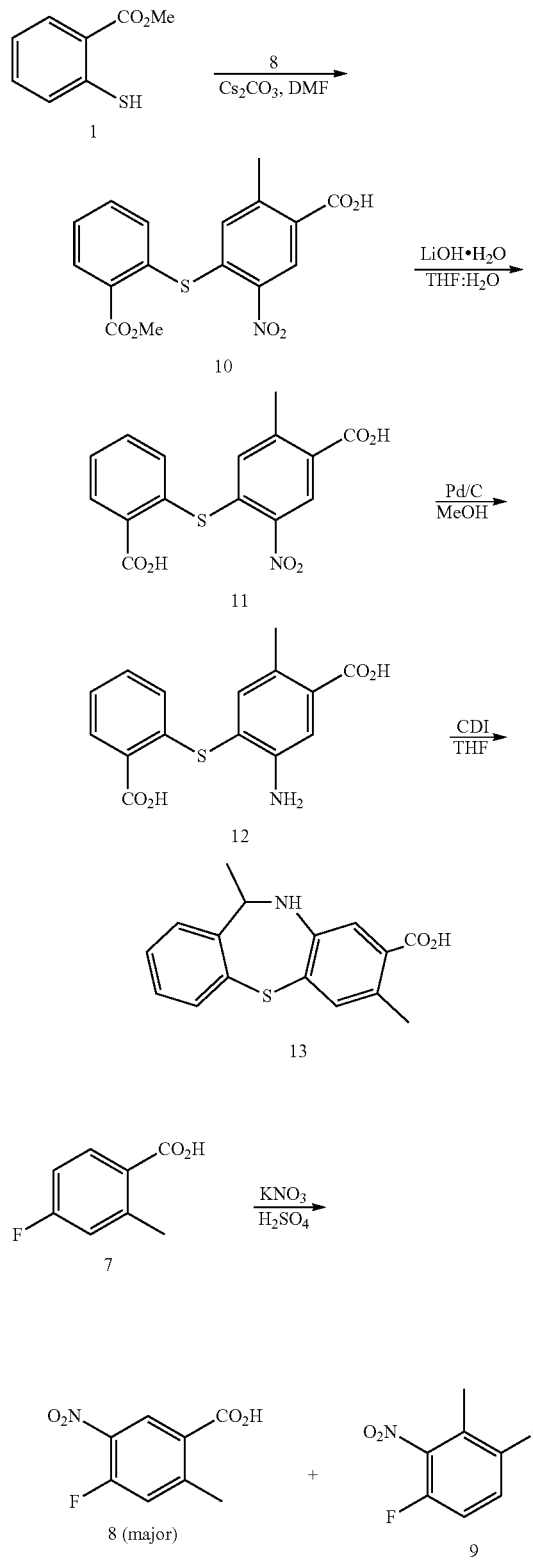

Synthesis of 4-((2-(methoxycarbonyl) phenyl) thio)-2-methyl-5-nitrobenzoic acid (10)

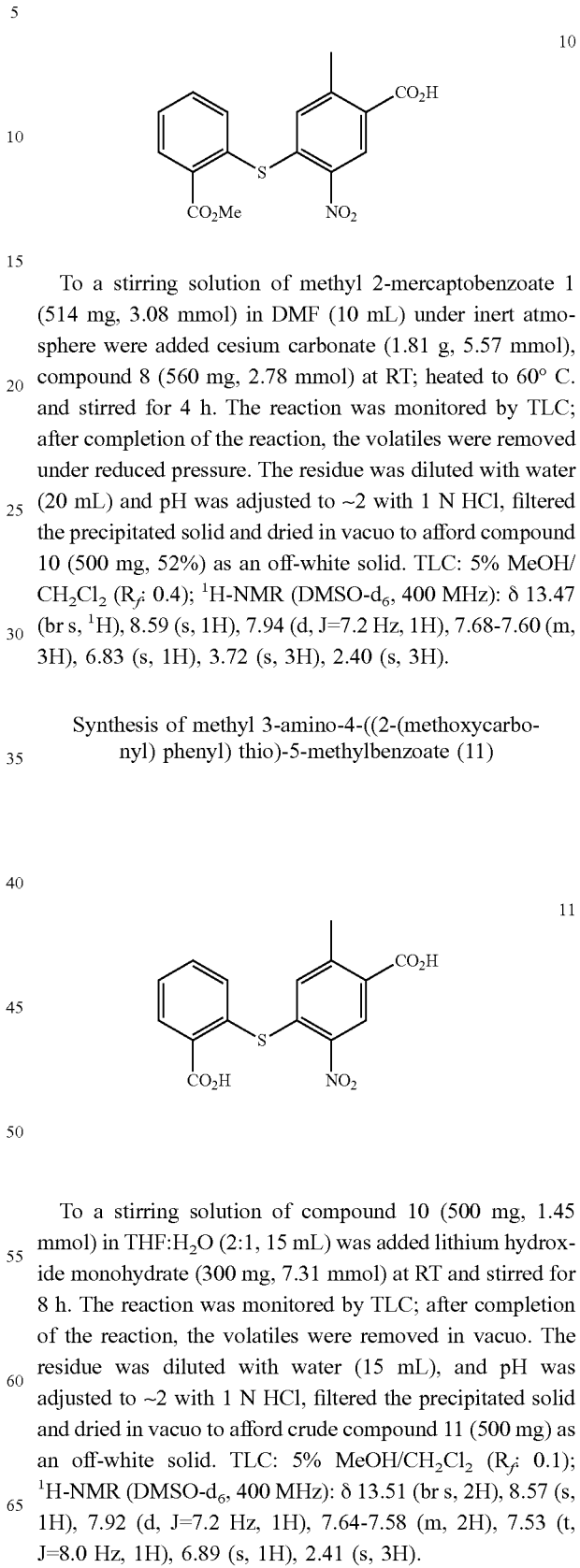

To a stirring solution of methyl 2-mercaptobenzoate 1 (514 mg, 3.08 mmol) in DMF (10 mL) under inert atmosphere were added cesium carbonate (1.81 g, 5.57 mmol), compound 8 (560 mg, 2.78 mmol) at RT; heated to 60° C. and stirred for 4 h. The reaction was monitored by TLC; after completion of the reaction, the volatiles were removed under reduced pressure. The residue was diluted with water (20 mL) and pH was adjusted to ~2 with 1 N HCl, filtered the precipitated solid and dried in vacuo to afford compound 10 (500 mg, 52%) as an off-white solid. TLC: 5% MeOH/$CH_2Cl_2$ ($R_f$: 0.4); $^1$H-NMR (DMSO-$d_6$, 400 MHz): δ 13.47 (br s, 1H), 8.59 (s, 1H), 7.94 (d, J=7.2 Hz, 1H), 7.68-7.60 (m, 3H), 6.83 (s, 1H), 3.72 (s, 3H), 2.40 (s, 3H).

Synthesis of methyl 3-amino-4-((2-(methoxycarbonyl) phenyl) thio)-5-methylbenzoate (11)

To a stirring solution of compound 10 (500 mg, 1.45 mmol) in THF:$H_2O$ (2:1, 15 mL) was added lithium hydroxide monohydrate (300 mg, 7.31 mmol) at RT and stirred for 8 h. The reaction was monitored by TLC; after completion of the reaction, the volatiles were removed in vacuo. The residue was diluted with water (15 mL), and pH was adjusted to ~2 with 1 N HCl, filtered the precipitated solid and dried in vacuo to afford crude compound 11 (500 mg) as an off-white solid. TLC: 5% MeOH/$CH_2Cl_2$ ($R_f$: 0.1); $^1$H-NMR (DMSO-$d_6$, 400 MHz): δ 13.51 (br s, 2H), 8.57 (s, 1H), 7.92 (d, J=7.2 Hz, 1H), 7.64-7.58 (m, 2H), 7.53 (t, J=8.0 Hz, 1H), 6.89 (s, 1H), 2.41 (s, 3H).

Synthesis of 5-amino-4-((2-carboxyphenyl) thio)-2-methylbenzoic acid (12)

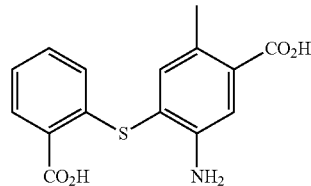

12

To a stirring solution of compound 11 (500 mg) in MeOH (15 mL) under inert atmosphere was added Pd/C (250 mg) at RT and stirred under hydrogen atmosphere for 16 h. The reaction was monitored by TLC; after completion of the reaction, the volatiles were removed in vacuo to afford crude compound 12 (430 mg) as an off-white solid. TLC: MeOH/CH$_2$Cl$_2$ (R$_f$: 0.1); LC-MS: 84.24%; 304.5 (M$^+$+1); (column; X-Select CSH C-18, (50×3.0 mm, 3.5 µm); RT 3.75 min. 0.05% TFA (Aq): ACN; 0.8 mL/min).

Synthesis of 7-methyl-11-oxo-10, 11-dihydrodibenzo [b, f] [1, 4] thiazepine-8-carboxylic acid (13)

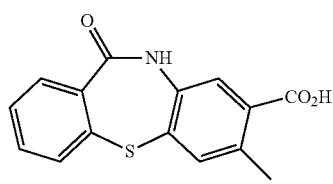

13

To a stirring solution of compound 12 (430 mg) in THF (20 mL) under inert atmosphere was added CDI (1.15 g, 7.09 mmol) at RT and stirred for 18 h. The reaction was monitored by TLC; after completion of the reaction, the volatiles were removed in vacuo and neutralized with 1 N HCl, filtered the precipitated solid and dried in vacuo to afford the crude compound 13 (290 mg) as an off-white solid. TLC: 10% MeOH/CH$_2$Cl$_2$ (R$_1$ 0.5); $^1$H-NMR (DMSO-d$_6$, 500 MHz): δ 13.15 (br s, 1H), 10.68 (s, 1H), 7.69-7.68 (m, 2H), 7.67-7.44 (m, 4H), 2.44 (s, 3H).

9-methyl-11-oxo-10, 11-dihydrodibenzo [b, f] [1, 4] thiazepine-8-carboxylic acid (20): A Common Intermediate

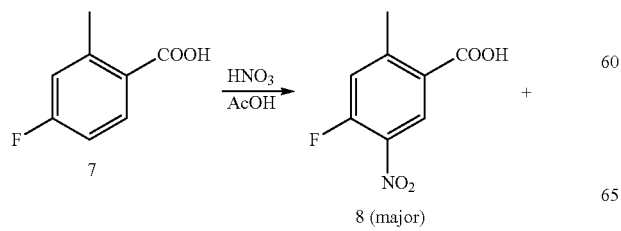

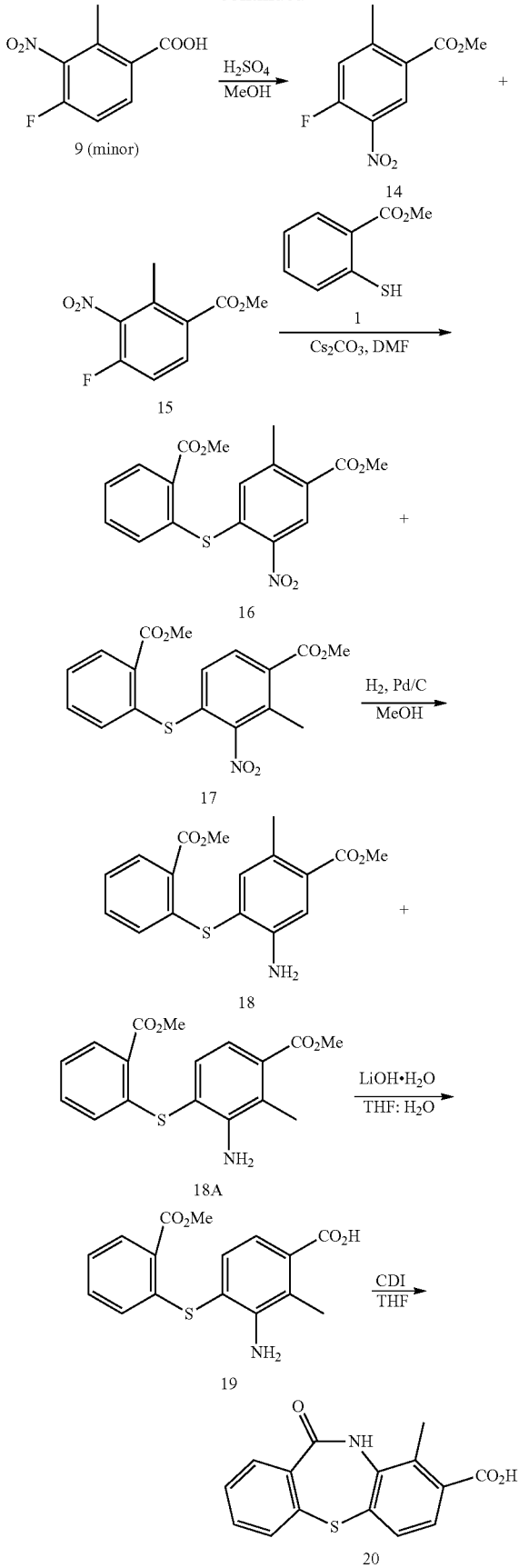

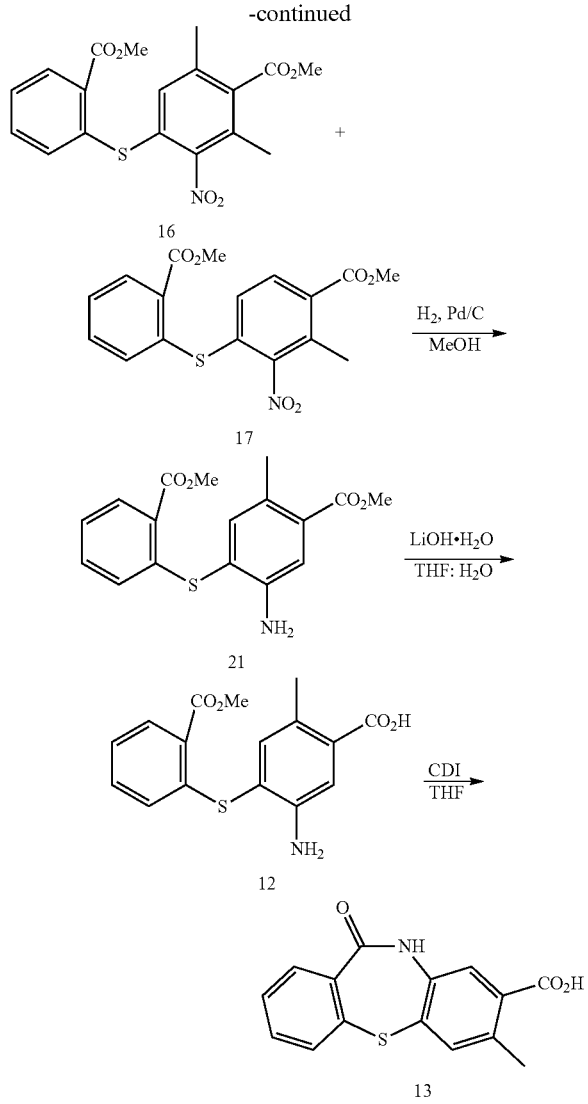

Synthesis of mixture of 4-fluoro-2-methyl-3-nitrobenzoic acid (8) and 4-fluoro-2-methyl-5-nitrobenzoic acid (9)

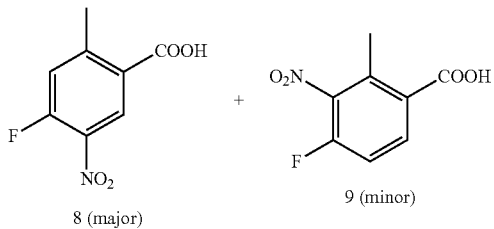

To a stirring solution of 4-fluoro-2-methylbenzoic acid 7 (10 g, 64.51 mmol) in acetic acid (50 mL) under inert atmosphere was added fuming nitric acid (50 mL) at RT and heated to 80° C. for 6 h. The reaction was monitored by TLC; after completion of the reaction, the reaction mixture was diluted with ice cold water (100 mL). The precipitate was filtered and dried in vacuo to afford mixture of compounds 8 and 9 (5.3 g, 40%) as white solid. TLC: 70% EtOAc/hexanes ($R_f$: 0.4); $^1$H NMR (DMSO-$d_6$, 400 MHz): δ 13.30 (br s, 2H), 8.52 (d, J=8.0 Hz, 2H), 8.10 (dd, J=8.9 5.9, Hz, 1H), 7.60 (d, J=12.5 Hz, 2H), 7.56 (t, J=9.3 Hz, 1H), 2.63 (s, 6H), 2.48 (s, 3H); NMR showed mixture of compounds 8 & 9 in the ratio of 2:1).

Synthesis of methyl 4-fluoro-2-methyl-3-nitrobenzoate (14) and methyl 4-fluoro-2-methyl-5-nitrobenzoate (15)

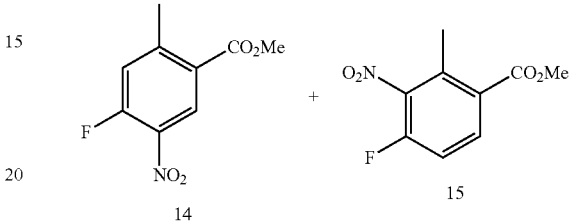

To a stirring solution of compound 8 & 9 (10 g) in MeOH (100 mL) under argon atmosphere was conc. sulfuric acid (20 mL) at 0° C. and heated to reflux for 48 h. The reaction was monitored by TLC; after completion of the reaction, the reaction mixture was diluted with water (100 mL) and extracted with EtOAc (2×100 mL). The combined organic extracts were dried over sodium sulfate, filtered and concentrated in vacuo to afford mixture of compounds 14 & 15 (6 g) as colorless thick syrup. TLC: 30% EtOAc/hexane ($R_f$: 0.5); $^1$H NMR (DMSO-$d_6$, 500 MHz): δ 8.51 (d, J=7.8 Hz, 1H), 8.09 (dd, J=8.8, 5.6 Hz, 0.5H), 7.63 (d, J=12.4 Hz, 1H), 7.58 (t, J=9.1 Hz, 0.5H), 3.87 (s, 4.5H), 2.62 (s, 3H), 2.45 (s, 1.5H); NMR showed mixture of compounds 14:15 in the ratio of 2:1).

Synthesis of methyl 4-((2-(methoxycarbonyl) phenyl) thio)-2-methyl-3-nitrobenzoate (16) and methyl 4-((2-(methoxycarbonyl) phenyl) thio)-2-methyl-5-nitrobenzoate (17)

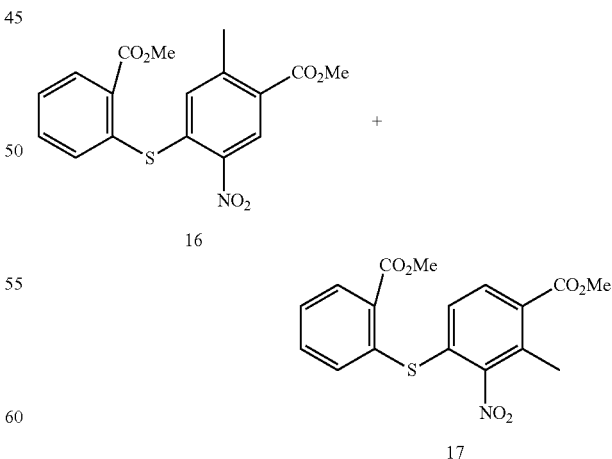

To a stirring solution of compounds 14 & 15 (11 g) in DMF (100 mL) under inert atmosphere were added methyl 2-mercaptobenzoate 1 (10.4 g, 61.97 mmol), cesium carbonate (18.5 g, 56.81 mmol) at 0° C.; heated to 80° C. and stirred for 4 h. The reaction was monitored by TLC; after completion of the reaction, the reaction mixture was diluted with ice cold water (100 mL) and extracted with EtOAc (2×100 mL). The combined organic extracts were washed with water (200 mL), brine (200 mL), dried over sodium sulfate, filtered and concentrated in vacuo to afford mixture of compounds 16 & 17 (12 g) as yellow solid. TLC: 20% EtOAc/hexanes ($R_f$: 0.2); LC-MS: 12.57%+81.14%; 370.8 ($M^++1$); (column; X-Select CSH C18, (50×3.0 mm, 3.5 μm); RT 2.77 min. 0.05% Aq. TFA: ACN; 0.8 mL/min); RT 4.05, 4.14 min.

Synthesis of methyl 5-amino-4-((2-(methoxycarbonyl) phenyl) thio)-2-methylbenzoate (18) and Synthesis of methyl 3-amino-4-((2-(methoxycarbonyl) phenyl) thio)-2-methylbenzoate (18A)

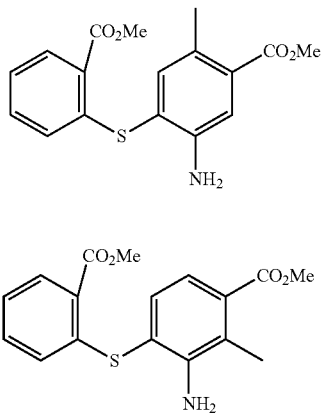

To a stirring solution of compound 16 & 17 (14 g, crude) in MeOH (500 mL) under inert atmosphere was added Pd/C (1.4 g, 50% wet) at RT and stirred under hydrogen atmosphere in an autoclave (6 kg/cm² pressure) for 18 h. The reaction was monitored by TLC; after completion of the reaction, the reaction mixture was filtered through celite, washed with MeOH (100 mL). The filtrate was concentrated in vacuo to obtain the crude. The crude was recrystallized with EtOH (20 mL) and further purified through silica gel column chromatography column chromatography using 10% EtOAc/hexanes to afford compound 18 (8 g, 63%%) and 18A (3 g, 30) as sticky off-white solids. TLC: 30% EtOAc/hexanes ($R_f$: 0.4);

$^1$H NMR (DMSO-$d_6$, 400 MHz) (18): δ 7.94 (d, J=7.1 Hz, 1H), 7.40 (t, J=7.3 Hz, 1H), 7.33-7.26 (m, 2H), 7.22 (dt, J=7.6, 1.1 Hz, 1H), 6.67 (dd, J=8.2, 0.8 Hz, 1H), 5.41 (s, 2H), 3.89 (s, 3H), 3.83 (s, 3H), 2.33 (s, 3H).

$^1$H NMR (DMSO-$d_6$, 400 MHz) (18A): δ 7.94 (dd, J=7.8, 1.4 Hz, 1H), 7.42-7.38 (m, 1H), 7.32 (s, 1H), 7.26 (s, 1H), 7.22 (td, J=7.5, 1.0 Hz, 1H), 6.67 (dd, J=8.1, 0.8 Hz, 1H), 5.41 (s, 2H), 3.88 (s, 2H), 3.82 (s, 3H), 2.33 (s, 3H).

Synthesis of 3-amino-4-((2-carboxyphenyl) thio)-2-methylbenzoic acid (19)

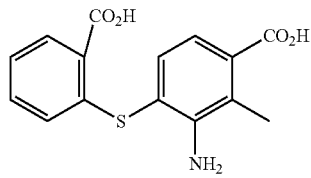

To a stirring solution of compound 18A (2 g, 6.04 mmol) in THF:H$_2$O (4:1, 50 mL) was added lithium hydroxide monohydrate (2.5 g, 10.0 mmol) at 0° C.; warmed to RT and stirred for 48 h. The reaction was monitored by TLC; after completion of the reaction, the volatiles were removed in vacuo. The residue was diluted with water (10 mL) and washed with diethyl ether (2×50 mL). The pH of the aqueous layer was acidified with 4 N HCl to ~1. The precipitated solid was filtered and dried in vacuo to afford compound 19 (1.2 g, 66%) as white solid. TLC: 2v60% MeOH/CH$_2$Cl$_2$ ($R_f$: 0.2); $^1$H NMR (DMSO-$d_6$, 400 MHz): δ 13.01 (br s, 2H), 7.94 (d, J=7.4 Hz, 1H), 7.36 (t, J=7.8 Hz, 1H), 7.28 (d, J=8.0 Hz, 1H), 7.20 (dt, J=7.4, 6.3 Hz, 1H), 6.95 (d, J=8.0 Hz, 1H), 6.61 (d, J=7.4 Hz, 1H), 5.25 (br s, 2H), 2.27 (s, 3H).

Synthesis of 9-methyl-11-oxo-10, 11-dihydrodibenzo [b, f] [1, 4] thiazepine-8-carboxylic acid (20)

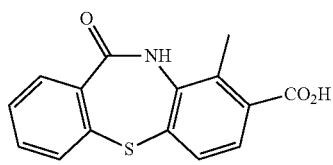

To a stirring solution of compound 19 (2.6 g, 4.30 mmol) in THF (30 mL) under argon atmosphere was added CDI (3.5 g, 21.50 mmol) at RT; heated to 80° C. and stirred for 16 h. The reaction was monitored by TLC; after completion of the reaction, the volatiles were removed in vacuo. The residue was diluted with water (20 mL) and pH was adjusted with 4 N HCl to ~2. The obtained solid was filtered, washed with diethyl ether and dried in vacuo to obtain compound 20 (1.6 g, 67%) as an off white solid. TLC: 15% MeOH/CH$_2$Cl$_2$ ($R_f$: 0.2); $^1$H NMR (DMSO-$d_6$, 400 MHz): δ 13.20 (br s, 1H), 10.23 (s, 1H), 7.74-7.60 (m, 1H), 7.56-7.51 (m, 2H), 7.50-7.42 (m, 3H), 2.47 (s, 3H).

Synthesis of 6-bromo-9-methyl-11-oxo-10, 11-dihydrodibenzo [b, f] [1, 4] thiazepine-8-carboxylic acid (32): A Common Intermediate

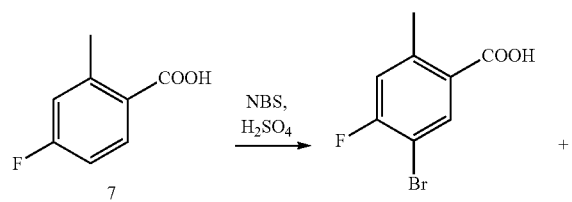

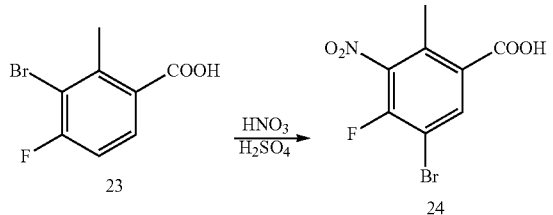

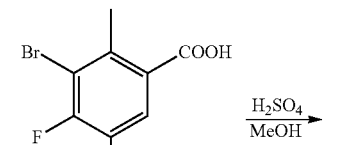

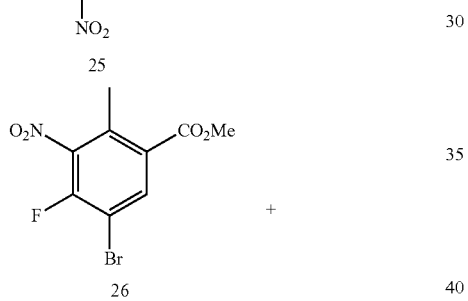

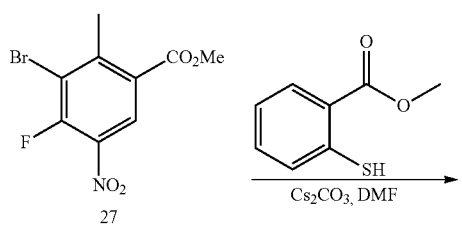

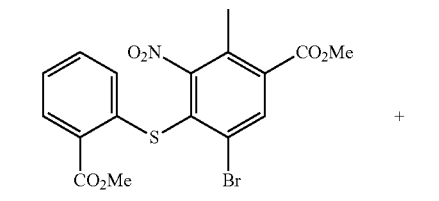

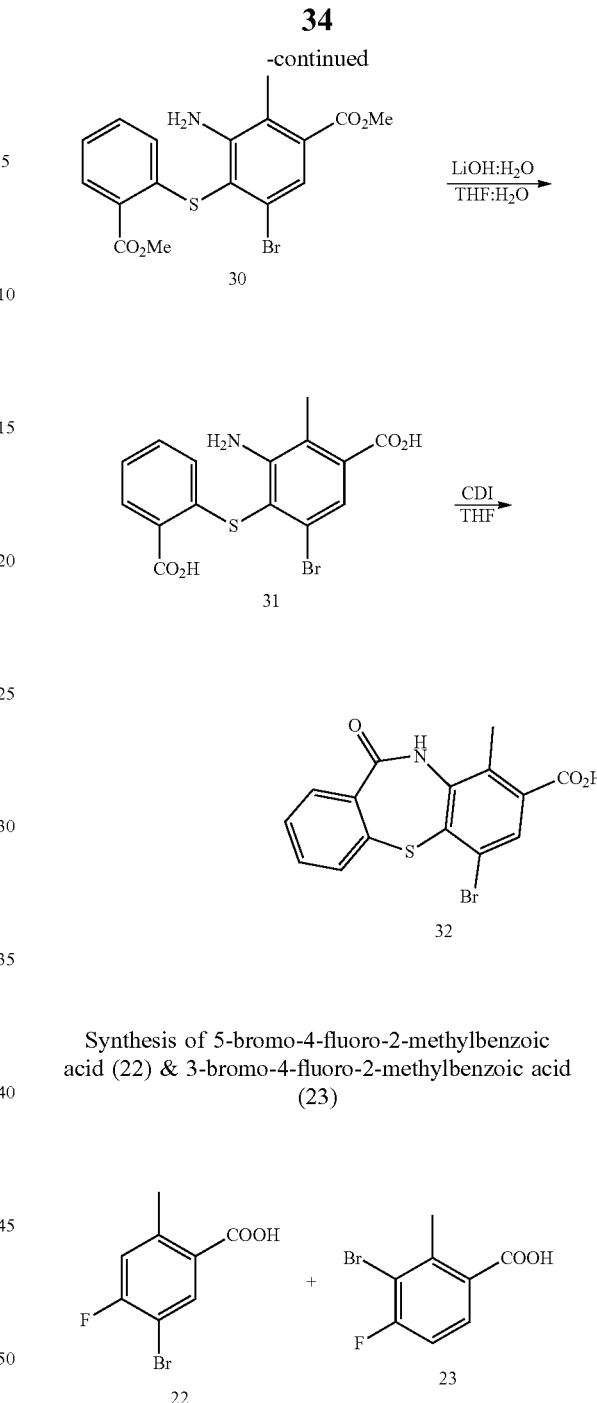

Synthesis of 5-bromo-4-fluoro-2-methylbenzoic acid (22) & 3-bromo-4-fluoro-2-methylbenzoic acid (23)

To a stirring solution of 4-fluoro-2-methylbenzoic acid 7 (10 g, 64.93 mmol) in $H_2SO_4$ (200 mL) at 0° C. under argon atmosphere was added N-bromosuccinimide (10.40 g, 58.44 mmol) portion wise for 15 min warmed to RT and stirred for 2 h. The reaction was monitored by TLC; after completion of the reaction, the reaction mixture was quenched with ice-cold water, the precipitated solid was filtered and dried in vacuo to afford mixture of compound 22 and 23 in the ratio of 2.5:1 (14 g) as an off-white solid. TLC: 30% EtOAc/hexanes ($R_f$: 0.3); $^1$H-NMR (DMSO-$d_6$, 400 MHz): δ 8.06 (d, J=7.4 Hz, 1H), 7.82 (dd, J=8.7, 5.9 Hz, 0.4H), 7.37 (d, J=9.9 Hz, 1H), 7.30 (t, J=8.4 Hz, 0.4H), 2.62 (s, 1.2H), 2.50 (s, 3H);

Synthesis of 5-bromo-4-fluoro-2-methyl-3-nitrobenzoic acid & 3-bromo-4-fluoro-2-methyl-5-nitrobenzoic acid (24 & 25)

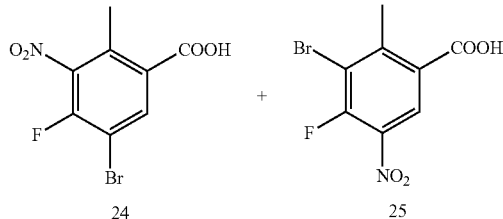

To a stirring solution of compound 22 & 23 (14 g, 60.34 mmol) in sulphuric acid (70 mL) under inert atmosphere at 0° C. was added fuming nitric acid (70 mL) dropwise for 30 min at 0° C. warmed to RT and stirred for 2 h. The reaction was monitored by TLC; after completion of the reaction, the reaction mixture was quenched with ice-cold water (100 mL). The precipitated solid was filtered, washed with water (100 mL) and dried in vacuo to afford mixture of compound 24 & 25 in the ratio of 2:1 (10 g) as pale yellow solid. TLC: 30% EtOAc/hexanes ($R_f$: 0.2). $^1$H NMR (DMSO-$d_6$, 400 MHz): δ 13.86 (br s, 3H), 8.47 (d, J=7.8 Hz, 1H), 8.30 (d, J=6.9 Hz, 2H), 2.72 (s, 3H), 2.44 (s, 8H);

Synthesis of methyl 5-bromo-4-fluoro-2-methyl-3-nitrobenzoate (26) & methyl 3-bromo-4-fluoro-2-methyl-5-nitrobenzoate (26&27)

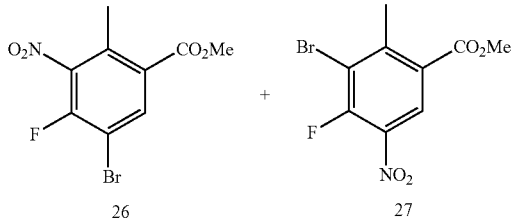 [SMILES: COC(=O)c1cc(Br)c(F)c([N+](=O)[O-])c1C ; COC(=O)c1cc([N+](=O)[O-])c(F)c(Br)c1C]

To a stirring solution of compound 24 & 25 (10 g, 35.9 mmol) in MeOH (200 mL) under inert atmosphere was added concentrated sulfuric acid (10 mL) dropwise for 15 min at 0° C.; heated to reflux and stirred for 16 h. The reaction was monitored by TLC; after completion of the reaction, the volatiles were removed in vacuo. The residue was diluted with ice-cold water (100 mL) and extracted with EtOAc (2×150 mL). The combined organic extracts were dried over sodium sulfate, filtered and concentrated in vacuo to obtain the crude. The crude was purified through silica gel column chromatography using 10% EtOAc/hexanes to afford mixture of compound 26 & 27 in 2:1 ratio (8 g) as an off-white solid. TLC: 10% EtOAc/hexanes ($R_f$: 0.5); $^1$H-NMR (DMSO-$d_6$, 400 MHz): δ 8.48 (d, J=7.7 Hz, 0.4H), 8.33 (d, J=7.0 Hz, 1H), 3.90 (s, 1.2H), 3.88 (s, 3H), 2.69 (s, 1.2H), 2.42 (s, 3H);

Synthesis of methyl 5-bromo-4-((2-(methoxycarbonyl) phenyl) thio)-2-methyl-3-nitrobenzoate (28) & methyl 3-bromo-4-((2-(methoxycarbonyl) phenyl) thio)-2-methyl-5-nitrobenzoate (29)

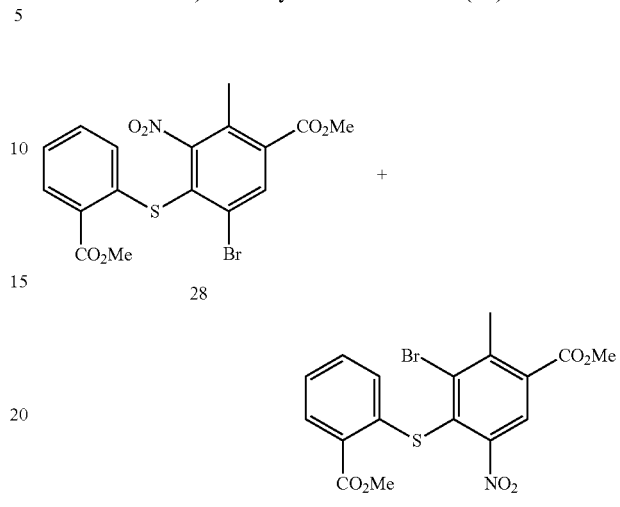

To a stirring solution of compound 26 & 27 (8 g, 27.49 mmol) in DMF (50 mL) under argon atmosphere were added methyl 2-mercaptobenzoate 1 (5.5 g, 32.98 mmol), cesium carbonate (9.8 g, 30.24 mmol) at RT; heated to 80° C. and stirred for 2 h. The reaction was monitored by TLC; after completion of the reaction, the reaction mixture was diluted with ice-cold water (150 mL). The precipitated solid was filtered, washed with water (100 mL) and dried in vacuo to obtain the crude which was triturated with EtOH (10 mL) & diethylether (25 mL) filtered and dried in vacuo to afford mixture of compound 28 and 29 (6 g) as pale yellow solid. TLC: 20% EtOAc/hexanes ($R_f$: 0.3); $^1$H NMR (DMSO-$d_6$, 400 MHz): δ 8.37 (s, 1H), 8.02 (dd, J=7.8, 1.4 Hz, 1H), 7.54-7.45 (m, 1H), 7.38-7.32 (m, 1H), 6.62 (d, J=7.8 Hz, 1H), 3.91 (d, J=2.8 Hz, 6H), 2.38 (s, 3H); LC-MS no ionization.

Synthesis of methyl 3-amino-5-bromo-4-((2-(methoxycarbonyl)phenyl)thio)-2-methylbenzoate (30)

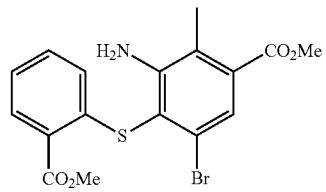

To a stirring solution of compound 28 & 29 (5 g, 11.39 mmol) in acetic acid (100 mL) was added iron powder (6.37 g, 113.89 mmol) at RT; heated to reflux and stirred for 16 h. The reaction was monitored by TLC; after completion, the reaction mixture was diluted with EtOAc (200 mL). The organic extract was dried over sodium sulfate, filtered and concentrated in vacuo to obtain the crude. The crude was triturated with EtOH (25 mL) and dried in vacuo to afford compound 30 (2.6 g, 55%) as pale yellow solid. TLC: 20%

EtOAc/hexanes (R$_f$: 0.4); $^1$H-NMR (DMSO-d$_6$, 400 MHz): δ 7.99 (dd, J=7.8, 1.4 Hz, 1H), 7.45-7.40 (m, 1H), 7.28-7.23 (m, 2H), 6.56 (dd, J=8.2, 0.8 Hz, 1H), 5.77 (s, 2H), 3.91 (s, 3H), 3.84 (s, 3H), 2.20 (s, 3H); LC-MS: 97.59%; 412.1 (M+2)$^+$; (column; Ascentis Express C18, (50×3.0 mm, 2.7 μm); RT 2.84 min. 0.025% Aq. TFA+5% ACN: ACN+5% 0.025% Aq. TFA, 1.2 mL/min).

Synthesis of 3-amino-5-bromo-4-((2-carboxyphenyl) thio)-2-methylbenzoic acid (31)

To a stirring solution of compound 30 (2 g, 4.89 mmol) in THF:H$_2$O (4:1, 25 mL) was added lithium hydroxide monohydrate (2.1 g, 50.00 mmol) portion wise for 10 min at 0° C.; warmed to RT and stirred for 48 h. The reaction was monitored by TLC; after completion of the reaction, the volatiles were removed in vacuo and the aqueous layer was washed with diethylether (2×5 mL) The pH of the aqueous layer was acidified with 2 N HCl to ~1. The precipitated solid was filtered and further dried by zoetrope using toluene (10 mL) to afford compound 31 (1.6 g 86%) as an off-white solid. TLC: 20% EtOAc/hexane (R$_f$: 0.2); $^1$H-NMR (DMSO-d$_6$, 500 MHz): δ 13.25 (br s, 2H), 7.98 (d, J=7.5 Hz, 1H), 7.38 (t, J=7.4 Hz, 1H), 7.27-7.19 (m, 2H), 6.54 (d, J=8.1 Hz, 1H), 5.67 (br s, 2H), 2.23 (s, 3H); LC-MS: 98.30%; 383.9 (M+2)$^+$; (column; Ascentis Express C18, (50×3.0 mm, 2.7 μm); RT 2.08 min. 0.025% Aq. TFA+5% ACN: ACN+5% 0.025% Aq. TFA, 1.2 mL/min).

Synthesis of 6-bromo-9-methyl-11-oxo-10, 11-dihydrodibenzo [b, f] [1, 4] thiazepine-8-carboxylic acid (32)

To a stirring solution of compound 31 (2 g, 5.25 mmol) in THF (100 mL) under inert atmosphere was added CDI (4.4 g, 26.25 mmol) at RT and stirred for 16 h. The reaction was monitored by TLC; after completion of the reaction, the reaction mixture was quenched with ice-cold-water (50 mL) and washed with EtOAc (2×75 mL). The pH of the residue was adjusted to ~2 using 1 N HCl. The precipitated solid was filtered, washed with water (50 mL) and further dried by azeotropic distillation using toluene to afford compound 32 (1.2 g, 63%) as an off-white solid. TLC: 10% MeOH/CH$_2$Cl$_2$ (R$_f$: 0.4); $^1$H NMR (DMSO-d$_6$, 400 MHz): δ 13.44 (br s, 1H), 10.36 (s, 1H), 7.78 (s, 1H), 7.70-7.64 (m, 1H), 7.56-7.51 (m, 1H), 7.51-7.44 (m, 2H), 2.40 (s, 3H); LC-MS: 97.42%; 363.9 (M$^+$+1); (column; Ascentis Express C18, (50×3.0 mm, 2.7 μm); RT 2.23 min. 0.025% Aq. TFA+5% ACN: ACN+5% 0.025% Aq. TFA, 1.2 mL/min).

Synthesis of 9-methyl-11-oxo-10, 11-dihydrodibenzo [b, f] [1, 4] thiazepine-8-carboxylic acid (20): (Alternate Approach)

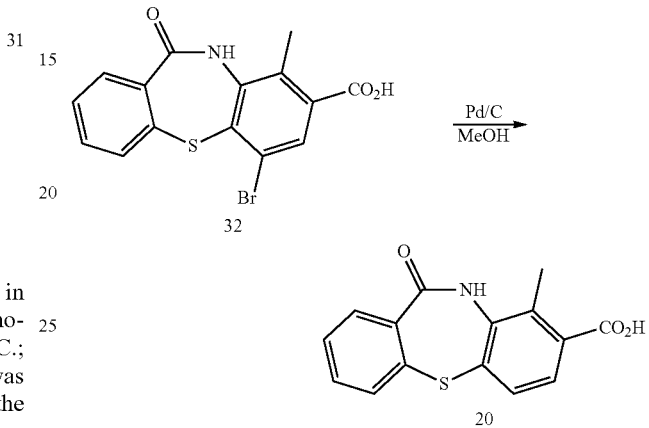

To a stirring solution of 6-bromo-9-methyl-11-oxo-10,11-dihydrodibenzo [b, f] [1, 4] thiazepine-8-carboxylic acid 32 (1 g, 2.75 mmol) in MeOH (20 mL) under inert atmosphere was added 10% Pd/C (1 g, 50% wet) at RT and stirred under hydrogen atmosphere at RT and stirred for 16 h. The reaction was monitored by TLC; after completion of the reaction, the reaction mixture was filtered through celite and eluted with 50% MeOH/CH$_2$Cl$_2$ (2×50 mL). The filtrate was concentrated in vacuo to obtain the crude. The crude was diluted with water (20 mL) and the obtained solid was filtered dried in vacuo to afford compound 20 (300 mg, 38%) as an off-white solid. TLC: 10% MeOH/CH$_2$Cl$_2$ (R$_f$: 0.4); $^1$H NMR (DMSO-d$_6$, 400 MHz): δ 13.15 (br s, 1H), 10.23 (s, 1H), 7.69-7.65 (m, 1H), 7.55-7.51 (m, 2H), 7.50-7.42 (m, 3H), 3.31 (s, 3H); LC-MS: 90.04%; 285.9 (M$^+$+1); (column; Ascentis Express C18, (50×3.0 mm, 2.7 μm); RT 2.01 min. 0.025% Aq. TFA+5% ACN: ACN+5% 0.025% Aq. TFA, 1.2 mL/min).

Synthesis of 2-chloro-11-oxo-10, 11-dihydrodibenzo [b, f] [1, 4] thiazepine-8-carboxylic acid (40): A Common Intermediate

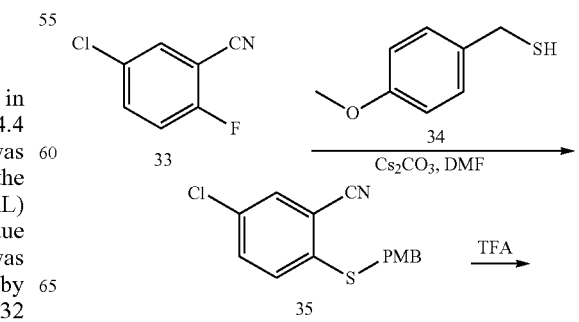

39

-continued

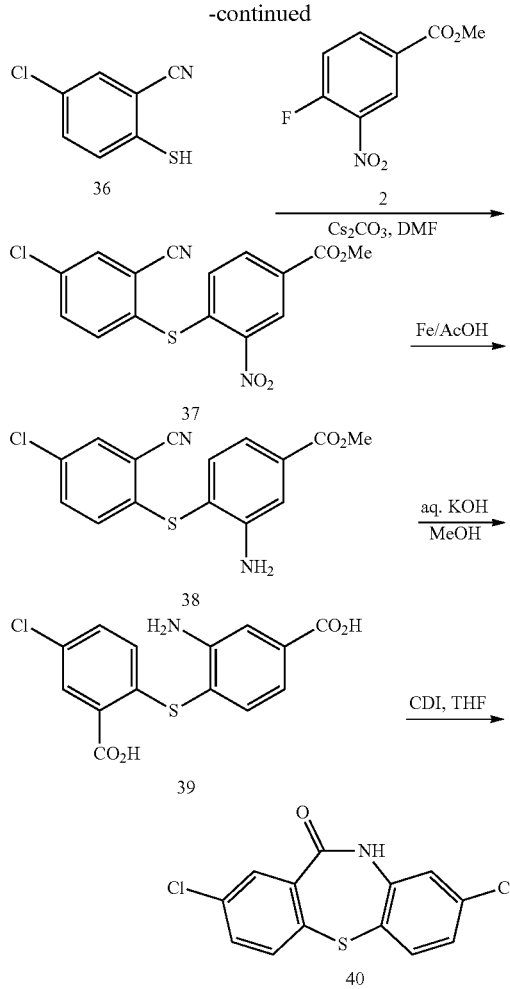

37

38

39

40

Synthesis of 5-chloro-2-((4-methoxybenzyl) thio) benzonitrile (35)

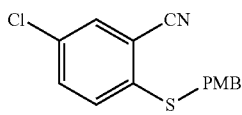

To a stirring solution of 5-chloro-2-fluorobenzonitrile 33 6.41 mmol) in DMF (10 mL) under inert atmosphere was added cesium carbonate (2.30 g, 7.05 mmol) at RT; heated to 40° C. and to this was added (4-methoxyphenyl) methanethiol 34 (1.08 g, 7.05 mmol); heated to 60° C. and stirred for 2 h. The reaction was monitored by TLC; after completion of the reaction, the reaction mixture was diluted with water (20 mL) and extracted with EtOAc (2×25 mL). The combined organic extracts were dried over sodium sulfate, filtered and concentrated in vacuo to obtain the crude. The crude was purified through silica gel column chromatography using 3-5% EtOAc/hexanes to afford compound 35 (1 g, 54%) as white solid. TLC: 10% EtOAc/hexanes ($R_f$: 0.6); $^1$H-NMR (CDCl$_3$, 500 MHz): δ 7.57 (s, 1H), 7.39 (d, J=8.0 Hz, 1H), 7.28-7.27 (m, 1H), 7.20 (d, J=9.0 Hz, 2H), 6.81 (d, J=9.0 Hz, 2H), 4.15 (s, 2H), 3.78 (s, 3H).

40

Synthesis of 5-chloro-2-mercaptobenzonitrile (36)

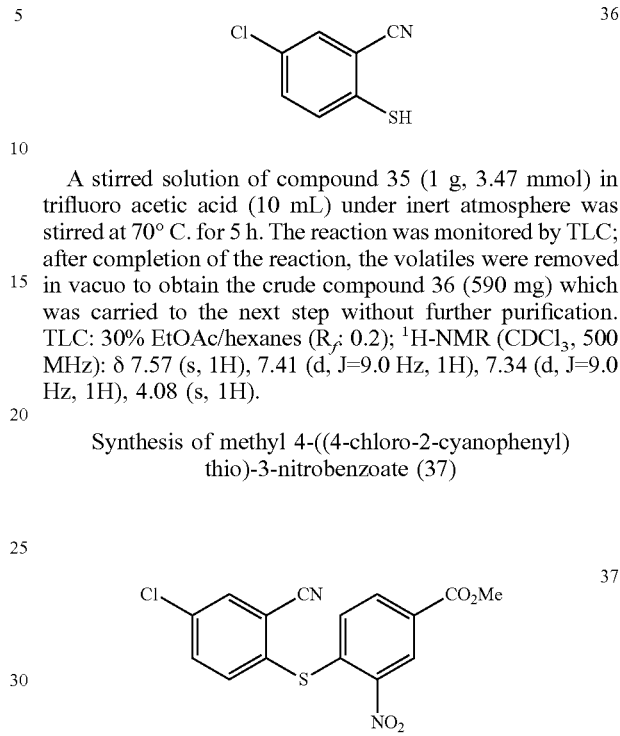

A stirred solution of compound 35 (1 g, 3.47 mmol) in trifluoro acetic acid (10 mL) under inert atmosphere was stirred at 70° C. for 5 h. The reaction was monitored by TLC; after completion of the reaction, the volatiles were removed in vacuo to obtain the crude compound 36 (590 mg) which was carried to the next step without further purification. TLC: 30% EtOAc/hexanes ($R_f$: 0.2); $^1$H-NMR (CDCl$_3$, 500 MHz): δ 7.57 (s, 1H), 7.41 (d, J=9.0 Hz, 1H), 7.34 (d, J=9.0 Hz, 1H), 4.08 (s, 1H).

Synthesis of methyl 4-((4-chloro-2-cyanophenyl) thio)-3-nitrobenzoate (37)

37

To a stirring solution of compound 36 (620 mg, 3.11 mmol) in DMF (10 mL) under inert atmosphere was added cesium carbonate (1.1 g, 3.42 mmol) at RT; heated to 40° C. and stirred for 10 min. To this was added methyl 4-fluoro-3-nitrobenzoate 2 (582 mg, 3.42 mmol) at 60° C. and stirred for 3 h. The reaction was monitored by TLC; after completion of the reaction, the reaction mixture was diluted with water (20 mL) and extracted with EtOAc (2×20 mL). The combined organic extracts were dried over sodium sulfate, filtered and concentrated in vacuo to obtain the crude. The crude was purified through silica gel column chromatography using 25% EtOAc/hexanes to afford compound 37 (600 mg, 55%) as pale yellow solid. TLC: 30% EtOAc/hexanes ($R_f$: 0.4); $^1$H-NMR (DMSO-d$_6$, 400 MHz): δ 8.66 (s, 1H), 8.33 (s, 1H), 8.05-8.03 (m, 1H), 7.98-7.92 (m, 2H), 7.02 (d, J=8.4 Hz, 1H), 3.86 (s, 3H).

Synthesis of methyl 3-amino-4-((4-chloro-2-cyanophenyl) thio) benzoate (38)

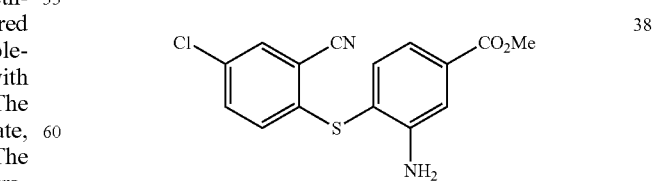

To a stirring solution of compound 37 (450 mg, 1.29 mmol) in acetic acid (15 mL) under inert atmosphere was added iron powder (724 mg, 12.9 mmol) at RT; heated to 90° C. and stirred for 3 h. The reaction was monitored by TLC;

after completion of the reaction, the volatiles were removed in vacuo. The residue was basified with saturated NaHCO$_3$ solution (15 mL) and extracted with CH$_2$Cl$_2$ (2×20 mL). The combined organic extracts were dried over sodium sulfate, filtered and concentrated in vacuo to obtain the crude. The crude was triturated with 3% EtOAc/hexanes (2×5 mL) to afford compound 38 (290 mg, 70%) as pale yellow solid. TLC: 20% MeOH/CH$_2$Cl$_2$ (R$_f$: 0.7); $^1$H-NMR (DMSO-d$_6$, 400 MHz): δ 8.05 (s, $^1$H), 7.63-7.60 (m, 1H), 7.48 (s, 1H), 7.43 (d, J=8.0 Hz, 1H), 7.14 (d, J=8.8 Hz, 1H), 6.75 (d, J=8.8 Hz, 1H), 5.88 (s, 2H), 3.84 (s, 3H).

Synthesis of 2-((2-amino-4-carboxyphenyl) thio)-5-chlorobenzoic acid (39)

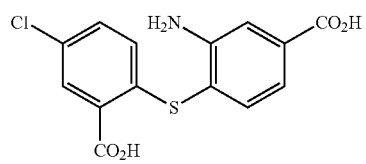

39

To a stirring solution of compound 38 (450 mg, 1.41 mmol) in MeOH (10 mL) was added potassium hydroxide (792 mg, 14.1 mmol) in water (3 mL) at 0° C.; heated to 90° C. and stirred for 9 h. The reaction was monitored by TLC; after completion of the reaction, the volatiles were removed in vacuo. The residue was acidified with 1 N HCl to pH~4.0. The obtained solid was filtered, washed with ether (2×5 mL) and dried in vacuo to afford compound 39 (350 mg, 76%) as an off-white solid. TLC: 20% MeOH/CH$_2$Cl$_2$ (R$_f$: 0.3); $^1$H-NMR (DMSO-d$_6$, 400 MHz): δ 12.92 (br s, 2H), 7.89 (s, 1H), 7.44-7.38 (m, 3H), 7.14 (d, J=8.8 Hz, 1H), 6.60 (d, J=8.8 Hz, 1H), 5.64 (br s, 2H).

Synthesis of 2-chloro-11-oxo-10, 11-dihydrodibenzo [b, f] [1, 4] thiazepine-8-carboxylic acid (40)

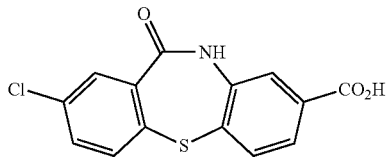

40

To a stirring solution of compound 39 (30 mg, 0.09 mmol) in THF (2 mL) under inert atmosphere was added CDI (45 mg, 0.27 mmol) at RT and stirred for 7 h. The reaction was monitored by TLC; after completion of the reaction, the volatiles were removed in vacuo. The residue was acidified with 2 N HCl to pH~4.0. The obtained solid was filtered, washed with ether (2×3 mL) and dried in vacuo to afford compound 40 (15 mg, 53%) as an off-white solid. TLC: 15% MeOH/CH$_2$Cl$_2$ (R$_f$: 0.5); $^1$H-NMR (DMSO-d$_6$, 400 MHz): δ 13.05 (br s, 1H), 10.98 (s, 1H), 7.80 (s, 1H), 7.72-7.70 (m, 3H), 7.64 (s, 2H).

Synthesis of 3-chloro-11-oxo-10, 11-dihydrodibenzo [b, f] [1, 4] thiazepine-8-carboxylic acid (47): A Common Intermediate

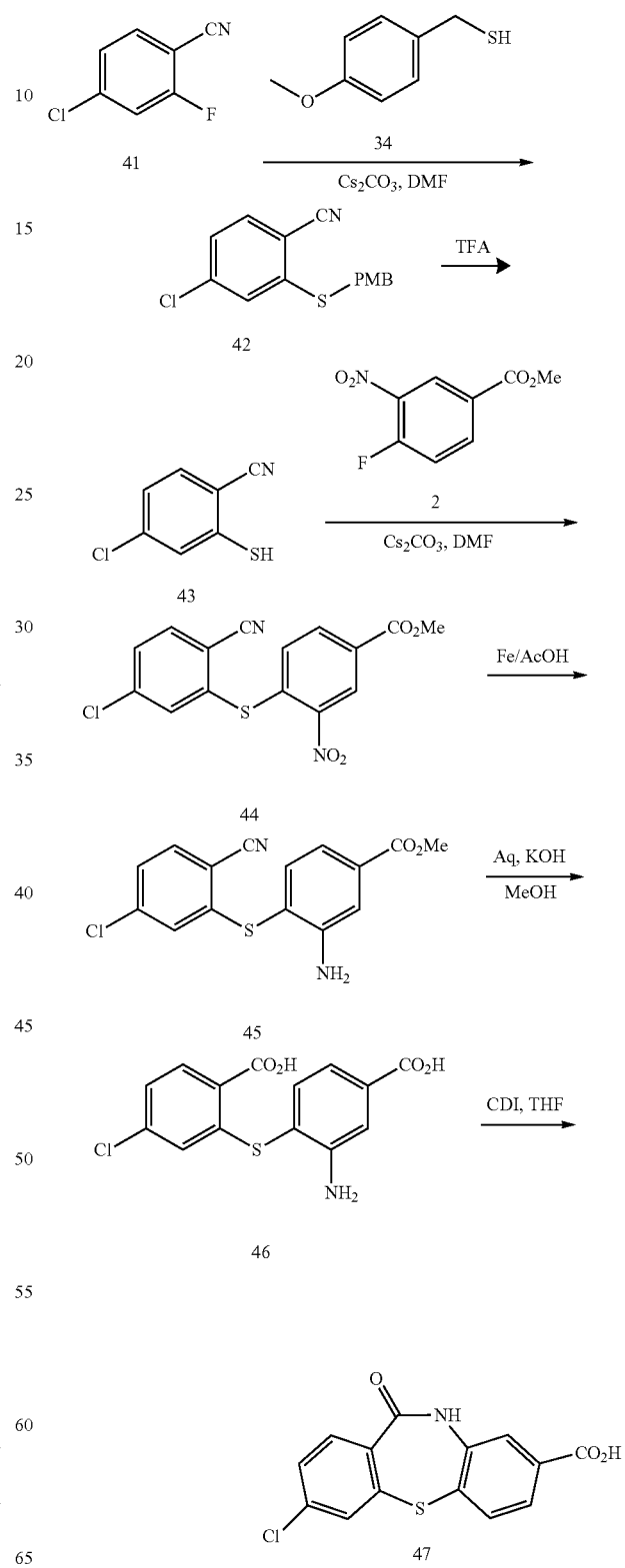

Synthesis of 4-chloro-2-((4-methoxybenzyl) thio) benzonitrile (42)

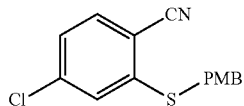

To a stirring solution of 4-chloro-2-fluorobenzonitrile 41 (1 g, 6.41 mmol) in DMF (25 mL) under inert atmosphere was added cesium carbonate (2.30 g, 7.05 mmol) at RT; heated to 40° C. and to this was added (4-methoxyphenyl) methanethiol 34 (1.08 g, 7.05 mmol); heated to 60° C. and stirred for 2 h. The reaction was monitored by TLC; after completion of the reaction, the reaction mixture was diluted with water (20 mL) and extracted with EtOAc (2×25 mL). The combined organic extracts were dried over sodium sulfate, filtered and concentrated in vacuo to obtain the crude. The crude was purified through silica gel column chromatography using 4% EtOAc/hexanes to afford compound 42 (900 mg, 48%) as white solid. TLC: 10% EtOAc/hexanes ($R_f$: 0.6); $^1$H-NMR (CDCl$_3$, 400 MHz): δ 7.51 (d, J=8.4 Hz, 1H), 7.33 (s, 1H), 7.23-7.20 (m, 3H), 6.84 (d, J=8.4 Hz, 2H), 4.19 (s, 2H), 3.79 (s, 3H).

Synthesis of 4-chloro-2-mercaptobenzonitrile (43)

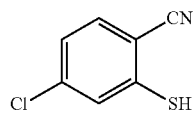

A stirred solution of compound 42 (900 mg, 3.11 mmol) in trifluoro acetic acid (10 mL) under inert atmosphere at RT was heated to 70° C. and stirred for 4 h. The reaction was monitored by TLC; after completion of the reaction, the volatiles were removed in vacuo to obtain the crude compound 43 (527 mg) as brown solid. The crude was carried to the next step without further purification. TLC: 5% MeOH/CH$_2$Cl$_2$ ($R_f$: 0.1); $^1$H-NMR (CDCl$_3$, 400 MHz): δ 7.52 (d, J=8.4 Hz, 1H), 7.41 (s, 1H), 7.22-7.19 (m, 1H), 4.13 (s, 1H).

Synthesis of methyl 4-((5-chloro-2-cyanophenyl) thio)-3-nitrobenzoate (44)

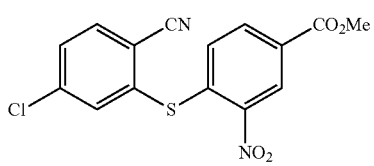

To a stirring solution of compound 43 (550 mg, 2.76 mmol) in DMF (15 mL) under inert atmosphere was added cesium carbonate (988 mg, 3.04 mmol) at RT; heated to 40° C. and stirred for 10 min. To this was added methyl 4-fluoro-3-nitrobenzoate 2 (515 mg, 3.04 mmol) at 60° C. and stirred for 3 h. The reaction was monitored by TLC; after completion of the reaction, the reaction mixture was diluted with water (20 mL). The obtained solid was filtered, washed with 15% EtOAc/hexanes (2×5 mL) and dried in vacuo to afford compound 44 (700 mg, 73%) as yellow solid. TLC: 20% EtOAc/hexanes ($R_f$: 0.3); $^1$H-NMR (DMSO-d$_6$, 500 MHz): δ 8.69 (s, 1H), 8.18-8.15 (m, 2H), 8.10 (d, J=8.5 Hz, 1H), 7.92 (d, J=8.5 Hz, 1H), 7.10 (d, J=9.0 Hz, 1H), 3.90 (s, 3H).

Synthesis of methyl 3-amino-4-((5-chloro-2-cyanophenyl) thio) benzoate (45)

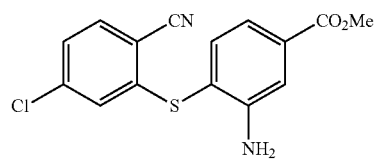

To a stirring solution of compound 44 (700 mg, 2.01 mmol) in acetic acid (15 mL) under inert atmosphere was added iron powder (1.12 g, 20.11 mmol) at RT; heated to 90° C. and stirred for 5 h. The reaction was monitored by TLC; after completion of the reaction, the volatiles were removed in vacuo. The residue was basified with 10% NaHCO$_3$ solution (20 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 20% EtOAc/hexanes to afford compound 45 (500 mg, 78%) as yellow solid. TLC: 30% EtOAc/hexanes ($R_f$: 0.8); $^1$H-NMR (DMSO-d$_6$, 500 MHz): δ 7.92 (d, J=7.5 Hz, 1H), 7.51-7.43 (m, 3H), 7.17 (d, J=8.0 Hz, 1H), 6.66 (s, 1H), 5.96 (s, 2H), 3.86 (s, 3H).

Synthesis of 2-((2-amino-4-carboxyphenyl) thio)-4-chlorobenzoic acid (46)

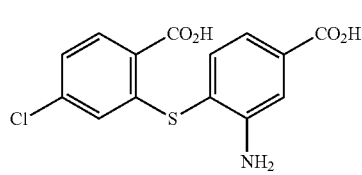

To a stirring solution of compound 45 (500 mg, 1.57 mmol) in MeOH (6 mL) was added potassium hydroxide (1.32 mg, 23.5 mmol) in water (6 mL) at 0° C.; heated to 90° C. and stirred for 24 h. The reaction was monitored by TLC; after completion of the reaction, the volatiles were removed in vacuo. The residue was diluted with water (20 mL) and extracted with EtOAc (2×25 mL). The aqueous layer was acidified with 1 N HCl to pH~6.0. The obtained solid was filtered, washed with ether (2×7 mL) and dried in vacuo to afford compound 46 (375 mg, 74%) as an off-white solid. TLC: 20% MeOH/CH$_2$Cl$_2$ ($R_f$: 0.2); $^1$H-NMR (CDCl$_3$, 400 MHz): δ 8.05 (d, J=8.4 Hz, 1H), 7.55-7.47 (m, 3H), 7.17-7.14 (m, 1H), 6.67 (s, 1H).

45

Synthesis of 3-chloro-11-oxo-10, 11-dihydrodibenzo [b, f] [1, 4] thiazepine-8-carboxylic acid (47)

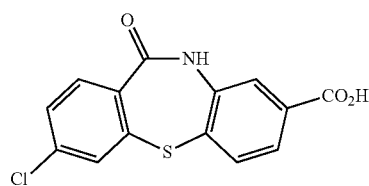

To a stirring solution of compound 46 (375 mg, 1.16 mmol) in THF (10 mL) under inert atmosphere was added CDI (564 mg, 3.48 mmol) at RT and stirred for 16 h. The reaction was monitored by TLC; after completion of the reaction, the volatiles were removed in vacuo. The residue was diluted with water (15 mL) and acidified with 6 N HCl to pH~1.0. The obtained solid was filtered, washed with ether (2×5 mL) and dried in vacuo to afford compound 47 (285 mg, 81%) as an off-white solid. TLC: 20% MeOH/CH$_2$Cl$_2$ (R$_f$: 0.4); $^1$H-NMR (DMSO-d$_6$, 400 MHz): δ 14.56 (br s, 2H), 10.90 (s, 1H), 9.11 (s, 1H), 7.71-7.65 (m, 4H).

Synthesis of 1-fluoro-11-oxo-10, 11-dihydrodibenzo [b, f] [1, 4] thiazepine-8-carboxylic acid (54): A Common Intermediate

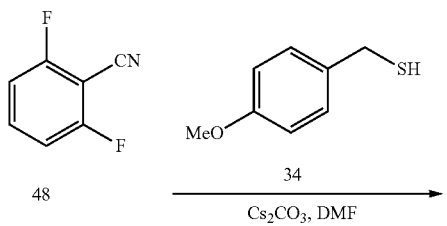

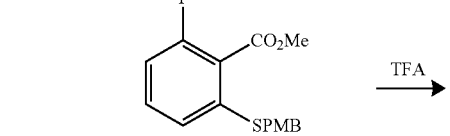

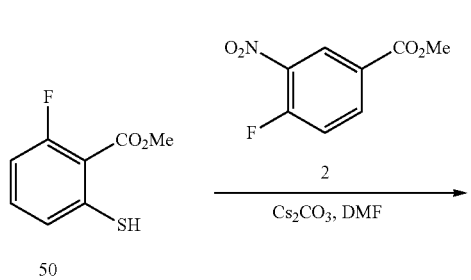

46

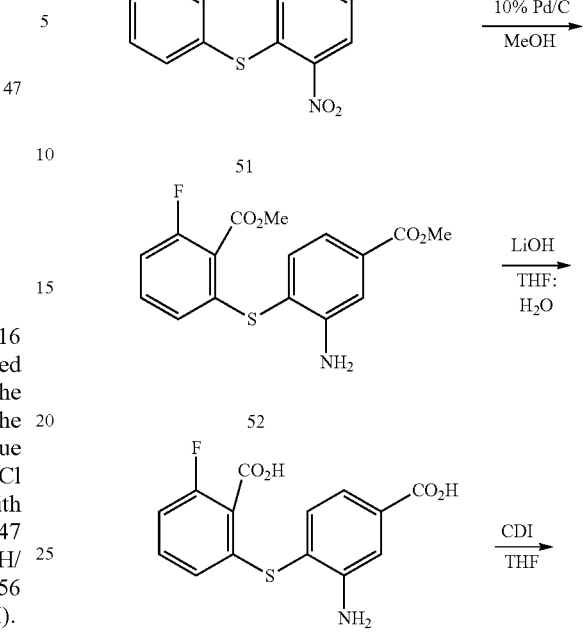

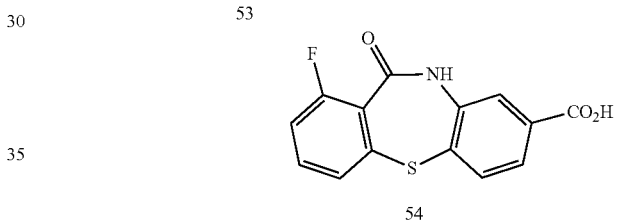

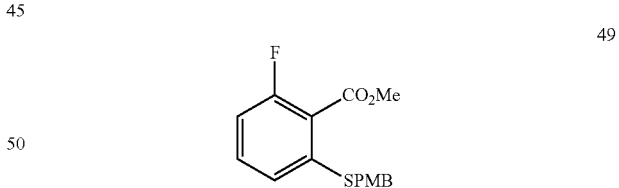

Synthesis of methyl 2-fluoro-6-((4-methoxybenzyl)thio) benzoate (49)

49

F, CO$_2$Me, SPMB

To a stirring solution of methyl 2, 6-difluorobenzoate 48 (10 g, 58.13 mmol) in DMF (100 mL) under inert atmosphere were added (4-methoxyphenyl) methanethiol 34 (8.96 g, 58.13 mmol), cesium carbonate (20.8 g, 63.95 mmol) at 0° C.; warmed to 10° C. and stirred for 2 h. The reaction was monitored by TLC; after completion of the reaction, the reaction mixture was diluted with water (200 mL) and extracted with EtOAc (2×800 mL). The combined organic extracts were dried over sodium sulfate, filtered and concentrated in vacuo to obtain the crude. The crude was purified through silica gel column chromatography using 10-15% EtOAc/hexanes to afford compound 49 (7.5 g, 42%) as white solid. TLC: 10% EtOAc/hexanes (R$_f$: 0.3); $^1$H NMR (DMSO-d$_6$, 400 MHz) δ 7.53-7.44 (m, 1H), 7.35 (d, J=8.0 Hz, 1H), 7.26 (d, J=8.6 Hz, 2H), 7.15 (t, J=9.0 Hz, 1H), 6.86 (d, J=8.7 Hz, 2H), 4.22 (s, 2H), 3.72 (s, 3H), 3.33 (s, 3H).

Synthesis of methyl 2-fluoro-6-mercaptobenzoate (50)

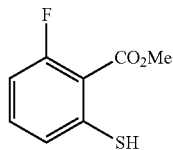

A stirred solution of compound 49 (7.5 g, 24.5 mmol) in trifluoro acetic acid (100 mL) at RT under inert atmosphere was heated to 60-65° C. and stirred for 5 h. The reaction was monitored by TLC; after completion of the reaction, the volatiles were removed and dried in vacuo to obtain compound 50 (4.6 g) as brown syrup. The crude was carried forward for next step without further purification. TLC: 10% EtOAc/hexanes ($R_f$: 0.7).

Synthesis of methyl 2-fluoro-6-((4-(methoxycarbonyl)-2-nitrophenyl) thio) benzoate (51)

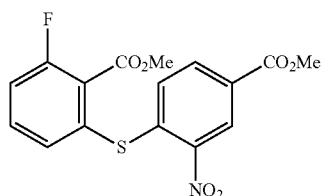

To a stirring solution of methyl 4-fluoro-3-nitrobenzoate 2 (4.5 g, 22.61 mmol) in DMF (100 mL) under inert atmosphere were added compound 50 (4.6 g, crude), cesium carbonate (11 g, 33.91 mmol) at RT; heated to 60-65° C. and stirred for 2 h. The reaction was monitored by TLC; after completion of the reaction, the reaction mixture was diluted with water (600 mL) and stirred for 1 h. The precipitated solid was filtered, titurated with 10% EtOAc/hexanes (2×20 mL) and dried in vacuo to afford compound 51 (7 g, 85%) as yellow solid. TLC: 20% EtOAc/hexanes ($R_f$: 0.3); $^1$H NMR (DMSO-$d_6$, 400 MHz): δ 8.65 (s, 1H), 8.08 (dd, J=8.6, 1.9 Hz, 1H), 7.79-7.72 (m, 1H), 7.67-7.61 (m, 2H), 7.01 (d, J=8.6 Hz, 1H), 3.88 (s, 3H), 3.72 (s, 3H).

Synthesis of methyl 2-((2-amino-4-(methoxycarbonyl) phenyl) thio)-6-fluorobenzoate (52)

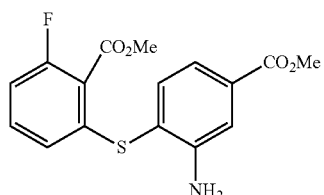

To a stirring solution of compound 51 (7.09 g, 19.17 mmol) in MeOH (200 mL) under inert atmosphere was added 10% Pd/C (3.5 g) at RT and stirred under hydrogen at 80 psi for 16 h in an autoclave. The reaction was monitored by TLC; after completion of the reaction, the reaction mixture was filtered through celite and washed with 40% MeOH/CH$_2$Cl$_2$ (3×500 mL). The combined organic extracts were dried over sodium sulfate, filtered and concentrated in vacuo to obtain the crude. The crude compound was triturated with 20% EtOAc/hexanes (200 mL) and dried in vacuo to afford compound 52 (5 g, 78%) as an off-white solid. TLC: 20% EtOAc/hexanes ($R_f$: 0.4); $^1$H NMR (DMSO-$d_6$, 400 MHz): δ 7.45-7.36 (m, 3H), 7.19-7.11 (m, 2H), 6.68 (d, J=7.7 Hz, 1H), 5.71 (s, 2H), 3.90 (s, 3H), 3.83 (s, 3H).

Synthesis of 2-((2-amino-4-carboxyphenyl) thio)-6-fluorobenzoic acid (53)

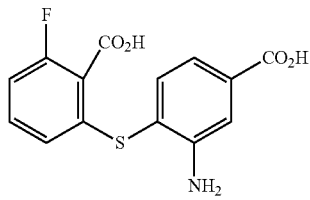

To a stirring solution of compound 52 (5 g, 14.92 mmol) in THF:H$_2$O (5:1, 90 mL) was added lithium hydroxide monohydrate (3.13 g, 74.62 mmol) at RT and stirred for 16 h and heated to 80° C. for 5 h. The reaction was monitored by TLC; after completion of the reaction, the volatiles were removed in vacuo. The residue was diluted with water (200 mL) and acidified with 2 N HCl to pH~4. The precipitated solid was filtered and dried in vacuo to afford compound 53 (4 g, 87%) as an off-white solid. TLC: 30% EtOAc/hexanes ($R_f$: 0.1); $^1$H NMR (DMSO-$d_6$, 400 MHz): δ 12.89 (br s, 1H), 7.42-7.36 (m, 2H), 7.35-7.31 (m, 1H), 7.14-7.08 (m, 2H), 6.63 (d, J=8.0 Hz, 1H), 5.75 (br s, 2H).

Synthesis of 1-fluoro-11-oxo-10, 11-dihydrodibenzo [b, f] [1, 4] thiazepine-8-carboxylic acid (54)

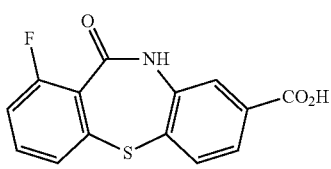

To a stirring solution of compound 53 (4 g, 13.02 mmol) in THF (100 mL) under inert atmosphere was added CDI (10.56 g, 65.1 mmol) at RT and stirred for 26 h. The reaction was monitored by TLC; after completion of the reaction, the volatiles were removed in vacuo. The residue was diluted with ice cold water (80 mL) and acidified with 2 N HCl to pH~4. The precipitated solid was filtered and dried in vacuo to afford compound 54 (3.3 g, 88%) as an off-white solid. TLC: 15% MeOH/CH$_2$Cl$_2$ ($R_f$: 0.2); $^1$H NMR (DMSO-$d_6$, 400 MHz): δ 13.33 (br s, 2H), 11.00 (s, 1H), 7.77 (s, 1H), 7.69-7.67 (m, 2H), 7.53-7.47 (m, 1H), 7.42-7.39 (m, 1H), 7.35-7.29 (m, 1H).

Synthesis of 2-fluoro-11-oxo-10, 11-dihydrodibenzo [b, f] [1, 4] thiazepine-8-carboxylic acid (61): A Common Intermediate

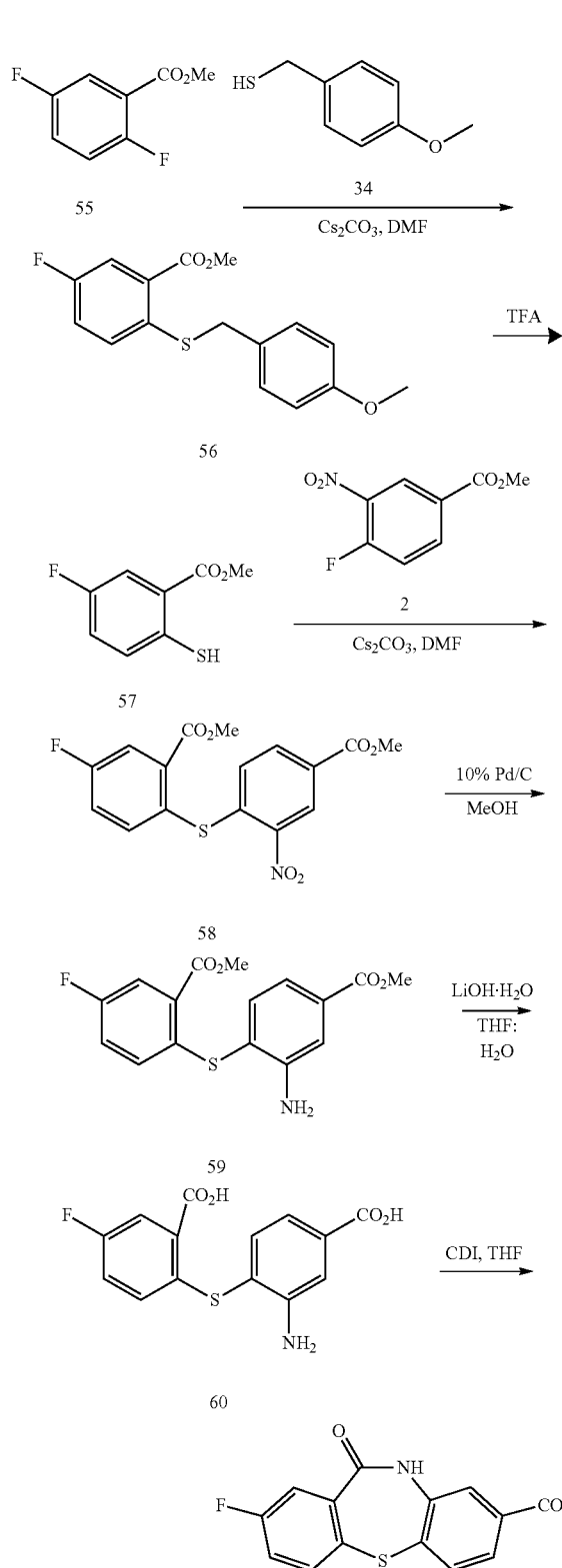

Synthesis of methyl-5-fluoro-2-((4-methoxybenzyl) thio) benzoate (56)

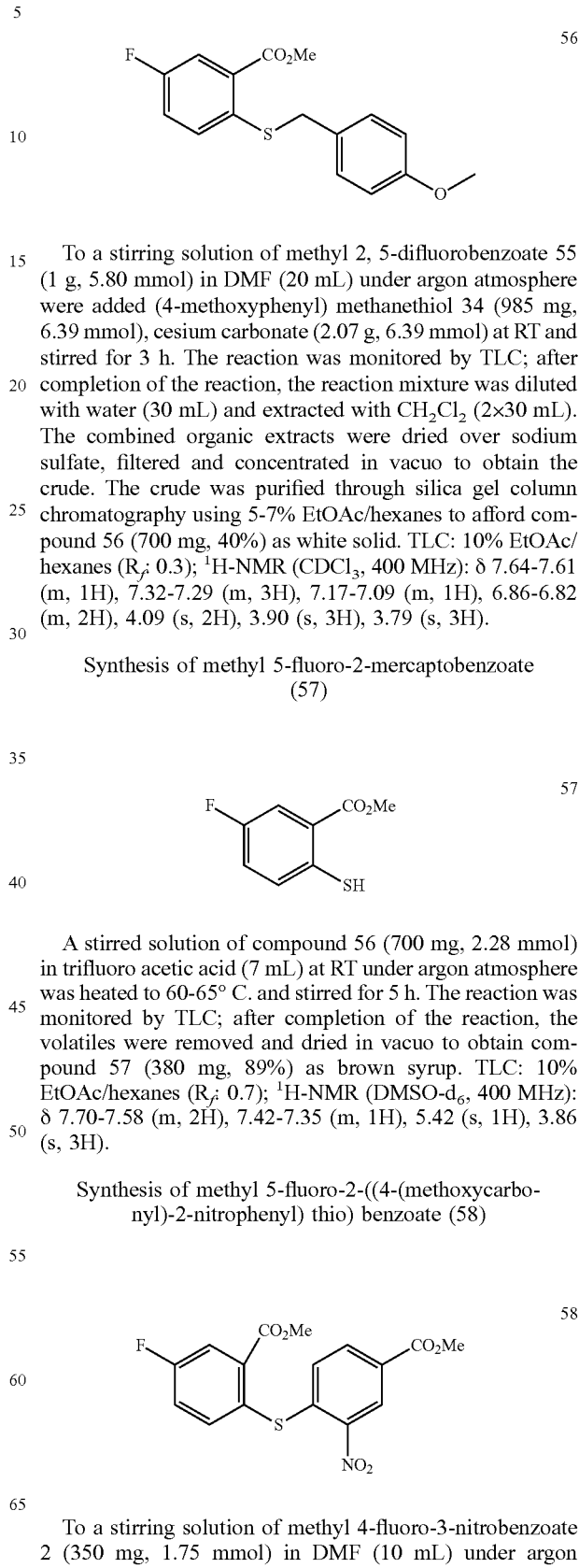

To a stirring solution of methyl 2, 5-difluorobenzoate 55 (1 g, 5.80 mmol) in DMF (20 mL) under argon atmosphere were added (4-methoxyphenyl) methanethiol 34 (985 mg, 6.39 mmol), cesium carbonate (2.07 g, 6.39 mmol) at RT and stirred for 3 h. The reaction was monitored by TLC; after completion of the reaction, the reaction mixture was diluted with water (30 mL) and extracted with $CH_2Cl_2$ (2×30 mL). The combined organic extracts were dried over sodium sulfate, filtered and concentrated in vacuo to obtain the crude. The crude was purified through silica gel column chromatography using 5-7% EtOAc/hexanes to afford compound 56 (700 mg, 40%) as white solid. TLC: 10% EtOAc/hexanes ($R_f$: 0.3); $^1$H-NMR ($CDCl_3$, 400 MHz): δ 7.64-7.61 (m, 1H), 7.32-7.29 (m, 3H), 7.17-7.09 (m, 1H), 6.86-6.82 (m, 2H), 4.09 (s, 2H), 3.90 (s, 3H), 3.79 (s, 3H).

Synthesis of methyl 5-fluoro-2-mercaptobenzoate (57)

A stirred solution of compound 56 (700 mg, 2.28 mmol) in trifluoro acetic acid (7 mL) at RT under argon atmosphere was heated to 60-65° C. and stirred for 5 h. The reaction was monitored by TLC; after completion of the reaction, the volatiles were removed and dried in vacuo to obtain compound 57 (380 mg, 89%) as brown syrup. TLC: 10% EtOAc/hexanes ($R_f$: 0.7); $^1$H-NMR (DMSO-$d_6$, 400 MHz): δ 7.70-7.58 (m, 2H), 7.42-7.35 (m, 1H), 5.42 (s, 1H), 3.86 (s, 3H).

Synthesis of methyl 5-fluoro-2-((4-(methoxycarbonyl)-2-nitrophenyl) thio) benzoate (58)

To a stirring solution of methyl 4-fluoro-3-nitrobenzoate 2 (350 mg, 1.75 mmol) in DMF (10 mL) under argon atmosphere were added compound 57 (360 mg, 1.93 mmol), cesium carbonate (1.14 g, 3.51 mmol) at RT; heated to 60-65° C. and stirred for 2 h. The reaction was monitored by TLC; after completion of the reaction, the reaction mixture was diluted with water (30 mL) and extracted with $CH_2Cl_2$ (2×40 mL). The combined organic extracts were dried over sodium sulfate, filtered and concentrated in vacuo to obtain the crude. The crude was purified through silica gel column chromatography using 7-10% EtOAc/hexanes to afford compound 58 (500 mg, 78%) as yellow solid. TLC: 10% EtOAc/hexanes ($R_f$: 0.3); $^1$H-NMR (DMSO-$d_6$, 400 MHz): δ 8.64 (s, 1H), 8.04-8.02 (m, 1H), 7.83-7.79 (m, 2H), 7.64-7.59 (m, 1H), 7.01 (d, J=8.4 Hz, 1H), 3.88 (s, 3H), 3.71 (s, 3H).

Synthesis of methyl 2-((2-amino-4-(methoxycarbonyl) phenyl) thio)-5-fluorobenzoate (59)

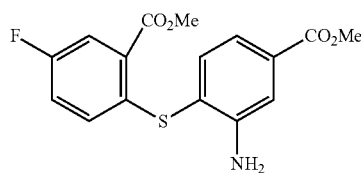

To a stirring solution of compound 58 (500 mg, 1.36 mmol) in MeOH (10 mL) under argon atmosphere was added 10% Pd/C (300 mg) at RT and stirred under hydrogen atmosphere (balloon pressure) for 16 h. The reaction was monitored by TLC; after completion of the reaction, the reaction mixture was filtered through celite and washed with 20% MeOH/$CH_2Cl_2$ (2×30 mL). The combined organic extracts were dried over sodium sulfate, filtered and concentrated in vacuo to obtain the crude. The crude was purified through silica gel column chromatography using 8-10% EtOAc/hexanes to afford compound 59 (300 mg, 66%) as pale yellow solid. TLC: 30% EtOAc/hexanes ($R_f$: 0.5); $^1$H-NMR (DMSO-$d_6$, 400 MHz): δ 7.78 (d, J=9.6 Hz, 1H), 7.45-7.41 (m, 2H), 7.35-7.30 (m, 1H), 7.14 (d, J=9.6 Hz, 1H), 6.68-6.65 (m, 1H), 5.70 (s, 2H), 3.89 (s, 3H), 3.83 (s, 3H).

Synthesis of 2-((2-amino-4-carboxyphenyl) thio)-5-fluorobenzoic acid (60)

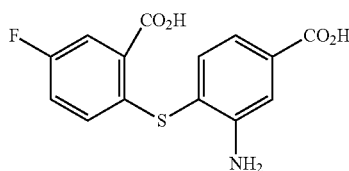

To a stirring solution of compound 59 (300 mg, 0.89 mmol) in THF:$H_2O$ (5:1, 6 mL) under argon atmosphere was added lithium hydroxide monohydrate (188 mg, 4.47 mmol) at RT and stirred for 16 h. The reaction was monitored by TLC; after completion of the reaction, the volatiles were removed in vacuo. The residue was diluted with water (15 mL) and acidified with 6 N HCl to pH~4. The precipitated solid was filtered and dried in vacuo to afford compound 60 (180 mg, 66%) as white solid. TLC: 50% EtOAc/hexanes ($R_f$: 0.2); $^1$H-NMR (DMSO-$d_6$, 400 MHz): δ 12.99-12.96 (m, 2H), 7.69 (d, J=6.8 Hz, 1H), 7.40 (t, J=7.2 Hz, 2H), 7.29 (t, J=7.2 Hz, 1H), 7.13 (d, J=7.2 Hz, 1H), 6.64-6.61 (m, 1H), 5.64-5.61 (m, 2H).

Synthesis of 2-fluoro-11-oxo-10, 11-dihydrodibenzo [b, f] [1, 4] thiazepine-8-carboxylic acid (61): A Common Intermediate

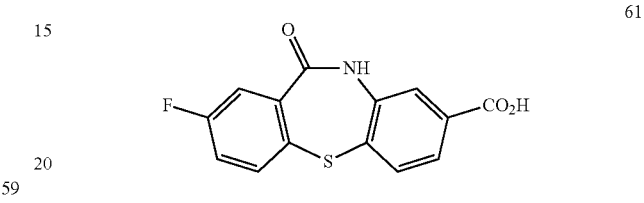

To a stirring solution of compound 60 (180 mg, 0.58 mmol) in THF (10 mL) under argon atmosphere was added CDI (284 mg, 1.75 mmol) at RT and stirred for 16 h. The reaction was monitored by TLC; after completion of the reaction, the volatiles were removed in vacuo. The residue was diluted with ice cold water (10 mL) and acidified with 6 N HCl to pH~4. The precipitated solid was filtered and dried in vacuo to afford compound 61 (80 mg, 47%) as an off-white solid. TLC: 10% MeOH/$CH_2Cl_2$ ($R_f$: 0.2); $^1$H-NMR (DMSO-$d_6$, 400 MHz): δ 13.30 (br s, 1H), 10.93 (s, 1H), 7.70 (s, 1H), 7.67 (d, J=7.6 Hz, 2H), 7.59 (t, J=7.6 Hz, 1H), 7.48 (t, J=7.6 Hz, 1H), 7.40-7.35 (m, 1H).

Synthesis of 3-fluoro-11-oxo-10, 11-dihydrodibenzo [b, f] [1, 4] thiazepine-8-carboxylic acid (68): A Common Intermediate

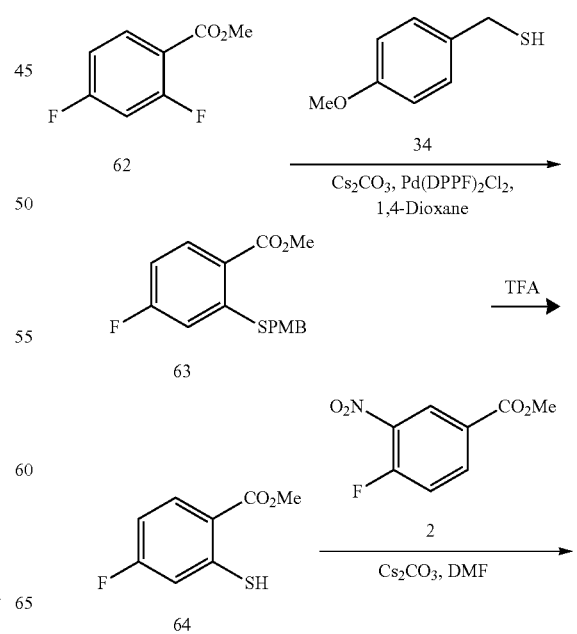

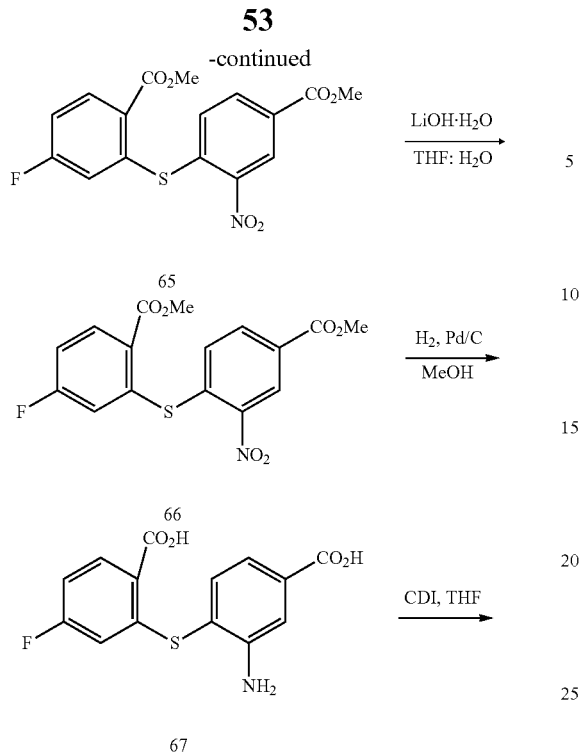

Synthesis of methyl 4-fluoro-2-mercaptobenzoate (64)

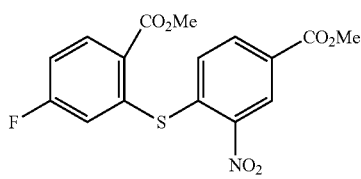

A stirred solution of compound 63 (2.2 g, 7.18 mmol) in trifluoro acetic acid (30 mL) at RT under inert atmosphere was heated to 90° C. and stirred for 3 h. The reaction was monitored by TLC; after completion of the reaction, the volatiles were removed in vacuo to obtain compound 64 (1.33 g, crude) as brown syrup. The crude was carried forward for next step without further purification. TLC: 10% EtOAc/hexanes ($R_f$: 0.8).

Synthesis of methyl 4-fluoro-2-((4-(methoxycarbonyl)-2-nitrophenyl) thio) benzoate (65)

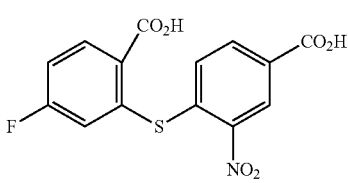

To a stirring solution of methyl 4-fluoro-3-nitrobenzoate 2 (1.29 g, 6.93 mmol) in DMF (50 mL) under inert atmosphere were added cesium carbonate (2.93 g, 9.01 mmol) and compound 64 (1.2 g, 6.03 mmol) at RT; heated to 55-60° C. and stirred for 2 h. The reaction was monitored by TLC; after completion of the reaction, the reaction mixture was diluted with water (20 mL), the precipitated solid was filtered to obtain the crude. The crude was washed with pentane (2×20 mL) and dried in vacuo to afford compound 65 (1.5 g, 68%) as yellow solid. TLC: 10% EtOAc/hexanes ($R_f$: 0.3); $^1$H-NMR (DMSO-$d_6$, 400 MHz): δ 8.63 (s, 1H), 8.13-8.04 (m, 2H), 7.53-7.46 (m, 2H), 7.24 (d, J=8.4 Hz, 1H), 3.89 (s, 3H), 3.72 (s, 3H).

Synthesis of 2-((4-carboxy-2-nitrophenyl) thio)-4-fluorobenzoic acid (66)

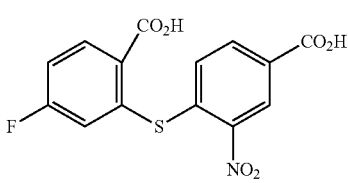

To a stirring solution of compound 65 (1.5 g, 4.10 mmol) in THF:H$_2$O (4:1, 20 mL) was added lithium hydroxide monohydrate (690 mg, 16.4 mmol) at RT, heated to 80° C. and stirred for 2 h. The reaction was monitored by TLC; after completion of the reaction, the volatiles were removed

Synthesis of methyl 4-fluoro-2-((4-methoxybenzyl) thio) benzoate (63)

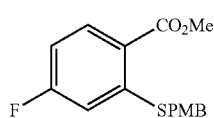

To a stirring solution of methyl 2-bromo-4-fluorobenzoate 62 (2 g, 8.58 mmol) in 1,4-dioxane (50 mL) under inert atmosphere were added (4-methoxyphenyl) methanethiol 34 (1.58 g, 10.25 mmol), cesium carbonate (4.18 g, 12.80 mmol) at RT and purged under argon atmosphere for 30 min. To this was added Pd(dppf)$_2$Cl$_2$ (306 mg, 0.42 mmol); heated to 120° C. and stirred for 16 h. The reaction was monitored by TLC; after completion of the reaction, the reaction mixture was diluted with water (20 mL) and extracted with EtOAc (2×250 mL). The combined organic extracts were dried over sodium sulfate, filtered and concentrated in vacuo to obtain the crude. The crude was purified through silica gel column chromatography using 7% EtOAc/hexanes to afford compound 63 (1.6 g, 61%) as an off-white solid. TLC: 10% EtOAc/hexanes ($R_f$: 0.4); $^1$H NMR (CDCl$_3$, 400 MHz): δ 8.01 (dd, J=8.7, 6.2 Hz, 1H), 7.34 (d, J=7.9 Hz, 2H), 7.04 (dd, J=10.3, 2.4 Hz, 1H), 6.88-6.80 (m, 3H), 4.09 (s, 2H), 3.88 (s, 3H), 3.80 (s, 3H).

in vacuo. The pH of the residue was acidified with 2 N HCl to 6. The precipitated solid was filtered and dried in vacuo to afford compound 66 (1.2 g, 86%) as an off-white solid. TLC: 5% MeOH/CH$_2$Cl$_2$ (R$_f$: 0.2); $^1$H-NMR (DMSO-d$_6$, 400 MHz): δ 13.46 (br s, 2H), 8.58 (s, 1H), 8.08-8.01 (m, 2H), 7.45-7.40 (m, 1H), 7.38-7.35 (m, 1H), 7.29 (d, J=8.4 Hz, 1H).

Synthesis of 2-((2-amino-4-carboxyphenyl) thio)-4-fluorobenzoic acid (67)

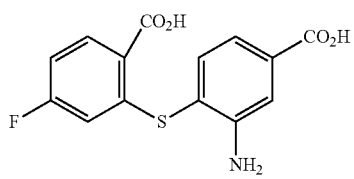

To a stirring solution of compound 66 (1.2 g, 3.56 mmol) in MeOH (50 mL) under inert atmosphere was added 10% Pd/C (300 mg) at RT and stirred under hydrogen atmosphere (balloon pressure) for 16 h. The reaction was monitored by TLC; after completion of the reaction, the reaction mixture was filtered through celite, washed with MeOH (20 mL). The filtrate was removed in vacuo to obtain the crude which as triturated with 10% EtOAc/n-pentane (50 mL) to afford compound 67 (1 g, 91%) as an off-white solid. TLC: 10% MeOH/CH$_2$Cl$_2$ (R$_f$: 0.3); $^1$H-NMR (DMSO-d$_6$, 400 MHz): δ 12.96 (br s, 2H), 8.06-8.02 (m, 1H), 7.46 (s, 1H), 7.40 (d, J=8.0 Hz, 1H), 7.16 (d, J=8.0 Hz, 1H), 7.07-7.02 (m, 1H), 6.24 (d, J=8.0 Hz, 1H), 5.67 (br s, 2H).

Synthesis of 3-fluoro-11-oxo-10, 11-dihydrodibenzo [b, f] [1, 4] thiazepine-8-carboxylic acid (68)

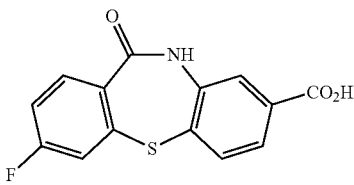

To a stirring solution of compound 67 (1 g, 3.25 mmol) in THF (30 mL) under inert atmosphere was added CDI (1.61 g, 9.77 mmol) at RT and stirred for 16 h. The reaction was monitored by TLC; after completion of the reaction, the reaction mixture was acidified with 2 N HCl to pH~4. The obtained solid was filtered, washed with water (20 mL), ether (2×5 mL) and dried in vacuo to afford compound 68 (760 mg, 80%) as white solid. TLC: 10% MeOH/CH$_2$Cl$_2$ (R$_f$: 0.3); $^1$H-NMR (DMSO-d$_6$, 400 MHz): δ 13.24 (br s, 1H), 10.83 (s, 1H), 7.78-7.74 (m, 2H), 7.69-7.66 (m, 2H), 7.47-7.44 (m, 1H), 7.35-7.30 (m, 1H).

Synthesis of 4-fluoro-11-oxo-10, 11-dihydrodibenzo [b, f] [1, 4] thiazepine-8-carboxylic acid (76): A Common Intermediate

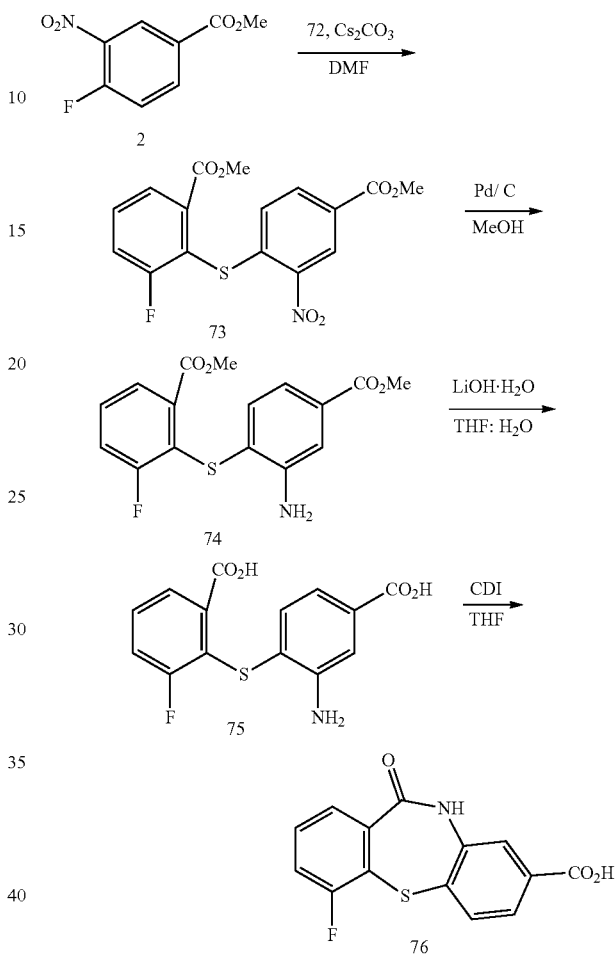

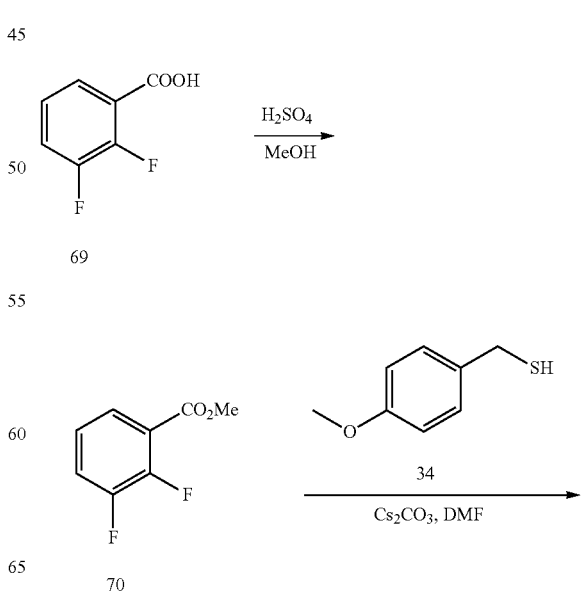

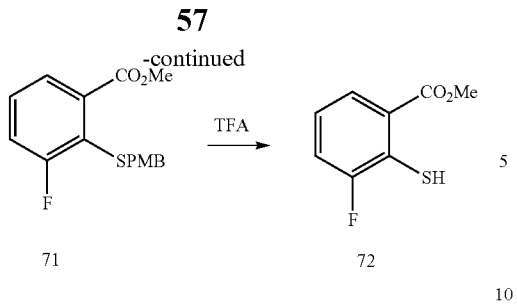

Synthesis of methyl 2, 3-difluorobenzoate (70)

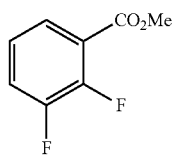

To a stirring solution of 2, 3-difluorobenzoic acid 69 (1 g, 6.28 mmol) in MeOH (10 mL) under inert atmosphere was added Conc. $H_2SO_4$ (5 mL) at 0° C. and heated to reflux for 36 h. The reaction was monitored by TLC; after completion of the reaction, the volatiles were removed in vacuo. The residue was diluted with water (25 mL) and pH adjusted to ~8 with saturated sodium bicarbonate solution (20 mL) and extracted with EtOAc (2×20 mL). The combined organic extracts were dried over sodium sulfate, filtered and concentrated in vacuo to obtain the crude. The crude was purified through silica gel column chromatography using 20% EtOAc/hexanes to afford compound 70 (800 mg, 74%) as an off-white solid. TLC: 40% EtOAc/hexanes ($R_f$: 0.8); $^1$H NMR (DMSO-$d_6$, 500 MHz) δ 7.80-7.65 (m, 2H), 7.41-7.23 (m, 1H), 3.88 (s, 3H).

Synthesis of methyl 3-fluoro-2-((4-methoxybenzyl) thio) benzoate (71)

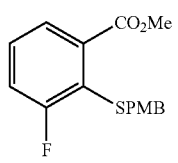

To a stirring solution of compound 70 (800 mg, 4.65 mmol) in DMF (10 mL) under inert atmosphere were added (4-methoxyphenyl) methanethiol 34 (282 mg, 5.11 mmol), cesium carbonate (1.66 g, 5.11 mmol) at RT and stirred for 6 h. The reaction was monitored by TLC; after completion of the reaction, the reaction mixture was diluted water (25 mL) and extracted with ether (2×40 mL). The combined organic extracts were dried over sodium sulfate, filtered and concentrated in vacuo to obtain the crude. The crude was purified through silica gel column chromatography using 20% EtOAc/hexanes to afford compound 71 (750 mg, 53%) as an off-white solid. TLC: 20% EtOAc/hexanes ($R_f$: 0.4); $^1$H NMR (DMSO-$d_6$, 500 MHz): δ 7.49-7.36 (m, 3H), 7.10 (d, J=8.9 Hz, 2H), 6.79 (d, J=8.9 Hz, 2H), 4.06 (s, 2H), 3.81 (s, 3H), 3.70 (s, 3H);

Synthesis of methyl 3-fluoro-2-mercaptobenzoate (72)

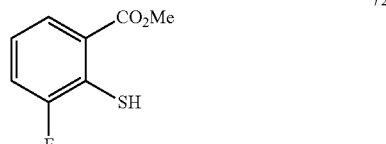

A stirred solution of compound 71 (750 mg, 2.45 mmol) in trifluoro acetic acid (7 mL) at RT under inert atmosphere was heated to 70° C. and stirred for 2 h. The reaction was monitored by TLC; after completion of the reaction, the volatiles were removed in vacuo to obtain compound 72 (1.1 g, crude) as colorless liquid. The crude was carried forward for next step. TLC: 30% EtOAc/hexanes ($R_f$: 0.8).

Synthesis of methyl 3-fluoro-2-((4-(methoxycarbonyl)-2-nitrophenyl) thio) benzoate (73)

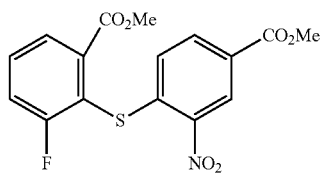

To a stirring solution of compound 72 (5.96 g, 3.20 mmol) in DMF (100 mL) under inert atmosphere were added methyl 4-fluoro-3-nitrobenzoate 2 (5.8 g, 2.91 mmol), cesium carbonate (10.41 g, 3.20 mmol) at RT; heated to 80° C. and stirred for 4 h. The reaction was monitored by TLC; after completion of the reaction, the reaction mixture was diluted with ice cold water (25 mL). The obtained solid was filtered, washed with hexane (2×10 mL) and dried in vacuo to afford compound 73 (7.8 g, 73%) as an pale yellow solid. TLC: 30% EtOAc/hexanes ($R_f$: 0.5); $^1$H NMR (DMSO-$d_6$, 500 MHz): δ 8.67 (s, 1H), 8.05 (dd, J=8.7, 1.7 Hz, 1H), 7.94-7.75 (m, 2H), 7.73-7.67 (m, 1H), 7.00 (d, J=8.4 Hz, 1H), 3.88 (s, 3H), 3.77-3.64 (m, 3H).

Synthesis of methyl 2-((2-amino-4-(methoxycarbonyl) phenyl) thio)-3-fluorobenzoate (74)

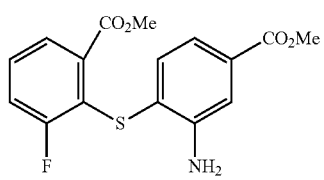

To a stirring solution of compound 73 (670 mg, 1.83 mmol) in MeOH (10 mL) under inert atmosphere was added 10% Pd/C (150 mg) at RT and stirred under hydrogen atmosphere (balloon pressure) for 12 h. The reaction was monitored by TLC; after completion of the reaction, the reaction mixture was filtered through celite and the filtrate was concentrated in vacuo to afford compound 74 (500 mg, 81%) as an off-white solid. TLC: 30% EtOAc/hexanes (R$_f$: 0.4); $^1$H NMR (DMSO-d$_6$, 400 MHz): δ 7.58-7.50 (m, 2H), 7.48-7.41 (m, 1H), 7.33 (s, 1H), 7.04 (s, 2H), 5.59 (br s, 2H), 3.82 (s, 3H), 3.79 (s, 3H).

Synthesis of 2-((2-amino-4-carboxyphenyl) thio)-3-fluorobenzoic acid (75)

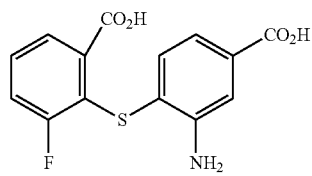

75

To a stirring solution of compound 74 (500 mg, 1.49 mmol) in THF:H$_2$O (4:1, 20 mL) was added lithium hydroxide monohydrate (376 mg, 8.95 mmol) at RT; heated to 80° C. and stirred for 3 h. The reaction was monitored by TLC; after completion of the reaction, the volatiles were removed in vacuo. The residue was diluted with water (25 mL) and washed with diethyl ether (2×25 mL). The aqueous layer was acidified with 2 N HCl to pH~4 and extracted with EtOAc (2×20 mL). The combined organic extracts were dried over sodium sulfate, filtered and concentrated in vacuo to obtain the crude which was washed with diethyl ether (2×5 mL) and dried in vacuo to afford compound 75 (300 mg, 65%) as an off-white solid. TLC: 10% MeOH/CH$_2$Cl$_2$ (R$_f$: 0.2); $^1$H NMR (DMSO-d$_6$, 500 MHz): δ 12.68 (br s, 2H), 7.54-7.45 (m, 2H), 7.39-7.32 (m, 1H), 7.28 (s, 1H), 7.09-7.06 (m, 1H), 7.02-6.96 (m, 1H), 5.56 (br s, 2H);

Synthesis of 4-fluoro-11-oxo-10, 11-dihydrodibenzo [b, f] [1, 4] thiazepine-8-carboxylic acid (76)

76

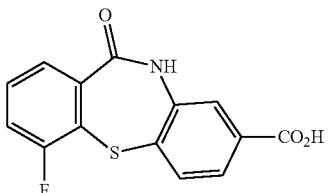

To a stirring solution of compound 75 (300 mg, 0.97 mmol) in THF (15 mL) under inert atmosphere was added CDI (474 mg, 2.92 mmol) at RT and stirred for 16 h. The reaction was monitored by TLC; after completion of the reaction, the volatiles were removed in vacuo. The pH of the residue was acidified with 4 N HCl to ~2. The obtained solid was filtered, washed with diethyl ether (2×5 mL) and dried in vacuo to afford compound 76 (150 mg, 53%) as an off-white solid. TLC: 15% MeOH/CH$_2$Cl$_2$ (R$_f$: 0.5); $^1$H NMR (DMSO-d$_6$ 400 MHz): δ 13.38 (br s, 1H), 10.92 (s, 1H), 7.79 (s, 1H), 7.75-7.66 (m, 2H), 7.55-7.46 (m, 3H).

Synthesis of 7-fluoro-11-oxo-10, 11-dihydrodibenzo [b, f] [1, 4] thiazepine-8-carboxylic acid (81): A Common Intermediate

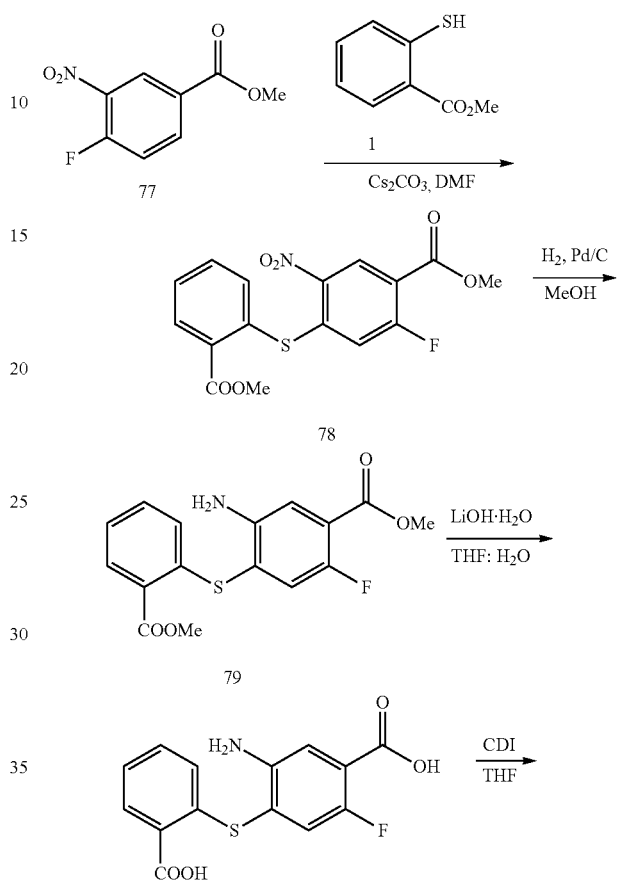

Synthesis of methyl 2-fluoro-4-((2-(methoxycarbonyl) phenyl) thio)-5-nitrobenzoate (78)

78

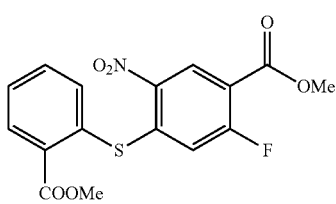

To a stirring solution of methyl 2, 4-difluoro-5-nitrobenzoate 77 (9.0 g, 41.45 mmol) in DMF (100 mL) under inert atmosphere were added methyl 2-mercaptobenzoate 1 (6.97 g, 41.45 mmol), cesium carbonate (14.82 g, 45.60 mmol) at 0° C.; warmed to 10° C. and stirred for 2 h. The reaction was monitored by TLC; after completion of the reaction, the reaction mixture was diluted with water (800 mL) and extracted with EtOAc (2×500 mL). The combined organic extracts were dried under sodium sulfate, filtered and concentrated in vacuo to obtain the crude. The crude was purified through silica gel column chromatography using 10% EtOAc/hexanes to afford compound 78 (11 g, 73%) as an off-white solid. TLC: 10% EtOAc/hexanes ($R_f$: 0.4); $^1$H NMR (DMSO-$d_6$, 400 MHz): δ 8.69 (d, J=6.8 Hz, 1H), 8.04-7.92 (m, 1H), 7.81-7.69 (m, 3H), 6.60 (d, J=11.5 Hz, 1H), 3.88 (s, 3H), 3.73 (s, 3H).

Synthesis of methyl 5-amino-2-fluoro-4-((2-(methoxycarbonyl) phenyl) thio) benzoate (79)

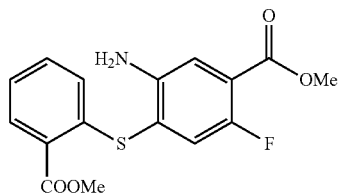

78

To a stirring solution of compound 78 (11 g, 30.13 mmol) in MeOH (400 mL) under inert atmosphere was added 10% Pd/C (5 g) at RT and stirred under hydrogen atmosphere (balloon pressure) for 24 h. The reaction was monitored by TLC; after completion of the reaction, the reaction mixture was filtered through celite, washed with 30% MeOH/CH$_2$Cl$_2$ (3×60 mL). The filtrate was removed in vacuo to afford compound 79 (6.5 g, 64%) as an off-white solid. TLC: 20% EtOAc/hexanes ($R_f$: 0.4); $^1$H NMR (DMSO-$d_6$, 400 MHz): δ 8.01-7.88 (m, 1H), 7.45-7.40 (m, 1H), 7.34-7.24 (m, 3H), 6.72 (dd, J=8.2, 0.8 Hz, 1H), 5.51 (s, 2H), 3.88 (s, 3H), 3.85 (s, 3H).

Synthesis of 5-amino-4-((2-carboxyphenyl) thio)-2-fluorobenzoic acid (80)

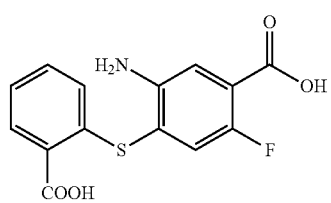

80

To a stirring solution of compound 79 (6.5 g, 19.4 mmol) in THF:H$_2$O (4:1, 90 mL) was added lithium hydroxide monohydrate (4 g, 97.01 mmol) at RT and stirred for 16 h. The reaction was monitored by TLC; after completion of the reaction, the volatiles were removed in vacuo. The pH of the residue was acidified with 2 N HCl to ~4. The precipitated solid was filtered and dried in vacuo to afford compound 80 (4.5 g, 75.6%) as an off-white solid. TLC: 30% EtOAc/hexane ($R_f$: 0.2); $^1$H NMR (DMSO-$d_6$, 400 MHz): δ 13.19 (br s, 2H), 7.96 (dd, J=7.7, 1.5 Hz, 1H), 7.39 (t, J=7.3 Hz, 1H), 7.30 (d, J=6.6 Hz, 1H), 7.27-7.20 (m, 2H), 6.68 (dd, J=8.2, 0.7 Hz, 1H), 5.42 (br s, 2H).

Synthesis of 7-fluoro-11-oxo-10, 11-dihydrodibenzo [b, f] [1, 4] thiazepine-8-carboxylic acid (81)

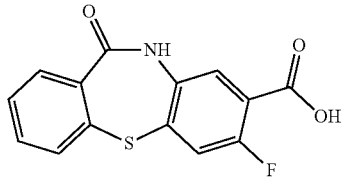

81

To a stirring solution of compound 80 (4.5 g, 14.65 mmol) in THF (100 mL) under inert atmosphere was added CDI (11.88 g, 73.28 mmol) at 0° C.; warmed to RT and stirred for 16 h. The reaction was monitored by TLC; after completion of the reaction, the reaction mixture was quenched with 2 N HCl to pH~4; the precipitated solid was filtered, dried in vacuo to afford compound 81 (3.5 g, 83%) as an off-white solid. TLC: 15% MeOH/CH$_2$Cl$_2$ ($R_f$: 0.2); $^1$H NMR (DMSO-$d_6$, 400 MHz): δ 13.61 (br s, 1H), 10.75 (s, 1H), 7.74-7.65 (m, 2H), 7.59-7.45 (m, 4H).

Synthesis of 7, 9-difluoro-11-oxo-10, 11-dihydrodibenzo [b, f] [1, 4] thiazepine-8-carboxylic acid (88): A Common Intermediate

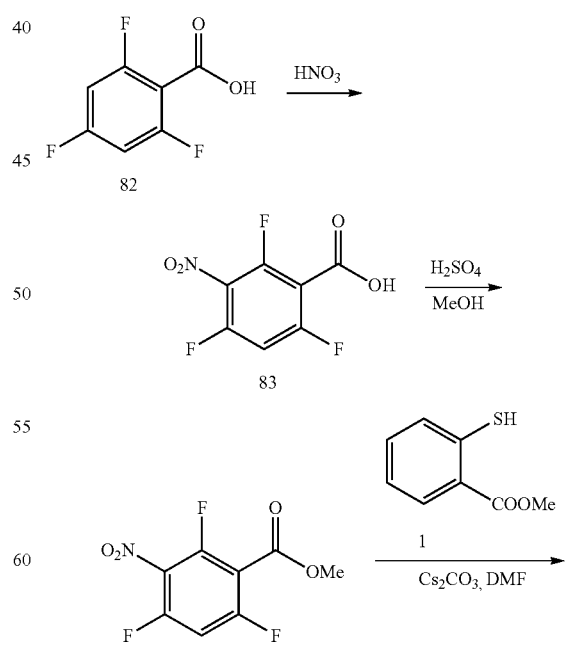

-continued

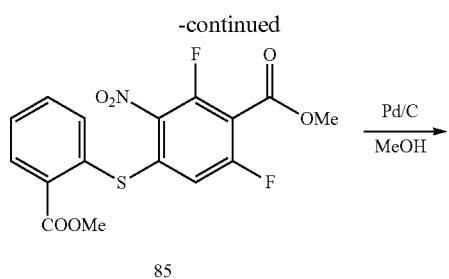

85

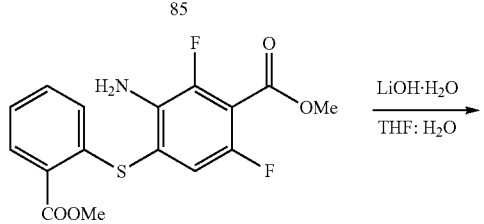

86

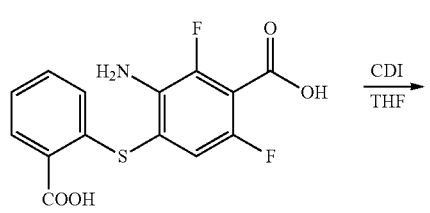

87

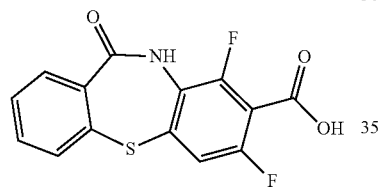

88

Synthesis of 2, 4, 6-trifluoro-3-nitrobenzoic acid (83)

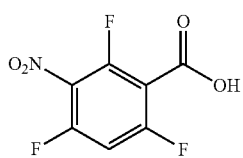

83

To 2, 4, 6-trifluorobenzoic acid 82 (15 g, 85.22 mmol) at 0° C., fuming nitric acid (20 mL) was added dropwise for 10 min; warmed to RT and stirred for 16 h. The reaction was monitored by TLC; after completion of the reaction, the reaction mixture was diluted with ice cold water (500 mL) and extracted with EtOAc (2×200 mL). The combined organic extracts were dried over sodium sulfate, filtered and concentrated in vacuo to afford compound 83 (20 g) as pale yellow liquid. TLC: 5% MeOH/CH$_2$Cl$_2$+0.05 mL CH$_3$COOH (R$_f$: 0.2); $^1$H NMR (DMSO-d$_6$, 400 MHz): δ 14.12 (br s, 1H), 7.83 (td, J=10.5, 2.1 Hz, 1H).

Synthesis of methyl 2, 4, 6-trifluoro-3-nitrobenzoate (84)

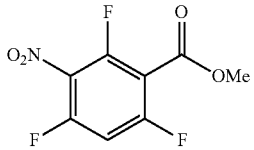

84

To a stirring solution of compound 83 (20 g) in MeOH (200 mL) under argon atmosphere was added concentrated sulfuric acid (20 mL) dropwise for 20 min at 0° C. and heated to reflux for 48 h. The reaction was monitored by TLC; after completion of the reaction, the volatiles were removed in vacuo. The residue was diluted with water (500 mL) and extracted with EtOAc (4×200 mL). The combined organic extracts were dried over sodium sulfate, filtered and concentrated in vacuo to obtain the crude. The crude was purified through silica gel column chromatography using 5-8% EtOAc/hexanes to afford compound 84 (14 g, 70% for 2 steps) as pale yellow syrup. TLC: 20% EtOAc/hexane (R$_f$: 0.8); $^1$H NMR (DMSO-d$_6$, 400 MHz): δ 7.88 (td, J=10.6, 2.2 Hz, 1H), 3.93 (s, 3H).

Synthesis of methyl 2, 6-difluoro-4-((2-(methoxycarbonyl) phenyl) thio)-3-nitrobenzoate (85)

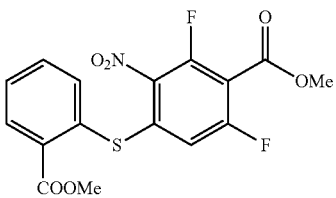

85

To a stirring solution of compounds 84 (14 g, 59.57 mmol) in DMF (300 mL) under inert atmosphere were added methyl 2-mercaptobenzoate 1 (11.1 g, 66.07 mmol), cesium carbonate (38.77 g, 119.14 mmol) at 0° C.; warmed to RT and stirred for 2 h. The reaction was monitored by TLC; after completion of the reaction, the reaction mixture was diluted with ice cold water (200 mL) and extracted with EtOAc (3×300 mL). The combined organic extracts were washed with water (200 mL), brine (200 mL), dried over sodium sulfate, filtered and concentrated in vacuo to obtain the crude. The crude was purified through silica gel column chromatography to afford compound 85 (14.5 g, 64%) as yellow syrup. TLC: 10% EtOAc/hexanes (R$_f$: 0.2); $^1$H NMR (DMSO-d$_6$, 500 MHz): δ 7.98 (dd, J=7.7, 1.3 Hz, 1H), 7.66-7.61 (m, 1H), 7.59-7.55 (m, 1H), 7.46 (d, J=7.8 Hz, 1H), 7.19 (d, J=9.3 Hz, 1H), 3.93 (s, 3H), 3.81 (s, 3H).

Synthesis of methyl 3-amino-2, 6-difluoro-4-((2-(methoxycarbonyl) phenyl) thio) benzoate (86)

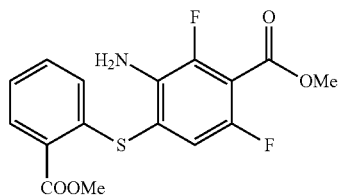

To a stirring solution of compound 85 (18 g, 46.99) in MeOH (400 mL) under inert atmosphere was added Pd/C (9 g, 50% wet) at RT and stirred under hydrogen atmosphere in an autoclave (5 kg/cm² pressure) for 16 h. The reaction was monitored by TLC; after completion of the reaction, the reaction mixture was filtered through celite, washed with MeOH (500 mL). The filtrate was concentrated in vacuo to afford compound 86 (15.1 g, 91%) as colorless semi solid. TLC: 20% EtOAc/hexanes ($R_f$: 0.5); $^1$H NMR (DMSO-$d_6$, 500 MHz): δ 8.00-7.93 (m, 1H), 7.48-7.42 (m, 1H), 7.31-7.21 (m, 2H), 6.76-6.64 (m, 1H), 5.54-5.47 (m, 2H), 3.91 (s, 3H), 3.89 (s, 3H).

Synthesis of 3-amino-4-((2-carboxyphenyl) thio)-2, 6-difluorobenzoic acid (87)

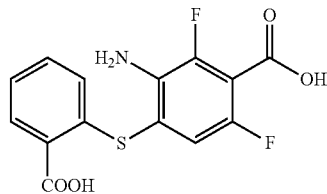

To a stirring solution of compound 86 (15.1 g, 39.42 mmol) in THF:H$_2$O (4:1, 250 mL) was added lithium hydroxide monohydrate (8.3 g, 197.61 mmol) at RT and stirred for 16 h. The reaction was monitored by TLC; after completion of the reaction, the volatiles were removed in vacuo, diluted with water (100 mL) and washed with EtOAc (2×100 mL). The pH of the aqueous layer was acidified with 4 N HCl to ~4. The precipitated solid was filtered, washed with water (100 mL), pentane (100 mL). The obtained solid was further dried using toluene (150 mL) to afford compound 87 (11 g, 79%) as an off-white solid. TLC: 20% EtOAc/hexanes ($R_f$: 0.2); $^1$H NMR (DMSO-$d_6$, 400 MHz): δ 13.24 (br s, 1H), 7.97 (dd, J=7.7, 1.4 Hz, 1H), 7.46-7.39 (m, 1H), 7.28-7.19 (m, 2H), 6.66 (d, J=8.2 Hz, 1H), 5.39 (br s, 2H).

Synthesis of 7, 9-difluoro-11-oxo-10, 11-dihydrodibenzo [b, f] [1, 4] thiazepine-8-carboxylic acid (88)

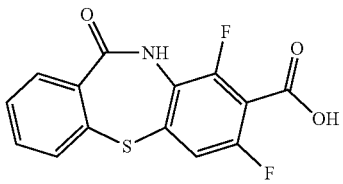

To a stirring solution of compound 87 (10 g, 30.76 mmol) in THF (200 mL) under argon atmosphere was added CDI (14.9 g, 81.97 mmol) at RT and stirred for 24 h. The reaction was monitored by TLC; after completion of the reaction, the volatiles were removed in vacuo. The residue was diluted with water (300 mL) and the pH was adjusted to ~3 with 2 N HCl. The obtained solid was filtered, washed with water (100 mL), pentane (50 mL) and diethyl ether (150 mL) and dried in vacuo to obtain compound 88 (2.83 g, 30%) as brick red solid. TLC: 15% MeOH/CH$_2$Cl$_2$ ($R_f$: 0.3); $^1$H NMR (DMSO-$d_6$, 500 MHz): δ 14.19 (br s, 1H), 10.64 (s, 1H), 7.73-7.66 (m, 2H), 7.58-7.48 (m, 3H).

Synthesis of 11-oxo-10, 11-dihydrodibenzo [b, f] [1, 4] thiazepine-8-carboxylic acid 5-oxide (89): A Common Intermediate

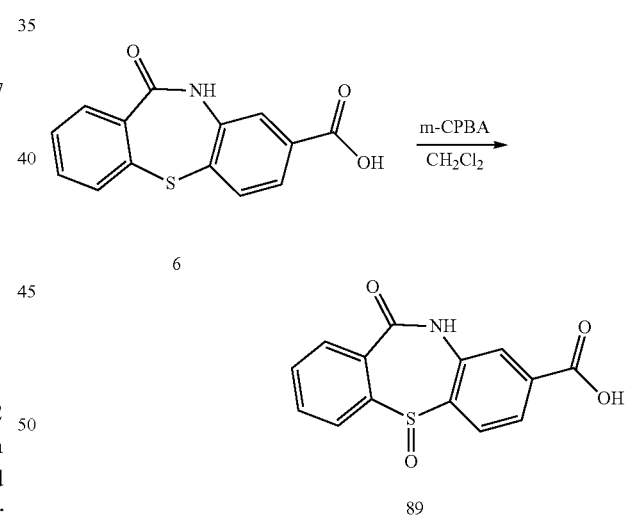

To a stirring solution of 6 (2.5 g, 9.21 mmol) in CH$_2$Cl$_2$ (50 mL) under inert atmosphere was added m-chloro perbenzoic acid (1.59 g, 9.21 mmol) at RT and stirred for 48 h. The reaction was monitored by TLC; after completion of the reaction, the reaction mixture was the volatiles were removed in vacuo to obtain the crude. The crude was triturated with 10% MeOH/CH$_2$Cl$_2$ (2×5 mL), isopropanol (10 mL) to afford compound 89 (2.3 g, 87%) as white solid. TLC: 10% MeOH/CH$_2$Cl$_2$+0.05 mL CH$_3$COOH ($R_f$: 0.4); $^1$H NMR (DMSO-$d_6$, 500 MHz): δ 13.36 (br s, 1H), 11.08 (s, 1H), 7.96 (d, J=7.8 Hz, 1H), 7.92-7.87 (m, 1H), 7.85-7.66 (m, 3H), 7.63 (t, J=7.8 Hz, 1H), 7.53 (t, J=7.8 Hz, 1H);

Synthesis of 11-oxo-10, 11-dihydrodibenzo [b, f] [1, 4] thiazepine-8-carboxylic acid 5, 5-dioxide (92): A Common Intermediate

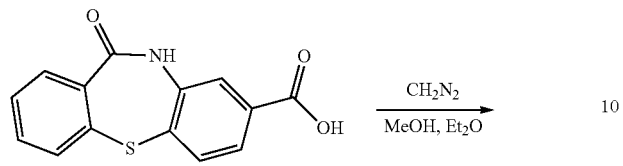

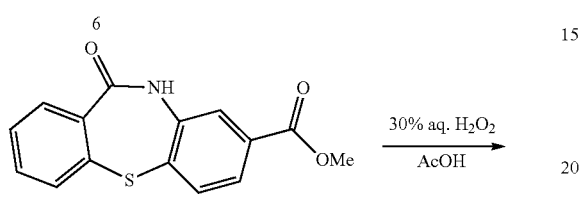

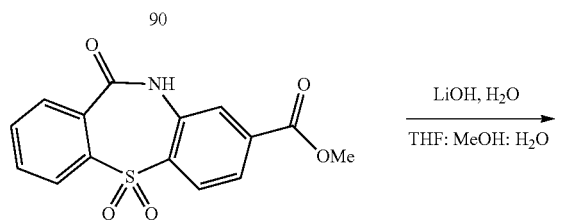

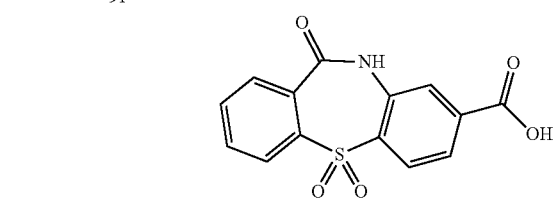

Synthesis of methyl 11-oxo-10, 11-dihydrodibenzo [b, f] [1, 4] thiazepine-8-carboxylate (90)

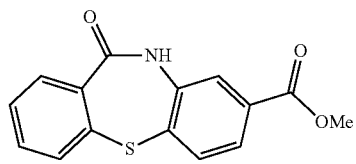

To a stirring solution of 6 (500 mg, 1.84 mmol) in MeOH:CH$_2$Cl$_2$ (1:1, 20 mL) under argon atmosphere was added CH$_2$N$_2$ (insitu prepared using N-nitrosomethyl urea (0.95 g, 9.2 mmol)+KOH (0.51 g, 9.22 mmol) at 0° C.; warmed to RT and stirred for 1 h. The reaction was monitored by TLC; after completion of the reaction, the volatiles were removed in vacuo to obtain the crude. The crude was purified through silica gel column chromatography using 20% EtOAc/hexanes to afford compound 90 (450 mg, 86%) as white solid. TLC: 30% EtOAc/hexanes (R$_f$: 0.5); $^1$H-NMR (DMSO-d$_6$, 500 MHz): δ 10.82 (s, 1H), 7.82 (s, 1H), 7.75-7.69 (m, 3H), 7.58-7.63 (m, 3H), 3.82 (s, 3H).

Synthesis of methyl 11-oxo-10, 11-dihydrodibenzo [b, f] [1, 4] thiazepine-8-carboxylate 5, 5-dioxide (91)

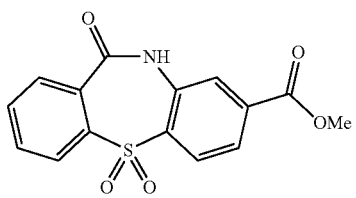

To a stirring solution of 90 (5 g, 17.54 mmol) in acetic acid (25 mL) was added 30% aqueous hydrogen peroxide (100 mL) at 0° C.; warmed to 50° C. and stirred for 72 h. The reaction was monitored by TLC; after completion of the reaction, the obtained solid was filtered, washed with water (100 mL), 10% EtOAc/hexanes (100 mL) and dried in vacuo to afford compound 91 (3.5 g, 64%) as white solid. TLC: 5% MeOH/CH$_2$Cl$_2$ (R$_f$: 0.3); $^1$H NMR (DMSO-d$_6$, 500 MHz): δ 11.58 (s, 1H), 8.09 (d, J=8.4 Hz, 1H), 8.01-7.95 (m, 3H), 7.93-7.83 (m, 3H), 3.88 (s, 3H);

Synthesis of 11-oxo-10, 11-dihydrodibenzo [b, f] [1, 4] thiazepine-8-carboxylic acid 5, 5-dioxide (92)

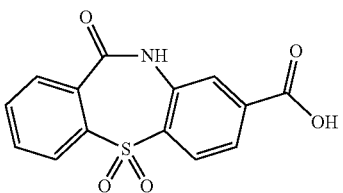

To a stirring solution of compound 91 (3.5 g, 11.04 mmol) in a mixture of THF:MeOH:H$_2$O (2:2:1, 25 mL) was added lithium hydroxide monohydrate (1.3 g, 33.12 mmol) portion wise for 10 min at 0° C.; warmed to RT and stirred for 3 h. The reaction was monitored by TLC; after completion of the reaction, the volatiles were removed in vacuo. The residue was diluted with water (20 mL) and acidified with 1 N HCl to pH~2. The obtained solid was filtered, washed with isopropyl alcohol (15 mL) and dried in vacuo to obtain compound 92 (2.8 g, 84%) as white solid. TLC: 5% MeOH/CH$_2$Cl$_2$ (R$_f$: 0.1); 41 NMR (DMSO-d$_6$, 400 MHz): δ 13.65 (br s, 1H), 11.55 (s, 1H), 8.07 (d, J=8.3 Hz, 1H), 8.03-7.82 (m, 6H).

Synthesis of 9-methyl-11-oxo-10, 11-dihydrodibenzo [b, f] [1, 4] thiazepine-8carboxylic acid 5, 5-dioxide (95): A Common Intermediate

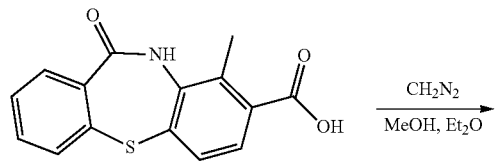

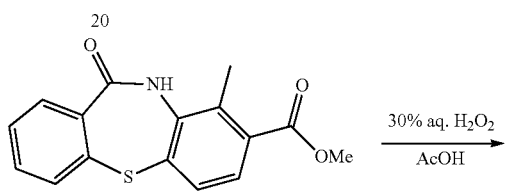

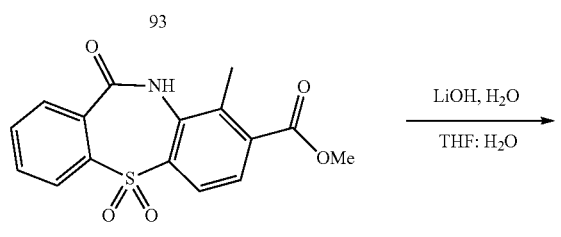

Synthesis of methyl 9-methyl-11-oxo-10, 11-dihydrodibenzo [b, f] [1, 4] thiazepine-8-carboxylate (93)

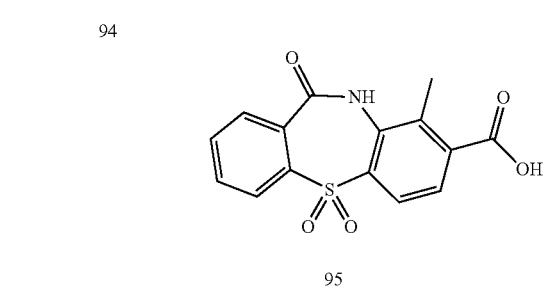

To a stirring solution of 9-methyl-11-oxo-10, 11-dihydrodibenzo [b, f] [1, 4] thiazepine-8-carboxylic acid 20 (400 mg, 1.40 mmol) in MeOH (30 mL) under argon atmosphere was added CH$_2$N$_2$ [insitu prepared using N-nitrosomethyl urea (723 mg, 7.01 mmol)+30% KOH solution (100 mL) in diethyl ether (200 mL)] at 0° C. and stirred for 3 h. The reaction was monitored by TLC; after completion of the reaction, the volatiles were removed in vacuo to obtain the crude, which was triturated with diethyl ether (2×20 mL) and dried in vacuo to afford compound 93 (300 mg, 71%) as an off-white solid. TLC: 5% MeOH/CH$_2$Cl$_2$ (R$_f$: 0.8); $^1$H-NMR (DMSO-d$_6$, 500 MHz): δ 10.40 (s, 1H), 7.83-7.79 (m, 1H), 7.72-7.65 (m, 2H), 7.64-7.56 (m, 3H), 3.95 (s, 3H), 2.58 (s, 3H); LC-MS: 95.08%; 299.8 (M$^+$+1); (column; Ascentis Express C18, (50×3.0 mm, 2.7 μm); RT 2.38 min. 0.025% Aq. TFA+5% ACN: ACN+5% 0.025% Aq. TFA, 1.2 mL/min).

Synthesis of methyl 9-methyl-11-oxo-10, 11-dihydrodibenzo [b, f] [1, 4] thiazepine-8-carboxylate 5, 5-dioxide (94)

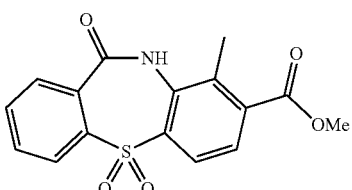

To a stirring solution of 93 (300 mg, 1.00 mmol) in acetic acid (4 mL) was added 30% hydrogen peroxide (8 mL) at 0° C.; warmed to 60° C. and stirred for 72 h. The reaction was monitored by TLC; after completion of the reaction, the reaction mixture was diluted with ice-cold water (50 mL), stirred for 15 min, the obtained solid was filtered, washed with water (100 mL) and dried in vacuo to afford compound 94 (210 mg, 63%) as an off-white solid. TLC: 5% MeOH/CH$_2$Cl$_2$ (R$_f$: 0.3); $^1$H NMR (DMSO-d$_6$, 500 MHz): δ 10.86 (s, 1H), 7.94-7.89 (m, 3H), 7.88-7.76 (m, 2H), 7.67 (d, J=8.4 Hz, 1H), 3.83 (s, 3H), 2.43 (s, 3H). LC-MS: 94.24%; 331.9 (M$^+$+1); (column; Ascentis Express C18, (50×3.0 mm, 2.7 μm); RT 2.22 min. 0.025% Aq. TFA+5% ACN: ACN+5% 0.025% Aq. TFA, 1.2 mL/min).

Synthesis of 9-methyl-11-oxo-10, 11-dihydrodibenzo [b, f] [1, 4] thiazepine-8-carboxylic acid 5, 5-dioxide (95)

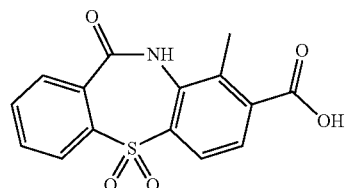

To a stirring solution of compound 94 (230 mg, 0.69 mmol) in THF:MeOH:H$_2$O (2:2:1, 20 mL) was added lithium hydroxide monohydrate (87 mg, 2.08 mmol) portion wise for 10 min at 0° C.; warmed to RT and stirred for 24 h. The reaction was monitored by TLC; after completion of the reaction, the volatiles were removed in vacuo. The residue was diluted with water (20 mL) and acidified with 3 N HCl to pH~3. The obtained solid was filtered, washed with water (20 mL) and dried in vacuo to obtain compound 95 (210 mg, 95%) as an off-white solid. TLC: 10% MeOH/CH$_2$Cl$_2$ (R$_f$: 0.1); $^1$H NMR (DMSO-d$_6$, 400 MHz): δ 13.62

(br s, 1H), 10.85 (s, 1H), 7.97-7.84 (m, 4H), 7.82-7.79 (m, 1H), 7.65 (d, J=8.4 Hz, 1H), 2.43 (s, 3H). LC-MS: 96.06%; 317.9 (M$^+$+1); (column; X Select CSH C-18, (50×3.0 mm, 2.5 μm); RT 1.68 min. 2.5 mM Aq. NH4OOCH+5% ACN: ACN+5% 2.5 mM Aq.NH4OOCH, 0.8 mL/min).

Synthesis 9-methyl-11-oxo-10, 11-dihydrodibenzo [b, f] [1, 4] thiazepine-8-carboxylic acid 5, 5-dioxide (104): A Common Intermediate

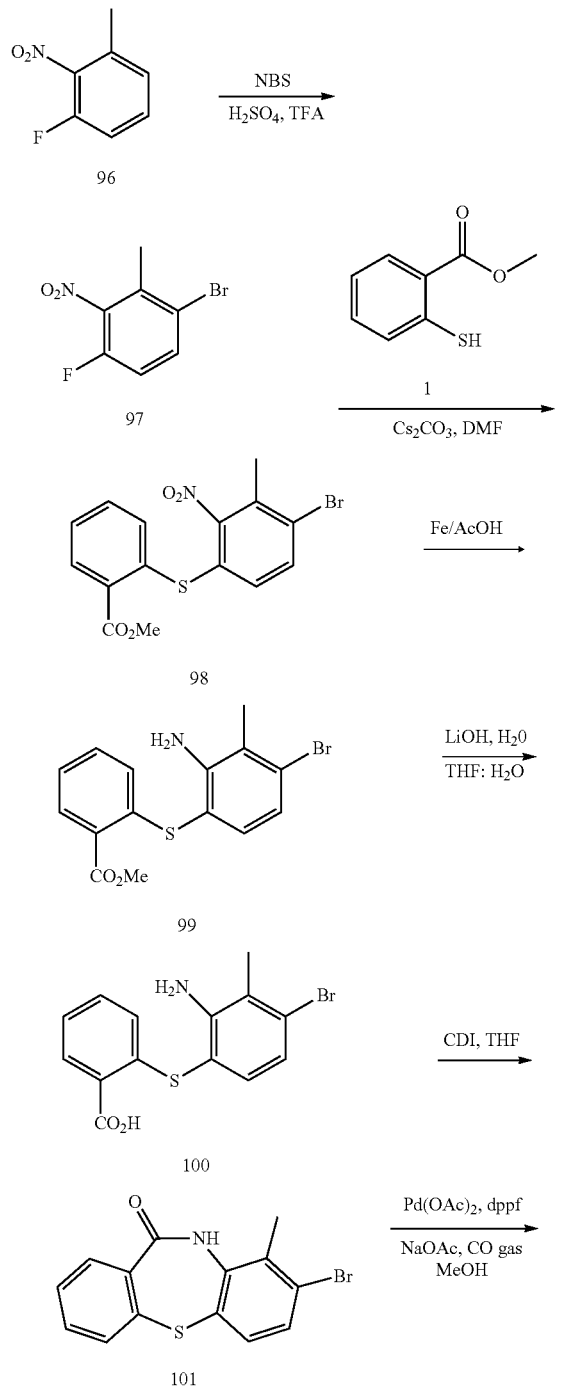

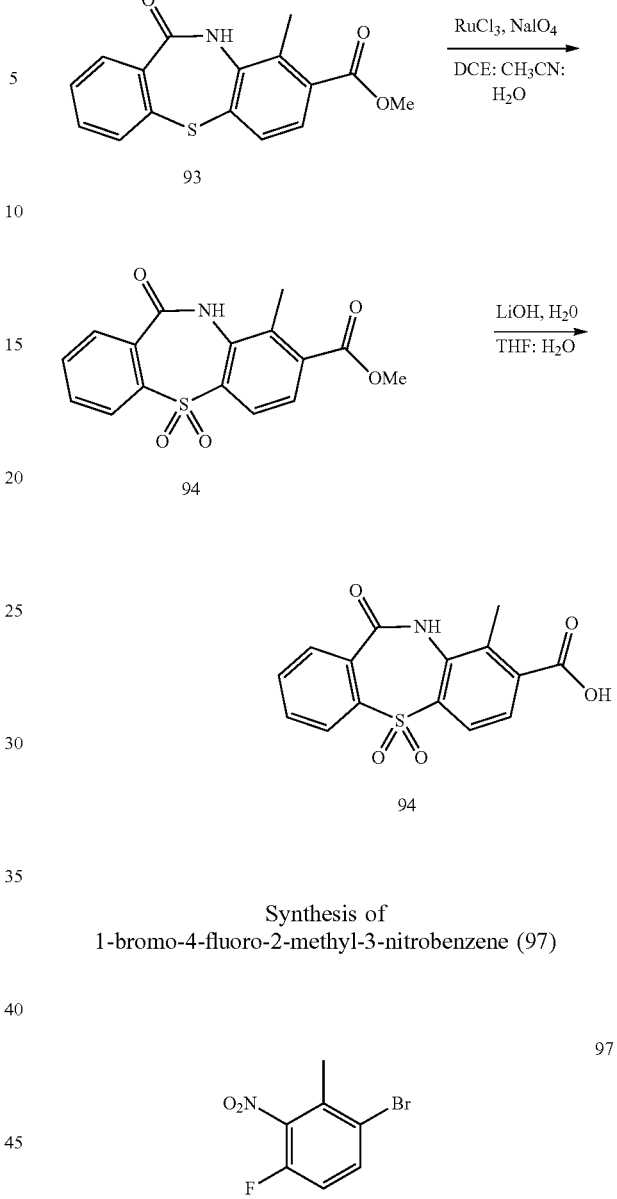

Synthesis of 1-bromo-4-fluoro-2-methyl-3-nitrobenzene (97)

To 1-fluoro-3-methyl-2-nitrobenzene 96 (5 g, 32.25 mmol) at 0° C. under argon atmosphere was added concentrated sulfuric acid:trifluoroacetic acid (1:2, 45 mL). To this was added N-bromosuccinimide (8.61 g, 48.37 mmol) portion wise for 15 min; warmed to RT and stirred for 5 h. The reaction was monitored by TLC; after completion of the reaction, the reaction mixture was poured into ice-cold water (200 mL), the precipitated solid was filtered, washed with water (100 mL) and dried in vacuo to afford the crude. The crude was purified through silica gel flash column chromatography using 1-2% EtOAc/hexanes to afford compound 97 (5.1 g, 68%). TLC: 5% EtOAc/hexanes (R$_f$: 0.8); TLC: 30% EtOAc/hexanes (R$_f$: 0.3). $^1$H NMR (DMSO-d$_6$, 400 MHz): δ 7.96 (dd, J=8.9, 5.2 Hz, 1H), 7.47 (t, J=9.2 Hz, 1H), 22.35 (m, 3H);

Synthesis of methyl 2-((4-bromo-3-methyl-2-nitrophenyl) thio) benzoate (98)

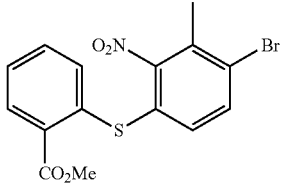

98

To a stirring solution of compound 97 (5.1 g, 21.79 mmol) in DMF (80 mL) under argon atmosphere were added cesium carbonate (10.62 g, 32.67 mmol), methyl 2-mercaptobenzoate 1 (4.03 g, 23.97 mmol) at RT and stirred for 2 h. The reaction was monitored by TLC; after completion of the reaction, the reaction mixture was diluted with ice-cold water (100 mL), the precipitated solid was filtered, washed with hexane (100 mL) and diethyl ether (100 mL) and dried in vacuo to afford compound 98 (7.0 g, 84%) as an off-white solid. TLC: 10% EtOAc/hexanes ($R_f$: 0.3); $^1$H NMR (DMSO-$d_6$, 400 MHz): δ 8.09-7.85 (m, 2H), 7.55-7.46 (m, 2H), 7.34 (td, J=7.6, 1.1 Hz, 1H), 6.81 (dd, J=8.2, 0.8 Hz, 1H), 3.87 (s, 3H), 2.35 (s, 3H); LC-MS: 98.98%; 383.2 (M+2)$^+$; (Column; X-select CSH C-18 (50×3.0 mm, 2.5 μm); RT 4.99 min. 2.5 mM Aq. NH$_4$OAc:ACN, 0.8 mL/min).

Synthesis of methyl 2-((2-amino-4-bromo-3-methylphenyl) thio) benzoate (99)

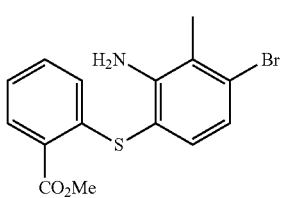

99

To a stirring solution of compound 98 (7 g, 18.32 mmol) in acetic acid (100 mL) was added iron powder (10.2 g, 182.7 mmol) at RT; heated to 80° C. and stirred for 16 h. The reaction was monitored by TLC and LC-MS; after completion of the reaction, the reaction mixture was filtered through celite, the filtrate was concentrated in vacuo. The residue was diluted with EtOAc (200 mL), washed with water (2×100 mL). The organic extract was dried over sodium sulfate, filtered and concentrated in vacuo to compound 99 (5.8 g, 90%) as an off-white solid. TLC: 10% EtOAc/hexanes ($R_f$: 0.2); LC-MS: 98.31%; 353.9 (M$^+$+2); (column; Ascentis Express C18, (50×3.0 mm, 2.7 μm); RT 3.06 min. 0.025% Aq. TFA+5% ACN: ACN+5% 0.025% Aq. TFA, 1.2 mL/min).

Synthesis of 2-((2-amino-4-bromo-3-methylphenyl) thio) benzoic acid (100)

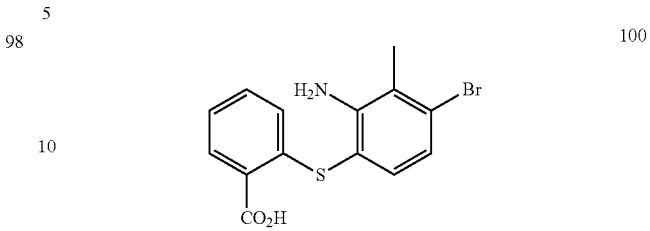

100

To a stirring solution of compound 99 (4.8 g, 13.63 mmol) in THF:H$_2$O (3:1, 120 mL) was added lithium hydroxide monohydrate (1.72 g, 40.95 mmol) at RT and stirred for 16 h. The reaction was monitored by TLC; after completion of the reaction, the volatiles were removed in vacuo. The residue was diluted with water (20 mL) and acidified with 2 N HCl to pH~4-5. The obtained solid was filtered, washed with (50 mL) and dried in vacuo to obtain compound 100 (4 g, 87%) as an off-white solid. TLC: 20% EtOAc/hexanes ($R_f$: 0.2); LC-MS: 98.82%; 339.9 (M$^+$+2); (column; Ascentis Express C18, (50×3.0 mm, 2.7 μm); RT 2.67 min. 0.025% Aq. TFA+5% ACN: ACN+5% 0.025% Aq. TFA, 1.2 mL/min).

Synthesis of 8-bromo-9-methyldibenzo [b, f] [1, 4] thiazepin-11(10H)-one (101)

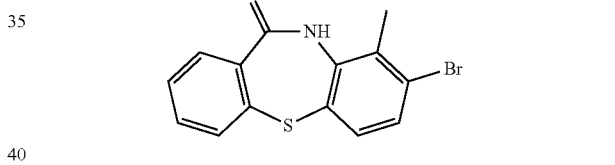

101

To a stirring solution of compound 100 (4.7 g, 13.90 mmol) in THF (100 mL) under inert atmosphere was added CDI (13.50 g, 83.32 mmol) at RT and stirred for 24 h. The reaction was monitored by TLC; after completion of the reaction, the volatiles were removed in vacuo. The pH of the residue was adjusted to ~2 using 2 N HCl. The precipitated solid was filtered, washed with water (50 mL) and dried in vacuo to afford compound 101 (3 g, 68%) as white solid. TLC: 30% EtOAc/hexanes ($R_f$: 0.4) $^1$H NMR (DMSO-$d_6$, 400 MHz): δ 10.36 (s, 1H), 7.68-7.63 (m, 1H), 7.54-7.49 (m, 1H), 7.49-7.36 (m, 4H), 2.41 (s, 3H);

Synthesis of methyl 9-methyl-11-oxo-10, 11-dihydrodibenzo [b, f] [1, 4] thiazepine-8-carboxylate (93)

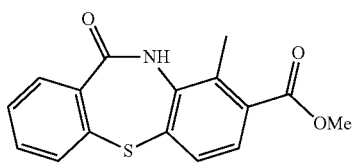

93

To a stirring solution of compound 101 (1.5 g, 4.68 mmol) in MeOH (30 mL) in a steel bomb under inert atmosphere were added dppf (259 mg, 0.46 mmol), sodium acetate (1.15 g, 14.02 mmol), Pd(OAc)$_2$ (105 mg, 0.46 mmol) at RT and heated to 100° C. under CO gas atmosphere (150 psi) and stirred for 24 h. The reaction was monitored by TLC; after completion of the reaction, the reaction mixture was filtered through celite. The filtrate was concentrated in vacuo to obtain the crude. The crude was purified through silica gel column flash chromatography using 10-20% EtOAc/hexanes to afford compound 93 (1.1 g, 79%). TLC: 20% EtOAc/hexanes (R$_f$: 0.2); LC-MS: 98.18%; 299.9 (M+1)$^+$; (column; Ascentis Express C18, (50×3.0 mm, 2.7 μm); RT 2.38 min. 0.025% Aq. TFA+5% ACN: ACN+5% 0.025% Aq. TFA, 1.2 mL/min).

Synthesis of methyl 9-methyl-11-oxo-10, 11-dihydrodibenzo [b, f] [1, 4] thiazepine-8-carboxylate 5, 5-dioxide (94)

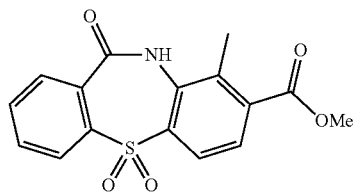

94

To a compound 93 (1.1 g, 3.67 mmol) in 1, 2 dichloro ethane:CH$_3$CN:H$_2$O (1:1:2, 40 mL) were added sodium metaperiodate (2.35 g, 11.03 mmol), ruthenium chloride (38 mg, 0.18 mmol) at RT and stirred for 16 h. The reaction was monitored by TLC; after completion, the reaction mixture was diluted with ice-cold water (50 mL) and extracted with EtOAc (2×75 mL). The combined organic extracts were dried over sodium sulfate, filtered and concentrated in vacuo to afford compound 94 (1 g, 83%) as an white solid. TLC: 40% EtOAc/hexanes (R$_f$: 0.2); $^1$H NMR (DMSO-d$_6$, 400 MHz): δ 10.87 (s, 1H), 7.95-7.84 (m, 4H), 7.83-7.78 (m, 1H), 7.68 (d, J=8.3 Hz, 1H), 3.85 (s, 3H), 2.45 (s, 3H); LC-MS: 98.10%; 332.0 (M+1)$^+$; (column; Ascentis Express C18, (50×3.0 mm, 2.7 μm); RT 2.16 min. 0.025% Aq. TFA+5% ACN: ACN+5% 0.025% Aq. TFA, 1.2 mL/min).

Synthesis of 9-methyl-11-oxo-10, 11-dihydrodibenzo [b, f] [1, 4] thiazepine-8-carboxylic acid 5, 5-dioxide (95)

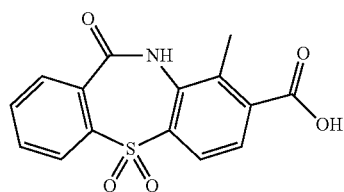

95

To a stirring solution of compound 94 (1.07 g, 3.23 mmol) in THF:H$_2$O (3:1, 18 mL) was added lithium hydroxide monohydrate (407 mg, 9.69 mmol) at 0° C.; warmed to RT and stirred for 16 h. The reaction was monitored by TLC; after completion of the reaction, the volatiles were removed in vacuo. The pH of the residue was acidified with 2 N HCl to ~2. The precipitated solid was filtered, washed with water (50 mL), hexane (20 mL) and dried in vacuo to afford 95 (950 mg, 93%) as white solid. TLC: 5% MeOH/CH$_2$Cl$_2$ (R$_f$: 0.1); $^1$H NMR (DMSO-d$_6$, 400 MHz): δ 3.63 (br s, 1H), 10.85 (s, 1H), 7.96-7.84 (m, 4H), 7.83-7.78 (m, 1H), 7.67 (d, J=8.1 Hz, 1H), 2.48 (s, 3H); LC-MS: 98.67%; 317.9 (M+1)$^+$; (column; Ascentis Express C18, (50×3.0 mm, 2.7 μm); RT 1.81 min. 0.025% Aq. TFA+5% ACN: ACN+5% 0.025% Aq. TFA, 1.2 mL/min).

Synthesis of 7-methyl-11-oxo-10, 11-dihydrodibenzo [b, f] [1, 4] thiazepine-8-carboxylic acid 5, 5-dioxide (105): A Common Intermediate

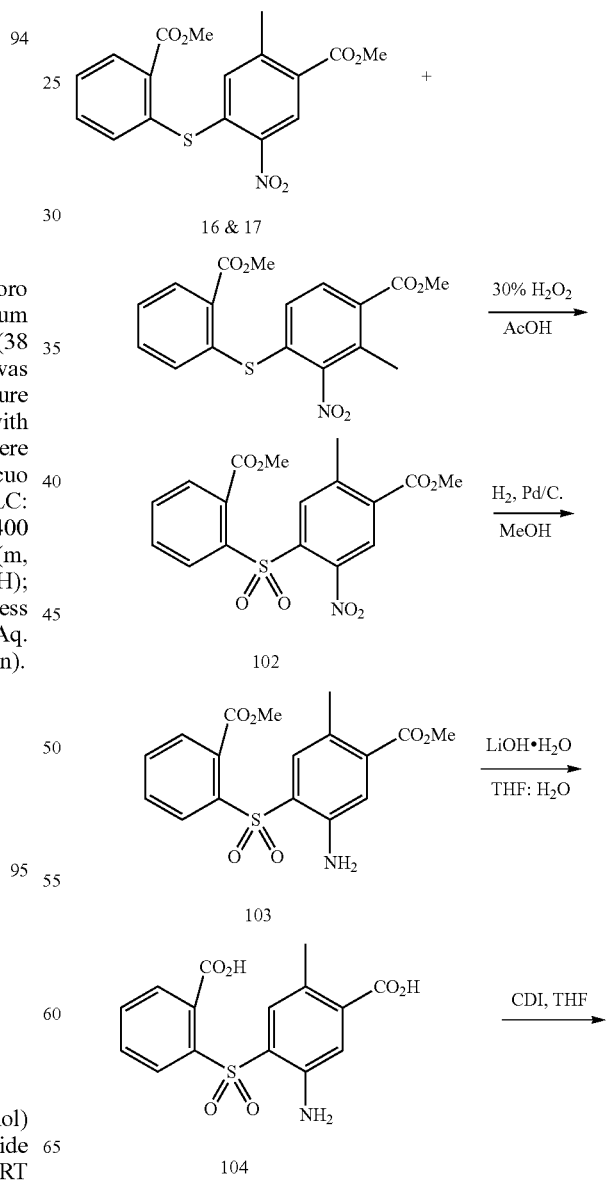

-continued

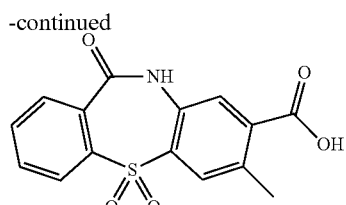

105

Synthesis of methyl 4-((2-(methoxycarbonyl) phenyl) sulfonyl)-2-methyl-5-nitrobenzoate (102)

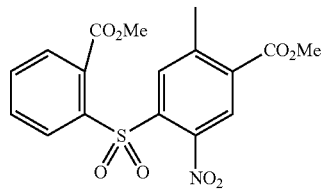

To a stirring solution of methyl 5-amino-4-((2-(methoxycarbonyl) phenyl) thio)-2-methylbenzoate 16 & 17 (4 g, 12.08 mmol) in acetic acid (25 mL) was added 30% $H_2O_2$ (20 mL) at 0° C.; heated to 70° C. and stirred for 16 h. The reaction was monitored by TLC; after completion of the reaction, the reaction mixture was diluted with water (20 mL) and the pH was adjusted to ~7 using 10% $Na_2CO_3$ solution (50 mL) and extracted with EtOAc (150 mL). The organic extract was dried over sodium sulfate, filtered and concentrated in vacuo to obtain the crude. The crude was purified by column chromatography using 30% EtOAc/hexanes to afford compound 102 (1.2 g) as yellow syrup. TLC: 40% EtOAc/hexanes ($R_f$: 0.4); LC-MS: 34.05%; 392.1 $(M-1)^+$; (column; X-select C18, (50×3.0 mm, 2.5 μm); RT 4.26 min. 2.5 mM Aq. $NH_4OAc$:ACN: 0.8 mL/min).

Synthesis of methyl 5-amino-4-((2-(methoxycarbonyl) phenyl) sulfonyl)-2-methylbenzoate (103)

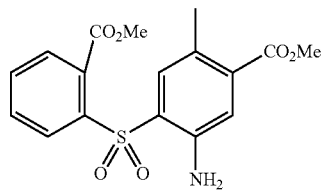

To a stirring solution of compound 102 (500 mg, 1.27 mmol) in MeOH (25 mL) under inert atmosphere was added 10% Pd/C (200 mg, 50% wet) at RT under hydrogen atmosphere (balloon pressure) and stirred for 16 h. The reaction was monitored by TLC; after completion of the reaction, the reaction mixture was filtered through celite, washed with MeOH (50 mL). The filtrate was removed in vacuo to obtain the crude compound 103 (300 mg, 60%, over 2 steps) as yellow syrup. TLC: 40% EtOAc/hexanes ($R_f$: 0.4); LC-MS: 98.20%; 364.1 $(M^++1)$; (column; Ascentis Express C18, (50×3.0 mm, 2.7 μm); RT 2.45 min. 0.025% Aq. TFA+5% ACN: ACN+5% 0.025% Aq. TFA, 1.2 mL/min). $^1H$ NMR (DMSO-$d_6$, 400 MHz): δ 8.11 (dd, J=7.8, 1.1 Hz, 1H), 7.84-7.70 (m, 2H), 7.65 (dd, J=7.5, 1.3 Hz, 1H), 7.52 (s, 1H), 7.28 (s, 1H), 6.14 (s, 2H), 3.83 (s, 3H), 3.81 (s, 3H), 2.35 (s, 3H);

Synthesis of 5-amino-4-((2-carboxyphenyl) sulfonyl)-2-methylbenzoic acid (104)

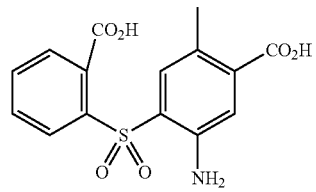

To a stirring solution of compound 103 (1.2 g, 3.26 mmol) in THF:$H_2O$ (3:1, 20 mL) was added lithium hydroxide monohydrate (692 mg, 16.48 mmol) at RT; heated to reflux and stirred for 32 h. The reaction was monitored by TLC; after completion of the reaction, the volatiles were removed in vacuo. The pH of the residue was acidified with 2 N HCl to ~2. The precipitated solid was filtered and dried in vacuo to afford compound 104 (600 mg, 59%) as an off-white solid. The crude was carried for next step without further purification. TLC: 30% EtOAc/hexanes ($R_f$: 0.3); LC-MS: 81.82%; 335.9 $(M^++1)$; (column; Ascentis Express C18, (50×3.0 mm, 2.7 μm); RT 1.78 min. 0.025% Aq. TFA+5% ACN: ACN+5% 0.025% Aq. TFA, 1.2 mL/min). $^1H$ NMR (DMSO-$d_6$, 400 MHz): δ 13.12 (br s, 1H), 8.05-7.97 (m, 1H), 7.74 (td, J=7.5, 1.1 Hz, 1H), 7.66 (td, J=7.7, 1.4 Hz, 1H), 7.60 (dd, J=7.5, 1.1 Hz, 1H), 7.56 (s, 1H), 7.23 (s, 1H), 6.13 (br s, 2H), 2.33 (s, 3H);

Synthesis of 7-methyl-11-oxo-10, 11-dihydrodibenzo [b, f] [1, 4] thiazepine-8-carboxylic acid 5, 5-dioxide (105)

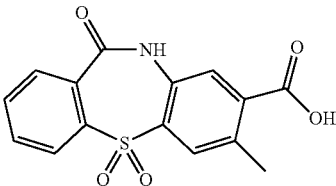

To a stirring solution of compound 104 (650 mg, 1.94 mmol) in THF (15 mL) under inert atmosphere was added CDI (1.59 g, 9.70 mmol) at 0° C.; warmed to RT and stirred for 16 h. The reaction was monitored by TLC; after completion of the reaction, the reaction mixture was acidified with 6 N HCl to pH~2. The obtained solid was filtered and further dried and dried in vacuo to afford compound 105 (350 mg, 59%) as an off-white solid. TLC: 10% MeOH/$CH_2Cl_2$ ($R_f$: 0.2); LC-MS: 71.53%; 317.9 $(M^++1)$; (column; Ascentis Express C18, (50×3.0 mm, 2.7 μm); RT 2.45 min. 0.025% Aq. TFA+5% ACN: ACN+5% 0.025% Aq. TFA, 1.2 mL/min).

Synthesis of 7-ethyl-11-oxo-10, 11-dihydrodibenzo [b, f] [1, 4] thiazepine-8-carboxylic acid 5, 5-dioxide (117): A Common Intermediate

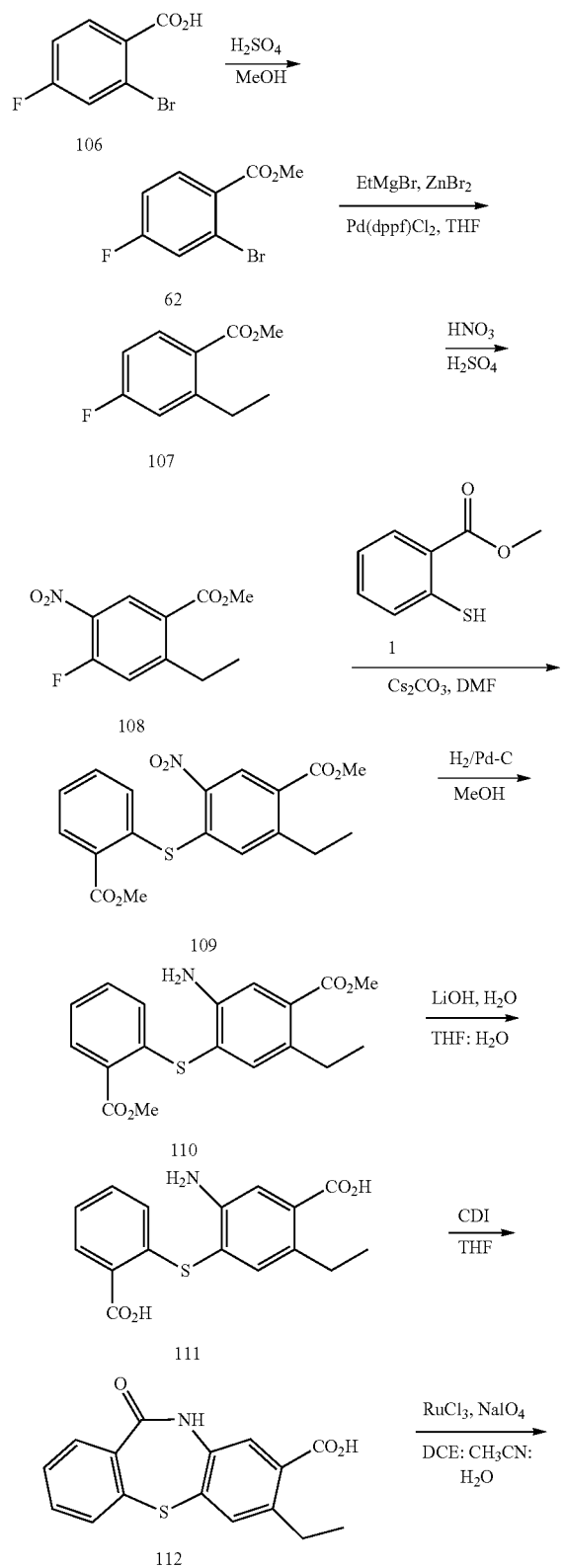

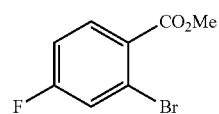

113

Synthesis of methyl 2-bromo-4-fluorobenzoate (62)

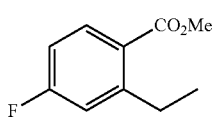

62

To a stirring solution of 2-bromo-4-fluorobenzoic acid 106 (20 g, 91.32 mmol) in MeOH (200 mL) under inert atmosphere was added concentrated sulfuric acid (100 mL) dropwise for 20 min at 0° C.; heated to reflux and stirred for 16 h. The reaction was monitored by TLC; after completion of the reaction, the volatiles were removed in vacuo. The residue was diluted with ice-cold water (100 mL) and extracted with EtOAc (300 mL). The organic extract was washed with saturated NaHCO$_3$ solution (2×100 mL), dried over sodium sulfate, filtered and concentrated in vacuo to afford compound 62 (16.5 g, 78%) as pale yellow oil. TLC: 10% EtOAc/hexanes ($R_f$: 0.8). $^1$H-NMR (DMSO-d$_6$, 500 MHz): δ 7.88 (dd, J=8.8, 6.2 Hz, 1H), 7.75 (dd, J=8.7, 2.6 Hz, 1H), 7.39 (td, J=8.5, 2.6 Hz, 1H), 3.85 (s, 3H).

Synthesis of methyl 2-ethyl-4-fluorobenzoate (107)

107

To a stirring solution of zinc(II) bromide (19.3 g, 85.77 mmol) in THF (200 mL) under argon atmosphere was added ethyl magnesium bromide (28.6 mL, 85.83 mmol, 3 M solution in Et$_2$O) dropwise for 10 min. The reaction mixture was cooled to −78° C., added Pd(ddpf)Cl$_2$ (3.13 g, 4.27 mmol) and compound 62 (10 g, 42.91 mmol), warmed to RT and stirred for 16 h. The reaction was monitored by TLC; after completion of the reaction, the reaction mixture was cooled to 0° C., quenched with saturated ammonium chloride solution (100 mL) and extracted with EtOAc (2×150 mL). The combined organic extracts were dried over sodium sulfate, filtered and concentrated in vacuo to obtain the crude. The crude was purified through silica gel flash column chromatography using 2-4% EtOAc/hexanes to afford compound 107 (6.5 g, 83%) as pale yellow liquid. TLC: 10% EtOAc/hexanes ($R_f$: 0.8). $^1$H-NMR (DMSO-d$_6$, 400 MHz): δ 7.86 (dd, J=8.8, 6.1 Hz, 1H), 7.22 (dd, J=10.2, 2.7 Hz, 1H), 7.14 (td, J=8.5, 2.7 Hz, 1H), 3.82 (s, 3H), 2.92 (q, J=7.4 Hz, 2H), 1.16 (t, J=7.5 Hz, 3H).

Synthesis of methyl 2-ethyl-4-fluoro-5-nitrobenzoate (108)

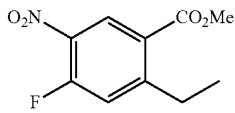

108

To a stirring solution of compound 107 (6.5 g, 35.71 mmol) in concentrated sulphuric acid (100 mL) under inert atmosphere at 0° C. was added fuming nitric acid (1.5 mL, 35.70 mmol) dropwise for 5 min, warmed to RT and stirred for 2 h. The reaction was monitored by TLC; after completion of the reaction, the reaction mixture was quenched with ice-cold water (300 mL), extracted with EtOAc (2×200 mL), washed with saturated NaHCO$_3$ solution (2×50 mL) and brine (50 mL). The organic extract was dried over sodium sulfate, filtered and concentrated in vacuo to obtain the crude. The crude was purified by combiflash chromatography using 5% EtOAc/hexanes to afford compound 108 (1.8 g, 22%) as colorless liquid. TLC: 5% EtOAc/hexanes ($R_f$: 0.4). $^1$H-NMR (DMSO-d$_6$, 500 MHz): δ 8.52 (d, J=8.1 Hz, 1H), 7.66 (d, J=12.8 Hz, 1H), 3.89 (s, 3H), 3.01 (q, J=7.5 Hz, 2H), 1.20 (t, J=7.5 Hz, 3H).

Synthesis of methyl 2-ethyl-4-((2-(methoxycarbonyl) phenyl) thio)-5-nitrobenzoate (109)

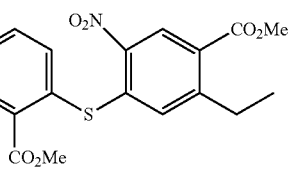

109

To a stirring solution of compound 108 (1.8 g, 7.92 mmol) in DMF (30 mL) under argon atmosphere were added methyl 2-hydroxybenzoate 1 (1.46 g, 8.72 mmol), cesium carbonate (3.90 g, 11.90 mmol) at 0° C.; warmed to RT and stirred for 4 h. The reaction was monitored by TLC; after completion of the reaction, the reaction mixture was diluted with water (100 mL) and extracted with EtOAc (2×100 mL). The combined organic extracts were dried over sodium sulfate, filtered and concentrated in vacuo to obtain the crude. The crude was purified by combiflash chromatography using 2-10% EtOAc/hexanes to afford compound 109 (2.4 g, 81%) as yellow solid. TLC: 20% EtOAc/hexanes ($R_f$: 0.4). $^1$H-NMR (DMSO-d$_6$, 500 MHz): δ 8.59 (s, 1H), 7.97-7.92 (m, 1H), 7.75-7.65 (m, 3H), 6.84 (s, 1H), 3.87 (s, 3H), 3.70 (s, 3H), 2.79 (q, J=7.5 Hz, 2H), 0.93 (t, J=7.2 Hz, 3H).

Synthesis of methyl 5-amino-2-ethyl-4-((2-(methoxycarbonyl) phenyl) thio) benzoate (110)

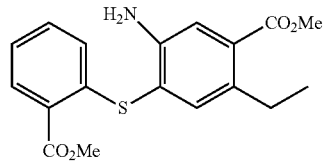

110

A stirring solution of compound 109 (2.4 g, 6.40 mmol) in MeOH (50 mL) was evacuated for 5 min and under inert atmosphere was added 10% Pd/C (1.2 g, 50% wet) at RT and stirred under hydrogen atmosphere (balloon pressure) at RT for 24 h. The reaction was monitored by TLC; after completion of the reaction, the reaction mixture was filtered through celite and washed with MeOH (100 mL). The crude was purified by combiflash chromatography using 5-20% EtOAc/hexanes to afford compound 110 (1.4 g, 63%) as white solid. TLC: 10% EtOAc/hexanes ($R_f$: 0.2); $^1$H NMR (DMSO-d$_6$, 400 MHz): δ 7.95 (dd, J=7.9, 1.4 Hz, 1H), 7.44-7.37 (m, 1H), 7.27-7.20 (m, 3H), 6.67 (dd, J=8.2, 0.9 Hz, 1H), 5.42 (s, 2H), 3.88 (s, 3H), 3.83 (s, 3H), 2.71 (q, J=7.5 Hz, 2H), 1.08 (t, J=7.4 Hz, 3H); LC-MS: 97.16%; 345.9 (M$^+$+1); (column; Ascentis Express C18, (50×3.0 mm, 2.7 μm); RT 2.88 min. 0.025% Aq. TFA+5% ACN: ACN+5% 0.025% Aq. TFA, 1.2 mL/min).

Synthesis of 5-amino-4-((2-carboxyphenyl) thio)-2-ethylbenzoic acid (111)

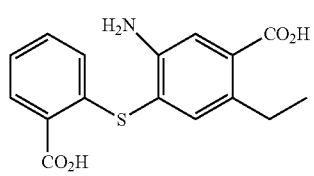

111

To a stirring solution of compound 110 (1.4 g, 4.05 mmol) in THF:H$_2$O (3:1, 40 mL) was added lithium hydroxide monohydrate (852 mg, 20.28 mmol) portion wise for 10 min at RT, heated to reflux and stirred for 24 h. The reaction was monitored by TLC and LC-MS; after completion of the reaction, the volatiles were removed in vacuo and the pH of the aqueous layer was acidified with 2 N HCl to ~3. The precipitated solid was filtered washed with water (50 mL), n-hexane (30 mL) dried in vacuo to afford compound 111 (1.0 g 78%) as an off-white solid. TLC: 20% EtOAc/hexanes ($R_f$: 0.1); $^1$H-NMR (DMSO-d$_6$, 400 MHz): δ 13.38-12.60 (m, 2H), 7.94 (dd, J=7.8, 1.4 Hz, 1H), 7.40-7.34 (m, 1H), 7.24 (d, J=11.2 Hz, 2H), 7.19 (td, J=7.5, 1.1 Hz, 1H), 6.65 (dd, J=8.2, 0.8 Hz, 1H), 5.33 (br s, 2H), 2.74 (q, J=7.5 Hz, 2H), 1.09 (t, J=7.4 Hz, 3H); LC-MS: 99.36%; 317.9 (M$^+$+1); (column; Ascentis Express C18, (50×3.0 mm, 2.7 μm); RT 2.09 min. 0.025% Aq. TFA+5% ACN: ACN+5% 0.025% Aq. TFA, 1.2 mL/min).

83

Synthesis of 7-ethyl-11-oxo-10, 11-dihydrodibenzo [b, f] [1, 4] thiazepine-8-carboxylic acid (112)

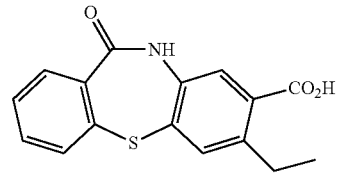

112

To a stirring solution of compound 111 (1 g, 3.15 mmol) in THF (20 mL) under inert atmosphere was added CDI (1.53 g, 9.46 mmol) at RT and stirred for 24 h. The reaction was monitored by TLC; after completion of the reaction, the volatiles were removed in vacuo. The residue was diluted with water (50 mL), cooled to 0° C. and the pH was adjusted to ~2 using 2 N HCl. The precipitated solid was filtered, washed with water (50 mL), hexane (20 mL) and dried in vacuo to afford compound 112 (710 mg, 75%) as white solid. TLC: 5% MeOH/CH$_2$Cl$_2$ (R$_f$: 0.3); $^1$H NMR (DMSO-d$_6$, 400 MHz): δ 13.12 (br s, 1H), 10.69 (s, 1H), 7.71-7.67 (m, 1H), 7.61 (s, 1H), 7.56-7.42 (m, 4H), 2.85 (q, J=7.4 Hz, 2H), 1.11 (t, J=7.5 Hz, 3H).

Synthesis of 7-ethyl-11-oxo-10, 11-dihydrodibenzo [b, f] [1, 4] thiazepine-8-carboxylic acid 5, 5-dioxide (113)

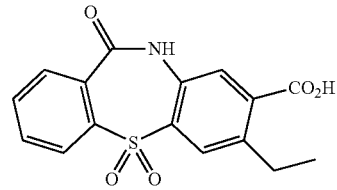

113

To a stirring solution of compound 112 (700 mg, 2.34 mmol) in 1, 2 dichloro ethane:CH$_3$CN:H$_2$O (1:1:2, 40 mL) were added sodium metaperiodate (1.49 g, 6.99 mmol), ruthenium chloride (26.3 mg, 0.11 mmol) at RT and stirred for 16 h. The reaction was monitored by TLC and LCMS; after completion the volatiles were removed in vacuo. The precipitated solid was filtered, washed with water (50 mL), hexane (20 mL) and diethylether (20 mL), dried in vacuo to afford compound 113 (650 mg, 84%) as pale brown solid. TLC: 10% MeOH/CH$_2$Cl$_2$ (R$_f$: 0.2); $^1$H-NMR (DMSO-d$_6$, 400 MHz): δ 11.39 (s, 1H), 8.00-7.95 (m, 2H), 7.93-7.84 (m, 2H), 7.83 (s, 1H), 7.70 (s, 1H), 2.91 (q, J=7.4 Hz, 2H), 1.14 (t, J=7.5 Hz, 3H); LC-MS: 86.02%; 331.9 (M$^+$+1); (column; Ascentis Express C18, (50×3.0 mm, 2.7 μm); RT 2.06 min. 0.025% Aq. TFA+5% ACN: ACN+5% 0.025% Aq. TFA, 1.2 mL/min).

84

Synthesis of 7-methoxy-11-oxo-10, 11-dihydrodibenzo [b, f] [1, 4] thiazepine-8-carboxylic acid 5, 5-dioxide (124): A Common Intermediate

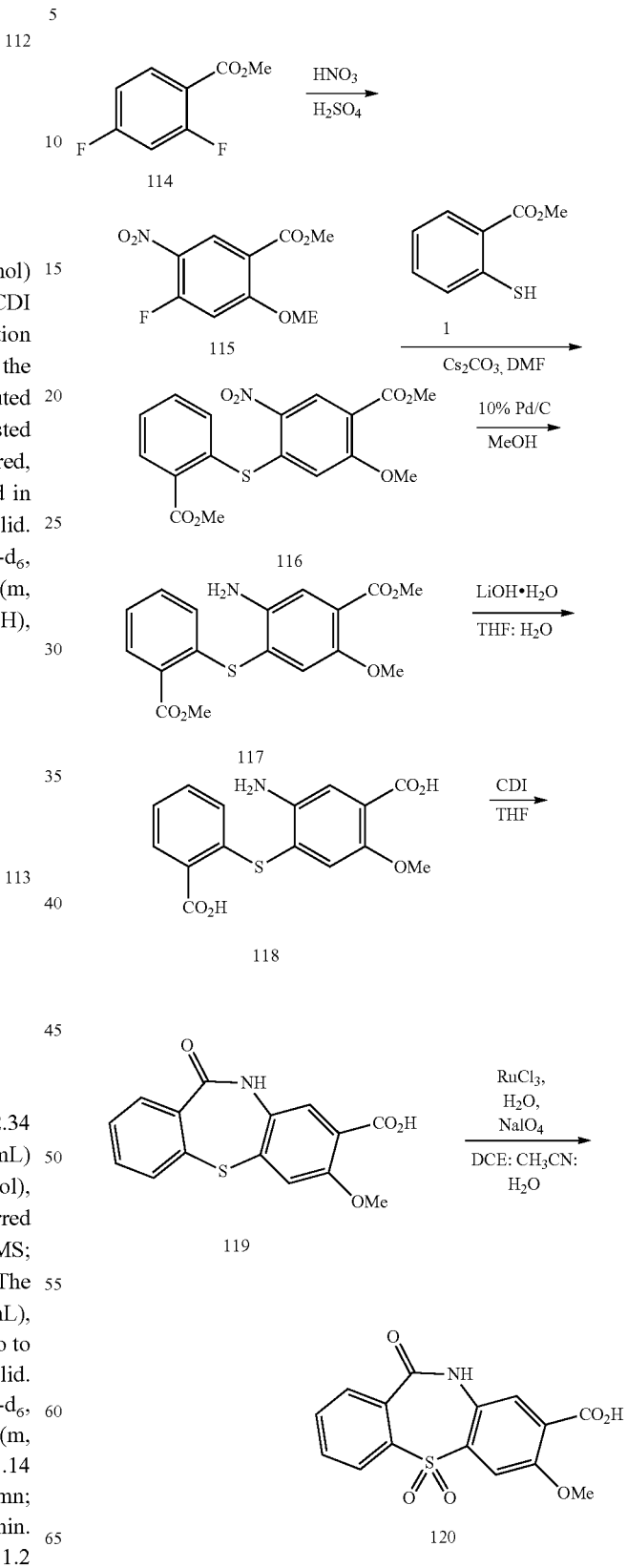

Synthesis of methyl 4-fluoro-2-methoxy-5-nitrobenzoate (115)

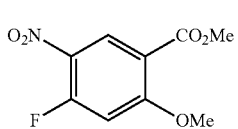

To a stirring solution of methyl 4-fluoro-2-methoxybenzoate 114 (10 g, 27.17 mmol) in sulfuric acid (14 mL) under inert atmosphere was added the mixture of nitric acid (0.90 mL, 21.73 mmol) and sulfuric acid (1 mL) at −5° C. and stirred for 5 min. The reaction was monitored by TLC; after completion of the reaction, the reaction mixture was diluted with water (25 mL) and extracted with $CH_2Cl_2$ (2×30 mL). The combined quenched with ice-cold water (100 mL) and extracted with EtOAc (2×200 mL). The combined organic extracts were washed with saturated $NaHCO_3$ solution (100 mL), dried over sodium sulfate, filtered and concentrated in vacuo to obtain the crude. The crude was purified through silica gel column chromatography using 20% EtOAc/hexanes to afford compound 115 (5 g, 40%) as colorless syrup. TLC: 20% EtOAc/hexanes ($R_f$: 0.4); $^1$H-NMR ($CDCl_3$, 400 MHz): δ 8.69 (d, J=8.8 Hz, 1H), 6.83 (d, J=12.8 Hz, 1H), 4.01 (s, 3H), 3.92 (s, 3H).

Synthesis of methyl 2-methoxy-4-((2-(methoxycarbonyl) phenyl) thio)-5-nitrobenzoate (116)

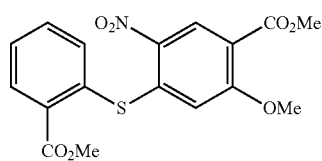

To a stirring solution of compound 115 (5 g, 21.8 mmol) in DMF (50 mL) under inert atmosphere were added methyl 2-mercaptobenzoate 1 (4 g, 24.01 mmol), cesium carbonate (8.5 g, 26.16 mmol) at RT; heated to 80° C. and stirred for 4 h. The reaction was monitored by TLC; after completion of the reaction, the reaction mixture was diluted with ice-cold water (250 mL) and extracted with EtOAc (2×100 mL). The combined organic extracts were dried over sodium sulfate, filtered and concentrated in vacuo to obtain the crude. The crude was purified through silica gel column chromatography using 25% EtOAc/hexanes to afford compound 116 (6 g, 79%) as an off-white solid. TLC: 30% EtOAc/hexanes ($R_f$: 0.3); $^1$H-NMR ($CDCl_3$, 400 MHz): δ 8.80 (s, 1H), 7.94-7.92 (m, 1H), 7.70 (t, J=8.0 Hz, 1H), 7.61-7.59 (m, 2H), 6.30 (s, 1H), 3.90 (s, 3H), 3.82 (s, 3H), 3.52 (s, 3H).

Synthesis of methyl 5-amino-2-methoxy-4-((2-(methoxycarbonyl) phenyl) thio) benzoate (117)

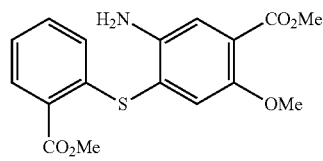

To a stirring solution of compound 116 (6 g, 0.53 mmol) in MeOH (50 mL) under inert atmosphere was added 10% Pd/C (600 mg) at RT and stirred under hydrogen atmosphere (balloon pressure) for 20 h. The reaction was monitored by TLC; after completion of the reaction, the reaction mixture was filtered through celite and the filtrate was concentrated in vacuo to obtain the crude. The crude was purified through silica gel column chromatography using 25% EtOAc/hexanes to afford compound 117 (2 g, 36%) as sticky solid. TLC: 40% EtOAc/hexanes ($R_f$: 0.5); $^1$H NMR ($CDCl_3$, 400 MHz): δ 8.04 (dd, J=7.8, 1.4 Hz, 1H), 7.32-7.28 (m, 1H), 7.28-7.26 (m, 1H), 7.19-7.14 (m, 1H), 7.13 (s, 1H), 6.76 (dd, J=8.2, 0.9 Hz, 1H), 4.06 (s, 2H), 3.97 (s, 3H), 3.91 (s, 3H), 3.81 (s, 3H); LC-MS: 95.75%; 347.9 ($M^+$+1); (column; Ascentis Express C18, (50×3.0 mm, 2.7 µm); RT 2.43 min. 0.025% Aq. TFA+5% ACN: ACN+5% 0.025% Aq. TFA, 1.2 mL/min).

Synthesis of 5-amino-4-((2-carboxyphenyl) thio)-2-methoxybenzoic acid (118)

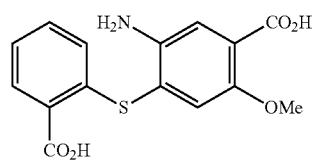

To a stirring solution of compound 117 (2 g, 5.76 mmol) in THF:$H_2O$ (4:1, 25 mL) was added lithium hydroxide monohydrate (1.69 g, 40.34 mmol) at RT; heated to 80° C. and stirred for 24 h. The reaction was monitored by TLC and LC-MS; after completion of the reaction, the volatiles were removed in vacuo. The pH of the aqueous layer was acidified with 2 N HCl to ~2. The precipitated solid was filtered, triturated with EtOAc (10 mL) and dried in vacuo to afford compound 118 (1.4 g 77%) as an off-white solid. TLC: 40% EtOAc/hexanes ($R_f$: 0.1); $^1$H NMR (DMSO-$d_6$, 400 MHz): δ 13.19 (br s, 1H), 7.96 (dd, J=7.8, 1.5 Hz, 1H), 7.44-7.37 (m, 2H), 7.24 (td, J=7.5, 1.0 Hz, 1H), 7.16 (s, 1H), 6.69 (dd, J=0.8, 8.1 Hz, 1H), 3.72 (s, 3H); LC-MS: 96.65%; 319.9 ($M^+$+1); (column; Ascentis Express C18, (50×3.0 mm, 2.7 µm); RT 1.81 min. 0.025% Aq. TFA+5% ACN: ACN+5% 0.025% Aq. TFA, 1.2 mL/min).

Synthesis of 7-methoxy-11-oxo-10, 11-dihydrodibenzo [b, f] [1, 4] thiazepine-8-carboxylic acid (119)

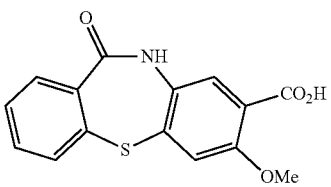

119

To a stirring solution of compound 118 (1.3 g, 4.07 mmol) in THF (25 mL) under inert atmosphere was added CDI (1.95 g, 12.22 mmol) at 0° C.; warmed to RT and stirred for 24 h. The reaction was monitored by TLC; after completion of the reaction, the volatiles were removed in vacuo. The pH of the residue was adjusted to ~2 using 6 N HCl. The precipitated solid was filtered, washed with water (2×20 mL) dried in vacuo and triturated with 50% EtOAc/hexanes (5 mL) and dried in vacuo to afford compound 119 (1 g, 82%) as an off-white solid. TLC: 10% MeOH/CH$_2$Cl$_2$ (R$_f$: 0.4); $^1$H NMR (DMSO-d$_6$, 500 MHz): δ 14.41 (br s, 1H), 10.55 (s, 1H), 7.71-7.67 (m, 1H), 7.56-7.44 (m, 4H), 7.28 (s, 1H), 3.81 (s, 3H);

Synthesis of 7-methoxy-11-oxo-10, 11-dihydrodibenzo [b, f] [1, 4] thiazepine-8-carboxylic acid 5, 5-dioxide (120)

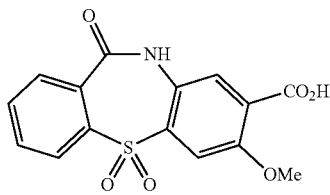

120

To a stirring solution of compound 119 (1 g, 3.32 mmol) in 1, 2 dichloro ethane:CH$_3$CN:H$_2$O (1:1:2, 40 mL) were added sodium metaperiodate (2.17 g, 9.96 mmol), ruthenium chloride (37.35 mg, 0.16 mmol) at 0° C.; warmed to RT and stirred for 16 h. The reaction was monitored by TLC; after completion the volatiles were removed in vacuo to obtain the crude. The crude was triturated with EtOAc (10 mL) and dried in vacuo to afford compound 120 (700 mg, 64%) as an off-white solid. TLC: 10% MeOH/CH$_2$Cl$_2$ (R$_f$: 0.1); TLC eluted twice; H NMR (DMSO-d$_6$, 500 MHz, DMSO-d$_6$): δ 13.37 (br s, 1H), 11.25 (s, 1H), 8.01-7.95 (m, 2H), 7.90 (t, J=7.5 Hz, 1H), 7.88-7.84 (m, 1H), 7.58 (s, 1H), 7.50 (s, 1H), 3.90 (s, 3H); LC-MS: 95.49%; 333.9 (M$^+$+1); (column; Ascentis Express C18, (50×3.0 mm, 2.7 μm); RT 1.79 min. 0.025% Aq. TFA+5% ACN: ACN+5% 0.025% Aq. TFA, 1.2 mL/min).

Synthesis of 7-chloro-11-oxo-10, 11-dihydrodibenzo [b, f] [1, 4] thiazepine-8-carboxylic acid 5, 5-dioxide (130): A Common Intermediate

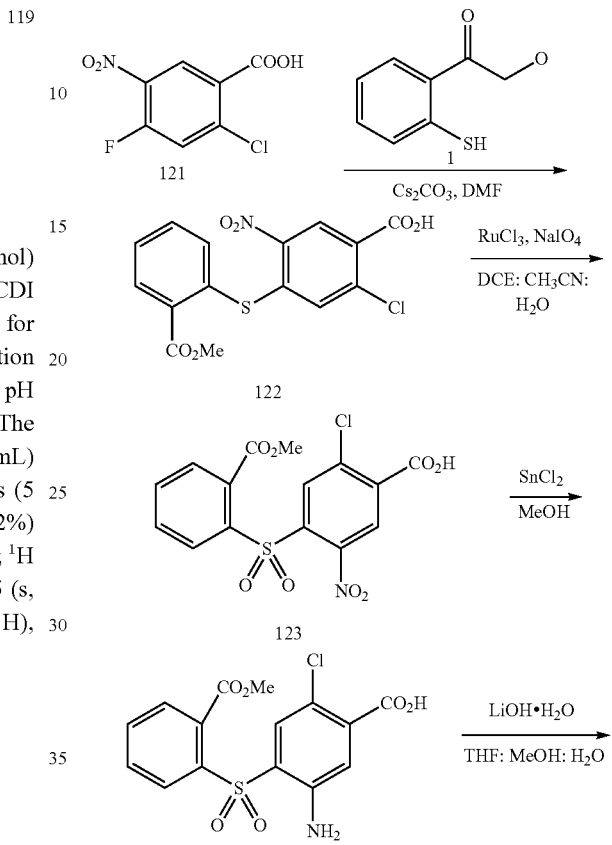

Synthesis of 2-chloro-4-((2-(methoxycarbonyl) phenyl) thio)-5-nitrobenzoic acid (122)

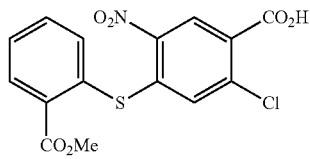

122

To a stirring solution of 2-chloro-4-fluoro-5-nitrobenzoic acid 121 (5 g, 22.76 mmol) in DMF (100 mL) under inert atmosphere were added methyl 2-mercaptobenzoate 1 (4.2 g, 25.04 mmol), cesium carbonate (3.1 g, 9.54 mmol) at RT and stirred for 12 h. The reaction was monitored by TLC; after completion of the reaction, the reaction mixture was diluted with ice-cold water (100 mL) and washed with EtOAc (2×250 mL). The pH of the aqueous layer was adjusted to ~2 with 2 N HCl and extracted with EtOAc (2×200 mL). The combined organic extracts were dried over sodium sulfate, filtered and concentrated in vacuo to obtain the crude. The crude was purified through silica gel column chromatography using 1-2 MeOH/CH$_2$Cl$_2$ to afford compound 122 (4 g, 48%) as yellow solid. TLC: 10% MeOH/CH$_2$Cl$_2$ (R$_f$: 0.5). $^1$H-NMR (DMSO-d$_6$, 500 MHz): δ 13.97 (br s, 1H), 8.62 (s, 1H), 7.99-7.94 (m, 1H), 7.77-7.69 (m, 3H), 6.87 (s, 1H), 3.75 (s, 3H); LC-MS (Agilent Ion trap): 77.39%; 366.1 (M−1)$^+$; (column; X-select C-18 (50×3.0 mm, 2.5 um); RT 3.18 min. 2.5 mM Aq. NH$_4$OAc:ACN; 0.8 mL/min).

Synthesis of 2-chloro-4-((2-(methoxycarbonyl) phenyl) sulfonyl)-5-nitrobenzoic acid (123)

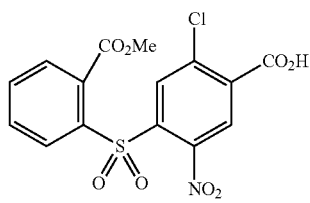

123

To a stirring solution of compound 122 (4 g, 10.89 mmol) in 1, 2 dichloro ethane:CH$_3$CN:H$_2$O (1:1:2, 40 mL) were added sodium metaperiodate (7 g, 32.72 mmol), ruthenium chloride (10 mg, 0.048 mmol) at 0° C.; warmed to RT and stirred for 16 h. The reaction was monitored by TLC; after completion the reaction mixture was diluted with water (100 mL) and washed with EtOAc (2×100 mL). The pH of the aqueous layer was adjusted to ~2 with 2 N HCl and extracted with EtOAc (2×200 mL). The combined organic extracts were dried over sodium sulfate, filtered and concentrated in vacuo to afford compound 123 (3.1 g, 72%) as an off-white solid. TLC: 10% MeOH/CH$_2$Cl$_2$ (R$_f$: 0.1); $^1$H-NMR (DMSO-d$_6$, 500 MHz): δ 14.53 (br s, 1H), 8.47 (s, 1H), 8.18-8.15 (m, 1H), 8.11 (s, 1H), 7.99-7.85 (m, 3H), 3.76 (s, 3H); LC-MS (Agilent Ion trap): 99.64%; 397.9 (M−1)$^+$; (column; X-select C-18 (50×3.0 mm, 2.5 um); RT 2.97 min. 2.5 mM Aq. NH$_4$OAc:ACN; 0.8 mL/min).

Synthesis of 5-amino-2-chloro-4-((2-(methoxycarbonyl) phenyl) sulfonyl) benzoic acid (124)

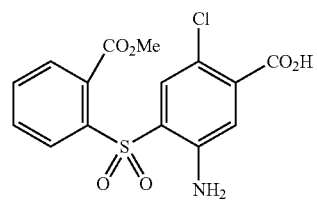

124

To a stirring solution of compound 123 (2.9 g, 7.26 mmol) in MeOH (30 mL) was added stannous chloride (4.1 g, 21.80 mmol) at RT; heated to 60° C. and stirred for 16 h. The reaction was monitored by TLC; after completion of the reaction, the volatiles were removed in vacuo. The residue was added water (100 mL) and extracted with EtOAc (2×100 mL). The organic extract was dried over sodium sulfate, filtered and concentrated in vacuo to afford compound 124 (1.2 g, 44%) as an off-white solid. TLC: 20% MeOH/CH$_2$Cl$_2$ (R$_f$: 0.3); $^1$H-NMR (DMSO-d$_6$, 400 MHz): δ 13.66 (br s, 1H), 8.26 (td, J=7.8, 1.1 Hz, 1H), 7.83 (td, J=7.4, 1.3 Hz, 1H), 7.77 (dd, J=7.9, 1.9 Hz, 1H), 7.69 (dd, J=7.5, 1.3 Hz, 1H), 7.63 (s, 1H), 7.18 (s, 1H), 6.44 (s, 2H), 3.86 (s, 3H); LC-MS: 92.25%; 369.9 (M$^+$+1); (column; Ascentis Express C18, (50×3.0 mm, 2.7 μm); RT 2.09 min. 0.025% Aq. TFA+5% ACN: ACN+5% 0.025% Aq. TFA, 1.2 mL/min).

Synthesis of 5-amino-4-((2-carboxyphenyl) sulfonyl)-2-chlorobenzoic acid (125)

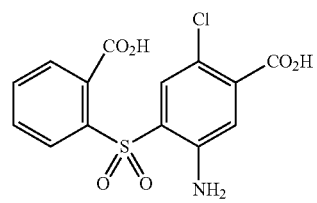

125

To a stirring solution of compound 124 (1 g, 2.71 mmol) in THF:H$_2$O (3:1, 20 mL) was added lithium hydroxide monohydrate (1.1 g, 27.10 mmol) portion wise at RT and stirred for 12 h. The reaction was monitored by TLC and LC-MS; after completion of the reaction, the volatiles were removed in vacuo. The pH of the aqueous layer was acidified with 2 N HCl to ~2. The precipitated solid was filtered and dried in vacuo to afford crude compound 125 (800 mg, 83%) as an off-white solid. TLC: 20% MeOH/CH$_2$Cl$_2$ (R$_f$: 0.3).

Synthesis of 7-chloro-11-oxo-10, 11-dihydrod-ibenzo [b, f] [1, 4] thiazepine-8-carboxylic acid 5, 5-dioxide (126)

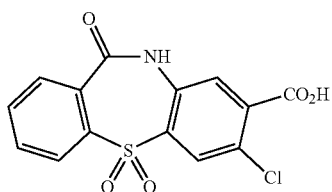

126

To a stirring solution of compound 125 (800 mg, 2.25 mmol) in THF (20 mL) under inert atmosphere was added CDI (1.85 g, 11.26 mmol) at 0° C.; warmed to RT and stirred for 16 h. The reaction was monitored by TLC; after completion of the reaction, the volatiles were removed in vacuo. The pH of the residue was adjusted to ~2 using 2 N HCl. The precipitated solid was filtered, washed with water (2×20 mL), hexanes (10 mL) and dried in vacuo to afford compound 126 (500 mg, 65%) as an off-white solid. TLC: 20% MeOH/CH$_2$Cl$_2$ (R$_f$: 0.4); $^1$H NMR (DMSO-d$_6$, 400 MHz): δ 14.08 (br s, 1H), 11.56 (s, 1H), 8.01-7.96 (m, 3H), 7.96-7.85 (m, 2H), 7.74 (s, 1H); LC-MS (Agilent Ion trap): 86.33%; 336.0 (M−1)$^+$; (column; X-select C-18 (50×3.0 mm, 2.5 um); RT 6.57 min. 2.5 mM Aq. NH$_4$OAc:ACN; 1.0 mL/min).

Synthesis of 9-chloro-11-oxo-10, 11-dihydrod-ibenzo [b, f] [1, 4] thiazepine-8-carboxylic acid 5, 5-dioxide (135): A Common Intermediate

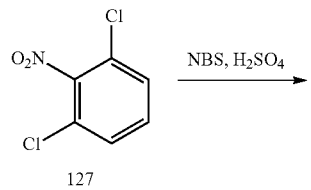

127

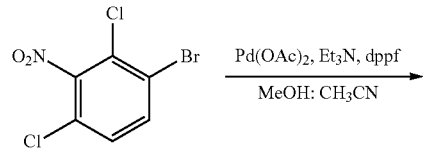

128

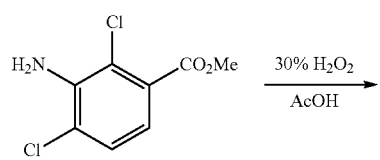

129

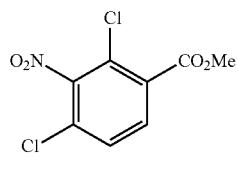

130

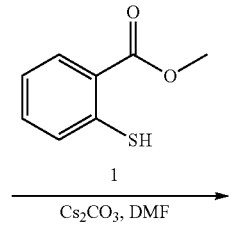

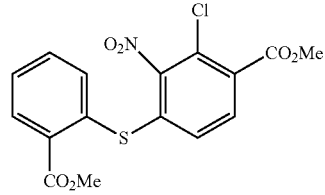

131

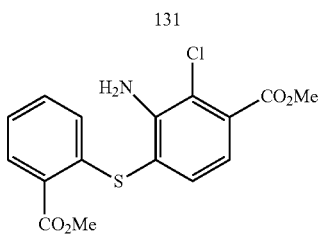

132

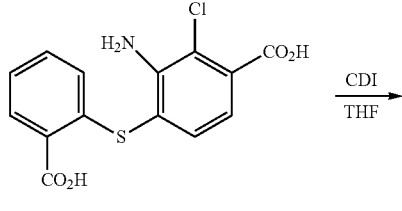

133

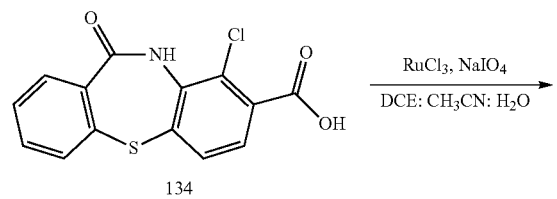

134

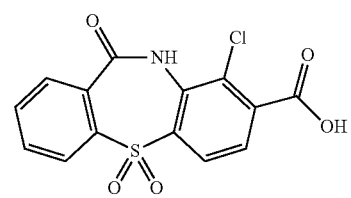

135

Synthesis of 1-bromo-2, 4-dichloro-3-nitrobenzene (128)

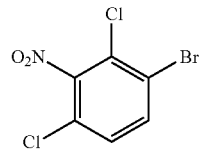

To a stirring solution of 1,3-dichloro-2-nitrobenzene 127 (5 g, 26.04 mmol) in concentrated sulfuric acid (150 mL) under inert atmosphere was added N-bromosuccinimide (4.6 g, 26.04 mmol) portion wise at RT and heated to 60° C. and stirred for 16 h. The reaction was poured into ice-cold water (100 mL) and extracted with EtOAc (2×100 mL). The combined organic extracts were dried over sodium sulfate, filtered and concentrated in vacuo to obtain the crude. The crude was purified through silica gel column chromatography using 2% EtOAc/hexanes to afford compound 128 (4.9 g, 70%). TLC: 5% EtOAc/hexanes ($R_f$: 0.5); $^1$H NMR (DMSO-$d_6$, 400 MHz): δ 8.11 (d, J=8.8 Hz, 1H), 7.79 (d, J=8.9 Hz, 1H).

Synthesis of methyl 3-amino-2, 4-dichlorobenzoate (129)

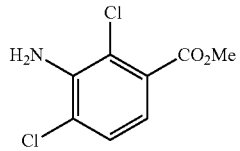

To a stirring solution of compound 128 (7.5 g, 27.77 mmol) in MeOH:CH$_3$CN (4:1, 100 mL) under inert atmosphere in a steel bomb were added triethylamine (12 mL, 83.33 mmol), dppf (1.53 g, 2.76 mmol), Pd(OAc)$_2$ (500 mg, 2.27 mmol) at RT; heated to 100° C., under CO gas atmosphere (150 psi) and stirred for 16 h. The reaction was monitored by TLC; after completion of the reaction, the reaction mixture was filtered through celite and the filtrate was concentrated in vacuo to obtain the crude. The crude was purified through silica gel column flash chromatography using 15% EtOAc/hexanes to afford compound 129 (5 g, 82%). TLC: 30% EtOAc/hexanes ($R_f$: 0.5); $^1$H NMR (DMSO-$d_6$, 400 MHz): δ 7.34 (d, J=8.1 Hz, 1H), 6.94 (d, J=8.1 Hz, 1H), 5.79 (s, 2H), 3.83 (s, 3H);

Synthesis of methyl 2, 4-dichloro-3-nitrobenzoate (130)

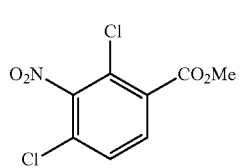

To a stirring solution of compound 129 (5 g, 22.72 mmol) in glacial acetic acid (25 mL) was added 30% H$_2$O$_2$ (25 mL) at 0° C.; warmed to RT and stirred for 16 h. The reaction was monitored by TLC; after completion of the reaction, the reaction mixture was diluted with water (100 mL) and EtOAc (200 mL). The organic extract was dried over sodium sulfate, filtered and concentrated in vacuo to afford compound 130 (4.1 g, 73%) as brown solid. TLC: 30% EtOAc/hexanes ($R_f$: 0.3); $^1$H NMR (DMSO-$d_6$, 400 MHz): δ 8.11 (d, J=8.5 Hz, 1H), 7.96 (d, J=8.7 Hz, 1H), 3.91 (s, 3H);

Synthesis of methyl 2-chloro-4-((2-(methoxycarbonyl) phenyl) thio)-3-nitrobenzoate (131)

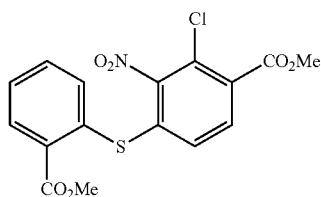

To a stirring solution of compound 130 (4.1 g, 16.40 mmol) in DMF (100 mL) under argon atmosphere were added methyl 2-mercaptobenzoate 1 (2.75 g, 16.40 mmol), cesium carbonate (16 g, 49.23 mmol) at 0° C.; warmed to RT and stirred for 16 h. The reaction was monitored by TLC; after completion of the reaction, the reaction mixture was diluted with water (500 mL) and extracted with EtOAc (200 mL). The organic extract was dried over sodium sulfate, filtered and concentrated in vacuo to compound 131 (1 g, 16%) as white solid. TLC: 30% EtOAc/hexanes ($R_f$: 0.3). $^1$H NMR (DMSO-$d_6$, 400 MHz): δ 8.08 (d, J=8.3 Hz, 1H), 7.98 (dd, J=7.8, 1.5 Hz, 1H), 7.73 (d, J=8.3 Hz, 1H), 7.58-7.52 (m, 1H), 7.43 (td, J=7.6, 1.1 Hz, 1H), 7.02 (dd, J=8.0, 0.6 Hz, 1H), 3.92 (s, 3H), 3.86 (s, 3H);

Synthesis of methyl 3-amino-2-chloro-4-((2-(methoxycarbonyl) phenyl) thio) benzoate (132)

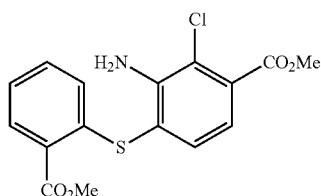

To a stirring solution of compound 131 (1 g, 2.62 mmol) in acetic acid (10 mL) was added iron powder (734 mg, 13.12 mmol) at RT; heated to 60° C. and stirred for 4 h. The reaction was monitored by TLC; after completion of the reaction, the volatiles were removed in vacuo and the residue was diluted with EtOAc (200 mL). The organic layer was washed with saturated sodium bicarbonate solution (100 mL) and dried over sodium sulfate, filtered and concentrated in vacuo to afford compound 132 (700 mg, 76%) as brown syrup. TLC: 40% EtOAc/hexanes ($R_f$: 0.7). $^1$H NMR (DMSO-$d_6$, 500 MHz): δ 7.97 (br d, J=7.5 Hz, 1H), 7.47-7.42 (m, 2H), 7.26 (br t, J=7.5 Hz, 1H), 6.97 (d, J=8.1 Hz, 1H), 6.65 (br d, J=8.1 Hz, 1H), 5.76-5.73 (m, 2H), 3.89 (s, 3H), 3.87 (s, 3H); LC-MS: 90.61%; 351.8 (M⁺+1); (column; Ascentis Express C18, (50×3.0 mm, 2.7 μm); RT 2.82 min. 0.025% Aq. TFA+5% ACN: ACN+5% 0.025% Aq. TFA, 1.2 mL/min).

Synthesis of 3-amino-4-((2-carboxyphenyl) thio)-2-chlorobenzoic acid (133)

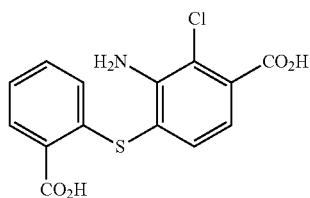

133

To a stirring solution of compound 132 (700 mg, 1.99 mmol) in THF:H₂O (1:1, 20 mL) was added lithium hydroxide monohydrate (837 mg, 19.94 mmol) portion wise for 10 min at RT and stirred for 16 h. The reaction was monitored by TLC; after completion of the reaction, the volatiles were removed in vacuo. The pH of the residue was adjusted to ~2 with 1 N HCl and extracted with EtOAc (2×50 mL) The organic layer was dried over sodium sulfate, filtered and concentrated in vacuo to compound 133 (500 mg, 78%) as a white solid. TLC: 40% EtOAc/hexanes (R$_f$: 0.2).

¹H NMR (DMSO-d₆, 400 MHz): δ 13.29 (br s, 2H), 7.97 (dd, J=7.8, 1.4 Hz, 1H), 7.44-7.38 (m, 2H), 7.26-7.21 (m, 1H), 6.95 (d, J=7.9 Hz, 1H), 6.63 (d, J=7.6 Hz, 1H), 5.62 (br s, 2H); LC-MS: 94.65%; 323.9 (M⁺+1); (column; Ascentis Express C18, (50×3.0 mm, 2.7 μm); RT 1.98 min. 0.025% Aq. TFA+5% ACN: ACN+5% 0.025% Aq. TFA, 1.2 mL/min).

Synthesis of 9-chloro-11-oxo-10, 11-dihydrodibenzo [b, f] [1, 4] thiazepine-8-carboxylic acid (134)

134

To a stirring solution of compound 133 (500 mg, 1.42 mmol) in THF (10 mL) under inert atmosphere was added CDI (2.30 g, 14.20 mmol) at RT and stirred for 16 h. The reaction was monitored by TLC; after completion of the reaction, the volatiles were removed in vacuo. The pH of the residue was adjusted to using 1 N HCl. The precipitated solid was filtered, washed with hexane (20 mL) and dried in vacuo to afford compound 134 (300 mg, 69%) as an off-white solid. TLC: 10% MeOH/CH₂Cl₂ (R$_f$: 0.4); ¹H NMR (DMSO-d₆, 400 MHz): δ 13.62 (br s, 1H), 10.41 (s, 1H), 7.72-7.63 (m, 2H), 7.58-7.54 (m, 1H), 7.53-7.46 (m, 3H); LC-MS: 93.51%; 305.9 (M⁺+1); (column; Ascentis Express C18, (50×3.0 mm, 2.7 μm); RT 2.02 min. 0.025% Aq. TFA+5% ACN: ACN+5% 0.025% Aq. TFA, 1.2 mL/min).

Synthesis of 9-chloro-11-oxo-10, 11-dihydrodibenzo [b, f] [1, 4] thiazepine-8-carboxylic acid 5, 5-dioxide (135)

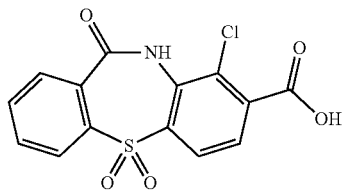

135

To a stirring solution of compound 134 (290 mg, 0.95 mmol) in 1, 2 dichloro ethane:CH₃CN:H₂O (1:1:2, 20 mL) were added sodium metaperiodate (622 mg, 2.85 mmol), ruthenium chloride (10.70 mg, 0.047 mmol) at RT and stirred for 16 h. The reaction was monitored by TLC; after completion, the volatiles were removed in vacuo and the residue was extracted with EtOAc (2×75 mL). The combined organic extracts were dried over sodium sulfate, filtered and concentrated in vacuo to obtain the crude. The crude was purified through silica gel column chromatography using 10% MeOH/CH₂Cl₂ to afford compound 135 (230 mg, 72%) as brown solid. TLC: 40% MeOH/CH₂Cl₂ (R$_f$: 0.3); ¹H NMR (DMSO-d₆, 400 MHz): δ 14.08 (br s, 1H), 11.13 (s, 1H), 8.01 (d, J=8.2 Hz, 1H), 7.98-7.89 (m, 3H), 7.85 (dd, J=7.5, 1.4 Hz, 1H), 7.71 (d, J=8.2 Hz, 1H); LC-MS: 99.61%; 335.9 (M−1)⁺; (column; Kinetex EVO C-18 (50×3.0 mm, 2.6 um); RT 1.15 min. 2.5 mM Aq. NH₄OOCH+5% ACN: ACN+5% 2.5 mM Aq.NH₄OOCH, 0.8 mL/min).

Synthesis of 11-oxo-7-(trifluoromethyl)-10, 11-dihydrodibenzo [b, f] [1, 4] thiazepine-8-carboxylic acid 5, 5-dioxide (143): A Common Intermediate

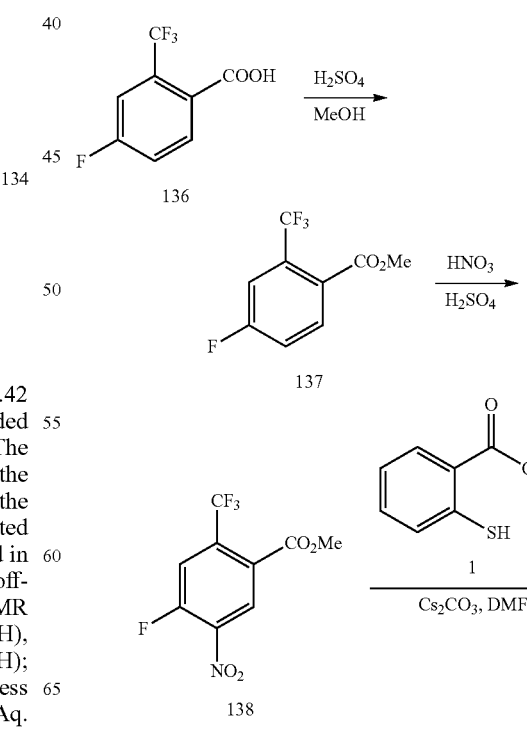

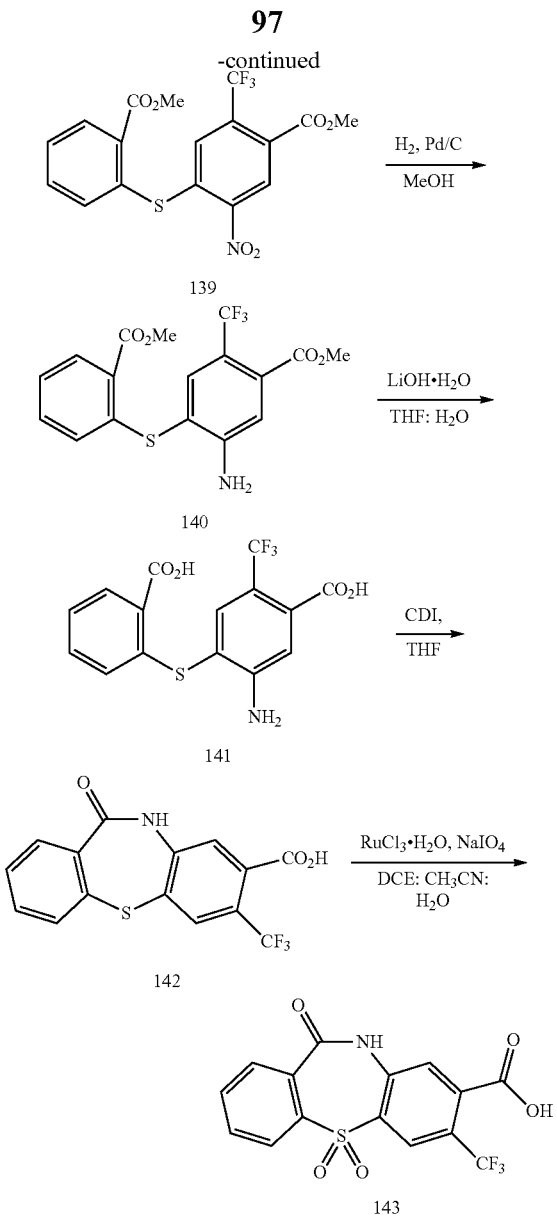

139

140

141

142

143

Synthesis of methyl 4-fluoro-2-(trifluoromethyl) benzoate (137)

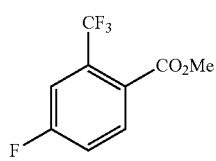

137

To a stirring solution of 4-fluoro-2-(trifluoromethyl) benzoic acid 136 (20 g, 96.10 mmol) in MeOH (200 mL) under inert atmosphere was added concentrated sulfuric acid (18.85 mL, 192.20 mmol) dropwise for 15 min at 0° C.; heated to reflux and stirred for 16 h. The reaction was monitored by TLC; after completion of the reaction, the volatiles were removed in vacuo. The residue was diluted with ice-cold water (300 mL) and extracted with diethyl ether (2×300 mL). The combined organic extracts were dried over sodium sulfate, filtered and concentrated in vacuo to afford mixture of compound 137 (10.8 g, 51%) as colorless syrup. TLC: 10% EtOAc/hexanes ($R_f$: 0.8). $^1$H NMR (400 MHz, DMSO-$d_6$): δ 7.96 (dd, J=8.7, 5.5 Hz, 1H), 7.81 (dd, J=9.3, 2.6 Hz, 1H), 7.68 (td, J=8.4, 2.5 Hz, 1H), 3.87 (s, 3H);

Synthesis of methyl 4-fluoro-5-nitro-2-(trifluoromethyl) benzoate (138)

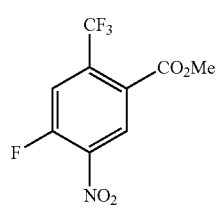

138

To a stirring solution of compound 137 (10.8 g, 48.64 mmol) in concentrated sulphuric acid (30 mL) under inert atmosphere at 0° C. was added fuming nitric acid (15 mL) dropwise for 30 min at 0° C.; heated to 65° C. and stirred for 16 h. The reaction was monitored by TLC; after completion of the reaction, the reaction mixture was cooled to 0° C. and slowly quenched with ice-cold water (300 mL) and extracted with EtOAc (2×300 mL). The combined organic extracts were washed with saturated NaHCO$_3$ solution (300 mL) and brine (300 mL), dried over sodium sulfate, filtered and concentrated in vacuo to obtain the crude. The crude was purified through silica gel column flash chromatography using 5% EtOAc/hexanes to afford compound 138 (3.5 g, 27%) as colorless syrup. TLC: 10% EtOAc/hexanes ($R_f$: 0.7). $^1$H NMR (400 MHz, DMSO-$d_6$): δ 8.63 (d, J=7.3 Hz, 1H), 8.30 (d, J=11.3 Hz, 1H), 3.92 (s, 3H);

Synthesis of methyl 4-((2-(methoxycarbonyl) phenyl) thio)-5-nitro-2-(trifluoromethyl) benzoate (139)

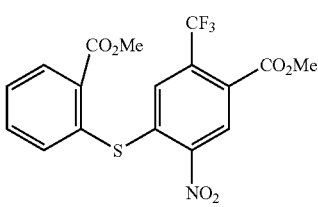

139

To a stirring solution of methyl 4-fluoro-5-nitro-2-(trifluoromethyl) benzoate 138 (4.00 g, 14.98 mmol) in DMF (80 mL) under inert atmosphere were added methyl 2-mercaptobenzoate 1 (2.52 g, 14.98 mmol) and cesium carbonate (7.32 g, 22.47 mmol) at 0° C.; warmed to RT and stirred for 2 h. The reaction was monitored by TLC; after completion of the reaction, the reaction mixture was diluted with water (200 mL) and extracted with EtOAc (2×200 mL). The combined organic extracts were dried over sodium sulfate, filtered and concentrated in vacuo to obtain the crude. The crude was purified through silica gel column chromatography using 5-7% EtOAc/hexanes to afford compound 139 (5 g, 81%) as yellow syrup. TLC: 20% EtOAc/hexanes (R$_f$: 0.5); $^1$H NMR (DMSO-d$_6$, 400 MHz): δ 8.68 (s, 1H), 8.03-7.96 (m, 1H), 7.77-7.70 (m, 3H), 7.25 (s, 1H), 3.90 (s, 3H), 3.74 (s, 3H);

Synthesis of methyl 5-amino-4-((2-(methoxycarbonyl) phenyl) thio)-2-(trifluoromethyl) benzoate (140)

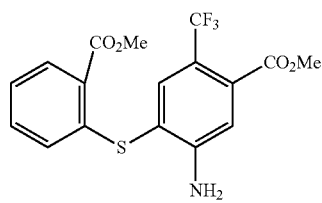

140

To a stirring solution of compound 139 (5 g, 12.04 mmol) in MeOH (100 mL) under inert atmosphere was added 10% Pd/C (2 g) at RT and stirred under hydrogen atmosphere (balloon pressure) at RT for 16 h. The reaction was monitored by TLC; after completion of the reaction, the reaction mixture was filtered through celite and eluted with 50% MeOH/CH$_2$Cl$_2$ (2×150 mL). The filtrate was concentrated in vacuo to obtain the crude. The crude was purified through silica gel column chromatography using 20-25% EtOAc/hexanes to afford compound 140 (3.5 g, 75%) as an off-white solid. TLC: 40% EtOAc/hexanes (R$_f$: 0.5); $^1$H NMR (400 MHz, DMSO-d$_6$): δ 7.96 (dd, J=7.8, 1.4 Hz, 1H), 7.67 (s, 1H), 7.46-7.41 (m, 1H), 7.27-7.23 (m, 1H), 7.15 (s, 1H), 6.65 (dd, J=8.1, 0.7 Hz, 1H), 6.40 (s, 2H), 3.88 (s, 3H), 3.84 (s, 3H);

Synthesis of 5-amino-4-((2-carboxyphenyl) thio)-2-(trifluoromethyl) benzoic acid (141)

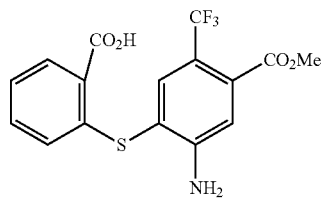

141

To a stirring solution of compound 140 (3.5 g, 9.09 mmol) in THF:H$_2$O (3:1, 40 mL) was added lithium hydroxide monohydrate (1.90 g, 45.45 mmol) at 0° C.; warmed to RT and stirred for 16 h. The reaction was monitored by TLC; after completion of the reaction, the volatiles were removed in vacuo. The residue was diluted with water (30 mL) and washed with diethylether (2×30 mL). The aqueous layer was acidified with 6 N HCl to pH~4. The precipitated solid was filtered and dried in vacuo to afford compound 141 (2.8 g, 86%) as an off-white solid. TLC: 40% EtOAc/hexanes (R$_f$: 0.2); $^1$H NMR (400 MHz, DMSO-d$_6$): δ 13.32 (br s, 2H), 7.97 (dd, J=7.8, 1.4 Hz, 1H), 7.64 (s, 1H), 7.45-7.38 (m, 1H), 7.27-7.20 (m, 1H), 7.15 (s, 1H), 6.63 (d, J=8.0 Hz, 1H), 6.25 (br s, 2H);

Synthesis of 11-oxo-7-(trifluoromethyl)-10, 11-dihydrodibenzo [b, f] [1, 4] thiazepine-8-carboxylic acid (142)

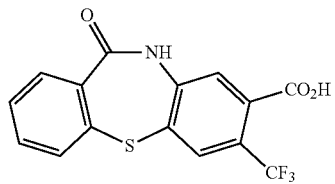

142

To a stirring solution of compound 141 (2.6 g, 7.28 mmol) in THF (50 mL) under inert atmosphere was added CDI (5.90 g, 36.41 mmol) at 0° C.; heated to 60° C. and stirred for 16 h. The reaction was monitored by TLC; after completion of the reaction, the volatiles were removed in vacuo. The residue was poured into ice-cold water (100 mL) and the pH was adjusted to ~2 using 6 N HCl. The precipitated solid was filtered and dried in vacuo to afford compound 142 (710 mg, 75%) as white solid. TLC: 5% MeOH/CH$_2$Cl$_2$ (R$_f$: 0.3); 41 NMR (400 MHz, DMSO-d$_6$): δ 13.82 (br s, 1H), 11.04 (s, 1H), 7.96 (s, 1H), 7.75-7.69 (m, 1H), 7.64-7.45 (m, 4H);

Synthesis of 11-oxo-7-(trifluoromethyl)-10, 11-dihydrodibenzo [b, f] [1, 4] thiazepine-8-carboxylic acid 5, 5-dioxide (143)

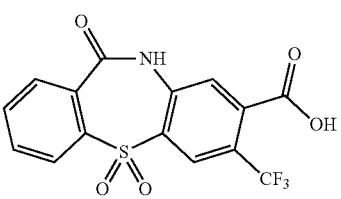

143

To a stirring solution of compound 142 (1.9 g, 5.60 mmol) in 1, 2 dichloro ethane:CH$_3$CN:H$_2$O (1:1:2, 100 mL) were added sodium metaperiodate (3.6 g, 16.81 mmol), ruthenium chloride (58 mg, 0.28 mmol) at 0° C.; warmed to RT and stirred for 16 h. The reaction was monitored by TLC; after completion, the volatiles were removed in vacuo. The solid obtained was filtered, washed with water (2×20 mL). The solid was dissolved in 20% MeOH/CH$_2$Cl$_2$ (100 mL) and filtered through celite. The filtrate was concentrated in vacuo to obtain the crude, which was triturated with n-hexane (20 mL) and dried in vacuo to afford compound 143 (1.6 g, 77%) as an off-white solid. TLC: 15% MeOH/CH$_2$Cl$_2$ (R$_f$: 0.2); $^1$H NMR (400 MHz, DMSO-d$_6$): δ 11.85 (s, 1H), 8.19 (s, 1H), 8.05-7.99 (m, 2H), 7.97-7.87 (m, 2H), 7.78 (s, 2H); LC-MS: 98.87%; 289.9 (M$^+$+1); (column; Ascentis Express C18, (50×3.0 mm, 2.7 μm); RT 2.08 min. 0.025% Aq. TFA+5% ACN: ACN+5% 0.025% Aq. TFA, 1.2 mL/min).

101
Synthesis of 4-fluoro-11-oxo-10, 11-dihydrodibenzo [b, f] [1, 4] thiazepine-8-carboxylic acid 5, 5-dioxide (144): A Common Intermediate

102
Synthesis of 11-oxo-10, 11-dihydrodibenzo [b, f] [1, 4] oxazepine-8-carboxylic acid (149): A Common Intermediate

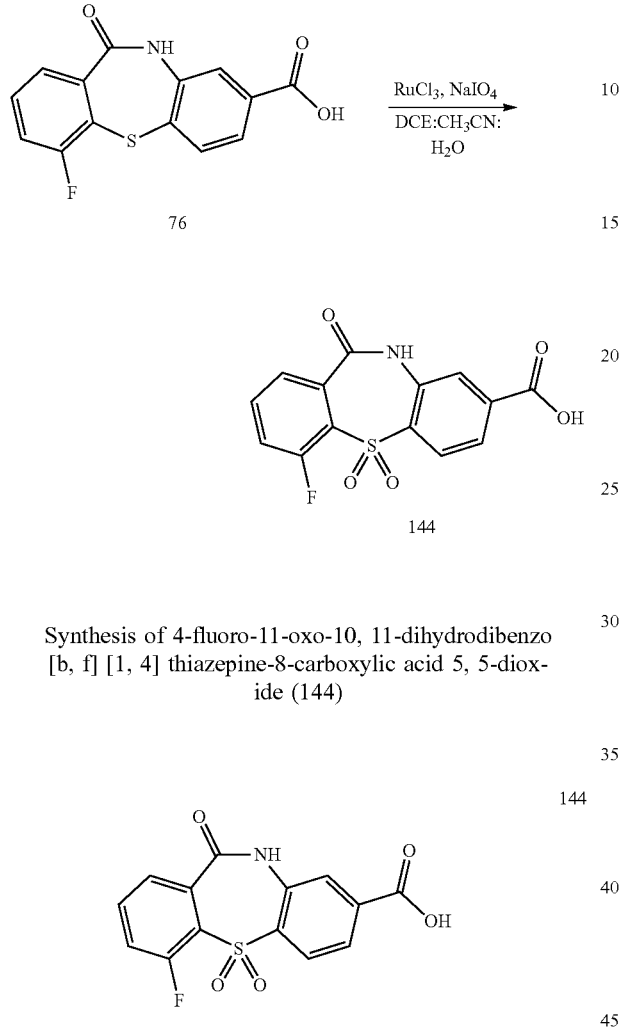

Synthesis of 4-fluoro-11-oxo-10, 11-dihydrodibenzo [b, f] [1, 4] thiazepine-8-carboxylic acid 5, 5-dioxide (144)

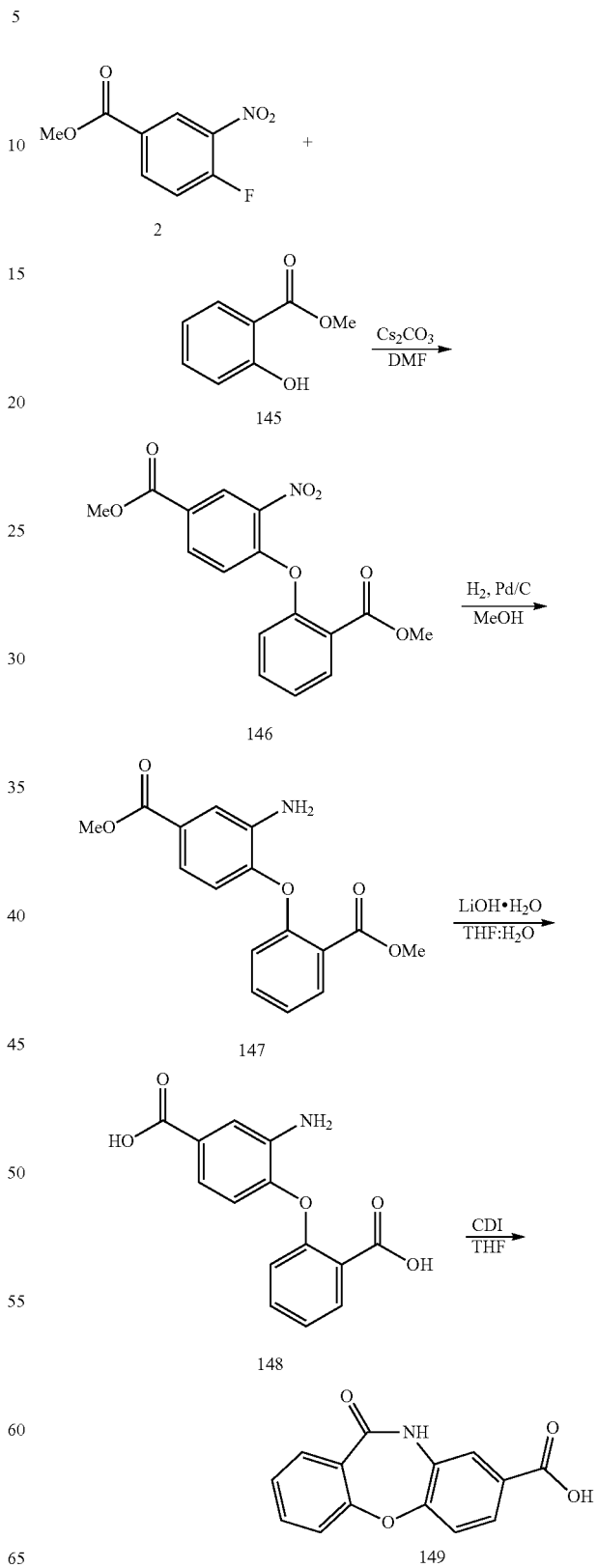

To a stirring solution of 4-fluoro-11-oxo-10, 11-dihydrodibenzo [b, f] [1, 4] thiazepine-8-carboxylic acid 76 (300 mg, 1.03 mmol) in 1, 2 dichloro ethane:CH$_3$CN:H$_2$O (1:1:2, 12 mL) were added sodium metaperiodate (663 mg, 3.11 mmol), ruthenium chloride (10.7 mg, 0.05 mmol) at RT and stirred for 16 h. The reaction was monitored by TLC; after completion the volatiles were removed in vacuo. The residue was diluted with water (50 mL) and extracted with EtOAc (3×50 mL). The combined organic extracts were dried over sodium sulfate, filtered and concentrated in vacuo to afford compound 144 (220 mg, 67%) as an off-white solid. TLC: 10% MeOH/CH$_2$Cl$_2$ (R$_f$: 0.2); $^1$H-NMR (DMSO-d$_6$, 400 MHz): δ 13.91-13.44 (m, 1H), 11.60 (s, 1H), 8.13 (d, J=8.2 Hz, 1H), 7.94-7.84 (m, 3H), 7.77-7.64 (m, 2H); LC-MS: 97.70%; 320.0 (M−1)$^+$; (column; Kinetex EVO C-18 (50× 3.0 mm, 2.6 um); RT 1.27 min. 2.5 mM Aq. NH$_4$OOCH+5% ACN: ACN+5% 2.5 mM Aq.NH$_4$OOCH, 0.8 mL/min).

Synthesis of methyl 4-(2-(methoxycarbonyl)phenoxy)-3-nitrobenzoate (146)

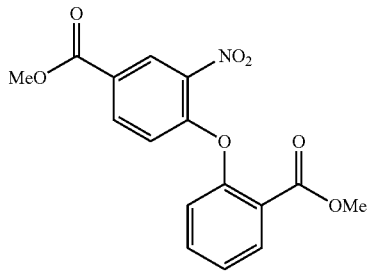

146

To a stirring solution of methyl 4-fluoro-3-nitrobenzoate 2 (5 g, 25.12 mmol) in DMF (75 mL) under argon atmosphere were added methyl 2-hydroxybenzoate 145 (4.2 g, 27.63 mmol), cesium carbonate (8.98 g, 27.64 mmol), at RT; heated to 100° C. and stirred for 2 h. The reaction was monitored by TLC; after completion of the reaction, the reaction mixture was diluted with ice-cold water (200 mL). The precipitated solid was filtered, washed with n-hexane (100 mL) and dried in vacuo to afford compound 146 (6.2 g, 75%) as an off-white solid. TLC: 30% EtOAc/hexanes ($R_f$: 0.4); $^1$H NMR (DMSO-$d_6$, 500 MHz): δ 8.54 (s, 1H), 8.11 (dd, J=8.8, 2.2 Hz, 1H), 8.02 (dd, J=7.7, 1.6 Hz, 1H), 7.80 (td, J=7.8, 1.7 Hz, 1H), 7.52 (t, J=7.4 Hz, 1H), 7.45 (d, J=7.8 Hz, 1H), 6.89 (d, J=8.7 Hz, 1H), 3.88 (s, 3H), 3.64 (s, 3H).

Synthesis of methyl 3-amino-4-(2-(methoxycarbonyl) phenoxy) benzoate (147)

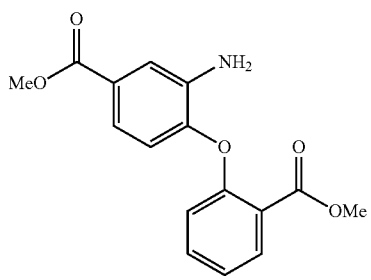

147

To a stirring solution of compound 146 (2 g, 6.04 mmol) in MeOH (50 mL) was evacuated for 5 min and added 10% Pd/C (1 g, 50% wet) under argon atmosphere at RT and stirred under hydrogen atmosphere (balloon pressure) at RT for 16 h. The reaction was monitored by TLC; after completion of the reaction, the reaction mixture was filtered through celite and washed with 20% MeOH/CH$_2$Cl$_2$ (200 mL). The filtrate was concentrated in vacuo to obtain the crude. The crude was purified by combiflash chromatography using 20% EtOAc/hexanes to afford compound 147 (1.4 g, 77%) as an off-white solid. TLC: 30% EtOAc/hexanes ($R_f$: 0.3); $^1$H NMR (DMSO-$d_6$, 400 MHz): δ 7.84 (dd, J=7.7, 1.6 Hz, 1H), 7.61-7.55 (m, 1H), 7.44 (s, 1H), 7.27 (t, J=7.2 Hz, 1H), 7.13 (dd, J=8.3, 2.0 Hz, 1H), 7.00 (d, J=8.0 Hz, 1H), 6.65 (d, J=8.3 Hz, 1H), 5.30 (br s, 2H), 3.80 (s, 3H), 3.74 (s, 3H).

Synthesis of 3-amino-4-(2-carboxyphenoxy) benzoic acid (148)

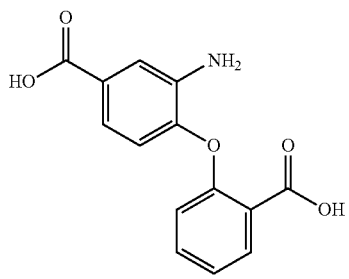

148

To a stirring solution of compound 147 (1.4 g, 4.65 mmol) in THF:H$_2$O (3:1, 40 mL) was added lithium hydroxide monohydrate (976 mg, 23.23 mmol) at RT; heated to reflux and stirred for 2 h. The reaction was monitored by TLC; after completion of the reaction, the volatiles were removed in vacuo. The pH of the residue was acidified to ~2 with 2 N HCl. The precipitated solid was filtered, washed with water (20 mL), n-pentane (20 mL) and dried in vacuo to afford compound 148 (700 mg, 56%) as an off-white solid. TLC: 30% EtOAc/hexanes ($R_f$: 0.0; $^1$H NMR (DMSO-$d_6$, 400 MHz): δ 7.86 (dd, J=7.7, 1.6 Hz, 1H), 7.63 (s, 1H), 7.62-7.57 (m, 1H), 7.37 (d, J=7.3 Hz, 1H), 7.31 (t, J=7.3 Hz, 1H), 7.06 (d, J=8.0 Hz, 1H), 6.69 (d, J=8.5 Hz, 1H).

Synthesis of 11-oxo-10, 11-dihydrodibenzo [b, f] [1, 4] oxazepine-8-carboxylic acid (149)

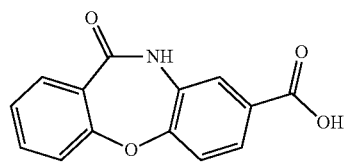

149

To a stirring solution of compound 148 (700 mg, 2.56 mmol) in THF (20 mL) under argon atmosphere was added CDI (2.07 g, 12.77 mmol) at RT and stirred for 24 h. The reaction was monitored by TLC; after completion of the reaction, the volatiles were removed in vacuo. The pH of the residue was acidified to ~2 using 2 N HCl. The precipitated solid was filtered, washed with n-pentane (50 mL) and dried in vacuo to afford compound 149 (450 mg, 69%) as an off-white solid. TLC: 10% MeOH/CH$_2$Cl$_2$ ($R_f$: 0.2); $^1$H NMR (DMSO-$d_6$, 400 MHz): δ 13.03 (br s, 1H), 10.65 (s, 1H), 7.81-7.76 (m, 2H), 7.70 (dd, J=8.4, 2.2 Hz, 1H), 7.67-7.61 (m, 1H), 7.43 (d, J=8.4 Hz, 1H), 7.40-7.31 (m, 2H).

Synthesis of 9-methyl-11-oxo-10, 11-dihydrodibenzo [b, f] [1, 4] oxazepine-8-carboxylic acid (153): A Common Intermediate

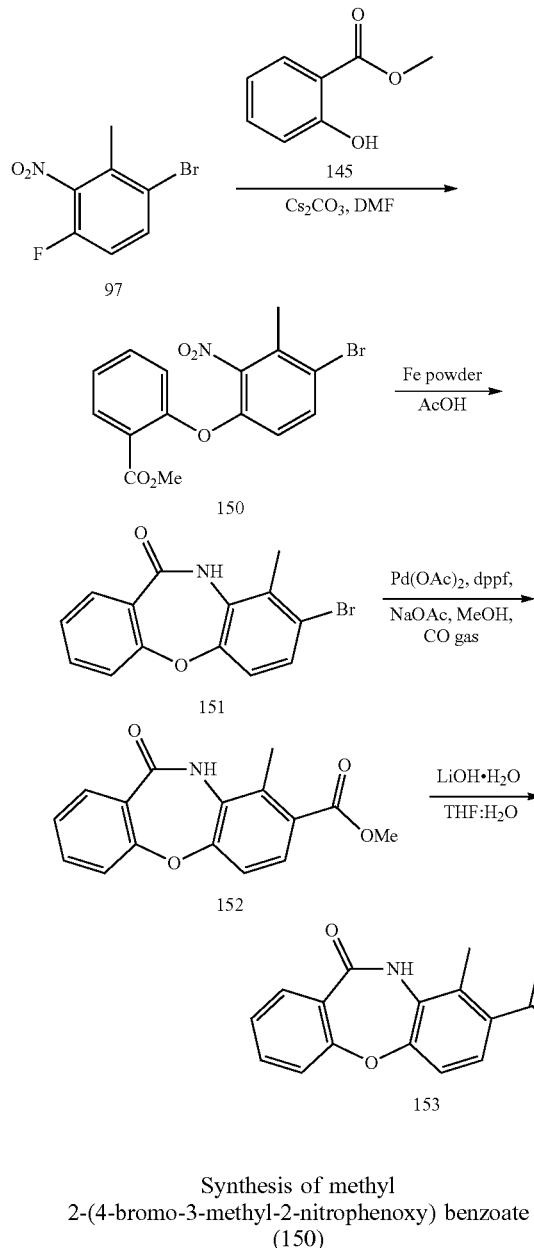

Synthesis of methyl 2-(4-bromo-3-methyl-2-nitrophenoxy) benzoate (150)

To a stirring solution of compound 97 (1.5 g, 6.41 mmol) in DMF (30 mL) under inert atmosphere were added cesium carbonate (3.1 g, 9.54 mmol), methyl 2-hydroxybenzoate 145 (974 mg, 6.41 mmol) at RT; heated to 70° C. and stirred for 2 h. The reaction was monitored by TLC; after completion of the reaction, the reaction mixture was diluted with ice-cold water (100 mL) and the precipitated solid was filtered, washed with water (20 mL), hexane (20 mL) and dried in vacuo to afford compound 150 (1.1 g, 48%) as a pale brown solid. TLC: 5% EtOAc/hexanes ($R_f$: 0.3); $^1$H NMR (DMSO-$d_6$, 400 MHz): δ 7.94 (dd, J=7.8, 1.8 Hz, 1H), 7.75-7.69 (m, 2H), 7.45 (td, J=7.6, 1.1 Hz, 1H), 7.27 (dd, J=8.2, 0.9 Hz, 1H), 6.65 (d, J=9.0 Hz, 1H), 3.71 (s, 3H), 2.35 (s, 3H); LC-MS: 97.42%; 364.0 (M–1)$^+$; 365.9 (M–2)$^+$; (column; Kinetex EVO C-18 (50×3.0 mm, 2.6 um); RT 3.78 min. 2.5 mM Aq. NH$_4$OOCH+5% ACN: ACN+5% 2.5 mM Aq.NH$_4$OOCH, 0.8 mL/min).

Synthesis of 8-bromo-9-methyldibenzo [b, f] [1, 4] oxazepin-11(10H)-one (151)

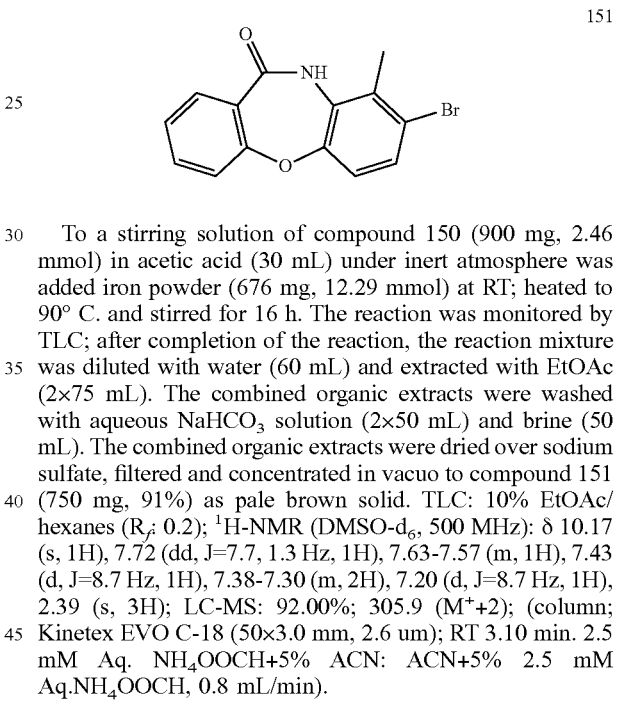

To a stirring solution of compound 150 (900 mg, 2.46 mmol) in acetic acid (30 mL) under inert atmosphere was added iron powder (676 mg, 12.29 mmol) at RT; heated to 90° C. and stirred for 16 h. The reaction was monitored by TLC; after completion of the reaction, the reaction mixture was diluted with water (60 mL) and extracted with EtOAc (2×75 mL). The combined organic extracts were washed with aqueous NaHCO$_3$ solution (2×50 mL) and brine (50 mL). The combined organic extracts were dried over sodium sulfate, filtered and concentrated in vacuo to compound 151 (750 mg, 91%) as pale brown solid. TLC: 10% EtOAc/hexanes ($R_f$: 0.2); $^1$H-NMR (DMSO-$d_6$, 500 MHz): δ 10.17 (s, 1H), 7.72 (dd, J=7.7, 1.3 Hz, 1H), 7.63-7.57 (m, 1H), 7.43 (d, J=8.7 Hz, 1H), 7.38-7.30 (m, 2H), 7.20 (d, J=8.7 Hz, 1H), 2.39 (s, 3H); LC-MS: 92.00%; 305.9 (M$^+$+2); (column; Kinetex EVO C-18 (50×3.0 mm, 2.6 um); RT 3.10 min. 2.5 mM Aq. NH$_4$OOCH+5% ACN: ACN+5% 2.5 mM Aq.NH$_4$OOCH, 0.8 mL/min).

Synthesis of methyl 9-methyl-11-oxo-10, 11-dihydrodibenzo [b, f] [1, 4] oxazepine-8-carboxylate (152)

To a stirring solution of compound 151 (800 mg, 2.63 mmol) in MeOH (80 mL) in a steel bomb were added dppf (145.7 mg, 0.26 mmol), sodium acetate (647 mg, 7.89 mmol), Pd(OAc)$_2$ (59 mg, 0.26 mmol) at RT; heated to 120° C. under CO gas atmosphere (80 psi) and stirred for 24 h.

The reaction was monitored by TLC; after completion of the reaction, the reaction mixture was filtered through celite and the filtrate was concentrated in vacuo to obtain the crude. The crude was purified through silica gel column flash chromatography using 10-20% EtOAc/hexanes to afford compound 152 (500 mg, 68%). TLC: 20% EtOAc/hexanes ($R_f$: 0.2); $^1$H NMR (DMSO-$d_6$, 400 MHz): δ 10.09 (s, 1H), 7.73 (dd, J=7.8, 1.6 Hz, 1H), 7.63-7.54 (m, 2H), 7.40-7.29 (m, 3H), 3.81 (s, 3H), 2.45 (s, 3H); LC-MS: 97.37%; 283.9 (M$^+$+1); (column; Kinetex EVO C-18 (50×3.0 mm, 2.6 um); RT 2.68 min. 2.5 mM Aq. NH$_4$OOCH+5% ACN: ACN+5% 2.5 mM Aq.NH$_4$OOCH, 0.8 mL/min).

Synthesis of 9-methyl-11-oxo-10, 11-dihydrodibenzo [b, f] [1, 4] oxazepine-8-carboxylic acid (153)

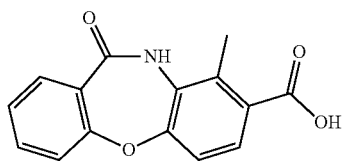

153

To a stirring solution of compound 152 (550 mg, 1.94 mmol) in THF:H$_2$O (4:1, 24 mL) was added lithium hydroxide monohydrate (245 mg, 5.83 mmol) RT and reflux for 16 h. The reaction was monitored by TLC; after completion of the reaction, the volatiles were removed in vacuo. The residue was diluted with water (20 mL) and acidified with 2 N HCl to pH~3-4. The obtained solid was filtered, washed with water (20 mL), n-hexane (20 mL), diethylether (20 mL) and dried in vacuo to obtain compound 153 (310 mg, 60%) as pale brown solid. TLC: 30% EtOAc/hexanes ($R_f$: 0.1); $^1$H NMR (DMSO-$d_6$, 400 MHz): δ 13.03 (br s, 1H), 10.05 (s, 1H), 7.73 (dd, J=7.7, 1.7 Hz, 1H), 7.63-7.53 (m, 2H), 7.39-7.26 (m, 3H), 2.47 (s, 3H); LC-MS: 99.95%; 269.9 (M$^+$+1); (column; Kinetex EVO C-18 (50×3.0 mm, 2.6 um); RT 1.17 min. 2.5 mM Aq. NH$_4$OOCH+5% ACN: ACN+5% 2.5 mM Aq.NH$_4$OOCH, 0.8 mL/min).

Synthesis of 7-chloro-11-oxo-10, 11-dihydrodibenzo [b, f] [1, 4] oxazepine-8-carboxylic acid (155): A Common Intermediate

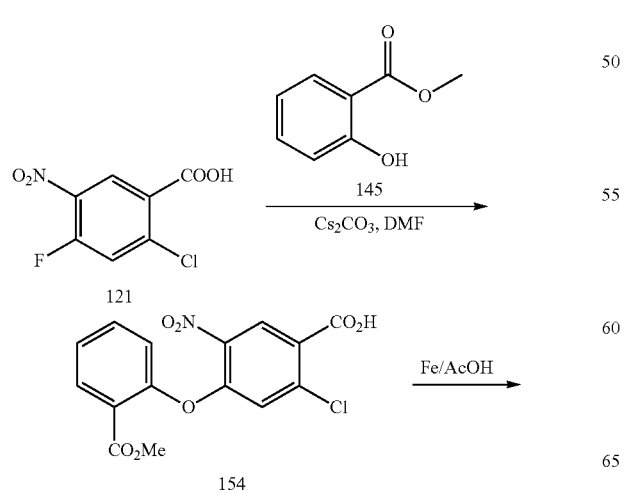

154

Synthesis of 2-chloro-4-(2-(methoxycarbonyl phenoxy)-5-nitrobenzoic acid (154)

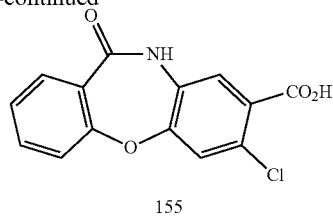

155

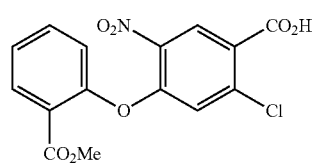

154

To a stirring solution of 2-chloro-4-fluoro-5-nitrobenzoic acid 121 (5 g, 22.76 mmol) in DMF (50 mL) under argon atmosphere were added methyl 2-hydroxybenzoate 145 (3.8 g, 25.04 mmol), cesium carbonate (14.8 g, 45.53 mmol) at 0° C.; warmed to RT and stirred for 16 h. The reaction was monitored by TLC; after completion of the reaction, the reaction mixture was diluted with water (100 mL) and washed with EtOAc (2×100 mL). The pH of the aqueous layer was acidified to ~2 with 2 N HCl and extracted with EtOAc (2×100 mL). The combined organic extracts were dried over sodium sulfate, filtered and concentrated in vacuo to obtain the crude. The crude was purified through silica gel chromatography using 2-10% MeOH/CH$_2$Cl$_2$ to afford compound 154 (6 g, 75%) as an off-white solid. TLC: 10% MeOH/to CH$_2$Cl$_2$ ($R_f$: 0.3). $^1$H-NMR (DMSO-$d_6$, 400 MHz): δ 13.79 (br s, 1H), 8.55 (s, 1H), 8.02 (dd, J=7.8, 1.8 Hz, 1H), 7.81-7.75 (m, 1H), 7.52 (td, J=7.7, 1.1 Hz, 1H), 7.45 (dd, J=8.2, 0.9 Hz, 1H), 6.85 (s, 1H), 3.69 (s, 3H); LC-MS (Agilent Ion trap): 94.80%; 352.7 (M$^+$+1); (Column; X-select CSH C-18 (50×3 mm, 2.5 μm); RT 3.02 min. 2.5% Aq. NH$_4$OAc:ACN; 0.8 mL/min).

Synthesis of 7-chloro-11-oxo-10, 11-dihydrodibenzo [b, f] [1, 4] oxazepine-8-carboxylic acid (155)

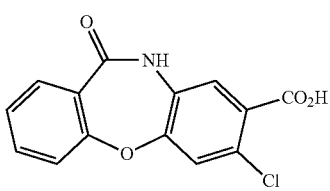

155

To a stirring solution of compound 154 (6 g, 17.09 mmol) in acetic acid (60 mL) was added iron powder (9.5 g, 170.94 mmol) at RT; heated to 100° C. and stirred for 16 h. The reaction was monitored by TLC; after completion of the reaction, the volatiles were removed in vacuo. The residue was diluted with water (50 mL) and the pH was adjusted to ~2 with 6 N HCl. The precipitated solid was filtered and dried in vacuo afford compound 155 (4 g, 81%) as an off-white solid. TLC: 10% MeOH/CH$_2$Cl$_2$ (R$_f$: 0.2); $^1$H-NMR (DMSO-d$_6$, 400 MHz): δ 13.46 (br s, 1H), 10.68 (s, 1H), 7.78 (dd, J=7.8, 1.6 Hz, 1H), 7.68-7.59 (m, 3H), 7.41-7.32 (m, 2H); LC-MS (Agilent Ion trap): 93.44%; 289.9 (M$^+$+1); (Column; X-select CSH C-18 (50×3 mm, 2.5 μm); RT 2.58 min. 2.5% Aq. NH$_4$OAc:ACN; 0.8 mL/min).

Synthesis of 11-oxo-7-(trifluoromethyl)-10, 11-dihydrodibenzo [b, f] [1, 4] oxazepine-8-carboxylic acid (158): A Common Intermediate

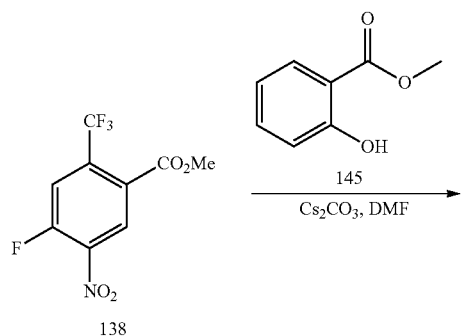

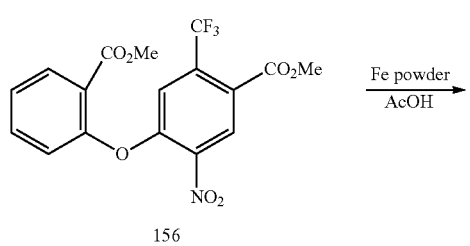

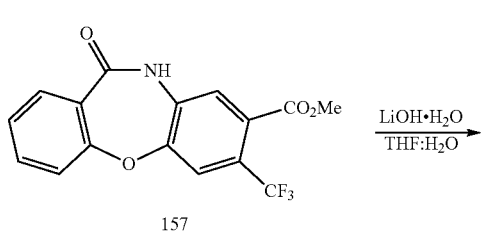

Synthesis of methyl 4-(2-(methoxycarbonyl) phenoxy)-5-nitro-2-(trifluoromethyl) benzoate (156)

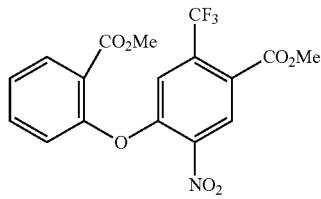

To a stirring solution of compound 138 (3 g, 11.23 mmol) in DMF (50 mL) under argon atmosphere were added methyl 2-hydroxybenzoate 145 (1.7 g, 11.23 mmol), cesium carbonate (5.49 g, 16.85 mmol) at 0° C.; warmed to RT and stirred for 2 h. The reaction was monitored by TLC; after completion of the reaction, the reaction mixture was diluted with water (500 mL) and stirred for 1 h. The precipitated solid was filtered, washed with hexane (2×50 mL) and dried in vacuo to afford compound 156 (3.5 g, 78%) as pale yellow solid. TLC: 30% EtOAc/hexanes (R$_f$: 0.4); $^1$H NMR (400 MHz, DMSO-d$_6$): δ 8.63 (s, 1H), 8.02 (dd, J=7.8, 1.8 Hz, 1H), 7.80 (td, J=7.8, 1.8 Hz, 1H), 7.58-7.48 (m, 2H), 7.10 (s, 1H), 3.90 (s, 3H), 3.68 (s, 3H); LC-MS: 99.37%; 399.9 (M$^+$+1); (column; Ascentis Express C18, (50×3.0 mm, 2.7 μm); RT 2.80 min. 0.025% Aq. TFA+5% ACN: ACN+5% 0.025% Aq. TFA, 1.2 mL/min).

Synthesis of methyl 11-oxo-7-(trifluoromethyl)-10, 11-dihydrodibenzo [b, f] [1, 4] oxazepine-8-carboxylate (157)

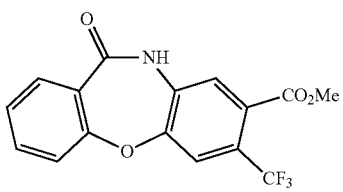

To a stirring solution of compound 156 (3.3 g, 8.27 mmol) in acetic acid (50 mL) were added iron powder (4.6 g, 82.70 mmol) at RT; heated to 80° C. and stirred for 16 h. The reaction was monitored by TLC; after completion of the reaction, the volatiles were removed in vacuo and the residue was diluted with EtOAc (200 mL) and filtered through celite. The filtrate was concentrated in vacuo to obtain the crude. The crude was purified through silica gel flash column chromatography using 30-35% EtOAc/hexanes to afford compound 157 (1.9 g, 68%) as white solid. TLC: 40% EtOAc/hexanes (R$_f$: 0.4). LC-MS: 98.04%; 338.2 (M$^+$+1); (column; Ascentis Express C18, (50×3.0 mm, 2.7 μm); RT 2.55 min. 0.025% Aq. TFA+5% ACN: ACN+5% 0.025% Aq. TFA, 1.2 mL/min).

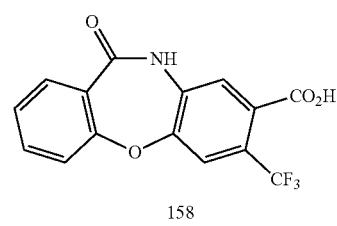

111

Synthesis of 11-oxo-7-(trifluoromethyl)-10, 11-dihydrodibenzo [b, f] [1, 4] oxazepine-8-carboxylic acid (158)

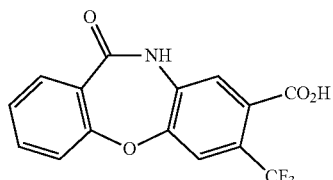

158

To a stirring solution of compound 157 (2.2 g, 6.52 mmol) in THF:$H_2O$ (3:1, 20 mL) was added lithium hydroxide monohydrate (1.37 g, 32.64 mmol) portion wise for 10 min at 0° C.; warmed to RT and stirred for 24 h. The reaction was monitored by TLC; after completion of the reaction, the volatiles were removed in vacuo. The residue was diluted with water (20 mL) and acidified with 6 N HCl to pH~4 and stirred for 2 h. The obtained solid was filtered, and dried in vacuo to obtain compound 158 (1.8 g, 86%) as white solid. TLC: 50% EtOAc/hexanes ($R_f$: 0.1); $^1$H NMR (DMSO-$d_6$, 400 MHz): δ 13.70 (br s, 1H), 10.91 (s, 1H), 7.84 (s, 1H), 7.80 (dd, J=7.8, 1.6 Hz, 1H), 7.70-7.62 (m, 2H), 7.47 (dd, J=8.1, 0.8 Hz, 1H), 7.37 (td, J=7.6, 1.1 Hz, 1H); LC-MS: 99.92%; 321.9 (M−1)$^+$; (column; Kinetex EVO C-18 (50× 3.0 mm, 2.6 um); RT 0.94 min. 2.5 mM Aq. $NH_4OOCH$+5% ACN: ACN+5% 2.5 mM Aq.$NH_4OOCH$, 0.8 mL/min);

Synthesis of 11-oxo-10, 11-dihydro-5H-dibenzo [b, e] [1, 4] diazepine-8-carboxylic acid (163): A Common Intermediate

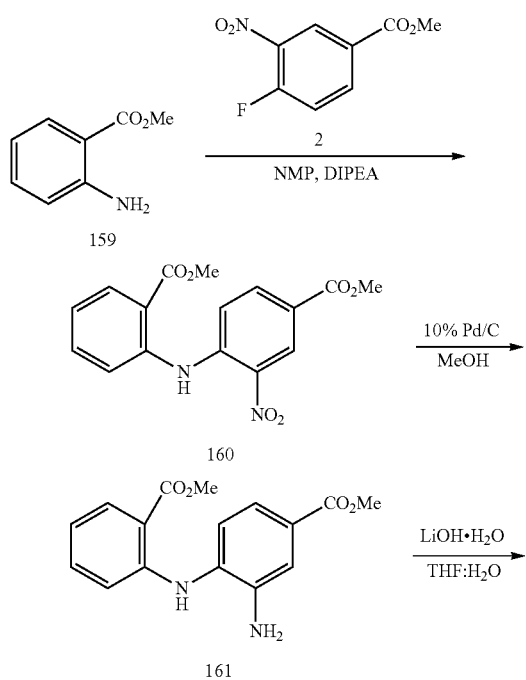

112

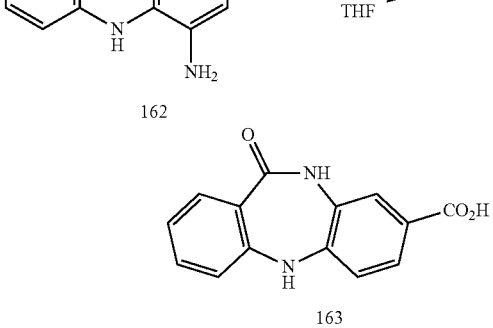

Synthesis of methyl 4-((2-(methoxycarbonyl) phenyl) amino)-3-nitrobenzoate (160)

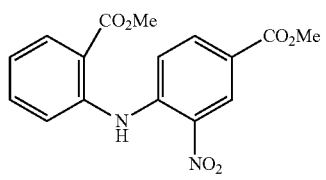

160

To a stirring solution of methyl 2-aminobenzoate 159 (5 g, 33.07 mmol) in N-Methyl-2-pyrrolidone (13 mL) under inert atmosphere were added diisopropylethylamine (18 mL, 103.46 mmol), methyl 4-fluoro-3-nitrobenzoate 2 (9.87 g, 49.21 mmol) at RT; heated to 120° C. in a sealed tube and stirred for 14 h. The reaction was monitored by TLC; after completion of the reaction, the reaction mixture was diluted with diethyl ether (100 mL) and stirred for 1 h. The obtained solid was filtered, washed with EtOAc (100 mL) and dried in vacuo to afford compound 160 (2.9 g, 26%) as yellow solid. TLC: 30% EtOAc/hexanes ($R_f$: 0.4); $^1$H NMR (DMSO-$d_6$, 400 MHz): δ 11.13 (s, 1H), 8.67 (s, 1H), 8.11-7.94 (m, 2H), 7.70-7.62 (m, 2H), 7.58 (d, J=9.0 Hz, 1H), 7.32-7.27 (m, 1H), 3.87 (s, 6H).

Synthesis of methyl 3-amino-4-((2-(methoxycarbonyl) phenyl) amino) benzoate (161)

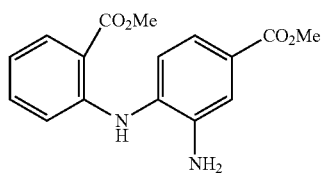

161

To a stirring solution of compound 160 (5 g, 15.15 mmol) in MeOH (150 mL) under inert atmosphere was added 10% Pd/C (2.5 g, 50% wet) at RT and stirred under hydrogen atmosphere (balloon pressure) at RT for 16 h. The reaction was monitored by TLC; after completion of the reaction, the reaction mixture was filtered through celite and washed with 20% MeOH/CH$_2$Cl$_2$ (600 mL). The filtrate was concentrated in vacuo to obtain the crude. The crude washed with diethyl ether:n-pentane (1:2, 30 mL) dried in vacuo to afford compound 161 (2.7 g, 60%) as yellow solid. TLC: 30% EtOAc/hexanes (R$_f$: 0.3); $^1$H NMR (DMSO-d$_6$, 400 MHz): δ 8.92 (s, 1H), 7.91 (dd, J=8.0, 1.6 Hz, 1H), 7.46-7.45 (m, 1H), 7.43-7.36 (m, 1H), 7.21 (s, 2H), 6.95 (dd, J=8.5, 0.6 Hz, 1H), 6.83-6.77 (m, 1H), 5.18 (s, 2H), 3.85 (s, 3H), 3.80 (s, 3H).

Synthesis of 3-amino-4-((2-carboxyphenyl) amino) benzoic acid (162)

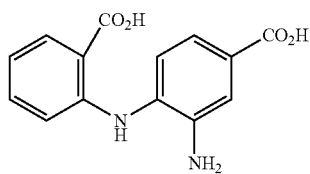

162

To a stirring solution of compound 161 (2.7 g, 9.00 mmol) in THF:H$_2$O (2.5:1, 210 mL) was added lithium hydroxide monohydrate (3.4 g, 81.00 mmol) at RT; heated to 65° C. and stirred for 5 h. The reaction was monitored by TLC; after completion of the reaction, the volatiles were removed in vacuo. The pH of the residue was acidified to ~4 with 2 N HCl. The precipitated solid was filtered, washed with water (20 mL) and dried in vacuo to afford compound 162 (2.4 g, crude) as an off-white solid. TLC: 30% EtOAc/hexanes (R$_f$: 0.1); $^1$H NMR (DMSO-d$_6$, 400 MHz): δ 12.65 (br s, 2H), 9.20 (br s, 1H), 7.90 (dd, J=8.0, 1.6 Hz, 1H), 7.44-7.42 (m, 1H), 7.39-7.35 (m, 1H), 7.20-7.18 (m, 2H), 6.92 (dd, J=8.5, 0.7 Hz, 1H), 6.79-6.75 (m, 1H), 5.08 (br s, 2H).

Synthesis of 11-oxo-10, 11-dihydro-5H-dibenzo [b, e] [1, 4] diazepine-8-carboxylic acid (163)

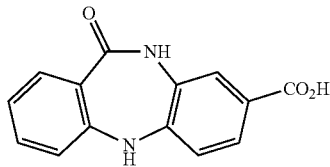

163

To a stirring solution of compound 162 (2.4 g, 8.82 mmol) in THF (80 mL) under inert atmosphere was added CDI (5.8 g, 35.29 mmol) at RT and stirred for 24 h. The reaction was monitored by TLC; after completion of the reaction, the volatiles were removed in vacuo. The pH of the residue was adjusted to ~2 using 2 N HCl. The precipitated solid was filtered, washed with n-pentane (50 mL) and dried in vacuo to afford compound 163 (1.9 g, 85%) as pale green solid. TLC: 10% MeOH/CH$_2$Cl$_2$ (R$_f$: 0.2); $^1$H NMR (DMSO-d$_6$, 400 MHz): δ 12.66 (br s, 1H), 9.93 (s, 1H), 8.26 (s, 1H), 7.70 (d, J=7.9 Hz, 1H), 7.58-7.50 (m, 2H), 7.36 (t, J=7.0 Hz, 1H), 7.02 (dd, J=17.4, 8.2 Hz, 2H), 6.91 (t, J=7.4 Hz, 1H).

Synthesis of 5-methyl-11-oxo-10, 11-dihydro-5H-dibenzo [b, e] [1, 4] diazepine-8-carboxylic acid (177): A Common Intermediate

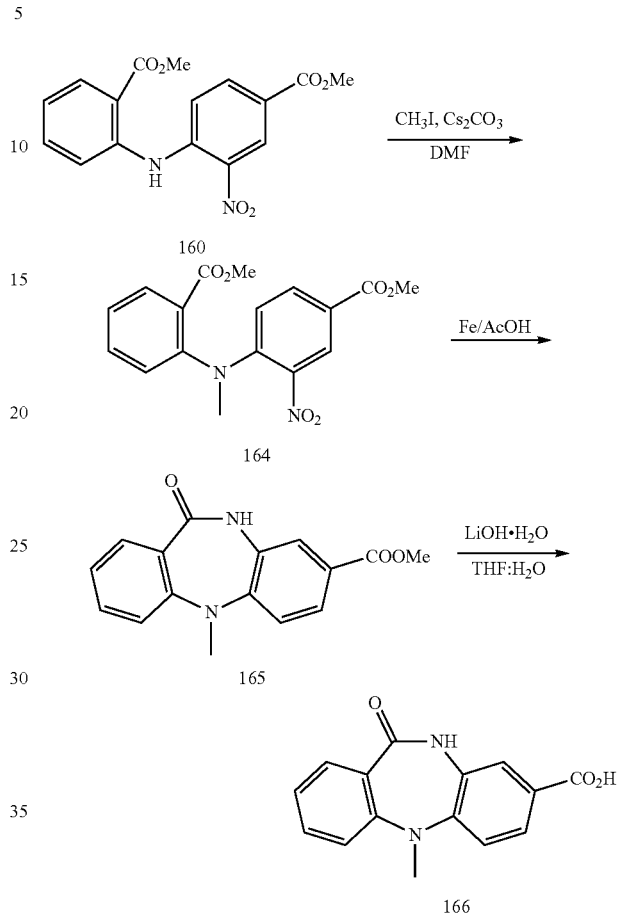

Synthesis of methyl 4-((2-(methoxycarbonyl) phenyl) (methyl) amino)-3-nitrobenzoate (164)

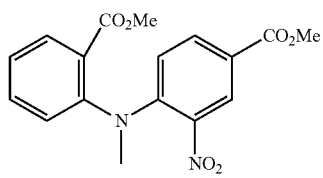

164

To a stirring solution of compound 160 (3 g, 9.09 mmol) in DMF (30 mL) under inert atmosphere were added cesium carbonate (5.9 g, 18.15 mmol), methyl iodide (0.84 mL, 13.59 mmol) at RT and stirred for 6 h. The reaction was monitored by TLC; after completion of the reaction, the reaction mixture was diluted with ice-cold water (60 mL) and extracted with EtOAc (2×100 mL). The combined organic extracts were dried over sodium sulfate, filtered and concentrated in vacuo to obtain the crude. The crude was purified through silica gel column chromatography using 20% EtOAc/hexanes to afford compound 164 (2.73 g, 88%) as yellow solid. TLC: 30% EtOAc/hexanes (R$_f$: 0.4); $^1$H NMR (DMSO-$d_6$, 400 MHz): δ 8.07 (s, 1H), 8.06 (d, J=7.8 Hz, 1H), 7.71 (dd, J=7.8, 1.5 Hz, 1H), 7.62 (t, J=7.3 Hz, 1H), 7.40-7.26 (m, 3H), 3.84 (s, 3H), 3.53 (s, 3H), 3.38 (s, 3H).

Synthesis of methyl 5-methyl-11-oxo-10, 11-dihydro-5H-dibenzo [b, e] [1, 4] diazepine-8-carboxylate (165)

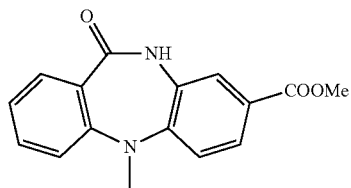

165

To a stirring solution of compound 164 (2.73 g, 7.93 mmol) in acetic acid (36 mL) under inert atmosphere was added iron powder (7 g, 127.2 mmol) at RT; heated to 80° C. and stirred for 4 h. The reaction was monitored by TLC; after completion of the reaction, the reaction mixture was diluted with $CH_2Cl_2$ (50 mL), stirred for 2 h and filtered through celite and the filtrate was concentrated in vacuo to obtain the crude. The crude was dissolved in $CH_2Cl_2$ (200 mL), washed with saturated aqueous $NaHCO_3$ solution (100 mL), brine (100 mL). The organic extract was dried over sodium sulfate, filtered and concentrated in vacuo to afford compound 165 (2 g, 91%) as an off-white solid. TLC: 30% EtOAc/hexanes ($R_f$: 0.4); $^1$H NMR (DMSO-$d_6$, 500 MHz): δ 10.33 (s, 1H), 7.68 (dd, J=8.5, 1.9 Hz, 1H), 7.65-7.61 (m, 2H), 7.50 (t, J=7.8 Hz, 1H), 7.28 (d, J=8.4 Hz, 1H), 7.21 (d, J=8.1 Hz, 1H), 7.10 (t, J=7.4 Hz, 1H), 3.80 (s, 3H), 3.33 (s, 3H).

Synthesis of 5-methyl-11-oxo-10, 11-dihydro-5H-dibenzo [b, e] [1, 4] diazepine-8-carboxylic acid (166)

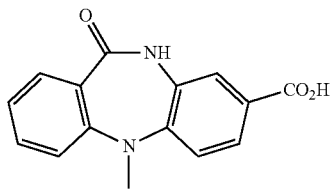

166

To a stirring solution of compound 165 (2 g, 7.09 mmol) in THF:$H_2O$ (1:1, 80 mL) was added lithium hydroxide monohydrate (900 mg, 21.42 mmol) at RT and stirred for 12 h. The reaction was monitored by TLC; after completion of the reaction, the volatiles were removed in vacuo. The pH of the residue was adjusted to ~2 with 2 N HCl. The precipitated solid was filtered and dried in vacuo to afford compound 166 (1.7 g, 89%) as an off-white solid. TLC: 40% EtOAc/hexanes ($R_f$: 0.2); $^1$H NMR (DMSO-$d_6$, 400 MHz): δ 12.82 (br s, 1H), 10.33 (s, 1H), 7.70-7.60 (m, 3H), 7.51 (t, J=7.8 Hz, 1H), 7.27 (d, J=8.5 Hz, 1H), 7.21 (d, J=7.8 Hz, 1H), 7.11 (t, J=7.2 Hz, 1H), 3.32 (s, 3H).

Synthesis of 5-ethyl-11-oxo-10, 11-dihydro-5H-dibenzo [b, e] [1, 4] diazepine-8-carboxylic acid (169): A Common Intermediate

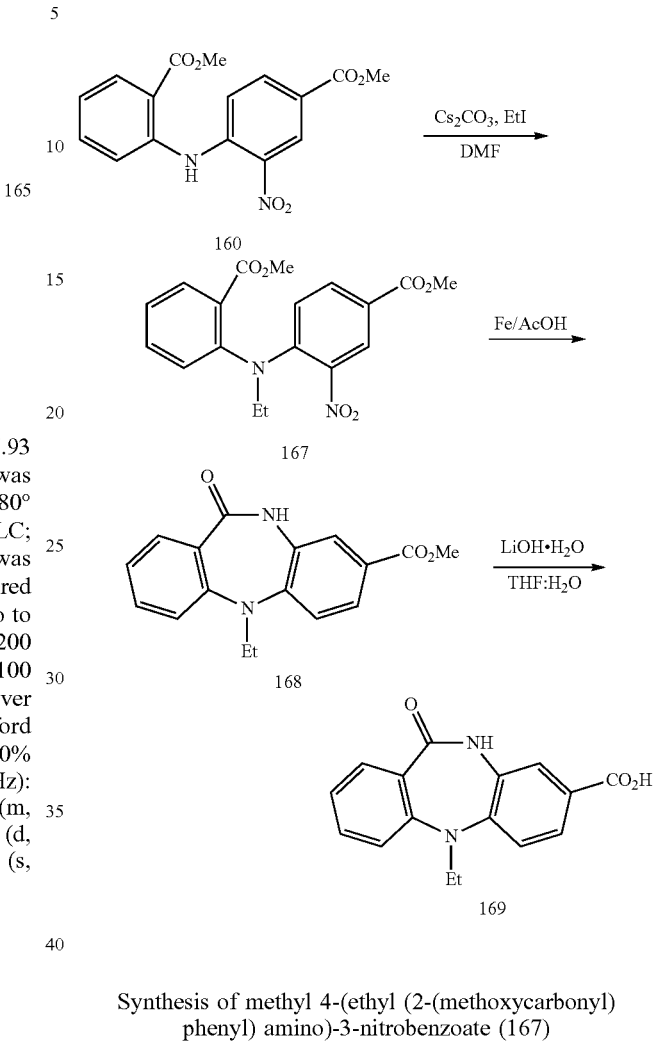

Synthesis of methyl 4-(ethyl (2-(methoxycarbonyl) phenyl) amino)-3-nitrobenzoate (167)

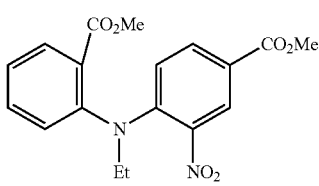

167

To a stirring solution of compound 160 (2.9 g, 8.78 mmol) in DMF (40 mL) under inert atmosphere were added cesium carbonate (6 g, 18.46 mmol), ethyl iodide (1.06 mL, 12.82 mmol) at RT and stirred for 5 h. The reaction was monitored by TLC; after completion of the reaction, the reaction mixture was diluted with ice-cold water (60 mL), extracted with EtOAc (2×100 mL). The combined organic extracts were dried over sodium sulfate, filtered and concentrated in vacuo to obtain the crude which was titurated with n-pentane (20 mL) to afford compound 167 (2.8 g, 89%) as pale yellow solid. TLC: 30% EtOAc/hexanes ($R_f$: 0.5); $^1$H NMR (DMSO-$d_6$, 500 MHz): δ 8.05 (dd, J=9.0, 2.0 Hz, 1H), 8.02

(s, 1H), 7.62-7.57 (m, 2H), 7.45 (d, J=9.0 Hz, 1H), 7.33 (d, J=8.1 Hz, 1H), 7.28 (t, J=7.5 Hz, 1H), 3.94 (q, J=7.1 Hz, 2H), 3.82 (s, 3H), 3.44 (s, 3H), 1.20 (t, J=7.1 Hz, 3H).

Synthesis of methyl 5-ethyl-11-oxo-10, 11-dihydro-5H-dibenzo [b, e] [1, 4] diazepine-8-carboxylate (168)

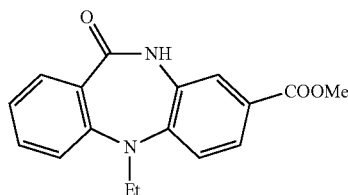

168

To a stirring solution of compound 167 (2.8 g, 7.82 mmol) in acetic acid (40 mL) under inert atmosphere was added iron powder (6.8 g, 125.1 mmol) at RT; heated to 80° C. and stirred for 4 h. The reaction was monitored by TLC; after completion of the reaction, the reaction mixture was diluted with CH$_2$Cl$_2$ (50 mL), stirred for 2 h and filtered through celite. The filtrate was concentrated in vacuo to obtain the crude. The crude was diluted with CH$_2$Cl$_2$ (200 mL), washed with saturated aqueous sodium bicarbonate solution (100 mL) and brine (100 mL). The organic extract was dried over sodium sulfate, filtered and concentrated in vacuo to afford compound 168 (2.2 g, 96%) as an off-white solid. TLC: 30% EtOAc/hexanes (R$_f$: 0.3); $^1$H NMR (DMSO-d$_6$, 500 MHz): δ 10.35 (br s, 1H), 7.70 (dd, J=8.5, 1.9 Hz, 1H), 7.67 (s, 1H), 7.62 (d, J=7.5 Hz, 1H), 7.51 (t, J=8.1 Hz, 1H), 7.29 (d, J=8.4 Hz, 1H), 7.22 (d, J=8.1 Hz, 1H), 7.12 (t, J=7.4 Hz, 1H), 3.31 (s, 5H), 1.11 (t, J=6.9 Hz, 3H).

Synthesis of 5-ethyl-11-oxo-10, 11-dihydro-5H-dibenzo [b, e] [1, 4] diazepine-8-carboxylic acid (169)

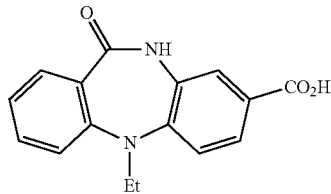

169

To a stirring solution of compound 168 (2.1 g, 7.09 mmol) in THF:H$_2$O (1:1, 60 mL) was added lithium hydroxide monohydrate (890 mg, 21.26 mmol) at RT and stirred for 12 h. The reaction was monitored by TLC; after completion of the reaction, the volatiles were removed in vacuo. The pH of the residue was acidified to ~2 with 2 N HCl. The precipitated solid was filtered, washed with water (50 mL) and dried in vacuo to afford compound 169 (1.6 g, 80%) as an off-white solid. TLC: 30% EtOAc/hexanes (R$_f$: 0.2); $^1$H NMR (DMSO-d$_6$, 400 MHz): δ 12.82 (br s, 1H), 10.33 (s, 1H), 7.69-7.59 (m, 3H), 7.53-7.48 (m, 1H), 7.24 (dd, J=19.7, 8.2 Hz, 2H), 7.12 (t, J=7.5 Hz, 1H), 3.79 (br s, 2H), 1.12 (t, J=7.0 Hz, 3H).

Synthesis of 11-oxo-5-propyl-10, 11-dihydro-5H-dibenzo [b, e] [1, 4] diazepine-8-carboxylic acid (172): A Common Intermediate

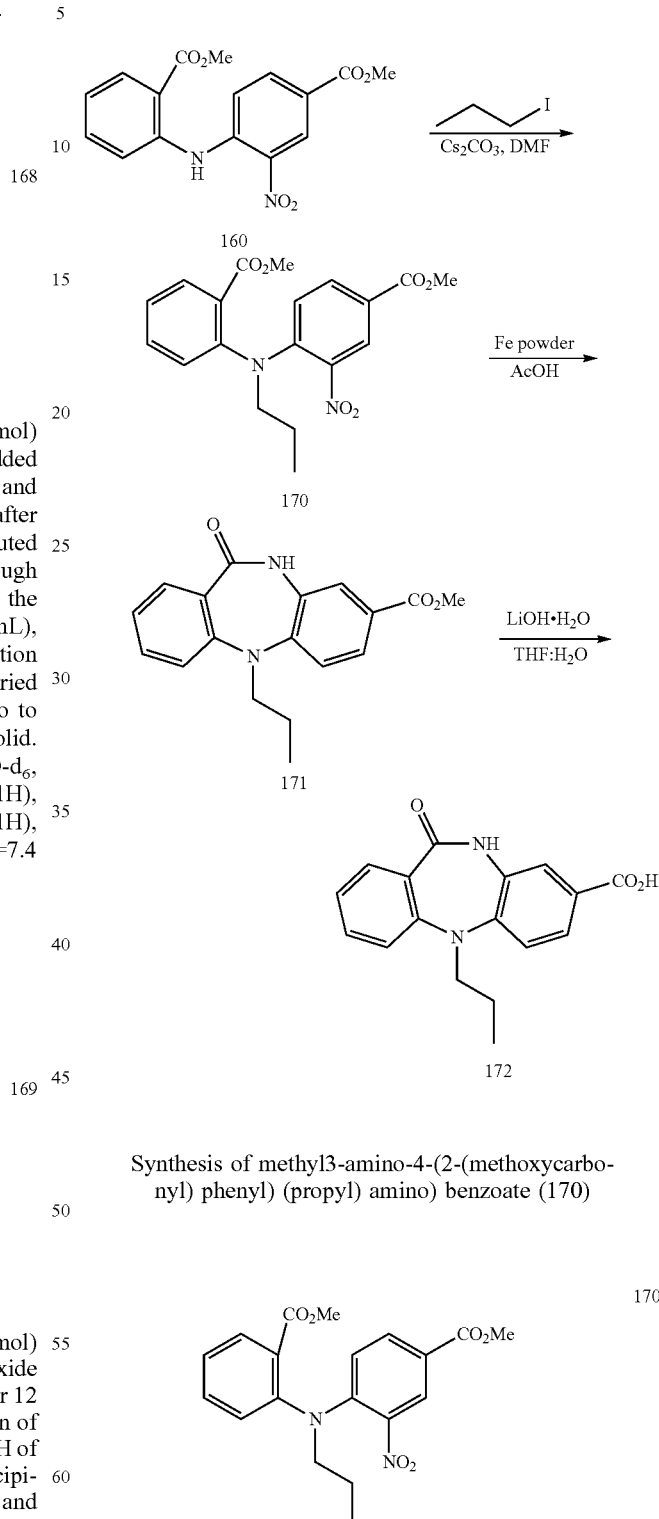

Synthesis of methyl3-amino-4-(2-(methoxycarbonyl) phenyl) (propyl) amino) benzoate (170)

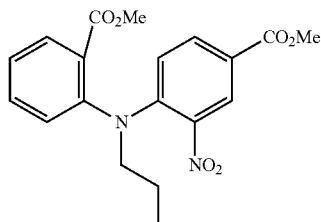

170

To a stirring solution of methyl methyl 4-((2-(methoxycarbonyl) phenyl) amino)-3-nitrobenzoate 160 (2 g, 6.06 mmol) in DMF (50 mL) under argon atmosphere were added cesium carbonate (5.9 g, 18.18 mmol), iodo propane (1.17 mL, 12.12 mmol) at RT; heated to 80° C. and stirred for 14 h. The reaction was monitored by TLC; after completion of the reaction, the reaction mixture was diluted with EtOAc (100 mL) and washed with water (75 mL), brine (75 mL). The organic layer was dried over sodium sulfate, filtered and concentrated in vacuo to obtain the crude. The crude was purified through silica gel column chromatography using 5-10% EtOAc/hexanes to afford compound 170 (1.2 g, 53%) as yellow solid. TLC: 10% EtOAc/hexanes ($R_f$: 0.4); $^1$H NMR (DMSO-$d_6$, 400 MHz): δ 8.07 (dd, J=8.9, 2.1 Hz, 1H), 8.01 (d, J=2.1 Hz, 1H), 7.64-7.54 (m, 2H), 7.48 (d, J=8.9 Hz, 1H), 7.36 (dd, J=8.2, 0.8 Hz, 1H), 7.27 (td, J=7.6, 1.1 Hz, 1H), 3.90-3.80 (m, 5H), 3.41 (s, 3H), 1.73-1.63 (m, 2H), 0.94 (t, J=7.3 Hz, 3H).

Synthesis of methyl 11-oxo-5-propyl-10, 11-dihydro-5H-dibenzo [b, e] [1,4] diazepine-8-carboxylate (171)

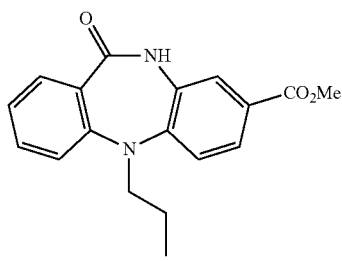

171

To a stirring solution of compound 170 (1.2 g, 3.22 mmol) in AcOH (12 mL) under argon atmosphere was added Iron powder (2.8 g, 51.6 mmol) at RT and heated to 80° C. and stirred for 4 h. The reaction was monitored by TLC; after completion of the reaction, the reaction mixture was diluted with $CH_2Cl_2$ filtered through celite and washed with $CH_2Cl_2$ (100 mL). The filtrate was concentrated in vacuo. The residue was dissolved in $CH_2Cl_2$ washed with saturated sodium bicarbonate solution (50 mL), brine solution (50 mL). The organic layer was dried over sodium sulfate, filtered and concentrated in vacuo to obtain the crude. The crude was triturated with diethyl ether:pentane (1:1, 50 mL) filtered finally washed with pentane (30 mL) to afford compound 171 (700 mg, 70%) as off white solid. TLC: 20% EtOAc/hexanes ($R_f$: 0.3); $^1$H NMR (DMSO-$d_6$, 400 MHz): δ 10.34 (s, 1H), 7.71-7.65 (m, 2H), 7.61 (dd, J=7.8, 1.6 Hz, 1H), 7.53-7.46 (m, 1H), 7.30 (d, J=8.4 Hz, 1H), 7.23 (d, J=8.0 Hz, 1H), 7.15-7.09 (m, 1H), 3.81 (s, 3H), 3.75-3.65 (br s, 2H), 1.54-1.55 (m, 2H), 0.87 (t, J=7.3 Hz, 3H); LC-MS: 93.58%; 310.9 (M$^+$+1); (column; Ascentis Express C-18 (50×3.0 mm, 2.7 μm); RT 2.45 min. 0.025% Aq. TFA+5% ACN: ACN+5% 0.025% Aq TFA, 1.2 mL/min).

Synthesis of 11-oxo-5-propyl-10, 11-dihydro-5H-dibenzo [b, e] [1, 4] diazepine-8-carboxylic acid (172)

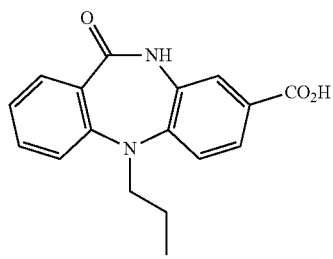

172

To a stirring solution of compound 171 (700 mg, 2.25 mmol) in THF:$H_2O$ (1:1, 20 mL) was added lithium hydroxide monohydrate (284 mg, 6.76 mmol) at RT; and stirred for 16 h. The reaction was monitored by TLC; after completion of the reaction, the volatiles were removed in vacuo. The pH of the residue was acidified to ~4 with 1 N HCl and stirred for 30 min. The precipitated solid was filtered, washed with water (30 mL) and dried in vacuo to afford compound 172 (550 mg, 82%) as an off-white solid. TLC: 20% EtOAc/hexanes ($R_f$: 0.1); $^1$H NMR (DMSO-$d_6$, 500 MHz): 12.81 (br s, 1H), 10.30 (s, 1H), 7.68-7.56 (m, 3H), 7.52-7.45 (m, 1H), 7.23 (dd, J=9.0, 8.1 Hz, 2H), 7.09 (t, J=7.4 Hz, 1H), 3.71 (br d, J=17.6 Hz, 2H), 1.53-1.46 (m, 2H), 0.86 (t, J=7.4 Hz, 3H); LC-MS: 96.38%; 296.9 (M$^+$+1); (column; Ascentis Express C-18 (50×3.0 mm, 2.7 μm); RT 2.14 min. 0.025% Aq. TFA+5% ACN: ACN+5% 0.025% Aq TFA, 1.2 mL/min).

Synthesis of 5-butyl-11-oxo-10, 11-dihydro-5H-dibenzo [b, e] [1, 4] diazepine-8-carboxylic acid (176): A Common Intermediate

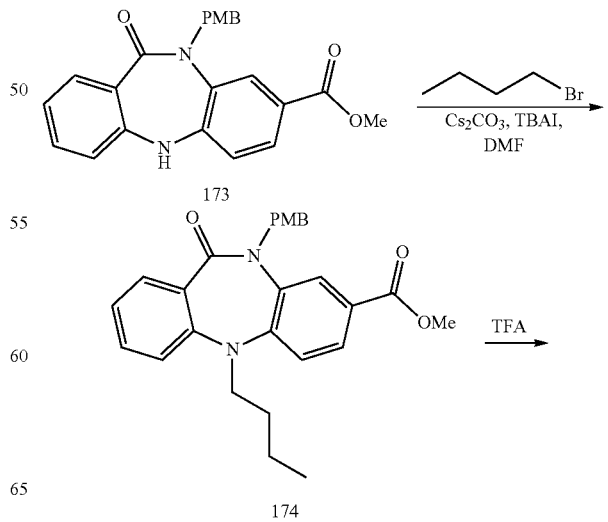

173

174

-continued

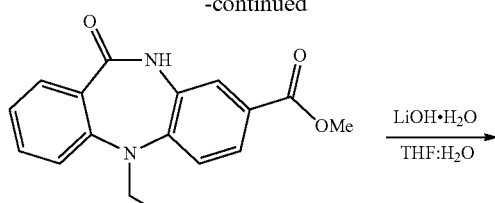

175

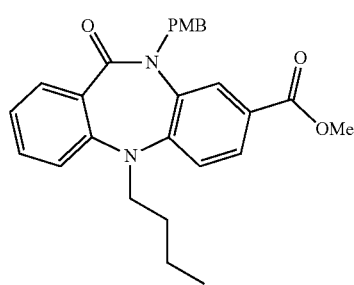

176

Synthesis of methyl 5-butyl-10-(4-methoxybenzyl)-11-oxo-10, 11-dihydro-5H-dibenzo [b, e] [1, 4] diazepine-8-carboxylate (174)

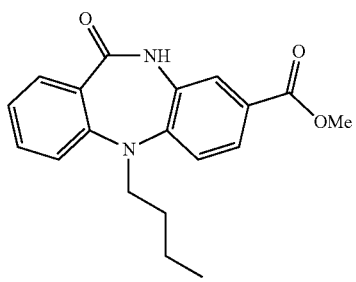

To a stirring solution of methyl 10-(4-methoxybenzyl)-11-oxo-10,11-dihydro-5H-dibenzo [b, e] [1, 4] diazepine-8-carboxylate 173 (500 mg, 1.28 mmol) in DMF (10 mL) under argon atmosphere were added cesium carbonate (1.25 g, 3.86 mmol), TBAI (cat 10 mg), bromo butane (1.4 mL, 12.8 mmol) in a sealed tube at RT; heated to 110° C. and stirred for 24 h. The reaction was monitored by TLC; after completion of the reaction, the reaction mixture was diluted with water and extracted with EtOAc (2×50 mL). The combined organic layer was washed with water and dried over sodium sulfate, filtered and concentrated in vacuo to obtain the crude. The crude was purified through silica gel column chromatography using 1% EtOAc/CH$_2$Cl$_2$ to afford compound 174 (300 mg, 28%) as an off white solid. TLC: 5% EtOAc/CH$_2$Cl$_2$ (R$_f$: 0.6); $^1$H NMR (400 MHz, DMSO-d$_6$): δ 7.96 (d, J=1.9 Hz, 1H), 7.69 (dd, J=8.5, 1.9 Hz, 1H), 7.59 (dd, J=7.7, 1.6 Hz, 1H), 7.48-7.42 (m, 1H), 7.33 (d, J=8.5 Hz, 1H), 7.21 (d, J=8.0 Hz, 1H), 7.18-7.09 (m, 3H), 6.79 (d, J=8.8 Hz, 2H), 5.60 (d, J=15.6 Hz, 1H), 4.88 (d, J=15.6 Hz, 1H), 3.80 (s, 3H), 3.71-3.70 (m, 1H), 3.68 (s, 3H), 3.66-3.60 (m, 1H), 1.56-1.49 (m, 1H), 1.41-1.23 (m, 3H), 0.82 (t, J=7.3 Hz, 3H); LC-MS: 91.60%; 445.2 (M++1); (column; Ascentis Express C-18 (50×3.0 mm, 2.7 μm); RT 3.04 min; 0.025% Aq. TFA+5% ACN: ACN+5% 0.025% Aq TFA, 1.2 mL/min).

Synthesis of methyl 5-butyl-11-oxo-10, 11-dihydro-5H-dibenzo [b, e] [1, 4] diazepine-8-carboxylate (175)

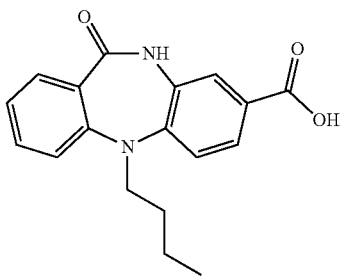

To a stirring solution of methyl 5-butyl-10-(4-methoxybenzyl)-11-oxo-10, 11-dihydro-5H-dibenzo [b, e] [1, 4] diazepine-8-carboxylate 174 (300 mg, 0.67 mmol) in trifluoroacetic acid (2 mL) at RT; heated to 60° C. and stirred for 3 h. The reaction was monitored by TLC; after completion of the reaction, the volatiles were removed in vacuo. The residue was diluted with saturated sodium bicarbonate solution (30 mL) and extracted with EtOAc (2×25 mL). The combined organic layer was washed with water and dried over sodium sulfate, filtered and concentrated in vacuo to afford compound 175 (200 mg crude) as an off white solid. TLC: 5% EtOAc/CH$_2$Cl$_2$ (R$_f$: 0.2); $^1$H NMR (DMSO-d$_6$, 400 MHz): δ 10.32 (br s, 1H), 7.71-7.64 (m, 2H), 7.61 (dd, J=7.7, 1.6 Hz, 1H), 7.53-7.45 (m, 1H), 7.31 (d, J=8.5 Hz, 1H), 7.24 (d, J=7.9 Hz, 1H), 7.15-7.09 (m, 1H), 3.81 (s, 3H), 3.77-3.58 (m, 2H), 1.58-1.44 (m, 2H), 1.39-1.29 (m, 2H), 0.82 (t, J=7.3 Hz, 3H); LC-MS: 89.47%; 325.3 (M$^+$+1); (column; X Select CSH C-18, (50×3.0 mm, 2.5 μm); RT 4.26 min; 2.5 mM Aq. NH4OOCH:ACN, 0.8 mL/min).

Synthesis of 5-butyl-11-oxo-10, 11-dihydro-5H-dibenzo [b, e] [1, 4] diazepine-8-carboxylic acid (176)

To a stirring solution of compound 175 (200 mg, 0.61 mmol) in THF:H$_2$O (1:1, 10 mL) was added lithium hydroxide monohydrate (78 mg, 1.85 mmol) at RT; heated to 60° C. and stirred for 2.5 h. The reaction was monitored by TLC; after completion of the reaction, the volatiles were removed in vacuo. The pH of the residue was acidified to ~4 with 1 N HCl and stirred for 10 min. The precipitated solid was filtered, washed with water (30 mL), ether (20 mL) and pentane (20 mL) and dried in vacuo to afford compound 176 (110 mg, 58%) as an off-white solid. TLC: 30% EtOAc/hexanes ($R_f$: 0.1); $^1$H NMR (DMSO-d$_6$, 400 MHz): δ 12.82 (br s, 1H), 10.30 (s, 1H), 7.69-7.61 (m, 3H), 7.54-7.46 (m, 1H), 7.29-7.23 (m, 2H), 7.11 (t, J=7.2 Hz, 1H), 3.86-3.64 (m, 2H), 1.55-1.43 (m, 2H), 1.40-1.29 (m, 2H), 0.82 (t, J=7.3 Hz, 3H); LC-MS: 99.00%; 311.0 (M$^+$+1); (column; Ascentis Express C-18 (50×3.0 mm, 2.7 μm); RT 2.28 min. 0.025% Aq. TFA+5% ACN: ACN+5% 0.025% Aq TFA, 1.2 mL/min).

Synthesis of 5-isobutyl-11-oxo-10, 11-dihydro-5H-dibenzo [b, e] [1, 4] diazepine-8-carboxylic acid (185): A Common Intermediate

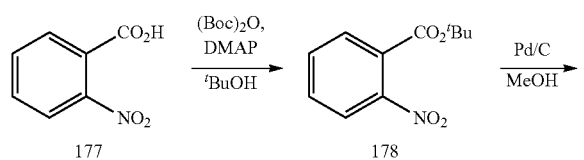

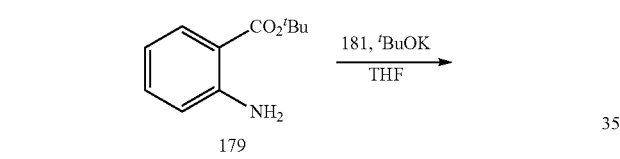

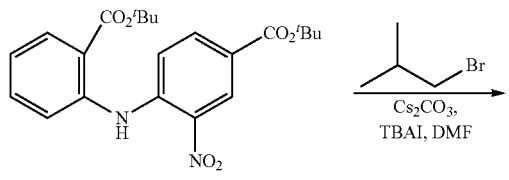

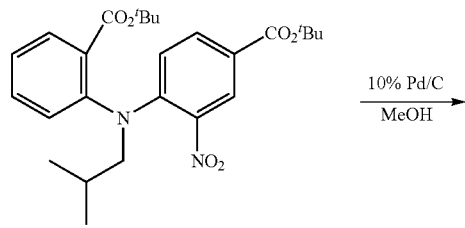

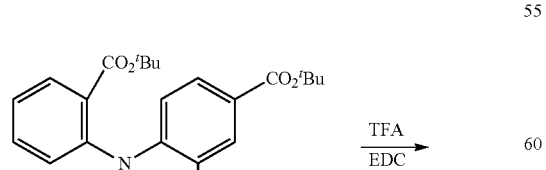

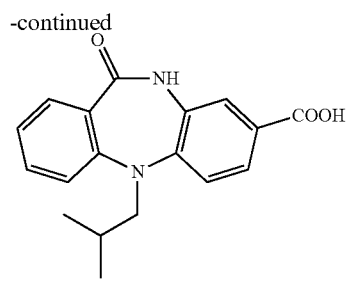

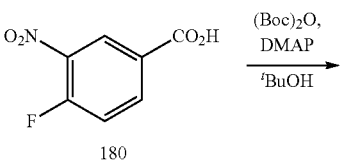

Synthesis of tert-butyl 2-nitrobenzoate (178)

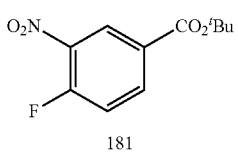

To a stirring solution of 2-nitrobenzoic acid 177 (20 g, 119.67 mmol) t-butanol (540 mL) under argon atmosphere were added Boc-anhydride (78.35 g, 359.02 mmol), DMAP (2.90 g, 23.93 mmol) at 0° C.; warmed to RT and stirred for 24 h. The reaction was monitored by TLC; after completion of the reaction, the volatiles were removed in vacuo. The residue was diluted with EtOAc (200 mL), washed with water (100 mL), brine (150 mL). The organic extract was dried over sodium sulfate, filtered and concentrated in vacuo to obtain the crude. The crude was purified through silica gel column chromatography using 2-5% EtOAc/hexanes to afford compound 178 (19 g, 71%) as colorless syrup. TLC: 10% EtOAc/hexanes ($R_f$: 0.6); $^1$H-NMR (DMSO-d$_6$, 500 MHz): δ 8.01 (d, J=7.8 Hz, 1H), 7.85-7.75 (m, 3H), 1.50 (s, 9H);

Synthesis of tert-butyl 2-aminobenzoate (179)

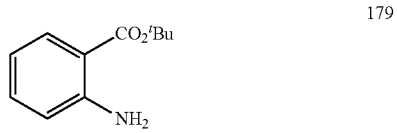 [SMILES: CC(C)(C)OC(=O)c1ccccc1[N+](=O)[O-]]

To a stirring solution of compound 178 (19 g, 85.11 mmol) in MeOH (200 mL) under inert atmosphere was added 10% Pd/C (10 g, 50% wet) at RT and stirred under hydrogen atmosphere (balloon pressure) at RT for 18 h. The reaction was monitored by TLC; after completion of the reaction, the reaction mixture was filtered through celite and washed with MeOH (100 mL). The filtrate was concentrated in vacuo to afford compound 179 (17 g, crude) as colorless syrup. TLC: 10% EtOAc/hexanes ($R_f$: 0.8); $^1$H NMR (400 MHz, DMSO-$d_6$): δ 7.64 (dd, J=8.1, 1.6 Hz, 1H), 7.23-7.18 (m, 1H), 6.73 (dd, J=8.4, 0.9 Hz, 1H), 6.56 (br s, 2H), 6.51-6.47 (m, 1H), 1.53 (s, 9H);

Synthesis of tert-butyl 4-fluoro-3-nitrobenzoate (181)

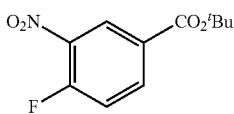

181

To a stirring solution of 4-fluoro-3-nitrobenzoic acid 180 (10 g, 54.05 mmol) t-butanol (270 mL) under argon atmosphere were added Boc-anhydride (35 g, 162.16 mmol), DMAP (1.3 g, 10.81 mmol) at 0° C.; warmed to RT and stirred for 16 h. The reaction was monitored by TLC; after completion of the reaction, the volatiles were removed in vacuo. The residue was diluted with EtOAc (150 mL), washed with water (75 mL), brine (100 mL). The organic extract was dried over sodium sulfate, filtered and concentrated in vacuo to obtain the crude. The crude was purified through silica gel column chromatography (100-200 mesh) using 2-5% EtOAc/hexanes to afford compound 181 (14 g, crude) as colorless syrup. TLC: 10% EtOAc/hexanes ($R_f$: 0.8);
$^1$H NMR (400 MHz, DMSO-$d_6$): δ 8.52 (dd, J=7.3, 2.3 Hz, 1H), 8.30-8.26 (m, 1H), 7.72 (dd, J=11.0, 8.7 Hz, 1H), 1.47 (s, 9H);

Synthesis of tert-butyl 4-((2-(tert-butoxycarbonyl) phenyl) amino)-3-nitrobenzoate (182)

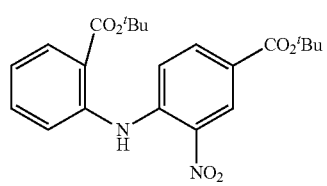

182

To a stirring solution of compound 181 (8 g, 42.42 mmol) in dry THF (150 mL) under argon atmosphere was added potassium tertbutoxide (82.9 mL, 82.90 mmol, 1.0 M sol. In THF) at 0° C. and stirred for 45 min; added compound 179 (15 g, 62.23 mmol) at 0° C.; warmed to RT and stirred for 16 h. The reaction was monitored by TLC; after completion of the reaction, the reaction mixture was diluted with ice-cold water (100 mL) and extracted with EtOAc (2×100 mL). The combined organic extracts were washed with water (100 mL), brine (100 mL) and dried over sodium sulfate, filtered and concentrated in vacuo to obtain the crude. The crude was purified through silica gel column chromatography (100-200 mesh) using 100% EtOAc to afford compound 182 (6 g 34%) as yellow liquid. TLC: 10% EtOAc/hexanes ($R_f$ 0.8); $^1$H NMR (500 MHz, DMSO-$d_6$): δ 10.94 (s, 1H), 8.60 (d, J=2.0 Hz, 1H), 8.00-7.92 (m, 2H), 7.65-7.54 (m, 2H), 7.46 (d, J=9.0 Hz, 1H), 7.30-7.25 (m, 1H), 1.56-1.49 (m, 18H);

Synthesis of tert-butyl 4-((2-(tert-butoxycarbonyl) phenyl) (isobutyl)amino)-3-nitrobenzoate (183)

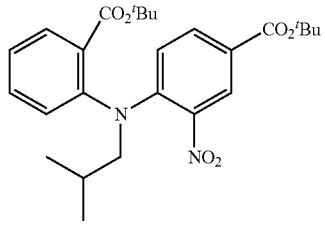

183

To a stirring solution of compound 182 (4 g, 9.65 mmol) in DMF (100 mL) under argon atmosphere were added cesium carbonate (6.28 g, 19.32 mmol), TBAI (713 mg, 1.93 mmol), 1-bromo-2-methylpropane (8.4 mL, 48.66 mmol) in a sealed tube at RT; heated to 85° C. and stirred for 16 h. The reaction was monitored by TLC; after 16 h, the reaction mixture was diluted EtOAc (2×75 mL) and washed with water (150 mL), brine (100 mL). The organic extract was dried over sodium sulfate, filtered and concentrated in vacuo to obtain the crude. The crude was purified through silica gel column chromatography (100-200 mesh) using 2-5% EtOAc/hexanes to afford compound 183 (1 g, 22%) as colorless syrup. TLC: 10% EtOAc/hexanes ($R_f$: 0.5); $^1$H NMR (400 MHz, DMSO-$d_6$): δ 7.98 (dd, J=8.9, 2.1 Hz, 1H), 7.90 (d, J=2.1 Hz, 1H), 7.59-7.52 (m, 1H), 7.46 (d, J=8.9 Hz, 1H), 7.40 (dd, J=7.8, 1.6 Hz, 1H), 7.33 (dd, J=8.2, 0.8 Hz, 1H), 7.18 (td, J=7.5, 1.0 Hz, 1H), 3.67 (d, J=7.4 Hz, 2H), 2.13-2.05 (m, 1H), 1.49 (s, 9H), 1.14 (s, 9H), 0.98 (d, J=6.7 Hz, 6H);

Synthesis of tert-butyl 3-amino-4-((2-(tert-butoxy-carbonyl) phenyl) (isobutyl) amino) benzoate (184)

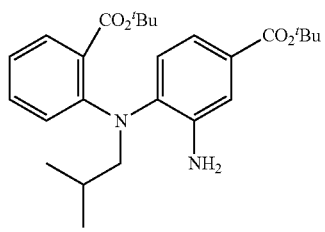

184

To a stirring solution of compound 183 (1.5 g, 3.19 mmol) in MeOH (100 mL) under inert atmosphere was added 10% Pd/C (1.5 g, 50% wet) at RT and stirred under hydrogen atmosphere (balloon pressure) at RT for 5 h. The reaction was monitored by TLC; after completion of the reaction, the reaction mixture was filtered through celite and washed with MeOH (100 mL). The filtrate was concentrated in vacuo to obtain the crude. The crude was purified through silica gel column chromatography using 5-10% EtOAc/hexanes to afford compound 184 (1.4 g, quantitative) as colorless syrup. TLC: 10% EtOAc/hexanes ($R_f$: 0.5); $^1$H NMR (500 MHz, DMSO-$d_6$): δ 7.42 (dd, J=7.5, 1.2 Hz, 1H), 7.35-7.29 (m, 1H), 7.21 (d, J=2.3 Hz, 1H), 7.10 (dd, J=8.4, 2.0 Hz, 1H), 7.02 (t, J=7.2 Hz, 1H), 6.93 (dd, J=11.6, 8.1 Hz, 2H), 5.13 (s, 2H), 3.17 (d, J=7.5 Hz, 2H), 1.86-1.8-0 (m, 1H), 1.49 (s, 9H), 1.42 (s, 9H), 0.83 (d, J=7.0 Hz, 6H);

Synthesis of 5-isobutyl-11-oxo-10, 11-dihydro-5H-dibenzo [b, e] [1, 4] diazepine-8-carboxylic acid (185)

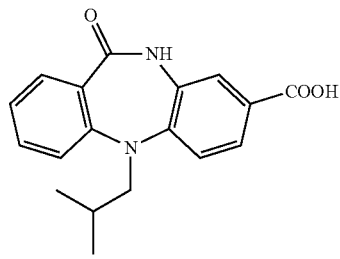

To a stirring solution of compound 184 (1 g, 2.27 mmol) in 1, 2-dichloroethane (25 mL) under inert atmosphere was added trifluoroacetic acid (3.5 mL, 45.55 mmol) at 0° C.; heated to 80° C. and stirred for 9 h. The reaction was monitored by TLC; after completion of the reaction, the volatiles were removed in vacuo. The pH of the residue was adjusted to ~8 using saturated sodium bicarbonate solution (10 mL), washed with EtOAc (2×75 mL). The pH of the aqueous layer was adjusted to ~1 with 1 N HCl and extracted with EtOAc (2×50 mL). The combined organic extracts were dried over sodium sulfate, filtered and concentrated in vacuo to afford compound 185 (500 mg, 60%) as brown solid. TLC: 30% EtOAc/hexanes ($R_f$: 0.2); $^1$H NMR (400 MHz, DMSO-$d_6$): δ 12.81 (br s, 1H), 10.31 (s, 1H), 7.69-7.59 (m, 3H), 7.52-7.45 (m, 1H), 7.28 (d, J=8.4 Hz, 1H), 7.23 (d, J=7.8 Hz, 1H), 7.14-7.07 (m, 1H), 3.63-3.46 (m, 2H), 1.83-1.70 (m, 1H), 0.89 (d, J=6.5 Hz, 6H);

Synthesis of 5-allyl-11-oxo-10, 11-dihydro-5H-dibenzo [b, e] [1, 4] diazepine-8-carboxylic acid (190): A Common Intermediate

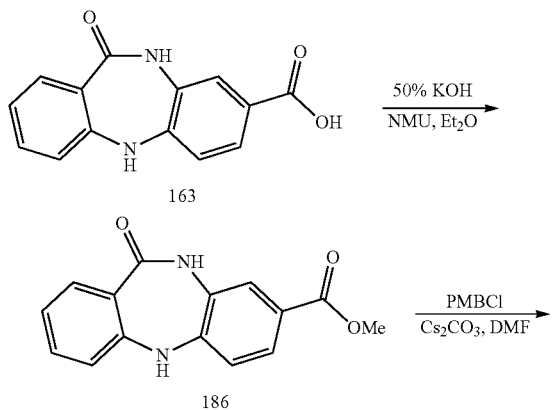

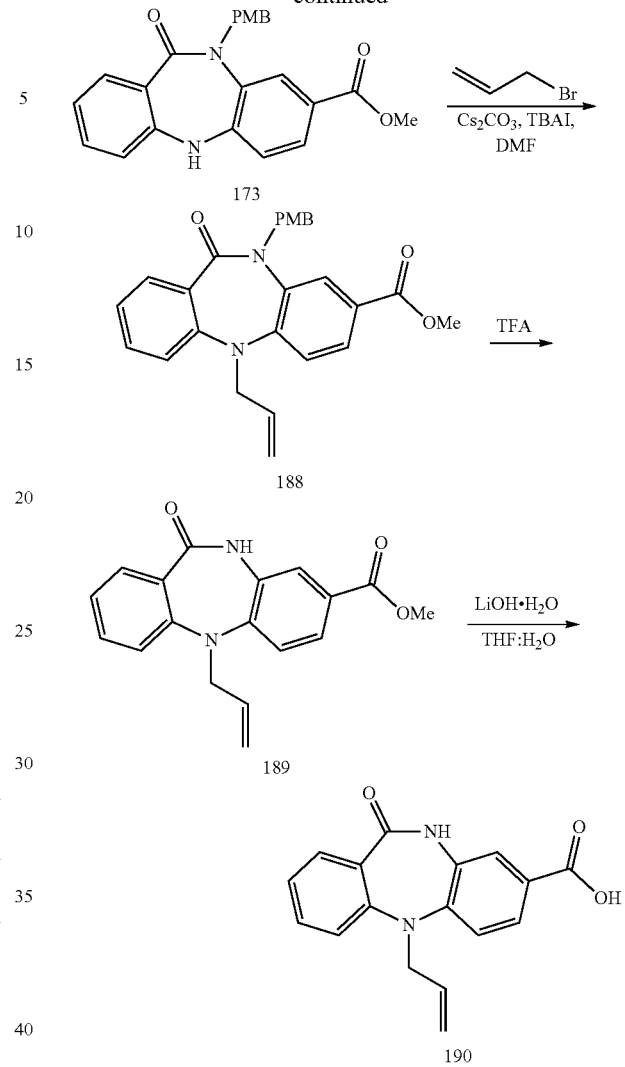

Synthesis of methyl 11-oxo-10, 11-dihydro-5H-dibenzo [b, e] [1, 4] diazepine-8-carboxylate (186)

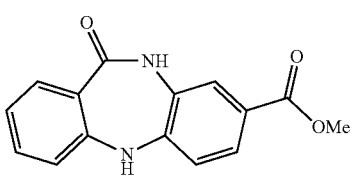

To a stirring solution of 11-oxo-10, 11-dihydro-5H-dibenzo [b, e] [1, 4] diazepine-8-carboxylic acid 163 (4.5 g, 17.71 mmol) in 50% MeOH/CH$_2$Cl$_2$ under argon atmosphere was added diazomethane in diethyl ether (freshly prepared by addition of N-nitrosomethyl urea (9.1 g, 88.58 mmol) to mixture of 50% KOH solution (100 mL) and diethylether (200 mL) at 0° C.) at 0° C.; warmed to RT and stirred for 3 h. The reaction was monitored by TLC; after completion of the reaction, the volatiles were removed in vacuo to obtain the crude. The crude was purified through silica gel column chromatography using 2% MeOH/CH$_2$Cl$_2$ to afford compound 186 (3 g, 64%) as an off white solid. TLC: 5% MeOH/CH$_2$Cl$_2$ (R$_f$: 0.6); $^1$H NMR (400 MHz, DMSO-d$_6$): δ 9.94 (s, 1H), 8.32 (s, 1H), 7.71 (dd, J=7.9, 1.6 Hz, 1H), 7.60-7.53 (m, 2H), 7.38-7.34 (m, 1H), 7.06 (d, J=8.3 Hz, 1H), 7.02-6.98 (m, 1H), 6.95-6.89 (m, 1H), 3.79 (s, 3H); LC-MS: 87.13%; 269.0 (M$^+$+1); (column; Ascentis Express C-18 (50×3.0 mm, 2.7 μm); RT 2.05 min. 0.025% Aq. TFA+5% ACN: ACN+5% 0.025% Aq TFA, 1.2 mL/min).

Synthesis of methyl 10-(4-methoxybenzyl)-11-oxo-10, 11-dihydro-5H-dibenzo [b, e] [1, 4] diazepine-8-carboxylate (173)

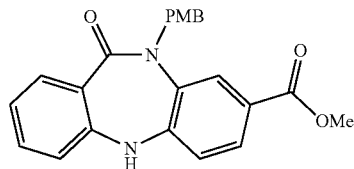

173

To a stirring solution of methyl 11-oxo-10, 11-dihydro-5H-dibenzo [b, e] [1, 4] diazepine-8-carboxylate 186 (3 g, 11.19 mmol) in DMF (30 mL) under inert atmosphere were added Cs$_2$CO$_3$ (4.3 g, 13.43 mmol), PMBCl (2.1 g, 13.43 mmol) at 0° C.; warmed to RT and stirred for 16 h. The reaction was monitored by TLC; after completion of the reaction, the reaction mixture was diluted with ice cold water and extracted with EtOAc (2×25 mL). The combined organic extracts were washed with water (100 ml) and dried over sodium sulfate, filtered and concentrated in vacuo to obtain the crude. The crude was purified through silica gel column chromatography using 2% EtOAc/CH$_2$Cl$_2$ to afford compound 173 (1.7 g, 40%) as an off white solid. TLC: 5% EtOAc/CH$_2$Cl$_2$ (R$_f$: 0.6); $^1$H NMR (400 MHz, DMSO-d$_6$): δ 8.32 (s, 1H), 7.85 (d, J=1.8 Hz, 1H), 7.68 (dd, J=7.8, 1.4 Hz, 1H), 7.62 (dd, J=8.3, 1.9 Hz, 1H), 7.41-7.35 (m, 1H), 7.20-7.18 (m, 3H), 7.09 (d, J=7.5 Hz, 1H), 7.05-6.99 (m, 1H), 6.84 (d, J=8.7 Hz, 2H), 5.16 (s, 2H), 3.77 (s, 3H), 3.70 (s, 3H); LC-MS: 94.69%; 389.1 (M$^+$+1); (column; Ascentis Express C-18 (50×3.0 mm, 2.7 μm); RT 2.55 min. 0.025% Aq. TFA+5% ACN: ACN+5% 0.025% Aq TFA, 1.2 mL/min).

Synthesis of methyl 5-allyl-10-(4-methoxybenzyl)-11-oxo-10, 11-dihydro-5H-dibenzo [b, e] [1, 4] diazepine-8-carboxylate (188)

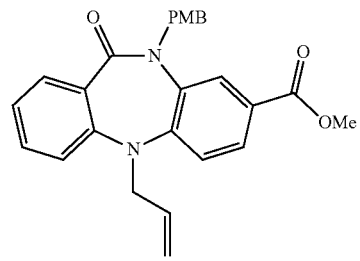

188

To a stirring solution of methyl 10-(4-methoxybenzyl)-11-oxo-10, 11-dihydro-5H-dibenzo [b, e] [1, 4] diazepine-8-carboxylate 173 (600 mg, 1.54 mmol) in DMF (10 mL) under argon atmosphere were added cesium carbonate (1.5 g, 4.63 mmol), TBAI (0.057 mg, 0.15 mmol), 3-bromoprop-1-ene (1.3 mL, 15.4 mmol) in a sealed tube at RT; heated to 120° C. and stirred for 24 h. The reaction was monitored by TLC; after completion of the reaction, the reaction mixture was diluted with ice cold water (50 mL) and extracted with EtOAc (2×25 mL). The combined organic extracts were washed with water (100 mL) and dried over sodium sulfate, filtered and concentrated in vacuo to obtain the crude. The crude was purified through silica gel column chromatography using 2% EtOAc/hexanes to afford compound 188 (555 mg, 84%) as an off-white solid. TLC: 5% EtOAc/hexanes (R$_f$: 0.6); $^1$H NMR (DMSO-d$_6$, 400 MHz): δ 7.95 (d, J=1.9 Hz, 1H), 7.67 (dd, J=8.5, 1.9 Hz, 1H), 7.61 (dd, J=7.7, 1.6 Hz, 1H), 7.48-7.42 (m, 1H), 7.32 (d, J=8.7 Hz, 1H), 7.23-7.10 (m, 4H), 6.81 (d, J=8.7 Hz, 2H), 5.71-5.57 (m, 2H), 5.30 (dd, J=17.3, 1.5 Hz, 1H), 5.12 (dd, J=10.4, 1.4 Hz, 1H), 4.91 (d, J=15.6 Hz, 1H), 4.41 (t, J=5.7 Hz, 2H), 3.79 (s, 3H), 3.69 (s, 3H); LC-MS: 96.23%; 429.1 (M$^+$+1); (column; Ascentis Express C-18 (50×3.0 mm, 2.7 μm); RT 2.81 min; 0.025% Aq. TFA+5% ACN: ACN+5% 0.025% Aq TFA, 1.2 mL/min).

Synthesis of methyl 5-allyl-11-oxo-10, 11-dihydro-5H-dibenzo [b, e] [1, 4] diazepine-8-carboxylate (189)

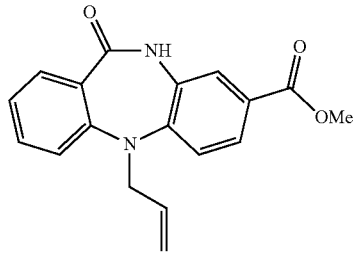

189

A mixture of methyl 5-allyl-10-(4-methoxybenzyl)-11-oxo-10, 11-dihydro-5H-dibenzo [b, e] [1, 4] diazepine-8-carboxylate 188 (550 mg, 1.28 mmol) in trifluoroacetic acid (3 mL) at RT was heated to 60° C. and stirred for 1.5 h. The reaction was monitored by TLC; after completion of the reaction, the volatiles were removed in vacuo. The residue was diluted with saturated sodium bicarbonate solution (30 mL) and extracted with EtOAc (2×25 mL). The combined organic layer was washed with water and dried over sodium sulfate, filtered and concentrated in vacuo to afford compound 189 (300 mg, 76%) as an off-white solid. TLC: 30% EtOAc/CH$_2$Cl$_2$ (R$_f$: 0.3); $^1$H NMR (500 MHz, DMSO-d$_6$): δ 10.38 (s, 1H), 7.70-7.66 (m, 2H), 7.62 (dd, J=7.7, 1.3 Hz, 1H), 7.51-7.46 (m, 1H), 7.29 (d, J=9.0 Hz, 1H), 7.22 (d, J=8.1 Hz, 1H), 7.12 (t, J=7.5 Hz, 1H), 5.79-5.65 (m, 1H), 5.33 (dd, J=17.2, 1.0 Hz, 1H), 5.14 (d, J=9.5 Hz, 1H), 4.48-4.44 (m, 2H), 3.81 (s, 3H); LC-MS: 99.27%; 309.0 (M$^+$+1); column; Ascentis Express C-18 (50×3.0 mm, 2.7 μm); RT 2.36 min; 0.025% Aq. TFA+5% ACN: ACN+5% 0.025% Aq TFA, 1.2 mL/min).

131

Synthesis of 5-allyl-11-oxo-10, 11-dihydro-5H-dibenzo [b, e] [1,4] diazepine-8-carboxylic acid (190)

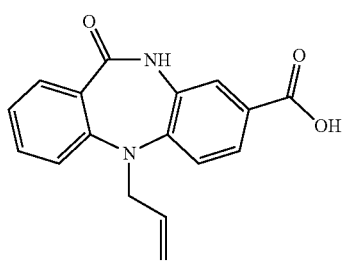
190

To a stirring solution of compound 189 (300 mg, 0.97 mmol) in THF:H$_2$O (1:1, 15 mL) was added lithium hydroxide monohydrate (122 mg, 2.92 mmol) at RT; heated to 70° C. and stirred for 2 h. The reaction was monitored by TLC; after completion of the reaction, the volatiles were removed in vacuo. The pH of the residue was acidified to ~4 with 1 N HCl and stirred for 15 min. The precipitated solid was filtered, washed with water (40 mL), diethylether (20 mL) and pentane (20 mL) and dried in vacuo to afford compound 190 (200 mg, 70%) as an off-white solid. TLC: 50% EtOAc/hexanes (R$_f$: 0.1); $^1$H NMR (400 MHz, DMSO-d$_6$): δ 12.85 (br s, 1H), 10.35 (s, 1H), 7.67-7.59 (m, 3H), 7.52-7.44 (m, 1H), 7.26 (d, J=8.9 Hz, 1H), 7.21 (d, J=8.0 Hz, 1H), 7.11 (t, J=7.2 Hz, 1H), 5.80-5.66 (m, 1H), 5.33 (dd, J=17.3, 1.6 Hz, 1H), 5.14 (dd, J=10.4, 1.4 Hz, 1H), 4.45 (d, J=2.4 Hz, 2H); LC-MS: 96.58%; 294.9 (M$^+$+1); (column; Ascentis Express C-18 (50×3.0 mm, 2.7 μm); RT 2.06 min. 0.025% Aq. TFA+5% ACN: ACN+5% 0.025% Aq TFA, 1.2 mL/min).

Synthesis of 5-(2-hydroxyethyl)-11-oxo-10, 11-dihydro-5H-dibenzo [b, e] [1, 4] diazepine-8-carboxylic acid (194): A Common Intermediate

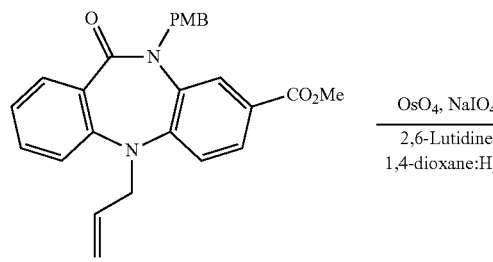
188

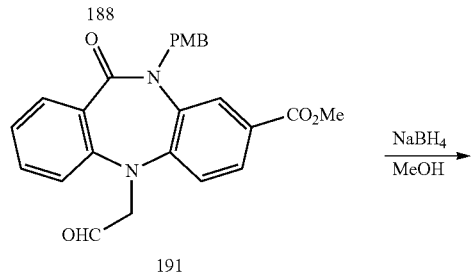
191

132

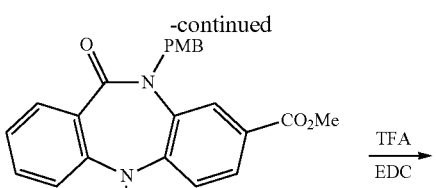
192

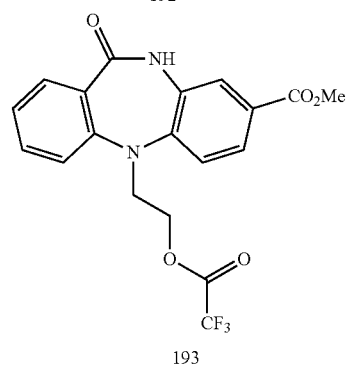
193

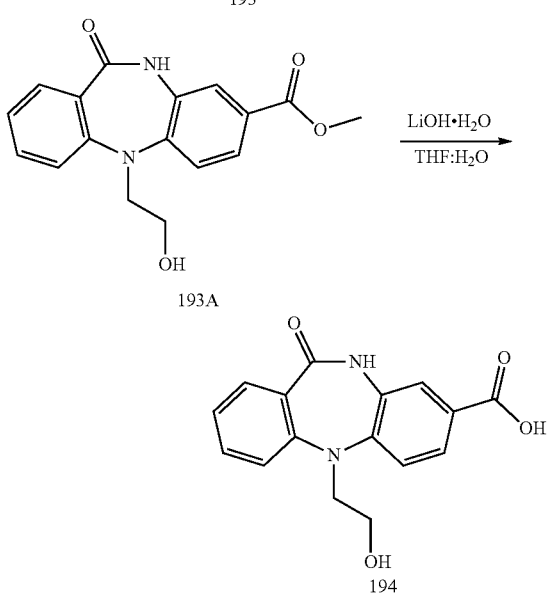
193A

194

Synthesis of methyl 10-(4-methoxybenzyl)-11-oxo-5-(2-oxoethyl)-10, 11-dihydro-5H-dibenzo [b, e] [1, 4] diazepine-8-carboxylate (191)

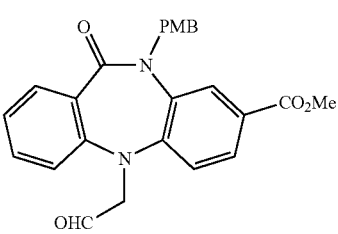
191

To a stirring solution of methyl 5-allyl-10-(4-methoxy-benzyl)-11-oxo-10, 11-dihydro-5H-dibenzo [b, e] [1, 4] diazepine-8-carboxylate 188 (500 mg, 1.16 mmol) in 1, 4 dioxane:H₂O (1:1:2, 40 mL) was added 2, 6-lutidine (0.27 mL, 2.30 mmol) at 25° C. followed by addition of osmium tetroxide (3.75 mL, 0.058 mmol, 0.4% solution in t-butanol), sodium metaperiodate (1 g, 4.67 mmol) and stirred at RT for 16 h. The reaction was monitored by TLC; after completion the reaction mixture was quenched with ice-cold water (10 mL) and extracted with CH₂Cl₂ (2×75 mL). The combined organic extracts were dried over sodium and concentrated in vacuo to afford crude compound 191 (600 mg) as pale brown solid. TLC: 30% EtOAc/hexanes (R$_f$: 0.4); LC-MS: 40.34%; 431.0 (M⁺+1); (column; Ascentis Express C18, (50×3.0 mm, 2.7 μm); RT 2.53 min. 0.025% Aq. TFA+5% ACN: ACN+ 5% 0.025% Aq. TFA, 1.2 mL/min).

Synthesis of methyl 5-(2-hydroxyethyl)-10-(4-methoxybenzyl)-11-oxo-10, 11-dihydro-5H-dibenzo [b, e] [1, 4] diazepine-8-carboxylate (192)

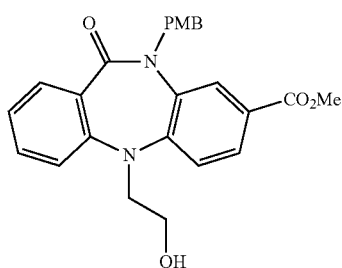

192

To a stirring solution of methyl 10-(4-methoxybenzyl)-11-oxo-5-(2-oxoethyl)-10, 11-dihydro-5H-dibenzo [b, e] [1, 4] diazepine-8-carboxylate 191 (1.15 g, crude) in MeOH (30 mL) under argon atmosphere was added sodium borohydride (203 mg, 5.34 mmol) at 0° C.; warmed to RT and stirred for 4 h. The reaction was monitored by TLC; after completion of the reaction, the reaction mixture was diluted with water (50 mL) and extracted with CH₂Cl₂ (2×100 mL). The combined organic extracts were dried over sodium sulfate and concentrated in vacuo to obtain the crude. The crude was purified through silicagel column chromatography (100-200 mesh) using 40-50% EtOAc/hexanes to afford compound 192 (400 mg, 40%, over 2 steps) as an off-white solid. TLC: 40% EtOAc/hexanes (R$_f$: 0.2); ¹H NMR (400 MHz, DMSO-d₆): δ 7.92 (d, J=1.8 Hz, 1H), 7.67 (dd, J=8.5, 1.9 Hz, 1H), 7.61 (dd, J=7.7, 1.6 Hz, 1H), 7.49-7.44 (m, 1H), 7.36 (d, J=8.5 Hz, 1H), 7.27-7.21 (m, 3H), 7.16-7.10 (m, 1H), 6.80 (d, J=8.9 Hz, 2H), 5.64 (d, J=15.7 Hz, 1H), 4.89 (d, J=15.9 Hz, 1H), 4.76 (t, J=5.3 Hz, 1H), 3.91-3.80 (m, 2H), 3.78 (s, 3H), 3.68 (s, 3H), 3.56-3.48 (m, 2H); LC-MS: 94.51%; 432.1 (M⁺+1); (column; Ascentis Express C-18, (50×3.0 mm, 2.7 μm); RT 2.35 min. 0.025% Aq. TFA+5% ACN: ACN+5% 0.025% Aq. TFA, 1.2 mL/min);

Synthesis of methyl 11-oxo-5-(2-(2, 2, 2-trifluoro-acetoxy) ethyl)-10, 11-dihydro-5H-dibenzo [b, e] [1, 4] diazepine-8-carboxylate (193)

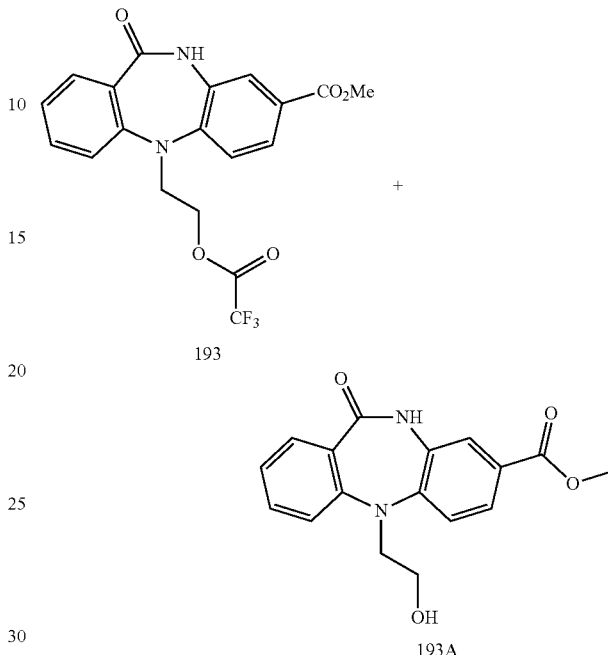

A mixture of methyl 5-(2-hydroxyethyl)-10-(4-methoxybenzyl)-11-oxo-10, 11-dihydro-5H-dibenzo [b, e] [1, 4] diazepine-8-carboxylate 192 (400 mg, 0.92 mmol) in trifluoroacetic acid (0.11 mL, 1.51 mmol) under inert atmosphere at RT was heated to 60° C. and stirred for 3 h. The reaction was monitored by TLC; after completion of the reaction, the volatiles were removed in vacuo to obtain the crude. The residue was diluted with CH₂Cl₂ (100 mL) and washed with saturated sodium bicarbonate solution (30 mL). The organic extracts were dried over sodium sulfate and concentrated in vacuo to afford 203 (450 mg, mixture of 193 (major) & 193A (minor)) as an off-white solid. TLC: 40% EtOAc/hexanes (R$_f$: 0.8); LC-MS: 80.01%; 409.0 (M⁺+1), 12.26%; 313.1 (M⁺+1); (column; Ascentis Express C18, (50×3.0 mm, 2.7 μm); RT 2.40 min, 1.91 min. 0.025% Aq. TFA+5% ACN: ACN+5% 0.025% Aq. TFA, 1.2 mL/min);

Synthesis of 5-(2-hydroxyethyl)-11-oxo-10, 11-dihydro-5H-dibenzo [b, e] [1, 4] diazepine-8-carboxylic acid (194)

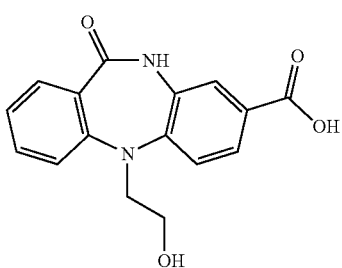

194

To a stirring solution of compound 193 & 193A (430 mg, mixture of compounds) in THF:H₂O (1:1, 14 mL) was added lithium hydroxide monohydrate (221 mg, 5.26 mmol) portion wise for 10 min at RT and stirred for 24 h. The reaction was monitored by TLC; after completion of the reaction, the volatiles were removed in vacuo. The pH of the residue was acidified with 2 M HCl to ~1. The obtained solid was filtered and dried in vacuo to afford compound 194 (250 mg, 80%) as an off-white solid. TLC: 50% EtOAc/hexanes ($R_f$: 0.1); $^1$H NMR (400 MHz, DMSO-$d_6$): δ 12.84 (br s, 1H), 10.30 (s, 1H), 7.68-7.59 (m, 3H), 7.54-7.47 (m, 1H), 7.29-7.23 (m, 2H), 7.14-7.08 (m, 1H), 4.66 (t, J=4.6 Hz, 1H), 3.89-3.79 (m, 2H), 3.54-3.48 (m, 2H); LC-MS: 92.62%; 298.9 (M$^+$+ 1); (column; Ascentis Express C18, (50×3.0 mm, 2.7 μm); RT 1.66 min, 0.025% Aq. TFA+5% ACN: ACN+5% 0.025% Aq. TFA, 1.2 mL/min);

Synthesis of 6-oxo-6, 11-dihydro-5H-dibenzo [b, e] azepine-3-carboxylic acid (210): A Common Intermediate

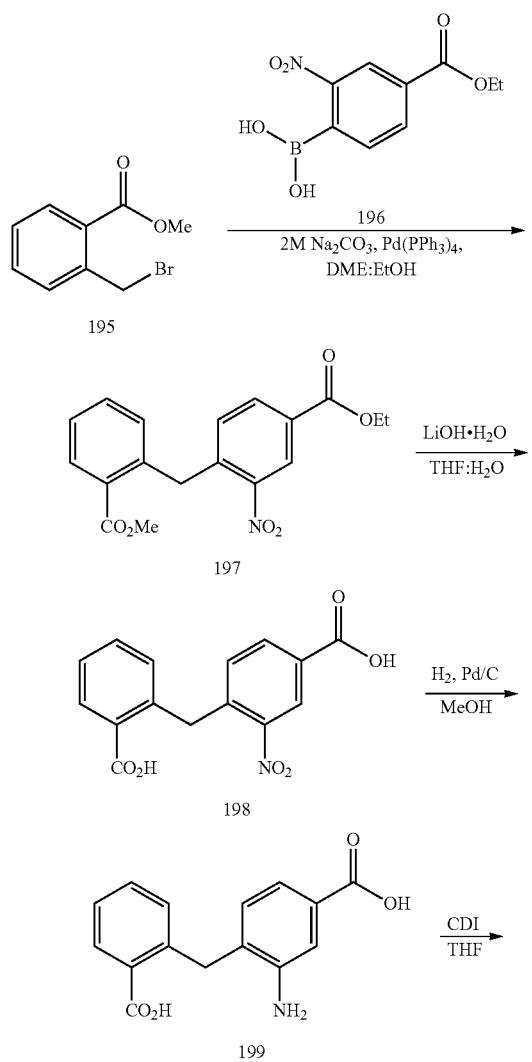

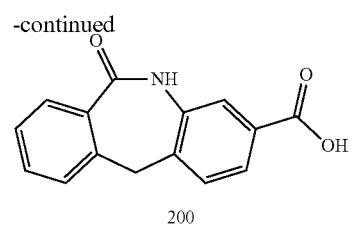

200

Synthesis of ethyl 4-(2-(methoxycarbonyl) benzyl)-3-nitrobenzoate (197)


To a stirring solution of methyl 2-(bromomethyl) benzoate 195 (9 g, 39.30 mmol) in 1, 2 dimethoxy ethane (72 mL) was added Pd(PPh₃)₄ (1.81 g, 1.57 mmol) and purged under argon atmosphere for 10 min. To this were added (4-(ethoxycarbonyl)-2-nitrophenyl) boronic acid 196 (10.6 g, 44.41 mmol) dissolved in 1, 2 dimethoxy ethane:EtOH (2:1, 108 mL) and 2 M sodium carbonate solution (72 mL) and purged under argon atmosphere for 15 min at RT and stirred for 2 h. The reaction was monitored by TLC; after completion the reaction the volatiles were removed in vacuo to obtain the crude. The crude was purified through silica gel column chromatography using 2-6% EtOAc/hexanes to afford compound 197 (5.6 g, 41%) as an off-white solid. TLC: 10% EtOAc/hexanes ($R_f$: 0.3); $^1$H-NMR (DMSO-$d_6$, 400 MHz): δ 8.45 (s, 1H), 8.11 (dd, J=8.1, 1.8 Hz, 1H), 7.93 (dd, J=7.8, 1.4 Hz, 1H), 7.59 (td, J=7.5, 1.5 Hz, 1H), 7.45 (td, J=7.6, 1.1 Hz, 1H), 7.29 (d, J=7.1 Hz, 1H), 7.21 (d, J=8.2 Hz, 1H), 4.63 (s, 2H), 4.36 (q, J=7.1 Hz, 2H), 3.70 (s, 3H), 1.33 (t, J=7.1 Hz, 3H).

Synthesis of 4-(2-carboxybenzyl)-3-nitrobenzoic acid (198)

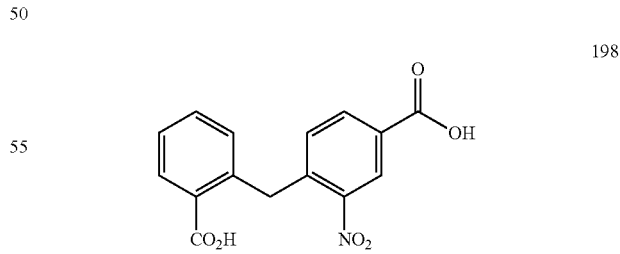

To a stirring solution of compound 197 (5.6 g, 16.23 mmol) in THF:H₂O (4:1, 615 mL) was added lithium hydroxide monohydrate (6.82 g, 162.31 mmol) portion wise for 10 min at RT heated to 60° C. and stirred for 2 h. The reaction was monitored by TLC; after completion of the reaction, the volatiles were removed in vacuo. The pH of the residue was acidified with 2 N HCl to ~1. The obtained solid was filtered and dried in vacuo to obtain compound 198 (3.2 g, 66%) as yellow solid. TLC: 10% EtOAc/hexanes ($R_f$: 0.1); $^1$H-NMR (CD$_3$OD-d$_4$, 400 MHz): δ 8.34 (s, 1H), 8.00 (d, J=8.0 Hz, 1H), 7.65-7.64 (m, 1H), 7.63 (t, J=6.0 Hz, 1H), 7.53 (t, J=6.0 Hz, 1H), 7.26 (d, J=7.6 Hz, 1H), 7.13 (d, J=8.0 Hz, 1H), 4.70 (s, 2H).

Synthesis of 3-amino-4-(2-carboxybenzyl) benzoic acid (199)

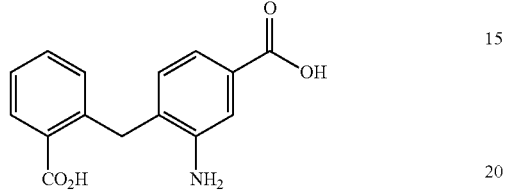

199

To a stirring solution of compound 198 (1 g, 3.32 mmol) in MeOH (20 mL) under inert atmosphere was added 10% Pd/C (200 mg) at RT and stirred under hydrogen atmosphere (balloon pressure) at RT for 18 h. The reaction was monitored by TLC; after completion of the reaction, the reaction mixture was filtered through celite and washed with MeOH (100 mL). The filtrate was concentrated in vacuo to obtain the crude. The crude washed with diethyl ether (30 mL) and dried in vacuo to afford compound 199 (830 mg, 92%) as pale brown solid. TLC: 10% MeOH/CH$_2$Cl$_2$ ($R_f$: 0.2); $^1$H NMR (DMSO-d$_6$, 400 MHz): δ 12.48 (br s, 1H), 7.81 (d, J=7.4 Hz, 1H), 7.43 (t, J=7.3 Hz, 1H), 7.31 (t, J=7.6 Hz, 1H), 7.24 (s, 1H), 7.13 (d, J=7.5 Hz, 1H), 7.02 (dd, J=7.8, 1.4 Hz, 1H), 3.17 (s, 2H); LC-MS: 91.07%; 271.9 (M$^+$+1); (column; X Select CSH C-18, (50×3.0 mm, 3.5 μm); RT 2.51 min. 0.05% Aq. TFA: ACN, 0.8 mL/min).

Synthesis of 6-oxo-6, 11-dihydro-5H-dibenzo [b, e] azepine-3-carboxylic acid (200)

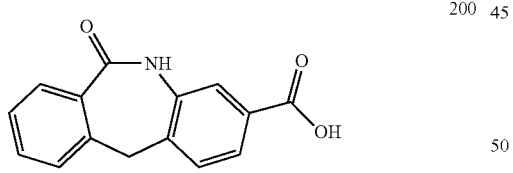

200

To a stirring solution of compound 199 (830 mg, 3.06 mmol) in THF (20 mL) under inert atmosphere was added CDI (2.02 g, 12.25 mmol) at RT and stirred for 18 h. The reaction was monitored by TLC; after completion of the reaction, the volatiles were removed in vacuo. The pH of the residue was adjusted to ~2 using 4 N HCl. The precipitated solid was filtered, washed with and dried in vacuo to afford compound 200 (515 mg, 66%) as an off-white solid. TLC: 10% MeOH/CH$_2$Cl$_2$ (R$_1$ 0.3); $^1$H NMR (DMSO-d$_6$, 400 MHz): δ 12.93 (br s, 1H), 10.57 (s, 1H), 7.74-7.67 (m, 2H), 7.64 (dd, J=7.8, 1.7 Hz, 1H), 7.52-7.44 (m, 2H), 7.42-7.38 (m, 1H), 7.34 (td J=7.5, 1.3 Hz, 1H), 3.98 (s, 2H); LC-MS: 99.31%; 253.9 (M$^+$+1); (column; X Select CSH C-18, (50×3.0 mm, 3.5 μm); RT 2.75 min. 0.05% Aq. TFA: ACN, 0.8 mL/min).

Synthesis of 11-methyl-6-oxo-6, 11-dihydro-5H-dibenzo [b, e] azepine-3-carboxylic acid (211): A Common Intermediate

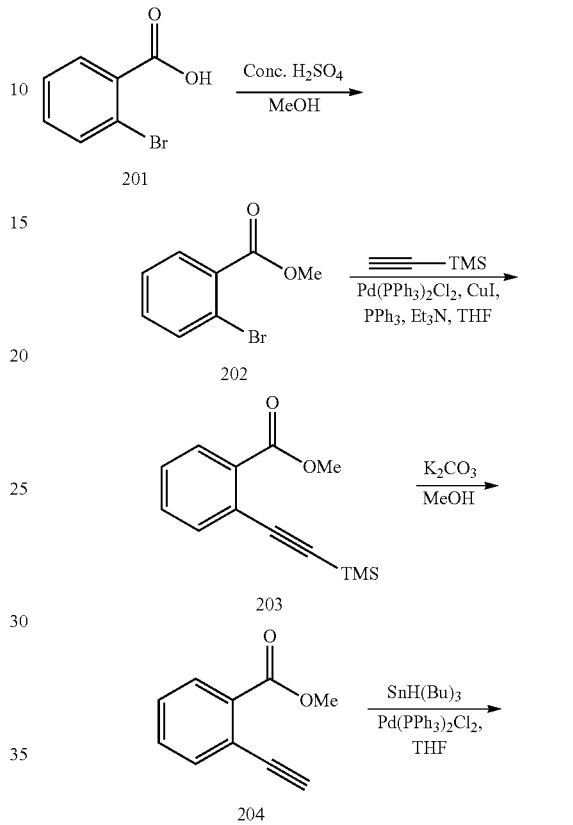

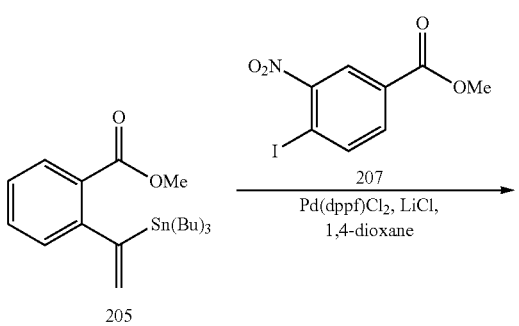

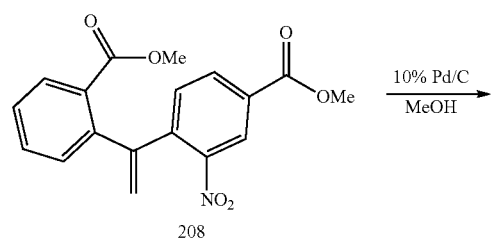

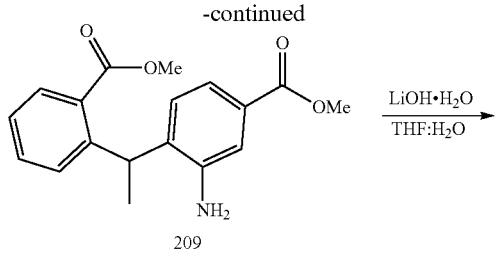

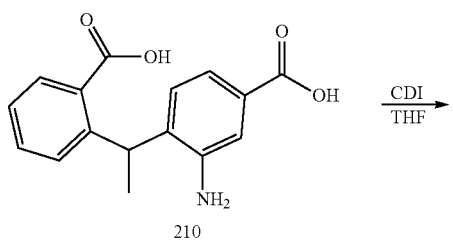

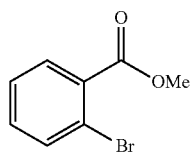

Synthesis of methyl 2-bromobenzoate (202)

202

To a stirring solution of 2-bromobenzoic acid 201 (15 g, 74.62 mmol) in MeOH (150 mL) under inert atmosphere was added concentrated sulfuric acid (4 mL, 75.04 mmol) dropwise for 5 min at 0° C.; heated to reflux and stirred for 18 h. The reaction was monitored by TLC; after completion of the reaction, the volatiles were removed in vacuo. The residue was diluted with ice-cold water (100 mL) and extracted with EtOAc (2×100 mL). The combined organic extracts were dried over sodium sulfate, filtered and concentrated in vacuo to afford compound 202 (14 g, 93%) as colorless syrup. TLC: 10% EtOAc/hexanes ($R_f$: 0.5). $^1$H NMR (CDCl$_3$, 400 MHz): δ 7.81-7.77 (m, 1H), 7.70-7.64 (m, 1H), 7.39-7.30 (m, 2H), 3.94 (s, 3H).

Synthesis of methyl 2-((trimethylsilyl) ethynyl) benzoate (203)

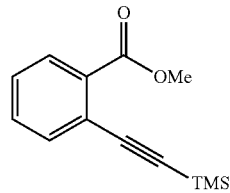

To a stirring solution of methyl 2-bromobenzoate 202 (14 g, 65.11 mmol) in THF (150 mL) under inert atmosphere were added triphenylphosphine (426 mg, 1.62 mmol), Pd(PPh$_3$)$_2$Cl$_2$ (4.57 g, 6.51 mmol), ethynyltrimethylsilane (18.4 mL, 130.23 mmol), triethyl amine (18.7 mL, 130.2 mmol) and purged under argon for 15 min. To this was added copper iodide (1.23 g, 6.51 mmol) at RT and stirred for 16 h. The reaction was monitored by TLC; after completion of the reaction, the reaction mixture was filtered through celite washed with EtOAc (200 mL). The filtrate was washed with water (150 mL), dried over sodium sulfate, filtered and concentrated in vacuo to obtain the crude. The crude was purified through silica gel column chromatography using 2% EtOAc/hexanes to afford compound 203 (11 g, 73%) a colorless syrup. TLC: 5% EtOAc/hexanes ($R_f$: 0.5); $^1$H NMR (CDCl$_3$, 400 MHz) δ 7.92-7.88 (m, 1H), 7.60-7.55 (m, 1H), 7.44 (td, J=7.6, 1.5 Hz, 1H), 7.36 (td, J=7.6, 1.3 Hz, 1H), 3.92 (s, 3H), 0.27 (s, 9H).

Synthesis of methyl 2-ethynylbenzoate (204)

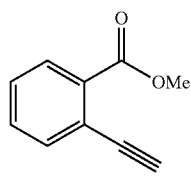

To a stirring solution of compound 203 (45 g, 193.96 mmol) in MeOH (500 mL) under inert atmosphere was added potassium carbonate (40 g, 290.94 mmol) at RT and stirred for 4 h. The reaction was monitored by TLC; after completion of the reaction, the reaction mixture was filtered through celite washed with CH$_2$Cl$_2$ (2×500 mL). The filtrate was removed in vacuo to obtain the crude. The crude was as purified through silica gel column chromatography using 2% EtOAc/hexanes to afford compound 204 (31 g, 33%) as colorless syrup. TLC: 5% EtOAc/hexanes ($R_f$: 0.5); $^1$H NMR (CDCl$_3$, 400 MHz): δ 7.97-7.91 (m, 1H), 7.62 (dd, J=7.7, 1.1 Hz, 1H), 7.47 (td, J=7.6, 1.5 Hz, 1H), 7.40 (td, J=7.7, 1.4 Hz, 1H), 3.38 (s, 1H), 3.91 (s, 3H).

Synthesis of methyl 2-(1-(tributylstannyl) vinyl) benzoate (205)

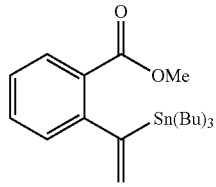

205

To a stirring solution of compound 204 (10 g, 62.5 mmol) and Pd(PPh₃)₂Cl₂ (877 mg, 1.25 mmol) in THF (37 mL) under inert atmosphere was added tributyltin hydride (20.43 mL, 75 mmol) at RT and stirred for 2.5 h. The reaction was monitored by TLC; after completion of the reaction, the volatiles were removed in vacuo to obtain the crude. The crude was purified through silica gel column chromatography using 2% EtOAc/hexanes to afford compound 205 (28 g, 54%) as colorless syrup. TLC: 5% EtOAc/hexanes ($R_f$: 0.8); ¹H NMR (CDCl₃, 400 MHz): δ 7.87 (dd, J=7.8, 0.9 Hz, 1H), 7.41 (td, J=7.6, 1.4 Hz, 1H), 7.21 (td, J=7.6, 1.3 Hz, 1H), 7.01 (dd, J=7.7, 0.9 Hz, 1H), 5.67 (d, J=2.8 Hz, 1H), 5.38 (d, J=2.9 Hz, 1H), 3.82 (s, 3H), 1.49-1.39 (m, 6H), 1.30-1.20 (m, 6H), 0.90-0.83 (m, 15H).

Synthesis of methyl 4-iodo-3-nitrobenzoate (207)

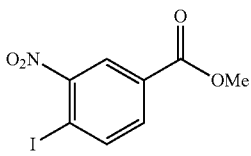

207

To a stirring solution of 4-iodo-3-nitrobenzoic acid 206 (15 g, 51.36 mmol) in MeOH (150 mL) under inert atmosphere was added concentrated sulphuric acid (15 mL) dropwise for 10 min at 0° C.; warmed to RT at stirred for 16 h. The reaction was monitored by TLC; after completion of the reaction, the volatiles were removed in vacuo. The residue was diluted with ice-cold water (500 mL) and extracted with EtOAc (3×100 mL). The combined organic extracts were washed saturated sodium bicarbonate solution (2×100 mL) dried over sodium sulfate, filtered and concentrated in vacuo to afford compound 207 (13 g, 83%) as an off-white solid. TLC: 30% EtOAc/hexanes ($R_f$: 0.8); ¹H NMR (CDCl₃, 500 MHz) δ 8.45 (s, 1H), 8.15 (d, J=8.4 Hz, 1H), 7.88 (dd, J=8.2, 1.9 Hz, 1H), 3.97 (s, 3H).

Synthesis of methyl 4-(1-(2-(methoxycarbonyl) phenyl) vinyl)-3-nitrobenzoate (208)

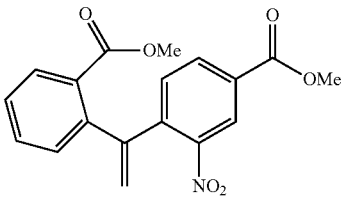

208

To a stirring solution of compound 205 (25 g, 5.52 mmol) in 1, 4-dioxane (40 mL) under inert atmosphere in a sealed tube were added methyl 4-iodo-3-nitrobenzoate 207 (1.86 g, 6.08 mmol), lithium chloride (813 mg, 19.35 mmol) and purged under argon for 20 min. To this was added Pd(dppf)Cl₂ (2 g, 2.76 mmol) at RT; heated to 120° C. and stirred for 16 h. The reaction was monitored by TLC; after completion of the reaction, the reaction mixture was filtered through celite washed with EtOAc (2×50 mL). The filtrate was washed with water (2×50 mL), dried over sodium sulfate, filtered and concentrated in vacuo to afford compound 208 (1.3 g, 70%) colorless syrup. TLC: 20% EtOAc/hexanes ($R_f$: 0.4); ¹H-NMR (CDCl₃, 400 MHz): δ 8.30 (s, 1H), 8.17 (dd, J=8.2, 1.8 Hz, 1H), 7.69-7.65 (m, 2H), 7.52-7.42 (m, 2H), 7.40-7.35 (m, 1H), 5.61 (s, 1H), 5.58 (s, 1H), 3.96 (s, 3H), 3.58 (s, 3H).

Synthesis of methyl 3-amino-4-(1-(2-(methoxycarbonyl) phenyl) ethyl) benzoate (209)

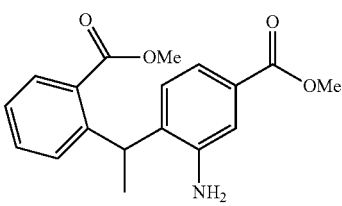

209

To a stirring solution of compound 208 (100 g, 0.29 mmol) in MeOH (10 mL) under inert atmosphere was added 10% Pd/C (40 mg, dry) at RT and stirred under hydrogen atmosphere (balloon pressure) for 16 h. The reaction was monitored by TLC; after completion of the reaction, the reaction mixture was filtered through celite, washed with CH₂Cl₂ (2×50 mL). The filtrate was concentrated in vacuo to afford compound 209 (70 mg, 77%) as colorless syrup. TLC: 20% EtOAc/hexanes ($R_f$: 0.7); ¹H-NMR (DMSO-d₆, 500 MHz): δ 7.68 (dd, J=7.8, 1.2 Hz, 1H), 7.46 (td, J=7.6, 1.4 Hz, 1H), 7.32 (td, J=7.5, 1.0 Hz, 1H), 7.24 (s, 1H), 7.21-7.15 (m, 2H), 7.14-7.10 (m, 1H), 5.09 (s, 2H), 4.85 (q, J=6.9 Hz, 1H), 3.79 (s, 6H), 1.46 (d, J=7.0 Hz, 3H).

143
Synthesis of 3-amino-4-(1-(2-carboxyphenyl) ethyl) benzoic acid (210)

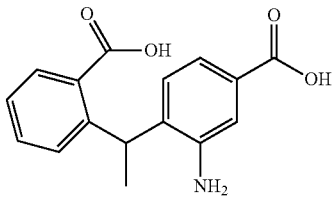
210

To a stirring solution of compound 209 (1.4 g, 4.47 mmol) in THF:H₂O (4:1, 20 mL) was added lithium hydroxide monohydrate (1.07 g, 22.3 mmol) at RT and heated to 70° C. and stirred for 6 h. The reaction was monitored by TLC; after completion of the reaction, the volatiles were removed in vacuo. The pH of the residue was acidified with 2 N HCl to ~4. The precipitated solid was filtered, washed with water (50 mL), n-pentane (30 mL) and dried in vacuo to afford compound 210 (900 mg, 71%) as an off-white solid. TLC: 10% MeOH/CH₂Cl₂ (R$_f$: 0.2); ¹H-NMR (DMSO-d₆, 500 MHz): δ 12.50 (br s, 1H), 7.70 (dd, J=7.8, 1.2 Hz, 1H), 7.40 (td, J=7.6, 1.3 Hz, 1H), 7.28-7.23 (m, 2H), 7.19-7.17 (m, 2H), 7.09 (d, J=7.8 Hz, 1H), 4.98 (q, J=6.9 Hz, 1H), 1.44 (d, J=6.9 Hz, 3H).

Synthesis of 11-methyl-6-oxo-6, 11-dihydro-5H-dibenzo [b, e] azepine-3-carboxylic acid (211)

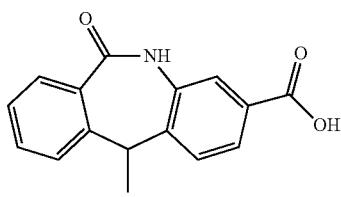
211

To a stirring solution of compound 210 (900 mg, 3.15 mmol) in THF (20 mL) under inert atmosphere was added CDI (2.5 g, 15.7 mmol) at RT and stirred for 16 h. The reaction was monitored by TLC; after completion of the reaction, the volatiles were removed in vacuo. The residue was diluted with water (15 mL) and pH was adjusted to ~4 with 2 N HCl. The obtained solid was filtered washed with water (30 mL), diethyl ether (20 mL) and dried in vacuo to afford compound 211 (750 mg, 89%) as an off-white solid. TLC: 10% MeOH/CH₂Cl₂ (R$_f$: 0.3); LC-MS: 96.89%; 267.9 (M⁺+1); (column; Ascentis Express C18, (50×3.0 mm, 2.7 µm); RT 2.14 min. 0.025% Aq. TFA+5% ACN: ACN+5% 0.025% Aq. TFA, 1.2 mL/min).

144
Synthesis of 6, 11-dioxo-6, 11-dihydro-5H-dibenzo [b, e] azepine-3-carboxylic acid (216): A Common Intermediate

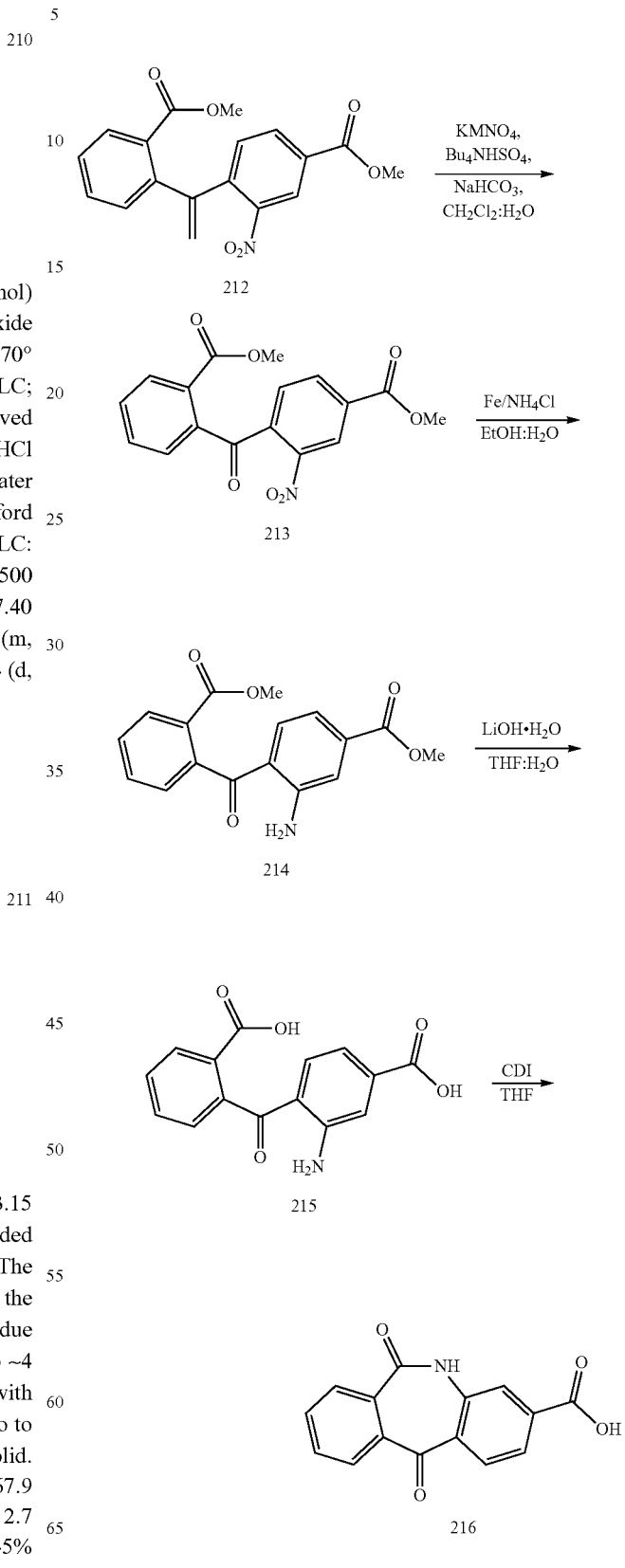

Synthesis of methyl 4-(2-(methoxycarbonyl) benzoyl)-3-nitrobenzoate (213)

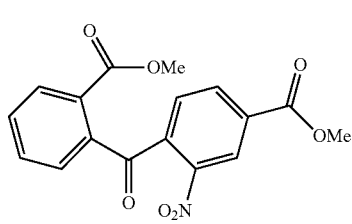

213

To a stirring solution of methyl 4-(1-(2-(methoxycarbonyl) phenyl) vinyl)-3-nitrobenzoate 212 (8 g, 23.46 mmol) in a mixture of $CH_2Cl_2$:$H_2O$ (1:1, 500 mL) were added $KMnO_4$ (37 g, 234.6 mmol), tetrabutylammonium hydrogensulfate (7.9 g, 23.46 mmol), sodium bicarbonate (9.8 g, 117.3 mmol) at RT and stirred for 16 h. The reaction was monitored by TLC; after completion of the reaction, the reaction mixture was quenched with acetic acid (20 mL) and 10% sodium bisulfate solution (50 mL) and extracted with $CH_2Cl_2$ (2×500 mL). The combined organic extracts were dried over sodium sulfate, filtered and concentrated in vacuo. The crude was purified through silica gel column chromatography using 40% EtOAc/hexanes to afford compound 213 (4 g, 50%) as colorless syrup. TLC: 30% EtOAc/hexanes ($R_f$: 0.5); $^1$H-NMR (DMSO-$d_6$, 500 MHz): δ 8.55 (s, 1H), 8.34 (dd, J=18.0, 1.6 Hz, 1H), 7.82-7.65 (m, 4H), 7.56 (d, J=7.5 Hz, 1H), 3.94 (s, 3H), 3.70 (s, 3H).

Synthesis of methyl 3-amino-4-(2-(methoxycarbonyl) benzoyl) benzoate (214)

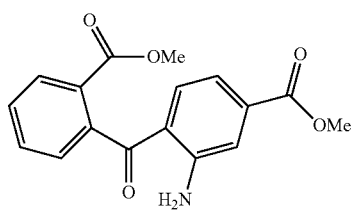

214

To a stirring solution of compound 213 (4 g, 11.66 mmol) in a mixture of EtOH:$H_2O$ (1:1, 60 mL) were added iron powder (6.5 g, 116.48 mmol) and ammonium chloride (6.1 g, 115.09 mmol) at RT; heated to 90° C. and stirred for 4 h. The reaction was monitored by TLC; after completion of the reaction, the reaction mixture was diluted with $CH_2Cl_2$ (200 mL), filtered through celite, washed with 20% MeOH/$CH_2Cl_2$ (50 mL). The combined organic extracts were dried over sodium sulfate, filtered and concentrated in vacuo to obtain the crude. The crude was purified through silica gel column chromatography using 1% MeOH/$CH_2Cl_2$ (50 mL) to afford compound 214 (2 g, 56%) as pale green solid. TLC: 20% MeOH/$CH_2Cl_2$ ($R_f$: 0.7); $^1$H-NMR (DMSO-$d_6$, 500 MHz): δ 7.99 (d, J=7.8 Hz, 1H), 7.75 (dd, J=7.8, 1.2 Hz, 1H), 7.65 (td, J=7.8, 1.2 Hz, 1H), 7.51 (s, 1H), 7.47-7.41 (m, 3H), 6.98 (d, J=8.4 Hz, 1H), 6.90 (dd, J=8.4, 1.4 Hz, 1H), 3.62 (s, 3H), 3.31 (s, 3H).

Synthesis of 3-amino-4-(2-carboxybenzoyl) benzoic acid (215)

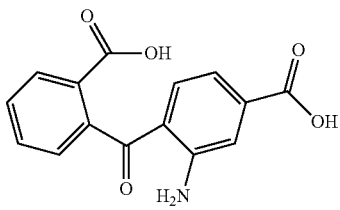

215

To a stirring solution of compound 214 (2 g, 6.38 mmol) in THF:$H_2O$ (4:1, 30 mL) was added lithium hydroxide monohydrate (1.34 g, 31.94 mmol) at 0° C.; warmed to RT and stirred for 16 h. The reaction was monitored by TLC; after completion of the reaction, the volatiles were removed in vacuo. The pH of the residue was acidified with 2 N HCl to ~4. The precipitated solid was filtered washed with water (50 mL), triturated with diethyl ether (2×20 mL) and dried in vacuo to afford compound 215 (1.5 g 84%) as an off-white solid. TLC: 10% MeOH/$CH_2Cl_2$ ($R_f$: 0.2); $^1$H-NMR (DMSO-$d_6$, 500 MHz): δ 13.04 (br s, 2H), 7.97 (d, J=7.5 Hz, 1H), 7.72-7.67 (m, 1H), 7.63-7.59 (m, 1H), 7.45 (s, 1H), 7.41 (br s, 2H), 7.35 (d, J=7.5 Hz, 1H), 6.97 (d, J=8.4 Hz, 1H), 6.89 (dd, J=8.4, 1.4 Hz, 1H).

Synthesis of 6, 11-dioxo-6, 11-dihydro-5H-dibenzo [b, e] azepine-3-carboxylic acid (216)

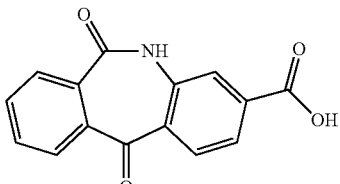

216

To a stirring solution of compound 215 (750 mg, 2.63 mmol) in THF (20 mL) under inert atmosphere was added CDI (2.13 g, 13.15 mmol) 0° C.; warmed to RT and stirred for 16 h. The reaction was monitored by TLC; after completion of the reaction, the volatiles were removed in vacuo. The residue was diluted with ice-cold water (15 mL) and the pH was adjusted to ~4 with 2 N HCl. The obtained solid was filtered washed with water (30 mL), diethylether (20 mL) and dried in vacuo to afford compound 216 (600 mg, 86%) as an off-white solid. TLC: 10% MeOH/$CH_2Cl_2$ ($R_f$: 0.3); $^1$H-NMR (DMSO-$d_6$, 500 MHz): δ 13.30 (br s, 1H), 11.25 (s, 1H), 8.19 (d, J=6.4 Hz, 1H), 7.96 (s, 1H), 7.89-7.79 (m, 4H), 7.72 (d, J=8.1 Hz, 1H).

Amines for Compounds:

Commercial Amines Used in the Preparation of Compounds:

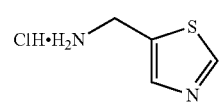

217

148

Synthesis of (2-chlorothiazol-5-yl) methanamine (223)

To a stirring solution of compound 222 (10 g, 57.47 mmol) in THF:H$_2$O (15:1, 160 mL) was added triphenyl phosphine (15.05 g, 57.45 mmol) portion wise for 15 min at RT and stirred for 3 h. The reaction was monitored by TLC; after completion of the reaction, the volatiles were removed in vacuo. The residue was diluted with EtOAc (3×100 mL). The combined organic extracts were dried over sodium sulfate, filtered and concentrated in vacuo to obtain the crude compound 223 (10 g) as an off-white solid; which was carried forward for next step without further purification. TLC: 10% EtOAc/hexanes (R$_f$: 0.2). LC-MS: 21.47%+ 7.59%; 149.0 (M$^+$+1); (column; X-select CSH C-18 (50×3.0 mm, 2.5 µm); RT 0.73 min & 0.82 min. 2.5 mM NH4OOCH (Aq)+5% ACN: ACN+5% 2.5 mM NH4OOCH (Aq); 0.8 mL/min).

Synthesis of tert-butyl ((2-chlorothiazol-5-yl) methyl) carbamate (224)

To a stirring solution of compound 223 (10 g, 67.56 mmol) in CH$_2$Cl$_2$ (150 mL) under argon atmosphere were added triethylamine (19.48 mL, 135.05 mmol) at 0° C. and stirred for 10 min. To this was added Boc-anhydride (17.67 g, 81.05 mmol) at the same temperature; warmed to RT and stirred for 16 h. The reaction was monitored by TLC; after completion of the reaction, the reaction mixture was diluted with water (200 mL) and extracted with CH$_2$Cl$_2$ (3×100 mL). The combined organic extracts were dried over sodium sulfate, filtered and concentrated in vacuo to obtain the crude. The crude was purified through silica gel flash column chromatography using 10-20% EtOAc/hexanes to afford compound 224 (8 g, 56% over 2 steps) as pale yellow liquid. TLC: 20% EtOAc/hexanes (R$_f$: 0.8); $^1$H-NMR (DMSO-d$_6$, 400 MHz): δ 7.57 (d, J=4.0 Hz, 1H), 7.49 (s, 1H), 4.24 (d, J=6.1 Hz, 2H), 1.39 (s, 9H).

Synthesis of tert-butyl ((2-(4-cyanophenyl) thiazol-5-yl) methyl) carbamate (226)

To a stirring solution of tert-butyl ((2-chlorothiazol-5-yl) methyl) carbamate 224 (1 g, 4.02 mmol) in 1, 2 dimethoxy ethane:H2O (4:1, 30 mL) were added sodium carbonate (1.49 g, 14.08 mmol), (4-cyanophenyl) boronic acid 225 (710 mg, 4.82 mmol) and purged under argon atmosphere for 30 min. To this was added Pd(PPh3)4 (464 mg, 0.40 mmol) at RT; heated to 100° C. and stirred for 16 h. The reaction was monitored by TLC; after completion of the reaction, the reaction mixture was poured into ice-cold water (100 mL) and extracted with EtOAc (2×150 mL). The combined organic extracts were dried over sodium sulfate, filtered and concentrated in vacuo to obtain the crude. The crude purified through silicagel column chromatography using 30% EtOAc/hexanes to afford compound 226 (550 mg, 43%) as an off-white solid. TLC: 30% EtOAc/hexanes (Rf: 0.3); 1H NMR (DMSO-d6, 500 MHz): δ 8.08 (d, J=8.5 Hz, 2H), 7.95 (d, J=8.6 Hz, 2H), 7.81 (s, 1H), 7.61 (t, J=5.9 Hz, 1H), 4.37 (d, J=5.9 Hz, 2H), 1.40 (s, 9H); LC-MS: 97.93%; 315.9 (M++1); (column; Ascentis Express C18, (50×3.0 mm, 2.7 µm); RT 2.52 min. 0.025% Aq. TFA+5% ACN: ACN+5% 0.025% Aq. TFA, 1.2 mL/min).

Synthesis of 4-(5-(aminomethyl) thiazol-2-yl) benzonitrile hydrochloride (227)

To a stirring solution of compound 226 (550 mg, 1.74 mmol) in CH$_2$Cl$_2$ (10 mL) under inert atmosphere was

147

-continued

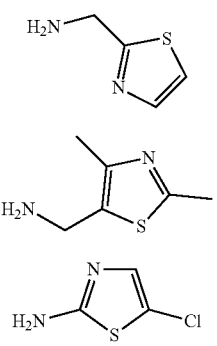

218

219

220

Preparation of the Amines:

Synthesis of 4-(5-(aminomethyl) thiazol-2-yl) benzonitrile hydrochloride (227)

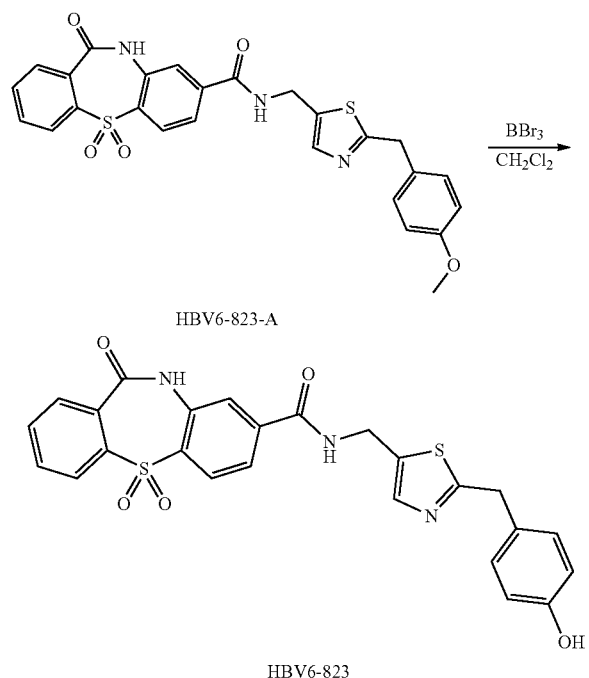

HBV6-823-A

HBV6-823

Synthesis of 5-(azidomethyl)-2-chlorothiazole (222)

To a stirring solution of 2-chloro-5-(chloromethyl) thiazole 221 (10 g, 59.52 mmol) in EtOH (150 mL) under argon atmosphere was added sodium azide (5.8 g, 89.23 mmol) at RT and heated to reflux for 4 h. The reaction was monitored by TLC; after completion of the reaction, the reaction mixture was filtered, washed with EtOAc (100 mL) and the filtrate was concentrated in vacuo to obtain the crude. The crude was purified through silica gel flash column chromatography using 5% EtOAc/hexanes to afford compound 222 (10 g, 97%) as pale yellow oil. TLC: 10% EtOAc/hexanes (R$_f$: 0.5); LC-MS: 99.33%; 174.7 (M$^+$+1); (column; Ascentis Express C18, (50×3.0 mm, 2.7 µm); RT 2.28 min. 0.025% Aq. TFA+5% ACN: ACN+5% 0.025% Aq. TFA, 1.2 mL/min).

added 4 N HCl in 1, 4-dioxane (5 mL) at 0° C.; warmed to RT and stirred for 2 h. The reaction was monitored by TLC; after completion of the reaction, the volatiles were removed in vacuo to obtain the crude. The crude was washed with EtOAc (2×10 mL) and dried in vacuo to afford compound 227 (400 mg, 92%) as an off-white solid. TLC: 10% MeOH/CH$_2$Cl$_2$ (R$_f$: 0.2); $^1$H-NMR (DMSO-d$_6$, 500 MHz): δ 8.68 (br s, 3H), 8.12 (s, 1H), 8.10 (d, J=4.3 Hz, 2H), 7.98 (d, J=8.4 Hz, 2H), 4.38 (q, J=5.4 Hz, 2H); LC-MS: 98.49%; 215.9 (M$^+$+1); (column; Ascentis Express C18, (50×3.0 mm, 2.7 μm); RT 1.43 min. 0.025% Aq. TFA+5% ACN: ACN+ 5% 0.025% Aq. TFA, 1.2 mL/min).

Synthesis of 5-(aminomethyl) thiazol-2-amine dihydrochloride (230)

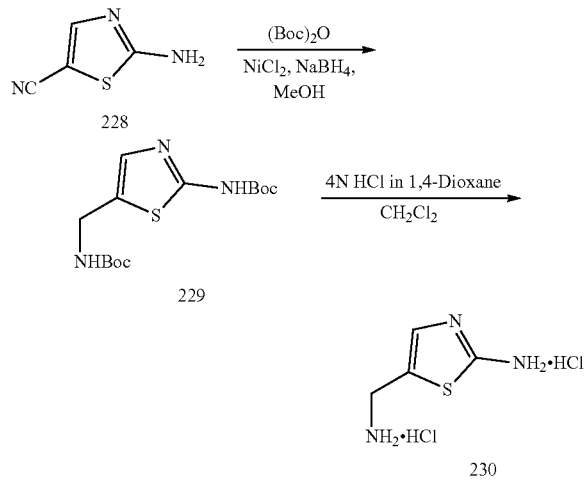

Synthesis of tert-butyl ((2-((tert-butoxycarbonyl) amino) thiazol-5-yl) methyl) carbamate (229)

To a stirring solution of 2-aminothiazole-5-carbonitrile 228 (300 mg, 2.40 mmol) in MeOH (50 mL) were added Boc-anhydride (1.5 mL, 7.20 mmol), nickel (II) chloride (571 mg, 2.40 mmol) at 0° C. To this was added sodium borohydride (638 mg, 16.80 mmol) portion wise for 10 min at 0° C.; warmed to RT and stirred for 18 h. The reaction was monitored by TLC; after completion of the reaction, the volatiles were removed in vacuo. The residue was diluted with EtOAc (100 mL) and water (75 mL), filtered through celite. The organic layer was dried over sodium sulphate, filtered and concentrated in vacuo to obtain compound 229 (300 mg) as colorless syrup. TLC: 10% MeOH/CH$_2$Cl$_2$ (R$_f$: 0.5); $^1$H NMR (DMSO-d$_6$, 500 MHz): δ 11.24 (br s, 1H), 7.38 (br s, 1H), 7.11 (s, 1H), 4.17 (d, J=5.5 Hz, 2H), 1.39 (s, 9H), 1.37 (s, 9H).

Synthesis of 5-(aminomethyl) thiazol-2-amine dihydrochloride (230)

To a stirring solution of compound 229 (300 mg) in CH$_2$Cl$_2$ (10 mL) was added 4 N HCl in 1, 4-dioxane (5 mL) under argon atmosphere at 0-5° C.; warmed to RT and stirred for 4 h. The reaction was monitored by TLC; after completion of the reaction, the volatiles were removed under reduced pressure. The obtained solid was washed with CH$_2$Cl$_2$ (5 mL), EtOAc (5 mL) and dried in vacuo to afford compound 230 (120 mg, HCl salt) as yellow solid. TLC: 10% MeOH/CH$_2$Cl$_2$ (R$_f$: 0.2); $^1$H NMR (DMSO-d$_6$, 500 MHz): δ 9.31 (br s, 1H), 8.53 (br s, 2H), 8.14 (br s, 1H), 7.37 (br s, 1H), 7.27 (br s, 1H), 7.17 (br s, 1H), 4.07 (d, J=5.5 Hz, 2H).

Synthesis of (2-ethylthiazol-5-yl) methanamine hydrochloride (239)

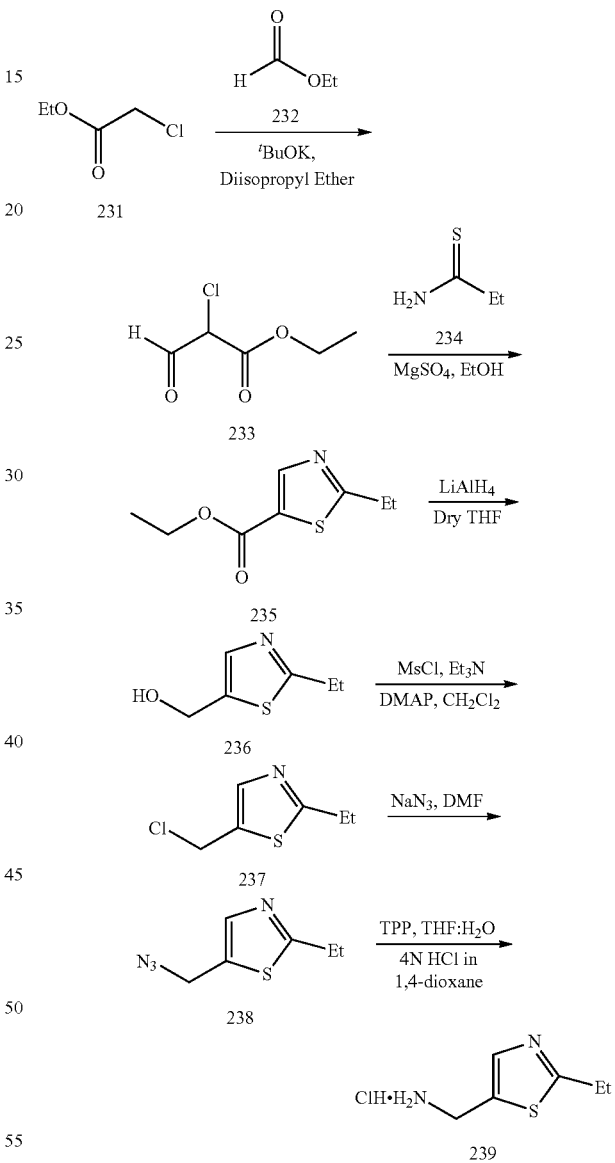

Synthesis of ethyl 2-chloro-3-oxopropanoate (233)

To a stirring solution of ethyl 2-chloroacetate 231 (5 g, 40.98 mmol) and 232 (3.03 g, 40.98 mmol) in diisopropyl ether (100 mL) under argon atmosphere was added potassium tert-butoxide (5.49 g, 45.08 mmol) portion wise for 10 min at 0° C.; warmed to RT and stirred for 24 h. The reaction was monitored by TLC; after completion of the reaction, the pH of the reaction mixture was adjusted to ~6 using 5 N HCl. The obtained solid was filtered, washed with diethyl ether (200 mL) and dried in vacuo to afford compound 233 (6 g) as pale brown syrup. TLC: 30% EtOAc/hexanes (R$_f$: 0.2); LC-MS: 21.49%+75.58%; 149.0 (M$^+$-1); (column; X-Select C-18, (50×3.0 mm, 3.5 μm); RT 0.56 min, 0.77 min. 5 Mm Aq.NH$_4$OAc:ACN 0.8 mL/min).

Synthesis of ethyl 2-ethylthiazole-5-carboxylate (235)

To a stirring solution of compound 233 (1 g) in ethanol (25 mL) under argon atmosphere were added propanethioamide 234 (594 mg, 6.67 mmol), dry magnesium sulfate (4 g) at RT and heated to reflux for 24 h. The reaction was monitored by TLC; after completion of the reaction, the volatiles were removed in vacuo, diluted with EtOAc (2×100 mL). The combined organic extracts were washed with saturated sodium bicarbonate solution (2×100 mL), brine (50 mL), dried over sodium sulfate, filtered and concentrated in vacuo to obtain the crude. The crude was purified through flash column chromatography using 6% EtOAc/hexanes to afford compound 235 (330 mg, 27%) as brown syrup. TLC: 10% EtOAc/hexanes (R$_f$: 0.4); $^1$H-NMR (DMSO-d$_6$, 400 MHz): δ 8.29 (s, 1H), 4.30 (q, J=7.1 Hz, 2H), 3.04 (q, J=7.5 Hz, 2H), 1.31 (t, J=7.3 Hz, 3H), 1.29 (t, J=7.3 Hz, 3H).

Synthesis of (2-ethylthiazol-5-yl) methanol (236)

To a stirring suspension of lithium aluminium hydride (205 mg, 5.40 mmol) in dry THF (15 mL) under inert atmosphere was added compound 235 (500 mg, 2.70 mmol) at 0° C.; warmed to RT and stirred for 16 h. The reaction was monitored by TLC; after completion of the reaction, the reaction mixture was cooled to 0° C., quenched with 20% aqueous sodium hydroxide solution (3 mL), filtered through celite and washed with EtOAc (3×100 mL). The filtrate was dried over sodium sulfate, filtered and concentrated in vacuo to afford compound 236 (310 mg, 80%) as pale yellow solid. TLC: 50% EtOAc/hexanes (R$_f$: 0.4). $^1$H-NMR (CDCl$_3$, 400 MHz): δ 7.51 (s, 1H), 4.82 (s, 2H), 3.01 (q, J=7.5 Hz, 2H), 1.38 (t, J=7.6 Hz, 3H).

Synthesis of 5-(chloromethyl)-2-ethylthiazole (237)

To a stirring solution of compound 236 (300 mg, 2.09 mmol) in CH$_2$Cl$_2$ (15 mL) under inert atmosphere were added triethyl amine (0.6 mL, 4.20 mmol), DMAP (25.6 mg, 0.21 mmol) and methanesulfonyl chloride (0.19 mL, 2.51 mmol) at 0° C.; warmed to RT and stirred for 2 h. The reaction was monitored by TLC; after completion of the reaction, the reaction mixture was diluted with water (50 mL) and extracted with CH$_2$Cl$_2$ (3×100 mL). The combined organic extracts were dried over sodium sulfate, filtered and concentrated in vacuo to afford compound 237 (500 mg, crude) as pale yellow syrup. TLC: 30% EtOAc/hexanes (R$_f$: 0.8); LC-MS: 30.71%; 162.0 (M$^+$+1); (column; Ascentis Express C18, (50×3.0 mm, 2.7 μm); RT 2.14 min. 0.025% Aq. TFA+5% ACN: ACN+5% 0.025% Aq. TFA, 1.2 mL/min).

Synthesis of 5-(azidomethyl)-2-ethylthiazole (238)

To a stirring solution of compound 237 (500 mg, 2.26 mmol) in DMF (20 mL) under inert atmosphere was added sodium azide (294 mg, 4.52 mmol) at RT and heated to 80° C. for 16 h. The reaction was monitored by TLC; after completion of the reaction, the reaction mixture was diluted with ice cold water (50 mL) and extracted with EtOAc (3×100 mL). The combined organic extracts were dried over sodium sulfate, filtered and concentrated in vacuo to obtain the crude. The crude was purified through flash column chromatography using 15% EtOAc/hexanes to afford compound 238 (250 mg, 71%) as pale yellow syrup. TLC: 20% EtOAc/hexanes (R$_f$: 0.4); $^1$H-NMR (CDCl$_3$, 400 MHz): δ 7.56 (s, 1H), 4.49 (s, 2H), 3.03 (q, J=7.6 Hz, 2H), 1.40 (t, J=7.6 Hz, 3H);

Synthesis of (2-ethylthiazol-5-yl) methanamine hydrochloride (239)

To a stirring solution of compound 238 (250 mg, 1.48 mmol) in THF:H$_2$O (5:1, 12 mL) was added triphenyl phosphine (780 mg, 2.97 mmol) at RT and stirred for 2 h. The reaction was monitored by TLC; after completion of the reaction, the volatiles were removed in vacuo to obtain the crude. The obtained solid was further dried using toluene (2×5 mL) to obtain the crude amine.

The above compound was dissolved in CH$_2$Cl$_2$ (5 mL) added 4 N HCl in 1, 4-dioxane (4 mL) under inert atmosphere at 0° C. and stirred for 30 min. The volatiles were removed in vacuo to obtain the crude, which was triturated with EtOAc (2 mL), diethyl ether (2 mL) and pentane (5 mL) to afford compound 239 (180 mg, 68%) as an off-white solid. TLC: 5% MeOH/CH$_2$Cl$_2$ (R$_f$: 0.2); $^1$H NMR (DMSO-d$_6$, 500 MHz): δ 8.48 (br s, 3H), 7.74 (s, 1H), 4.25 (q, J=5.5 Hz, 2H), 2.98 (q, J=7.5 Hz, 2H), 1.28 (t, J=7.5 Hz, 3H);

Synthesis of 4-(aminomethyl)-N-methylthiazol-2-amine hydrochloride (242)

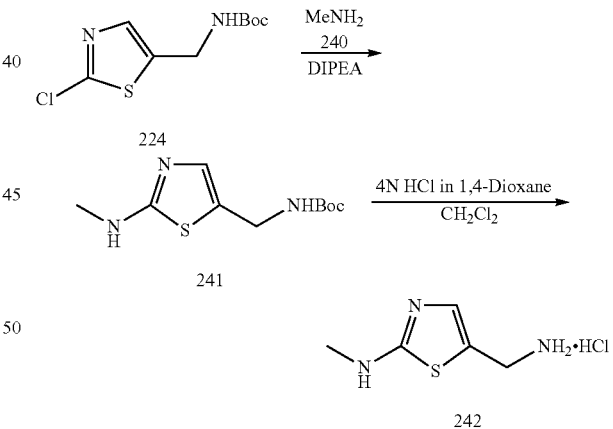

Synthesis of tert-butyl ((2-(methylamino) thiazol-4-yl) methyl) carbamate (241)

A mixture of compound 224 (100 mg, 0.41 mmol) and methyl amine 240 (5 mL, 33% solution in EtOH) in a sealed tube under argon atmosphere was added diisopropyl ethylamine (0.2 mL, 1.21 mmol) under argon atmosphere at RT and heated to 120° C. for 16 h. The reaction was monitored by TLC; after completion of the reaction, the volatiles were removed in vacuo. The crude was purified through silica gel column chromatography using 70% EtOAc/hexanes to afford compound 241 (90 mg, 92%) as colorless sticky solid. TLC: 50% EtOAc/hexanes ($R_f$ 0.2); $^1$H NMR (DMSO-$d_6$, 400 MHz): δ 7.26 (d, J=5.6 Hz, 2H), 6.77 (s, 1H), 4.05 (d, J=5.7 Hz, 2H), 2.76 (d, J=4.8 Hz, 3H), 1.38 (s, 9H).

Synthesis of 4-(aminomethyl)-N-methylthiazol-2-amine hydrochloride (242)

To a stirring solution of compound 241 (90 mg, 0.37 mmol) in $CH_2Cl_2$ (3 mL) under argon atmosphere was added 4 N HCl in 1, 4-dioxane (3 mL) at 0° C.; warmed to RT and stirred for 4 h. The reaction was monitored by TLC; after completion of the reaction, the volatiles were removed in vacuo. The crude was titurated with diethyl ether (5 mL) and dried in vacuo to afford compound 242 (70 mg, HCl salt) as brown solid. TLC: 30% EtOAc/hexanes ($R_f$ 0.1); $^1$H NMR (DMSO-$d_6$, 400 MHz): δ 9.73-9.27 (m, 1H), 8.39 (br s, 3H), 7.35 (s, 1H), 4.08 (q, J=5.3 Hz, 2H), 2.95 (s, 3H).

Synthesis of 4-(aminomethyl)-N,N-dimethylthiazol-2-amine hydrochloride (245)

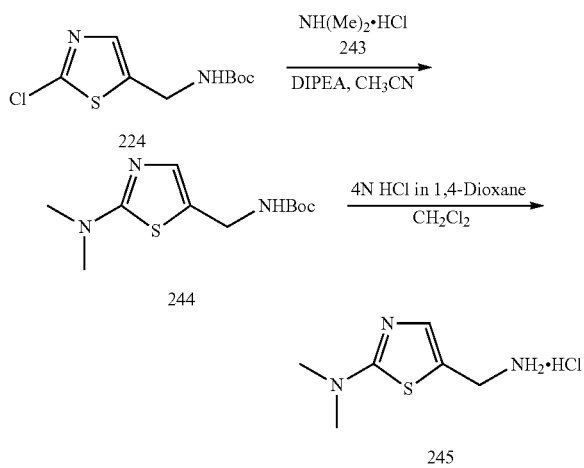

Synthesis of tert-butyl ((2-(dimethylamino) thiazol-4-yl) methyl) carbamate (244)

To a stirring solution of compound 224 (100 mg, 0.41 mmol) in $CH_3CN$ (3 mL) under argon atmosphere were added dimethyl amine hydrochloride 243 (648 mg, 8.06 mmol) and diisopropyl ethylamine (0.2 mL, 1.21 mmol) in a sealed tube at RT and heated to 120° C. for 54 h. The reaction was monitored by TLC; after completion of the reaction, the reaction mixture was diluted with EtOAc (2×50 mL) washed with water (20 mL). The organic extract was dried over sodium sulphate, filtered and concentrated in vacuo to obtain the crude. The crude was purified through silica gel column chromatography using 20% EtOAc/hexanes to afford compound 244 (80 mg, 77%) as an off-white solid. TLC: 30% EtOAc/hexanes ($R_f$: 0.2); $^1$H NMR (DMSO-$d_6$, 400 MHz): δ 7.29 (t, J=4.8 Hz, 1H), 6.89 (s, 1H), 4.08 (d, J=5.9 Hz, 2H), 2.97 (s, 6H), 1.38 (s, 9H).

Synthesis of 4-(aminomethyl)-N,N-dimethylthiazol-2-amine hydrochloride (245)

To a stirring solution of compound 244 (100 mg, 0.38 mmol) in $CH_2Cl_2$ (3 mL) under argon atmosphere was added 4 N HCl in 1, 4-dioxane (3 mL) at 0° C.; warmed to RT and stirred for 4 h. The reaction was monitored by TLC; after completion of the reaction, the volatiles were removed in vacuo. The crude was titurated with diethyl ether (5 mL) and dried in vacuo to afford compound 245 (75 mg, HCl salt) as an off-white solid. TLC: 50% EtOAc/hexanes ($R_1$. 0.1); $^1$H NMR (DMSO-$d_6$, 400 MHz): δ 8.44 (br s, 3H), 7.38 (s, 1H), 4.10 (q, J=5.6 Hz, 2H), 3.14 (s, 6H).

Synthesis of (2-isopropylthiazol-5-yl) methanamine hydrochloride (251)

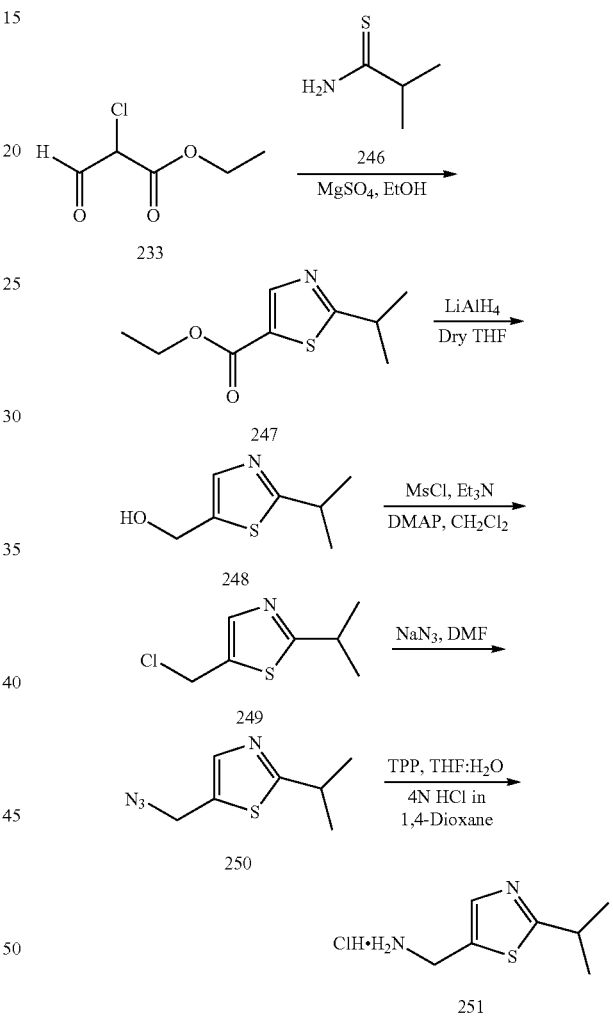

Synthesis of ethyl 2-isopropylthiazole-5-carboxylate (247)

To a stirring solution of compound 233 (3.05 g) in ethanol (60 mL) under argon atmosphere were added 2-methylpropanethioamide 246 (1.5 g, 14.56 mmol), dry magnesium sulfate (5 g) at RT and heated to reflux for 24 h. The reaction was monitored by TLC; after completion of the reaction, the volatiles were removed in vacuo. The residue was diluted with saturated sodium bicarbonate solution (100 mL), extracted with EtOAc (3×100 mL). The combined organic extracts were dried over sodium sulfate, filtered and concentrated in vacuo to obtain the crude. The crude was purified through flash column chromatography using 2% EtOAc/hexanes to afford compound 247 (550 mg, 17%) as brown syrup. TLC: 10% EtOAc/hexanes ($R_f$: 0.5); $^1$H NMR (500 MHz, DMSO-$d_6$) δ 8.31 (s, 1H), 4.30 (q, J=7.0 Hz, 2H), 3.36-3.29 (m, 1H), 1.34 (d, J=6.9 Hz, 6H), 1.29 (t, J=7.1 Hz, 3H).

Synthesis of (2-isopropylthiazol-5-yl) methanol (248)

To a stirring solution of compound 247 (550 mg, 2.76 mmol) in dry THF (10 mL) under inert atmosphere was added lithium aluminium hydride (210 mg, 5.52 mmol) at 0° C.; warmed to RT and stirred for 16 h. The reaction was monitored by TLC; after completion of the reaction, the reaction mixture was cooled to 0° C., quenched with 15% aqueous sodium hydroxide solution (3 mL), filtered through celite and washed with EtOAc (100 mL). The filtrate was dried over sodium sulfate, filtered and concentrated in vacuo to afford compound 248 (360 mg, 83%) as pale yellow syrup. TLC: 50% EtOAc/hexanes ($R_f$: 0.3). $^1$H NMR (400 MHz, DMSO-$d_6$) δ 7.47 (s, 1H), 5.43 (t, J=5.7 Hz, 1H), 4.61 (dd, J=5.6, 0.6 Hz, 2H), 3.26-3.19 (m, 1H), 1.30 (d, J=6.9 Hz, 6H).

Synthesis of 5-(chloromethyl)-2-isopropylthiazole (249)

To a stirring solution of compound 248 (350 mg, 2.23 mmol) in CH$_2$Cl$_2$ (20 mL) under inert atmosphere were added triethyl amine (0.64 mL, 4.45 mmol), DMAP (27.2 mg, 0.22 mmol) and methanesulfonyl chloride (0.2 mL, 2.67 mmol) at 0° C.; warmed to RT and stirred for 3 h. The reaction was monitored by TLC; after completion of the reaction, the reaction mixture was diluted with water (50 mL) and extracted with CH$_2$Cl$_2$ (2×100 mL). The combined organic extracts were dried over sodium sulfate, filtered and concentrated in vacuo to afford compound 249 (500 mg, crude) as pale yellow syrup. TLC: 40% EtOAc/hexanes ($R_f$: 0.8); LC-MS: 70.54%; 175.8 (M$^+$+1); (column; Ascentis Express C18, (50×3.0 mm, 2.7 μm); RT 2.34 min. 0.025% Aq. TFA+5% ACN: ACN+5% 0.025% Aq. TFA, 1.2 mL/min).

Synthesis of 5-(azidomethyl)-2-isopropylthiazole (250)

To a stirring solution of compound 249 (500 mg, 2.26 mmol) in DMF (20 mL) under inert atmosphere was added sodium azide (445 mg, 6.85 mmol) at RT and heated to 80° C. for 16 h. The reaction was monitored by TLC; after completion of the reaction, the reaction mixture was diluted with ice cold water (100 mL) and extracted with EtOAc (2×100 mL). The combined organic extracts were dried over sodium sulfate, filtered and concentrated in vacuo to obtain the crude. The crude was purified through column chromatography using 8% EtOAc/hexanes to afford compound 250 (255 mg, 63%) as colorless liquid. TLC: 10% EtOAc/hexanes ($R_f$: 0.4); $^1$H NMR (500 MHz, DMSO-$d_6$): δ=7.67 (s, 1H), 4.69 (s, 2H), 3.29-3.24 (m, 1H), 1.32 (d, J=6.9 Hz, 8H).

Synthesis of (2-isopropylthiazol-5-yl) methanamine hydrochloride (251)

To a stirring solution of compound 250 (250 mg, 1.37 mmol) in THF:H$_2$O (5:1, 12 mL) was added triphenyl phosphine (720 mg, 2.74 mmol) at RT and stirred for 2 h. The reaction was monitored by TLC; after completion of the reaction, the volatiles were removed in vacuo to obtain the crude. The obtained solid was further dried using toluene (2×5 mL) to obtain the crude amine.

The above crude compound was dissolved in CH$_2$Cl$_2$ (5 mL) added 4 N HCl in 1, 4-dioxane (10 mL) under inert atmosphere at 0° C. and stirred for 30 min. The volatiles were removed in vacuo to obtain the crude, which was triturated with EtOAc (2 mL), diethyl ether (2 mL) and pentane (5 mL) to afford compound 251 (170 mg, 65%) as low melting hygroscopic solid. TLC: 5% MeOH/CH$_2$Cl$_2$ ($R_f$: 0.2); $^1$H NMR (500 MHz, DMSO-$d_6$): δ 8.29 (br s, 2H), 7.72 (s, 1H), 4.25 (d, J=5.8 Hz, 2H), 3.29-3.24 (m, 1H), 1.30 (d, J=6.9 Hz, 6H)

Synthesis of (2-(trifluoromethyl) thiazol-5-yl) methanamine (255)

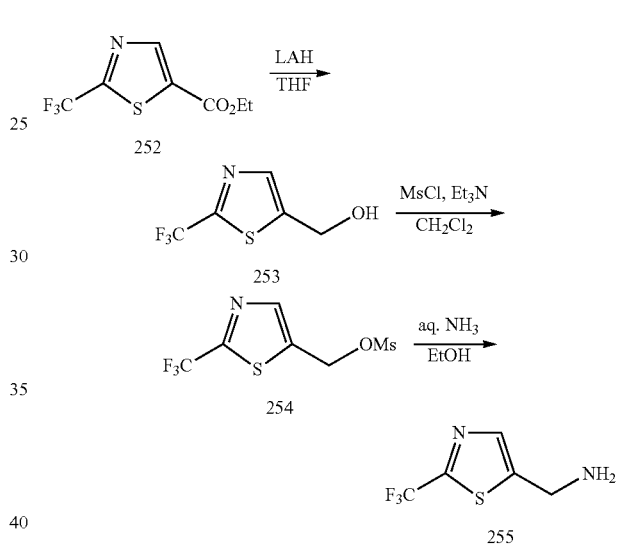

Synthesis of (2-(trifluoromethyl) thiazol-5-yl) methanol (253)

To a stirring solution of ethyl 2-(trifluoromethyl) thiazole-5-carboxylate 252 (500 mg, 2.22 mmol) in THF (25 mL) under inert atmosphere was added lithium aluminium hydride (126 mg, 3.33 mmol) at 0° C.; warmed to RT and stirred for 3 h. The reaction was monitored by TLC; after completion of the reaction, the reaction mixture was cooled to 0° C., quenched with ice-cold water (5 mL), followed by 10% aqueous sodium hydroxide solution (3 mL), filtered through celite and washed with THF (10 mL). The filtrate was dried over sodium sulfate, filtered and concentrated in vacuo to afford compound 253 (300 mg, 73%) as pale yellow liquid. $^1$H NMR (DMSO-$d_6$, 400 MHz): δ 7.98 (s, 1H), 5.90 (t, J=5.7 Hz, 2H), 4.79 (d, J=5.6 Hz, 3H).

Synthesis of (2-(trifluoromethyl) thiazol-5-yl) methyl methanesulfonate (254)

To a stirring solution of compound 253 (200 mg, 1.09 mmol) in CH$_2$Cl$_2$ (10 mL) under inert atmosphere were added triethyl amine (0.47 mL, 3.27 mmol), methanesulfonyl chloride (0.16 mL, 2.18 mmol) at 0° C.; warmed to RT and stirred for 16 h. The reaction was monitored by TLC; after completion of the reaction, the reaction mixture was diluted with CH$_2$Cl$_2$ (100 mL), washed with 10% NaHCO$_3$ solution (50 mL). The organic extract was dried over sodium sulfate, filtered and concentrated in vacuo to afford crude compound 254 (200 mg) as yellow liquid. TLC: 40% EtOAc/hexanes (R$_f$: 0.2); LC-MS: 24.48%; 261.8 (M$^+$+1); (column; Ascentis Express C18, (50×3.0 mm, 2.7 µm); RT 2.29 min. 0.025% Aq. TFA+5% ACN: ACN+5% 0.025% Aq. TFA, 1.2 mL/min).

Synthesis of (2-(trifluoromethyl) thiazol-5-yl) methanamine (255)

To a stirring solution of compound 254 (200 mg, crude) in EtOH (10 mL) was added aqueous ammonia (10 mL) at 0° C.; heated to 100° C. and stirred for 16 h in a sealed tube. The reaction was monitored by TLC; after completion of the reaction, the volatiles were removed in vacuo to obtain the crude. The crude was purified through silica gel column chromatography using 10% MeOH/CH$_2$Cl$_2$ to afford compound 255 (56 mg) as pale yellow sticky solid. 41 NMR (DMSO-d$_6$, 400 MHz): δ 7.92 (s, 1H), 6.80 (br s, 2H), 4.01 (s, 2H).

Synthesis of (4-(trifluoromethyl) thiazol-5-yl) methanamine (263)

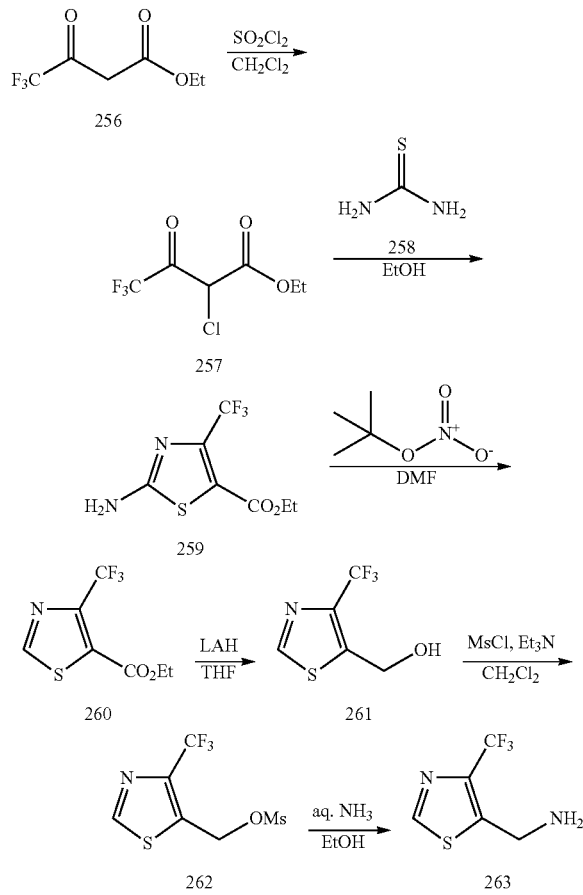

Synthesis of ethyl 2-chloro-4, 4, 4-trifluoro-3-oxobutanoate (257)

To a stirring solution of ethyl 4, 4, 4-trifluoro-3-oxobutanoate 256 (10 g, 54.2 mmol) in CH$_2$Cl$_2$ (25 mL) under inert atmosphere was added sulfuryl chloride (5.2 mL, 65.0 mmol) at 0° C.; warmed to RT and stirred for 16 h. The reaction was monitored by TLC; after completion of the reaction, the volatiles were removed in vacuo at RT to afford compound 257 (5 g) as yellow liquid. TLC: 10% EtOAc/hexanes (R$_f$: 0.5). $^1$H NMR (CDCl$_3$, 400 MHz): δ 5.62 (s, 1H), 4.29 (q, J=7.2 Hz, 2H), 1.33 (t, J=7.2 Hz, 3H).

Synthesis of ethyl 2-amino-4-(trifluoromethyl) thiazole-5-carboxylate (259)

To a stirring solution of compound 257 (5 g, crude) in ethanol (25 mL) under inert atmosphere was added thiourea 258 (3.3 g, 45.8 mmol) at RT and heated to reflux for 16 h. The reaction was monitored by TLC; after completion of the reaction, the volatiles were removed in vacuo. The residue was diluted with diethyl ether (200 mL) and washed with water (100 mL). The organic extract was dried over sodium sulfate, filtered and concentrated in vacuo to obtain the crude. The crude was purified through silica gel column chromatography using 10-15% EtOAc/hexanes to afford compound 259 (2.7 g, 49%) as pale yellow solid. TLC: 30% EtOAc/hexanes (R$_f$: 0.5); $^1$H NMR (DMSO-d$_6$, 400 MHz): δ 8.21 (s, 2H), 4.21 (q, J=7.0 Hz, 2H), 1.24 (t, J=7.1 Hz, 3H).

Synthesis of ethyl 4-(trifluoromethyl) thiazole-5-carboxylate (260)

To a stirring solution of compound 259 (2.7 g, 11.25 mmol) in DMF (10 mL) under inert atmosphere was added tert-butyl nitrate (5.8 g, 56.25 mmol) at 0° C.; heated to 100° C. and stirred for 4 h. The reaction was monitored by TLC; after completion of the reaction, the reaction mixture was diluted with diethyl ether (2×100 mL). The combined organic extracts were dried over sodium sulfate, filtered and concentrated in vacuo to afford the crude. The crude was purified through silica gel column chromatography using 5-10% EtOAc/hexanes to afford compound 260 (1.5 g, 60%) as pale yellow solid. TLC: 20% EtOAc/hexanes (R$_f$: 0.7); $^1$H NMR (DMSO-d$_6$, 400 MHz): 9.41 (s, 1H), 4.35 (q, J=7.0 Hz, 2H), 1.32 (t, J=7.1 Hz, 3H).

Synthesis of (4-(trifluoromethyl) thiazol-5-yl) methanol (261)

To a stirring solution of compound 260 (500 mg, 2.22 mmol) in THF (20 mL) under inert atmosphere was added lithium aluminium hydride (169 mg, 4.44 mmol) portion wise at 0° C.; warmed to RT and stirred for 6 h. The reaction was monitored by TLC; after completion of the reaction, the reaction mixture was cooled to 0° C., quenched with ice-cold water (1 mL), followed by 15% aqueous sodium hydroxide solution (1.5 mL), filtered through celite and washed with THF (10 mL). The filtrate was dried over sodium sulfate, filtered and concentrated in vacuo to obtain the crude. The crude was purified through silica gel column chromatography using 30% EtOAc/hexanes to afford compound 261 (205 mg, 50%) as colorless liquid. $^1$H NMR (DMSO-d$_6$, 400 MHz): δ 9.12 (s, 1H), 6.15 (t, J=5.6 Hz, 1H), 4.85-4.83 (m, 2H).

Synthesis of (4-(trifluoromethyl) thiazol-5-yl) methyl methanesulfonate (262)

To a stirring solution of compound 261 (200 mg, 1.09 mmol) in CH$_2$Cl$_2$ (10 mL) under inert atmosphere were added triethyl amine (0.47 mL, 3.27 mmol), methanesulfonyl chloride (0.23 mL, 2.73 mmol) at 0° C.; warmed to RT and stirred for 6 h. The reaction was monitored by TLC; after completion of the reaction, the reaction mixture was diluted with CH$_2$Cl$_2$ (2×50 mL), washed with water (100 mL). The organic extract was dried over sodium sulfate, filtered and concentrated in vacuo to afford compound 262 (210 mg) as yellow liquid. TLC: 30% EtOAc/hexanes (R$_f$: 0.3); $^1$H NMR (DMSO-d$_6$, 400 MHz): δ 9.29 (s, 1H), 5.64 (s, 2H), 3.34 (s, 3H).

Synthesis of (4-(trifluoromethyl) thiazol-5-yl) methanamine (263)

To a stirring solution of compound 262 (200 mg, 0.76 mmol) in EtOH (10 mL) was added aqueous ammonia (10 mL) at 0° C.; warmed to RT and stirred for 16 h. The reaction was monitored by TLC; after completion of the reaction, the volatiles were removed in vacuo to obtain the crude. The crude was purified through silica gel column chromatography using 10% MeOH/CH$_2$Cl$_2$ to afford compound 263 (85 mg, 61%) as pale yellow sticky solid. $^1$H NMR (DMSO-d$_6$, 400 MHz): 9.21 (s, 1H), 7.27 (br s, 2H), 4.32 (s, 2H).

Synthesis of 2-(thiazol-5-yl) propan-2-amine hydrochloride (270)

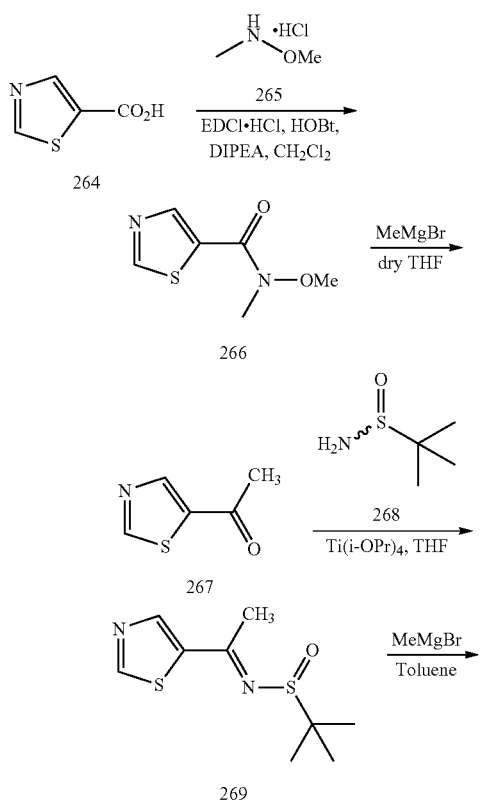

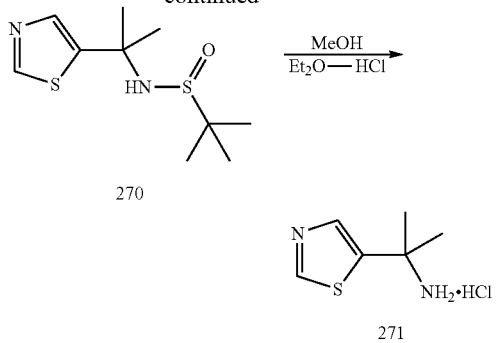

Synthesis of N-methoxy-N-methylthiazole-5-carboxamide (266)

To a stirring solution of thiazole-5-carboxylic acid 264 (2 g, 15.44 mmol) in CH$_2$Cl$_2$ (40 mL) under inert atmosphere were added EDCI.HCl (3.26 g, 17.04 mmol), HOBt (1 g, 7.74 mmol), N,O-dimethyl hydroxylamine hydrochloride 265 (1.81 g, 18.59 mmol) and diisopropylethylamine (13.4 mL, 77.45 mmol) at 0° C.; warmed to RT and stirred for 16 h. The reaction was monitored by TLC; after completion of the reaction, the reaction mixture was diluted with water (70 mL) and extracted with CH$_2$Cl$_2$ (3×70 mL). The combined organic extracts were dried over sodium sulfate, filtered and concentrated in vacuo to obtain the crude. The crude was purified through silica gel flash column chromatography using 30-40% EtOAc/hexanes to afford compound 266 (1.6 g, 60%) as white solid. TLC: 5% MeOH/CH$_2$Cl$_2$ (R$_f$: 0.6); $^1$H NMR (DMSO-d$_6$, 400 MHz): 9.32 (s, 1H), 8.52 (s, 1H), 3.77 (s, 3H), 3.30 (s, 3H).

Synthesis of 1-(thiazol-5-yl) ethan-1-one (267)

To a stirring solution of compound 266 (1.6 g, 9.30 mmol) in dry THF (20 mL) under inert atmosphere was added methyl magnesium bromide (4.65 mL, 13.95 mmol, 3 M solution in Et$_2$O) dropwise for 10 min at −10° C.; warmed to RT and stirred for 16 h. The reaction was monitored by TLC; after completion of the reaction, the reaction mixture was quenched with saturated ammonium chloride (30 mL) and extracted with EtOAc (2×60 mL). The combined organic extracts were dried over sodium sulfate, filtered and concentrated in vacuo to obtain the crude. The crude was purified through silica gel flash column chromatography using 25-30% EtOAc/hexanes to afford compound 267 (1 g, 85%) as white solid. TLC: 50% EtOAc/hexanes (R$_f$: 0.8); $^1$H NMR (DMSO-d$_6$, 400 MHz): δ 9.40 (s, 1H), 8.71 (s, 1H), 2.60 (s, 3H).

Synthesis of 2-methyl-N-(1-(thiazol-5-yl) ethylidene) propane-2-sulfinamide (269)

To a stirring solution of compound 267 (500 mg, 3.93 mmol) in THF (20 mL) under inert atmosphere was added 2-methylpropane-2-sulfinamide 268 (570 mg, 4.70 mmol) and titanium (IV) isopropoxide (2.23 g, 7.87 mmol) at RT and heated to reflux and stirred for 16 h. The reaction was monitored by TLC; after completion of the reaction, the reaction mixture was diluted diethyl ether (300 mL) and water (10 mL) and stirred for 10 min. The organic extract was dried over sodium sulfate, filtered and concentrated in vacuo to obtain the crude. The crude was purified through silica gel flash column chromatography using 35-40% EtOAc/hexanes to afford compound 269 (600 mg, 66%) as brown syrup. TLC: 40% EtOAc/hexanes ($R_f$: 0.3); $^1$H NMR (DMSO-$d_6$, 400 MHz): δ 9.29 (s, 1H), 8.58 (s, 1H), 2.75 (s, 3H), 1.15 (s, 9H).

Synthesis of 2-methyl-N-(2-(thiazol-5-yl) propan-2-yl) propane-2-sulfinamide (270)

To a stirring solution of compound 269 (300 mg, 1.30 mmol) in Toluene (10 mL) under inert atmosphere was added methyl magnesium bromide (2.6 mL, 7.82 mmol, 3 M solution in Et$_2$O) dropwise for 10 min at −70° C.; warmed to RT and stirred for 16 h. The reaction was monitored by TLC; after completion of the reaction, the reaction mixture was quenched with saturated ammonium chloride (30 mL) and extracted with EtOAc (2×60 mL). The combined organic extracts were dried over sodium sulfate, filtered and concentrated in vacuo to obtain the crude. The crude was purified through silica gel flash column chromatography using 60-70% EtOAc/hexanes to afford compound 270 (140 mg, 44%) as yellow syrup. TLC: 5% MeOH/CH$_2$Cl$_2$ ($R_f$: 0.3); $^1$H NMR (DMSO-$d_6$, 400 MHz): δ 8.99 (s, 1H), 7.81 (s, 1H), 5.54 (s, $^1$H), 1.68 (s, 3H), 1.61 (s, 3H), 1.32 (s, 9H).

Synthesis of 2-(thiazol-5-yl) propan-2-amine hydrochloride (271)

To a stirring solution of compound 270 (100 mg, 0.40 mmol) in MeOH (4 mL) under inert atmosphere was added 2 M HCl in diethyl ether (4 mL) at 0° C.; warmed to RT and stirred for 2 h. The reaction was monitored by TLC; after completion of the reaction, the volatiles were removed in vacuo to obtain the crude which was washed with diethyl ether (2×10 mL) to afford compound 271 (65 mg, 90%) as an off-white solid. TLC: 5% MeOH/CH$_2$Cl$_2$ ($R_f$: 0.1); $^1$H NMR (DMSO-$d_6$, 400 MHz): δ 9.11 (s, 1H), 8.99 (br s, 3H), 8.04 (s, 1H), 1.78 (s, 6H).

Synthesis of (2-(tert-butyl) thiazol-5-yl) methanamine hydrochloride (277)

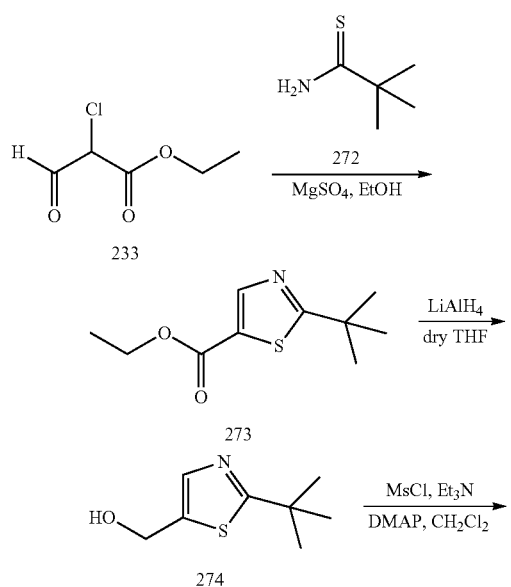

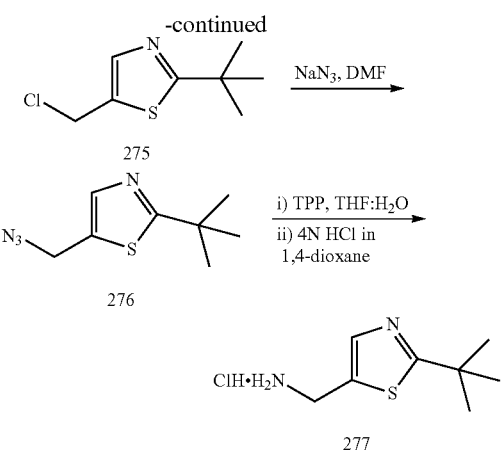

Synthesis of ethyl 2-(tert-butyl) thiazole-5-carboxylate (273)

To a stirring solution of compound 233 (11.2 g, 74.66 mmol) in ethanol (100 mL) under argon atmosphere were added 2,2-dimethylpropanethioamide 272 (8.73 g, 74.66 mmol) and dry magnesium sulfate (20 g) at RT and heated to reflux for 24 h. The reaction was monitored by TLC; after completion of the reaction, the volatiles were removed in vacuo, diluted with water (200 mL) and extracted with EtOAc (2×200 mL). The combined organic extracts were dried over sodium sulfate, filtered and concentrated in vacuo to obtain the crude. The crude was purified through silica gel column chromatography using 2-15% EtOAc/hexanes to afford compound 273 (3.7 g, 23%) as pale yellow syrup. TLC: 20% EtOAc/hexanes ($R_f$: 0.6); $^1$H-NMR (DMSO-$d_6$, 500 MHz): δ 8.29 (s, 1H), 4.28 (q, J=7.2 Hz, 2H), 1.38 (s, 9H), 1.27 (t, J=7.1 Hz, 3H).

Synthesis of (2-(tert-butyl) thiazol-5-yl) methanol (274)

To a stirring solution of compound 273 (3.7 g, 20.10 mmol) in dry THF (50 mL) under inert atmosphere was added lithium aluminium hydride (1.5 g, 40.21 mmol) portion wise for 10 min at 0° C.; warmed to RT and stirred for 16 h. The reaction was monitored by TLC; after completion of the reaction, the reaction mixture was cooled to 0° C., quenched with ice cold water (100 mL), filtered through celite and washed with EtOAc (2×100 mL). The filtrate was removed in vacuo to obtain the crude. The crude was purified through silica gel column chromatography using 5-20% EtOAc/hexanes to afford compound 274 (1.7 g, 50%) as pale yellow thick syrup. TLC: 30% EtOAc/hexanes ($R_f$: 0.4). $^1$H-NMR (DMSO-$d_6$, 500 MHz): δ 7.46 (s, 1H), 5.42 (t, J=5.6 Hz, 1H), 4.60 (d, J=5.5 Hz, 2H), 1.34 (s, 9H).

Synthesis of 2-(tert-butyl)-5-(chloromethyl) thiazole (275)

To a stirring solution of compound 274 (1.7 g, 13.17 mmol) in CH$_2$Cl$_2$ (50 mL) under inert atmosphere were added triethyl amine (2.3 mL, 19.76 mmol) and methanesulfonyl chloride (1.30 mL, 15.81 mmol) at 0° C.; warmed to RT and stirred for 4 h. The reaction was monitored by TLC; after completion of the reaction, the reaction mixture was quenched with saturated sodium carbonate (100 mL)

and extracted with $CH_2Cl_2$ (2×100 mL). The combined organic extracts were dried over sodium sulfate, filtered and concentrated in vacuo to afford compound 275 (2.5 g, crude) as colorless syrup. TLC: 30% EtOAc/hexanes ($R_f$: 0.8); LC-MS: 61.93%; 190.2 ($M^++1$); (column; X-select C18, (50×3.0 mm, 2.5 μm); RT 4.43 min. 2.5 mM Aq. $NH_4OAc$: ACN: 0.8 mL/min).

Synthesis of 5-(azidomethyl)-2-(tert-butyl) thiazole (276)

To a stirring solution of compound 275 (2.5 g, crude) in DMF (25 mL) under inert atmosphere was added sodium azide (1.71 g, 26.45 mmol) at RT and heated to 80° C. for 16 h. The reaction was monitored by TLC; after completion of the reaction, the reaction mixture was diluted with ice cold water (50 mL) and extracted with EtOAc (2×100 mL). The combined organic extracts were dried over sodium sulfate, filtered and concentrated in vacuo to obtain the crude. The crude was purified through silica gel column chromatography using 5-10% EtOAc/hexanes to afford compound 276 (1 g, 38%) as colorless syrup. TLC: 20% EtOAc/hexanes ($R_f$: 0.5); $^1$H-NMR (DMSO-$d_6$, 500 MHz): 7.66 (s, 1H), 4.69 (s, 2H), 1.37 (s, 9H).

Synthesis of (2-(tert-butyl) thiazol-5-yl) methanamine hydrochloride (277)

To a stirring solution of compound 276 (1 g, 5.10 mmol) in THF:$H_2O$ (4:1, 20 mL) was added triphenyl phosphine (2.67 g, 10.20 mmol) at 0° C. portion wise for 15 min; warmed to RT and stirred for 2 h. The reaction was monitored by TLC; after completion of the reaction, the volatiles were removed in vacuo to obtain the crude. The obtained solid was further dried using toluene (2×5 mL) to obtain the crude amine.

The above compound (600 mg, crude) was dissolved in $CH_2Cl_2$ (5 mL) under inert atmosphere was added 4 N HCl in 1, 4-dioxane (10 mL) at 0° C.; warmed to RT and stirred for 3 h. The volatiles were removed in vacuo to obtain the crude. The crude was washed with $CH_2Cl_2$ (10 mL), diethyl ether (10 mL) and dried in vacuo to afford compound 277 (700 mg, 96%) as an off-white solid. TLC: 20% EtOAc/hexanes ($R_f$: 0.2); 41 NMR (DMSO-$d_6$, 500 MHz): δ 8.49 (br s, 3H), 7.75 (s, 1H), 4.25 (q, J=5.6 Hz, 2H), 1.37 (s, 9H).

Synthesis of 5-(aminomethyl) thiazole-2-carbonitrile (282)

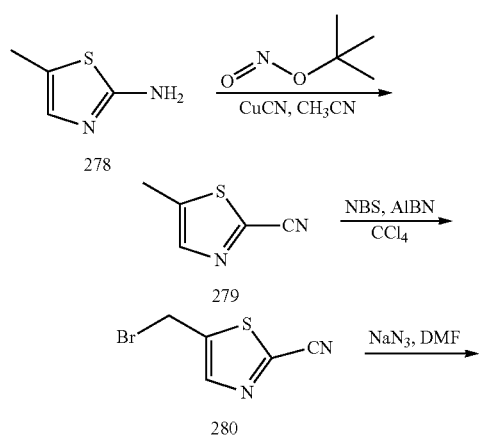

Synthesis of 5-methylthiazole-2-carbonitrile (279)

To a stirring solution of 5-methylthiazol-2-amine 278 (10 g, 87.71 mmol) in $CH_3CN$ (100 mL) under argon atmosphere were added tert-butyl nitrite (18 g, 17.54 mmol), copper (I) cyanide (23.6 g, 263.51 mmol) at RT; heated to reflux and stirred for 2 h. The reaction was monitored by TLC; after completion of the reaction, the volatiles were removed in vacuo to obtain the crude, which was purified through silica gel column chromatography using 20% EtOAc/hexanes to afford compound 279 (2 g, 20%) as white solid. TLC: 30% EtOAc/hexanes ($R_f$: 0.3); $^1$H-NMR (DMSO-$d_6$, 400 MHz): δ 7.98 (s, 1H), 2.59 (s, 3H).

Synthesis of 5-(bromomethyl) thiazole-2-carbonitrile (280)

To a stirring solution of compound 279 (2.4 g, 19.35 mmol) in $CCl_4$ (50 mL) under argon atmosphere was added N-bromosuccinimide (3.4 g, 19.35 mmol), azobisisobutyronitrile (317 mg, 1.93 mmol) at RT; heated to reflux and stirred for 8 h. The reaction was monitored by TLC; after completion of the reaction, the volatiles were removed in vacuo to obtain the crude. The crude was purified through silica gel column chromatography using 15% EtOAc/hexanes to afford compound 280 (2 g, 51%) as yellow solid. TLC: 10% EtOAc/hexanes ($R_f$: 0.5); $^1$H-NMR (DMSO-$d_6$, 400 MHz): δ 8.26 (s, 1H), 5.14 (s, 2H).

Synthesis of 5-(azidomethyl) thiazole-2-carbonitrile (281)

To a stirring solution of compound 280 (2 g, 9.85 mmol) in DMF (25 mL) under inert atmosphere was added sodium azide (1.9 g, 29.55 mmol) at 0° C.; warmed to RT and stirred for 2 h. The reaction was monitored by TLC; after completion of the reaction, the reaction mixture was diluted with ice cold water (50 mL) and extracted with EtOAc (3×100 mL). The combined organic extracts were dried over sodium sulfate, filtered and concentrated in vacuo to obtain the crude. The crude was purified through silica gel column chromatography using 30% EtOAc/hexanes to afford compound 281 (1 g, 62%) as yellow syrup. TLC: 30% EtOAc/hexanes ($R_f$: 0.4); $^1$H-NMR (DMSO-$d_6$, 500 MHz): δ 7.95 (s, 1H), 4.95 (s, 2H).

Synthesis of 5-(aminomethyl) thiazole-2-carbonitrile (282)

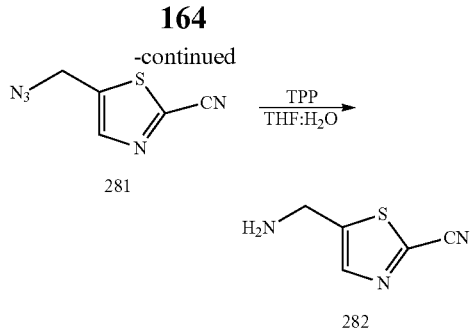

To a stirring solution of compound 281 (1 g, 6.06 mmol) in THF:$H_2O$ (3:1, 20 mL) was added triphenyl phosphine (3.1 g, 12.12 mmol) at 0° C.; warmed to RT and stirred for 16 h. The reaction was monitored by TLC; after completion of the reaction, the volatiles were removed in vacuo to obtain the crude, The crude was purified through silica gel column chromatography using 50% EtOAc/hexanes to afford compound 282 (1 g, 62%) as yellow syrup. TLC: 80% EtOAc/hexanes ($R_f$: 0.4); $^1$H-NMR (DMSO-$d_6$, 400 MHz): δ 8.01 (s, 1H), 4.04 (s, 2H).

Synthesis of (2-(4-fluorophenyl) thiazol-5-yl) methanamine hydrochloride (285)

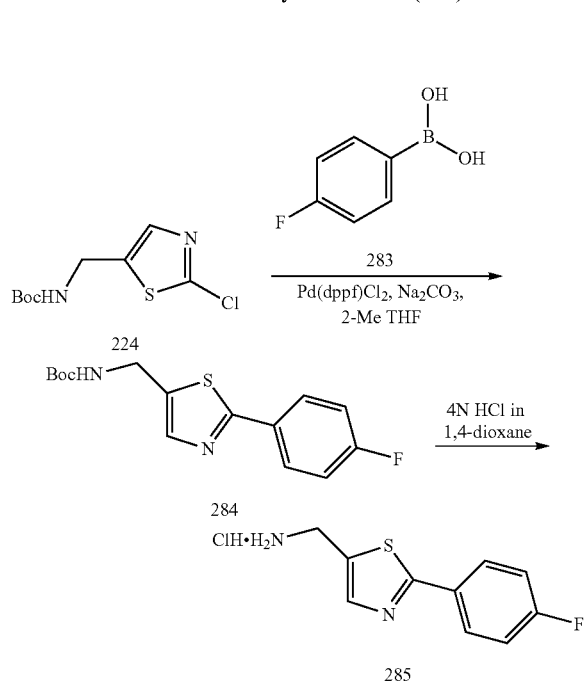

Synthesis of tert-butyl ((2-(4-fluorophenyl) thiazol-5-yl) methyl) carbamate (284)

To a stirring solution of compound 224 (500 mg, 2.01 mmol) in 2-methyltetrahydrofuran (50 mL) under argon atmosphere were added (4-fluorophenyl) boronic acid 283 (309 mg, 2.25 mmol), sodium carbonate (535 mg, 5.05 mmol) at RT and purged under argon atmosphere for 10 min. To this was added Pd(dppf)Cl$_2$ (73.5 mg, 0.10 mmol); heated to 110° C. and stirred for 16 h. The reaction was monitored by TLC; after completion of the reaction, the volatiles were removed in vacuo to obtain the crude. The crude was purified through silica gel column chromatography using 40% EtOAc/hexanes to afford compound 284 (160 mg, 25%) as yellow solid. TLC: 40% EtOAc/hexanes ($R_f$: 0.4); $^1$H-NMR (DMSO-$d_6$, 400 MHz): δ 7.94 (dd, J=8.7, 5.5 Hz, 2H), 7.68 (s, 1H), 7.56 (t, J=4.9 Hz, 1H), 7.32 (t, J=8.7 Hz, 2H), 4.33 (d, J=5.8 Hz, 2H), 1.40 (s, 9H).

Synthesis of (2-(4-fluorophenyl) thiazol-5-yl) methanamine hydrochloride (285)

To a stirring solution of compound 284 (160 mg, 0.51 mmol) in CH$_2$Cl$_2$ (5 mL) was added 4 N HCl in 1, 4-dioxane (2 mL) under argon atmosphere at 0° C.; warmed to RT and stirred for 2 h. The reaction was monitored by TLC; after completion of the reaction, the volatiles were removed in vacuo to afford compound 285 (100 mg, 94%) as pink solid. TLC: 40% EtOAc/hexanes ($R_f$: 0.1); $^1$H-NMR (DMSO-$d_6$, 400 MHz): δ 8.55 (br s, 3H), 8.01-7.96 (m, 3H), 7.36 (t, J=8.8 Hz, 2H), 4.34 (q, J=5.7 Hz, 2H).

Synthesis of 2-((5-(aminomethyl) thiazol-2-yl) thio)-N, N-dimethylethan-1-amine hydrochloride (288)

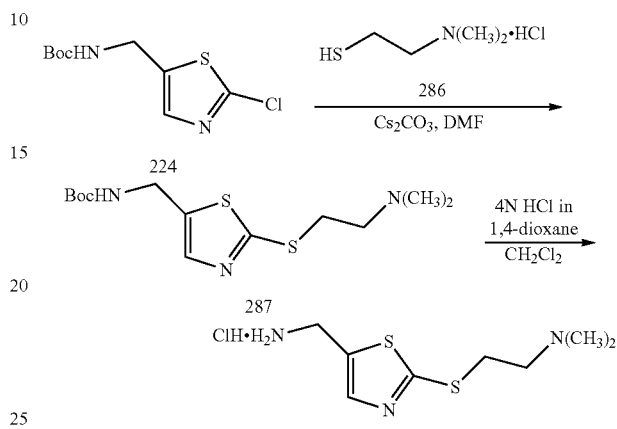

Synthesis of tert-butyl ((2-((2-(dimethylamino) ethyl) thio) thiazol-5-yl) methyl) carbamate (287)

To a stirring solution of tert-butyl ((2-chlorothiazol-5-yl) methyl) carbamate 224 (1 g, 4.03 mmol) in DMF (20 mL) under inert atmosphere was added 2-(dimethylamino) ethane-1-thiol hydrochloride 286 (1.1 g, 8.06 mmol) and cesium carbonate (4 g, 12.09 mmol) at RT in a sealed tube; heated to 100° C. and stirred for 16 h. The reaction was monitored by TLC; after completion of the reaction, the reaction mixture was poured into ice-cold water (20 mL) and extracted with EtOAc (2×50 mL). The combined organic extracts were dried over sodium sulfate, filtered and concentrated in vacuo to afford compound 287 (1.1 g, 87%) as brown syrup. TLC: 10% MeOH/CH$_2$Cl$_2$ ($R_f$: 0.2); $^1$H-NMR (DMSO-$d_6$, 500 MHz): δ 7.46 (s, 1H), 4.22 (d, J=5.5 Hz, 2H), 3.28 (t, J=7.1 Hz, 2H), 2.56 (t, J=7.1 Hz, 2H), 2.16 (s, 6H), 1.38 (s, 9H).

Synthesis of 2-((5-(aminomethyl) thiazol-2-yl) thio)-N, N-dimethylethan-1-amine hydrochloride (288)

To a stirring solution of compound 287 (1.1 g, 3.47 mmol) in CH$_2$Cl$_2$ (5 mL) was added 4 N HCl in 1, 4-dioxane (10 mL) under inert atmosphere at 0° C.; warmed to RT and stirred for 4 h. The reaction was monitored by TLC; after completion of the reaction, the volatiles were removed in vacuo. The crude was washed with diethyl ether (2×10 mL), n-pentane (2×10 mL) and dried in vacuo to afford compound 288 (700 mg, HCl salt) as an off-white solid. TLC: 30% 10% MeOH/CH$_2$Cl$_2$ ($R_f$: 0.2); $^1$H-NMR (DMSO-$d_6$, 500 MHz): δ 8.67 (br s, 3H), 7.83 (s, 1H), 4.23 (q, J=4.9 Hz, 2H), 3.63-3.57 (m, 2H), 3.41-3.34 (m, 2H), 2.77 (d, J=4.6 Hz, 6H).

Synthesis of (2-phenylthiazol-5-yl) methanamine hydrochloride (291)

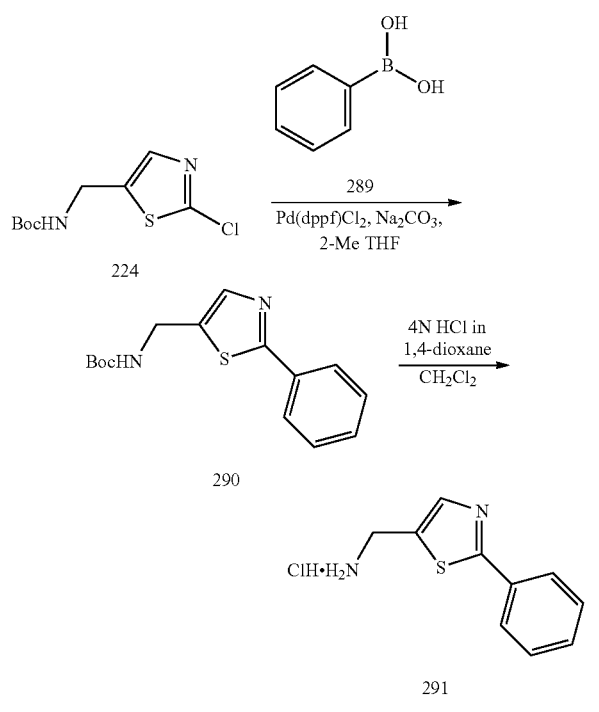

Synthesis of tert-butyl ((2-phenylthiazol-5-yl)methyl) carbamate (290)

To a stirring solution of compound 224 (250 mg, 1.00 mmol) in 2-methyltetrahydrofuran (10 mL) under argon atmosphere were added phenylboronic acid 289 (136 mg, 1.10 mmol), sodium carbonate (265 mg, 2.50 mmol) at RT and purged under argon atmosphere for 20 min. To this was added Pd(dppf)Cl$_2$ (36.5 mg, 0.05 mmol) at RT; heated to 110° C. and stirred for 16 h. The reaction was monitored by TLC; after completion of the reaction, the volatiles were removed in vacuo to obtain the crude. The crude was purified through silica gel column chromatography using 20% EtOAc/hexanes to afford compound 290 (110 mg, 37%) as an off-white solid. TLC: 30% EtOAc/hexanes (R$_f$: 0.4); $^1$H-NMR (DMSO-d$_6$, 500 MHz): δ 7.89 (d, J=6.4 Hz, 2H), 7.69 (s, 1H), 7.56 (t, J=6.4 Hz, 1H), 7.51-7.46 (m, 3H), 4.34 (d, J=5.8 Hz, 2H), 1.40 (s, 9H).

Synthesis of (2-phenylthiazol-5-yl) methanamine hydrochloride (291)

To a stirring solution of compound 290 (1.6 g, 5.51 mmol) in CH$_2$Cl$_2$ (25 mL) under inert atmosphere was added 4 N HCl in 1,4-dioxane (10 mL) at 0° C.; warmed to RT and stirred for 3 h. The reaction was monitored by TLC; after completion of the reaction, the volatiles were removed in vacuo to obtain the crude. The crude was washed with diethyl ether (2×5 mL) and dried in vacuo to afford compound 291 (1 g, 83%) as an off-white solid. TLC: 30% EtOAc/hexanes (R$_f$: 0.2); $^1$H-NMR (DMSO-d$_6$, 400 MHz): δ 8.25 (br s, 2H), 7.98 (s, 1H), 7.94-7.92 (m, 2H), 7.54-7.51 (m, 3H), 4.35 (q, J=6.0 Hz, 2H).

Synthesis of (2-methylthiazol-5-yl) methanamine hydrochloride (297)

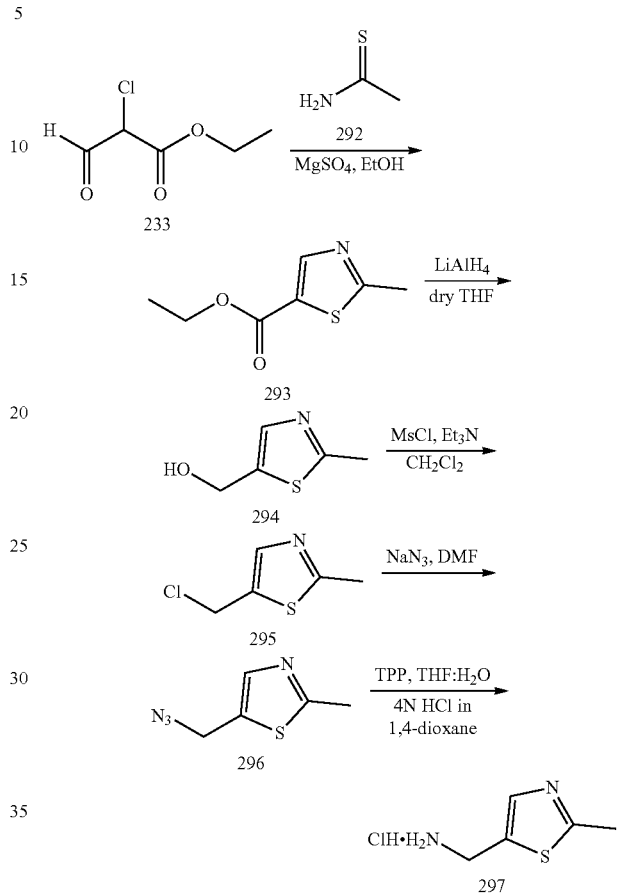

Synthesis of ethyl 2-methylthiazole-5-carboxylate (293)

To a stirring solution of ethyl 2-chloro-3-oxopropanoate 233 (26 g, 173.33 mmol) in ethanol (200 mL) under argon atmosphere were added ethanethioamide 292 (10 g, 133.33 mmol), dry magnesium sulfate (10 g) at RT and heated to reflux for 24 h. The reaction was monitored by TLC; after completion of the reaction, the volatiles were removed in vacuo, diluted with EtOAc (500 mL). The combined organic extracts were washed with saturated sodium bicarbonate solution (2×200 mL), brine (200 mL), dried over sodium sulfate, filtered and concentrated in vacuo to obtain the crude. The crude was purified through flash column chromatography using 6% EtOAc/hexanes to afford compound 293 (8 g, 35%) as brown syrup. TLC: 25% EtOAc/hexanes (R$_f$: 0.7); $^1$H-NMR (DMSO-d$_6$, 500 MHz): δ 8.24 (s, 1H), 4.27 (q, J=7.2 Hz, 2H), 2.70 (s, 3H), 1.27 (t, J=7.1 Hz, 3H).

Synthesis of (2-methylthiazol-5-yl) methanol (294)

To a stirring suspension of lithium aluminium hydride (3.1 g, 93.56 mmol) in dry THF (10 mL) under inert atmosphere was added compound 293 (8 g, 46.78 mmol) in dry THF (50 mL) dropwise for 15 min at 0° C.; warmed to RT and stirred for 16 h. The reaction was monitored by TLC;

after completion of the reaction, the reaction mixture was cooled to 0° C., quenched with 15% aqueous sodium hydroxide solution (10 mL), filtered through celite and washed with EtOAc (3×100 mL). The filtrate was dried over sodium sulfate, filtered and concentrated in vacuo to afford compound 294 (5 g, 83%) as an off-white solid. TLC: 50% EtOAc/hexanes ($R_f$: 0.3). LC-MS: 97.32%; 130.22 ($M^+$+1); (column; X-select CSH C18, (50×3.0 mm, 2.5 μm); RT 0.65 min. 2.5 mM Aq. NH$_4$OAc:ACN: 0.8 mL/min).

Synthesis of 5-(chloromethyl)-2-methylthiazole (295)

To a stirring solution of compound 294 (5 g, 38.75 mmol) in CH$_2$Cl$_2$ (150 mL) under inert atmosphere were added triethyl amine (8.3 mL, 58.13 mmol), methanesulfonyl chloride (4.6 mL, 46.51 mmol) at 0° C.; warmed to RT and stirred for 4 h. The reaction was monitored by TLC; after completion of the reaction, the reaction mixture was diluted with water (50 mL) and extracted with CH$_2$Cl$_2$ (2×100 mL). The combined organic extracts were dried over sodium sulfate, filtered and concentrated in vacuo to afford compound 295 (5 g, 87%) as pale yellow syrup. TLC: 30% EtOAc/hexanes ($R_f$: 0.8); LC-MS: 77.92%; 147.7 ($M^+$+1); (column; Ascentis Express C18, (50×3.0 mm, 2.7 μm); RT 1.71 min. 0.025% Aq. TFA+5% ACN: ACN+5% 0.025% Aq. TFA, 1.2 mL/min).

Synthesis of 5-(azidomethyl)-2-methylthiazole (296)

To a stirring solution of compound 295 (5 g, 34.01 mmol) in DMF (100 mL) under inert atmosphere was added sodium azide (2.21 g, 34.01 mmol) at RT and heated to 80° C. for 6 h. The reaction was monitored by TLC; after completion of the reaction, the reaction mixture was diluted with ice cold water (50 mL) and extracted with EtOAc (3×100 mL). The combined organic extracts were dried over sodium sulfate, filtered and concentrated in vacuo to obtain the crude. The crude was purified through silica gel column chromatography using 10% EtOAc/hexanes to afford compound 296 (2.3 g, 44%) as off-white thick syrup. TLC: 20% EtOAc/hexanes ($R_f$: 0.5); $^1$H-NMR (DMSO-d$_6$, 500 MHz): δ 7.64 (s, 1H), 4.67 (s, 2H), 2.65 (s, 3H).

Synthesis of (2-methylthiazol-5-yl) methanamine hydrochloride (297)

To a stirring solution of compound 296 (2.3 g, 14.93 mmol) in THF:H$_2$O (5:1, 80 mL) was added triphenyl phosphine (7.8 g, 29.87 mmol) at 0° C.; warmed to RT and stirred for 16 h. The reaction was monitored by TLC; after completion of the reaction, the volatiles were removed in vacuo to obtain the crude, which was triturated with diethyl ether (20 mL) to afford amine (900 mg, 47%) as colorless syrup. TLC: 10% MeOH/CH$_2$Cl$_2$ ($R_f$: 2);

The above compound was dissolved in CH$_2$Cl$_2$ (10 mL) added 4 N HCl in 1, 4-dioxane (5 mL) under inert atmosphere at 0° C.; warmed to RT and stirred for 3 h. The volatiles were removed in vacuo to obtain the crude, which was triturated with EtOAc (2 mL), diethyl ether (2 mL) to afford compound 297 (1.1 g, 95%) as an off-white solid. TLC: 10% MeOH/CH$_2$Cl$_2$ ($R_f$: 0.2); $^1$H NMR (DMSO-d$_6$, 500 MHz): δ 8.59 (br. s, 3H), 7.74 (s, 1H), 4.23 (q, J=5.6 Hz, 2H), 2.66 (s, 3H)

Synthesis of (4'-fluoro-[1,1'-biphenyl]-3-yl) methanamine hydrochloride (301)

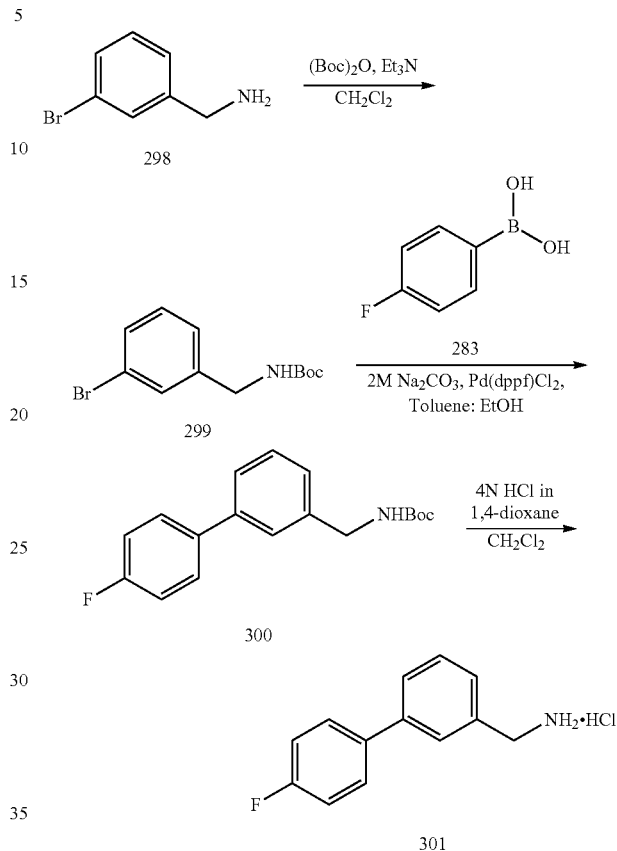

Synthesis of tert-butyl (3-bromobenzyl) carbamate (299)

To a stirring solution of (3-bromophenyl) methanamine 298 (5 g, 26.88 mmol) in CH$_2$Cl$_2$ (50 mL) under argon atmosphere were added triethylamine (1.16 mL, 80.59 mmol), Boc-anhydride (5.8 mL, 26.88 mmol) at 0° C.; warmed to RT and stirred for 16 h. The reaction was monitored by TLC; after completion of the reaction, the reaction mixture was diluted with water (100 mL) and extracted with CH$_2$Cl$_2$ (2×100 mL). The combined organic extracts were washed with water (25 mL), dried over sodium sulfate, filtered and concentrated in vacuo to obtain the crude. The crude was purified through silica gel column chromatography using 5% EtOAc/hexanes to afford compound 299 (5 g, 65%) as white solid. TLC: 10% EtOAc/hexanes ($R_f$: 0.6); $^1$H-NMR (DMSO-d$_6$, 400 MHz): δ 7.45-7.37 (m, 3H), 7.32-7.20 (m, 2H), 4.12 (d, J=6.1 Hz, 2H), 1.39 (s, 9H).

Synthesis of tert-butyl ((4'-fluoro-[1, 1'-biphenyl]-3-yl) methyl) carbamate (300)

To a stirring solution of tert-butyl (3-bromobenzyl) carbamate 299 (100 mg, 0.34 mmol) in a mixture of toluene: EtOH (4:1, 2.5 mL) under inert atmosphere were added 2 M aqueous sodium carbonate solution (0.5 mL) and (4-fluorophenyl) boronic acid 283 (58 mg, 0.41 mmol) and at RT and purged under argon atmosphere for 15 min. To this was added Pd(dppf)Cl$_2$ (7.6 mg, 0.01 mmol) and heated to 80° C. for 6 h. The reaction was monitored by TLC; after completion of the reaction, the organic layer was separated dried over sodium sulphate, filtered and concentrated in vacuo to obtain the crude. The crude was purified through silica gel column chromatography using 2-8% EtOAc/hexanes to afford compound 300 (100 mg, 95%) as an off-white solid. TLC: 10% EtOAc/hexanes (R$_f$: 0.3); $^1$H-NMR (DMSO-d$_6$, 400 MHz): 7.67 (dd, J=8.7, 5.4 Hz, 2H), 7.52-7.48 (m, 2H), 7.40 (t, J=7.7 Hz, 2H), 7.29 (t, J=8.8 Hz, 2H), 7.23 (d, J=7.3 Hz, 1H), 4.19 (d, J=6.0 Hz, 2H), 1.40 (s, 9H).

Synthesis of (4'-fluoro-[1, r-biphenyl]-3-yl) methanamine hydrochloride (301)

To a stirring solution of compound 300 (130 mg, 0.43 mmol) in CH$_2$Cl$_2$ (2 mL) under inert atmosphere was added 4 N HCl in 1, 4-dioxane (2 mL) at 0° C.; warmed to RT and stirred for 2 h. The reaction was monitored by TLC; after completion of the reaction, the volatiles were removed in vacuo to afford compound 301 (90 mg, 88%) as an off-white solid. TLC: 30% EtOAc/hexanes (R$_f$: 0.1); LC-MS: 98.27%; 201.9 (M$^+$+1); (column; Ascentis Express C18, (50×3.0 mm, 2.7 μm); RT 1.76 min. 0.025% Aq. TFA+5% ACN: ACN+ 5% 0.025% Aq. TFA, 1.2 mL/min).

Synthesis of (2-morpholinothiazol-5-yl) methanamine hydrochloride (389)

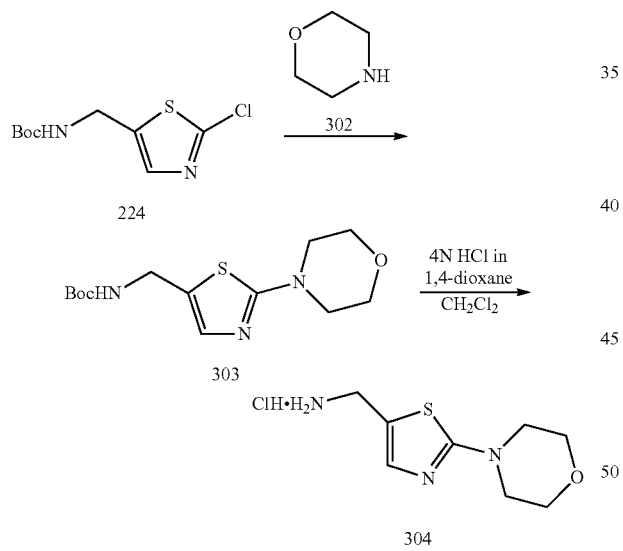

Synthesis of tert-butyl ((2-morpholinothiazol-5-yl) methyl) carbamate (303)

A stirred solution of compound 224 (300 mg, 1.21 mmol) in morpholine 302 (3 mL) under argon atmosphere was heated to 100° C. and stirred for 6 h. The reaction was monitored by TLC; after completion of the reaction, the reaction mixture was diluted with water (20 mL) and extracted with EtOAc (2×100 mL). The combined organic extracts were washed with water (50 mL) and brine (50 mL), dried over sodium sulphate, filtered and concentrated in vacuo to afford compound 303 (250 mg, 69%) as a colorless semi solid. TLC: 30% EtOAc/hexanes (R$_f$: 0.3); $^1$H-NMR (DMSO-d$_6$, 400 MHz): 7.31 (t, J=5.1 Hz, 1H), 6.94 (s, 1H), 4.09 (d, J=5.8 Hz, 2H), 3.70-3.62 (m, 4H), 3.29-3.27 (m, 4H), 1.36 (s, 9H).

Synthesis of (2-morpholinothiazol-5-yl) methanamine hydrochloride (304)

To a stirring solution of compound 303 (250 mg, 0.83 mmol) in CH$_2$Cl$_2$ (20 mL) under inert atmosphere was added 4 N HCl in 1, 4-dioxane (10 mL) at 0° C.; warmed to RT and stirred for 4 h. The reaction was monitored by TLC; after completion of the reaction, the volatiles were removed in vacuo to obtain the crude. The crude was washed with diethyl ether (2×5 mL) and dried in vacuo to afford compound 304 (200 mg, HCl salt) as an off-white solid. TLC: 30% EtOAc/hexanes (R$_f$: 0.1); $^1$H-NMR (DMSO-d$_6$, 500 MHz): δ 8.36 (br s, 3H), 7.31 (s, 1H), 4.11 (q, J=5.4 Hz, 2H), 3.75-3.67 (m, 4H), 3.45-3.37 (m, 4H).

Synthesis of (2-(4-methylpiperazin-1-yl) thiazol-5-yl) methanamine hydrochloride (307)

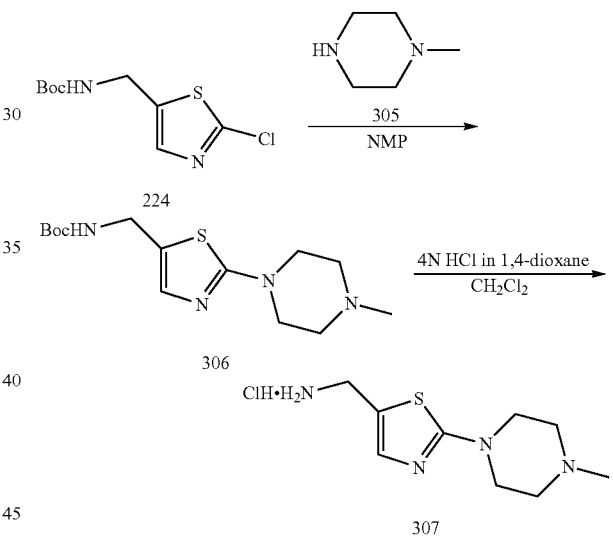

Synthesis of tert-butyl ((2-(4-methylpiperazin-1-yl) thiazol-5-yl) methyl) carbamate (306)

A stirred solution of tert-butyl ((2-chlorothiazol-5-yl) methyl) carbamate 224 (200 mg, 0.80 mmol) in N-methyl-2-pyrrolidone (5 mL) was added 1-methylpiperazine 305 (5 mL) in a sealed tube under argon atmosphere was heated to 100° C. and stirred for 16 h. The reaction was monitored by TLC; after completion of the reaction, the reaction mixture was diluted with water (20 mL) and extracted with EtOAc (2×100 mL). The combined organic extracts were dried over sodium sulphate, filtered and concentrated in vacuo to obtain the crude. The crude was purified through silica gel column chromatography using 5% MeOH/CH$_2$Cl$_2$ to afford compound 306 (200 mg, 80%) as colorless syrup. TLC: 10% MeOH/CH$_2$Cl$_2$ (R$_f$: 0.5); $^1$H NMR (DMSO-d$_6$, 500 MHz): 7.31 (t, J=6.1 Hz, 1H), 6.92 (s, 1H), 4.09 (d, J=5.5 Hz, 2H), 3.35-3.31 (m, 4H), 2.39 (t, J=4.8 Hz, 4H), 2.21 (s, 3H), 1.38 (s, 9H).

Synthesis of (2-(4-methylpiperazin-1-yl) thiazol-5-yl) methanamine hydrochloride (307)

To a stirring solution of compound 306 (200 mg, 0.64 mmol) in $CH_2Cl_2$ (5 mL) under inert atmosphere was added 4 N HCl in 1, 4-dioxane (5 mL) at 0° C.; warmed to RT and stirred for 4 h. The reaction was monitored by TLC; after completion of the reaction, the volatiles were removed in vacuo to obtain the crude. The crude was washed with diethyl ether (2×5 mL) and dried in vacuo to afford compound 307 (240 mg, as HCl salt) as an off-white solid. TLC: 30% EtOAc/hexanes ($R_f$: 0.1); $^1$H-NMR (DMSO-$d_6$, 500 MHz): δ 11.37 (br s, 1H), 8.37 (br s, 3H), 7.29 (s, 1H), 4.12 (q, J=5.4 Hz, 2H), 4.00-3.98 (m, 2H), 3.50-3.41 (m, 4H), 3.23-3.02 (m, 2H), 2.80 (s, 3H).

Synthesis of 4-(5-(aminomethyl) thiazol-2-yl)-N,N-dimethylaniline hydrochloride (312)

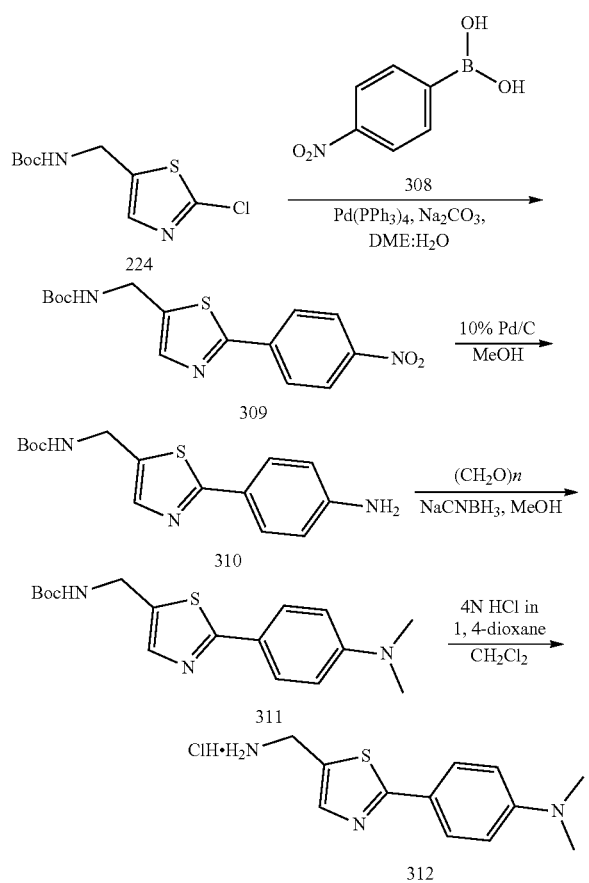

Synthesis of tert-butyl ((2-(4-nitrophenyl) thiazol-5-yl) methyl) carbamate (309)

To a stirring solution of tert-butyl ((2-chlorothiazol-5-yl) methyl) carbamate 224 (1 g, 4.02 mmol) in 1, 2 dimethoxy ethane:$H_2O$ (4:1, 20 mL) was added sodium carbonate (1.5 g, 14.08 mmol) and purged under argon atmosphere for 30 min. To this was added Pd(PPh$_3$)$_4$ (464 mg, 0.40 mmol) and (4-nitrophenyl) boronic acid (308) at RT and stirred for 16 h. The reaction was monitored by TLC; after completion the reaction, the reaction mixture was diluted with water (50 mL) and extracted with EtOAc (2×100 mL). The combined organic extracts were dried over sodium sulfate, filtered and concentrated in vacuo to obtain the crude. The crude was purified through silica gel column chromatography using 30% EtOAc/hexanes to afford compound 309 (650 mg, 48%) as yellow solid. TLC: 30% EtOAc/hexanes ($R_f$: 0.4); $^1$H NMR (DMSO-$d_6$, 400 MHz): δ 8.32 (d, J=9.0 Hz, 2H), 8.16 (d, J=8.9 Hz, 2H), 7.84 (s, 1H), 7.63 (t, J=5.7 Hz, 1H), 4.38 (d, J=6.0 Hz, 2H), 1.40 (s, 9H); LC-MS: 92.61%; 335.9 ($M^+$+1); (column; Ascentis Express C18, (50×3.0 mm, 2.7 μm); RT 2.66 min. 0.025% Aq. TFA+5% ACN: ACN+5% 0.025% Aq. TFA, 1.2 mL/min).

Synthesis of tert-butyl ((2-(4-aminophenyl) thiazol-5-yl) methyl) carbamate (310)

To a stirring solution of compound 309 (500 mg, 1.49 mmol) in MeOH (20 mL) under inert atmosphere was added 10% Pd/C (150 mg) at RT and stirred under hydrogen atmosphere (balloon pressure) at RT for 16 h. The reaction was monitored by TLC; after completion of the reaction, the reaction mixture was filtered through celite and washed with MeOH (50 mL). The filtrate was concentrated in vacuo to obtain the crude. The crude washed with 10% EtOAc/hexanes (20 mL) and dried in vacuo to afford compound 310 (350 mg, 77%) as an off-white solid. TLC: 30% EtOAc/hexanes ($R_f$: 0.2); $^1$H NMR (DMSO-$d_6$, 400 MHz): δ 7.54 (d, J=8.6 Hz, 2H), 7.48 (s, 2H), 6.59 (d, J=8.6 Hz, 2H), 5.64 (br s, 2H), 4.26 (d, J=5.9 Hz, 2H), 1.39 (s, 9H); LC-MS: 98.14%; 305.9 ($M^+$+1); (column; Ascentis Express C18, (50×3.0 mm, 2.7 μm); RT 2.06 min. 0.025% Aq. TFA+5% ACN: ACN+5% 0.025% Aq. TFA, 1.2 mL/min).

Synthesis of tert-butyl ((2-(4-(dimethylamino) phenyl) thiazol-5-yl) methyl) carbamate (311)

To a stirring solution of compound 310 (200 mg, 0.65 mmol) in MeOH (10 mL) under inert atmosphere were added paraformaldehyde (98 mg, 3.27 mmol) and sodium cyanoborohydride (206 mg, 3.27 mmol) at RT and stirred for 16 h. The reaction was monitored by TLC; after completion of the reaction, the reaction mixture was quenched with ice-cold water (10 mL) and extracted with 10% MeOH/$CH_2Cl_2$ (2×100 mL). The combined organic extracts were dried over sodium sulfate, filtered and concentrated in vacuo to obtain the crude. The crude was purified through silica gel column chromatography using 20% EtOAc/hexanes to afford compound 311 (120 mg, 55%) as white solid. TLC: 30% EtOAc/hexanes ($R_f$: 0.8); $^1$H NMR (DMSO-$d_6$, 500 MHz): δ 7.69 (d, J=9.0 Hz, 2H), 7.52 (s, 1H), 7.49 (t, J=5.5 Hz, 1H), 6.76 (d, J=9.0 Hz, 2H), 4.28 (d, J=5.8 Hz, 2H), 2.97 (s, 6H), 1.40 (s, 9H); LC-MS: 98.93%; 334.1 ($M^+$+1); (column; Ascentis Express C18, (50×3.0 mm, 2.7 μm); RT 2.06 min. 0.025% Aq. TFA+5% ACN: ACN+5% 0.025% Aq. TFA, 1.2 mL/min).

Synthesis of 4-(5-(aminomethyl) thiazol-2-yl)-N,N-dimethylaniline hydrochloride (312)

To a stirring solution of compound 311 (120 mg, 0.36 mmol) in $CH_2Cl_2$ (5 mL) under inert atmosphere was added 4 N HCl in 1, 4-dioxane (1 mL) at 0° C.; warmed to RT and stirred for 2 h. The reaction was monitored by TLC; after completion of the reaction, the volatiles were removed in vacuo to obtain the crude. The crude was washed with diethylether (2×5 mL) and dried in vacuo to afford compound 312 (90 mg, 93%) as white solid. TLC: 10% MeOH/ CH$_2$Cl$_2$ (R$_f$: 0.2); $^1$H-NMR (DMSO-d$_6$, 500 MHz): δ 8.53 (br s, 3H), 7.83 (s, 1H), 7.76 (d, J=8.7 Hz, 2H), 6.86 (d, J=7.2 Hz, 2H), 4.27 (q, J=5.4 Hz, 2H), 2.99 (s, 6H); LC-MS: 98.98%; 233.8 (M$^+$+1); (column; Ascentis Express C18, (50×3.0 mm, 2.7 μm); RT 1.51 min. 0.025% Aq. TFA+5% ACN: ACN+5% 0.025% Aq. TFA, 1.2 mL/min).

Synthesis of 4-(5-(aminomethyl) thiazol-2-yl)-3-fluorobenzonitrile hydrochloride (316)

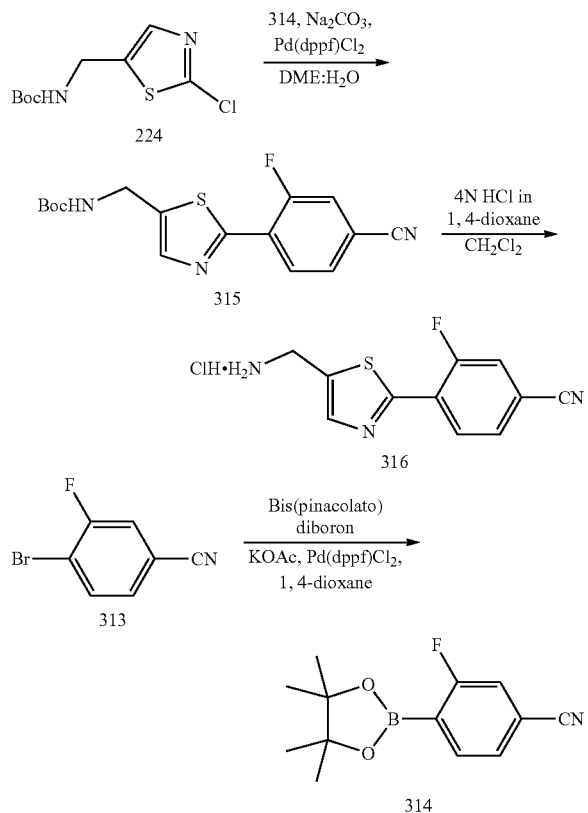

Synthesis of 3-fluoro-4-(4, 4, 5, 5-tetramethyl-1, 3, 2-dioxaborolan-2-yl) benzonitrile (314)

To a stirring solution of 4-bromo-3-fluorobenzonitrile 313 (15 g, 75.0 mmol) in 1,4-dioxane (200 mL) under inert atmosphere were added bis pinacolato diboron (28.56 g, 112.5 mmol), potassium acetate (25.76 g, 262.5 mmol) at RT and purged under argon atmosphere for 20 min; to this was added Pd(dppf)$_2$Cl$_2$ (5.5 g, 7.51 mmol) and purged under argon atmosphere for 20 min, heated to 100° C. and stirred for 16 h. The reaction was monitored by TLC; after completion of the reaction, the reaction mixture was filtered through celite, washed with EtOAc (2×500 mL). The filtrate was concentrated in vacuo and the residue was diluted with H$_2$O (500 mL) and extracted with EtOAc (2×700 mL). The combined organic extracts were dried over sodium sulfate, filtered and concentrated in vacuo to obtain the crude. The crude was purified through silica gel flash column chromatography using 15-20% EtOAc/hexanes to afford compound 314 (10.2 g, 55%) as an off-white solid. TLC: 20% EtOAc/hexanes (R$_f$: 0.3); $^1$H-NMR (DMSO-d$_6$, 400 MHz): δ 7.82-7.75 (m, 2H), 7.67 (dd, J=7.7, 1.4 Hz, 1H), 1.30 (s, 12H).

Synthesis of tert-butyl ((2-(4-cyano-2-fluorophenyl) thiazol-5-yl) methyl) carbamate (315)

To a stirring solution of compound 224 (8 g, 32.16 mmol) in 1, 2-dimethoxy ethane:H$_2$O (4:1, 100 mL) under inert atmosphere were added compound 314 (10.4 g, 42.09 mmol), sodium carbonate (12 g, 113.20 mmol) in a sealed tube at RT and purged under argon atmosphere for 15 min, added Pd(dppf)Cl$_2$ (2.36 g, 3.22 mmol) and heated to 100° C. and stirred for 16 h. The reaction was monitored by TLC; after completion of the reaction, the reaction mixture was diluted with water (100 mL) and extracted with EtOAc (2×800 mL). The combined organic extracts were dried over sodium sulfate, filtered and concentrated in vacuo to obtain the crude. The crude was purified through silica gel flash column chromatography using 25-30% EtOAc/hexanes and triturated using 10% EtOAc/hexanes to afford compound 315 (6.5 g, 61%) as an off-white solid. TLC: 30% EtOAc/hexanes (R$_f$: 0.3); $^1$H-NMR (DMSO-d$_6$, 400 MHz): δ 8.36 (t, J=7.9 Hz, 1H), 8.10 (dd, J=11.3, 1.4 Hz, 1H), 7.91 (d, J=2.4 Hz, 1H), 7.83 (dd, J=8.2, 1.6 Hz, 1H), 7.62 (br t, J=5.5 Hz, 1H), 4.40 (br d, J=5.9 Hz, 2H), 1.40 (s, 9H); LC-MS: 94.47%; 333.9 (M$^+$+1); (column; Ascentis Express C18, (50×3.0 mm, 2.7 μm); RT 2.61 min. 0.025% Aq. TFA+5% ACN: ACN+5% 0.025% Aq. TFA, 1.2 mL/min).

Synthesis of 4-(5-(aminomethyl) thiazol-2-yl)-3-fluorobenzonitrile hydrochloride (316)

To a stirring solution of compound 315 (6.5 g, 19.51 mmol) in CH$_2$Cl$_2$ (70 mL) was added 4 N HCl in 1, 4-dioxane (70 mL) under argon atmosphere at 0° C.; warmed to RT and stirred for 2 h. The reaction was monitored by TLC; after completion of the reaction, the volatiles were removed in vacuo. The crude washed with EtOAc (2×100 mL) and dried in vacuo to afford compound 316 (4.7 g; 89% as HCl salt) as white solid. TLC: 30% EtOAc/hexanes (R$_f$: 0.2); $^1$H-NMR (DMSO-d$_6$, 400 MHz): δ 8.60 (br s, 3H), 8.39 (t, J=7.9 Hz, 1H), 8.23-8.08 (m, 2H), 7.87 (dd, J=8.2, 1.5 Hz, 1H), 4.42 (br s, 2H); LC-MS: 98.68%; 234.9 (M$^+$+1); (column; Ascentis Express C18, (50×3.0 mm, 2.7 μm); RT 1.40 min. 0.025% Aq. TFA+5% ACN: ACN+ 5% 0.025% Aq. TFA, 1.2 mL/min).

Synthesis of 5-(5-(aminomethyl) thiazol-2-yl) indolin-2-one hydrochloride (319)

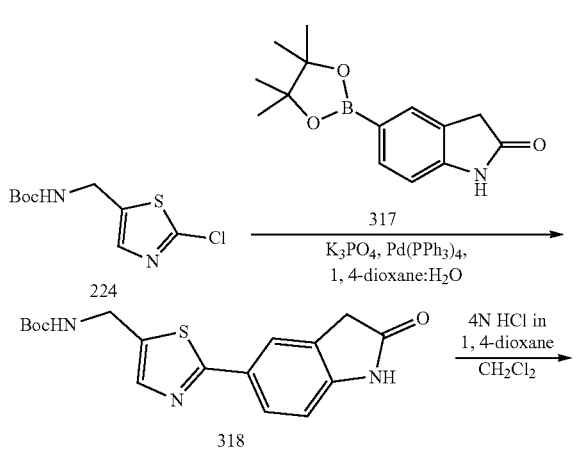

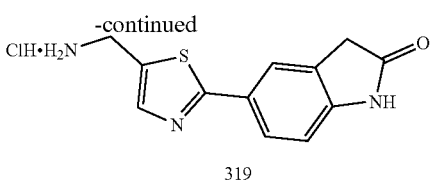

319

Synthesis of tert-butyl ((2-(2-oxoindolin-5-yl) thiazol-5-yl) methyl) carbamate (318)

To a stirring solution of tert-butyl ((2-chlorothiazol-5-yl) methyl) carbamate 224 (1 g, 4.03 mmol) in 1, 4-dioxane:H$_2$O (4:1, 30 mL) under inert atmosphere were added 5-(4, 4, 5, 5-tetramethyl-1, 3, 2-dioxaborolan-2-yl) indolin-2-one 317 (1.3 g, 5.02 mmol) and potassium phosphate (2.60 g, 12.26 mmol) in sealed tube at RT and purged under inert atmosphere for 20 min. To this was added Pd(PPh$_3$)$_4$ (465 mg, 0.40 mmol) and heated to 110° C. and stirred for 16 h. The reaction was monitored by TLC; after completion of the reaction, the volatiles were removed in vacuo to obtain the crude. The crude was purified through silica gel flash column chromatography using 2-4% MeOH/CH$_2$Cl$_2$ to afford compound 318 (600 mg, 43%) as pale yellow solid. TLC: 5% MeOH/CH$_2$Cl$_2$ (R$_f$: 0.2). $^1$H-NMR (DMSO-d$_6$, 400 MHz): δ 10.58 (s, 1H), 7.71 (d, J=5.1 Hz, 2H), 7.59 (s, 1H), 7.52 (t, J=5.8 Hz, 1H), 6.88 (d, J=8.5 Hz, 1H), 4.29 (d, J=5.8 Hz, 2H), 3.54 (s, 2H), 1.39 (s, 9H); LC-MS: 91.80%; 346.9 (M$^+$+1); (column; Kinetex EVO C-18 (50×3.0 mm, 2.6 um); RT 2.31 min. 2.5 mM Aq. NH$_4$OOCH+5% ACN:ACN+5% 2.5 mM Aq.NH$_4$OOCH, 0.8 mL/min).

Synthesis of 5-(5-(aminomethyl) thiazol-2-yl) indolin-2-one hydrochloride (319)

To a stirring solution of compound 318 (600 mg, 1.74 mmol) in CH$_2$Cl$_2$ (10 mL) under inert atmosphere was added 4 N HCl in 1, 4-dioxane (10 mL) at 0° C.; warmed to RT and stirred for 4 h. The reaction was monitored by TLC; after completion of the reaction, the volatiles were removed in vacuo to obtain the crude which was triturated with EtOAc (2×5 mL) and dried in vacuo to afford compound 319 (600 mg; crude) as yellow solid. TLC: 10% MeOH/to CH$_2$Cl$_2$ (R$_f$: 0.1); $^1$H-NMR (DMSO-d$_6$, 400 MHz): δ 10.69 (s, 1H), 8.58 (br s, 3H), 7.90 (s, 1H), 7.80-7.73 (m, 2H), 6.93 (d, J=8.7 Hz, 1H), 4.31 (q, J=5.5 Hz, 2H), 3.57 (s, 2H);

Synthesis of (2-(4-methoxybenzyl) thiazol-5-yl) methanamine hydrochloride (326)

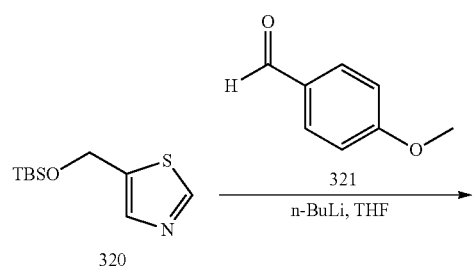

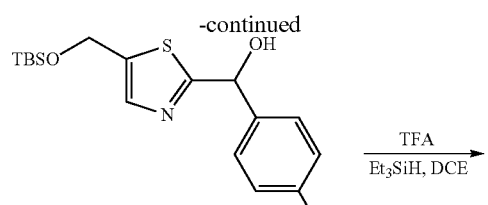

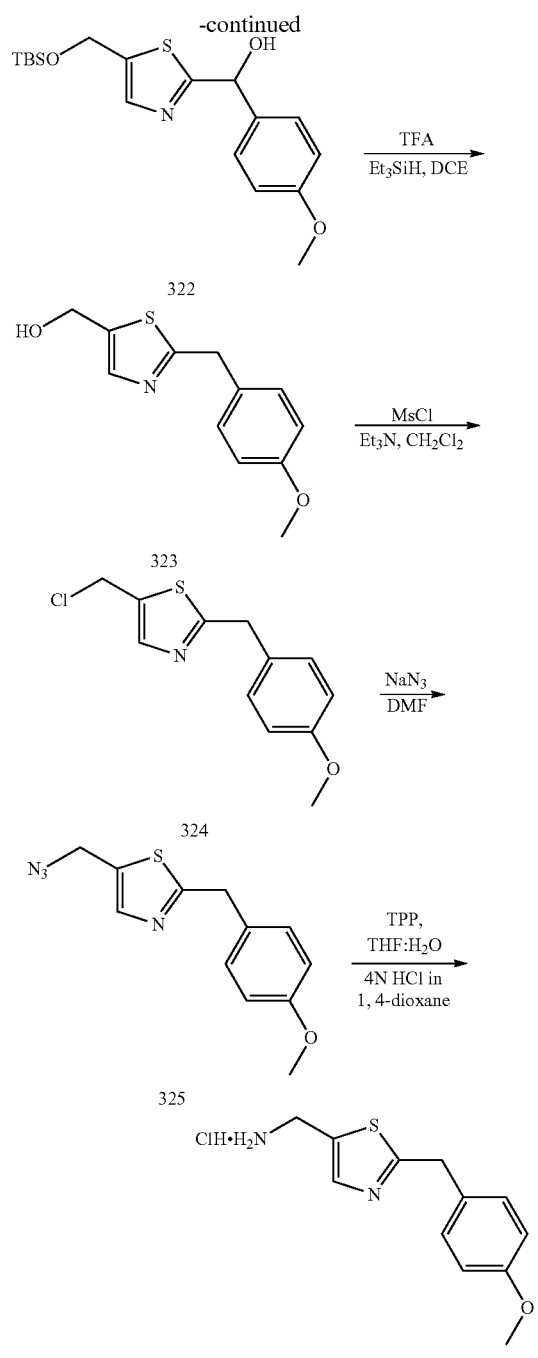

Synthesis of (5-(((tert-butyldimethylsilyl) oxy) methyl) thiazol-2-yl) (4methoxyphenyl) methanol (322)

To a stirring solution 5-(((tert-butyldimethylsilyl) oxy) methyl) thiazole 320 (6 g, 26.20 mmol) in dry THF (100 mL) under inert atmosphere was added n-butyl lithium (1.6 M solution in hexane, 24 mL, 39.30 mmol) dropwise for 10 min at −78° C. and stirred for 30 min. To this was added 4-methoxybenzaldehyde 321 (3.9 g, 28.80 mmol) at −78° C. and stirred at the same temperature for 3 h. The reaction was monitored by TLC; after completion of the reaction, the reaction mixture was quenched with saturated ammonium chloride solution (50 mL) and extracted with EtOAc (2×200 mL). The combined organic extracts were dried over sodium sulfate, filtered and concentrated in vacuo to obtain the crude. The crude was purified through silica gel column chromatography using 20% EtOAc/hexanes to afford compound 322 (6 g, 63%) as colorless liquid. TLC: 20% EtOAc/hexanes ($R_f$: 0.2); $^1$H NMR (500 MHz, DMSO-$d_6$): δ 7.51 (s, 1H), 7.31 (d, J=8.7 Hz, 2H), 6.89 (d, J=8.4 Hz, 2H), 6.61 (d, J=4.6 Hz, 1H), 5.81 (d, J=4.3 Hz, 1H), 4.83 (s, 2H), 3.72 (s, 3H), 0.88-0.85 (m, 9H), 0.07 (s, 6H).

Synthesis of (2-(4-methoxybenzyl) thiazol-5-yl) methanol (323)

To a stirring solution of compound 322 (6 g, 16.43 mmol) in 1, 2-dichloroethane (30 mL) under inert atmosphere were added trieythlsilane (2.65 mL, 82.19 mmol), trifluoroacetic acid (6.28 mL, 82.19 mmol) at 0° C.; heated to 60° C. and stirred for 8 h. The reaction was monitored by TLC; after completion of the reaction, the volatiles were removed in vacuo to obtain the crude. The crude was purified through silica gel column chromatography using 60% EtOAc/hexanes to afford compound 323 (2.8 g, 73%) as sticky solid. TLC: 40% EtOAc/hexanes ($R_f$: 0.2); $^1$H NMR (500 MHz, DMSO-$d_6$): δ 7.48 (s, 1H), 7.22 (d, J=8.7 Hz, 2H), 6.88 (d, J=8.4 Hz, 2H), 5.41 (br s, 1H), 4.57 (s, 2H), 4.18 (s, 2H), 3.72 (s, 3H); LC-MS: 90.27%; 235.9 (M$^+$+1); (column; Kinetex EVO C-18 (50×3.0 mm, 2.6 um); RT 2.03 min. 2.5 mM Aq. NH$_4$OOCH+5% ACN: ACN+5% 2.5 mM Aq.NH$_4$OOCH; 0.8 mL/min).

Synthesis of 5-(chloromethyl)-2-(4-methoxybenzyl) thiazole (324)

To a stirring solution of compound 323 (2.8 g, 11.90 mmol) in CH$_2$Cl$_2$ (30 mL) under inert atmosphere were added triethylamine (5.0 mL, 35.70 mmol), methanesulfonyl chloride (1.16 mL, 14.29 mmol) at 0° C.; warmed to RT and stirred for 4 h. The reaction was monitored by TLC; after completion of the reaction, the reaction mixture was quenched with CH$_2$Cl$_2$ (100 mL) and washed with water (75 mL). The combined organic extracts were dried over sodium sulfate, filtered and concentrated in vacuo to afford crude compound 324 (2.1 g) as colorless liquid. TLC: 30% EtOAc/hexanes ($R_f$: 0.8); $^1$H NMR (500 MHz, DMSO-$d_6$): δ 7.70 (s, 1H), 7.24 (d, J=8.4 Hz, 2H), 6.89 (d, J=8.4 Hz, 2H), 5.00 (s, 2H), 4.22 (s, 2H), 3.73 (s, 3H)

Synthesis of 5-(azidomethyl)-2-(4-methoxybenzyl) thiazole (325)

To a stirring solution of compound 324 (2.1 g, crude) in DMF (20 mL) under inert atmosphere was added sodium azide (1.61 g, 24.90 mmol) at 0° C.; warmed to RT and stirred for 4 h. The reaction was monitored by TLC; after completion of the reaction, the reaction mixture was diluted with water (100 mL) and extracted with EtOAc (2×100 mL). The combined organic extracts were dried over sodium sulphate, filtered and concentrated in vacuo to afford compound 325 (1.5 g) as colorless sticky solid. TLC: 20% EtOAc/hexanes ($R_f$: 0.4); 41 NMR (400 MHz, DMSO-$d_6$): δ 7.68 (s, 1H), 7.25 (d, J=8.8 Hz, 2H), 6.90 (d, J=8.7 Hz, 2H), 4.65 (s, 2H), 4.24 (s, 2H), 3.73 (s, 3H); LC-MS: 89.03%; 260.9 (M$^+$+1); (column; Kinetex EVO C-18 (50× 3.0 mm, 2.6 um); RT 2.96 min. 2.5 mM Aq. NH$_4$OOCH+5% ACN: ACN+5% 2.5 mM Aq.NH$_4$OOCH; 0.8 mL/min).

Synthesis of (2-(4-methoxybenzyl) thiazol-5-yl) methanamine hydrochloride (326)

To a stirring solution of compound 325 (1.5 g, crude) in THF:H$_2$O (10:1, 22 mL) was added triphenyl phosphine (1.5 g, 5.76 mmol) at 0° C.; warmed to RT and stirred for 16 h. The reaction was monitored by TLC; after completion of the reaction; the volatiles were removed in vacuo to obtain the crude amine (1.3 g crude).

To the above crude amine (1.3 g) in CH$_2$Cl$_2$ (10 mL) was added 4 N HCl in 1, 4-dioxane (3 mL) under inert atmosphere at 0° C. and stirred for 1 h. The reaction was monitored by TLC; after completion of the reaction, the volatiles were removed in vacuo. The crude washed with triturated with EtOAc (5 mL), CH$_2$Cl$_2$ (5 mL) and dried in vacuo to afford compound 326 (830 mg, 53% HCl salt) as an off-white solid. TLC: 5% MeOH/CH$_2$Cl$_2$ ($R_f$: 0.1); $^1$H NMR (400 MHz, DMSO-$d_6$): δ 8.33 (br s, 1H), 7.73 (s, 1H), 7.25 (d, J=8.7 Hz, 2H), 6.91 (d, J=8.8 Hz, 2H), 4.33-4.11 (m, 6H), 3.73 (s, 3H)

Synthesis of (5-(aminomethyl) thiazol-2-yl) (phenyl) methanone (332)

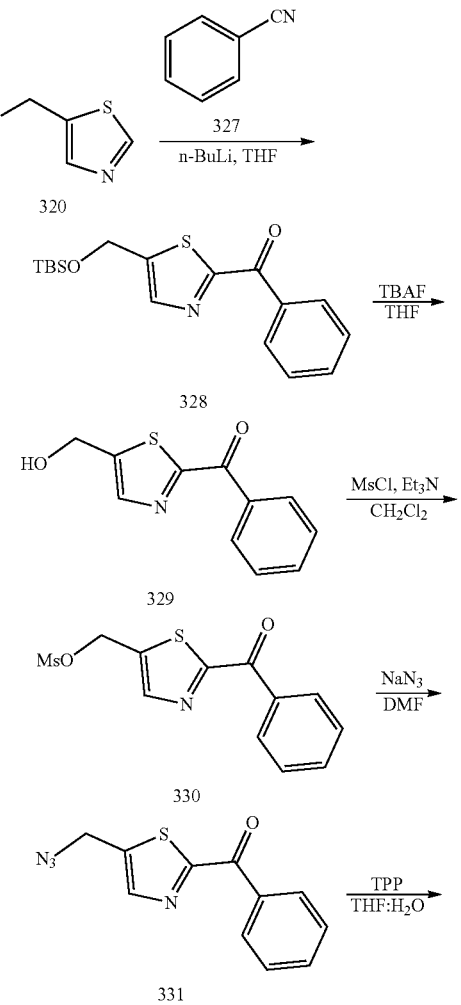

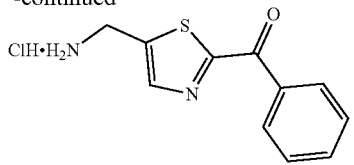

332

Synthesis of (5-(((tert-butyldimethylsilyl) oxy) methyl) thiazol-2-yl) (phenyl) methanone (328)

To a stirring solution of 5-(((tert-butyldimethylsilyl) oxy) methyl) thiazole 320 (200 mg, 0.87 mmol) in dry THF (15 mL) under inert atmosphere was added n-butyl lithium (1.6 M solution in hexane, 0.82 mL, 1.30 mmol) dropwise for 5 min at −78° C. and stirred for 1 h. To this was added benzonitrile 327 (180 mg, 1.74 mmol) at −78° C. and stirred for 2 h. The reaction was monitored by TLC; after completion of the reaction, the reaction mixture was quenched with 1 N aqueous HCl (10 mL) at −78° C. and extracted with EtOAc (2×50 mL). The combined organic extracts were dried over sodium sulfate, filtered and concentrated in vacuo to obtain the crude. The crude was purified through silica gel flash column chromatography using 5-10% EtOAc/hexanes to afford crude compound 328 (300 mg) as pale yellow liquid. TLC: 20% EtOAc/hexanes ($R_f$: 0.8); $^1$H-NMR (DMSO-$d_6$, 500 MHz): δ 8.36 (d, J=7.5 Hz, 2H), 8.08 (s, 1H), 7.86-7.82 (m, 2H), 7.76-7.69 (m, 1H), 5.04 (s, 2H), 0.91 (s, 9H), 0.12 (s, 6H);

Synthesis of (5-(hydroxymethyl) thiazol-2-yl) (phenyl) methanone (329)

To a stirring solution of compound 328 (300 mg, 0.90 mmol) in THF (5 mL) under inert atmosphere was added tetrabutylammonium fluoride (1.0 M solution in THF, 1.35 mL, 1.35 mmol) at 0° C. and stirred for 1 h. The reaction was monitored by TLC; after completion of the reaction, the reaction mixture was quenched with water (20 mL) and extracted with EtOAc (2×50 mL). The combined organic extracts were dried over sodium sulfate, filtered and concentrated in vacuo to obtain the crude. The crude was purified through silica gel flash column chromatography using 10% EtOAc/hexanes to afford crude compound 329 (100 mg, 52% over 2 steps) as pale yellow solid. TLC: 20% EtOAc/hexanes ($R_f$: 0.1); LC-MS: 99.90%; 219.9 (M$^+$+1); (column; Ascentis Express C18, (50×3.0 mm, 2.7 μm); RT 2.02 min. 0.025% Aq. TFA+5% ACN: ACN+5% 0.025% Aq. TFA, 1.2 mL/min). $^1$H-NMR (DMSO-$d_6$, 400 MHz): δ 8.38-8.33 (m, 2H), 8.09-8.02 (m, 1H), 7.75-7.70 (m, 1H), 7.62-7.57 (m, 2H), 5.86 (t, J=5.8 Hz, 1H), 4.81 (dd, J=5.7, 0.9 Hz, 2H).

Synthesis of (2-benzoylthiazol-5-yl) methyl methanesulfonate (330)

To a stirring solution of compound 329 (100 mg, 0.45 mmol) in CH$_2$Cl$_2$ (5 mL) under inert atmosphere were added triethyl amine (2.5 mL, 17.32 mmol) at 0° C. and stirred for 10 min. To this was added methanesulfonyl chloride (0.13 mL, 0.08 mmol) at 0° C.; warmed to RT and stirred for 16 h. The reaction was monitored by TLC; after completion of the reaction, the reaction mixture was diluted with water (50 mL), extracted with CH$_2$Cl$_2$ (2×50 mL), washed with saturated NaHCO$_3$ solution (30 mL) and brine (20 mL). The combined organic extracts were dried over sodium sulfate, filtered and concentrated in vacuo to afford crude compound 330 (150 mg) as pale yellow liquid. TLC: 20% EtOAc/ hexanes ($R_f$: 0.1); $^1$H-NMR (DMSO-$d_6$, 400 MHz): δ 8.38-8.33 (m, 2H), 8.25 (s, 1H), 7.76-7.71 (m, 1H), 7.64-7.56 (m, 2H), 5.22 (s, 2H), 2.42 (s, 3H).

Synthesis of (5-(azidomethyl) thiazol-2-yl) (phenyl) methanone (331)

To a stirring solution of compound 330 (150 mg, 0.50 mmol) in DMF (150 mL) under inert atmosphere was added sodium azide (49 mg, 0.75 mmol) at RT and stirred for 16 h. The reaction was monitored by TLC and LC-MS; after completion of the reaction, the reaction mixture was diluted with EtOAc (100 mL) and washed with ice-cold water (2×50 mL). The combined organic extracts were dried over sodium sulphate, filtered and concentrated in vacuo to obtain the crude. The crude was purified through silica gel flash column chromatography using 5-10% EtOAc/hexanes to afford compound 331 (100 mg, 89%, over 2 steps) as pale yellow solid. TLC: 20% EtOAc/hexanes ($R_f$: 0.6); $^1$H-NMR (DMSO-$d_6$, 400 MHz): δ 8.40-8.38 (m, 2H), 8.23 (s, 1H), 7.79-7.74 (m, 1H), 7.65-7.60 (m, 2H), 4.94 (s, 2H). LC-MS: 94.73%; 244.9 (M$^+$+1); (column; Ascentis Express C18, (50×3.0 mm, 2.7 μm); RT 2.65 min. 0.025% Aq. TFA+5% ACN: ACN+5% 0.025% Aq. TFA, 1.2 mL/min).

Synthesis of (5-(aminomethyl) thiazol-2-yl) (phenyl) methanone (332)

To a stirring solution of compound 331 (100 mg, 0.41 mmol) in THF:H$_2$O (5:1, 12 mL) was added triphenyl phosphine (161 mg, 0.61 mmol) at 0° C.; warmed to RT and stirred for 20 h. The reaction was monitored by TLC; after completion of the reaction, the volatiles were removed in vacuo, further dried by azeotropic distillation using toluene (2×5 mL) to obtain the crude.

The above crude compound was diluted with CH$_2$Cl$_2$ (1 mL) and under inert atmosphere was added 4 N HCl in 1,4-dioxane (1 mL) at 0° C., warmed to RT and stirred for 1 h. The volatiles were removed in vacuo and the crude was washed with diethyl ether (10 mL), hexane (10 mL) and triturated with CH$_2$Cl$_2$:hexanes (4:1, 5 mL) to afford compound 332 (100 mg, 96%) as pale yellow solid. TLC: 5% MeOH/CH$_2$Cl$_2$ ($R_f$: 0.2); LC-MS: 30.80%; 218.8 (M$^+$+1); (column; Ascentis Express C18, (50×3.0 mm, 2.7 μm); RT 1.51 min. 0.025% Aq. TFA+5% ACN: ACN+5% 0.025% Aq. TFA, 1.2 mL/min).

Synthesis of 1-(2-(5-(aminomethyl) thiazol-2-yl) phenyl)-2-methylpropan-2-ol hydrochloride (338)

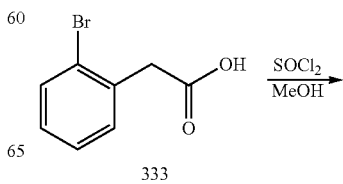

333

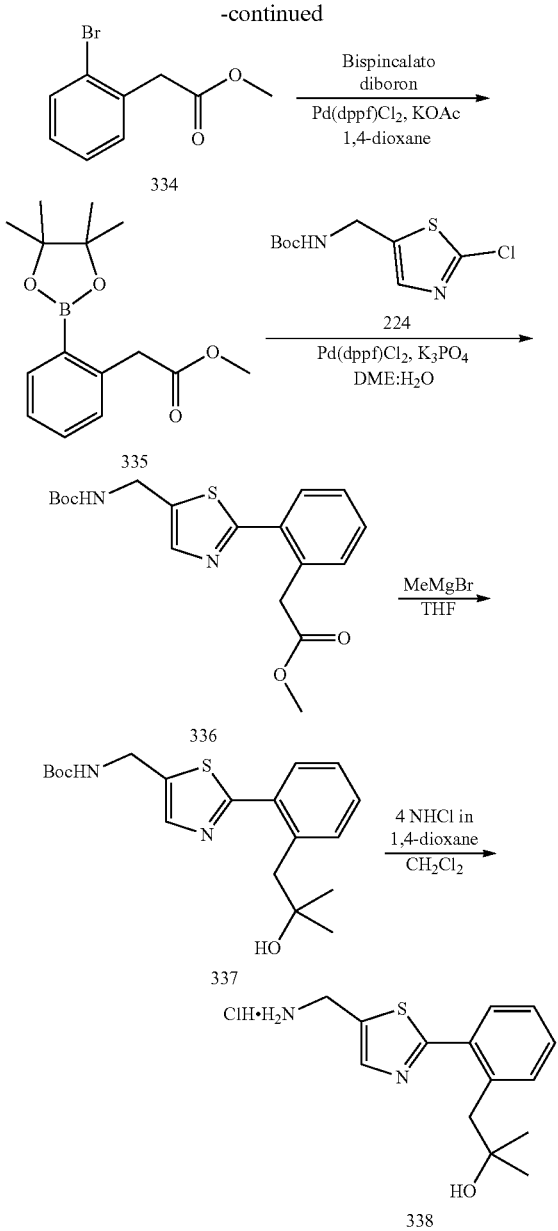

Synthesis of methyl 2-(2-bromophenyl) acetate (334)

To a stirring solution of 2-(2-bromophenyl) acetic acid 333 (5 g, 23.25 mmol) in MeOH (100 mL) under inert atmosphere was added thionyl chloride (2.00 mL, 27.90 mmol) dropwise at 0° C. for 15 min; warmed to RT and stirred for 16 h. The reaction was monitored by TLC; after completion of the reaction, the volatiles were removed in vacuo. The residue was diluted with $CH_2Cl_2$ (300 mL) and the pH was neutralized with saturated $NaHCO_3$ solution (200 mL). The organic layer was separated dried over sodium sulphate, filtered and concentrated in vacuo to afford compound 334 (5 g, 94%) as colorless thick syrup. TLC: 20% EtOAc/hexanes ($R_f$: 0.8); $^1$H-NMR (DMSO-d$_6$, 400 MHz): δ 7.62 (dd, J=8.0, 1.1 Hz, 1H), 7.43-7.39 (m, 1H), 7.36 (td, J=7.4, 1.1 Hz, 1H), 7.23 (td, J=7.6, 1.8 Hz, 1H), 3.83 (s, 2H), 3.63 (s, 3H);

Synthesis of methyl 2-(2-(4, 4, 5, 5-tetramethyl-1, 3, 2-dioxaborolan-2-yl) phenyl) acetate (335)

To a stirring solution of compound 334 (4.5 g, 19.65 mmol) in 1, 4-dioxane (100 mL) under inert atmosphere were added bispinacolato diboron (5.98 g, 23.58 mmol), potassium acetate (8.30 g, 84.50 mmol) at RT and purged under argon atmosphere for 15 min; to this was added Pd(dppf)Cl$_2$ (1.43 g, 1.96 mmol) and purged under argon atmosphere for 5 min, heated to 80° C. and stirred for 16 h. The reaction was monitored by TLC; after completion of the reaction, the reaction mixture was filtered through celite, washed with 50% MeOH/CH$_2$Cl$_2$ (2×80 mL). The filtrate was concentrated in vacuo to obtain the crude. The crude was purified through silica gel flash column chromatography using 10-12% EtOAc/hexanes to afford compound 335 (3 g, 55%) as colorless syrup. TLC: 10% EtOAc/hexanes ($R_f$: 0.4); $^1$H-NMR (CDCl$_3$, 400 MHz): δ 7.85 (br d, J=7.2 Hz, 1H), 7.42-7.38 (m, 1H), 7.32-7.26 (m, 1H), 7.21 (br d, J=7.5 Hz, 1H), 4.00 (s, 2H), 3.68 (s, 3H), 1.34 (s, 12H);

Synthesis of methyl 2-(2-(5-(((tert-butoxycarbonyl) amino) methyl) thiazol-2-yl) phenyl) acetate (336)

To a stirring solution of tert-butyl ((2-chlorothiazol-5-yl) methyl) carbamate 224 (1 g, 4.02 mmol) in 1, 2-dimethoxy ethane:H$_2$O (4:1, 30 mL) under inert atmosphere were added compound 335 (1.33 g, 4.82 mmol) and potassium phosphate (2.55 g, 12.06 mmol) in sealed tube at RT and purged under argon atmosphere for 15 min. To this was added Pd(dppf)Cl$_2$ (294 mg, 0.40 mmol) and heated to 100° C. and stirred for 16 h. The reaction was monitored by TLC; after completion of the reaction, the volatiles were removed in vacuo to obtain the crude. The crude was purified through silica gel flash column chromatography using 10-15% EtOAc/hexanes to afford compound 336 (700 mg, 48%) as an off-white solid. TLC: 30% EtOAc/hexanes ($R_f$: 0.4). $^1$H-NMR (DMSO-d$_6$, 400 MHz): δ 7.71-7.64 (m, 2H), 7.56 (t, J=5.6 Hz, 1H), 7.45-7.37 (m, 3H), 4.33 (d, J=5.9 Hz, 2H), 4.06 (s, 2H), 3.52 (s, 3H), 1.40 (s, 9H);

Synthesis of tert-butyl ((2-(2-(2-hydroxy-2-methylpropyl) phenyl) thiazol-5-yl) methyl) carbamate (337)

To a stirring solution of compound 336 (700 mg, 1.93 mmol) in anhydrous THF (20 mL) under inert atmosphere was added methylmagnesium bromide (5.79 mL, 17.40 mmol, 3 M sol. In diethylether) at −10° C.; warmed to RT and stirred for 16 h. The reaction was monitored by TLC; after completion of the reaction, the reaction mixture was quenched with aqueous saturated ammonium chloride solution (70 mL) and extracted with EtOAc (2×70 mL). The combined organic extracts were dried over sodium sulfate, filtered and concentrated in vacuo to obtain the crude. The crude was purified through silica gel (100-200 mesh) column chromatography using 30-40% EtOAc/hexanes to afford compound 337 (200 mg, 29%) as an off-white solid. TLC: 30% EtOAc/hexanes ($R_f$: 0.4); $^1$H-NMR (DMSO-d$_6$, 400 MHz): δ 7.72 (s, 1H), 7.56 (t, J=5.6 Hz, 1H), 7.52 (dd, J=7.7, 1.1 Hz, 1H), 7.46-7.38 (m, 2H), 7.34 (dd, J=7.5, 1.9 Hz, 1H), 4.99 (s, 1H), 4.35 (d, J=5.8 Hz, 2H), 3.07 (s, 2H), 1.40 (s, 9H), 1.00 (s, 6H);

Synthesis of 1-(2-(5-(aminomethyl) thiazol-2-yl) phenyl)-2-methylpropan-2-ol hydrochloride (338)

To a stirring solution of compound 337 (200 mg, 0.55 mmol) in CH$_2$Cl$_2$ (10 mL) under inert atmosphere was added 4 N HCl in 1, 4-dioxane (2 mL) at 0° C.; warmed to RT and stirred for 3 h. The reaction was monitored by TLC; after completion of the reaction, the volatiles were removed in vacuo. The crude was triturated with diethyl ether (2×10 mL) and dried in vacuo to afford compound 338 (160 mg, HCl salt) as an off-white solid. TLC: 40% EtOAc/hexanes (R$_f$: 0.1); $^1$H-NMR (DMSO-d$_6$, 400 MHz): δ 8.45 (br s, 3H), 8.00 (s, 1H), 7.53 (dd, J=7.7, 1.1 Hz, 1H), 7.50-7.41 (m, 2H), 7.39-7.34 (m, 1H), 4.37 (q, J=5.7 Hz, 2H), 3.11 (s, 2H), 0.99 (s, 6H);

Synthesis of [2, 2'-bithiazol]-5-ylmethanamine hydrochloride (345)

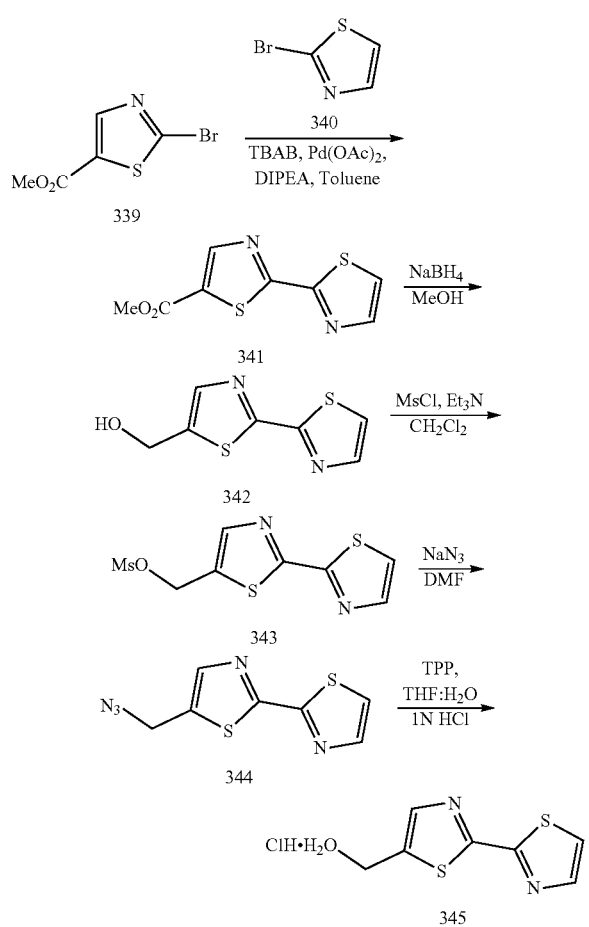

Synthesis of methyl [2, 2'-bithiazole]-5-carboxylate (341)

To a stirring solution of methyl 2-bromothiazole-5-carboxylate 339 (3 g, 13.51 mmol) in Toulene (50 mL) under inert atmosphere in a sealed tube were added 2-bromothiazole 340 (5.9 g, 40.41 mmol), diisopropylethylamine (1.7 mL, 13.50 mmol), tetrabutylammonium bromide (2.10 g, 6.52 mmol), Pd(OAc)$_2$ (150 mg, 0.66 mmol) at RT; heated to 100° C. and stirred for 24 h. The reaction was monitored by TLC; after completion of the reaction, the reaction mixture was filtered through celite and the filtrate was concentrated in vacuo to obtain the crude. The crude was purified through silica gel column flash chromatography using 20% EtOAc/hexanes to afford crude compound 341 (1.5 g, crude) which was carried to next step without further purification. TLC: 40% EtOAc/hexanes (R$_f$: 0.5);

Synthesis of [2, 2'-bithiazol]-5-ylmethanol (342)

To a stirring solution of compound 341 (1.5 g, 6.63 mmol) in MeOH (10 mL) under inert atmosphere was added sodium borohydride (1.5 g, 39.82 mmol) portion wise for 15 min at 0° C.; warmed to RT and stirred for 16 h. The reaction was monitored by TLC; after completion of the reaction, the volatiles were removed in vacuo. The crude was diluted with EtOAc (100 mL) and washed with water (2×50 mL). The combined organic extracts were dried over sodium sulfate and concentrated in vacuo to obtain the crude. The crude was purified through silica gel column flash chromatography using 20% EtOAc/hexanes to afford compound 342 (800 mg, 30%, over 2 steps) as colorless liquid. TLC: 40% EtOAc/hexanes (R$_f$: 0.4); $^1$H-NMR (DMSO-d$_6$, 400 MHz): δ 7.97 (d, J=3.2 Hz, 1H), 7.90 (d, J=3.05 Hz, 1H), 7.80 (s, 1H), 5.72 (t, J=5.8 Hz, 1H), 4.73 (dd, J=5.8, 0.9 Hz, 2H); LC-MS: 60.68%; 234.9 (M$^+$+1); (column; Ascentis Express C18, (50×3.0 mm, 2.7 μm); RT 1.44 min. 0.025% Aq. TFA+5% ACN: ACN+5% 0.025% Aq. TFA, 1.2 mL/min).

Synthesis of [2, 2'-bithiazol]-5-ylmethyl methanesulfonate (343)

To a stirring solution of compound 342 (800 mg, 4.04 mmol) in CH$_2$Cl$_2$ (10 mL) under inert atmosphere were added triethyl amine (1.73 mL, 12.12 mmol) and methanesulfonyl chloride (0.13 mL, 0.08 mmol) at 0° C.; warmed to RT and stirred for 16 h. The reaction was monitored by TLC; after completion of the reaction, the reaction mixture was diluted with water (50 mL), extracted with EtOAc (2×50 mL) The combined organic extracts were dried over sodium sulfate, filtered and concentrated in vacuo to afford crude compound 343 (1.1 g, 99%) as brown liquid. TLC: 20% EtOAc/hexanes (R$_f$: 0.1); $^1$H-NMR (DMSO-d$_6$, 400 MHz): δ 8.02-7.99 (m, 2H), 7.96 (d, J=3.2 Hz, 1H), 5.16 (s, 2H), 2.45 (s, 3H); LC-MS 88.94%; 278.9 (M$^+$+1); (column; Ascentis Express C18, (50×3.0 mm, 2.7 μm); RT 2.26 min. 0.025% Aq. TFA+5% ACN: ACN+5% 0.025% Aq. TFA, 1.2 mL/min).

Synthesis of 5-(azidomethyl)-2, 2'-bithiazole (344)

To a stirring solution of compound 343 (1.1 g, 3.98 mmol) in DMF (10 mL) under inert atmosphere was added sodium azide (778 mg, 11.95 mmol) at RT; heated to 60° C. and stirred for 4 h. The reaction was monitored by TLC; after completion of the reaction, the reaction mixture was diluted with water (50 mL) and extracted with EtOAc (100 mL) The combined organic extracts were dried over sodium sulphate, filtered and concentrated in vacuo to afford compound 344 (600 mg, 67%) as colorless liquid. TLC: 5% MeOH/CH$_2$Cl$_2$ (R$_f$: 0.2); $^1$H-NMR (DMSO-d$_6$, 400 MHz): δ 8.00 (d, J=3.2 Hz, 1H), 7.98 (s, 1H), 7.95 (d, J=3.1 Hz, 1H), 4.82 (s, 2H); LC-MS: 88.41%; 223.8 (M$^+$+1); (column; Ascentis Express C18, (50×3.0 mm, 2.7 μm); RT 2.20 min. 0.025% Aq. TFA+5% ACN: ACN+5% 0.025% Aq. TFA, 1.2 mL/min).

Synthesis of [2, 2'-bithiazol]-5-ylmethanamine hydrochloride (345)

To a stirring solution of compound 344 (600 mg, 2.69 mmol) in THF:H$_2$O (4:1, 5 mL) was added triphenyl phosphine (846 mg, 3.22 mmol) at 0° C.; warmed to RT and stirred for 2 h. The reaction was monitored by TLC; after completion of the reaction, the volatiles were removed in vacuo. The pH of the residue was adjusted to 2 with 1 N HCl. The aqueous layer was washed with EtOAc (2×25 mL). The aqueous layer was concentrated in vacuo and further dried by azeotropic distillation using toluene (10 mL) to afford compound 345 (600 mg, crude) as pale yellow solid. The crude was taken forward for next step without further purification. TLC: 5%

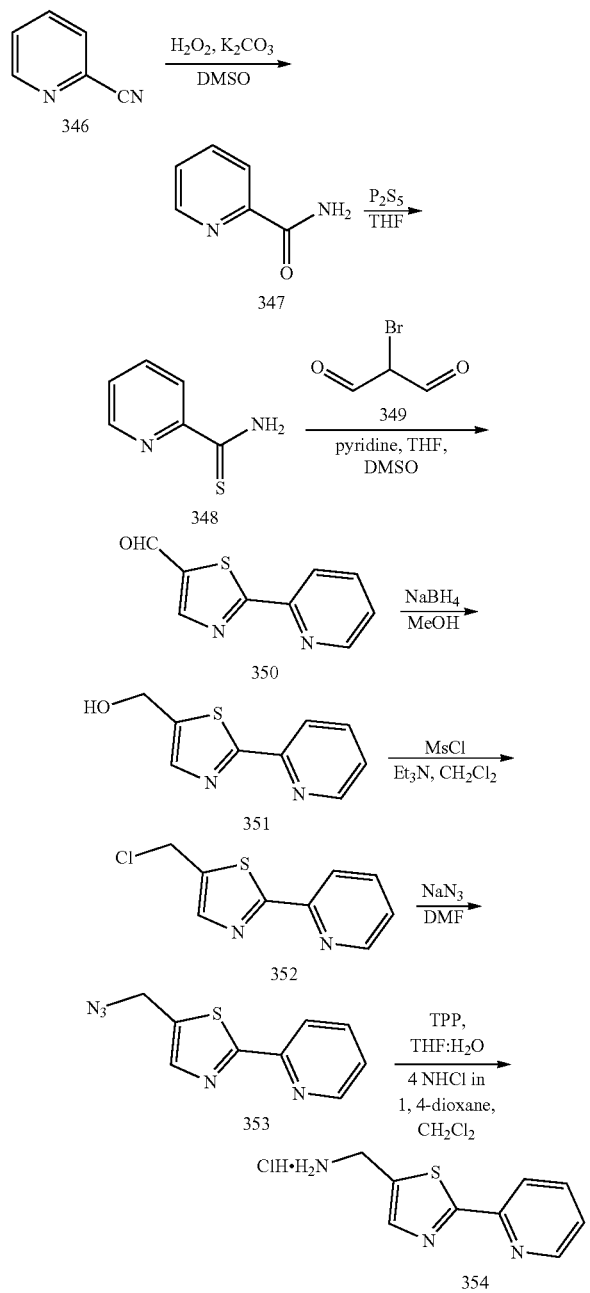

Synthesis of picolinamide (347)

To a stirring solution of picolinonitrile 346 (30 g, 296.91 mmol) in DMSO (300 mL) was added potassium carbonate (39.8 g, 288.35 mmol) followed by slow addition of 30% $H_2O_2$ (300 mL, 10 vol) for 20 min at 0° C.; warmed to RT and stirred for 3 h. The reaction was monitored by TLC; after completion of the reaction, the reaction mixture was diluted with EtOAc (200 mL) and washed with water (2×100 mL). The aqueous layer was extracted with EtOAc (4×100 mL). The combined organic extracts were dried over sodium sulfate, filtered and concentrated in vacuo to afford crude compound 347 (45 g) as an off-white solid. TLC: 50% EtOAc/hexanes ($R_f$: 0.2).

Synthesis of pyridine-2-carbothioamide (348)

To a stirring solution of compound 347 (45 g, 368.45 mmol) in THF (500 mL) under inert atmosphere was added $P_2S_5$ (81.97 g, 368.85 mmol) at 0° C., RT; heated to reflux and stirred for 16 h. The reaction was monitored by TLC after 16 h, the reaction mixture was diluted with EtOAc (200 mL), washed with saturated $NaHCO_3$ solution (2×80 mL). The aqueous layer was extracted with EtOAc (3×100 mL). The combined organic extracts were dried over sodium sulfate, filtered and concentrated in vacuo to obtain the crude. The crude was purified through silica gel column chromatography using 10% EtOAc/hexanes to afford compound 348 (13 g, 26%) as pale yellow solid. TLC: 40% EtOAc/hexanes ($R_f$: 0.8). $^1$H NMR (400 MHz, DMSO-$d_6$): δ 10.17 (br s, 1H), 9.91 (br s, 1H), 8.64-8.57 (m, 1H), 8.50 (td J=8.0, 1.0 Hz, 1H), 7.97 (td, J=7.8, 1.8 Hz, 1H), 7.61-7.57 (m, 1H).

Synthesis of 2-(pyridin-2-yl) thiazole-5-carbaldehyde (350)

A mixture of compound 348 (6 g, 43.41 mmol) and pyridine (12 mL) in THF (120 mL) was heated to 50° C. for 15 min, added 2-bromomalonaldehyde 349 (9.2 g, 60.92 mmol), heated to reflux and stirred for 16 h. The reaction was monitored by TLC; after completion of the reaction, the reaction mixture was diluted with EtOAc (100 mL) and washed with water (30 mL), brine (30 mL). The combined organic extracts were dried over sodium sulfate, filtered and concentrated in vacuo to obtain the crude. The crude was purified through silicagel flash column chromatography using 5-20% EtOAc/hexanes to afford compound 350 as brown solid. TLC: 20% EtOAc/hexanes ($R_f$: 0.3). $^1$H NMR (400 MHz, DMSO-$d_6$): δ 10.11 (s, 1H), 8.82 (s, 1H), 8.73-8.70 (m, 1H), 8.24 (d, J=7.9 Hz, 1H), 8.07-8.03 (m, 1H), 7.63-7.60 (m, 1H); LC-MS: 94.69%; 190.8 (M$^+$+1); (column; Ascentis Express C18, (50×3.0 mm, 2.7 μm); RT 1.93 min. 0.025% Aq. TFA+5% ACN: ACN+5% 0.025% Aq. TFA, 1.2 mL/min).

Synthesis of (2-(pyridin-2-yl) thiazol-5-yl) methanol (351)

To a stirring solution of compound 350 (1.5 g, 7.81 mmol) in MeOH (50 mL) under inert atmosphere was added sodium borohydride (600 mg, 15.78 mmol) portion wise for 15 min at 0° C.; warmed to RT and stirred for 3 h. The reaction was monitored by TLC; after completion of the reaction, the volatiles were removed in vacuo. The crude was diluted with EtOAc (100 mL) and washed with water (2×25 mL). The combined organic extracts were dried over sodium sulfate and concentrated in vacuo to obtain the crude. The crude was purified through silica gel flash column chromatography using 10-40% EtOAc/hexanes to afford compound 351 (1 g, 30%, over 2 steps) as pale brown solid. TLC: 30% EtOAc/hexanes (R_f: 0.2); ¹H NMR (400 MHz, DMSO-d_6): δ 8.65-8.58 (m, 1H), 8.10 (d, J=7.9 Hz, 1H), 7.97-7.92 (m, 1H), 7.80 (s, 1H), 7.49-7.45 (m, 1H), 5.63 (t, J=5.7 Hz, 1H), 4.72 (d, J=5.6 Hz, 2H); LC-MS: 99.64%; 192.9 (M⁺+1); (column; Ascentis Express C18, (50×3.0 mm, 2.7 μm); RT 1.47 min. 0.025% Aq. TFA+5% ACN: ACN+5% 0.025% Aq. TFA, 1.2 mL/min).

Synthesis of 5-(chloromethyl)-2-(pyridin-2-yl) thiazole (352)

To a stirring solution of compound 351 (1.0 g, 5.20 mmol) in CH_2Cl_2 (20 mL) under inert atmosphere were added triethylamine (1.46 mL, 10.41 mmol), methanesulfonyl chloride (712 mg, 6.25 mmol) at 0° C.; warmed to RT and stirred for 16 h. The reaction was monitored by TLC; after completion of the reaction, the reaction mixture was diluted with CH_2Cl_2 (100 mL), washed with saturated NaHCO_3 solution (2×50 mL), brine (50 mL). The combined organic extracts were dried over sodium sulfate, filtered and concentrated in vacuo to afford crude compound 352 (900 mg, 83%) as pale brown solid. TLC: 50% EtOAc/hexanes (R_f: 0.8); ¹H NMR (400 MHz, DMSO-d_6): δ 8.70-8.60 (m, 1H), 8.13 (d, J=7.9 Hz, 1H), 8.03 (s, 1H), 8.01-7.97 (m, 1H), 7.55-7.52 (m, 1H), 5.17 (d, J=0.6 Hz, 2H); LC-MS: 97.86%; 210.9 (M⁺+1); (column; Ascentis Express C-18, (50×3.0 mm, 2.7 μm); RT 2.27 min. 0.025% Aq. TFA+5% ACN: ACN+5% 0.025% Aq. TFA, 1.2 mL/min).

Synthesis of 5-(azidomethyl)-2-(pyridin-2-yl) thiazole (353)

To a stirring solution of compound 352 (900 mg, 4.28 mmol) in DMF (20 mL) under inert atmosphere was added sodium azide (557 mg, 8.56 mmol) at 0° C.; heated to 70° C. and stirred for 16 h. The reaction was monitored by TLC; after completion of the reaction, the reaction mixture was diluted with EtOAc (2×75 mL) washed with water (50 mL), brine (20 mL). The combined organic extracts were dried over sodium sulfate, filtered and concentrated in vacuo to obtain the crude compound 353 (850 mg, 91%) as pale brown solid. TLC: 20% EtOAc/hexanes (R_f: 0.5); ¹H NMR (400 MHz, DMSO-d_6): δ 8.66-8.61 (m, 1H), 8.12 (d, J=7.9 Hz, 1H), 8.00-7.95 (m, 2H), 7.53-7.51 (m, 1H), 4.80 (s, 2H); LC-MS: 96.94%; 217.8 (M⁺+1); (column; Ascentis Express C18, (50×3.0 mm, 2.7 μm); RT 2.21 min. 0.025% Aq. TFA+5% ACN: ACN+5% 0.025% Aq. TFA, 1.2 mL/min).

Synthesis of (2-(pyridin-2-yl) thiazol-5-yl) methanamine hydrochloride (354)

To a stirring solution of compound 353 (850 mg, 3.91 mmol) in THF:H_2O (15:5, 25 mL) was added triphenyl phosphine (1.23 g, 4.69 mmol) at 0° C.; warmed to RT and stirred for 4 h. The reaction was monitored by TLC; after completion of the reaction; the volatiles were removed in vacuo to obtain the crude amine (1.02 g crude). TLC: 20% EtOAc/hexanes (R_f: 0.1);
To the above crude amine (1.02 g) in CH_2Cl_2 (50 mL) was added 4 N HCl in 1, 4-dioxane (5 mL) under inert atmosphere at 0° C. and stirred for 1 h. The reaction was monitored by TLC; after completion of the reaction, the volatiles were removed in vacuo to obtain the crude. The crude was triturated with diethyl ether (2×50 mL), CH_2Cl_2 (2×60 mL), EtOAc (2×50 mL) and dried in vacuo to afford compound 354 (850 mg, 96%; HCl salt) as an hygroscopic off-white solid. TLC: 5% MeOH/CH_2Cl_2 (R_f: 0.2); ¹H NMR (400 MHz, DMSO-d_6): δ 8.65 (br s, 3H), 8.12 (d, J=7.0 Hz, 1H), 8.04 (s, 1H), 8.01-7.94 (m, 1H), 7.69-7.46 (m, 2H), 4.36-4.32 (m, 2H); LC-MS: 86.55%; 191.8 (M⁺+1); (column; Kinetex EVO C-18 (50×3.0 mm, 2.6 um); RT 1.09 min. 2.5 mM Aq. NH_4OOCH+5% ACN:ACN: 5% 2.5 mM Aq. NH4OOCH; 0.8 mL/min).

Synthesis of 4-(5-(aminomethyl) thiazol-2-yl) phenol hydrochloride (357)

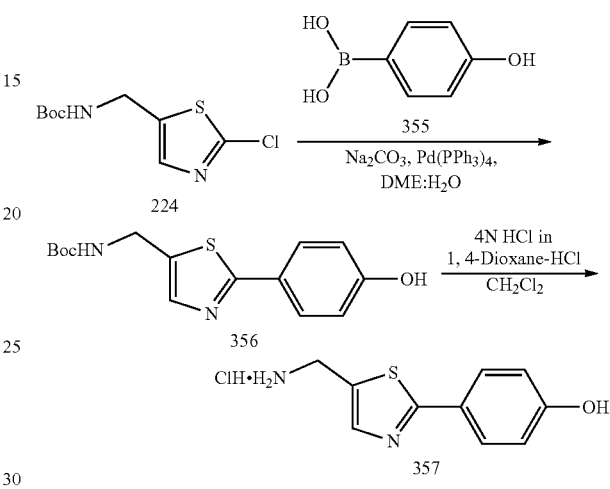

Synthesis of tert-butyl ((2-(4-hydroxyphenyl) thiazol-5-yl) methyl) carbamate (356)

To a stirring solution of tert-butyl ((2-chlorothiazol-5-yl) methyl) carbamate 224 (500 mg, 2.01 mmol) in 1, 2-dimethoxy ethane:H_2O (4:1, 20 mL) were added sodium carbonate (640 mg, 6.03 mmol) and (4-hydroxyphenyl) boronic acid 355 (416 mg, 3.01 mmol) and purged under argon atmosphere for 30 min in a sealed tube. To this was added Pd(PPh_3)_4 (231 mg, 0.20 mmol) at RT; heated to 90° C. and stirred for 6 h. The reaction was monitored by TLC; after completion of the reaction, the volatiles were removed in vacuo. The residue was diluted with EtOAc (200 mL), washed with water (100 mL). The organic extract was dried over sodium sulfate, filtered and concentrated in vacuo to obtain the crude. The crude was purified through silica gel column chromatography using 40% EtOAc/hexanes to afford compound 356 (250 mg, 41%) as an off-white solid. TLC: 50% EtOAc/hexanes (R_f: 0.5); ¹H-NMR (DMSO-d_6, 500 MHz): 9.92 (s, 1H), 7.69 (d, J=8.4 Hz, 2H), 7.55 (s, 1H), 7.50 (t, J=5.5 Hz, 1H), 6.83 (d, J=8.7 Hz, 2H), 4.28 (d, J=5.8 Hz, 2H), 1.38 (s, 9H).

Synthesis of 4-(5-(aminomethyl) thiazol-2-yl) phenol hydrochloride (357)

To a stirring solution of compound 356 (150 mg, 0.49 mmol) in CH_2Cl_2 (4 mL) was added 4 N HCl in 1, 4-Dioxane (1.25 mL, 4.90 mmol) under inert atmosphere at 0° C.; warmed to RT and stirred for 2 h. The reaction was monitored by TLC; after completion of the reaction, the volatiles were removed in vacuo. The crude was washed with diethyl ether (2×10 mL) and dried in vacuo to afford compound 357 (110 mg, 93%; HCl salt) as white solid. TLC: 30% EtOAc/hexanes (R_f: 0.2); ¹H-NMR (DMSO-d_6, 400

MHz): δ 10.07 (br s, 1H), 8.51 (br s, 3H), 7.84 (s, 1H), 7.74 (d, J=8.4 Hz, 2H), 6.88 (d, J=8.7 Hz, 2H), 4.28 (q, J=5.4 Hz, 2H).

Synthesis of 2-(4-(5-(aminomethyl) thiazol-2-yl) phenoxy)-N, N-dimethylethan-1-amine hydrochloride (360)

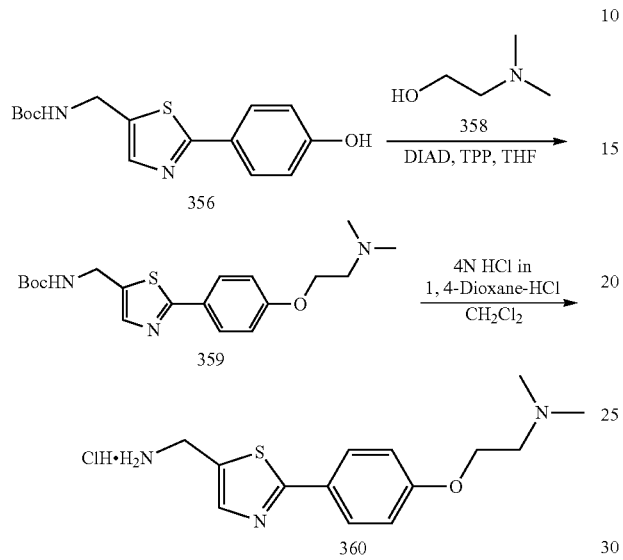

Synthesis of tert-butyl ((2-(4-(2-(dimethylamino) ethoxy) phenyl) thiazol-5-yl) methyl) carbamate (359)

To a mixture of tert-butyl ((2-(4-hydroxyphenyl) thiazol-5-yl) methyl) carbamate 356 (100 mg, 0.32 mmol) and 2-(dimethylamino) ethan-1-ol 358 (43 mg, 0.49 mmol) in THF (5 mL) under inert atmosphere were added diisopropyl azodicarboxylate (198 mg, 0.98 mmol) and triphenyl phosphine (256 mg, 0.98 mmol) at 0° C.; warmed to RT and stirred for 16 h. The reaction was monitored by TLC; after completion of the reaction, the volatiles were removed in vacuo. The residue was diluted with $CH_2Cl_2$ (100 mL) and washed with water (2×50 mL). The organic extract was dried over sodium sulfate, filtered and concentrated in vacuo to obtain the crude. The crude was purified through silica gel column chromatography using 3% MeOH/$CH_2Cl_2$ to afford compound 359 (60 mg, 49%) as white solid. TLC: 5% MeOH/$CH_2Cl_2$ ($R_f$: 0.2); $^1$H NMR (DMSO-$d_6$, 500 MHz): δ 7.83 (d, J=8.7 Hz, 2H), 7.61 (s, 1H), 7.53 (t, J=5.2 Hz, 1H), 7.06 (d, J=9.0 Hz, 2H), 4.31 (d, J=5.8 Hz, 2H), 4.19 (t, J=5.4 Hz, 2H), 2.91 (br s, 2H), 2.42 (br s, 6H), 1.40 (s, 9H).

Synthesis of 2-(4-(5-(aminomethyl) thiazol-2-yl) phenoxy)-N, N-dimethylethan-1-amine hydrochloride (360)

To a stirring solution of compound 359 (60 mg, 0.15 mmol) in $CH_2Cl_2$ (3 mL) was added 4 N HCl in 1, 4-Dioxane (0.4 mL) under inert atmosphere at 0° C.; warmed to RT and stirred for 3 h. The reaction was monitored by TLC; after completion of the reaction, the volatiles were removed in vacuo. The crude was washed with diethyl ether (2×5 mL) and dried in vacuo to afford compound 360 (45 mg, 90%; HCl salt) as white solid. TLC: 10% MeOH/$CH_2Cl_2$ ($R_f$: 0.2); LC-MS: 94.06%; 277.9 ($M^+$+1); (column; Ascentis Express C18, (50×3.0 mm, 2.7 μm); RT 0.42 min. 0.025% Aq. TFA+5% ACN: ACN+5% 0.025% Aq. TFA, 1.2 mL/min).

Synthesis of (2-(4-methoxyphenyl) thiazol-5-yl) methanamine hydrochloride (363)

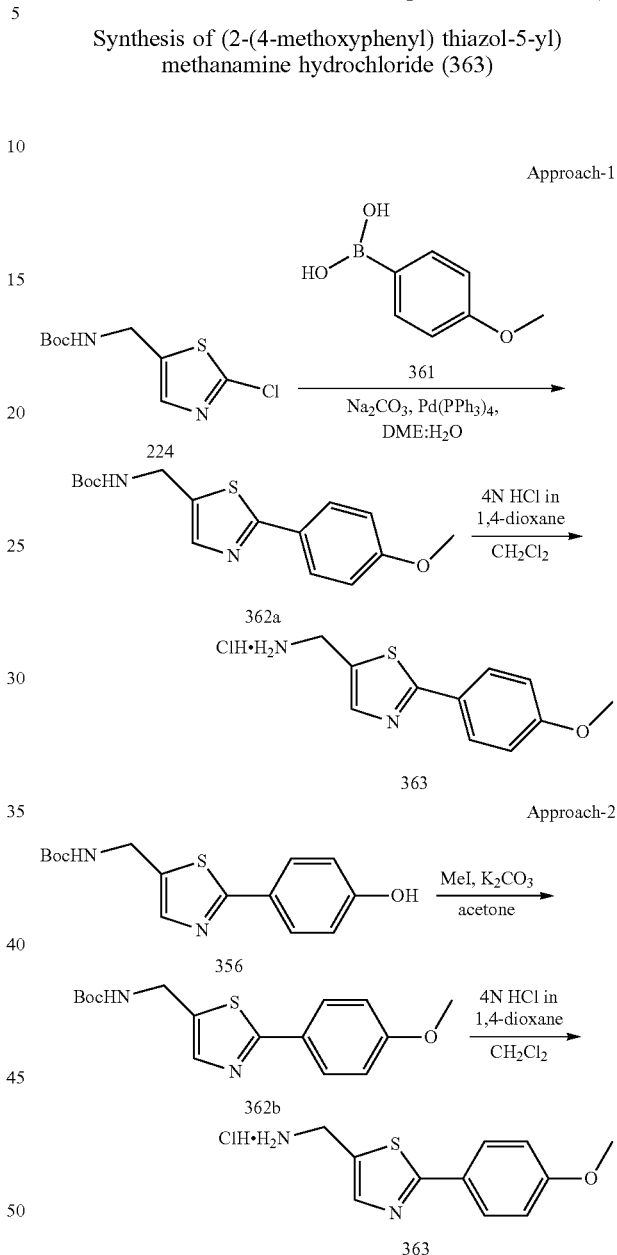

Synthesis of tert-butyl ((2-(4-methoxyphenyl) thiazol-5-yl) methyl) carbamate (362a)

To a stirring solution of tert-butyl ((2-chlorothiazol-5-yl) methyl) carbamate 224 (1 g, 4.02 mmol) in DMF:$H_2O$ (4:1, 20 mL) were added sodium carbonate (464 mg, 0.40 mmol) and (4-methoxyphenyl) boronic acid 361 (734 mg, 4.82 mmol) and purged under argon atmosphere for 20 min. To this was added Pd(PPh$_3$)$_4$ (464 mg, 0.40 mmol) at RT; heated to 80° C. and stirred for 16 h. The reaction was monitored by TLC; after completion of the reaction, the volatiles were removed in vacuo. The residue was diluted with EtOAc (200 mL), washed with water (75 mL). The organic extract was dried over sodium sulfate, filtered and concentrated in vacuo to obtain the crude. The crude was purified through silica gel column chromatography using 40% EtOAc/hexanes to afford compound 362a (700 mg, 58%) as yellow solid. TLC: 30% EtOAc/hexanes (R$_f$: 0.2); $^1$H-NMR (DMSO-d$_6$, 500 MHz): δ 7.81 (d, J=8.7 Hz, 2H), 7.59 (s, 1H), 7.51 (t, J=6.1 Hz, 1H), 7.02 (d, J=8.7 Hz, 2H), 4.29 (d, J=5.5 Hz, 2H), 3.80 (s, 3H), 1.38 (s, 9H).

Synthesis of (2-(4-methoxyphenyl) thiazol-5-yl) methanamine hydrochloride (363)

To a stirring solution of compound 362a (700 mg, 2.18 mmol) in CH$_2$Cl$_2$ (20 mL) under argon atmosphere was added 4 N HCl in 1, 4-dioxane (2 mL) at 0° C.; warmed to RT and stirred for 4 h. The reaction was monitored by TLC; after completion of the reaction, the volatiles were removed in vacuo to afford compound 363 (550 mg, 99%) as an off-white solid. TLC: 40% EtOAc/hexanes (R$_f$: 0.1); $^1$H-NMR (DMSO-d$_6$, 500 MHz): δ 8.52 (br s, 3H), 7.90 (s, 1H), 7.87 (d, J=9.0 Hz, 2H), 7.07 (d, J=8.7 Hz, 2H), 4.32 (q, J=5.7 Hz, 2H), 3.83 (s, 3H).

Synthesis of tert-butyl ((2-(4-methoxyphenyl) thiazol-5-yl) methyl) carbamate (362b)

To a stirring solution of tert-butyl ((2-(4-hydroxyphenyl) thiazol-5-yl) methyl) carbamate 356 (150 mg, 0.49 mmol) in acetone (10 mL) under inert atmosphere were added potassium carbonate (203 mg, 1.47 mmol) and methyl iodide (0.09 mL, 1.47 mmol) at 0° C.; heated to 70° C. and stirred for 2 h. The reaction was monitored by TLC; after completion of the reaction, the volatiles were removed in vacuo. The residue was diluted with water (100 mL) and extracted with EtOAc (2×50 mL). The organic extract was dried over sodium sulfate, filtered and concentrated in vacuo to obtain the crude. The crude was purified through silica gel column chromatography using 20% EtOAc/hexanes to afford compound 362b (105 mg, 67%) as white solid. TLC: 40% EtOAc/hexanes (R$_f$: 0.8); $^1$H NMR (DMSO-d$_6$, 400 MHz): δ 7.82 (d, J=8.7 Hz, 2H), 7.61 (s, 1H), 7.53 (t, J=5.5 Hz, 1H), 7.04 (d, J=8.7 Hz, 2H), 4.31 (d, J=5.8 Hz, 2H), 3.81 (s, 3H), 1.40 (s, 9H).

Synthesis of (2-(4-methoxyphenyl) thiazol-5-yl) methanamine hydrochloride (363)

To a stirring solution of compound 362b (100 mg, 0.31 mmol) in CH$_2$Cl$_2$ (5 mL) under inert atmosphere was added 4 N HCl in 1, 4-Dioxane (0.78 mL) at 0° C.; warmed to RT and stirred for 3 h. The reaction was monitored by TLC; after completion of the reaction, the volatiles were removed in vacuo to obtain the crude. The crude was washed with diethyl ether (10 mL) and dried in vacuo to afford compound 363 (65 mg, 81%) as white solid. TLC: 5% MeOH/CH$_2$Cl$_2$ (R$_f$: 0.2); $^1$H-NMR (DMSO-d$_6$, 500 MHz): δ 8.49 (br s, 3H), 7.90 (s, 1H), 7.87 (d, J=8.7 Hz, 2H), 7.07 (d, J=9.0 Hz, 2H), 4.32 (q, J=5.4 Hz, 2H), 3.83 (s, 3H).

Synthesis of 3-(4-(5-(aminomethyl) thiazol-2-yl) phenoxy)-N, N-dimethylpropan-1-amine hydrochloride (367)

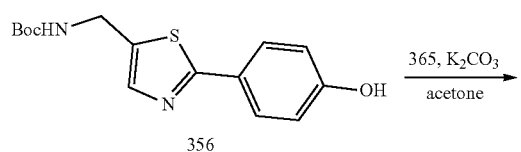

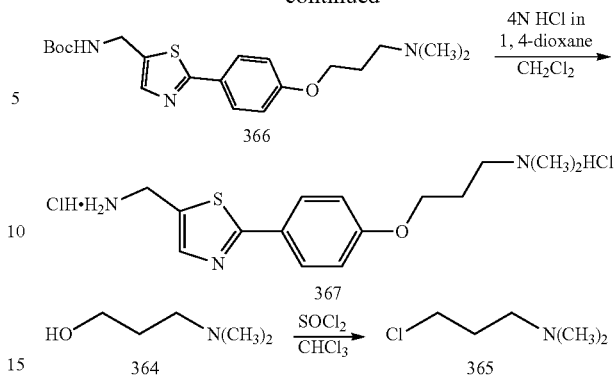

Synthesis of 3-chloro-N, N-dimethylpropan-1-amine (365)

To a stirring solution of 3-(dimethylamino) propan-1-ol 364 (2.0 g, 1.94 mmol) in CHCl$_3$ (50 mL) under inert atmosphere was added thionyl chloride (4.22 mL, 58.23 mmol) at 0° C.; heated to 70° C. and stirred for 4 h. The reaction was monitored by TLC; after completion of the reaction, the volatiles were removed in vacuo to obtain the crude. The crude was washed with diethyl ether (2×30 mL) to afford compound 365 (2.5 g, 83%) as white solid. TLC: 5% MeOH/CH$_2$Cl$_2$ (R$_f$: 0.2); $^1$H-NMR (DMSO-d$_6$, 500 MHz): δ 10.97 (br s, 1H), 3.74 (t, J=6.4 Hz, 2H), 3.12 (t, J=7.8 Hz, 2H), 2.72 (s, 6H), 2.20-2.12 (m, 2H).

Synthesis of tert-butyl ((2-(4-(3-(dimethylamino) propoxy) phenyl) thiazol-5-yl) methyl) carbamate (366)

To a stirring solution of compound 356 (400 mg, 1.30 mmol) and compound 365 (411 mg, 2.61 mmol) in acetone (20 mL) under inert atmosphere was added potassium carbonate (541 mg, 3.91 mmol) at RT; heated to 80° C. and stirred for 8 h. The reaction was monitored by TLC; after completion of the reaction, the volatiles were removed in vacuo. The residue was diluted with water (100 mL) and extracted with EtOAc (2×100 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 366 (350 mg, 68%) as off-white sticky solid. TLC: 5% MeOH/CH$_2$Cl$_2$ (R$_f$: 0.1); $^1$H NMR (DMSO-d$_6$, 400 MHz): δ 7.81 (d, J=8.8 Hz, 2H), 7.60 (s, 1H), 7.53 (t, J=5.5 Hz, 1H), 7.02 (d, J=8.8 Hz, 2H), 4.31 (d, J=5.7 Hz, 2H), 4.06 (t, J=6.3 Hz, 2H), 2.52-2.48 (m, 2H), 2.28 (s, 6H), 1.96-1.87 (m, 2H), 1.40 (s, 9H).

Synthesis of 3-(4-(5-(aminomethyl) thiazol-2-yl) phenoxy)-N, N-dimethylpropan-1-amine hydrochloride (367)

To a stirring solution of compound 366 (350 mg, 0.89 mmol) in CH$_2$Cl$_2$ (5 mL) under inert atmosphere was added 4 N HCl in 1, 4-dioxane (2 mL) at 0° C.; warmed to RT and stirred for 2 h. The reaction was monitored by TLC; after completion of the reaction, the volatiles were removed in vacuo to obtain the crude. The crude was washed with EtOAc (2×5 mL) and dried in vacuo to afford compound 367 (300 mg, 92%) as an off-white solid. TLC: 10% MeOH/

CH$_2$Cl$_2$ (R$_f$: 0.2); $^1$H-NMR (DMSO-d$_6$, 400 MHz): δ 10.86 (br s, 1H), 8.65 (br s, 3H), 7.91 (s, 1H), 7.87 (d, J=8.9 Hz, 2H), 7.08 (d, J=8.8 Hz, 2H), 4.31 (q, J=5.6 Hz, 2H), 4.14 (t, J=6.1 Hz, 2H), 3.28-3.15 (m, 2H), 2.76 (s, 3H), 2.77 (s, 3H), 2.23-2.14 (m, 2H).

Synthesis of 4-(5-((methylamino) methyl) thiazol-2-yl) phenol (369)

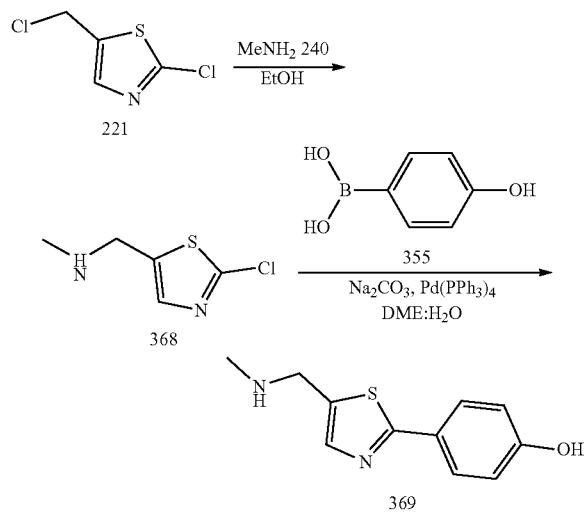

Synthesis of 1-(2-chlorothiazol-5-yl)-N-methylmethanamine (368)

To a stirring solution of 2-chloro-5-(chloromethyl) thiazole 221 (2 g, 11.90 mmol) in EtOH (15 mL) in a sealed tube under inert atmosphere were added methyl amine 240 (2 M in THF, 1.8 mL, 14.28 mmol) at 0° C.; warmed to RT and stirred for 16 h. The reaction was monitored by TLC; after completion of the reaction, the reaction mixture was diluted with water (10 mL) extracted with EtOAc (2×50 mL). The combined organic extracts were dried over sodium sulphate, filtered and concentrated in vacuo to obtain the crude. The crude was purified through silica gel column chromatography using 5% MeOH/CH$_2$Cl$_2$ to afford compound 368 (600 mg, 31%) as colorless liquid. TLC: 30% EtOAc/hexanes (R$_f$: 0.7); $^1$H NMR (DMSO-d$_6$, 400 MHz): δ 7.57 (s, 1H), 4.08 (br s, 1H), 3.91 (s, 2H), 3.17 (s, 3H).

Synthesis of 4-(5-((methylamino) methyl) thiazol-2-yl) phenol (369)

To a stirring solution of 1-(2-chlorothiazol-5-yl)-N-methylmethanamine 368 (200 mg, 1.23 mmol) in 1, 2 dimethoxy ethane:H$_2$O (4:1, 15 mL) were added (4-hydroxyphenyl) boronic acid 355 (170 mg, 1.923 mmol), sodium carbonate (342 mg, 3.70 mmol) and purged under argon atmosphere for 30 min. To this was added Pd(PPh$_3$)$_4$ (142 mg, 0.12 mmol) at RT; heated to 100° C. and stirred for 16 h. The reaction was monitored by TLC; after completion the reaction mixture was diluted with water (50 mL) and extracted with EtOAc (2×100 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 369 (70 mg, 25%) as an off-white solid. TLC: 10% MeOH/CH$_2$Cl$_2$ (R$_f$: 0.3); $^1$H-NMR (DMSO-d$_6$, 500 MHz): 9.96 (br s, 1H), 7.72 (d, J=8.8 Hz, 2H), 7.63 (s, 1H), 6.85 (d, J=8.8 Hz, 2H), 4.08 (br s, 1H), 3.91 (s, 2H), 3.17 (s, 3H).

Synthesis of (2-(4-(2-morpholinoethoxy) phenyl) thiazol-5-yl) methanamine hydrochloride (372)

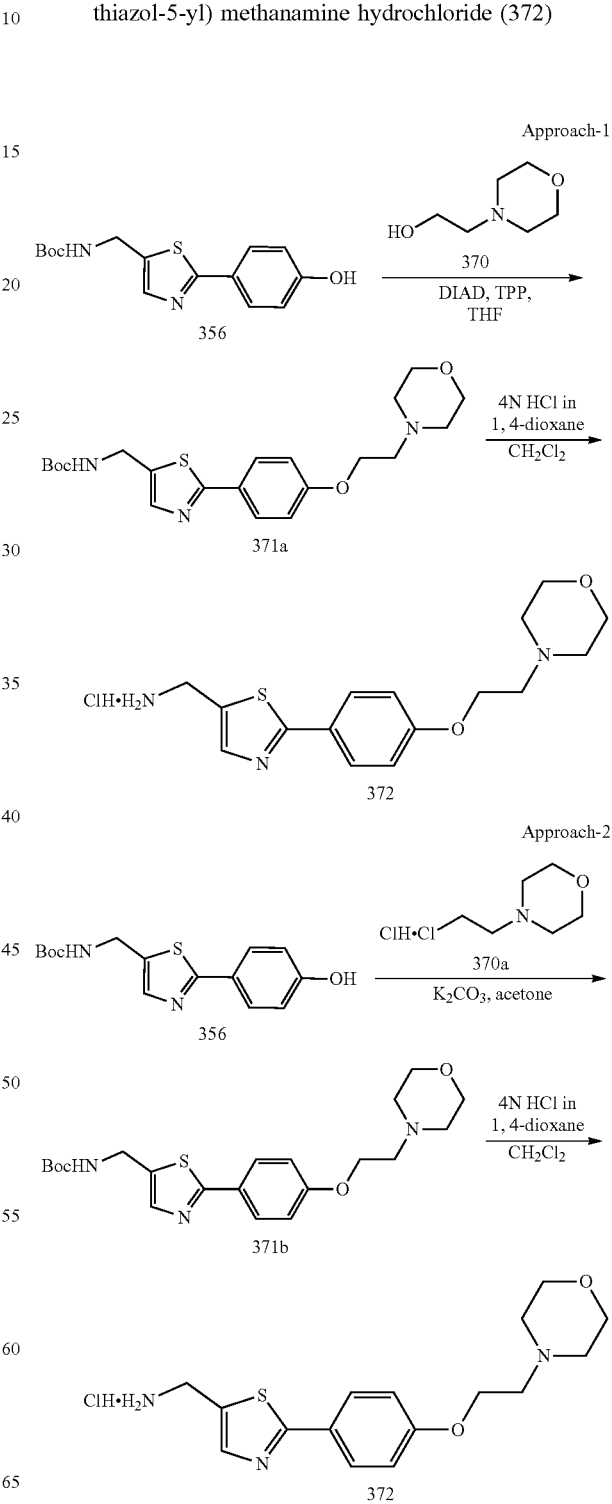

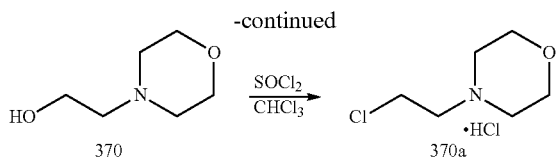

Synthesis of tert-butyl ((2-(4-(2-morpholinoethoxy) phenyl) thiazol-5-yl) methyl) carbamate (371a)

To a mixture of tert-butyl ((2-(4-hydroxyphenyl) thiazol-5-yl) methyl) carbamate 356 (250 mg, 0.81 mmol) in THF (5 mL) under inert atmosphere was added diisopropyl azodicarboxylate (495 mg, 2.45 mmol) and triphenyl phosphine (642 mg, 2.45 mmol) at 0° C. and stirred for 10 min. To this was added 2-morpholinoethan-1-ol 370 (128 mg, 0.98 mmol) at 0° C.; warmed to RT and stirred for 16 h. The reaction was monitored by TLC; after completion of the reaction, the volatiles were removed in vacuo. The residue was diluted with CH$_2$Cl$_2$ (100 mL) and washed with water (2×50 mL). The combined organic extracts were dried over sodium sulfate, filtered and concentrated in vacuo to obtain the crude. The crude was purified through silica gel column chromatography using 3% MeOH/CH$_2$Cl$_2$ to afford compound 371a (170 mg, 50%) as white solid. TLC: 50% EtOAc/hexanes (R$_f$: 0.4); $^1$H NMR (DMSO-d$_6$, 400 MHz): δ 7.79 (d, J=8.7 Hz, 2H), 7.59 (s, 1H), 7.51 (t, J=5.5 Hz, 1H), 7.03 (d, J=9.0 Hz, 2H), 5.74 (s, 1H), 4.29 (d, J=6.1 Hz, 2H), 4.13 (t, J=5.8 Hz, 2H), 3.59-3.54 (m, 4H), 2.69 (t, J=5.8 Hz, 2H), 2.52-2.42 (m, 4H), 1.38 (s, 9H).

Synthesis of (2-(4-(2-morpholinoethoxy) phenyl) thiazol-5-yl) methanamine hydrochloride (372)

To a stirring solution of compound 371a (170 mg, 0.40 mmol) in CH$_2$Cl$_2$ (10 mL) was added 4 N HCl in 1, 4-Dioxane (1 mL) under inert atmosphere at 0° C.; warmed to RT and stirred for 3 h. The reaction was monitored by TLC; after completion of the reaction, the volatiles were removed in vacuo. The crude was washed with EtOAc (5 mL) and dried in vacuo to afford compound 372 (100 mg, 56%; HCl salt) as white solid. TLC: 10% MeOH/CH$_2$Cl$_2$ (R$_f$: 0.2); $^1$H-NMR (DMSO-d$_6$, 500 MHz): δ 8.56 (br s, 3H), 7.92 (s, 1H), 7.90 (d, J=8.7 Hz, 2H), 7.14 (d, J=8.7 Hz, 2H), 4.52 (t, J=4.8 Hz, 2H), 4.35-4.30 (m, 2H), 4.00-3.94 (m, 2H), 3.85 (t, J=11.3 Hz, 2H), 3.60-3.55 (m, 2H), 3.50-3.47 (m, 2H), 3.25-3.15 (m, 2H).

Synthesis of (2-(4-(2-morpholinoethoxy) phenyl) thiazol-5-yl) methanamine hydrochloride (372): Approach-2

Synthesis of 4-(2-chloroethyl) morpholine hydrochloride (370a)

To a stirring solution of 3-(dimethylamino) propan-1-ol 370 (3.0 g, 23.07 mmol) in CHCl$_3$ (50 mL) under inert atmosphere was added thionyl chloride (6.88 mL, 69.23 mmol) at 0° C.; heated to 70° C. and stirred for 1 h. The reaction was monitored by TLC; after completion of the reaction, the volatiles were removed in vacuo to obtain the crude. The crude was washed with diethyl ether (2×30 mL) to afford compound 370a (3 g, 88%) as white solid. TLC: 5% MeOH/CH$_2$Cl$_2$ (R$_f$: 0.2); $^1$H-NMR (DMSO-d$_6$, 500 MHz): 11.65 (br s, 1H), 10.81 (br s, 1H), 4.06 (t, J=6.8 Hz, 1H), 3.98-3.90 (m, 2H), 3.86-3.77 (m, 2H), 3.54-3.36 (m, 3H), 3.22-3.03 (m, 2H).

Synthesis of tert-butyl ((2-(4-(2-morpholinoethoxy) phenyl) thiazol-5-yl) methyl) carbamate (371b)

To a stirring solution of tert-butyl ((2-(4-hydroxyphenyl) thiazol-5-yl) methyl) carbamate 356 (150 mg, 0.49 mmol) and 4-(2-chloroethyl) morpholine hydrochloride 370a (145 mg, 0.98 mmol) in acetone (15 mL) under inert atmosphere was added potassium carbonate (203 mg, 2.45 mmol) at RT; heated to 70-80° C. and stirred for 16 h. The reaction was monitored by TLC; after completion of the reaction, the volatiles were removed in vacuo. The residue was diluted with water (100 mL) and extracted with EtOAc (2×100 mL). The combined organic extracts were dried over sodium sulfate, filtered and concentrated in vacuo to obtain the crude. The crude was purified through silica gel column chromatography using 3% MeOH/CH$_2$Cl$_2$ to afford compound 371b (175 mg, 85%) as colorless thick syrup. TLC: 3% MeOH/CH$_2$Cl$_2$(R$_f$: 0.5); $^1$H NMR (DMSO-d$_6$, 400 MHz): δ 7.79 (d, J=8.7 Hz, 2H), 7.59 (s, 1H), 7.51 (t, J=5.5 Hz, 1H), 7.03 (d, J=9.0 Hz, 2H), 5.74 (s, 1H), 4.29 (d, J=6.1 Hz, 2H), 4.13 (t, J=5.8 Hz, 2H), 3.59-3.54 (m, 4H), 2.69 (t, J=5.8 Hz, 2H), 2.52-2.42 (m, 4H), 1.38 (s, 9H).

Synthesis of (2-(4-(2-morpholinoethoxy) phenyl) thiazol-5-yl) methanamine hydrochloride (372)

To a stirring solution of compound 371b (175 mg, 0.40 mmol) in CH$_2$Cl$_2$ (5 mL) was added 4 N HCl in 1, 4-Dioxane (5 mL) under inert atmosphere at 0° C.; warmed to RT and stirred for 2 h. The reaction was monitored by TLC; after completion of the reaction, the volatiles were removed in vacuo. The crude was washed with diethyl ether (5 mL) and dried in vacuo to afford compound 372 (155 mg, 95%; HCl salt) as white solid. TLC: 10% MeOH/CH$_2$Cl$_2$ (R$_f$: 0.2); $^1$H-NMR (DMSO-d$_6$, 500 MHz): δ 8.56 (br s, 3H), 7.92 (s, 1H), 7.90 (d, J=8.7 Hz, 2H), 7.14 (d, J=8.7 Hz, 2H), 4.52 (t, J=4.8 Hz, 2H), 4.35-4.30 (m, 2H), 4.00-3.94 (m, 2H), 3.85 (t, J=11.3 Hz, 2H), 3.60-3.55 (m, 2H), 3.50-3.47 (m, 2H), 3.25-3.15 (m, 2H).

Synthesis of (2-(4-(3-(piperidin-1-yl) propoxy) phenyl) thiazol-5-yl) methanamine hydrochloride (375)

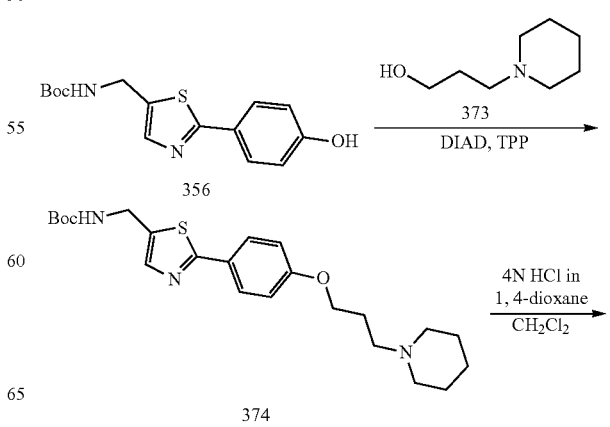

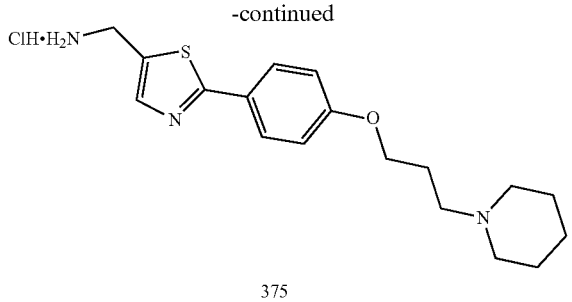

375

Synthesis of tert-butyl ((2-(4-(3-(piperidin-1-yl) propoxy) phenyl) thiazol-5-yl) methyl) carbamate (374)

To a stirring solution of tert-butyl ((2-(4-hydroxyphenyl) thiazol-5-yl) methyl) carbamate 356 (200 mg, 0.65 mmol) in diethyl ether (10 mL) under argon atmosphere were added triphenylphosphine (256 mg, 0.98 mmol), DIAD (198 mg, 0.98 mmol) and 3-(piperidin-1-yl) propan-1-ol 373 (112 mg, 0.78 mmol) at 0° C.; warmed to RT and stirred for 6 h. The reaction was monitored by TLC; after completion of the reaction, the volatiles were removed in vacuo to obtain the crude. The crude was purified through silica gel column chromatography using 10% MeOH/CH$_2$Cl$_2$+5 mL aqueous ammonia to afford compound 374 (280 mg, 80%) as an off white solid. TLC: 10% MeOH/CH$_2$Cl$_2$ (R$_f$ 0.2); $^1$H NMR (400 MHz, DMSO-d$_6$): δ 7.81 (d, J=8.8 Hz, 2H), 7.60 (s, 1H), 7.53 (t, J=5.0 Hz, 1H), 7.02 (d, J=8.8 Hz, 2H), 4.31 (d, J=5.8 Hz, 2H), 4.06 (t, J=6.3 Hz, 2H), 2.45-2.19 (m, 6H), 1.95-1.85 (m, 2H), 1.57-1.45 (m, 4H), 1.40 (s, 9H), 1.25-1.11 (m, 2H); LC-MS: 98.75%; 432.1 (M$^+$+1); (column; Ascentis Express C-18 (50×3.0 mm, 2.7 μm); RT 1.94 min. 0.025% Aq. TFA+5% ACN: ACN+5% 0.025% Aq TFA, 1.2 mL/min).

Synthesis of (2-(4-(3-(piperidin-1-yl) propoxy) phenyl) thiazol-5-yl) methanamine hydrochloride (375)

To a stirring solution of compound 374 (270 mg, 0.62 mmol) in CH$_2$Cl$_2$ (5 mL) was added 4 N HCl in 1, 4-dioxane (5 mL) under argon atmosphere at 0° C.; warmed to RT and stirred for 4 h. The reaction was monitored by TLC; after completion of the reaction, the volatiles were removed in vacuo. The crude washed with diethyl ether (5 mL), pentane (5 mL) and dried in vacuo to afford compound 375 (190 mg; 83%) as an off white solid. TLC: 10% MeOH/CH$_2$Cl$_2$ (R$_f$: 0.2); $^1$H NMR (400 MHz, DMSO-d$_6$): δ 10.20 (br s, 1H), 8.48 (br s, 3H), 7.92-7.84 (m, 3H), 7.08 (d, J=8.9 Hz, 2H), 4.32 (q, J=5.5 Hz, 2H), 4.14 (t, J=6.1 Hz, 2H), 3.48-3.43 (m, 2H), 3.22-3.13 (m, 2H), 2.94-2.81 (m, 2H), 2.26-2.16 (m, 2H), 1.85-1.67 (m, 6H); LC-MS: 99.67%; 332.1 (M$^+$+1); (column; Ascentis Express C18, (50×3.0 mm, 2.7 μm); RT 1.05 min. 0.025% Aq. TFA+5% ACN: ACN+5% 0.025% Aq. TFA, 1.2 mL/min).

Synthesis of (2-(4-(3-morpholinopropoxy) phenyl) thiazol-5-yl) methanamine hydrochloride (378)

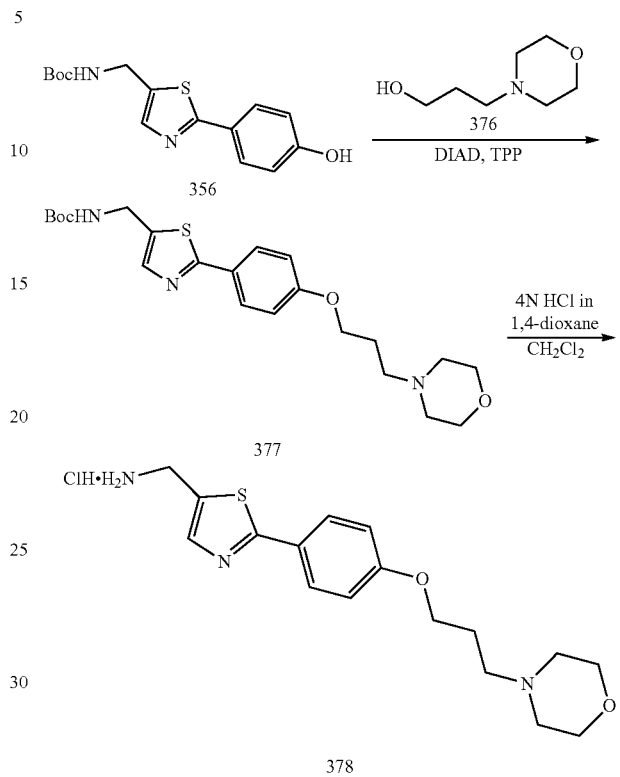

Synthesis of tert-butyl ((2-(4-(3-morpholino-propoxy)phenyl) thiazol-5-yl)methyl) carbamate (377)

To a stirring solution tert-butyl ((2-(4-hydroxyphenyl) thiazol-5-yl) methyl) carbamate 356 (200 mg, 0.65 mmol) in THF (10 mL) under argon atmosphere were added triphenyl phosphine (342 mg, 1.30 mmol), DIAD (258 mg, 1.30 mmol) and 3-morpholinopropan-1-ol 376 (0.13 mL, 0.98 mmol) at 0° C.; warmed to RT and stirred for 16 h. The reaction was monitored by TLC; after completion of the reaction, the volatiles were removed in vacuo. The residue was diluted with water (20 mL) and extracted with EtOAc (3×20 mL). The combined organic extracts were dried over sodium sulfate, filtered and concentrated to obtain crude. The crude was purified through silica gel column chromatography using 100% EtOAc to afford compound 377 (250 mg crude) as an off-white solid. TLC: 100% EtOAc (R$_f$: 0.2). LC-MS: 66.02%; 434.1 (M$^+$+1); (column; Ascentis Express C-18 (50×3.0 mm, 2.7 μm); RT 1.87 min. 0.025% Aq. TFA+5% ACN: ACN+5% 0.025% Aq TFA, 1.2 mL/min).

Synthesis of (2-(4-(3-morpholinopropoxy) phenyl) thiazol-5-yl) methanamine hydrochloride (378)

To a stirring solution of compound 377 (250 mg, 0.57 mmol) in CH$_2$Cl$_2$ (5 mL) under argon atmosphere was added 4 N HCl in 1, 4-dioxane (4 mL) at 0° C.; warmed to RT and stirred for 2 h. The reaction was monitored by TLC; after completion of the reaction, the volatiles were removed in vacuo. The crude washed with diethyl ether (20 mL), EtOAc (10 mL) and dried in vacuo to afford compound 378 (125 mg; 83%) as an off white solid. TLC: 10% MeOH/CH$_2$Cl$_2$ (R$_f$: 0.2); $^1$H NMR (400 MHz, DMSO-d$_6$): δ 9.29 (br s, 1H), 8.98-8.89 (m, 2H), 7.81 (d, J=8.8 Hz, 2H), 7.60 (s, 1H), 7.02 (d, J=8.9 Hz, 2H), 4.34-4.30 (m, 2H), 4.11-3.99 (m, 4H), 3.60-3.53 (m, 8H), 1.94-1.86 (m, 2H); LC-MS: 96.49%; 334 (M$^+$+1); (column; Kinetex EVO C-18 (50×3.0 mm, 2.6 um); RT 1.51 min. 2.5 mM Aq.NH$_4$OOCH+5% ACN:CAN+5% 2.5 mM Aq.NH$_4$OOCH; 1.2 mL/min).

Synthesis of 3-(4-(5-(aminomethyl) thiazol-2-yl) phenoxy)-N-methyl-N-(2, 2, 2-trifluoroethyl) propan-1-amine hydrochloride (383)

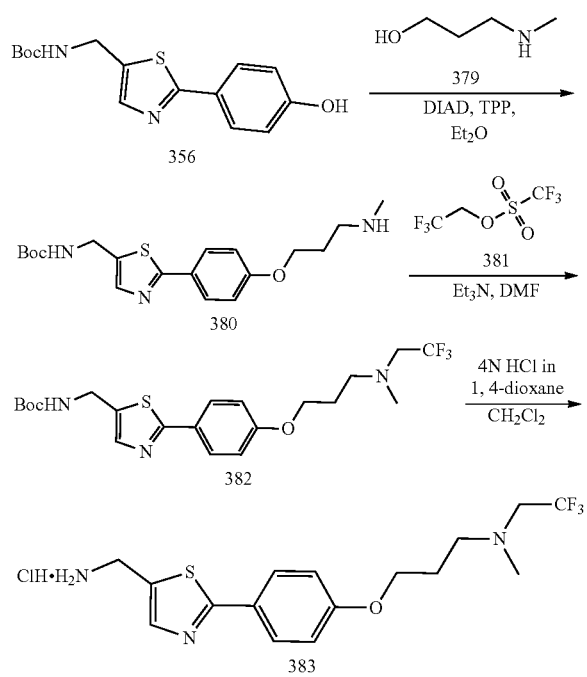

Synthesis of tert-butyl ((2-(4-(3-(methylamino) propoxy) phenyl) thiazol-5-yl) methyl) carbamate (380)

To a stirring solution of tert-butyl ((2-(4-hydroxyphenyl) thiazol-5-yl) methyl) carbamate 356 (1 g, 3.26 mmol) in dry diethyl ether (50 mL) under argon atmosphere were added triphenyl phosphine (2.56 g, 9.80 mmol), 3-(methylamino) propan-1-ol 379 (0.36 mL, 3.92 mmol) and diisopropyl azodicarboxylate (1.98 g, 9.80 mmol) at 0° C.; warmed to RT and stirred for 16 h. The reaction was monitored by TLC; after completion of the reaction, the reaction mixture was diluted with water (50 mL) and extracted with EtOAc (2×50 mL). The combined organic extracts were dried over sodium sulfate, filtered and concentrated in vacuo to obtain the crude. The crude was purified through silicagel column chromatography using 15% MeOH/CH$_2$Cl$_2$ to afford compound 380 (600 mg, 49%) as an off-white solid. TLC: 10% MeOH/CH$_2$Cl$_2$ (R$_f$: 0.2); LC-MS: 93.67%; 378.1 (M$^+$+1); (column; Ascentis Express C18, (50×3.0 mm, 2.7 μm); RT 1.84 min. 0.025% Aq. TFA+5% ACN: ACN+5% 0.025% Aq. TFA, 1.2 mL/min).

Synthesis of tert-butyl ((2-(4-(3-(methyl(2, 2, 2-trifluoroethyl) amino) propoxy) phenyl) thiazol-5-yl) methyl) carbamate (382)

To a stirring solution of tert-butyl ((2-(4-(3-(methylamino) propoxy) phenyl) thiazol-5-yl) methyl) carbamate 380 (400 mg, 1.06 mmol) in DMF (8 mL) under inert atmosphere were added triethylamine (0.44 mL, 3.18 mmol), 2, 2, 2-trifluoroethyl trifluoromethanesulfonate 381 (0.22 mL, 1.59 mmol) at RT and stirred for 4 h. The reaction was monitored by TLC; after completion of the reaction, the reaction mixture was diluted with water (100 mL) and extracted with EtOAc (2×80 mL). The combined organic extracts were dried over sodium sulfate, filtered and concentrated in vacuo to obtain the crude. The crude was purified through silicagel column chromatography using 5-10% MeOH/CH$_2$Cl$_2$ to afford compound 382 (200 mg, 41%) as pale yellow liquid. TLC: 10% MeOH/CH$_2$Cl$_2$ (R$_f$: 0.8). LC-MS: 88.52%; 181.9 (M$^+$+1); (column; Ascentis Express C18, (50×3.0 mm, 2.7 μm); RT 0.37 min. 0.025% Aq. TFA+5% ACN: ACN+5% 0.025% Aq. TFA, 1.2 mL/min).

Synthesis of 3-(4-(5-(aminomethyl) thiazol-2-yl) phenoxy)-N-methyl-N-(2, 2, 2-trifluoroethyl) propan-1-amine hydrochloride (383)

To a stirring solution of compound 382 (100 mg, 0.21 mmol) in CH$_2$Cl$_2$ (2 mL) under inert atmosphere was added 4 N HCl in 1, 4-dioxane (2 mL) at 0° C.; warmed to RT and stirred for 2 h. The reaction was monitored by TLC; after completion of the reaction, the volatiles were removed in vacuo to obtain the crude, which was triturated with diethyl ether (2×5 mL) and dried in vacuo to afford compound 383 (70 mg, HCl salt) as white solid. TLC: 30% EtOAc/hexanes (R$_f$: 0.2); LC-MS: 99.39%; 360.0 (M$^+$+1); (column; Ascentis Express C18, (50×3.0 mm, 2.7 μm); RT 1.57 min. 0.025% Aq. TFA+5% ACN: ACN+5% 0.025% Aq. TFA, 1.2 mL/min).

Synthesis of 3-(4-(5-(aminomethyl) thiazol-2-yl) phenoxy)-N, N-diethylpropan-1-amine hydrochloride (389)

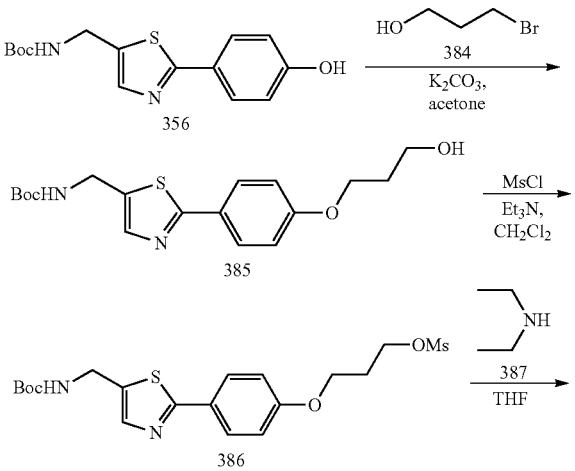

203

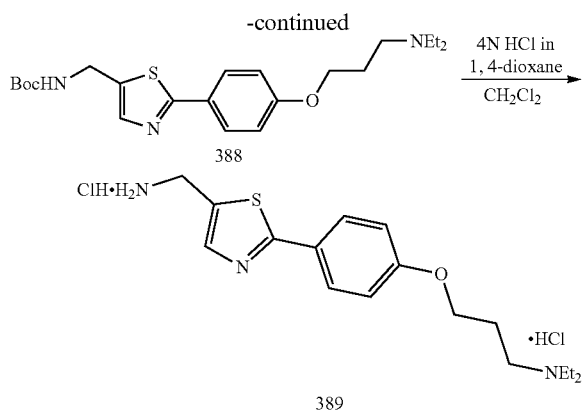

Synthesis of tert-butyl ((2-(4-(3-hydroxypropoxy) phenyl) thiazol-5-yl) methyl) carbamate (385)

To a stirring solution of tert-butyl ((2-(4-hydroxyphenyl) thiazol-5-yl) methyl) carbamate 356 (500 mg, 1.63 mmol) in acetone (10 mL) under inert atmosphere were added potassium carbonate (676 mg, 4.90 mmol), 3-bromopropan-1-ol 384 (0.22 mL, 2.45 mmol) and at RT; heated to 60° C. and stirred for 8 h. The reaction was monitored by TLC; after completion of the reaction, the reaction mixture was diluted with water (30 mL) and extracted with EtOAc (2×25 mL). The combined organic extracts were dried over sodium sulfate, filtered and concentrated in vacuo to obtain the crude. The crude was purified through silica gel flash column chromatography using 50% EtOAc/hexanes to afford compound 385 (400 mg, 67%) as an off-white solid. TLC: 60% EtOAc/hexanes ($R_f$: 0.2). $^1$H NMR (500 MHz, DMSO-$d_6$): δ 7.81 (d, J=8.7 Hz, 2H), 7.60 (s, 1H), 7.52 (t, J=5.5 Hz, 1H), 7.03 (d, J=9.3 Hz, 2H), 4.55 (t, J=5.2 Hz, 1H), 4.31 (d, J=5.8 Hz, 2H), 4.09 (t, J=6.4 Hz, 2H), 3.61-3.52 (m, 2H), 1.90-1.85 (m, 2H), 1.40 (s, 9H); LC-MS: 95.79%; 365.0 (M$^+$+1); (column; Ascentis Express C18, (50×3.0 mm, 2.7 μm); RT 2.24 min. 0.025% Aq. TFA+5% ACN: ACN+5% 0.025% Aq. TFA, 1.2 mL/min).

Synthesis of 3-(4-(5-(((tert-butoxycarbonyl) amino) methyl) thiazol-2-yl) phenoxy) propyl methanesulfonate (386)

To a stirring solution of compound 385 (300 mg, 0.82 mmol) in CH$_2$Cl$_2$ (10 mL) under inert atmosphere were added triethylamine (0.23 mL, 1.64 mmol), methanesulfonyl chloride (0.07 mL, 0.98 mmol) at 0° C.; warmed to RT and stirred for 3 h. The reaction was monitored by TLC; after completion of the reaction, the reaction mixture was diluted with water (50 mL) and extracted with CH$_2$Cl$_2$ (2×50 mL). The combined organic extracts were dried over sodium sulfate, filtered and concentrated in vacuo to afford crude compound 386 (350 mg, 96%) as pale yellow liquid. TLC: 60% EtOAc/hexanes ($R_f$: 0.6); $^1$H NMR (400 MHz, DMSO-$d_6$): δ 7.82 (d, J=8.8 Hz, 2H), 7.61 (s, 1H), 7.55-7.46 (m, 1H), 7.06 (d, J=8.9 Hz, 2H), 4.37 (t, J=6.3 Hz, 2H), 4.31 (d, J=6.0 Hz, 2H), 4.14 (t, J=6.2 Hz, 2H), 3.18 (s, 3H), 2.16 (t, J=6.2 Hz, 2H), 1.40 (s, 9H); LC-MS: 97.12%; 443.0 (M$^+$+1); (column; Ascentis Express C-18, (50×3.0 mm, 2.7 μm); RT 2.50 min. 0.025% Aq. TFA+5% ACN: ACN+5% 0.025% Aq. TFA, 1.2 mL/min).

204

Synthesis of tert-butyl ((2-(4-(3-(diethylamino) propoxy) phenyl) thiazol-5-yl) methyl) carbamate (388)

To a stirring solution of compound 386 (350 mg, 0.79 mmol) in THF (5 mL) in a sealed tube under inert atmosphere was added diethylamine 387 (0.41 mL, 3.96 mmol) at RT; heated to 70° C. and stirred for 24 h. The reaction was monitored by TLC; after completion of the reaction, the volatiles were removed in vacuo. The residue was diluted with water (50 mL) and extracted with EtOAc (2×75 mL). The combined organic extracts were dried over sodium sulfate, filtered and concentrated in vacuo to obtain the crude. The crude was purified through silica gel column chromatography using 5-10% MeOH/CH$_2$Cl$_2$ to afford compound 388 (220 mg, 66%) as pale yellow liquid. TLC: 10% MeOH/CH$_2$Cl$_2$ ($R_f$: 0.2); $^1$H NMR (400 MHz, CD$_3$OD): δ 7.82 (d, J=8.9 Hz, 2H), 7.59 (s, 1H), 7.02 (d, J=8.9 Hz, 2H), 4.41 (s, 2H), 4.11 (t, J=6.0 Hz, 2H), 2.88-2.85 (m, 2H), 2.78 (q, J=7.3 Hz, 4H), 2.10-1.97 (m, 2H), 1.46 (s, 9H), 1.15 (t, J=7.2 Hz, 6H); LC-MS: 96.43%; 420.1 (M$^+$+1); (column; Ascentis Express C18, (50×3.0 mm, 2.7 μm); RT 1.94 min. 0.025% Aq. TFA+5% ACN: ACN+5% 0.025% Aq. TFA, 1.2 mL/min).

Synthesis of 3-(4-(5-(aminomethyl) thiazol-2-yl) phenoxy)-N, N-diethylpropan-1-amine dihydrochloride (389)

To a stirring solution of compound 388 (300 mg, 0.71 mmol) in CH$_2$Cl$_2$ (5 mL) under inert atmosphere was added 4 N HCl in 1, 4-dioxane (5 mL) at 0° C.; warmed to RT and stirred for 2 h. The reaction was monitored by TLC; after completion of the reaction, the volatiles were removed in vacuo to obtain the crude, which was triturated with diethyl ether (2×20 mL) and dried in vacuo to afford compound 389 (200 mg, 79%; HCl salt) as white solid. TLC: 10% MeOH/CH$_2$Cl$_2$ ($R_f$: 0.2); $^1$H NMR (400 MHz, DMSO-$d_6$) δ 10.53 (br s, 1H), 8.58 (br s, 3H), 7.91 (s, 1H), 7.87 (d, J=8.9 Hz, 2H), 7.08 (d, J=8.9 Hz, 2H), 4.32 (q, J=5.5 Hz, 2H), 4.16 (t, J=6.1 Hz, 2H), 3.22-3.04 (m, 6H), 2.20-2.10 (m, 2H), 1.24 (t, J=7.2 Hz, 6H); LC-MS: 98.14%; 320.1 (M$^+$+1); (column; Ascentis Express C18, (50×3.0 mm, 2.7 μm); RT 1.03 min. 0.025% Aq. TFA+5% ACN: ACN+5% 0.025% Aq. TFA, 1.2 mL/min).

Synthesis of 4-(4-(5-(aminomethyl) thiazol-2-yl) phenoxy)-N, N-dimethylbutan-1-amine hydrochloride (394)

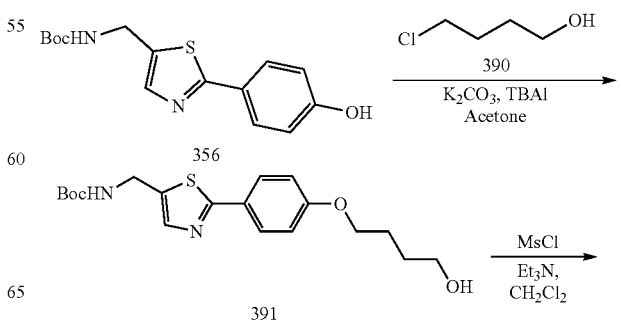

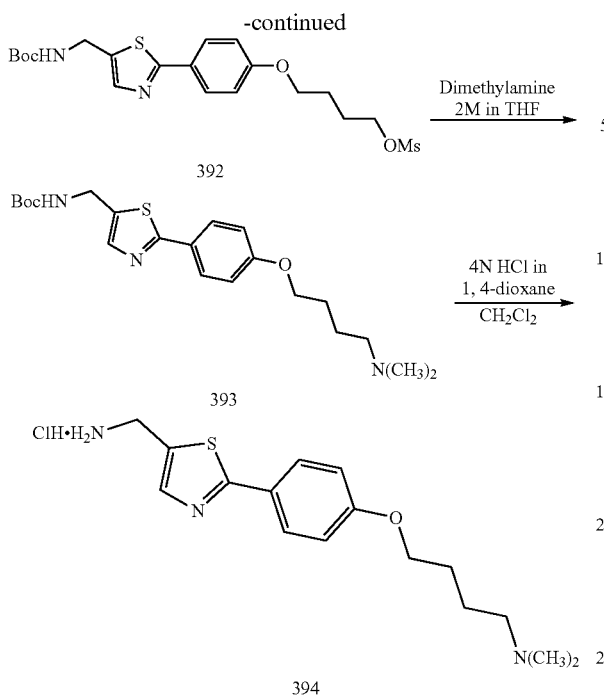

Synthesis of tert-butyl ((2-(4-(4-hydroxybutoxy) phenyl) thiazol-5-yl) methyl) carbamate (391)

To a stirring solution of tert-butyl ((2-(4-hydroxyphenyl) thiazol-5-yl) methyl) carbamate 356 (60 mg, 0.19 mmol) in acetone (5 mL) under inert atmosphere were added potassium carbonate (81 mg, 0.58 mmol), TBAI (7.2 mg, 0.019 mmol) and 4Chlorobutanol 390 (0.49 mL, 4.90 mmol) at RT; heated to reflux and stirred for 16 h. The reaction was monitored by TLC; after completion of the reaction, the reaction mixture was filtered through celite and washed with $CH_2Cl_2$ (40 mL). The filtrate was concentrated in vacuo to obtain the crude. The crude was purified through silicagel flash column chromatography using 50% EtOAc/hexanes; to afford compound 391 (40 mg, 54%) as brown syrup. TLC: 50% EtOAc/hexanes ($R_f$: 0.5); LC-MS: 99.31%; 379.1 ($M^+$+1); (column; Ascentis Express C18, (50×3.0 mm, 2.7 μm); RT 2.29 min. 0.025% Aq. TFA+5% ACN: ACN+5% 0.025% Aq. TFA, 1.2 mL/min).

Synthesis of 4-(4-(5-(((tert-butoxycarbonyl) amino) methyl) thiazol-2-yl) phenoxy) butyl methanesulfonate (392)

To a stirring solution of compound 391 (200 mg, 0.52 mmol) in $CH_2Cl_2$ (5 mL) under inert atmosphere were added triethylamine (106 mg, 1.05 mmol), methanesulfonyl chloride (90 mg, 0.79 mmol) at 0° C.; warmed to RT and stirred for 4 h. The reaction was monitored by TLC; after completion of the reaction, the reaction mixture was diluted with water (20 mL) and extracted with $CH_2Cl_2$ (2×20 mL). The combined organic extracts were washed with saturated sodium bicarbonate solution (30 mL) and water (30 mL); dried over sodium sulfate, filtered and concentrated in vacuo to afford crude compound 392 (220 mg, 91%) as brown syrup. TLC: 5% MeOH/$CH_2Cl_2$ ($R_f$: 0.3); LC-MS: 97.66%; 457.1 ($M^+$+1); (column; Ascentis Express C-18, (50×3.0 mm, 2.7 μm); RT 2.56 min. 0.025% Aq. TFA+5% ACN: ACN+5% 0.025% Aq. TFA, 1.2 mL/min);

Synthesis of tert-butyl ((2-(4-(4-(dimethylamino) butoxy) phenyl) thiazol-5-yl) methyl) carbamate (393)

To a stirring solution of compound 392 (220 mg, crude 0.48 mmol)) in THF (2 mL) in a sealed tube was added 2 M dimethylamine in THF (3 mL) at RT and heated to 60° C. for 6 h. The reaction was monitored by TLC; after completion the volatiles were removed in vacuo to obtain the crude. The crude was either purified through silica gel column chromatography using 5% MeOH/$CH_2Cl_2$ to afford 393 (180 mg, 84%) as brown syrup. TLC: 5% MeOH/$CH_2Cl_2$ ($R_f$: 0.3); $^1$H NMR (400 MHz, DMSO-$d_6$): δ 7.80 (d, J=8.9 Hz, 2H), 7.60 (s, 1H), 7.52 (t, J=5.2 Hz, 1H), 7.02 (d, J=8.9 Hz, 2H), 4.31 (d, J=5.8 Hz, 2H), 4.04 (t, J=6.5 Hz, 2H), 2.24 (t, J=7.2 Hz, 2H), 2.12 (s, 6H), 1.78-1.68 (m, 2H), 1.58-1.50 (m, 2H), 1.40 (s, 9H); LC-MS: 98.90%; 406.1 ($M^+$+1); (column; Ascentis Express C18, (50×3.0 mm, 2.7 μm); RT 1.92 min. 0.025% Aq. TFA+5% ACN: ACN+5% 0.025% Aq. TFA, 1.2 mL/min).

Synthesis of 4-(4-(5-(aminomethyl) thiazol-2-yl) phenoxy)-N, N-dimethylbutan-1-amine hydrochloride (394)

To a stirring solution of compound 393 (230 mg, 0.56 mmol) in $CH_2Cl_2$ (5 mL) was added 4 N HCl in 1, 4-dioxane (6 mL) under argon atmosphere at 0° C.; warmed to RT and stirred for 4 h. The reaction was monitored by TLC; after completion of the reaction, the volatiles were removed in vacuo. The crude washed with diethyl ether (5 mL) and dried in vacuo to afford 394 (135 mg; 70%) as an off white solid. TLC: 5% MeOH/$CH_2Cl_2$ ($R_f$: 0.1); $^1$H NMR (400 MHz, DMSO-$d_6$): δ 10.41 (br s, 1H), 8.54 (br s, 3H), 7.95-7.84 (m, 3H), 7.11-7.05 (m, 2H), 4.32 (q, J=5.5 Hz, 2H), 4.17-4.09 (m, 2H), 3.14-3.03 (m, 2H), 2.74 (s, 3H), 2.73 (s, 3H), 1.89-1.74 (m, 4H);

Synthesis of 3-(4-(5-(aminomethyl) thiazol-2-yl) phenoxy)-N, N-dimethylbutan-1-amine hydrochloride (402)

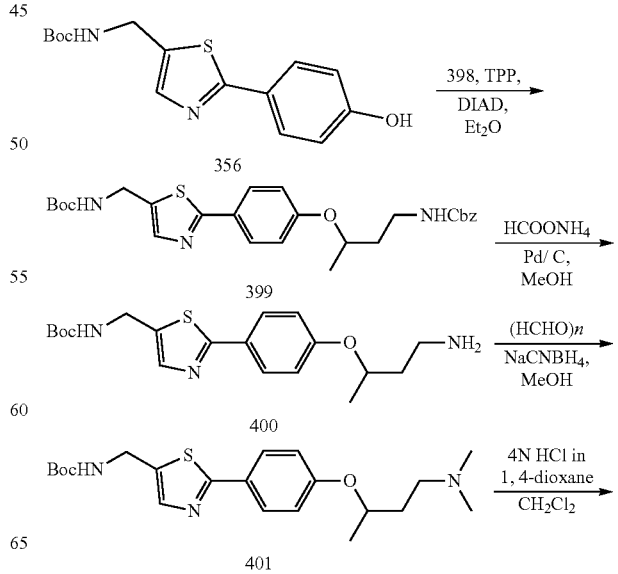

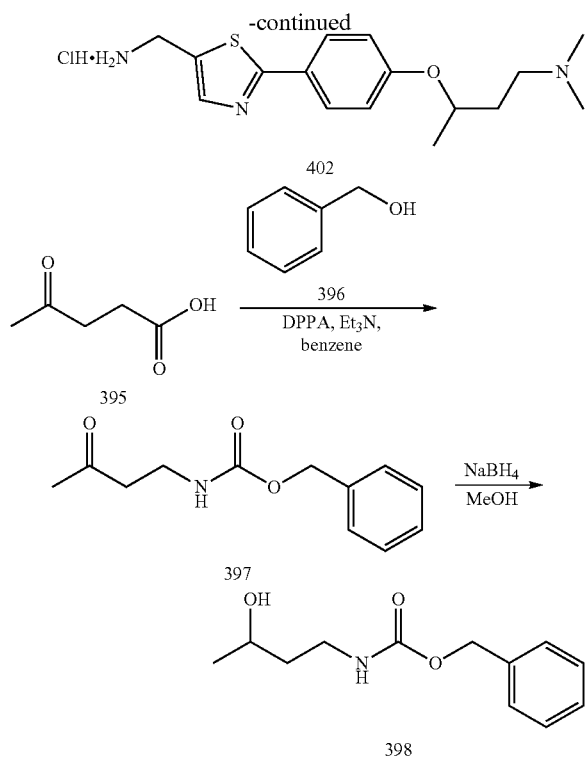

Synthesis of benzyl (3-oxobutyl) carbamate (397)

To a stirring solution of 4-oxopentanoic acid 395 (3.5 g, 30.15 mmol) in benzene (50 mL) were added diphenyl phosphonic azide (8.30 g, 30.17 mmol) and triethylamine (4.4 mL, 30.17 mmol) at RT; heated to 50° C. for 30 min. To this was added benzyl alcohol 396 (4.8 g, 45.26 mmol) and heated to reflux and stirred for 16 h. The reaction was monitored by TLC; after completion of the reaction, the volatiles were removed in vacuo to obtain the crude. The residue was diluted with EtOAc (100 mL), washed with 5% citric acid solution (50 mL), saturated sodium bicarbonate solution (50 mL), water (50 mL), brine (100 mL). The organic extract was dried over sodium sulfate, filtered and concentrated in vacuo to afford the crude. The crude was purified through silica gel column chromatography using 30% EtOAc/hexanes to afford compound 397 (3 g, 45%) as pale yellow solid. TLC: 5% MeOH/CH$_2$Cl$_2$ (R$_f$: 0.5); $^1$H-NMR (DMSO-d$_6$, 400 MHz): δ 7.40-7.27 (m, 5H), 7.20 (t, J=5.3 Hz, 1H), 5.00 (s, 2H), 3.23-3.17 (m, 2H), 2.60 (t, J=6.8 Hz, 2H), 2.08 (s, 3H); LC-MS: 80.94%; 222.0 (M$^+$+1); (column; Ascentis Express C18, (50×3.0 mm, 2.7 μm); RT 1.98 min. 0.025% Aq. TFA+5% ACN: ACN+5% 0.025% Aq. TFA, 1.2 mL/min);

Synthesis of benzyl (3-hydroxybutyl) carbamate (398)

To a stirring solution of benzyl (3-oxobutyl) carbamate 397 (2 g, 9.05) in MeOH (50 mL) under argon atmosphere was added sodium borohydride (687 mg, 18.09 mmol) at 0° C.; warmed to RT and stirred for 4 h. The reaction was monitored by TLC; after completion of the reaction, reaction mixture was diluted with water (50 mL) and extracted with CH$_2$Cl$_2$ (2×100 mL). The combined organic extracts were dried over sodium sulfate and concentrated in vacuo to crude compound 398 (1.8 g, 90%) as colorless liquid. TLC: 30% EtOAc/hexanes (R$_f$: 0.2); $^1$H NMR (DMSO-d$_6$, 400 MHz): δ 7.41-7.27 (m, 5H), 7.15 (t, J=4.9 Hz, 1H), 5.00 (s, 2H), 4.41 (d, J=4.6 Hz, 1H), 3.66-3.56 (m, 1H), 3.11-3.00 (m, 2H), 1.49-1.42 (m, 2H), 1.04 (d, J=5.8 Hz, 3H); LC-MS: 96.96%; 223.7 (M$^+$+1); (column; Ascentis Express C-18, (50×3.0 mm, 2.7 μm); RT 1.99 min. 0.025% Aq. TFA+5% ACN: ACN+5% 0.025% Aq. TFA, 1.2 mL/min);

Synthesis of tert-butyl ((2-(4-((4-(((benzyloxy) carbonyl) amino) butan-2-yl) oxy) phenyl) thiazol-5-yl) methyl) carbamate (399)

To a stirring solution of tert-butyl ((2-(4-hydroxyphenyl) thiazol-5-yl) methyl) carbamate 398 (2 g, 8.97 mmol) in diethyl ether (50 mL) under argon atmosphere were added triphenylphosphine (7.1 g, 26.91 mmol), DIAD (5.4 g, 26.91 mmol) and benzyl (3-hydroxybutyl) carbamate 356 (2.74 g, 8.97 mmol) at RT and stirred for 16 h. The reaction was monitored by TLC; after completion of the reaction, the volatiles were removed in vacuo to obtain the crude. The crude was purified through silica gel column chromatography using 20-50% EtOAc/hexanes to afford compound 399 (1.2 g, crude) as brown color sticky solid. TLC: 50% EtOAc/hexanes (R$_f$: 0.4); LC-MS: 67.64%; 512.1 (M$^+$+1); (column; Ascentis Express C-18 (50×3.0 mm, 2.7 μm); RT 2.87 min. 0.025% Aq.TFA+5% ACN: ACN+5% 0.025% Aq TFA, 1.2 mL/min).

Synthesis of tert-butyl ((2-(4-((4-aminobutan-2-yl) oxy) phenyl) thiazol-5-yl) methyl) carbamate (400)

To a stirring solution of tert-butyl ((2-(4-((4-(((benzyloxy) carbonyl) amino) butan-2-yl) oxy) phenyl) thiazol-5-yl) methyl) carbamate 399 (600 mg, 1.17 mmol) in MeOH (50 mL) under inert atmosphere was added 10% Pd/C (50% wet, 600 mg), ammonium formate (2.95 g, 46.96 mmol) at RT; heated to reflux and stirred for 24 h. The reaction was monitored by TLC; after completion of the reaction, the reaction mixture was filtered through celite washed with 20% MeOH/CH$_2$Cl$_2$ (20 mL). The filtrate was concentrated in vacuo to obtain the crude. The crude was diluted with EtOAc (100 mL), washed with water (50 mL). The aqueous layer was extracted with EtOAc (2×50 mL). The combined organic extracts were dried over sodium sulfate and concentrated in vacuo to obtain the crude. The crude was purified through silica gel (100-200 mesh) column chromatography using 10% MeOH/CH$_2$Cl$_2$ to afford compound 400 (120 mg, 30%) as an colorless liquid. TLC: 15% MeOH/CH$_2$Cl$_2$ (R$_f$: 0.2); $^1$H NMR (DMSO-d$_6$, 400 MHz): δ 7.79 (d, J=8.9 Hz, 2H), 7.53 (t, J=5.3 Hz, 1H), 7.02 (d, J=8.9 Hz, 2H), 4.70-4.60 (m, 1H), 4.31 (d, J=5.8 Hz, 2H), 2.76-2.64 (m, 2H), 1.87-1.75 (m, 1H), 1.72-1.61 (m, 1H), 1.40 (s, 9H), 1.26 (d, J=6.1 Hz, 3H); LC-MS: 96.47%; 378.0 (M$^+$+1); (column; Ascentis Express C-18 (50×3.0 mm, 2.7 μm); RT 1.90 min. 0.025% Aq. TFA+5% ACN: ACN+5% 0.025% Aq TFA, 1.2 mL/min).

Synthesis of tert-butyl ((2-(4-((4-(dimethylamino) butan-2-yl) oxy) phenyl) thiazol-5-yl) methyl) carbamate (401)

To a stirring solution of tert-butyl ((2-(4-((4-aminobutan-2-yl) oxy) phenyl) thiazol-5-yl) methyl) carbamate 400 (180 mg, 0.47 mmol) in MeOH (25 mL) under inert atmosphere were added paraformaldehyde (143 mg, 4.77 mmol) and sodium cyanoborohydride (150 mg, 2.39 mmol) portion wise for 5 min at 0° C.; warmed to RT and stirred for 16 h. The reaction was monitored by TLC; after completion of the reaction, the reaction mixture was diluted with EtOAc (100 mL) and washed with water (50 mL), washed with saturated sodium bicarbonate solution (50 mL). The organic extract was dried over sodium sulfate, filtered and concentrated in vacuo to obtain the crude. The crude was purified through silica gel column chromatography using 10% MeOH/CH$_2$Cl$_2$ (5% aqueous ammonia) to afford compound 401 (90 mg, crude) as yellow solid. TLC: 10% MeOH/CH$_2$Cl$_2$ (R$_f$: 0.3); LC-MS: 54.78%; 406.1 (M$^+$+1); (column; Ascentis Express C-18 (50×3.0 mm, 2.7 μm); RT 1.92 min. 0.025% Aq. TFA+5% ACN: ACN+5% 0.025% Aq TFA, 1.2 mL/min).

Synthesis of 3-(4-(5-(aminomethyl) thiazol-2-yl) phenoxy)-N, N-dimethylbutan-1-amine hydrochloride (402)

To a stirring solution of tert-butyl ((2-(4-((4-(dimethylamino) butan-2-yl) oxy) phenyl) thiazol-5-yl) methyl) carbamate 401 (90 mg, 0.22 mmol) in CH$_2$Cl$_2$ (5 mL) was added 4 N HCl in 1, 4-dioxane (0.5 mL) under inert atmosphere at 0° C.; warmed to RT and stirred for 4 h. The reaction was monitored by TLC; after completion of the reaction, the volatiles were removed in vacuo to afford crude compound 402 (70 mg; HCl salt) as yellow sticky solid. TLC: 50% EtOAc/hexanes (R$_f$: 0.1); LC-MS: 79.21%; 306.0 (M$^+$+1); (column; Ascentis Express C18, (50×3.0 mm, 2.7 μm); RT 1.03 min. 0.025% Aq. TFA+5% ACN: ACN+5% 0.025% Aq. TFA, 1.2 mL/min).

Synthesis of 3-(4-(5-(aminomethyl) thiazol-2-yl) phenoxy)-N-(2, 2, 2-trifluoroethyl) propan-1-amine hydrochloride (406)

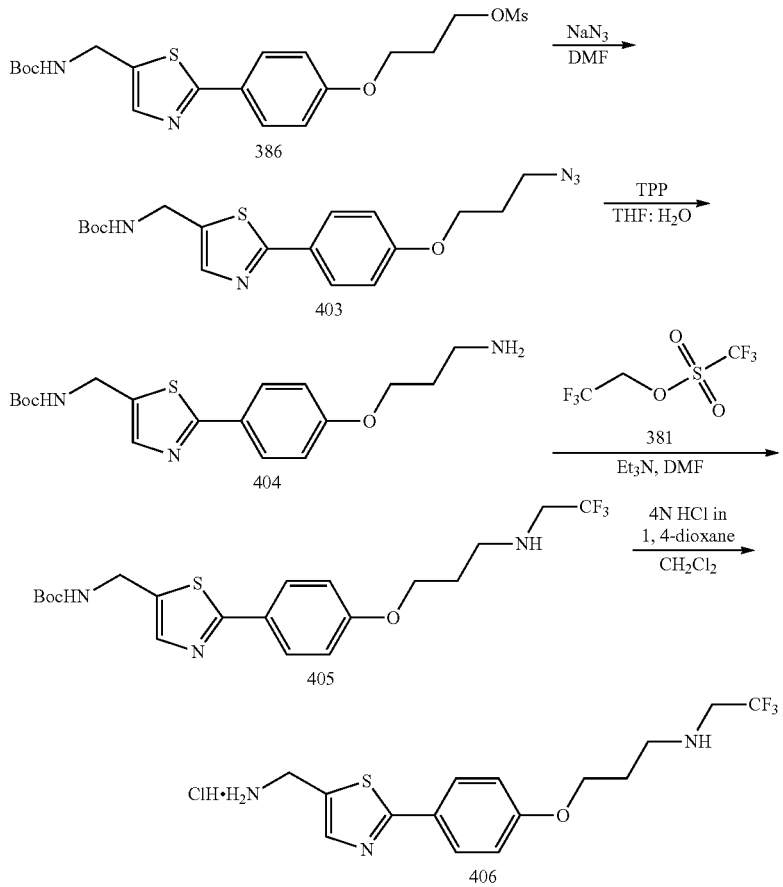

Synthesis of tert-butyl ((2-(4-(3-azidopropoxy) phenyl) thiazol-5-yl) methyl) carbamate (403)

To a stirring solution of 4 3-(4-(5-(((tert-butoxycarbonyl) amino) methyl) thiazol-2-yl) phenoxy) propyl methanesulfonate 386 (1 g, 2.26 mmol) in DMF (10 mL) under inert atmosphere was added sodium azide (441 mg, 6.70 mmol) at 0° C.; warmed to RT and stirred for 16 h. The reaction was monitored by TLC; after completion of the reaction, the reaction mixture was diluted water (50 mL) and extracted with EtOAc (2×75 mL). The combined organic extracts were dried over sodium sulfate, filtered and concentrated in vacuo to obtain the crude which was triturated with diethylether (10 mL) and dried in vacuo to afford compound 403 (900 mg, 68%) as sticky solid. TLC: 3% MeOH/CH$_2$Cl$_2$ (R$_f$: 0.8); 41 NMR (DMSO-d$_6$, 500 MHz): δ 7.82 (d, J=8.7 Hz, 2H), 7.61 (s, 1H), 7.53 (t, J=5.5 Hz, 1H), 7.05 (d, J=9.3 Hz, 2H), 4.31 (d, J=5.8 Hz, 2H), 4.10 (t, J=6.1 Hz, 2H), 3.52 (t, J=6.7 Hz, 2H), 2.03-1.97 (m, 2H), 1.40 (s, 9H); LC-MS: 96.94%; 390.0 (M$^+$+1); (column; Ascentis Express C18, (50×3.0 mm, 2.7 µm); RT 2.82 min. 0.025% Aq. TFA+5% ACN: ACN+5% 0.025% Aq. TFA, 1.2 mL/min).

Synthesis of tert-butyl ((2-(4-(3-aminopropoxy) phenyl) thiazol-5-yl) methyl) carbamate (404)

To a stirring solution of compound 403 (900 mg, crude) in THF:H$_2$O (4:1, 12.5 mL) was added triphenyl phosphine (606 mg, 2.31 mmol) at RT and stirred for 16 h. The reaction was monitored by TLC; after completion of the reaction, the volatiles were removed in vacuo to obtain the crude. The crude was purified through silica gel column chromatography using 10% MeOH/CH$_2$Cl$_2$ (10 mL aqueous ammonia) to afford compound 404 (530 mg, 63%) as an off-white solid. TLC: 10% MeOH/CH$_2$Cl$_2$ (R$_f$: 0.2); $^1$H-NMR (DMSO-d$_6$, 500 MHz): δ 8.42 (s, 1H), 7.82 (d, J=8.7 Hz, 2H), 7.61 (s, 1H), 7.54 (t, J=5.5 Hz, 2H), 7.04 (d, J=8.7 Hz, 2H), 4.31 (d, J=5.8 Hz, 2H), 4.11 (t, J=6.4 Hz, 2H), 2.88 (t, J=7.2 Hz, 2H), 1.97 (p, J=6.7 Hz, 2H), 1.40 (s, 9H); LC-MS: 99.67%; 364.0 (M$^+$+1); (column; Ascentis Express C18, (50×3.0 mm, 2.7 µm); RT 1.84 min. 0.025% Aq. TFA+5% ACN: ACN+5% 0.025% Aq. TFA, 1.2 mL/min).

Synthesis of tert-butyl ((2-(4-(3-((2, 2, 2-trifluoroethyl) amino) propoxy) phenyl) thiazol-5-yl) methyl) carbamate (405)

To a stirring solution of compound 404 (400 mg, 1.10 mmol) in DMF (5 mL) under inert atmosphere were added triethylamine (0.46 mL, 3.30 mmol), 2, 2, 2-trifluoroethyl trifluoromethanesulfonate (0.47 mL, 3.30 mmol) at RT and stirred for 4 h. The reaction was monitored by TLC; after completion of the reaction, the reaction mixture was diluted with water (100 mL) and extracted with EtOAc (2×80 mL). The combined organic extracts were dried over sodium sulfate, filtered and concentrated in vacuo to obtain the crude. The crude was purified through silica gel column chromatography using 2% MeOH/CH$_2$Cl$_2$ to afford compound 405 (300 mg, 61%) as an off-white solid. TLC: 10% MeOH/CH$_2$Cl$_2$ (R$_f$: 0.7). LC-MS: 98.65%; 446.1 (M$^+$+1); (column; Ascentis Express C18, (50×3.0 mm, 2.7 µm); RT 1.98 min. 0.025% Aq. TFA+5% ACN: ACN+5% 0.025% Aq. TFA, 1.2 mL/min).

Synthesis of 3-(4-(5-(aminomethyl) thiazol-2-yl) phenoxy)-N-(2, 2, 2-trifluoroethyl) propan-1-amine hydrochloride (406)

To a stirring solution of compound 405 (300 mg, 0.67 mmol) in CH$_2$Cl$_2$ (5 mL) under inert atmosphere was added 4 N HCl in 1, 4-dioxane (3 mL) at 0° C.; warmed to RT and stirred for 2 h. The reaction was monitored by TLC; after completion of the reaction, the volatiles were removed in vacuo to obtain the crude, which was triturated with diethyl ether (2×10 mL) and dried in vacuo to afford compound 406 (230 mg, 89%; HCl salt) as brown solid. TLC: 10% MeOH/ CH$_2$Cl$_2$ (R$_f$: 0.2); $^1$H NMR (400 MHz, DMSO-d$_6$): δ 10.15 (br, 2H), 8.56 (br s, 3H), 7.94-7.81 (m, 3H), 7.07 (d, J=8.9 Hz, 2H), 4.92 (s, 2H), 4.32 (q, J=5.4 Hz, 2H), 4.21-4.08 (m, 2H), 3.21 (t, J=7.5 Hz, 2H), 2.27-2.18 (m, 2H); LC-MS: 98.51%; 346.0 (M$^+$+1); (column; Kinetex EVO C-18 (50× 3.0 mm, 2.6 um); RT 1.97 min. 2.5 mM Aq. NH$_4$OOCH: 5% ACN; 0.8 mL/min).

Synthesis of N-(3-(4-(5-(aminomethyl) thiazol-2-yl) phenoxy) propyl) acetamide hydrochloride (408)

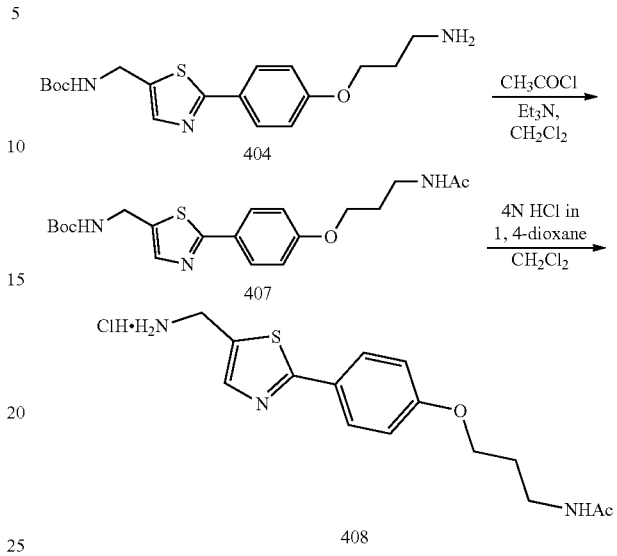

Synthesis of tert-butyl ((2-(4-(3-acetamidopropoxy) phenyl) thiazol-5-yl) methyl) carbamate (407)

To a stirring solution of tert-butyl ((2-(4-(3-aminopropoxy) phenyl) thiazol-5-yl) methyl) carbamate 404 (250 mg, 0.68 mmol) in CH$_2$Cl$_2$ (20 mL) under inert atmosphere were added triethylamine (0.25 mL, 1.70 mmol), acetylchloride (0.053 mL, 0.75 mmol) at 0° C.; warmed to RT and stirred for 3 h. The reaction was monitored by TLC; after completion of the reaction, the reaction mixture was diluted with CH$_2$Cl$_2$ (100 mL), washed with water (75 mL). The organic extract was dried over sodium sulfate, filtered and concentrated in vacuo to afford crude which was triturated with 10% EtOAc/hexanes (10 mL), diethylether (5 mL) and dried in vacuo to afford compound 407 (220 mg, 79%) as colorless liquid. TLC: 10% MeOH/CH$_2$Cl$_2$ (R$_f$: 0.6); $^1$H-NMR (DMSO-d$_6$, 500 MHz): δ 8.11-8.02 (m, 0.6H), 7.90 (t, J=4.6 Hz, 0.4H), 7.81 (d, J=8.7 Hz, 2H), 7.61 (s, 1H), 7.53 (t, J=5.5 Hz, 1H), 7.03 (dd, J=9.0, 2.6 Hz, 2H), 4.31 (d, J=5.8 Hz, 2H), 4.08-4.00 (m, 2H), 3.28-3.16 (m, 2H), 1.91-1.82 (m, 3.5H), 1.80 (s, 1.5H), 1.40 (s, 9H); LC-MS: 98.81%; 406.1 (M$^+$+1); (column; Ascentis Express C-18, (50×3.0 mm, 2.7 µm); RT 2.18 min. 0.025% Aq. TFA+5% ACN: ACN+5% 0.025% Aq. TFA, 1.2 mL/min);

Synthesis of N-(3-(4-(5-(aminomethyl) thiazol-2-yl) phenoxy) propyl) acetamide hydrochloride (408)

To a stirring solution of compound 407 (210 mg, 0.48 mmol) in CH$_2$Cl$_2$ (5 mL) under inert atmosphere was added 4 N HCl in 1, 4-dioxane (3 mL) at 0° C.; warmed to RT and stirred for 4 h. The reaction was monitored by TLC; after completion of the reaction, the volatiles were removed in vacuo to obtain the crude, which was triturated with diethyl ether (2×50 mL), n-hexane (25 mL) and dried in vacuo to afford compound 408 (160 mg, 91%; HCl salt) as an off-white solid. TLC: 10% MeOH/CH$_2$Cl$_2$ (R$_f$: 0.2); $^1$H-NMR (DMSO-d$_6$, 500 MHz): δ 8.52 (br s, 3H), 7.90 (s, 1H), 7.86 (d, J=8.7 Hz, 2H), 7.06 (dd, J=8.7, 2.9 Hz, 2H), 4.32 (q, J=5.8 Hz, 2H), 4.06 (q, J=5.8 Hz, 2H), 3.29-3.14 (m, 2H), 1.92-1.83 (m, 2H), 1.80 (s, 3H);

Synthesis of 2, 2'-((3-(4-(5-(aminomethyl) thiazol-2-yl) phenoxy) propyl) azanediyl) bis (ethan-1-ol) hydrochloride (411)

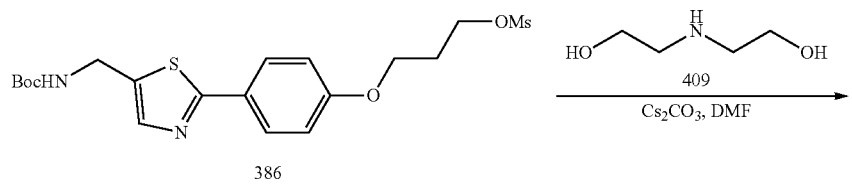

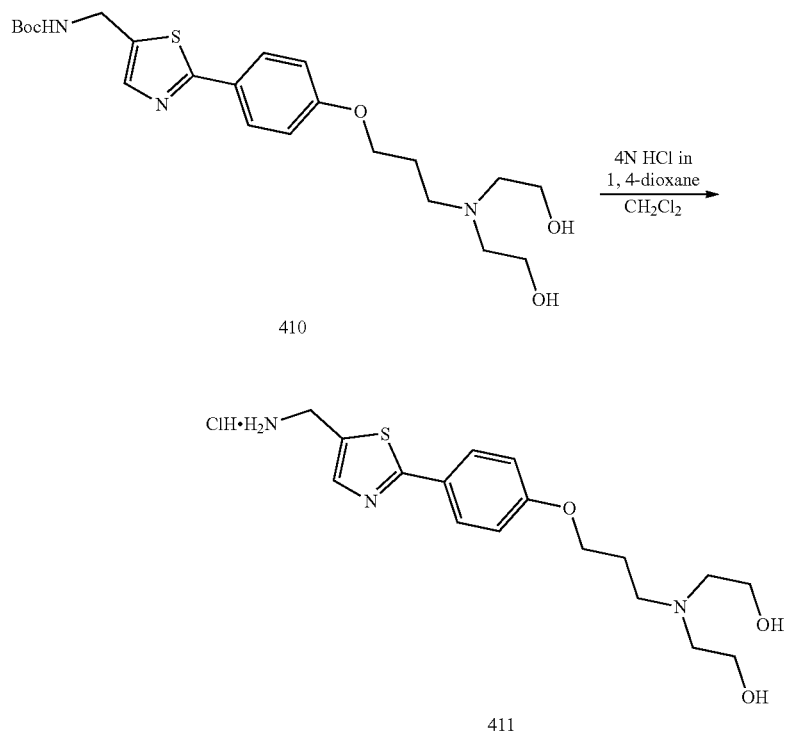

Hz, 2H), 3.55 (q, J=5.8 Hz, 2H), 1.89-1.84 (m, 2H), 1.39 (s, 9H); LC-MS: 89.41%; 452.1 (M$^+$+1); (column; Ascentis Express C18, (50×3.0 mm, 2.7 µm); RT 1.80 min. 0.025% Aq. TFA+5% ACN: ACN+5% 0.025% Aq. TFA, 1.2 mL/min).

Synthesis of tert-butyl ((2-(4-(3-(bis(2-hydroxyethyl) amino) propoxy) phenyl) thiazol-5-yl) methyl) carbamate (410)

To a stirring solution of compound 386 (1.7 g, 3.84 mmol) in DMF (30 mL) under inert atmosphere were added 2,2'-azanediylbis(ethan-1-ol) 409 (807 mg, 7.69 mmol) and potassium carbonate (1.6 g, 11.52 mmol) at RT; heated to 100° C. and stirred for 24 h. The reaction was monitored by TLC; after completion of the reaction, the reaction mixture was diluted with 10% MeOH/CH$_2$Cl$_2$ and washed with water. The organic extract was dried over sodium sulfate, filtered and concentrated in vacuo to obtain the crude. The crude was purified through silica gel column chromatography using 10% MeOH/CH$_2$Cl$_2$ to afford compound 410 (400 mg, 23%) as sticky solid. TLC:MeOH/CH$_2$Cl$_2$ (R$_f$: 0.3); $^1$H NMR (500 MHz, DMSO-d$_6$): δ 7.80 (d, J=8.7 Hz, 2H), 7.59 (s, 1H), 7.52 (br t, J=5.5 Hz, 1H), 7.02 (d, J=8.7 Hz, 2H), 4.54 (t, J=4.9 Hz, 1H), 4.30 (d, J=5.8 Hz, 2H), 4.08 (t, J=6.4

Synthesis of 2, 2'-((3-(4-(5-(aminomethyl) thiazol-2-yl) phenoxy) propyl) azanediyl) bis (ethan-1-ol) hydrochloride (411)

To a stirring solution of compound 410 (400 mg, 0.88 mmol) in CH$_2$Cl$_2$ (10 mL) was added 4 N HCl in 1, 4-dioxane (2 mL) under argon atmosphere at 0° C.; warmed to RT and stirred for 3 h. The reaction was monitored by TLC; after completion of the reaction, the volatiles were removed in vacuo. The crude was triturated with isopropanol (3 mL), EtOAc (7 mL) and dried in vacuo to afford compound 411 (350 mg crude, HCl salt) as an off white solid. TLC: 10% MeOH/CH$_2$Cl$_2$ (R$_f$: 0.1); $^1$H NMR (400 MHz, DMSO-d$_6$): δ 11.53 (s, 1H), 9.49 (t, J=5.7 Hz, 1H), 8.92-8.83 (m, 1H), 8.75-8.63 (m, 1H), 8.06 (d, J=8.2 Hz, 1H), 8.01-7.96 (m, 2H), 7.92-7.80 (m, 6H), 7.73 (s, 1H), 7.03 (d, J=8.9 Hz, 2H), 4.66 (d, J=5.5 Hz, 2H), 4.04-3.89 (m, 2H), 3.38-3.32 (m, 1H), 3.28-3.20 (m, 1H), 2.85-2.71 (m, 2H), 2.28-2.18 (m, 1H), 1.89-1.79 (m, 2H), 1.73-1.63 (m, 1H), 1.41-1.28 (m, 1H);

Synthesis of 3-(4-(5-(aminomethyl) thiazol-2-yl) phenoxy)-N-isopropyl-N-methylpropan-1-amine hydrochloride (414)

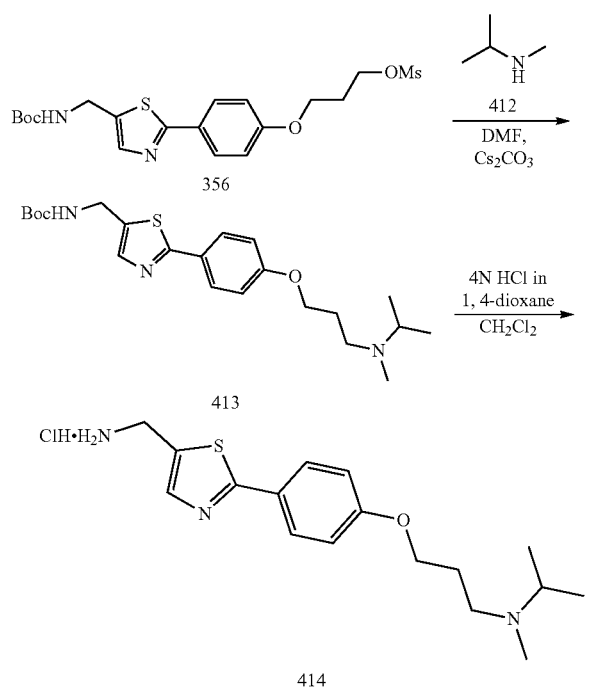

Synthesis of tert-butyl ((2-(4-(3-(isopropyl (methyl) amino) propoxy) phenyl) thiazol-5-yl) methyl) carbamate (413)

To a stirring solution of 3-(4-(5-(((tert-butoxy carbonyl) amino) methyl) thiazol-2-yl) phenoxy) propyl methanesulfonate 356 (1.3 g, 2.94 mmol) in DMF (20 mL) under inert atmosphere were added potassium carbonate (1.22 g, 8.82 mmol), N-methylpropan-2-amine 412 (430 mg, 5.89 mmol) at RT and stirred for 48 h. The reaction was monitored by TLC; after completion of the reaction, the reaction mixture was diluted with EtOAc (2×75 mL), washed with water (50 mL). The organic extract was dried over sodium sulfate, filtered and concentrated in vacuo to obtain the crude. The crude was purified through silica gel flash column chromatography using 6% EtOAc/hexanes to afford compound 413 (300 mg, 32%) as an off-white solid. TLC: 5% MeOH/CH2Cl2 ($R_f$: 0.4). LC-MS: 96.38%; 420.1 ($M^+$+1); (column; Ascentis Express C18, (50×3.0 mm, 2.7 nm); RT 1.92 min. 0.025% Aq. TFA+5% ACN: ACN+5% 0.025% Aq. TFA, 1.2 mL/min).

Synthesis of 3-(4-(5-(aminomethyl) thiazol-2-yl) phenoxy)-N-isopropyl-N-methylpropan-1-amine hydrochloride (414)

To a stirring solution of compound 413 (300 mg, 0.71 mmol) in CH2Cl2 (10 mL) under inert atmosphere was added 4 N HCl in 1, 4-dioxane (1 mL) at 0° C.; warmed to RT and stirred for 3 h. The reaction was monitored by TLC; after completion of the reaction, the volatiles were removed in vacuo to obtain the crude, which was triturated with diethyl ether (2×10 mL) and dried in vacuo to afford compound 414 (260 mg, HCl salt) as an off-white solid. TLC: 5% MeOH/CH$_2$Cl$_2$ ($R_f$: 0.2); $^1$H-NMR (DMSO-$d_6$, 400 MHz): 10.41 (br s, 1H), 8.54 (br s, 3H), 7.92-7.85 (m, 3H), 7.08 (d, J=8.7 Hz, 2H), 4.32 (q, J=5.8 Hz, 2H), 4.15 (t, J=6.1 Hz, 2H), 3.58-3.54 (m, 2H), 3.29-3.21 (m, 1H), 3.14-3.05 (m, 1H), 2.29-2.14 (m, 2H), 1.28 (d, J=7.0 Hz, 3H), 1.23 (d, J=6.4 Hz, 3H); Mass: 320.1 ($M^+$+1);

Synthesis of N-(3-(4-(5-(aminomethyl) thiazol-2-yl) phenoxy) propyl)-N-methylcyclopropanamine hydrochloride (417)

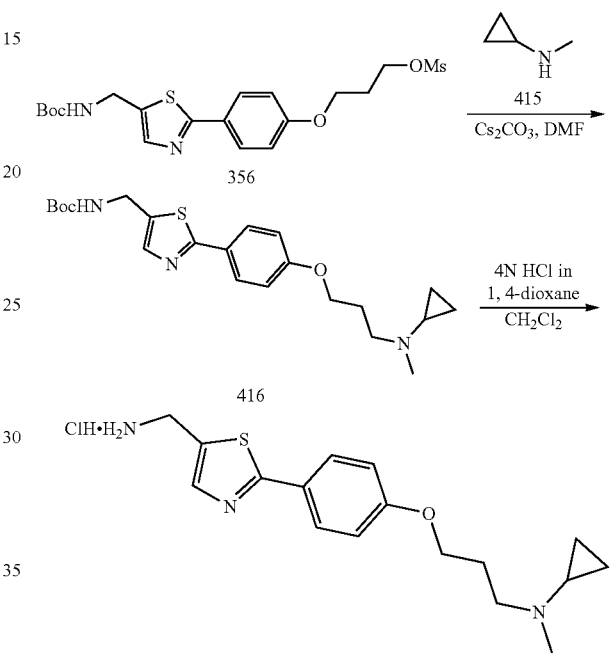

Synthesis of tert-butyl ((2-(4-(3-(cyclopropyl (methyl) amino) propoxy) phenyl) thiazol-5-yl) methyl) carbamate (416)

To a stirring solution of 3-(4-(5-(((tert-butoxy carbonyl) amino) methyl) thiazol-2-yl) phenoxy) propyl methanesulfonate 356 (1.0 g, 2.26 mmol) in DMF (10 mL) under inert atmosphere were added potassium carbonate (935 mg, 13.57 mmol), N-methylcyclopropanamine 415 (963 mg, 13.57 mmol) at 0° C.; heated to 70° C. and stirred for 24 h. The reaction was monitored by TLC; after completion of the reaction, the reaction mixture was diluted with EtOAc (2×75 mL), washed with water (50 mL). The organic extract was dried over sodium sulfate, filtered and concentrated in vacuo to obtain the crude. The crude was purified through silica gel flash column chromatography using 5% MeOH/CH$_2$Cl$_2$ to afford compound 416 (180 mg, 19%) as sticky solid. TLC: 5% MeOH/CH$_2$Cl$_2$ ($R_f$: 0.4). LC-MS: 96.38%; 418.1 ($M^+$+1); (column; Ascentis Express C18, (50×3.0 mm, 2.7 μm); RT 1.94 min. 0.025% Aq. TFA+5% ACN: ACN+5% 0.025% Aq. TFA, 1.2 mL/min). $^1$H-NMR (DMSO-$d_6$, 400 MHz): δ 7.80 (d, J=8.7 Hz, 2H), 7.60 (s, 1H), 7.53 (d, J=5.8 Hz, 1H), 7.02 (d, J=8.7 Hz, 2H), 4.31 (d, J=5.8 Hz, 2H), 4.02 (t, J=6.4 Hz, 2H), 2.62 (t, J=7.0 Hz, 2H), 2.26 (s, 3H), 1.88 (p, J=6.8 Hz, 2H), 1.65-1.60 (m, 1H), 1.40 (s, 9H), 0.45-0.38 (m, 2H), 0.29-0.24 (m, 2H);

Synthesis of N-(3-(4-(5-(aminomethyl) thiazol-2-yl) phenoxy) propyl)-N-methylcyclopropanamine hydrochloride (417)

To a stirring solution of compound 416 (180 mg, 0.43 mmol) in CH$_2$Cl$_2$ (5 mL) under inert atmosphere was added 4 N HCl in 1, 4-dioxane (0.5 mL) at 0° C.; warmed to RT and stirred for 3 h. The reaction was monitored by TLC; after completion of the reaction, the volatiles were removed in vacuo to obtain the crude, which was triturated with diethyl ether (2×10 mL) and dried in vacuo to afford compound 417 (160 mg, HCl salt) as sticky solid. TLC: 5% MeOH/CH$_2$Cl$_2$ (R$_f$: 0.1); $^1$H-NMR (DMSO-d$_6$, 500 MHz): 11.00 (br s, 1H), 8.65 (br s, 3H), 7.91 (s, 1H), 7.87 (d, J=8.7 Hz, 2H), 7.08 (d, J=8.7 Hz, 2H), 4.31 (q, J=5.8 Hz, 2H), 4.16 (t, J=6.1 Hz, 2H), 3.40-3.26 (m, 2H), 2.90-2.84 (m, 1H), 2.82 (d, J=4.6 Hz, 3H), 2.35-2.19 (m, 2H), 1.25-1.04 (m, 2H), 0.94-0.73 (m, 2H); LC-MS (Agilent Ion Trap): 90.32%; 318.3 (M$^+$+1); (column; Kinetex EVO C-18 (50×3.0 mm, 2.6 um); RT 2.72 min. 2.5 mM Aq. NH$_4$OAc:ACN; 0.8 mL/min).

Synthesis of tert-butyl ((2-(4-((4-(diethylamino) butan-2-yl) oxy) phenyl) thiazol-5-yl) methyl) carbamate (419)

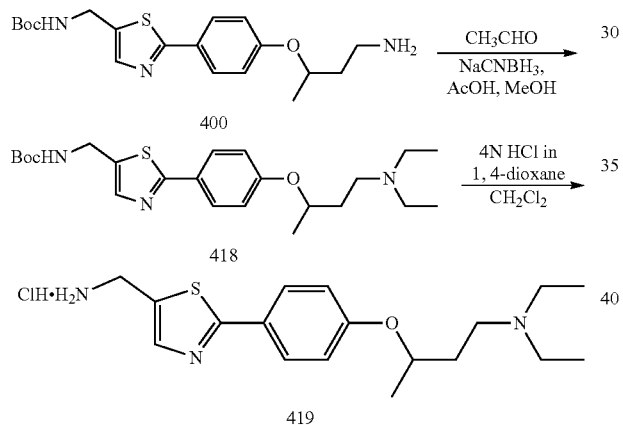

Synthesis of tert-butyl ((2-(4-((4-(diethylamino) butan-2-yl) oxy) phenyl) thiazol-5-yl) methyl) carbamate (418)

To a stirring solution of tert-butyl ((2-(4-((4-aminobutan-2-yl) oxy) phenyl) thiazol-5-yl) methyl) carbamate 400 (200 mg, 0.53 mmol) in MeOH (20 mL) under inert atmosphere were added acetaldehyde (116 mg, 2.65 mmol), acetic acid (0.05 mL) and sodium cyanoborohydride (167 mg, 2.65 mmol) at 0° C.; warmed to RT and stirred for 16 h. The reaction was monitored by TLC; after completion of the reaction, the volatiles were removed in vacuo. The residue was diluted with water (100 mL) and extracted with EtOAc (2×50 mL). The combined organic extracts were washed with brine, dried over sodium sulfate, filtered and concentrated in vacuo to afford compound 418 (200 mg, 87%) as colorless syrup. TLC: 10% MeOH/CH$_2$Cl$_2$ (R$_f$: 0.4); $^1$H NMR (DMSO-d$_6$, 400 MHz): δ 7.82 (d, J=8.8 Hz, 2H), 7.61 (s, 1H), 7.53 (t, J=5.8 Hz, 1H), 7.04 (d, J=8.9 Hz, 2H), 4.74-4.50 (m, 1H), 4.31 (d, J=5.9 Hz, 2H), 3.14-2.93 (m, 6H), 1.41-1.38 (m, 11H), 1.30 (d, J=6.1 Hz, 3H), 1.17 (t, J=7.1 Hz, 6H); LC-MS: 87.75%; 434.1 (M$^+$+1); (column; Ascentis Express C-18 (50×3.0 mm, 2.7 μm); RT 2.03 min. 0.025% Aq. TFA+5% ACN: ACN+5% 0.025% Aq TFA, 1.2 mL/min).

Synthesis of 3-(4-(5-(aminomethyl) thiazol-2-yl) phenoxy)-N,N-diethylbutan-1-amine hydrochloride (419)

To a stirring solution of tert-butyl ((2-(4-((4-(diethylamino) butan-2-yl) oxy) phenyl) thiazol-5-yl) methyl) carbamate 418 (200 mg, 0.46 mmol) in CH$_2$Cl$_2$ (20 mL) was added 4 N HCl in 1, 4-dioxane (2 mL) under inert atmosphere at 0° C.; warmed to RT and stirred for 4 h. The reaction was monitored by TLC; after completion of the reaction, the volatiles were removed in vacuo to afford crude compound 419 (200 mg) as yellow sticky solid. TLC: 10% MeOH/CH$_2$Cl$_2$ (R$_f$: 0.1); LC-MS: 89.46%; 334.0 (M$^+$+1); (column; Ascentis Express C18, (50×3.0 mm, 2.7 μm); RT 1.00 min. 0.025% Aq. TFA+5% ACN: ACN+5% 0.025% Aq. TFA, 1.2 mL/min).

Synthesis of 1-(((2-(4-(3-(azetidin-1-yl) propoxy) phenyl) thiazol-5-yl) methyl)-14-azanyl)-2, 2, 2-trifluoroethan-1-one (422)

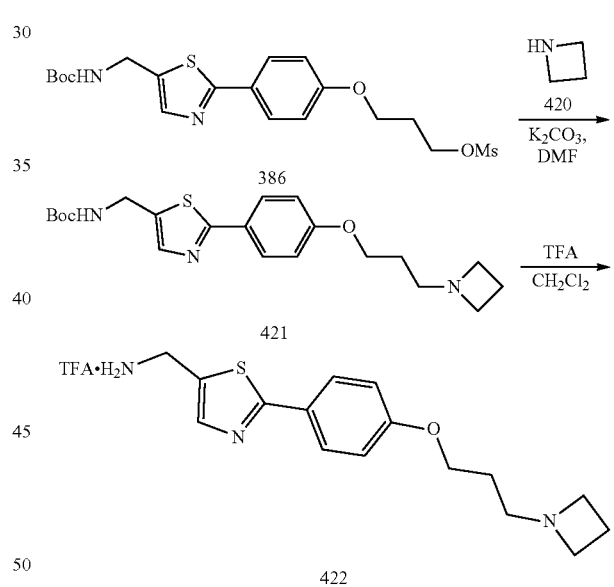

Synthesis of tert-butyl ((2-(4-(3-(azetidin-1-yl) propoxy) phenyl) thiazol-5-yl) methyl) carbamate (421)

To a stirring solution of compound 386 (1 g, 2.47 mmol) in DMF (30 mL) were added potassium carbonate (1.7 g, 12.37 mmol) and azetidine 420 (705 mg, 12.37 mmol) at RT under inert atmosphere. The reaction mixture was heated to 80° C. and stirred for 16 h. The reaction was monitored by TLC; after completion of the reaction, the reaction mixture was diluted with water (30 mL) and extracted with EtOAc (2×30 mL). The combined organic extracts were dried over sodium sulfate, filtered and concentrated in vacuo to obtain the crude. The crude was purified through silica gel column chromatography using 10% MeOH/CH$_2$Cl$_2$ to afford crude compound 421 (130 mg) as yellow syrup. $^1$H NMR (400 MHz, DMSO-d$_6$): δ 7.79 (d, J=8.9 Hz, 2H), 7.59 (s, 1H), 7.54-7.48 (m, 1H), 7.00 (d, J=8.8 Hz, 2H), 4.29 (d, J=5.9 Hz, 2H), 4.04-3.97 (m, 2H), 3.08-3.05 (m, 4H), 2.47-2.42 (m, 2H), 1.96-1.90 (m, 2H), 1.69-1.67 (m, 2H), 1.38 (s, 9H); LC-MS: 70.31%; 404.1 (M$^+$+1) (column; Ascentis Express C-18, (50×3.0 mm, 2.7 μm); RT 1.89 min. 0.025% Aq. TFA+5% ACN: ACN+5% 0.025% Aq. TFA, 1.2 mL/min).

Synthesis of 1-(((2-(4-(3-(azetidin-1-yl) propoxy) phenyl) thiazol-5-yl) methyl)-14-azanyl)-2, 2, 2-trifluoroethan-1-one (422)

To a stirring solution of compound 421 (130 mg, 0.29 mmol) in CH$_2$Cl$_2$ (10 mL) was added trifluoroacetic acid (0.06 mL, 0.87 mmol) at 0° C. under inert atmosphere. The reaction mixture was gradually warmed to RT and stirred for 16 h. The reaction was monitored by TLC; after completion of the reaction, the volatiles were removed in vacuo to afford crude compound 422 (100 mg) as an off-white solid. This crude material was taken to next step without further purification. TLC: 70% EtOAc/Hexane (R$_f$: 0.1); LC-MS: 24.00%; 304.1 (M$^+$+1); (column; Kinetex EVO C-18 (50× 3.0 mm, 2.6 um); RT 1.07 min. 2.5 mM NH$_4$OOCH in water+5% ACN: ACN+5% 2.5 mM NH$_4$OOCH in water, 0.8 mL/min).

Synthesis of 1-(1-((4-(5-(aminomethyl) thiazol-2-yl) phenoxy) methyl) cyclopropyl)-N, N-dimethylmethanamine hydrochloride (431)

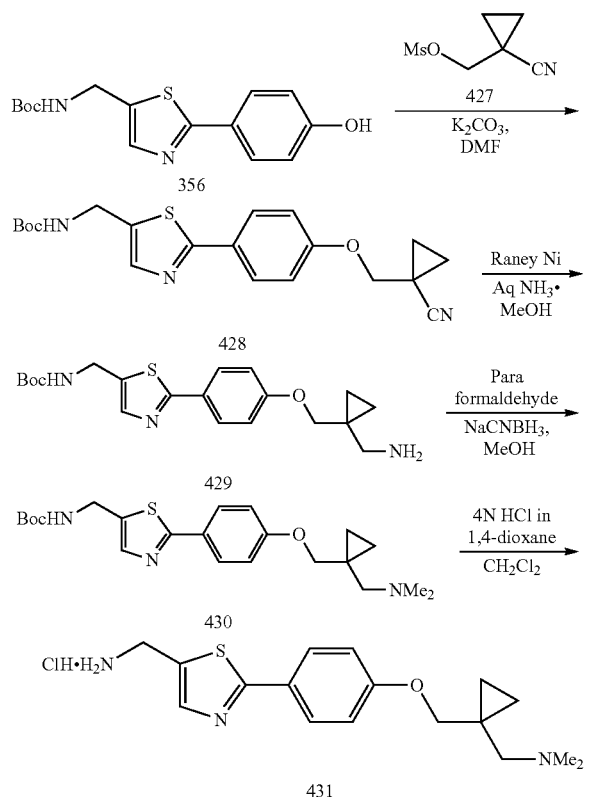

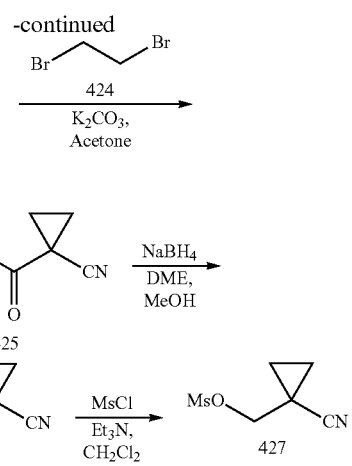

Synthesis of ethyl 1-cyanocyclopropane-1-carboxylate (425)

To a stirring solution of ethyl 2-cyanoacetate 423 (5 g, 44.20 mmol) in acetone (100 mL) were added potassium carbonate (18.3 g, 132.60 mmol) and 1,2-dibromo ethane (8 mL, 88.4 mmol) 424 at RT under inert atmosphere. The reaction mixture was heated to 70° C. and stirred for 16 h. The reaction was monitored by TLC; after completion of the reaction, the reaction mixture was filtered through celite and washed with acetone (200 mL). The filtrate was dried over sodium sulfate, filtered and concentrated in vacuo to obtain the compound 425 (10 g, crude) as brown liquid. $^1$H NMR (400 MHz, CDCl$_3$): δ 4.27 (q, J=7.2 Hz, 2H), 1.68 (t, J=3.5 Hz, 2H), 1.68 (t, J=3.5 Hz, 2H), 1.34 (t, J=7.2 Hz, 3H)

Synthesis of 1-(hydroxymethyl) cyclopropane-1-carbonitrile (426)

To a stirring solution of compound 425 (4 g, 28.78 mmol) in 1, 2-dimethoxy ethane:MeOH (9:1, 88 mL) was added sodium borohydride (8.7 g, 228.90 mmol) at RT under inert atmosphere. The reaction mixture was stirred at RT for 48 h. The reaction was monitored by TLC; after completion of the reaction, the reaction mixture was quenched with saturated sodium bicarbonate solution (50 mL) and extracted with 10% MeOH/CH$_2$Cl$_2$ (2×50 mL). The combined organic extracts were dried over sodium sulfate, filtered and concentrated in vacuo to afford compound 426 (1.4 g, 54%) as yellow color liquid. $^1$H NMR (400 MHz, CDCl$_3$): δ 4.25 (br s, 1H), 3.63 (s, 2H), 1.32-1.24 (m, 2H), 1.02-0.92 (m, 2H)

Synthesis of 1-(hydroxymethyl) cyclopropane-1-carbonitrile (427)

To a stirring solution of compound 426 (1 g, 10.31 mmol) in CH$_2$Cl$_2$ (20 mL) under inert atmosphere were added triethyl amine (4.5 mL, 30.93 mmol), methane sulfonyl chloride (1.68 mL, 20.62 mmol) at 0° C.; stirred RT for 2 h. The reaction was monitored by TLC; after completion of the reaction, the reaction mixture was quenched with water (20 mL) and extracted with CH$_2$Cl$_2$ (2×20 mL). The combined organic extracts were washed with sodium bicarbonate solution (20 mL), brine (20 mL) dried over sodium sulfate, filtered and concentrated in vacuo to obtain the crude compound 427 (1.5 g) as brown liquid. TLC: 30% EtOAc/

Hexane (R$_f$: 0.5); $^1$H NMR (400 MHz, CDCl$_3$): δ 4.19 (s, 2H), 3.15 (s, 3H), 1.49-1.44 (m, 2H), 1.21-1.16 (m, 2H)

Synthesis of tert-butyl ((2-(4-((1-cyanocyclopropyl) methoxy) phenyl) thiazol-5-yl) methyl) carbamate (428)

To a stirring solution of tert-butyl ((2-(4-hydroxyphenyl) thiazol-5-yl) methyl) carbamate 356 (500 mg, 1.64 mmol) in DMF (10 mL) were added compound 427 (858 mg, 4.90 mmol) and potassium carbonate (1.13 g, 5.0 mmol) at RT under inert atmosphere. The reaction mixture was heated to 70° C. and stirred for 16 h. The reaction was monitored by TLC; after completion of the reaction, the reaction mixture was mixture was diluted with ice cold water (20 mL) and extracted with EtOAc (2×20 mL). The combined organic extracts were dried over sodium sulfate, filtered and concentrated in vacuo to obtain the crude. The crude was purified through column chromatography using 2-5% MeOH/CH$_2$Cl$_2$ to afford compound 428 (500 mg, 79%) as colorless liquid. TLC: 5% MeOH/CH$_2$Cl$_2$ (R$_f$: 0.6); $^1$H NMR (500 MHz, DMSO-d$_6$): δ 7.83 (d, J=8.7 Hz, 2H), 7.62 (s, 1H), 7.54-7.52 (m, 1H), 7.06 (d, J=8.7 Hz, 2H), 4.31 (d, J=5.8 Hz, 2H), 4.10 (s, 2H), 1.40 (s, 9H), 1.21-1.12 (m, 4H); LC-MS: 85.37%; 386.1 (M$^+$+1) (column; Ascentis Express C-18, (50×3.0 mm, 2.7 μm); RT 0.58 min. 0.025% Aq. TFA+5% ACN: ACN+5% 0.025% Aq. TFA, 1.2 mL/min);

Synthesis of tert-butyl ((2-(4-((1-(aminomethyl) cyclopropyl) methoxy) phenyl) thiazol-5-yl) methyl) carbamate (429)

To a stirring solution of compound 428 (400 mg, 1.04 mmol) in a mixture of methanol and ammonia (9:1, 50 mL) was added Raney Ni (100 mg) at RT under inert atmosphere. The reaction mixture was stirred under hydrogen atmosphere (balloon pressure) at RT for 16 h. The reaction was monitored by TLC; after completion of the reaction, the reaction mixture was filtered through a pad of celite and the celite bed was washed with 10% MeOH/CH$_2$Cl$_2$ (50 mL). The filtrate was concentrated in vacuo to obtain the crude. The crude was purified through neutral alumina column chromatography using 10% MeOH/CH$_2$Cl$_2$ to afford compound 429 (250 mg, 62%) as an off-white solid. TLC: 10% MeOH/CH$_2$Cl$_2$ (R$_f$: 0.2); $^1$H NMR (500 MHz, DMSO-d$_6$): δ 8.01-7.91 (m, 1H), 7.82 (d, J=8.7 Hz, 2H), 7.60 (s, 1H), 7.57-7.55 (m, 1H), 7.03 (d, J=8.7 Hz, 2H), 4.29 (d, J=5.8 Hz, 2H), 4.11-4.03 (m, 1H), 3.97 (s, 2H), 2.91 (s, 2H), 1.38 (s, 9H), 0.79-0.72 (m, 2H), 0.70-0.64 (m, 2H); LC-MS: 89.88%; 390.1 (M$^+$+1); (column; Kinetex EVO C-18 (50× 3.0 mm, 2.6 um); RT 2.33 min. 2.5 mM NH$_4$OOCH in water+5% ACN: ACN+5% 2.5 mM NH$_4$OOCH in water, 0.8 mL/min).

Synthesis of tert-butyl ((2-(4-((1-((dimethylamino) methyl) cyclopropyl) methoxy) phenyl) thiazol-5-yl) methyl) carbamate (430)

To a stirring solution of compound 429 (250 mg, 0.64 mmol) in methanol (25 mL) were added paraformaldehyde (96 mg, 3.21 mmol) and sodium cyanoborohydride (202 mg, 3.21 mmol) at 0° C. under inert atmosphere. The reaction mixture was gradually warmed to RT and stirred for 16 h. The reaction was monitored by TLC; after completion of the reaction, the volatiles were removed in vacuo. The residue was dilute with saturated sodium bicarbonate solution (20 mL) and extracted with EtOAc (2×30 mL). The combined organic extracts were dried over sodium sulfate, filtered and concentrated in vacuo to obtain the crude. The crude was purified through column chromatography using 2-5% MeOH/CH$_2$Cl$_2$ to afford compound 430 (160 mg, 59%) as an off white solid. TLC: 10% MeOH/CH$_2$Cl$_2$ (R$_f$: 0.5); LC-MS: 84.53%; 418.1 (M$^+$+1); (column; Kinetex EVO C-18 (50×3.0 mm, 2.6 um); RT 2.55 min. 2.5 mM NH$_4$OOCH in water+5% ACN: ACN+5% 2.5 mM NH$_4$OOCH in water, 0.8 mL/min).

1-(1-((4-(5-(aminomethyl) thiazol-2-yl) phenoxy) methyl) cyclopropyl)-N, N-dimethylmethanamine hydrochloride (431)

To a stirring solution of compound 430 (160 mg, 0.38 mmol) in CH$_2$Cl$_2$ (20 mL) was added 4 N HCl in 1, 4-dioxane (2 mL) under argon atmosphere at 0° C.; warmed to RT and stirred for 4 h. The reaction was monitored by TLC; after completion of the reaction, the volatiles were removed in vacuo. The crude washed with ether (20 mL) to afford compound 431 (150 mg, HCl salt) as an off-white solid. TLC: 40% EtOAc/Hexane (R$_f$: 0.1); $^1$H NMR (400 MHz, DMSO-d$_6$): δ), 8.60 (br s, 3H), 7.90 (s, 1H), 7.87 (d, J=8.8 Hz, 2H), 7.06 (d, J=8.9 Hz, 2H), 4.35-4.29 (m, 2H), 4.04 (s, 2H), 3.26-3.18 (m, 2H), 2.82 (d, J=4.9 Hz, 6H), 0.82 (s, 4H); LC-MS: 94.00%; 318.3 (M$^+$+1) (des-Boc); (column; Cortecs C18, (50×3.0 mm, 2.7 μm); RT 3.05 min. 2.5 mM Aq NH$_4$HCO$_3$:ACN, 0.8 mL/min);

Synthesis of 1-(1-((4-(5-(aminomethyl) thiazol-2-yl) phenoxy) methyl) cyclobutyl)-N, N-dimethylmethanamine hydrochloride (439)

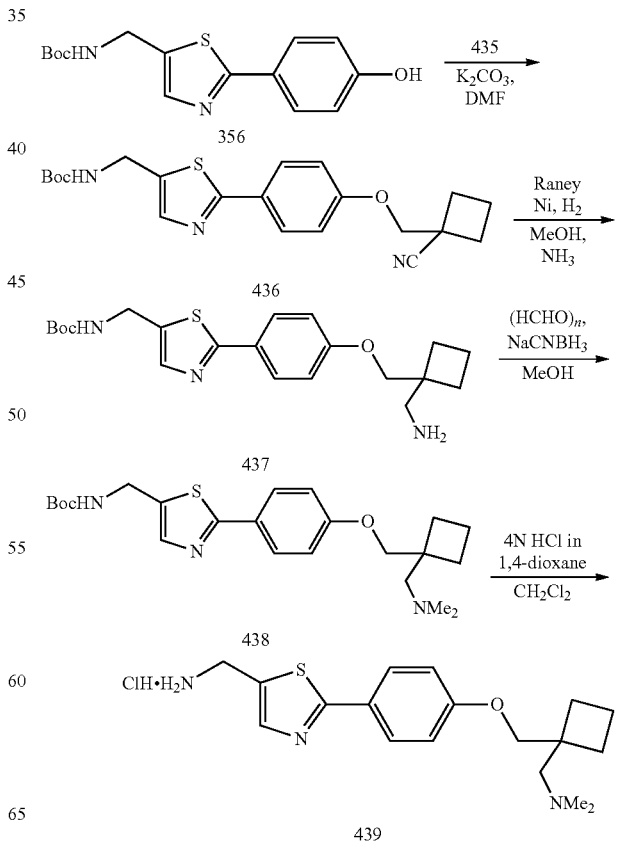

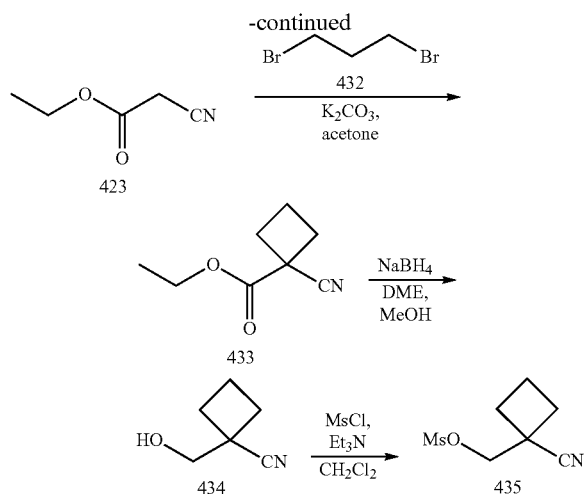

Synthesis of ethyl 1-cyanocyclobutane-1-carboxylate (433)

To a stirring solution of ethyl 2-cyanoacetate 423 (7 g, 61.95 mmol) in acetone (300 mL) were added 1,3-dibromopropane 432 (9.47 mL, 92.92 mmol) and potassium carbonate (25.6 g, 185.84 mmol) at RT under inert atmosphere. The reaction mixture was heated to 70-80° C. and stirred for 16 h. The reaction was monitored by TLC; after completion of the reaction, the reaction mixture was filtered through a pad of celite and the celite bed was washed with EtOAc (100 mL). The filtrate was concentrated in vacuo to afford compound 433 (10 g) as pale yellow liquid. This crude material was taken to next step without further purification. TLC: 30% EtOAc/hexanes ($R_f$: 0.5).

Synthesis of 1-(hydroxymethyl) cyclobutane-1-carbonitrile (434)

To a stirring solution of compound 433 (5 g, crude) in a mixture of DME/MeOH (10:1, 110 mL) was added sodium borohydride (10 g, 261.44 mmol) portion wise at 0° C. under inert atmosphere. The reaction mixture was gradually warmed to RT and stirred for 16 h. The reaction was monitored by TLC; after completion of the reaction, the reaction mixture was quenched slowly with aqueous sodium bicarbonate solution (50 mL) and extracted with 10% MeOH/CH$_2$Cl$_2$ (2×50 mL). The combined organic extracts were dried over sodium sulfate, filtered and concentrated in vacuo to afford compound 434 (2 g) as pale yellow liquid. This crude material was taken to next step without further purification. TLC: 30% EtOAc/hexanes ($R_f$: 0.3).

Synthesis of (1-cyanocyclobutyl) methyl methanesulfonate (435)

To a stirring solution of compound 434 (500 mg, crude) in CH$_2$Cl$_2$ (10 mL) were added methanesulfonyl chloride (0.4 mL, 5.4 mmol) and triethylamine (0.94 mL, 6.75 mmol) at 0° C. under inert atmosphere. The reaction mixture was gradually warmed to RT and stirred for 3 h. The reaction was monitored by TLC; after completion of the reaction, the reaction mixture was poured into aqueous sodium bicarbonate solution (30 mL) and extracted with EtOAc (2×30 mL). The combined organic extracts were dried over sodium sulfate, filtered and concentrated in vacuo to afford compound 435 (600 mg) as pale yellow liquid. This crude material was taken to next step without further purification. TLC: 30% EtOAc/hexanes ($R_f$: 0.4).

Synthesis of tert-butyl ((2-(4-((1-cyanocyclobutyl) methoxy) phenyl) thiazol-5-yl) methyl) carbamate (436)

To a stirring solution of tert-butyl ((2-(4-hydroxyphenyl) thiazol-5-yl) methyl) carbamate 356 (1.5 g, 4.9 mmol) in DMF (40 mL) were added compound 435 (3.24 g, 17.16 mmol) and potassium carbonate (2.03 g, 14.7 mmol) at RT under inert atmosphere. The reaction mixture was heated to 80° C. and stirred for 16 h. The reaction was monitored by TLC; after completion of the reaction, the reaction mixture was mixture was diluted with ice cold water (30 mL) and extracted with EtOAc (2×40 mL). The combined organic extracts were dried over sodium sulfate, filtered and concentrated in vacuo to obtain the crude. The crude was purified through column chromatography using 3% MeOH/CH$_2$Cl$_2$ to afford compound 436 (1.2 g, 61%) as an off white solid. TLC: 5% MeOH/CH$_2$Cl$_2$ ($R_f$: 0.7); LC-MS: 87.97%; 400.1 (M$^+$+1); (column; Kinetex EVO C-18 (50×3.0 mm, 2.6 um); RT 3.38 min. 2.5 mM NH$_4$OOCH in water+5% ACN: ACN+5% 2.5 mM NH$_4$OOCH in water, 0.8 mL/min).

Synthesis of tert-butyl ((2-(4-((1-(aminomethyl) cyclobutyl) methoxy) phenyl) thiazol-5-yl) methyl) carbamate (437)

To a stirring solution of compound 436 (900 mg, 2.25 mmol) in a mixture of methanol and ammonia (10:1, 66 mL) was added Raney Ni (200 mg) at RT under inert atmosphere. The reaction mixture was stirred under hydrogen atmosphere (balloon pressure) at RT for 16 h. The reaction was monitored by TLC; after completion of the reaction, the reaction mixture was filtered through a pad of celite and the celite bed was washed with 10% MeOH/CH$_2$Cl$_2$ (50 mL). The filtrate was concentrated in vacuo to afford compound 437 (800 mg) as pale yellow sticky syrup. This crude material was taken to next step without further purification. TLC: 5% MeOH/CH$_2$Cl$_2$ ($R_f$: 0.2); $^1$H NMR (500 MHz, DMSO-d$_6$): δ 7.96 (s, 1H), 7.84-7.81 (m, 2H), 7.53 (br s, 1H), 7.10-7.06 (m, 2H), 4.30 (d, J=4.6 Hz, 2H), 3.32-3.22 (m, 2H), 2.43-2.31 (m, 2H), 2.08-1.79 (m, 6H), 1.39 (s, 9H); LC-MS: 78.30%; 404.2 (M$^+$+1); (column; Ascentis Express C18, (50×3.0 mm, 2.7 µm); RT 2.03 min. 0.025% Aq. TFA+5% ACN: ACN+5% 0.025% Aq. TFA, 1.2 mL/min).

Synthesis of tert-butyl ((2-(4-((1-((dimethylamino) methyl) cyclobutyl) methoxy) phenyl) thiazol-5-yl) methyl) carbamate (438)

To a stirring solution of compound 437 (800 mg, crude) in methanol (30 mL) were added paraformaldehyde (297 mg, 9.92 mmol) and sodium cyanoborohydride (615 mg, 9.92 mmol) at 0° C. under inert atmosphere. The reaction mixture was gradually warmed to RT and stirred for 16 h. The reaction was monitored by TLC; after completion of the reaction, the volatiles were removed in vacuo. The residue was dilute with water (30 mL) and extracted with EtOAc (2×40 mL). The combined organic extracts were dried over sodium sulfate, filtered and concentrated in vacuo to obtain the crude. The crude was purified through column chromatography using 8% MeOH/CH$_2$Cl$_2$ to afford compound 438 (560 mg, 65%) as an off white solid. TLC: 5% MeOH/CH$_2$Cl$_2$ ($R_f$: 0.5); $^1$H NMR (500 MHz, DMSO-d$_6$): δ 7.83 (d, J=8.7 Hz, 2H), 7.61 (s, 1H), 7.53 (t, J=5.2 Hz, 1H), 7.08 (d, J=8.1 Hz, 2H), 4.31 (d, J=5.8 Hz, 2H), 4.16-4.05 (m, 2H), 3.17 (d, J=5.2 Hz, 2H), 2.33-2.07 (m, 4H), 2.05-1.77 (m, 8H), 1.40 (s, 9H); LC-MS: 97.54%; 432.2 (M⁺+1); (column; Ascentis Express C18, (50×3.0 mm, 2.7 µm); RT 2.00 min. 0.025% Aq. TFA+5% ACN: ACN+5% 0.025% Aq. TFA, 1.2 mL/min).

Synthesis of 1-(1-((4-(5-(aminomethyl) thiazol-2-yl) phenoxy) methyl) cyclobutyl)-N, N-dimethylmethanamine hydrochloride (439)

To a stirring solution of compound 438 (560 mg, 1.3 mmol) in CH₂Cl₂ (13 mL) was added 4 N HCl in 1, 4-dioxane (3 mL) at 0° C. under inert atmosphere. The reaction mixture was gradually warmed to RT and stirred for 2 h. The reaction was monitored by TLC; after completion of the reaction, the volatiles were removed in vacuo to obtain the crude. The crude was triturated with EtOAc (20 mL), diethylether (20 mL) and dried in vacuo to afford compound 439 (450 mg, HCl salt) as an off white solid. TLC: 5% MeOH/CH₂Cl₂ (R_f: 0.1); ¹H NMR (500 MHz, DMSO-d₆): δ 8.65 (br s, 3H), 7.94-7.86 (m, 3H), 7.15 (d, J=8.7 Hz, 2H), 4.31 (q, J=5.2 Hz, 2H), 4.27 (s, 2H), 3.35 (d, J=5.8 Hz, 2H), 2.78 (s, 3H), 2.77 (s, 3H), 2.14-1.88 (m, 6H); LC-MS: 98.70%; 332.1 (M⁺+1); (column; Ascentis Express C18, (50×3.0 mm, 2.7 µm); RT 1.39 min. 0.025% Aq. TFA+5% ACN: ACN+5% 0.025% Aq. TFA, 1.2 mL/min).

Synthesis of 1-((4-(5-(aminomethyl) thiazol-2-yl) phenoxy) methyl) cyclobutane-1-carbonitrile hydrochloride (440)

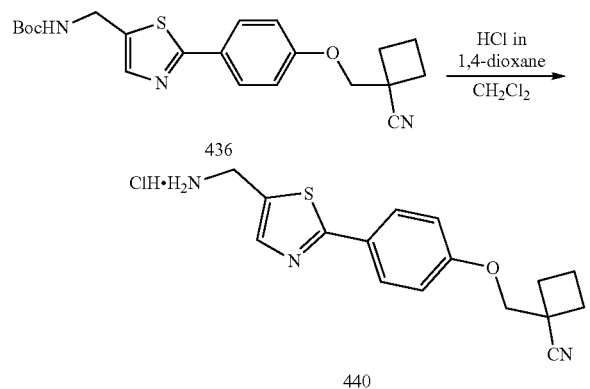

Synthesis of 1-((4-(5-(aminomethyl) thiazol-2-yl) phenoxy) methyl) cyclobutane-1-carbonitrile hydrochloride (440)

To a stirring solution of compound 436 (300 mg, 0.75 mmol) in CH2Cl2 (10 mL) was added 4 N HCl in 1, 4-dioxane (1 mL) under argon atmosphere at 0° C.; warmed to RT and stirred for 2 h. The reaction was monitored by TLC; after completion of the reaction, the volatiles were removed in vacuo. The crude washed with diethyl ether (10 mL), EtOAc (10 mL) and dried in vacuo to afford compound 440 (150 mg; HCl salt) as pale yellow solid. TLC: 5% MeOH/CH2Cl2 (R_f: 0.1); 1H NMR (400 MHz, DMSO-d6): δ 8.60 (br s, 3H), 7.92 (s, 1H), 7.89 (d, J=8.9 Hz, 2H), 7.14 (d, J=8.9 Hz, 2H), 4.34 (s, 2H), 4.32 (d, J=5.6 Hz, 2H), 2.56-2.50 (m, 2H), 2.33-2.19 (m, 2H), 2.17-2.07 (m, 2H); LC-MS: 98.63%; 299.9 (M++1); (column; Kinetex EVO C-18 (50×3.0 mm, 2.6 um); RT 2.05 min. 2.5 mM NH4OOCH in water+5% ACN: ACN+5% 2.5 mM NH4OOCH in water, 0.8 mL/min).

Synthesis of 4-(1-(5-(aminomethyl) thiazol-2-yl)-1H-pyrazol-4-yl)-N, N-dimethylbutan-1-amine hydrochloride (448) and 4-(1-(5-(aminomethyl)thiazol-2-yl)-1H-pyrazol-4-yl)-N,N-diethyl butan-1-amine hydrochloride (448A)

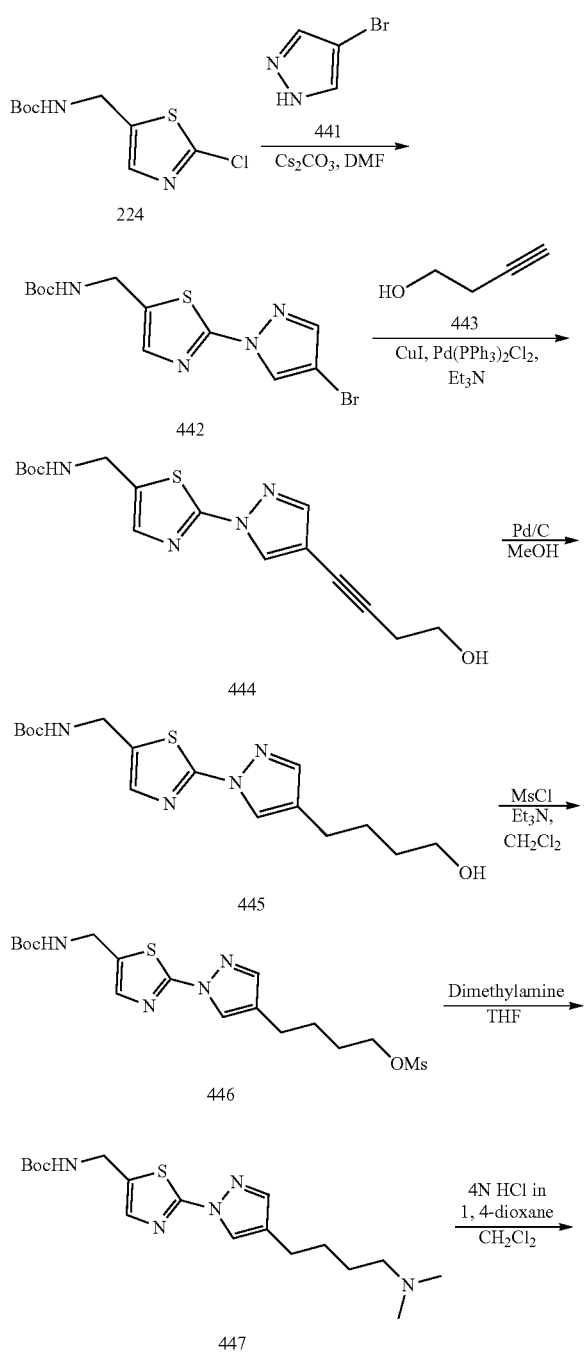

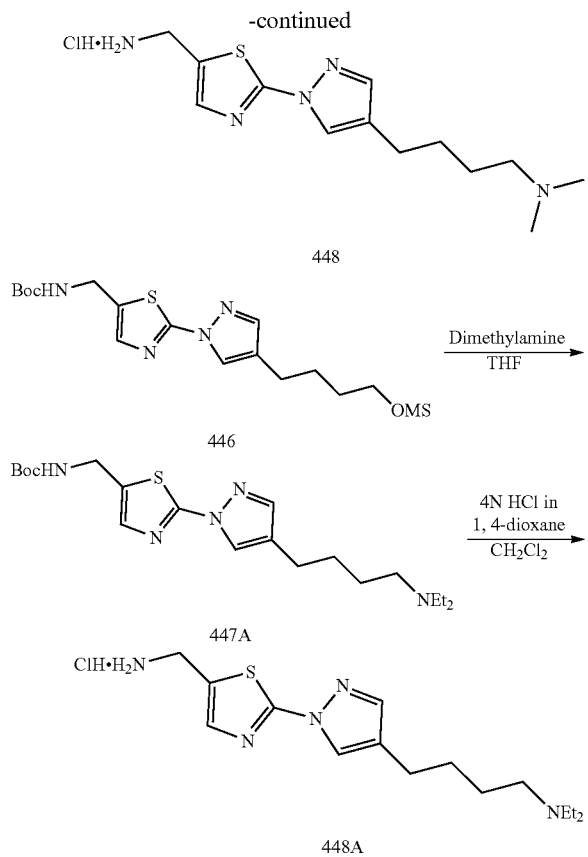

Synthesis of tert-butyl ((2-(4-bromo-1H-pyrazol-1-yl) thiazol-5-yl) methyl) carbamate (442)

To a stirring solution of tert-butyl ((2-chlorothiazol-5-yl) methyl) carbamate 224 (10 g, 40.32 mmol) in DMF (100 mL) under inert atmosphere were added 4-bromo-1H-pyrazole 441 (5.92 g, 40.29 mmol), cesium carbonate (39.4 g, 120.96 mmol) at RT; heated to 80° C. and stirred for 16 h. The reaction was monitored by TLC; after completion of the reaction, the reaction mixture was diluted with ice-cold water (500 mL) and extracted with EtOAc (2×200 mL). The combined organic extracts were dried over sodium sulfate, filtered and concentrated in vacuo to obtain the crude. The crude was purified through silicagel column chromatography using 30% EtOAc/hexanes to afford compound 442 (4.1 g, 29%) as an off-white solid. TLC: 30% EtOAc/hexanes ($R_f$: 0.3). $^1$H-NMR (DMSO-$d_6$, 500 MHz): δ 8.74 (s, 1H), 7.99 (s, 1H), 7.57 (t, J=5.2 Hz, 1H), 7.46 (s, 1H), 4.27 (d, J=6.4 Hz, 2H), 1.40 (s, 9H); LC-MS: 83.58%; 359.0 (M$^+$+1); (column; Ascentis Express C18, (50×3.0 mm, 2.7 μm); RT 2.69 min. 0.025% Aq. TFA+5% ACN: ACN+5% 0.025% Aq. TFA, 1.2 mL/min).

Synthesis of tert-butyl 42-(4-(4-hydroxybut-1-yn-1-yl)-1H-pyrazol-1-yl) thiazol-5-yl) methyl) carbamate (444)

To a stirring solution of compound 442 (4.1 g, 11.45 mmol) in triethylamine (50 mL) were added but-3-yn-1-ol 443 (1.2 g, 17.18 mmol), Copper(I) iodide (22 mg, 0.11 mmol) and purged under argon atmosphere for 20 min. To this was added Pd(PPh$_3$)$_2$Cl$_2$ (160 mg, 0.22 mmol) and purged under argon atmosphere for 10 min; heated to 80° C. and stirred for 2 h. The reaction was monitored by TLC; after completion the reaction mixture was diluted with water (75 mL) and extracted with EtOAC (2×100 mL). The combined organic extracts were dried over sodium sulfate, filtered and concentrated in vacuo to obtain the crude. The crude was purified through silica gel column chromatography using 40% EtOAc/hexanes to afford compound 444 (2.7 g, crude) as an off-white solid. TLC: 50% EtOAc/hexanes ($R_f$: 0.4); LC-MS: 62.79%; 349.0 (M$^+$+1); (column; Ascentis Express C18, (50×3.0 mm, 2.7 μm); RT 2.25 min. 0.025% Aq. TFA+5% ACN: ACN+5% 0.025% Aq. TFA, 1.2 mL/min).

Synthesis of tert-butyl ((2-(4-(4-hydroxybutyl)-1H-pyrazol-1-yl) thiazol-5-yl) methyl) carbamate (445)

To a stirring solution of compound 444 (2.7 g, 7.75 mmol) in MeOH (30 mL) under inert atmosphere was added 10% Pd/C (800 mg, 50% w/w) at RT and stirred under hydrogen atmosphere (balloon pressure) at RT for 16 h. The reaction was monitored by TLC; after completion of the reaction, the reaction mixture was filtered through celite and eluted with 10% MeOH/CH$_2$Cl$_2$ (100 mL). The filtrate was concentrated in vacuo to obtain the crude. The crude was purified through silica gel column chromatography using 50% EtOAc/hexanes to afford compound 445 (1.8 g, 67%) as colorless thick syrup. TLC: 50% EtOAc/hexanes ($R_f$: 0.6); $^1$H NMR (DMSO-$d_6$, 500 MHz): δ 8.22 (s, 1H), 7.69 (s, 1H), 7.57-7.51 (m, 1H), 7.39 (s, 1H), 4.36 (t, J=4.9 Hz, 1H), 4.25 (d, J=5.8 Hz, 2H), 3.39-3.34 (m, 2H), 2.49-2.46 (m, 2H), 1.63-1.54 (m, 2H), 1.49-1.43 (m, 2H), 1.40 (s, 9H); LC-MS: 99.7\5%; 353.1 (M$^+$+1); (column; Ascentis Express C18, (50×3.0 mm, 2.7 μm); RT 2.19 min. 0.025% Aq. TFA+5% ACN: ACN+5% 0.025% Aq. TFA, 1.2 mL/min).

Synthesis of 4-(1-(5-(((tert-butoxycarbonyl) amino) methyl) thiazol-2-yl)-1H-pyrazol-4-yl) butyl methanesulfonate (446)

To a stirring solution of compound 445 (1.8 g, 5.11 mmol) in CH$_2$Cl$_2$ (20 mL) under inert atmosphere were added triethylamine (1.5 mL, 10.22 mmol), methanesulfonyl chloride (0.62 mL, 7.67 mmol) at 0° C.; warmed to RT and stirred for 4 h. The reaction was monitored by TLC; after completion of the reaction, the reaction mixture was diluted with water (75 mL) extracted with CH$_2$Cl$_2$ (2×25 mL). The combined organic extracts were dried over sodium sulfate, filtered and concentrated in vacuo to afford crude. The crude was purified through silica gel column chromatography using 50% EtOAc/hexanes to afford crude compound 446 (2 g) as an off-white solid. TLC: 50% EtOAc/to hexanes ($R_f$: 0.6); $^1$H NMR (DMSO-$d_6$, 500 MHz): δ 8.27 (s, 1H), 7.71 (s, 1H), 7.58-7.51 (m, 1H), 7.39 (s, 1H), 4.27-4.20 (m, 4H), 3.15 (s, 3H), 2.56-2.51 (m, 2H), 1.73-1.61 (m, 4H), 1.40 (s, 9H); LC-MS: 95.12%; 431.1 (M$^+$+1); (column; Ascentis Express C-18, (50×3.0 mm, 2.7 μm); RT 2.53 min. 0.025% Aq. TFA+5% ACN: ACN+5% 0.025% Aq. TFA, 1.2 mL/min).

Synthesis of tert-butyl ((2-(4-(4-(dimethylamino) butyl)-1H-pyrazol-1-yl) thiazol-5-yl) methyl) carbamate (447)

To a stirring solution of compound 446 (1.4 g, 3.25 mmol) in THF (10 mL) in a sealed tube under inert atmosphere was added dimethylamine (5 mL) at RT; heated to 80° C. and stirred for 16 h. The reaction was monitored by TLC; after completion of the reaction, the volatiles were removed in vacuo. The crude was purified through silica gel column chromatography using 5% MeOH/CH$_2$Cl$_2$ to afford compound 447 (220 mg, 69%) as brown syrup. TLC: 10% MeOH/CH$_2$Cl$_2$ (R$_f$: 0.2); $^1$H NMR (DMSO-d$_6$, 500 MHz): δ 8.23 (s, 1H), 7.69 (s, 1H), 7.58-7.52 (m, 1H), 7.39 (s, 1H), 4.25 (d, J=5.8 Hz, 2H), 2.76-2.71 (m, 2H), 2.51-2.44 (m, 2H), 2.21 (t, J=7.2 Hz, 2H), 2.10 (s, 6H), 1.56 (p, J=7.5 Hz, 2H), 1.40 (s, 9H); LC-MS: 97.07%; 380.1 (M$^+$+1); (column; Ascentis Express C18, (50×3.0 mm, 2.7 μm); RT 1.85 min. 0.025% Aq. TFA+5% ACN: ACN+5% 0.025% Aq. TFA, 1.2 mL/min).

Synthesis of 4-(1-(5-(aminomethyl) thiazol-2-yl)-1H-pyrazol-4-yl)-N, N-dimethylbutan-1-amine hydrochloride (448)

To a stirring solution of compound 447 (1 g, 2.63 mmol) in CH$_2$Cl$_2$ (10 mL) under inert atmosphere was added 4 N HCl in 1, 4-dioxane (3 mL) at 0° C.; warmed to RT and stirred for 4 h. The reaction was monitored by TLC; after completion of the reaction, the volatiles were removed in vacuo to obtain the crude, which was triturated with diethyl ether (2×5 mL), hexane (5 mL) and dried in vacuo to afford crude compound 448 (750 mg, HCl salt) as an off-white solid. TLC: 10% MeOH/CH$_2$Cl$_2$ (R$_f$: 0.1); LC-MS: 57.57%; 315.1 (M$^+$+1); (column; Ascentis Express C18, (50×3.0 mm, 2.7 μm); RT 0.31 min. 0.025% Aq. TFA+5% ACN: ACN+5% 0.025% Aq. TFA, 1.2 mL/min).

Synthesis of tert-butyl 42-(4-(4-(diethylamino) butyl)-1H-pyrazol-1-yl)thiazol-5-yl)methyl)carbamate (447A)

To a stirring solution of compound 446 (2.0 g, 4.65 mmol) in THF (10 mL) in a sealed tube under inert atmosphere was added diethylamine (5 mL) at RT; heated to 80° C. and stirred for 16 h. The reaction was monitored by TLC; after completion of the reaction, the volatiles were removed in vacuo. The crude was purified through silica gel column chromatography using 6% MeOH/CH$_2$Cl$_2$ to afford compound 447A (1.6 g, 85%) as pale brown syrup. TLC: 10% MeOH/CH$_2$Cl$_2$ (R$_f$: 0.2); LC-MS: 99.53%; 408.2 (M$^+$+1); (column; Ascentis Express C18, (50×3.0 mm, 2.7 μm); RT 2.00 min. 0.025% Aq. TFA+5% ACN: ACN+5% 0.025% Aq. TFA, 1.2 mL/min).

Synthesis of 4-(1-(5-(aminomethyl)thiazol-2-yl)-1H-pyrazol-4-yl)-N,N-diethyl butan-1-amine hydrochloride (448A)

To a stirring solution of compound 447A (1.6 g, 3.93 mmol) in CH$_2$Cl$_2$ (20 mL) under inert atmosphere was added 4 N HCl in 1, 4-dioxane (5 mL) at 0° C.; warmed to RT and stirred for 4 h. The reaction was monitored by TLC; after completion of the reaction, the volatiles were removed in vacuo to obtain the crude, which was triturated with diethyl ether (2×5 mL), hexane (5 mL) and dried in vacuo to afford crude compound 448A (750 mg, HCl salt) as an off-white solid. TLC: 10% MeOH/CH$_2$Cl$_2$ (R$_f$: 0.1); LC-MS: 57.57%; 315.1 (M$^+$+1); (column; Ascentis Express C18, (50×3.0 mm, 2.7 μm); RT 0.31 min. 0.025% Aq. TFA+5% ACN: ACN+5% 0.025% Aq. TFA, 1.2 mL/min).

Synthesis of ethyl (E)-3-(1-(5-(aminomethyl) thiazol-2-yl)-1H-pyrazol-4-yl) acrylate hydrochloride (451)

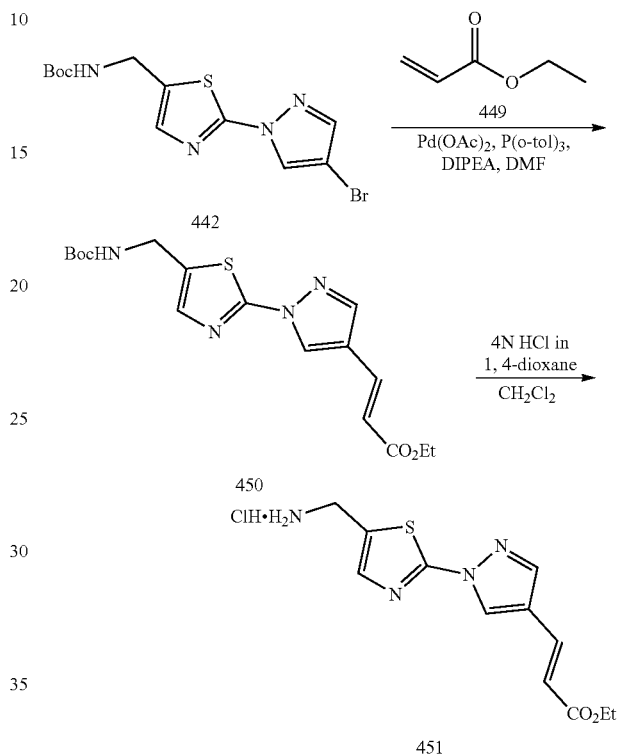

Synthesis of ethyl (E)-3-(1-(5-(((tert-butoxycarbonyl) amino) methyl) thiazol-2-yl)-1H-pyrazol-4-yl) acrylate (450)

To a stirring solution of methyl tert-butyl ((2-(4-bromo-1H-pyrazol-1-yl) thiazol-5-yl) methyl) carbamate 442 (1.3 g, 3.61 mmol) in DMF (50 mL) under inert atmosphere in a sealed tube were added ethyl acrylate 449 (1.81 g, 18.10 mmol), diisopropylethylamine (2.0 mL, 10.86 mmol), purged under argon atmosphere for 30 min. To this were added P(o-tol)$_3$ (330 mg, 1.08 mmol), Pd(OAc)$_2$ (243 mg, 0.36 mmol) at RT; heated to 100° C. and stirred for 16 h. The reaction was monitored by TLC; after completion of the reaction, the reaction mixture was poured into ice-cold water (150 mL) and extracted with EtOAc (2×150 mL). The combined organic extracts were dried over sodium sulfate, filtered and concentrated in vacuo to afford crude. The crude was purified through silica gel column chromatography using 30% EtOAc/hexanes to afford compound 450 (550 mg, 40%) as an off-white solid. TLC: 40% EtOAc/hexanes (R$_f$: 0.4); $^1$H NMR (400 MHz, DMSO-d$_6$): δ 8.90 (s, 1H), 8.32 (s, 1H), 7.65-7.55 (m, 2H), 7.47 (s, 1H), 6.58 (d, J=16.1 Hz, 1H), 4.27 (d, J=5.9 Hz, 2H), 4.17 (q, J=7.1 Hz, 2H), 1.40 (s, 9H), 1.25 (t, J=7.2 Hz, 3H); LC-MS: 89.66%; 379.0 (M$^+$+1); (column; Kinetex EVO C-18 (50×3.0 mm, 2.6 um); RT 1.97 min. 2.5 mM Aq. NH$_4$OOCH+5% ACN:ACN: 5%2.5 mM Aq. NH$_4$OOCH; 0.8 mL/min).

Synthesis of ethyl (E)-3-(1-(5-(aminomethyl) thiazol-2-yl)-1H-pyrazol-4-yl) acrylate hydrochloride (451)

To a stirring solution of compound 450 (150 mg, 0.39 mmol) in CH$_2$Cl$_2$ (5 mL) under inert atmosphere was added 4 N HCl in 1, 4-dioxane (1 mL) at 0° C.; warmed to RT and stirred for 2 h. The reaction was monitored by TLC; after completion of the reaction, the volatiles were removed in vacuo to obtain the crude, which was triturated with diethyl ether (2×5 mL), dried in vacuo to afford compound 451 (110 mg, 89%; HCl salt) as white solid. TLC: 30% EtOAc/hexanes (R$_f$: 0.1); $^1$H NMR (500 MHz, DMSO-d$_6$): δ 8.93 (s, 1H), 8.45 (br s, 3H), 8.37 (s, 1H), 7.74 (s, 1H), 7.61 (d, J=15.6 Hz, 1H), 6.59 (d, J=16.2 Hz, 1H), 4.31-4.30 (m, 2H), 4.17 (q, J=7.0 Hz, 2H), 1.24 (t, J=7.0 Hz, 3H);

Synthesis of (2-(1H-pyrazol-1-yl) thiazol-5-yl) methanamine hydrochloride (455)

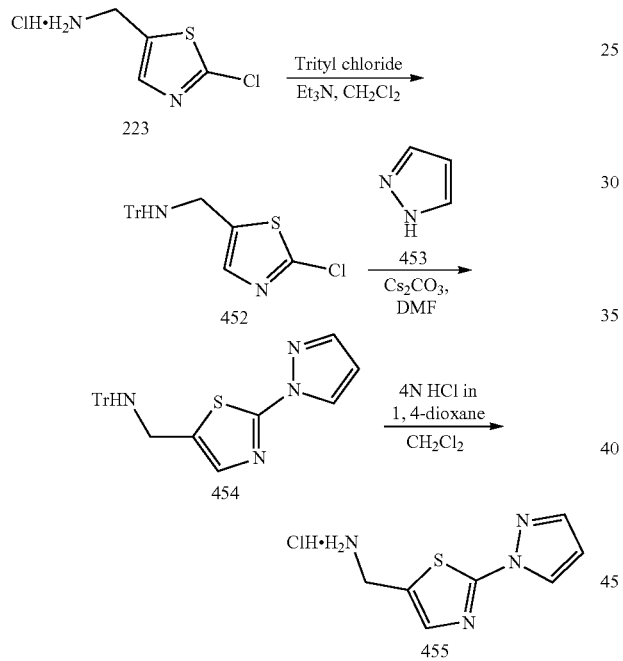

Synthesis of N-((2-chlorothiazol-5-yl) methyl)-1, 1, 1-triphenylmethanamine (452)

To a stirring solution of (2-chlorothiazol-5-yl) methanamine hydrochloride 223 (1.0 g, 5.43 mmol) in CH$_2$Cl$_2$ (40 mL) under inert atmosphere were added triethyl amine (1.57 mL, 10.86 mmol), trityl chloride (1.57 mL, 6.46 mmol) at 0° C.; warmed to RT and stirred for 2 h. The reaction was monitored by TLC; after completion of the reaction, the volatiles were removed in vacuo to obtain the crude. The crude was purified through silica gel column chromatography using 10% EtOAc/hexanes to afford compound 452 (1.5 g, 71%) as white solid. TLC: 10% EtOAc/ (R$_f$: 0.8); $^1$H-NMR (DMSO-d$_6$, 500 MHz): δ 7.46-7.40 (m, 5H), 7.36-7.27 (m, 5H), 7.26-7.17 (m, 5H), 3.97 (br t, J=8.4 Hz, 1H), 3.34-3.27 (m, 2H);

Synthesis of N-((2-(1H-pyrazol-1-yl) thiazol-5-yl) methyl)-1, 1, 1-triphenylmethanamine (454)

To a stirring solution of compound 452 (2 g, 0.51 mmol) in DMF (15 mL) under inert atmosphere were added 1H-pyrazole 453 (70 mg, 1.02 mmol), cesium carbonate (333 mg, 1.02 mmol) at RT; heated to 100° C. and stirred for 16 h. The reaction was monitored by TLC; after completion of the reaction, the reaction mixture was diluted with water (30 mL) and extracted with EtOAc (2×60 mL). The combined organic extracts were dried over sodium sulfate, filtered and concentrated in vacuo to obtain the crude. The crude was purified through silica gel column flash chromatography using 5-7% EtOAc/hexanes to afford compound 454 (110 mg, 51%) as an off-white solid. TLC: 15% EtOAc/hexanes (R$_f$: 0.4). $^1$H-NMR (DMSO-d$_6$, 400 MHz): δ 8.46 (d, J=2.6, 0.6 Hz, 1H), 7.86 (d, J=1.7 Hz, 1H), 7.48-7.44 (m, 6H), 7.38-7.30 (m, 7H), 7.24-7.19 (m, 3H), 6.62 (dd, J=2.5, 1.8 Hz, 1H), 3.87 (t, J=8.4 Hz, 1H), 3.31 (s, 2H); LC-MS (Agilent 6310 Ion trap): 99.52%; 423.2 (M+1)$^+$; (column; Kinetex EVO C-18 (50×3.0 mm, 2.6 um); RT 5.33 min. 2.5 mM Aq. NH$_4$OOCH:ACN; 0.8 mL/min).

Synthesis of (2-(1H-pyrazol-1-yl) thiazol-5-yl) methanamine hydrochloride (455)

To a stirring solution of compound 454 (200 mg, 0.47 mmol) in CH$_2$Cl$_2$ (5 mL) was added 4 N HCl in 1, 4-dioxane (1 mL) under inert atmosphere at 0° C.; warmed to RT and stirred for 2 h. The reaction was monitored by TLC; after completion of the reaction, the volatiles were removed in vacuo to obtain the crude, which was triturated with diethyl ether (2×10 mL) and dried in vacuo to afford compound 455 (90 mg, 88%; HCl salt) as an off-white solid. TLC: 5% MeOH/CH$_2$Cl$_2$ (R$_f$: 0.1); $^1$H-NMR (DMSO-d$_6$, 400 MHz): δ 8.56 (br s, 2H), 8.50 (d, J=2.6 Hz, 1H), 7.88 (d, J=1.5 Hz, 1H), 7.72 (s, 1H), 6.66-6.64 (m, 1H), 4.28 (br s, 2H); LC-MS: 95.50%; 181.9 (M+1)$^+$; (column; Kinetex EVO C-18 (50×3.0 mm, 2.6 um); RT 0.69 min. 2.5 mM Aq. NH$_4$OOCH+5% ACN: ACN+5% 2.5 mM Aq.NH$_4$OOCH, 0.8 mL/min).

Synthesis of (2-(2H-1, 2, 3-triazol-2-yl) thiazol-5-yl) methanamine hydrochloride (458A)

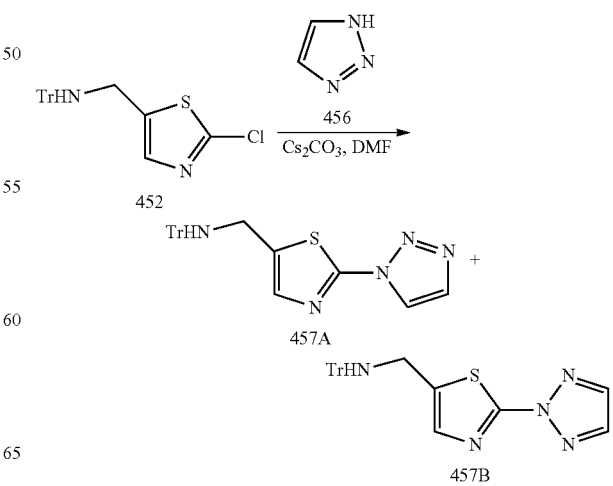

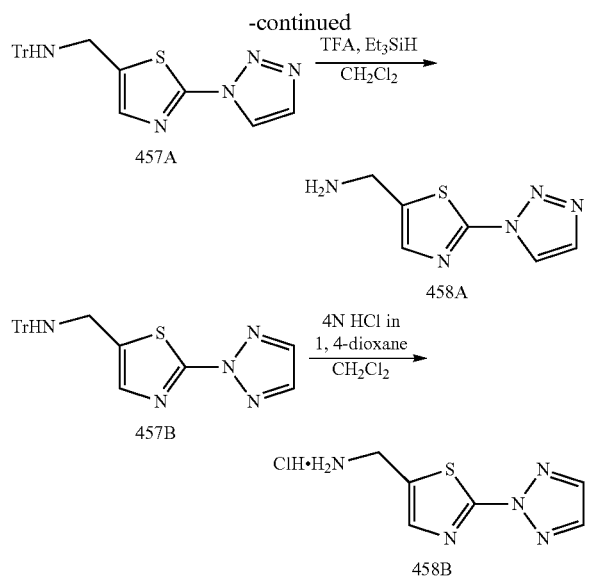

Synthesis of N-((2-(1H-1, 2, 3-triazol-1-yl) thiazol-5-yl)methyl)-1, 1, 1-triphenylmethanamine (457A) & N-((2-(2H-1, 2, 3-triazol-2-yl) thiazol-5-yl) methyl)-1, 1, 1-triphenylmethanamine (457B)

To a stirring solution of N-((2-chlorothiazol-5-yl) methyl)-1, 1, 1-triphenylmethanamine 452 (1 g, 2.56 mmol) in DMF (15 mL) under inert atmosphere were added 1H-1, 2, 3-triazole 456 (354 mg, 5.12 mmol), cesium carbonate (2.5 g, 7.69 mmol) at RT; heated to 110° C. and stirred for 32 h. The reaction was monitored by TLC; after completion of the reaction, the reaction mixture was diluted with water (100 mL) and extracted with EtOAc (2×80 mL). The combined organic extracts were dried over sodium sulfate, filtered and concentrated in vacuo to obtain the crude. The crude was purified through neutral alumina flash column chromatography using 5-10% EtOAc/hexanes to afford compound 457A (250 mg) and 457B (230 mg) as white solids.

Analytical Data of 457A: TLC: 20% EtOAc/hexanes ($R_f$: 0.3). $^1$H NMR (400 MHz, DMSO-$d_6$): δ 8.87 (d, J=1.2 Hz, 1H), 8.05 (d, J=1.2 Hz, 1H), 7.58 (s, 1H), 7.50-7.44 (m, 6H), 7.37-7.30 (m, 6H), 7.26-7.19 (m, 3H), 4.07 (t, J=8.4 Hz, 1H), 3.40 (d, J=8.4 Hz, 2H);

Analytical Data of 457B: TLC: 20% EtOAc/hexanes ($R_f$: 0.3). $^1$H-NMR (DMSO-$d_6$, 400 MHz): δ 8.25 (s, 2H), 7.50 (s, 1H), 7.48-7.44 (m, 6H), 7.34 (t, J=7.7 Hz, 6H), 7.25-7.20 (m, 3H), 4.02 (t, J=8.4 Hz, 1H), 3.38 (d, J=8.2 Hz, 2H).

Synthesis of (2-(1H-1, 2, 3-triazol-1-yl) thiazol-5-yl) methanamine TFA salt (458A)

To a stirring solution of compound 457A (200 mg, 0.47 mmol) in CH$_2$Cl$_2$ (10 mL) under inert atmosphere were added trieythlsilane (0.15 mL, 0.94 mmol), trifluoroacetic acid (0.2 mL, 2.36 mmol) at 0° C.; warmed to RT and stirred for 1 h. The reaction was monitored by TLC; after completion of the reaction, the volatiles were removed in vacuo to obtain the crude, which was washed with n-hexane to afford compound 458A (85 mg, 71) as white solid. TLC: 30% EtOAc/hexanes ($R_f$: 0.2); $^1$H-NMR (DMSO-$d_6$, 400 MHz): δ 8.92 (s, 1H), 8.46 (br s, 2H), 8.07 (s, 1H), 7.89 (s, 1H), 4.39 (br s, 2H); LC-MS: 88.52%; 181.9 (M$^+$+1); (column; Ascentis Express C18, (50×3.0 mm, 2.7 µm); RT 0.37 min. 0.025% Aq. TFA+5% ACN: ACN+5% 0.025% Aq. TFA, 1.2 mL/min).

Synthesis of (2-(2H-1, 2, 3-triazol-2-yl) thiazol-5-yl) methanamine hydrochloride (458B)

To a stirring solution of N-((2-(2H-1, 2, 3-triazol-2-yl) thiazol-5-yl) methyl)-1, 1, 1-triphenylmethanamine 457B (230 mg, 0.54 mmol) in CH$_2$Cl$_2$ (5 mL) under inert atmosphere was added 4 N HCl in 1, 4-dioxane (3 mL) at 0° C.; warmed to RT and stirred for 3 h. The reaction was monitored by TLC; after completion of the reaction, the volatiles were removed in vacuo to obtain the crude, which was triturated with diethyl ether (2×10 mL) and dried in vacuo to afford compound 458B (90 mg, 76%; HCl salt) as white solid. TLC: 30% EtOAc/hexanes ($R_f$: 0.2); $^1$H-NMR (DMSO-$d_6$, 400 MHz): δ 8.56 (br s, 3H), 8.28 (s, 2H), 7.83 (s, 1H), 4.34 (s, 2H); LC-MS (Agilent 6310 Ion trap): 95.92%; 182.1 (M$^+$+1); (column; X-Select CSH C-18, (150× 4.6 mm, 3.5 µm); RT 5.53 min. 2.5 mM Aq. NH$_4$OAc:ACN; 1.0 mL/min).

Synthesis of ethyl 1-(5-(aminomethyl) thiazol-2-yl)-1H-pyrazole-4-carboxylate TFA salt (461)

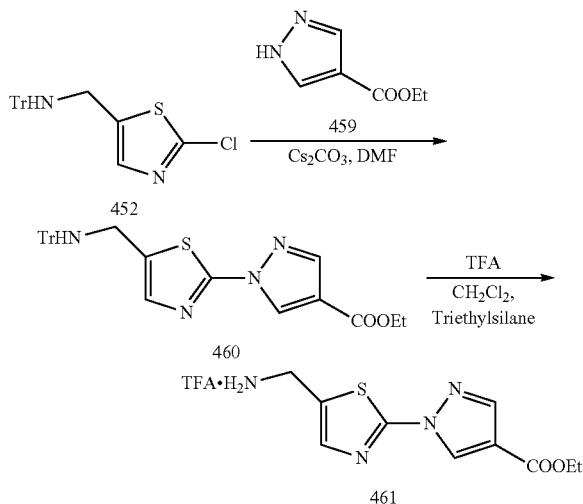

Synthesis of ethyl 1-(5-(((tritylamino) methyl) thiazol-2-yl)-1H-pyrazole-4-carboxylate (460)

To a stirring solution of N-((2-chlorothiazol-5-yl) methyl)-1, 1, 1-triphenylmethanamine 452 (500 mg, 1.28 mmol) in DMF (10 mL) under inert atmosphere were added ethyl 1H-pyrazole-4-carboxylate 459 (180 mg, 1.28 mmol), cesium carbonate (833 mg, 2.56 mmol) at RT; heated to 90° C. and stirred for 10 h. The reaction was monitored by TLC; after completion of the reaction, the reaction mixture was diluted with water (30 mL) and extracted with EtOAc (2×60 mL). The combined organic extracts were dried over sodium sulfate, filtered and concentrated in vacuo to obtain the crude. The crude was purified through silica gel flash column chromatography using 20-25% EtOAc/hexanes to afford compound 460 (200 mg, 32%) as white solid. TLC:

20% EtOAc/hexanes ($R_f$: 0.3). $^1$H-NMR (DMSO-$d_6$, 400 MHz): δ 8.85 (s, 1H), 8.25 (s, 1H), 7.45 (br d, J=7.4 Hz, 6H), 7.32 (t, J=7.7 Hz, 6H), 7.21 (t, J=7.3 Hz, 3H), 4.27 (q, J=7.2 Hz, 2H), 3.96 (t, J=8.4 Hz, 1H), 3.34 (d, J=8.4 Hz, 3H), 1.30 (t, J=7.1 Hz, 3H);

Synthesis of ethyl 1-(5-(aminomethyl) thiazol-2-yl)-1H-pyrazole-4-carboxylate TFA Salt (461)

To a stirring solution of compound 460 (200 mg, 0.40 mmol) in CH$_2$Cl$_2$ (20 mL) under inert atmosphere were added trieythlsilane (0.12 mL, 0.80 mmol), trifluoroacetic acid (0.16 mL, 2.02 mmol) at 0° C.; warmed to RT and stirred for 3 h. The reaction was monitored by TLC; after completion of the reaction, the volatiles were removed in vacuo to obtain the crude, which was washed diethylether (2×10 mL) and dried in vacuo to afford compound 461 (100 mg, 71) as white solid. TLC: 30% EtOAc/hexanes ($R_f$: 0.2); $^1$H-NMR (DMSO-$d_6$, 400 MHz): δ 8.91 (br s, 1H), 8.34 (br s, 2H), 8.28 (s, 1H), 7.78 (s, 1H), 4.34 (d, J=4.0 Hz, 2H), 4.28 (q, J=7.2 Hz, 2H), 1.30 (t, J=7.1 Hz, 3H).

Synthesis of 2-(4-(4-morpholinobutyl) phenyl) thiazol-5-yl) methanamine hydrochloride (468)

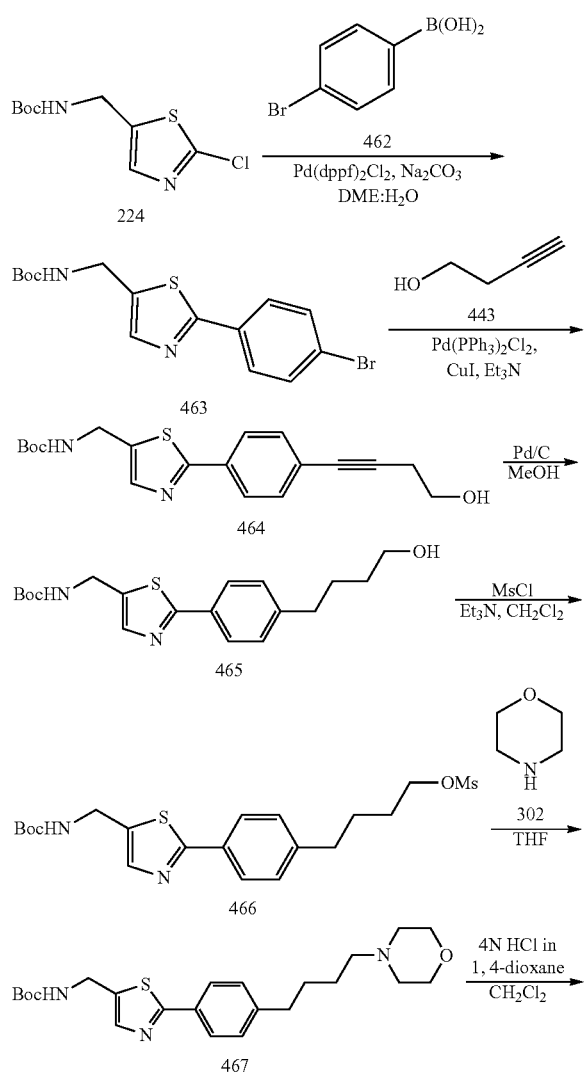

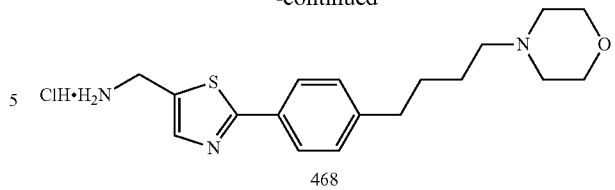

Synthesis of tert-butyl ((2-(4-bromophenyl) thiazol-5-yl) methyl) carbamate (463)

To a stirring solution of tert-butyl ((2-chlorothiazol-5-yl) methyl) carbamate 224 (10 g, 40.29) in DME:H$_2$O (4:1, 100 mL) were added (4-bromophenyl) boronic acid 462 (6.43 g, 32.16 mmol) and sodium carbonate (14.91 g, 140.73 mmol) in a sealed tube at RT and purged under argon for 30 min. Then Pd(dppf)Cl$_2$ (2.94 g, 4.02 mmol) was added at RT. The reaction mixture was heated to 100° C. and stirred for 16 h. The reaction was monitored by TLC; after completion of the reaction, the reaction mixture was diluted with water (200 mL), and extracted with EtOAc (2×200 mL). The combined organic extracts were washed with brine (100 mL), dried over sodium sulfate, filtered and concentrated in vacuo to obtain the crude. The crude was purified through silica gel column chromatography using 5% EtOAc/Hexane to afford compound 463 (2.5 g, 17%) as white solid. TLC: 20% EtOAc/hexanes ($R_f$: 0.5). $^1$H NMR (500 MHz, DMSO-$d_6$): δ 7.84 (d, J=8.1 Hz, 2H), 7.70 (d, J=9.3 Hz, 2H), 7.67 (s, 1H), 7.57 (br s, 1H), 4.34 (br d, J=5.8 Hz, 2H), 1.39 (s, 9H)

Synthesis of tert-butyl ((2-(4-(4-hydroxybut-1-yn-1-yl) phenyl) thiazol-5-yl)methyl) carbamate (464)

To a stirring solution of compound 463 (2.5 g, 3.79 mmol) in triethyl amine (30 mL) were added prop-2-yn-1-ol 443 (456 mg, 8.15 mmol), and copper iodide (12 mg, 0.06 mmol) at RT in a sealed tube and purged under argon atmosphere for 15 min. To this were added Pd(PPh$_3$)$_2$Cl$_2$ (95 mg, 1.13 mmol) at RT; heated to 60° C. and stirred for 16 h. The reaction was monitored by TLC; after completion of the reaction, the volatiles removed under reduced pressure. The residue was diluted with water (20 mL), and extracted with EtOAc (2×30 mL). The combined organic extracts were washed with brine (30 mL), dried over sodium sulfate, filtered and concentrated in vacuo to obtain the crude. The crude was purified through silica gel column chromatography using 40-50% EtOAc/Hexane to afford crude compound 464 (2.8 g, crude) as pale yellow solid. TLC: 50% EtOAc/hexanes ($R_f$: 0.3); LC-MS: 92.51%; 359.50 (M$^+$+1); (column; Ascentis Express C18, (50×3.0 mm, 2.7 μm); RT 2.37 min. 0.025% Aq. TFA+5% ACN: ACN+5% 0.025% Aq. TFA, 1.2 mL/min).

Synthesis of tert-butyl ((2-(4-(4-hydroxybutyl) phenyl) thiazol-5-yl) methyl) carbamate (465)

To a stirring solution of tert-butyl ((2-(4-(4-hydroxybut-1-yn-1-yl) phenyl) thiazol-5-yl) methyl) carbamate 464 (1.3 g, 3.62 mmol) in MeOH (150 mL) under inert atmosphere was added 10% Pd/C (700 mg, 50% w/w) at RT and stirred under hydrogen atmosphere (balloon pressure) at RT for 16 h. The reaction was monitored by TLC; after completion of the reaction, the reaction mixture was filtered through celite and eluted with 20% MeOH/CH$_2$Cl$_2$ (200 mL). The filtrate was concentrated in vacuo to obtain the crude. The crude was triturated with diethyl ether (15 mL) and dried in vacuo to afford compound 465 (800 mg, 61%) as colorless thick syrup. TLC: 5% MeOH/CH$_2$Cl$_2$ (R$_f$: 0.4); $^1$H NMR (400 MHz, DMSO-d$_6$): δ 7.79 (d, J=8.2 Hz, 2H), 7.65 (s, 1H), 7.59-7.52 (m, 1H), 7.30 (d, J=8.2 Hz, 2H), 4.40-4.27 (m, 3H), 3.41 (t, J=6.3 Hz, 2H), 2.62 (t, J=7.6 Hz, 2H), 1.68-1.53 (m, 2H), 1.51-1.41 (m, 2H), 1.40 (s, 9H);

Synthesis of 4-(4-(5-(((tert-butoxycarbonyl) amino) methyl) thiazol-2-yl) phenyl) butyl methanesulfonate (466)

To a stirring solution of compound 465 (250 mg, 0.69 mmol) in CH$_2$Cl$_2$ (15 mL) under inert atmosphere were added triethyl amine (0.19 mL, 1.38 mmol) and methanesulfonyl chloride (94 mg, 0.82 mmol) at 0° C.; warmed to RT and stirred for 3 h. The reaction was monitored by TLC; after completion of the reaction, the reaction mixture was diluted with water (50 mL), extracted with EtOAc (2×50 mL). The combined organic extracts were dried over sodium sulfate, filtered and concentrated in vacuo to afford crude compound 466 (400 mg) as an off-white solid. TLC: 5% MeOH/CH$_2$Cl$_2$ (R$_f$: 0.8); LC-MS: 93.89%; 441.0 (M$^+$+1); (column; Ascentis Express C18, (50×3.0 mm, 2.7 μm); RT 2.63 min. 0.025% Aq. TFA+5% ACN: ACN+5% 0.025% Aq. TFA, 1.2 mL/min).

Synthesis of tert-butyl ((2-(4-(4-morpholinobutyl) phenyl) thiazol-5-yl) methyl) carbamate (467)

To a stirring solution of compound 466 (330 mg, crude) in THF (10 mL) in a sealed tube under inert atmosphere was added morpholine 302 (326 mg, 3.75 mmol) at RT; heated to 70° C. and stirred for 8 h. The reaction was monitored by TLC; after completion of the reaction, the volatiles were removed in vacuo. The residue was diluted with EtOAc (50 mL), washed with water (50 mL). The organic extract was dried over sodium sulfate, filtered and concentrated in vacuo to obtain the crude. The crude was purified through silica gel column chromatography using 3% MeOH/CH$_2$Cl$_2$ to afford compound 467 (210 mg, 70%, over 2 steps) as colorless thick syrup. TLC: 5% MeOH/CH$_2$Cl$_2$ (R$_f$: 0.2); LC-MS: 97.07%; 432.1 (M$^+$+1); (column; Ascentis Express C18, (50×3.0 mm, 2.7 μm); RT 1.95 min. 0.025% Aq. TFA+5% ACN: ACN+5% 0.025% Aq. TFA, 1.2 mL/min).

Synthesis of (2-(4-(4-morpholinobutyl) phenyl) thiazol-5-yl) methanamine hydrochloride (468)

To a stirring solution of compound 467 (210 mg, 0.48 mmol) in CH$_2$Cl$_2$ (10 mL) was added 4 N HCl in 1, 4-dioxane (2 mL) under inert atmosphere at 0° C.; warmed to RT and stirred for 2 h. The reaction was monitored by TLC; after completion of the reaction, the volatiles were removed in vacuo to obtain the crude, which was triturated with EtOAc (2×5 mL), diethyl ether (5 mL) and dried in vacuo to afford compound 468 (160 mg, 90%; HCl salt) as an off-white solid. TLC: 10% MeOH/CH$_2$Cl$_2$ (R$_f$: 0.2); $^1$H NMR (400 MHz, DMSO-d$_6$): δ 11.06 (br s, 1H), 8.57 (br s, 3H), 7.95 (s, 1H), 7.85 (d, J=8.2 Hz, 2H), 7.38 (d, J=8.2 Hz, 2H), 4.33 (q, J=5.4 Hz, 2H), 3.97-3.88 (m, 2H), 3.86-3.74 (m, 2H), 3.42-3.32 (m, 2H), 3.16-2.91 (m, 4H), 2.71-2.62 (m, 2H), 1.80-1.57 (m, 4H);

Synthesis of 4-(4-(5-(aminomethyl) thiazol-2-yl) phenyl)-N-(tert-butyl) butan-1-amine hydrochloride (471)

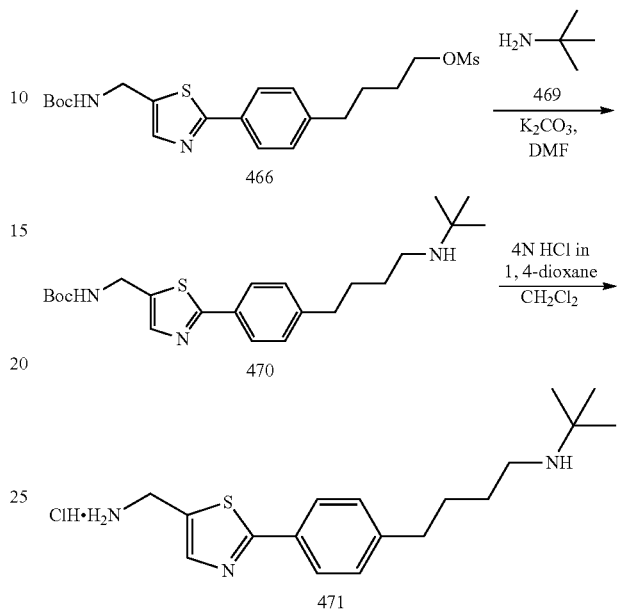

Synthesis of tert-butyl ((2-(4-(4-(tert-butylamino) butyl) phenyl) thiazol-5-yl) methyl) carbamate (470)

To a stirring solution of 4-(4-(5-(((tert-butoxycarbonyl) amino) methyl) thiazol-2-yl) phenyl) butyl methanesulfonate 466 (400 mg, 0.90 mmol) in DMF (10 mL) under inert atmosphere were added 2-methylpropan-2-amine 469 (663 mg, 9.08 mmol) and potassium carbonate (250 mg, 1.81 mmol) in a sealed tube at RT; heated to 70° C. and stirred for 16 h. The reaction was monitored by TLC; after completion of the reaction, the reaction mixture was diluted with water (100 mL) and extracted with EtOAc (2×50 mL). The combined organic extracts were dried over sodium sulfate, filtered and concentrated in vacuo to obtain the crude. The crude was purified through silica gel column chromatography using 8% MeOH/CH$_2$Cl$_2$ to afford crude compound 470 (260 mg) as colorless syrup. TLC: 10% MeOH/CH$_2$Cl$_2$ (R$_f$: 0.3). $^1$H NMR (400 MHz, DMSO-d$_6$): δ 7.95 (s, 1H), 7.79 (d, J=8.2 Hz, 2H), 7.65 (s, 1H), 7.54 (t, J=4.1 Hz, 1H), 7.31 (d, J=8.2 Hz, 2H), 4.32 (d, J=5.8 Hz, 2H), 3.22-3.10 (m, 2H), 2.62 (t, J=7.6 Hz, 2H), 1.67-1.59 (m, 2H), 1.40 (s, 9H), 1.34-1.24 (m, 2H), 1.01 (s, 9H); LC-MS: 98.88%; 191.0 (M$^+$+1); (column; Ascentis Express C18, (50×3.0 mm, 2.7 μm); RT 2.04 min. 0.025% Aq. TFA+5% ACN: ACN+5% 0.025% Aq. TFA, 1.2 mL/min).

Synthesis of 4-(4-(5-(aminomethyl) thiazol-2-yl) phenyl)-N-(tert-butyl) butan-1-amine hydrochloride (471)

To a stirring solution of compound 470 (260 mg, 0.62 mmol) in CH$_2$Cl$_2$ (10 mL) under inert atmosphere was added 4 N HCl in 1, 4-dioxane (5 mL) at 0° C.; warmed to RT and stirred for 3 h. The reaction was monitored by TLC;

after completion of the reaction, the volatiles were removed in vacuo to obtain the crude, which was triturated with diethyl ether (5 mL) and dried in vacuo to afford compound 471 (190 mg, 86%; HCl salt) as an off-white solid. TLC: 10% MeOH/CH$_2$Cl$_2$ (R$_f$: 0.2); $^1$H NMR (500 MHz, DMSO-d$_6$): δ 8.89-8.54 (m, 3H), 7.96 (s, 1H), 7.85 (d, J=8.1 Hz, 2H), 7.38 (d, J=8.1 Hz, 2H), 4.64 (br s, 2H), 4.37-4.31 (m, 2H), 2.89-2.79 (m, 2H), 2.70-2.66 (m, 2H), 1.27 (s, 13H); LC-MS: 98.49%; 318.1 (M$^+$+1); (column; Ascentis Express C18, (50×3.0 mm, 2.7 μm); RT 1.37 min. 0.025% Aq.TFA+5% ACN: ACN+5% 0.025% Aq. TFA, 1.2 mL/min).

Synthesis of (2-(4-(4-(piperidin-1-yl) butyl) phenyl) thiazol-5-yl) methanamine hydrochloride (474)

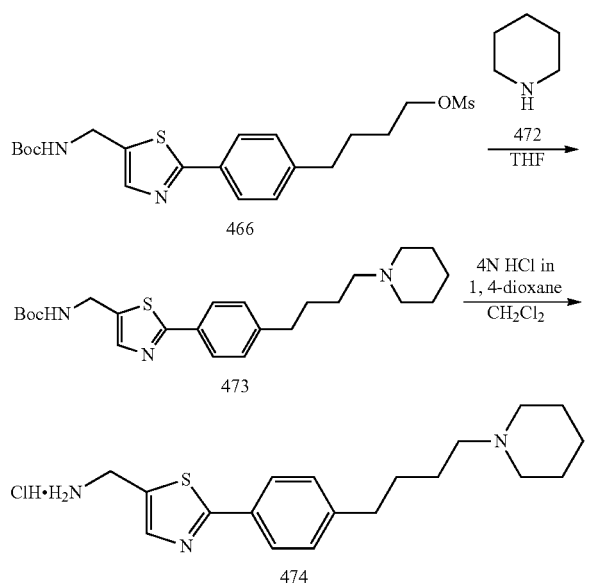

Synthesis of tert-butyl 42-(4-(4-(piperidin-1-yl) butyl) phenyl) thiazol-5-yl) methyl) carbamate (473)

To a stirring solution of 4-(4-(5-(((tert-butoxycarbonyl) amino) methyl) thiazol-2-yl) phenyl) butyl methanesulfonate 466 (330 mg, 0.75 mmol) in THF (5 mL) in a sealed tube under inert atmosphere was added piperidine 472 (2 mL) at RT; heated to 90° C. and stirred for 6 h. The reaction was monitored by TLC; after completion of the reaction, the volatiles were removed in vacuo. The crude was purified through silica gel column chromatography using 5% MeOH/CH$_2$Cl$_2$ to afford compound 473 (220 mg, 69%) as brown syrup. TLC: 10% MeOH/CH$_2$Cl$_2$ (R$_f$: 0.2); $^1$H NMR (DMSO-d$_6$, 400 MHz): δ 7.79 (d, J=8.2 Hz, 2H), 7.65 (s, 1H), 7.54 (t, J=5.0 Hz, 1H), 7.30 (d, J=8.2 Hz, 2H), 4.32 (d, J=6.0 Hz, 2H), 2.62 (t, J=7.5 Hz, 2H), 2.31-2.15 (m, 4H), 1.63-1.55 (m, 2H), 1.50-1.42 (m, 6H), 1.40 (s, 9H), 1.37-1.32 (m, 4H); LC-MS: 97.07%; 432.1 (M$^+$+1); (column; Ascentis Express C18, (50×3.0 mm, 2.7 μm); RT 1.95 min. 0.025% Aq. TFA+5% ACN: ACN+5% 0.025% Aq. TFA, 1.2 mL/min).

Synthesis of (2-(4-(4-(piperidin-1-yl) butyl) phenyl) thiazol-5-yl) methanamine hydrochloride (474)

To a stirring solution of compound 473 (210 mg, 0.48 mmol) in CH$_2$Cl$_2$ (5 mL) under inert atmosphere was added 4 N HCl in 1, 4-dioxane (3 mL) at 0° C.; warmed to RT and stirred for 4 h. The reaction was monitored by TLC; after completion of the reaction, the volatiles were removed in vacuo to obtain the crude, which was triturated with diethyl ether (2×50 mL), hexane (25 mL) and dried in vacuo to afford compound 474 (170 mg, HCl salt) as brown solid. TLC: 10% MeOH/CH$_2$Cl$_2$ (R$_f$: 0.2); $^1$H NMR (400 MHz, DMSO-d$_6$): δ 10.34 (br s, 1H), 8.63 (br s, 3H), 7.96 (s, 1H), 7.85 (d, J=8.2 Hz, 2H), 7.37 (d, J=8.2 Hz, 2H), 4.33 (q, J=5.6 Hz, 2H), 3.42-3.30 (m, 2H), 3.06-2.92 (m, 2H), 2.86-2.75 (m, 2H), 2.67 (t, J=7.5 Hz, 2H), 1.85-1.59 (m, 10H);

Synthesis of 4-(4-(5-(aminomethyl) thiazol-2-yl) phenyl)-N, N-diethylbutan-1-amine hydrochloride (476)

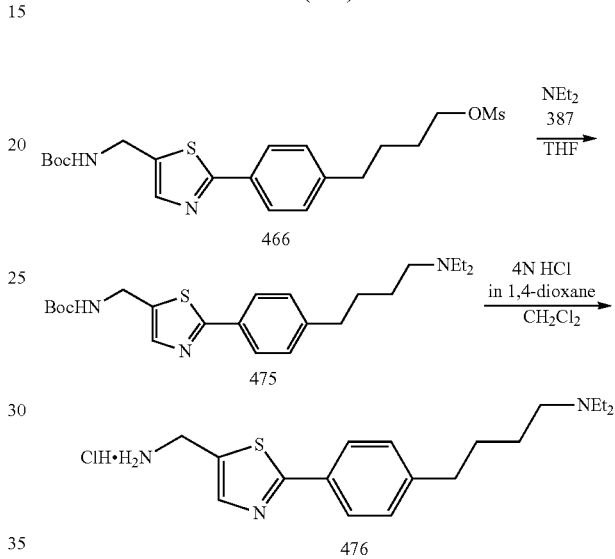

Synthesis of tert-butyl ((2-(4-(4-(diethylamino) butyl) phenyl) thiazol-5-yl) methyl) carbamate (475)

To a stirring solution of 4-(4-(5-(((tert-butoxycarbonyl) amino) methyl) thiazol-2-yl) phenyl) butyl methanesulfonate 466 (340 mg, 0.77 mmol) in THF (10 mL) under inert atmosphere was added diethylamine 387 (3 mL) in a sealed tube at RT; heated to 90° C. and stirred for 6 h. The reaction was monitored by TLC; after completion of the reaction, the volatiles were removed in vacuo to obtain the crude. The crude was purified through silica gel column chromatography using 5% MeOH/CH$_2$Cl$_2$+aqueous ammonia (0.5 mL) to afford compound 475 (250 mg, 78%) as colorless syrup. TLC: 10% MeOH/CH$_2$Cl$_2$ (R$_f$: 0.2). $^1$H-NMR (DMSO-d$_6$, 400 MHz): δ 7.77 (d, J=8.1 Hz, 2H), 7.63 (s, 1H), 7.52 (t, J=5.5 Hz, 1H), 7.28 (d, J=8.1 Hz, 2H), 4.30 (d, J=5.8 Hz, 2H), 2.60 (t, J=7.6 Hz, 2H), 2.42-2.26 (m, 8H), 1.56 (p, J=7.5 Hz, 2H), 1.37 (s, 9H), 0.90 (t, J=7.1 Hz, 6H); LC-MS: 99.61%; 418.2 (M$^+$+1); (column; Ascentis Express C18, (50×3.0 mm, 2.7 μm); RT 2.04 min. 0.025% Aq. TFA+5% ACN: ACN+5% 0.025% Aq. TFA, 1.2 mL/min).

Synthesis of 4-(4-(5-(aminomethyl) thiazol-2-yl) phenyl)-N, N-diethylbutan-1-amine hydrochloride (476)

To a stirring solution of compound 475 (250 mg, 0.59 mmol) in CH$_2$Cl$_2$ (5 mL) under inert atmosphere was added 4 N HCl in 1, 4-dioxane (2 mL) at 0° C.; warmed to RT and stirred for 4 h. The reaction was monitored by TLC; after completion of the reaction, the volatiles were removed in vacuo to obtain the crude, which was triturated with diethyl ether (5 mL), n-hexane (5 mL) and dried in vacuo to afford compound 476 (150 mg, 71%; HCl salt) as an off-white solid. TLC: 10% MeOH/CH$_2$Cl$_2$ (R$_f$: 0.2); $^1$H-NMR (DMSO-d$_6$, 400 MHz): δ 10.51-10.23 (m, 1H), 8.63 (br s, 2H), 7.96 (s, 1H), 7.85 (d, J=8.2 Hz, 2H), 7.38 (d, J=8.2 Hz, 2H), 4.33 (q, J=5.5 Hz, 2H), 3.12-2.99 (m, 6H), 2.71-2.65 (m, 2H), 1.75-1.61 (m, 4H), 1.20 (t, J=7.2 Hz, 6H); LC-MS: 99.36%; 318.1 (M$^+$+1); (column; Ascentis Express C18, (50×3.0 mm, 2.7 μm); RT 1.35 min. 0.025% Aq. TFA+5% ACN: ACN+5% 0.025% Aq. TFA, 1.2 mL/min).

Synthesis of N-(4-(4-(5-(aminomethyl) thiazol-2-yl) phenyl) butyl) acetamide hydrochloride (480)

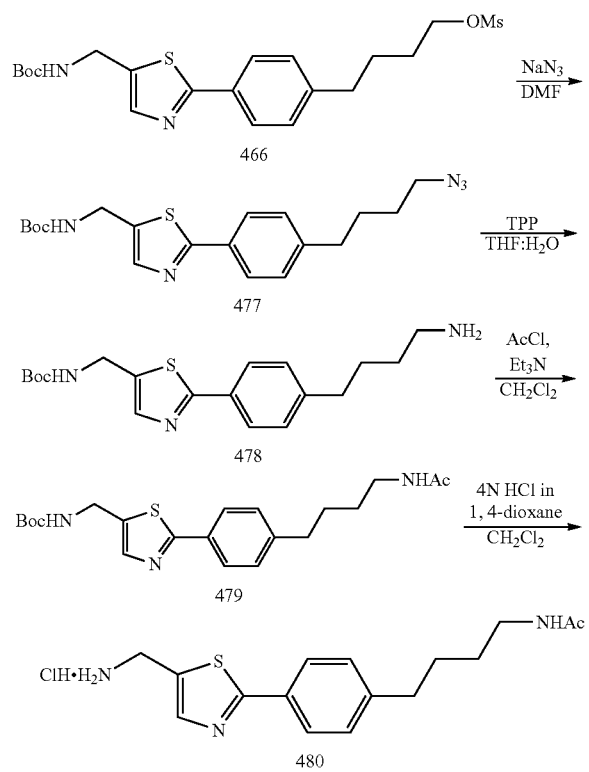

Synthesis of tert-butyl ((2-(4-(4-azidobutyl) phenyl) thiazol-5-yl) methyl) carbamate (477)

To a stirring solution of 4-(4-(5-(((tert-butoxycarbonyl) amino) methyl) thiazol-2-yl) phenyl) butyl methanesulfonate 466 (510 mg, 1.15 mmol) in DMF (10 mL) under inert atmosphere was added sodium azide (113 mg, 1.70 mmol) at RT and heated to 70° C. and stirred for 16 h. The reaction was monitored by TLC; after completion of the reaction, the reaction mixture was diluted water (50 mL) and extracted with EtOAc (2×75 mL). The combined organic extracts were dried over sodium sulfate, filtered and concentrated in vacuo to obtain crude compound 477 (550 mg) as pale yellow oil. TLC: 5% MeOH/CH$_2$Cl$_2$ (R$_f$: 0.8);

Synthesis of tert-butyl ((2-(4-(4-aminobutyl) phenyl) thiazol-5-yl) methyl) carbamate (478)

To a stirring solution of compound 477 (550 mg, crude) in THF:H$_2$O (4:1, 30 mL) was added triphenyl phosphine (446 mg, 1.70 mmol) at 0° C.; warmed to RT and stirred for 16 h. The reaction was monitored by TLC; after completion of the reaction, the volatiles were removed in vacuo. The residue was diluted water (50 mL) and extracted with 10% MeOH/CH$_2$Cl$_2$ (2×50 mL). The combined organic extracts were dried over sodium sulfate, filtered and concentrated to obtain the crude. The crude was purified through silica gel column chromatography using 10% MeOH/CH$_2$Cl$_2$ to afford compound 478 (160 mg, 31%) as an off-white solid. TLC: 10% MeOH/CH$_2$Cl$_2$ (R$_f$: 0.2); LC-MS: 97.99%; 362.1 (M$^+$+1); (column; Ascentis Express C18, (50×3.0 mm, 2.7 μm); RT 1.95 min. 0.025% Aq. TFA+5% ACN: ACN+5% 0.025% Aq. TFA, 1.2 mL/min).

Synthesis of tert-butyl ((2-(4-(4-acetamidobutyl) phenyl) thiazol-5-yl) methyl) carbamate (479)

To a stirring solution of compound 478 (160 mg, 0.44 mmol) in CH$_2$Cl$_2$ (10 mL) under inert atmosphere were added triethyl amine (0.12 mL, 0.88 mmol), acetyl chloride (52 mg, 0.66 mmol) at 0° C.; warmed to RT and stirred for 4 h. The reaction was monitored by TLC; after completion of the reaction, the reaction mixture was quenched with ice-cold water (50 mL) and extracted with EtOAc (2×75 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 479 (140 mg, 78%) as thick syrup. TLC: 10% MeOH/CH$_2$Cl$_2$ (R$_f$: 0.8); LC-MS: 98.01%; 404.1 (M$^+$+1); (column; Ascentis Express C-18, (50×3.0 mm, 2.7 μm); RT 2.29 min. 0.025% Aq. TFA+5% ACN: ACN+5% 0.025% Aq. TFA, 1.2 mL/min);

Synthesis of N-(4-(4-(5-(aminomethyl) thiazol-2-yl) phenyl) butyl) acetamide hydrochloride (480)

To a stirring solution of compound 479 (140 mg, 0.34 mmol) in CH$_2$Cl$_2$ (10 mL) under inert atmosphere was added 4 N HCl in 1, 4-dioxane (3 mL) at 0° C.; warmed to RT and stirred for 3 h. The reaction was monitored by TLC; after completion of the reaction, the volatiles were removed in vacuo to obtain the crude, which was triturated with EtOAc (2×5 mL), diethyl ether (2×5 mL) and dried in vacuo to afford compound 480 (100 mg, 89%; HCl salt) as an off-white solid. TLC: 5% MeOH/CH$_2$Cl$_2$ (R$_f$: 0.2); $^1$H NMR (DMSO-d$_6$, 400 MHz) δ=8.64 (br s, 3H), 7.95 (s, 1H), 7.83 (d, J=7.9 Hz, 2H), 7.34 (d, J=8.0 Hz, 2H), 4.32 (q, J=5.5 Hz, 2H), 3.09-3.00 (m, 2H), 2.63 (t, J=7.6 Hz, 2H), 1.78 (s, 3H), 1.59 (p, J=7.4 Hz, 2H), 1.41 (p, J=7.2 Hz, 2H); LC-MS: 98.49%; 304.1 (M$^+$+1); (column; Ascentis Express C18, (50×3.0 mm, 2.7 μm); RT 1.48 min. 0.025% Aq. TFA+5% ACN: ACN+5% 0.025% Aq. TFA, 1.2 mL/min).

Synthesis of 4-(4-(5-(aminomethyl) thiazol-2-yl) phenyl)-N-isopropyl-N-methylbutan-1-amine hydrochloride (482)

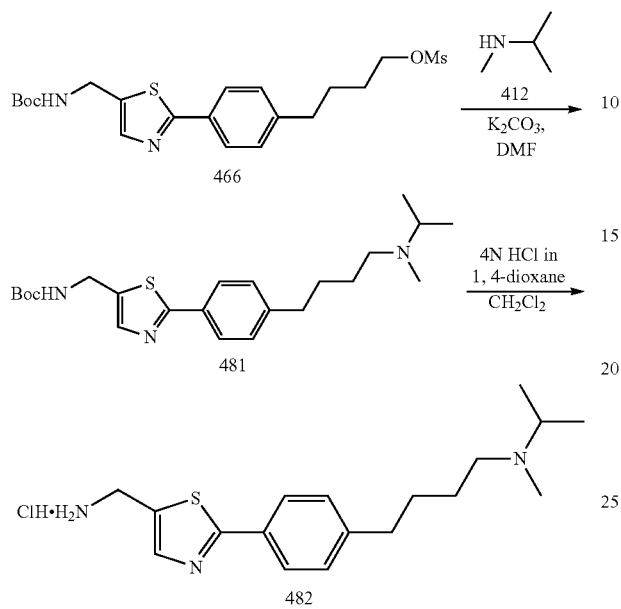

Synthesis of tert-butyl ((2-(4-(4-(isopropyl(methyl) amino) butyl) phenyl) thiazol-5-yl) methyl) carbamate (481)

To a stirring solution of 4-(4-(5-(((tert-butoxycarbonyl) amino) methyl) thiazol-2-yl) phenyl) butyl methanesulfonate 466 (100 mg, 0.22 mmol) in DMF (5 mL) under inert atmosphere were added N-methylpropan-2-amine 412 (50 mg, 0.68 mmol) and potassium carbonate (62 mg, 0.45 mmol) in a sealed tube at RT and stirred for 16 h. The reaction was monitored by TLC; after completion of the reaction, the reaction mixture was diluted with water (50 mL) and extracted with EtOAc (2×50 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 481 (80 mg) as colorless syrup. TLC: 5% MeOH/CH$_2$Cl$_2$ (R$_f$: 0.2). LC-MS: 80.36%; 418.1 (M$^+$+1); (column; Ascentis Express C18, (50×3.0 mm, 2.7 µm); RT 2.00 min. 0.025% Aq. TFA+5% ACN: ACN+5% 0.025% Aq. TFA, 1.2 mL/min).

Synthesis of 4-(4-(5-(aminomethyl) thiazol-2-yl) phenyl)-N-isopropyl-N-methylbutan-1-amine hydrochloride (482)

To a stirring solution of compound 481 (80 mg, 0.19 mmol) in CH$_2$Cl$_2$ (5 mL) was added 4 N HCl in 1, 4-dioxane (1 mL) under inert atmosphere at 0° C.; warmed to RT and stirred for 2 h. The reaction was monitored by TLC; after completion of the reaction, the volatiles were removed in vacuo to obtain the crude, which was triturated with EtOAc (2×4 mL), diethyl ether (2×4 mL) and dried in vacuo to afford compound 482 (60 mg, HCl salt) as an off-white solid. TLC: 10% MeOH/CH$_2$Cl$_2$ (R$_f$: 0.2); $^1$H-NMR (DMSO-d$_6$, 400 MHz): δ 10.02 (br s, 1H), 8.53 (br s, 3H), 7.95 (s, 1H), 7.86 (d, J=8.1 Hz, 2H), 7.38 (d, J=8.7 Hz, 2H), 4.34 (q, J=5.2 Hz, 2H), 3.53-3.45 (m, 2H), 3.13-3.03 (m, 1H), 2.99-2.88 (m, 1H), 2.68 (br t, J=7.5 Hz, 2H), 2.60 (d, J=4.6 Hz, 3H), 1.79-1.54 (m, 4H), 1.31-1.17 (m, 6H); LC-MS: 83.54%; 318.1 (M$^+$+1); (column; Ascentis Express C18, (50×3.0 mm, 2.7 µm); RT 1.33 min. 0.025% Aq. TFA+5% ACN: ACN+5% 0.025% Aq. TFA, 1.2 mL/min).

Synthesis of N-(4-(4-(5-(aminomethyl) thiazol-2-yl) phenyl) butyl)-N-methylcyclopropanamine hydrochloride (484)

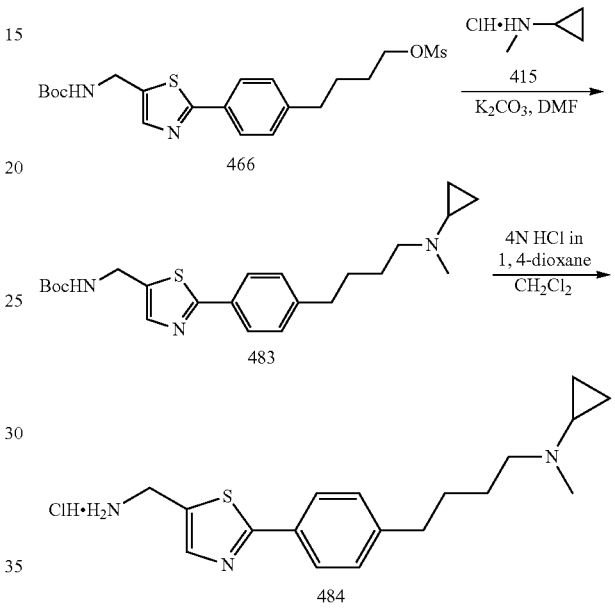

Synthesis of tert-butyl ((2-(4-(4-(cyclopropyl (methyl) amino) butyl) phenyl) thiazol-5-yl) methyl) carbamate (483)

To a stirring solution of 4-(4-(5-(((tert-butoxy carbonyl) amino) methyl) thiazol-2-yl) phenyl) butyl methanesulfonate 466 (200 mg, 0.45 mmol) in DMF (5 mL) under inert atmosphere were added N-methylcyclopropanamine hydrochloride 415 (98 mg, 0.90 mmol) and potassium carbonate (125 mg, 0.90 mmol) in a sealed tube at RT and stirred for 48 h. The reaction was monitored by TLC; after completion of the reaction, the reaction mixture was diluted with water (100 mL) and extracted with EtOAc (2×75 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 483 (80 mg, 43%) as colorless thick syrup. TLC: 10% MeOH/CH$_2$Cl$_2$ (R$_f$: 0.2). LC-MS: 99.65%; 416.1 (M$^+$+1); (column; Ascentis Express C18, (50×3.0 mm, 2.7 µm); RT 2.02 min. 0.025% Aq. TFA+5% ACN: ACN+5% 0.025% Aq. TFA, 1.2 mL/min).

Synthesis of N-(4-(4-(5-(aminomethyl) thiazol-2-yl) phenyl) butyl)-N-methylcyclopropanamine hydrochloride (484)

To a stirring solution of compound 483 (220 mg, 0.53 mmol) in CH$_2$Cl$_2$ (10 mL) was added 4 N HCl in 1, 4-dioxane (3 mL) under inert atmosphere at 0° C.; warmed to RT and stirred for 2 h. The reaction was monitored by TLC; after completion of the reaction, the volatiles were removed in vacuo to obtain the crude, which was triturated with EtOAc (2×10 mL), diethyl ether (2×10 mL) and dried in vacuo to afford compound 484 (125 mg, 72%; HCl salt) as colorless thick syrup. TLC: 10% MeOH/CH$_2$Cl$_2$ (R$_f$: 0.2); $^1$H NMR (DMSO-d$_6$, 400 MHz): δ 10.14 (br s, 1H), 8.45 (br s, 3H), 7.94 (s, 1H), 7.86 (d, J=8.3 Hz, 2H), 7.38 (d, J=8.3 Hz, 2H), 4.34 (q, J=5.5 Hz, 2H), 3.24-3.14 (m, 2H), 2.78 (d, J=4.8 Hz, 3H), 2.72-2.65 (m, 2H), 1.86-1.57 (m, 4H), 1.13-0.91 (m, 2H), 0.89-0.70 (m, 2H); LC-MS: 94.90%; 316.1 (M$^+$+1); (column; Ascentis Express C18, (50×3.0 mm, 2.7 μm); RT 1.34 min. 0.025% Aq. TFA+5% ACN: ACN+5% 0.025% Aq. TFA, 1.2 mL/min).

Synthesis of 1-(5-(aminomethyl) thiazol-2-yl) piperidin-4-one hydrochloride (488)

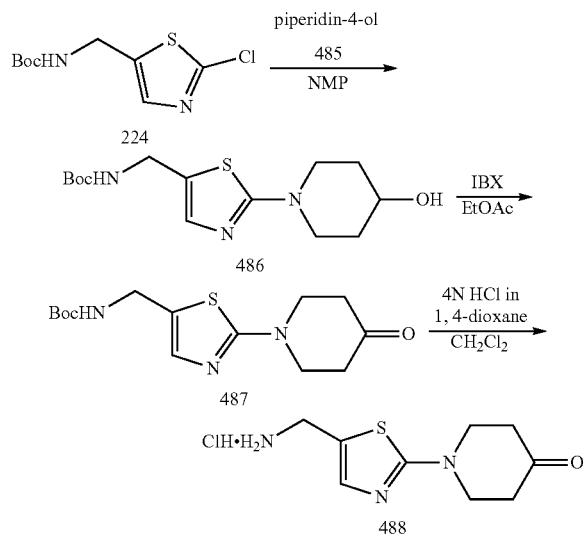

Synthesis of tert-butyl ((2-(4-hydroxypiperidin-1-yl) thiazol-5-yl) methyl) carbamate (486)

To a stirring solution tert-butyl ((2-chlorothiazol-5-yl) methyl) carbamate 224 (500 mg, 2.01 mmol) in N-methyl pyrrolidinone (10 mL) under inert atmosphere were added piperidin-4-ol 485 (408 mg, 4.03 mmol) and diisopropylethylamine (1.8 mL, 10.08 mmol) in a sealed tube and heated to 160° C. and stirred for 16 h. The reaction was monitored by TLC and LC-MS; after completion the reaction mixture was diluted with water (50 mL) and extracted with EtOAc (2×50 mL). The combined organic extracts were dried over sodium sulphate, filtered and concentrated in vacuo to obtain the crude. The crude was purified through silica gel column chromatography using 4% MeOH/CH$_2$Cl$_2$ to afford compound 486 (350 mg, 55%) as sticky solid. TLC: 5% MeOH/CH$_2$Cl$_2$ (R$_f$: 0.3); $^1$H-NMR (DMSO-d$_6$, 500 MHz): δ 7.29 (t, J=5.5 Hz, 1H), 6.88 (s, 1H), 4.74 (d, J=4.0 Hz, 1H), 4.08 (d, J=5.8 Hz, 2H), 4.05-4.01 (m, 1H), 3.72-3.60 (m, 3H), 3.15-3.07 (m, 2H), 1.85-1.71 (m, 2H), 1.45-1.40 (m, 2H), 1.38 (s, 9H); LC-MS: 99.03%; 314.0 (M$^+$+1); (column; Ascentis Express C18, (50×3.0 mm, 2.7 μm); RT 1.54 min. 0.025% Aq. TFA+5% ACN: ACN+5% 0.025% Aq. TFA, 1.2 mL/min).

Synthesis of tert-butyl ((2-(4-oxopiperidin-1-yl) thiazol-5-yl) methyl) carbamate (487)

To a stirring solution of compound 486 (1.7 g, 5.43 mmol) in EtOAc (40 mL) under inert atmosphere was added iodoxybenzoic acid (3.04 g, 10.86 mmol) at 0° C.; heated to 70° C. and stirred for 16 h. The reaction was monitored by TLC; after completion of the reaction, the reaction mixture was filtered through celite. The titrate was concentrated in vacuo to obtain the crude. The crude was purified through silica gel column chromatography using 3% MeOH/CH$_2$Cl$_2$ to afford compound 487 (650 mg, crude) as colorless syrup. TLC: 5% MeOH/CH$_2$Cl$_2$ (R$_f$: 0.6); LC-MS: 48.21%; 312.2 (M$^+$+1); (Column; X-select CSH C-18 (50×3 mm, 2.5 μm); RT 3.37 min. 0.025% Aq. TFA+5% ACN: ACN+5% 0.025% Aq. TFA, 1.0 mL/min).

Synthesis of 1-(5-(aminomethyl) thiazol-2-yl) piperidin-4-one hydrochloride (488)

To a stirring solution of compound 487 (750 mg, crude) in CH$_2$Cl$_2$ (10 mL) under inert atmosphere was added 4 N HCl in 1, 4-dioxane (1 mL) at 0° C.; warmed to RT and stirred for 3 h. The reaction was monitored by TLC; after completion of the reaction, the volatiles were removed in vacuo. The crude was washed with EtOAc (5 mL) and dried in vacuo to afford compound 488 (450 mg, 76%, HCl salt) as an off-white solid. TLC: 5% MeOH/CH$_2$Cl$_2$ (R$_f$: 0.1); $^1$H-NMR (DMSO-d$_6$, 500 MHz): δ 8.36 (br s, 3H), 7.30 (s, 1H), 4.10 (q, J=5.6 Hz, 2H), 3.83-3.78 (m, 4H), 2.52-2.49 (m, 4H);

Synthesis of 1-(5-(aminomethyl) thiazol-2-yl)-1, 4-diazepan-5-one hydrochloride (492)

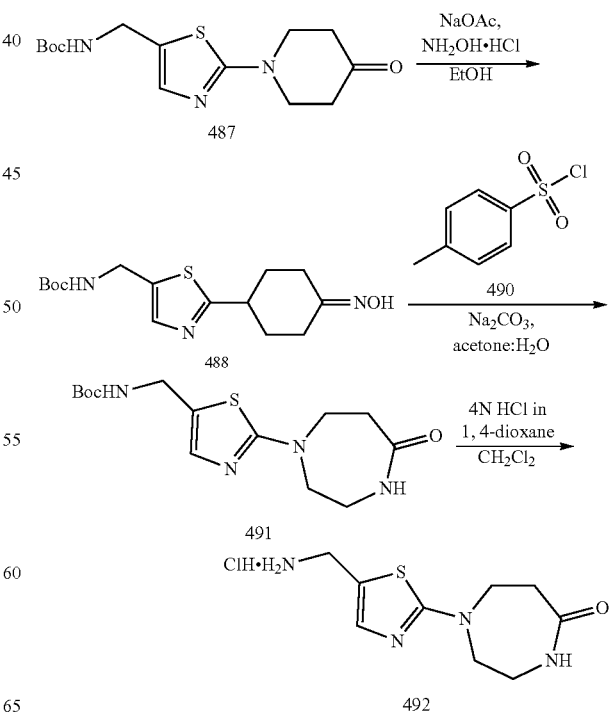

Synthesis of tert-butyl ((2-(4-(hydroxyimino) cyclohexyl) thiazol-5-yl) methyl) carbamate (488)

To a stirring solution of compound 487 (900 mg, 2.89 mmol) in EtOH (25 mL) under argon atmosphere were added hydroxylamine hydrochloride (402 mg, 5.78 mmol) and sodium acetate (474 mg, 5.78 mmol) at RT; heated to reflux and stirred for 12 h. The reaction was monitored by TLC; after completion of the reaction, the reaction mixture was filtered washed with EtOAc and filtrate was concentrated in vacuo. The residue was diluted with water (20 mL) and extracted with EtOAc (2×20 mL). The combined organic extracts were washed with water and dried over sodium sulfate, filtered and concentrated in vacuo to afford compound 488 (920 mg crude) as brown syrupy. TLC: 5% MeOH/CH$_2$Cl$_2$ (R$_f$: 0.4); $^1$H-NMR (DMSO-d$_6$, 500 MHz): δ 13.15 (br s, 1H), 8.29 (br s, 3H), 8.14 (s, 1H), 8.05 (s, 1H), 7.76 (d, J=8.1 Hz, 2H), 7.69 (dd, J=8.4, 1.7 Hz, 1H), 7.65-7.62 (m, 1H), 7.56 (d, J=8.4 Hz, 2H), 4.07 (q, J=5.8 Hz, 2H); LC-MS: 65.42%; 327.0 (M$^+$+2); (column; Ascentis Express C18, (50×3.0 mm, 2.7 μm); RT 1.63 min. 0.025% Aq. TFA+5% ACN: ACN+5% 0.025% Aq. TFA, 1.2 mL/min).

Synthesis of tert-butyl ((2-(5-oxo-1, 4-diazepan-1-yl) thiazol-5-yl) methyl) carbamate (491)

To a stirring solution of compound 488 (900 mg, 2.75 mmol) in acetone (5 mL) was added sodium carbonate (875 mg, 8.25 mmol in 15 mL water) in water (15 mL) and stirred for 5 min. To this was added p-toluene sulfonyl chloride 490 (786 mg, 4.12 mmol) at RT; and stirred for 16 h. The reaction was monitored by TLC; after completion of the reaction, the volatiles were removed in vacuo. The residue was diluted with water (20 mL) and extracted with CH$_2$Cl$_2$ (2×20 mL). The combined organic extracts were dried over sodium sulfate, filtered and concentrated in vacuo to obtain the crude. The crude was purified through silica gel column chromatography using 8% MeOH/CH$_2$Cl$_2$ to afford compound 491 (460 mg, 51%) as an off-white solid. TLC: 5% MeOH/CH$_2$Cl$_2$ (R$_f$: 0.4); $^1$H-NMR (DMSO-d$_6$, 500 MHz): δ 13.15 (br s, 1H), 8.29 (br s, 3H), 8.14 (s, 1H), 8.05 (s, 1H), 7.76 (d, J=8.1 Hz, 2H), 7.69 (dd, J=8.4, 1.7 Hz, 1H), 7.65-7.62 (m, 1H), 7.56 (d, J=8.4 Hz, 2H), 4.07 (q, J=5.8 Hz, 2H); LC-MS: 87.76%; 327.0 (M$^+$+1); (column; Ascentis Express C18, (50×3.0 mm, 2.7 μm); RT 1.56 min. 0.025% Aq. TFA+5% ACN: ACN+5% 0.025% Aq. TFA, 1.2 mL/min).

Synthesis of 1-(5-(aminomethyl) thiazol-2-yl)-1, 4-diazepan-5-one hydrochloride (492)

To a stirring solution of compound 491 (450 mg, 1.38 mmol) in CH$_2$Cl$_2$ (10 mL) under argon atmosphere was added 4 N HCl in 1, 4-dioxane (15 mL) at 0° C.; warmed to RT and stirred for 6 h. The reaction was monitored by TLC; after completion of the reaction, the volatiles were removed in vacuo. The crude washed with diethyl ether (40 mL), hexane (30 mL) and dried in vacuo to afford compound 492 (300 mg crude) as off-white solid. TLC: 10% MeOH/CH$_2$Cl$_2$ (R$_f$: 0.4); $^1$H-NMR (DMSO-d$_6$, 500 MHz): δ 13.15 (br s, 1H), 8.29 (br s, 3H), 8.14 (s, 1H), 8.05 (s, 1H), 7.76 (d, J=8.1 Hz, 2H), 7.69 (dd, J=8.4, 1.7 Hz, 1H), 7.65-7.62 (m, 1H), 7.56 (d, J=8.4 Hz, 2H); LC-MS: 85.76%; 227 (M$^+$+1); (column; Kinetex EVO C-18, (50×3.0 mm, 2.6 μm); RT 0.36 min. 2.5 mM Aq. NH4OOCH+5% ACN: ACN+5% 2.5 mM Aq.NH$_4$OOCH, 0.8 mL/min).

Synthesis of (2-(morpholinomethyl) thiazol-5-yl) methanamine (500)

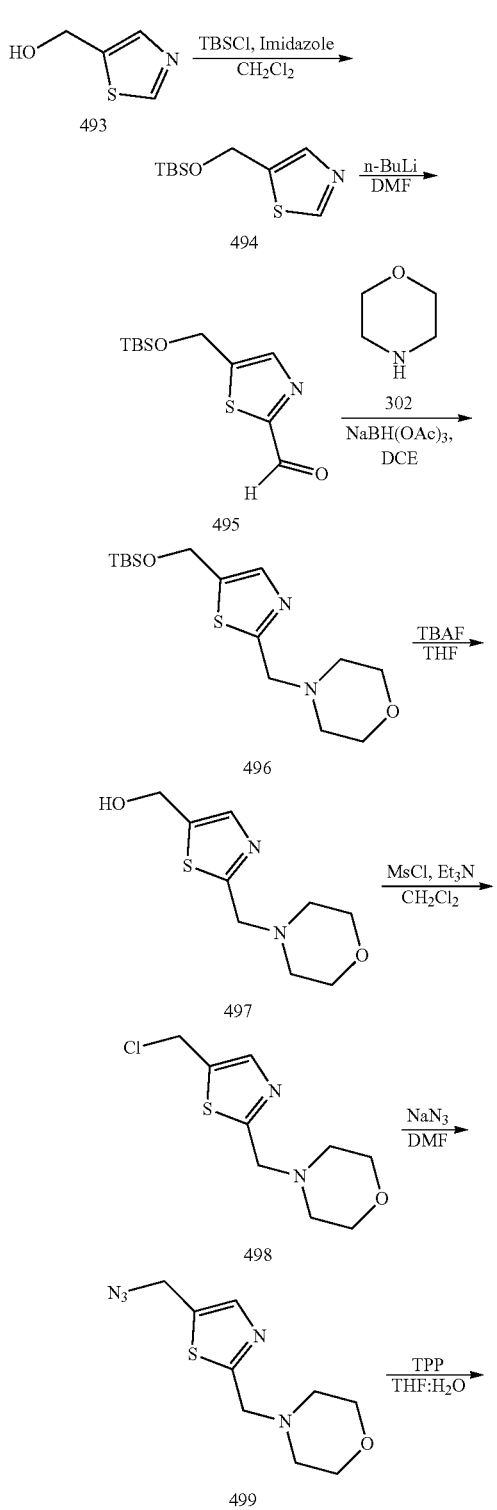

-continued

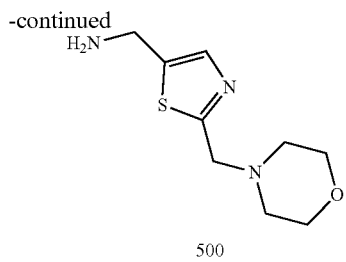

500

Synthesis of 5-(((tert-butyldimethylsilyl) oxy) methyl) thiazole (494)

To a stirring solution of thiazol-5-ylmethanol 493 (10 g, 86.95 mmol) in CH$_2$Cl$_2$ (100 mL) under inert atmosphere were added imidazole (11.82 g, 173.9 mmol) and tert-Butyldimethylsilyl chloride (15.72 g, 104.31 mmol) at 0° C.; warmed to RT and stirred for 2 h. The reaction was monitored by TLC; after completion of the reaction, the reaction mixture was diluted with water (200 mL) and extracted with CH$_2$Cl$_2$ (2×200 mL). The combined organic extracts were dried over sodium sulfate, filtered and concentrated in vacuo to afford compound 494 (19 g, 95%) as pale yellow liquid. TLC: 20% EtOAc/hexanes (R$_f$: 0.4); $^1$H-NMR (DMSO-d$_6$, 400 MHz): δ 9.02 (s, 1H), 7.79 (s, 1H), 4.92 (s, 2H), 0.87 (s, 9H), 0.07 (s, 6H); LC-MS: 99.03%; 229.9 (M$^+$+1); (column; Ascentis Express C18, (50×3.0 mm, 2.7 μm); RT 2.91 min. 0.025% Aq.TFA+5% ACN: ACN+5% 0.025% Aq. TFA, 1.2 mL/min).

Synthesis of 5-(((tert-butyldimethylsilyl) oxy) methyl) thiazole-2-carbaldehyde (495)

To a stirring solution of 5-(((tert-butyldimethylsilyl) oxy) methyl) thiazole compound 494 (2 g, 8.71 mmol) in dry THF (20 mL) under inert atmosphere was added n-butyl lithium (1.6 M solution in hexane, 8.16 mL, 13.07 mmol) dropwise for 10 min at −78° C. and stirred for 1 h. To this was added DMF (1.35 mL, 17.43 mmol) at −78° C. and stirred at the same temperature for 2 h. The reaction was monitored by TLC; after completion of the reaction, the reaction mixture was quenched with saturated ammonium chloride solution (10 mL) and extracted with EtOAc (2×100 mL). The combined organic extracts were dried over sodium sulfate, filtered and concentrated in vacuo to afford compound 495 (2 g, 89%) as colorless liquid. TLC: 30% EtOAc/hexanes (R$_f$: 0.4); $^1$H-NMR (DMSO-d$_6$, 400 MHz): δ 9.89 (s, 1H), 8.10 (s, 1H), 5.02 (s, 2H), 0.89 (s, 9H), 0.10 (s, 6H); LC-MS (Agilent 6310 Ion trap): 98.45%; 258.2 (M$^+$+1); (column; X Select C-18 (50×3.0 mm, 2.5 um); RT 5.02 min. 2.5 mM Aq. NH$_4$OOCH:ACN, 0.8 mL/min).

Synthesis of 4-((5-(((tert-butyldimethylsilyl) oxy) methyl) thiazol-2-yl) methyl) morpholine (496)

To a stirring solution of compound 495 (2 g, 7.78 mmol) in 1, 2-dichloroethane (20 mL) under inert atmosphere were added morpholine (812 mg, 9.33 mmol) and sodium triacetoxyborohydride (3.3 g, 15.56 mmol) at 0° C.; warmed to RT and stirred for 16 h. The reaction was monitored by TLC; after completion of the reaction, the reaction mixture was quenched with ice-cold water (100 mL) and extracted with CH$_2$Cl$_2$ (2×100 mL). The combined organic extracts were dried over sodium sulfate, filtered and concentrated in vacuo to obtain the crude. The crude was purified through silica gel column chromatography using 10-50% EtOAc/hexanes to afford compound 496 (1.3 g, 51%) as colorless thick syrup. TLC: 30% EtOAc/hexanes (R$_f$: 0.1); $^1$H NMR (DMSO-d$_6$, 500 MHz): δ 7.54 (s, 1H), 4.85 (s, 2H), 3.76 (s, 2H), 3.62-3.53 (m, 4H), 2.49-2.45 (m, 4H), 0.86 (s, 9H), 0.07 (s, 6H); LC-MS: 94.28%; 329.0 (M$^+$+1); (column; Ascentis Express C18, (50×3.0 mm, 2.7 μm); RT 2.06 min. 0.025% Aq. TFA+5% ACN: ACN+5% 0.025% Aq. TFA, 1.2 mL/min).

Synthesis of (2-(morpholinomethyl) thiazol-5-yl) methanol (497)

To a stirring solution of compound 496 (1.3 g, 3.96 mmol) in THF (30 mL) under inert atmosphere was added tetra-butylammonium fluoride (1.0 M solution in THF, 3.96 mL, 5.94 mmol) at 0° C.; warmed to RT and stirred for 2 h. The reaction was monitored by TLC; after completion of the reaction, the reaction mixture was quenched with water (100 mL) and extracted with EtOAc (2×100 mL). The combined organic extracts were dried over sodium sulfate, filtered and concentrated in vacuo to obtain the crude. The crude was purified through silica gel flash column chromatography using 10-50% EtOAc/hexanes to afford compound 497 (700 mg, 82%) as thick syrup. TLC: 50% EtOAc/hexanes (R$_f$: 0.1); $^1$H-NMR (DMSO-d$_6$, 400 MHz): δ 7.51 (s, 1H), 5.48 (t, J=5.7 Hz, 1H), 4.63 (dd, J=5.6, 0.8 Hz, 2H), 3.76 (s, 2H), 3.61-3.57 (m, 4H), 2.49-2.45 (m, 4H); LC-MS: 98.60%; 215.0 (M$^+$+1); (column; Kinetex EVO C-18 (50×3.0 mm, 2.6 um); RT 0.94 min. 2.5 mM Aq. NH$_4$OOCH+5% ACN: ACN+5% 2.5 mM Aq.NH$_4$OOCH, 0.8 mL/min);

Synthesis of 4-((5-(chloromethyl) thiazol-2-yl) methyl) morpholine (498)

To a stirring solution of compound 497 (700 mg, 3.25 mmol) in CH$_2$Cl$_2$ (20 mL) under inert atmosphere were added triethyl amine (1.38 mL, 9.74 mmol) at 0° C. and stirred for 10 min. To this was added methanesulfonyl chloride (0.3 mL, 3.90 mmol) at 0° C.; warmed to RT and stirred for 2 h. The reaction was monitored by TLC; after completion of the reaction, the reaction mixture was quenched with saturated NaHCO$_3$ solution (50 mL) and extracted with EtOAc (2×100 mL). The combined organic extracts were dried over sodium sulfate, filtered and concentrated in vacuo to afford crude compound 498 (700 mg, 93%) as pale brown liquid. TLC: 30% EtOAc/hexanes (R$_f$: 0.4); LC-MS: 89.79%; 232.9 (M$^+$+1); (column; Ascentis Express C-18, (50×3.0 mm, 2.7 μm); RT 0.58 min. 0.025% Aq. TFA+5% ACN: ACN+5% 0.025% Aq. TFA, 1.2 mL/min).

Synthesis of 4-((5-(azidomethyl) thiazol-2-yl) methyl) morpholine (499)

To a stirring solution of compound 498 (700 mg, 3.01 mmol) in DMF (20 mL) under inert atmosphere was added sodium azide (580 mg, 9.05 mmol) at 0° C.; warmed to RT and stirred for 16 h. The reaction was monitored by TLC and LC-MS; after completion of the reaction, the reaction mixture was diluted with ice-cold water (100 mL) and extracted with EtOAc (2×100 mL). The combined organic extracts were dried over sodium sulphate, filtered and concentrated in vacuo to obtain the crude. The crude was purified through silica gel flash column chromatography using 10-30% EtOAc/hexanes to afford compound 499 (400 mg, 70%) as colorless thick syrup. TLC: 30% EtOAc/hexanes ($R_f$: 0.5); $^1$H-NMR (DMSO-$d_6$, 400 MHz): δ 7.70 (s, 1H), 4.70 (s, 2H), 3.80 (s, 2H), 3.62-3.58 (m, 4H), 2.51-2.49 (m, 4H);

Synthesis of (2-(morpholinomethyl) thiazol-5-yl) methanamine (500)

To a stirring solution of compound 499 (400 mg, 1.67 mmol) in THF:H$_2$O (4:1, 10 mL) was added triphenyl phosphine (877 mg, 3.34 mmol) at RT and stirred for 16 h. The reaction was monitored by TLC and LC-MS; after completion of the reaction, the reaction mixture was quenched with water (100 mL) and extracted with EtOAc (2×100 mL). The combined organic extracts were dried over sodium sulphate, filtered and concentrated in vacuo to obtain the crude. The crude was purified through silica gel flash column chromatography using 4-5% MeOH/CH$_2$Cl$_2$ to afford compound 500 (200 mg, 56%) as colorless thick syrup. TLC: 10% MeOH/CH$_2$Cl$_2$ ($R_f$: 0.2); $^1$H-NMR (DMSO-$d_6$, 400 MHz): δ 7.48 (s, 1H), 3.90 (s, 2H), 3.74 (s, 2H), 3.63-3.56 (m, 4H), 2.97-2.72 (m, 2H), 2.48-2.45 (m, 4H); LC-MS: 99.68%; 213.9 (M$^+$+1); (Column; X-select CSH C-18 (150×4.6 mm, 3.5 μm); RT 1.31 min. 0.025% Aq. TFA+5% ACN: ACN+5% 0.025% Aq. TFA, 1.0 mL/min).

Synthesis of azepan-3-ol hydrochloride (503)

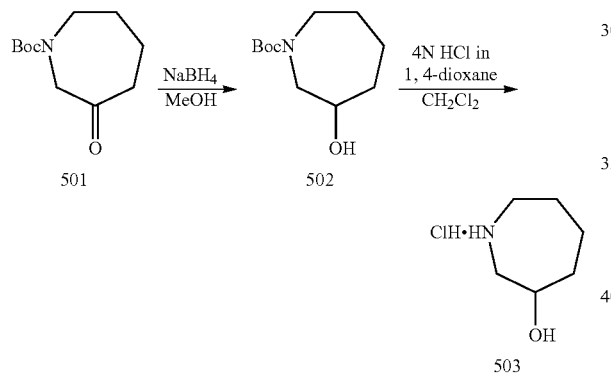

Synthesis of tert-butyl 3-hydroxyazepane-1-carboxylate (502)

To a stirring solution of tert-butyl 3-oxoazepane-1-carboxylate 501 (500 mg, 2.34 mmol) in MeOH (10 mL) under argon atmosphere was added sodium borohydride (134 mg, 3.52 mmol) at 0° C.; warmed to RT and stirred for 4 h. The reaction was monitored by TLC; after completion of the reaction, the reaction mixture was quenched with ice-cold water (20 mL) and extracted with CH$_2$Cl$_2$ (2×50 mL). The combined organic extracts were dried over sodium sulfate and concentrated in vacuo to afford compound 502 (450 mg, 89%) as colorless thick syrup. TLC: 30% EtOAc/hexanes ($R_f$: 0.4); $^1$H-NMR (DMSO-$d_6$, 400 MHz): δ 4.67 (t, J=4.4 Hz, 1H), 3.81-3.43 (m, 3H), 3.08-2.88 (m, 1H), 2.80-2.65 (m, 1H), 1.72-1.58 (m, 4H), 1.56-1.33 (m, 9H), 1.30-1.17 (m, 1H).

Synthesis of azepan-3-ol hydrochloride (503)

To a stirring solution of compound 502 (450 mg, 2.09 mmol) in CH$_2$Cl$_2$ (10 mL) was added 4 N HCl in 1,4-dioxane (2 mL) under inert atmosphere at 0° C.; warmed to RT and stirred for 4 h. The reaction was monitored by TLC; after completion of the reaction, the volatiles were removed in vacuo. The crude was washed with CH$_2$Cl$_2$ (5 mL), n-pentane (10 mL) and dried in vacuo to afford compound 503 (200 mg, 63%) as an off-white solid. TLC: 30% EtOAc/hexanes ($R_f$: 0.1); $^1$H-NMR (DMSO-$d_6$, 400 MHz): δ 9.27 (br s, 1H), 8.52 (br s, 1H), 5.35-5.25 (m, 1H), 4.03-3.96 (m, 1H), 3.15-2.94 (m, 4H), 1.85-1.44 (m, 6H).

Synthesis of (2-(oxazol-5-yl) thiazol-5-yl) methanamine (508)

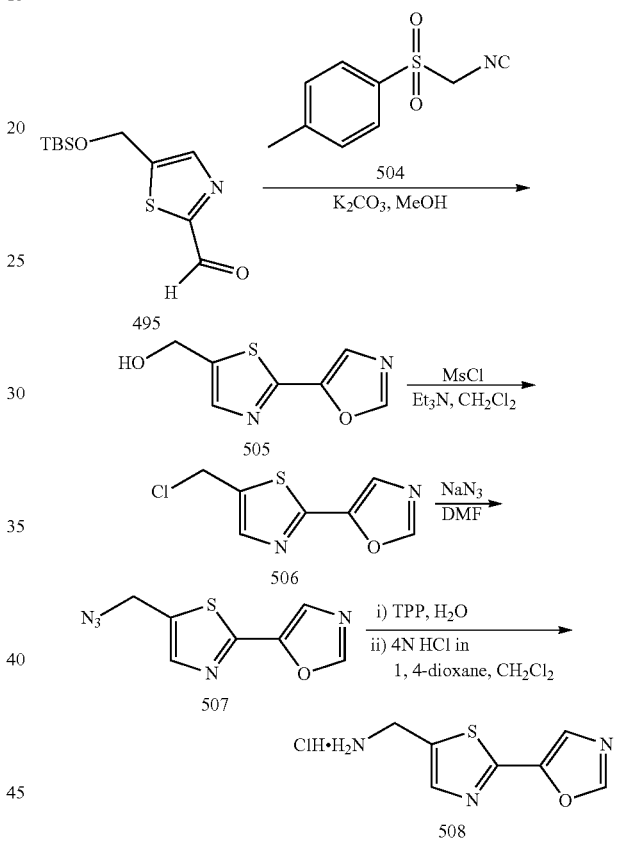

Synthesis of (2-(oxazol-5-yl)thiazol-5-yl)methanol (505)

To a stirring solution of 5-(((tert-butyldimethylsilyl) oxy) methyl) thiazole-2-carbaldehyde 495 (600 mg, 2.33 mmol) in dry THF (20 mL) under inert atmosphere were added 1-((isocyanomethyl) sulfonyl)-4-methylbenzene 504 (455 mg, 2.33 mmol) and potassium carbonate (322 mg, 2.33 mmol) at RT; heated to 80° C. and stirred for 3 h. The reaction was monitored by TLC; after completion of the reaction, the reaction mixture poured into ice-cold water (10 mL) and extracted with CH$_2$Cl$_2$ (2×100 mL). The combined organic extracts were dried over sodium sulfate, filtered and concentrated in vacuo to obtain the crude. The crude was purified through silica gel column chromatography using 3% MeOH/CH$_2$Cl$_2$ to afford compound 505 (200 mg, 53%) as white semi solid. TLC: 50% EtOAc/hexanes ($R_f$: 0.4); $^1$H-NMR (DMSO-$d_6$, 400 MHz): δ 8.56 (s, 1H), 7.80-7.78

(m, 2H), 5.70 (t, J=5.7 Hz, 1H), 4.73 (dd, J=5.6, 0.9 Hz, 2H); LC-MS: 94.97%; 182.9 (M⁺+1); (column; Kinetex EVO C-18 (50×3.0 mm, 2.6 um); RT 1.066 min. 2.5 mM Aq. NH₄OOCH+5% ACN: ACN+5% 2.5 mM Aq.NH₄OOCH, 0.8 mL/min).

Synthesis of 5-(5-(chloromethyl) thiazol-2-yl) oxazole (506)

To a stirring solution of compound 505 (200 mg, 1.09 mmol) in CH₂Cl₂ (5 mL) under inert atmosphere were added triethyl amine (0.317 mL, 2.19 mmol), methanesulfonyl chloride (0.168 mL, 2.19 mmol) at 0° C.; warmed to RT and stirred for 1 h. The reaction was monitored by TLC; after completion of the reaction, the reaction mixture was poured into ice-cold water (50 mL) and extracted with CH₂Cl₂ (2×25 mL). The combined organic extracts were dried over sodium sulfate, filtered and concentrated in vacuo to afford crude compound 506 (200 mg) as colorless syrup. Which was taken forward for next step without further purification. TLC: 20% EtOAc/hexanes (R$_f$: 0.8);

Synthesis of 5-(5-(azidomethyl) thiazol-2-yl) oxazole (507)

To a stirring solution of compound 506 (200 mg, crude) in DMF (5 mL) under inert atmosphere was added sodium azide (130 mg, 2.00 mmol) at 0° C.; warmed to RT and stirred for 16 h. The reaction was monitored by TLC; after completion of the reaction, the reaction mixture was poured into ice-cold water (50 mL) and extracted with EtOAc (2×100 mL). The combined organic extracts were dried over sodium sulfate, filtered and concentrated in vacuo to obtain the crude. The crude was purified through silica gel column chromatography using 20% EtOAc/hexanes to afford compound 507 (100 mg, 48%) as thick brown syrup. TLC: 20% EtOAc/hexanes (R$_f$: 0.6); ¹H-NMR (DMSO-d₆, 400 MHz): δ 8.60 (s, 1H), 7.98 (s, 1H), 7.86 (s, 1H), 4.83 (s, 2H); LC-MS: 95.22%; 207.9 (M⁺+1); (column; Kinetex EVO C-18 (50×3.0 mm, 2.6 um); RT 2.00 min. 2.5 mM Aq. NH₄OOCH+5% ACN: ACN+5% 2.5 mM Aq.NH₄OOCH, 0.8 mL/min).

Synthesis of (2-(oxazol-5-yl) thiazol-5-yl) methanamine hydrochloride (508)

To a stirring solution of compound 507 (100 mg, 0.48 mmol) in THF:H₂O (4:1, 5 mL) was added triphenyl phosphine (253 mg, 0.96 mmol) at RT and stirred for 6 h. The reaction was monitored by TLC and LC-MS; after completion of the reaction; the volatiles were removed in vacuo to obtain the crude amine (200 mg crude).

To the above crude amine (200 mg) in CH₂Cl₂ (5 mL) was added 4 N HCl in 1, 4-dioxane (1 mL) under inert atmosphere at 0° C.; warmed to RT and stirred for 1 h. The reaction was monitored by TLC; after completion of the reaction, the volatiles were removed in vacuo. The crude washed with EtOAc (5 mL) and dried in vacuo to afford compound 508 (85 mg, HCl salt, crude) as an off-white solid. TLC: 5% MeOH/CH₂Cl₂ (R$_f$: 0.1);

Synthesis of (2-(oxazol-2-yl) thiazol-5-yl) methanamine hydrochloride (512)

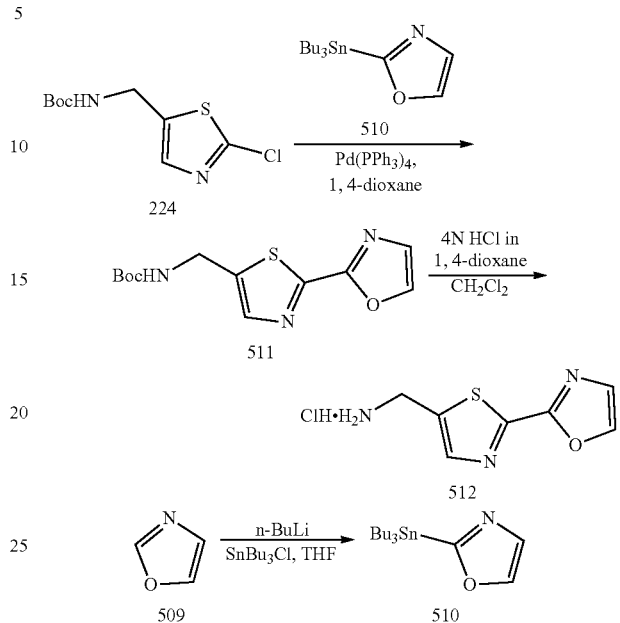

Synthesis of 2-(tributylstannyl) oxazole (510)

To a stirring solution of oxazole 509 (2 g, 28.98 mmol) in dry THF (50 mL) under inert atmosphere was added n-butyl lithium (19.9 mL, 31.88 mmol, 1.6 M solution in hexane) at −78° C. and stirred for 1 h. To this was added a tributyltin chloride (7.85 mL, 28.98 mmol) at −78° C.; warmed to RT and stirred for 2 h.

The reaction was monitored by TLC; after completion of the reaction, the volatiles were removed in vacuo. The residue was diluted with hexane (100 mL), the obtained solid was filtered through celite and the filtrate was concentrated in vacuo to afford crude compound 510 (8 g) as colorless liquid which was taken for next step without further purification. TLC: 10% EtOAc/hexanes (R$_f$: 0.8);

Synthesis of tert-butyl ((2-(oxazol-2-yl) thiazol-5-yl) methyl) carbamate (511)

To a stirring solution of tert-butyl ((2-chlorothiazol-5-yl) methyl) carbamate 224 (750 mg, 3.01 mmol) in 1, 4-dioxane (20 mL) was added 2-(tributylstannyl) oxazole 510 (4.32 g, 12.07 mmol) and purged under argon atmosphere for 30 min. To this was added Pd(PPh₃)₄ (348 mg, 0.30 mmol) at RT; heated to 100° C. and stirred for 16 h. The reaction was monitored by TLC; after completion the reaction the volatiles were removed in vacuo to obtain the crude. The crude was purified through silica gel column chromatography using 30% EtOAc/hexanes and further purified by preparative HPLC purification to afford compound 511 (100 mg, 12%) as thick syrup. TLC: 30% EtOAc/hexanes (R$_f$: 0.2); ¹H-NMR (DMSO-d₆, 500 MHz): δ 8.32 (s, 1H), 7.83 (s, 1H), 7.63 (t, J=6.1 Hz, 1H), 7.46 (s, 1H), 4.37 (br d, J=5.8 Hz, 2H), 1.40 (s, 9H); LC-MS: 99.93%; 281.9 (M⁺+1); (column; Ascentis Express C18, (50×3.0 mm, 2.7 µm); RT 2.06 min. 0.025% Aq. TFA+5% ACN: ACN+5% 0.025% Aq. TFA, 1.2 mL/min).

Synthesis of (2-(oxazol-2-yl) thiazol-5-yl) methanamine hydrochloride (512)

To a stirring solution of compound 511 (100 mg, 0.35 mmol) in $CH_2Cl_2$ (5 mL) was added 4 N HCl in 1, 4-dioxane (0.5 mL) under inert atmosphere at 0° C.; warmed to RT and stirred for 1 h. The reaction was monitored by TLC; after completion of the reaction, the volatiles were removed in vacuo to obtain the crude which was washed with EtOAc (10 mL) and dried in vacuo to afford compound 512 (70 mg, 90%; HCl salt) as an off-white solid. TLC: 5% MeOH/to $CH_2Cl_2$ ($R_f$: 0.1); $^1$H-NMR (DMSO-$d_6$, 400 MHz): δ 8.55 (br s, 3H), 8.37 (s, 1H), 8.10 (s, $^1$H), 7.51 (d, 1H), 4.40 (q, J=5.6 Hz, 2H); LC-MS: 97.38%; 181.9 (M$^+$+1); (column; Ascentis Express C18, (50×3.0 mm, 2.7 μm); RT 0.29 min. 0.025% Aq. TFA+5% ACN: ACN+5% 0.025% Aq. TFA, 1.2 mL/min).

Synthesis of methyl (3-(4-(5-(aminomethyl) thiazol-2-yl) phenoxy) propyl)-L-prolinate hydrochloride (517)

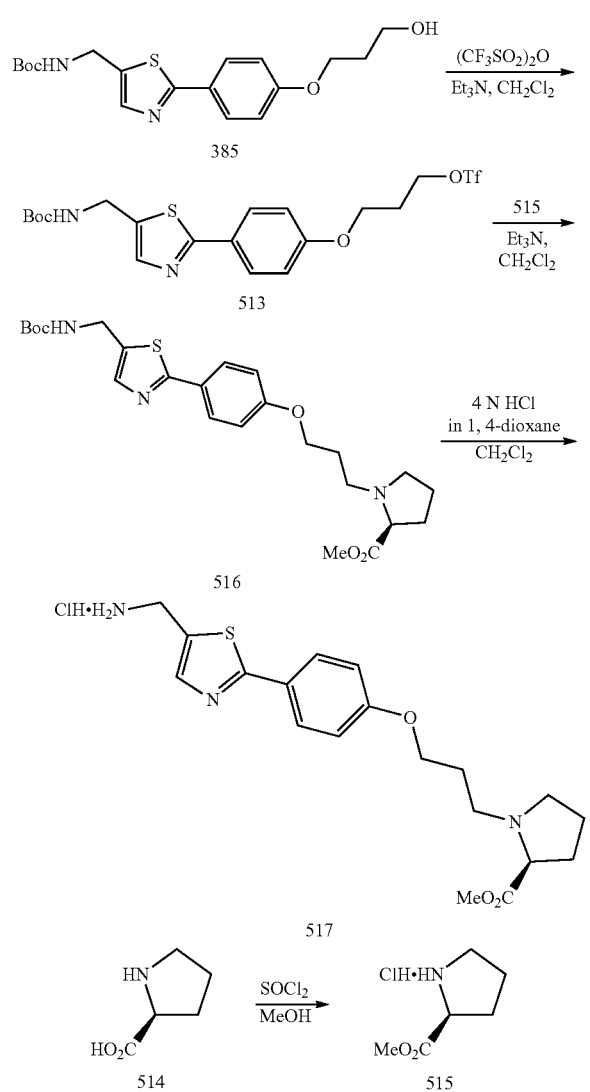

Synthesis of methyl L-prolinate hydrochloride (515)

To a stirring solution of L-proline 514 (5 g, 43.47 mmol) in MeOH (75 mL) under inert atmosphere was added thionyl chloride (3.15 mL, 65.21 mmol) drop wise at 0° C. for 15 min; and heated to reflux for 3 h. The reaction was monitored by TLC; after completion of the reaction, the volatiles were removed in vacuo to obtain the crude compound 515 (6 g salt, quantitative) as colourless liquid. This material was taken to next step without further purification. TLC: 10% MeOH/$CH_2Cl_2$ ($R_f$: 0.4); $^1$H NMR (400 MHz, DMSO-$d_6$): δ 10.85-10.21 (m, 1H), 9.33-8.59 (m, 1H), 4.40-4.18 (m, 1H), 4.05-3.82 (m, 1H), 3.75 (s, 3H), 3.29-3.16 (m, 2H), 2.32-2.18 (m, 1H), 2.06-1.82 (m, 2H);

Synthesis of 3-(4-(5-(((tert-butoxycarbonyl) amino) methyl) thiazol-2-yl) phenoxy) propyl trifluoromethanesulfonate (513)

To a stirring solution of compound 385 (100 mg, 0.27 mmol) in $CH_2Cl_2$ (10 mL) under argon atmosphere were added triethylamine (0.11 mL, 0.82 mmol) and triflic anhydride (0.1 mL, 0.54 mmol), at −40° C. and stirred for 2 h. The reaction was monitored by TLC; after completion of the reaction, the reaction mixture was diluted with water (20 mL) and extracted with $CH_2Cl_2$ (2×20 mL). The combined organic extracts were dried over sodium sulfate, filtered and concentrated in vacuo to obtain the crude compound 513 (120 mg) as viscous syrup. TLC: 5% MeOH/$CH_2Cl_2$ ($R_f$: 0.6);

Synthesis of methyl (3-(4-(5-(((tert-butoxycarbonyl) amino) methyl) thiazol-2-yl) phenoxy) propyl)-L-prolinate (516)

To a stirring solution of compound 513 (2.7 g, 5.44 mmol) in $CH_2Cl_2$ (20 mL) under argon atmosphere were added triethylamine (1.5 mL, 10.88 mmol) and compound 515 (1.4 g, 10.88 mmol), at −40° C. and stirred for 5 min. warmed to RT and stirred for 16 h. The reaction was monitored by TLC; after completion of the reaction, the reaction mixture was diluted with water (50 mL) and extracted with $CH_2Cl_2$ (2×60 mL). The combined organic extracts were dried over sodium sulfate, filtered and concentrated in vacuo to obtain the crude. The crude was purified through silica gel flash column chromatography using 2% MeOH/$CH_2Cl_2$ to afford compound 516 (1.1 g, 42% for 2 steps) as viscous syrup. TLC: 5% MeOH/$CH_2Cl_2$ ($R_f$: 0.4); $^1$H NMR (400 MHz, DMSO-$d_6$): δ 7.81 (d, J=8.9 Hz, 2H), 7.60 (s, 1H), 7.52 (t, J=5.6 Hz, 1H), 7.01 (d, J=8.8 Hz, 2H), 4.30 (d, J=5.9 Hz, 2H), 4.06 (t, J=6.3 Hz, 2H), 3.56 (s, 3H), 3.23-3.14 (m, 1H), 3.03-3.00 (m, 1H), 2.82-2.73 (m, 1H), 2.56-2.53 (m, 1H), 2.40-2.33 (m, 1H), 2.07-1.89 (m, 1H), 1.90-1.73 (m, 5H), 1.40 (s, 9H); LC-MS: 96.16%; 476.2 (M$^+$+1); (column; Ascentis Express C18, (50×3.0 mm, 2.7 μm); RT 1.97 min. 0.025% Aq. TFA+5% ACN: ACN+; 5% 0.025% Aq. TFA, 1.2 mL/min).

Synthesis of methyl (3-(4-(5-(aminomethyl) thiazol-2-yl) phenoxy) propyl)-L-prolinate hydrochloride (517)

To a stirring solution of compound 516 (100 mg, 0.21 mmol) in $CH_2Cl_2$ (5 mL) was added 4 N HCl in 1, 4-dioxane (1 mL) under argon atmosphere at 0° C.; warmed to RT and stirred for 2 h. The reaction was monitored by TLC; after completion of the reaction, the volatiles were removed in vacuo. The crude was triturated with diethyl ether (5 mL) and EtOAc (5 mL) and dried in vacuo to afford compound 517 (60 mg salt; 69%) as thick syrup. TLC: 10% MeOH/ CH$_2$Cl$_2$ (R$_f$: 0.2); $^1$H NMR (500 MHz, DMSO-d$_6$): δ 8.54 (br s, 3H), 7.92-7.85 (m, 3H), 7.08 (d, J=8.7 Hz, 2H), 4.51 (q, J=7.9 Hz, 1H), 4.32 (q, J=5.2 Hz, 2H), 4.15 (t, J=5.8 Hz, 2H), 3.79 (s, 3H), 3.75-3.64 (m, 2H), 3.56-3.47 (m, 1H), 3.35-3.18 (m, 2H), 2.47-2.37 (m, 1H), 2.21-2.04 (m, 4H); LC-MS: 94.78%; 376.1 (M$^+$+1); (column; Ascentis Express C18, (50×3.0 mm, 2.7 µm); RT 1.23 min. 0.025% Aq. TFA+5% ACN: ACN+; 5% 0.025% Aq. TFA, 1.2 mL/min);

Synthesis of 2, 2, 2-trifluoro-1-(((2-(4-isopropyl-1H-pyrazol-1-yl) thiazol-5-yl) methyl)-14-azanyl) ethan-1-one (519)

lane (0.2 mL, 1.25 mmol) at 0° C.; warmed to RT and stirred for 1 h. The reaction was monitored by TLC; after completion of the reaction, the volatiles were removed in vacuo to obtain the crude, which was washed diethylether (2×10 mL) and dried in vacuo to afford crude compound 519 (150 mg, 68%) as white solid. TLC: 30% EtOAc/hexanes (R$_f$: 0.2); 41 NMR (DMSO-d$_6$, 400 MHz): δ 8.37 (br s, 3H), 8.26 (s, 1H), 7.80 (s, 1H), 7.66 (s, 1H), 4.30 (s, 2H), 2.91-2.84 (m, 1H), 1.22 (d, J=6.9 Hz, 6H); LC-MS: 82.87%; 223.1 (M+1)$^+$; (column; Kinetex EVO C-18 (50×3.0 mm, 2.6 um); RT 2.62 min. 2.5 mM Aq. NH$_4$OOCH:ACN; 0.8 mL/min).

Synthesis of Synthesis of 1-(((2-(4-((3-(dimethylamino) azetidin-1-yl) methyl) phenyl) thiazol-5-yl) methyl)-14-azanyl)-2, 2, 2-trifluoroethan-1-one (524A)

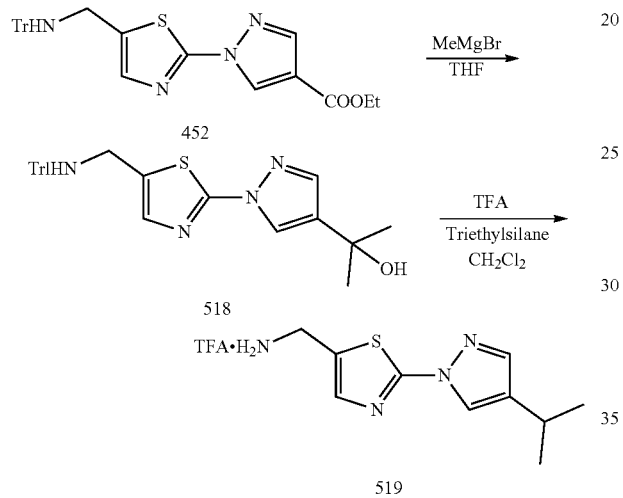

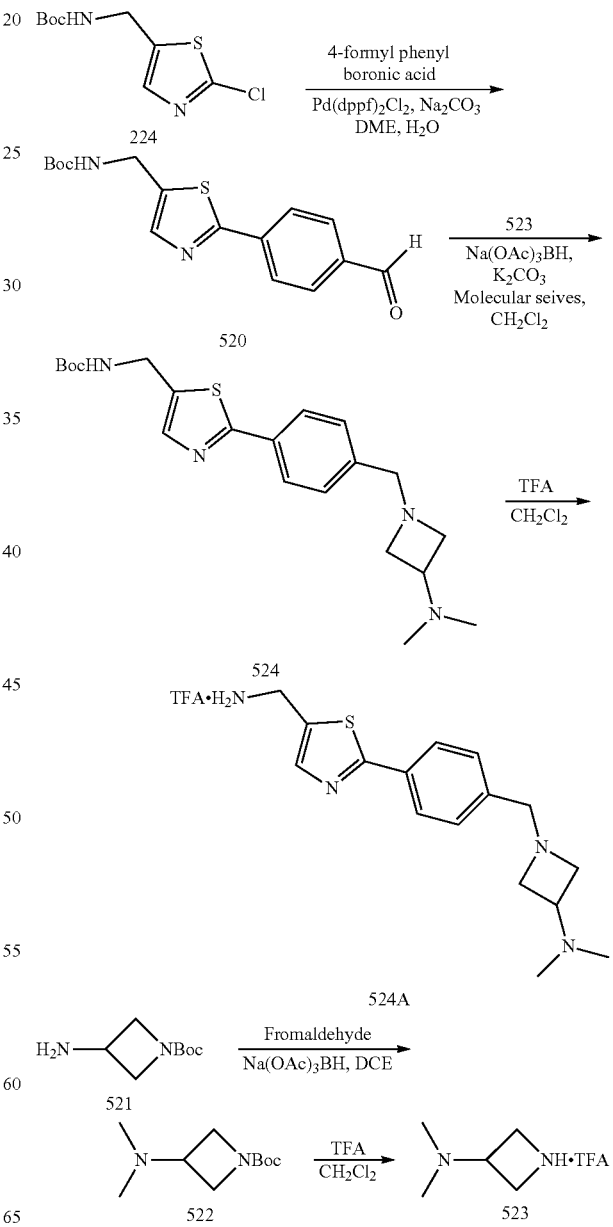

Synthesis of 2-(1-(5-((tritylamino) methyl) thiazol-2-yl)-1H-pyrazol-4-yl) propan-2-ol (518)

To a stirring solution of ethyl 1-(5-((tritylamino) methyl) thiazol-2-yl)-1H-pyrazole-4-carboxylate 452 (2.5 g, 5.06 mmol) in anhydrous THF (20 mL) under inert atmosphere was added methylmagnesium bromide (13 mL, 25.30 mmol, 2 M sol. In diethylether) at −10° C.; warmed to RT and stirred for 16 h. The reaction was monitored by TLC; after completion of the reaction, the reaction mixture was quenched with saturated ammonium chloride solution (60 mL) and extracted with EtOAc (2×100 mL). The combined organic extracts were dried over sodium sulfate, filtered and concentrated in vacuo to obtain the crude. The crude was purified through silica gel flash column chromatography using 20-25% EtOAc/hexanes to afford compound 518 (1 g, 42%) as an off-white solid. TLC: 20% EtOAc/hexanes (R$_f$: 0.2); $^1$H NMR (DMSO-d$_6$, 400 MHz): δ 8.23 (s, 1H), 7.79 (s, 1H), 7.47-7.45 (m, 5H), 7.38-7.30 (m, 8H), 7.26-7.19 (m, 4H), 3.34-3.31 (m, 2H), 5.07 (s, 1H), 1.46 (s, 6H);

Synthesis of (2-(4-isopropyl-1H-pyrazol-1-yl) thiazol-5-yl) methanamineTFA salt (519)

To a stirring solution of compound 518 (300 mg, 0.62 mmol) in CH$_2$Cl$_2$ (10 mL) under inert atmosphere were added trifluoroacetic acid (0.24 mL, 3.12 mmol), trieythlsi-

Synthesis of tert-butyl ((2-(4-formylphenyl) thiazol-5-yl) methyl) carbamate (520)

To a stirring solution of tert-butyl ((2-chlorothiazol-5-yl) methyl) carbamate 224 (1 g, 4.02 mmol) in DME:H₂O (4:1, 15 mL) were added (4-formylphenyl) boronic acid (905 mg, 6.03 mmol) and sodium carbonate (1.49 g, 14.08 mmol) in a sealed tube at RT and purged under argon for 30 min. Then Pd(dppf)Cl₂ (294 mg, 0.40 mmol) was added at RT. The reaction mixture was heated to 90-95° C. and stirred for 16 h. The reaction was monitored by TLC; after completion of the reaction, the reaction mixture was diluted with water (30 mL), and extracted with EtOAc (2×30 mL). The combined organic extracts were washed with brine (30 mL), water (10 mL), dried over sodium sulfate, filtered and concentrated in vacuo to obtain the crude. The crude was purified through silica gel column chromatography using 15% EtOAc/Hexane to afford compound 520 (600 mg, 47%) as pale yellow solid. TLC: 40% EtOAc/hexanes ($R_f$: 0.4). ¹H NMR (500 MHz, DMSO-$d_6$): δ 10.05 (s, 1H), 8.12 (d, J=8.1 Hz, 2H), 8.01 (d, J=8.1 Hz, 2H), 7.80 (s, 1H), 7.60 (br s, 1H), 4.37 (d, J=5.8 Hz, 2H), 1.40 (s, 9H); LC-MS: 93.26%; 318.9 (M⁺+1) (column; Kinetex EVO C-18 (50×3.0 mm, 2.6 um); RT 2.91 min. 2.5 mM NH₄OOCH in water+5% ACN: ACN+5% 2.5 mM NH₄OOCH in water, 0.8 mL/min).

Synthesis of tert-butyl 3-(dimethylamino) azetidine-1-carboxylate (522)

To a stirring solution of compound 521 (2.5 g, 14.53 mmol) in 1, 2-dichloro ethane (25 mL) were added formaldehyde solution (36% in H₂O) (4.25 mL) and sodium triacetoxy borohydride (27.7 g, 13.08 mmol) at RT under inert atmosphere. The reaction mixture was stirred at RT for 2 h. The reaction was monitored by TLC; after completion of the reaction, the reaction mixture was diluted with water (30 mL), basified with saturated sodium bicarbonate solution (20 mL) to pH~8 and extracted with EtOAc (2×30 mL). The combined organic extracts were dried over sodium sulfate, filtered and concentrated in vacuo to obtain the crude compound 522 (2.2 g, 75%) as pale yellow liquid. LC-MS: 88.00%; 101.3 (M⁺+1) (des-boc) (column; Kinetex EVO C-18 (50×3.0 mm, 2.6 um); RT 0.36 min. 5 mM Aq NH₄OAc+ACN: 0.8 mL/min).

Synthesis of 1-(3-(dimethylamino)-1l4-azetidin-1-yl)-2, 2, 2-trifluoroethan-1-one (523)

To a stirring solution of compound 522 (2.2 g, 11 mmol) in CH₂Cl₂ (20 mL) was added trifluoroacetic acid (6 mL) at 0° C. under inert atmosphere. The reaction mixture was gradually warmed to RT and stirred for 8 h. The reaction was monitored by TLC; after completion of the reaction, the volatiles were removed in vacuo. The crude washed with triturated with ether (20 mL) and dried in vacuo to obtain crude compound 523 (1.8 g, 76%) as white solid. TLC: 10% MeOH/CH₂Cl₂ ($R_f$: 0.1); LC-MS: 80.67%; 101.3 (M⁺+1) (column; Atlantis T3, (150×4.6 mm, 3 μm); RT 2.41 min. 2.5 mM Aq NH₄OAc:ACN, 1.0 mL/min).

Synthesis of tert-butyl ((2-(4-((3-(dimethylamino) azetidin-1-yl) methyl) phenyl) thiazol-5-yl) methyl) carbamate (524)

To a stirring solution of compound 520 (500 mg, 1.57 mmol) and compound 523 (235 mg, 2.35 mmol) in CH₂Cl₂ (15 mL) were added potassium carbonate (260 mg, 1.88 mmol), sodium triacetoxy borohydride (666 mg, 3.14 mmol) and molecular sieves (500 mg) at RT under inert atmosphere. The reaction mixture was stirred at RT for 16 h. The reaction was monitored by TLC; after completion of the reaction, the reaction mixture was diluted with water (15 mL), basified with saturated sodium bicarbonate solution (15 mL) to pH~8 and extracted with EtOAc (2×15 mL). The combined organic extracts were dried over sodium sulfate, filtered and concentrated in vacuo to obtain the crude. The crude was purified through silica gel column chromatography using 6-10% MeOH/CH₂Cl₂ to afford compound 524 (400 mg, 63%) as pale yellow syrup. ¹H NMR (500 MHz, DMSO-$d_6$): δ 7.83 (d, J=7.5 Hz, 2H), 7.67 (s, 1H), 7.58-7.53 (m, 1H), 7.38 (d, J=8.1 Hz, 2H), 4.33 (d, J=5.2 Hz, 2H), 3.63 (s, 2H), 3.66-3.59 (m, 2H), 2.93-2.81 (m, 3H), 2.03 (s, 6H), 1.40 (s, 9H); LC-MS: 98.20%; 403.2 (M⁺+1) (column; Ascentis Express C-18, (50×3.0 mm, 2.7 μm); RT 1.69 min. 0.025% Aq. TFA+5% ACN: ACN+5% 0.025% Aq. TFA, 1.2 mL/min).

Synthesis of 1-(((2-(4-((3-(dimethylamino) azetidin-1-yl) methyl) phenyl) thiazol-5-yl) methyl)-14-aza-nyl)-2, 2, 2-trifluoroethan-1-one (524A)

To a stirring solution of compound 524 (500 mg, 1.24 mmol) in CH₂Cl₂ (5 mL) was added trifluoroacetic acid (2 mL) at 0° C. under inert atmosphere. The reaction mixture was gradually warmed to RT and stirred for 8 h. The reaction was monitored by TLC; after completion of the reaction, the volatiles were removed in vacuo. The crude washed with triturated with ether (10 mL) and dried in vacuo to obtain crude compound 524A (390 mg, 75%) as pale yellow solid. TLC: 10% MeOH/CH₂Cl₂ ($R_f$: 0.1); LC-MS: 94.59%; 303.2 (M⁺+1); (column; Atlantis T3, (150×4.6 mm, 3 μm); RT 6.45 min. 2.5 mM Aq NH₄OAc:ACN, 1.0 mL/min).

Synthesis of (2-(1-methyl-1H-pyrazol-3-yl) thiazol-5-yl) methanamine TFA Salt (528)

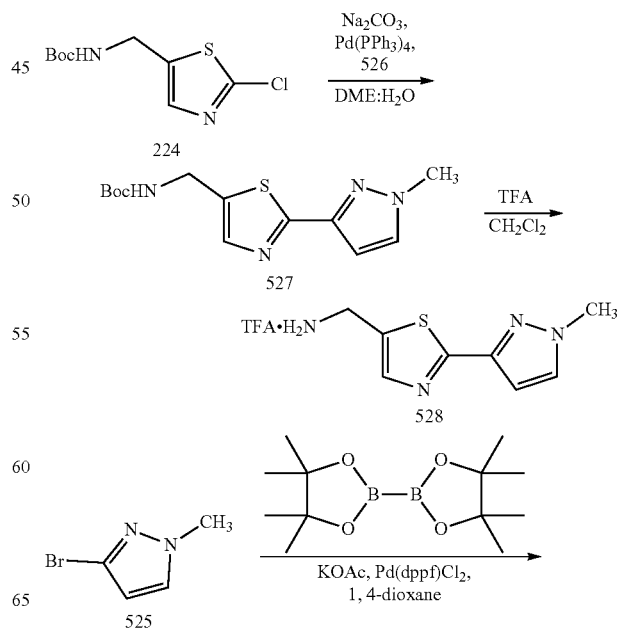

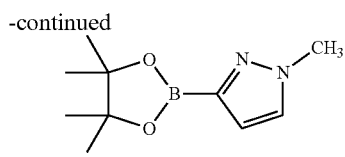

526

Synthesis of 1-methyl-3-(4, 4, 5, 5-tetramethyl-1, 3, 2-dioxaborolan-2-yl)-1H-pyrazole (526)

To a stirring solution of 3-bromo-1-methyl-1H-pyrazole 525 (1 g, 6.25 mmol) in 1, 4-dioxane (60 mL) under inert atmosphere were added bispinacolato diboron (1.73 g, 6.83 mmol), potassium acetate (1.82 g, 18.63 mmol) at RT and purged under argon atmosphere for 20 min, added Pd(dppf)Cl$_2$ (454 mg, 0.62 mmol) and heated to 120° C. and stirred for 3 h. The reaction was monitored by TLC; after completion of the reaction, the reaction mixture was filtered through celite. The filtrate was concentrated in vacuo to obtain the crude. The crude was purified through silica gel column chromatography using 20% EtOAc/hexanes to afford compound 526 (2.4 g, crude) as brown thick syrup. The crude was carried forward for next step without further purification. TLC: 50% EtOAc/hexanes (R$_f$: 0.3);

Synthesis of tert-butyl 42-(1-methyl-1H-pyrazol-3-yl) thiazol-5-yl) methyl) carbamate (527)

To a stirring solution of tert-butyl ((2-chlorothiazol-5-yl) methyl) carbamate 224 (500 mg, 2.01 mmol) in 1, 2 dimethoxy ethane:H$_2$O (4:1, 75 mL) under inert atmosphere were added 1-methyl-3-(4, 4, 5, 5-tetramethyl-1, 3, 2-dioxaborolan-2-yl)-1H-pyrazole 526 (3.9 g, crude), sodium carbonate (750 mg, 7.08 mmol) and purged under argon atmosphere for 20 min. To this was added Pd(PPh$_3$)$_4$ (270 mg, 0.23 mmol) at RT; heated to 110° C. and stirred for 16 h. The reaction was monitored by TLC; after completion the volatiles were removed in vacuo to obtain the crude. The residue was diluted with water (50 mL) and extracted with EtOAc (3×50 mL). The combined organic extracts were dried over sodium sulfate and concentrated in vacuo to obtain the crude. The crude was purified by preparative HPLC purification to afford compound 527 (160 mg, 27%) as an off-white solid. TLC: 70% EtOAc/hexanes (R$_f$: 0.4); $^1$H-NMR (DMSO-d$_6$, 400 MHz): δ 7.80 (d, J=2.3 Hz, 1H), 7.59 (s, 1H), 7.52 (br t, J=5.3 Hz, 1H), 6.67 (d, J=2.3 Hz, 1H), 4.30 (br d, J=5.8 Hz, 2H), 3.31 (s, 3H), 1.40 (s, 9H); LC-MS: 96.60%; 294.9 (M$^+$+1); (column; Ascentis Express C18, (50×3.0 mm, 2.7 μm); RT 2.04 min. 0.025% Aq. TFA+5% ACN: ACN+5% 0.025% Aq. TFA, 1.2 mL/min).

Synthesis of (2-(1-methyl-1H-pyrazol-3-yl) thiazol-5-yl) methanamine TFA salt (528)

To a stirring solution of tert-butyl ((2-(1-methyl-1H-pyrazol-3-yl) thiazol-5-yl) methyl) carbamate 527 (50 mg, 0.17 mmol) in CH$_2$Cl$_2$ (3 mL) under inert atmosphere was added trifluoroacetic acid (0.06 mL) at 0° C.; warmed to RT and stirred for 8 h. The reaction was monitored by TLC; after completion of the reaction, the volatiles were removed in vacuo to obtain the crude. The crude was titurated with diethylether (2×5 mL) and dried in vacuo to afford compound 528 (380 mg, 84%; HCl salt) as white solid. TLC: 40% EtOAc/hexanes (R$_f$: 0.1); $^1$H-NMR (DMSO-d$_6$, 400 MHz): δ 8.29 (br s, 3H), 7.84 (s, 1H), 7.82 (d, J=2.1 Hz, 1H), 6.70 (d, J=2.3 Hz, 1H), 4.31 (s, 2H), 3.89 (s, 3H); LC-MS (Agilent 6310 Ion Trap): 99.97%; 195.2 (M$^+$+1); (column; X-Select HSS T3 (150×3 mm, 2.5 μm); RT 0.62 min. 2.5 mM Aq. NH$_4$OAc:ACN; 0.6 mL/min).

Synthesis of tert-butyl (1-((5-(aminomethyl) thiazol-2-yl) methyl) piperidin-4-yl) carbamate (534)

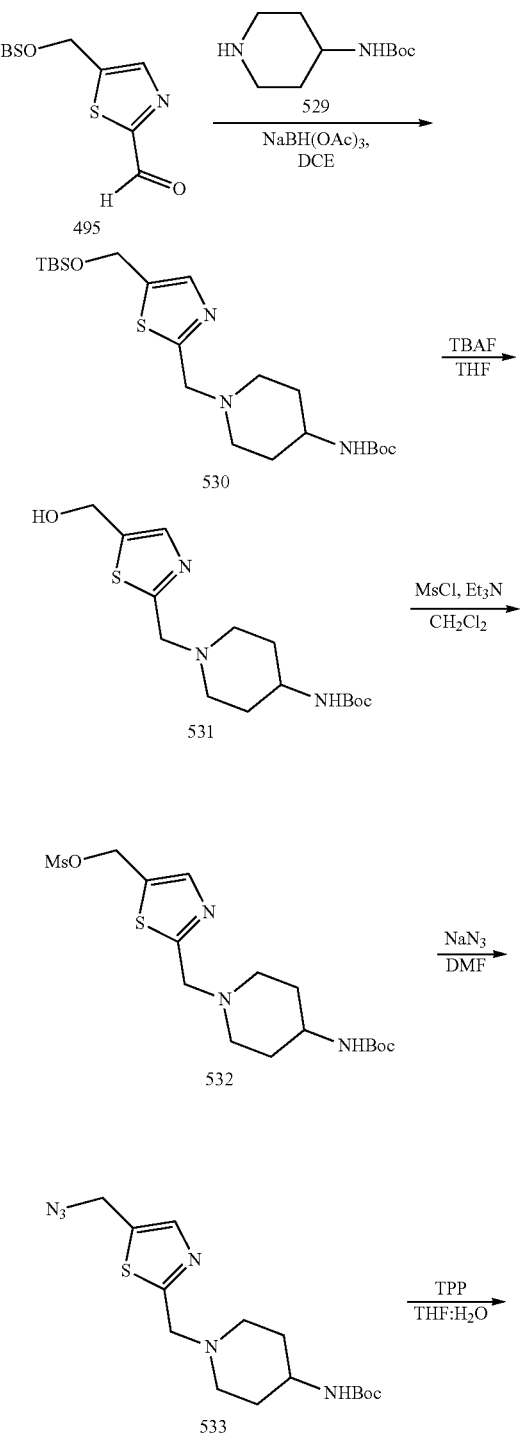

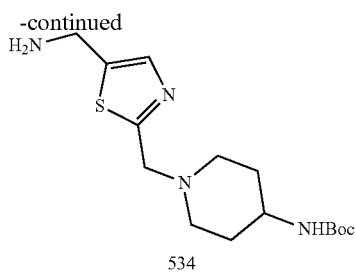

534

Synthesis of tert-butyl (1-((5-(((tert-butyldimethylsilyl) oxy) methyl) thiazol-2-yl) methyl) piperidin-4-yl) carbamate (530)

To a stirring solution of 5-(((tert-butyldimethylsilyl) oxy) methyl) thiazole-2-carbaldehyde 495 (1.2 g, 4.66 mmol) in 1, 2-dichloroethane (50 mL) under inert atmosphere were added tert-butyl piperidin-4-ylcarbamate 529 (1.12 g, 5.60 mmol) and sodium triacetoxyborohydride (2.96 g, 14.00 mmol) at 0° C.; warmed to RT and stirred for 16 h. The reaction was monitored by TLC; after completion of the reaction, the reaction mixture was diluted with $CH_2Cl_2$ (200 mL), washed with water (100 mL) and brine (100 mL). The organic extract was dried over sodium sulfate, filtered and concentrated in vacuo to obtain the crude. The crude was purified through silica gel column chromatography using 30% EtOAc/hexanes to afford compound 530 (800 mg, 49%) as a pale yellow thick syrup. TLC: 20% EtOAc/hexanes ($R_f$: 0.1); $^1$H NMR (DMSO-$d_6$, 500 MHz): δ 7.52 (s, 1H), 6.76 (br d, J=7.2 Hz, 1H), 4.85 (s, 2H), 3.72 (s, 2H), 3.24-3.21 (m, 1H), 2.83-2.79 (m, 2H), 2.14-2.07 (m, 2H), 1.70-1.66 (m, 2H), 1.47-1.39 (m, 11H), 0.86 (s, 9H), 0.07 (s, 6H); LC-MS: 93.12%; 442.2 ($M^+$+1); (column; Ascentis Express C18, (50×3.0 mm, 2.7 μm); RT 2.18 min. 0.025% Aq. TFA+5% ACN: ACN+5% 0.025% Aq. TFA, 1.2 mL/min).

Synthesis of tert-butyl (1-((5-(hydroxymethyl) thiazol-2-yl) methyl) piperidin-4-yl) carbamate (531)

To a stirring solution of compound 530 (800 mg, 1.81 mmol) in THF (15 mL) under inert atmosphere was added tetrabutylammonium fluoride (1.0 M solution in THF, 2.72 mL, 2.72 mmol) at 0° C. and stirred at the same temperature for 1 h. The reaction was monitored by TLC; after completion of the reaction, the reaction mixture was quenched with ice-cold water (100 mL) and extracted with EtOAc (2×75 mL). The combined organic extracts were dried over sodium sulfate, filtered and concentrated in vacuo to obtain the crude. The crude was purified through silica gel column chromatography using 4% MeOH/$CH_2Cl_2$ to afford compound 531 (650 mg, quantitative) as thick syrup. TLC: 5% MeOH/$CH_2Cl_2$ ($R_f$: 0.1); $^1$H-NMR (DMSO-$d_6$, 500 MHz): δ 7.48 (s, 1H), 6.77 (br d, J=6.7 Hz, 1H), 5.46 (br t, J=5.5 Hz, 1H), 4.62 (br d, J=5.8 Hz, 2H), 3.71 (br s, 2H), 3.03-3.01 (m, 1H), 2.84-2.80 (m, 2H), 2.14-2.08 (m, 2H), 1.75-1.54 (m, 2H), 1.47-1.37 (m, 11H); LC-MS: 94.85%; 328.0 ($M^+$+1); (column; Ascentis Express C18, (50×3.0 mm, 2.7 μm); RT 1.40 min. 0.025% Aq. TFA+5% ACN: ACN+5% 0.025% Aq. TFA, 1.2 mL/min).

Synthesis of (2-((4-(((tert-butoxycarbonyl) amino) piperidin-1-yl) methyl) thiazol-5-yl) methyl methanesulfonate (532)

To a stirring solution of compound 531 (650 mg, 1.98 mmol) in $CH_2Cl_2$ (30 mL) under inert atmosphere were added triethyl amine (1.43 mL, 9.93 mmol) at 0° C. and stirred for 10 min. To this was added methanesulfonyl chloride (453.2 mg, 3.97 mmol) at 0° C.; warmed to RT and stirred for 3 h. The reaction was monitored by TLC; after completion of the reaction, the reaction mixture was quenched with ice-cold water (2×50 mL) and extracted with $CH_2Cl_2$ (2×100 mL). The combined organic extracts were dried over sodium sulfate, filtered and concentrated in vacuo to afford crude compound 532 (600 mg) as pale brown liquid. The crude taken forward for next step with out further purification. TLC: 10% MeOH/$CH_2Cl_2$ ($R_f$: 0.4);

Synthesis of tert-butyl (1-((5-(azidomethyl) thiazol-2-yl) methyl) piperidin-4-yl) carbamate (533)

To a stirring solution of compound 532 (600 mg, 1.48 mmol) in DMF (10 mL) under inert atmosphere was added sodium azide (284 mg, 4.44 mmol) at RT and stirred for 16 h. The reaction was monitored by TLC and LC-MS; after completion of the reaction, the reaction mixture was diluted with ice-cold water (100 mL) and extracted with EtOAc (2×75 mL). The combined organic extracts were dried over sodium sulphate, filtered and concentrated in vacuo to obtain the crude. The crude was purified through silica gel flash column chromatography using 70% EtOAc/hexanes to afford compound 533 (400 mg, 76%) as thick syrup. TLC: 70% EtOAc/hexanes ($R_f$: 0.4); $^1$H-NMR (DMSO-$d_6$, 500 MHz): δ 7.67 (s, 1H), 6.78 (br d, J=7.5 Hz, 1H), 4.69 (s, 2H), 3.76 (s, 2H), 3.28-3.19 (m, 1H), 2.85-2.80 (m, 2H), 2.18-2.11 (m, 2H), 1.71-1.67 (m, 2H), 1.48-1.32 (m, 11H); LC-MS: 92.56%; 353.0 ($M^+$+1); (column; Ascentis Express C-18, (50×3.0 mm, 2.7 μm); RT 1.80 min. 0.025% Aq. TFA+5% ACN: ACN+5% 0.025% Aq. TFA, 1.2 mL/min);

Synthesis of tert-butyl (1-((5-(aminomethyl) thiazol-2-yl) methyl) piperidin-4-yl) carbamate (534)

To a stirring solution of compound 533 (300 mg, 0.85 mmol) in THF:$H_2O$ (4:1, 5 mL) was added triphenyl phosphine (446 mg, 1.70 mmol) at RT and stirred for 16 h. The reaction was monitored by TLC and LC-MS; after completion of the reaction, the volatiles were removed in vacuo to obtain the crude. The crude was purified through silica gel column chromatography using 4-5% MeOH/$CH_2Cl_2$ to afford compound 534 (250 mg, 91%) as semi solid. TLC: 5% MeOH/$CH_2Cl_2$ ($R_f$: 0.2); $^1$H-NMR (DMSO-$d_6$, 400 MHz): δ=7.43 (s, 1H), 3.86 (s, 1H), 3.69 (s, 1H), 3.30-3.12 (m, 3H), 2.84-2.79 (m, 2H), 2.17-2.03 (m, 2H), 1.70-1.67 (m, 2H), 1.37 (s, 9H); LC-MS: 81.58%; 327.1 ($M^+$+1); (column; Kinetex EVOC-18 (50×3.0 mm, 2.6 μm); RT 1.60 min. 2.5 mM Aq. NH4OOCH+5% ACN: ACN+5% 2.5 mM Aq.$NH_4OOCH$, 0.8 mL/min).

Compound Preparation

Acids similar to compound 6 (compounds 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194) were synthesized as mentioned above and converted to final products either using commercially available amines or prepared amines employing typical procedures A and B, and the results are captured in the Table 1:

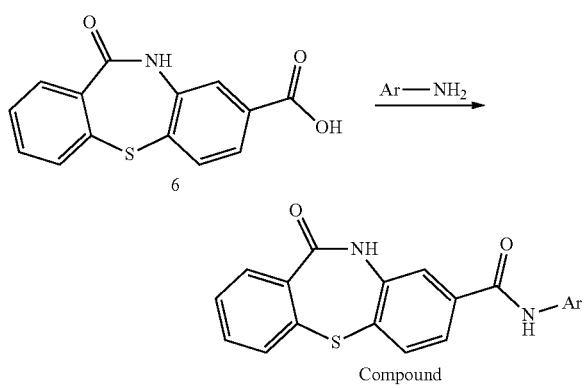

Typical Procedure A:

To a stirring solution of compound 6 (100 mg, 0.36 mmol) in DMF (5 mL) under in inert atmosphere were added EDCI.HCl (105 mg, 0.55 mmol), HOBt (75 mg, 0.55 mmol), compound 255 (80 mg, 0.44 mmol) and diisopropylethylamine (0.19 mL, 1.10 mmol) at 0° C. warmed to RT and stirred for 16 h. The reaction was monitored by TLC; after completion of the reaction, the volatiles were removed in vacuo to obtain the crude. The crude was either directly dried in vacuo or triturated or purified through silica gel column chromatography to afford the desired compound.

Typical Procedure B:

To a stirring solution of acid 105 (130 mg, 0.41 mmol) in DMF (6 mL) under inert atmosphere were added HATU (187 mg, 0.49 mmol) and stirred for 10 min. To this were added and compound 255 (83 mg, 0.49 mmol) and diisopropylethylamine (0.21 mL, 1.23 mmol) at 0° C. warmed to RT and stirred for 16 h. The reaction was monitored by TLC; after completion of the reaction, the diluted with water (10 mL) and extracted with 5% MeOH/CH$_2$Cl$_2$ (2×10 mL). The combined organic extracts were dried over sodium sulfate, filtered and concentrated in vacuo to obtain the crude. The crude was either directly dried in vacuo or triturated or purified through silica gel column chromatography or preparative HPLC purification to afford the desired compound.

TABLE 1

Synthesis from compound 13, 20, 32, 40, 47, 54, 61, 68, 76, 81, 88, 92, 95, 105, 113, 120, 126, 135, 143, 144, 149, 153, 155, 158, 200, 211, 216, 89, 163, 169, 172, 176, 185, 190, 194 and various commercial and synthesized amines.

| Example | Structure | Procedure, Interemediate, amine | Rx. Yield (%) | Mass Spec. Found | Mass Spec. Calculated | 1H-NMR |
|---|---|---|---|---|---|---|
| 1421 | 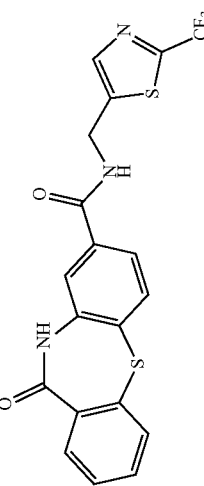 | A, 6, 255 | 21 | 435.9 (M+ + 1); | 435.03 for $C_{19}H_{12}F_3N_3O_2S_2$ | 1H-NMR (DMSO-d6, 400 MHz): δ 10.77 (s, 1H), 9.38 (t, J = 5.7 Hz, 1H), 8.05 (s, 1H), 7.72-7.66 (m, 3H), 7.60 (dd, J = 8.0, 1.8 Hz, 1H), 7.53 (td, J = 7.1, 1.6 Hz, 1H), 7.50-7.43 (m, 2H), 4.72 (d, J = 5.6 Hz, 2H); |
| 1431 | 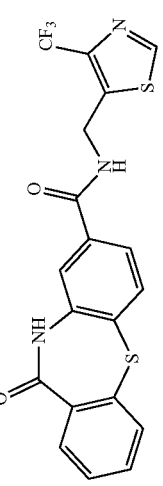 | A, 6, 263 | 23 | 435.9 (M+ + 1); | 435.03 for $C_{19}H_{12}F_3N_3O_2S_2$ | 1H-NMR (DMSO-d6, 400 MHz): δ 10.80 (s, 1H), 9.45 (t, J = 5.3 Hz, 1H), 9.09 (s, 1H), 7.70 (d, J = 8.0 Hz, 3H), 7.64-7.43 (m, 4H), 4.77 (d, J = 4.8 Hz, 2H); |
| 1424 | 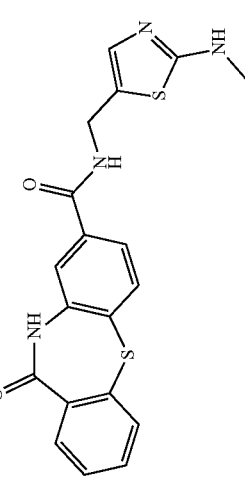 | A, 6, 242 | 53 | 396.9 (M+ + 1); | 396.07 $C_{19}H_{16}N_4O_2S_2$ | 1H NMR (DMSO-d6, 500 MHz): δ 10.77 (s, 1H), 9.03 (t, J = 5.6 Hz, 1H), 7.69-7.62 (m, 3H), 7.59-7.42 (m, 4H), 7.34-7.30 (m, 1H), 6.87 (s, 1H), 4.36 (d, J = 5.8 Hz, 2H), 2.72 (d, J = 4.9 Hz, 3H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various 149, 153, 155, 158, 200, 211, 216, commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1425 | 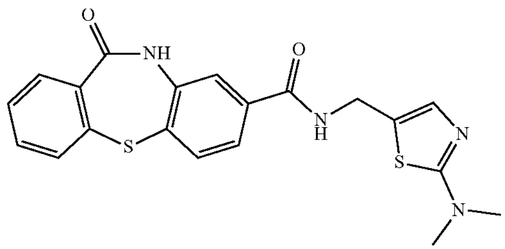 [SMILES: CN(C)c1ncc(CNC(=O)c2ccc3c(c2)NC(=O)c2ccccc2S3)s1] | A, 6, 245 | 61 | 411.0 (M$^+$ + 1); | $C_{20}H_{18}N_4O_2S_2$ 410.09 | $^1$H NMR (DMSO-d$_6$, 400 MHz): δ 10.75 (s, 1H), 9.05 (t, J = 5.7 Hz, 1H), 7.72-7.62 (m, 3H), 7.59-7.42 (m, 4H), 6.99 (s, 1H), 4.41 (d, J = 5.5 Hz, 2H), 2.95 (s, 6H); |
| 1473 | 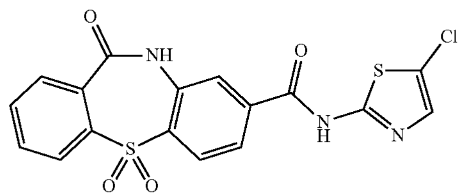 [SMILES: O=C(Nc1ncc(Cl)s1)c1ccc2c(c1)NC(=O)c1ccccc1S2(=O)=O] | A, 92, 220 | 18 | 419.8 (M$^+$ + 1); | $C_{17}H_{10}ClN_3O_4S_2$ 418.98 | 1H NMR (DMSO-d6, 400 MHz): δ 13.19 (br s, 1H), 11.62 (s, 1H), 8.10 (d, J = 8.2 Hz, 1H), 8.07-7.97 (m, 4H), 7.95-7.85 (m, 2H), 7.63 (s, 1H); |
| 1496 | 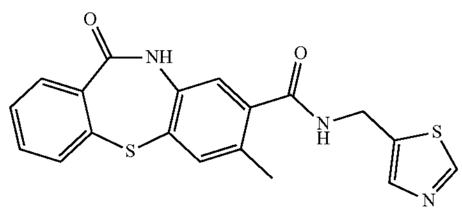 [SMILES: Cc1cc2c(cc1C(=O)NCc1cncs1)NC(=O)c1ccccc1S2] | A, 13, 217 | 34 | 381.9 (M$^+$ + 1) | $C_{19}H_{15}N_3O_2S_2$ 381.06 | 1H NMR (DMSO-d6, 400 MHz): δ 10.63 (s, 1H), 9.00-8.95 (m, 2H), 7.79 (s, 1H), 7.66 (dd, J = 7.5, 1.5 Hz, 1H), 7.54-7.41 (m, 4H), 7.15 (s, 1H), 4.61 (d, J = 5.7 Hz, 2H), 2.23 (s, 3H); |
| 1549 | 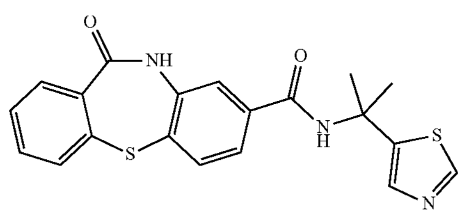 [SMILES: CC(C)(NC(=O)c1ccc2c(c1)NC(=O)c1ccccc1S2)c1cncs1] | A, 6, 271 | 21 | 396.0 (M$^+$ + 1); | 395.08 for $C_{20}H_{17}N_3O_2S_2$ | $^1$H NMR (DMSO-d$_6$, 400 MHz): 10.72 (s, 1H), 8.87 (s, 1H), 8.62 (s, 1H), 7.72-7.60 (m, 4H), 7.58-7.42 (m, 4H), 1.74 (s, 6H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1555 | 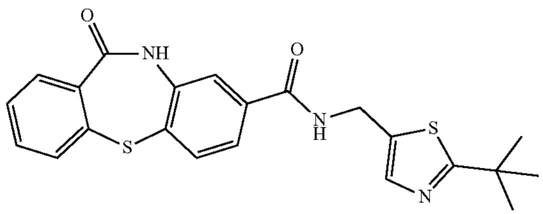 [SMILES: CC(C)(C)c1ncc(CNC(=O)c2ccc3c(c2)NC(=O)c2ccccc2S3)s1] | A, 6, 277 | 38 | 424.0 (M$^+$ + 1); | 423.11 for C$_{22}$H$_{21}$N$_3$O$_2$S$_2$ | $^1$H-NMR (DMSO-d$_6$, 400 MHz): δ 10.78 (s, 1H), 9.19 (t, J = 5.6 Hz, 1H), 7.72-7.64 (m, 3H), 7.59 (dd, J = 8.2, 1.9 Hz, 1H), 7.56-7.51 (m, 2H), 7.50-7.43 (m, 2H), 4.57 (d, J = 5.6 Hz, 2H), 1.32 (s, 9H); |
| 1556 | 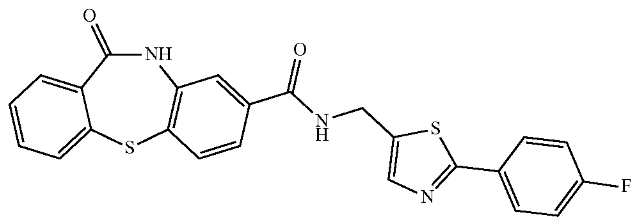 [SMILES: O=C(NCc1cnc(-c2ccc(F)cc2)s1)c1ccc2c(c1)NC(=O)c1ccccc1S2] | A, 6, 285 | 38 | 461.9 (M$^+$ + 1); | 461.07 for C$_{24}$H$_{16}$FN$_3$O$_2$S$_2$ | $^1$H-NMR (DMSO-d$_6$, 400 MHz): δ 10.78 (s, 1H), 9.28 (t, J = 5.3 Hz, 1H), 7.93 (dd, J = 8.9, 5.3 Hz, 2H), 7.78 (s, 1H), 7.73-7.65 (m, 3H), 7.60 (dd, J = 8.3, 1.8 Hz, 1H), 7.56-7.43 (m, 3H), 7.31 (t, J = 8.9 Hz, 2H), 4.65 (d, J = 5.6 Hz, 2H); |
| 1598 | 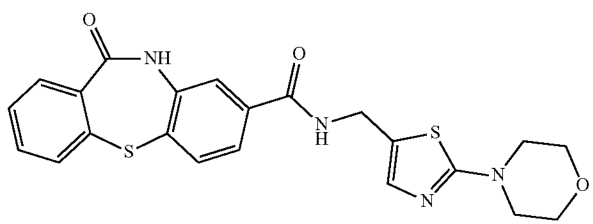 | A, 6, 304 | 48 | 452.9 (M$^+$ + 1); | 452.10 for C$_{22}$H$_{20}$N$_4$O$_3$S$_2$ | $^1$H-NMR (DMSO-d$_6$, 500 MHz): δ 10.76 (s, 1H), 9.08 (t, J = 5.5 Hz, 1H), 7.70-7.63 (m, 3H), 7.60-7.42 (m, 4H), 7.05 (s, 1H), 4.42 (d, J = 5.5 Hz, 2H), 3.68-3.64 (m, 4H), 3.35-3.25 (m, 4H) |
| 1604 | 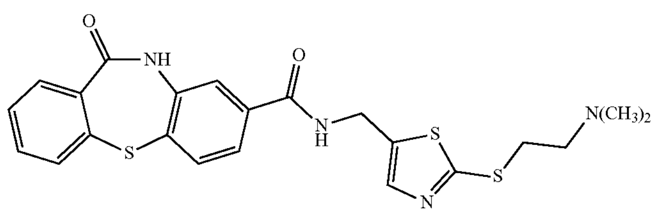 | A, 6, 288 | 39 | 471.2 (M$^+$ + 1); | 470.09 for C$_{22}$H$_{22}$N$_4$O$_2$S$_3$ | $^1$H-NMR (DMSO-d$_6$, 500 MHz): δ 10.77 (s, 1H), 9.20 (t, J = 5.6 Hz, 1H), 7.72-7.64 (m, 3H), 7.59-7.43 (m, 5H), 4.54 (d, J = 5.5 Hz, 2H), 3.27 (t, J = 6.9 Hz, 2H), 2.56 (t, J = 6.8 Hz, 2H), 2.16 (s, 6H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1605 | (structure with phenol-thiazole-benzothiazepinone) | A, 6, 357 | 38 | 459.9 (M$^+$ + 1); | 459.07 for $C_{24}H_{17}N_3O_3S_2$ | $^1$H-NMR (DMSO-$d_6$, 500 MHz): δ 10.77 (s, 1H), 9.94 (s, 1H), 9.24 (t, J = 5.8 Hz, 1H), 7.72-7.65 (m, 5H), 7.62-7.43 (m, 5H), 6.83 (d, J = 8.7 Hz, 2H), 4.62 (d, J = 5.5 Hz, 2H); |
| 1606 | (structure with methoxyphenyl-thiazole-benzothiazepinone) | A, 6, 363 | 49 | 473.9 (M$^+$ + 1); | 473.09 for $C_{25}H_{19}N_3O_3S_2$ | $^1$H-NMR (DMSO-$d_6$, 500 MHz): δ 10.78 (s, 1H), 9.25 (t, J = 5.6 Hz, 1H), 7.81 (d, J = 8.7 Hz, 2H), 7.73-7.65 (m, 4H), 7.63-7.43 (m, 4H), 7.02 (d, J = 8.7 Hz, 2H), 4.63 (d, J = 5.5 Hz, 2H), 3.80 (s, 3H); |
| 1608 | (structure with N(CH$_3$)$_2$ ethoxyphenyl-thiazole-benzothiazepinone) | A, 6, 360 | 23 | 531.0 (M$^+$ + 1); | 530.14 for $C_{28}H_{26}N_4O_3S_2$ | $^1$H NMR (DMSO-$d_6$, 500 MHz): δ 10.77 (s, 1H), 9.28 (t, J = 5.1 Hz, 1H), 7.78 (d, J = 8.7 Hz, 2H), 7.72-7.59 (m, 5H), 7.55-7.41 (m, 3H), 7.01 (d, J = 8.7 Hz, 2H), 4.62 (d, J = 5.5 Hz, 2H), 4.10 (t, J = 5.6 Hz, 2H), 2.67 (t, J = 5.2 Hz, 2H), 2.24 (s, 6H); |
| 1627 | (structure with cyanothiazole-benzothiazepinone) | A, 6, 282 | 26 | 393.0 (M$^+$ + 1); | 392.04 for $C_{19}H_{12}N_4O_2S_2$ | $^1$H-NMR (DMSO-$d_6$, 400 MHz): δ 10.77 (br s, 1H), 9.38 (t, J = 4.8 Hz, 1H), 8.12 (s, 1H), 7.72-7.65 (m, 4H), 7.63-7.42 (m, 3H), 4.72 (d, J = 5.4 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | 1H-NMR |
|---|---|---|---|---|---|---|
| 1758 | 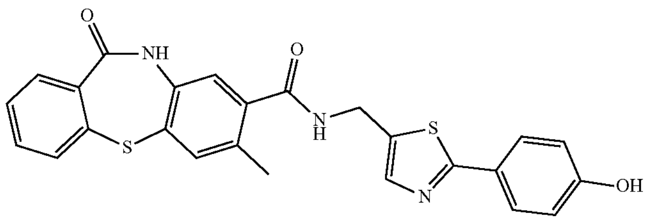 | A, 13, 357 | 22 | 474.0 (M+ + 1); | 473.09 for $C_{25}H_{19}N_3O_3S_2$ | 1H-NMR (DMSO-d6, 400 MHz): δ 10.63 (s, 1H), 9.97 (br s, 1H), 8.98 (t, J = 5.9 Hz, 1H), 7.72 (d, J = 8.8 Hz, 2H), 7.68-7.64 (m, 2H), 7.54-7.42 (m, 4H), 7.16 (s, 1H), 6.85 (d, J = 8.7 Hz, 2H), 4.58 (d, J = 5.8 Hz, 2H), 2.25 (s, 3H); |
| 1910 | 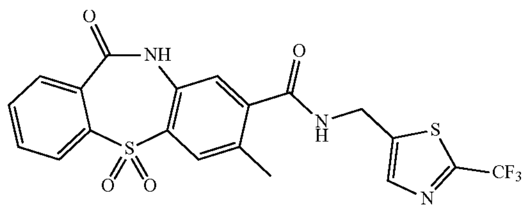 [SMILES: Cc1cc2c(cc1C(=O)NCc1cnc(C(F)(F)F)s1)NC(=O)c1ccccc1S2(=O)=O] | B$^a$, 105, 255 | 10 | 482.1 (M+ + 1); | 481.04 for $C_{20}H_{14}F_3N_3O_4S_2$ | 1H NMR (400 MHz, DMSO-d6): δ 11.35 (s, 1H), 9.28-9.26 (m, 1H), 8.06 (s, 1H), 7.99-7.94 (m, 2H), 7.91-7.81 (m, 3H), 7.32 (s, 1H), 4.73 (d, J = 4.0 Hz, 2H), 2.32 (s, 3H); |
| 1911 | 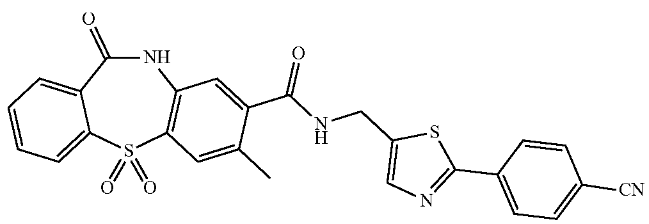 [SMILES: Cc1cc2c(cc1C(=O)NCc1cnc(-c3ccc(C#N)cc3)s1)NC(=O)c1ccccc1S2(=O)=O] | A, 105, 227 | 13 | 515.1 (M+ + 1); | 514.08 for $C_{26}H_{18}N_4O_4S_2$ | 1H NMR (400 MHz, DMSO-d6): δ 11.35 (s, 1H), 9.21 (t, J = 5.9 Hz, 1H), 8.09 (d, J = 8.5 Hz, 2H), 7.99-7.93 (m, 4H), 7.92-7.81 (m, 4H), 7.32 (s, 1H), 4.69 (d, J = 5.9 Hz, 2H), 2.34 (s, 3H); |
| 1915 | 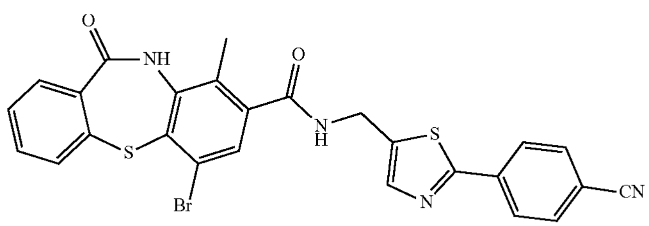 [SMILES: Cc1c(C(=O)NCc2cnc(-c3ccc(C#N)cc3)s2)cc(Br)c2c1NC(=O)c1ccccc1S2] | A, 32 227 | 52 | 561.0 (M+ + 1); | 560.00 for $C_{26}H_{17}BrN_4O_2S_2$ | 1H-NMR (DMSO-d6, 400 MHz): δ 10.39 (s, 1H), 9.18 (t, J = 5.3 Hz, 1H), 8.09 (d, J = 8.0 Hz, 2H), 7.98-7.88 (m, 3H), 7.71-7.66 (m, 1H), 7.59-7.44 (m, 4H), 4.65 (d, J = 5.0 Hz, 2H), 2.25 (s, 3H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 11106-A | 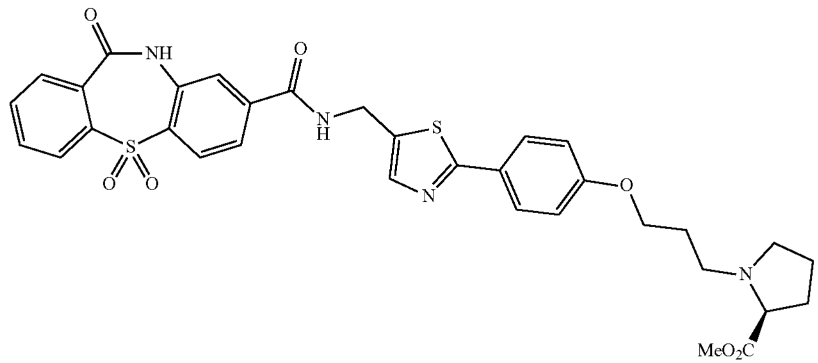 [SMILES: COC(=O)[C@@H]1CCCN1CCCOc1ccc(-c2ncc(CNC(=O)c3ccc4c(c3)NC(=O)c3ccccc3S4(=O)=O)s2)cc1] | A, 92, 517 | 40 | 661.1 ($M^+ + 1$) | 660.17 for $C_{33}H_{32}N_4O_7S_2$ | $^1$H NMR (500 MHz, DMSO-$d_6$): δ 11.51 (s, 1H), 9.44 (t, J = 5.8 Hz, 1H), 8.06 (d, J = 8.1 Hz, 1H), 8.01-7.96 (m, 2H), 7.93-7.77 (m, 6H), 7.72 (s, 1H), 7.00 (d, J = 8.7 Hz, 2H), 4.66 (t, J = 5.8 Hz, 2H), 4.05 (t, J = 6.1 Hz, 2H), 3.56 (s, 3H), 3.21-3.18 (m, 1H), 3.06-2.99 (m, 1H), 2.82-2.74 (m, 1H), 2.56-2.52 (m, 1H), 2.39-2.34 (m, 1H), 2.07-1.98 (m, 1H), 1.88-1.70 (m, 5H); |
| 1914 | 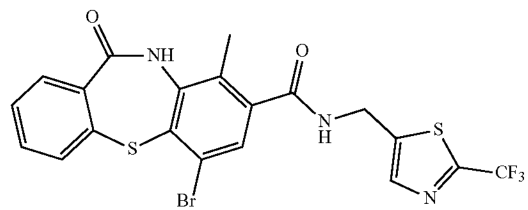 [SMILES: Cc1c(C(=O)NCc2cnc(C(F)(F)F)s2)cc(Br)c2c1NC(=O)c1ccccc1S2] | A, 32, 255 | 94 | 528.3 ($M^+ + 1$); $C_{20}H_{13}BrF_3N_3O_2S_2$ | 526.96 for | $^1$H-NMR (DMSO-$d_6$, 400 MHz): δ 10.39 (s, 1H), 9.24 (t, J = 5.6 Hz, 1H), 8.05 (s, 1H), 7.71-7.66 (m, 1H), 7.61-7.44 (m, 4H), 4.68 (d, J = 5.6 Hz, 2H), 2.23 (s, 3H); |
| 1535 | 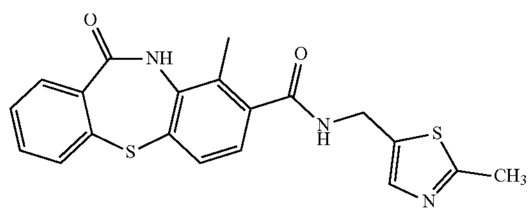 [SMILES: Cc1ncc(CNC(=O)c2ccc3c(c2C)NC(=O)c2ccccc2S3)s1] | A, 20, 297 | 69 | 395.8 ($M^+ + 1$); | 395.08 for $C_{20}H_{17}N_3O_2S_2$ | $^1$H-NMR (DMSO-$d_6$, 400 MHz): δ 10.24 (s, 1H), 8.96 (t, J = 6.0 Hz, 1H), 7.67-7.63 (m, 1H), 7.55-7.40 (m, 5H), 7.05 (d, J = 7.8 Hz, 1H), 4.51 (d, J = 5.9 Hz, 2H), 2.59 (s, 3H), 2.27 (s, 3H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1755 | 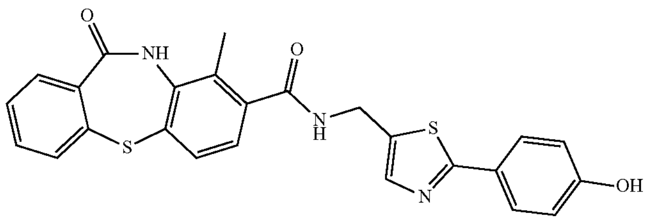 [SMILES: Cc1c(C(=O)NCc2cnc(-c3ccc(O)cc3)s2)ccc2c1NC(=O)c1ccccc1S2] | A, 20, 357 | 9 | 474.1 (M$^+$ + 1) | 473.09 for $C_{25}H_{19}N_3O_3S_2$ | $^1$H-NMR (DMSO-d$_6$, 400 MHz): δ 10.24 (s, 1H), 9.96 (s, 1H), 9.01 (t, J = 5.8 Hz, 1H), 7.72 (d, J = 8.5 Hz, 2H), 7.67-7.62 (m, 2H), 7.54-7.40 (m, 4H), 7.08 (d, J = 8.0 Hz, 1H), 6.85 (d, J = 8.7 Hz, 2H), 4.58 (d, J = 5.6 Hz, 2H), 2.29 (s, 3H); |
| 1766 | 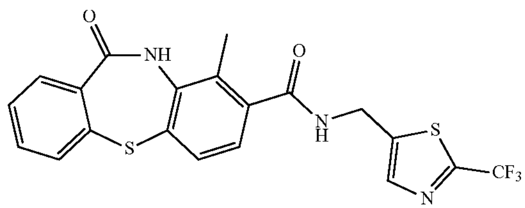 [SMILES: Cc1c(C(=O)NCc2cnc(C(F)(F)F)s2)ccc2c1NC(=O)c1ccccc1S2] | A, 20, 255 | 41 | 448.1 (M$^+$ − 1) | 449.05 for $C_{20}H_{14}F_3N_3O_2S_2$ | $^1$H-NMR (DMSO-d$_6$, 500 MHz): δ 10.24 (s, 1H), 9.15 (t, J = 5.8 Hz, 1H), 8.04 (s, 1H), 7.67-7.63 (m, 1H), 7.54-7.49 (m, 2H), 7.48-7.41 (m, 2H), 7.11 (d, J = 7.8 Hz, 1H), 4.69 (d, J = 5.8 Hz, 2H), 2.28 (s, 3H); |
| 1767 | 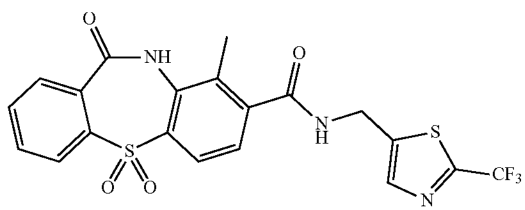 [SMILES: Cc1c(C(=O)NCc2cnc(C(F)(F)F)s2)ccc2c1NC(=O)c1ccccc1S2(=O)=O] | A, 95, 255 | 26 | 481.9 (M$^+$ + 1) | 481.04 for $C_{20}H_{14}F_3N_3O_4S_2$ | $^1$H-NMR (DMSO-d$_6$, 400 MHz): δ 10.86 (br s, 1H), 9.30 (t, J = 5.8 Hz, 1H), 8.06 (s, 1H), 7.95-7.84 (m, 4H), 7.80 (td, J = 7.5, 1.4 Hz, 1H), 7.38 (d, J = 8.2 Hz, 1H), 4.72 (d, J = 5.6 Hz, 2H), 2.31 (s, 3H); |
| 1752 | 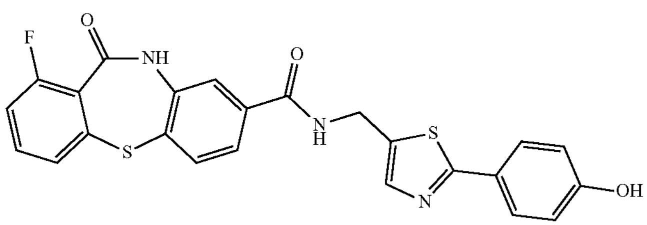 [SMILES: O=C(NCc1cnc(-c2ccc(O)cc2)s1)c1ccc2c(c1)NC(=O)c1c(F)cccc1S2] | A, 54, 357 | 7 | 477.9 (M$^+$ + 1) | 477.06 for $C_{24}H_{16}FN_3O_3S_2$ | $^1$H-NMR (DMSO-d$_6$, 400 MHz): δ 10.97 (br s, 1H), 9.95 (s, 1H), 9.27 (t, J = 5.5 Hz, 1H), 7.73-7.65 (m, 5H), 7.61 (dd, J = 8.3, 1.9 Hz, 1H), 7.52-7.46 (m, 1H), 7.40 (d, J = 7.4 Hz, 1H), 7.34-7.28 (m, 1H), 6.82 (d, J = 8.7 Hz, 2H), 4.62 (d, J = 5.5 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1746 | 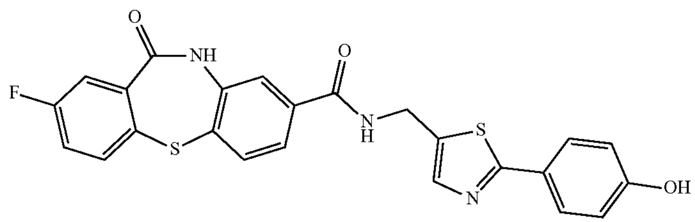 [SMILES: O=C(NCc1cnc(-c2ccc(O)cc2)s1)c1ccc2c(c1)NC(=O)c1cc(F)ccc1S2] | A, 61, 357 | 9 | 477.9 (M$^+$ + 1); | 477.06 for C$_{24}$H$_{16}$FN$_3$O$_3$S$_2$ | $^1$H-NMR (DMSO-d$_6$, 400 MHz): δ 10.91 (s, 1H), 9.94 (s, 1H), 9.25 (br t, J = 5.6 Hz, 1H), 7.76-7.31 (m, 9H), 6.83 (d, J = 8.7 Hz, 2H), 4.62 (br d, J = 5.6 Hz, 2H); |
| 1747 | 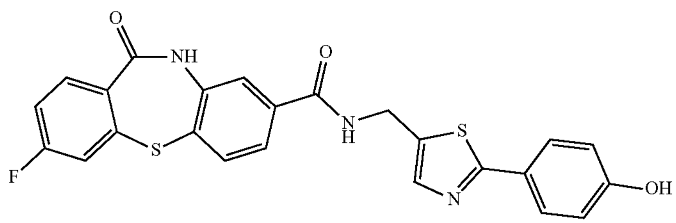 [SMILES: O=C(NCc1cnc(-c2ccc(O)cc2)s1)c1ccc2c(c1)NC(=O)c1ccc(F)cc1S2] | A, 68, 357 | 9 | 477.9 (M$^+$ + 1); | 477.06 for C$_{24}$H$_{16}$FN$_3$O$_3$S$_2$ | $^1$H-NMR (DMSO-d$_6$, 400 MHz): δ 10.80 (s, 1H), 9.92 (br s, 1H), 9.23 (t, J = 5.4 Hz, 1H), 7.76-7.57 (m, 7H), 7.43 (dd, J = 2.3, 8.4, 2.3 Hz, 1H), 7.30 (td, J = 8.5, 2.4 Hz, 1H), 6.80 (d, J = 8.5 Hz, 2H), 4.60 (d, J = 5.4 Hz, 2H); |
| 1753 | 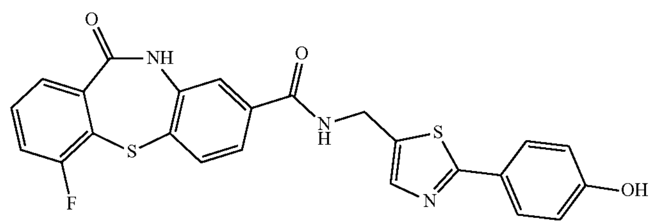 [SMILES: O=C(NCc1cnc(-c2ccc(O)cc2)s1)c1ccc2c(c1)NC(=O)c1cccc(F)c1S2] | A, 76, 357 | 12 | 477.9 (M$^+$ + 1); | 477.06 for C$_{24}$H$_{16}$FN$_3$O$_3$S$_2$ | $^1$H-NMR (DMSO-d$_6$, 400 MHz): δ 10.90 (s, 1H), 9.95 (s, 1H), 9.26 (t, J = 5.5 Hz, 1H), 7.74-7.59 (m, 6H), 7.54-7.44 (m, 3H), 6.83 (d, J = 8.6 Hz, 2H), 4.62 (d, J = 5.5 Hz, 2H); |
| 1904 | 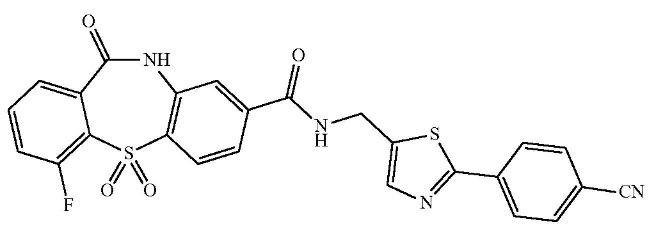 [SMILES: N#Cc1ccc(-c2ncc(CNC(=O)c3ccc4c(c3)NC(=O)c3cccc(F)c3S4(=O)=O)s2)cc1] | A$^c$, 144, 227 | 51 | 519.0 (M$^+$ + 1); | 518.05 for C$_{25}$H$_{15}$FN$_4$O$_4$S$_2$ | $^1$H-NMR (DMSO-d$_6$, 400 MHz): δ 1.58 (br s, 1H), 9.54 (t, J = 5.6 Hz, 1H), 8.13 (d, J = 8.7 Hz, 1H), 8.07 (d, J = 8.5 Hz, 2H), 7.93 (d, J = 8.8 Hz, 3H), 7.90-7.82 (m, 3H), 7.73 (d, J = 7.4 Hz, 1H), 7.70-7.64 (m, 1H), 4.72 (br d, J = 5.6 Hz, 2H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | 1H-NMR |
|---|---|---|---|---|---|---|
| 1749 | 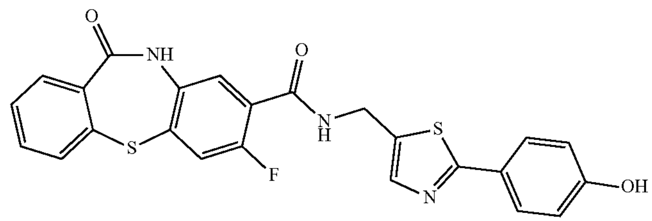 [SMILES: O=C(NCc1cnc(-c2ccc(O)cc2)s1)c1cc2c(cc1F)Sc1ccccc1C(=O)N2] | A, 81, 357 | 14 | 477.9 (M+ + 1); | 477.06 for $C_{24}H_{16}FN_3O_3S_2$ | 1H-NMR (DMSO-d6, 400 MHz): δ 10.72 (s, 1H), 9.96 (s, 1H), 9.04 (t, J = 5.3 Hz, 1H), 7.73-7.64 (m, 4H), 7.60-7.43 (m, 5H), 6.84 (d, J = 8.7 Hz, 2H), 4.61 (d, J = 5.8 Hz, 2H); |
| 1750 | 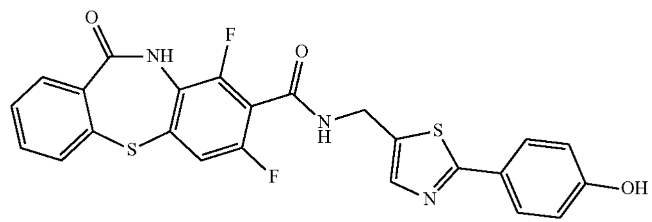 [SMILES: O=C1Nc2c(cc(F)c(C(=O)NCc3cnc(-c4ccc(O)cc4)s3)c2F)Sc2ccccc21] | A, 88, 357 | 10 | 495.9 (M+ + 1); | 495.05 for $C_{24}H_{15}F_2N_3O_3S_2$ | 1H-NMR (DMSO-d6, 400 MHz): δ 10.65 (br s, 1H), 9.96 (br s, 1H), 9.39 (t, J = 5.8 Hz, 1H), 7.74-7.64 (m, 4H), 7.58-7.46 (m, 4H), 6.85 (d, J = 8.7 Hz, 2H), 4.63 (d, J = 5.6 Hz, 2H); |
| 1541 | 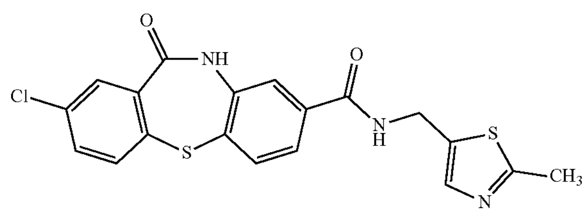 [SMILES: Cc1ncc(CNC(=O)c2ccc3c(c2)NC(=O)c2cc(Cl)ccc2S3)s1] | A, 40, 297 | 59 | 415.9 (M+ + 1); | 415.02 for $C_{20}H_{14}ClN_3O_2S_2$ | 1H NMR (DMSO-d6, 400 MHz): δ 10.91 (s, 1H), 9.20 (t, J = 5.9 Hz, 1H), 7.71-7.64 (m, 3H), 7.62-7.55 (m, 3H), 7.49 (s, 1H), 4.55 (d, J = 5.7 Hz, 2H), 2.57 (s, 3H); |
| 1760 | 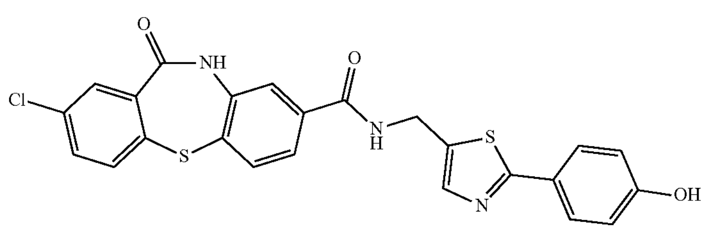 [SMILES: O=C(NCc1cnc(-c2ccc(O)cc2)s1)c1ccc2c(c1)NC(=O)c1cc(Cl)ccc1S2] | A$^d$, 40, 357 | 12 | 493.9 (M+ + 1); | 493.03 for $C_{24}H_{16}ClN_3O_3S_2$ | 1H-NMR (DMSO-d6, 400 MHz): δ 10.93 (br s, 1H), 9.95 (br s, 1H), 9.27 (t, J = 5.7 Hz, 1H), 7.74-7.60 (m, 7H), 7.57 (s, 2H), 6.83 (d, J = 8.7 Hz, 2H), 4.62 (d, J = 5.6 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1544 | (structure) | A, 47, 297 | 57 | 415.9 (M$^+$ + 1) | 415.02 for $C_{19}H_{14}ClN_3O_2S_2$ | $^1$H-NMR (DMSO-d$_6$, 400 MHz): δ 10.86 (s, 1H), 9.20 (t, J = 5.7 Hz, 1H), 7.71-7.64 (m, 4H), 7.62-7.58 (m, 1H), 7.54 (dd, J = 8.4, 2.1 Hz, 1H), 7.49 (s, 1H), 4.55 (d, J = 5.7 Hz, 2H), 2.57 (s, 3H); |
| 1761 | (structure) | A, 47, 357 | 12 | 494.0 (M$^+$ + 1) | 493.03 for $C_{24}H_{16}ClN_3O_3S_2$ | $^1$H-NMR (DMSO-d$_6$, 400 MHz): δ 10.86 (s, 1H), 9.94 (s, 1H), 9.25 (t, J = 5.9 Hz, 1H), 7.71 (dd, J = 6.4, 1.8 Hz, 2H), 7.68 (s, 2H), 7.67-7.60 (m, 4H), 7.53 (dd, J = 8.3, 2.1 Hz, 1H), 6.83 (d, J = 8.7 Hz, 2H), 4.62 (d, J = 5.6 Hz, 2H); |
| 1772 | (structure) | A$^a$, 89, 255 | 54 | 451.9 (M$^+$ + 1) | 451.03 for $C_{19}H_{12}F_3N_3O_3S_2$ | $^1$H-NMR (DMSO-d$_6$, 400 MHz): δ 11.06 (s, 1H), 9.46 (t, J = 5.8 Hz, 1H), 8.05 (s, 1H), 7.88 (dd, J = 8.2, 1.5 Hz, 1H), 7.84-7.77 (m, 2H), 7.76-7.68 (m, 3H), 7.63 (td, J = 7.5, 1.3 Hz, 1H), 4.72 (d, J = 5.6 Hz, 2H); |
| 1526 | (structure) | A, 89, 297 | 21 | 397.9 (M$^+$ + 1) | 397.06 for $C_{19}H_{15}N_3O_3S_2$ | $^1$H-NMR (DMSO-d$_6$, 400 MHz): δ 11.05 (s, 1H), 9.26 (t, J = 5.7 Hz, 1H), 7.85 (dd, J = 8.3, 1.5 Hz, 1H), 7.80 (dd, J = 7.6, 3.9 Hz, 2H), 7.76-7.67 (m, 3H), 7.63 (td, J = 8.4, 1.1 Hz, 1H), 7.49 (s, 1H), 4.56 (d, J = 5.7 Hz, 2H), 2.56 (s, 3H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 163, 169, 172, 176, 185, 190, 194 and various commercial and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1528 | 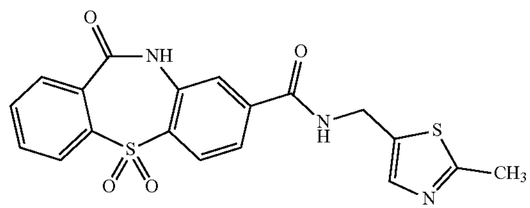 [SMILES: Cc1ncc(CNC(=O)c2ccc3c(c2)NC(=O)c2ccccc2S3(=O)=O)s1] | A, 92, 297 | 33 | 413.9 ($M^+$ + 1); | 413.05 for $C_{19}H_{15}N_3O_4S_2$ | $^1$H-NMR (DMSO-d$_6$, 400 MHz): δ 11.50 (br s, 1H), 9.37 (t, J = 5.7 Hz, 1H), 8.05 (d, J = 8.3 Hz, 1H), 8.01-7.95 (m, 2H), 7.93-7.82 (m, 3H), 7.78 (dd, J = 8.3, 1.4 Hz, 1H), 7.50 (s, 1H), 4.58 (d, J = 5.6 Hz, 2H), 2.57 (s, 3H); |
| 1529 | 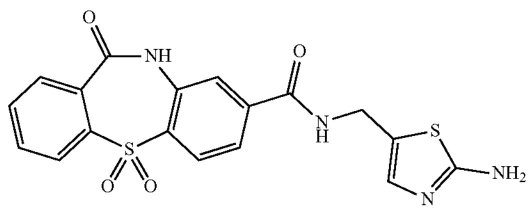 [SMILES: Nc1ncc(CNC(=O)c2ccc3c(c2)NC(=O)c2ccccc2S3(=O)=O)s1] | A, 92, 230 | 22 | 414.9 ($M^+$ + 1); | 414.05 for $C_{18}H_{14}N_4O_4S_2$ | $^1$H-NMR (DMSO-d$_6$, 400 MHz): 11.49 (br s, 1H), 9.18 (d, J = 5.4 Hz, 1H), 8.03 (d, J = 8.3 Hz, 1H), 7.98 (td, J = 7.3, 1.0 Hz, 2H), 7.93-7.81 (m, 3H), 7.77 (dd, J = 8.3, 1.3 Hz, 1H), 6.80 (s, 1H), 6.79 (br s, 2H), 4.38 (d, J = 5.5 Hz, 2H); |
| 1525 | 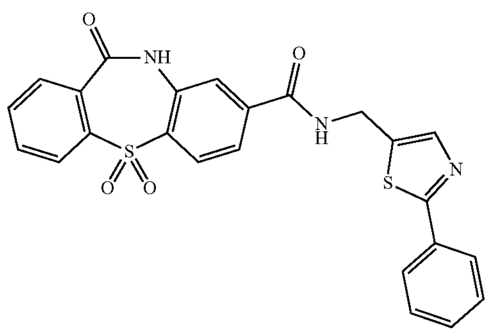 [SMILES: O=C(NCc1cnc(-c2ccccc2)s1)c1ccc2c(c1)NC(=O)c1ccccc1S2(=O)=O] | A, 92, 291 | 32 | 475.9 ($M^+$ + 1); | 475.07 for $C_{24}H_{17}N_3O_4S_2$ | $^1$H-NMR (DMSO-d$_6$, 400 MHz): δ 11.52 (s, 1H), 9.47 (t, J = 5.7 Hz, 1H), 8.06 (d, J = 8.3 Hz, 1H), 7.98 (td, J = 7.6, 1.0 Hz, 2H), 7.93-7.79 (m, 7H), 7.54-7.39 (m, 3H), 4.69 (d, J = 5.6 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various 149, 153, 155, 158, 200, 211, 216, commerical and synthesized amines.

| Example | Structure | Procedure, Intermediate, amine | Rx. Yield (%) | Mass Spec. Found | Mass Spec. Calculated | ¹H-NMR |
|---|---|---|---|---|---|---|
| 1550 | 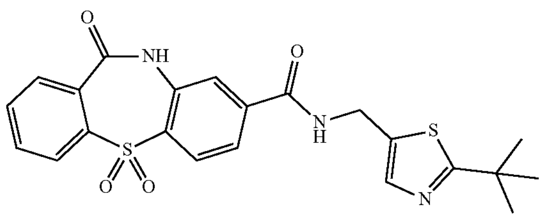 [SMILES: CC(C)(C)c1ncc(CNC(=O)c2ccc3c(c2)NC(=O)c2ccccc2S3(=O)=O)s1] | A, 92, 277 | 26 | 455.9 (M⁺ + 1); | 455.10 for $C_{22}H_{21}N_3O_4S_2$ | ¹H-NMR (DMSO-d₆, 500 MHz): δ 11.50 (s, 1H), 9.38 (t, J = 5.8 Hz, 1H), 8.05 (d, J = 8.4 Hz, 1H), 8.00-7.96 (m, 2H), 7.90 (td, J = 7.4, 1.3 Hz, 1H), 7.88-7.83 (m, 2H), 7.80 (dd, J = 8.2, 1.3 Hz, 1H), 7.54 (s, 1H), 4.60 (d, J = 5.8 Hz, 2H), 1.33 (s, 9H); |
| 1551 | 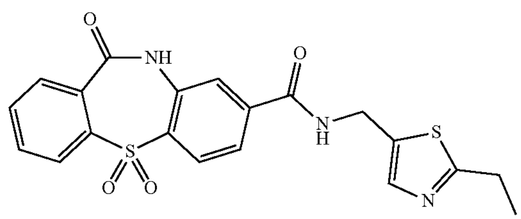 [SMILES: CCc1ncc(CNC(=O)c2ccc3c(c2)NC(=O)c2ccccc2S3(=O)=O)s1] | A, 92, 239 | 42 | 427.9 (M⁺ + 1); | 427.07 for $C_{20}H_{17}N_3O_4S_2$ | ¹H-NMR (DMSO-d₆, 500 MHz): δ 11.52 (s, 1H), 9.40 (t, J = 5.8 Hz, 1H), 8.04 (d, J = 8.4 Hz, 1H), 7.97 (t, J = 8.4 Hz, 2H), 7.90 (t, J = 7.1 Hz, 1H), 7.87-7.81 (m, 2H), 7.78 (d, J = 8.1 Hz, 1H), 7.53 (s, 1H), 4.58 (d, J = 5.8 Hz, 2H), 2.89 (q, J = 7.5 Hz, 2H), 1.23 (t, J = 7.5 Hz, 3H); |
| 1552 | 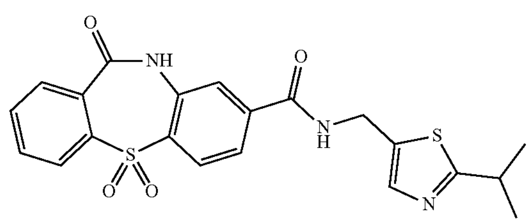 [SMILES: CC(C)c1ncc(CNC(=O)c2ccc3c(c2)NC(=O)c2ccccc2S3(=O)=O)s1] | A, 92, 251 | 34 | 441.9 (M⁺ + 1); | 441.08 for $C_{21}H_{19}N_3O_4S_2$ | ¹H-NMR (DMSO-d₆, 400 MHz): δ 11.50 (s, 1H), 9.38 (t, J = 5.8 Hz, 1H), 8.05 (d, J = 8.3 Hz, 1H), 8.01-7.95 (m, 2H), 7.93-7.82 (m, 3H), 7.79 (dd, J = 8.3, 1.6 Hz, 1H), 7.54 (s, 1H), 4.60 (d, J = 5.7 Hz, 2H), 3.24-3.15 (m, 1H), 1.27 (d, J = 6.9 Hz, 6H); |
| 1553 | 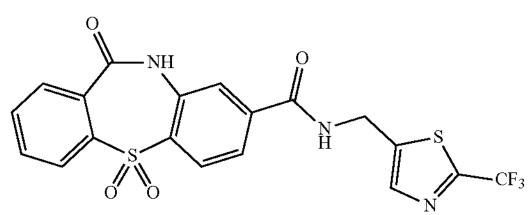 [SMILES: O=C(NCc1cnc(C(F)(F)F)s1)c1ccc2c(c1)NC(=O)c1ccccc1S2(=O)=O] | A, 92, 255 | 16 | 468.3 (M⁺ + 1); | 467.02 for $C_{19}H_{12}FN_3O_4S_2$ | ¹H-NMR (DMSO-d₆, 400 MHz): δ 11.50 (s, 1H), 9.56 (t, J = 5.6 Hz, 1H), 8.08-8.04 (m, 2H), 7.98 (td, J = 7.7, 0.9 Hz, 2H), 7.94-7.83 (m, 3H), 7.81 (dd, J = 8.2, 1.4 Hz, 1H), 4.75 (d, J = 5.5 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commercial and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1566 | 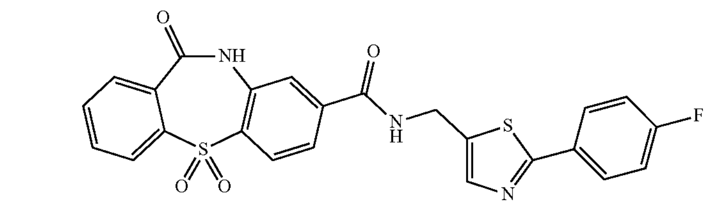 [SMILES: O=C(NCc1cnc(-c2ccc(F)cc2)s1)c1ccc2c(c1)NC(=O)c1ccccc1S2(=O)=O] | A, 92, 285 | 34 | 486.9 (M$^+$ + 1); | 486.10 for $C_{27}H_{19}FN_2O_4S$ | $^1$H-NMR (DMSO-d$_6$, 400 MHz): δ 11.52 (s, 1H), 9.31 (t, J = 5.7 Hz, 1H), 8.06 (d, J = 8.5 Hz, 1H), 8.01-7.95 (m, 2H), 7.93-7.82 (m, 4H), 7.66 (dd, J = 8.8, 5.5 Hz, 2H), 7.59-7.56 (m, 1H), 7.52 (d, J = 7.8 Hz, 1H), 7.41 (t, J = 7.6 Hz, 1H), 7.32-7.25 (m, 3H), 4.54 (d, J = 5.9 Hz, 2H); |
| 1584 | 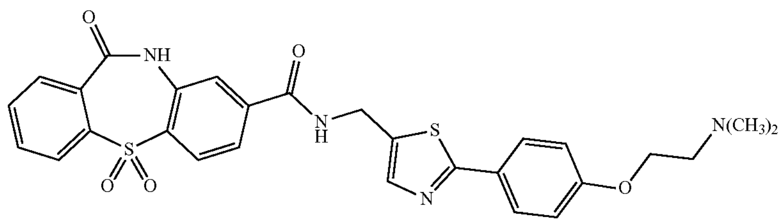 [SMILES: CN(C)CCOc1ccc(-c2ncc(CNC(=O)c3ccc4c(c3)NC(=O)c3ccccc3S4(=O)=O)s2)cc1] | A, 92, 360 | 47 | 563.0 (M$^+$ + 1); | 562.13 for $C_{28}H_{26}N_4O_5S_2$ | $^1$H NMR (DMSO-d$_6$, 400 MHz): δ 11.52 (br s, 1H), 9.47 (t, J = 5.4 Hz, 1H), 8.05 (d, J = 8.3 Hz, 1H), 7.98 (td, J = 7.5, 1.0 Hz, 2H), 7.90 (td, J = 7.4, 1.3 Hz, 1H), 7.87-7.82 (m, 3H), 7.80 (d, J = 8.9 Hz, 2H), 7.72 (s, 1H), 7.02 (d, J = 8.8 Hz, 2H), 4.66 (d, J = 5.5 Hz, 2H), 4.09 (t, J = 5.8 Hz, 2H), 2.63 (t, J = 5.8 Hz, 2H), 2.21 (s, 6H); |
| 1595 | 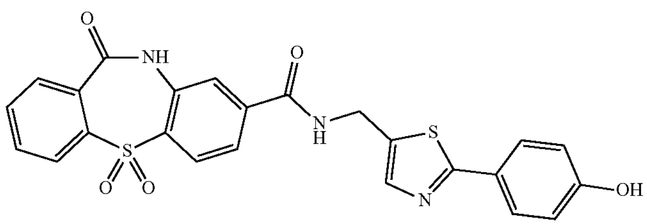 [SMILES: O=C(NCc1cnc(-c2ccc(O)cc2)s1)c1ccc2c(c1)NC(=O)c1ccccc1S2(=O)=O] | A, 92, 357 | 50 | 492.0 (M$^+$ + 1); | 491.06 for $C_{24}H_{17}N_3O_5S_2$ | $^1$H NMR (DMSO-d$_6$, 500 MHz): δ 11.51 (s, 1H), 9.94 (s, 1H), 9.43 (t, J = 5.8 Hz, 1H), 8.05 (d, J = 8.4 Hz, 1H), 8.00-7.96 (m, 2H), 7.90 (td, J = 7.5, 1.2 Hz, 1H), 7.87-7.83 (m, 2H), 7.81 (dd, J = 8.2, 1.3 Hz, 1H), 7.71-7.67 (m, 3H), 6.83 (d, J = 8.4 Hz, 2H), 4.65 (d, J = 5.5 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commercial and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 1596 | 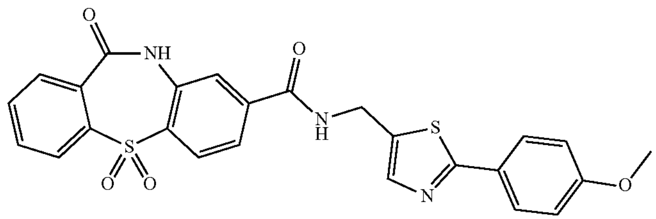 [SMILES: COc1ccc(-c2ncc(CNC(=O)c3ccc4c(c3)NC(=O)c3ccccc3S4(=O)=O)s2)cc1] | A, 92, 363 | 60 | 506.0 ($M^+ + 1$); | 505.08 for $C_{25}H_{19}N_3O_5S_2$ | $^1$H NMR (DMSO-$d_6$, 500 MHz): δ 11.51 (s, 1H), 9.45 (t, J = 5.6 Hz, 1H), 8.06 (d, J = 8.4 Hz, 1H), 7.98 (t, J = 8.5 Hz, 2H), 7.93-7.78 (m, 6H), 7.72 (s, 1H), 7.02 (d, J = 9.0 Hz, 2H), 4.66 (d, J = 5.5 Hz, 2H), 3.80 (s, 3H); |
| 1587 | 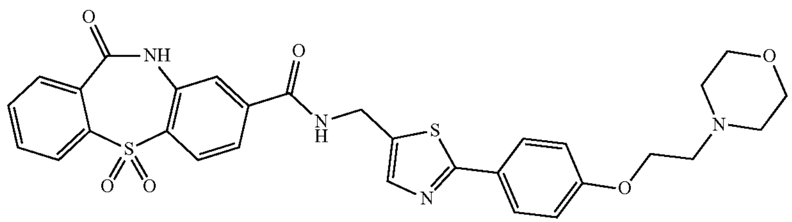 [SMILES: O=C(NCc1cnc(-c2ccc(OCCN3CCOCC3)cc2)s1)c1ccc2c(c1)NC(=O)c1ccccc1S2(=O)=O] | A, 92, 372 | 58 | 605.0 ($M^+ + 1$); | 604.15 for $C_{30}H_{28}N_4O_6S_2$ | $^1$H NMR (DMSO-$d_6$, 400 MHz): δ 11.51 (s, 1H), 9.44 (t, J = 5.7 Hz, 1H), 8.06 (d, J = 8.2 Hz, 1H), 8.00-7.96 (m, 2H), 7.90 (td, J = 7.5, 1.5 Hz, 1H), 7.87-7.77 (m, 5H), 7.72 (s, 1H), 7.03 (d, J = 8.9 Hz, 2H), 4.66 (t, J = 5.6 Hz, 2H), 4.14 (t, J = 5.7 Hz, 2H), 3.59-3.55 (m, 4H), 2.70 (t, J = 5.7 Hz, 2H), 2.48-2.46 (m, 4H); |
| 1590 | 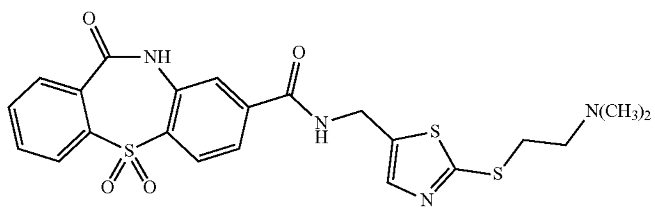 [SMILES: CN(C)CCSc1ncc(CNC(=O)c2ccc3c(c2)NC(=O)c2ccccc2S3(=O)=O)s1] | A, 92, 288 | 36 | 502.9 ($M^+ + 1$); | 502.08 for $C_{22}H_{22}N_4O_4S_3$ | $^1$H-NMR (DMSO-$d_6$, 500 MHz): δ 11.50 (br s, 1H), 9.39 (t, J = 5.5 Hz, 1H), 8.04 (d, J = 8.4 Hz, 1H), 7.97 (t, J = 8.1 Hz, 2H), 7.93-7.75 (m, 4H), 7.57 (s, 1H), 4.57 (d, J = 5.8 Hz, 2H), 3.29-3.25 (m, 2H), 2.55 (t, J = 6.9 Hz, 2H), 2.15 (s, 6H); |
| 1628 | 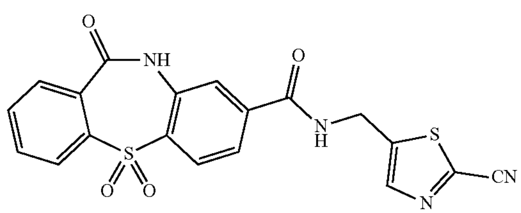 [SMILES: N#Cc1ncc(CNC(=O)c2ccc3c(c2)NC(=O)c2ccccc2S3(=O)=O)s1] | A, 92, 282 | 20 | 424.9 ($M^+ + 1$); | 424.03 for $C_{19}H_{12}N_4O_4S_2$ | $^1$H-NMR (DMSO-$d_6$, 400 MHz): δ 11.53 (s, 1H), 9.59 (t, J = 5.4 Hz, 1H), 8.14 (s, 1H), 8.07 (d, J = 8.3 Hz, 1H), 7.98 (t, J = 7.3 Hz, 2H), 7.94-7.83 (m, 3H), 7.80 (d, J = 8.3 Hz, 1H), 7.82-7.78 (m, 1H), 4.76 (d, J = 5.5 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 163, 169, 172, 176, 185, 190, 194 and various commercial and synthesized amines.

| Example | Structure | Procedure, Intermediate, amine | Rx. Yield (%) | Mass Spec. Found | Mass Spec. Calculated | ¹H-NMR |
|---|---|---|---|---|---|---|
| 1645 | 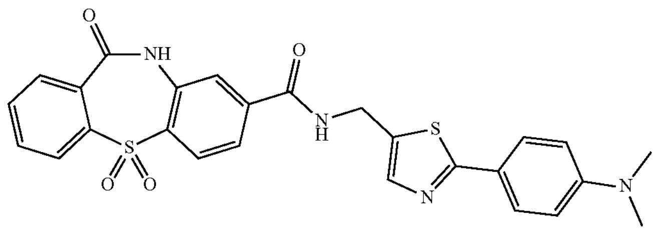 [SMILES: CN(C)c1ccc(-c2ncc(CNC(=O)c3ccc4c(c3)NC(=O)c3ccccc3S4(=O)=O)s2)cc1] | A, 92, 312 | 40 | 519.0 (M⁺ + 1); | 518.11 for $C_{26}H_{22}N_4O_4S_2$ | ¹H-NMR (DMSO-d₆, 400 MHz): δ 11.51 (s, 1H), 9.41 (t, J = 5.6 Hz, 1H), 8.05 (d, J = 8.4 Hz, 1H), 7.98 (t, J = 8.7 Hz, 2H), 7.90 (t, J = 7.1 Hz, 1H), 7.87-7.79 (m, 3H), 7.68 (d, J = 9.0 Hz, 2H), 7.63 (s, 1H), 6.74 (d, J = 9.0 Hz, 2H), 4.63 (d, J = 5.8 Hz, 2H), 2.96 (s, 6H); |
| 1648 | 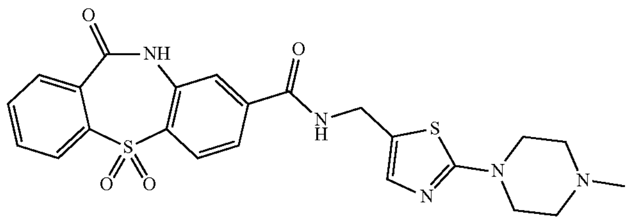 [SMILES: CN1CCN(c2ncc(CNC(=O)c3ccc4c(c3)NC(=O)c3ccccc3S4(=O)=O)s2)CC1] | A, 92, 307 | 21 | 498.0 (M⁺ + 1); | 497.12 for $C_{23}H_{23}N_5O_4S_2$ | ¹H-NMR (DMSO-d₆, 400 MHz): δ 11.50 (s, 1H), 9.27 (t, J = 5.7 Hz, 1H), 8.07-7.75 (m, 7H), 7.04 (s, 1H), 4.44 (d, J = 5.6 Hz, 2H), 3.33-3.31 (m, 4H), 2.40-2.34 (m, 4H), 2.19 (s, 3H); |
| 1650 | 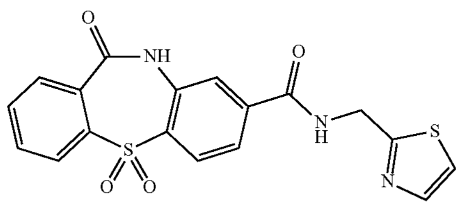 [SMILES: O=C(NCc1nccs1)c1ccc2c(c1)NC(=O)c1ccccc1S2(=O)=O] | A, 92, 218 | 35 | 399.9 (M⁺ + 1); | 399.03 for $C_{18}H_{13}N_3O_3S_2$ | ¹H-NMR (DMSO-d₆, 400 MHz): δ 11.53 (br s, 1H), 9.66-9.58 (m, 1H), 8.08 (d, J = 8.2 Hz, 1H), 8.02-7.96 (m, 2H), 7.94-7.82 (m, 4H), 7.73 (d, J = 3.2 Hz, 1H), 7.63 (d, J = 6.1 Hz, 1H), 4.75 (d, J = 6.1 Hz, 2H); |
| 1679 | 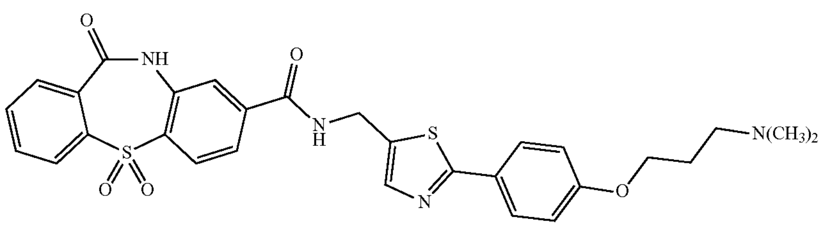 [SMILES: CN(C)CCCOc1ccc(-c2ncc(CNC(=O)c3ccc4c(c3)NC(=O)c3ccccc3S4(=O)=O)s2)cc1] | A, 92, 367 | 24 | 577.1 (M⁺ + 1); | 576.15 for $C_{29}H_{28}N_4O_5S_2$ | ¹H NMR (DMSO-d₆, 400 MHz): δ 11.52 (br s, 1H), 9.44 (t, J = 5.7 Hz, 1H), 8.05 (d, J = 8.3 Hz, 1H), 8.00-7.95 (m, 2H), 7.93-7.84 (m, 3H), 7.72 (s, 1H), 7.00 (d, J = 8.9 Hz, 2H), 4.66 (d, J = 5.5 Hz, 2H), 4.04 (t, J = 6.4 Hz, 2H), 2.34 (t, J = 7.1 Hz, 2H), 2.13 (s, 6H), 1.89-1.80 (m, 2H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commercial and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 1763 | (structure) | A, 92, 219 | 89 | 427.9 (M$^+$ + 1); | 427.07 for $C_{20}H_{17}N_3O_4S_2$ | $^1$H-NMR (DMSO-d6, 400 MHz): δ 11.50 (br s, 1H), 9.29 (t, J = 5.6 Hz, 1H), 8.04 (d, J = 8.3 Hz, 1H), 7.98 (td, J = 7.5, 0.9 Hz, 2H), 7.93-7.75 (m, 4H), 4.49 (d, J = 5.6 Hz, 2H), 2.50 (s, 3H), 2.30 (s, 3H); |
| 1814 | (structure) | A$^b$, 92, 316 | 88 | 519.1 (M$^+$ + 1); | 518.05 for $C_{25}H_{15}FN_4O_4S_2$ | $^1$H-NMR (DMSO-d$_6$, 400 MHz): δ 11.47 (br s, 1H), 9.53 (t, J = 5.7 Hz, 1H), 8.35 (t, J = 7.9 Hz, 1H), 8.11-7.95 (m, 5H), 7.93-7.79 (m, 5H), 4.75 (d, J = 5.6 Hz, 2H); |
| 1661 | (structure) | A, 92, 369 | 24 | 505.9 (M$^+$ + 1); | 505.08 for $C_{25}H_{19}N_3O_5S_2$ | $^1$H-NMR (DMSO-d$_6$, 500 MHz) (rotamers): δ 11.44 (br s, 1H), 10.00 (br s, 1H), 7.94-8.04-7.96 (m, 3H), 7.94-7.82 (m, 2H), 7.81-7.71 (m, 3H), 7.49-7.38 (m, 2H), 6.86 (d, J = 8.4 Hz, 2H), 4.82, 4.59 (s, 2H), 2.95, 2.76 (s, 3H); |
| 1821 | (structure) | A$^b$, 92, 319 | 29 | 531.1 (M$^+$ + 1); | 530.07 for $C_{26}H_{18}N_4O_5S_2$ | $^1$H-NMR (DMSO-d$_6$, 500 MHz): δ 11.52 (s, 1H), 10.60 (s, 1H), 9.45 (t, J = 5.3 Hz, 1H), 8.06 (d, J = 8.2 Hz, 1H), 8.01-7.94 (m, 2H), 7.93-7.79 (m, 5H), 7.72 (d, J = 3.5 Hz, 3H), 6.88 (d, J = 8.3 Hz, 1H), 4.66 (d, J = 5.1 Hz, 2H), 3.54 (s, 2H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 163, 169, 172, 176, 185, 190, 194 and various commerical and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 1823-A | 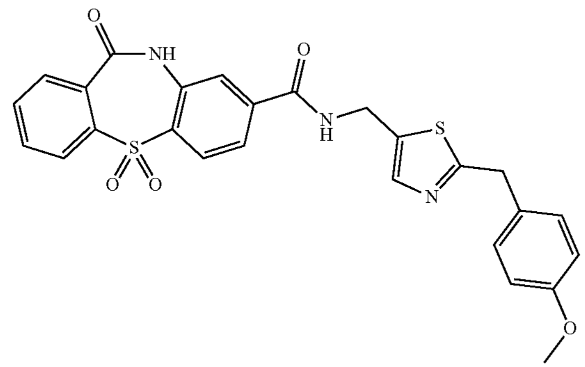 [SMILES: COc1ccc(Cc2ncc(CNC(=O)c3ccc4c(c3)NC(=O)c3ccccc3S4(=O)=O)s2)cc1] | A$^c$, 92, 326 | 32 | 520.1 (M$^+$ + 1); | 519.09 for $C_{26}H_{21}N_3O_5S_2$ | $^1$H NMR (DMSO-d$_6$, 500 MHz): δ 11.48 (br s, 1H), 9.35 (t, J = 5.5 Hz, 1H), 8.03 (d, J = 8.4 Hz, 1H), 7.97 (t, J = 8.1 Hz, 2H), 7.92-7.80 (m, 3H), 7.76 (d, J = 8.4 Hz, 1H), 7.55 (s, 1H), 7.21 (d, J = 8.4 Hz, 2H), 6.87 (d, J = 8.7 Hz, 2H), 4.56 (d, J = 5.8 Hz, 2H), 4.16 (s, 2H), 3.71 (s, 3H); |
| 1840 | 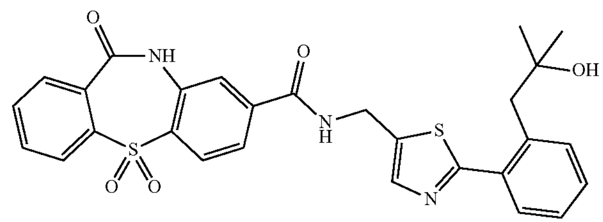 [SMILES: CC(C)(O)Cc1ccccc1-c1ncc(CNC(=O)c2ccc3c(c2)NC(=O)c2ccccc2S3(=O)=O)s1] | A, 92, 338 | 19 | 548.1 (M$^+$ + 1); | 547.12 for $C_{28}H_{25}N_3O_5S_2$ | $^1$H NMR (400 MHz, DMSO-d$_6$) δ 11.52 (s, 1H), 9.49 (t, J = 5.8 Hz, 1H), 8.06 (d, J = 8.3 Hz, 1H), 7.98 (td, J = 7.8, 1.3 Hz, 2H), 7.93-7.79 (m, 5H), 7.50 (dd, J = 7.5, 0.9 Hz, 1H), 7.45-7.37 (m, 2H), 7.34-7.29 (m, 1H), 5.00 (s, 1H), 4.70 (d, J = 5.6 Hz, 2H), 3.07 (s, 2H), 0.99 (s, 6H); |
| 1882 | 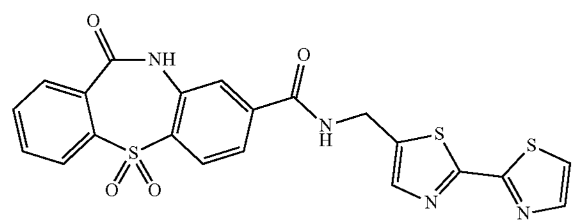 [SMILES: O=C(NCc1cnc(-c2nccs2)s1)c1ccc2c(c1)NC(=O)c1ccccc1S2(=O)=O] | A$^b$, 92, 345 | 29 | 483.0 (M$^+$ + 1); | 482.02 for $C_{21}H_{14}N_4O_4S_3$ | $^1$H NMR (DMSO-d$_6$, 400 MHz): δ 11.51 (s, 1H), 9.50 (t, J = 5.6 Hz, 1H), 8.06 (d, J = 8.4 Hz, 1H), 8.01-7.94 (m, 3H), 7.93-7.78 (m, 6H), 4.70 (d, J = 5.6 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commerical and synthesized amines. 149, 153, 155, 158, 200, 211, 216,

| Example | Structure | Procedure, Intermediate, amine | Rx. Yield (%) | Mass Spec. Found | Mass Spec. Calculated | $^1$H-NMR |
|---|---|---|---|---|---|---|
| 1906 | 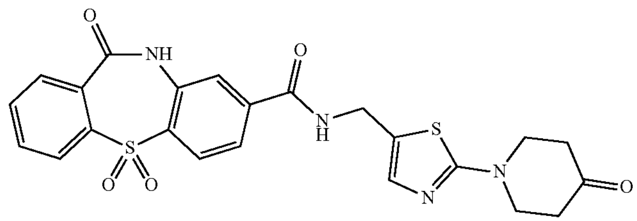 [SMILES: O=C1CCN(c2ncc(CNC(=O)c3ccc4c(c3)NC(=O)c3ccccc3S4(=O)=O)s2)CC1] | A$^c$, 92, 488 | 9 | 497.0 (M$^+$ + 1); | 496.09 for $C_{23}H_{20}N_4O_5S_2$ | $^1$H NMR (400 MHz, DMSO-d$_6$): δ 11.51 (s, 1H), 9.33 (t, J = 5.8 Hz, 1H), 8.05 (d, J = 8.3 Hz, 1H), 8.00-7.96 (m, 2H), 7.93-7.83 (m, 3H), 7.79 (dd, J = 8.3, 1.6 Hz, 1H), 7.13 (s, 1H), 4.47 (d, J = 5.6 Hz, 2H), 3.74 (t, J = 6.2 Hz, 4H), 2.48-2.45 (m, 4H); |
| 1973 | 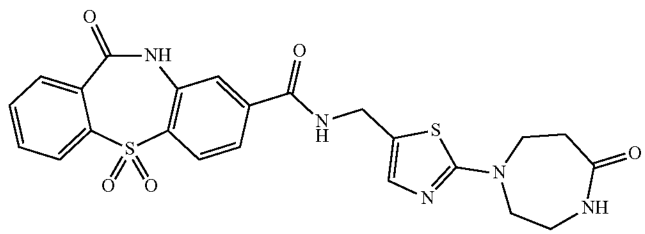 [SMILES: O=C1CCN(c2ncc(CNC(=O)c3ccc4c(c3)NC(=O)c3ccccc3S4(=O)=O)s2)CCN1] | A, 92, 492 | 48 | 512.1 (M$^+$ + 1); | 511.10 for $C_{23}H_{21}N_5O_5S_2$ | $^1$H NMR (400 MHz, DMSO-d$_6$): δ 11.51 (s, 1H), 9.28 (t, J = 5.8 Hz, 1H), 8.04 (d, J = 8.3 Hz, 1H), 8.01-7.95 (m, 2H), 7.94-7.83 (m, 3H), 7.79 (dd, J = 8.3, 1.5 Hz, 1H), 7.67 (t, J = 5.3 Hz, 1H), 7.03 (s, 1H), 4.45 (d, J = 5.5 Hz, 2H), 3.65-3.53 (m, 4H), 3.34-3.39 (m, 2H), 3.23-3.17 (m, 2H); |
| 1927 | 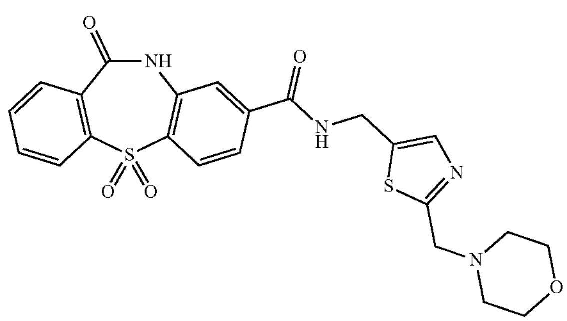 [SMILES: O=C(NCc1cnc(CN2CCOCC2)s1)c1ccc2c(c1)NC(=O)c1ccccc1S2(=O)=O] | A, 92, 500 | 40 | 499.0 (M$^+$ + 1); | 498.10 for $C_{23}H_{22}N_4O_5S_2$ | $^1$H-NMR (DMSO-d$_6$, 400 MHz): δ 11.51 (s, 1H), 9.39 (t, J = 5.6 Hz, 1H), 8.05 (br d, J = 8.2 Hz, 1H), 7.98 (t, J = 7.0 Hz, 2H), 7.93-7.77 (m, 4H), 7.57 (s, 1H), 4.61 (br d, J = 4.9 Hz, 2H), 3.73 (s, 2H), 3.59-3.54 (m, 4H), 2.47-2.43 (m, 4H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various 149, 153, 155, 158, 200, 211, 216, commerical and synthesized amines.

| Example | Structure | Procedure, Interemediate, amine | Rx. Yield (%) | Mass Spec. Found | Mass Spec. Calculated | 1H-NMR |
|---|---|---|---|---|---|---|
| 1885-A | 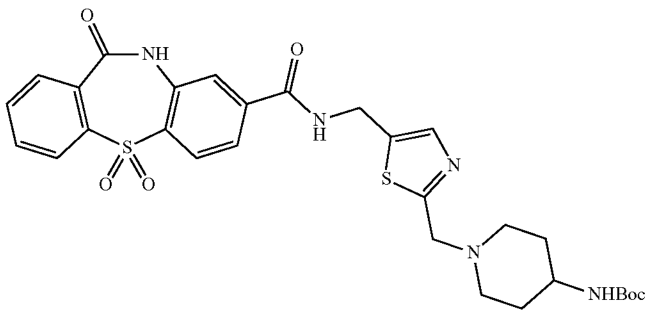 [SMILES: CC(C)(C)OC(=O)NC1CCN(Cc2ncc(CNC(=O)c3ccc4c(c3)NC(=O)c3ccccc3S4(=O)=O)s2)CC1] | A, 92, 534 | 25 | 612.1 (M+ + 1); | 611.19 for $C_{29}H_{33}N_5O_6S_2$ | 1H NMR (DMSO-d6, 400 MHz): δ 11.50 (s, 1H), 9.38 (t, J = 5.7 Hz, 1H), 8.05 (d, J = 8.3 Hz, 1H), 7.98 (dt, J = 7.5, 1.0 Hz, 2H), 7.94-7.82 (m, 3H), 7.79 (dd, J = 8.3, 1.5 Hz, 1H), 7.55 (s, 1H), 6.74 (d, J = 7.5 Hz, 1H), 4.60 (d, J = 5.6 Hz, 2H), 3.69 (s, 2H), 3.26-3.08 (m, 2H), 2.84-2.75 (m, 2H), 2.15-2.04 (m, 2H), 1.74-1.60 (m, 2H), 1.43-1.33 (m, 11H); |
| 1929 | 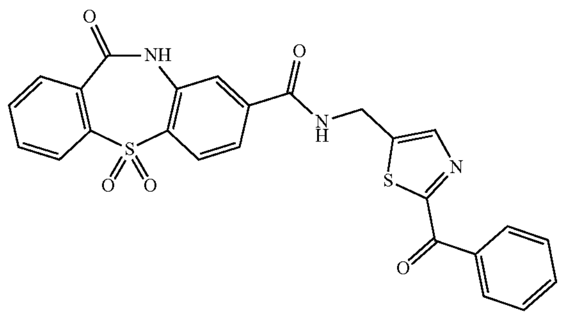 [SMILES: O=C(NCc1cnc(C(=O)c2ccccc2)s1)c1ccc2c(c1)NC(=O)c1ccccc1S2(=O)=O] | A$^c$, 92, 332 | 19 | 503.7 (M+ + 1); | 503.06 for $C_{25}H_{17}N_3O_5S_2$ | 1H-NMR (DMSO-d6, 400 MHz): δ 11.52 (s, 1H), 9.57 (t, J = 5.8 Hz, 1H), 8.36-8.30 (m, 2H), 8.12 (s, 1H), 8.07 (d, J = 8.3 Hz, 1H), 7.98 (td, J = 7.5, 1.1 Hz, 2H), 7.93-7.80 (m, 4H), 7.74-7.69 (m, 1H), 7.61-7.53 (m, 2H), 4.78 (d, J = 5.6 Hz, 2H); |
| 1957 | 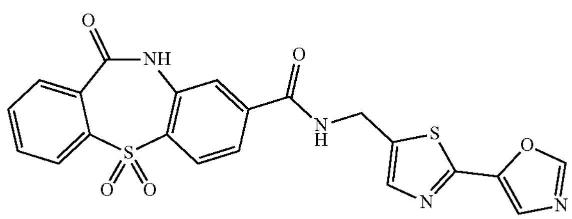 [SMILES: O=C(NCc1cnc(-c2cnco2)s1)c1ccc2c(c1)NC(=O)c1ccccc1S2(=O)=O] | A$^c$, 92, 508 | 26 | 467.0 (M+ + 1); | 466.04 for $C_{21}H_{14}N_4O_5S_2$ | 1H-NMR (DMSO-d6, 400 MHz): δ 11.51 (s, 1H), 9.51 (br t, J = 5.5 Hz, 1H), 8.55 (s, 1H), 8.06 (d, J = 8.3 Hz, 1H), 8.01-7.95 (m, 2H), 7.93-7.77 (m, 6H), 4.70 (br d, J = 5.5 Hz, 2H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1958 | 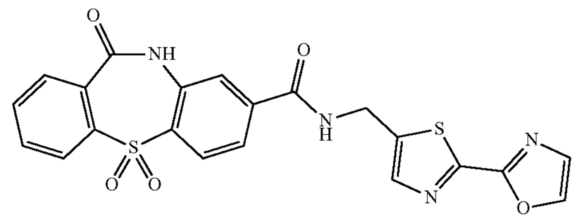 [SMILES: O=C(NCc1cnc(-c2ncco2)s1)c1ccc2c(c1)NC(=O)c1ccccc1S2(=O)=O] | A$^c$, 92, 512 | 48 | 466.9 (M$^+$ + 1); | 466.04 for $C_{21}H_{14}N_4O_5S_2$ | $^1$H-NMR (DMSO-d$_6$, 400 MHz): δ 11.51 (s, 1H), 9.52 (t, J = 5.7 Hz, 1H), 8.31 (s, 1H), 8.06 (d, J = 8.3 Hz, 1H), 7.98 (td, J = 7.4, 1.0 Hz, 2H), 7.95-7.88 (m, 2H), 7.87-7.79 (m, 3H), 7.45 (s, 1H), 4.72 (d, J = 5.6 Hz, 2H); |
| 1991 | 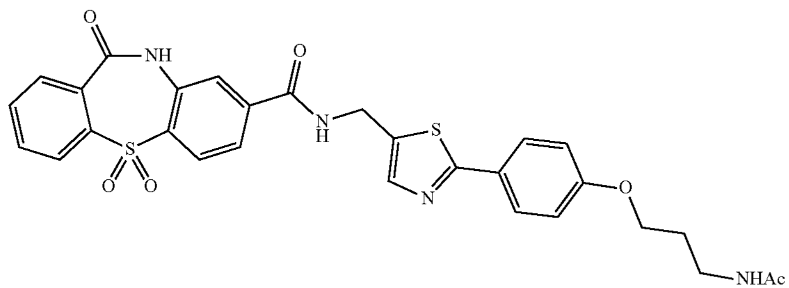 [SMILES: CC(=O)NCCCOc1ccc(-c2ncc(CNC(=O)c3ccc4c(c3)NC(=O)c3ccccc3S4(=O)=O)s2)cc1] | A$^c$, 92, 408 | 44 | 591.4 (M$^+$ + 1); | 590.13 for $C_{29}H_{26}N_4O_6S_2$ | $^1$H-NMR (DMSO-d$_6$, 400 MHz): δ 11.51 (s, 1H), 9.45 (t, J = 5.6 Hz, 1H), 8.06 (d, J = 8.2 Hz, 1H), 8.03-7.95 (m, 3H), 7.93-7.84 (m, 3H), 7.84-7.78 (m, 3H), 7.72 (s, 1H), 7.01 (dd, J = 8.9, 2.2 Hz, 2H), 4.66 (d, J = 5.5 Hz, 2H), 4.06-4.01 (m, 2H), 3.28-3.14 (m, 2H), 1.91-1.81 (m, 2H), 1.79 (s, 3H); |
| 1992 | 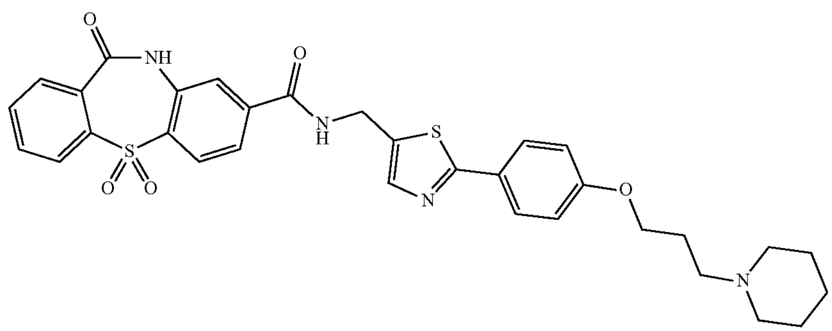 [SMILES: O=C(NCc1cnc(-c2ccc(OCCCN3CCCCC3)cc2)s1)c1ccc2c(c1)NC(=O)c1ccccc1S2(=O)=O] | A$^c$, 92, 375 | 45 | 617.1 (M$^+$ + 1); | 616.18 for $C_{32}H_{32}N_4O_5S_2$ | $^1$H-NMR (DMSO-d$_6$, 400 MHz): δ 11.52 (br s, 1H), 9.46 (t, J = 5.8 Hz, 1H), 8.06 (d, J = 8.3 Hz, 1H), 7.98 (td, J = 7.5, 1.0 Hz, 2H), 7.93-7.79 (m, 6H), 7.72 (s, 1H), 7.02 (d, J = 8.9 Hz, 2H), 4.66 (d, J = 5.5 Hz, 2H), 4.08 (t, J = 5.9 Hz, 2H), 3.04-2.70 (m, 4H), 2.30-2.14 (m, 2H), 2.12-1.93 (m, 2H), 1.75-1.18 (m, 6H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | 1H-NMR |
|---|---|---|---|---|---|---|
| 1993 | 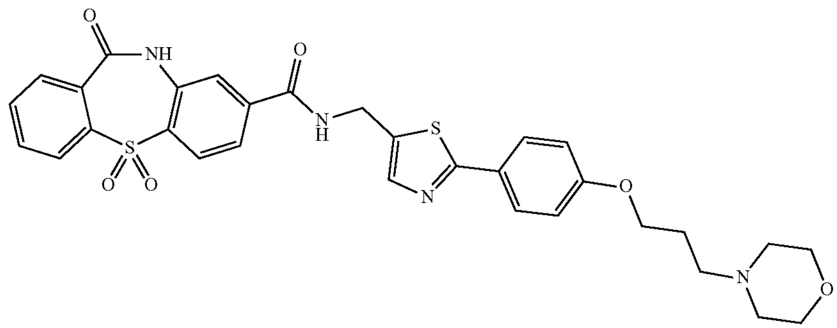 [SMILES: O=C(NCc1cnc(-c2ccc(OCCCN3CCOCC3)cc2)s1)c1ccc2c(c1)NC(=O)c1ccccc1S2(=O)=O] | A, 92, 378 | 35 | 619.3 (M+ + 1); | 618.16 $C_{31}H_{30}N_4O_6S_2$ | 1H-NMR (DMSO-d6, 400 MHz): δ 11.51 (s, 1H), 9.44 (t, J = 5.8 Hz, 1H), 8.06 (d, J = 8.3 Hz, 1H), 8.01-7.95 (m, 2H), 7.92-7.84 (m, 3H), 7.84-7.77 (m, 3H), 7.72 (s, 1H), 7.01 (d, J = 9.0 Hz, 2H), 4.66 (d, J = 5.6 Hz, 2H), 4.06 (t, J = 6.4 Hz, 2H), 3.59-3.53 (m, 4H), 2.41 (t, J = 7.2 Hz, 2H), 2.37-2.33 (m, 4H), 1.92-1.84 (m, 2H); |
| 1994 | 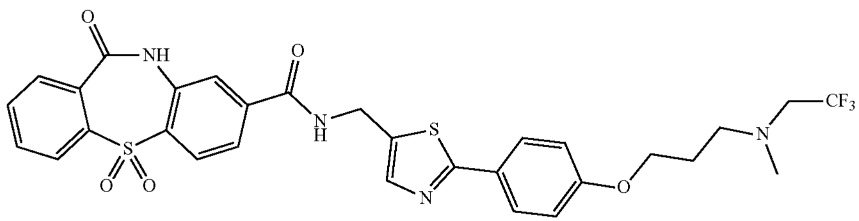 [SMILES: CN(CCCOc1ccc(-c2ncc(CNC(=O)c3ccc4c(c3)NC(=O)c3ccccc3S4(=O)=O)s2)cc1)CC(F)(F)F] | A$^c$, 92, 383 | 38 | 645.0 (M+ + 1); | 644.14 for $C_{30}H_{27}F_3N_4O_5S_2$ | 1H-NMR (DMSO-d6, 400 MHz): δ 11.51 (br s, 1H), 9.44 (t, J = 5.6 Hz, 1H), 8.05 (d, J = 8.2 Hz, 1H), 7.98 (td, J = 7.5, 0.8 Hz, 2H), 7.93-7.84 (m, 3H), 7.84-7.78 (m, 3H), 7.72 (s, 1H), 7.00 (d, J = 8.7 Hz, 2H), 4.66 (d, J = 5.5 Hz, 2H), 4.04 (t, J = 6.2 Hz, 2H), 3.18 (q, J = 10.1 Hz, 2H), 2.67 (t, J = 7.0 Hz, 2H), 2.37 (s, 3H), 1.91-1.83 (m, 2H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | ¹H-NMR |
|---|---|---|---|---|---|---|
| 1998 | 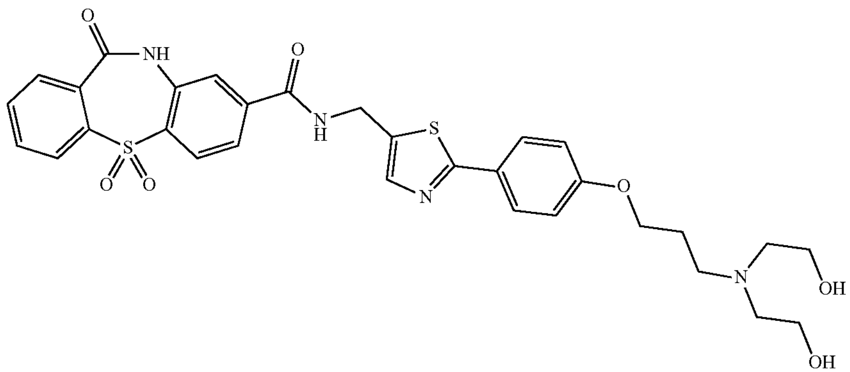 [SMILES: O=C(NCc1cnc(-c2ccc(OCCCN(CCO)CCO)cc2)s1)c1ccc2c(c1)NC(=O)c1ccccc1S2(=O)=O] | A[b], 92, 411 | 71 | 637.1 (M⁺ + 1); | 636.17 for $C_{31}H_{32}N_4O_7S_2$ | ¹H-NMR (DMSO-d₆, 400 MHz): δ 11.34 (br s, 1H), 9.45 (t, J = 5.8 Hz, 1H), 8.05 (d, J = 8.3 Hz, 1H), 7.98 (td, J = 7.4, 1.1 Hz, 2H), 7.93-7.84 (m, 3H), 7.84-7.77 (m, 3H), 7.72 (s, 1H), 7.01 (d, J = 8.9 Hz, 2H), 4.66 (d, J = 5.5 Hz, 2H), 4.42-4.25 (m, 2H), 4.06 (t, J = 6.4 Hz, 2H), 3.41 (t, J = 6.2 Hz, 4H), 2.61 (t, J = 6.8 Hz, 2H), 2.55-2.51 (m, 4H), 1.83 (p, J = 6.7 Hz, 2H); |
| 11047 | 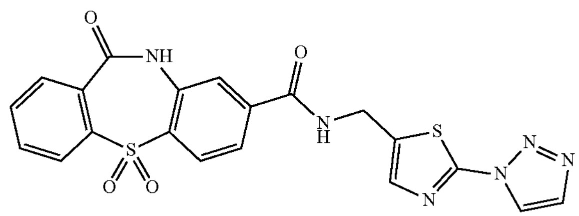 [SMILES: O=C(NCc1cnc(-n2ccnn2)s1)c1ccc2c(c1)NC(=O)c1ccccc1S2(=O)=O] | A[c], 92, 458A | 39 | 467.0 (M⁺ + 1); | 466.05 for $C_{20}H_{14}N_6O_4S_2$ | ¹H-NMR (DMSO-d₆, 400 MHz): δ 11.52 (s, 1H), 9.56 (t, J = 5.7 Hz, 1H), 8.85 (s, 1H), 8.06 (d, J = 8.2 Hz, 1H), 8.03 (s, 1H), 7.98 (dd, J = 7.5, 1.2 Hz, 2H), 7.93-7.80 (m, 4H), 7.76 (s, 1H), 4.68 (d, J = 5.6 Hz, 2H); |
| 11048 | 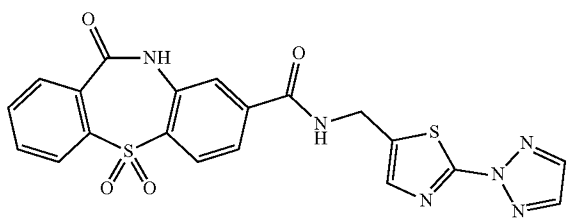 [SMILES: O=C(NCc1cnc(-n2nccn2)s1)c1ccc2c(c1)NC(=O)c1ccccc1S2(=O)=O] | A[c], 92, 458B | 23 | 467.0 (M⁺ + 1); | 466.05 for $C_{20}H_{14}N_6O_4S_2$ | ¹H-NMR (DMSO-d₆, 400 MHz): δ 11.51 (s, 1H), 9.52 (t, J = 5.6 Hz, 1H), 8.22 (s, 2H), 8.06 (d, J = 8.2 Hz, 1H), 7.98 (td, J = 7.6, 1.1 Hz, 2H), 7.93-7.79 (m, 4H), 7.67 (s, 1H), 4.66 (d, J = 5.6 Hz, 2H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commercial and synthesized amines.

| Example | Structure | Procedure, Interemediate, amine | Rx. Yield (%) | Mass Spec. Found | Mass Spec. Calculated | ¹H-NMR |
|---|---|---|---|---|---|---|
| 11053 | 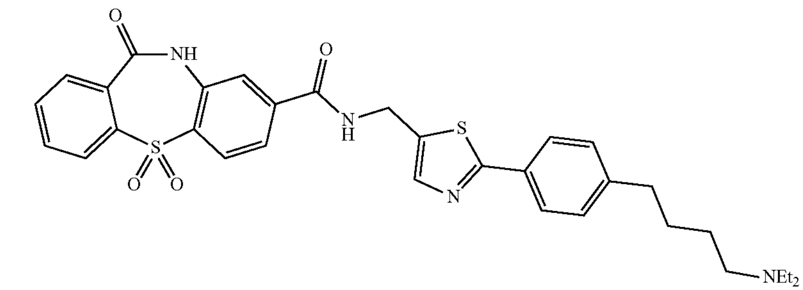 | A^c, 92, 476 | 41 | 603.20 (M⁺ + 1); | 602.20 for $C_{32}H_{34}N_4O_4S_2$ | ¹H-NMR (DMSO-d₆, 400 MHz): δ 11.50 (br s, 1H), 9.46 (t, J = 5.8 Hz, 1H), 8.06 (d, J = 8.1 Hz, 1H), 8.00-7.96 (m, 2H), 7.93-7.74 (m, 7H), 7.29 (d, J = 8.1 Hz, 2H), 4.68 (d, J = 5.2 Hz, 2H), 2.62 (t, J = 7.5 Hz, 2H), 2.46-2.33 (m, 6H), 1.58 (p, J = 7.5 Hz, 2H), 1.44-1.36 (m, 2H), 0.92 (t, J = 7.0 Hz, 6H); |
| 11054 | 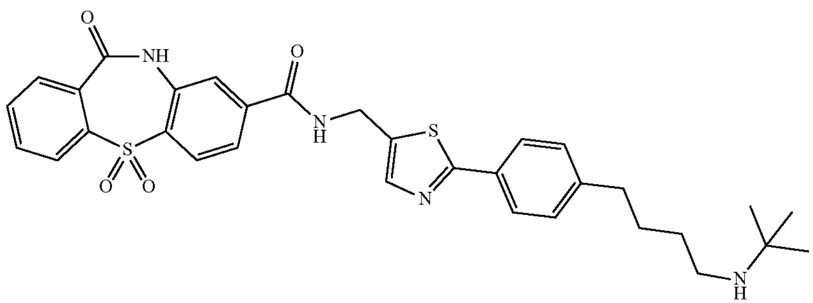 [SMILES: CC(C)(C)NCCCCc1ccc(-c2ncc(CNC(=O)c3ccc4c(c3)NC(=O)c3ccccc3S4(=O)=O)s2)cc1] | A^c, 92, 471 | 23 | 603.20 (M⁺ + 1); | 602.20 for $C_{32}H_{34}N_4O_4S_2$ | ¹H-NMR (DMSO-d₆, 400 MHz): δ 9.45 (t, J = 5.6 Hz, 1H), 8.04 (d, J = 8.3 Hz, 1H), 7.97 (td, J = 7.9, 1.3 Hz, 2H), 7.92-7.75 (m, 7H), 7.29 (d, J = 8.3 Hz, 2H), 4.67 (d, J = 5.5 Hz, 2H), 2.61 (t, J = 7.6 Hz, 2H), 2.54-2.44 (m, 3H), 1.62 (p, J = 7.7 Hz, 2H), 1.37 (td, J = 15.0, 7.3 Hz, 2H), 1.00 (s, 9H); |
| 11055 | 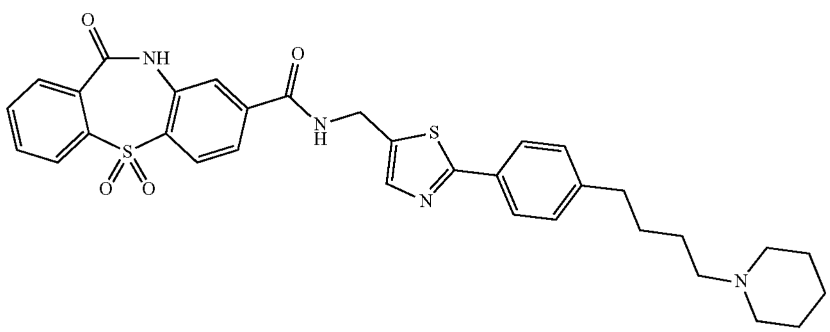 | A^c, 92, 474 | 53 | 615.1 (M⁺ + 1); | 614.20 for $C_{33}H_{34}N_4O_4S_2$ | ¹H-NMR (DMSO-d₆, 400 MHz): δ 11.50 (br s, 1H), 9.46 (t, J = 5.8 Hz, 1H), 8.06 (d, J = 8.2 Hz, 1H), 7.98 (td, J = 7.6, 1.1 Hz, 2H), 7.93-7.76 (m, 7H), 7.29 (d, J = 8.2 Hz, 2H), 4.68 (d, J = 5.6 Hz, 2H), 2.61 (t, J = 7.5 Hz, 2H), 2.30-2.19 (m, 6H), 1.57 (p, J = 7.5 Hz, 2H), 1.49-1.31 (m, 8H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 11056 | (structure) | A, 92, 468 | 8 | 617.1 (M$^+$ + 1); | 616.18 for $C_{32}H_{32}N_4O_5S_2$ | $^1$H NMR (400 MHz, DMSO-d$_6$): δ 11.52 (s, 1H), 9.46 (t, J = 5.6 Hz, 1H), 8.06 (d, J = 8.2 Hz, 1H), 8.01-7.95 (m, 2H), 7.93-7.88 (m, 1H), 7.87-7.76 (m, 6H), 7.29 (d, J = 8.1 Hz, 2H), 4.68 (t, J = 5.5 Hz, 2H), 3.53 (t, J = 4.4 Hz, 4H), 2.62 (t, J = 7.5 Hz, 2H), 2.35-2.22 (m, 6H), 1.65-1.53 (m, 2H), 1.49-1.37 (m, 2H); |
| 11057 | (structure) | A, 92, 480 | 26 | 589.1 (M$^+$ + 1); | 588.15 for $C_{30}H_{28}N_4O_5S_2$ | $^1$H-NMR (DMSO-d$_6$ 400 MHz): δ 11.52 (s, 1H), 9.46 (t, J = 5.8 Hz, 1H), 8.06 (d, J = 8.4 Hz, 1H), 7.98 (td, J = 1.1, 7.5 Hz, 2H), 7.90 (td, J = 7.5, 1.4 Hz, 1H), 7.87-7.75 (m, 7H), 7.29 (d, J = 8.2 Hz, 2H), 4.68 (d, J = 5.5 Hz, 2H), 3.07-3.00 (m, 2H), 2.61 (t, J = 7.6 Hz, 2H), 1.77 (s, 3H), 1.57 (td, J = 15.1, 7.6 Hz, 2H), 1.39 (p, J = 7.3 Hz, 2H); |
| 11073 | (structure) | A$^c$, 92, 389 | 12 | 605.1 (M$^+$ + 1); | 604.18 for $C_{31}H_{32}N_4O_5S_2$ | $^1$H NMR (400 MHz, Acetic acid): δ 8.16 (d, J = 8.7 Hz, 1H), 8.11-8.08 (m, 2H), 7.93-7.88 (m, 3H), 7.87-7.79 (m, 4H), 7.03 (d, J = 9.0 Hz, 2H), 4.87 (s, 2H), 4.18 (t, J = 5.7 Hz, 2H), 3.46-3.22 (m, 6H), 2.34-2.23 (m, 2H), 1.35-1.28 (m, 6H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various 149, 153, 155, 158, 200, 211, 216, commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 11080 | 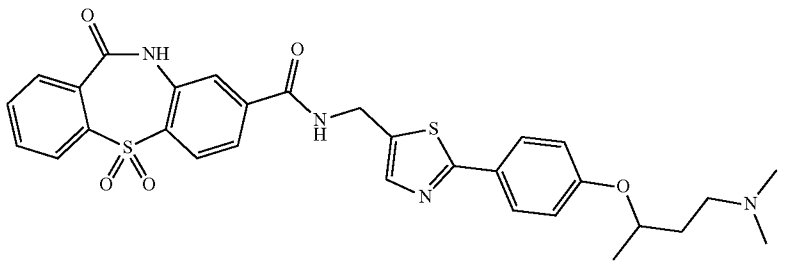 [SMILES: CC(CCN(C)C)Oc1ccc(-c2ncc(CNC(=O)c3ccc4c(c3)NC(=O)c3ccccc3S4(=O)=O)s2)cc1] | A, 92, 402 | 18 | 591.1 (M$^+$ + 1); | 590.17 for $C_{30}H_{30}N_4O_5S_2$ | $^1$H-NMR (DMSO-d$_6$, 400 MHz): δ 11.47 (m, 1H), 9.44 (t, J = 5.7 Hz, 1H), 8.17 (s, 1H), 8.06 (d, J = 8.2 Hz, 1H), 7.98 (t, J = 7.6 Hz, 2H), 7.93-7.76 (m, 6H), 7.72 (s, 1H), 7.00 (d, J = 8.7 Hz, 2H), 4.66 (d, J = 5.5 Hz, 2H), 4.57 (q, J = 5.5 Hz, 1H), 2.38 (t, J = 7.2 Hz, 2H), 2.17 (s, 6H), 1.87-1.66 (m, 2H), 1.26 (d, J = 6.0 Hz, 3H); |
| 11091 | 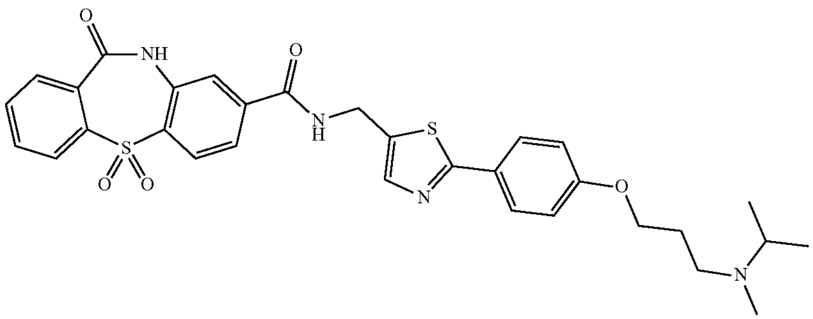 [SMILES: CC(C)N(C)CCCOc1ccc(-c2ncc(CNC(=O)c3ccc4c(c3)NC(=O)c3ccccc3S4(=O)=O)s2)cc1] | B$^a$, 92, 414 | 55 | 605.1 (M$^+$ + 1); | 604.18 for $C_{31}H_{32}N_4O_5S_2$ | $^1$H-NMR (400 MHz, DMSO-d$_6$): δ 11.50 (br s, 1H), 9.44 (t, J = 5.8 Hz, 1H), 8.05 (d, J = 8.3 Hz, 1H), 7.98 (td, J = 7.5, 1.1 Hz, 2H), 7.92-7.84 (m, 3H), 7.83-7.76 (m, 3H), 7.72 (s, 1H), 7.00 (d, J = 8.8 Hz, 2H), 4.66 (d, J = 5.5 Hz, 2H), 4.04 (t, J = 6.3 Hz, 2H), 2.79-2.73 (m, 1H), 2.48-2.41 (m, 2H), 2.13 (s, 3H), 1.85-1.78 (m, 2H), 0.92 (d, J = 6.5 Hz, 6H); |
| 11092 | 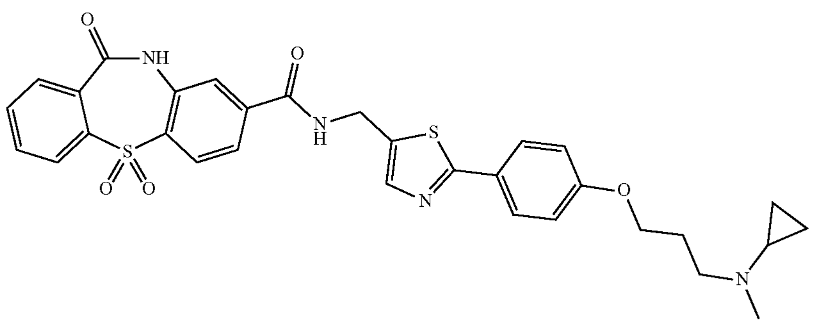 [SMILES: CN(CCCOc1ccc(-c2ncc(CNC(=O)c3ccc4c(c3)NC(=O)c3ccccc3S4(=O)=O)s2)cc1)C1CC1] | B$^a$, 92, 417 | 37 | 603.2 (M$^+$ + 1); | 602.17 for $C_{31}H_{30}N_4O_5S_2$ | $^1$H NMR (400 MHz, CD$_3$COOD): δ 8.14 (d, J = 8.5 Hz, 1H), 8.10-8.07 (m, 2H), 7.93-7.86 (m, 3H), 7.86-7.78 (m, 4H), 7.02 (d, J = 8.8 Hz, 2H), 4.86 (s, 2H), 4.16 (t, J = 5.8 Hz, 2H), 3.57-3.48 (m, 2H), 3.03 (s, 3H), 2.81-2.76 (m, 1H), 2.43-2.32 (m, 2H), 1.33-1.22 (m, 2H), 0.94-0.92 (m, 2H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commercial and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 11093 | 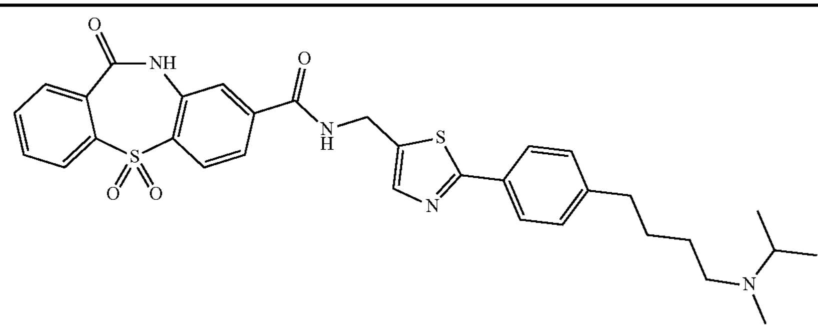 | A, 92, 482 | 13 | 603.1 (M$^+$ + 1); | 602.20 C$_{32}$H$_{34}$N$_4$O$_4$S$_2$ | $^1$H NMR (500 MHz, DMSO-d$_6$): δ 11.50 (br s, 1H), 9.46 (t, J = 5.8 Hz, 1H), 8.05 (d, J = 8.7 Hz, 1H), 7.99-7.77 (m, 9H), 7.29 (d, J = 8.1 Hz, 2H), 4.68 (d, J = 5.8 Hz, 2H), 2.76-2.68 (m, 1H), 2.65-2.57 (m, 2H), 2.30 (t, J = 7.2 Hz, 2H), 2.05 (s, 3H), 1.61-1.54 (m, 2H), 1.41-1.36 (m, 2H), 0.90 (d, J = 7.0 Hz, 6H); |
| 11099 | 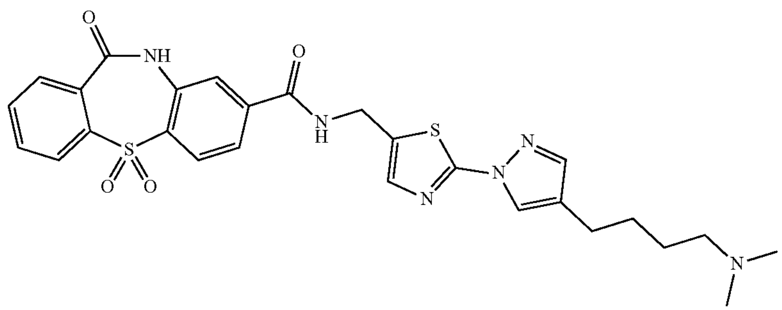 [SMILES: CN(C)CCCCc1cnn(-c2ncc(CNC(=O)c3ccc4c(c3)NC(=O)c3ccccc3S4(=O)=O)s2)c1] | A$^c$, 92, 448 | 41 | 565.6 (M$^+$ + 1); | 564.16 for C$_{27}$H$_{28}$N$_6$O$_4$S$_2$ | $^1$H-NMR (DMSO-d$_6$, 400 MHz): δ 11.48 (br s, 1H), 9.45 (t, J = 5.7 Hz, 1H), 8.22 (s, 1H), 8.05 (d, J = 8.3 Hz, 1H), 8.00-7.95 (m, 2H), 7.93-7.83 (m, 3H), 7.80 (dd, J = 8.3, 1.6 Hz, 1H), 7.68 (s, 1H), 7.50 (s, 1H), 4.59 (d, J = 5.6 Hz, 2H), 2.48-2.45 (m, 2H), 2.21 (t, J = 7.2 Hz, 2H), 2.10 (s, 6H), 1.55 (p, J = 7.5 Hz, 2H), 1.46-1.36 (m, 2H); |
| 11100 | 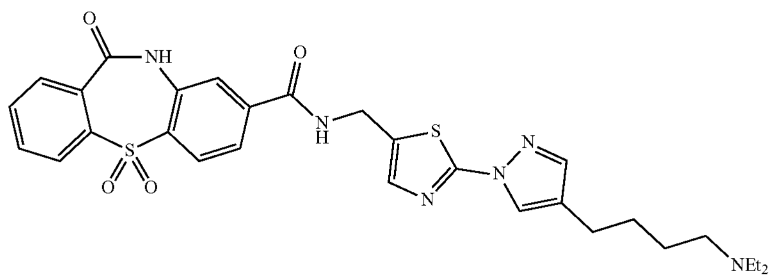 | A, 92, 448A | 38 | 593.1 (M$^+$ + 1); | 592.19 for C$_{29}$H$_{32}$N$_6$O$_4$S$_2$ | $^1$H NMR (400 MHz, DMSO-d$_6$): δ 11.56 (br s, 1H), 9.46 (t, J = 5.8 Hz, 1H), 8.22 (s, 1H), 8.05 (d, J = 8.2 Hz, 1H), 8.01-7.95 (m, 2H), 7.92-7.77 (m, 4H), 7.68 (s, 1H), 7.50 (s, 1H), 4.59 (d, J = 5.6 Hz, 2H), 3.30-3.14 (m, 8H), 1.58-1.51 (m, 2H), 1.45-1.36 (m, 2H), 0.93 (t, J = 7.0 Hz, 6H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 11101 | 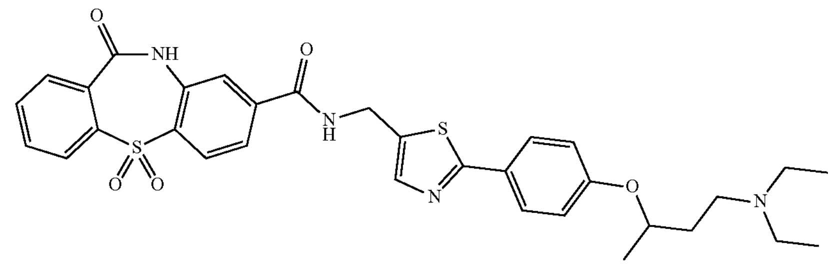 [SMILES: CCN(CC)CCC(C)Oc1ccc(-c2ncc(CNC(=O)c3ccc4c(c3)NC(=O)c3ccccc3S4(=O)=O)s2)cc1] | A, 92, 419 | 32 | 619.1 (M$^+$ + 1) | 618.20 for C$_{32}$H$_{34}$N$_4$O$_5$S$_2$ | $^1$H NMR (400 MHz, CD$_3$COOD): δ 8.15 (d, J = 8.9 Hz, 1H), 8.11-8.06 (m, 2H), 7.93-7.88 (m, 3H), 7.86-7.77 (m, 4H), 7.03 (d, J = 8.9 Hz, 2H), 4.87 (s, 2H), 4.73-4.63 (m, 1H), 3.43-3.22 (m, 6H), 2.26-2.15 (m, 2H), 1.37 (d, J = 6.0 Hz, 3H), 1.35-1.30 (m, 6H); |
| 11102 | 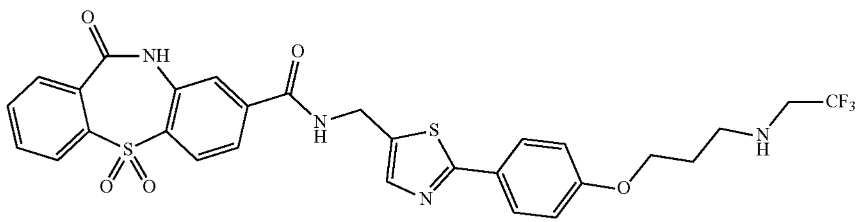 [SMILES: O=C(NCc1cnc(-c2ccc(OCCCNCC(F)(F)F)cc2)s1)c1ccc2c(c1)NC(=O)c1ccccc1S2(=O)=O] | A$^c$, 92, 406 | 14 | 631.1 (M$^+$ + 1) | 630.12 for C$_{29}$H$_{25}$F$_3$N$_4$O$_5$S$_2$ | $^1$H NMR (400 MHz, DMSO-d$_6$): δ 11.52 (s, 1H), 9.45 (t, J = 5.8 Hz, 1H), 8.06 (d, J = 8.4 Hz, 1H), 8.00-7.98 (m, 2H), 7.92-7.79 (m, 6H), 7.72 (s, 1H), 7.01 (d, J = 8.9 Hz, 2H), 4.66 (d, J = 5.5 Hz, 2H), 4.07 (t, J = 6.3 Hz, 2H), 3.27-3.17 (m, 2H), 2.76 (s, 2H), 1.90-1.83 (m, 2H); |
| 11105 | 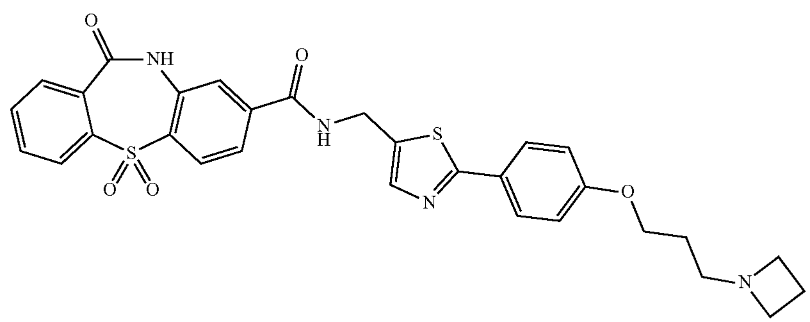 [SMILES: O=C(NCc1cnc(-c2ccc(OCCCN3CCC3)cc2)s1)c1ccc2c(c1)NC(=O)c1ccccc1S2(=O)=O] | A, 92, 411 | 10 | 589.1 (M$^+$ + 1) | 588.15 for C$_{30}$H$_{28}$N$_4$O$_5$S$_2$ | $^1$H NMR (400 MHz, DMSO-d$_6$): δ 11.52 (br s, 1H), 9.46 (t, J = 5.8 Hz, 1H), 8.05 (d, J = 8.3 Hz, 1H), 7.99-7.95 (m, 2H), 7.93-7.77 (m, 6H), 7.71 (s, 2H), 7.00 (d, J = 5.5 Hz, 2H), 4.65 (d, J = 5.5 Hz, 2H), 4.04-4.01 (m, 2H), 3.48-3.35 (m, 4H), 2.78-2.69 (m, 2H), 2.10-2.02 (m, 2H), 1.81-1.71 (m, 2H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 163, 169, 172, 176, 185, 190, 194 and various commerical and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 11116 | (structure) | A$^c$, 92, 461 | 45 | 538.0 (M$^+$ + 1) | 537.08 for $C_{24}H_{19}N_5O_6S_2$ | $^1$H-NMR (DMSO-d$_6$, 400 MHz): δ 11.47 (br s, 1H), 9.51 (t, J = 5.6 Hz, 1H), 8.84 (s, 1H), 8.21 (s, 1H), 8.06 (d, J = 8.2 Hz, 1H), 8.00-7.95 (m, 2H), 7.93-7.77 (m, 4H), 7.63 (s, 1H), 4.64 (d, J = 5.5 Hz, 2H), 4.26 (q, J = 7.1 Hz, 2H), 1.29 (t, J = 7.0 Hz, 3H); |
| 11112 | (structure) | A$^b$, 92, 431 | 17 | 603.1 (M$^+$ + 1) | 602.17 for $C_{31}H_{30}N_4O_5S_2$ | $^1$H NMR (400 MHz, DMSO-d$_6$): δ 11.52 (s, 1H), 9.46 (t, J = 5.6 Hz, 1H), 8.06 (d, J = 8.2 Hz, 1H), 8.01-7.95 (m, 2H), 7.93-7.77 (m, 6H), 7.72 (s, 1H), 7.00 (d, J = 8.9 Hz, 2H), 4.66 (d, J = 5.6 Hz, 2H), 3.90 (br s, 2H), 2.97-2.69 (m, 2H), 2.31-1.97 (m, 6H), 0.69-0.30 (m, 4H); |
| 11113 | (structure) | A$^b$, 92, 439 | 61 | 617.1 (M$^+$ + 1) | 616.18 for $C_{32}H_{32}N_4O_5S_2$ | $^1$H NMR (400 MHz, DMSO-d$_6$): δ 11.52 (br s, 1H), 9.46 (t, J = 5.8 Hz, 1H), 8.05 (d, J = 8.2 Hz, 1H), 7.99-7.94 (m, 2H), 7.92-7.83 (m, 3H), 7.83-7.78 (m, 3H), 7.71 (s, 1H), 7.04 (d, J = 8.8 Hz, 2H), 4.65 (d, J = 5.6 Hz, 2H), 4.07 (br s, 2H), 2.57-2.51 (m, 1H), 2.46-2.29 (m, 2H), 2.27-2.06 (m, 4H), 2.02-1.79 (m, 7H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 11118 | 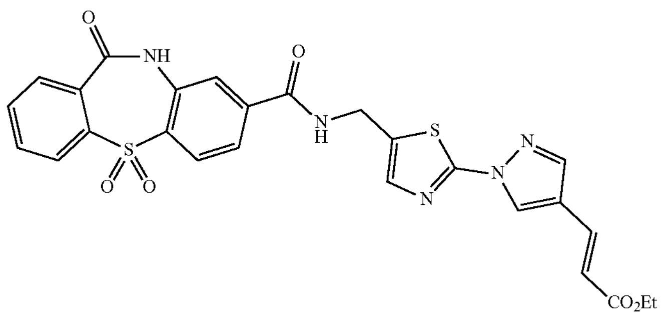 [SMILES: CCOC(=O)/C=C/c1cnn(-c2ncc(CNC(=O)c3ccc4c(c3)NC(=O)c3ccccc3S4(=O)=O)s2)c1] | A$^c$, 92, 451 | 27 | 564.1 (M$^+$ + 1); | 563.09 for $C_{26}H_{21}N_5O_6S_2$ | $^1$H NMR (400 MHz, DMSO-d$_6$): δ 11.51 (s, 1H), 9.48 (t, J = 5.7 Hz, 1H), 8.89 (s, 1H), 8.31 (s, 1H), 8.06 (d, J = 8.3 Hz, 1H), 8.00-7.79 (m, 6H), 7.62 (s, 1H), 7.59-7.57 (m, 1H), 6.56 (d, J = 16.1 Hz, 1H), 4.62 (d, J = 5.4 Hz, 2H), 4.19-4.14 (m, 2H), 1.24 (t, J = 7.1 Hz, 3H); |
| 11142 | 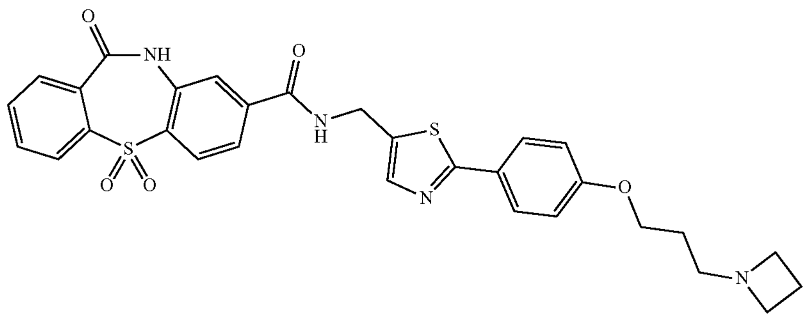 [SMILES: O=C(NCc1cnc(-c2ccc(OCCCN3CCC3)cc2)s1)c1ccc2c(c1)NC(=O)c1ccccc1S2(=O)=O] | A$^b$, 92, 422 | 48 | 635.1 (M$^+$ + 1) | 588.15 for $C_{30}H_{28}N_4O_5S_2$ | $^1$H NMR (400 MHz, DMSO-d$_6$): δ 11.52 (s, 1H), 9.45 (t, J = 5.8 Hz, 1H), 8.06 (d, J = 8.3 Hz, 1H), 8.00-7.96 (m, 2H), 7.92-7.77 (m, 6H), 7.72 (s, 1H), 7.00 (d, J = 8.9 Hz, 2H), 4.66 (d, J = 5.5 Hz, 2H), 4.04 (t, J = 6.3 Hz, 2H), 2.70-2.55 (m, 8H), 2.47-2.45 (m, 2H), 1.89-1.83 (m, 2H); |
| 1901-A | 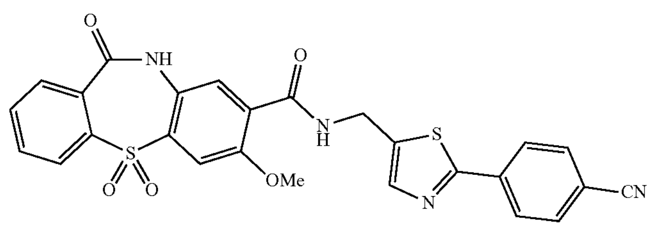 [SMILES: COc1cc2c(cc1C(=O)NCc1cnc(-c3ccc(C#N)cc3)s1)NC(=O)c1ccccc1S2(=O)=O] | A$^c$, 120, 227 | 57 | 531.1 (M$^+$ + 1); | 530.07 for $C_{26}H_{18}N_4O_5S_2$ | 1H-NMR (DMSO-d6, 400 MHz): δ 11.25 (br s, 1H), 9.07 (t, J = 6.0 Hz, 1H), 8.07 (d, J = 8.5 Hz, 2H), 8.01-7.82 (m, 7H), 7.66 (s, 1H), 7.51 (s, 1H), 4.70 (d, J = 5.6 Hz, 2H), 3.94 (s, 3H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various 149, 153, 155, 158, 200, 211, 216, commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1768 | 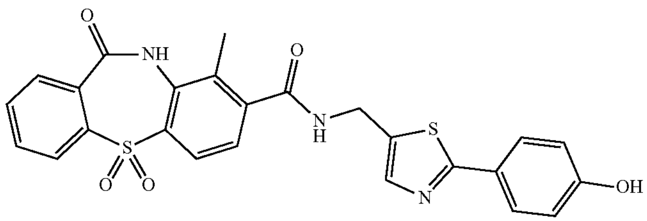 [SMILES: Cc1c(C(=O)NCc2cnc(-c3ccc(O)cc3)s2)ccc2c1NC(=O)c1ccccc1S2(=O)=O] | A, 95 357 | 12 | 506.1 (M$^+$ + 1); | 505.08 for C$_{25}$H$_{19}$N$_3$O$_5$S$_2$ | $^1$H-NMR (DMSO-d$_6$, 400 MHz): δ 10.86 (br s, 1H), 10.00 (br s, 1H), 9.17 (br s, 1H), 7.98-7.77 (m, 5H), 7.75-7.65 (m, 3H), 7.35 (d, J = 7.2 Hz, 1H), 6.85 (d, J = 7.9 Hz, 2H), 4.60 (br s, 2H), 2.32 (br s, 3H); |
| 1877 | 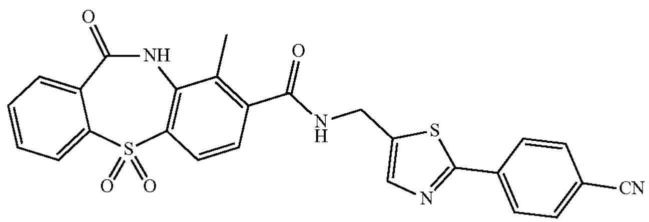 [SMILES: Cc1c(C(=O)NCc2cnc(-c3ccc(C#N)cc3)s2)ccc2c1NC(=O)c1ccccc1S2(=O)=O] | A, 95, 227 | 68 | 515.1 (M$^+$ + 1); | 514.08 for C$_{26}$H$_{18}$N$_4$O$_4$S$_2$ | $^1$H-NMR (DMSO-d$_6$, 500 MHz): δ 10.85 (s, 1H), 9.22 (t, J = 5.8 Hz, 1H), 8.08 (d, J = 8.1 Hz, 2H), 7.96-7.88 (m, 5H), 7.87-7.82 (m, 2H), 7.80-7.76 (m, 1H), 7.35 (d, J = 8.1 Hz, 1H), 4.67 (d, J = 5.8 Hz, 2H), 2.31 (s, 3H); |
| 11046 | 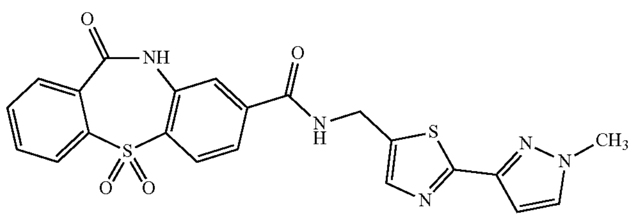 [SMILES: Cn1ccc(-c2ncc(CNC(=O)c3ccc4c(c3)NC(=O)c3ccccc3S4(=O)=O)s2)n1] | A$^c$, 92, 528 | 70 | 480.0 (M$^+$ + 1); | 479.07 for C$_{22}$H$_{17}$N$_5$O$_4$S$_2$ | 1H-NMR (DMSO-d6, 400 MHz): δ 11.52 (br s, 1H), 9.43 (t, J = 5.7 Hz, 1H), 8.05 (d, J = 8.2 Hz, 1H), 7.97 (dd, J = 8.4, 1.7 Hz, 2H), 7.92-7.81 (m, 3H), 7.81-7.77 (m, 2H), 7.70 (s, 1H), 6.66 (d, J = 2.3 Hz, 1H), 4.65 (d, J = 5.8 Hz, 2H), 3.87 (s, 3H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commercial and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 11158 | 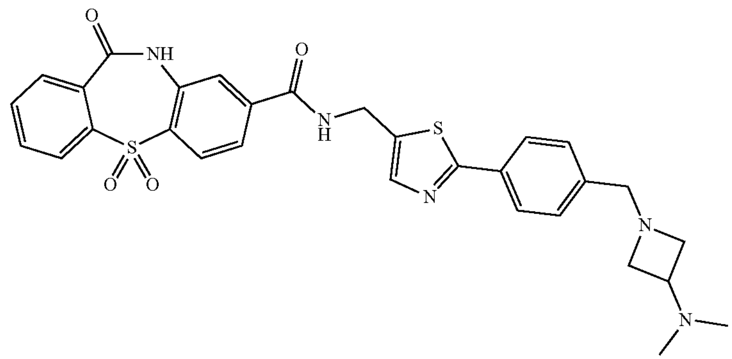 [SMILES: CN(C)C1CN(Cc2ccc(-c3ncc(CNC(=O)c4ccc5c(c4)NC(=O)c4ccccc4S5(=O)=O)s3)cc2)C1] | $A^C$, 92, 524A | 26 | 588.2 (M$^+$ + 1); | 587.17 for $C_{30}H_{29}N_5O_4S_2$ | $^1$H NMR (400 MHz, DMSO-d$_6$): δ 11.52 (br s, 1H), 9.47 (t, J = 5.8 Hz, 1H), 8.06 (d, J = 8.3 Hz, 1H), 8.01-7.95 (m, 2H), 7.93-7.77 (m, 7H), 7.36 (d, J = 8.2 Hz, 2H), 4.68 (d, J = 5.6 Hz, 2H), 3.62 (s, 2H), 3.39 (s, 2H), 2.87-2.85 (m, 3H), 2.03 (s, 6H); |
| 11182 | 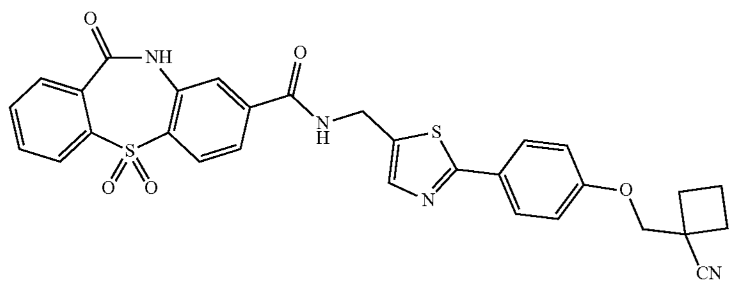 [SMILES: N#CC1(COc2ccc(-c3ncc(CNC(=O)c4ccc5c(c4)NC(=O)c4ccccc4S5(=O)=O)s3)cc2)CCC1] | $A^C$, 92, 440 | 37 | 585.1 (M$^+$ + 1) | 584.12 for $C_{30}H_{24}N_4O_5S_2$ | $^1$H NMR (400 MHz, DMSO-d$_6$): δ 11.52 (s, 1H), 9.46 (t, J = 5.8 Hz, 1H), 8.06 (d, J = 8.3 Hz, 1H), 8.00-7.96 (m, 2H), 7.93-7.78 (m, 6H), 7.74 (s, 1H), 7.09 (d, J = 8.9 Hz, 2H), 4.67 (d, J = 5.6 Hz, 2H), 4.32 (s, 2H), 2.43-2.40 (m, 2H), 2.31-2.21 (m, 2H), 2.17-2.01 (m, 2H); |
| 11074 | 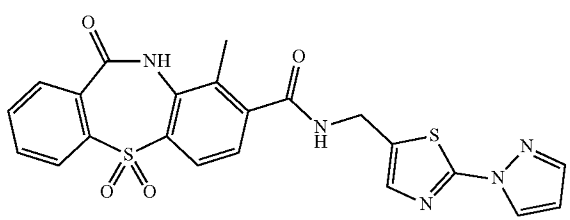 [SMILES: Cc1c(C(=O)NCc2cnc(-n3cccn3)s2)ccc2c1NC(=O)c1ccccc1S2(=O)=O] | $A^C$, 95, 455 | 50 | 480.0 (M$^+$ + 1); | 497.07 for $C_{22}H_{17}N_5O_4S_2$ | $^1$H-NMR (DMSO-d$_6$, 400 MHz): δ 10.86 (s, 1H), 9.20 (t, J = 5.8 Hz, 1H), 8.47 (d, J = 2.3 Hz, 1H), 7.95-7.83 (m, 5H), 7.80 (td, J =, 7.6, 1.5 Hz, 1H), 7.54 (s, 1H), 7.35 (d, J = 8.1 Hz, 1H), 6.62 (dd, J = 2.5, 1.8 Hz, 1H), 4.58 (d, J = 5.6 Hz, 2H), 2.32 (s, 3H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 163, 169, 172, 176, 185, 190, 194 and various commercial and synthesized amines.

| Example | Structure | Procedure, Intermediate, amine | Rx. Yield (%) | Mass Spec. Found | Mass Spec. Calculated | ¹H-NMR |
|---|---|---|---|---|---|---|
| 11077 | (structure) | A$^c$, 95, 354 | 57 | 491.08 (M$^+$ + 1); | 490.08 for C$_{24}$H$_{18}$N$_4$O$_4$S$_2$ | ¹H NMR (400 MHz, DMSO-d$_6$) δ 10.86 (br s, 1H), 9.21 (t, J = 5.3 Hz, 1H), 8.62 (d, J = 4.4 Hz, 1H), 8.09 (d, J = 7.9 Hz, 1H), 7.99-7.77 (m, 7H), 7.52-7.44 (m, 1H), 7.36 (d, J = 8.1 Hz, 1H), 4.67 (d, J = 5.6 Hz, 2H), 2.33 (s, 3H); |
| 11041 | (structure) | A, 113, 255 | 37 | 496.0 (M$^+$ + 1); | 495.05 for C$_{21}$H$_{16}$F$_3$N$_3$O$_4$S$_2$ | ¹H NMR (DMSO-d$_6$, 400 MHz): δ 11.37 (s, 1H), 9.31 (br t, J = 5.8 Hz, 1H), 8.06 (s, 1H), 8.00-7.94 (m, 2H), 7.92-7.81 (m, 3H), 7.30 (s, 1H), 4.73 (br d, J = 5.6 Hz, 2H), 2.75-2.63 (m, 2H), 1.07 (t, J = 7.5 Hz, 3H); |
| 11042 | (structure) | A$^c$, 113 316 | 19 | 547.0 (M$^+$ + 1); | 546.08 for C$_{27}$H$_{19}$FN$_4$O$_4$S$_2$ | ¹H NMR (DMSO-d$_6$ 500 MHz): δ 11.15 (br s, 1H), 9.04 (br t, J = 5.8 Hz, 1H), 8.15 (t, J = 8.1 Hz, 1H), 7.90 (br d, J = 11.0 Hz, 1H), 7.80-7.72 (m, 3H), 7.70-7.59 (m, 4H), 7.07 (s, 1H), 4.51 (br d, J = 5.8 Hz, 2H), 2.52-2.44 (m, 2H), 0.87 (t, J = 7.5 Hz, 3H); |
| 11082 | (structure) | A, 135, 255 | 32 | 503.9 (M$^+$ + 1); | 500.98 for C$_{19}$H$_{11}$ClF$_3$N$_3$O$_4$S$_2$ | ¹H NMR (400 MHz, DMSO-d$_6$) δ 11.18 (br s, 1H), 9.40 (t, J = 5.8 Hz, 1H), 8.06 (s, 1H), 8.02-7.93 (m, 3H), 7.90 (td, J = 7.5, 1.3 Hz, 1H), 7.84 (dd, J = 7.5, 1.7 Hz, 1H), 7.52 (d, J = 8.1 Hz, 1H), 4.75 (d, J = 5.6 Hz, 2H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | ¹H-NMR |
|---|---|---|---|---|---|---|
| 11083 | 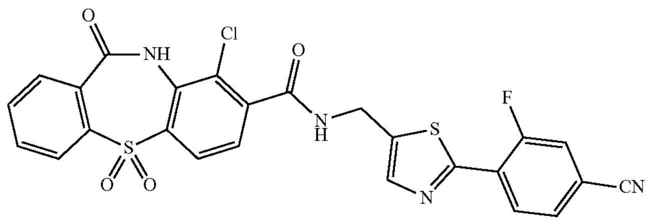 [SMILES: N#Cc1ccc(-c2ncc(CNC(=O)c3ccc4c(c3Cl)NC(=O)c3ccccc3S4(=O)=O)s2)c(F)c1] | A, 135, 316 | 43 | 553.0 (M⁺ + 1) | 552.01 for $C_{25}H_{14}ClFN_4O_4S_2$ | ¹H NMR (400 MHz, DMSO-$d_6$): δ 11.19 (s, 1H), 9.35 (t, J = 5.9 Hz, 1H), 8.37 (t, J = 7.9 Hz, 1H), 8.11 (dd, J = 11.2, 1.4 Hz, 1H), 8.03-7.93 (m, 4H), 7.90 (td, J = 7.5, 1.4 Hz, 1H), 7.87-7.80 (m, 2H), 7.50 (d, J = 8.2 Hz, 1H), 4.74 (d, J = 5.8 Hz, 2H); |
| 1936 | 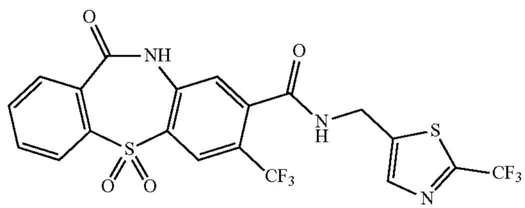 [SMILES: O=C(NCc1cnc(C(F)(F)F)s1)c1cc2c(cc1C(F)(F)F)S(=O)(=O)c1ccccc1C(=O)N2] | A$^a$, 143, 255 | 49 | 536.0 (M⁺ + 1) | 535.01 for $C_{20}H_{11}F_6N_3O_4S_2$ | ¹H-NMR (DMSO-$d_6$, 400 MHz): δ 11.82 (br s, 1H), 9.47 (t, J = 5.5 Hz, 1H), 8.17 (s, 1H), 8.09-7.84 (m, 5H), 7.52 (s, 1H), 4.76 (br d, J = 5.3 Hz, 2H); |
| 1734 | 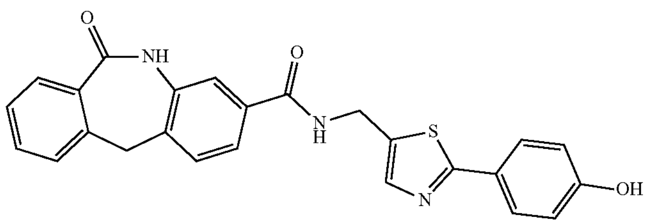 [SMILES: O=C(NCc1cnc(-c2ccc(O)cc2)s1)c1ccc2c(c1)NC(=O)c1ccccc1C2] | A, 200, 357 | 6 | 442.0 (M⁺ + 1) | 441.11 for $C_{25}H_{19}N_3O_3S$ | ¹H-NMR (DMSO-$d_6$, 500 MHz): δ 10.52 (s, 1H), 9.91 (s, 1H), 9.09 (t, J = 5.8 Hz, 1H), 7.71-7.60 (m, 5H), 7.54 (d, J = 7.8 Hz, 1H), 7.46 (t, J = 7.2 Hz, 1H), 7.42 (d, J = 8.1 Hz, 1H), 7.37 (d, J = 7.5 Hz, 1H), 7.31 (t, J = 8.7 Hz, 2H), 6.81 (d, J = 5.8 Hz, 2H), 4.59 (d, J = 5.8 Hz, 2H), 3.94 (s, 2H); |
| 1557 | 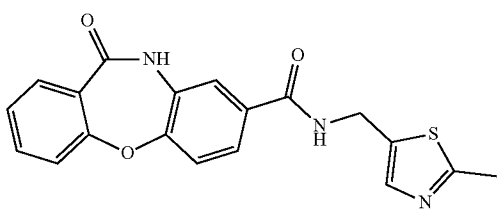 [SMILES: Cc1ncc(CNC(=O)c2ccc3c(c2)NC(=O)c2ccccc2O3)s1] | A, 149, 297 | 48 | 365.8 (M⁺ + 1) | 365.08 for $C_{19}H_{15}N_3O_3S$ | ¹H-NMR (DMSO-$d_6$, 400 MHz): δ 10.62 (s, 1H), 9.12 (t, J = 5.9 Hz, 1H), 7.78 (dd, J = 7.7, 1.7 Hz, 1H), 7.67 (s, 1H), 7.65-7.58 (m, 2H), 7.49 (s, 1H), 7.41 (d, J = 8.4 Hz, 1H), 7.38-7.31 (m, 2H), 4.55 (d, J = 5.7 Hz, 2H), 2.57 (s, 3H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1558 | 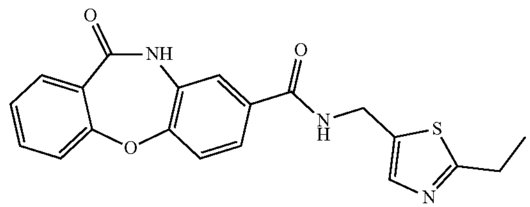 [SMILES: CCc1ncc(CNC(=O)c2ccc3c(c2)NC(=O)c2ccccc2O3)s1] | A, 149, 239 | 56 | 379.9 (M$^+$ + 1); | 379.10 for $C_{20}H_{17}N_3O_3S$ | $^1$H-NMR (DMSO-d$_6$, 400 MHz): δ 10.62 (s, 1H), 9.12 (t, J = 5.6 Hz, 1H), 7.78 (dd, J = 7.5, 1.4 Hz, 1H), 7.69-7.58 (m, 3H), 7.52 (s, 1H), 7.41 (d, J = 8.3 Hz, 1H), 7.39-7.31 (m, 2H), 4.56 (d, J = 5.6 Hz, 2H), 2.90 (q, J = 7.5 Hz, 2H), 1.24 (t, J = 7.5 Hz, 3H); |
| 1559 | 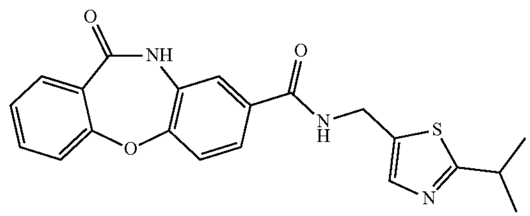 [SMILES: CC(C)c1ncc(CNC(=O)c2ccc3c(c2)NC(=O)c2ccccc2O3)s1] | A, 149, 251 | 41 | 393.9 (M$^+$ + 1); | 393.11 for $C_{21}H_{19}N_3O_3S$ | $^1$H-NMR (DMSO-d$_6$, 400 MHz): δ 10.62 (s, 1H), 9.12 (t, J = 5.7 Hz, 1H), 7.78 (dd, J = 7.8, 1.6 Hz, 1H), 7.68 (s, 1H), 7.66-7.59 (m, 2H), 7.53 (s, 1H), 7.42 (d, J = 8.4 Hz, 1H), 7.38-7.30 (m, 2H), 4.57 (d, J = 5.7 Hz, 2H), 3.24-3.19 (m, 1H), 1.27 (d, J = 6.9 Hz, 6H); |
| 1561 | 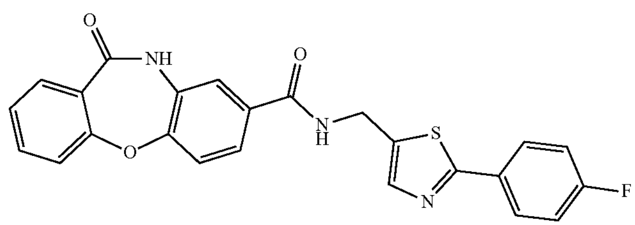 [SMILES: O=C(NCc1cnc(-c2ccc(F)cc2)s1)c1ccc2c(c1)NC(=O)c1ccccc1O2] | A, 149, 285 | 8 | 446.0 (M$^+$ + 1); | 445.09 for $C_{24}H_{16}FN_3O_3S$ | $^1$H NMR (DMSO-d$_6$, 500 MHz): δ 10.64 (s, 1H), 9.22 (t, J = 4.8 Hz, 1H), 7.93 (dd, J = 8.0, 5.6 Hz, 2H), 7.78 (br s, 2H), 7.70 (s, 1H), 7.63 (d, J = 3.5 Hz, 2H), 7.43 (d, J = 8.4 Hz, 1H), 7.38-7.28 (m, 4H), 4.66 (d, J = 5.2 Hz, 2H) |
| 1562 | 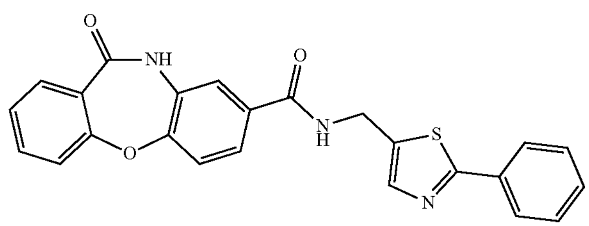 [SMILES: O=C(NCc1cnc(-c2ccccc2)s1)c1ccc2c(c1)NC(=O)c1ccccc1O2] | A, 149, 291 | 36 | 428.3 (M$^+$ + 1); | 427.10 for $C_{24}H_{17}N_3O_3S$ | $^1$H-NMR (DMSO-d$_6$, 400 MHz): δ 10.59 (s, 1H), 9.18 (t, J = 5.7 Hz, 1H), 7.88-7.84 (m, 2H), 7.78-7.73 (m, 2H), 7.68 (s, 1H), 7.63-7.57 (m, 2H), 7.49-7.38 (m, 4H), 7.36-7.28 (m, 2H), 4.64 (d, J = 5.6 Hz, 2H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 1611 | 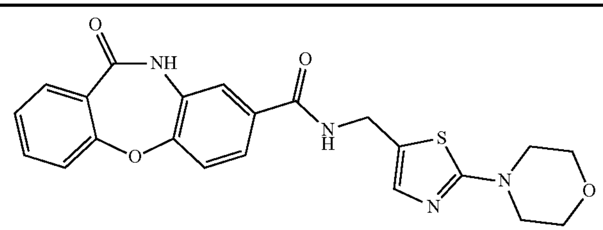 | A, 149, 304 | 48 | 436.9 (M$^+$ + 1); | 436.12 for $C_{22}H_{20}N_4O_4S$ | $^1$H-NMR (DMSO-d$_6$, 500 MHz): δ 10.62 (s, 1H), 9.02 (t, J = 5.2 Hz, 1H), 7.78 (d, J = 7.2 Hz, 1H), 7.66 (s, 1H), 7.65-7.57 (m, 2H), 7.40 (d, J = 8.4 Hz, 1H), 7.38-7.30 (m, 2H), 7.06 (s, 1H), 4.43 (d, J = 5.2 Hz, 2H), 3.68-3.63 (m, 4H), 3.31-3.28 (m, 4H); |
| 1617 | 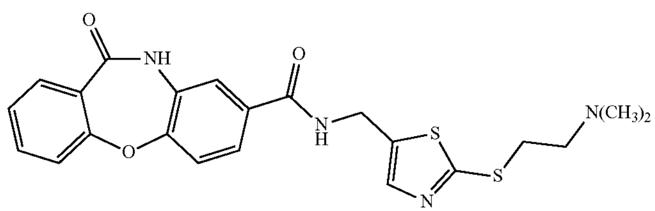 [SMILES: CN(C)CCSc1ncc(CNC(=O)c2ccc3c(c2)NC(=O)c2ccccc2O3)s1] | A, 149, 288 | 14 | 455.3 (M$^+$ + 1); | 454.11 for $C_{22}H_{22}N_4O_3S_2$ | $^1$H-NMR (DMSO-d$_6$, 500 MHz): δ 10.63 (s, 1H), 9.14 (t, J = 5.6 Hz, 1H), 7.78 (d, J = 6.9 Hz, 1H), 7.70-7.54 (m, 4H), 7.42 (d, J = 8.4 Hz, 1H), 7.39-7.31 (m, 2H), 4.54 (d, J = 5.8 Hz, 2H), 3.27 (t, J = 6.9 Hz, 2H), 2.55 (t, J = 6.9 Hz, 2H), 2.15 (s, 6H); |
| 1618 | 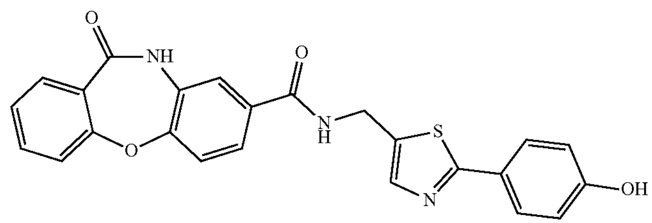 [SMILES: O=C(NCc1cnc(-c2ccc(O)cc2)s1)c1ccc2c(c1)NC(=O)c1ccccc1O2] | A, 149, 357 | 34 | 444.0 (M$^+$ + 1); | 443.09 for $C_{24}H_{17}N_3O_4S$ | $^1$H-NMR (DMSO-d$_6$, 500 MHz): δ 10.63 (s, 1H), 9.93 (s, 1H), 9.17 (t, J = 5.6 Hz, 1H), 7.78 (d, J = 6.7 Hz, 1H), 7.72-7.59 (m, 6H), 7.42 (d, J = 8.4 Hz, 1H), 7.38-7.31 (m, 2H), 6.83 (d, J = 8.7 Hz, 2H), 4.62 (d, J = 5.5 Hz, 2H); |
| 1619 | 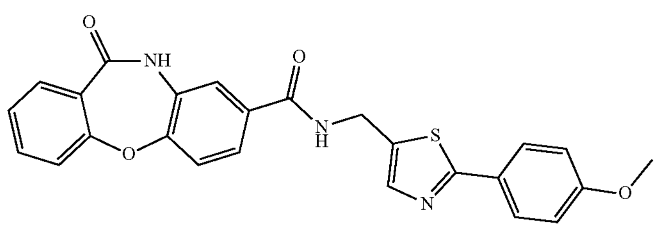 [SMILES: COc1ccc(-c2ncc(CNC(=O)c3ccc4c(c3)NC(=O)c3ccccc3O4)s2)cc1] | A, 149, 363 | 35 | 458.0 (M$^+$ + 1); | 457.11 for $C_{25}H_{19}N_3O_4S$ | $^1$H-NMR (DMSO-d$_6$, 500 MHz): δ 10.63 (s, 1H), 9.19 (t, J = 5.8 Hz, 1H), 7.82 (d, J = 8.7 Hz, 2H), 7.78 (dd, J = 7.7, 1.6 Hz, 1H), 7.72-7.69 (m, 2H), 7.66-7.61 (m, 2H), 7.42 (d, J = 8.4 Hz, 1H), 7.38-7.31 (m, 2H), 7.02 (d, J = 9.0 Hz, 2H), 4.64 (d, J = 5.5 Hz, 2H), 3.80 (s, 3H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1621 | 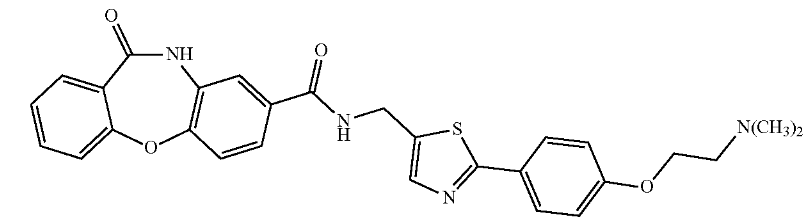 [SMILES: CN(C)CCOc1ccc(-c2ncc(CNC(=O)c3ccc4c(c3)NC(=O)c3ccccc3O4)s2)cc1] | A, 149, 360 | 14 | 515.1 ($M^+ + 1$) | 514.17 for $C_{28}H_{26}N_2O_4S$ | $^1$H-NMR (DMSO-d$_6$, 400 MHz): δ 10.61 (s, 1H), 9.17 (t, J = 5.3 Hz, 1H), 7.81-7.74 (m, 3H), 7.68 (d, J = 6.7 Hz, 2H), 7.61 (d, J = 7.5 Hz, 2H), 7.41 (d, J = 8.4 Hz, 1H), 7.36-7.29 (m, 2H), 7.01 (d, J = 8.4 Hz, 2H), 4.62 (d, J = 5.5 Hz, 2H), 4.11 (t, J = 5.5 Hz, 2H), 2.75-2.68 (m, 2H), 2.27 (br s, 6H); |
| 1629 | 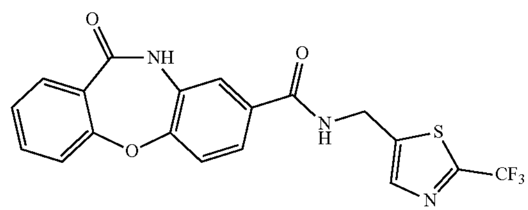 [SMILES: O=C(NCc1cnc(C(F)(F)F)s1)c1ccc2c(c1)NC(=O)c1ccccc1O2] | A, 149, 255 | 9 | 419.9 ($M^+ + 1$) | 419.06 for $C_{19}H_{12}F_3N_3O_3S$ | $^1$H-NMR (DMSO-d$_6$, 400 MHz): δ 10.64 (s, 1H), 9.33 (t, J = 5.6 Hz, 1H), 8.05 (s, 1H), 7.78 (dd, J = 7.7, 1.6 Hz, 1H), 7.69 (d, J = 8.4 Hz, 1H), 7.66-7.60 (m, 2H), 7.43 (d, J = 8.4 Hz, 1H), 7.39-7.31 (m, 2H), 4.72 (d, J = 5.6 Hz, 2H); |
| 1698 | 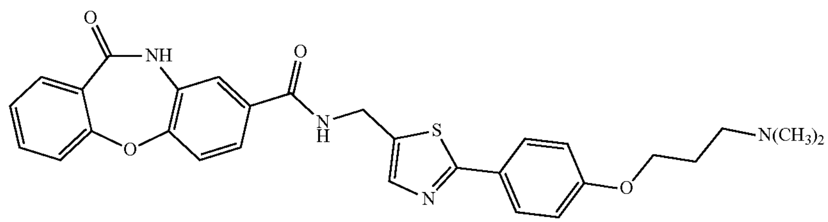 [SMILES: CN(C)CCCOc1ccc(-c2ncc(CNC(=O)c3ccc4c(c3)NC(=O)c3ccccc3O4)s2)cc1] | A, 149, 367 | 48 | 529.1 ($M^+ + 1$) | 528.18 for $C_{29}H_{28}N_4O_4S$ | $^1$H NMR (DMSO-d$_6$, 400 MHz): δ 10.63 (s, 1H), 9.19 (t, J = 5.8 Hz, 1H), 7.82-7.76 (m, 3H), 7.71-7.69 (m, 2H), 7.66-7.60 (m, 2H), 7.42 (d, J = 8.4 Hz, 1H), 7.39-7.30 (m, 2H), 7.00 (d, J = 8.9 Hz, 2H), 4.63 (d, J = 5.7 Hz, 2H), 4.04 (t, J = 6.5 Hz, 2H), 2.34 (t, J = 7.1 Hz, 2H), 2.13 (s, 6H), 1.89-1.80 (m, 2H); |
| 1769 | 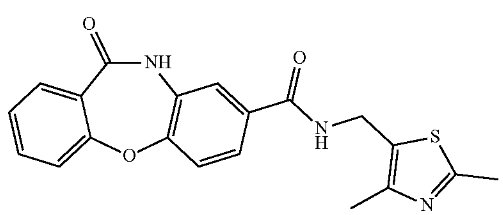 [SMILES: Cc1nc(C)c(CNC(=O)c2ccc3c(c2)NC(=O)c2ccccc2O3)s1] | A$^a$, 149, 219 | 72 | 380.0 ($M^+ + 1$) | 379.10 for $C_{20}H_{17}N_3O_3S$ | $^1$H-NMR (DMSO-d$_6$, 500 MHz): δ 10.62 (s, 1H), 9.04 (t, J = 5.6 Hz, 1H), 7.78 (dd, J = 7.7, 1.5 Hz, 1H), 7.67-7.56 (m, 3H), 7.41 (d, J = 8.4 Hz, 1H), 7.38-7.30 (m, 2H), 4.47 (d, J = 5.6 Hz, 2H), 2.54-2.50 (m, 3H), 2.30 (s, 3H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various 149, 153, 155, 158, 200, 211, 216, commerical and synthesized amines.

| Example | Structure | Procedure, Interemediate, amine | Rx. Yield (%) | Mass Spec. Found | Mass Spec. Calculated | 1H-NMR |
|---|---|---|---|---|---|---|
| 1833 | 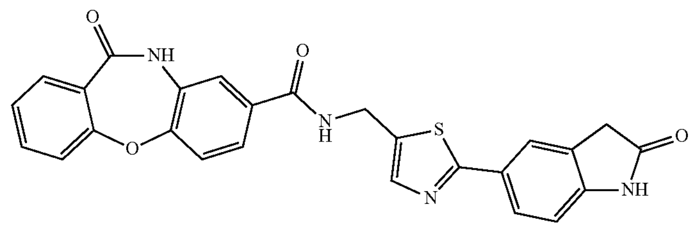 [SMILES: O=C1Cc2cc(-c3ncc(CNC(=O)c4ccc5c(c4)NC(=O)c4ccccc4O5)s3)ccc2N1] | A[b], 149, 319 | 70 | 483.1 (M+ + 1); | 482.51 for $C_{26}H_{18}N_4O_4S$ | 1H-NMR (DMSO-d6, 500 MHz): δ 10.74-10.46 (m, 2H), 9.20 (br s, 1H), 7.82-7.58 (m, 6H), 7.47-7.29 (m, 4H), 6.88 (d, J = 7.2 Hz, 1H), 4.64 (br s, 2H), 3.54 (br s, 2H); |
| 1835-A | 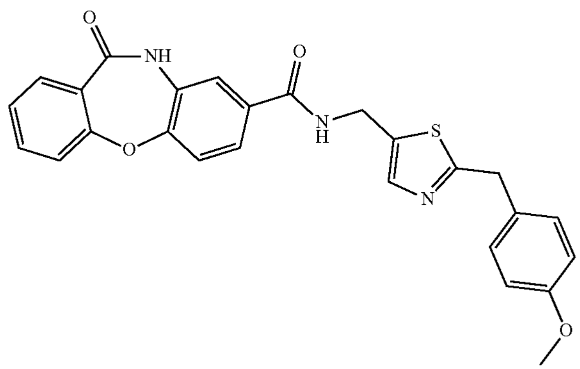 [SMILES: COc1ccc(Cc2ncc(CNC(=O)c3ccc4c(c3)NC(=O)c3ccccc3O4)s2)cc1] | A[c], 149, 326 | 32 | 472.1 (M+ + 1); | 471.13 for $C_{26}H_{21}N_3O_4S$ | 1H NMR (500 MHz, DMSO-d6): δ 10.60 (s, 1H), 9.09 (t, J = 5.5 Hz, 1H), 7.79-7.76 (m, 1H), 7.66-7.53 (m, 4H), 7.40 (d, J = 8.4 Hz, 1H), 7.37-7.31 (m, 2H), 7.21 (d, J = 8.4 Hz, 2H), 6.87 (d, J = 8.4 Hz, 2H), 4.53 (d, J = 5.5 Hz, 2H), 4.16 (s, 2H), 3.71 (s, 3H); |
| 1941 | 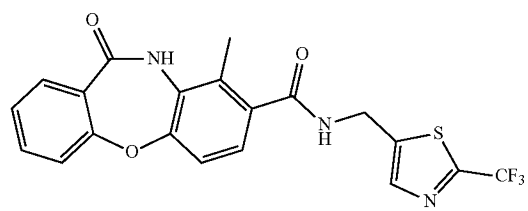 | A, 153, 255 | 55 | 434.0 (M+ + 1); | 433.07 for $C_{20}H_{14}F_3N_3O_3S$ | 1H NMR (DMSO-d6, 400 MHz): δ 10.06 (s, 1H), 9.10 (t, J = 5.8 Hz, 1H), 8.04 (s, 1H), 7.72 (dd, J = 7.7, 1.7 Hz, 1H), 7.62-7.57 (m, 1H), 7.40-7.23 (m, 3H), 7.14 (d, J = 8.3 Hz, 1H), 4.69 (d, J = 5.8 Hz, 2H), 2.28 (s, 3H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 163, 169, 172, 176, 185, 190, 194 and various commercial and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 1913 | 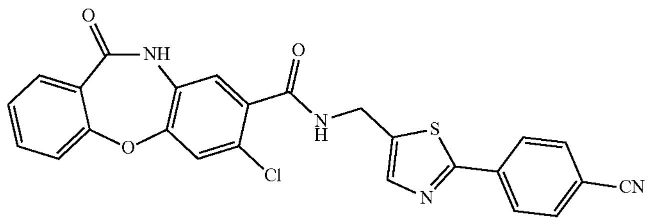 | A, 155, 227 | 23 | 487.1 (M$^+$ + 1); | 486.06 for C$_{25}$H$_{15}$ClN$_4$O$_3$S | $^1$H-NMR (DMSO-d$_6$, 400 MHz): δ 10.64 (br s, 1H), 9.19 (br t, J = 5.4 Hz, 1H), 8.09 (br d, J = 8.0 Hz, 2H), 7.96 (br d, J = 8.2 Hz, 2H), 7.91 (s, 1H), 7.78 (br d, J = 7.3 Hz, 1H), 7.65 (br t, J = 7.3 Hz, 1H), 7.60 (s, 1H), 7.44-7.32 (m, 2H), 7.23 (s, 1H), 4.68 (br d, J = 5.4 Hz, 2H); |
| 1732 | 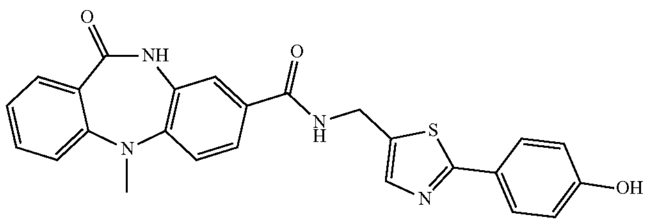 [SMILES: CN1c2ccc(C(=O)NCc3cnc(-c4ccc(O)cc4)s3)cc2NC(=O)c2ccccc21] | A, 166, 357 | 21 | 457.0 (M$^+$ + 1); | 456.13 for C$_{25}$H$_{20}$N$_4$O$_3$S | $^1$H-NMR (DMSO-d$_6$, 400 MHz): δ 10.29 (s, 1H), 9.93 (s, 1H), 9.08 (t, J = 5.6 Hz, 1H), 7.72-7.54 (m, 6H), 7.53-7.47 (m, 1H), 7.25 (d, J = 8.7 Hz, 1H), 7.20 (d, J = 8.1 Hz, 1H), 7.10 (t, J = 7.4 Hz, 1H), 6.82 (d, J = 8.7 Hz, 2H), 4.61 (d, J = 5.5 Hz, 2H); |
| 1751 | 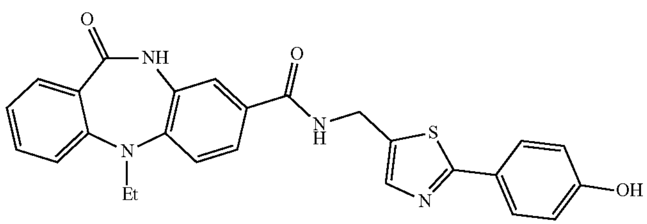 [SMILES: CCN1c2ccc(C(=O)NCc3cnc(-c4ccc(O)cc4)s3)cc2NC(=O)c2ccccc21] | A, 169, 357 | 14 | 471.0 (M$^+$ + 1); | 470.14 for C$_{26}$H$_{22}$N$_4$O$_3$S | $^1$H-NMR (DMSO-d$_6$, 400 MHz): δ 10.30 (s, 1H), 9.95 (br s, 1H), 9.07 (t, J = 5.8 Hz, 1H), 7.69 (d, J = 8.8 Hz, 2H), 7.65 (s, 1H), 7.63-7.57 (m, 3H), 7.52-7.46 (m, 1H), 7.24 (d, J = 8.4 Hz, 1H), 7.20 (d, J = 8.0 Hz, 1H), 7.13-7.08 (m, 1H), 6.82 (d, J = 8.8 Hz, 2H), 4.61 (d, J = 5.6 Hz, 2H), 3.78 (br d, J = 5.5 Hz, 2H), 1.12 (t, J = 7.0 Hz, 3H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 163, 169, 172, 176, 185, 190, 194 and various commerical and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 11043 | 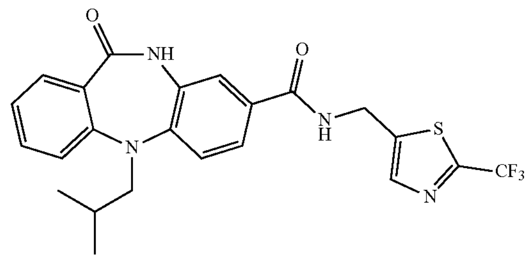 [SMILES: CC(C)CN1c2ccc(C(=O)NCc3cnc(C(F)(F)F)s3)cc2NC(=O)c2ccccc21] | A$^c$, 185 255 | 15 | 475.0 (M$^+$ + 1); | 474.13 for $C_{23}H_{21}F_3N_4O_2S$ | $^1$H-NMR (DMSO-d$_6$, 400 MHz): δ 10.29 (s, 1H), 9.22 (t, J = 5.6 Hz, 1H), 8.04 (s, 1H), 7.63-7.54 (m, 3H), 7.51-7.44 (m, 1H), 7.27 (d, J = 8.4 Hz, 1H), 7.21 (d, J = 8.1 Hz, 1H), 7.10 (t, J = 7.4 Hz, 1H), 4.70 (d, J = 5.5 Hz, 2H), 3.54 (d, J = 7.0 Hz, 2H), 1.81-1.69 (m, 1H), 0.89 (dd, J = 5.3, 4.1 Hz, 6H); |
| 11044 | 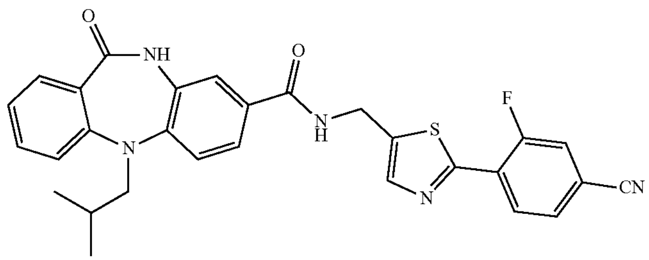 [SMILES: CC(C)CN1c2ccc(C(=O)NCc3cnc(-c4ccc(C#N)cc4F)s3)cc2NC(=O)c2ccccc21] | A$^b$, 185, 316 | 15 | 526.1 (M$^+$ + 1); | 525.16 for $C_{29}H_{24}FN_5O_2S$ | $^1$H NMR (400 MHz, DMSO-d$_6$): δ 10.28 (s, 1H), 9.16 (t, J = 5.3 Hz, 1H), 8.35 (t, J = 7.9 Hz, 1H), 8.09 (d, J = 11.3 Hz, 1H), 7.99 (s, 1H), 7.82 (d, J = 7.8 Hz, 1H), 7.71-7.70 (m, 1H), 7.64-7.51 (m, 3H), 7.47 (t, J = 7.0 Hz, 1H), 7.33-7.18 (m, 2H), 7.09 (t, J = 7.4 Hz, 1H), 4.70 (br d, J = 5.2 Hz, 2H), 3.54 (d, J = 5.5 Hz, 2H), 1.84-1.69 (m, 1H), 0.89 (s, 6H); |
| 1920 | 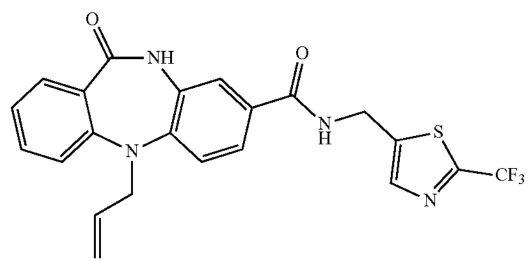 [SMILES: C=CCN1c2ccc(C(=O)NCc3cnc(C(F)(F)F)s3)cc2NC(=O)c2ccccc21] | A, 190, 255 | 47 | 459.1 (M$^+$ + 1); | 458.10 for $C_{22}H_{17}F_3N_4O_2S$ | $^1$H NMR (400 MHz, DMSO-d$_6$): δ 10.33 (s, 1H), 9.23 (br t, J = 5.6 Hz, 1H), 8.04 (s, 1H), 7.63-7.55 (m, 3H), 7.51-7.43 (m, 1H), 7.29-7.18 (m, 2H), 7.11 (t, J = 7.6 Hz, 1H), 5.78-5.66 (m, 1H), 5.33 (dd, J = 17.4, 1.2 Hz, 1H), 5.16-5.10 (m, 1H), 4.70 (d, J = 5.4 Hz, 2H), 4.45 (d, J = 5.3 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various 149, 153, 155, 158, 200, 211, 216, 217 commercial and synthesized amines.

| Example | Structure | Procedure, Interemediate, amine | Rx. Yield (%) | Mass Spec. Found | Mass Spec. Calculated | ¹H-NMR |
|---|---|---|---|---|---|---|
| 1546 | 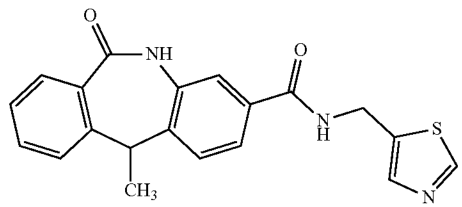 [SMILES: CC1c2ccc(C(=O)NCc3cncs3)cc2NC(=O)c2ccccc21] | A, 211, 217 | 48% | 364.0 (M⁺ + 1); | 363.10 for $C_{20}H_{17}N_3O_2S$ | ¹H-NMR (DMSO-d₆, 400 MHz): δ 10.64-10.51 (m, 1H), 9.10 (t, J = 4.4 Hz, 1H), 8.95 (d, J = 2.7 Hz, 1H), 7.82-7.75 (m, 1.5 H), 7.69-7.57 (m, 2H), 7.55-7.46 (m, 1.5 H), 7.43-7.29 (m, 3H), 4.64 (d, J = 2.8 Hz, 2H), 4.27-4.09 (m, 1H), 1.77, 1.44 (d, J = 7.1 Hz, 3H); |
| 1548 | 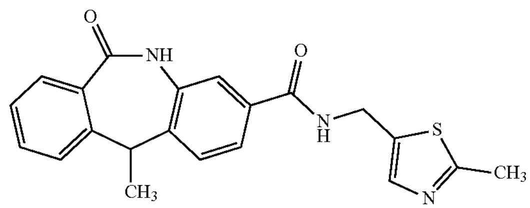 [SMILES: Cc1ncc(CNC(=O)c2ccc3c(c2)NC(=O)c2ccccc2C3C)s1] | A, 211 297 | 48% | 377.9 (M⁺ + 1); | 377.12 for $C_{21}H_{19}N_3O_2S$ | ¹H-NMR (DMSO-d₆, 400 MHz): δ 10.69-10.44 (m, 1H), 9.05 (t, J = 4.5 Hz, 1H), 7.77 (d, J = 7.1 Hz, 0.5H), 7.65 (d, J = 6.6 Hz, 0.5H), 7.62-7.57 (m, 1.5 H), 7.54-7.46 (m, 2.5H), 7.43-7.29 (m, 3H), 4.58-4.49 (m, 2H), 4.28-4.07 (m, 1H), 2.56 (d, J = 2.6 Hz, 3H), 1.77, 1.43 (d, J = 7.3 Hz, 3H); |
| 1697 | 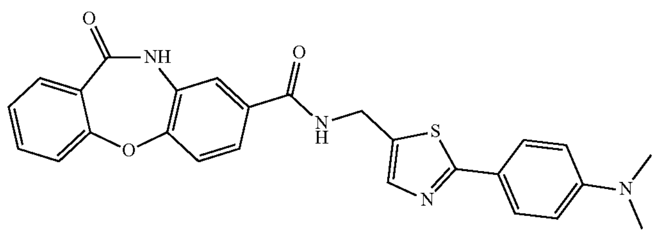 [SMILES: CN(C)c1ccc(-c2ncc(CNC(=O)c3ccc4c(c3)NC(=O)c3ccccc3O4)s2)cc1] | A, 149, 312 | 68 | 471.0 (M⁺ + 1); | 470.14 for $C_{26}H_{22}N_4O_3S$ | 1H-NMR (DMSO-d6, 400 MHz): δ 10.77 (s, 1H), 9.29 (t, J = 5.6 Hz, 1H), 7.95-7.90 (m, 1H), 7.85-7.74 (m, 6H), 7.56 (d, J = 8.4 Hz, 1H), 7.52-7.44 (m, 2H), 6.88 (d, J = 9.0 Hz, 2H), 4.74 (d, J = 5.8 Hz, 2H), 3.10 (s, 6H); |
| 1754 | 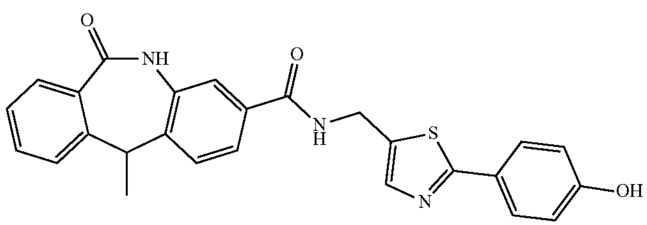 [SMILES: CC1c2ccc(C(=O)NCc3cnc(-c4ccc(O)cc4)s3)cc2NC(=O)c2ccccc21] | A, 211, 357 | 37 | 456.0 (M⁺ + 1); | 455.13 for $C_{26}H_{21}N_3O_3S$ | ¹H-NMR (rotamers): δ 10.74-10.45 (m, 1H), 9.93 (br s, 1H), 9.11 (t, J = 4.8 Hz, 1H), 7.80-7.46 (m, 7H), 7.43-7.28 (m, 3H), 6.83 (dd, J = 9.2, 2.5 Hz, 2H), 4.66-4.57 (m, 2H), 4.27-4.09 (m, 1H), 1.77, 1.44 (d, J = 7.3 Hz, 3H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | ¹H-NMR |
|---|---|---|---|---|---|---|
| 1592 | 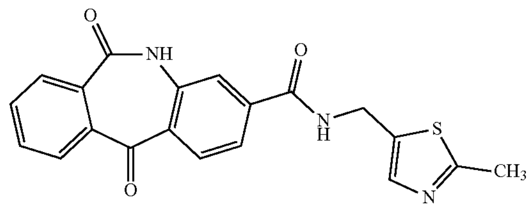 [SMILES: Cc1ncc(CNC(=O)c2ccc3c(=O)c4ccccc4c(=O)[nH]c3c2)s1] | A, 216, 297 | 42 | 377.8 (M⁺ + 1); | 377.08 for $C_{20}H_{15}N_3O_3S$ | ¹H-NMR (DMSO-d₆, 500 MHz): 11.19 (s, 1H), 9.28 (t, $J = 5.8$ Hz, 1H), 8.20-8.14 (m, 1H), 7.87-7.76 (m, 5H), 7.60 (dd, $J = 8.2$, 1.3 Hz, 1H), 7.50 (s, 1H), 4.57 (d, $J = 5.8$ Hz, 2H), 2.57 (s, 3H); |
| 1594 | 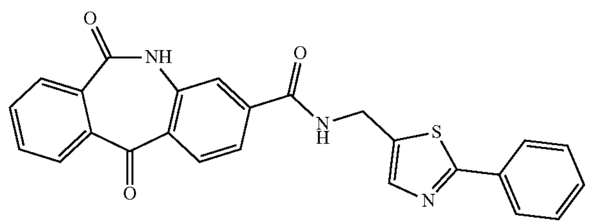 [SMILES: O=C(NCc1cnc(-c2ccccc2)s1)c1ccc2c(=O)c3ccccc3c(=O)[nH]c2c1] | A, 216, 291 | 30 | 440.5 (M⁺ + 1); | 439.10 for $C_{25}H_{17}N_3O_3S$ | ¹H NMR (400 MHz, DMSO-d₆): δ 11.21 (br s, 1H), 9.40 (t, $J = 5.6$ Hz, 1H), 8.21-8.16 (m, 1H), 7.93-7.79 (m, 8H), 7.65 (dd, $J = 8.3$, 1.5 Hz, 1H), 7.52-7.44 (m, 3H), 4.70 (d, $J = 5.5$ Hz, 2H); |
| 1916 | 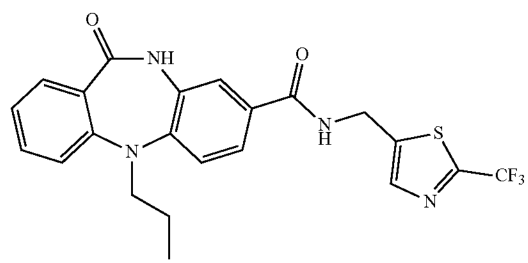 [SMILES: CCCN1c2ccc(C(=O)NCc3cnc(C(F)(F)F)s3)cc2NC(=O)c2ccccc21] | Aᶜ, 172, 255 | 58 | 461.1 (M⁺ + 1); | 460.12 $C_{22}H_{19}F_3N_4O_2S$ | 1H-NMR (DMSO-d6, 400 MHz): δ 10.29 (s, 1H), 9.22 (t, $J = 5.8$ Hz, 1H), 8.04 (s, 1H), 7.62-7.56 (m, 3H), 7.51-7.45 (m, 1H), 7.27 (d, $J = 8.4$ Hz, 1H), 7.21 (d, $J = 7.8$ Hz, 1H), 7.13-7.08 (m, 1H), 4.70 (d, $J = 5.5$ Hz, 2H), 3.72 (t, $J = 5.7$ Hz, 2H), 1.57-1.44 (m, 2H), 0.87 (t, $J = 7.3$ Hz, 3H); |
| 1917 | 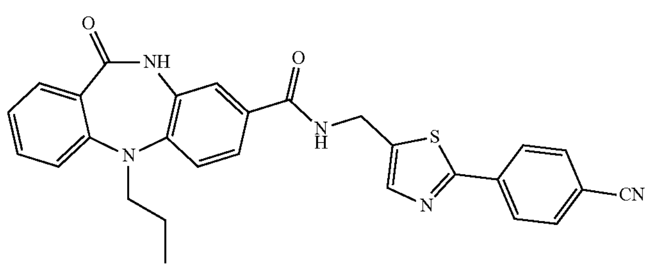 [SMILES: CCCN1c2ccc(C(=O)NCc3cnc(-c4ccc(C#N)cc4)s3)cc2NC(=O)c2ccccc21] | Aᶜ, 172, 227 | 30 | 494.1 (M⁺ + 1); | 493.16 $C_{28}H_{23}N_5O_2S$ | ¹H NMR (400 MHz, DMSO-d₆): δ 10.29 (s, 1H), 9.15 (t, $J = 5.7$ Hz, 1H), 8.06 (d, $J = 8.4$ Hz, 2H), 7.96-7.88 (m, 3H), 7.64-7.56 (m, 3H), 7.51-7.44 (m, 1H), 7.29-7.18 (m, 2H), 7.10 (t, $J = 7.4$ Hz, 1H), 4.68 (d, $J = 5.8$ Hz, 2H), 3.77-3.69 (m, 2H), 1.55-1.47 (m, 2H), 0.87 (t, $J = 7.3$ Hz, 3H); |

TABLE 1-continued

Synthesis from compound 13, 20, 32, 40, 47, 54, 61, 68, 76, 81, 88, 149, 153, 155, 158, 200, 211, 216, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1921 | 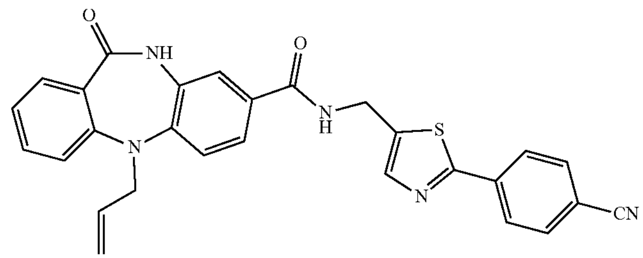 [SMILES: C=CCN1c2ccc(C(=O)NCc3cnc(-c4ccc(C#N)cc4)s3)cc2NC(=O)c2ccccc21] | A$^c$, 190, 227 | 46 | 492.1 (M$^+$ + 1); | 491.14 $C_{28}H_{21}N_5O_2S$ | $^1$H NMR (400 MHz, DMSO-d$_6$): δ 10.34 (s, 1H), 9.16 (t, J = 5.5 Hz, 1H), 8.06 (d, J = 8.3 Hz, 2H), 7.95-7.88 (m, 3H), 7.64-7.56 (m, 3H), 7.48 (t, J = 7.1 Hz, 1H), 7.29-7.17 (m, 2H), 7.10 (t, J = 7.5 Hz, 1H), 5.79-5.66 (m, 1H), 5.33 (d, J = 17.3 Hz, 1H), 5.13 (d, J = 10.2 Hz, 1H), 4.68 (d, J = 5.3 Hz, 2H), 4.44 (d, J = 4.9 Hz, 2H); |
| 1922 | 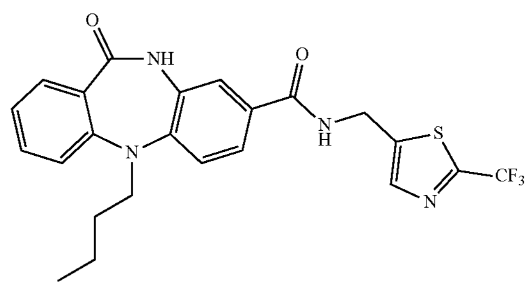 [SMILES: CCCCN1c2ccc(C(=O)NCc3cnc(C(F)(F)F)s3)cc2NC(=O)c2ccccc21] | A, 176, 255 | | 475.1 (M$^+$ + 1); | 474.13 for $C_{23}H_{21}F_3N_4O_2S$ | $^1$H NMR (400 MHz, DMSO-d$_6$): δ 10.28 (s, 1H), 9.22 (t, J = 5.8 Hz, 1H), 8.04 (d, J = 0.9 Hz, 1H), 7.62-7.56 (m, 3H), 7.50-7.47 (m, 1H), 7.27 (d, J = 8.4 Hz, 1H), 7.21 (d, J = 7.8 Hz, 1H), 7.13-7.07 (m, 1H), 4.70 (d, J = 5.6 Hz, 2H), 3.79-3.72 (m, 2H), 1.53-1.43 (m, 2H), 1.38-1.28 (m, 2H), 0.82 (t, J = 7.3 Hz, 3H); |
| 1934 | 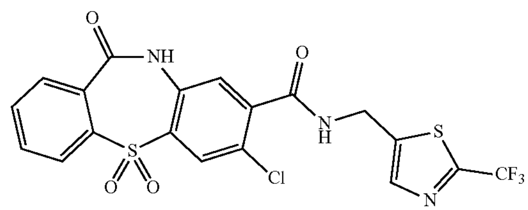 [SMILES: O=C(NCc1cnc(C(F)(F)F)s1)c1cc2c(cc1Cl)S(=O)(=O)c1ccccc1C(=O)N2] | A, 126, 255 | 20 | 501.9 (M$^+$ + 1); | 500.98 for $C_{19}H_{11}ClF_3N_3O_4S_2$ | 1H-NMR (DMSO-d6, 400 MHz): δ 11.50 (br s, 1H), 9.43 (t, J = 5.8 Hz, 1H), 8.06 (s, 1H), 8.02-7.96 (m, 3H), 7.95-7.85 (m, 2H), 7.43 (s, 1H), 4.76 (d, J = 5.8 Hz, 2H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various 149, 153, 155, 158, 200, 211, 216, commerical and synthesized amines.

| Example | Structure | Procedure, Interemediate, amine | Rx. Yield (%) | Mass Spec. Found | Mass Spec. Calculated | $^1$H-NMR |
|---|---|---|---|---|---|---|
| 1935 | 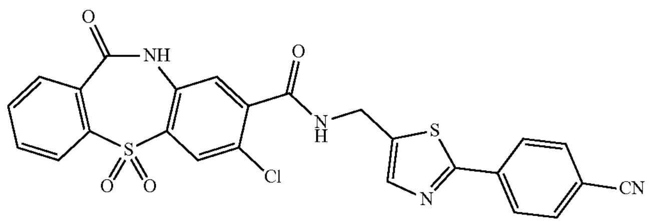 [SMILES: N#Cc1ccc(-c2ncc(CNC(=O)c3cc4c(cc3Cl)S(=O)(=O)c3ccccc3C(=O)N4)s2)cc1] | A, 126, 227 | 35 | 535.1 (M$^+$ + 1); | 534.02 for $C_{25}H_{15}ClN_4O_4S_2$ | 1H NMR (400 MHz, DMSO-d6): δ 11.52 (s, 1H), 9.36 (t, J = 5.8 Hz, 1H), 8.10 (d, J = 8.4 Hz, 2H), 8.02-7.94 (m, 5H), 7.93-7.85 (m, 3H), 7.43 (s, 1H), 4.72 (d, J = 5.8 Hz, 2H); |
| 1942 | 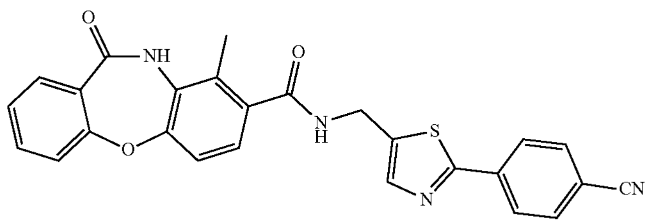 [SMILES: Cc1c(C(=O)NCc2cnc(-c3ccc(C#N)cc3)s2)ccc2c1NC(=O)c1ccccc1O2] | A$^c$, 153, 227 | 59 | 467.0 (M$^+$ + 1); | 466.11 for $C_{26}H_{18}N_4O_3S$ | 1H-NMR (DMSO-d6, 400 MHz): δ 10.05 (s, 1H), 9.04 (t, J = 5.9 Hz, 1H), 8.09 (d, J = 8.5 Hz, 2H), 7.95 (d, J = 8.5 Hz, 2H), 7.89 (s, 1H), 7.72 (dd, J = 7.7, 1.6 Hz, 1H), 7.64-7.55 (m, 1H), 7.38-7.29 (m, 2H), 7.26 (d, J = 8.3 Hz, 1H), 7.13 (d, J = 8.3 Hz, 1H) 4.65 (d, J = 5.8 Hz, 2H), 2.29 (s, 3H); |
| 1971 | 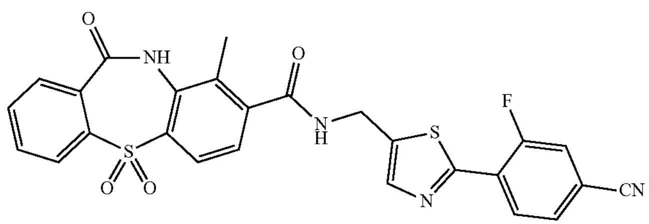 [SMILES: Cc1c(C(=O)NCc2cnc(-c3ccc(C#N)cc3F)s2)ccc2c1NC(=O)c1ccccc1S2(=O)=O] | A, 95, 316 | 64 | 533.0 (M$^+$ + 1); | 532 for $C_{26}H_{17}FN_4O_4S_2$ | $^1$H NMR (400 MHz, DMSO-d$_6$): δ 10.29 (s, 1H), 9.15 (t, J = 5.7 Hz, 1H), 8.06 (d, J = 8.4 Hz, 2H), 7.96-7.88 (m, 3H), 7.64-7.56 (m, 3H), 7.51-7.44 (m, 1H), 7.29-7.18 (m, 2H), 7.10 (t, J = 7.4 Hz, 1H), 4.68 (d, J = 5.8 Hz, 2H), 3.77-3.69 (m, 2H), 1.55-1.47 (m, 2H), 0.87 (t, J = 7.3 Hz, 3H); |
| 1974 | 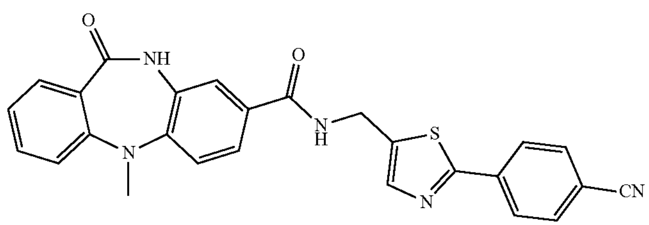 [SMILES: CN1c2ccc(C(=O)NCc3cnc(-c4ccc(C#N)cc4)s3)cc2NC(=O)c2ccccc21] | A, 166, 227 | 23 | 466.1 (M$^+$ + 1); | 465.13 for $C_{26}H_{19}N_5O_2S$ | 1H-NMR (DMSO-d6, 400 MHz): δ 10.30 (s, 1H), 9.17 (t, J = 5.5 Hz, 1H), 8.07 (d, J = 8.3 Hz, 2H), 7.92 (t, J = 8.5 Hz, 3H), 7.66-7.57 (m, 3H), 7.54-7.47 (m, 1H), 7.23 (t, J = 8.8 Hz, 2H), 7.10 (t, J = 7.4 Hz, 1H), 4.68 (d, J = 5.6 Hz, 2H), 3.31 (s, 3H); |

TABLE 1-continued

Synthesis from compound 13, 20, 32, 40, 47, 54, 61, 68, 76, 81, 88, 92, 95, 105, 113, 120, 126, 135, 143, 144, 163, 169, 172, 176, 185, 190, 194 and various commercial and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 1975 | 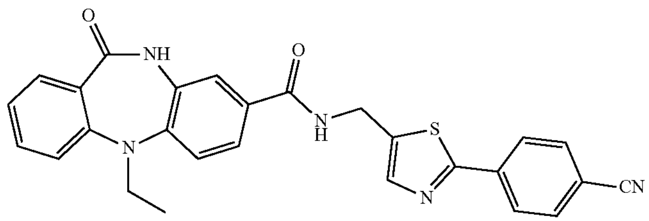 [SMILES: CCN1c2ccc(C(=O)NCc3cnc(-c4ccc(C#N)cc4)s3)cc2NC(=O)c2ccccc21] | A, 169, 227 | 24 | 480.1 (M$^+$ + 1); | 479.14 for $C_{27}H_{21}N_5O_2S$ | 1H-NMR (DMSO-d6, 400 MHz): δ 10.31 (s, 1H), 9.17 (t, J = 5.5 Hz, 1H), 8.06 (d, J = 8.3 Hz, 2H), 7.95-7.87 (m, 3H), 7.66-7.56 (m, 3H), 7.49 (t, J = 7.0 Hz, 1H), 7.27-7.17 (m, 2H), 7.10 (t, J = 7.5 Hz, 1H), 4.68 (d, J = 5.4 Hz, 2H), 3.80-3.77 (m, 2H), 1.12 (t, J = 6.9 Hz, 3H); |
| 11001 | 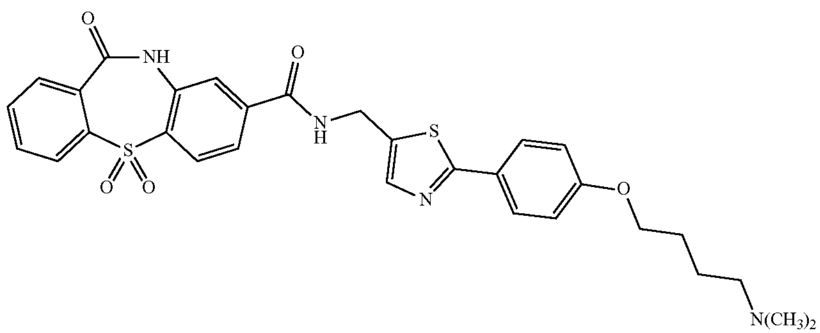 [SMILES: CN(C)CCCCOc1ccc(-c2ncc(CNC(=O)c3ccc4c(c3)NC(=O)c3ccccc3S4(=O)=O)s2)cc1] | A, 92, 394 | 40 | 591.1 (M$^+$ + 1); | 590.17 for $C_{30}H_{30}N_4O_5S_2$ | $^1$H NMR (400 MHz, DMSO-d$_6$): δ 11.47 (br s, 1H), 9.44 (t, J = 5.7 Hz, 1H), 8.05 (d, J = 8.2 Hz, 1H), 8.01-7.95 (m, 2H), 7.93-7.77 (m, 6H), 7.72 (s, 1H), 7.01 (d, J = 8.9 Hz, 2H), 4.66 (d, J = 5.5 Hz, 2H), 4.03 (t, J = 6.5 Hz, 2H), 2.24 (t, J = 7.2 Hz, 2H), 2.12 (s, 6H), 1.77-1.68 (m, 2H), 1.58-1.49 (m, 2H); |
| 11117-A | 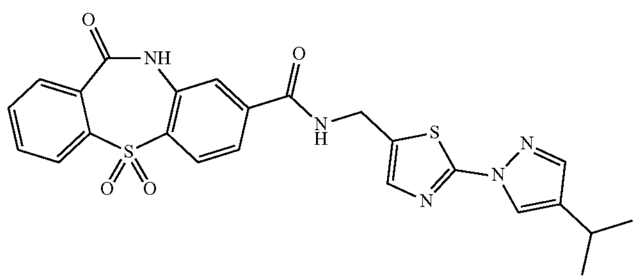 [SMILES: CC(C)c1cnn(-c2ncc(CNC(=O)c3ccc4c(c3)NC(=O)c3ccccc3S4(=O)=O)s2)c1] | A$^c$, 92, 519 | 26 | 508.0 (M$^+$ + 1); | 507.10 for $C_{24}H_{21}N_5O_4S_2$ | $^1$H NMR (400 MHz, DMSO-d$_6$): δ 11.52 (s, 1H), 9.46 (t, J = 5.8 Hz, 1H), 8.21 (s, 1H), 8.06 (d, J = 8.3 Hz, 1H), 8.01-7.95 (m, 2H), 7.93-7.78 (m, 4H), 7.73 (s, 1H), 7.50 (s, 1H), 4.60 (d, J = 5.5 Hz, 2H), 2.88-2.81 (m, 1H), 1.20 (d, J = 6.9 Hz, 6H); |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commerical and synthesized amines.

| Example | Structure | Procedure, Intermediate, amine | Rx. Yield (%) | Mass Spec. Found | Mass Spec. Calculated | $^1$H-NMR |
|---|---|---|---|---|---|---|
| 11078 | 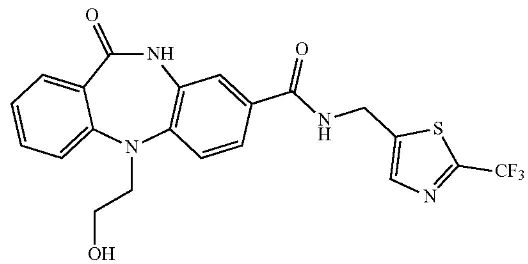 [SMILES: O=C(NCc1cnc(C(F)(F)F)s1)c1ccc2c(c1)NC(=O)c1ccccc1N2CCO] | A$^c$, 194, 255 | 19 | 463.1 (M$^+$ + 1); | 462.10 for C$_{21}$H$_{17}$F$_3$N$_4$O$_3$S | $^1$H NMR (400 MHz, DMSO-d$_6$): δ 10.27 (s, 1H), 9.22 (t, J = 5.8 Hz, 1H), 8.04 (s, 1H), 7.63-7.56 (m, 3H), 7.52-7.46 (m, 1H), 7.31-7.21 (m, 2H), 7.11 (t, J = 7.5 Hz, 1H), 4.70 (d, J = 5.6 Hz, 2H), 4.66 (t, J = 5.4 Hz, 1H), 3.86-3.82 (m, 2H), 3.51 (q, J = 6.1 Hz, 2H); |
| 11079 | 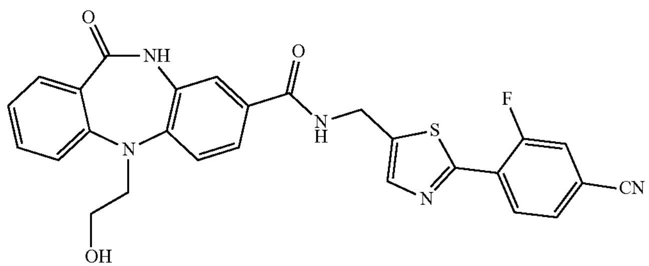 [SMILES: N#Cc1ccc(-c2ncc(CNC(=O)c3ccc4c(c3)NC(=O)c3ccccc3N4CCO)s2)c(F)c1] | A$^c$, 194, 316 | 26 | 514.1 (M$^+$ + 1); | 513.13 for C27H20FN5O3S | $^1$H NMR (400 MHz, DMSO-d$_6$): δ 10.27 (s, 1H), 9.17 (t, J = 5.9 Hz, 1H), 8.35 (t, J = 7.9 Hz, 1H), 8.09 (dd, J = 11.1, 1.4 Hz, 1H), 7.99 (d, J = 2.3 Hz, 1H), 7.82 (dd, J = 8.2, 1.5 Hz, 1H), 7.62-7.56 (m, 3H), 7.52-7.46 (m, 1H), 7.28 (d, J = 8.4 Hz, 1H), 7.23 (d, J = 8.1 Hz, 1H), 7.10 (t, J = 7.2 Hz, 1H), 4.71 (d, J = 5.6 Hz, 2H), 4.66 (t, J = 5.4 Hz, 1H), 3.86-3.82 (m, 2H), 3.51 (q, J = 6.2 Hz, 2H); |
| 11094 | 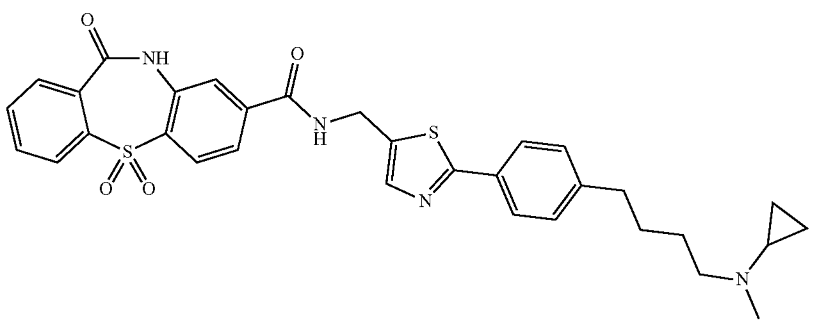 [SMILES: CN(CCCCc1ccc(-c2ncc(CNC(=O)c3ccc4c(c3)NC(=O)c3ccccc3S4(=O)=O)s2)cc1)C1CC1] | A, 92, 484 | 38 | 601.1 (M$^+$ + 1); | 600.19 for C$_{32}$H$_{32}$N$_4$O$_4$S$_2$ | $^1$H NMR (400 MHz, DMSO-d$_6$): δ 11.51 (s, 1H), 9.46 (t, J = 5.8 Hz, 1H), 8.06 (d, J = 8.3 Hz, 1H), 7.98 (td, J = 7.4, 1.4 Hz, 2H), 7.90 (td, J = 1.5, 7.5 Hz, 1H), 7.87-7.75 (m, 6H), 7.28 (d, J = 8.3 Hz, 2H), 4.68 (d, J = 5.6 Hz, 2H), 2.60 (t, J = 7.5 Hz, 2H), 2.47-2.47 (m, 2H), 2.19 (br s, 3H), 1.55 (td, J = 7.3, 14.7 Hz, 3H), 1.48-1.39 (m, 2H), 0.38 (br d, J = 4.0 Hz, 2H), 0.24 (br s, 2H); |

TABLE 1-continued

Synthesis from compound 13, 20, 32, 40, 47, 54, 61, 68, 76, 81, 88, 89, 92, 95, 105, 113, 120, 126, 135, 143, 144, 149, 153, 155, 158, 200, 211, 216, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | ¹H-NMR |
|---|---|---|---|---|---|---|
| C20-01 | 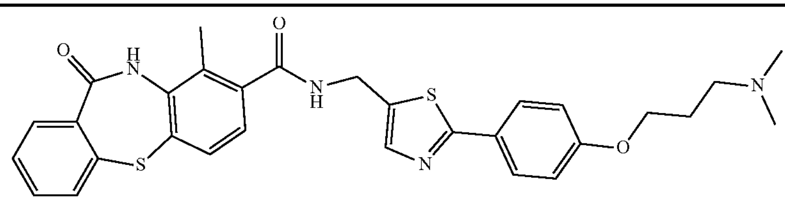 | B, 20, 367 | 46 | 559.20 (M⁺ + 1) | 558.18 for $C_{30}H_{30}N_4O_3S_2$ | ¹H NMR (400 MHz, DMSO-$d_6$): δ 10.25 (s, 1H), 9.03 (t, J = 5.6 Hz, 1H), 7.81 (d, J = 8.8 Hz, 2H), 7.68-7.64 (m, 2H), 7.53-7.43 (m, 4H), 7.10-7.01 (m, 3H), 4.59 (d, J = 5.6 Hz, 2H), 4.06 (t, J = 6.4 Hz, 2H), 2.45 (t, J = 6.4 Hz, 2H), 2.29 (s, 3H), 2.25 (s, 6H), 1.88 (t, J = 6.4 Hz, 2H) |
| C20-02 | 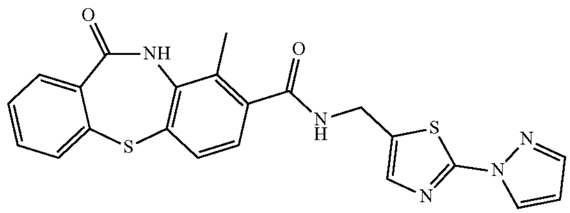 [SMILES: Cc1c(C(=O)NCc2cnc(-n3cccn3)s2)ccc2c1NC(=O)c1ccccc1S2] | B, 20, 455 | 64 | 448.05 (M⁺ + 1) | 447.08 for $C_{22}H_{17}N_5O_2S_2$ | ¹H NMR (400 MHz, DMSO-$d_6$): δ 10.26 (s, 1H), 9.07 (t, J = 5.6 Hz, 1H), 8.47 (d, J = 1.6 Hz, 1H), 7.84 (s, 1H), 7.68-7.64 (m, 1H), 7.52-7.43 (m, 5H), 7.08 (d, J = 8.4 Hz, 1H), 6.62 (s, 1H), 4.56 (d, J = 5.6 Hz, 2H), 2.29 (s, 3H) |
| C38-01 | 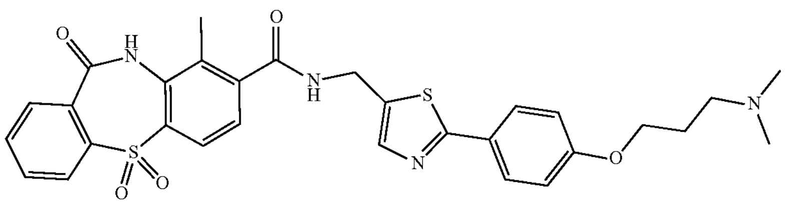 [SMILES: Cc1c(C(=O)NCc2cnc(-c3ccc(OCCCN(C)C)cc3)s2)ccc2c1NC(=O)c1ccccc1S2(=O)=O] | B, 95, 367 | 21 | 591.15 (M⁺ + 1) | 590.17 for $C_{30}H_{30}N_4O_5S_2$ | ¹H NMR (400 MHz, DMSO-$d_6$): δ 10.87 (s, 1H), 9.18 (t, 1H), 7.94-7.77 (m, 7H), 7.71 (s, 1H), 7.35 (d, J = 8.0 Hz, 1H), 7.03 (d, J = 8.0 Hz, 2H), 4.62 (d, J = 5.6 Hz, 2H), 4.08 (t, J = 6.0 Hz, 2H), 2.72-2.70 (m, 2H), 2.43 (s, 6H), 2.32 (s, 3H), 1.97-1.94 (m, 2H) |
| C38-02 | 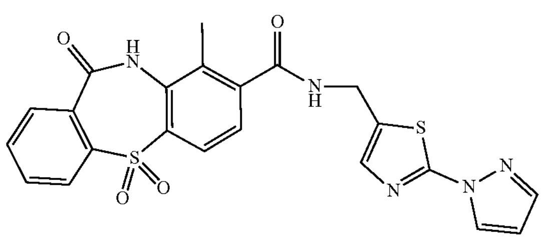 [SMILES: Cc1c(C(=O)NCc2cnc(-n3cccn3)s2)ccc2c1NC(=O)c1ccccc1S2(=O)=O] | B, 95, 455 | 23 | 480.10 (M⁺ + 1) | 479.07 for $C_{22}H_{17}N_5O_4S_2$ | ¹H NMR (400 MHz, DMSO-$d_6$): δ 10.87 (s, 1H), 9.21 (t, J = 5.6 Hz, 1H), 8.47 (s, 1H), 7.94-7.77 (m, 5H), 7.54 (s, 1H), 7.35 (d, J = 8.4 Hz, 1H), 6.62 (s, 1H), 4.58 (d, J = 5.6 Hz, 2H), 2.32 (s, 3H) |

TABLE 1-continued

Synthesis from compound 13, 20, 32, 40, 47, 54, 61, 68, 76, 81, 88, 89, 92, 95, 105, 113, 120, 126, 135, 143, 144, 163, 169, 172, 176, 185, 190, 194 and various commerical and synthesized amines.

| Example | Structure | Procedure, Interemediate, amine | Rx. Yield (%) | Mass Spec. Found | Mass Spec. Calculated | 1H-NMR |
|---|---|---|---|---|---|---|
| C44-01 | 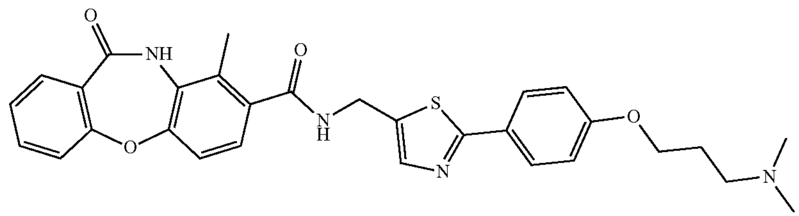 [SMILES: Cc1c(C(=O)NCc2cnc(-c3ccc(OCCCN(C)C)cc3)s2)ccc2c1NC(=O)c1ccccc1O2] | B, 153, 367 | 20 | 543 (M+ + 1) | 542.20 for $C_{30}H_{30}N_4O_4S$ | 1H NMR (400 MHz, DMSO-$d_6$): δ 10.05 (s, 1H), 8.97 (t, J = 5.9 Hz, 1H), 7.85-7.76 (m, 2H), 7.74-7.65 (m, 2H), 7.58 (td, J = 7.7, 1.8 Hz, 1H), 7.37-7.21 (m, 2H), 7.10 (d, J = 8.3 Hz, 1H), 7.05-6.97 (m, 2H), 4.58 (d, J = 5.8 Hz, 2H), 4.04 (t, J = 6.4 Hz, 2H), 2.40 (t, J = 7.2 Hz, 2H), 2.27 (s, 3H), 2.18 (s, 6H), 1.86 (p, J = 6.6 Hz, 2H) |
| C51-01 | 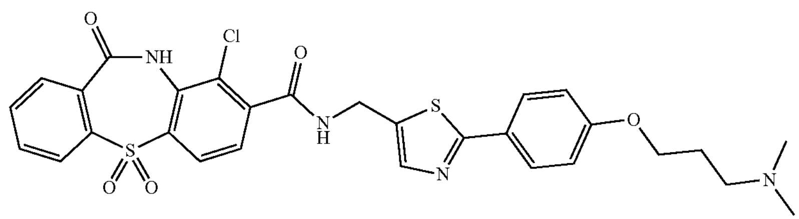 [SMILES: CN(C)CCCOc1ccc(-c2ncc(CNC(=O)c3ccc4c(c3Cl)NC(=O)c3ccccc3S4(=O)=O)s2)cc1] | B, 135, 367 | 27 | 611 (M+ + 1) | 610.11 for $C_{29}H_{27}ClN_4O_5S_2$ | 1H NMR (400 MHz, DMSO-$d_6$) δ 9.26 (t, J = 5.8 Hz, 1H), 8.00-7.76 (m, 7H), 7.71 (s, 1H), 7.41 (d, J = 8.0 Hz, 1H), 7.06-6.98 (m, 2H), 4.64 (d, J = 5.6 Hz, 2H), 4.05 (t, J = 6.4 Hz, 2H), 2.37 (t, J = 6.8 Hz, 2H), 2.15 (s, 6H), 1.89-1.83 (m, 2H) |
| C51-02 | 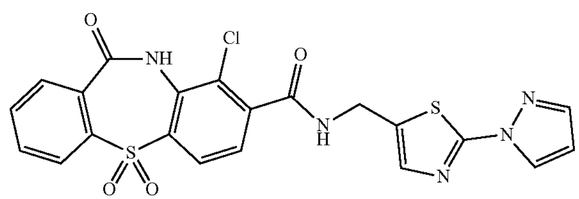 [SMILES: O=C1Nc2c(ccc(C(=O)NCc3cnc(-n4cccn4)s3)c2Cl)S(=O)(=O)c2ccccc21] | B, 135, 455 | 20 | 500 (M+ + 1) | 499.02 for $C_{21}H_{14}ClN_5O_4S_2$ | 1H NMR (400 MHz, DMSO-$d_6$): δ 11.21 (s, 1H), 9.30 (t, J = 5.8 Hz, 1H), 8.47 (d, J = 2.6 Hz, 1H), 8.03-7.79 (m, 6H), 7.57-7.45 (m, 2H), 6.62 (s, 1H), 4.60 (d, J = 5.8 Hz, 2H) |

A[a]: DIPEA (2 equiv);
A[b]: EDCl (2 equiv), HOBt (2 equiv), DIPEA (5 equiv);
A[c]: DIPEA (5 equiv);
A[d]: Column purification done in neutral alumina (Eluent: 1:1:50, MeOH:NH4OH:CH2Cl2);
B[e]: HATU (1.5 equiv), Amine (1.1 equiv), DIPEA (3 equiv)

Synthesis of N-((2-chlorothiazol-5-yl) methyl)-11-oxo-10, 11-dihydrodibenzo [b, f] [1, 4] thiazepine-8-carboxamide 5, 5-dioxide (535): A Common Intermediate

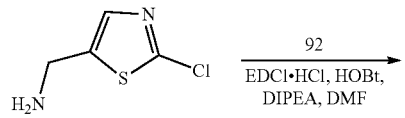

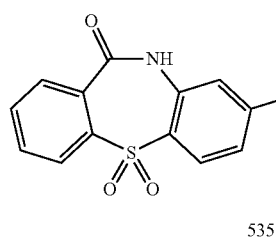

Synthesis of N-((2-chlorothiazol-5-yl) methyl)-11-oxo-10, 11-dihydrodibenzo [b, f][1, 4] thiazepine-8-carboxamide 5, 5-dioxide (535)

To a stirring solution of compound 92 (600 mg, 1.65 mmol) in DMF (15 mL) under inert atmosphere were added compound 223 (362 mg, 1.98 mmol), EDCI.HCl (597 mg, 3.30 mmol), HOBt (445 mg, 3.30 mmol) and diisopropylethylamine (1.5 mL, 8.25 mmol) at 0° C.; warmed to RT and stirred for 16 h. The reaction was monitored by TLC; after completion of the reaction, the reaction mixture was diluted with water (100 mL) and extracted with EtOAc (2×100 mL). The combined organic extracts were dried over sodium sulphate, filtered and concentrated in vacuo to obtain the crude. The crude was triturated with EtOAc (10 mL), diethyl ether (10 mL), n-hexane (20 mL) and dried in vacuo to afford compound 535 (700 mg, 82%) as an off-white solid. TLC: 10% MeOH/CH$_2$Cl$_2$ (R$_f$: 0.4); $^1$H-NMR (DMSO-d$_6$ 400 MHz): δ 11.51 (br s, 1H), 9.48 (t, J=5.5 Hz, 1H), 8.06 (d, J=8.3 Hz, 1H), 7.98 (td, J=7.4, 1.1 Hz, 2H), 7.93-7.83 (m, 3H), 7.79 (dd, J=8.3, 1.5 Hz, 1H), 7.61 (s, 1H), 4.59 (d, J=5.5 Hz, 2H).

Synthesis of N-((2-chlorothiazol-5-yl) methyl)-9-methyl-11-oxo-10, 11-dihydrodibenzo [b, f] [1, 4] thiazepine-8-carboxamide 5, 5-dioxide (536): A Common Intermediate

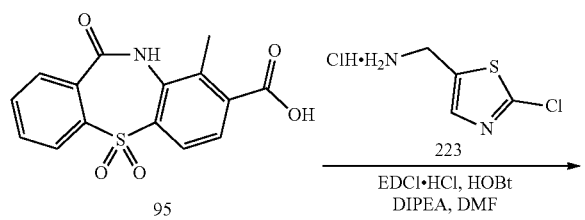

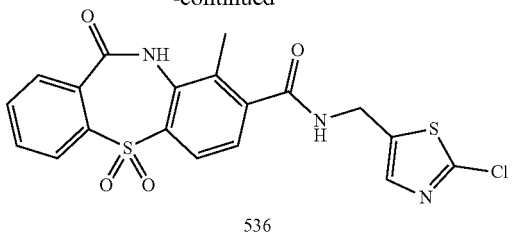

Synthesis of N-((2-chlorothiazol-5-yl) methyl)-9-methyl-11-oxo-10, 11-dihydrodibenzo [b, f] [1, 4] thiazepine-8-carboxamide 5, 5-dioxide (536)

To a stirring solution of compound 95 (1.5 g, 4.73 mmol) in DMF (15 mL) under inert atmosphere were added EDCI.HCl (1.36 g, 7.09 mmol), HOBt (960 mg, 7.09 mmol), (2-chlorothiazol-5-yl) methanamine hydrochloride 223 (963 mg, 7.09 mmol) and diisopropylethylamine (4.1 mL, 23.65 mmol) at 0° C.; warmed to RT and stirred for 16 h. The reaction was monitored by TLC; after completion of the reaction, the reaction mixture was poured into ice-cold water (100 mL) and extracted with EtOAc (2×60 mL) and dried in vacuo to afford compound 536 (1.2 g, 57%) as white solid. TLC: 5% MeOH/CH$_2$Cl$_2$ (R$_f$: 0.3); $^1$H NMR (DMSO-d$_6$, 400 MHz): δ 10.86 (s, 1H), 9.21 (t, J=5.8 Hz, 1H), 7.95-7.90 (m, 2H), 7.89-7.84 (m, 2H), 7.82-7.77 (m, 1H), 7.60 (s, 1H), 7.35 (d, J=8.2 Hz, 1H), 4.56 (d, J=5.6 Hz, 2H), 2.31 (s, 3H); LC-MS: 99.42%; 448.0 (M$^+$+1); (column; Ascentis Express C18, (50×3.0 mm, 2.7 μm); RT 2.08 min. 0.025% Aq. TFA+5% ACN: ACN+5% 0.025% Aq. TFA, 1.2 mL/min).

Synthesis of N-((2-(4-bromophenyl) thiazol-5-yl) methyl)-11-oxo-10, 11-dihydrodibenzo [b, f] [1, 4] thiazepine-8-carboxamide 5, 5-dioxide (538): A Common Intermediate

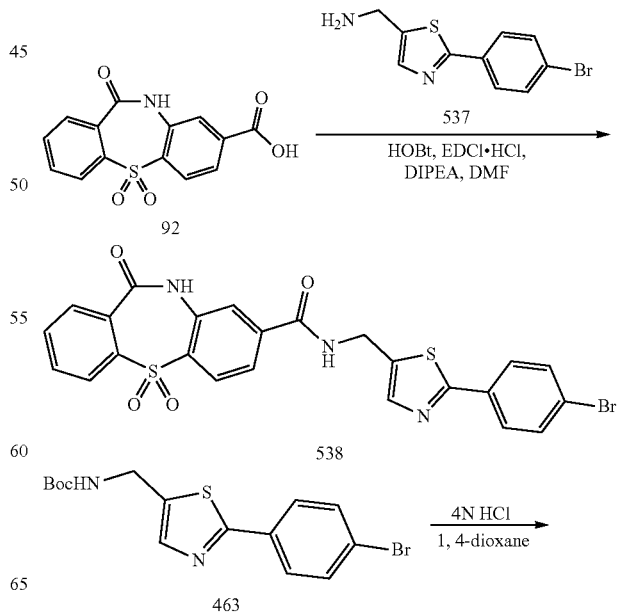

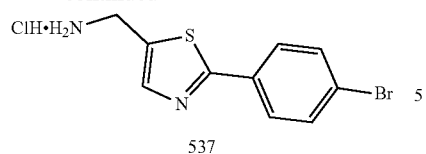

537

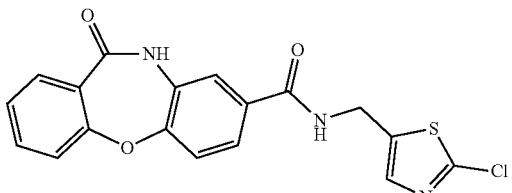

539

Synthesis of (2-(4-bromophenyl) thiazol-5-yl) methanamine hydrochloride (537)

To a stirring solution of compound 463 (700 mg, 1.89 mmol) in $CH_2Cl_2$ mL) was added 4 N HCl in 1, 4-dioxane (3 mL) under inert atmosphere at 0° C.; warmed to RT and stirred for 3-4 h. The reaction was monitored by TLC; after completion of the reaction, the volatiles were removed in vacuo. The crude was triturated with diethyl ether (2×5 mL) and dried in vacuo to afford compound 537 (680 mg, HCl salt) as an off-white solid. TLC: 10% $MeOH/CH_2Cl_2$ ($R_f$: 0.2); $^1H$ NMR (DMSO-$d_6$, 400 MHz): δ 8.64 (br s, 3H), 8.00 (s, 1H), 7.88 (d, J=8.5 Hz, 2H), 7.72 (d, J=8.7 Hz, 2H), 4.34 (q, J=5.6 Hz, 2H);

Synthesis of N-((2-(4-bromophenyl) thiazol-5-yl) methyl)-11-oxo-10, 11-dihydrodibenzo [b, f] [1, 4] thiazepine-8-carboxamide 5, 5-dioxide (538)

To a stirring solution of 92 (400 mg, 1.32 mmol) in DMF (15 mL) under inert atmosphere were added HOBt (268 mg, 1.98 mmol), EDCI.HCl (380 mg, 1.98 mmol), ((2-(4-bromophenyl) thiazol-5-yl) methanamine 537 (402 mg, 1.32 mmol) and diisopropylethylamine (1.2 mL, 6.60 mmol) at 0° C.; warmed to RT and stirred for 16 h. The reaction was monitored by TLC; after completion of the reaction, the reaction mixture was diluted with water (50 mL) and extracted with EtOAc (2×50 mL). The combined organic extracts were dried over sodium sulfate, filtered and concentrated in vacuo to obtain the crude, which was triturated with EtOAc (20 mL) and dried in vacuo to afford compound 538 (500 mg, 68%) as an off-white solid. TLC: 5% $MeOH/CH_2Cl_2$ ($R_f$: 0.5); $^1H$ NMR (DMSO-$d_6$, 400 MHz): δ 11.12 (br s, 1H), 9.48 (t, J=5.8 Hz, 1H), 8.06 (d, J=8.2 Hz, 1H), 7.98 (td, J=7.4, 1.1 Hz, 2H), 7.93-7.79 (m, 7H), 7.67 (d, J=8.7 Hz, 2H), 4.69 (d, J=5.6 Hz, 2H); LC-MS: 97.62%; 555.9 (M+2)$^+$; (column; Ascentis Express C18, (50×3.0 mm, 2.7 μm); RT 2.57 min. 0.025% Aq. TFA+5% ACN: ACN+ 5% 0.025% Aq. TFA, 1.2 mL/min).

Synthesis of N-((2-chlorothiazol-5-yl) methyl)-11-oxo-10, 11-dihydrodibenzo [b, f] [1, 4] oxazepine-8-carboxamide (539): A Common Intermediate

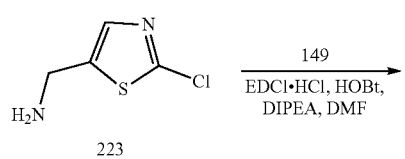

223

Synthesis of N-((2-chlorothiazol-5-yl) methyl)-11-oxo-10, 11-dihydrodibenzo [b, f] [1, 4] oxazepine-8-carboxamide (539)

To a stirring solution of compound 149 (500 mg, 1.96 mmol) in DMF (10 mL) under inert atmosphere were added compound 223 (398 mg, 2.15 mmol), EDCI.HCl (561 mg, 2.94 mmol), HOBt (397 mg, 2.94 mmol) and diisopropylethylamine (1.75 mL, 9.80 mmol) at 0° C.; warmed to RT and stirred for 16 h. The reaction was monitored by TLC; after completion of the reaction, the reaction mixture was diluted with ice cold-water (50 mL), extracted with EtOAc (2×100 mL). The combined organic extracts were dried over sodium sulfate, filtered and concentrated in vacuo to obtain the crude. The crude was purified through silica gel column chromatography using 8% $MeOH/CH_2Cl_2$ to afford compound 539 (390 mg, 52%) as an off-white solid. TLC: 10% $MeOH/CH_2Cl_2$ ($R_f$: 0.4); $^1H$-NMR (DMSO-$d_6$ 500 MHz): δ 10.63 (s, 1H), 9.23 (t, J=5.6 Hz, 1H), 7.78 (dd, J=7.7, 1.6 Hz, 1H), 7.68 (s, 1H), 7.65-7.58 (m, 3H), 7.43 (d, J=8.4 Hz, 1H), 7.39-7.31 (m, 2H), 4.56 (d, J=5.8 Hz, 2H).

The common intermediates 535, 536, 538 & 539 were converted to final products through the displacement reaction using amines or were coupled with either commercially available coupling reagents or prepared coupling reagents.

Commercially Available Amines for Displacement Reaction:

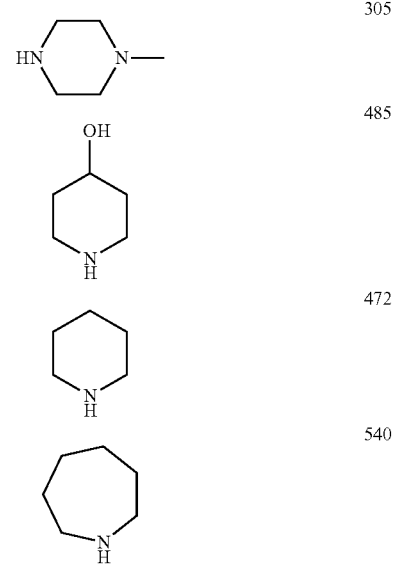

305

485

472

540

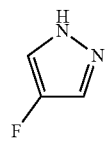
541

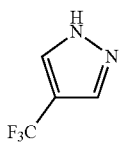
542

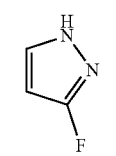
543

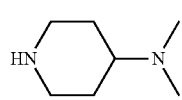
544

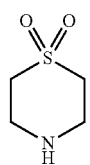
545

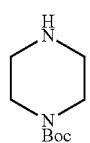
546

Preparation of Amines for Displacement Reaction:

Synthesis of (3S,6S)-azepane-3, 6-diol (550)

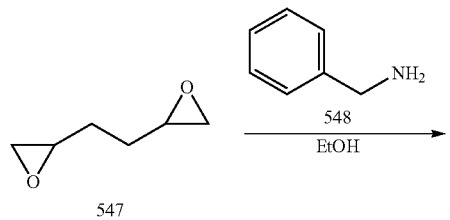

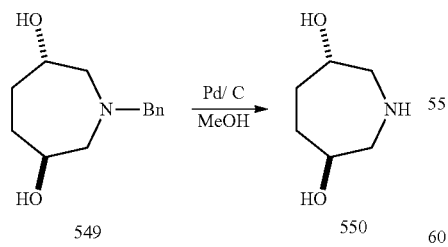

Synthesis of (3S,6S)-1-benzylazepane-3, 6-diol (549)

To a stirring solution of 1, 2-di(oxiran-2-yl) ethane 547 (1.5 g, 13.14 mmol) in EtOH (40 mL) under argon atmosphere was added benzyl amine 548 (1.53 mL, 14.46 mmol) at RT and heated to reflux for 16 h. The reaction was monitored by TLC; after completion of the reaction, the volatiles were concentrated in vacuo to obtain the crude. The crude was purified preparative HPLC purification to afford compound 549 (600 mg, crude) as colorless liquid. TLC: 10% MeOH/CH$_2$Cl$_2$ (R$_f$: 0.5); $^1$H NMR (DMSO-d$_6$, 400 MHz): δ 7.36-7.28 (m, 4H), 7.26-7.19 (m, 1H), 4.38 (d, J=4.8 Hz, 2H), 3.72-3.50 (m, 4H), 2.73-2.69 (m, 2H), 2.40-2.37 (m, 2H), 1.88-1.67 (m, 2H), 1.48-1.27 (m, 2H); LC-MS: 89.13%; 222.2 (M$^+$+1); (Column; X-select CSH C-18 (150×4.6 mm, 3.5 μm); RT 7.28 min. 2.5 mM (NH$_4$)$_2$CO$_3$:ACN, 1.0 mL/min).

Synthesis of (3S, 6S)-azepane-3,6-diol (550)

To a stirring solution of compound 549 (500 mg, 0.22 mmol) in MeOH (25 mL) under inert atmosphere was added 10% Pd/C (50 mg, 50% wet) at RT and stirred under hydrogen atmosphere (balloon pressure) for 16 h. The reaction was monitored by TLC; after completion of the reaction, the reaction mixture was filtered through celite, and eluted with MeOH (10 mL). The filtrate was concentrated in vacuo to afford compound 550 (250 mg, 84%) as pale yellow solid. TLC: 10% MeOH/CH$_2$Cl$_2$ (R$_f$, 0.1); $^1$H-NMR (DMSO-d$_6$, 400 MHz): δ 4.55-4.22 (m, 2H), 3.59-3.51 (m, 2H), 2.87-2.83 (m, 2H), 2.48-2.43 (m, 2H), 1.80-1.71 (m, 2H), 1.40-1.27 (m, 2H); Mass (Agilent 6310 Ion trap): 132.3 (M$^+$+1);

Synthesis of 3, 3-dimethylpyrrolidine (554)

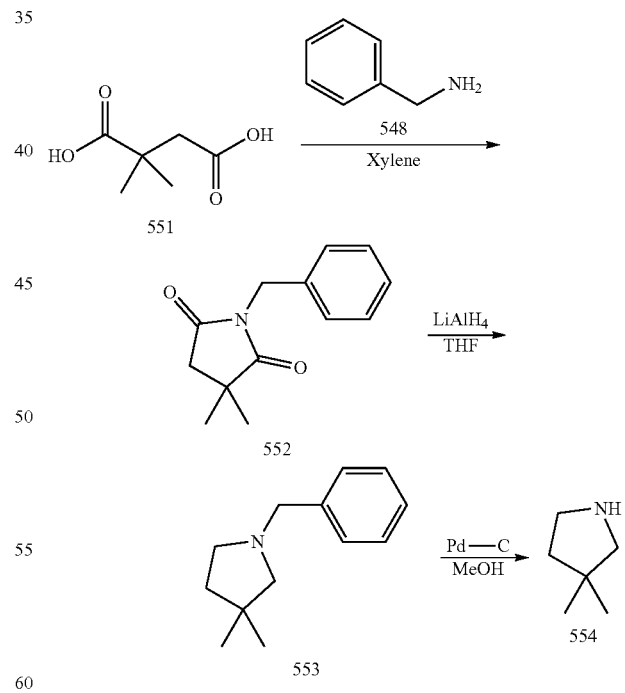

Synthesis of 1-benzyl-3, 3-dimethylpyrrolidine-2, 5-dione (552)

To a stirring solution of 2, 2-dimethylsuccinic acid 551 (5 g, 34.21 mmol) in xylene (50 mL) under inert atmosphere was added benzyl amine 548 (4.03 g, 37.63 mmol) at RT; heated to 120° C. and stirred for 3 h. The reaction was monitored by TLC; after completion of the reaction, the volatiles were removed in vacuo. The residue was diluted with EtOAc (100 mL), washed with 5% sodium bicarbonate solution. The organic extract was dried over sodium sulfate, filtered and concentrated in vacuo to obtain the crude. The crude compound was precipitated in isopropanol (100 mL) at −40° C. The solvent was decanted and the obtained solid was and dried in vacuo to afford compound 552 (3 g, 40%) as white solid. TLC: 20% EtOAc/hexanes ($R_f$: 0.8); $^1$H-NMR (DMSO-$d_6$, 400 MHz): δ 7.35-7.20 (m, 5H), 4.55 (s, 2H), 2.65 (s, 2H), 1.22 (s, 6H); LC-MS: 99.27%; 217.9 (M$^+$+1); (column; Ascentis Express C18, (50×3.0 mm, 2.7 μm); RT 2.27 min. 0.025% Aq. TFA+5% ACN: ACN+5% 0.025% Aq. TFA, 1.2 mL/min).

Synthesis of 1-benzyl-3, 3-dimethylpyrrolidine (553)

To a stirring solution of compound 552 (3.0 g, 13.82 mmol) in THF (50 mL) under argon atmosphere was added lithium aluminium hydride (1.57 g, 41.47 mmol) portion wise for 10 min at 0° C.; warmed to RT and stirred for 16 h. The reaction was monitored by TLC; after completion of the reaction, the reaction mixture was cooled to 0° C., quenched with saturated sodium sulfate and stirred for 20 min, filtered through celite. The celite pad was eluted with EtOAc (30 mL). The filtrate was dried over sodium sulfate, filtered and concentrated in vacuo to afford compound 553 (2.2 g, 85%) as colorless thick syrup. $^1$H NMR (DMSO-$d_6$, 400 MHz): δ 7.32-7.27 (m, 4H), 7.25-7.19 (m, 1H), 3.52 (s, 2H), 2.56-2.47 (m, 2H), 2.21 (s, 2H), 1.51 (t, J=7.1 Hz, 2H), 1.03 (s, 6H); LC-MS: 92.64%; 190.0 (M$^+$+1); (column; Ascentis Express C18, (50×3.0 mm, 2.7 μm); RT 1.47 min. 0.025% Aq. TFA+5% ACN: ACN+5% 0.025% Aq. TFA, 1.2 mL/min).

Synthesis of 3, 3-dimethylpyrrolidine (554)

To a stirring solution of compound 553 (1.5 g, 7.98 mmol) in MeOH (20 mL) under inert atmosphere was added 10% Pd/C (500 mg) at RT and stirred under hydrogen atmosphere (70 psi) at RT; heated to 75° C. for 24 h. The reaction was monitored by TLC; after completion of the reaction, the reaction mixture was filtered through celite and eluted with 20% MeOH/CH$_2$Cl$_2$ (2×80 mL). The filtrate was concentrated in vacuo to afford compound 554 (500 mg, 64%) as colorless thick syrup. TLC: 5% MeOH/CH$_2$Cl$_2$ ($R_f$: 0.2); $^1$H NMR (DMSO-$d_6$, 400 MHz): δ 3.03 (t, J=7.4 Hz, 2H), 2.65 (s, 2H), 1.55 (t, J=7.3 Hz, 2H), 1.45-1.40 (m, 1H), 1.04 (s, 6H).

Commercially Available Cross Coupling Reagents Used for Preparing Compounds:

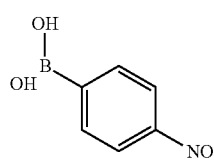

308

-continued

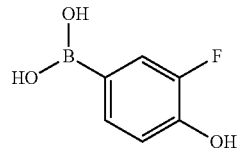

555

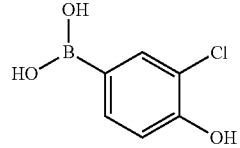

556

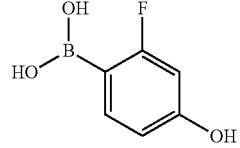

557

225

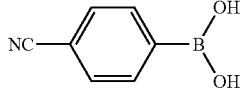

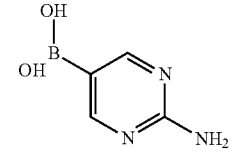

558

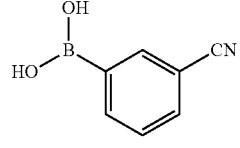

559

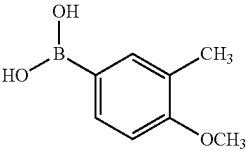

560

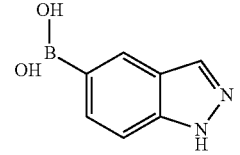

561

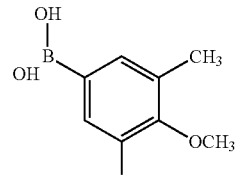

562

563

-continued

| 564 | 6-quinolinylboronic acid |
| 565 | 6-isoquinolinylboronic acid |
| 566 | (2-(hydroxymethyl)phenyl)boronic acid |
| 567 | (4-(methylsulfonyl)phenyl)boronic acid |
| 568 | (4-(methylsulfonamido)phenyl)boronic acid |
| 569 | 7-(4,4,5,5-tetramethyl-1,3,2-dioxaborolan-2-yl)indolin-2-one |
| 570 | 2-chloro-4-(4,4,5,5-tetramethyl-1,3,2-dioxaborolan-2-yl)benzonitrile |
| 571 | (2-(dimethylamino)pyrimidin-5-yl)boronic acid |
| 572 | (1H-indol-5-yl)boronic acid |
| 573 | (1H-benzimidazol-5-yl)boronic acid |
| 574 | 3-chloro-4-(4,4,5,5-tetramethyl-1,3,2-dioxaborolan-2-yl)phenol |
| 575 | (4-cyano-2-fluorophenyl)boronic acid |
| 576 | (4-sulfamoylphenyl)boronic acid |
| 577 | (2-chloro-4-cyanophenyl)boronic acid |
| 578 | (1H-pyrazol-3-yl)boronic acid |
| 579 | pyridin-3-ylboronic acid |
| 580 | pyridin-4-ylboronic acid |
| 581 | pyrimidin-5-ylboronic acid |

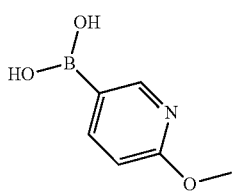

582

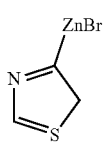

583

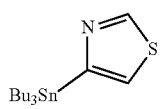

584

Preparation of Cross Coupling Reagents Used in the Preparation of Compounds:

Synthesis of 2, 6-difluoro-4-(4, 4, 5, 5-tetramethyl-1, 3, 2-dioxaborolan-2-yl) phenol (586)

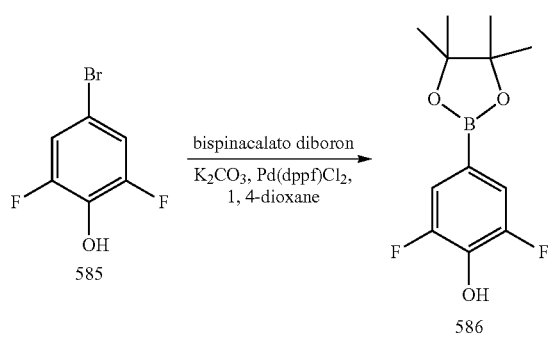 [SMILES: Oc1c(F)cc(Br)cc1F ; CC1(C)OB(c2cc(F)c(O)c(F)c2)OC1(C)C]

Synthesis of 2, 6-difluoro-4-(4, 4, 5, 5-tetramethyl-1, 3, 2-dioxaborolan-2-yl) phenol (586)

To a stirring solution of 4-bromo-2, 6-difluorophenol 585 (1 g, 4.80 mmol) in 1, 4-dioxane (25 mL) under inert atmosphere were added bis pinacolato diboron (1.83 g, 7.21 mmol), potassium carbonate (1.98 g, 14.40 mmol) and purged under argon atmosphere for 10 min. To this was added Pd(dppf)Cl$_2$ (350 mg, 0.48 mmol) and the reaction mixture was heated to 100° C. for 4 h. The reaction was monitored by TLC; after completion of the reaction, the reaction mixture was filtered through celite, eluted with CH$_2$Cl$_2$ (75 mL). The filtrate was concentrated in vacuo to obtain the crude. The crude was purified through silica gel column chromatography using 2-5% EtOAc/hexanes to compound 586 (620 mg, 50%) TLC: 10% EtOAc/hexanes (R$_f$: 0.5).

Synthesis of (6-(dimethylamino) pyridin-3-yl) boronic acid hydrochloride (588)

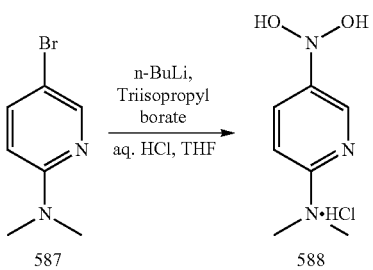

Synthesis of (6-(dimethylamino) pyridin-3-yl) boronic acid hydrochloride (588)

To a stirring solution of 5-bromo-N, N-dimethylpyridin-2-amine 587 (250 mg, 1.24 mmol) in dry THF (10 mL) under inert atmosphere was added n-butyl lithium (1.6 M solution in hexane, 0.93 mL, 1.49 mmol) drop wise for 5 min at −78° C. and stirred for 30 min. To this was added triisopropyl borate (0.43 mL, 1.86 mmol) in dry THF (4 mL) at −78° C.; warmed to RT and stirred for 16 h. The reaction was monitored by TLC; after completion of the reaction, the reaction mixture was quenched with 2 N aqueous HCl (10 mL). The volatiles were removed in vacuo to obtain the crude, which washed with diethylether (2×10 mL) to afford compound 588 (250 mg, crude) as an off-white thick syrup. TLC: 10% MeOH/CH$_2$Cl$_2$ (R$_f$: 0.1); LC-MS: 74.20%; 166.7 (M$^+$+1); (column; Ascentis Express C18, (50×3.0 mm, 2.7 µm); RT 0.48 min. 0.025% Aq. TFA+5% ACN: ACN+5% 0.025% Aq. TFA, 1.2 mL/min).

Synthesis of (6-((tert-butoxycarbonyl) amino) pyridin-3-yl) boronic acid (591)

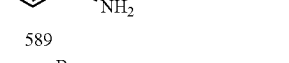

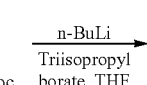

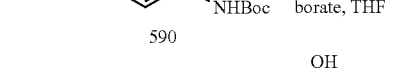

Synthesis of tert-butyl (5-bromopyridin-2-yl) carbamate (590)

To a stirring solution of 5-bromopyridin-2-amine 589 (1 g, 5.78 mmol) in THF (20 mL) under argon atmosphere were added triethyl amine (2.5 mL, 17.32 mmol), Boc-anhydride (1.51 g, 6.92 mmol) and DMAP (70 mg, 0.57 mmol) at 0° C.; heated to reflux and stirred for 16 h. The reaction was monitored by TLC; after completion of the reaction, the volatiles were removed in vacuo to obtain the crude. The crude was purified through silica gel flash column chromatography using 2-5% EtOAc/hexanes to afford compound 590 (900 mg, 57%) as white solid. TLC: 5% EtOAc/hexanes ($R_f$: 0.8); $^1$H-NMR (CDCl$_3$, 400 MHz): δ 8.32 (d, J=2.4 Hz, 1H), 8.02 (br s, 1H), 7.91 (d, J=9.0 Hz, 1H), 7.75 (dd, J=8.9, 2.4 Hz, 1H), 1.54 (s, 9H).

Synthesis of (6-((tert-butoxycarbonyl) amino) pyridin-3-yl) boronic acid (591)

To a stirring solution of compound 590 (250 mg, 0.91 mmol) and in dry THF (10 mL) under inert atmosphere was added n-butyl lithium (1.6 M solution in hexane, 1.72 mL, 2.74 mmol) drop wise for 10 min at −78° C. and stirred for 1 h. To this was added triisopropyl borate (0.31 mL, 1.37 mmol) at −78° C. and stirred for 1 h; warmed to RT and stirred for 16 h. The reaction was monitored by TLC; after completion of the reaction, the reaction mixture was quenched with water (5 mL) and the volatiles were removed in vacuo to obtain the crude. The pH of the crude was adjusted to ~5-6 with 1 N HCl. The volatiles were removed in vacuo to afford compound 591 (300 mg, crude) as white semi solid. TLC: 5% EtOAc/hexanes ($R_f$: 0.1); LC-MS: 30.85%; 239.0 (M$^+$+1); (column; X Select CSH C-18, (50×3.0 mm, 2.5 μm); RT 2.54 min. 2.5 mM Aq. NH$_4$OOCH+5% ACN: ACN+5% 2.5 mM Aq.NH$_4$OOCH, 0.8 mL/min).

Synthesis of 2-methoxy-5-(4, 4, 5, 5-tetramethyl-1, 3, 2-dioxaborolan-2-yl) pyrimidine (594)

Synthesis of 5-bromo-2-methoxypyrimidine (593)

Sodium metal (230 mg, 1.03 mmol) was dissolved in MeOH (25 mL) under inert atmosphere at 0° C.; warmed to RT and stirred for 1 h. To this was added 5-bromo-2-chloropyrimidine 592 (1 g, 0.51 mmol) at RT and stirred for 4 h. The reaction was monitored by TLC; after completion the volatiles were removed in vacuo to obtain the crude. The crude was diluted with ice-cold water (30 mL) and extracted with EtOAc (2×50 mL). The combined organic extracts were dried over sodium sulphate, filtered and concentrated in vacuo to afford compound 593 (900 mg, 92%). TLC: 10% EtOAc/hexanes ($R_f$: 0.3); $^1$H NMR (CDCl$_3$, 500 MHz): δ 8.59 (s, 2H), 4.01 (s, 3H).

Synthesis of 2-methoxy-5-(4, 4, 5, 5-tetramethyl-1, 3, 2-dioxaborolan-2-yl) pyrimidine (594)

To a stirring solution of 5-bromo-2-methoxypyrimidine 593 (500 mg, 2.65 mmol) in 1, 4-dioxane (25 mL) under inert atmosphere were added bis pinacolato diboron (1.34 g, 5.29 mmol), potassium acetate (779 mg, 7.95 mmol) at RT and stirred under argon atmosphere for 15 min. To this was added Pd(dppf)Cl$_2$ (193 mg, 0.26 mmol) and heated to 90-100° C. and stirred for 16 h. The reaction was monitored by TLC; after completion of the reaction, the reaction mixture was filtered through celite, washed with EtOAc (2×75 mL). The filtrate was concentrated in vacuo to obtain the crude. The crude was purified through silica gel column chromatography using 20-30% EtOAc/hexanes to afford compound 594 (700 mg, crude). TLC: 20% EtOAc/hexanes ($R_f$: 0.3); $^1$H NMR (CDCl$_3$, 400 MHz): δ 8.81 (s, 2H), 4.03 (s, 3H), 1.21 (s, 12H).

Synthesis of N-(4-(4, 4, 5, 5-tetramethyl-1, 3, 2-dioxaborolan-2-yl) phenyl) cyclopropanecarboxamide (598)

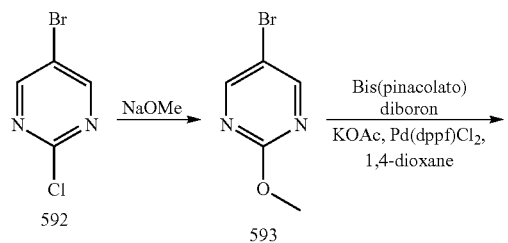

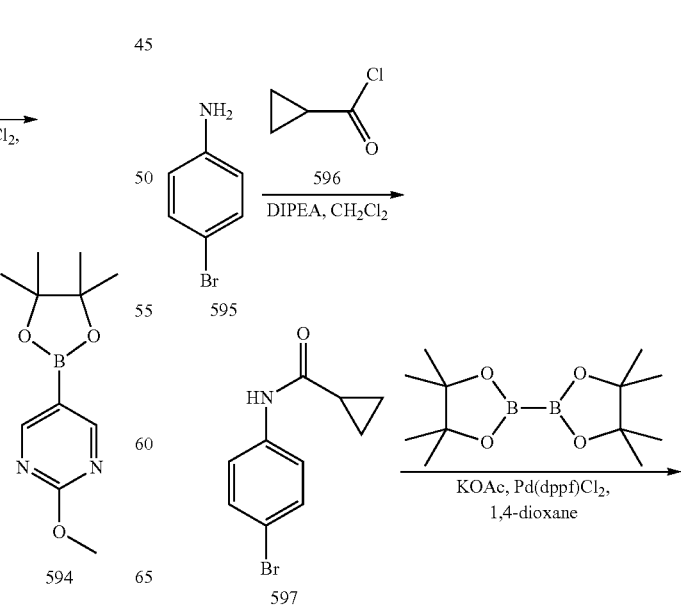

Synthesis of N-(4-bromophenyl) cyclopropanecarboxamide (597)

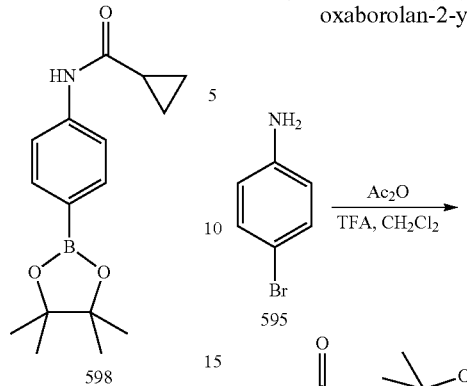

To a stirring solution of 4-bromoaniline 595 (1 g, 5.81 mmol) in CH$_2$Cl$_2$ (50 mL) under argon atmosphere were added diisopropylamine (2.1 mL, 11.62 mmol), cyclopropanecarbonyl chloride 596 (604 mg, 5.81 mmol) at 0° C., warmed to RT and stirred for 2.5 h. The reaction was monitored by TLC; after completion of the reaction, the reaction mixture was diluted with saturated sodium bicarbonate solution (30 mL) and extracted with CH$_2$Cl$_2$ (25 mL). The organic layer was washed with water (30 mL) and dried over sodium sulfate, filtered and concentrated in vacuo to obtain the crude. The crude was purified through silica gel column chromatography using 40% EtOAc/hexanes to afford compound 597 (1.15 g, 83%) as an off-white solid. TLC: 40% EtOAc/hexanes (R$_f$: 0.3); $^1$H NMR (DMSO-d$_6$, 400 MHz): δ 10.29 (s, 1H), 7.58-7.54 (m, 2H), 7.48-7.44 (m, 2H), 1.79-1.72 (m, 1H), 0.82-0.78 (m, 4H); LC-MS: 99.73%; 239.7 (M$^+$+1); (column; Kinetex EVO C-18, (50× 3.0 mm, 2.6 μm); RT 2.71 min. 2.5 mM Aq. NH$_4$OOCH+5% ACN: ACN+5% 2.5 mM Aq.NH$_4$OOCH, 0.8 mL/min).

Synthesis of N-(4-(4, 4, 5, 5-tetramethyl-1, 3, 2-dioxaborolan-2-yl) phenyl) cyclopropanecarboxamide (598)

To a stirring solution of N-(4-bromophenyl) cyclopropanecarboxamide 597 (500 mg, 2.08 mmol) in 1, 4-dioxane (15 mL) under argon atmosphere were added bis pinacolato diboron (632 mg, 2.50 mmol), potassium acetate (510 mg, 5.20 mmol) at RT in a sealed tube and purged under argon atmosphere for 15 min. To this was added Pd(dppf)Cl$_2$ (15 mg, 0.02 mmol) and purged under argon atmosphere for 10 min and heated to 110° C. and stirred for 16 h. The reaction was monitored by TLC; after completion of the reaction, the reaction mixture diluted with water (20 mL) and extracted with EtOAc (2×25 mL). The combined organic extracts were dried over sodium sulfate, filtered and concentrated in vacuo to obtain the crude. The crude was purified through silica gel column chromatography using 40% EtOAc/hexanes to afford compound 598 (520 mg, 87%) as an off-white solid. TLC: 40% EtOAc/hexanes (R$_f$: 0.3); $^1$H NMR (DMSO-d$_6$, 400 MHz): δ 10.28 (s, 1H), 7.61-7.58 (m, 4H), 1.83-1.74 (m, 1H), 1.28 (s, 12H), 0.84-0.77 (m, 4H);

Synthesis of N-(4-(4, 4, 5, 5-tetramethyl-1, 3, 2-dioxaborolan-2-yl) phenyl) acetamide (600)

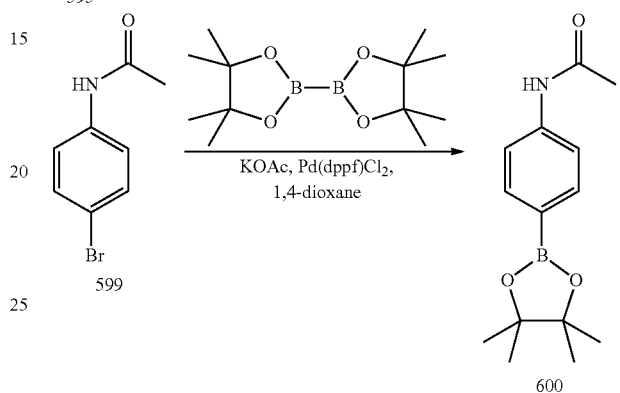

Synthesis of N-(4-bromophenyl) acetamide (599)

To a stirring solution of 4-bromoaniline 595 (1 g, 5.81 mmol) in CH$_2$Cl$_2$ (50 mL) under argon atmosphere were added trifluoroacetic acid (1.6 mL, 11.62 mmol), acetic anhydride (0.6 mL, 5.81 mmol) at 0° C., warmed to RT and stirred for 2 h. The reaction was monitored by TLC; after completion of the reaction, the reaction mixture was diluted with water (50 mL) and extracted with CH$_2$Cl$_2$ (2×60 mL). The combined organic extracts were washed with saturated sodium bicarbonate (50 mL), brine (50 mL). The organic layer was dried over sodium sulfate, filtered and concentrated in vacuo to obtain the crude. The crude was purified through silica gel column chromatography using 40% EtOAc/hexanes to afford compound 599 (1.1 g, 92%) as an off white solid. TLC: 40% EtOAc/hexanes (R$_f$: 0.3); $^1$H NMR (DMSO-d$_6$, 400 MHz): δ 10.04 (br s, 1H), 7.57-7.53 (m, 2H), 7.48-7.44 (m, 2H), 2.04 (s, 3H); LC-MS: 99.65%; 211.9 (M−1)$^+$; (column; Kinetex EVO C-18, (50×3.0 mm, 2.6 μm); RT 2.21 min. 2.5 mM Aq. NH$_4$OOCH+5% ACN: ACN+5% 2.5 mM Aq.NH$_4$OOCH, 0.8 mL/min).

Synthesis of N-(4-(4, 4, 5, 5-tetramethyl-1, 3, 2-dioxaborolan-2-yl) phenyl) acetamide (600)

To a stirring solution of N-(4-bromophenyl) acetamide 599 (500 mg, 2.33 mmol) in 1, 4-dioxane (15 mL) under argon atmosphere were added bis pinacolato diboron (709 mg, 2.80 mmol), potassium acetate (572 mg, 5.84 mmol) at RT and purged under argon atmosphere for 15 min. To this was added Pd(dppf)Cl$_2$ (17 mg, 0.02 mmol) and purged under argon atmosphere for 20 min and heated to 100° C. and stirred for 16 h. The reaction was monitored by TLC; after completion of the reaction, the volatiles were removed in vacuo to obtain the crude. The crude was purified through silica gel column chromatography using 40% EtOAc/ hexanes to afford compound 600 (510 mg, 84%) as an off-white solid. TLC: 40% EtOAc/hexanes (R$_f$: 0.3); $^1$H NMR (DMSO-d$_6$, 500 MHz): δ 10.02 (s, 1H), 7.60-7.58 (m, 4H), 2.05 (s, 3H), 1.28 (s, 12H); LC-MS: 96.10%; 262 (M$^+$+1); (column; Kinetex EVO C-18, (50×3.0 mm, 2.6 µm); RT 2.63 min. 2.5 mM Aq. NH$_4$OOCH+5% ACN: ACN+5% 2.5 mM Aq.NH$_4$OOCH, 0.8 mL/min).

Synthesis of 1-(4-(4, 4, 5, 5-tetramethyl-1, 3, 2-dioxaborolan-2-yl) phenyl) pyrrolidin-2-one (602)

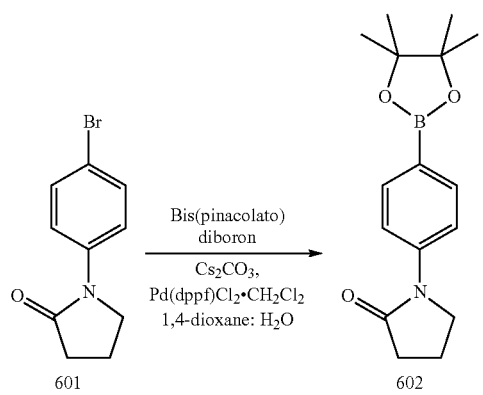 [SMILES: O=C1CCCN1c1ccc(Br)cc1 ; CC1(C)OB(c2ccc(N3CCCC3=O)cc2)OC1(C)C]

Synthesis of 1-(4-(4, 4, 5, 5-tetramethyl-1, 3, 2-dioxaborolan-2-yl) phenyl) pyrrolidin-2-one (602)

To a stirring solution of 1-(4-bromophenyl) pyrrolidin-2-one 601 (1 g, 4.16 mmol) in 1, 4-dioxane:H$_2$O (10:1, 22 mL) in a sealed tube under inert atmosphere were added bis pinacolato diboron (1.27 g, 4.99 mmol), cesium carbonate (1.62 g, 4.99 mmol) at RT and purged under argon atmosphere for 15 min. To this was added Pd(dppf)Cl$_2$.CH$_2$Cl$_2$ (304 mg, 0.41 mmol) and purged under argon atmosphere for 30 min, heated to 100° C. and stirred for 24 h. The reaction was monitored by TLC; after completion of the reaction, the volatiles were removed in vacuo to obtain the crude. The crude was purified through silica gel column chromatography using 20% EtOAc/hexanes to afford compound 602 (800 mg, 66%). TLC: 30% EtOAc/hexanes (R$_f$: 0.3); LC-MS: 54.37%; 287.9 (M$^+$+1); (column; Ascentis Express C18, (50×3.0 mm, 2.7 µm); RT 2.50 min. 0.025% Aq. TFA+5% ACN: ACN+5% 0.025% Aq. TFA, 1.2 mL/min);

Synthesis of 6-(4, 4, 5, 5-tetramethyl-1, 3, 2-dioxaborolan-2-yl)-3, 4-dihydroquinolin-2(1H)-one (604)

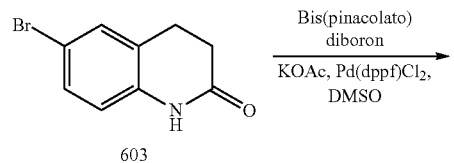

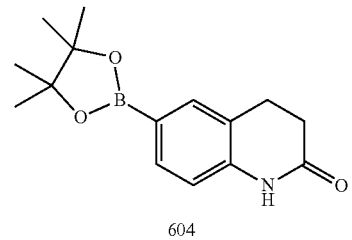

Synthesis of 6-(4, 4, 5, 5-tetramethyl-1, 3, 2-dioxaborolan-2-yl)-3, 4-dihydroquinolin-2(1H)-one (604)

To a stirring solution of 6-bromo-3, 4-dihydroquinolin-2 (1H)-one 603 (500 mg, 2.21 mmol) in DMSO (25 mL) under inert atmosphere were added bis pinacolato diboron (671 mg, 2.65 mmol), potassium acetate (650 mg, 6.63 mmol) at RT and purged under argon atmosphere for 10 min. To this was added Pd(dppf)$_2$Cl$_2$ (161 mg, 0.22 mmol) and purged under argon atmosphere for 5 min; heated to 90° C. and stirred for 16 h. The reaction was monitored by TLC; after completion of the reaction, the reaction mixture was diluted with EtOAc (100 mL), washed ice-cold water (2×30 mL), brine (30 mL). The organic extract was dried over sodium sulphate, filtered and concentrated in vacuo to obtain the crude. The crude was purified through silica gel flash column chromatography using 20-30% EtOAc/hexanes to afford compound 604 (300 mg, crude) as semi-solid. TLC: 30% EtOAc/hexanes (R$_f$: 0.3); $^1$H NMR (DMSO-d$_6$, 400 MHz): δ 10.21 (s, 1H), 7.50-7.39 (m, 2H), 6.83 (d, J=7.8 Hz, 1H), 2.92-2.84 (m, 2H), 2.46-2.42 (m, 2H), 1.27 (s, 12H).

Synthesis of 5-fluoro-2-lithium tri isopropyl borate salt (606)

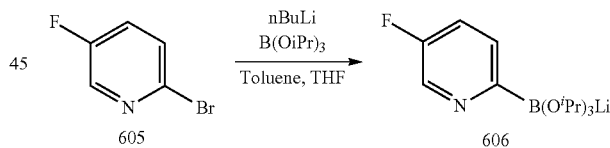

Synthesis of 5-fluoro-2-lithium tri isopropyl borate salt (606)

To a stirring solution of 2-bromo-5-fluoropyridine 605 (500 mg, 2.84 mmol) and triisopropyl borate (0.8 mL, 3.4 mmol) in dry toluene (10 mL), dry THF (2 mL) under inert atmosphere was added n-butyl lithium (2.5 M solution in hexane, 2.3 mL, 5.68 mmol) drop wise for 1.5 h at −78° C. and stirred for 30 min and warmed to RT and stirred for 16 h. The reaction was monitored by TLC; after completion of the reaction, the volatiles were removed in vacuo to obtain the crude, which washed with hexane (2×10 mL) to afford compound 606 (800 mg salt, crude) as brown solid. This crude salt was taken up for the next reaction without purification. TLC: 10% EtOAc/to hexanes (R$_f$: 0.1);

Synthesis of 5-fluoro-2-lithium tri isopropyl borate salt (608)

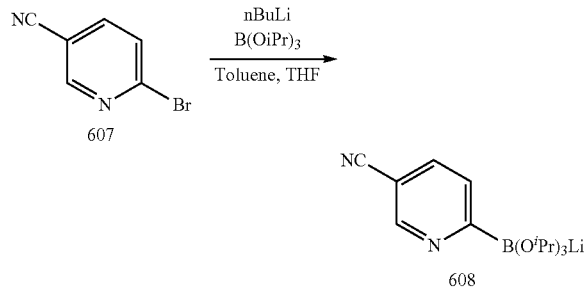

Synthesis of 5-cyano-2-lithium triisopropyl borate salt (608)

To a stirring solution of 2-bromo-5-cyanopyridine 607 (1 g, 5.46 mmol) and triisopropyl borate (1.52 mL, 6.55 mmol) in dry toluene:dry THF (1:4; 25 mL) under inert atmosphere was added n-butyl lithium (2.5 M solution in hexane, 3.4 mL, 5.46 mmol) drop wise for 1.5 h at −78° C. and stirred for 30 min and warmed to RT and stirred for 16 h. The reaction was monitored by TLC; after completion of the reaction, the volatiles were removed in vacuo to obtain the crude, which washed with hexane (2×10 mL) to afford compound 608 (1.6 g salt, crude) as yellow solid. The crude was taken forward next reaction without further purification. TLC: 10% MeOH/CH$_2$Cl$_2$ (R$_f$: 0.2).

Synthesis of 2-(tributylstannyl) thiazole (610)

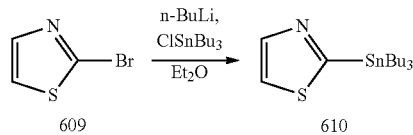

Synthesis of 2-(tributylstannyl) thiazole (610)

To a stirring solution of 2-bromothiazole 609 (5 g, 30.48 mmol) in diethyl ether (50 mL) under inert atmosphere was added n-butyl lithium (12.2 mL, 33.53 mmol, 2.5 M solution in hexane) dropwise for 15 min at −70° C. and stirred for 30 min. To this a solution of tributyltin chloride (10 mL, 30.48 mmol) in diethyl ether (15 mL) was added dropwise for 10 min at −70° C. and stirred at the same temperature for 4 h. The reaction was monitored by TLC; after completion of the reaction, the reaction mixture was diluted with water (50 mL) and extracted with diethylether (3×50 mL), washed with saturated potassium fluoride solution (50 mL). The combined organic extracts were dried over sodium sulfate, filtered and concentrated in vacuo to afford crude compound 610 (11 g) as brown color syrup. The crude was carried forward for next step without further purification. TLC: 30% EtOAc/hexanes (R$_f$: 0.2); $^1$H NMR (CDCl$_3$, 400 MHz): δ 8.17 (d, J=3.0 Hz, 1H), 7.54 (d, J=3.0 Hz, 1H), 1.58-1.50 (m, 6H), 1.34-1.27 (m, 6H), 1.16-1.10 (m, 6H), 0.89-0.83 (m, 9H) (NMR shows excess of tin reagent as impurity in the aliphatic region).

Synthesis of 5-(tributylstannyl) thiazole (611)

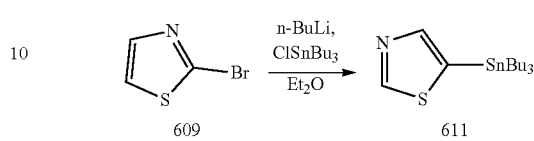

To a stirring solution of 2-bromothiazole 609 (5 g, 30.48 mmol) in diethyl ether (35 mL) under inert atmosphere was added n-butyl lithium (12.2 mL, 33.53 mmol, 2.5 M solution in hexane) at −70° C. and stirred for 30 min. To this was added a solution of tributyltin chloride (10 mL, 30.48 mmol) in diethyl ether (15 mL) dropwise for 10 min at −70° C. and stirred at the same temperature for 4 h; warmed to RT and stirred for 2 h. The reaction was monitored by TLC; after completion of the reaction, the reaction mixture was diluted with water (100 mL) and extracted with diethylether (3×50 mL) and washed with saturated potassium fluoride solution (50 mL). The combined organic extracts were dried over sodium sulfate, filtered and concentrated in vacuo to obtain the crude. The crude was purified through column chromatography using 25-30% EtOAc/hexanes to afford compound 611 (3.5 g, 31%) as white solid. TLC: 30% EtOAc/hexanes (R$_f$: 0.4); $^1$H NMR (DMSO-d$_6$, 400 MHz): δ 9.35 (s, 1H), 7.89 (s, 1H), 1.58-1.47 (m, 6H), 1.34-1.24 (m, 6H), 1.13 (t, J=8.0 Hz, 6H), 0.85 (t, J=7.3 Hz, 9H).

Synthesis of 5-methoxy-2-(tributylstannyl) pyridine (613)

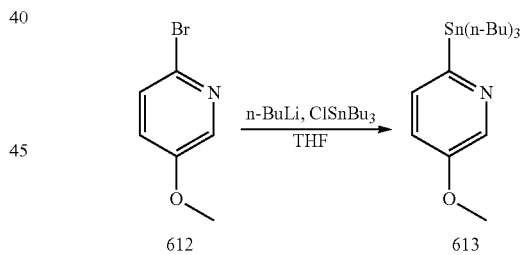

Synthesis of 5-methoxy-2-(tributylstannyl) pyridine (613)

To a stirring solution of 2-bromo-5-methoxypyridine 612 (2 g, 10.64 mmol) in THF (25 mL) under inert atmosphere was added n-butyl lithium (8.9 mL, 10.64 mmol, 1.6 M solution in hexane) at −78° C. and stirred for 30 min. To this was added tributyltin chloride (3.5 g, 10.64 mmol) drop wise for 10 min at −78° C.; warmed to RT and stirred for 2 h; warmed to RT and stirred for 2 h. The reaction was monitored by TLC; after completion of the reaction, the reaction mixture was quenched with saturated ammonium chloride (100 mL) and extracted with EtOAc (3×75 mL). The combined organic extracts were dried over sodium sulfate, filtered and concentrated in vacuo to obtain the crude. The crude was purified through neutral alumina column chromatography using 10% EtOAc/hexanes to afford compound 613 (3 g) as pale yellow liquid. TLC: 10% EtOAc/hexanes (R$_f$: 0.5); LC-MS: 75.23%; 400.1 (M$^+$+1); (column; Ascentis Express C18, (50×3.0 mm, 2.7 µm); RT 2.56 min. 0.025% Aq. TFA+5% ACN: ACN+5% 0.025% Aq. TFA, 1.2 mL/min).

Synthesis of 4-fluoro-2-(tributylstannyl) pyridine (615)

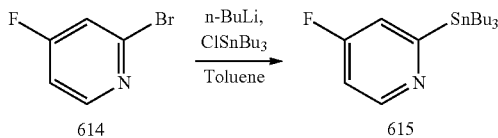

Synthesis of 4-fluoro-2-(tributylstannyl) pyridine (615)

To a stirring solution of 2-bromo-4-fluoropyridine 614 (300 mg, 1.70 mmol) in toluene (10 mL) under inert atmosphere was added n-butyl lithium (1.2 mL, 2.04 mmol, 1.6 M solution in hexane) at −78° C. and stirred for 75 min. To this was added tributyltin chloride (0.55 mL, 2.04 mmol) drop wise for 10 min at −78° C. and stirred at the same temperature for 30 min; warmed to RT and stirred for 30 min. The reaction was monitored by TLC; after completion of the reaction, the reaction mixture was quenched with saturated ammonium chloride solution (100 mL) and extracted with EtOAc (2×15 mL). The combined organic extracts were dried over sodium sulfate, filtered and concentrated in vacuo to afford compound 615 (700 mg, crude) as colorless syrup. TLC: 10% EtOAc/hexanes (R$_f$: 0.8); $^1$H NMR (DMSO-d$_6$, 400 MHz): δ 9.35 (s, 1H), 7.89 (s, 1H), 1.58-1.47 (m, 6H), 1.34-1.24 (m, 6H), 1.13 (t, J=8.0 Hz, 6H), 0.85 (t, J=7.3 Hz, 9H).

Synthesis of 2-(trimethylstannyl) isonicotinonitrile (617)

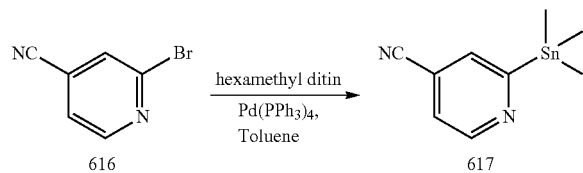

Synthesis of 2-(trimethylstannyl) isonicotinonitrile (617)

To a stirring solution of 2-bromoisonicotinonitrile 616 (1.3 g, 7.10 mmol) in toluene (20 mL) under argon atmosphere was added hexamethyl ditin (1.7 mL, 8.52 mmol) at RT and purged under argon atmosphere for 20 min, added Pd(PPh$_3$)$_4$ (410 mg, 0.35 mmol) purged under argon atmosphere for 15 min; heated to 100° C. and stirred for 16 h. The reaction was monitored by TLC; after completion of the reaction, the reaction mixture was filtered through celite, eluted with EtOAc (50 mL). The filtrate was concentrated in vacuo to afford crude compound 617 (2 g) as brown syrup which was carried forward for next step without further purification. TLC: 5% MeOH/CH$_2$Cl$_2$ (R$_f$: 0.3).

Preparation

Compound 535, 536, 538 & 539 was synthesized as mentioned above and converted to final products through displacement reaction or cross coupling reaction employing typical procedures D, E, F, G, H, I, J and K and the results are captured in the Table 2:

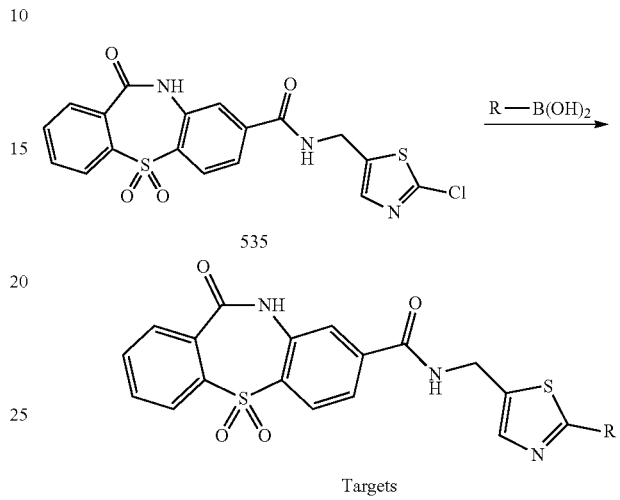

Targets

Typical Procedure D:

To a stirring solution of N-((2-chlorothiazol-5-yl) methyl)-11-oxo-10, 11-dihydrodibenzo [b, f] [1, 4] thiazepine-8-carboxamide 5, 5-dioxide 536 (150 mg, 0.34 mmol) in 1, 2 dimethoxy ethane:H$_2$O (4:1, 8 mL) were added sodium carbonate (124 mg, 1.17 mmol), (3-chloro-4-hydroxyphenyl) boronic acid 556 (80.4 mg, 0.46 mmol) and purged under argon atmosphere for 20 min. To this was added Pd(dppf)Cl$_2$ (45 mg, 0.039 mmol) at RT; heated to 100-110° C. and stirred for 16 h. The reaction was monitored by TLC; after completion the volatiles were removed in vacuo to obtain the crude. The crude was either directly dried in vacuo or triturated or purified through silica gel column chromatography to afford the desired compound.

Typical Procedure E:

To a stirring solution of N-((2-chlorothiazol-5-yl) methyl)-11-oxo-10, 11-dihydrodibenzo [b, f] [1, 4] thiazepine-8-carboxamide 5, 5-dioxide 536 (150 mg, 0.34 mmol) in 1, 4 dioxane:H$_2$O (3:1, 10 mL) were added cesium carbonate (341 mg, 1.04 mmol), (3-fluoro-4-hydroxyphenyl) boronic acid 555 (54 mg, 0.34 mmol) and purged under argon atmosphere for 15 min. To this was added Pd(dppf)Cl$_2$ (27 mg, 0.034 mmol) at RT; heated to 100° C. and stirred for 16 h. The reaction was monitored by TLC; after completion the volatiles were removed in vacuo to obtain the crude. The crude was either directly dried in vacuo or triturated or purified through silica gel column chromatography to afford the desired compound.

Typical Procedure F:

A mixture of N-((2-chlorothiazol-5-yl) methyl)-11-oxo-10, 11-dihydrodibenzo [b, 1] [1, 4] thiazepine-8-carboxamide 5, 5-dioxide 536 (100 mg, 0.23 mmol) and piperidine 472 (2 mL) in a sealed tube was heated to 120° C. and stirred for 4 h. The reaction was monitored by TLC; after completion the volatiles were removed in vacuo to obtain the crude. The crude was either directly dried in vacuo or triturated or purified through silica gel column chromatography to afford the desired compound.

Typical Procedure G:

To a solution of mixture N-((2-chlorothiazol-5-yl) methyl)-11-oxo-10, 11-dihydrodibenzo [b, f] [1, 4] thiazepine-8-carboxamide 5, 5-dioxide 536 (150 mg, 0.34 mmol) in N-methyl pyrrolidinone (5 mL) were added azepan-3-ol hydrochloride 503 (57.7 mg, 0.39 mmol) and diisopropylethylamine (0.23 mL, 1.73 mmol) in a sealed tube and heated to 160° C. and stirred for 24 h. The reaction was monitored by TLC and LC-MS; after completion the reaction mixture was diluted with water (50 mL) and extracted with 10% MeOH/$CH_2Cl_2$ (2×50 mL). The combined organic extracts were dried over sodium sulphate, filtered and concentrated in vacuo to obtain the crude. The crude was either directly dried in vacuo or triturated or purified through silica gel column chromatography to afford the desired compound.

Typical Procedure H:

To a stirring solution of N-((2-chlorothiazol-5-yl) methyl)-11-oxo-10, 11-dihydrodibenzo [b, f] [1, 4] thiazepine-8-carboxamide 5, 5-dioxide 536 (250 mg, 0.57 mmol) in 1,4-dioxane (20 mL) under argon atmosphere in a sealed tube were added 5-(tributylstannyl) thiazole 611 (324 mg, 0.86 mmol) at RT and purged under argon atmosphere for 15 min; to this was added Pd(dppf)$Cl_2$ (42.2 mg, 0.057 mmol) at RT; heated to 110° C. and stirred for 16 h. The reaction was monitored by TLC; after completion of the reaction, the reaction mixture was filtered through celite, washed with 20% MeOH/$CH_2Cl_2$ (2×80 mL). The filtrate was concentrated in vacuo to obtain the crude. The crude was purified through silica gel flash column chromatography using 10-12% EtOAc/hexanes and further purified by preparative HPLC purification to afford the desired compound.

Typical Procedure I:

To a stirring solution of N-((2-chlorothiazol-5-yl) methyl)-11-oxo-10, 11-dihydrodibenzo [b, f] [1, 4] thiazepine-8-carboxamide 5, 5-dioxide 536 (100 mg, 0.23 mmol) in DMF (10 mL) under argon atmosphere in a sealed tube were added 4-fluoro-1H-pyrazole 541 (40 mg, 0.46 mmol), cesium carbonate (150 mg, 0.46 mmol) at RT in a sealed tube and heated to 110° C. and stirred for 16 h. The reaction was monitored by TLC; after completion of the reaction, after completion the reaction mixture was diluted with water (50 mL) and extracted with EtOAc (2×40 mL). The combined organic extracts were dried over sodium sulphate, filtered and concentrated in vacuo to obtain the crude. The crude was either directly dried in vacuo or triturated or purified through silica gel column chromatography/flash column chromatography to afford the desired compound.

Typical Procedure J:

To a stirring solution of N-((2-chlorothiazol-5-yl) methyl)-11-oxo-10, 11-dihydrodibenzo [b, f] [1, 4] thiazepine-8-carboxamide 5, 5-dioxide 536 (200 mg, 0.36 mmol) in 1, 4-dioxane (20 mL) under argon atmosphere was added cesium carbonate (450 mg, 1.38 mmol) in sealed tube at RT and purged under argon for 20 min. To this were added $Pd_2(dba)_3$ (23 mg, 0.023 mmol), t-BuXphos (14 mg, 0.032 mmol), 3,3-dimethylpyrrolidine 554 (137 mg, 1.38 mmol), at RT and purged under argon for 5 min; heated to 100° C. and stirred for 16 h. The reaction was monitored by TLC; after completion of the reaction, the reaction mixture was filtered through celite and eluted with EtOAc (2×30 mL). The filtrate was concentrated in vacuo to obtain the crude. The crude was either directly dried in vacuo or triturated or purified through silica gel column chromatography to afford the desired compound.

Typical Procedure K:

To a stirring solution N-((2-chlorothiazol-5-yl) methyl)-11-oxo-10, 11-dihydrodibenzo [b, f] [1, 4] oxazepine-8-carboxamide 536 (150 mg, 0.38 mmol) in N-methyl-2-pyrrolidone (1 mL) under argon atmosphere was added N, N-dimethylpiperidin-4-amine 544 (46 mg, 0.46 mmol) in sealed tube at RT; heated to 100° C. and stirred for 16 h. The reaction was monitored by TLC; after completion of the reaction, the reaction mixture was diluted with water (25 mL), the precipitated solid was filtered, washed with $CH_3CN$ (5 mL), diethyl ether (10 mL) and dried in vacuo to afford to afford the desired compound.

TABLE 2

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 1624 | (3-pyridyl thiazole structure) | D$^f$, 535, 579 | 23 | 476.9 (M$^+$ + 1); | 476.06 for C$_{23}$H$_{16}$N$_4$O$_4$S$_2$ | ¹H-NMR (DMSO-d$_6$, 400 MHz): δ 11.52 (s, 1H), 9.51 (t, J = 5.6 Hz, 1H), 9.08 (br s, 1H), 8.65 (d, J = 4.1 Hz, 1H), 8.24 (d, J = 7.9 Hz, 1H), 8.06 (d, J = 8.3 Hz, 1H), 7.98 (td, J = 7.5, 1.0 Hz, 2H), 7.93-7.79 (m, 5H), 7.51 (dd, J = 7.9, 4.8 Hz, 1H), 4.72 (d, J = 5.5 Hz, 2H); |
| 1625 | (4-pyridyl thiazole structure) | D$^f$, 535, 580 | 10 | 476.9 (M$^+$ + 1); | 476.06 for C$_{23}$H$_{16}$N$_4$O$_4$S$_2$ | ¹H-NMR (DMSO-d$_6$, 400 MHz): δ 11.52 (s, 1H), 9.52 (t, J = 5.5 Hz, 1H), 8.68 (d, J = 5.3 Hz, 2H), 8.06 (d, J = 8.2 Hz, 1H), 8.01-7.94 (m, 3H), 7.93-7.88 (m, 1H), 7.88-7.80 (m, 5H), 4.73 (d, J = 5.7 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | 1H-NMR |
|---|---|---|---|---|---|---|
| 1626 | 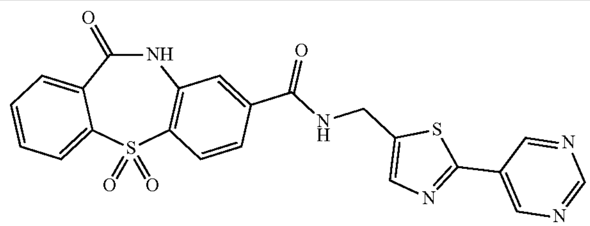 [SMILES: O=C(NCc1cnc(-c2cncnc2)s1)c1ccc2c(c1)NC(=O)c1ccccc1S2(=O)=O] | D*f*, 535, 581 | 27 | 477.9 (M+ +1); | 476.06 for $C_{22}H_{15}N_5O_4S_2$ | 1H-NMR (DMSO-d6, 400 MHz): δ 11.53 (s, 1H), 9.54 (t, J = 5.6 Hz, 1H), 9.26 (s, 2H), 9.25 (s, 1H), 8.07 (d, J = 8.3 Hz, 1H), 8.01-7.95 (m, 3H), 7.90 (td, J = 7.5, 1.6 Hz, 1H), 7.87-7.80 (m, 3H), 4.74 (d, J = 5.6 Hz, 2H); |
| 1636 | 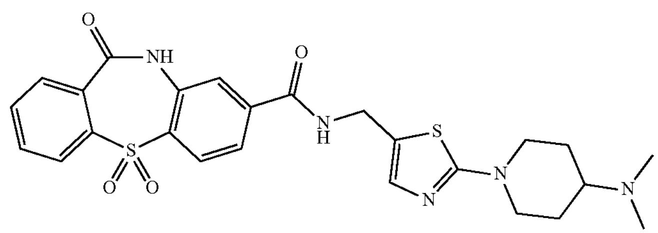 [SMILES: CN(C)C1CCN(c2ncc(CNC(=O)c3ccc4c(c3)NC(=O)c3ccccc3S4(=O)=O)s2)CC1] | G*d*, 535, 544 | 63 | 526.0 (M+ +1); | 525.15 for $C_{25}H_{27}N_5O_4S_2$ | 1H-NMR (500 MHZ, DMSO-d6): δ 11.49 (br s, 1H), 9.26 (t, J = 5.6 Hz, 1H), 8.04 (d, J = 8.4 Hz, 1H), 8.00-7.95 (m, 2H), 7.93-7.82 (m, 3H), 7.78 (dd, J = 8.4, 1.4 Hz, 1H), 7.02 (s, 1H), 4.44 (d, J = 5.5 Hz, 2H), 3.83-3.79 (m, 2H), 2.97-2.90 (m, 2H), 2.34-2.28 (m, 1H), 2.18 (br s, 6H), 1.81-1.77 (m, 2H), 1.45-1.32 (m, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | 1H-NMR |
|---|---|---|---|---|---|---|
| 1637 | 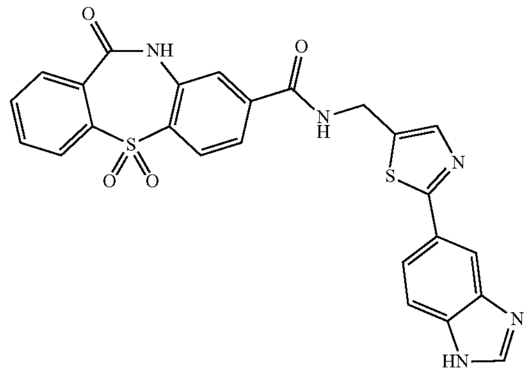 [SMILES: O=C(NCc1cnc(-c2ccc3[nH]cnc3c2)s1)c1ccc2c(c1)NC(=O)c1ccccc1S2(=O)=O] | D$^f$, 535, 573 | 15 | 516.0 (M$^+$ + 1) | 515.07 for C$_{25}$H$_{17}$N$_5$O$_4$S$_2$ | 1H-NMR (DMSO-d$_6$, 400 MHz): δ 12.62 (d, J = 11.5 Hz, 1H), 11.48 (br s, 1H), 9.46 (t, J = 5.1 Hz, 1H), 8.31 (br s, 1H), 8.12 (br s, 1H), 8.06 (d, J = 8.3 Hz, 1H), 8.01-7.95 (m, 2H), 7.93-7.80 (m, 4H), 7.80-7.54 (m, 3H), 4.69 (d, J = 5.3 Hz, 2H); |
| 1645-A | 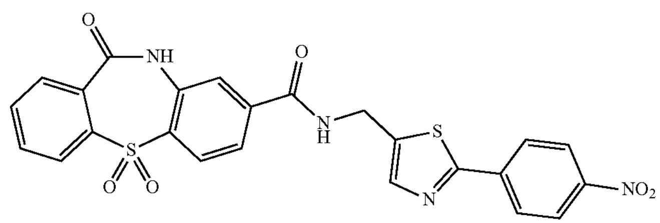 [SMILES: O=C(NCc1cnc(-c2ccc([N+](=O)[O-])cc2)s1)c1ccc2c(c1)NC(=O)c1ccccc1S2(=O)=O] | D$^a$, 535, 308 | 19 | 521.0 (M$^+$ + 1) | 520.05 for C$_{24}$H$_{16}$N$_4$O$_6$S$_2$ | 1H-NMR (DMSO-d$_6$, 400 MHz): δ 11.51 (br s, 1H), 9.52 (t, J = 4.8 Hz, 1H), 8.31 (d, J = 8.8 Hz, 2H), 8.15 (d, J = 8.9 Hz, 2H), 8.06 (d, J = 8.3 Hz, 1H), 8.01-7.95 (m, 3H), 7.93-7.80 (m, 4H), 4.73 (d, J = 5.5 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1654-A | (structure with 4-cyanophenyl thiazole) | D$^a$, 535, 225 | 40 | 501.0 (M$^+$ + 1) | 500.06 for C$_{25}$H$_{16}$N$_4$O$_4$S$_2$ | $^1$H-NMR (DMSO-d$_6$, 400 MHz): δ 11.52 (s, 1H), 9.51 (t, J = 5.8 Hz, 1H), 8.09-8.04 (m, 3H), 8.01-7.79 (m, 9H), 4.72 (d, J = 5.6 Hz, 2H); |
| 1664 | (structure with 3-fluoro-4-hydroxyphenyl thiazole) | E, 535, 555 | 14 | 509.9 (M$^+$ + 1) | 509.05 for C$_{24}$H$_{16}$FN$_3$O$_5$S$_2$ | $^1$H-NMR (DMSO-d$_6$, 400 MHz): δ 11.52 (br s, 1H), 10.43 (br s, 1H), 9.45 (t, J = 5.8 Hz, 1H), 8.05 (d, J = 8.3 Hz, 1H), 7.98 (td, J = 7.6, 0.8 Hz, 2H), 7.90 (td, J = 7.4, 1.2 Hz, 1H), 7.87-7.78 (m, 3H), 7.72 (s, 1H), 7.62 (dd, J = 12.1, 1.9 Hz, 1H), 7.51 (dd, J = 8.7, 1.4 Hz, 1H), 7.02 (t, J = 8.7 Hz, 1H), 4.66 (d, J = 5.5 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---------|-----------|------------------------------------------------------------|-----------|------------------|------------------------|-----------|
| 1665 | (structure with 3,5-difluoro-4-hydroxyphenyl thiazole) | E$^b$, 535, 586 | 25 | 527.9 (M$^+$ + 1) | 527.04 for C$_{24}$H$_{15}$F$_2$N$_3$O$_5$S$_2$ | $^1$H-NMR (DMSO-d$_6$, 500 MHz): δ 11.52 (s, 1H), 10.79 (br s, 1H), 9.47 (t, J = 5.6 Hz, 1H), 8.06 (d, J = 8.1 Hz, 1H), 7.98 (t, J = 8.4 Hz, 2H), 7.93-7.79 (m, 4H), 7.76 (s, 1H), 7.53 (d, J = 7.5 Hz, 2H), 4.67 (d, J = 5.2 Hz, 2H); |
| 1667 | (structure with 3-chloro-4-hydroxyphenyl thiazole) | D$^b$, 535, 556 | 10 | 525.9 (M$^+$ + 1) | 525.02 for C$_{24}$H$_{16}$ClN$_3$O$_5$S$_2$ | $^1$H-NMR (DMSO-d$_6$, 400 MHz): δ 11.52 (br s, 1H), 10.79 (br s, 1H), 9.46 (t, J = 5.5 Hz, 1H), 8.05 (d, J = 8.3 Hz, 1H), 8.01-7.95 (m, 2H), 7.93-7.78 (m, 5H), 7.72 (s, 1H), 7.65 (dd, J = 8.5, 2.1 Hz, 1H), 7.03 (d, J = 8.5 Hz, 1H), 4.66 (d, J = 5.4 Hz, 2H); |
| 1668 | (structure with 2-chloro-4-hydroxyphenyl thiazole) | D$^d$, 535, 574 | 44 | 525.9 (M$^+$ + 1) | 525.02 for C$_{24}$H$_{16}$ClN$_3$O$_5$S$_2$ | $^1$H-NMR (DMSO-d$_6$, 400 MHz): δ 11.49 (s, 1H), 10.39 (s, 1H), 9.44 (t, J = 5.6 Hz, 1H), 8.04 (d, J = 8.4 Hz, 1H), 7.99-7.93 (m, 3H), 7.88 (t, J = 7.4 Hz, 1H), 7.85-7.78 (m, 4H), 6.93 (d, J = 2.3 Hz, 1H), 6.85 (dd, J = 8.8, 2.2 |

TABLE 2-continued

Synthesis from compound 535, 536, 538, 539 common intermediates

| Example | Structure | Procedure, Intermediate, or boronic acid or boronate esters | Rx. Yield | Mass Spec. Found | Mass Spec. Calculated | 1H-NMR |
|---|---|---|---|---|---|---|
| 1670 | (structure with 2-fluoro-4-hydroxyphenyl) | D[b], 535, 557 | 19 | 510.0 (M[+] + 1) | 509.05 for $C_{24}H_{16}FN_3O_5S_2$ | 1H-NMR (DMSO-d$_6$, 400 MHz): δ 11.51 (s, 1H), 10.46 (s, 1H), 9.44 (t, J = 5.8 Hz, 1H), 8.05 (d, J = 8.3 Hz, 1H), 8.01-7.95 (m, 3H), 7.93-7.77 (m, 5H), 6.77-6.67 (m, 2H), 4.68 (d, J = 5.6 Hz, 2H); |
| 1671-A | (structure with 2-methoxypyrimidine) | E[b], 535, 594 | 51 | 507.9 (M[+] + 1) | 507.07 for $C_{23}H_{17}N_5O_5S_2$ | 1H-NMR (DMSO-d$_6$, 400 MHz): δ 11.52 (s, 1H), 9.51 (t, J = 5.5 Hz, 1H), 9.06 (s, 2H), 8.06 (d, J = 8.3 Hz, 1H), 8.01-7.95 (m, 2H), 7.93-7.80 (m, 5H), 4.70 (d, J = 5.6 Hz, 2H), 3.98 (s, 3H); |
| 1672 | (structure with 6-aminopyridine) | D[c], 535, 591 | 53 | 491.9 (M[+] + 1) | 491.07 for $C_{23}H_{17}N_5O_4S_2$ | 1H-NMR (DMSO-d$_6$, 400 MHz): δ 11.52 (s, 1H), 9.43 (t, J = 5.8 Hz, 1H), 8.41 (d, J = 2.4 Hz, 1H), 8.05 (d, J = 8.3 Hz, 1H), 8.00-7.95 (m, 2H), 7.93-7.78 (m, 5H), 7.66 (s, 1H), 6.51-6.44 (m, 3H), 4.64 (d, J = 5.6 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | 1H-NMR |
|---|---|---|---|---|---|---|
| 1673 | 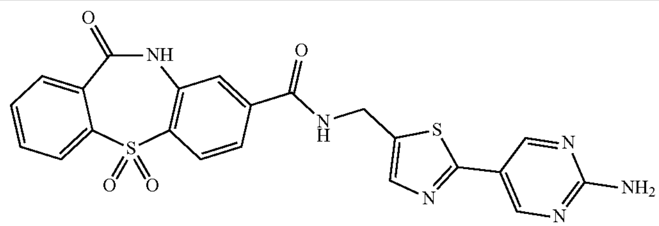 [SMILES: Nc1ncc(-c2ncc(CNC(=O)c3ccc4c(c3)NC(=O)c3ccccc3S4(=O)=O)s2)cn1] | D$^e$, 535, 558 | 47 | 493.0 (M$^+$ + 1) | 492.07 for C$_{22}$H$_{16}$N$_6$O$_4$S$_2$ | 1H-NMR (DMSO-d$_6$, 400 MHz): δ 11.52 (s, 1H), 9.46 (t, J = 5.8 Hz, 1H), 8.68 (s, 2H), 8.05 (d, J = 8.3 Hz, 1H), 8.00-7.95 (m, 2H), 7.90 (td, J = 7.5, 1.5 Hz, 1H), 7.88-7.79 (m, 3H), 7.72 (s, 1H), 7.19 (s, 2H), 4.66 (d, J = 5.8 Hz, 2H); |
| 1674 | 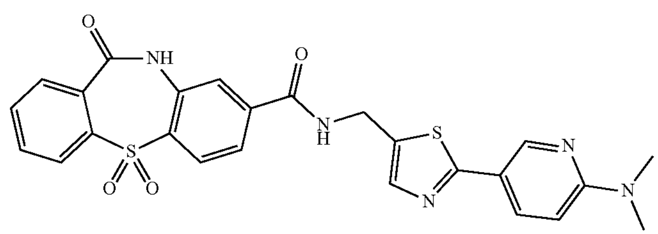 [SMILES: CN(C)c1ccc(-c2ncc(CNC(=O)c3ccc4c(c3)NC(=O)c3ccccc3S4(=O)=O)s2)cn1] | D$^f$, 535, 588 | 6 | 520.0 (M$^+$ + 1) | 519.10 for C$_{25}$H$_{21}$N$_5$O$_4$S$_2$ | 1H-NMR (DMSO-d$_6$, 400 MHz): δ 11.52 (s, 1H), 9.43 (br t, J = 5.6 Hz, 1H), 8.58 (d, J = 2.3 Hz, 1H), 8.05 (d, J = 8.2 Hz, 1H), 8.01-7.79 (m, 7H), 7.68 (s, 1H), 6.70 (d, J = 8.9 Hz, 1H), 4.65 (br d, J = 5.6 Hz, 2H), 3.08 (s, 6H); |
| 1675 | 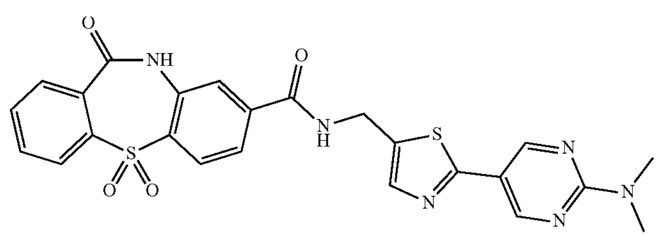 | D$^e$, 535, 571 | 42 | 521.0 (M$^+$ + 1) | 520.10 for C$_{24}$H$_{20}$N$_6$O$_4$S$_2$ | 1H-NMR (DMSO-d$_6$, 400 MHz): δ 11.52 (s, 1H), 9.45 (t, J = 5.8 Hz, 1H), 8.79 (s, 2H), 8.05 (d, J = 8.3 Hz, 1H), 7.98 (dd, J = 7.7, 1.1 Hz, 2H), 7.90 (td, J = 7.4, 1.4 Hz, 1H), 7.87-7.79 (m, 3H), 7.74 (s, 1H), 4.66 (d, J = 5.6 Hz, 2H), 3.18 (s, |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | 1H-NMR |
|---|---|---|---|---|---|---|
| 1677-A | 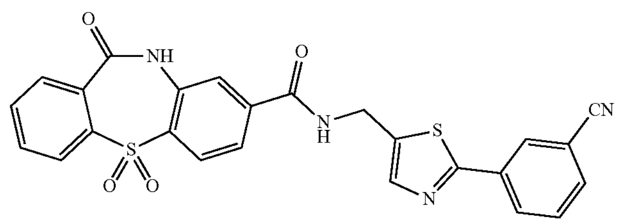 [SMILES: N#Cc1cccc(-c2ncc(CNC(=O)c3ccc4c(c3)NC(=O)c3ccccc3S4(=O)=O)s2)c1] | D', 535, 559 | 55 | 500.9 (M+ + 1); | 500.06 for $C_{25}H_{16}N_4O_4S_2$ | 1H-NMR (DMSO-d6, 400 MHz): δ 11.52 (s, 1H), 9.51 (t, J = 5.8 Hz, 1H), 8.30 (s, 1H), 8.20 (dt, J = 8.3, 1.3 Hz, 1H), 8.06 (d, J = 8.2 Hz, 1H), 7.98 (dt, J = 7.5, 1.1 Hz, 2H), 7.94-7.79 (m, 6H), 7.69 (t, J = 7.8 Hz, 1H), 4.71 (d, J = 5.6 Hz, 2H), 6H); |
| 1972 | 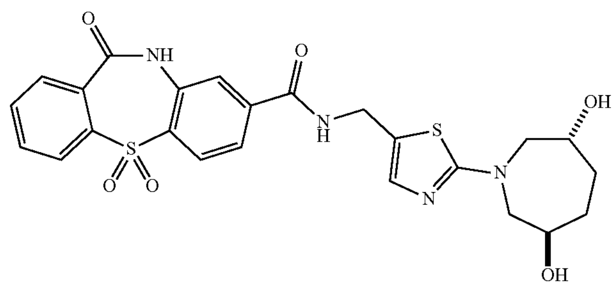 [SMILES: O=C(NCc1cnc(N2C[C@H](O)CC[C@@H](O)C2)s1)c1ccc2c(c1)NC(=O)c1ccccc1S2(=O)=O] | F$^a$, 535, 550 | 53 | 529.1 (M+ + 1); | 528.11 for $C_{24}H_{24}N_4O_6S$ | 1H NMR (400 MHz, DMSO-d6): δ = 11.50 (s, 1H), 9.25 (t, J = 5.7 Hz, 1H), 8.04 (d, J = 8.2 Hz, 1H), 8.01-7.95 (m, 2H), 7.93-7.82 (m, 3H), 7.79 (dd, J = 8.3, 1.4 Hz, 1H), 6.95 (s, 1H), 4.87 (d, J = 4.6 Hz, 2H), 4.42 (d, J = 5.6 Hz, 2H), 3.74 (br s, 2H), 3.78-3.71 (m, 2H), 3.18-3.15 (m, 2H), 1.81-1.79 (m, 2H), 1.40-1.20 (m, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 1804-A | 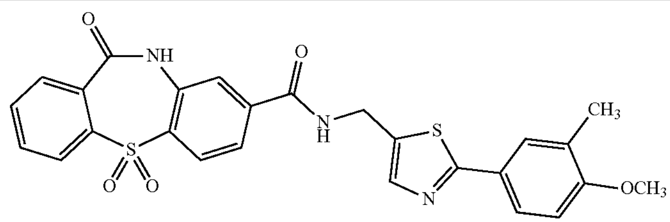 [SMILES: COc1ccc(-c2ncc(CNC(=O)c3ccc4c(c3)NC(=O)c3ccccc3S4(=O)=O)s2)cc1C] | D, 535, 560 | 37 | 520.0 (M⁺ + 1); | 519.09 for $C_{26}H_{21}N_3O_5S_2$ | ¹H-NMR (DMSO-d₆, 400 MHz): δ 11.52 (s, 1H), 9.45 (t, J = 5.6 Hz, 1H), 8.06 (d, J = 8.3 Hz, 1H), 7.97 (dd, J = 7.3 1.1 Hz 2H), 7.93-7.79 (m, 4H), 7.72-7.65 (m, 3H), 7.01 (d, J = 8.4 Hz, 1H), 4.66 (d, J = 5.6 Hz, 2H), 3.83 (s, 3H), 2.19 (s, 3H); |
| 1805 | 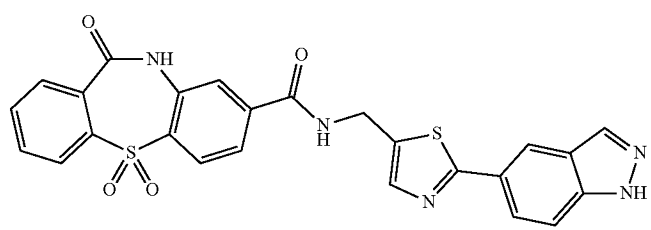 [SMILES: O=C(NCc1cnc(-c2ccc3[nH]ncc3c2)s1)c1ccc2c(c1)NC(=O)c1ccccc1S2(=O)=O] | D, 535, 561 | 38 | 516.0 (M⁺ + 1); | 515.07 for $C_{25}H_{17}N_5O_4S_2$ | ¹H-NMR (DMSO-d₆, 400 MHz): δ 13.26 (s, 1H), 11.52 (s, 1H), 9.47 (t, J = 5.9 Hz, 1H), 8.31-8.28 (m, 1H), 8.16 (s, 1H), 8.06 (d, J = 8.3 Hz, 1H), 8.00-7.95 (m, 2H), 7.93-7.88 (m, 2H), 7.87 (s, 1H), 7.86-7.81 (m, 2H), 7.76 (s, 1H) 7.61 (d, J = 8.8 Hz, 1H), 4.69 (d, J = 5.6 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 1806-A | (structure with 3,5-dimethyl-4-methoxyphenyl thiazole) | D$^g$, 535, 562 | 40 | 534.0 (M⁺ + 1) | 533.11 for $C_{27}H_{23}N_3O_5S_2$ | ¹H-NMR (DMSO-d$_6$, 400 MHz): δ 11.52 (s, 1H), 9.46 (t, J = 5.8 Hz, 1H), 8.06 (d, J = 8.3 Hz, 1H), 7.98 (td, J = 1.0, 7.3 Hz, 2H), 7.93-7.80 (m, 4H), 7.74 (s, 1H), 7.55 (s, 2H), 4.67 (d, J = 5.5 Hz, 2H), 3.68 (s, 3H), 2.26 (s, 6H); |
| 1815 | (structure with 3-fluoro-4-cyanophenyl thiazole) | D, 535, 563 | 17 | 519.0 (M⁺ + 1) | 518.05 for $C_{25}H_{15}FN_4O_4S_2$ | ¹H-NMR (DMSO-d$_6$, 400 MHz): δ 11.53 (s, 1H), 9.53 (t, J = 5.8 Hz, 1H), 8.08-7.94 (m, 6H), 7.93-7.80 (m, 5H), 4.73 (d, J = 5.6 Hz, 2H); |
| 1816 | (structure with 2-chloro-4-cyanophenyl thiazole) | D$^g$, 535, 577 | 8 | 535.0 (M⁺ + 1) | 534.02 for $C_{25}H_{15}ClN_4O_4S_2$ | ¹H NMR (DMSO-d$_6$, 400 MHz): δ 11.51 (br s, 1H), 9.53 (t, J = 5.8 Hz, 1H), 8.36 (d, J = 8.4 Hz, 1H), 8.26 (d, J = 1.5 Hz, 1H), 8.06 (d, J = 8.3 Hz, 1H), 8.02 (s, 1H), 8.00-7.95 (m, 2H), 7.95-7.84 (m, 4H), 7.83-7.79 (m, 1H), 4.76 (d, J = 5.6 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1817 | 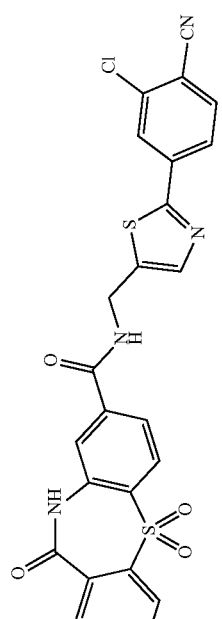 | D$^p$, 535, 570 | 16 | 535.0 (M$^+$ + 1); | 534.02 for C$_{25}$H$_{15}$ClN$_4$O$_4$S$_2$ | $^1$H-NMR (DMSO-d$_6$, 400 MHz): δ 11.52 (br s, 1H), 9.54 (t, J = 5.8 Hz, 1H), 8.19 (s, 1H), 8.08-8.05 (m, 2H), 8.03-7.95 (m, 4H), 7.93-7.78 (m, 4H), 4.73 (d, J = 5.6 Hz, 2H); |
| 1819 | 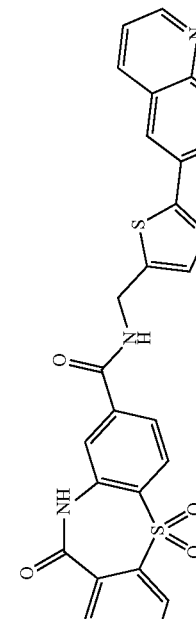 | D$^p$, 535, 564 | 30 | 527.1 (M$^+$ + 1); | 526.08 for C$_{27}$H$_{18}$N$_4$O$_4$S$_2$ | $^1$H-NMR (DMSO-d$_6$, 400 MHz): δ 11.53 (s, 1H), 9.53 (t, J = 5.7 Hz, 1H), 8.93 (dd, J = 4.2, 1.7 Hz, 1H), 8.54 (s, 1H), 8.50 (dd, J = 8.5, 1.0 Hz, 1H), 8.28 (dd, J = 8.8, 2.1 Hz, 1H), 8.08 (t, J = 7.8 Hz, 2H), 7.98 (td, J = 7.8, 1.0 Hz, 2H), 7.94-7.81 (m, 5H), 7.59 (dd, J = 8.3, 4.2 Hz, 1H), 4.73 (d, J = 5.6 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | 1H-NMR |
|---|---|---|---|---|---|---|
| 1820 | 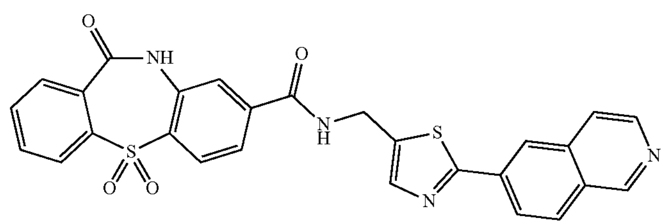 [SMILES: O=C(NCc1cnc(-c2ccc3cnccc3c2)s1)c1ccc2c(c1)NC(=O)c1ccccc1S2(=O)=O] | D', 535, 565 | 17 | 527.1 (M+ + 1); | 526.08 for $C_{27}H_{18}N_4O_4S_2$ | 1H NMR (DMSO-d6, 400 MHz): δ 11.53 (br s, 1H), 9.54 (t, J = 5.8 Hz, 1H), 9.34 (s, 1H), 8.56-8.50 (m, 2H), 8.23-8.18 (m, 2H), 8.07 (d, J = 8.3 Hz, 1H), 8.01-7.81 (m, 8H), 4.74 (d, J = 5.6 Hz, 2H); |
| 1826 | 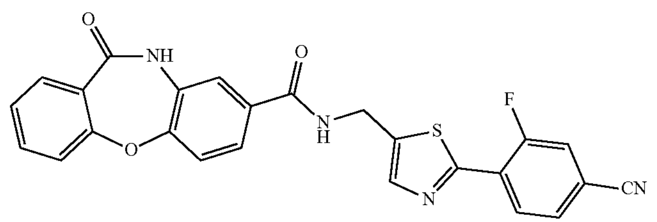 [SMILES: N#Cc1ccc(-c2ncc(CNC(=O)c3ccc4c(c3)NC(=O)c3ccccc3O4)s2)c(F)c1] | D', 539, 575 | 16 | 471.6 (M+ + 1); | 470.08 for $C_{25}H_{15}FN_4O_3S$ | 1H NMR (DMSO-d6, 400 MHz): δ = 10.63 (s, 1H), 9.27 (t, J = 5.8 Hz, 1H), 8.35 (t, J = 7.9 Hz, 1H), 8.09 (dd, J = 11.3, 1.5 Hz, 1H), 8.01 (d, J = 2.4 Hz, 1H), 7.84-7.77 (m, 2H), 7.70 (d, J = 2.0 Hz, 1H), 7.67-7.60 (m, 2H), 7.43 (d, J = 8.4 Hz, 1H), 7.39-7.30 (m, 2H), 4.72 (d, J = 5.6 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 1838 | 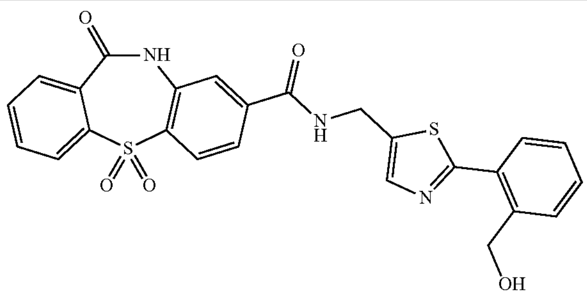 [SMILES: O=C(NCc1cnc(-c2ccccc2CO)s1)c1ccc2c(c1)NC(=O)c1ccccc1S2(=O)=O] | D°, 535, 566 | 61 | 506.0 (M⁺ + 1) | 505.08 for $C_{25}H_{19}N_3O_5S_2$ | ¹H-NMR (DMSO-d₆, 400 MHz): δ 11.52 (s, 1H), 9.49 (t, J = 5.7 Hz, 1H), 8.06 (d, J = 8.3 Hz, 1H), 8.01-7.95 (m, 2H), 7.94-7.80 (m, 5H), 7.69-7.63 (m, 2H), 7.47 (td J = 7.6, 1.1 Hz, 1H), 7.39-7.34 (m, 1H), 5.31 (t, J = 5.9 Hz, 1H), 4.79-4.66 (m, 4H); |
| 1855 | 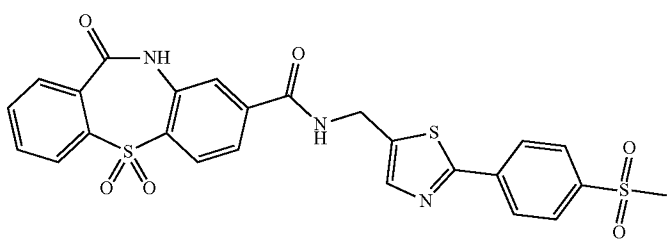 [SMILES: CS(=O)(=O)c1ccc(-c2ncc(CNC(=O)c3ccc4c(c3)NC(=O)c3ccccc3S4(=O)=O)s2)cc1] | D°, 535, 567 | 40 | 554.0 (M⁺ + 1) | 553.04 for $C_{25}H_{19}N_3O_6S_3$ | ¹H NMR (DMSO-d₆, 500 MHz): δ 11.58 (br s, 1H), 9.52 (t, J = 5.8 Hz, 1H), 8.18 (d, J = 8.2 Hz, 2H), 8.10-8.04 (m, 1H), 8.01-7.94 (m, 4H), 7.92-7.82 (m, 5H), 4.72 (d, J = 5.5 Hz, 2H), 3.23 (s, 3H); |
| 1856 | 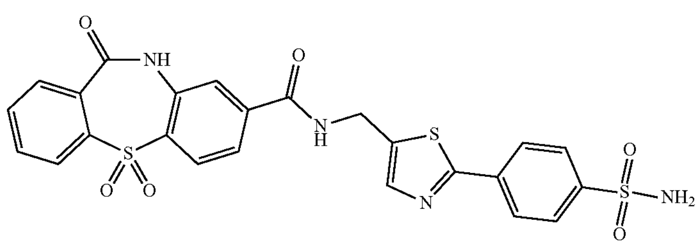 [SMILES: NS(=O)(=O)c1ccc(-c2ncc(CNC(=O)c3ccc4c(c3)NC(=O)c3ccccc3S4(=O)=O)s2)cc1] | D°, 535, 576 | 11 | 555.0 (M⁺ + 1) | 554.04 for $C_{24}H_{18}N_4O_6S_3$ | ¹H NMR (DMSO-d₆, 400 MHz): δ 11.52 (br s, 1H), 9.52 (t, J = 5.8 Hz, 1H), 8.10-8.05 (m, 3H), 8.01-7.95 (m, 2H), 7.86-7.80 (m, 5H), 7.45 (s, 2H), 4.71 (d, J = 5.5 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | 1H-NMR |
|---|---|---|---|---|---|---|
| 1857 | 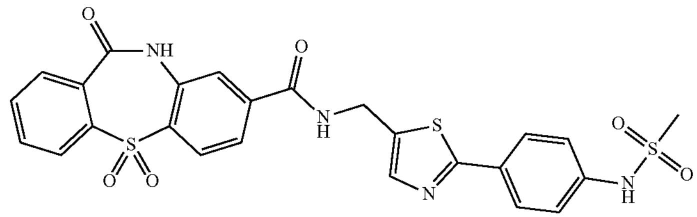 [SMILES: CS(=O)(=O)Nc1ccc(-c2ncc(CNC(=O)c3ccc4c(c3)NC(=O)c3ccccc3S4(=O)=O)s2)cc1] | D^o, 535, 568 | 22 | 569.1 (M+ + 1) | 568.05 C25H20N4O6S3 | 1H NMR (DMSO-d6, 400 MHz): δ 11.51 (br s, 1H), 10.08 (br s, 1H), 9.46 (t, J = 5.8 Hz, 1H), 8.06 (d, J = 8.3 Hz, 1H), 8.01-7.95 (m, 2H), 7.93-7.79 (m, 6H), 7.75 (s, 1H), 7.27 (d, J = 8.7 Hz, 2H), 4.67 (d, J = 5.5 Hz, 2H), 3.05 (s, 3H); |
| 1860 | 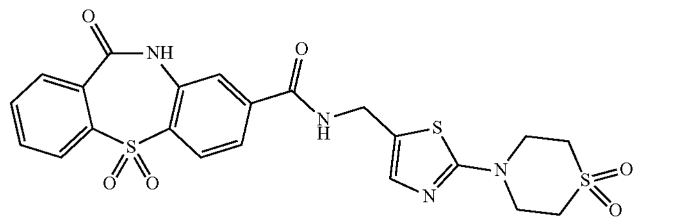 [SMILES: O=C(NCc1cnc(N2CCS(=O)(=O)CC2)s1)c1ccc2c(c1)NC(=O)c1ccccc1S2(=O)=O] | J^a, 535, 545 | 14 | 533.0 (M+ + 1) | 532.05 for C22H20N4O6S3 | 1H NMR (DMSO-d6, 400 MHz): δ 11.51 (s, 1H), 9.31 (t, J = 5.7 Hz, 1H), 8.05 (d, J = 8.3 Hz, 1H), 8.01-7.95 (m, 2H), 7.93-7.82 (m, 3H), 7.79 (d, J = 8.2 Hz, 1H), 7.09 (s, 1H), 4.46 (d, J = 5.6 Hz, 2H), 3.90-3.84 (m, 4H), 3.22-3.15 (m, 4H); |
| 1879-A | 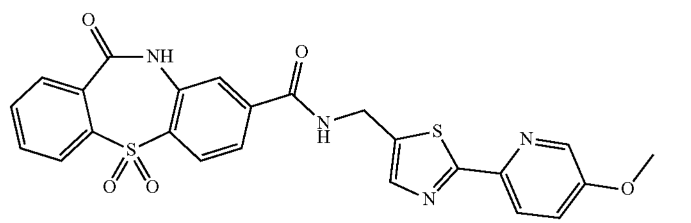 [SMILES: COc1ccc(-c2ncc(CNC(=O)c3ccc4c(c3)NC(=O)c3ccccc3S4(=O)=O)s2)nc1] | H^c, 535, 613 | 26 | 507.0 (M+ + 1) | 506.07 for C24H18N4O5S2 | 1H-NMR (DMSO-d6, 400 MHz): δ 11.51 (br s, 1H), 9.44 (t, J = 5.5 Hz, 1H), 8.30 (d, J = 2.6 Hz, 1H), 8.11-7.93 (m, 5H), 7.92-7.77 (m, 6H), 7.52 (dd, J = 8.7, 2.8 Hz, 1H), 4.67 (d, J = 5.4 Hz, 2H), 3.88 (s, 3H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 1881 | (structure with 5-cyanopyridinyl-thiazole) | D$^s$, 535, 608 | 26 | 542 (M$^+$ + 1); | 501.06 for C$_{24}$H$_{15}$N$_5$O$_4$S$_2$ | ¹H NMR (DMSO-d$_6$, 400 MHz): δ 11.51 (s, 1H), 9.52 (t, J = 5.7 Hz, 1H), 9.05 (d, J = 1.2 Hz, 1H), 8.42 (dd, J = 8.3, 2.1 Hz, 1H), 8.22 (d, J = 8.2 Hz, 1H), 8.06 (d, J = 8.2 Hz, 1H), 8.01-7.95 (m, 3H), 7.93-7.79 (m, 4H), 4.73 (d, J = 5.6 Hz, 2H); |
| 1905 | (structure with piperidinyl-thiazole) | F, 535, 472 | 68 | 483.1 (M$^+$ + 1); | 482.11 for C$_{23}$H$_{22}$N$_4$O$_4$S$_2$ | ¹H-NMR (DMSO-d$_6$, 400 MHz): δ 11.50 (s, 1H), 9.25 (t, J = 5.2 Hz, 1H), 8.04 (d, J = 8.2 Hz, 1H), 8.00-7.95 (m, 2H), 7.93-7.81 (m, 3H), 7.78 (d, J = 8.4 Hz, 1H), 7.01 (s, 1H), 4.44 (d, J = 5.4 Hz, 2H), 3.35-3.30 (m, 4H), 1.56-1.52 (m, 6H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 1907 | 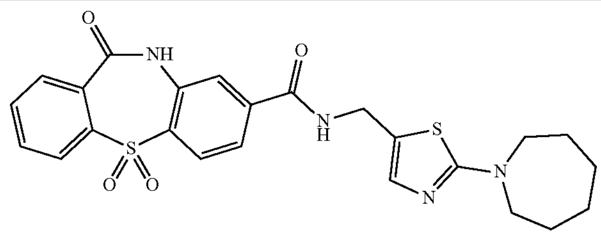 [SMILES: O=C(NCc1cnc(N2CCCCCC2)s1)c1ccc2c(c1)NC(=O)c1ccccc1S2(=O)=O] | G[b], 535, 540 | 26 | 497.1 (M⁺ + 1); | 496.12 for $C_{24}H_{24}N_4O_4S_2$ | ¹H NMR (400 MHz, DMSO-d₆): δ 11.50 (s, 1H), 9.23 (t, J = 5.6 Hz, 1H), 8.04 (d, J = 8.2 Hz, 1H), 8.00-7.95 (m, 2H), 7.92-7.81 (m, 3H), 7.79 (dd, J = 8.3, 1.4 Hz, 1H), 4.43 (d, J = 5.6 Hz, 2H), 3.48-3.43 (m, 4H), 1.74-1.66 (m, 4H), 1.52-1.43 (m, 4H); |
| 1908 | 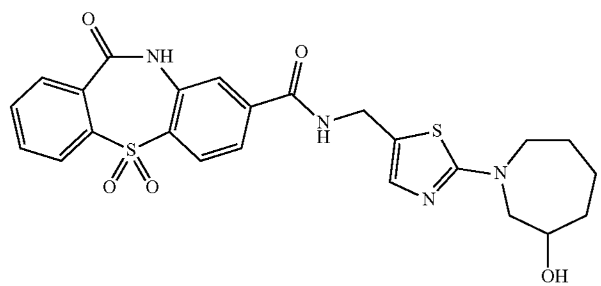 [SMILES: O=C(NCc1cnc(N2CCCCC(O)C2)s1)c1ccc2c(c1)NC(=O)c1ccccc1S2(=O)=O] | G, 535, 503 | 28 | 513.1 (M⁺ + 1); | 512.12 for $C_{24}H_{24}N_4O_5S_2$ | ¹H NMR (400 MHz, DMSO-d₆): δ 11.50 (s, 1H), 9.24 (br t, J = 5.6 Hz, 1H), 8.04 (d, J = 8.3 Hz, 1H), 8.00-7.95 (m, 2H), 7.93-7.82 (m, 3H), 7.79 (dd, J = 8.3, 1.3 Hz, 1H), 6.96 (s, 1H), 4.83 (d, J = 4.4 Hz, 1H), 4.43 (br d, J = 5.5 Hz, 2H), 3.81-3.66 (m, 2H), 3.52-3.43 (m, 1H), 3.40-3.35 (m, 1H), 3.20-3.10 (m, 1H), 1.85-1.56 (m, 4H), 1.48-1.36 (m, 1H), 1.29-1.17 (m, 1H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---------|-----------|---------|-----------|----------|------------|---------|
| 1858 | 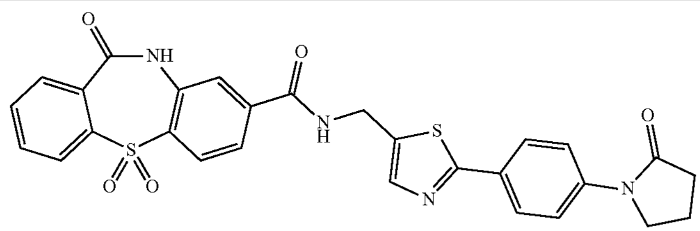 [SMILES: O=C(NCc1cnc(-c2ccc(N3CCCC3=O)cc2)s1)c1ccc2c(c1)NC(=O)c1ccccc1S2(=O)=O] | D*, 535, 602 | 26 | 559.1 (M⁺ + 1) | 558.10 for $C_{28}H_{22}N_4O_5S_2$ | 1H-NMR (DMSO-d6, 400 MHz): δ 11.42 (br s, 1H), 9.46 (t, J = 5.8 Hz, 1H), 8.06 (d, J = 8.2 Hz, 1H), 8.01-7.95 (m, 2H), 7.93-7.75 (m, 9H), 4.68 (d, J = 5.6 Hz, 2H), 3.86 (t, J = 7.1 Hz, 2H), 2.52-2.50 (m, 2H), 2.12-2.03 (m, 2H); |
| 1859 | 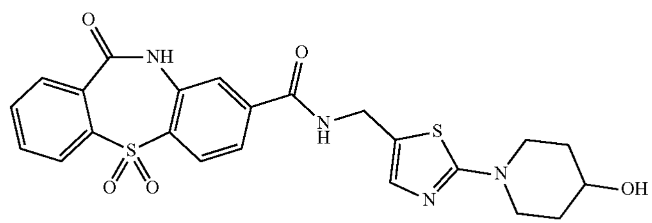 [SMILES: O=C(NCc1cnc(N2CCC(O)CC2)s1)c1ccc2c(c1)NC(=O)c1ccccc1S2(=O)=O] | G*, 535, 485 | 10 | 499.1 (M⁺ + 1) | 498.10 for $C_{23}H_{22}N_4O_5S_2$ | 1H NMR (DMSO-d6, 400 MHz): δ 11.50 (s, 1H), 9.25 (t, J = 5.6 Hz, 1H), 8.05-7.95 (m, 1H), 7.93-7.82 (m, 3H), 7.78 (d, J = 8.3 Hz, 1H), 7.01 (s, 1H), 4.74 (br s, 1H), 4.44 (d, J = 5.5 Hz, 2H), 3.72-3.58 (m, 3H), 3.15-3.06 (m, 2H), 1.79-1.74 (m, 2H), 1.44-1.34 (m, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 1864 | 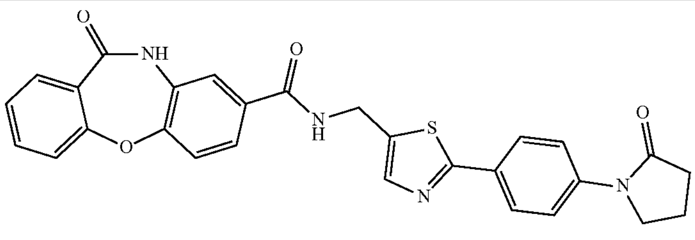 [SMILES: O=C(NCc1cnc(-c2ccc(N3CCCC3=O)cc2)s1)c1ccc2c(c1)NC(=O)c1ccccc1O2] | D°, 539, 602 | 18 | 511.2 (M⁺ + 1); | 510.14 for $C_{28}H_{22}N_4O_4S$ | 1H NMR ((DMSO-d6, 400 MHz): δ 10.64 (s, 1H), 9.21 (t, J = 5.8 Hz, 1H), 7.90-7.86 (m, 2H), 7.80-7.74 (m, 4H), 7.70 (d, J = 2.0 Hz, 1H), 7.66-7.60 (m, 2H), 7.43 (d, J = 8.4 Hz, 1H), 7.39-7.30 (m, 2H), 4.65 (d, J = 5.6 Hz, 2H), 3.86 (t, J = 7.0 Hz, 2H), 2.52-2.50 (m, 2H), 2.07 (p, J = 7.5 Hz, 2H); |
| 1930 | 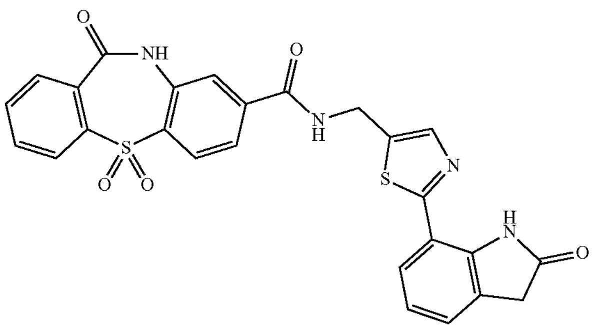 [SMILES: O=C1Cc2cccc(-c3ncc(CNC(=O)c4ccc5c(c4)NC(=O)c4ccccc4S5(=O)=O)s3)c2N1] | D°, 535, 569 | 27 | 531.0 (M⁺ + 1); | 530.07 for $C_{26}H_{18}N_4O_5S_2$ | ¹H NMR (DMSO-d6, 400 MHz): δ 11.52 (s, 1H), 9.98 (s, 1H), 9.50 (t, J = 5.8 Hz, 1H), 8.06 (d, J = 8.3 Hz, 1H), 8.01-7.95 (m, 2H), 7.93-7.80 (m, 5H), 7.57-7.54 (m, 1H), 7.31 (d, J = 7.3 Hz, 1H), 7.06 (t, J = 7.7 Hz, 1H), 4.71 (d, J = 5.5 Hz, 2H), 3.61 (s, 2H); |

TABLE 2-continued
Synthesis from compound 535, 536, 538, 539 common intermediates
| Example | Structure | Procedure, Intermediate, boronic acid or boronate esters | Rx. Yield | Mass Spec. Found | Mass Spec. Calculated | 1H-NMR |
|---|---|---|---|---|---|---|
| 1931 | 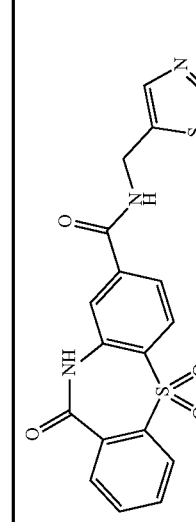 | D$^p$, 535, 598 | 16 | 559.1 (M$^+$ + 1); | 558.10 C$_{28}$H$_{22}$N$_4$O$_5$S$_2$ | 1H NMR (DMSO-d$_6$, 400 MHz): δ 11.51 (br s, 1H), 10.40 (s, 1H), 9.45 (t, J = 5.8 Hz, 1H), 8.05 (d, J = 8.2 Hz, 1H), 8.00-7.95 (m, 2H), 7.92-7.78 (m, 6H), 7.74 (s, 1H), 7.68 (d, J = 8.8 Hz, 2H), 4.67 (d, J = 5.6 Hz, 2H), 1.84-1.76 (m, 1H), 0.84-0.79 (m, 4H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1932 | 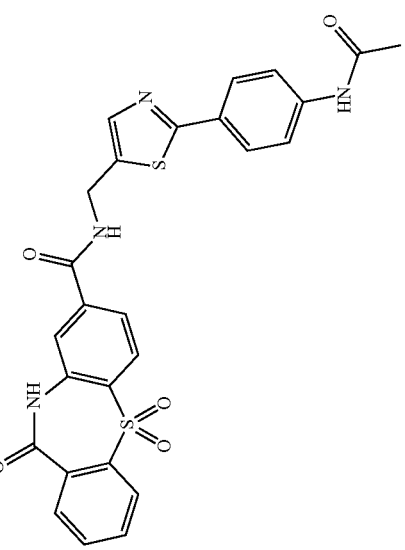 | D$^p$, 535, 600 | 38 | 533.1 (M$^+$ + 1); | 532.09 $C_{26}H_{20}N_4O_5S_2$ | $^1$H NMR (DMSO-d$_6$, 400 MHz): δ 11.51 (s, 1H), 10.14 (s, 1H), 9.45 (t, J = 5.7 Hz, 1H), 8.06 (d, J = 8.3 Hz, 1H), 8.00-7.95 (m, 2H), 7.93-7.84 (m, 3H), 7.83-7.79 (m, 3H), 7.74 (s, 1H), 7.67 (d, J = 8.8 Hz, 2H), 4.67 (d, J = 5.5 Hz, 2H), 2.06 (s, 3H); |
| 1951 | 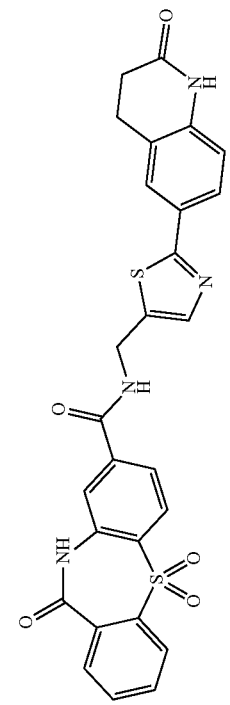 | D$^j$, 535, 604 | 56 | 545.1 (M$^+$ + 1); | 544.09 for $C_{27}H_{20}N_4O_5S_2$ | $^1$H NMR (DMSO-d$_6$, 400 MHz): δ 11.52 (s, 1H), 10.29 (s, 1H), 9.46 (t, J = 5.7 Hz, 1H), 8.06 (d, J = 8.3 Hz, 1H), 8.00-7.95 (m, 2H), 7.93-7.80 (m, 4H), 7.73-7.64 (m, 3H), 6.91 (d, J = 8.3 Hz, 1H), 4.66 (d, J = 5.6 Hz, 2H), 2.94 (t, J = 7.5 Hz, 2H), 2.48-2.46 (m, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1953 | 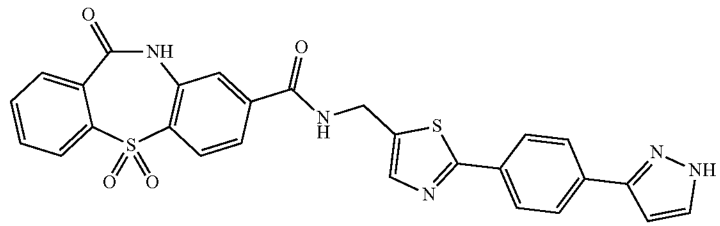 [SMILES: O=C(NCc1cnc(-c2ccc(-c3cc[nH]n3)cc2)s1)c1ccc2c(c1)NC(=O)c1ccccc1S2(=O)=O] | D, 538, 578 | 27 | 542.0 (M$^+$ + 1); | 541 for C$_{27}$H$_{19}$N$_5$O$_4$S$_2$ | $^1$H NMR (DMSO-d$_6$, 400 MHz): δ 13.45-12.95 (m, 1H), 11.52 (br s, 1H), 9.49 (t, J = 4.8 Hz, 1H), 8.06 (d, J = 8.3 Hz, 1H), 8.01-7.95 (m, 2H), 7.94-7.90 (m, 4H), 7.89-7.83 (m, 4H), 7.82-7.80 (m, 2H), 6.78 (s, 1H), 4.70 (d, J = 5.3 Hz, 2H); |
| 1954 | 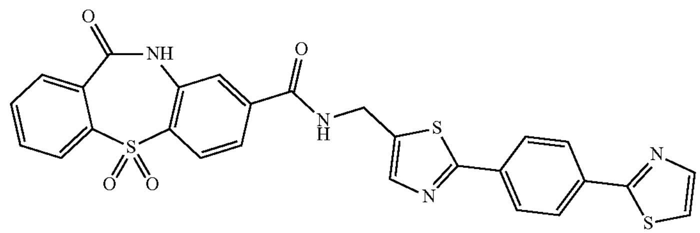 [SMILES: O=C(NCc1cnc(-c2ccc(-c3nccs3)cc2)s1)c1ccc2c(c1)NC(=O)c1ccccc1S2(=O)=O] | H$^d$, 538, 610 | 20 | 559.0 (M$^+$ + 1); | 558 for C$_{27}$H$_{18}$N$_4$O$_4$S$_3$ | 1H NMR (DMSO-d6, 400 MHz): δ 11.51 (br s, 1H), 9.50 (t, J = 5.7 Hz, 1H), 8.08-8.04 (m, 3H), 8.03-7.95 (m, 5H), 7.93-7.80 (m, 6H), 4.71 (d, J = 5.6 Hz, 2H); |
| 1959 | 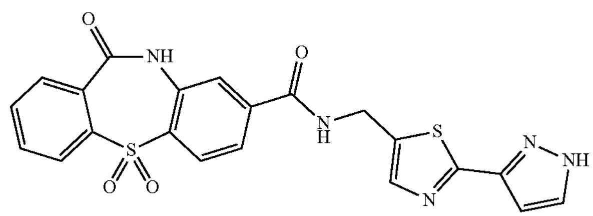 [SMILES: O=C(NCc1cnc(-c2cc[nH]n2)s1)c1ccc2c(c1)NC(=O)c1ccccc1S2(=O)=O] | D$^d$, 535, 578 | 11 | 466.0 (M$^+$ + 1); | 465.06 C$_{21}$H$_{15}$N$_5$O$_4$S$_2$ | 1H NMR DMSO-d6, 400 MHz): δ 13.16 (br s, 1H), 11.51 (s, 1H), 9.43 (br t, J = 5.8 Hz, 1H), 8.05 (d, J = 8.3 Hz, 1H), 7.98 (td, J = 7.7, 1.1 Hz, 2H), 7.93-7.79 (m, 5H), 7.70 (s, 1H), 6.69 (t, J = 2.1 Hz, 1H), 4.65 (d, J = 5.8 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1956 | 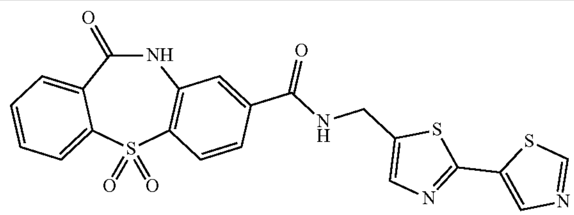 [SMILES: O=C(NCc1cnc(-c2cncs2)s1)c1ccc2c(c1)NC(=O)c1ccccc1S2(=O)=O] | H, 535, 611 | 6 | 483.0 (M$^+$ + 1) | 482.02 for C$_{21}$H$_{14}$N$_4$O$_4$S$_3$ | $^1$H NMR (DMSO-d$_6$, 400 MHz): δ 11.52 (br s, 1H), 9.50 (t, J = 5.8 Hz, 1H), 9.17 (s, 1H), 8.42 (s, 1H), 8.06 (d, J = 8.3 Hz, 1H), 8.01-7.96 (m, 2H), 7.90 (td, J = 7.5, 1.5 Hz, 1H), 7.87-7.80 (m, 3H), 7.78 (s, 1H), 4.68 (d, J = 5.6 Hz, 2H); |
| 1960 | 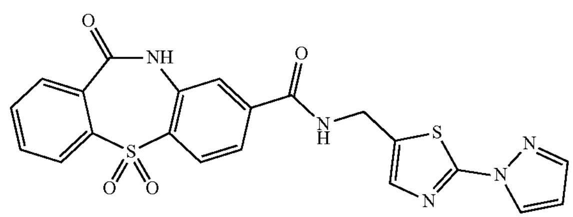 [SMILES: O=C(NCc1cnc(-n2cccn2)s1)c1ccc2c(c1)NC(=O)c1ccccc1S2(=O)=O] | K$^a$, 535, 453 | 56 | 466.3 (M$^+$ + 1) | 465.06 for C$_{21}$H$_{15}$N$_5$O$_4$S$_2$ | $^1$H NMR (DMSO-d$_6$, 500 MHz): δ 11.52 (s, 1H), 9.48 (t, J = 5.5 Hz, 1H), 8.46 (d, J = 2.9 Hz, 1H), 8.07 (d, J = 8.1 Hz, 1H), 7.99 (t, J = 8.7 Hz, 2H), 7.94-7.80 (m, 5H), 7.55 (s, 1H), 6.61 (d, J = 1.7 Hz, 1H), 4.62 (d, J = 5.8 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | 1H-NMR |
|---|---|---|---|---|---|---|
| 1981 | 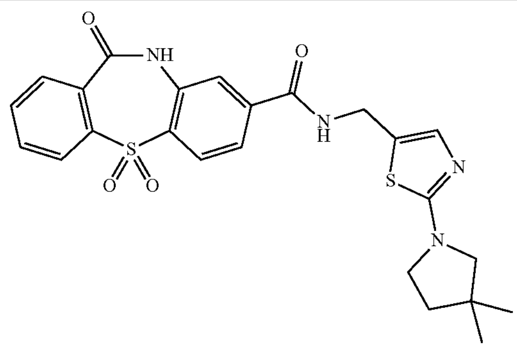 [SMILES: CC1(C)CCN(c2ncc(CNC(=O)c3ccc4c(c3)NC(=O)c3ccccc3S4(=O)=O)s2)C1] | J, 535, 554 | 35 | 497.0 (M+ + 1) | 496.12 for $C_{24}H_{24}N_4O_4S_2$ | 1H NMR (DMSO-d6, 400 MHz): δ 11.50 (s, 1H), 9.24 (t, J = 5.7 Hz, 1H), 8.04 (d, J = 8.2 Hz, 1H), 8.00-7.95 (m, 2H), 7.92-7.82 (m, 3H), 7.78 (dd, J = 8.3, 1.4 Hz, 1H), 6.99 (s, 1H), 4.43 (d, J = 5.5 Hz, 2H), 3.38 (t, J = 6.9 Hz, 2H), 3.08 (s, 2H), 1.75 (t, J = 7.0 Hz, 2H), 1.06 (s, 6H); |
| 11038 | 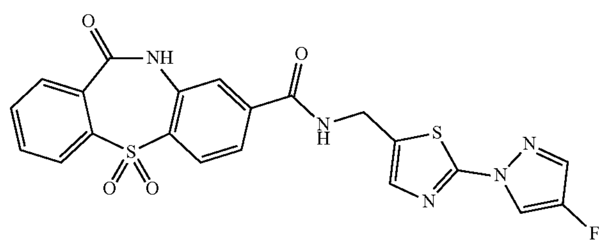 [SMILES: O=C(NCc1cnc(-n2cc(F)cn2)s1)c1ccc2c(c1)NC(=O)c1ccccc1S2(=O)=O] | I, 535, 541 | 48 | 483.9 (M+ + 1) | 483.05 for $C_{21}H_{14}FN_5O_4S_2$ | 1H-NMR (DMSO-d6, 400 MHz): δ 11.51 (s, 1H), 9.48 (t, J = 5.6 Hz, 1H), 8.64 (d, J = 4.1 Hz, 1H), 8.06 (d, J = 8.2 Hz, 1H), 8.01-7.95 (m, 3H), 7.93-7.78 (m, 4H), 7.55 (s, 1H), 4.61 (br d, J = 5.6 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 11039 | (structure with CF₃-pyrazole-thiazole-methylamide-dibenzothiazepine sulfone) | I<sup>a</sup>, 535, 542 | 46 | 534.0 (M⁺ + 1) | 533.04 for $C_{22}H_{14}F_3N_5O_4S_2$ | ¹H-NMR (DMSO-d₆, 400 MHz): δ 11.51 (s, 1H), 9.51 (t, J = 5.6 Hz, 1H), 9.16 (s, 1H), 8.32 (s, 1H), 8.06 (d, J = 8.2 Hz, 1H), 7.98 (dd, J = 7.5, 1.2 Hz, 2H), 7.93–7.84 (m, 3H), 7.81 (td, J = 4.9, 1.5 Hz, 1H), 7.65 (s, 1H), 4.64 (d, J = 5.5 Hz, 2H); |
| 11040 | (structure with 5-fluoropyridine-thiazole-methylamide-dibenzothiazepine sulfone) | D<sup>a</sup>, 535, 606 | 9 | 495 (M⁺ + 1) | 494.05 for $C_{23}H_{15}FN_4O_4S_2$ | ¹H NMR (DMSO-d₆, 400 MHz): δ 11.49 (s, 1H), 9.45 (t, J = 5.9 Hz, 1H), 8.59 (d, J = 2.9 Hz, 1H), 8.12 (dd, J = 8.8, 4.6 Hz, 1H), 8.03 (d, J = 8.2 Hz, 1H), 7.98–7.93 (m, 2H), 7.90–7.76 (m, 6H), 4.66 (d, J = 5.6 Hz, 2H); |
| 11045 | (structure with 3-fluoropyrazole-thiazole-methylamide-dibenzothiazepine sulfone) | I, 535, 543 | 18 | 483.9 (M⁺ + 1) | 483.05 for $C_{21}H_{14}FN_5O_4S_2$ | ¹H-NMR (DMSO-d₆, 400 MHz): δ 11.51 (s, 1H), 9.48 (t, J = 5.6 Hz, 1H), 8.44 (d, J = 8.2 Hz, 1H), 8.06 (d, J = 8.2 Hz, 1H), 7.98 (t, J = 6.9 Hz, 2H), 7.94–7.77 (m, 4H), 7.54 (s, 1H), 6.46 (dd, J = 5.3, 2.7 Hz, 1H), 4.61 (d, J = 5.5 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 11049 | 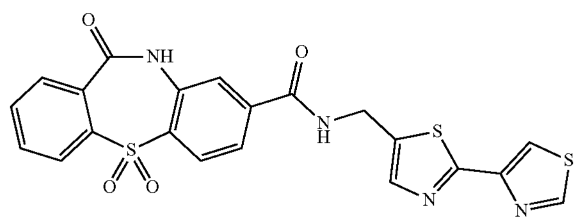 [SMILES: O=C(NCc1cnc(-c2cscn2)s1)c1ccc2c(c1)NC(=O)c1ccccc1S2(=O)=O] | H, 535, 584 | 19 | 483.1 (M$^+$ + 1); | 482.02 for $C_{21}H_{14}N_4O_4S_3$ | $^1$H-NMR (DMSO-d$_6$, 400 MHz): δ 11.51 (s, 1H), 9.46 (t, J = 5.8 Hz, 1H), 9.20 (d, J = 2.0 Hz, 1H), 8.25 (d, J = 2.0 Hz, 1H), 8.06 (d, J = 8.3 Hz, 1H), 7.98 (td, J = 1.3, 8.3 Hz, 2H), 7.94-7.84 (m, 3H), 7.847.79 (m, 2H), 4.69 (d, J = 5.8 Hz, 2H); |
| 11050 | 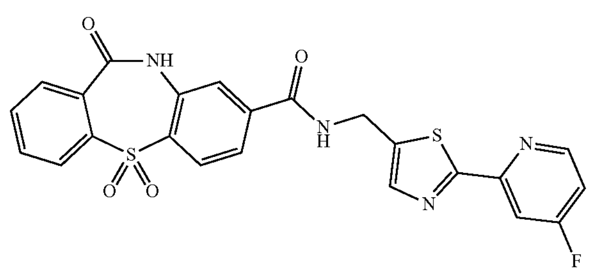 [SMILES: O=C(NCc1cnc(-c2cc(F)ccn2)s1)c1ccc2c(c1)NC(=O)c1ccccc1S2(=O)=O] | H$^a$, 535, 615 | 17 | 495.0 (M$^+$ + 1); | 494.05 for $C_{23}H_{15}FN_4O_4S_2$ | $^1$H-NMR (DMSO-d$_6$, 400 MHz): δ 11.51 (s, 1H), 9.49 (t, J = 5.7 Hz, 1H), 8.64 (dd, J = 8.4, 5.6 Hz, 1H), 8.06 (d, J = 8.2 Hz, 1H), 8.01-7.95 (m, 2H), 7.93-7.78 (m, 6H), 7.45-7.39 (m, 1H), 4.71 (d, J = 5.8 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 11051 | 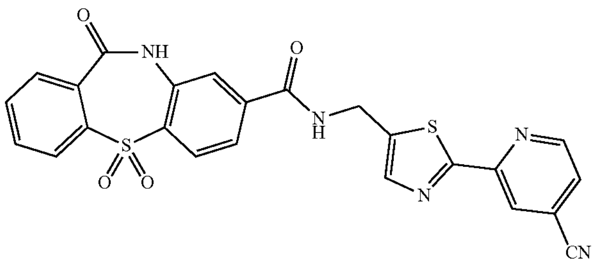 [SMILES: N#Cc1ccnc(-c2ncc(CNC(=O)c3ccc4c(c3)NC(=O)c3ccccc3S4(=O)=O)s2)c1] | H$^b$, 535, 617 | 18 | 502.0 (M$^+$ + 1); | 501.06 for C$_{24}$H$_{15}$N$_5$O$_4$S$_2$ | $^1$H NMR (DMSO-d$_6$, 400 MHz): δ 11.51 (s, 1H), 9.51 (t, J = 5.7 Hz, 1H), 8.84 (dd, J = 5.0, 0.8 Hz, 1H), 8.39 (s, 1H), 8.06 (d, J = 8.2 Hz, 1H), 8.01-7.94 (m, 3H), 7.94-7.90 (m, 2H), 7.89-7.84 (m, 2H), 7.81 (dd, J = 8.2, 1.4 Hz, 1H), 4.72 (d, J = 5.6 Hz, 2H); |
| 11150 | 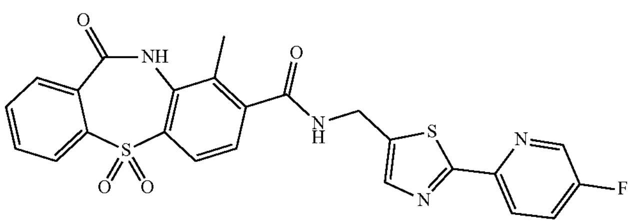 [SMILES: Cc1c(C(=O)NCc2cnc(-c3ccc(F)cn3)s2)ccc2c1NC(=O)c1ccccc1S2(=O)=O] | D$^f$, 536, 606 | 20 | 509.1 (M$^+$ + 1); | 508.07 for C$_{24}$H$_{17}$FN$_4$O$_4$S$_2$ | $^1$H NMR (DMSO-d$_6$, 400 MHz): δ 10.85 (s, 1H), 9.21 (t, J = 5.8 Hz, 1H), 8.65 (d, J = 2.8 Hz, 1H), 8.16 (dd, J = 8.8, 4.6 Hz, 1H), 7.96-7.83 (m, 6H), 7.82-7.76 (m, 1H), 7.36 (d, J = 8.2 Hz, 1H), 4.66 (d, J = 6.0 Hz, 2H), 2.32 (s, 3H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 11152 | 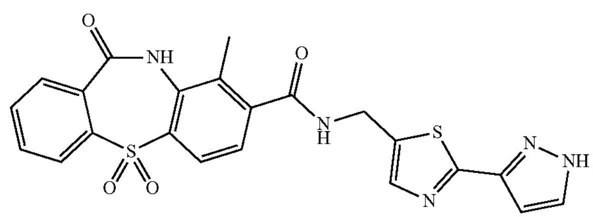 [SMILES: Cc1c(C(=O)NCc2cnc(-c3cc[nH]n3)s2)ccc2c1NC(=O)c1ccccc1S2(=O)=O] | D, 536, 578 | 34 | 480.1 (M⁺ + 1); | 479.07 for $C_{22}H_{17}N_5O_4S_2$ | ¹H NMR (DMSO-d₆, 400 MHz): δ 10.85 (s, 1H), 9.16 (t, J = 5.8 Hz, 1H), 7.94-7.90 (m, 2H), 7.89-7.84 (m, 3H), 7.82-7.77 (m, 1H), 7.70 (s, 1H), 7.35 (d, J = 8.2 Hz, 1H), 6.71 (d, J = 2.4 Hz, 1H), 4.63 (d, J = 5.9 Hz, 2H), 2.32 (s, 3H); |
| 11148 | 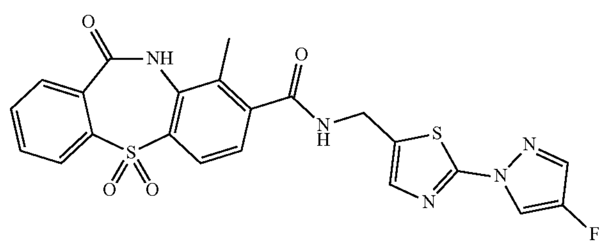 [SMILES: Cc1c(C(=O)NCc2cnc(-n3cc(F)cn3)s2)ccc2c1NC(=O)c1ccccc1S2(=O)=O] | I^b, 536, 541 | 23 | 498.0 (M⁺ + 1); | 497.06 for $C_{22}H_{16}FN_5O_4S_2$ | ¹H-NMR (DMSO-d₆, 400 MHz): δ 10.87 (s, 1H), 9.21 (t, J = 5.8 Hz, 1H), 8.67 (d, J = 4.1 Hz, 1H), 8.00 (d, J = 4.0 Hz, 1H), 7.94-7.89 (m, 2H), 7.89-7.84 (m, 2H), 7.79 (td, J = 7.8, 1.6 Hz, 1H), 7.55 (s, 1H), 7.35 (d, J = 8.2 Hz, 1H), 4.58 (d, J = 5.8 Hz, 2H), 2.32 (s, 3H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 11149 | 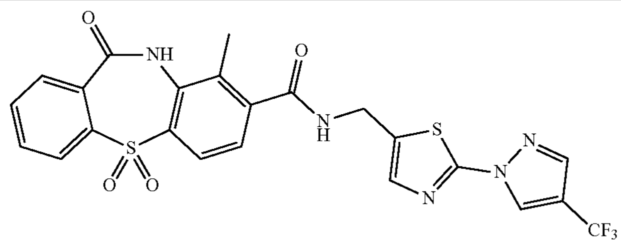 [SMILES: Cc1c(C(=O)NCc2cnc(-n3cc(C(F)(F)F)cn3)s2)ccc2c1NC(=O)c1ccccc1S2(=O)=O] | I$^b$, 536, 542 | 19 | 548.1 (M$^+$ + 1) | 547.06 for $C_{23}H_{16}F_3N_5O_4S_2$ | $^1$H NMR (400 MHz, DMSO-d$_6$) δ 10.87 (br s, 1H), 9.25 (t, J = 5.3 Hz, 1H), 9.18 (s, 1H), 8.34 (s, 1H), 8.00-7.75 (m, 5H), 7.64 (s, 1H), 7.36 (d, J = 8.0 Hz, 1H), 4.61 (d, J = 5.3 Hz, 2H), 2.32 (s, 3H); |
| 1694 | 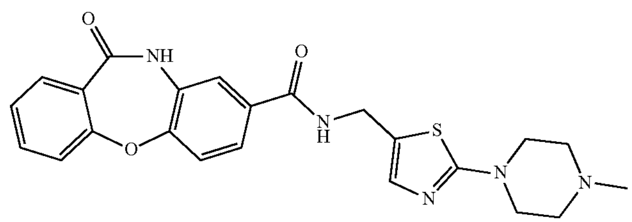 | K, 539, 305 | 23 | 450.0 (M$^+$ + 1) | 934.28 for $C_{46}H_{47}ClN_{10}O_6S_2$ | $^1$H-NMR (DMSO-d$_6$, 500 MHz): δ 10.62 (s, 1H), 9.01 (t, J = 5.8 Hz, 1H), 7.78 (dd, J = 7.8, 1.4 Hz, 1H), 7.68-7.58 (m, 3H), 7.41 (d, J = 8.4 Hz, 1H), 7.38-7.31 (m, 2H), 7.03 (s, 1H), 4.42 (d, J = 5.8 Hz, 2H), 3.34-3.29 (m, 4H), 2.44-2.37 (m, 4H), 2.22 (br s, 3H); |

TABLE 2-continued

Synthesis from compound 535, 536, 538, 539 common intermediates

| Example | Structure | Procedure, Intermediate, or boronic acid or boronate esters | Rx. Yield | Mass Spec. Found | Mass Spec. Calculated | ¹H-NMR |
|---|---|---|---|---|---|---|
| 1695 | 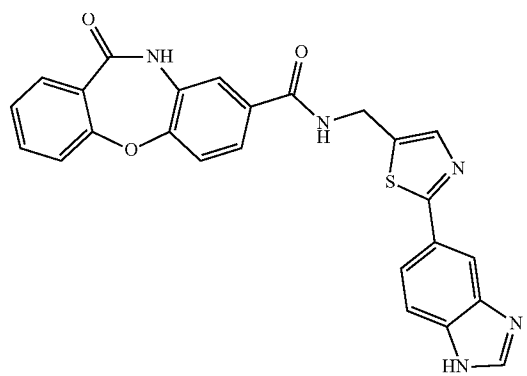 [SMILES: O=C(NCc1cnc(-c2ccc3[nH]cnc3c2)s1)c1ccc2c(c1)NC(=O)c1ccccc1O2] | E, 539, 573 | 14 | 468.0 (M⁺ + 1); | 467.11 for $C_{25}H_{17}N_5O_3S$ | ¹H-NMR (DMSO-d₆, 400 MHz): δ 10.64 (s, 1H), 9.23 (t, J = 5.3 Hz, 1H), 8.66 (br s, 1H), 8.14 (s, 1H), 7.84 (br d, J = 8.7 Hz, 1H), 7.80-7.69 (m, 5H), 7.66-7.60 (m, 2H), 7.43 (d, J = 8.4 Hz, 1H), 7.39-7.31 (m, 2H), 4.67 (br d, J = 5.5 Hz, 2H); |
| 1696 | 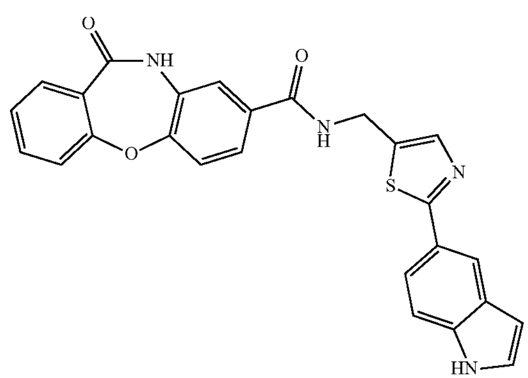 [SMILES: O=C(NCc1cnc(-c2ccc3[nH]ccc3c2)s1)c1ccc2c(c1)NC(=O)c1ccccc1O2] | D^f, 539, 572 | 41 | 467.0 (M⁺ + 1); | 466.11 $C_{26}H_{18}N_4O_3S$ | ¹H-NMR (DMSO-d₆, 400 MHz): δ 11.31 (br s, 1H), 10.64 (s, 1H), 9.19 (t, J = 5.7 Hz, 1H), 8.08 (s, 1H), 7.78 (dd, J = 7.7, 1.7 Hz, 1H), 7.71-7.69 (m, 2H), 7.66-7.61 (m, 3H), 7.46-7.40 (m, 3H), 7.38-7.31 (m, 2H), 6.52 (t, J = 2.1 Hz, 1H), 4.64 (d, J = 5.6 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | 1H-NMR |
|---|---|---|---|---|---|---|
| 1700 | (structure shown) | E$^c$, 539, 555 | 8 | 461.9 (M$^+$ + 1); | 461.08 for C$_{24}$H$_{16}$FN$_3$O$_4$S | 1H-NMR (DMSO-d$_6$, 400 MHz): δ 10.64 (s, 1H), 10.50 (br s, 1H), 9.19 (t, J = 5.8 Hz, 1H), 7.78 (dd, J = 7.7, 1.6 Hz, 1H), 7.71-7.69 (m, 2H), 7.66-7.59 (m, 3H), 7.51 (dd, J = 8.4, 1.5 Hz, 1H), 7.42 (d, J = 8.4 Hz, 1H), 7.38-7.30 (m, 2H), 7.00 (t, J = 8.7 Hz, 1H), 4.63 (br d, J = 5.6 Hz, 2H); |
| 1701 | (structure shown) | E$^b$, 539, 586 | 30 | 479.9 (M$^+$ + 1); | 479.08 for C$_{24}$H$_{15}$F$_2$N$_3$O$_4$S | 1H-NMR (DMSO-d$_6$, 400 MHz): δ 10.65 (s, 1H), 9.21 (t, J = 5.6 Hz, 1H), 7.82 (d, J = 8.1 Hz, 1H), 7.40-7.31 (m, 4H), 7.70-7.60 (m, 5H), 4.67 (d, J = 5.2 Hz, 2H); |

TABLE 2-continued

Synthesis from compound 535, 536, 538, 539 common intermediates

| Example | Structure | Procedure, Intermediate, or boronic acid or boronate esters | Rx. Yield | Mass Spec. Found | Mass Spec. Calculated | 1H-NMR |
|---|---|---|---|---|---|---|
| 1702 | (structure) | D[b], 539, 556 | 64 | 477.9 (M+ + 1); | 477.06 for $C_{24}H_{16}ClN_3O_4S$ | 1H-NMR (DMSO-d6, 500 MHz): δ 10.78 (br s, 1H), 10.64 (s, 1H), 9.21 (t, J = 5.5 Hz, 1H), 7.83-7.76 (m, 2H), 7.72-7.60 (m, 5H), 7.42 (d, J = 8.4 Hz, 1H), 7.38-7.31 (m, 2H), 7.05 (d, J = 8.4 Hz, 1H), 4.63 (d, J = 5.5 Hz, 2H); |
| 1703 | (structure) | D[b], 539, 574 | 62 | 477.9 (M+ + 1); | 477.06 for $C_{24}H_{16}ClN_3O_4S$ | 1H-NMR (DMSO-d6, 400 MHz): δ 10.64 (s, 1H), 10.41 (s, 1H), 9.21 (t, J = 5.7 Hz, 1H), 7.97 (d, J = 8.8 Hz, 1H), 7.80-7.76 (m, 2H), 7.69 (s, 1H), 7.66-7.60 (m, 2H), 7.43 (d, J = 8.3 Hz, 1H), 7.38-7.31 (m, 2H), 6.94 (d, J = 2.5 Hz, 1H), 6.87 (dd, J = 8.8, 2.4 Hz, 1H), 4.67 (d, J = 5.6 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---|---|---|---|---|---|---|
| 1704 | (structure: fluorophenol-thiazole-methylamide-dibenzoxazepinone) | D[b], 539, 557 | 13 | 461.9 (M⁺ + 1); | 461.08 for $C_{24}H_{16}FN_3O_4S$ | ¹H-NMR (DMSO-d₆, 500 MHz): δ 10.62 (s, 1H), 10.45 (s, 1H), 9.19 (t, J = 5.8 Hz, 1H), 7.98 (t, J = 9.0 Hz, 1H), 7.80-7.74 (m, 2H), 7.69 (d, J = 2.0 Hz, 1H), 7.65-7.60 (m, 2H), 7.42 (d, J = 8.4 Hz, 1H), 7.38-7.31 (m, 2H), 6.77-6.67 (m, 2H), 4.65 (d, J = 5.5 Hz, 2H); |
| 1708 | (structure: dimethylaminopyridine-phenyl-thiazole-methylamide-dibenzoxazepinone) | D[j], 539, 588 | 25 | 472.0 (M⁺ + 1); | 471.14 for $C_{25}H_{21}N_5O_3S$ | ¹H NMR (DMSO-d₆, 500 MHz): δ 10.63 (s, 1H), 9.17 (t, J = 5.6 Hz, 1H), 8.58 (d, J = 2.0 Hz, 1H), 7.92 (dd, J = 9.0, 2.3 Hz, 1H), 7.78 (d, J = 7.2 Hz, 1H), 7.70-7.59 (m, 4H), 7.42 (d, J = 8.4 Hz, 1H), 7.39-7.31 (m, 2H), 6.70 (d, J = 9.0 Hz, 1H), 4.62 (br d, J = 5.5 Hz, 2H), 3.08 (s, 6H); |

TABLE 2-continued

Synthesis from compound 535, 536, 538, 539 common intermediates

| Example | Structure | Procedure, Intermediate, or boronic acid or boronate esters | Rx. Yield | Mass Spec. Found | Mass Spec. Calculated | ¹H-NMR |
|---|---|---|---|---|---|---|
| 1709-A | (structure with OCH₃-pyridine-thiazole-methylamide-dibenzoxazepinone) | D[i], 539, 594 | 27 | 460.0 (M⁺ + 1) | 459.10 for $C_{23}H_{17}N_5O_4S$ | ¹H NMR (DMSO-$d_6$, 400 MHz): δ 10.64 (s, 1H), 9.25 (t, J = 5.8 Hz, 1H), 9.06 (s, 2H), 7.85 (s, 1H), 7.78 (dd, J = 7.8, 1.6 Hz, 1H), 7.70 (d, J = 2.1 Hz, 1H), 7.66-7.60 (m, 2H), 7.43 (d, J = 8.4 Hz, 1H), 7.39-7.31 (m, 2H), 4.68 (d, J = 5.6 Hz, 2H), 3.98 (s, 3H); |
| 1710 | (structure with NH₂-pyridine-thiazole-methylamide-dibenzoxazepinone) | E[a], 539, 558 | 6 | 445.0 (M⁺ + 1) | 444.10 for $C_{22}H_{16}N_6O_3S$ | ¹H-NMR (DMSO-$d_6$, 400 MHz): δ 10.63 (s, 1H), 9.20 (t, J = 5.8 Hz, 1H), 8.68 (s, 2H), 7.78 (dd, J = 7.7, 1.6 Hz, 1H), 7.73-7.68 (m, 2H), 7.66-7.59 (m, 2H), 7.42 (d, J = 8.3 Hz, 1H), 7.39-7.31 (m, 2H), 7.17 (s, 2H), 4.63 (d, J = 5.6 Hz, 2H) |

TABLE 2-continued

Synthesis from compound 535, 536, 538, 539 common intermediates

| Example | Structure | Procedure, Intermediate, or boronic acid or boronate esters | Rx. Yield | Mass Spec. Found | Mass Spec. Calculated | ¹H-NMR |
|---------|-----------|---------------|-----------|------------------|----------------------|--------|
| 1711 | (structure with dimethylamino-pyrimidine-thiazole-dibenzoxazepinone) | D$^f$, 539, 571 | 14 | 473.0 (M$^+$ + 1); | 472.13 for C$_{24}$H$_{20}$N$_6$O$_3$S | ¹H-NMR (DMSO-d$_6$, 400 MHz): δ 10.63 (s, 1H), 9.20 (t, J = 5.7 Hz, 1H), 8.79 (s, 2H), 7.78 (dd, J = 7.8, 1.6 Hz, 1H), 7.73-7.68 (m, 2H), 7.66-7.60 (m, 2H), 7.42 (d, J = 8.4 Hz, 1H), 7.38-7.31 (m, 2H), 4.64 (d, J = 5.5 Hz, 2H), 3.18 (s, 6H); |
| 1714-A | (structure with 3-cyanophenyl-thiazole-dibenzoxazepinone) | D$^b$, 539, 559 | 71 | 452.9 (M$^+$ + 1); | 452.09 for C$_{25}$H$_{16}$N$_4$O$_3$S | ¹H-NMR (DMSO-d$_6$, 400 MHz): δ 10.64 (s, 1H), 9.26 (t, J = 5.6 Hz, 1H), 8.30 (s, 1H), 8.21 (d, J = 7.8 Hz, 1H), 7.92 (d, J = 7.8 Hz, 1H), 7.87 (s, 1H), 7.78 (dd, J = 7.7, 1.3 Hz, 1H), 7.71-7.61 (m, 4H), 7.43 (d, J = 8.4 Hz, 1H), 7.38-7.32 (m, 2H), 4.69 (d, J = 5.8 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1736-A | (structure) | D, 539, 560 | 49 | 472.0 (M$^+$ + 1) | 471.13 $C_{26}H_{21}N_3O_4S$ | $^1$H-NMR (DMSO-d$_6$, 500 MHz): δ 10.64 (s, 1H), 9.19 (t, J = 5.3 Hz, 1H), 7.78 (d, J = 7.2 Hz, 1H), 7.73-7.60 (m, 6H), 7.42 (d, J = 8.1 Hz, 1H), 7.39-7.31 (m, 2H), 7.01 (d, J = 8.4 Hz, 1H), 4.63 (d, J = 5.5 Hz, 2H), 3.83 (s, 3H), 2.19 (s, 3H); |
| 1737 | (structure) | E$^d$, 539, 561 | 11 | 486.0 (M$^+$ + 1) | 467.11 for $C_{25}H_{17}N_5O_3S$ | $^1$H-NMR (DMSO-d$_6$, 400 MHz): δ 13.26 (br s, 1H), 10.64 (br s, 1H), 9.22 (t, J = 5.8 Hz, 1H), 8.30 (s, 1H), 8.16 (s, 1H), 7.90 (dd, J = 8.7, 1.4 Hz, 1H), 7.80-7.74 (m, 2H), 7.71 (s 1H), 7.67-7.58 (m, 3H), 7.43 (d, J = 8.4 Hz, 1H), 7.39-7.30 (m, 2H), 4.66 (d, J = 5.6 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | 1H-NMR |
|---|---|---|---|---|---|---|
| 1738-A | 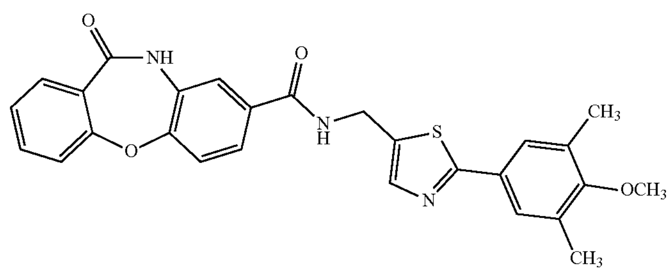 [SMILES: COc1c(C)cc(-c2ncc(CNC(=O)c3ccc4c(c3)NC(=O)c3ccccc3O4)s2)cc1C] | D°, 539, 562 | 68 | 486.0 (M+ + 1); | 485.14 for C27H23N3O4S | 1H-NMR (DMSO-d6, 500 MHz): δ 10.64 (s, 1H), 9.21 (t, J = 5.8 Hz, 1H), 7.78 (dd, J = 7.7, 1.6 Hz, 1H), 7.73-7.69 (m, 2H), 7.66-7.60 (m, 2H), 7.56 (s, 2H), 7.43 (d, J = 8.4 Hz, 1H), 7.37 (d, J = 7.8 Hz, 1H), 7.34 (t, J = 7.5 Hz, 1H), 4.64 (d, J = 5.8 Hz, 2H), 3.68 (s, 3H), 2.26 (s, 6H); |
| 1831 | 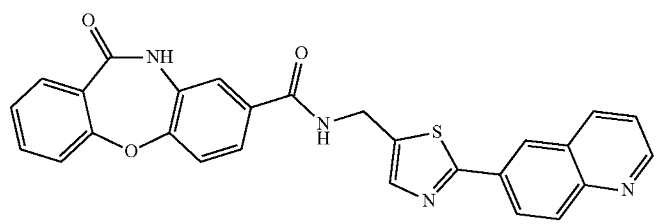 [SMILES: O=C(NCc1cnc(-c2ccc3ncccc3c2)s1)c1ccc2c(c1)NC(=O)c1ccccc1O2] | D°, 539, 564 | 16 | 479.1 (M+ + 1); | 478.11 for C27H18N4O3S | 1H NMR (DMSO-d6, 400 MHz): δ 10.65 (s, 1H), 9.27 (t, J = 5.8 Hz, 1H), 8.93 (dd, J = 4.3, 1.8 Hz, 1H), 8.54 (d, J = 2.0 Hz, 1H), 8.50 (dd, J = 0.9, 8.6 Hz, 1H), 8.29 (dd, J = 8.8, 2.1 Hz, 1H), 8.09 (d, J = 8.8 Hz, 1H), 7.88 (s, 1H), 7.79 (dd, J = 7.7, 1.7 Hz, 1H), 7.72 (d, J = 2.0 Hz, 1H), 7.68-7.56 (m, 3H), 7.44 (d, J = 8.4 Hz, 1H), 7.39-7.31 (m, 2H), 4.71 (d, J = 5.6 Hz, 2H) |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1832 | 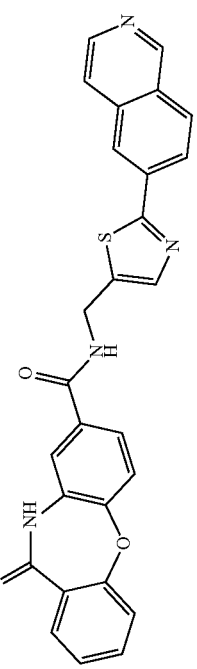 | D$^o$, 539, 565 | 10 | 479.1 (M$^+$ + 1); | 478.11 for $C_{27}H_{18}N_4O_3S$ | $^1$H NMR (DMSO-d$_6$, 400 MHz): δ 10.65 (s, 1H), 9.34 (s, 1H), 9.29 (br t, J = 5.7 Hz, 1H), 8.55 (d, J = 5.8 Hz, 1H), 8.51 (s, 1H), 8.21 (s, 2H), 7.95 (d, J = 5.6 Hz, 1H), 7.92 (s, 1H), 7.79 (dd, J = 7.7, 1.6 Hz, 1H), 7.72 (d, J = 2.0 Hz, 1H), 7.68-7.60 (m, 2H), 7.44 (d, J = 8.4 Hz, 1H), 7.40-7.29 (m, 2H), 4.72 (d, J = 5.5 Hz, 2H); |
| 1861 | 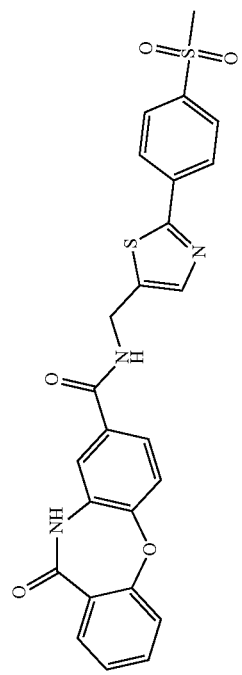 | D$^o$, 539, 567 | 31 | 506.1 (M$^+$ + 1); | 505.08 for $C_{25}H_{19}N_3O_5S_2$ | $^1$H NMR (DMSO-d$_6$, 400 MHz): δ 10.63 (s, 1H), 9.25 (t, J = 5.8 Hz, 1H), 8.13 (d, J = 8.4 Hz, 2H), 7.99 (d, J = 8.4 Hz, 2H), 7.89 (s, 1H), 7.77 (dd, J = 7.8, 1.4 Hz, 1H), 7.69 (d, J = 1.7 Hz, 1H), 7.61 (dd, J = 9.0, 2.0 Hz, 2H), 7.42 (d, J = 8.4 Hz, 1H), 7.35 (d, J = 8.1 Hz, 1H), 7.32 (t, J = 7.7 Hz, 1H), 4.68 (d, J = 5.5 Hz, 2H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1862 | 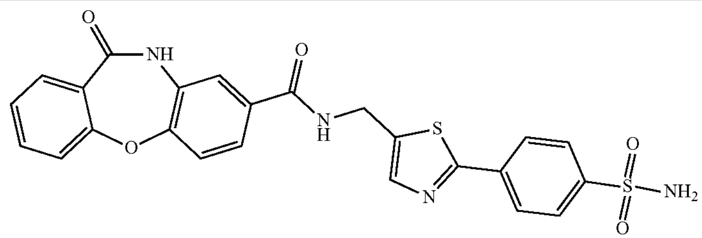 [SMILES: NS(=O)(=O)c1ccc(-c2ncc(CNC(=O)c3ccc4c(c3)NC(=O)c3ccccc3O4)s2)cc1] | D, 539, 576 | 15 | 507.1 (M$^+$ + 1); | 506.07 for $C_{24}H_{18}N_4O_5S_2$ | $^1$H NMR (DMSO-d$_6$, 400 MHz): δ 10.64 (s, 1H), 9.26 (t, J = 5.7 Hz, 1H), 8.07 (d, J = 8.5 Hz, 2H), 7.93-7.86 (m, 3H), 7.78 (dd, J = 7.7, 1.4 Hz, 1H), 7.70 (d, J = 1.8 Hz, 1H), 7.67-7.59 (m, 2H), 7.49-7.40 (m, 3H), 7.39-7.30 (m, 2H), 4.69 (d, J = 5.6 Hz, 2H); |
| 1863 | 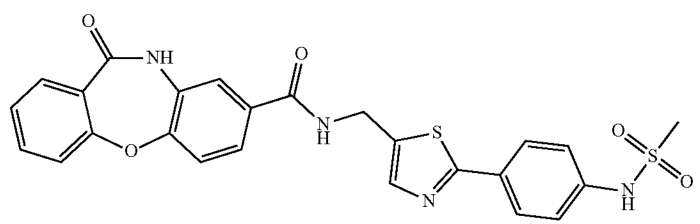 [SMILES: CS(=O)(=O)Nc1ccc(-c2ncc(CNC(=O)c3ccc4c(c3)NC(=O)c3ccccc3O4)s2)cc1] | D$^p$, 539, 568 | 25 | 521.0 (M$^+$ + 1); | 520.09 for $C_{25}H_{20}N_4O_5S_2$ | $^1$H NMR (400 MHz, DMSO-d$_6$) δ 10.63 (s, 1H), 10.05 (s, 1H), 9.20 (t, J = 5.8 Hz, 1H), 7.83 (d, J = 8.8 Hz, 2H), 7.77 (dd, J = 7.7, 1.7 Hz, 1H), 7.73 (s, 1H), 7.69 (d, J = 2.1 Hz, 1H), 7.65-7.60 (m Hz, 2H), 7.42 (d, J = 8.4 Hz, 1H), 7.37-7.30 (m, 2H), 7.26 (d, J = 8.8 Hz, 2H), 4.64 (d, J = 5.5 Hz, 2H), 3.04 (s, 3H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1865 | 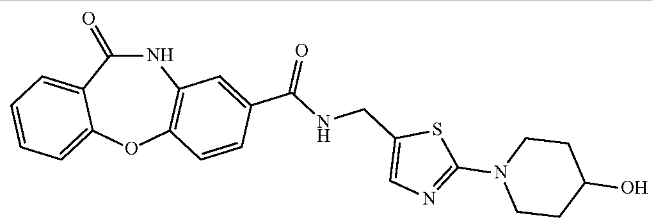 [SMILES: O=C(NCc1cnc(N2CCC(O)CC2)s1)c1ccc2c(c1)NC(=O)c1ccccc1O2] | G$^a$, 539, 485 | 34 | 451.1 (M$^+$ + 1); | 450.14 for C$_{23}$H$_{22}$N$_4$O$_4$S | $^1$H NMR (DMSO-d$_6$, 400 MHz): δ 10.62 (s, 1H), 9.05-8.93 (m, 1H), 7.78 (dd, J = 7.7, 1.6 Hz, 1H), 7.71-7.55 (m, 3H), 7.44-7.28 (m, 3H), 6.99 (s, 1H), 4.73 (d, J = 4.1 Hz, 1H), 4.41 (d, J = 5.5 Hz, 2H), 3.76-3.52 (m, 3H), 3.14-3.05 (m, 2H), 1.82-1.70 (m, 2H), 1.46-1.33 (m, 2H); |
| 1866 | 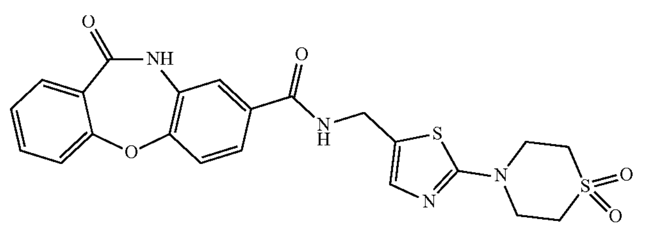 [SMILES: O=C(NCc1cnc(N2CCS(=O)(=O)CC2)s1)c1ccc2c(c1)NC(=O)c1ccccc1O2] | M$^a$, 539, 545 | 14 | 485.1 (M$^+$ + 1); | 484.09 C$_{22}$H$_{20}$N$_4$O$_5$S$_2$ | $^1$H NMR (DMSO-d$_6$, 400 MHz): δ 10.63 (s, 1H), 9.06 (t, J = 5.6 Hz, 1H), 7.78 (d, J = 6.7 Hz, 1H), 7.69-7.58 (m, 3H), 7.41 (d, J = 8.3 Hz, 1H), 7.38-7.30 (m, 2H), 7.07 (s, 1H), 4.44 (d, J = 5.5 Hz, 2H), 3.91-3.84 (m, 4H), 3.23-3.14 (m, 4H); |

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | $^1$H-NMR |
|---|---|---|---|---|---|---|
| 1893 | (structure) | H, 539, 610 | 9 | 435.0 (M$^+$ + 1) | 434.05 C$_{21}$H$_{14}$N$_4$O$_3$S$_2$ | $^1$H NMR (DMSO-d$_6$, 400 MHz): δ 10.63 (s, 1H), 9.25 (t, J = 5.5 Hz, 1H), 7.95 (d, J = 3.1 Hz, 1H), 7.90 (d, J = 3.1 Hz, 1H), 7.86 (s, 1H), 7.78 (dd, J = 7.7, 1.6 Hz, 1H), 7.69 (d, J = 2.0 Hz, 1H), 7.66-7.60 (m, 2H), 7.43 (d, J = 8.3 Hz, 1H), 7.39-7.31 (m, 2H), 4.67 (d, J = 5.5 Hz, 2H); |

D$^a$: Pd(PPh$_3$)$_4$ (0.1 equiv), reaction temp 90-100° C.;
D$^b$: Pd(PPh$_3$)$_4$ (0.1 equiv), Na$_2$CO$_3$ (3.0 equiv);
D$^c$: Pd(PPh$_3$)$_4$ (0.1 equiv), boronic acid (2 equiv), Na$_2$CO$_3$ (5 equiv), reaction time 4 h;
D$^d$: Pd(PPh$_3$)$_4$ (0.1 equiv), reaction temp 110° C.;
D$^e$: 1,4-dioxane: H$_2$O (4:1);
D$^f$: Pd(PPh$_3$)$_4$ (0.1 equiv), reaction performed in a sealed tube;
D$^g$: reaction performed at 80° C.;
D$^h$: boronate ester (2 equiv);
D$^i$: Pd(PPh$_3$)$_4$ (0.1 equiv), boronic acid (2.5 equiv), Na$_2$CO$_3$ (5 equiv), 80-90° C.;
D$^j$: Pd(PPh$_3$)$_4$ (0.1 equiv), boronic acid (2 equiv), Na$_2$CO$_3$ (5 equiv), reaction time 16 h;
D$^o$: Reaction performed in a sealed tube;
D$^p$: DME:H$_2$O (3:1), Na$_2$CO$_3$ (3 equiv), boronic acid/Ester (1.2 equiv), reaction performed in sealed tube, reaction temp 120° C., 16 h;
D$^q$: Reaction time 24 h;
D$^r$: Cs$_2$CO$_3$ (3 equiv), reaction performed in sealed tube at 120° C, reaction time 16 h;
D$^s$: Na$_2$CO$_3$ (3.5 equiv), boronic acid (3 equiv), Pd(dppf)Cl$_2$ (0.1 equiv), DME, sealed tube, 120° C, 16 h;
E$^a$: boronate ester (2.5 equiv), reaction time 16 h at 120° C., sealed tube;
E$^c$: Pd(PPh$_3$)$_4$ (0.1 equiv), 100° C., reaction time 24 h;
E$^d$: Pd(PPh$_3$)$_4$ (0.1 equiv), 120° C., reaction time 48 h;
F$^a$: Amine (3 equiv), 160° C., 16 h;
G$^a$: Amine (3 equiv), DIPEA (3 equiv), 100° C., 20 h;
G$^b$: Amine (1.5 equiv), 110° C., 16 h;
G$^c$: Amine (2 equiv), 160° C., 20 h;
G$^d$: Amine (2 equiv), DIPEA (3 equiv), 160° C., 16 h;

TABLE 2-continued

Synthesis from compound 535, 536, 538, 539 common intermediates

| Example | Structure | Procedure, Intermediate, boronic acid or boronate esters | Rx. Yield | Mass Spec. Found | Mass Spec. Calculated | ¹H-NMR |
|---------|-----------|------|-----------|------------------|----------------------|--------|

H$^a$: 700 mg of crude tin reagent was taken for the 200 mg batch;
H$^b$: 2 g of crude tin reagent was taken for the 200 mg batch, Pd(dppf)Cl$_2$ (0.1 equiv), 100° C., reaction time 16 h;
H$^c$: tin reagent (1 equiv), Pd(dppf)Cl$_2$ (0.1 equiv), 1,4-dioxane, 110° C., 16 h;
H$^d$: tin reagent (5 equiv), 120° C.;
I$^a$: amine (1.2 equiv), Cs$_2$CO$_3$ (3 equiv);
I$^b$: Cs$_2$CO$_3$ (2 equiv);
J$^a$: amine (1.5 equiv), Xantphos (0.05 equiv), Pd$_2$(dba)$_3$ (0.025 equiv), Cs$_2$CO$_3$ (3.5 equiv) conventional heating, 100-110° C.; 16 h;
J$^b$: Cs$_2$CO$_3$ (3 equiv), t-BuXphos (0.07 equiv), Pd$_2$(dba)$_3$ (0.05 equiv), 1,4-dioxane, sealed tube, 100° C., 16 h;
J$^c$: Cs$_2$CO$_3$ (5 equiv); NMP, sealed tube 120° C., 16 h;
K$^a$: amine (2 equiv), Cs$_2$CO$_3$ (5 equiv); NMP, sealed tube 120° C., 16 h;

Synthesis of 1432 & 1433

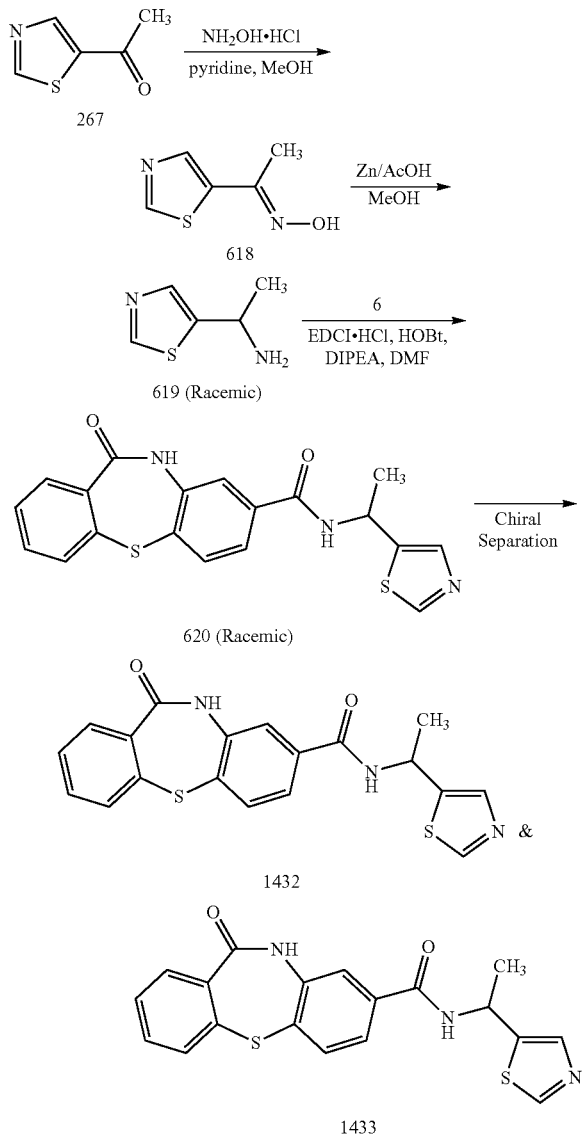

620 (Racemic)

1432

1433

Synthesis of 1-(thiazol-5-yl) ethan-1-one oxime (618)

To a stirring solution of compound 267 (800 mg, 6.29 mmol) in MeOH (20 mL) under inert atmosphere was added hydroxyl amine hydrochloride (875 mg, 12.59 mmol) and pyridine (2 mL) dropwise for 5 min at 0° C. warmed to RT and stirred for 16 h. The reaction was monitored by TLC; after completion of the reaction, the volatiles were removed in vacuo diluted with water (50 mL) and stirred for 30 min. The precipitated solid was filtered dried in vacuo to afford compound 618 (800 mg, 90%) as white solid. TLC: 40% EtOAc/hexanes ($R_f$: 0.4, 0.6); 41 NMR (DMSO-$d_6$, 400 MHz) (Mixture of E/Z isomers): δ 11.86 (s, 1H), 11.41 (s, 0.6H), 9.19 (s, 1H), 9.01 (s, 0.56H), 8.35 (s, 1H), 8.15 (s, 0.65H), 2.31 (s, 3H), 2.21 (s, 2H).

Synthesis of 1-(thiazol-5-yl) ethan-1-amine (619)

To a stirring solution of compound 618 (800 mg, 5.63 mmol) in MeOH:acetic acid (1:1, 20 mL) under inert atmosphere were zinc powder (2.2 g, 33.80 mmol) at RT; heated at 50° C. and stirred for 4 h. The reaction was monitored by TLC; after completion of the reaction, the reaction mixture was filtered through celite washed with MeOH (3×10 mL). The filtrate was removed in vacuo, the residue was diluted with water (20 mL), basified with aqueous ammonia (15 mL) and extracted with EtOAc (3×50 mL). The combined organic extracts were dried over sodium sulfate, filtered and concentrated in vacuo to obtain the crude compound 619 (racemic) (700 mg, 92%) as brown syrup. TLC: 5% MeOH/CH$_2$Cl$_2$ ($R_f$: 0.4, 0.6); $^1$H NMR (DMSO-$d_6$, 400 MHz): δ 8.90 (s, 1H), 7.71 (s, 1H), 4.33-4.28 (m, 1H), 3.38 (t, J=6.4 Hz, 1H), 1.87 (s, 3H).

Synthesis of 11-oxo-N-(1-(thiazol-5-yl) ethyl)-10,11-dihydrodibenzo [b, f] [1, 4] thiazepine-8-carboxamide (620 Racemic)

Using typical procedure A the title compound was prepared with DBT-Acid (150 mg, 0.55 mmol) and compound 619 racemic (109 mg, 0.66) to afford compound 620 (Racemic) (100 mg, 48%); TLC: 5% MeOH/CH$_2$Cl$_2$ ($R_f$: 0.5); $^1$H NMR (DMSO-$d_6$, 400 MHz): δ 10.87 (br s, 1H), 9.14 (d, J=8.0 Hz, 1H), 8.95 (s, 1H), 7.79 (d, J=3.6 Hz, 2H), 7.70-7.58 (m, 3H), 7.56-7.42 (m, 3H), 5.48-5.41 (m, 1H), 1.60 (s, 3H); LC-MS: 98.31%; 381.9 (M$^+$+1); (column; Ascentis Express C18, (50×3.0 mm, 2.7 μm); RT 2.03 min. 0.025% Aq. TFA+5% ACN: ACN+5% 0.025% Aq. TFA, 1.2 mL/min); HPLC (purity): 97.68%; (column; Eclipse XDB C-18 (150×4.6 mm, 5.0 μm); RT 7.58 min. ACN: 0.05% TFA (Aq); 1.0 mL/min) (IP14012554); Chiral HPLC: 35.10%, R$_t$=9.01 min (Chiralpak-IA, 250×4.6 mm, 5 μm); mobile phase (A) 0.1% DEA in n-Hexane (B) CH$_2$Cl$_2$:MeOH (50:50) (A:B:: 63:35); Flow Rate: 1.0 mL/min).

The racemic compound 620 (100 mg) was separated by preparative HPLC using a CHIRALPAK-IC column (250× 20 mm×5 μm) (10 mg loading; mobile phase (A) 0.1% DEA in n-Hexane (B) CH$_2$Cl$_2$:MeOH:DMF (65:35:05) (A:B:: 75:25) to afford 1432 (10 mg) and 1433 (15 mg) as an off-white solids.

Analytical Data of 1432

TLC: 5% MeOH/CH$_2$Cl$_2$ ($R_f$: 0.5); $^1$H NMR (DMSO-$d_6$, 400 MHz): δ 10.75 (s, 1H), 9.02 (d, J=7.8 Hz, 1H), 8.95 (s, 1H), 7.79 (s, 1H), 7.72-7.64 (m, 3H), 7.62-7.58 (m, 1H), 7.56-7.41 (m, 3H), 5.45 (t, J=7.0 Hz, 1H), 1.57 (d, J=6.8 Hz, 3H); LC-MS: 96.06%; 381.8 (M$^+$+1); (column; Ascentis Express C18, (50×3.0 mm, 2.7 μm); RT 2.03 min. 0.025% Aq. TFA+5% ACN: ACN+5% 0.025% Aq. TFA, 1.2 mL/min); HPLC (purity): 95.02%; (column; Zorbax SB C-18 (150×4.6 mm, 3.5 μm); RT 7.79 min. ACN: 0.05% TFA (Aq); 1.0 mL/min) (IP15010530); Chiral HPLC: 96.24%, R$_t$=14.33 min (Chiralpak-IA, 250×4.6 mm, 5 μm); mobile phase (A) 0.1% DEA in n-Hexane (B) CH$_2$Cl$_2$:MeOH:DMF (65:35:05) (A:B: 75:25); Flow Rate: 1.0 mL/min).

Analytical Data of 1433

TLC: 5% MeOH/CH$_2$Cl$_2$ ($R_f$: 0.5); $^1$H NMR (DMSO-$d_6$, 400 MHz): δ 10.75 (s, 1H), 9.03 (d, J=8.3 Hz, 1H), 8.95 (s, 1H), 7.79 (s, 1H), 7.71-7.63 (m, 3H), 7.62-7.58 (m, 1H), 7.56-7.42 (m, 3H), 5.48-5.47 (m, 1H), 1.57 (d, J=6.9 Hz, 3H); LC-MS: 96.65%; 381.9 (M$^+$+1); (column; Ascentis Express C18, (50×3.0 mm, 2.7 μm); RT 2.68 min. 0.025% Aq. TFA+5% ACN: ACN+5% 0.025% Aq. TFA, 1.2 mL/min); HPLC (purity): 98.53%; (column; Zorbax SB C-18 (150×4.6 mm, 3.5 μm); RT 7.76 min. ACN: 0.05% TFA (Aq); 1.0 mL/min) (IP15010229). Chiral HPLC: 99.87%, R$_t$=16.90 min (Chiralpak-IA, 250×4.6 mm, 5 μm); mobile phase (A) 0.1% DEA in n-Hexane (B) CH$_2$Cl$_2$: MeOH:DMF (65:35:05) (A:B: 75:25); Flow Rate: 1.0 mL/min).

Synthesis of 1602

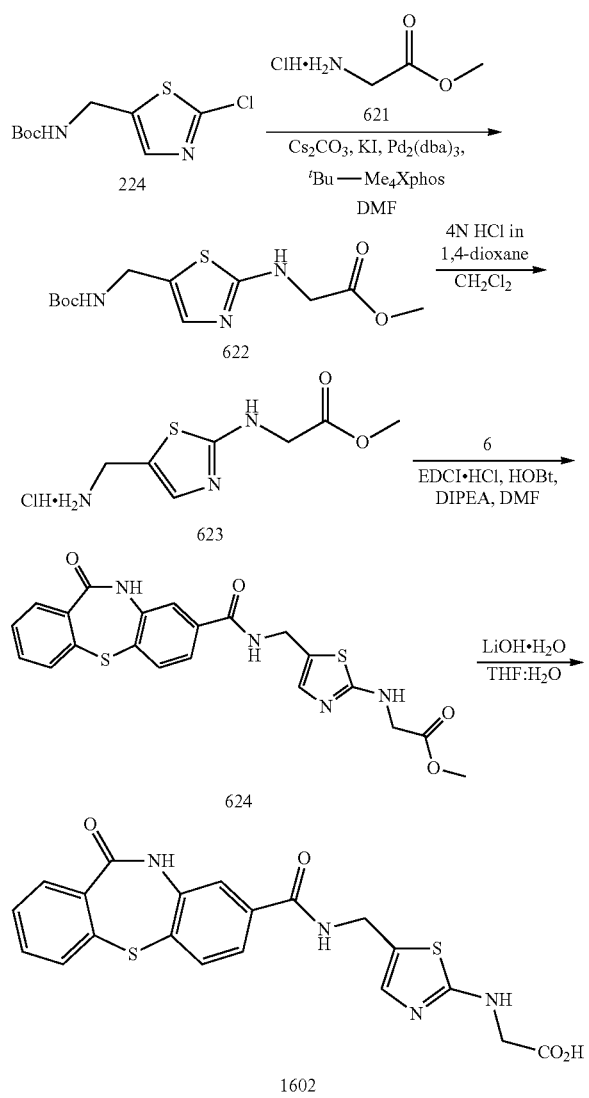

Synthesis of methyl (5-(((tert-butoxycarbonyl) amino) methyl) thiazol-2-yl) glycinate (622)

To a stirring solution of tert-butyl ((2-chlorothiazol-5-yl) methyl) carbamate 224 (500 mg, 2.01 mmol) in DMF (10 mL) were added methyl glycinate hydrochloride 621 (506 mg, 4.03 mmol), potassium iodide (334 mg, 2.01 mmol) and purged under argon atmosphere for 15 min in a sealed tube. To this were added and cesium carbonate (1.97 g, 6.04 mmol) purged under argon atmosphere for 5 min; followed by addition of Pd$_2$(dba)$_3$ (92.3 mg, 0.10 mmol), $^t$Bu-Me$_4$Xphos (96.9 mg, 0.20 mmol) at RT; heated to 100° C. and stirred for 18 h. The reaction was monitored by TLC; after completion of the reaction, the reaction mixture diluted with water (100 mL) and extracted with EtOAc (2×100 mL). The combined organic extracts were washed with water (100 mL) and brine (50 mL), dried over sodium sulfate, filtered and concentrated in vacuo to obtain the crude. The crude was purified through silica gel column chromatography using 40% EtOAc/hexanes further purified by preparative HPLC purification to afford compound 622 (210 mg, 9%) as an off-white solid. TLC: 30% EtOAc/hexanes (R$_f$: 0.5); $^1$H-NMR (DMSO-d$_6$, 500 MHz): 7.81 (t, J=5.2 Hz, 1H), 7.28 (t, J=5.5 Hz, 1H), 6.75 (s, 1H), 4.04 (d, J=5.5 Hz, 2H), 3.99 (d, J=6.1 Hz, 2H), 3.62 (s, 3H), 1.38 (s, 9H).

Synthesis of methyl (5-(aminomethyl) thiazol-2-yl) glycinate hydrochloride (623)

To a stirring solution of compound 622 (200 mg, 0.66 mmol) in CH$_2$Cl$_2$ (5 mL) was added 4 N HCl in 1, 4-dioxane (5 mL) under inert atmosphere at 0° C.; warmed to RT and stirred for 16 h. The reaction was monitored by TLC; after completion of the reaction, the volatiles were removed in vacuo. The crude was triturated with diethyl ether (2×5 mL) and dried in vacuo to afford compound 623 (190 mg, HCl salt) as an off-white solid. TLC: 40% EtOAc/hexanes (R$_f$: 0.2); $^1$H-NMR (DMSO-d$_6$, 400 MHz): δ 8.69 (br s, 1H), 8.23 (br s, 3H), 7.15 (s, 1H), 4.14-4.11 (m, 2H), 4.05 (q, J=5.4 Hz, 2H), 3.64 (s, 3H).

Synthesis of methyl (5-((11-oxo-10, 11-dihydrodibenzo [b, f] [1, 4] thiazepine-8-carboxamido) methyl) thiazol-2-yl) glycinate (624)

To a stirring solution of compound 6 (100 mg, 0.49 mmol) in DMF (5 mL) under inert atmosphere were added compound 623 (90 mg, 0.37 mmol), EDCI.HCl (137 mg, 0.75 mmol), HOBt (102 mg, 0.75 mmol) and diisopropylethylamine (0.35 mL, 1.89 mmol) at 0° C.; warmed to RT and stirred for 16 h. The reaction was monitored by TLC; after completion of the reaction, the reaction mixture was diluted with ice-cold water (50 mL). The obtained solid was filtered and dried in vacuo to obtain the crude. The crude was purified through silicagel column chromatography using 4-10% MeOH/CH$_2$Cl$_2$ to afford compound 624 (95 mg, 57%) as pale yellow solid. TLC: 10% MeOH/CH$_2$Cl$_2$ (R$_f$: 0.4); $^1$H-NMR (DMSO-d$_6$ 500 MHz): δ 10.75 (s, 1H), 9.03 (t, J=6.1 Hz, 1H), 7.83 (t, J=6.2 Hz, 1H), 7.72-7.63 (m, 3H), 7.59-7.42 (m, 4H), 6.86 (s, 1H), 4.37 (d, J=5.8 Hz, 2H), 3.99 (d, J=6.1 Hz, 2H), 3.61 (s, 3H).

Synthesis of (5-((11-oxo-10, 11-dihydrodibenzo [b, f] [1, 4] thiazepine-8-carboxamido) methyl) thiazol-2-yl) glycine (1602)

To a stirring solution of compound 624 (90 mg, 0.19 mmol) in THF:H$_2$O (1:1, 10 mL) was added lithium hydroxide monohydrate (46 mg, 0.99 mmol) at RT and stirred for 4 h. The reaction was monitored by TLC; after completion of the reaction, the reaction mixture was diluted with water (50 mL), washed with EtOAc (2×10 mL). The pH of the aqueous layer was acidified with 4 N HCl to ~2. The precipitated solid was filtered, washed with water (10 mL)

and triturated with CH$_3$CN (5 mL) and dried in vacuo to afford 1602 (60 mg, 69%) as an off-white solid. TLC: 10% MeOH/CH$_2$Cl$_2$ (R$_f$: 0.2); $^1$H-NMR (DMSO-d$_6$, 500 MHz): δ 10.75 (s, 1H), 9.02 (t, J=5.5 Hz, 1H), 7.71-7.62 (m, 3H), 7.60-7.43 (m, 5H), 6.85 (s, 1H), 4.37 (d, J=5.5 Hz, 2H), 3.76 (d, J=4.3 Hz, 2H); LC-MS: 93.40%; 440.9 (M$^+$+1); (column; Ascentis Express C18, (50×3.0 mm, 2.7 μm); RT 1.77 min. 0.025% Aq. TFA+5% ACN: ACN+5% 0.025% Aq. TFA, 1.2 mL/min); HPLC (purity): 94.16%; (column; X-select CSH C-18 (150×4.6 mm, 3.5 μm); RT 5.80 min. 0.05% TFA (Aq): ACN; 1.0 mL/min).

Synthesis of 1603

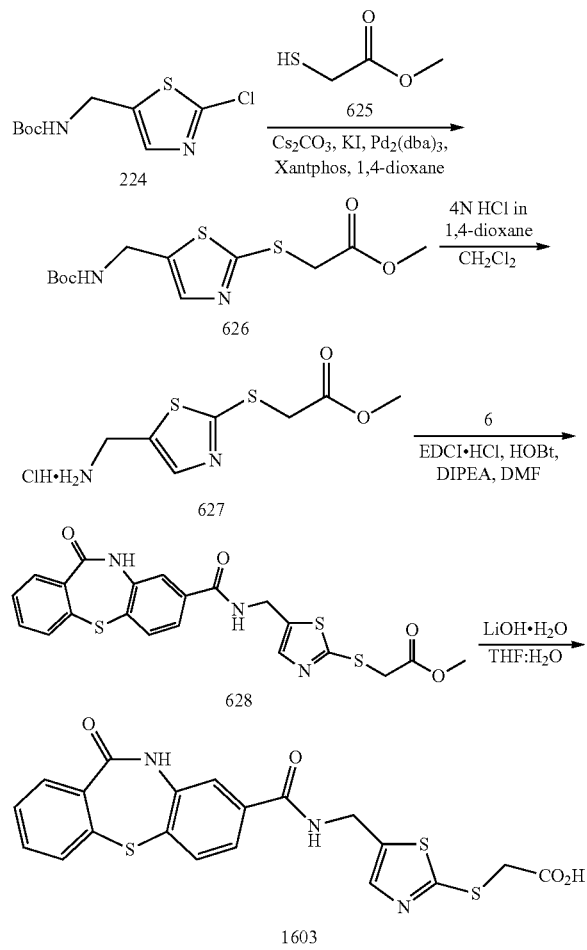

Synthesis of methyl 2-((5-(((tert-butoxycarbonyl) amino) methyl) thiazol-2-yl) thio) acetate (626)

To a stirring solution of tert-butyl ((2-chlorothiazol-5-yl) methyl) carbamate 224 (1 g, 4.03 mmol) in 1, 4-dioxane (10 mL) was added methyl thioglycolate 625 (1.3 mL, 12.09 mmol), potassium iodide (1.34 g, 8.06 mmol) and cesium carbonate (2.62 g, 8.06 mmol) at RT in a sealed tube and purged under argon atmosphere for 15 min. To this were added Pd$_2$(dba)$_3$ (184 mg, 0.20 mmol), Xantphos (163 mg, 0.28 mmol) at RT; heated to 120° C. and stirred for 18 h. The reaction was monitored by TLC; after completion of the reaction, the volatiles were removed in vacuo. The residue was diluted with EtOAc (200 mL), washed with water (100 mL) and brine (50 mL). The organic extract was dried over sodium sulfate, filtered and concentrated in vacuo to obtain the crude. The crude was purified through silica gel column chromatography using 20-30% EtOAc/hexanes to afford compound 626 (620 mg, 48%) as pale yellow thick syrup. TLC: 30% EtOAc/hexanes (R$_f$: 0.2); $^1$H-NMR (DMSO-d$_6$, 500 MHz): δ 7.49 (t, J=6.1 Hz, 1H), 7.47 (s, 1H), 4.22 (d, J=5.8 Hz, 2H), 4.12 (s, 2H), 3.65 (s, 3H), 1.38 (s, 9H).

Synthesis of methyl 2-((5-(aminomethyl) thiazol-2-yl) thio) acetate hydrochloride (627)

To a stirring solution of compound 626 (500 mg, 1.57 mmol) in CH$_2$Cl$_2$ (2 mL) was added 4 N HCl in 1, 4-dioxane (5 mL) under inert atmosphere at 0° C.; warmed to RT and stirred for 4 h. The reaction was monitored by TLC; after completion of the reaction, the volatiles were removed in vacuo. The crude was triturated with diethyl ether (2×5 mL) and dried in vacuo to afford compound 627 (400 mg, HCl salt) as an off-white solid. TLC: 30% EtOAc/hexanes (R$_f$: 0.2); $^1$H-NMR (DMSO-d$_6$, 500 MHz): δ 8.47 (br s, 3H), 7.75 (s, 1H), 4.24 (q, J=5.7 Hz, 2H), 4.18 (s, 2H), 3.66 (s, 3H).

Synthesis of methyl 2-((5-((11-oxo-10, 11-dihydrodibenzo [b, f] [1, 4] thiazepine-8-carboxamido) methyl) thiazol-2-yl) thio) acetate (628)

To a stirring solution of compound 6 (150 mg, 0.58 mmol) in DMF (5 mL) under inert atmosphere were added compound 627 (139 mg, 0.64 mmol), EDCI.HCl (224 mg, 1.17 mmol), HOBt (158 mg, 1.17 mmol) and diisopropylethylamine (0.30 mL, 1.76 mmol) at 0° C.; warmed to RT and stirred for 16 h. The reaction was monitored by TLC; after completion of the reaction, the reaction mixture was diluted with water (50 mL), the precipitated solid was filtered and dried in vacuo to afford compound 628 (180 mg, 65%) as an off-white solid. TLC: 10% MeOH/CH$_2$Cl$_2$ (R$_f$: 0.4); $^1$H-NMR (DMSO-d$_6$ 500 MHz): δ 10.75 (br s, 1H), 9.20 (t, J=4.6 Hz, 1H), 7.71-7.62 (m, 3H), 7.59-7.40 (m, 5H), 4.53 (d, J=5.2 Hz, 2H), 4.10 (s, 2H), 3.62 (s, 3H).

Synthesis of 2-((5-((11-oxo-10, 11-dihydrodibenzo [b, f] [1, 4] thiazepine-8-carboxamido) methyl) thiazol-2-yl) thio) acetic acid (1603)

To a stirring solution of compound 628 (100 mg, 0.21 mmol) in THF:H$_2$O (5:1, 6 mL) was added lithium hydroxide monohydrate (15 mg, 0.31 mmol) at 0° C.; warmed to RT and stirred for 2 h. The reaction was monitored by TLC; after completion of the reaction, the reaction mixture was volatiles were removed in vacuo. The crude was diluted with water (20 mL) and washed with EtOAc (2×10 mL). The pH of the aqueous layer was adjusted with 4 N HCl to ~2. The precipitated solid was filtered and dried in vacuo to afford 1603 (42 mg, 43%) as an off-white solid. TLC: 10% MeOH/CH$_2$Cl$_2$ (R$_f$: 0.2); $^1$H-NMR (DMSO-d$_6$, 500 MHz): δ 10.76 (s, 1H), 9.21 (t, J=5.8 Hz, 1H), 7.71-7.64 (m, 3H), 7.61-7.42 (m, 5H), 4.54 (d, J=4.9 Hz, 2H), 3.99 (s, 2H); LC-MS: 95.88%; 457.9 (M$^+$+1); (column; Ascentis Express C18, (50×3.0 mm, 2.7 μm); RT 2.11 min. 0.025% Aq. TFA+5% ACN: ACN+5% 0.025% Aq. TFA, 1.2 mL/min); HPLC (purity): 92.76%; (column; X-select CSH C-18 (150× 4.6 mm, 3.5 μm); RT 7.99 min. ACN+0.5% TFA (Aq)+0.5% TFA (Aq)+5% ACN; 1.0 mL/min).

Synthesis of 1735

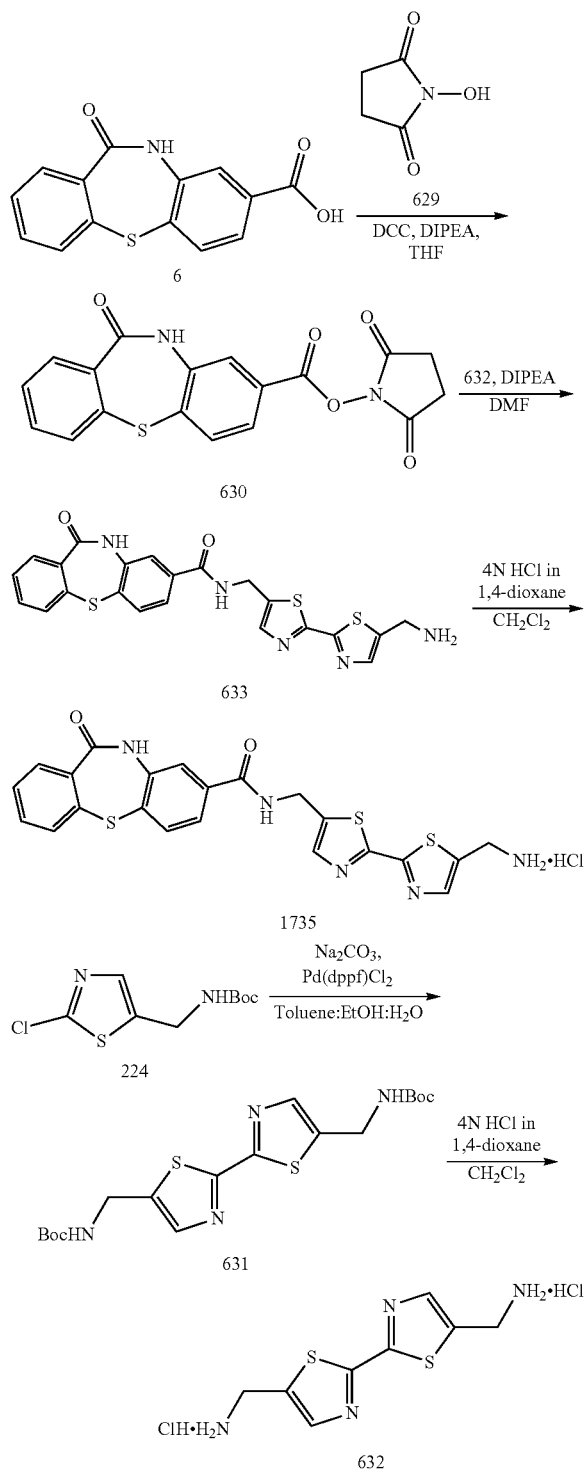

Synthesis of di-tert-butyl ([2, 2'-bithiazole]-5, 5'-diylbis (methylene)) dicarbamate (631)

To a stirring solution of tert-butyl ((2-chlorothiazol-5-yl) methyl) carbamate 224 (2 g, 8.06 mmol) in Toluene:EtOH: H$_2$O (2:2:1, 25 mL) under inert atmosphere was sodium carbonate (1.70 g, 16.12 mmol) at RT and purged under argon atmosphere for 30 min; added Pd(dppf)Cl$_2$ (589 mg, 0.80 mmol) and heated to 100° C. and stirred for 16 h. The reaction was monitored by TLC; after completion of the reaction, the reaction mixture was filtered through celite. The filtrate was concentrated in vacuo to obtain the crude. The crude was purified through silica gel column chromatography using 25% EtOAc/hexanes to afford compound 631 (650 mg) as an off-white solid. TLC: 40% EtOAc/hexanes (R$_f$: 0.3); $^1$H-NMR (DMSO-d$_6$, 500 MHz): δ 7.74 (s, 2H), 7.60 (br s, 2H), 4.34 (d, J=6.1 Hz, 4H), 1.40 (s, 18H); LC-MS: 80.62%; 427.0 (M$^+$+1); (column; Ascentis Express C18, (50×3.0 mm, 2.7 μm); RT 2.56 min. 0.025% Aq. TFA+5% ACN: ACN+5% 0.025% Aq. TFA, 1.2 mL/min).

Synthesis of [2, 2'-bithiazole]-5, 5'-diyldimethanamine dihydrochloride (632)

To a stirring solution of compound 631 (650 mg, 0.52 mmol) in CH$_2$Cl$_2$ (15 mL) under inert atmosphere was added 4 N HCl in 1, 4-dioxane (1 mL) at 0° C.; warmed to RT and stirred for 16 h. The reaction was monitored by TLC; after completion of the reaction, the volatiles were removed in vacuo to obtain the crude. The crude was titurated with CH$_2$Cl$_2$ (2×5 mL) and dried in vacuo to afford compound 632 (380 mg, 84%; HCl salt) as white solid. TLC: 40% EtOAc/hexanes (R$_f$: 0.1); LC-MS: 99.31%; 227.2 (M$^+$+1); (column; Atlantis T3 (150×4.6 mm, 3 μm); RT 5.96 min. 2.5 mM Aq. NH$_4$OAc:ACN; 1.0 mL/min).

Synthesis of 2, 5-dioxopyrrolidin-1-yl 11-oxo-10, 11-dihydrodibenzo [b, f] [1, 4] thiazepine-8-carboxylate (630)

To a stirring solution of 6 (1 g, 3.69 mmol) in THF (20 mL) under inert atmosphere were added diisopropylethylamine (1.98 mL, 11.07 mmol), CDI (910 mg, 4.42 mmol) and N-hydroxysuccinimide 629 (509 mg, 4.42 mmol) at 0° C.; warmed to RT and stirred for 16 h. The reaction was monitored by TLC; after completion of the reaction, the reaction mixture was filtered through celite. The filtrate was diluted with EtOAc (2×50 mL) washed with water (50 mL). The organic extract was dried over sodium sulfate, filtered and concentrated in vacuo to obtain the crude, which was titurated with 10% diethylether/pentane (10 mL) and dried in vacuo to afford compound 630 (1 g, 74%) as an white solid. TLC: 10% MeOH/CH$_2$Cl$_2$ (R$_f$: 0.8); $^1$H NMR (DMSO-d$_6$, 500 MHz): δ 10.89 (s, 1H), 7.91 (s, 1H), 7.85-7.80 (m, 2H), 7.71 (dd, J=7.5, 1.2 Hz, 1H), 7.60-7.47 (m, 3H), 2.88 (s, 4H); LC-MS: 96.35%; 368.9 (M$^+$+1); (column; Ascentis Express C18, (50×3.0 mm, 2.7 μm); RT 2.25 min. 0.025% Aq.TFA+5% ACN: ACN+5% 0.025% Aq. TFA, 1.2 mL/min).

Synthesis of N-((5'-(aminomethyl)-[2, 2'-bithiazol]-5-yl) methyl)-11-oxo-10, 11-dihydrodibenzo [b, f] [1, 4] thiazepine-8-carboxamide (633)

To a stirring solution of compound 630 (365 mg, 1.22 mmol) in DMF (15 mL) under inert atmosphere was added diisopropylethylamine (0.43 mL, 2.43 mmol) at 0° C. stirred for 10 min; added compound 632 (300 mg, 0.81 mmol), heated to 50° C. and stirred for 16 h. The reaction was monitored by TLC; after completion of the reaction, the reaction mixture was diluted with ice-cold water (100 mL)

and extracted with 10% MeOH/CH$_2$Cl$_2$ (2×50 mL). The combined organic extracts were dried over sodium sulfate, filtered and concentrated in vacuo to obtain the crude with titurated with CH$_2$Cl$_2$ (20 mL) and dried in vacuo to afford crude compound 633 (250 mg) as an off-white solid. TLC: 10% MeOH/CH$_2$Cl$_2$ (R$_f$: 0.2); LC-MS: 40.20%; 480.0 (M$^+$+1); (column; Ascentis Express C18, (50×3.0 mm, 2.7 μm); RT 1.80 min. 0.025% Aq. TFA+5% ACN: ACN+5% 0.025% Aq. TFA, 1.2 mL/min).

Synthesis of N-((5'-(aminomethyl)-[2,2'-bithiazol]-5-yl) methyl)-11-oxo-10, 11-dihydrodibenzo [b, f] [1, 4] thiazepine-8-carboxamide hydrochloride (1735)

To a stirring solution of compound 633 (250 mg, 0.52 mmol) in CH$_2$Cl$_2$ (15 mL) under inert atmosphere was added 4 N HCl in 1, 4-dioxane (0.4 mL) at 0° C.; warmed to RT and stirred for 1 h. The reaction was monitored by TLC; after completion of the reaction, the volatiles were removed in vacuo to obtain the crude. The crude was triturated with CH$_2$Cl$_2$ (10 mL), MeOH (5 mL) and further purified by preparative HPLC purification to afford 1735 (28 mg, 4%) as an off-white solid. TLC: 10% MeOH/CH$_2$Cl$_2$ (eluted 2 times) (R$_f$: 0.1); $^1$H-NMR (DMSO-d$_6$, 500 MHz): δ 10.79 (s, 1H), 9.33 (t, J=5.8 Hz, 1H), 8.25 (br s, 3H), 7.97 (s, 1H), 7.88 (s, 1H), 7.72-7.67 (m, 3H), 7.60 (dd, J=8.4, 2.0 Hz, 1H), 7.56-7.44 (m, 3H), 4.67 (d, J=5.8 Hz, 2H), 4.37 (s, 2H); LC-MS: 99.23%; 480.0 (M$^+$+1); (column; Ascentis Express C18, (50×3.0 mm, 2.7 μm); RT 1.77 min. 0.025% Aq. TFA+5% ACN: ACN+5% 0.025% Aq. TFA, 1.2 mL/min); HPLC (purity): 96.62%; (column; X-select CSH C-18 (150×4.6 mm, 3.5 μm); RT 5.52 min. ACN+5% 0.05% TFA (Aq): 0.5% TFA (Aq)+5% ACN; 1.0 mL/min, Diluent: DMSO:ACN:water).

Synthesis of 1599-A & 1599

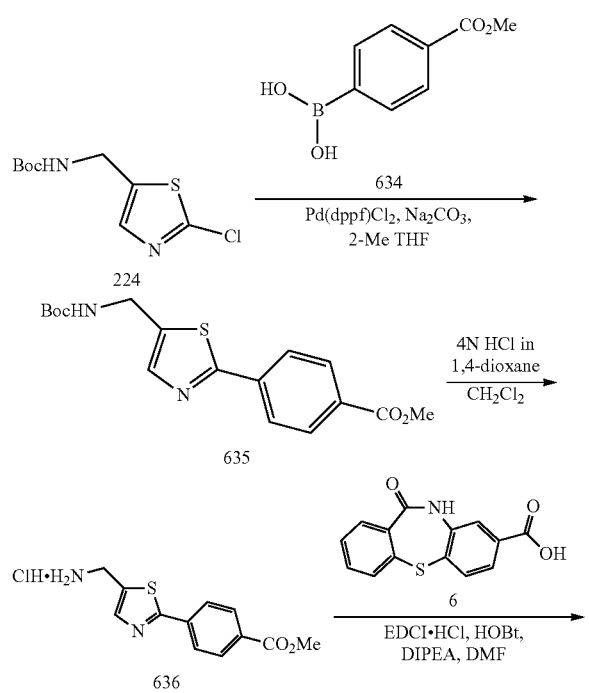

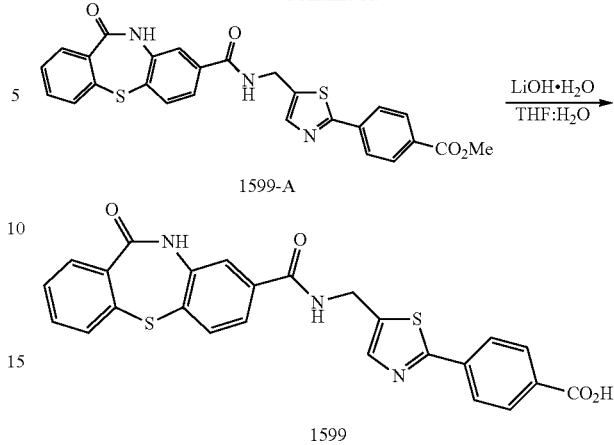

Synthesis of methyl 4-(5-(((tert-butoxycarbonyl) amino) methyl) thiazol-2-yl) benzoate (635)

To a stirring solution of tert-butyl ((2-chlorothiazol-5-yl) methyl) carbamate 224 (500 mg, 2.01 mmol) in 2-methyl-tetrahydrofuran (10 mL) under argon atmosphere were added (4-(methoxycarbonyl) phenyl) boronic acid 634 (435 mg, 2.41 mmol), sodium carbonate (427 mg, 4.02 mmol) at RT in a sealed tube and purged under argon atmosphere for 10 min. To this was added Pd(dppf)Cl$_2$ (73.7 mg, 0.10 mmol); heated to 100° C. and stirred for 16 h. The reaction was monitored by TLC; after completion of the reaction, the reaction mixture was diluted with EtOAc (100 mL), washed with water (50 mL). The organic extract was dried over sodium sulfate, filtered and concentrated in vacuo to obtain the crude. The crude was purified through mobile phase liquid chromatography using 10% EtOAc/hexanes to afford compound 635 (280 mg, 40%) as pale yellow solid. TLC: 30% EtOAc/hexanes (R$_f$: 0.3); $^1$H-NMR (DMSO-d$_6$, 500 MHz): δ 8.05-8.02 (m, 4H), 7.76 (s, 1H), 7.58 (t, J=5.6 Hz, 1H), 4.35 (d, J=6.1 Hz, 2H), 3.86 (s, 3H), 1.39 (s, 9H).

Synthesis of methyl 4-(5-(aminomethyl) thiazol-2-yl) benzoate hydrochloride (636)

To a stirring solution of compound 635 (280 mg, 0.80 mmol) in CH$_2$Cl$_2$ (10 mL) under inert atmosphere was added 4 N HCl in 1, 4-dioxane (10 mL) at 0° C.; warmed to RT and stirred for 3 h. The reaction was monitored by TLC; after completion of the reaction, the volatiles were removed in vacuo to obtain the crude. The crude was washed with diethyl ether (2×30 mL) and dried in vacuo to afford compound 636 (200 mg, 88%) as pale brown solid. TLC: 30% EtOAc/hexanes (R$_f$: 0.2); $^1$H-NMR (DMSO-d$_6$, 500 MHz): δ 8.57 (br s, 3H), 8.10-8.09 (m, 4H), 8.06 (s, 1H), 4.38 (d, J=4.0 Hz, 2H), 3.89 (s, 3H).

Synthesis of methyl 4-(5-((11-oxo-10, 11-dihydrodibenzo [b, f] [1, 4] thiazepine-8-carboxamido) methyl) thiazol-2-yl) benzoate (1599-A)

To a stirring solution of compound 636 (200 mg, 0.74 mmol) in DMF (8 mL) under inert atmosphere were added EDCI.HCl (211 mg, 1.10 mmol), HOBt (149 mg, 1.10 mmol), compound 248 (250 mg, 0.88 mmol) and diisopropylethylamine (0.70 mL, 3.69 mmol) at 0° C.; warmed to RT and stirred for 16 h. The reaction was monitored by TLC; after completion of the reaction, the reaction mixture was poured into ice-cold water (50 mL) and stirred for 10 min. The precipitated solid was filtered and dried in vacuo to obtain the crude. The crude was washed with diethyl ether (2×10 mL), n-pentane (2×10 mL) and dried in vacuo to afford compound 1599-A (140 mg, 38%) as an off-white solid. TLC: 10% MeOH/CH$_2$Cl$_2$ (R$_f$: 0.5); $^1$H NMR (DMSO-d$_6$, 400 MHz): δ 10.78 (s, 1H), 9.31 (t, J=5.5 Hz, 1H), 8.03 (s, 4H), 7.87 (s, 1H), 7.74-7.66 (m, 3H), 7.63-7.59 (m, 1H), 7.57-7.41 (m, 3H), 4.68 (d, J=5.5 Hz, 2H), 3.87 (s, 3H); LC-MS: 94.78%; 502.3 (M$^+$+1); (column; X-select CSH C-18 (50×3.0 mm, 2.5 μm); RT 3.95 min. 2.5 mM Aq NH$_4$OAc:ACN; 0.8 mL/min). HPLC (purity): 91.89%; (column; Zorbax SB C-18 (150×4.6 mm, 3.5 μm); RT 9.46 min. ACN: 0.05% TFA (Aq); 1.0 mL/min, Diluent: ACN:water).

Synthesis of 4-(5-((11-oxo-10, 11-dihydrodibenzo [b, f] [1, 4] thiazepine-8-carboxamido) methyl) thiazol-2-yl) benzoic acid (1599)

To a stirring solution of 1599-A (100 mg, 0.419 mmol) in THF:H$_2$O (4:1, 5 mL) was added lithium hydroxide monohydrate (21 mg, 0.49 mmol) at RT and stirred for 16 h. The reaction was monitored by TLC; after completion of the reaction, the reaction mixture was diluted with ice-cold water (10 mL) and the pH was adjusted to 2 N with 2 N HCl to ~4. The precipitated solid was filtered washed with water (50 mL) 20% EtOAc/hexanes (5 mL), diethyl ether (5 mL), n-pentane (10 mL) and dried in vacuo to afford 1599 (70 mg, 72%) as an off-white solid. TLC: 10% MeOH/CH$_2$Cl$_2$ (R$_f$: 0.2); $^1$H NMR (DMSO-d$_6$, 400 MHz): δ 13.10 (br s, 1H), 10.79 (s, 1H), 9.31 (t, J=5.7 Hz, 1H), 8.04-7.96 (m, 4H), 7.86 (s, 1H), 7.75-7.64 (m, 3H), 7.61 (dd, J=8.0, 1.7 Hz, 1H), 7.57-7.42 (m, 3H), 4.68 (d, J=5.6 Hz, 2H). LC-MS: 92.86%; 488.3 (M$^+$+1); (column; X-select CSH C-18 (50×3.0 mm, 2.5 μm); RT 2.93 min. 2.5 mM Aq NH$_4$OAc:ACN; 0.8 mL/min). HPLC (purity): 95.00%; (column; Zorbax SB C-18 (150×4.6 mm, 3.5 μm); RT 7.21 min. ACN+5% 5 mM Aq NH$_4$OAc: 5 mM Aq NH$_4$OAc+5% ACN; 0.8 mL/min), Diluent: ACN:water).

Synthesis of 1607

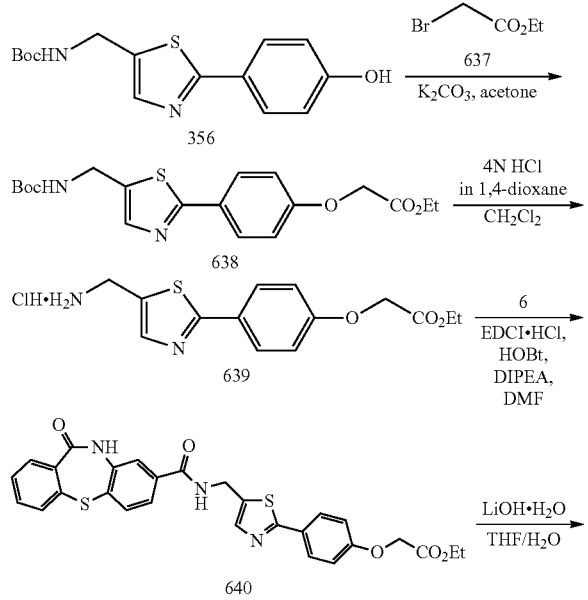

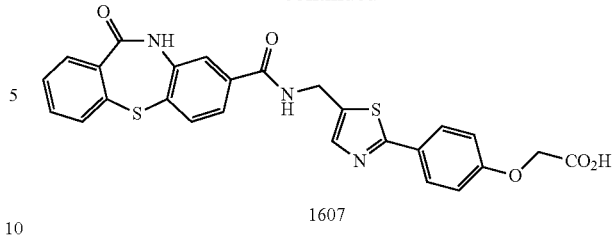

Synthesis of ethyl 2-(4-(5-(((tert-butoxycarbonyl) amino) methyl) thiazol-2-yl) phenoxy) acetate (638)

To a stirring solution of tert-butyl ((2-(4-hydroxyphenyl) thiazol-5-yl) methyl) carbamate 356 (250 mg, 0.81 mmol) and ethyl 2-bromoacetate 637 (204 mg, 1.22 mmol) in acetone (15 mL) under inert atmosphere was added potassium carbonate (338 mg, 2.45 mmol) at RT; heated to 70° C. and stirred for 16 h. The reaction was monitored by TLC; after completion of the reaction, the volatiles were removed in vacuo. The residue was diluted with water (100 mL) and extracted with EtOAc (2×150 mL). The combined organic extracts were dried over sodium sulfate, filtered and concentrated in vacuo to obtain the crude. The crude was purified through silica gel column chromatography using 20% EtOAc/hexanes to afford compound 638 (250 mg, 78%) as an off-white solid. TLC: 20% EtOAc/hexanes (R$_f$: 0.5); $^1$H NMR (DMSO-d$_6$, 500 MHz): δ 7.82 (d, J=8.7 Hz, 2H), 7.62 (s, 1H), 7.53 (t, J=5.5 Hz, 1H), 7.03 (d, J=9.0 Hz, 2H), 4.85 (s, 2H), 4.31 (d, J=5.8 Hz, 2H), 4.18 (q, J=7.2 Hz, 2H), 1.40 (s, 9H), 1.22 (t, J=7.1 Hz, 3H).

Synthesis of ethyl 2-(4-(5-(aminomethyl) thiazol-2-yl) phenoxy) acetate hydrochloride (639)

To a stirring solution of compound 638 (250 mg, 0.63 mmol) in CH$_2$Cl$_2$ (10 mL) under inert atmosphere was added 4 N HCl in 1, 4-dioxane (10 mL) at 0° C.; warmed to RT and stirred for 3 h. The reaction was monitored by TLC; after completion of the reaction, the volatiles were removed in vacuo to obtain the crude. The crude was washed with diethyl ether (10 mL) and dried in vacuo to afford compound 639 (190 mg, 90%) as white solid. TLC: 10% MeOH/CH$_2$Cl$_2$ (R$_f$: 0.2); $^1$H-NMR (DMSO-d$_6$, 500 MHz): δ 8.55 (br s, 3H), 7.90 (s, 1H), 7.84 (d, J=8.7 Hz, 2H), 7.04 (d, J=8.7 Hz, 2H), 4.85 (s, 2H), 4.30 (q, J=5.4 Hz, 2H), 4.16 (q, J=7.2 Hz, 2H), 1.20 (t, J=7.1 Hz, 3H).

Synthesis of ethyl 2-(4-(5-((5, 5-dioxido-11-oxo-10, 11-dihydrodibenzo [b, f] [1, 4] thiazepine-8-carboxamido) methyl) thiazol-2-yl) phenoxy) acetate (640)

To a stirring solution of compound 6 (75 mg, 0.27 mmol) in DMF (5 mL) under inert atmosphere were added compound 639 (100 mg, 0.30 mmol), EDCI.HCl (80 mg, 0.41 mmol), HOBt (56 mg, 0.41 mmol), and diisopropylethylamine (0.27 mL, 1.47 mmol) at 0° C.; warmed to RT and stirred for 16 h. The reaction was monitored by TLC; after completion of the reaction, the reaction mixture was poured into ice-cold water (50 mL) and extracted with EtOAc (2×150 mL). The combined organic extracts were dried over sodium sulfate, filtered and concentrated in vacuo to obtain the crude. The crude was purified through silica gel column chromatography using 3% MeOH/CH$_2$Cl$_2$ to afford compound 640 (80 mg, 53%) as white solid. TLC: 5% MeOH/

CH$_2$Cl$_2$ (R$_f$: 0.4); $^1$H NMR (DMSO-d$_6$, 500 MHz): δ 10.77 (s, 1H), 9.25 (t, J=4.9 Hz, 1H), 7.80 (d, J=8.4 Hz, 2H), 7.74-7.65 (m, 4H), 7.60 (d, J=7.8 Hz, 1H), 7.56-7.43 (m, 3H), 7.01 (d, J=8.4 Hz, 2H), 4.84 (s, 2H), 4.64 (d, J=5.2 Hz, 2H), 4.17 (q, J=6.8 Hz, 2H), 1.21 (t, J=6.9 Hz, 3H).

Synthesis of 2-(4-(5-((11-oxo-10, 11-dihydrodibenzo [b, f] [1, 4] thiazepine-8-carboxamido) methyl) thiazol-2-yl) phenoxy) acetic acid (1607)

To a stirring solution of compound 640 (80 mg, 0.15 mmol) in THF:H$_2$O (4:1, 10 mL) was added lithium hydroxide monohydrate (32 mg, 0.77 mmol) at RT and stirred for 2 h. The reaction was monitored by TLC; after completion of the reaction, the volatiles were removed in vacuo. The residue was diluted water (50 mL) and the pH was acidified with 2 N HCl to ~6. The precipitated solid was filtered and dried in vacuo to afford 1607 (70 mg, 80%) as white solid. TLC: 10% MeOH/CH$_2$Cl$_2$ (R$_f$ 0.2); $^1$H-NMR (DMSO-d$_6$, 500 MHz): δ 13.06 (br s, 1H), 10.77 (s, 1H), 9.25 (t, J=5.6 Hz, 1H), 7.80 (d, J=9.0 Hz, 2H), 7.72-7.65 (m, 4H), 7.62-7.59 (m, 1H), 7.55-7.43 (m, 3H), 6.99 (d, J=9.0 Hz, 2H), 4.73 (s, 2H), 4.63 (d, J=5.5 Hz, 2H); LC-MS: 96.16%; 517.9 (M$^+$+1); (column; Ascentis Express C18, (50×3.0 mm, 2.7 μm); RT 2.17 min. 0.025% Aq. TFA+5% ACN: ACN+5% 0.025% Aq. TFA, 1.2 mL/min); HPLC (purity): 97.19%; (column; Zorbax SB C-18 (150×4.6 mm, 3.5 μm); RT 7.98 min; 0.05% TFA (Aq): 5% ACN; 1.0 mL/min, Diluent: ACN:water).

Synthesis of 1909

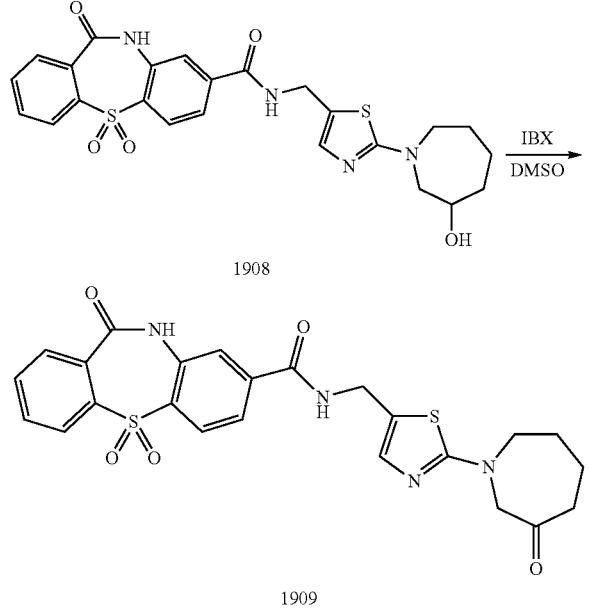

Synthesis of 11-oxo-N-((2-(3-oxoazepan-1-yl) thiazol-5-yl) methyl)-10, 11-dihydrodibenzo [b, f] [1, 4] thiazepine-8-carboxamide 5, 5-dioxide (1909)

To a stirring solution of 1908 (100 mg, 0.19 mmol) in DMSO (10 mL) under inert atmosphere was added iodoxybenzoic acid (218 mg, 0.97 mmol) at RT and stirred for 24 h. The reaction was monitored by TLC; after completion of the reaction, the reaction mixture was diluted with ice-cold water (50 mL) and extracted with 10% MeOH/CH$_2$Cl$_2$ (2×50 mL). The combined organic extracts were dried over sodium sulfate, filtered and concentrated in vacuo to obtain the crude. The crude was purified through silica gel column chromatography using 5% MeOH/CH$_2$Cl$_2$ to afford 1909 (60 mg, 60%) as an off-white solid. TLC: 10% MeOH/CH$_2$Cl$_2$ (R$_f$: 0.5); $^1$H-NMR (DMSO-d$_6$, 400 MHz): δ 11.50 (s, 1H), 9.29 (t, J=5.7 Hz, 1H), 8.04 (d, J=8.3 Hz, 1H), 8.01-7.95 (m, 2H), 7.93-7.77 (m, 4H), 7.03 (s, 1H), 4.45 (d, J=5.6 Hz, 2H), 4.15 (s, 2H), 3.66-3.59 (m, 2H), 2.28-2.23 (m, 2H), 1.86-1.64 (m, 4H); LC-MS: 91.22%; 511.1 (M$^+$+1); (column; Ascentis Express C-18, (50×3.0 mm, 2.7 μm); RT 1.93 min. 0.025% Aq. TFA+5% ACN: ACN+5% 0.025% Aq. TFA, 1.2 mL/min); HPLC (purity): 91.03%; (column; X-select CSH-C18 (150×4.6 mm, 3.5 μm); RT 9.10 min. 5 mM NH$_4$OAc: ACN; 1.0 mL/min, Diluent: DMSO:ACN: water).

Synthesis of 1822

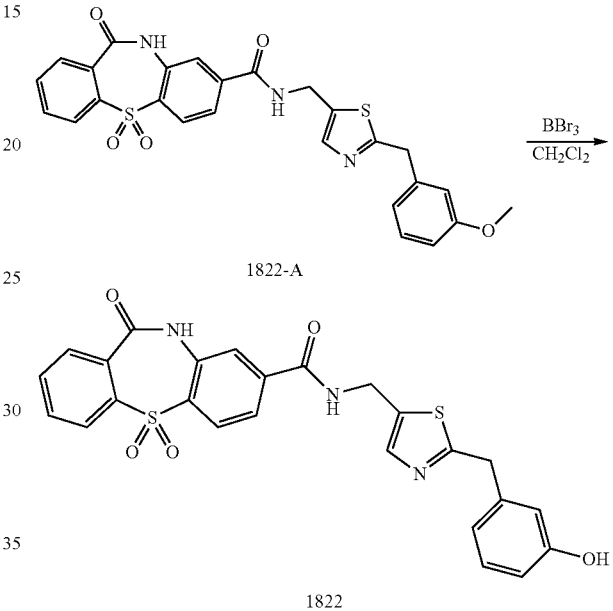

Synthesis of N-((2-(3-methoxybenzyl) thiazol-5-yl) methyl)-11-oxo-10, 11-dihydrodibenzo [b, f] [1, 4] thiazepine-8-carboxamide 5, 5-dioxide (1822)

To a stirring solution N-((2-(3-methoxybenzyl) thiazol-5-yl) methyl)-11-oxo-10, 11-dihydrodibenzo [b, f] [1, 4] thiazepine-8-carboxamide 5, 5-dioxide (1822-A) (150 mg, 0.28 mmol) in CH$_2$Cl$_2$ (15 mL) under inert atmosphere was added BBr$_3$ (0.082 mL, 0.86 mmol) at 0° C.; warmed to RT and stirred for 8 h. The reaction was monitored by TLC; after completion of the reaction, the reaction mixture was quenched with ice-cold water (10 mL) and extracted with 10% MeOH/CH$_2$Cl$_2$ (50 mL). The precipitated solid was filtered, and washed with 10% NaHCO$_3$ solution (20 mL). The organic extract was dried over sodium sulfate and concentrated in vacuo to obtain the crude. The crude was purified through silicagel column chromatography using 4% MeOH/CH$_2$Cl$_2$, and further purified by second column chromatography using 8% isopropanol/CH$_2$Cl$_2$ to afford 1822 (50 mg, 34%) as an off-white solid. TLC: 10% MeOH/CH$_2$Cl$_2$ (R$_f$: 0.4); $^1$H-NMR (DMSO-d$_6$, 500 MHz): δ 11.47 (s, 1H), 9.34 (t, J=5.8 Hz, 1H), 8.03 (d, J=8.1 Hz, 1H), 7.97 (br t, J=8.1 Hz, 2H), 7.92-7.82 (m, 2H), 7.81 (s, 1H), 7.76 (br d, J=8.1 Hz, 1H), 7.55 (s, 1H), 7.08 (br d, J=8.1 Hz, 2H), 6.69 (br d, J=8.1 Hz, 2H), 4.55 (d, J=5.2 Hz, 2H), 4.10 (s, 2H); LC-MS: 93.47%; 506.1 (M+1)$^+$ column; Ascentis Express C18, (50×3.0 mm, 2.7 μm); RT 2.01 min. 0.025% Aq. TFA+5% ACN: ACN+5% 0.025% Aq. TFA, 1.2 mL/min); HPLC (purity): 93.81%; (column; X-select CSH C-18 (150×4.6 mm, 3.5 μm); RT 7.53 min. 0.05% TFA+5% ACN: ACN+5% 0.05% TFA; 1.0 mL/min, Diluent: DMSO: ACN:water).

481
Synthesis of 1823

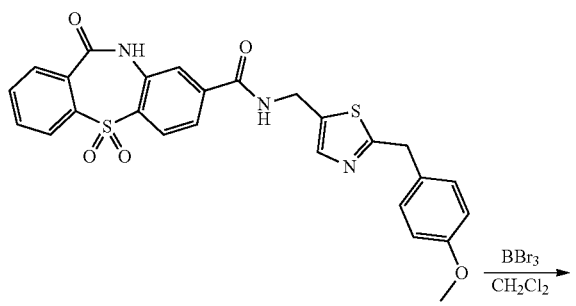

1823-A

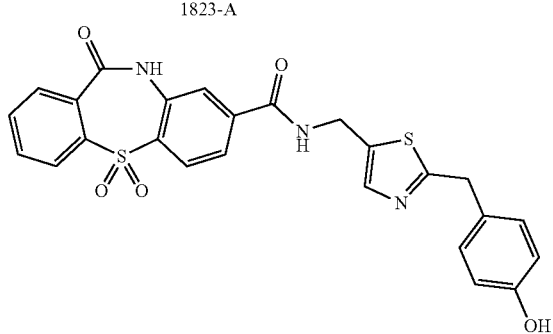

1823

482
Synthesis of N-((2-(4-hydroxybenzyl) thiazol-5-yl) methyl)-11-oxo-10, 11-dihydrodibenzo [b, f] [1, 4] thiazepine-8-carboxamide 5, 5-dioxide (1823)

To a stirring solution of N-((2-(4-methoxybenzyl) thiazol-5-yl) methyl)-11-oxo-10, 11-dihydrodibenzo [b, 1] [1, 4] thiazepine-8-carboxamide 5, 5-dioxide (1823-A) (80 mg, 0.15 mmol) in $CH_2Cl_2$ (6 mL) under inert atmosphere was added $BBr_3$ (0.029 mL, 0.30 mmol) at 0° C.; warmed to RT and stirred for 24 h. The reaction was monitored by TLC; after completion of the reaction, the reaction mixture was quenched with ice-cold water (10 mL) and the precipitated solid was filtered, and washed with 10% $NaHCO_3$ solution (20 mL). This was titurated with 30% isopropanol/EtOAc (30 mL) to afford 1823 (68 mg, 87%) as an off-white solid. TLC: 10% $MeOH/CH_2Cl_2$ ($R_f$: 0.4); $^1$H-NMR (DMSO-$d_6$, 500 MHz): δ 11.47 (s, 1H), 9.34 (t, J=5.8 Hz, 1H), 8.03 (d, J=8.1 Hz, 1H), 7.97 (br t, J=8.1 Hz, 2H), 7.92-7.82 (m, 2H), 7.81 (s, 1H), 7.76 (br d, J=8.1 Hz, 1H), 7.55 (s, 1H), 7.08 (br d, J=8.1 Hz, 2H), 6.69 (br d, J=8.1 Hz, 2H), 4.55 (d, J=5.2 Hz, 2H), 4.10 (s, 2H); LC-MS: 93.47%; 506.1 $(M+1)^+$ column; Ascentis Express C18, (50×3.0 mm, 2.7 μm); RT 2.01 min. 0.025% Aq. TFA+5% ACN: ACN+5% 0.025% Aq. TFA, 1.2 mL/min); HPLC (purity): 93.81%; (column; X-select CSH C-18 (150×4.6 mm, 3.5 μm); RT 7.53 min. 0.05% TFA+5% ACN: ACN+5% 0.05% TFA; 1.0 mL/min, Diluent: DMSO:ACN:water).

Synthesis of 1653

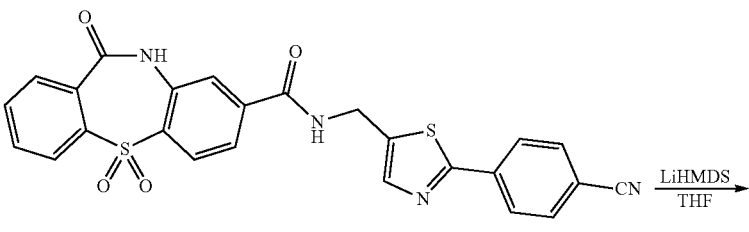

1654-A

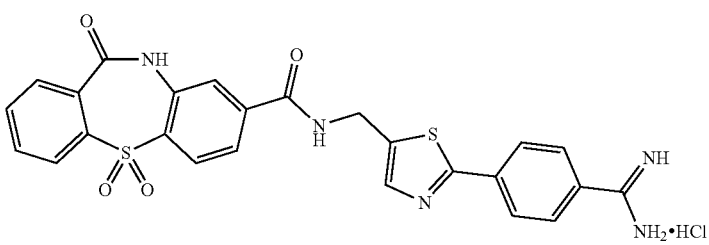

1653

Synthesis of N-((2-(4-carbamimidoylphenyl) thiazol-5-yl) methyl)-11-oxo-10, 11-dihydrodibenzo [b, f] [1, 4] thiazepine-8-carboxamide 5, 5-dioxide hydrochloride (1653)

To a stirring solution of N-((2-(4-cyanophenyl) thiazol-5-yl) methyl)-11-oxo-10, 11-dihydrodibenzo [b, f] [1, 4] thiazepine-8-carboxamide 5, 5-dioxide 1654-A (175 mg, 0.35 mmol) in dry THF (5 mL) under inert atmosphere was added LiHMDS (1 M solution in THF, 3.5 mL) at 0° C.; warmed to RT and stirred for 16 h. The reaction was monitored by TLC; after completion of the reaction, the reaction mixture was quenched with ice-cold water (10 mL), diluted with EtOAc (10 mL). The precipitated solid was filtered and dried in vacuo to obtain the crude. The crude was purified using preparative HPLC to afford 1653 (30 mg, 16%) as white solid. TLC: 10% MeOH/CH$_2$Cl$_2$ (R$_f$: 0.4); $^1$H-NMR (DMSO-d$_6$, 400 MHz): δ 11.54 (s, 1H), 9.54 (t, J=5.7 Hz, 1H), 9.37 (s, 2H), 9.00 (br s, 2H), 8.12 (d, J=8.5 Hz, 2H), 8.07 (d, J=8.3 Hz, 1H), 8.01-7.96 (m, 2H), 7.93-7.86 (m, 5H), 7.84 (td, J=7.9, 1.3 Hz, 2H), 4.72 (d, J=5.6 Hz, 2H); LC-MS: 94.34%; 518.1 (M$^+$+1); (column; Ascentis Express C18, (50×3.0 mm, 2.7 μm); RT 1.75 min. 0.025% Aq. TFA+5% ACN: ACN+5% 0.025% Aq. TFA, 1.2 mL/min); HPLC (purity): 90.29%; (column; Zorbax SB-C-18 (150×4.6 mm, 3.5 μm); RT 5.56 min. ACN+5% 0.05% TFA (Aq): 0.05% TFA (Aq)+5% ACN; 1.0 mL/min, Diluent: ACN:water).

Synthesis of 1677-B

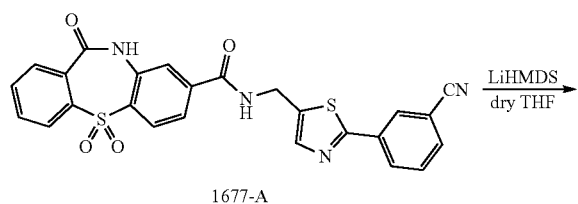

1677-A

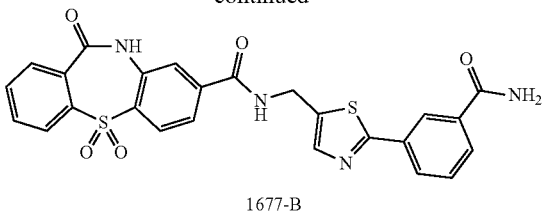

1677-B

Synthesis of N-((2-(3-carbamoylphenyl)thiazol-5-yl) methyl)-11-oxo-10, 11-dihydrodibenzo [b, f] [1, 4] thiazepine-8-carboxamide 5, 5-dioxide (1677-B)

To a stirring solution of N-((2-(3-cyanophenyl) thiazol-5-yl) methyl)-11-oxo-10, 11-dihydrodibenzo [b, 1] [1, 4] thiazepine-8-carboxamide 5, 5-dioxide 1677-A (226 mg, 0.45 mmol) in dry THF (8 mL) under inert atmosphere was added LiHMDS (1 M solution in THF, 4.5 mL) at 0° C.; warmed to RT and stirred for 18 h. The reaction was monitored by TLC; after completion of the reaction, the reaction mixture was quenched with ice-cold water (10 mL) and stirred for 30 min. The precipitated solid was filtered, washed with water and dried in vacuo to afford 1677-B (30 mg, 13%) as an off-white solid. TLC: 10% MeOH/CH$_2$Cl$_2$ (R$_f$: 0.2); $^1$H-NMR (DMSO-d$_6$, 400 MHz): δ 11.40 (br s, 1H), 9.50 (br t, J=4.8 Hz, 1H), 8.34 (s, 1H), 8.16 (br s, 1H), 8.04 (br t, J=7.6 Hz, 2H), 8.00-7.78 (m, 8H), 7.56 (br t, J=7.7 Hz, 1H), 7.47 (br s, 1H), 4.71 (br d, J=5.3 Hz, 2H); LC-MS: 98.51%; 518.9 (M$^+$+1); (column; Ascentis Express C18, (50×3.0 mm, 2.7 nm); RT 1.97 min. 0.025% Aq. TFA+5% ACN: ACN+5% 0.025% Aq. TFA, 1.2 mL/min); HPLC (purity): 97.86%; (column; X-Select CSH C-18 (150×4.6 mm, 3.5 nm); RT 7.12 min. ACN+5% 0.05% TFA (Aq): 0.05% TFA (Aq)+5% ACN; 1.0 mL/min, Diluent: DMSO: ACN:water).

Synthesis of 1901-B

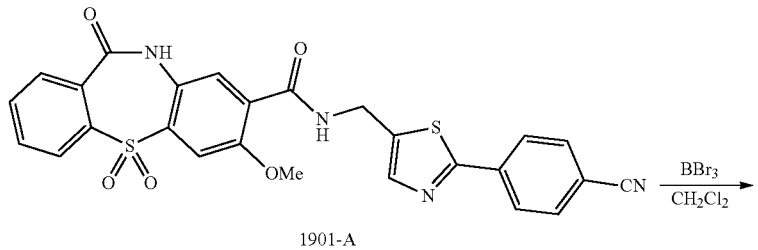

1901-A

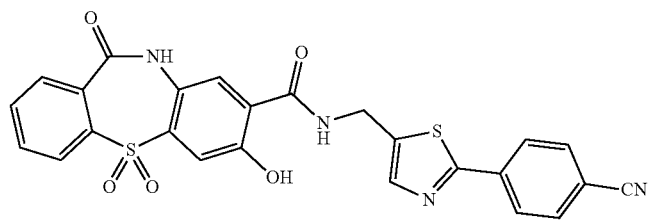

1901-B

485

Synthesis of N-((2-(4-cyanophenyl) thiazol-5-yl) methyl)-7-hydroxy-11-oxo-10, 11-dihydrodibenzo [b, f] [1, 4] thiazepine-8-carboxamide 5, 5-dioxide (1901-B)

To a stirring solution of N-((2-(4-cyanophenyl)-5-yl) methyl)-7-methoxy-11-oxo-10, 11-dihydrodibenzo [b, f] [1, 4] thiazepine-8-carboxamide 5, 5-dioxide (1901-A) (150 mg, 0.28 mmol) in $CH_2Cl_2$ (10 mL) under inert atmosphere was added $BBr_3$ (0.13 mL, 1.41 mmol) at 0° C.; warmed to RT and stirred for 16 h. The reaction was monitored by TLC; after completion of the reaction, the reaction mixture was quenched with ice-cold water (10 mL) and extracted with 10% $MeOH/CH_2Cl_2$ (2×50 mL). The combined organic extracts were dried over sodium sulfate, filtered and concentrated in vacuo to obtain the crude. The crude was purified through silica gel column chromatography using 2% $MeOH/CH_2Cl_2$ and triturated EtOAc (5 mL), dried in vacuo to afford 1901-B (120 mg, 82%) as white solid. TLC: 5% $MeOH/CH_2Cl_2$ ($R_f$: 0.5); $^1$H-NMR (DMSO-$d_6$, 400 MHz): δ 11.82 (br s, 1H), 11.09 (s, 1H), 9.56 (br s, 1H), 8.06 (d, J=8.3 Hz, 2H), 7.97-7.85 (m, 6H), 7.84-7.76 (m, 2H), 7.44 (s, 1H), 4.74 (d, J=4.4 Hz, 2H); LC-MS: 97.63%; 517.0 ($M^+$+1); (column; Ascentis Express C18, (50×3.0 mm, 2.7 μm); RT 2.32 min. 0.025% Aq. TFA+5% ACN: ACN+5% 0.025% Aq. TFA, 1.2 mL/min); HPLC (purity): 97.29%; (column; X-select CSH C-18 (150×4.6 mm, 3.5 μm); RT 9.48 min. ACN+5% 0.05% TFA 0.05% TFA+5% ACN; 1.0 mL/min, Diluent: DMSO:ACN:water)

486

Synthesis of N-((2-(4-carbamoyl-2-fluorophenyl) thiazol-5-yl)methyl)-11-oxo-10, 11-dihydrodibenzo [b, f] [1, 4] thiazepine-8-carboxamide 5, 5-dioxide (1970)

To a stirring solution of 1814 (100 mg, 0.19 mmol) in DMSO (5 mL) were added 30% $H_2O_2$ (2 mL, 20 vol) and potassium carbonate (267 mg, 1.93 mmol) at 0° C.; warmed to RT and stirred for 16 h. The reaction was monitored by TLC; after completion of the reaction, the reaction mixture diluted with water (30 mL) and stirred for 1 h. The precipitated solid was filtered, dried in vacuo to obtain the crude, which was triturated with EtOAc (2×20 mL) and dried in vacuo to afford 1970 (80 mg, 78%) as an off-white solid. TLC: 5% $MeOH/CH_2Cl_2$ ($R_f$: 0.4); $^1$H-NMR (DMSO-$d_6$, 400 MHz): δ 11.50 (br s, 1H), 9.51 (br t, J=5.4 Hz, 1H), 8.25 (br t, J=8.0 Hz, 1H), 8.13 (br s, 1H), 8.06 (br d, J=8.3 Hz, 1H), 8.01-7.94 (m, 3H), 7.93-7.79 (m, 6H), 7.61 (br s, 1H), 4.74 (br d, J=5.1 Hz, 2H); LC-MS: 98.08%; 537.1 ($M^+$+1); (column; Ascentis Express C18, (50×3.0 mm, 2.7 μm); RT 1.98 min. 0.025% Aq. TFA+5% ACN: ACN+5% 0.025% Aq. TFA, 1.2 mL/min); HPLC (purity): 96.22%; (column; X-select CSH C-18 (150×4.6 mm, 3.5 μm); RT 7.37 min. 0.05% TFA+5% ACN: ACN+0.05% TFA+5%; 1.0 mL/min; Diluent: DMSO:ACN:water).

Synthesis of 1970

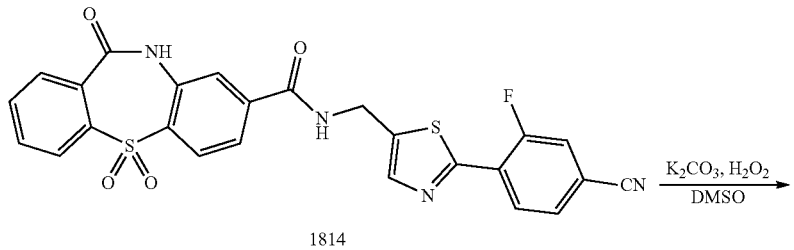

1814

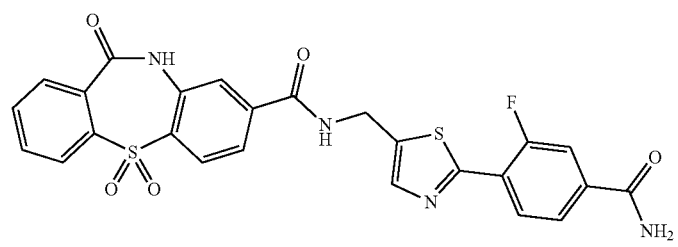

1970

Synthesis of 1952

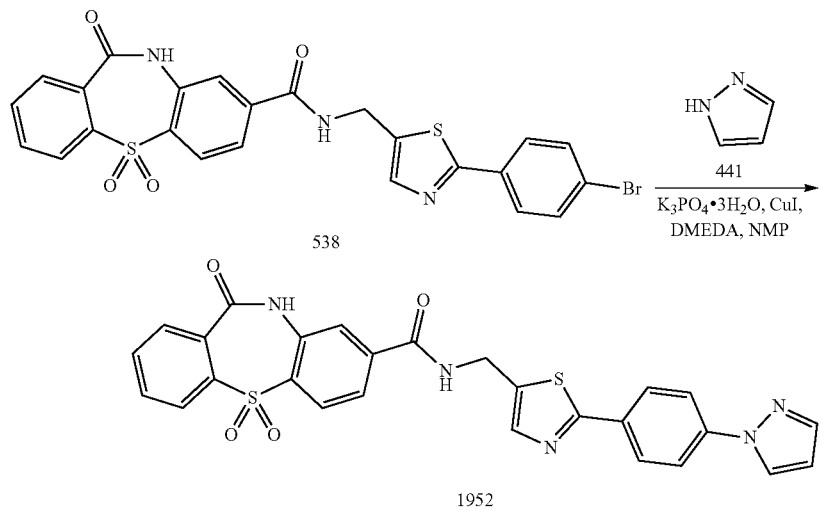

Synthesis of N-((2-(4-(1H-pyrazol-1-yl) phenyl) thiazol-5-yl) methyl)-11-oxo-10, 11-dihydrodibenzo [b, f] [1, 4] thiazepine-8-carboxamide 5, 5-dioxide (1952)

To a stirring solution of N-((2-(4-bromophenyl) thiazol-5-yl) methyl)-11-oxo-10, 11-dihydrodibenzo [b, 1] [1, 4] thiazepine-8-carboxamide 5, 5-dioxide 538 (100 mg, 0.18 mmol) in N-methyl-2-pyrrolidone (4 mL) under inert atmosphere were added 1H-pyrazole 441 (24 mg, 0.35 mmol) and potassium phosphate tribasic (115 mg, 0.54 mmol), copper (I) iodide (17 mg, 0.09 mmol) in a sealed tube at RT and purged under argon atmosphere for 15 min; heated to 150° C. and stirred for 16 h. The reaction was monitored by TLC; after completion of the reaction, the reaction mixture was filtered through celite. The filtrate was concentrated in vacuo to obtain the crude. The crude was purified through silica gel column chromatography using 3-5% MeOH/CH$_2$Cl$_2$ and triturated with diethylether (5 mL) to afford 1952 (30 mg, 31%) as an off-white solid. TLC: 5% MeOH/CH$_2$Cl$_2$ (R$_f$: 0.5); $^1$H-NMR (DMSO-d$_6$, 500 MHz): δ 11.52 (br s, 1H), 9.49 (t, J=5.5 Hz, 1H), 8.58 (d, J=2.3 Hz, 1H), 8.10-7.94 (m, 7H), 7.93-7.76 (m, 6H), 6.58 (s, 1H), 4.70 (d, J=5.2 Hz, 2H); LC-MS: 95.99%; 542.0 (M$^+$+1); (column; Ascentis Express C18, (50×3.0 mm, 2.7 μm); RT 2.31 min. 0.025% Aq. TFA+5% ACN: ACN+5% 0.025% Aq. TFA, 1.2 mL/min); HPLC (purity): 92.85%; (Column; X-select CSH C-18 (150×4.6 mm, 3.5 μm); RT 10.00 min. 5 mM NH$_4$OAc: ACN; 1.0 mL/min, Diluent: DMSO:ACN:water).

Synthesis of 1806

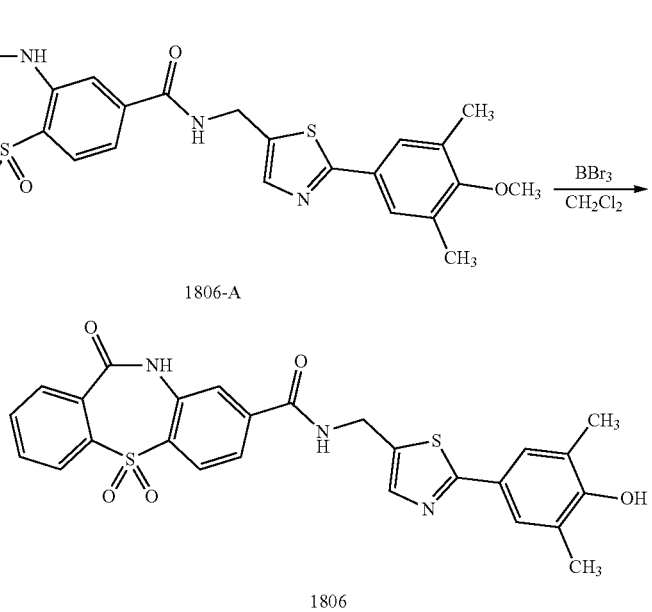

489

Synthesis of N-((2-(4-hydroxy-3, 5-dimethylphenyl) thiazol-5-yl) methyl)-11-oxo-10, 11-dihydrodibenzo [b, f] [1, 4] thiazepine-8-carboxamide 5, 5-dioxide (1806)

To a stirring solution of N-((2-(4-methoxy-3, 5-dimethylphenyl) thiazol-5-yl)methyl)-11-oxo-10, 11-dihydrodibenzo [b, f] [1, 4] thiazepine-8-carboxamide 5,5-dioxide (1806-A) (60 mg, 0.11 mmol) in $CH_2Cl_2$ (10 mL) was added $BBr_3$ (0.03 mL, 0.33 mmol) at 0° C.; warmed to RT and stirred for 24 h. The reaction was monitored by TLC; after completion of the reaction, the reaction mixture was quenched with ice-cold water (10 mL) the precipitated solid was filtered and dried in vacuo to obtain the crude which was titurated with MeOH (2 mL) and dried in vacuo to afford 1806 (30 mg, 52%) as an off-white solid. TLC: 5% MeOH/$CH_2Cl_2$ ($R_f$: 0.5); $^1$H-NMR (DMSO-$d_6$, 400 MHz): δ 11.52 (s, 1H), 9.43 (t, J=5.5 Hz, 1H), 8.75 (br s, 1H), 8.05 (d, J=8.3 Hz, 1H), 8.01-7.95 (m, 2H), 7.93-7.79 (m, 4H), 7.66 (s, 1H), 7.45 (s, 2H), 4.64 (d, J=5.4 Hz, 2H), 2.19 (s, 6H); LC-MS: 97.68%; 520.0 (M$^+$+1); (column; Ascentis Express C18, (50×3.0 mm, 2.7 µm); RT 2.24 min. 0.025% Aq. TFA+5% ACN: ACN+5% 0.025% Aq. TFA, 1.2 mL/min); HPLC (purity): 97.67%; X-select CSH C-18 (150×4.6 mm, 3.5 µm); RT 8.43 min. 5% 0.05% TFA+5% ACN: ACN+5% 0.05% TFA (Aq); 1.0 mL/min, Diluent: DMSO: ACN:water).

490

Synthesis of N-((2-(4-hydroxy-3-methylphenyl) thiazol-5-yl) methyl)-11-oxo-10, 11-dihydrodibenzo [b, f] [1, 4] thiazepine-8-carboxamide 5, 5-dioxide (1804)

To a stirring solution of N-((2-(4-methoxy-3-methylphenyl) thiazol-5-yl) methyl)-11-oxo-10, 11-dihydrodibenzo [b, f] [1, 4] thiazepine-8-carboxamide 5, 5-dioxide (1804-A) (80 mg, 0.15 mmol) in $CH_2Cl_2$ (10 mL) was added $BBr_3$ (0.07 mL, 0.77 mmol) at 0° C.; warmed to RT and stirred for 16 h. The reaction was monitored by TLC; after completion of the reaction, the reaction mixture was quenched with ice-cold water (10 mL). The aqueous layer was basified with saturated sodium bicarbonate solution (10 mL) and the precipitated solid was filtered washed with diethyl ether (2×10 mL) and dried in vacuo to afford 1804 (40 mg, 52%) as an off-white solid. TLC: 5% MeOH/$CH_2Cl_2$ ($R_f$: 0.3); $^1$H NMR (DMSO-$d_6$, 400 MHz): δ 11.51 (s, 1H), 9.85 (s, 1H), 9.43 (t, J=5.7 Hz, 1H), 8.05 (d, J=8.3 Hz, 1H), 8.01-7.95 (m, 2H), 7.92-7.79 (m, 4H), 7.66 (s, 1H), 7.59 (s, 1H), 7.53 (dd, J=8.3, 2.1 Hz, 1H), 6.83 (d, J=8.4 Hz, 1H), 4.64 (d, J=5.6 Hz, 2H), 2.15 (s, 3H); LC-MS: 99.14%; 506.1 (M$^+$+1); (column; Ascentis Express C18, (50×3.0 mm, 2.7 µm); RT 2.15 min. 0.025% Aq. TFA+5% ACN: ACN+5% 0.025% Aq. TFA, 1.2 mL/min); HPLC (purity): 99.24%; (column; X-select CSH C-18 (150×4.6 mm, 3.5 µm); RT 8.13 min. 5% 0.05% TFA+5% ACN: ACN+5% 0.05% TFA (Aq); 1.0 mL/min, Diluent: DMSO:ACN:water).

Synthesis of 1804

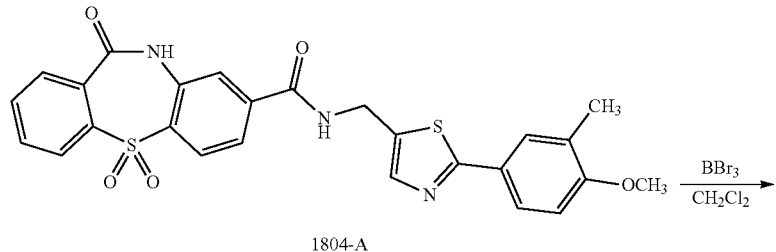

1804-A

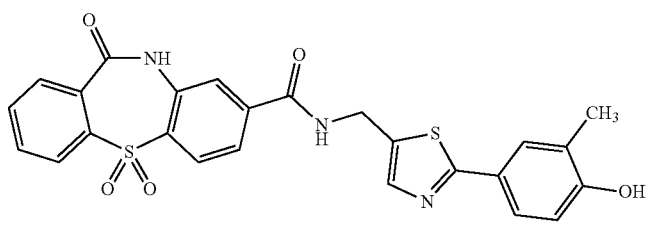

1804

Synthesis of 1879

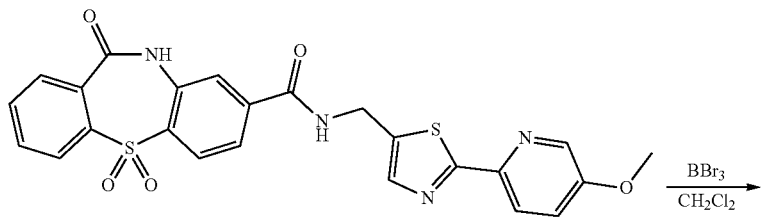

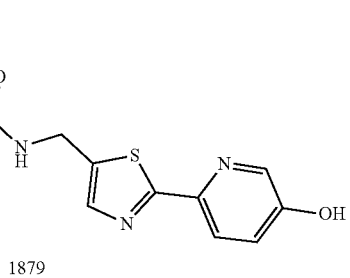

Synthesis of N-((2-(5-hydroxypyridin-2-yl) thiazol-5-yl) methyl)-11-oxo-10, 11-dihydrodibenzo [b, f] [1, 4] thiazepine-8-carboxamide 5, 5-dioxide (1879)

To a stirring solution of 1879-A (50 mg, 0.098 mmol) in CH$_2$Cl$_2$ (5 mL) was under inert atmosphere was added BBr$_3$ (1 mL) at 0° C.; warmed to RT and stirred for 120 h. The reaction was monitored by TLC; after completion of the reaction, the reaction mixture was quenched with ice-cold water (10 mL). The volatiles were concentrated in vacuo. The pH of the residue was adjusted to ~7.0 with saturated NaHCO$_3$ solution (20 mL). The precipitated solid was filtered and dried in vacuo to obtain the crude. The crude was purified through silicagel column chromatography using 3-5% MeOH/CH$_2$Cl$_2$ to afford compound 1879 (20 mg, 42%) as an off-white solid. TLC: 5% MeOH/CH$_2$Cl$_2$ (R$_f$: 0.4); $^1$H-NMR (DMSO-d$_6$, 500 MHz): δ 10.64 (s, 1H), 9.84 (s, 1H), 9.17 (t, J=5.2 Hz, 1H), 7.78 (d, J=6.9 Hz, 1H), 7.72-7.58 (m, 5H), 7.53 (d, J=8.2 Hz, 1H), 7.42 (d, J=8.3 Hz, 1H), 7.38-7.31 (m, 2H), 6.83 (d, J=8.3 Hz, 1H), 4.62 (d, J=5.1 Hz, 2H), 2.15 (s, 3H); LC-MS: 95.08%; 457.9 (M$^+$+ 1); (column; Ascentis Express C18, (50×3.0 mm, 2.7 µm); RT 2.19 min. 0.025% Aq. TFA+5% ACN: ACN+5% 0.025% Aq. TFA, 1.2 mL/min); HPLC (purity): 97.99%; (column; Zorbax SB C-18 (150×4.6 mm, 3.5 µm); RT 7.56 min. ACN+5% 0.05% TFA (Aq): 0.05% TFA (Aq)+5% ACN; 1.0 mL/min, Diluent: DMSO:ACN:water).

Synthesis of 1671

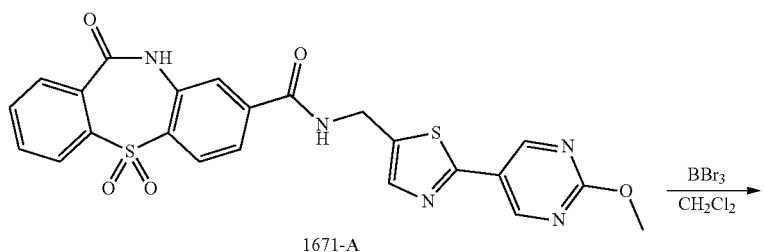

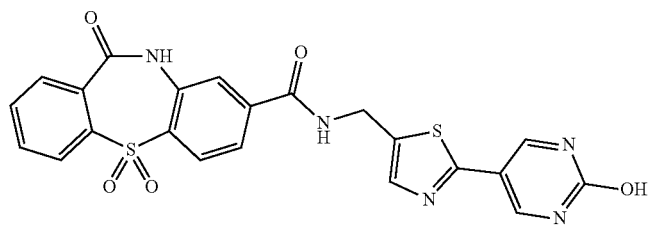

Synthesis of N-((2-(2-hydroxypyrimidin-5-yl) thiazol-5-yl)methyl)-11-oxo-10, 11-dihydrodibenzo [b, f] [1, 4] thiazepine-8-carboxamide 5, 5-dioxide (1671)

To a stirring solution of N-((2-(2-methoxypyrimidin-5-yl) thiazol-5-yl) methyl)-11-oxo-10, 11-dihydrodibenzo [b, f] [1, 4] thiazepine-8-carboxamide 5, 5-dioxide (1671-A) (80 mg, 0.15 mmol) in CH$_2$Cl$_2$ (10 mL) was added BBr$_3$ (0.14 mL, 0.78 mmol) at 0° C.; warmed to RT and stirred for 24 h. The reaction was monitored by TLC; after completion of the reaction, the reaction mixture was quenched with ice-cold water (2 mL) and stirred for 10 min. The pH was adjusted to ~7 with saturated sodium bicarbonate solution. The precipitated solid was filtered, washed with water and dried in vacuo to afford 1671 (45 mg, 58%) as an off-white solid. TLC: 10% MeOH/CH$_2$Cl$_2$ (R$_f$: 0.5); $^1$H-NMR (DMSO-d$_6$, 400 MHz): δ 12.43 (br s, 1H), 11.55 (br s, 1H), 9.48 (br s, 1H), 8.77-8.58 (m, 1H), 8.11-7.72 (m, 9H), 4.68-4.63 (m, 2H); LC-MS: 96.68%; 494.0 (M$^+$+1); (column; Ascentis Express C18, (50×3.0 mm, 2.7 μm); RT 1.78 min. 0.025% Aq. TFA+5% ACN: ACN+5% 0.025% Aq. TFA, 1.2 mL/min); HPLC (purity): 93.58%; (column; X-select CSH C-18 (150×4.6 mm, 3.5 μm); RT 5.70 min. ACN+5% 0.05% TFA: 0.05% TFA+5% ACN; 1.0 mL/min, Diluent: DMSO:ACN:water).

Synthesis of N-((2-(4-carbamoylphenyl) thiazol-5-yl) methyl)-9-methyl-11-oxo-10, 11-dihydrodibenzo [b, f] [1, 4] thiazepine-8-carboxamide 5, 5-dioxide (1878)

To a stirring solution of 1877 (100 mg, 0.19 mmol) in DMSO (2 mL) were added potassium carbonate (134 mg, 0.97 mmol) and 30% H$_2$O$_2$ (0.22 mL, 1.95 mmol) at 0° C.; warmed to RT and stirred for 4 h. The reaction was monitored by TLC; after completion of the reaction, the reaction mixture was diluted with water (100 mL), the precipitated solid was filtered and dried in vacuo to afford 1878 (75 mg, 73%) as an off-white solid. TLC: 10% MeOH/CH$_2$Cl$_2$ (R$_f$: 0.3); $^1$H-NMR (DMSO-d$_6$, 400 MHz): δ 10.86 (br s, 1H), 9.20 (t, J=5.6 Hz, 1H), 8.07 (br s, 1H), 7.98-7.87 (m, 4H), 7.94-7.75 (m, 6H), 7.46 (br s, 1H), 7.34 (d, J=7.9 Hz, 1H), 4.67 (d, J=5.6 Hz, 2H), 2.32 (s, 3H); LC-MS: 98.06%; 533.1 (M$^+$+1); (column; Ascentis Express C18, (50×3.0 mm, 2.7 μm); RT 1.87 min. 0.025% Aq. TFA+5% ACN: ACN+5% 0.025% Aq. TFA, 1.2 mL/min); HPLC (purity): 97.87%; (column; X select CSH C-18 (150×4.6 mm, 3.5 μm); RT 6.99 min. 0.05% TFA+5% ACN: ACN+5% 0.05% TFA; 1.0 mL/min, Diluent: DMSO:ACN:water).

Synthesis of 1878

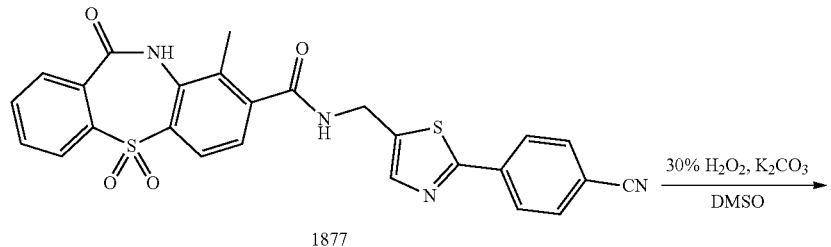

1877

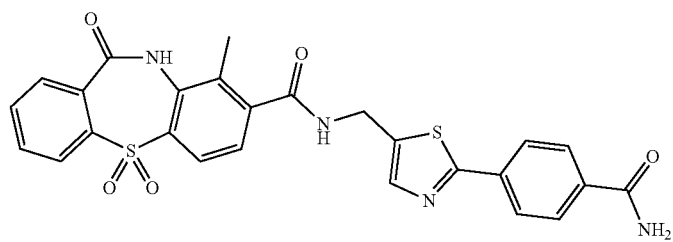

1878

Synthesis of 11106

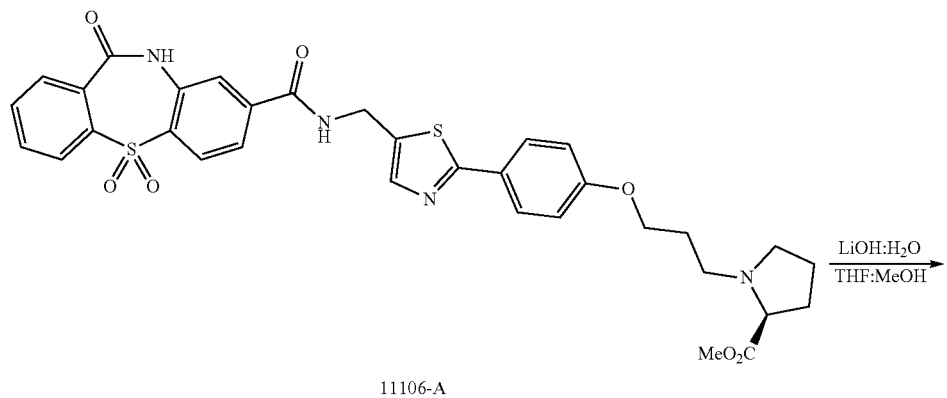

11106-A

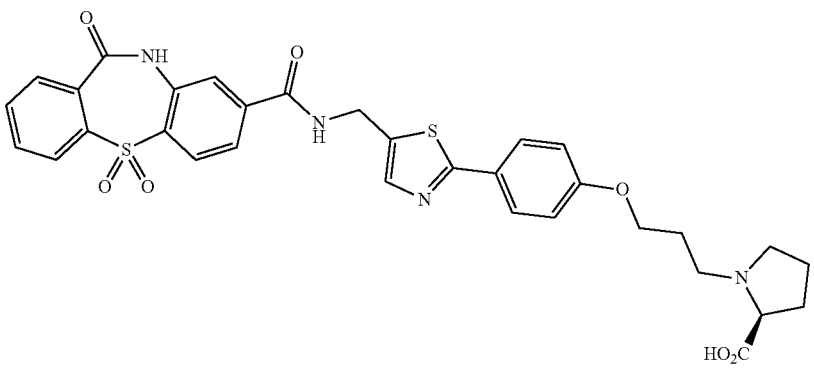

1879

Synthesis of (3-(4-(5-((5,5-dioxido-11-oxo-10, 11-dihydrodibenzo [b, f] [1, 4]thiazepine-8-carboxamido) methyl) thiazol-2-yl) phenoxy)propyl)-L-proline (5) (11106)

To a stirring solution of 11106-A (90 mg, 0.13 mmol) in THF:MeOH:H$_2$O (2:1:1, 8 mL) was added lithium hydroxide monohydrate (17 mg, 0.40 mmol) at 0° C.; warmed to RT, and stirred for 2 h. The reaction was monitored by TLC; after completion of the reaction, the volatiles were removed in vacuo and the pH of the residue was acidified with 2 N HCl to pH~5-6. The obtained solid was filtered, washed with water (20 mL), diethyl ether (10 mL) and dried in vacuo to obtain 11106 (50 mg, 56%) as an off-white solid. TLC: 10% MeOH/CH$_2$Cl$_2$ (R$_f$ 0.1); $^1$H NMR (400 MHz, DMSO-d$_6$): δ 11.52 (s, 1H), 9.47 (t, J=5.7 Hz, 1H), 8.05 (d, J=8.3 Hz, 1H), 8.01-7.95 (m, 2H), 7.93-7.79 (m, 6H), 7.72 (s, 1H), 7.02 (d, J=8.9 Hz, 2H), 4.66 (d, J=5.5 Hz, 2H), 4.10 (t, J=6.1 Hz, 2H), 3.52-3.46 (m, 2H), 3.18-3.12 (m, 1H), 3.04-2.98 (m, 1H), 2.85-2.78 (m, 1H), 2.20-2.10 (m, 1H), 2.06-2.00 (m, 2H), 1.97-1.83 (m, 2H), 1.75-1.65 (m, 1H); LC-MS: 95.82%; 647.1 (M+1)$^+$; (column; Ascentis Express C-18 (50×3.0 mm, 2.7 μm); RT 1.84 min. 0.025% Aq. TFA+5% ACN: ACN+5% 0.025% Aq TFA, 1.2 mL/min); HPLC (purity): 95.18%; (column; X-Select CSH-C-18 (150×4.6 mm, 3.5 μm); RT 6.28 min. 0.05% TFA+5% ACN: ACN+5% 0.05% TFA; 1.0 mL/min, Diluent: ACN:H$_2$O).

Synthesis of 11032-A

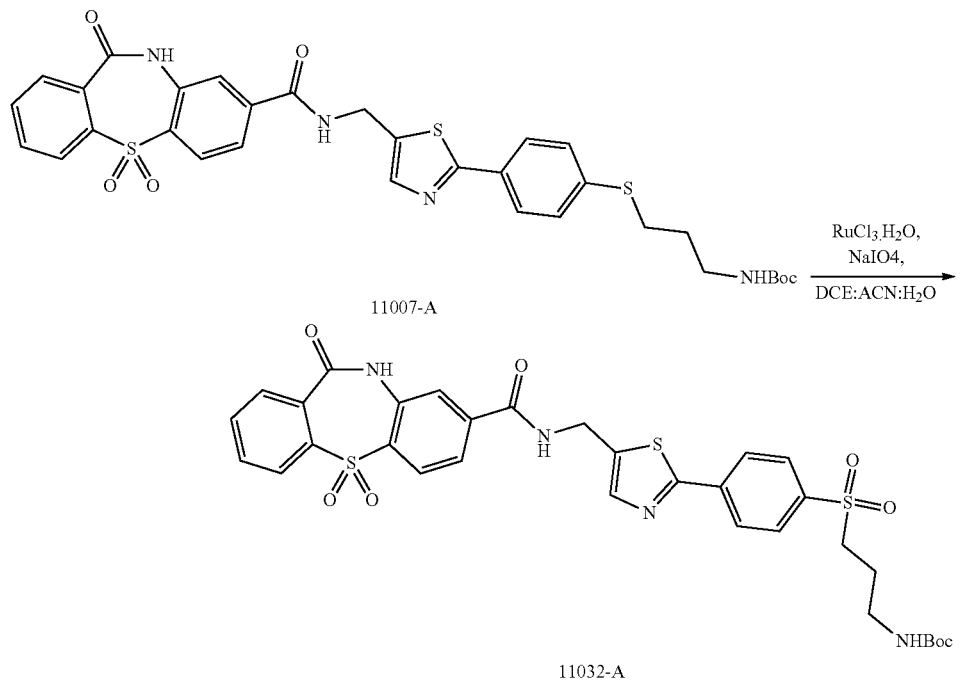

Synthesis of tert-butyl (3-((4-(5-((5, 5-dioxido-11-oxo-10, 11-dihydrodibenzo [b, f] [1, 4] thiazepine-8-carboxamido) methyl) thiazol-2-yl) phenyl) sulfonyl) propyl) carbamate (11032-A)

To a stirring solution of 11007-A (110 mg, 0.16 mmol) in 1, 2 dichloro ethane: $CH_3CN:H_2O$ (1:1:2, 4 mL) were added sodium metaperiodate (106 mg, 0.49 mmol), ruthenium chloride (1.7 mg, 0.05 mmol) at RT and stirred for 16 h. The reaction was monitored by TLC; after completion, the volatiles were removed in vacuo. The residue was diluted with water (50 mL) and extracted with $CH_2Cl_2$ (2×100 mL). The combined organic extracts were dried over sodium sulfate, filtered and concentrated in vacuo to obtain the crude. The crude was purified through silicagel column chromatography using 3% $MeOH/CH_2Cl_2$ to afford 11032-A (15 mg, 13%) as white solid. TLC: 5% $MeOH/CH_2Cl_2$ ($R_f$: 0.4); $^1$H-NMR (DMSO-$d_6$, 400 MHz): 11.52 (s, 1H), 9.52 (t, J=5.8 Hz, 1H), 8.15 (d, J=8.4 Hz, 2H), 8.01-7.94 (m, 4H), 7.93-7.81 (m, 5H), 7.65 (br s, 1H), 6.90-6.84 (m, 1H), 4.73 (d, J=5.6 Hz, 2H), 3.37-3.30 (m, 2H), 2.96 (q, J=5.6 Hz, 2H), 1.70-1.59 (m, 2H), 1.33 (s, 9H); LC-MS: 97.78%; 695.1 (M−1)$^+$, (column; Kinetex EVO C-18 (50×3.0 mm, 2.6 um); RT 2.91 min. 2.5 mM Aq. $NH_4OOCH$+5% ACN: ACN+5% 2.5 mM Aq.$NH_4OOCH$, 0.8 mL/min). HPLC (purity): 94.67%; (column; X-select CSH C-18 (150×4.6 mm, 3.5 µm); RT 9.28 min. 0.05% TFA (Aq)+5% ACN: ACN+5% 0.5% TFA (Aq); 1.0 mL/min, Diluent: DMSO:ACN:water).

Synthesis of 1583

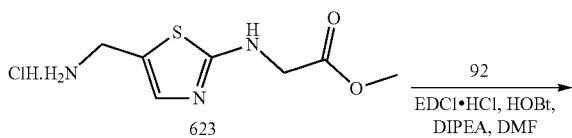

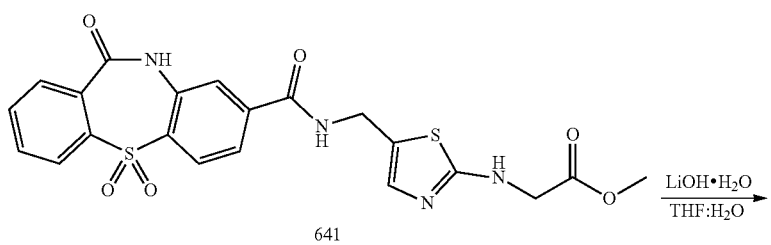

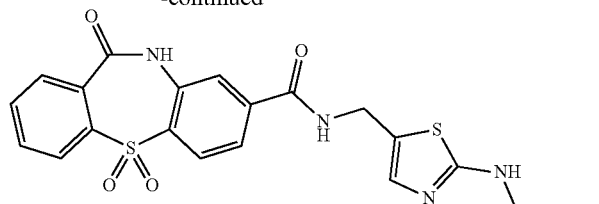

1583

Synthesis of methyl (5-((5, 5-dioxido-11-oxo-10, 11-dihydrodibenzo [b, f] [1, 4] thiazepine-8-carboxamido) methyl) thiazol-2-yl) glycinate (641)

To a stirring solution of compound 623 (150 mg, 0.49 mmol) in DMF (10 mL) under inert atmosphere were added EDCI.HCl (179 mg, 0.99 mmol), HOBt (133 mg, 0.99 mmol) and diisopropylethylamine (0.45 mL, 5.00 mmol) and methyl 5-(aminomethyl) thiazol-2-yl) glycinate hydrochloride 92 (109 mg, 0.55 mmol) at 0° C.; warmed to RT and stirred for 16 h. The reaction was monitored by TLC; after completion of the reaction, the reaction mixture was diluted with water (50 mL) and extracted with EtOAc (2×100 mL). The combined organic extracts were washed with water (50 mL), brine (50 mL), dried over sodium sulfate, filtered and concentrated in vacuo to obtain the crude. The crude was triturated with diethyl ether: $CH_3CN$ (4:1, 10 mL) and the obtained solid was dried in vacuo to afford 641 (85 mg, 35%) as an off-white solid. TLC: 10% MeOH/$CH_2Cl_2$ ($R_f$: 0.4); $^1$H-NMR (DMSO-$d_6$ 400 MHz): δ 11.50 (s, 1H), 9.23 (t, J=5.7 Hz, 1H), 8.03 (d, J=8.3 Hz, 1H), 7.98 (dd, J=9.3, 1.8 Hz, 2H), 7.93-7.81 (m, 4H), 7.77 (dd, J=8.3, 1.5 Hz, 1H), 6.88 (s, 1H), 4.40 (d, J=5.6 Hz, 2H), 3.99 (d, J=6.2 Hz, 2H), 3.61 (s, 3H).

Synthesis of (5-((5, 5-dioxido-11-oxo-10, 11-dihydrodibenzo [b, f] [1, 4] thiazepine-8-carboxamido) methyl) thiazol-2-yl) glycine (1583)

To a stirring solution of compound 641 (70 mg, 0.14 mmol) in THF:$H_2O$ (3:1, 8 mL) was added lithium hydroxide monohydrate (13.8 mg, 0.28 mmol) at RT and stirred for 6 h. The reaction was monitored by TLC; after completion of the reaction, the reaction mixture was diluted with water (50 mL) and washed with EtOAc (2×50 mL). The pH of the aqueous layer was acidified with 4 N HCl to ~2. The precipitated solid was filtered and dried in vacuo to afford 1583 (37 mg, 54%) as an off-white solid. TLC: 10% MeOH/$CH_2Cl_2$ ($R_f$: 0.2); $^1$H-NMR (DMSO-$d_6$, 500 MHz): δ 12.50 (br s, 1H), 11.49 (s, 1H), 9.23 (t, J=5.4 Hz, 1H), 8.03 (d, J=8.3 Hz, 1H), 7.98 (td, J=7.4, 0.9 Hz, 2H), 7.90 (td, J=7.5, 1.3 Hz, 1H), 7.87-7.81 (m, 2H), 7.77 (dd, J=8.2, 1.2 Hz, 1H), 7.73 (t, J=5.7 Hz, 1H), 6.88 (s, 1H), 4.40 (d, J=5.5 Hz, 2H), 3.88 (d, J=6.0 Hz, 2H); LC-MS: 95.64%; 472.9 (M$^+$+1); (column; Ascentis Express C18, (50×3.0 mm, 2.7 µm); RT 1.75 min. 0.025% Aq. TFA+5% ACN: ACN+5% 0.025% Aq. TFA, 1.2 mL/min); HPLC (purity): 97.00%; (column; Zorbax SB C-18 (150×4.6 mm, 3.5 µm); RT 4.87 min. ACN+5% 0.05% TFA (Aq): 0.05% TFA (Aq)+5% ACN; 1.0 mL/min).

Synthesis of 1580

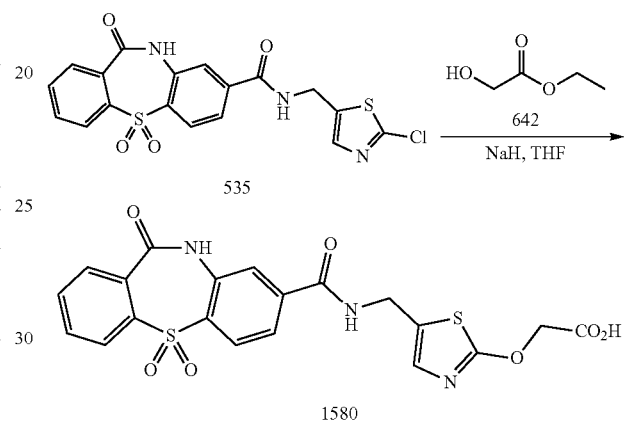

Synthesis of 2-((5-((5, 5-dioxido-11-oxo-10, 11-dihydrodibenzo [b, f] [1, 4] thiazepine-8-carboxamido) methyl) thiazol-2-yl) oxy) acetic acid (1580)

To a stirring suspension of added sodium hydride (60%, 27.7 mg, 1.15 mmol) in THF (15 mL) under argon atmosphere was added ethyl 2-hydroxyacetate 642 (48 mg, 0.46 mmol) at 0° C. and stirred for 1 h. To this was added compound 535 (100 mg, 0.23 mmol) at 0° C.; heated to 60° C. and stirred for 16 h. The reaction was monitored by TLC and LC-MS; after completion of the reaction, the reaction mixture was diluted with water (20 mL) and the extracted with EtOAc (2×10 mL). The pH of the aqueous layer was adjusted to ~4 using 2 N HCl and extracted with 5% MeOH/$CH_2Cl_2$ (3×50 mL). The combined organic extracts were dried over sodium sulfate, filtered and concentrated in vacuo to obtain the crude. The crude compound was purified by preparative HPLC purification to afford 1580 (10 mg, 9%) as an off-white solid. TLC: 5% MeOH/$CH_2Cl_2$+0.1 mL $CH_3COOH$ ($R_f$: 0.2); $^1$H-NMR (DMSO-$d_6$, 400 MHz): δ 9.32 (br s, 1H), 8.03 (d, J=8.3 Hz, 1H), 7.98 (td, J=7.4, 1.1 Hz, 2H), 7.93-7.82 (m, 4H), 7.78 (dd, J=8.3, 1.6 Hz, 1H), 7.00 (s, 1H), 4.49 (br s, 2H), 4.45 (d, J=4.7 Hz, 2H); LC-MS: 95.67%; 473.8 (M$^+$+1); (column; Ascentis Express C18, (50×3.0 mm, 2.7 µm); RT 1.96 min. 0.025% Aq. TFA+5% ACN: ACN+5% 0.025% Aq. TFA, 1.2 mL/min); HPLC (purity): 94.09%; (column; X-select CSH C-18 (150×4.6 mm, 3.5 µm); RT 7.17 min. ACN: 0.05% TFA (Aq); 1.0 mL/min).

Synthesis of 1586

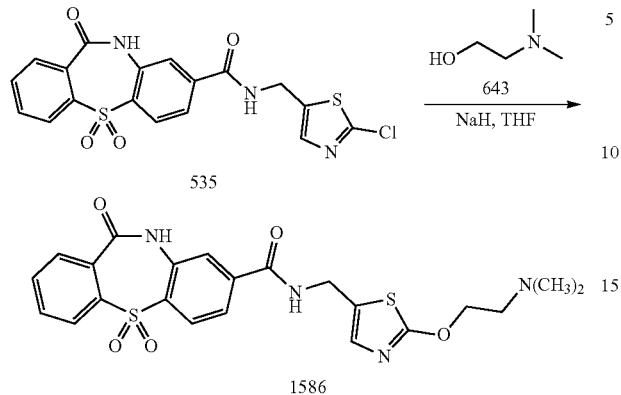

Synthesis of N-((2-(2-(dimethylamino) ethoxy) thiazol-5-yl) methyl)-11-oxo-10, 11-dihydrodibenzo [b, f] [1, 4] thiazepine-8-carboxamide 5, 5-dioxide (1586)

To a stirring solution of 2-(dimethylamino) ethan-1-ol 643 (62 mg, 0.69 mmol) in dry THF (10 mL) was added sodium hydride (60%, 25 mg, 0.69 mmol) under argon atmosphere was added at 0° C. and stirred for 10 min. To this was added N-((2-chlorothiazol-5-yl) methyl)-11-oxo-10, 11-dihydrodibenzo [b, f] [1, 4] thiazepine-8-carboxamide 5, 5-dioxide 535 (150 mg, 0.34 mmol) at 0° C.; heated to 60° C. and stirred for 24 h. The reaction was monitored by TLC; after completion of the reaction, the reaction mixture was diluted with ice-cold water (20 mL) and the extracted with EtOAc (2×10 mL). The combined organic extracts were dried over sodium sulfate, filtered and concentrated in vacuo to obtain the crude. The crude was purified through silica gel column chromatography using 10% MeOH/CH$_2$Cl$_2$ to afford compound to afford 1586 (40 mg, 24%) as an off-white solid. TLC: 10% MeOH/CH$_2$Cl$_2$ (R$_f$: 0.4); $^1$H-NMR (DMSO-d$_6$, 400 MHz): δ 11.51 (br s, 1H), 9.36 (t, J=5.6 Hz, 1H), 8.05 (d, J=8.4 Hz, 1H), 8.01-7.95 (m, 2H), 7.93-7.83 (m, 3H), 7.78 (dd, J=8.2, 1.3 Hz, 1H), 7.08 (s, 1H), 4.47 (d, J=5.8 Hz, 2H), 4.43 (t, J=5.5 Hz, 2H), 2.81-2.73 (m, 2H), 2.28 (s, 6H); LC-MS: 95.67%; 487.0 (M$^+$+1); (column; Ascentis Express C18, (50×3.0 mm, 2.7 µm); RT 1.58 min. 0.025% Aq. TFA+5% ACN: ACN+5% 0.025% Aq. TFA, 1.2 mL/min); HPLC (purity): 97.75%; (column; Zorbax SB C-18 (150×4.6 mm, 3.5 µm); RT 5.23 min. ACN: 0.05% TFA (Aq); 1.0 mL/min).

Synthesis of 1680

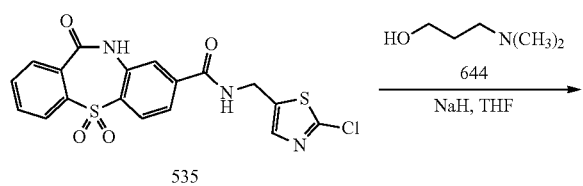

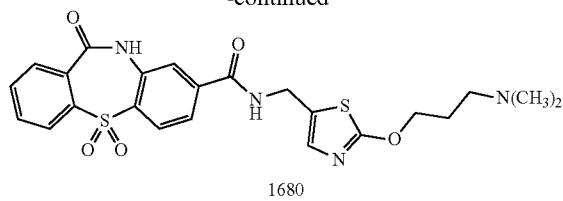

Synthesis of N-((2-(3-(dimethylamino) propoxy) thiazol-5-yl) methyl)-11-oxo-10, 11-dihydrodibenzo [b, f] [1, 4] thiazepine-8-carboxamide 5, 5-dioxide (1680)

To a stirring suspension of 3-(dimethylamino) propan-1-ol 644 (57 mg, 0.55 mmol) in THF (20 mL) under argon atmosphere was added sodium hydride (60%, 55 mg, 1.38 mmol) at 0° C. and stirred for 20 min. To this was added N-((2-chlorothiazol-5-yl) methyl)-11-oxo-10, 11-dihydrodibenzo [b, f] [1, 4] thiazepine-8-carboxamide 5, 5-dioxide 535 (200 mg, 0.46 mmol) at 0° C.; heated to 50-60° C. and stirred for 12 h. The reaction was monitored by TLC; after completion of the reaction, the reaction mixture was quenched with saturated citric acid solution (10 mL) and extracted with 10% n-butanol/EtOAc (2×40 mL). The combined organic extracts were dried over sodium sulfate, filtered and concentrated in vacuo to obtain the crude. The crude was purified through basic alumina flash column chromatography using 5% MeOH/CH2Cl2, triturated with 20% CH2Cl2/n-pentane (10 mL) and dried in vacuo to afford 1680 (80 mg, 35%) as white solid. TLC: 10% MeOH/CH2Cl2 (R$_f$: 0.2); 1H-NMR (DMSO-d6, 400 MHz): δ 11.50 (br s, 1H), 9.33 (t, J=5.7 Hz, 1H), 8.04 (d, J=8.3 Hz, 1H), 8.01-7.95 (m, 2H), 7.90 (td, J=7.5, 1.5 Hz, 1H), 7.86 (dd, J=7.5, 1.6 Hz, 1H), 7.83 (s, 1H), 7.78 (dd, J=8.3, 1.5 Hz, 1H), 7.07 (s, 1H), 4.46 (d, J=5.5 Hz, 2H), 4.32 (t, J=6.5 Hz, 2H), 2.28 (t, J=7.0 Hz, 2H), 2.10 (s, 6H), 1.87-1.79 (m, 2H); LC-MS: 95.84%; 501.0 (M++1); (column; Ascentis Express C18, (50×3.0 mm, 2.7 µm); RT 1.70 min. 0.025% Aq. TFA+5% ACN: ACN+5% 0.025% Aq. TFA, 1.2 mL/min); HPLC (purity): 94.58%; (column; Zorbax SBC C-18 (150× 4.6 mm, 3.5 µm); RT 5.73 min. ACN: 0.05% TFA (Aq); 1.0 mL/min, Diluent: ACN:water).

Synthesis of 1660

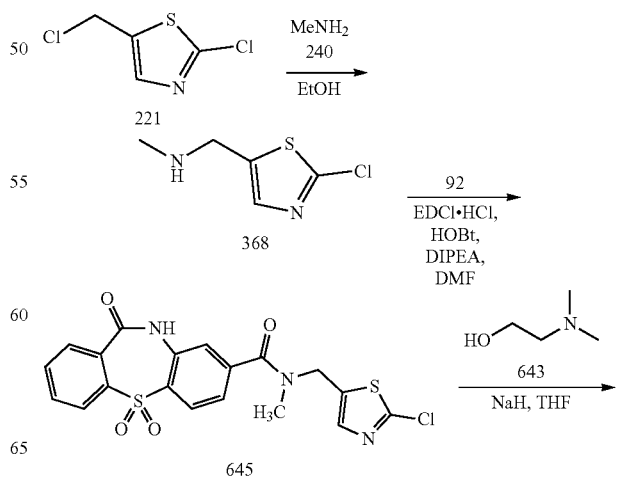

503

-continued

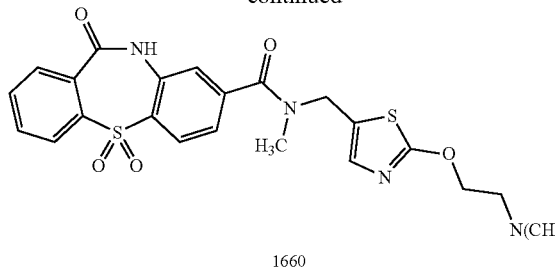

1660

Synthesis of N-((2-chlorothiazol-5-yl) methyl)-N-methyl-11-oxo-10, 11-dihydrodibenzo [b, f] [1, 4] thiazepine-8-carboxamide 5, 5-dioxide (645)

To a stirring solution of 92 (200 mg, 0.66 mmol) in DMF (10 mL) under inert atmosphere were added EDCI.HCl (190 mg, 0.99 mmol), HOBt (133 mg, 0.99 mmol), compound 368 (117 mg, 0.72 mmol) and diisopropylethylamine (0.36 mL, 1.98 mmol) at 0° C.; warmed to RT and stirred for 16 h. The reaction was monitored by TLC; after completion of the reaction, the reaction mixture was diluted with water (70 mL) and extracted with EtOAc (2×50 mL). The combined organic extracts were dried over sodium sulfate, filtered and concentrated in vacuo to obtain the crude. The crude was purified through silicagel column chromatography using 5% MeOH/CH$_2$Cl$_2$ to afford compound 645 (100 mg, 33%) as an off-white solid. TLC: 10% MeOH/CH$_2$Cl$_2$ ($R_f$: 0.6); $^1$H NMR (DMSO-d$_6$, 400 MHz): δ 11.44 (br s, 1H), 8.03-7.96 (m, 3H), 7.93-7.83 (m, 2H), 7.72 (s, 1H), 7.46-7.39 (m, 2H), 4.75 (s, 2H), 2.85 (s, 3H); LC-MS: 96.84%; 448.0 (M$^+$+1); (column; Ascentis Express C18, (50×3.0 mm, 2.7 μm); RT 2.19 min. 0.025% Aq.TFA+5% ACN: ACN+5% 0.025% Aq. TFA, 1.2 mL/min).

Synthesis of N-((2-(2-(dimethylamino) ethoxy) thiazol-5-yl) methyl)-N-methyl-11-oxo-10, 11-dihydrodibenzo [b, f] [1, 4] thiazepine-8-carboxamide 5, 5-dioxide (1660)

To a stirring solution of 2-(dimethylamino) ethan-1-ol 643 (176 mg, 0.98 mmol) in THF (20 mL) under argon atmosphere was added sodium hydride (60%, 47 mg, 1.98 mmol) at 0° C. and stirred for 20 min. To this was added compound 645 (300 mg, 0.99 mmol) at 0° C.; heated to 60° C. and stirred for 6 h. The reaction was monitored by TLC; after completion of the reaction, the reaction mixture was quenched with ice-cold water (1 mL). The volatiles were removed in vacuo to obtain the crude. The crude compound was purified through basis alumina column chromatography using 3% MeOH/CH$_2$Cl$_2$ to afford 1660 (20 mg, 4%) as an off-white solid. TLC: 10% MeOH/CH$_2$Cl$_2$ ($R_f$: 0.2); $^1$H-NMR (DMSO-d$_6$, 500 MHz) (rotamers): δ 11.43 (br s, 1H), 8.04-7.96 (m, 3H), 7.94-7.83 (m, 2H), 7.44-7.37 (m, 2H), 7.19, 7.01 (s, 1H), 4.63 (s, 1.5H), 4.41 (t, J=5.4 Hz, 2.5H), 2.91, 2.81 (s, 3H), 2.65-2.60 (m, 2H), 2.19 (s, 6H); LC-MS: 95.12%; 501.0 (M$^+$+1); (column; Ascentis Express C18, (50×3.0 mm, 2.7 μm); RT 1.71 min. 0.025% Aq. TFA+5% ACN: ACN+5% 0.025% Aq. TFA, 1.2 mL/min); HPLC (purity): 97.19%; (column; X-select CSH C-18 (150× 4.6 mm, 3.5 μm); RT 5.09 min. ACN+5% 0.05% TFA (Aq): 0.05% TFA (Aq)+5% ACN; 1.0 mL/min, Diluent: ACN: water).

Synthesis of 1589

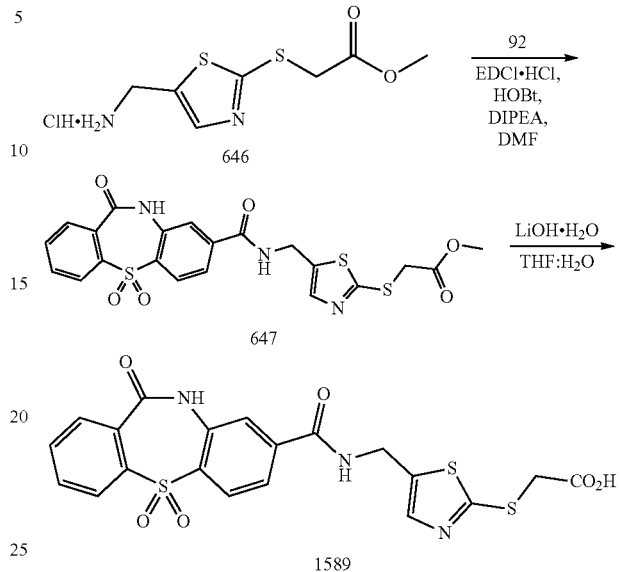

Synthesis of methyl 2-((5-((5, 5-dioxido-11-oxo-10, 11-dihydrodibenzo [b, f] [1, 4] thiazepine-8-carboxamido) methyl) thiazol-2-yl) thio) acetate (647)

To a stirring solution of compound 92 (200 mg, 0.66 mmol) in DMF (5 mL) under inert atmosphere were added EDCI.HCl (179 mg, 0.99 mmol), HOBt (133 mg, 0.99 mmol) and diisopropylethylamine (0.4 mL, 1.76 mmol) and methyl 2-((5-(aminomethyl) thiazol-2-yl) thio) acetate hydrochloride 646 (183 mg, 0.73 mmol) at 0° C.; warmed to RT and stirred for 16 h. The reaction was monitored by TLC; after completion of the reaction, the reaction mixture was diluted with water (50 mL), the precipitated solid was filtered and dried in vacuo to afford compound 647 (160 mg, 48%) as pale brown solid. TLC: 10% MeOH/CH$_2$Cl$_2$ ($R_f$: 0.4); $^1$H-NMR (DMSO-d$_6$ 500 MHz): δ 11.50 (s, 1H), 9.41 (t, J=5.6 Hz, 1H), 8.05 (d, J=8.1 Hz, 1H), 7.98 (t, J=8.4 Hz, 2H), 7.90 (t, J=7.1 Hz, 1H), 7.88-7.82 (m, 2H), 7.78 (d, J=8.1 Hz, 1H), 7.59 (s, 1H), 4.57 (d, J=5.5 Hz, 2H), 4.12 (s, 2H), 3.64 (s, 3H).

Synthesis of 2-((5-((5, 5-dioxido-11-oxo-10, 11-dihydrodibenzo [b, f] [1, 4] thiazepine-8-carboxamido) methyl) thiazol-2-yl) thio) acetic acid (1589)

To a stirring solution of compound 647 (100 mg, 0.19 mmol) in THF:H$_2$O (1:1, 10 mL) was added lithium hydroxide monohydrate (10 mg, 0.28 mmol) at RT and stirred for 6 h. The reaction was monitored by TLC; after completion of the reaction, the volatiles were removed in vacuo. The pH of the residue was acidified with 4 N HCl to ~4. The precipitated solid was filtered and dried in vacuo to afford 1589 (60 mg, 51%) as an off-white solid. TLC: 10% MeOH/CH$_2$Cl$_2$ ($R_f$: 0.2); $^1$H-NMR (DMSO-d$_6$, 500 MHz): δ 12.89 (br s, 1H), 11.50 (s, 1H), 9.41 (t, J=5.4 Hz, 1H), 8.04 (d, J=8.4 Hz, 1H), 8.01-7.95 (m, 2H), 7.93-7.81 (m, 3H), 7.78 (d, J=8.4 Hz, 1H), 7.58 (s, 1H), 4.57 (d, J=5.5 Hz, 2H), 4.02 (s, 2H); LC-MS: 98.73%; 490.0 (M$^+$+1); (column;

X-select CSH C18, (50×3.0 mm, 2.5 μm); RT 2.10 min. 2.5 mM Aq.NH₄OOCH+5% ACN+5% 2.5 mM Aq.NH₄OOCH; 0.0.8 mL/min); HPLC (purity): 99.17%; (column; Zorbax SB C-18 (150×4.6 mm, 3.5 μm); RT 6.59 min. ACN+5% 0.05% TFA (Aq): 0.05% TFA (Aq)+5% ACN; 1.0 mL/min).

Synthesis of 1585

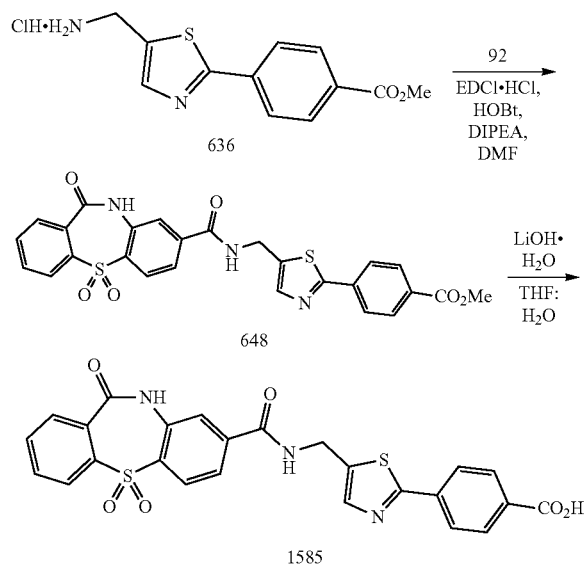

Synthesis of methyl 4-(5-((5, 5-dioxido-11-oxo-10, 11-dihydrodibenzo [b, f] [1, 4] thiazepine-8-carboxamido) methyl) thiazol-2-yl) benzoate (648)

To a stirring solution of compound 92 (200 mg, 0.66 mmol) in DMF (10 mL) under inert atmosphere were added EDCI.HCl (189.1 mg, 0.99 mmol), HOBt (133.6 mg, 0.99 mmol) at RT and stirred for 5 min. To this was added methyl 4-(5-(aminomethyl) thiazol-2-yl) benzoate hydrochloride 636 (196.4 mg, 0.79 mmol) and diisopropylethylamine (0.59 mL, 3.29 mmol) at RT and stirred for 16 h. The reaction was monitored by TLC; after completion of the reaction, the reaction mixture was diluted with ice-cold water (100 mL) and extracted with EtOAc (2×100 mL). The combined organic extracts were dried over sodium sulfate, filtered and concentrated in vacuo to obtain the crude. The crude was purified through silica gel flash column chromatography using 2% MeOH/CH₂Cl₂ to afford compound 648 (130 mg, 37%) as an off-white solid. TLC: 5% MeOH/CH₂Cl₂ (R$_f$: 0.3); ¹H-NMR (DMSO-d₆, 500 MHz): δ 11.52 (br s, 1H), 9.51 (t, J=5.6 Hz, 1H), 8.08-8.01 (m, 5H), 7.98 (t, J=8.5 Hz, 2H), 7.92-7.80 (m, 5H), 4.71 (d, J=5.8 Hz, 2H), 3.87 (s, 3H).

Synthesis of 4-(5-((5, 5-dioxido-11-oxo-10, 11-dihydrodibenzo [b, f] [1, 4] thiazepine-8-carboxamido) methyl) thiazol-2-yl) benzoic acid (1585)

To a stirring solution of compound 648 (80 mg, 0.15 mmol) in THF:H₂O (5:1, 6 mL) was added lithium hydroxide monohydrate (19 mg, 0.45 mmol) at 0° C.; warmed to RT and stirred for 16 h. The reaction was monitored by TLC; after completion of the reaction, volatiles were removed in vacuo. The crude was washed with EtOAc (2×10 mL). The obtained solid was dissolved in water (20 mL) and pH was adjusted to ~2 using 2 N HCl. The precipitated solid was filtered, washed with water (20 mL), n-pentane (50 mL) and dried in vacuo to afford 1585 (60 mg, 77%) as an off-white solid. TLC: 5% MeOH/CH₂Cl₂ (R$_f$: 0.2); ¹H-NMR (DMSO-d₆, 500 MHz): δ 13.18 (br s, 1H), 11.52 (s, 1H), 9.51 (t, J=5.6 Hz, 1H), 8.09-7.95 (m, 7H), 7.93-7.80 (m, 5H), 4.71 (d, J=5.8 Hz, 2H); LC-MS: 92.54%; 519.9 (M⁺+1); (column; Ascentis Express C18, (50×3.0 mm, 2.7 μm); RT 2.22 min. 0.025% Aq. TFA+5% ACN: ACN+5% 0.025% Aq. TFA, 1.2 mL/min); HPLC (purity): 93.48%; (column; Zorbax SB C-18 (150×4.6 mm, 3.5 μm); RT 7.41 min. ACN+5% 0.05% TFA (Aq): 0.05% TFA (Aq)+5% ACN; 1.0 mL/min).

Synthesis of 1645-B

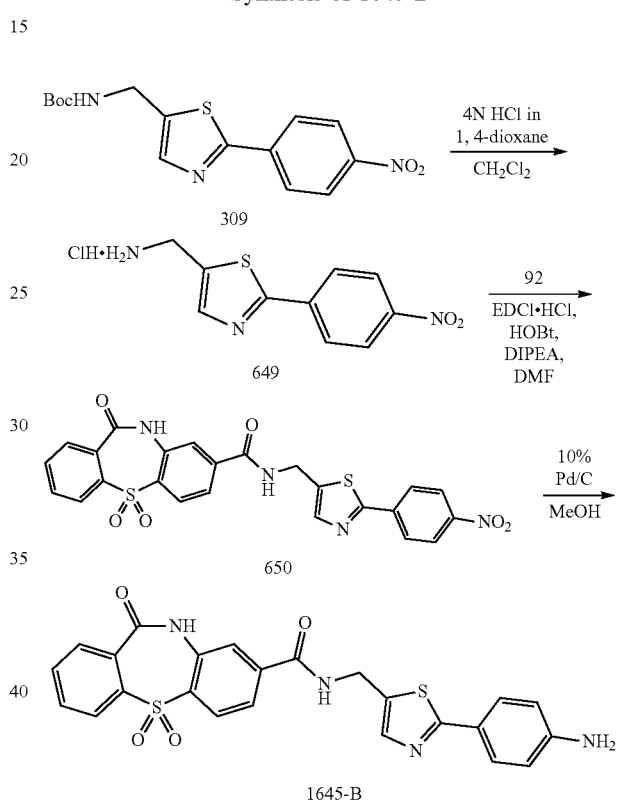

Synthesis of (2-(4-nitrophenyl) thiazol-5-yl) methanamine hydrochloride (649)

To a stirring solution of tert-butyl ((2-(4-nitrophenyl) thiazol-5-yl) methyl) carbamate 309 (150 mg, 0.44 mmol) in CH₂Cl₂ (5 mL) under inert atmosphere was added 4 N HCl in 1, 4-dioxane (1.5 mL) at 0° C.; warmed to RT and stirred for 2 h. The reaction was monitored by TLC; after completion of the reaction, the volatiles were removed in vacuo to obtain the crude. The crude was washed with diethylether (2×5 mL) and dried in vacuo to afford compound 649 (110 mg, 91%) as yellow solid. TLC: 5% MeOH/CH₂Cl₂ (R$_f$: 0.2); ¹H-NMR (DMSO-d₆, 500 MHz): δ 8.52 (br s, 3H), 8.36 (d, J=9.0 Hz, 2H), 8.21 (d, J=9.0 Hz, 2H), 8.12 (s, 1H), 4.41 (br s, 2H).

Synthesis of N-((2-(4-nitrophenyl) thiazol-5-yl) methyl)-11-oxo-10, 11-dihydrodibenzo [b, f] [1, 4] thiazepine-8-carboxamide 5, 5-dioxide (650)

To a stirring solution of 92 (100 mg, 0.33 mmol) in DMF (5 mL) under inert atmosphere were added EDCI.HCl (95 mg, 0.49 mmol), HOBt (67 mg, 0.49 mmol), compound 649 (108 mg, 0.39 mmol) and diisopropylethylamine (0.18 mL, 0.99 mmol) at 0° C.; warmed to RT and stirred for 16 h. The reaction was monitored by TLC; after completion of the reaction, the reaction mixture was diluted with water (50 mL) and extracted with EtOAc (2×100 mL). The combined organic extracts were dried over sodium sulfate, filtered and concentrated in vacuo to obtain the crude. The crude was purified through silicagel column chromatography using 3% MeOH/CH$_2$Cl$_2$ to afford compound 650 (80 mg, 47%) as an off-white solid. TLC: 5% MeOH/CH$_2$Cl$_2$ (R$_f$: 0.5); $^1$H NMR (DMSO-d$_6$, 500 MHz): δ11.52 (br s, 1H), 9.53 (t, J=5.5 Hz, 1H), 8.31 (d, J=8.7 Hz, 2H), 8.15 (d, J=8.7 Hz, 2H), 8.06 (d, J=8.4 Hz, 1H), 8.01-7.95 (m, 3H), 7.92-7.79 (m, 4H), 4.73 (d, J=5.5 Hz, 2H); LC-MS: 93.76%; 520.9 (M$^+$+1); (column; Ascentis Express C18, (50×3.0 mm, 2.7 μm); RT 2.46 min. 0.025% Aq. TFA+5% ACN: ACN+5% 0.025% Aq. TFA, 1.2 mL/min).

Synthesis of N-((2-(4-aminophenyl) thiazol-5-yl) methyl)-11-oxo-10, 11-dihydrodibenzo [b, f] [1, 4] thiazepine-8-carboxamide 5, 5-dioxide (1645-B)

To a stirring solution of compound 650 (75 mg, 0.14 mmol) in MeOH (10 mL) under inert atmosphere was added 10% Pd/C (30 mg) at RT and stirred under hydrogen atmosphere (balloon pressure) at RT for 16 h. The reaction was monitored by TLC; after completion of the reaction, the reaction mixture was filtered through celite and washed with MeOH (100 mL). The filtrate was concentrated in vacuo to obtain the crude, which was titurated with diethyl ether:n-pentane (1:1, 20 mL) and followed by silicagel column chromatography using 2-3% MeOH/CH$_2$Cl$_2$ to afford 1645-B (22 mg, 32%) as an off-white solid. TLC: 10% MeOH/CH$_2$Cl$_2$ (R$_f$: 0.2); 41 NMR (DMSO-d$_6$, 400 MHz): δ 11.48 (br s, 1H), 9.40 (t, J=5.5 Hz, 1H), 8.05 (d, J=8.3 Hz, 1H), 7.98 (td, J=7.5, 0.9 Hz, 2H), 7.94-7.78 (m, 4H), 7.59 (s, 1H), 7.53 (d, J=8.5 Hz, 2H), 6.57 (d, J=8.6 Hz, 2H), 5.62 (s, 2H), 4.62 (d, J=5.5 Hz, 2H); LC-MS: 97.21%; 491.0 (M$^+$+1); (column; Ascentis Express C18, (50×3.0 mm, 2.7 μm); RT 1.97 min. 0.025% Aq. TFA+5% ACN: ACN+5% 0.025% Aq. TFA, 1.2 mL/min); HPLC (purity): 96.45%; (column; X-select CSH C-18 (150×4.6 mm, 3.5 μm); RT 9.06 min. ACN+5 mM NH$_4$OAc: ACN; 1.0 mL/min, Diluent: ACN:water).

Synthesis of 1764

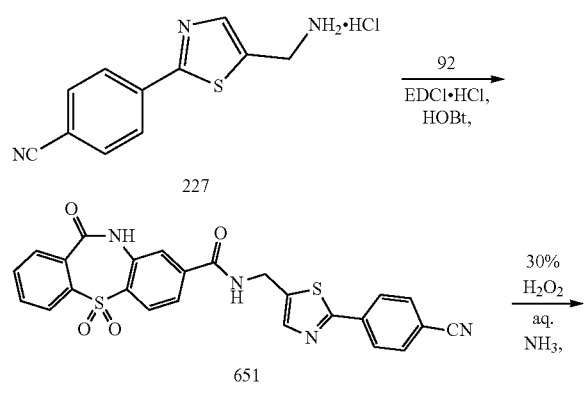

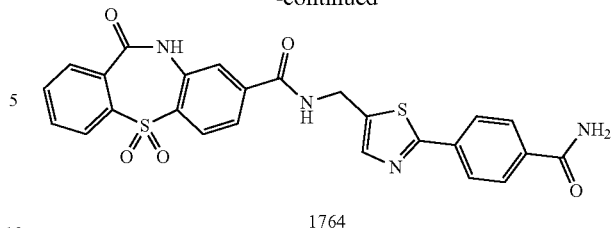

1764

Synthesis of N-((2-(4-cyanophenyl) thiazol-5-yl) methyl)-11-oxo-10, 11-dihydrodibenzo [b, f] [1, 4] thiazepine-8-carboxamide 5, 5-dioxide (651)

To a stirring solution of 92 (300 mg, 0.99 mmol) in DMF (15 mL) under inert atmosphere were added EDCI.HCl (283 mg, 1.48 mmol), HOBt (200 mg, 1.48 mmol), compound 227 (274 mg, 1.08 mmol) and diisopropylethylamine (0.55 mL, 2.95 mmol) at 0° C.; warmed to RT and stirred for 16 h. The reaction was monitored by TLC; after completion of the reaction, the reaction mixture was diluted with ice-cold water (100 mL) and extracted with EtOAc (2×150 mL). The combined organic extracts were dried over sodium sulfate, filtered and concentrated in vacuo to obtain the crude. The crude was purified through silicagel column chromatography using 3% MeOH/CH$_2$Cl$_2$ to afford compound 651 (250 mg, 50%) as white solid. TLC: 5% MeOH/CH$_2$Cl$_2$ (R$_f$: 0.6); $^1$H NMR (DMSO-d$_6$, 400 MHz): δ 11.52 (s, 1H), 9.52 (t, J=5.7 Hz, 1H), 8.08-7.79 (m, 11H), 4.72 (d, J=5.6 Hz, 2H); LC-MS: 99.46%; 501.0 (M$^+$+1); (column; Ascentis Express C18, (50×3.0 mm, 2.7 μm); RT 2.30 min. 0.025% Aq. TFA+5% ACN: ACN+5% 0.025% Aq. TFA, 1.2 mL/min).

Synthesis of N-((2-(4-carbamoylphenyl) thiazol-5-yl) methyl)-11-oxo-10, 11 dihydrodibenzo [b, f] [1, 4] thiazepine-8-carboxamide 5, 5-dioxide (1764)

To a stirring solution of compound 651 (100 mg, 0.20 mmol) in EtOH (5 mL) were added 30% H$_2$O$_2$ (5 mL) and 30% aqueous ammonia (5 mL) at 0° C. warmed to RT and stirred for 2 h. The reaction was monitored by TLC; after completion of the reaction, the reaction mixture was diluted with water (100 mL) and extracted with CH$_2$Cl$_2$ (2×50 mL). The combined organic extracts were dried over sodium sulfate, filtered, concentrated in vacuo to obtain the crude. The crude was washed with EtOAc (2×10 mL) and dried in vacuo to afford 1764 (55 mg, 53%) as white solid. TLC: 7% MeOH/CH$_2$Cl$_2$ (R$_f$: 0.4); $^1$H-NMR (DMSO-d$_6$, 400 MHz): δ 11.48 (br s, 1H), 9.50 (t, J=5.8 Hz, 1H), 8.08-8.04 (m, 2H), 8.00-7.94 (m, 6H), 7.90 (td, J=7.5, 1.4 Hz, 1H), 7.87-7.80 (m, 4H), 7.44 (br s, 1H), 4.71 (d, J=5.6 Hz, 2H); LC-MS: 98.11%; 519.0 (M$^+$+1); (column; Ascentis Express C18, (50×3.0 mm, 2.7 μm); RT 1.98 min. 0.025% Aq. TFA+5% ACN: ACN+5% 0.025% Aq. TFA, 1.2 mL/min); HPLC (purity): 98.61%; (column; X select CSH C-18 (150×4.6 mm, 3.5 μm); RT 6.87 min. ACN+5% 0.05% TFA (Aq): 0.05% TFA (Aq)+5% ACN; 1.0 mL/min, Diluent: ACN:water).

Synthesis of 1666 and 1669

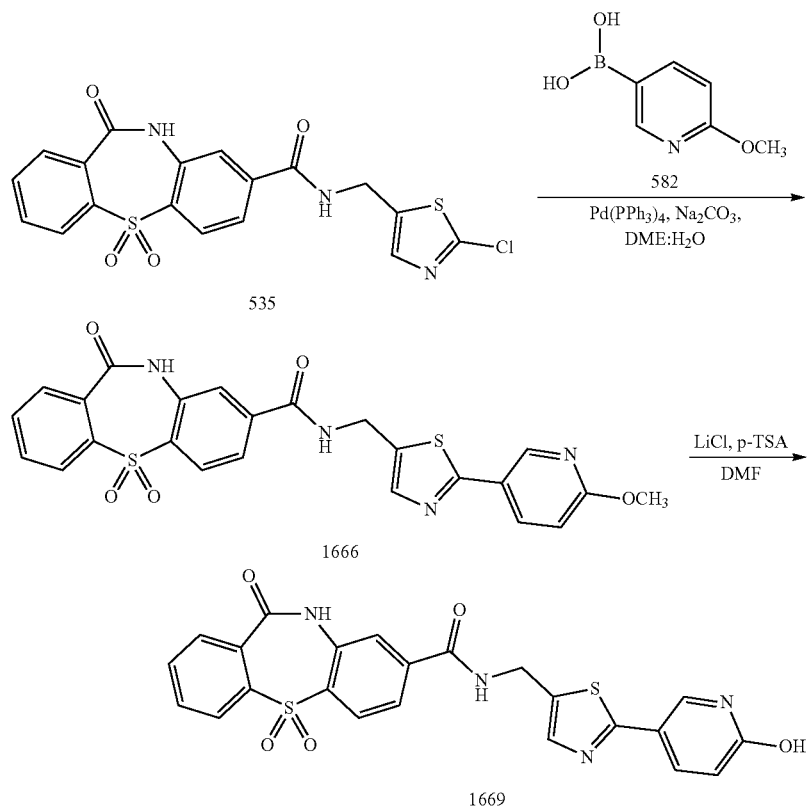

Synthesis of N-((2-(6-methoxypyridin-3-yl) thiazol-5-yl) methyl)-11-oxo-10, 11-dihydrodibenzo [b, f] [1, 4] thiazepine-8-carboxamide 5, 5-dioxide (1666)

To a stirring solution of N-((2-chlorothiazol-5-yl) methyl)-11-oxo-10, 11-dihydrodibenzo [b, f] [1, 4] thiazepine-8-carboxamide 5, 5-dioxide 535 (300 mg, 0.69 mmol) in 1, 2 dimethoxy ethane:$H_2O$ (4:1, 10 mL) were added (6-methoxypyridin-3-yl) boronic acid 582 (127 mg, 0.84 mmol), sodium carbonate (220 mg, 2.07 mmol) in a sealed tube and purged under argon atmosphere for 15 min. To this was added Pd(PPh$_3$)$_4$ (80 mg, 0.069 mmol) at RT; heated to 110° C. and stirred for 16 h. The reaction was monitored by TLC; after completion the reaction mixture was diluted with water (50 mL) and extracted with 5% MeOH/$CH_2Cl_2$ (100 mL). The combined organic extracts were dried over sodium sulfate, filtered and concentrated in vacuo to obtain the crude. The crude was purified through silica gel column chromatography using 2-8% MeOH/$CH_2Cl_2$ to afford compound 1666 (140 mg, 27%) as an off-white solid. TLC: 5% MeOH/$CH_2Cl_2$ ($R_f$: 0.4); $^1$H-NMR (DMSO-$d_6$, 500 MHz): δ 11.52 (s, 1H), 9.47 (t, J=6.1 Hz, 1H), 8.68 (d, J=2.3 Hz, 1H), 8.16 (dd, J=8.7, 2.3 Hz, 1H), 8.06 (d, J=8.1 Hz, 1H), 7.98 (t, J=8.2 Hz, 2H), 7.93-7.78 (m, 5H), 6.92 (d, J=8.7 Hz, 1H), 4.68 (d, J=5.5 Hz, 2H), 3.90 (s, 3H); LC-MS: 96.23%; 507.0 (M$^+$+1); (column; Ascentis Express C18, (50×3.0 mm, 2.7 μm); RT 2.23 min. 0.025% Aq. TFA+5% ACN: ACN+5% 0.025% Aq. TFA, 1.2 mL/min) HPLC (purity): 94.46%; (column; X-select CSH C-18 (150×4.6 mm, 3.5 μm); RT 8.40 min. ACN+5% 0.5% TFA (Aq): 0.5% TFA (Aq)+5% ACN; 1.0 mL/min, Diluent: ACN:water).

Synthesis of N-((2-(6-hydroxypyridin-3-yl) thiazol-5-yl) methyl)-11-oxo-10, 11-dihydrodibenzo [b, f] [1, 4] thiazepine-8-carboxamide 5, 5-dioxide (1669)

To a stirring solution of 1666 (100 mg, 0.19 mmol) in DMF (5 mL) under inert atmosphere were added lithium chloride (43 mg, 0.99 mmol), p-toluene sulfonic acid (4 mg, 0.019 mmol) at RT in a sealed tube; heated to 110° C. and stirred for 16 h. The reaction was monitored by TLC and LC-MS; after completion the reaction mixture was diluted with water (50 mL) and the precipitated was filtered, washed with $CH_2Cl_2$ (5 mL) and dried in vacuo to afford 1669 (60 mg, 62%) as an off-white solid. TLC: 5% MeOH/$CH_2Cl_2$ ($R_f$: 0.4); $^1$H-NMR (DMSO-$d_6$, 500 MHz): δ 11.96 (br s, 1H), 11.52 (br s, 1H), 9.45 (t, J=5.2 Hz, 1H), 8.05 (d, J=8.1 Hz, 1H), 7.98 (t, J=8.1 Hz, 2H), 7.94-7.83 (m, 5H), 7.80 (d, J=8.1 Hz, 1H), 7.68 (s, 1H), 6.43 (d, J=9.5 Hz, 1H), 4.64 (d, J=5.5 Hz, 2H); LC-MS: 97.01%; 492.9 (M$^+$+1); (column; Ascentis Express C18, (50×3.0 mm, 2.7 μm); RT 1.83 min. 0.025% Aq. TFA+5% ACN: ACN+5% 0.025% Aq. TFA, 1.2 mL/min); HPLC (purity): 93.66%; (column; Zorbax SBC C-18 (150×4.6 mm, 3.5 μm); RT 5.81 min. ACN+5% 0.05% TFA (Aq): 0.05% TFA (Aq)+5% ACN; 1.0 mL/min, Diluent: DMSO:ACN:water).

Synthesis of 1880 & 1880-A

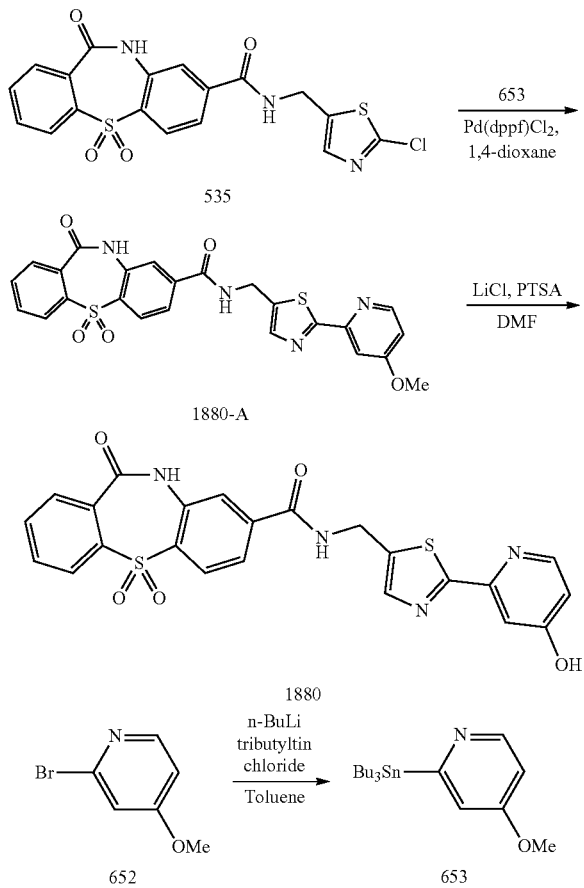

Synthesis of 4-methoxy-2-(tributylstannyl) pyridine (653)

To a stirring solution of 2-bromo-4-methoxypyridine 652 (1 g, 5.39 mmol) in dry Toluene (40 mL) under inert atmosphere was added n-butyl lithium (3.98 mL, 6.38 mmol, 1.6 M solution in hexane) at −78° C. and stirred for 1 h. To this was added tributyltin chloride (7.85 mL, 28.98 mmol) at −78° C.; warmed to RT and stirred for 30 min. The reaction was monitored by TLC; after completion of the reaction, the reaction mixture was quenched with ice-cold water (50 mL) and extracted with EtOAc (2×100 mL). The combined organic extracts were dried over sodium sulfate, filtered and concentrated in vacuo to afford compound 653 (1.5 g, 71%) as yellow liquid which was taken for next step without further purification. TLC: 20% EtOAc/hexanes ($R_f$: 0.8);

Synthesis of N-((2-(4-methoxypyridin-2-yl) thiazol-5-yl) methyl)-11-oxo-10, 11-dihydrodibenzo [b, f] [1, 4] thiazepine-8-carboxamide 5, 5-dioxide (1880-A)

To a stirring solution of N-((2-chlorothiazol-5-yl) methyl)-11-oxo-10, 11-dihydrodibenzo [b, 1] [1, 4] thiazepine-8-carboxamide 5, 5-dioxide 535 (500 mg, 1.15 mmol) in 1, 4-dioxane (30 mL) under argon atmosphere were added compound 653 (1.37 g, 3.46 mmol) and purged under argon atmosphere for 30 min, added Pd(dppf)Cl$_2$ (84 mg, 0.11 mmol) and heated to 110° C. and stirred for 16 h. The reaction was monitored by TLC; after completion of the reaction, the volatiles were removed in vacuo to obtain the crude. The crude was purified through silica gel column chromatography using 3% MeOH/CH$_2$Cl$_2$ to afford 1880-A (125 mg, 21%) as an off-white solid. TLC: 5% MeOH/CH$_2$Cl$_2$ ($R_f$: 0.5); $^1$H-NMR (DMSO-d$_6$, 400 MHz): δ 11.51 (s, 1H), 9.47 (t, J=5.8 Hz, 1H), 8.40 (d, J=5.6 Hz, 1H), 8.06 (d, J=8.3 Hz, 1H), 8.01-7.95 (m, 2H), 7.90 (td, J=7.5, 1.4 Hz, 1H), 7.87-7.83 (m, 3H), 7.81 (dd, J=8.3, 1.5 Hz, 1H), 7.58 (d, J=2.4 Hz, 1H), 7.04 (dd, J=5.7, 2.6 Hz, 1H), 4.69 (d, J=5.6 Hz, 2H), 3.90 (s, 3H); LC-MS: 97.10%; 507.0 (M$^+$+1); (column; Ascentis Express C18, (50×3.0 mm, 2.7 μm); RT 2.05 min. 0.025% Aq. TFA+5% ACN: ACN+5% 0.025% Aq. TFA, 1.2 mL/min); HPLC (purity): 96.24%; (column; X-select CSH C-18 (150×4.6 mm, 3.5 μm); RT 7.21 min. 0.05% TFA (Aq)+5% ACN: ACN+5% 0.05% ACN; 1.0 mL/min, Diluent: DMSO:ACN:water).

Synthesis of N-((2-(4-hydroxypyridin-2-yl) thiazol-5-yl) methyl)-11-oxo-10, 11-dihydrodibenzo [b, f] [1, 4] thiazepine-8-carboxamide 5, 5-dioxide (1880)

To a stirring solution of 1880-A (120 mg, 0.23 mmol) in DMF (10 mL) under inert atmosphere were added lithium chloride (206 mg, 4.74 mmol), p-toluenesulfonic acid (20 mg, 0.11 mmol) at RT; heated to 120-130° C. and stirred for 24 h. The reaction was monitored by TLC and LC-MS; after completion the reaction mixture was poured into ice-cold water (50 mL) and extracted with EtOAc (2×150 mL). The combined organic extracts were dried over sodium sulfate, filtered and concentrated in vacuo to obtain the crude. The crude was purified through silica gel column chromatography twice using 3% MeOH/CH$_2$Cl$_2$ to afford 1880 (15 mg, 13%) as an off-white solid. TLC: 5% MeOH/CH$_2$Cl$_2$ ($R_f$: 0.4); $^1$H-NMR (DMSO-d$_6$, 400 MHz): δ 11.51 (br s, 1H), 10.96 (br s, 1H), 9.48-9.43 (m, 1H), 8.26 (br d, J=3.5 Hz, 1H), 8.06 (br d, J=8.2 Hz, 1H), 7.98 (br t, J=7.3 Hz, 2H), 7.93-7.78 (m, 5H), 7.46 (br s, 1H), 6.81 (s, 1H), 4.68 (br d, J=4.1 Hz, 2H); LC-MS: 99.60%; 492.9 (M$^+$+1); (column; Ascentis Express C18, (50×3.0 mm, 2.7 μm); RT 1.76 min. 0.025% Aq. TFA+5% ACN: ACN+5% 0.025% Aq. TFA, 1.2 mL/min); HPLC (purity): 99.70%; (column; X-select CSH C-18 (150×4.6 mm, 3.5 μm); RT 5.94 min. 0.05% TFA (Aq)+5% ACN: ACN+5% 0.05% ACN; 1.0 mL/min, Diluent: DMSO:ACN:water).

Synthesis of 1889

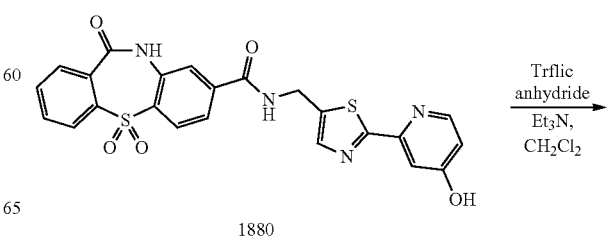

513

-continued

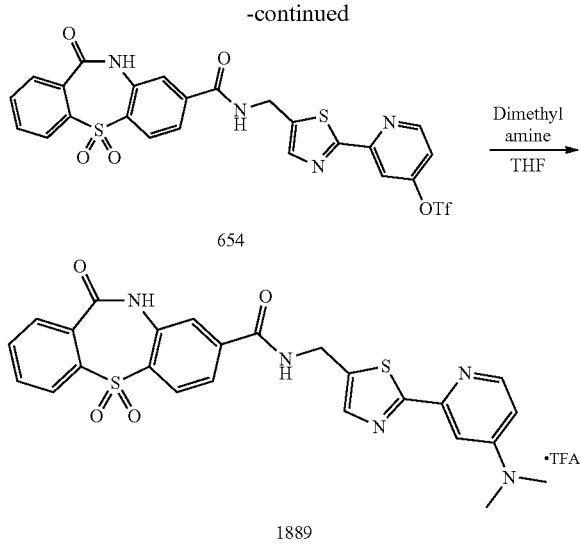

654

1889

Synthesis of 2-(5-((5,5-dioxido-11-oxo-10,11-dihydrodibenzo [b, f] [1, 4] thiazepine-8-carboxamido) methyl) thiazol-2-yl) pyridin-4-yl trifluoromethanesulfonate (654)

To a stirring solution of 1880 (200 mg, 0.40 mmol) in $CH_2Cl_2$ (10 mL) under inert atmosphere were added triethyl amine (1.67 mL, 1.21 mmol), triflic anhydride (0.1 mL, 0.60 mmol) at 0° C.; and stirred for 30 min. The reaction was monitored by TLC; after completion of the reaction, the reaction mixture was diluted with ice-cold water (30 mL) and extracted with $CH_2Cl_2$ (2×40 mL). The combined organic extracts were dried over sodium sulfate, filtered and concentrated in vacuo to afford compound 654 (210 mg crude) as an off white solid. The crude was taken forward next reaction without further purification. TLC: 5% MeOH/ $CH_2Cl_2$ ($R_f$: 0.7); LC-MS: 41%; 624.9 ($M^+$+1); (column; Ascentis Express C-18, (50×3.0 mm, 2.7 μm); RT 2.56 min, 0.025% Aq. TFA+5% ACN: ACN+5% 0.025% Aq. TFA, 1.2 mL/min);

Synthesis of N-((2-(4-(dimethylamino) pyridin-2-yl) thiazol-5-yl) methyl)-11-oxo-10,11-dihydrodibenzo [b, f] [1, 4] thiazepine-8-carboxamide 5,5-dioxide (1889)

To a stirring solution of compound 654 (210 mg crude, 0.33 mmol) in THF (5 mL) in a sealed tube was added 2 M dimethylamine in THF (0.36 mL, 0.67 mmol) at RT and stirred for 16 h. The reaction was monitored by TLC; after completion the volatiles were removed in vacuo to obtain the crude. The crude was purified through silica gel column chromatography using 3-4% MeOH/$CH_2Cl_2$ and further purified by preparative HPLC purification to afford 1889 (10 mg, 6%) as an off-white solid. TLC: 10% MeOH/$CH_2Cl_2$ ($R_f$: 0.4); $^1$H-NMR (DMSO-$d_6$, 400 MHz): δ 11.54 (s, 1H), 9.56 (br s, 1H), 8.10 (dd, J=16.7, 7.6 Hz, 2H), 7.98 (td, J=7.4, 1.1 Hz, 3H), 7.93-7.81 (m, 4H), 7.30 (d, J=2.6 Hz, 1H), 6.88 (br s, 1H), 4.74 (br d, J=5.5 Hz, 2H), 3.17 (br s, 6H); LC-MS: 95.94%; 520.0 ($M^+$+1); (column; Kinetex EVO C-18 (50×3.0 mm, 2.6 um); RT 2.47 min. 2.5 mM Aq. $NH_4OOCH$+5% ACN: ACN+5% 2.5 mM Aq. $NH_4OOCH$, 0.8 mL/min). HPLC (purity): 99.48%; (column; X select

514

CSH C-18 (150×4.6 mm, 3.5 μm); RT 5.73 min. 0.05% TFA+5% ACN: ACN+5% 0.05% TFA; 1.0 mL/min, Diluent: DMSO:ACN:water).

Synthesis of 1886

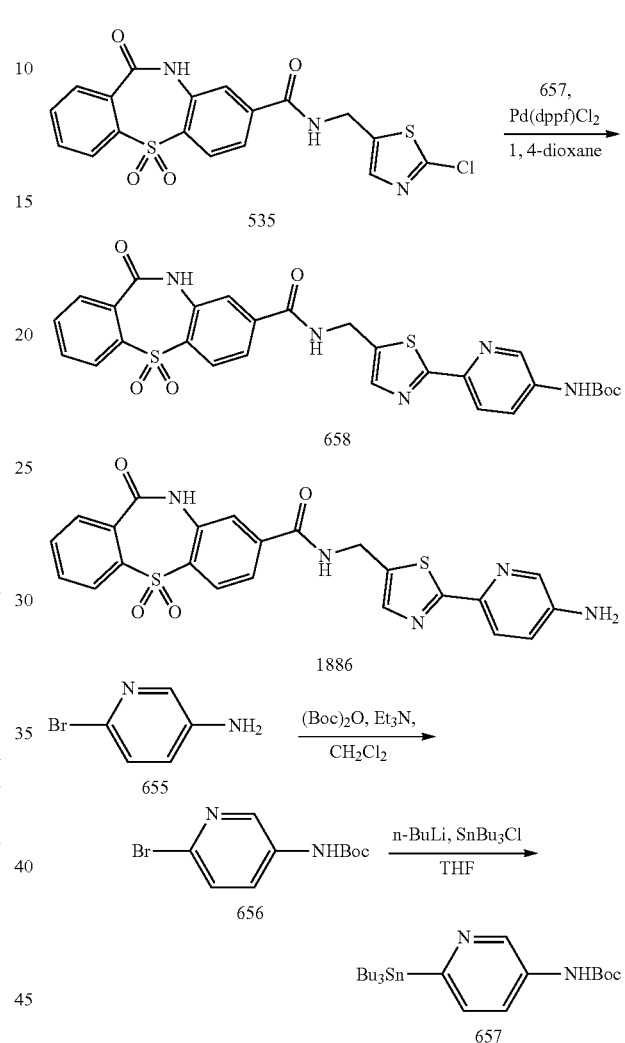

Synthesis of tert-butyl (6-bromopyridin-3-yl) carbamate (656)

To a stirring solution of 6-bromopyridin-3-amine 655 (5 g, 28.90 mmol) in $CH_2Cl_2$ (50 mL) under argon atmosphere were added Boc-anhydride (7.6 g, 34.86 mmol) and triethylamine (6.17 mL, 43.35 mmol) at 0 to 10° C.; warmed to RT and stirred for 16 h. The reaction was monitored by TLC; after completion of the reaction, the reaction mixture was diluted with water (100 mL), filtered through celite and eluted with $CH_2Cl_2$ (3×80 mL). The filtrate was dried over sodium sulfate, filtered and concentrated in vacuo to obtain the crude. The crude was purified through silica gel flash column chromatography using 5-7% EtOAc/hexanes to afford compound 656 (5 g, 64%) as white solid. TLC: 20% EtOAc/hexanes ($R_f$: 0.8); $^1$H-NMR (DMSO-$d_6$, 500 MHz): δ 9.72 (br s, 1H), 8.45 (s, 1H), 7.82 (dd, J=8.4, 2.0 Hz, 1H), 7.53 (d, J=8.7 Hz, 1H), 1.48 (s, 9H); LC-MS: 91.60%; 272.9

(M++1); (column; Ascentis Express C18, (50×3.0 mm, 2.7 µm); RT 2.48 min. 0.025% Aq. TFA+5% ACN: ACN+5% 0.025% Aq. TFA, 1.2 mL/min).

Synthesis of tert-butyl (6-(tributylstannyl) pyridin-3-yl) carbamate (657)

To a stirring solution of compound 656 (5 g, 18.31 mmol) in THF (50 mL) under argon atmosphere was added n-butyl lithium (23 mL, 36.63 mmol, 1.6 M solution in hexane) dropwise for 40 min at −78° C. and warmed to −10° C. and stirred for 40 min. To this was added tributylchlorostannane (8.92 g, 27.47 mmol) in THF (10 mL) at −78° C. and stirred for 1 h at the same temperature. The reaction was monitored by TLC; after completion of the reaction, the reaction mixture was quenched with saturated ammonium chloride solution (50 mL) and extracted with EtOAc (2×200 mL). The combined organic extracts were washed with saturated potassium fluoride solution (100 mL), dried over sodium sulfate, filtered and concentrated in vacuo to obtain the crude. The crude was purified through silicagel flash column chromatography using 5-7% EtOAc/hexanes to afford compound 657 (3 g, 34%) as yellow solid. TLC: 20% EtOAc/hexanes ($R_f$: 0.2); $^1$H-NMR (DMSO-$d_6$, 400 MHz): δ 9.42 (s, 1H), 8.70 (s, 1H), 7.73 (dd, J=8.0, 2.3 Hz, 1H), 7.33 (d, J=8.2 Hz, 1H), 1.64-1.54 (m, 6H), 1.47 (s, 9H), 1.38-1.22 (m, 6H), 1.14-1.08 (m, 6H), 0.87 (t, J=7.3 Hz, 9H); The aliphatic region shows tin reagent as impurity; LC-MS: 68.59%; 485.2 (M++1); (column; Ascentis Express C18, (50×3.0 mm, 2.7 µm); RT 2.78 min. 0.025% Aq. TFA+5% ACN: ACN+5% 0.025% Aq. TFA, 1.2 mL/min).

Synthesis of tert-butyl (6-(5-((5, 5-dioxido-11-oxo-10, 11-dihydrodibenzo [b, f] [1, 4] thiazepine-8-carboxamido) methyl) thiazol-2-yl) pyridin-3-yl) carbamate (658)

To a stirring solution of compound 535 (200 mg, 0.46 mmol) in 1, 4-dioxane (10 mL) under inert atmosphere were added compound 657 (670 mg, 1.38 mmol) and purged under argon atmosphere for 15 min, added Pd(dppf)Cl$_2$ (34 mg, 0.046 mmol) and heated to 100° C. and stirred for 16 h. The reaction was monitored by TLC; after completion of the reaction, the reaction mixture was filtered through celite washed with EtOAc (2×50 mL). The combined organic extracts were dried over sodium sulfate, filtered and concentrated in vacuo to obtain the crude. The crude was purified through silica gel flash column chromatography using 2-5% MeOH/CH$_2$Cl$_2$. The obtained compound was precipitated using 20% EtOAc/hexanes to afford compound 658 (50 mg, 18%) as an off-white solid. TLC: 5% MeOH/CH$_2$Cl$_2$ ($R_f$: 0.5); $^1$H-NMR (DMSO-$d_6$, 400 MHz): δ 11.50 (s, 1H), 9.81 (s, 1H), 9.44 (t, J=5.5 Hz, 1H), 8.59 (s, 1H), 8.07-7.76 (m, 10H), 4.66 (d, J=5.3 Hz, 2H), 1.48 (s, 9H); LC-MS: 96.84%; 592.1 (M++1); (column; Ascentis Express C18, (50×3.0 mm, 2.7 µm); RT 2.43 min. 0.025% Aq. TFA+5% ACN: ACN+5% 0.025% Aq. TFA, 1.2 mL/min).

Synthesis of N-((2-(5-aminopyridin-2-yl) thiazol-5-yl) methyl)-11-oxo-10, 11-dihydrodibenzo [b, f] [1, 4] thiazepine-8-carboxamide 5, 5-dioxide (1886)

To a stirring solution of compound 658 (50 mg, 0.08 mmol) in CH$_2$Cl$_2$ (5 mL) was added 4 N HCl in 1, 4-dioxane (1 mL) under argon atmosphere at 0° C.; warmed to RT and stirred for 2 h. The reaction was monitored by TLC; after completion of the reaction, the volatiles were removed in vacuo to obtain the crude. The compound was dissolved in CH$_2$Cl$_2$ (1 mL) and precipitated using n-hexane (10 mL) to afford 35 mg of semi-purified material. This was further purified by precipitation in N-methyl pyrrolidinone: H$_2$O (1:20, 21 mL) and stirred for 16 h. The solid obtained was filtered and dried in vacuo to afford 1886 (25 mg, 61%) as an off-white solid. TLC: 5% MeOH/CH$_2$Cl$_2$ ($R_f$: 0.3); $^1$H-NMR (DMSO-$d_6$, 400 MHz): δ 11.52 (s, 1H), 9.43 (t, J=5.6 Hz, 1H), 8.05 (d, J=8.3 Hz, 1H), 7.98 (td, J=7.6, 1.1 Hz, 2H), 7.93-7.79 (m, 5H), 7.77 (d, J=8.5 Hz, 1H), 7.68 (s, 1H), 7.02 (dd, J=8.5, 2.6 Hz, 1H), 4.63 (d, J=5.6 Hz, 2H); LC-MS: 94.26%; 492.0 (M++1); (column; Ascentis Express C18, (50×3.0 mm, 2.7 µm); RT 2.26 min. 0.025% Aq. TFA+5% ACN: ACN+5% 0.025% Aq. TFA, 1.2 mL/min). HPLC (purity): 93.39%; (column; X-select CSH-C18 (150× 4.6 mm, 3.5 µm); RT 8.69 min. 5 mM NH4OAc: ACN; 1.0 mL/min, Diluent: DMSO:ACN:water).

Synthesis of 1888

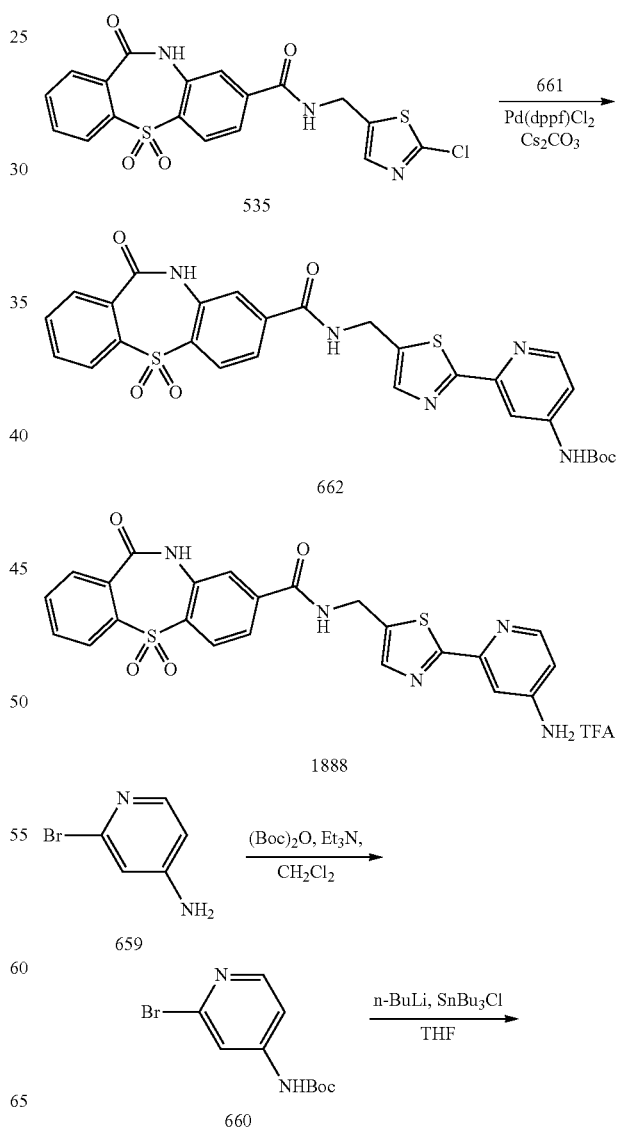

517
-continued

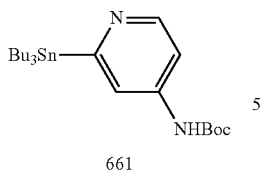

661

Synthesis of tert-butyl (2-bromopyridin-4-yl) carbamate (660)

To a stirring solution of 2-bromopyridin-4-amine 659 (5 g, 28.90 mmol) in 1, 2-dichloro ethane (80 mL) under inert atmosphere were added triethylamine (9.53 mL, 86.70 mmol) Boc-anhydride (7.56 g, 34.67 mmol) at 0° C.; heated to 70° C. and stirred for 16 h. The reaction was monitored by TLC; after completion of the reaction, the reaction the volatiles were concentrated in vacuo. The residue was diluted $CH_2Cl_2$ (20 mL), washed with water (100 mL). The organic extract was dried over sodium sulfate, filtered and concentrated in vacuo to obtain the crude. The crude was purified through silica gel flash column chromatography using 5-20% EtOAc/hexanes to afford compound 660 (3.5 g, 44%) as an off white solid. TLC: 40% EtOAc/hexanes ($R_f$: 0.7); LC-MS: 99.62%; 274.8 ($M^+$+1); (column; Ascentis Express C18, (50×3.0 mm, 2.7 µm); RT 2.40 min. 0.025% Aq. TFA+5% ACN: ACN+5% 0.025% Aq. TFA, 1.2 mL/min).

Synthesis of tert-butyl (2-(triisopropoxy-14-boranyl) pyridin-4-yl) carbamate, lithium salt (661)

To a stirring solution of tert-butyl (2-bromopyridin-4-yl) carbamate 660 (5 g, 18.31 mmol) and triisopropyl borate (1.52 mL, 6.55 mmol) in dry toluene: THF (4:1; 100 mL) under inert atmosphere was added n-butyl lithium (2.5 M solution in hexane, 24.92 mL, 5.46 mmol) drop wise for 1.5 h at −78° C. and stirred for 30 min. To this was added triisopropyl borate (4.13 g, 21.97 mmol) and warmed to RT and stirred for 16 h. The reaction was monitored by TLC; after completion of the reaction, the volatiles were removed in vacuo to afford compound 661 (7.2 g crude salt) as yellow solid. The crude was carried forward for next reaction without purification. TLC: 10% MeOH/$CH_2Cl_2$ ($R_f$: 0.1);

518

Synthesis of tert-butyl (2-(5-((5, 5-dioxido-11-oxo-10, 11-dihydrodibenzo [b, f] [1, 4] thiazepine-8-carboxamido) methyl) thiazol-2-yl) pyridin-4-yl) carbamate (662)

To a stirring solution of N-((2-chlorothiazol-5-yl) methyl)-11-oxo-10, 11-dihydrodibenzo [b, 1] [1, 4] thiazepine-8-carboxamide 5, 5-dioxide 535 (2 g, 4.61 mmol) in 1, 2 dimethoxy ethane: $H_2O$ (4:1, 80 mL) were added sodium carbonate (1.46 g, 13.85 mmol), compound 661 (7.37 g crude) and purged under argon atmosphere for 20 min. To this was added Pd(dppf)$Cl_2$ (337 mg, 0.46 mmol) at RT; heated to 100° C. and stirred for 16 h. The reaction was monitored by TLC; after completion of the reaction; the reaction mixture was filtered through celite and washed with 10% MeOH/$CH_2Cl_2$ (2×100 mL). The filtrate was concentrated in vacuo to obtain the crude. The crude was purified through silica gel flash column chromatography using 3% MeOH/$CH_2Cl_2$ to afford compound 662 (380 mg) as brown solid. LC-MS: 67.12%; 542 ($M^+$+1); (column; Ascentis Express C18, (50×3.0 mm, 2.7 µm); RT 2.20 min. 0.025% Aq. TFA+5% ACN: ACN+5% 0.025% Aq. TFA, 1.2 mL/min);

Synthesis of N-((2-(4-aminopyridin-2-yl) thiazol-5-yl) methyl)-11-oxo-10,11-dihydrodibenzo [b, f] [1, 4] thiazepine-8-carboxamide 5,5-dioxide, TFA Salt (1888)

To a stirring solution of compound 662 (380 mg crude) in $CH_2Cl_2$ (15 mL) under inert atmosphere was added 4 N HCl in 1, 4-dioxane (4 mL) at 0° C.; warmed to RT and stirred for 3 h. The reaction was monitored by TLC; after completion of the reaction, the volatiles were removed in vacuo. The crude was triturated with diethyl ether (5 mL), n-pentane (10 mL) and further purified by preparative HPLC purification to afford 1888 (45 mg, 14%) as an off-white solid. $^1$H-NMR (DMSO-$d_6$, 400 MHz): δ 13.68 (br s, 1H), 11.55 (s, 1H), 9.65-9.56 (m, 1H), 8.10-8.02 (m, 3H), 7.98 (br t, J=7.3 Hz, 2H), 7.91 (td, J=7.0, 1.1 Hz, 1H), 7.88-7.80 (m, 3H), 7.29 (d, J=2.1 Hz, 1H), 6.78 (br d, J=5.3 Hz, 1H), 4.75 (br d, J=5.6 Hz, 2H); LC-MS: 99.93%; 492.0 ($M^+$+1); (column; Ascentis Express C18, (50×3.0 mm, 2.7 µm); RT 1.62 min. 0.025% Aq. TFA+5% ACN: ACN+5% 0.025% Aq. TFA, 1.2 mL/min); HPLC (purity): 99.71%; (column; X select CSH C-18 (150×4.6 mm, 3.5 µm); RT 5.27 min. 0.05% TFA+5% ACN: ACN+5% 0.05% TFA; 1.0 mL/min, Diluent: DMSO:ACN:water).

Synthesis of 11019 & 11019-A

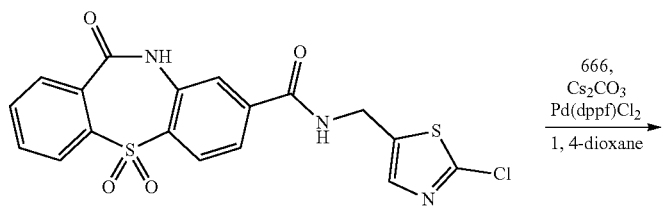

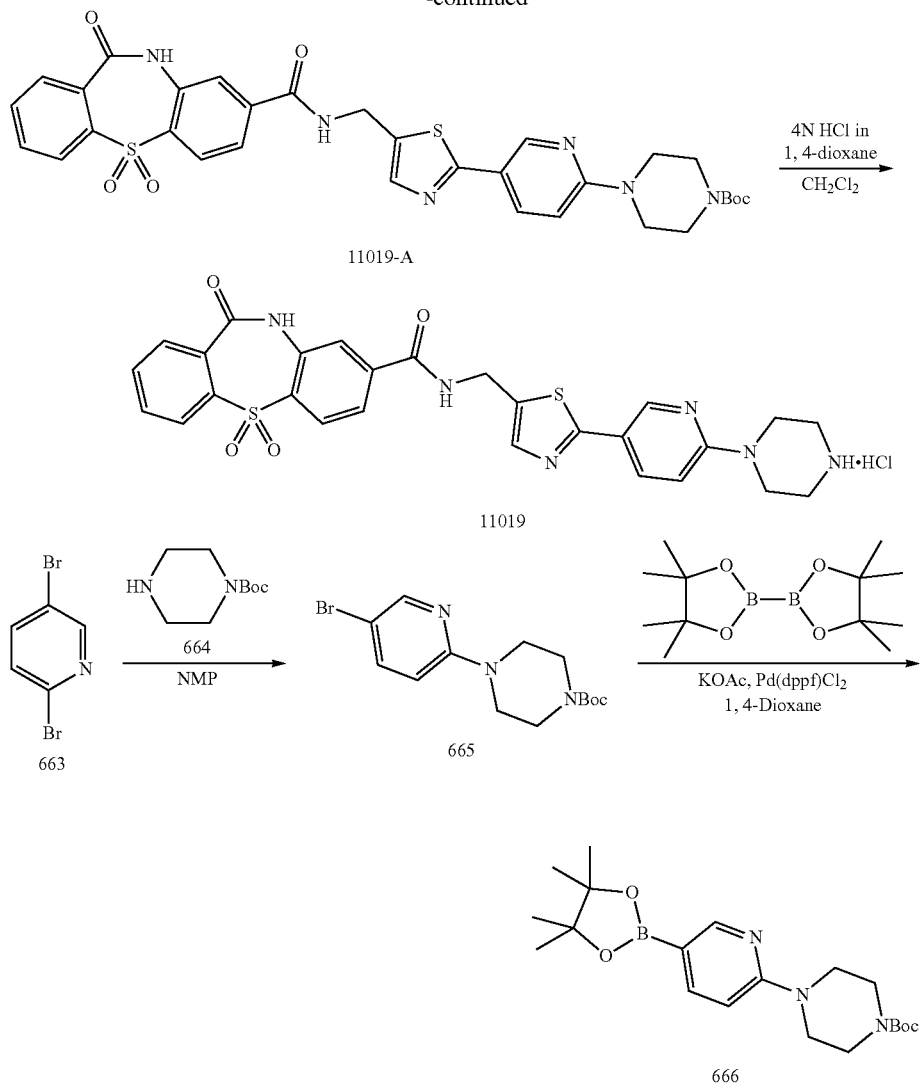

Synthesis of tert-butyl 4-(5-bromopyridin-2-yl) piperazine-1-carboxylate (665)

To a stirring solution 2, 5-dibromopyridine 663 (500 mg, 2.11 mmol) in N-methyl pyrrolidinone (2 mL) under inert atmosphere was added tert-butyl piperazine-1-carboxylate 664 (786 mg, 4.2 mmol) in a sealed tube and heated to 140° C. and stirred for 16 h. The reaction was monitored by TLC and LC-MS; after completion the reaction mixture was diluted with EtOAc (100 mL) and washed with water (50 mL). The organic extract was dried over sodium sulphate, filtered and concentrated in vacuo to obtain the crude. The crude was purified through silica gel column chromatography using 30% EtOAc/hexanes to afford compound 665 (400 mg, 56%) as an off-white solid. TLC: 30% EtOAc/hexanes ($R_f$: 0.2); $^1$H-NMR (DMSO-$d_6$, 400 MHz): δ 8.18 (d, J=2.3 Hz, 1H), 7.70 (dd, J=9.3, 2.6 Hz, 1H), 6.83 (d, J=9.0 Hz, 1H), 3.49-3.44 (m, 4H), 3.42-3.37 (m, 4H), 1.42 (s, 9H); LC-MS: 99.81%; 341.9 (M$^+$+1); (column; Kinetex EVO C-18 (50×3.0 mm, 2.6 um); RT 3.62 min. 2.5 mM Aq. NH$_4$OOCH+5% ACN: ACN+5% 2.5 mM Aq.NH$_4$OOCH, 0.8 mL/min).

Synthesis of tert-butyl 4-(5-(4, 4, 5, 5-tetramethyl-1, 3, 2-dioxaborolan-2-yl) pyridin-2-yl) piperazine-1-carboxylate (666)

To a stirring solution of compound 665 (400 mg, 1.16 mmol) in 1, 4-dioxane (25 mL) under inert atmosphere were added bispinacolato diboron (594 mg, 2.33 mmol), potassium acetate 343 mg, 3.50 mmol) at RT and purged under argon atmosphere for 15 min; to this was added Pd(dppf)Cl$_2$ (85 mg, 0.11 mmol) and purged under argon atmosphere for 5 min, heated to reflux and stirred for 16 h. The reaction was monitored by TLC; after completion of the reaction, the volatiles were concentrated in vacuo to obtain the crude. The crude was purified through silica gel column chromatography using 10-50% EtOAc/hexanes to afford compound 666 (420 mg, 43%) as an off-white solid. TLC: 5% MeOH/CH$_2$Cl$_2$ ($R_f$: 0.4); LC-MS: 98.83%; 307.9 (M$^+$+1) (Boronic acid); (column; Ascentis Express C18, (50×3.0 mm, 2.7 μm); RT 1.60 min. 0.025% Aq. TFA+5% ACN: ACN+5% 0.025% Aq. TFA, 1.2 mL/min).

Synthesis of tert-butyl 4-(5-(5-(((5, 5-dioxido-11-oxo-10, 11-dihydrodibenzo [b, f] [1, 4] thiazepine-8-carboxamido) methyl) thiazol-2-yl) pyridin-2-yl) piperazine-1-carboxylate (11019-A)

To a stirring solution of N-((2-chlorothiazol-5-yl) methyl)-11-oxo-10, 11-dihydrodibenzo [b, f] [1, 4] thiazepine-8-carboxamide 5, 5-dioxide 535 (300 mg, 0.73 mmol) in 1, 4-dioxane: $H_2O$ (4:1, 12 mL) under inert atmosphere were added compound 666 (410 mg, 1.46 mmol), cesium carbonate (714 mg, 2.19 mmol) in a sealed tube at RT and purged under argon atmosphere for 15 min, added Pd(dppf) $Cl_2$ (54 mg, 0.073 mmol) and heated to 110° C. and stirred for 16 h. The reaction was monitored by TLC; after completion of the reaction, the reaction was monitored by TLC; after completion of the reaction, the volatiles were concentrated in vacuo to obtain the crude. The crude was purified through silica gel column chromatography using 10-50% EtOAc/hexanes, triturated using $CH_2Cl_2$: hexanes (10 mL) and dried in vacuo to afford 11019-A (150 mg, 33%) as an off-white solid. TLC: 10% MeOH/$CH_2Cl_2$ ($R_f$: 0.4); $^1$H-NMR (DMSO-$d_6$, 400 MHz): δ 11.52 (s, 1H), 9.44 (t, J=5.8 Hz, 1H), 8.61 (d, J=2.1 Hz, 1H), 8.05 (d, J=8.3 Hz, 1H), 8.01-7.95 (m, 3H), 7.90 (td, J=7.5, 1.4 Hz, 1H), 7.87-7.83 (m, 2H), 7.81 (dd, J=8.3, 1.5 Hz, 1H), 7.71 (s, 1H), 6.90 (d, J=9.0 Hz, 1H), 4.66 (d, J=5.5 Hz, 2H), 3.61-3.57 (m, 4H), 3.45-3.40 (m, 4H), 1.42 (s, 9H); LC-MS: 96.01%; 661.1 ($M^+$+1) (column; Ascentis Express C18, (50×3.0 mm, 2.7 μm); RT 2.34 min. 0.025% Aq. TFA+5% ACN: ACN+5% 0.025% Aq. TFA, 1.2 mL/min). HPLC (purity): 95.67%; (column; X-select CSH-C18 (150×4.6 mm, 3.5 μm); RT 8.38 min. 0.05% TFA (Aq)+5% ACN: ACN+5% 0.05% TFA (Aq): 1.0 mL/min, Diluent: ACN:water).

Synthesis of 11-oxo-N-((2-(6-(piperazin-1-yl) pyridin-3-yl) thiazol-5-yl) methyl)-10, 11-dihydrodibenzo [b, f] [1, 4] thiazepine-8-carboxamide 5, 5-dioxide hydrochloride (11019)

To a stirring solution of 11019-A (50 mg, 0.075 mmol) in $CH_2Cl_2$ (5 mL) was added 4 N HCl in 1, 4-dioxane (5 mL) under argon atmosphere at 0° C.; warmed to RT and stirred for 4 h. The reaction was monitored by TLC; after completion of the reaction, the volatiles were removed in vacuo. The crude washed with $CH_2Cl_2$: n-hexane (1:1, 10 mL) and lyophilized for 12 h to afford compound 11019 (40 mg; HCl salt) as an off-white solid. TLC: 10% MeOH/$CH_2Cl_2$ ($R_f$: 0.1); $^1$H-NMR (DMSO-$d_6$, 400 MHz): δ 11.53 (s, 1H), 9.49 (t, J=5.7 Hz, 1H), 9.09 (br s, 2H), 8.64 (d, J=2.5 Hz, 1H), 8.07-8.01 (m, 2H), 8.00-7.95 (m, 2H), 7.90 (td, J=7.5, 1.5 Hz, 1H), 7.88-7.83 (m, 3H), 7.73 (s, 1H), 7.01 (d, J=9.0 Hz, 1H), 4.66 (d, J=5.5 Hz, 2H), 3.86-3.80 (m, 4H), 3.21-3.14 (m, 4H); LC-MS: 95.23%; 561.1 ($M^+$+1); (column; Ascentis Express C18, (50×3.0 mm, 2.7 μm); RT 1.74 min. 0.025% Aq. TFA+5% ACN: ACN+5% 0.025% Aq. TFA, 1.2 mL/min). HPLC (purity): 96.14%; (column; X-select CSH-C18 (150×4.6 mm, 3.5 μm); RT 5.46 min. 0.05% TFA (Aq)+5% ACN: ACN+5% 0.05% TFA (Aq): 1.0 mL/min, Diluent: ACN:water).

Synthesis of 11016 & 11016-A

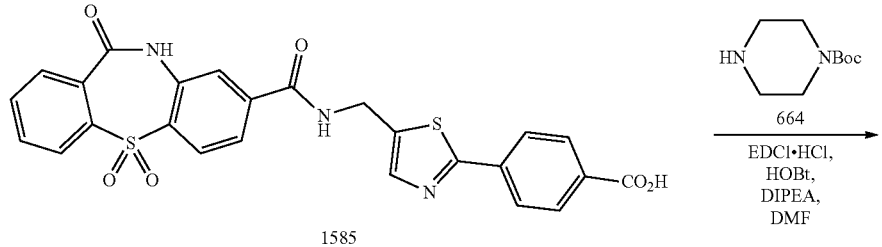

1585

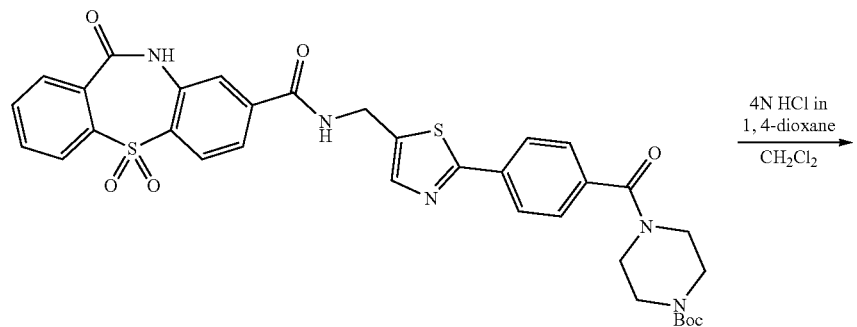

11016-A

-continued

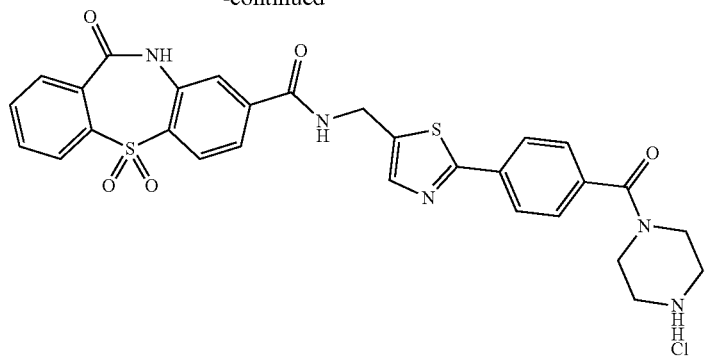

11016

Synthesis of tert-butyl 4-(4-(5-((5, 5-dioxido-11-oxo-10, 11-dihydrodibenzo [b, f] [1, 4] thiazepine-8-carboxamido) methyl) thiazol-2-yl) benzoyl) piperazine-1-carboxylate (11016-A)

To a stirring solution of 1585 (300 mg, 0.57 mmol) in DMF (10 mL) under inert atmosphere were added EDCI.HCl (166 mg, 0.86 mmol), HOBt (117 mg, 0.86 mmol), tert-butyl piperazine-1-carboxylate 664 (119 mg, 0.63 mmol) and diisopropylethylamine (0.28 mL, 1.98 mmol) at 0° C.; warmed to RT and stirred for 16 h. The reaction was monitored by TLC; after completion of the reaction, the reaction mixture was diluted with water (100 mL) and extracted with EtOAc (2×100 mL). The combined organic extracts were dried over sodium sulfate, filtered and concentrated in vacuo to obtain the crude. The crude was purified through silicagel column chromatography using 3-4% MeOH/CH$_2$Cl$_2$ to afford 11016-A (150 mg, 37%) as an off-white solid. TLC: 10% MeOH/CH$_2$Cl$_2$ (R$_f$: 0.6); $^1$H NMR (DMSO-d$_6$, 400 MHz): δ 11.52 (br s, 1H), 9.49 (t, J=5.8 Hz, 1H), 8.06 (d, J=8.2 Hz, 1H), 8.02-7.92 (m, 4H), 7.91-7.80 (m, 5H), 7.51 (d, J=8.4 Hz, 2H), 4.70 (br d, J=5.6 Hz, 2H), 3.66-3.30 (m, 8H), 1.40 (s, 9H); LC-MS: 97.25%; 686.1 (M−1)$^+$; (column; Kinetex EVO C-18 (50×3.0 mm, 2.6 um); RT 2.88 min. 2.5 mM Aq. NH$_4$OOCH+5% ACN: ACN+5% 2.5 mM Aq.NH$_4$OOCH, 0.8 mL/min); HPLC (purity): 97.43%; (column; X-Select CSH-C-18 (150×4.6 mm, 3.5 μm); RT 10.12 min. 5 mM NH$_4$OAc: ACN; 1.0 mL/min, Diluent: DMSO:ACN:water).

Synthesis of 11-oxo-N-((2-(4-(piperazine-1-carbonyl) phenyl)thiazol-5-yl) methyl)-10, 11-dihydrodibenzo [b, f] [1, 4] thiazepine-8-carboxamide 5, 5-dioxide hydrochloride (11016)

To a stirring solution of 11016-A (100 mg, 0.19 mmol) in CH$_2$Cl$_2$ (10 mL) was added 4 N HCl in 1, 4-dioxane (0.5 mL) under inert atmosphere at 0° C.; warmed to RT and stirred for 3 h. The reaction was monitored by TLC; after completion of the reaction, the volatiles were removed in vacuo. The crude washed with diethyl ether (5 mL) and dried in vacuo to afford 11016 (80 mg; 66% HCl salt) as an off-white solid. TLC: 10% MeOH/CH$_2$Cl$_2$ (R$_f$: 0.1); $^1$H-NMR (DMSO-d$_6$, 400 MHz): δ 11.50 (s, 1H), 9.49 (t, J=5.8 Hz, 1H), 8.94 (br s, 2H), 8.04 (d, J=8.3 Hz, 1H), 7.98-7.92 (m, 4H), 7.90-7.78 (m, 5H), 7.54 (d, J=8.5 Hz, 2H), 4.68 (d, J=5.6 Hz, 2H), 3.85-3.49 (m, 4H), 3.18-3.10 (m, 4H); LC-MS: 98.26%; 588.1 (M$^+$+1); (column; Ascentis Express C18, (50×3.0 mm, 2.7 μm); RT 1.73 min. 0.025% Aq. TFA+5% ACN: ACN+5% 0.025% Aq. TFA, 1.2 mL/min); HPLC (purity): 98.88%; (column; X-Select CSH-C-18 (150×4.6 mm, 3.5 μm); RT 5.61 min. ACN+5% 0.05% TFA (Aq): 0.05% TFA (Aq)+5% ACN; 1.0 mL/min, Diluent: DMSO:ACN:water).

Synthesis of 1585

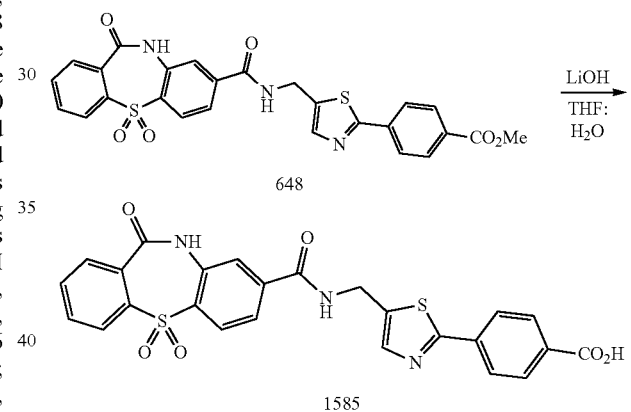

Synthesis of 4-(5-((5, 5-dioxido-11-oxo-10, 11-dihydrodibenzo [b, f] [1, 4] thiazepine-8-carboxamido) methyl) thiazol-2-yl) benzoic acid (1585)

To a stirring solution of compound 648 (80 mg, 0.15 mmol) in THF:H$_2$O (5:1, 6 mL) was added lithium hydroxide monohydrate (19 mg, 0.45 mmol) at 0° C.; warmed to RT and stirred for 16 h. The reaction was monitored by TLC; after completion of the reaction, volatiles were removed in vacuo. The crude was washed with EtOAc (2×10 mL). The obtained solid was dissolved in water (20 mL) and pH was adjusted to ~2 using 2 N HCl. The precipitated solid was filtered, washed with water (20 mL), n-pentane (50 mL) and dried in vacuo to afford 1585 (60 mg, 77%) as an off-white solid. TLC: 5% MeOH/CH$_2$Cl$_2$ (R$_f$: 0.2); $^1$H-NMR (DMSO-d$_6$, 500 MHz): δ 13.18 (br s, 1H), 11.52 (s, 1H), 9.51 (t, J=5.6 Hz, 1H), 8.09-7.95 (m, 7H), 7.93-7.80 (m, 5H), 4.71 (d, J=5.8 Hz, 2H); LC-MS: 92.54%; 519.9 (M$^+$+1); (column; Ascentis Express C18, (50×3.0 mm, 2.7 μm); RT 2.22 min. 0.025% Aq. TFA+5% ACN: ACN+5% 0.025% Aq. TFA, 1.2 mL/min); HPLC (purity): 93.48%; (column; Zorbax SB C-18 (150×4.6 mm, 3.5 μm); RT 7.41 min. ACN+5% 0.05% TFA (Aq): 0.05% TFA (Aq)+5% ACN; 1.0 mL/min).

Preparation 1585 was synthesized as mentioned above and converted to final products as using commercially available amines employing typical procedure C and the results are captured in the Table 3:

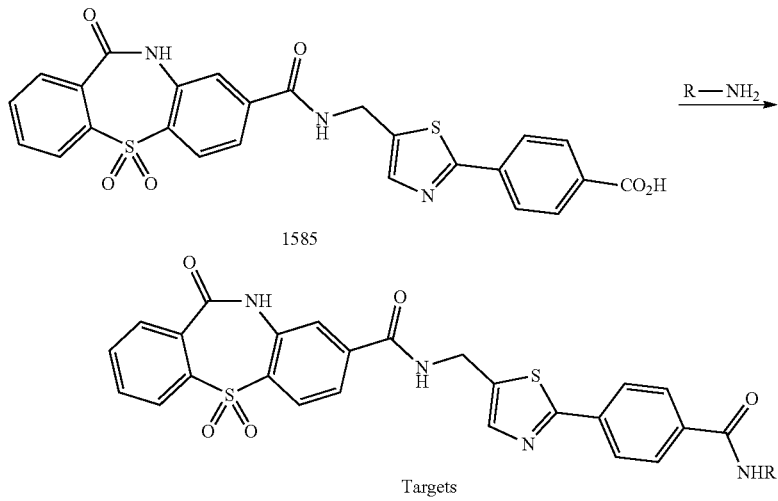
1585

Targets

Typical Procedure C:

To a stirring solution of 1585 (200 mg, 0.38 mmol) in DMF (5 mL) under inert atmosphere were added EDCI.HCl (110 mg, 0.57 mmol), HOBt (77 mg, 0.57 mmol), and diisopropylethylamine (0.20 mL, 1.15 mmol) at 0° C. and stirred for 10 min; added compound 240 (2 M sol. in THF, 0.1 mL, 1.15 mmol) at the same temperature; warmed to RT and stirred for 16 h. The reaction was monitored by TLC; after completion of the reaction, the volatiles were removed in vacuo to obtain the crude. The crude was either directly dried in vacuo or triturated or purified through silica gel column chromatography to afford the desired compound.

Commercial Amines Used in Preparation:

 240

-continued

 243

 469

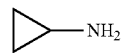 667

TABLE 3

Synthesis from 1585 using various amines

| Example | Structure | Procedure, Intermediate, amine | Rx. Yield (%) | Mass Spec. Found | Mass Spec. Calculated | $^1$H-NMR |
|---|---|---|---|---|---|---|
| 1943 | 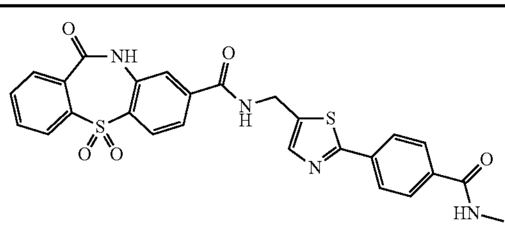 | C, 1585, 240 | 59 | 533.1 (M$^+$ + 1) | 532 for $C_{26}H_{20}N_4O_5S_2$ | $^1$H NMR (DMSO-$d_6$, 400 MHz): δ 11.52 (br s, 1H), 9.50 (br t, J = 5.7 Hz, 1H), 8.52 (q, J = 4.2 Hz, 1H), 8.06 (d, J = 8.3 Hz, 1H), 8.02-7.94 (m, 4H), 7.93-7.89 (m, 3H), 7.89-7.81 (m, 4H), 4.71 (br d, J = 5.6 Hz, 2H), 2.79 (d, J = 4.5 Hz, 3H); |

TABLE 3-continued

Synthesis from 1585 using various amines

| Example | Structure | Procedure, Intermediate, amine | Rx. Yield (%) | Mass Spec. Found | Mass Spec. Calculated | ¹H-NMR |
|---|---|---|---|---|---|---|
| 1944 | 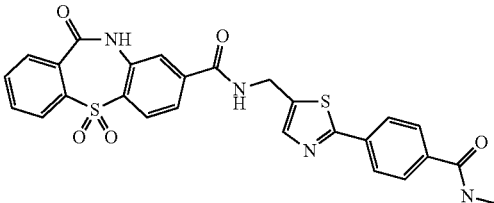 | C 1585, 243 | 71 | 547.1 (M⁺ + 1) | 546 for $C_{27}H_{22}N_4O_5S_2$ | ¹H NMR (DMSO-$d_6$, 400 MHz): δ 11.52 (s, 1H), 9.49 (t, J = 5.7 Hz, 1H), 8.06 (d, J = 8.2 Hz, 1H), 8.01-7.95 (m, 2H), 7.95-7.80 (m, 7H), 7.49 (d, J = 8.2 Hz, 2H), 4.70 (d, J = 5.6 Hz, 2H), 3.04-2.82 (m, 6H); |
| 1947 | 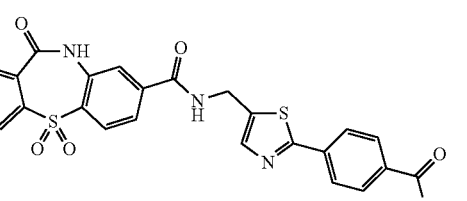 | C$^a$ 1585, 469 | 41 | 575.1 (M⁺ + 1) | 574 for $C_{29}H_{26}N_4O_5S_2$ | ¹H NMR (DMSO-$d_6$, 500 MHz): δ 11.51 (br s, 1H), 9.48 (br t, J = 5.6 Hz, 1H), 8.05 (d, J = 8.1 Hz, 1H), 7.99-7.94 (m, 2H), 7.93-7.79 (m, 10H), 4.69 (br d, J = 5.8 Hz, 2H), 1.37 (s, 9H); |
| 1949 | 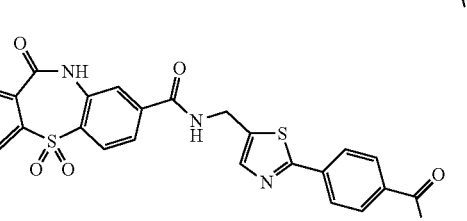 | C, 1585, 667 | 67 | 559.1 (M⁺ + 1) | 558 for $C_{28}H_{22}N_4O_5S_2$ | ¹H NMR (DMSO-$d_6$, 400 MHz): δ 11.52 (br s, 1H), 9.49 (br t, J = 5.4 Hz, 1H), 8.52 (br d, J = 3.5 Hz, 1H), 8.06 (d, J = 8.1 Hz, 1H), 8.02-7.76 (m, 11H), 4.70 (br d, J = 5.5 Hz, 2H), 2.93-2.78 (m, 1H), 0.74-0.52 (m, 4H); |

C$^a$: Reaction time 18 h

Synthesis of 11017 & 11017-A

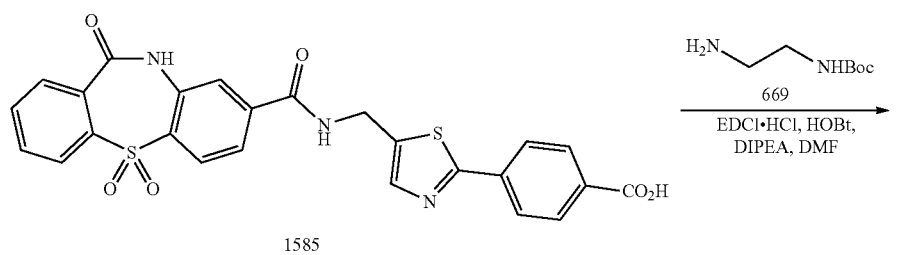

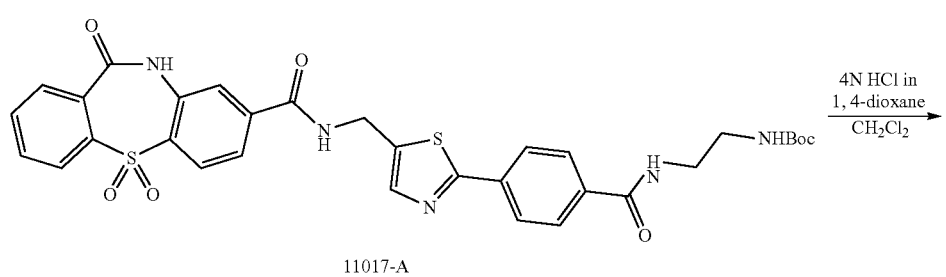

-continued

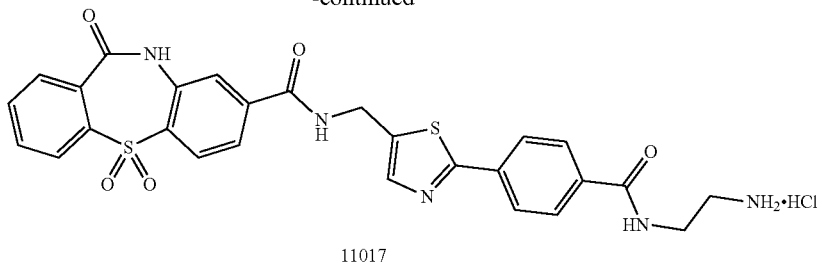

11017

Synthesis of tert-butyl (2-(4-(5-((5, 5-dioxido-11-oxo-10, 11-dihydrodibenzo [b, f][1, 4] thiazepine-8-carboxamido) methyl) thiazol-2-yl) benzamido) ethyl)carbamate (11017-A)

To a stirring solution of 1585 (300 mg, 0.57 mmol) in DMF (10 mL) under inert atmosphere were added EDCI.HCl (166 mg, 0.86 mmol), HOBt (117 mg, 0.86 mmol), tert-butyl (2-aminoethyl) carbamate 669 (102 mg, 0.63 mmol) and diisopropylethylamine (0.28 mL, 1.98 mmol) at 0° C.; warmed to RT and stirred for 16 h. The reaction was monitored by TLC; after completion of the reaction, the reaction mixture was diluted with water (100 mL) and extracted with EtOAc (2×100 mL). The combined organic extracts were dried over sodium sulfate, filtered and concentrated in vacuo to obtain the crude. The crude was purified through silicagel column chromatography using 3-4% MeOH/CH$_2$Cl$_2$ and triturated with 5% MeOH/CH$_2$Cl$_2$ (2 mL) and n-pentane (5 mL) and crystallized using N-methyl pyrrolidinone: H$_2$O (10 mL) to afford 11017-A (150 mg, 39%) as an off-white solid. TLC: 10% MeOH/CH$_2$Cl$_2$ (R$_f$: 0.6); $^1$H NMR (DMSO-d$_6$, 400 MHz): δ 11.52 (br s, 1H), 9.50 (br t, J=5.8 Hz, 1H), 8.54 (br t, J=4.9 Hz, 1H), 8.06 (d, J=8.3 Hz, 1H), 8.02-7.80 (m, 11H), 6.90 (br t, J=5.3 Hz, 1H), 4.71 (br d, J=5.5 Hz, 2H), 3.31-3.27 (m, 2H), 3.15-3.05 (m, 2H), 1.37 (s, 9H); LC-MS: 99.83%; 660.1 (M−1)$^+$; (column; Kinetex EVO C-18 (50×3.0 mm, 2.6 um); RT 2.67 min. 2.5 mM Aq. NH$_4$OOCH+5% ACN: ACN+5% 2.5 mM Aq.NH$_4$OOCH, 0.8 mL/min); HPLC (purity): 99.17%; (column; X-Select CSH-C-18 (150×4.6 mm, 3.5 µm); RT 8.58 min. 0.05% TFA (Aq)+5% ACN: ACN+5% 0.05% TFA (Aq); 1.0 mL/min, Diluent: DMSO:ACN).

Synthesis of N-((2-(4-((2-aminoethyl) carbamoyl) phenyl) thiazol-5-yl) methyl)-11-oxo-10, 11-dihydrodibenzo [b, f] [1, 4] thiazepine-8-carboxamide 5, 5-dioxide hydrochloride (11017)

To a stirring solution of 11017-A (100 mg, 0.15 mmol) in CH$_2$Cl$_2$ (10 mL) was added 4 N HCl in 1, 4-dioxane (0.5 mL) under inert atmosphere at 0° C.; warmed to RT and stirred for 3 h. The reaction was monitored by TLC; after completion of the reaction, the volatiles were removed in vacuo. The crude washed with diethyl ether (5 mL) and dried in vacuo to afford 11017 (80 mg; 88% HCl salt) as an off-white solid. TLC: 10% MeOH/CH$_2$Cl$_2$ (R$_f$: 0.1); $^1$H-NMR (DMSO-d$_6$, 400 MHz): δ 11.53 (s, 1H), 9.53 (t, J=5.8 Hz, 1H), 8.74 (t, J=5.5 Hz, 1H), 8.06 (d, J=8.2 Hz, 1H), 8.03-7.95 (m, 6H), 7.93-7.81 (m, 8H), 4.71 (br d, J=5.6 Hz, 2H), 3.55-3.49 (m, 2H), 3.02-2.96 (m, 2H); LC-MS: 98.39%; 562.1 (M$^+$+1); (column; Ascentis Express C18, (50×3.0 mm, 2.7 µm); RT 1.74 min. 0.025% Aq. TFA+5% ACN: ACN+5% 0.025% Aq. TFA, 1.2 mL/min); HPLC (purity): 99.17%; (column; X-Select CSH-C-18 (150×4.6 mm, 3.5 µm); RT 8.58 min. 0.05% TFA (Aq)+5% ACN: ACN+5% 0.05% TFA (Aq); 1.0 mL/min, Diluent: ACN: DMSO: MeOH).

Synthesis of 11018 & 11018-A

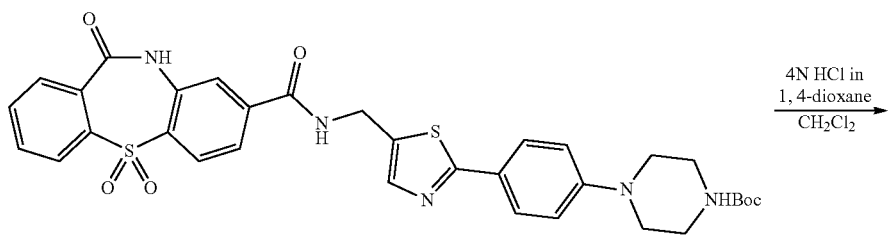

11018-A

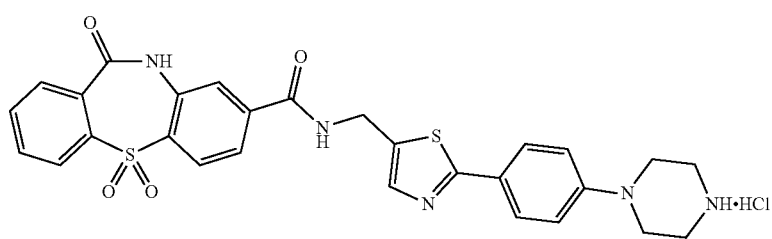

11018

Synthesis of 11-oxo-N-((2-(4-(piperazin-1-yl) phenyl) thiazol-5-yl) methyl)-10, 11-dihydrodibenzo [b, f] [1, 4] thiazepine-8-carboxamide 5, 5-dioxide hydrochloride (11018)

To a stirring solution of 11018-A (100 mg, 0.15 mmol) in CH$_2$Cl$_2$ (10 mL) was added 4 N HCl in 1, 4-dioxane (1 mL) under argon atmosphere at 0° C.; warmed to RT and stirred for 2 h. The reaction was monitored by TLC; after completion of the reaction, the volatiles were removed in vacuo. The crude washed with EtOAc (2×5 mL) and dried in vacuo to afford 1 1018 (75 mg, 88%; HCl salt) as yellow solid. TLC: 5% MeOH/CH$_2$Cl$_2$ (R$_f$: 0.1); $^1$H-NMR (DMSO-d$_6$, 400 MHz): δ 11.53 (s, 1H), 9.49 (t, J=5.8 Hz, 1H), 9.18 (br s, 2H), 8.05 (d, J=8.3 Hz, 1H), 7.98 (td, J=7.4, 1.1 Hz, 2H), 7.93-7.81 (m, 4H), 7.76 (d, J=8.9 Hz, 2H), 7.70 (s, 1H), 7.05 (d, J=8.9 Hz, 2H), 4.65 (br d, J=5.6 Hz, 2H), 3.51-3.44 (m, 4H), 3.24-3.17 (m, 4H); LC-MS: 98.17%; 560.1 (M$^+$+1); (column; Ascentis Express C18, (50×3.0 mm, 2.7 μm); RT 1.77 min. 0.025% Aq. TFA+5% ACN: ACN+5% 0.025% Aq. TFA, 1.2 mL/min). HPLC (purity): 97.26%; (column; X-select CSH C-18 (150×4.6 mm, 3.5 μm); RT 6.21 min. 0.05% TFA+5% ACN: ACN+0.05% TFA+5%; 1.0 mL/min; Diluent: ACN:water).

Synthesis of 1581 after completion of the reaction, the reaction mixture was poured into ice-cold water (50 mL) and extracted with EtOAc (3×150 mL). The combined organic extracts were dried over sodium sulfate, filtered and concentrated in vacuo to obtain the crude. The crude was purified through silica gel column chromatography using 3% MeOH/CH$_2$Cl$_2$ to afford compound 670 (110 mg, 39%) as white solid. TLC: 7% MeOH/CH$_2$Cl$_2$ (R$_f$: 0.4); $^1$H NMR (DMSO-d$_6$, 500 MHz): δ 11.51 (s, 1H), 9.45 (t, J=5.8 Hz, 1H), 8.05 (d, J=8.1 Hz, 1H), 8.00-7.95 (m, 2H), 7.90 (td, J=7.4, 1.3 Hz, 1H), 7.87-7.85 (m, 2H), 7.84-7.79 (m, 3H), 7.73 (s, 1H), 7.02 (d, J=9.0 Hz, 2H), 4.85 (s, 2H), 4.67 (d, J=5.8 Hz, 2H), 4.17 (q, J=6.9 Hz, 2H), 1.21 (t, J=7.1 Hz, 3H).

Synthesis of 2-(4-(5-((5, 5-dioxido-11-oxo-10, 11-dihydrodibenzo [b, f] [1, 4] thiazepine-8-carboxamido) methyl) thiazol-2-yl) phenoxy) acetic acid (1581)

To a stirring solution of compound 670 (80 mg, 0.13 mmol) in THF:H$_2$O (4:1, 10 mL) was added lithium hydroxide monohydrate (18 mg, 0.42 mmol) at RT and stirred for 4 h. The reaction was monitored by TLC; after completion of the reaction, the volatiles were removed in vacuo. The pH of the residue was acidified with 2 N HCl to ~6. The precipitated solid was filtered triturated with 20% EtOAc/hexanes (10 mL) and dried in vacuo to afford 1581 (60 mg,

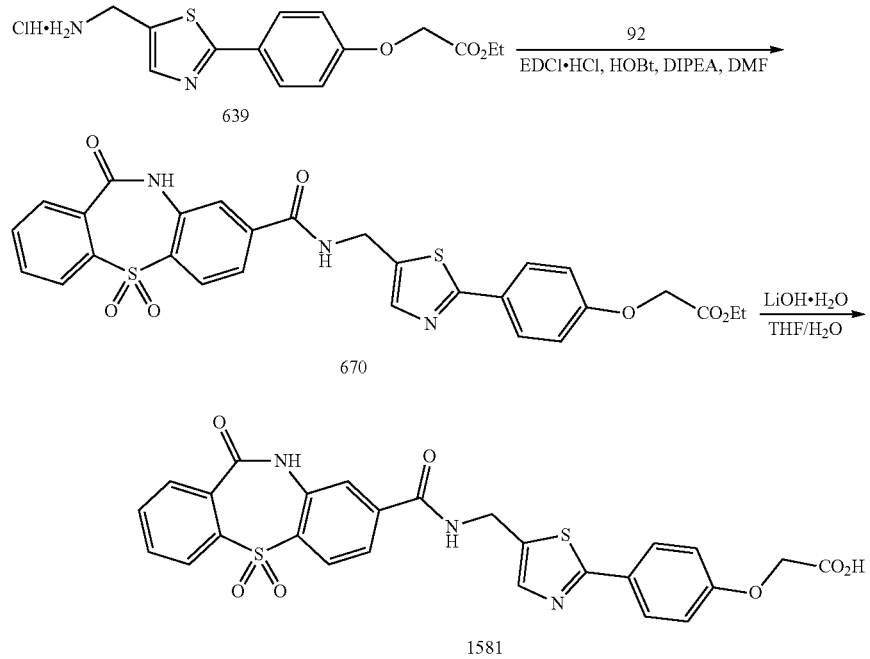

Synthesis of ethyl 2-(4-(5-((5, 5-dioxido-11-oxo-10, 11-dihydrodibenzo [b, f] [1, 4] thiazepine-8-carboxamido) methyl) thiazol-2-yl) phenoxy) acetate (670)

To a stirring solution of compound 92 (150 mg, 0.49 mmol) in DMF (10 mL) under inert atmosphere were added EDCl.HCl (142 mg, 0.29 mmol), HOBt (100 mg, 0.74 mmol), ethyl 2-(4-(5-(aminomethyl) thiazol-2-yl) phenoxy) acetate 639 (195 mg, 0.59 mmol) and diisopropylethylamine (0.45 mL, 2.47 mmol) at 0° C.; warmed to RT and stirred for 16 h. The reaction was monitored by TLC;

79%) as an off-white solid. TLC: 10% MeOH/CH$_2$Cl$_2$ (R$_f$: 0.2); $^1$H-NMR (DMSO-d$_6$, 500 MHz): δ 11.51 (s, 1H), 9.46 (t, J=5.6 Hz, 1H), 8.04 (d, J=8.4 Hz, 1H), 7.97 (t, J=8.4 Hz, 2H), 7.89 (t, J=7.1 Hz, 1H), 7.86-7.78 (m, 5H), 7.72 (s, 1H), 6.99 (d, J=8.7 Hz, 2H), 4.73 (s, 2H), 4.65 (d, J=5.5 Hz, 2H); LC-MS: 100%; 549.9 (M$^+$+1); (column; Ascentis Express C18, (50×3.0 mm, 2.7 μm); RT 2.06 min. 0.025% Aq. TFA+5% ACN: ACN+5% 0.025% Aq. TFA, 1.2 mL/min); HPLC (purity): 99.71%; (column; Zorbax SB C-18 (150×4.6 mm, 3.5 μm); RT 7.22 min. ACN: 0.05% TFA (Aq); 1.0 mL/min, Diluent: ACN:water).

Synthesis of 1995 and 1995-A

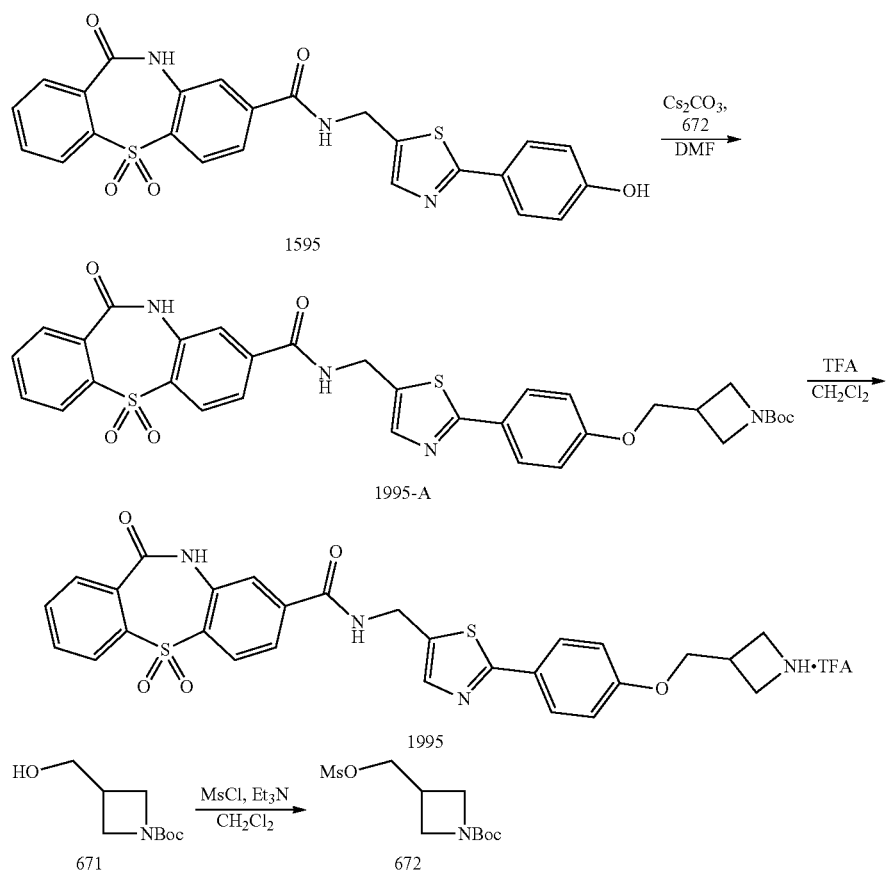

Synthesis of tert-butyl 3-(((methylsulfonyl) oxy) methyl) azetidine-1-carboxylate (1595)

To a stirring solution of tert-butyl 3-(hydroxymethyl) azetidine-1-carboxylate 671 (500 mg, 2.67 mmol) in $CH_2Cl_2$ (10 mL) under inert atmosphere were added triethylamine (0.77 mL, 5.34 mmol), methanesulfonyl chloride (0.24 mL, 2.94 mmol) at 0° C.; warmed to RT and stirred for 2 h. The reaction was monitored by TLC; after completion of the reaction, the reaction mixture was diluted with $CH_2Cl_2$ (75 mL), washed with water (2×50 mL) The organic extract was dried over sodium sulfate, filtered and concentrated in vacuo to afford crude compound 672 (580 mg) as sticky solid. TLC: 60% EtOAc/hexanes ($R_f$: 0.4); $^1$H NMR (DMSO-$d_6$, 500 MHz): δ 4.34 (d, J=6.4 Hz, 2H), 3.95-3.87 (m, 2H), 3.65-3.56 (m, 2H), 3.21 (s, 3H), 2.95-2.84 (m, 1H), 1.37 (s, 9H);

Synthesis of tert-butyl 3-((4-(5-((5, 5-dioxido-11-oxo-10, 11-dihydrodibenzo [b, f] [1, 4] thiazepine-8-carboxamido) methyl) thiazol-2-yl) phenoxy) methyl) azetidine-1-carboxylate (1995-A)

To a stirring solution of N-((2-(4-hydroxyphenyl) thiazol-5-yl) methyl)-11-oxo-10, 11-dihydrodibenzo [b, f] [1, 4] thiazepine-8-carboxamide 5, 5-dioxide 1595 (600 mg, 1.22 mmol) in DMF (100 mL) under inert atmosphere were added 4-bromo-1H-pyrazole 672 (5.92 g, 40.29 mmol), cesium carbonate (39.4 g, 120.96 mmol) at RT; heated to 80° C. and stirred for 16 h. The reaction was monitored by TLC; after completion of the reaction, the reaction mixture was diluted with ice-cold water (500 mL) and extracted with EtOAc (2×200 mL). The combined organic extracts were dried over sodium sulfate, filtered and concentrated in vacuo to obtain the crude. The crude was purified through silicagel column chromatography using 30% EtOAc/hexanes to afford 1995-A (4.1 g, 29%) as an off-white solid. TLC: 30% EtOAc/hexanes ($R_f$: 0.3). $^1$H-NMR (DMSO-$d_6$, 400 MHz): δ 11.52 (s, 1H), 9.46 (t, J=5.7 Hz, 1H), 8.59 (d, J=5.5 Hz, 1H), 8.06 (d, J=8.1 Hz, 1H), 7.98 (t, J=7.5 Hz, 1H), 7.93-7.79 (m, 5H), 7.73 (s, 1H), 7.07 (d, J=8.7 Hz, 2H), 4.66 (d, J=5.3 Hz, 2H), 4.18 (d, J=5.3 Hz, 2H), 4.12-4.04 (m, 2H), 3.93-3.81 (m, 2H), 3.27-3.16 (m, 1H); LC-MS: 97.70%; 659.1 (M−1)$^+$; (column; Kinetex EVO C-18 (50×3.0 mm, 2.6 um); RT 1.27 min. 2.5 mM Aq. $NH_4OOCH$+5% ACN: ACN+5% 2.5 mM Aq.$NH_4OOCH$, 0.8 mL/min); HPLC (purity): 99.67%; (column; X select CSH C-18 (150×4.6 mm, 3.5 nm); RT 10.33 min. 0.05% TFA+5% ACN: ACN+ 5% 0.05% TFA; 1.0 mL/min, Diluent: ACN:water).

Synthesis of N-((2-(4-(azetidin-3-ylmethoxy) phenyl) thiazol-5-yl) methyl)-11-oxo-10, 11-dihydrodibenzo [b, f] [1, 4] thiazepine-8-carboxamide 5, 5-dioxide TFA salt (1995)

To stirred solution of tert-butyl 3-((4-(5-((5, 5-dioxido-11-oxo-10, 11-dihydrodibenzo [b, f] [1, 4] thiazepine-8-carboxamido) methyl) thiazol-2-yl) phenoxy) methyl) azetidine-1-carboxylate (1995-A) (200 mg, 0.30 mmol) in CH$_2$Cl under inert atmosphere was added trifluoroacetic acid (0.11 mL, 1.51 mmol) at 0° C.; warmed to RT and stirred for 24 h. The reaction was monitored by TLC; after completion of the reaction, the volatiles were removed in vacuo to obtain the crude, which was triturated with EtOAc (2×10 mL) and dried in vacuo to afford 1995 (90 mg, 43%, TFA salt) as an off-white solid. TLC: 10% MeOH/CH$_2$Cl$_2$ (R$_f$: 0.1); $^1$H-NMR (DMSO-d$_6$, 400 MHz): δ 11.52 (s, 1H), 9.46 (t, J=5.7 Hz, 1H), 8.60 (br s, 2H), 8.06 (d, J=8.1 Hz, 1H), 7.98 (t, J=7.5 Hz, 2H), 7.93-7.79 (m, 6H), 7.73 (s, 1H), 7.07 (d, J=8.7 Hz, 2H), 4.66 (d, J=5.3 Hz, 2H), 4.18 (d, J=5.3 Hz, 2H), 4.12-4.04 (m, 2H), 3.93-3.81 (m, 2H), 3.27-3.16 (m, 1H); LC-MS: 96.93%; 491.0 (M$^+$+1); (column; Ascentis Express C18, (50×3.0 mm, 2.7 μm); RT 1.80 min. 0.025% Aq. TFA+5% ACN: ACN+5% 0.025% Aq. TFA, 1.2 mL/min); HPLC (purity): 95.81%; (column; X-select CSH C-18 (150×4.6 mm, 3.5 μm); RT 9.23 min. ACN+5 mM NH$_4$OAc: ACN; 1.0 mL/min, Diluent: DMSO:ACN:water).

Synthesis of 1997

Synthesis of tert-butyl 3-(hydroxymethyl) piperidine-1-carboxylate (674)

To a stirring solution of piperidin-3-ylmethanol 673 (1 g, 8.69 mmol) in CH$_2$Cl$_2$ (10 mL) under argon atmosphere were added triethylamine (3.66 mL, 26.08 mmol), Boc-anhydride (2.39 mL, 10.43 mmol) at 0° C.; warmed to RT and stirred for 5 h. The reaction was monitored by TLC; after completion of the reaction, the reaction mixture was diluted with water (30 mL) and extracted with CH$_2$Cl$_2$ (2×30 mL). The combined organic extracts were washed with water (40 mL) and brine (40 mL); dried over sodium sulfate, filtered and concentrated in vacuo to afford compound 674 (1.6 g, 86%) as pale yellow liquid. TLC: 5% MeOH/CH$_2$Cl$_2$ (R$_f$: 0.5); $^1$H-NMR (DMSO-d$_6$, 400 MHz): δ 4.49 (t, J=5.3 Hz, 1H), 4.04-3.87 (m, 1H), 3.81-3.76 (m, 1H), 3.30-3.25 (m, 1H), 3.20-3.14 (m, 1H), 2.77-2.61 (m, 1H), 1.75-1.62 (m, 1H), 1.62-1.53 (m, 1H), 1.51-1.42 (m, 1H), 1.39 (s, 9H), 1.36-1.18 (m, 1H), 1.14-1.01 (m, 1H);

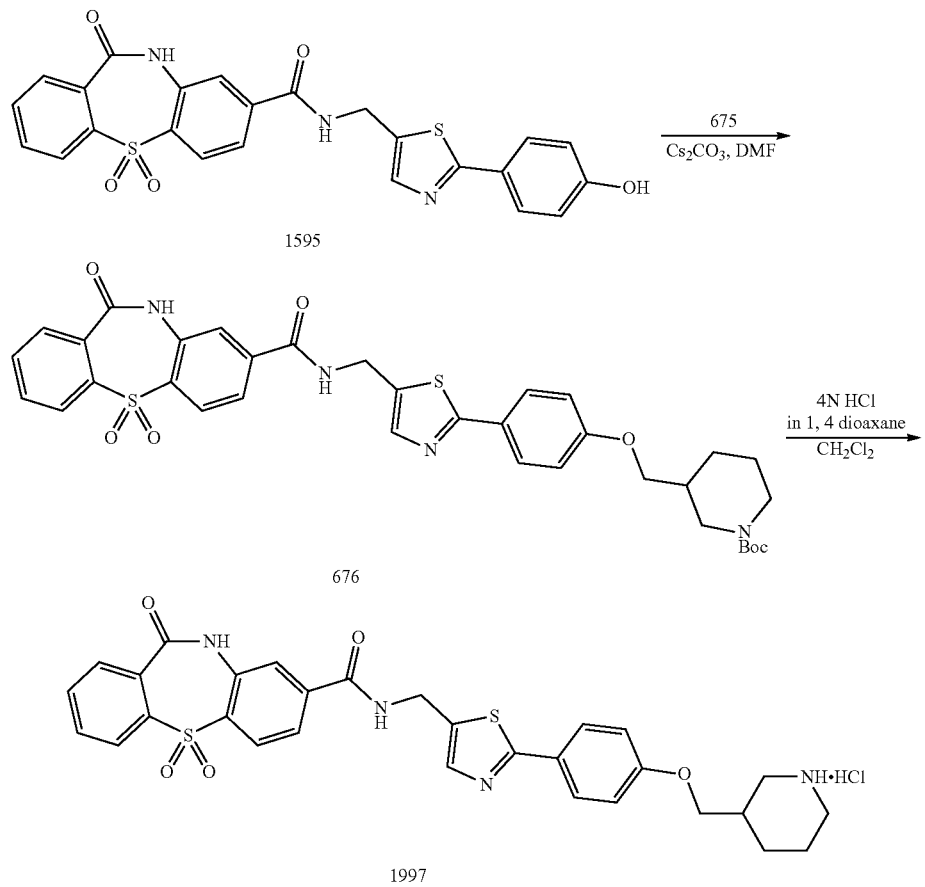

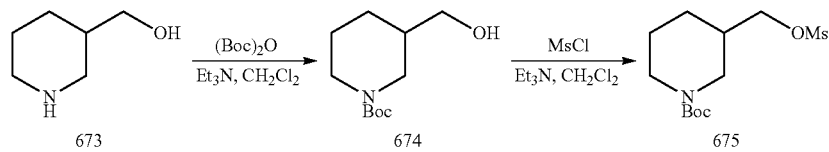

Synthesis of tert-butyl 3-(((methylsulfonyl) oxy) methyl) piperidine-1-carboxylate (675)

To a stirring solution of compound 674 (500 mg, 2.487 mmol) in $CH_2Cl_2$ (15 mL) under inert atmosphere were added triethylamine (1.04 mL, 7.46 mmol), methanesulfonyl chloride (0.24 mL, 3.73 mmol) at 0° C.; warmed to RT and stirred for 3 h. The reaction was monitored by TLC; after completion of the reaction, the reaction mixture was diluted with water (25 mL) and extracted with $CH_2Cl_2$ (2×30 mL). The combined organic extracts were washed with water (20 mL) and brine (20 mL); dried over sodium sulfate, filtered and concentrated in vacuo to afford crude compound 675 (600 mg crude) as pale yellow liquid. TLC: 30% EtOAc/hexanes ($R_f$: 0.5); $^1$H-NMR (DMSO-$d_6$, 400 MHz): δ 4.13-4.02 (m, 2H), 3.73-3.69 (m, 1H), 3.17 (s, 3H), 2.92-2.78 (m, 2H), 1.85-1.67 (m, 3H), 1.65-1.55 (m, 1H), 1.39 (s, 9H), 1.36-1.12 (m, 2H);

Synthesis of tert-butyl 3-((4-(5-(((5, 5-dioxido-11-oxo-10, 11-dihydrodibenzo [b f] [1, 4] thiazepine-8-carboxamido) methyl) thiazol-2-yl) phenoxy) methyl) piperidine-1-carboxylate (676)

To a stirring solution of N-((2-(4-hydroxyphenyl) thiazol-5-yl) methyl)-11-oxo-10, 11-dihydrodibenzo [b, f] [1, 4] thiazepine-8-carboxamide 5, 5-dioxide 1 595 (400 mg, 0.81 mmol) in DMF (8 mL) were added cesium carbonate (796 mg, 2.44 mmol), compound 675 (272 mg, 0.97 mmol) under argon atmosphere at RT; heated to 70° C. in a sealed tube and stirred for 16 h. The reaction was monitored by TLC; after completion, the reaction mixture was diluted with water (30 mL) and extracted with EtOAc (2×40 mL). The combined organic extracts were washed with water (40 mL) and brine (40 mL); dried over sodium sulfate, filtered and concentrated in vacuo to obtain the crude. The crude was purified through silica gel column chromatography using 3% MeOH/$CH_2Cl_2$ to afford compound 676 (50 mg, 9%) as pale yellow solid. TLC: 10% MeOH/$CH_2Cl_2$ ($R_f$: 0.6); $^1$H NMR (400 MHz, DMSO-$d_6$): δ 11.51 (s, 1H), 9.45 (t, J=5.7 Hz, 1H), 8.05 (d, J=8.3 Hz, 1H), 8.00-7.95 (m, 2H), 7.93-7.84 (m, 3H), 7.84-7.78 (m, 3H), 7.72 (s, 1H), 7.02 (d, J=8.9 Hz, 2H), 4.66 (d, J=5.6 Hz, 2H), 3.95-3.84 (m, 2H), 3.74-3.60 (m, 1H), 2.98-2.82 (m, 2H), 1.93-1.86 (m, 1H), 1.83-1.75 (m, 1H), 1.66-1.59 (m, 1H), 1.42-1.29 (m, 12H); LC-MS: 92.11%; 589.1 (M$^+$+1) des BOC; (column; Ascentis Express C-18, (50×3.0 mm, 2.7 μm); RT 2.74 min. 0.025% Aq. TFA+5% ACN: ACN+5% 0.025% Aq. TFA, 1.2 mL/min);

Synthesis of 11-oxo-N-((2-(4-(piperidin-3-yl-methoxy) phenyl) thiazol-5-yl) methyl)-10, 11-dihydrodibenzo [b, f] [1, 4] thiazepine-8-carboxamide 5, 5-dioxide hydrochloride (1997)

To a stirring solution of compound 675 (38 mg, 0.055 mmol) in $CH_2Cl_2$ (2 mL) was added 4 N HCl in 1, 4-dioxane (1 mL) under argon atmosphere at 0° C.; warmed to RT and stirred for 1 h. The reaction was monitored by TLC; after completion of the reaction, the volatiles were removed in vacuo. The crude washed with diethyl ether (5 mL) and dried in vacuo to afford 1997 (20 mg; 58%) as white solid. TLC: 10% MeOH/$CH_2Cl_2$ ($R_f$: 0.1); $^1$H NMR (400 MHz, DMSO-$d_6$): δ 11.53 (s, 1H), 9.49 (t, J=5.7 Hz, 1H), 8.92-8.83 (m, 1H), 8.75-8.63 (m, 1H), 8.06 (d, J=8.2 Hz, 1H), 8.01-7.96 (m, 2H), 7.92-7.80 (m, 6H), 7.73 (s, 1H), 7.03 (d, J=8.9 Hz, 2H), 4.66 (d, J=5.5 Hz, 2H), 4.04-3.89 (m, 2H), 3.38-3.32 (m, 1H), 3.28-3.20 (m, 1H), 2.85-2.71 (m, 2H), 2.28-2.18 (m, 1H), 1.89-1.79 (m, 2H), 1.73-1.63 (m, 1H), 1.41-1.28 (m, 1H); LC-MS: 99.93%; 589.1 (M$^+$+1); (column; Ascentis Express C-18, (50×3.0 mm, 2.7 μm); RT 1.86 min. 0.025% Aq. TFA+5% ACN: ACN+5% 0.025% Aq. TFA, 1.2 mL/min); HPLC (purity): 97.78%; (column; X select CSH C-18 (150×4.6 mm, 3.5 μm); RT 5.74 min. 0.05% TFA+5% ACN: ACN+5% 0.05% TFA; 1.0 mL/min, Diluent: ACN: water).

Synthesis of 11137 & 11138

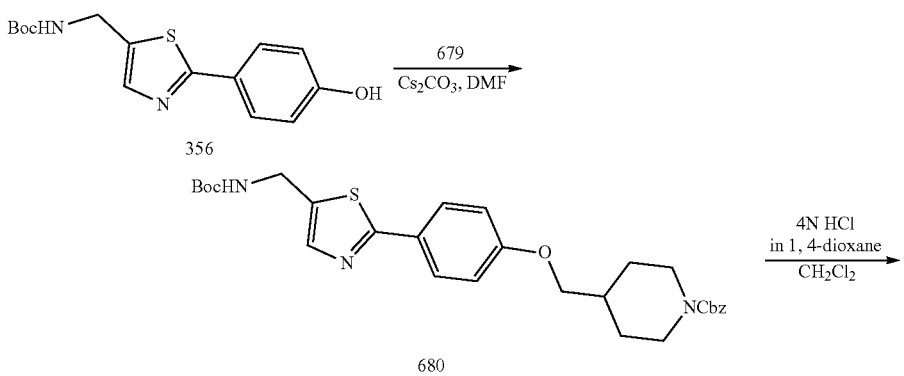

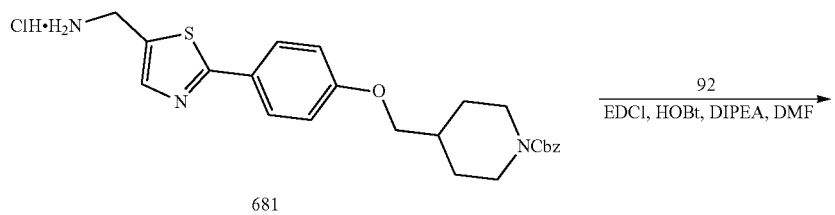

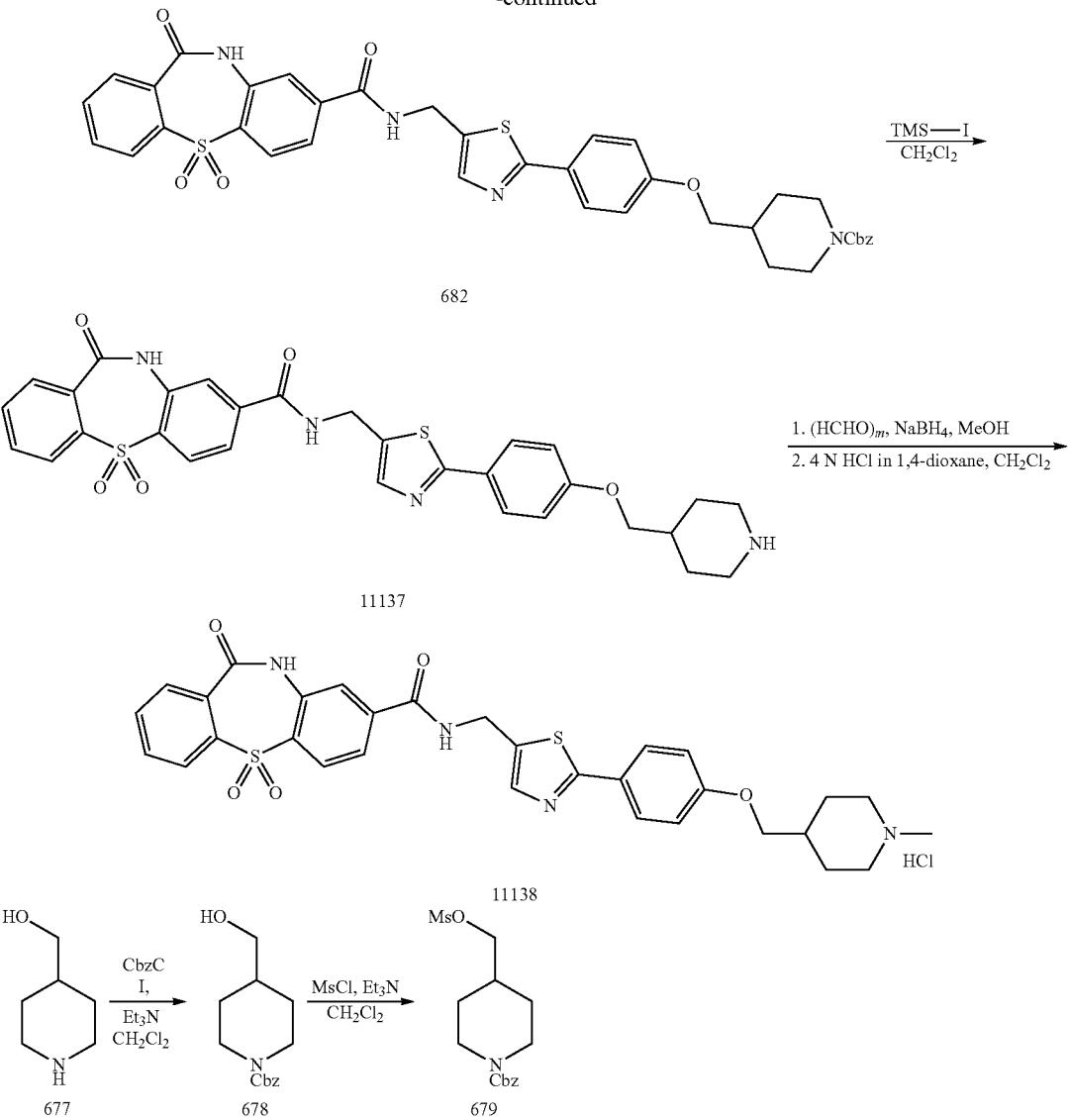

Synthesis of benzyl 4-(hydroxymethyl) piperidine-1-carboxylate (678)

To a stirring solution of piperidin-4-ylmethanol 677 (4 g, 34.72 mmol) in $CH_2Cl_2$ (100 mL) were added triethylamine (15 mL, 104.17 mmol) followed by benzyl chloroformate (50% in toluene, 13 mL, 38.19 mmol) at 0° C. under inert atmosphere. The reaction mixture was gradually warmed to RT and stirred for 16 h. The reaction was monitored by TLC; after completion of the reaction, the reaction mixture was quenched with aqueous saturated sodium bicarbonate solution (40 mL) and extracted with EtOAC (2×40 mL). The combined organic extracts were washed dried over sodium sulfate, filtered and concentrated in vacuo to obtain the crude. The crude was purified through column chromatography using 50% EtOAc/hexanes to afford compound 678 (5 g, 58%) as Pale yellow liquid. TLC: 50% EtOAc/hexanes ($R_f$: 0.3); $^1H$ NMR (500 MHz, DMSO-$d_6$): δ 7.44-7.27 (m, 5H), 5.06 (s, 2H), 4.46 (t, J=5.2 Hz, 1H), 4.03-3.98 (m, 2H), 3.24 (t, J=5.8 Hz, 2H), 2.79-2.75 (m, 2H), 1.67-1.62 (m, 2H), 1.58-1.50 (m, 1H), 1.05-0.96 (m, 2H); LC-MS: 89.34%; 250.1 ($M^+$+1); (column; Ascentis Express C18, (50×3.0 mm, 2.7 μm); RT 2.06 min. 0.025% Aq. TFA+5% ACN: ACN+5% 0.025% Aq. TFA, 1.2 mL/min).

Synthesis of benzyl 4-(((methylsulfonyl) oxy) methyl) piperidine-1-carboxylate (679)

To a stirring solution of compound 678 (1.25 g, 5.02 mmol) in $CH_2Cl_2$ (20 mL) were added methanesulfonyl chloride (0.5 mL, 6.02 mmol) and triethylamine (1.08 mL, 7.53 mmol) at 0° C. under inert atmosphere. The reaction mixture was gradually warmed to RT and stirred for 2 h. The reaction was monitored by TLC; after completion of the reaction, the reaction mixture was poured slowly into aqueous saturated sodium bicarbonate solution (20 mL) and extracted with EtOAc (2×35 mL). The combined organic extracts were washed dried over sodium sulfate, filtered and concentrated in vacuo to afford compound 679 (1.5 g) as pale yellow liquid. This crude material was taken to next step without further purification. TLC: 50% EtOAc/hexanes ($R_f$: 0.8); $^1H$ NMR (500 MHz, DMSO-$d_6$): δ 7.45-7.26 (m, 5H), 5.07 (s, 2H), 4.11-3.99 (m, 4H), 3.17 (s, 3H), 2.89-2.72 (m, 2H), 1.94-1.83 (m, 1H), 1.70-1.66 (m, 2H), 1.22-1.05 (m, 2H); LC-MS: 91.59%; 328.0 (M$^+$+1); (column; Ascentis Express C18, (50×3.0 mm, 2.7 µm); RT 2.37 min. 0.025% Aq. TFA+5% ACN: ACN+5% 0.025% Aq. TFA, 1.2 mL/min).

Synthesis of benzyl 4-((4-(5-(((tert-butoxycarbonyl) amino) methyl) thiazol-2-yl) phenoxy) methyl) piperidine-1-carboxylate (680)

To a stirring solution of tert-butyl ((2-(4-hydroxyphenyl) thiazol-5-yl) methyl) carbamate 356 (1 g, 3.27 mmol) in DMF (15 mL) were added compound 679 (1.17 g, crude) and cesium carbonate (2.66 g, 8.17 mmol) at RT under inert atmosphere. The reaction mixture was heated to 70° C. and stirred for 16 h. The reaction was monitored by TLC; after completion of the reaction, the reaction mixture was diluted with ice cold water (30 mL) and extracted with EtOAc (2×50 mL). The combined organic extracts were washed dried over sodium sulfate, filtered and concentrated in vacuo to obtain the crude. The crude was purified through column chromatography using 2% MeOH/CH$_2$Cl$_2$ to afford compound 680 (1.3 g, 74%) as an off white solid. TLC: 40% EtOAc/ hexanes (R$_f$: 0.7); $^1$H NMR (400 MHz, DMSO-d$_6$): δ 7.80 (d, J=8.8 Hz, 2H), 7.60 (s, 1H), 7.53 (t, J=5.7 Hz, 1H), 7.40-7.29 (m, 5H), 7.02 (d, J=8.9 Hz, 2H), 5.08 (s, 2H), 4.31 (d, J=5.9 Hz, 2H), 4.09-4.03 (m, 2H), 3.90 (d, J=6.4 Hz, 2H), 2.85-2.79 (m, 2H), 2.04-1.92 (m, 1H), 1.82-1.75 (m, 2H), 1.40 (s, 9H), 1.26-1.15 (m, 2H); LC-MS: 90.14%; 538.3 (M$^+$+1); (column; Ascentis Express C18, (50×3.0 mm, 2.7 µm); RT 3.06 min. 0.025% Aq. TFA+5% ACN: ACN+5% 0.025% Aq. TFA, 1.2 mL/min).

Synthesis of benzyl 4-((4-(5-(aminomethyl) thiazol-2-yl) phenoxy) methyl) piperidine-1-carboxylate hydrochloride (681)

To a stirring solution of compound 680 (1.3 g, 2.42 mmol) in CH$_2$Cl$_2$ (15 mL) was added 4 N HCl in 1, 4-dioxane (4 mL) at 0° C. under inert atmosphere. The reaction mixture was gradually warmed to RT and stirred for 2 h. The reaction was monitored by TLC; after completion of the reaction, the volatiles were removed in vacuo to obtain the crude. The crude was triturated with EtOAc (30 mL), diethylether (30 mL) and dried in vacuo to afford compound 681 (1.1 g, HCl salt) as an off white solid. TLC: 40% EtOAc/hexanes (R$_f$: 0.1); $^1$H NMR (500 MHz, DMSO-d$_6$): δ 8.64 (br s, 3H), 7.91 (s, 1H), 7.85 (d, J=8.7 Hz, 2H), 7.41-7.29 (m, 5H), 7.06 (d, J=8.7 Hz, 2H), 5.08 (s, 2H), 4.31 (q, J=5.2 Hz, 2H), 4.08-4.03 (m, 2H), 3.91 (d, J=6.4 Hz, 2H), 2.96-2.78 (m, 2H), 2.03-1.92 (m, 1H), 1.80-1.76 (m, 2H), 1.27-1.15 (m, 2H); LC-MS: 99.39%; 438.1 (M$^+$+1); (column; Ascentis Express C18, (50×3.0 mm, 2.7 µm); RT 2.07 min. 0.025% Aq. TFA+5% ACN: ACN+5% 0.025% Aq. TFA, 1.2 mL/min).

Synthesis of benzyl 4-((4-(5-((5, 5-dioxido-11-oxo-10, 11-dihydrodibenzo [b, f] [1, 4] thiazepine-8-carboxamido) methyl) thiazol-2-yl) phenoxy) methyl) piperidine-1-carboxylate (682)

To a stirring solution of 11-oxo-10, 11-dihydrodibenzo [b, f] [1, 4] thiazepine-8-carboxylic acid 5, 5-dioxide 92 (200 mg, 0.66 mmol) in DMF (15 mL) were added compound 681 (312 mg, 0.66 mmol), EDCI.HCl (189 mg, 0.99 mmol), HOBt (135 mg, 0.99 mmol) and diisopropylethylamine (0.6 mL, 0.33 mmol) at 0° C. under inert atmosphere. The reaction mixture was gradually warmed to RT and stirred for 16 h. The reaction was monitored by TLC; after completion of the reaction, the reaction mixture was diluted with ice cold water (20 mL) and extracted with EtOAc (2×30 mL). The combined organic extracts were dried over sodium sulfate, filtered and concentrated in vacuo to obtain the crude. The crude was purified through column chromatography using 4% MeOH/CH$_2$Cl$_2$ to afford compound 682 (310 mg, 65%) as an off white solid. TLC: 6% MeOH/ CH$_2$Cl$_2$ (R$_f$: 0.5); $^1$H NMR (500 MHz, DMSO-d$_6$): δ 11.51 (s, 1H), 9.44 (t, J=5.5 Hz, 1H), 8.06 (d, J=8.1 Hz, 1H), 8.01-7.95 (m, 2H), 7.93-7.83 (m, 3H), 7.83-7.77 (m, 3H), 7.72 (s, 1H), 7.40-7.30 (m, 5H), 7.01 (d, J=9.3 Hz, 2H), 5.07 (s, 2H), 4.66 (d, J=5.8 Hz, 2H), 4.07-4.03 (m, 2H), 3.89 (d, J=6.4 Hz, 2H), 2.93-2.77 (m, 2H), 2.01-1.93 (m, 1H), 1.79-1.75 (m, 2H), 1.25-1.15 (m, 2H); LC-MS: 93.17%; 723.2 (M$^+$+1); (column; Ascentis Express C18, (50×3.0 mm, 2.7 µm); RT 2.83 min. 0.025% Aq. TFA+5% ACN: ACN+5% 0.025% Aq. TFA, 1.2 mL/min).

Synthesis of 11-oxo-N-((2-(4-(piperidin-4-ylmethoxy) phenyl) thiazol-5-yl) methyl)-10, 11-dihydrodibenzo [b, f] [1, 4] thiazepine-8-carboxamide 5, 5-dioxide (11137)

To a stirring solution of compound 682 (200 mg, 0.28 mmol) in CH$_2$Cl$_2$ (5 mL) was added trimethylsilyl iodide (0.04 mL, 0.28 mmol) at 0° C. under inert atmosphere. The reaction mixture was gradually warmed to RT and stirred for 1 h. The reaction was monitored by TLC; after completion of the reaction, the reaction mixture was diluted with saturated sodium bicarbonate solution (20 mL) and extracted with EtOAc (2×30 mL). The combined organic extracts were dried over sodium sulfate, filtered and concentrated in vacuo to obtain the crude. The crude was purified through column chromatography using 8% MeOH/CH$_2$Cl$_2$ to afford 11137 (83 mg, 50%) as an off white solid. TLC: 10% MeOH/CH$_2$Cl$_2$ (R$_f$: 0.2); $^1$H NMR (400 MHz, DMSO-d$_6$): δ 9.45 (t, J=5.6 Hz, 1H), 8.05 (d, J=8.3 Hz, 1H), 7.97 (td, J=7.6, 1.1 Hz, 2H), 7.93-7.77 (m, 6H), 7.72 (s, 1H), 7.01 (d, J=8.8 Hz, 2H), 4.66 (d, J=5.6 Hz, 2H), 3.85 (d, J=6.3 Hz, 2H), 3.03-2.98 (m, 2H), 2.60-2.53 (m, 2H), 1.86-1.84 (m, 1H), 1.74-1.69 (m, 2H), 1.27-1.14 (m, 2H); LC-MS: 98.61%; 589.1 (M$^+$+1); (column; Ascentis Express C18, (50×3.0 mm, 2.7 µm); RT 1.84 min. 0.025% Aq. TFA+5% ACN: ACN+5% 0.025% Aq. TFA, 1.2 mL/min).

Synthesis of N-((2-(4-((1-methylpiperidin-4-yl) methoxy) phenyl) thiazol-5-yl) methyl)-11-oxo-10, 11-dihydrodibenzo [b, f] [1, 4] thiazepine-8-carboxamide 5, 5-dioxide hydrochloride (11138)

To a stirring solution of 11-oxo-N-((2-(4-(piperidin-4-ylmethoxy) phenyl) thiazol-5-yl) methyl)-10, 11-dihydrodibenzo [b, f] [1, 4] thiazepine-8-carboxamide 5, 5-dioxide 11137 (75 mg, 0.13 mmol) in methanol (5 mL) were added paraformaldehyde (19 mg, 0.64 mmol) and sodium cyanoborohydride (39 mg, 0.64 mmol) at 0° C. under inert atmosphere. The reaction mixture was gradually warmed to RT and stirred for 16 h. The reaction was monitored by TLC; after completion of the reaction, the volatiles were removed in vacuo. The residue was dilute with ice cold water (20 mL) and extracted with 10% MeOH/CH$_2$Cl$_2$ (2×30 mL). The combined organic extracts were dried over sodium sulfate, filtered and concentrated in vacuo to obtain the crude. The crude was purified through column chromatography using 8% MeOH/CH$_2$Cl$_2$ to afford N-methylated compound (50 mg) as an off white solid. TLC: 10% MeOH/CH$_2$Cl$_2$ (R$_f$: 0.7). This was taken forward for next step.

To a stirring solution of above N-methylated compound (50 mg) in CH$_2$Cl$_2$ (2 mL) was added 4 N HCl in 1,4-dioxane (0.5 mL) at 0° C. under inert atmosphere. The reaction mixture was gradually warmed to RT and stirred for 1 h. The reaction was monitored by TLC; after completion of the reaction, the volatiles were removed in vacuo to obtain the crude. The crude was triturated with EtOAc (10 mL), diethylether (10 mL), followed by preparative HPLC purification to afford 11138 (38 mg, 46%, for two steps) as an off white solid. TLC: 10% MeOH/CH$_2$Cl$_2$ (R$_f$: 0.1); $^1$H NMR (400 MHz, DMSO-d$_6$): δ 11.53 (s, 1H), 9.47 (t, J=5.6 Hz, 1H), 9.29 (br s, 1H), 8.06 (d, J=8.2 Hz, 1H), 8.00-7.95 (m, 2H), 7.92-7.79 (m, 6H), 7.73 (s, 1H), 7.02 (d, J=8.9 Hz, 2H), 4.66 (d, J=5.5 Hz, 2H), 3.92 (d, J=5.6 Hz, 2H), 3.48-3.43 (m, 2H), 3.29-3.12 (m, 1H), 3.02-2.91 (m, 2H), 2.76 (d, J=4.6 Hz, 3H), 2.02-1.94 (m, 2H), 1.56-1.43 (m, 2H); LC-MS: 99.63%; 603.1 (M$^+$+1); (column; Ascentis Express C18, (50×3.0 mm, 2.7 μm); RT 1.85 min. 0.025% Aq. TFA+5% ACN: ACN+5% 0.025% Aq. TFA, 1.2 mL/min); HPLC (purity): 99.37%; (column; X-Select CSH-C-18 (150×4.6 mm, 3.5 μm); RT 6.14 min. 0.05% TFA+5% ACN: ACN+5% 0.05% TFA; 1.0 mL/min, Diluent: ACN:H$_2$O).

Synthesis of tert-butyl (R)-2-(hydroxymethyl) pyrrolidine-1-carboxylate (684)

To a stirring solution of (R)-pyrrolidin-2-ylmethanol 683 (1 g, 9.88 mmol) in CH$_2$Cl$_2$ (20 mL) under inert atmosphere was added triethylamine (1.57 mL, 10.89 mmol) at 0° C., followed by addition of Boc-anhydride (2.5 mL, 10.89 mmol) at the same temperature; warmed to RT and stirred for 4 h. The reaction was monitored by TLC; after completion of the reaction, the reaction mixture was diluted with water (20 mL), diluted with 1 N HCl (10 mL). The aqueous layer was concentrated in vacuo to afford crude compound 684 (1.9 g) as colorless syrup which was carried forward for next step without further purification. TLC: 20% EtOAc/hexanes (R$_f$: 0.4); $^1$H NMR (CDCl$_3$, 400 MHz): δ 4.74 (br d, J=5.5 Hz, 1H), 4.01-3.98 (m, 1H), 3.73-3.56 (m, 2H), 3.54-3.44 (m, 1H), 3.36-3.33 (m, 1H), 2.09-1.97 (m, 1H), 1.89-1.84 (m, 2H), 1.50 (s, 9H);

Synthesis of tert-butyl (R)-2-(((methylsulfonyl)oxy) methyl) pyrrolidine-1-carboxylate (685)

To a stirring solution of compound 684 (1 g, crude) in CH$_2$Cl$_2$ (20 mL) under inert atmosphere were added triethylamine (1.40 mL, 9.95 mmol), methanesulfonyl chloride (0.68 mL, 8.45 mmol) at 0° C.; warmed to RT and stirred for Synthesis of 11104-A & 11104

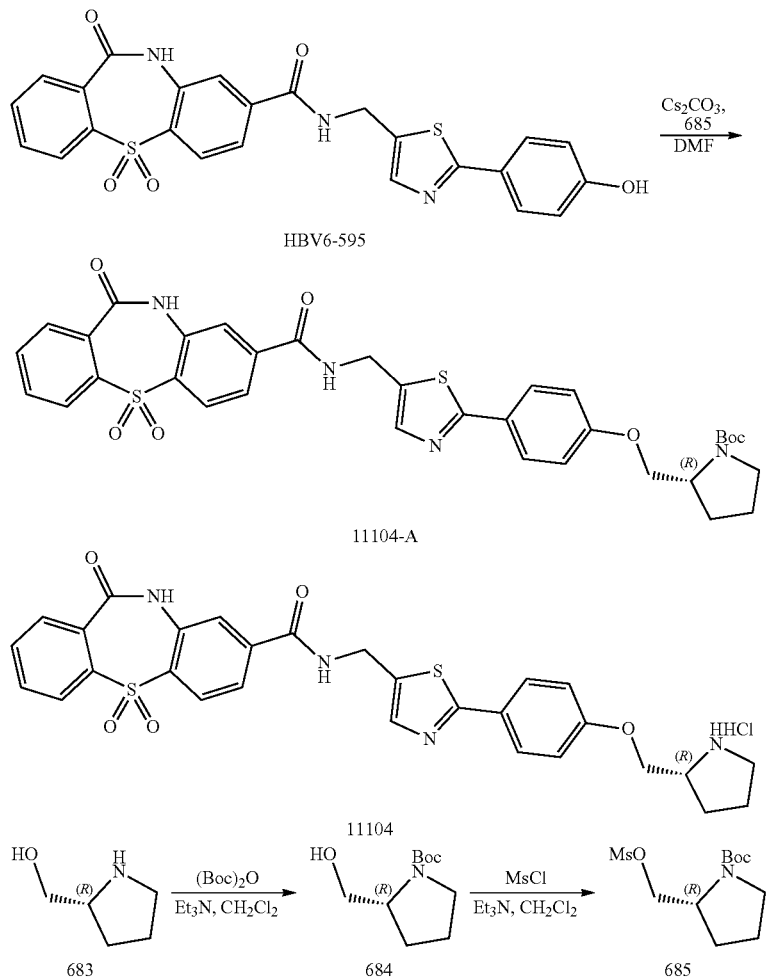

3 h. The reaction was monitored by TLC; after completion of the reaction, the reaction mixture was diluted with water (50 mL) and extracted with $CH_2Cl_2$ (2×50 mL). The combined organic extracts were dried over sodium sulfate, filtered and concentrated in vacuo to obtain the crude. The crude was purified through silicagel column chromatography using 20% EtOAc/hexanes to afford compound 685 (1.05 g, 38%, over 2 steps) as colorless liquid. TLC: 20% EtOAc/hexanes ($R_f$: 0.5); $^1$H NMR ($CDCl_3$, 400 MHz): δ 4.39-4.22 (m, 1.6H), 4.16-3.98 (m, 1.4H), 3.53-3.29 (m, 2H), 3.02 (s, 3H), 2.12-1.81 (m, 4H), 1.60 (s, 9H);

Synthesis of tert-butyl (R)-2-((4-(5-((5, 5-dioxido-11-oxo-10, 11-dihydrodibenzo [b, f] [1, 4] thiazepine-8-carboxamido) methyl) thiazol-2-yl) phenoxy) methyl) pyrrolidine-1-carboxylate (11104-A)

To a stirring solution of N-((2-(4-hydroxyphenyl) thiazol-5-yl) methyl)-11-oxo-10, 11-dihydrodibenzo [b, f] [1, 4] thiazepine-8-carboxamide 5, 5-dioxide 1595 (1 g, 2.03 mmol) in DMF (3 mL) under inert atmosphere were added ter t-butyl (R)-2-(((methylsulfonyl) oxy) methyl) pyrrolidine-1-carboxylate 685 (568 mg, 2.03 mmol), cesium carbonate (1.99 g, 6.10 mmol) at RT; heated to 80° C. and stirred for 16 h. The reaction was monitored by TLC; after completion of the reaction, the reaction mixture was diluted with water (50 mL) and extracted with EtOAc (2×25 mL). The combined organic extracts were dried over sodium sulfate, filtered and concentrated in vacuo to obtain the crude. The crude was purified through silicagel column chromatography using 3% $MeOH/CH_2Cl_2$ to afford 11104-A (460 mg, 35%) as an off-white solid. TLC: 5% $MeOH/CH_2Cl_2$ ($R_f$: 0.6); $^1$H NMR (DMSO-$d_6$, 400 MHz): δ 11.51 (s, 1H), 9.44 (t, J=5.6 Hz, 1H), 8.05 (d, J=8.2 Hz, 1H), 8.01-7.94 (m, 2H), 7.93-7.77 (m, 6H), 7.72 (s, 1H), 7.05 (d, J=8.9 Hz, 2H), 4.66 (d, J=5.6 Hz, 2H), 4.14-3.91 (m, 3H), 3.29-3.25 (m, 2H), 2.05-1.75 (m, 4H), 1.40 (s, 9H); LC-MS: 94.40%; 619.1 (M-$^t$Bu)$^+$ (Column; X-select CSH C-18 (150×3.0 mm, 2.7 μm); RT 2.70 min. 0.025% Aq. TFA+5% ACN: ACN+5% 0.025% Aq. TFA, 1.0 mL/min); HPLC (purity): 96.20%; (column; X-Select CSH-C-18 (150×4.6 mm, 3.5 μm); RT 10.64 min. 0.05% TFA (Aq)+5% ACN: ACN+5% 0.05% TFA (Aq); 1.0 mL/min, Diluent: ACN:$H_2O$).

Synthesis of (R)-11-oxo-N-((2-(4-(pyrrolidin-2-ylmethoxy) phenyl) thiazol-5-yl) methyl)-10, 11-dihydrodibenzo [b, f] [1, 4] thiazepine-8-carboxamide 5, 5-dioxide hydrochloride (11104)

To a stirring solution of 11104-A (450 mg, 0.66 mmol) in $CH_2Cl_2$ (10 mL) under inert atmosphere was added 4 N HCl in 1, 4-dioxane (4 mL) at 0° C.; warmed to RT and stirred for 4 h. The reaction was monitored by TLC; after completion of the reaction, the volatiles were removed in vacuo. The crude washed with diethyl ether (5 mL), EtOAc (5 mL), n-pentane (5 mL) and dried in vacuo to afford 1 1104 (280 mg, 69%; HCl salt) as an off-white solid. TLC: 5% MeOH/$CH_2Cl_2$ ($R_f$: 0.0; $^1$H NMR (DMSO-$d_6$, 400 MHz): δ 11.53 (s, 1H), 9.48 (t, J=5.8 Hz, 1H), 9.38-9.28 (m, 1H), 8.91-8.76 (m, 1H), 8.06 (d, J=8.2 Hz, 1H), 8.01-7.96 (m, 2H), 7.93-7.80 (m, 6H), 7.74 (s, 1H), 7.08 (d, J=8.9 Hz, 2H), 4.66 (d, J=5.6 Hz, 2H), 4.32 (dd, J=3.5, 10.7 Hz, 1H), 4.16 (dd, J=8.5, 10.6 Hz, 1H), 3.99-3.87 (m, 1H), 3.27-3.16 (m, 2H), 2.18-2.09 (m, 1H), 2.04-1.86 (m, 2H), 1.79-1.70 (m, 1H); LC-MS: 94.56%; 575.1 (M$^+$+1); (column; Ascentis Express C18, (50×3.0 mm, 2.7 μm); RT 1.82 min. 0.025% Aq. TFA+5% ACN: ACN+5% 0.025% Aq. TFA, 1.2 mL/min). HPLC (purity): 95.85%; (column; X-Select CSH-C-18 (150×4.6 mm, 3.5 μm); RT 5.86 min. 0.05% TFA (Aq)+5% ACN: ACN+5% 0.05% TFA (Aq); 1.0 mL/min, Diluent: ACN:$H_2O$).

Synthesis of 11131

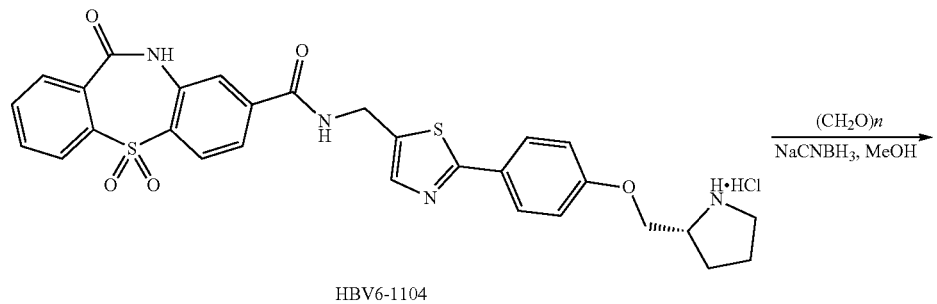

HBV6-1104

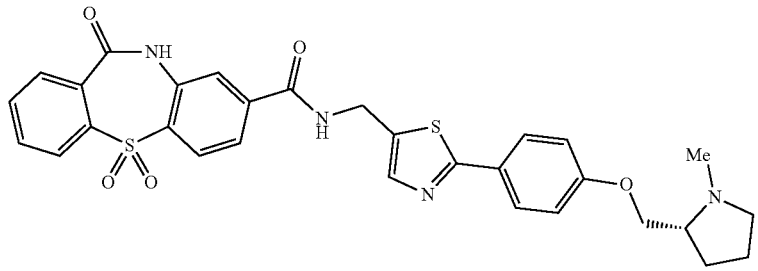

HBV6-1131

Synthesis of (R)—N-((2-(4-((1-methylpyrrolidin-2-yl) methoxy) phenyl) thiazol-5-yl)methyl)-11-oxo-10,11-dihydrodibenzo [b, f] [1, 4] thiazepine-8-carboxamide 5,5-dioxide (11131)

To a stirring solution of 11104 (120 mg, 0.19 mmol) in MeOH (10 mL) under inert atmosphere were added paraformaldehyde (29 mg, 0.98 mmol) and sodium cyanoborohydride (62 mg, 0.98 mmol) at RT and stirred for 6 h. The reaction was monitored by TLC; after completion of the reaction, the reaction mixture was quenched with ice-cold water (10 mL) and extracted with $CH_2Cl_2$ (3×15 mL). The combined organic extracts were dried over sodium sulfate, filtered and concentrated in vacuo to obtain the crude. The crude was purified through silica gel column chromatography using 4% MeOH/$CH_2Cl_2$ and 2 mL aqueous ammonia to obtain semi solid, which was washed further with diethyl ether and hexane and dried in vacuo to afford 11131 (100 mg, 63%) as an off whit solid. TLC: 10% MeOH/$CH_2Cl_2$ ($R_f$: 0.6); $^1$H NMR (DMSO-$d_6$, 400 MHz): δ 11.51 (br s, 1H), 9.44 (t, J=5.7 Hz, 1H), 8.05 (d, J=8.3 Hz, 1H), 7.98 (dd J=7.5, 1.0 Hz, 2H), 7.93-7.76 (m, 6H), 7.72 (m, 1H), 7.02 (d, J=8.9 Hz, 1H), 4.66 (br d, J=5.6 Hz, 2H), 4.01 (dd, J=5.3, 9.6 Hz, 1H), 3.87 (dd, J=6.0, 9.6 Hz, 1H), 2.99-2.92 (m, 1H), 2.70-2.65 (m, 1H), 2.62-2.54 (m, 1H), 2.25-2.14 (m, 1H), 2.02-1.90 (m, 1H), 1.73-1.64 (m, 2H), 1.63-1.53 (m, 1H); LC-MS: 97.99%; 589.1 (M$^+$+1); (column; Ascentis Express C18, (50×3.0 mm, 2.7 μm); RT 1.67 min. 0.025% Aq. TFA+5% ACN: ACN+5% 0.025% Aq. TFA, 1.2 mL/min). HPLC (purity): 98.46%; (column; X-Select CSH-C-18 (150×4.6 mm, 3.5 μm); RT 5.90 min. 0.05% TFA (Aq)+5% ACN: ACN+5% 0.05% TFA (Aq); 1.0 mL/min, Diluent: ACN:$H_2O$).

Synthesis of 11029

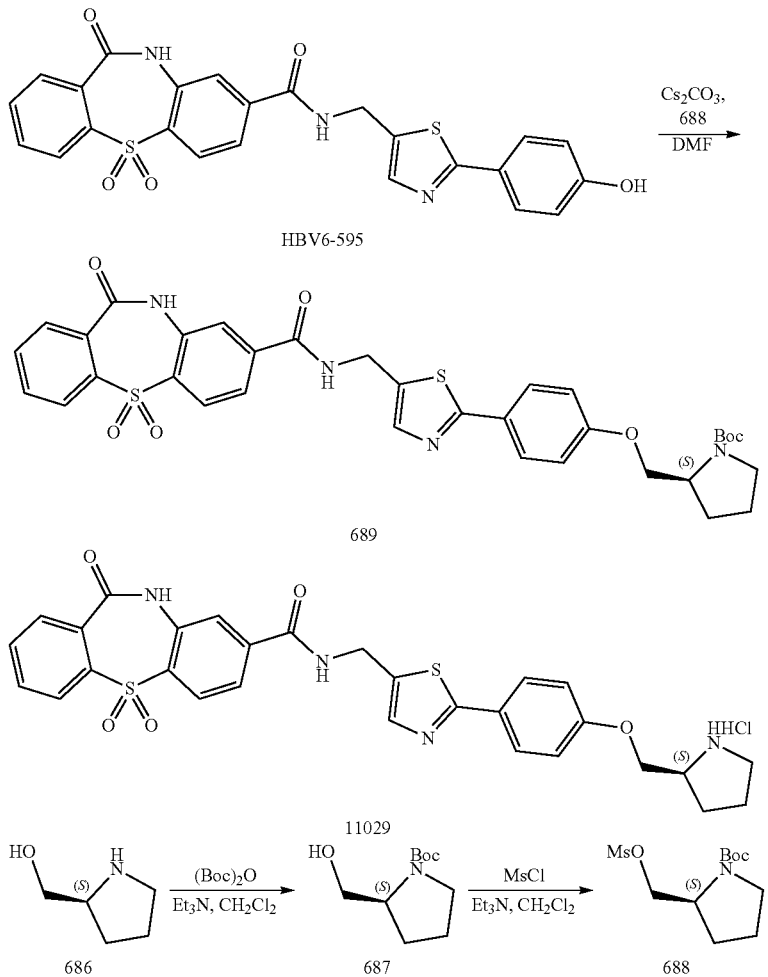

Synthesis of tert-butyl (S)-2-(hydroxymethyl) pyrrolidine-1-carboxylate (687)

To a stirring solution of (S)-pyrrolidin-2-ylmethanol 686 (1 g, 9.88 mmol) in $CH_2Cl_2$ (20 mL) under inert atmosphere was added triethylamine (1.57 mL, 10.89 mmol) at 0° C., followed by addition of Boc-anhydride (2.5 mL, 10.89 mmol) at the same temperature; warmed to RT and stirred for 6 h. The reaction was monitored by TLC; after completion of the reaction, the reaction mixture was diluted with water (20 mL), diluted with 1 N HCl (20 mL). The aqueous layer was concentrated in vacuo to afford crude compound 687 (1.9 g) as colorless syrup which was carried forward for next step without further purification. TLC: 20% EtOAc/hexanes ($R_f$: 0.4); $^1$H-NMR (CDCl$_3$, 500 MHz): δ 4.74-4.70

(m, 1H), 3.97 (d, J=5.2 Hz, 1H), 3.68-3.54 (m, 2H), 3.49-3.42 (m, 1H), 3.36-3.28 (m, 1H), 2.07-1.94 (m, 1H), 1.90-1.74 (m, 2H), 1.47 (s, 9H);

Synthesis of tert-butyl (S)-2-(((methylsulfonyl) oxy) methyl) pyrrolidine-1-carboxylate (688)

To a stirring solution of compound 687 (1 g, crude) in CH$_2$Cl$_2$ (20 mL) under inert atmosphere were added triethylamine (1.40 mL, 9.95 mmol), methanesulfonyl chloride (0.68 mL, 8.45 mmol) at 0° C.; warmed to RT and stirred for 3 h. The reaction was monitored by TLC; after completion of the reaction, the reaction mixture was diluted with water (50 mL) and extracted with CH$_2$Cl$_2$ (2×50 mL). The combined organic extracts were dried over sodium sulfate, filtered and concentrated in vacuo to afford compound 688 (570 mg, crude) as colorless liquid. TLC: 20% EtOAc/hexanes (R$_f$: 0.5); The crude was carried forward for next step without further purification.

Synthesis of tert-butyl (S)-2-((4-(5-((5, 5-dioxido-11-oxo-10, 11-dihydrodibenzo [b, f] [1, 4] thiazepine-8-carboxamido) methyl) thiazol-2-yl) phenoxy) methyl) pyrrolidine-1-carboxylate (689)

To a stirring solution of N-((2-(4-hydroxyphenyl) thiazol-5-yl) methyl)-11-oxo-10, 11-dihydrodibenzo [b, f] [1, 4] thiazepine-8-carboxamide 5, 5-dioxide 1 595 (1 g, 2.03 mmol) in DMF (20 mL) under inert atmosphere were added tert-butyl (S)-2-(((methylsulfonyl) oxy) methyl) pyrrolidine-1-carboxylate 688 (568 mg, crude), cesium carbonate (1.99 g, 6.10 mmol) at RT and stirred for 16 h. The reaction was monitored by TLC; after completion of the reaction, the reaction mixture was diluted with water (50 mL) and extracted with EtOAc (2×30 mL). The combined organic extracts were dried over sodium sulfate, filtered and concentrated in vacuo to obtain the crude. The crude was purified through silicagel column chromatography using 2% MeOH/CH$_2$Cl$_2$ to afford compound 689 (210 mg, 16%) as yellow solid. TLC: 5% MeOH/CH$_2$Cl$_2$ (R$_f$: 0.4); LC-MS: 94.40%; 619.1 (M$^+$+1) (–$^t$Bu) (Column; X-select CSH C-18 (150×3.0 mm, 2.7 μm); RT 2.70 min. 0.025% Aq. TFA+5% ACN: ACN+5% 0.025% Aq. TFA, 1.0 mL/min). $^1$H-NMR (DMSO-d$_6$, 400 MHz): δ 11.51 (s, 1H), 9.44 (t, J=5.8 Hz, 1H), 8.05 (d, J=8.2 Hz, 1H), 8.01-7.95 (m, 2H), 7.93-7.77 (m, 6H), 7.72 (s, 1H), 7.05 (d, J=8.9 Hz, 2H), 4.66 (d, J=5.6 Hz, 2H), 4.16-3.88 (m, 3H), 3.29-3.25 (m, 2H), 2.05-1.75 (m, 4H), 1.40 (s, 9H); LC-MS: 93.14%; 675.2 (M$^+$+1); (column; Kinetex EVO C-18 (50×3.0 mm, 2.6 um); RT 3.43 min. 2.5 mM Aq. NH$_4$OOCH+5% ACN: ACN+5% 2.5 mM Aq.NH$_4$OOCH, 0.8 mL/min).

Synthesis of (S)-11-oxo-N-((2-(4-(pyrrolidin-2-yl-methoxy) phenyl) thiazol-5-yl) methyl)-10, 11-dihydrodibenzo [b, f] [1, 4] thiazepine-8-carboxamide 5, 5-dioxide hydrochloride (11029)

To a stirring solution of compound 689 (200 mg, 0.29 mmol) in CH$_2$Cl$_2$ (10 mL) was added 4 N HCl in 1, 4-dioxane (10 mL) under inert atmosphere at 0° C.; warmed to RT and stirred for 4 h. The reaction was monitored by TLC; after completion of the reaction, the volatiles were removed in vacuo. The crude was washed with diethyl ether (5 mL), EtOAc (5 mL), hexane (5 mL) and dried in vacuo to afford 11029 (130 mg, HCl salt) as an off-white solid. TLC: 10% MeOH/CH$_2$Cl$_2$ (R$_f$: 0.1); $^1$H NMR (DMSO-d$_6$, 400 MHz): δ 11.53 (s, 1H), 9.48 (t, J=5.8 Hz, 1H), 9.42-9.28 (m, 1H), 8.94-8.73 (m, 1H), 8.06 (d, J=8.3 Hz, 1H), 8.00-7.95 (m, 2H), 7.93-7.80 (m, 6H), 7.74 (s, 1H), 7.08 (d, J=8.9 Hz, 2H), 4.66 (d, J=5.6 Hz, 2H), 4.32 (dd, J=10.7, 3.5 Hz, 1H), 4.17 (dd, J=10.5, 8.4 Hz, 1H), 3.97-3.89 (m, 1H), 3.28-3.17 (m, 2H), 2.16-2.08 (m, 1H), 2.05-1.95 (m, 1H), 1.95-1.84 (m, 1H), 1.80-1.68 (m, 1H); LC-MS: 93.84%; 575.1 (M$^+$+1); (column; Ascentis Express C18, (50×3.0 mm, 2.7 μm); RT 1.82 min. 0.025% Aq. TFA+5% ACN: ACN+5% 0.025% Aq. TFA, 1.2 mL/min). HPLC (purity): 93.14%; (column; X-select CSH-C18 (150×4.6 mm, 3.5 μm); RT 5.83 min. 0.05% TFA (Aq)+5% ACN: ACN+5% 0.05% TFA (Aq); 1.0 mL/min, Diluent: DMSO:ACN:water).

Synthesis of 11135

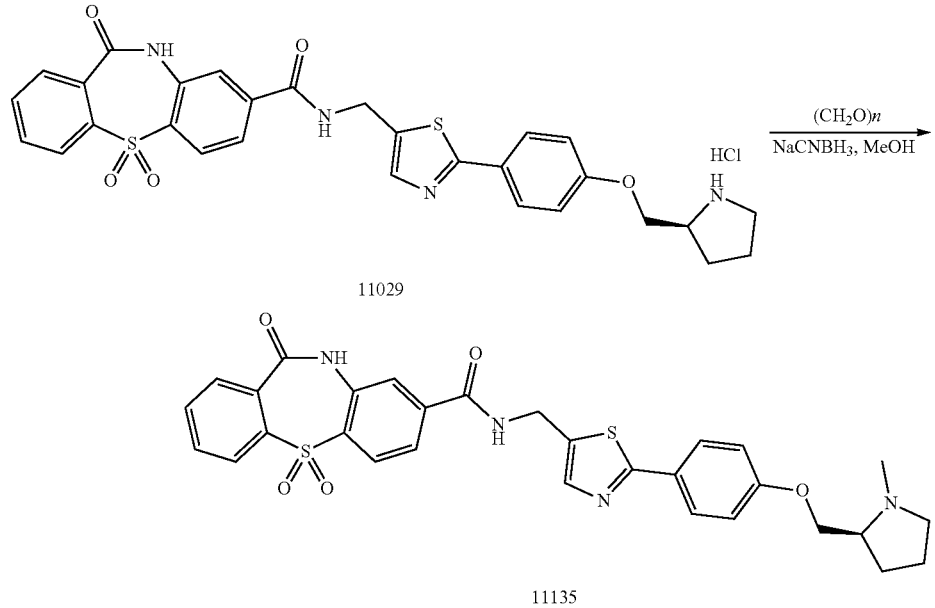 [SMILES: O=C(NCc1cnc(-c2ccc(OC[C@@H]3CCCN3)cc2)s1)c1ccc2c(c1)NC(=O)c1ccccc1S2(=O)=O ; Cl ; CN1CCC[C@H]1COc1ccc(-c2ncc(CNC(=O)c3ccc4c(c3)NC(=O)c3ccccc3S4(=O)=O)s2)cc1]

Synthesis of (S)—N-((2-(4-((1-methylpyrrolidin-2-yl) methoxy) phenyl) thiazol-5-yl)methyl)-11-oxo-10,11-dihydrodibenzo [b, f] [1, 4] thiazepine-8-carboxamide 5,5-dioxide (11135)

To a stirring solution of 11029 (90 mg, 0.14 mmol) in MeOH (5 mL) under inert atmosphere were added paraformaldehyde (22 mg, 0.73 mmol) and sodium cyanoborohydride (46 mg, 0.73 mmol) at RT and stirred for 16 h. The reaction was monitored by TLC; after completion of the reaction, the reaction mixture was quenched with ice-cold water (10 mL) and extracted with $CH_2Cl_2$ (3×20 mL). The combined organic extracts were dried over sodium sulfate, filtered and concentrated in vacuo to obtain the crude. The crude was purified through silica gel column chromatography using 5% MeOH/$CH_2Cl_2$ and 2 mL aqueous ammonia to afford 11135 (73 mg, 83%) as an off white solid. TLC: 10% MeOH/ $CH_2Cl_2$($R_f$: 0.6); 41 NMR (DMSO-$d_6$, 400 MHz): δ 11.51 (br s, 1H), 9.45 (t, J=5.7 Hz, 1H), 8.06 (d, J=8.3 Hz, 1H), 8.02-7.95 (m, 2H), 7.92-7.78 (m, 6H), 7.72 (s, 1H), 7.02 (d, J=8.7 Hz, 2H), 4.66 (d, J=5.6 Hz, 2H), 4.02 (dd, J=9.6, 5.5 Hz, 1H), 3.94-3.85 (m, 1H), 3.01-2.96 (m, 1H), 2.65-2.56 (m, 1H), 2.38 (br s, 3H), 2.27-2.16 (m, 1H), 2.01-1.92 (m, 1H), 1.76-1.55 (m, 3H); LC-MS: 96.81%; 589.1 (M$^+$+1); (column; Ascentis Express C18, (50×3.0 mm, 2.7 μm); RT 1.83 min. 0.025% Aq. TFA+5% ACN: ACN+5% 0.025% Aq. TFA, 1.2 mL/min); HPLC (purity): 97.00%; (column; X-select CSH-C18 (150×4.6 mm, 3.5 μm); RT 5.98 min. 0.05% TFA (Aq)+5% ACN: ACN+5% 0.05% TFA (Aq); 1.0 mL/min, Diluent: DMSO:ACN:water).

Synthesis of 11139

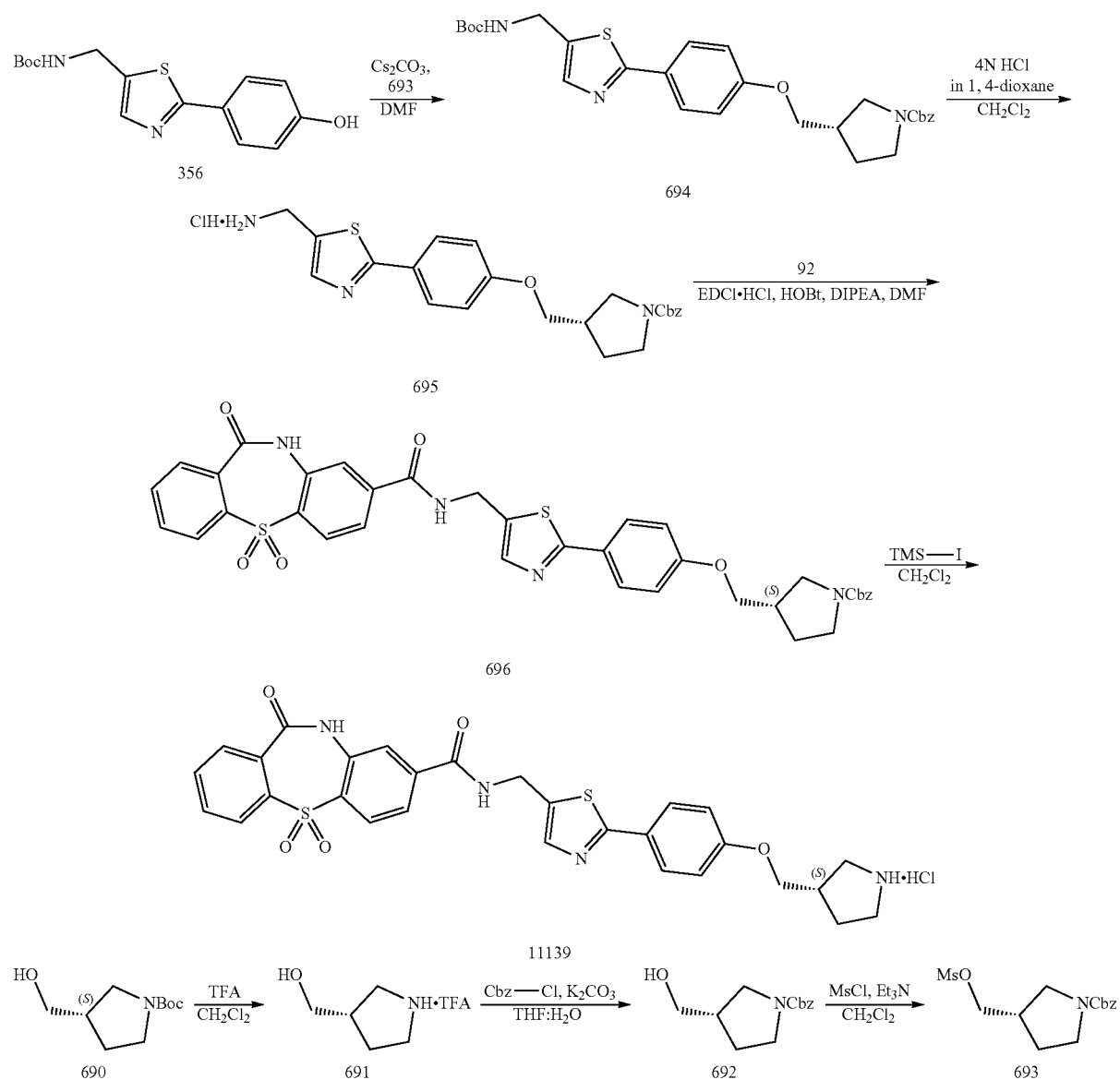

Synthesis of (S)-pyrrolidin-3-ylmethanol TFA Salt (691)

To a stirring solution of tert-butyl (S)-3-(hydroxymethyl) pyrrolidine-1-carboxylate 690 (2 g, 14.90 mmol) in $CH_2Cl_2$ (30 mL) under inert atmosphere was added trifluoroacetic acid (30 mL) at 0° C. and stirred for 30 min. The reaction was monitored by TLC; after completion of the reaction, the reaction mixture was diluted with water (100 mL) and extracted with $CH_2Cl_2$ (2×75 mL). The combined organic extracts were dried over sodium sulfate, filtered and concentrated in vacuo to afford crude compound 691 (2 g) as yellow syrup. TLC: 20% EtOAc/hexanes ($R_f$: 0.2).

Synthesis of benzyl (S)-3-(hydroxymethyl) pyrrolidine-1-carboxylate (692)

To a stirring solution of compound 691 (2 g, 19.77 mmol) in THF:$H_2O$ (4:1, 60 mL) was added potassium carbonate (5.4 g, 31.67 mmol) portion wise for 10 min at 0° C.; warmed to RT and stirred for 16 h. The reaction was monitored by TLC; after completion of the reaction, the reaction mixture was diluted with water (100 mL) and extracted with EtOAc (2×75 mL). The combined organic extracts were dried over sodium sulfate, filtered and concentrated in vacuo to obtain the crude. The crude was purified through silica gel column chromatography using 20% EtOAc/hexanes to afford compound 692 (1.1 g, crude) as yellow syrup. TLC: 40% EtOAc/hexanes ($R_f$: 0.2); LC-MS: 67.76%; 236.0 ($M^+$+1); (column; X Select CSH C-18, (50×3.0 mm, 2.5 µm); RT 2.12 min. 2.5 mM Aq. $NH_4OOCH$+5% ACN: ACN+5% 2.5 mM Aq.$NH_4OOCH$, 0.8 mL/min).

Synthesis of benzyl (S)-3-(((methylsulfonyl) oxy) methyl) pyrrolidine-1-carboxylate (693)

To a stirring solution of compound 692 (1.2 g, crude) in $CH_2Cl_2$ (10 mL) under inert atmosphere were added triethylamine (2.11 mL, 15.31 mmol), methanesulfonyl chloride (0.67 mL, 7.65 mmol) at 0° C.; warmed to RT and stirred for 4 h. The reaction was monitored by TLC; after completion of the reaction, the reaction mixture was diluted with water (50 mL) and extracted with $CH_2Cl_2$ (2×50 mL). The combined organic extracts were dried over sodium sulfate, filtered and concentrated in vacuo to afford crude compound 693 (2 g) as brown liquid. TLC: 40% EtOAc/hexanes ($R_f$: 0.4); LC-MS: 80.20%; 313.9 ($M^+$+1); (column; Kinetex EVO C-18 (50×3.0 mm, 2.6 um); RT 1.27 min. 2.5 mM Aq. $NH_4OOCH$+5% ACN: ACN+5% 2.5 mM Aq.$NH_4OOCH$, 0.8 mL/min).

Synthesis of benzyl (S)-3-((4-(5-(((tert-butoxycarbonyl) amino) methyl) thiazol-2-yl) phenoxy) methyl) pyrrolidine-1-carboxylate (694)

To a stirring solution of compound 693 (230 mg, 0.98 mmol) in DMF (3 mL) under inert atmosphere were added tert-butyl ((2-(4-hydroxyphenyl) thiazol-5-yl) methyl carbamate 356 (200 mg, 0.65 mmol), cesium carbonate (424 mg, 1.36 mmol) at RT and stirred for 16 h. The reaction was monitored by TLC; after completion of the reaction, the reaction mixture was diluted with water (50 mL) and extracted with EtOAc (2×75 mL). The combined organic extracts were dried over sodium sulfate, filtered and concentrated in vacuo to afford crude compound 694 (300 mg) as yellow solid. TLC: 40% EtOAc/hexanes ($R_f$: 0.4); LC-MS: 63.70%; 524.5 ($M^+$+1); (column; Kinetex EVO C-18 (50×3.0 mm, 2.6 um); RT 1.27 min. 2.5 mM Aq. $NH_4OAc$: ACN, 0.8 mL/min).

Synthesis of benzyl (S)-3-((4-(5-(aminomethyl) thiazol-2-yl) phenoxy) methyl) pyrrolidine-1-carboxylate hydrochloride (695)

To a stirring solution of compound 694 (1.4 g, crude) in $CH_2Cl_2$ (10 mL) was added 4 N HCl in 1, 4-dioxane (10 mL) under inert atmosphere at 0° C.; warmed to RT and stirred for 3 h. The reaction was monitored by TLC; after completion of the reaction, the volatiles were removed in vacuo. The crude washed with diethyl ether (5 mL), EtOAc (5 mL) and dried in vacuo to afford compound 695 (1 g, crude) as brown solid. TLC: 5% MeOH/$CH_2Cl_2$ ($R_f$: 0.1); LC-MS: 69.41%; 424.1 ($M^+$+1); (column; Ascentis Express C18, (50×3.0 mm, 2.7 µm); RT 2.08 min. 0.025% Aq. TFA+5% ACN: ACN+5% 0.025% Aq. TFA, 1.2 mL/min).

Synthesis of benzyl (S)-3-((4-(5-((5, 5-dioxido-11-oxo-10, 11-dihydrodibenzo [b, f] [1, 4] thiazepine-8-carboxamido) methyl) thiazol-2-yl) phenoxy) methyl) pyrrolidine-1-carboxylate (696)

To a stirring solution of 92 (400 mg, 1.32 mmol) in DMF (5 mL) under inert atmosphere were added HOBt (356 mg, 2.64 mmol), EDCI.HCl (506 mg, 2.64 mmol), diisopropyl ethyl amine (0.68 mL, 3.96 mmol) and compound 695 (722 mg, crude) at 0° C.; warmed to RT and stirred for 16 h. The reaction was monitored by TLC; after completion of the reaction, the reaction mixture was diluted with ice-cold water (50 mL) and extracted with EtOAc (2×75 mL). The combined organic extracts were dried over sodium sulfate, filtered and concentrated in vacuo to obtain the crude. The crude was purified through silica gel column chromatography using 2% MeOH/$CH_2Cl_2$ to afford compound 696 (400 mg, 43%) as an off-white solid. TLC: 5% MeOH/$CH_2Cl_2$ ($R_f$: 0.4); $^1$H-NMR (DMSO-$d_6$, 400 MHz): δ 11.52 (s, 1H), 9.45 (t, J=5.8 Hz, 1H), 8.06 (d, J=8.2 Hz, 1H), 7.98 (td, J=7.7, 1.3 Hz, 2H), 7.93-7.84 (m, 3H), 7.84-7.77 (m, 3H), 7.72 (s, 1H), 7.38-7.33 (m, 4H), 7.33-7.28 (m, 1H), 7.07-6.98 (m, 2H), 5.06 (s, 2H), 4.66 (d, J=5.6 Hz, 2H), 4.13-3.93 (m, 2H), 3.61-3.41 (m, 2H), 3.40-3.34 (m, 1H), 3.25-3.13 (m, 1H), 2.71-2.60 (m, 1H), 2.12-1.96 (m, 1H), 1.83-1.68 (m, 1H); LC-MS: 84.44%; 709.2 ($M^+$+1); (column; Ascentis Express C18, (50×3.0 mm, 2.7 µm); RT 1.98 min. 0.025% Aq. TFA+5% ACN: ACN+5% 0.025% Aq. TFA, 1.2 mL/min).

Synthesis of (S)-11-oxo-N-((2-(4-(pyrrolidin-3-ylmethoxy) phenyl) thiazol-5-yl) methyl)-10, 11-dihydrodibenzo [b, f] [1, 4] thiazepine-8-carboxamide 5, 5-dioxide hydrochloride (11139)

To a stirring solution of compound 696 (200 mg, 0.28 mmol) in $CH_2Cl_2$ (10 mL) was added trimethylsilyl iodide (0.03 mL, 0.211 mmol) under inert atmosphere at 0° C.; warmed to RT and stirred for 4 h. The reaction was monitored by TLC; after completion of the reaction, the volatiles were removed in vacuo. The crude washed with EtOAc (10 mL) and dried in vacuo to afford crude amine.

To the above crude amine (150 mg) in $CH_2Cl_2$ (5 mL) under inert atmosphere was added 4 N HCl in 1, 4-dioxane (3 mL) at 0° C. and stirred for 1 h. The reaction was monitored by TLC; after completion of the reaction, the volatiles were removed in vacuo. The crude washed with triturated with diethylether (10 mL) and dried in vacuo to afford crude compound HCl (140 mg) which was further purified by preparative HPLC purification to afford 11139 (89 mg, HCl salt, 36%) as an off-white solid. TLC: 5%

MeOH/CH$_2$Cl$_2$ (R$_f$: 0.2); $^1$H-NMR (DMSO-d$_6$, 400 MHz): δ 11.51 (s, 1H), 9.45 (t, J=5.8 Hz, 1H), 8.67 (br s, 2H), 8.05 (d, J=8.2 Hz, 1H), 7.97 (td, J=7.5, 1.3 Hz, 2H), 7.92-7.78 (m, 6H), 7.72 (s, 1H), 7.03 (d, J=8.9 Hz, 2H), 4.65 (d, J=5.6 Hz, 2H), 4.13-3.90 (m, 2H), 3.44-3.35 (m, 1H), 3.21-3.12 (m, 2H), 3.06-2.98 (m, 1H), 2.78-2.70 (m, 1H), 2.19-1.98 (m, 1H), 1.83-1.66 (m, 1H); LC-MS: 98.88%; 575.1 (M$^+$+1); (column; Ascentis Express C18, (50×3.0 mm, 2.7 µm); RT 1.98 min. 0.025% Aq.TFA+5% ACN: ACN+5% 0.025% Aq. TFA, 1.2 mL/min); HPLC (purity): 99.73%; (column; X-Select CSH-C-18 (150×4.6 mm, 3.5 µm); RT 5.61 min. 0.05% TFA (Aq)+5% ACN: ACN+5% 0.05% TFA (Aq); 1.0 mL/min, Diluent: ACN:H$_2$O:DMSO).

Synthesis of 11140

Synthesis of (R)-pyrrolidin-3-ylmethanol.TFA Salt (698)

To a stirring solution of tert-butyl (R)-3-(hydroxymethyl) pyrrolidine-1-carboxylate 697 (2 g, 9.95 mmol) in CH$_2$Cl$_2$ (20 mL) was added trifluoroacetic acid (20 mL) at 0° C. under inert atmosphere. The reaction mixture was gradually warmed to RT and stirred for 3 h. The reaction was monitored by TLC; after completion of the reaction, the volatiles were removed in vacuo. The crude was triturated with diethylether (20 mL), n-hexane (30 mL) and dried under vacuum to afford crude compound 698 (1.8 g) as pale yellow sticky syrup. This crude material was taken to next step without further purification. TLC: 5% MeOH/CH$_2$Cl$_2$ (R$_f$: 0.1); LC-MS (Agilent 6310 Ion trap): 32.89%; 102.3 (M$^+$+1); (column; X-select CSH C-18 (150×4.6 mm, 3.5 um); RT 1.95 min. 2.5 mM Aq. NH$_4$OAc: ACN; 1.0 mL/min).

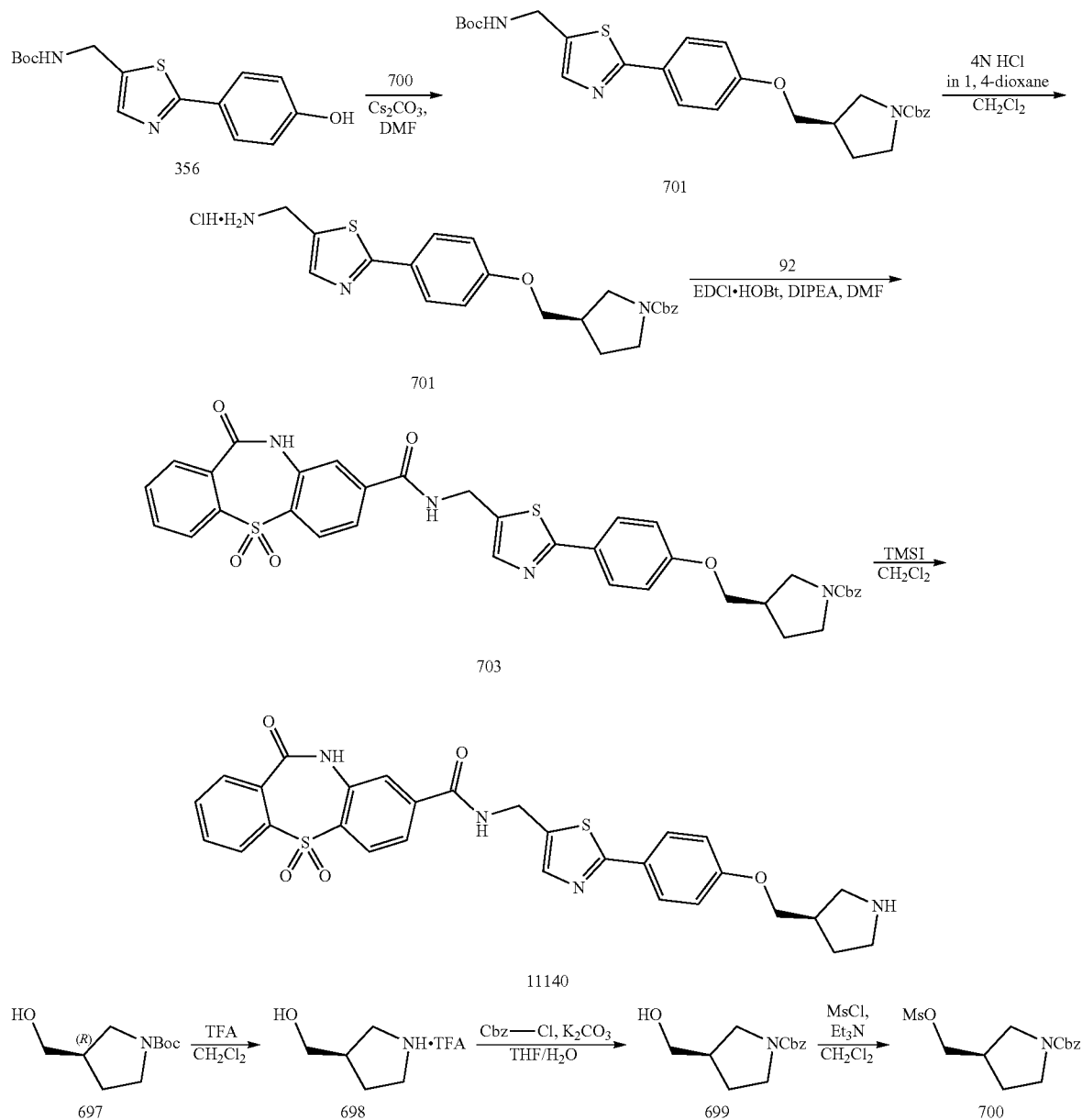

Synthesis of benzyl (R)-3-(hydroxymethyl) pyrrolidine-1-carboxylate (699)

To a stirring solution of compound 698 (1.8 g, crude) in a mixture of THF:$H_2O$ (1:1, 60 mL) were added potassium carbonate (4.92 g, 35.64 mmol) and benzyl chloroformate (50% in toluene, 10.22 mL, 35.64 mmol) at 0° C. The reaction mixture was gradually warmed to RT and stirred for 16 h. The reaction was monitored by TLC; after completion of the reaction, the reaction mixture was diluted with EtOAc (100 mL) and washed with water (50 mL). The organic layer was separated, dried over sodium sulfate, filtered and concentrated in vacuo to obtain the crude. The crude was purified through silica gel column chromatography using 50% EtOAc/hexanes to afford compound 699 (1.3 g) as pale yellow liquid. This material with minor impurity was taken to next step. TLC: 10% MeOH/$CH_2Cl_2$ ($R_f$: 0.3); $^1$H NMR (500 MHz, DMSO-$d_6$): δ 7.44-7.25 (m, 5H), 5.05 (s, 2H), 4.66 (q, J=4.6 Hz, 1H), 3.52-3.34 (m, 4H), 3.30-3.20 (m, 1H), 3.10-3.06 (m, 1H), 2.37-2.20 (m, 1H), 1.92-1.82 (m, 1H), 1.66-1.54 (m, 1H); LC-MS: 76.88%; 236.0 ($M^+$+1); (column; Kinetex EVO C-18 (50×3.0 mm, 2.6 um); RT 2.13 min. 2.5 mM $NH_4OOCH$ in water+5% ACN: ACN+5% 2.5 mM $NH_4OOCH$ in water, 0.8 mL/min).

Synthesis of benzyl (R)-3-(((methylsulfonyl) oxy) methyl) pyrrolidine-1-carboxylate (700)

To a stirring solution of compound 699 (1.3 g, 5.53 mmol) in $CH_2Cl_2$ (30 mL) were added triethylamine (2.32 mL, 16.59 mmol) and methanesulfonyl chloride (0.51 mL, 6.64 mmol) at 0° C. under inert atmosphere. The reaction mixture was gradually warmed to RT and stirred for 4 h. The reaction was monitored by TLC; after completion of the reaction, the reaction mixture was diluted with $CH_2Cl_2$ (50 mL) and washed with water (50 mL). The organic layer was separated, dried over sodium sulfate, filtered and concentrated in vacuo to afford compound 700 (1.5 g) as pale yellow viscous syrup. This crude material was taken to next step without further purification. TLC: 50% EtOAc/hexanes ($R_f$: 0.3); LC-MS: 81.89%; 313.9 ($M^+$+1); (column; Kinetex EVO C-18 (50×3.0 mm, 2.6 um); RT 2.64 min. 2.5 mM $NH_4OOCH$ in water+5% ACN: ACN+5% 2.5 mM $NH_4OOCH$ in water, 0.8 mL/min).

Synthesis of benzyl (R)-3-((4-(5-(((tert-butoxycarbonyl) amino) methyl) thiazol-2-yl) phenoxy) methyl) pyrrolidine-1-carboxylate (701)

To a stirring solution of tert-butyl ((2-(4-hydroxyphenyl) thiazol-5-yl) methyl) carbamate 356 (800 mg, 2.61 mmol) in DMF (15 mL) were added compound 700 (1.53 g, crude) and cesium carbonate (1.7 g, 5.23 mmol) at RT in a sealed tube under inert atmosphere. The reaction mixture was heated to 70° C. and stirred for 16 h. The reaction was monitored by TLC; after completion of the reaction, the reaction mixture was diluted with water (50 mL) and extracted with EtOAc (2×150 mL). The combined organic extracts were dried over sodium sulfate, filtered and concentrated in vacuo to afford compound 701 (800 mg) as pale yellow viscous syrup. This crude material was taken to next step without further purification. TLC: 5% MeOH/$CH_2Cl_2$ ($R_f$: 0.6); LC-MS: 53.55%; 524.2 ($M^+$+1); (column; Kinetex EVO C-18 (50×3.0 mm, 2.6 um); RT 3.73 min. 2.5 mM $NH_4OOCH$ in water+5% ACN: ACN+5% 2.5 mM $NH_4OOCH$ in water, 0.8 mL/min).

Synthesis of benzyl (R)-3-((4-(5-(aminomethyl) thiazol-2-yl) phenoxy) methyl) pyrrolidine-1-carboxylate hydrochloride (702)

To a stirring solution of compound 701 (500 mg, crude) in $CH_2Cl_2$ (10 mL) was added 4 N HCl in 1, 4-dioxane (5 mL) at 0° C. under inert atmosphere. The reaction mixture was gradually warmed to RT and stirred for 3 h. The reaction was monitored by TLC; after completion of the reaction, the volatiles were removed in vacuo. The crude was triturated with diethyl ether (10 mL), n-pentane (10 mL) and dried in vacuo to afford compound 702 (450 mg) as colorless sticky solid. This crude material was taken to next step without further purification. TLC: 5% MeOH/$CH_2Cl_2$ ($R_f$: 0.1); LC-MS (Agilent 6310 Ion trap): 66.70%; 424.3 ($M^+$+1); (column; Kinetex EVO C-18 (50×3.0 mm, 2.6 um); RT 3.53 min. 5 mM Aq. $NH_4OAc$: ACN, 0.8 mL/min).

Synthesis of benzyl (R)-3-((4-(5-(((5, 5-dioxido-11-oxo-10, 11-dihydrodibenzo [b, f] [1, 4] thiazepine-8-carboxamido) methyl)thiazol-2-yl) phenoxy) methyl) pyrrolidine-1-carboxylate (703)

To a stirring solution of 11-oxo-10, 11-dihydrodibenzo [b, f] [1, 4] thiazepine-8-carboxylic acid 5, 5-dioxide 92 (250 mg, 0.82 mmol) in DMF (10 mL) were added compound 702 (419 mg, crude) and HOBt (167 mg, 1.24 mmol), EDCI.HCl (238 mg, 1.24 mmol) followed by diisopropylethylamine (0.72 mL, 4.12 mmol) at 0° C. under inert atmosphere. The reaction mixture was gradually warmed to RT and stirred for 16 h. The reaction was monitored by TLC; after completion of the reaction, the reaction mixture was diluted with water (50 mL) and extracted with EtOAc (2×150 mL). The combined organic extracts were dried over sodium sulfate, filtered and concentrated in vacuo to obtain the crude. The crude was triturated with EtOAc (20 mL), $CH_2Cl_2$ (20 mL), n-pentane (20 mL) and dried under vacuum to afford compound 703 (230 mg) as colorless sticky solid. This crude material was taken to next step without further purification. TLC: 5% MeOH/$CH_2Cl_2$ ($R_f$: 0.5); $^1$H NMR (500 MHz, DMSO-$d_6$): δ 11.51 (br s, 1H), 9.45 (t, J=5.5 Hz, 1H), 8.06 (d, J=8.1 Hz, 1H), 7.98 (t, J=8.7 Hz, 2H), 7.90 (t, J=7.2 Hz, 1H), 7.87-7.78 (m, 6H), 7.72 (s, 1H), 7.38-7.29 (m, 4H), 7.03 (J=8.1 Hz, 2H), 5.06 (s, 2H), 4.72-4.64 (m, 2H), 4.11-3.97 (m, 2H), 3.61-3.46 (m, 2H), 3.24-3.16 (m, 1H), 3.00-2.94 (m, 2H), 1.82-1.71 (m, 1H), 1.50-1.45 (m, 1H); LC-MS: 68.55%; 709.1 ($M^+$+1); (column; Ascentis Express C18, (50×3.0 mm, 2.7 μm); RT 2.71 min. 0.025% Aq. TFA+5% ACN: ACN+5% 0.025% Aq. TFA, 1.2 mL/min).

Synthesis of (R)-11-oxo-N-((2-(4-(pyrrolidin-3-ylmethoxy) phenyl) thiazol-5-yl) methyl)-10, 11-dihydrodibenzo [b, f] [1, 4] thiazepine-8-carboxamide 5, 5-dioxide (11140)

To a stirring solution of compound 703 (230 mg, crude) in $CH_2Cl_2$ (5 mL) was added trimethylsilyl iodide (0.06 mL, 0.45 mmol) at 0° C. under inert atmosphere and stirred at the same temperature for 3 h. The reaction was monitored by TLC; after completion of the reaction, the volatiles were removed in vacuo. The residue was diluted with $CH_2Cl_2$ (30 mL) and washed with saturated sodium bicarbonate solution (20 mL). The organic layer was separated, dried over sodium sulfate, filtered and concentrated in vacuo to obtain the crude. The crude was purified through silica gel column chromatography in basic $Al_2O_3$ using 10% MeOH/$CH_2Cl_2$ to afford 11140 (18 mg, 8%) as an off white solid. TLC: 10%

MeOH/CH$_2$Cl$_2$ (R$_f$: 0.1); $^1$H NMR (400 MHz, DMSO-d$_6$): δ 9.45 (t, J=5.5 Hz, 1H), 8.05 (d, J=8.2 Hz, 1H), 8.01-7.95 (m, 2H), 7.93-7.78 (m, 6H), 7.72 (s, 1H), 7.02 (d, J=8.8 Hz, 2H), 4.66 (d, J=5.4 Hz, 2H), 4.00-3.89 (m, 2H), 3.46-3.37 (m, 1H), 3.03-2.89 (m, 2H), 2.83-2.80 (m, 1H), 2.73-2.66 (m, 1H), 1.95-1.84 (m, 1H), 1.53-1.45 (m, 1H); LC-MS: 96.04%; 575.1 (M$^+$+1); (column; Ascentis Express C18, (50×3.0 mm, 2.7 μm); RT 1.82 min. 0.025% Aq. TFA+5% ACN: ACN+5% 0.025% Aq. TFA, 1.2 mL/min); HPLC (purity): 95.84%; (column; X-Select CSH-C-18 (150×4.6 mm, 3.5 μm); RT 5.64 min. 0.05% TFA+5% ACN: ACN+5% 0.05% TFA; 1.0 mL/min, Diluent: ACN:H$_2$O).
Synthesis of 11103
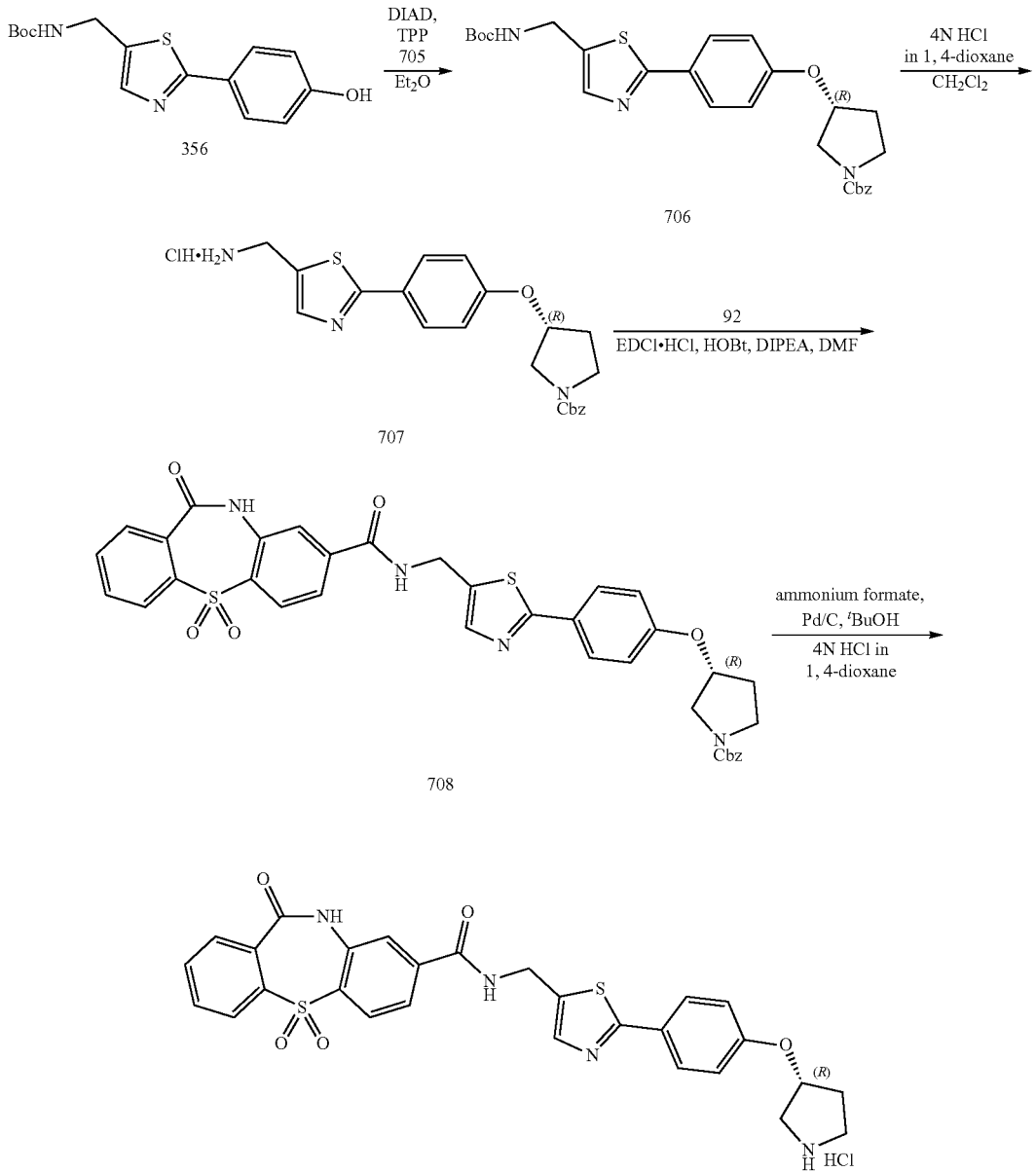
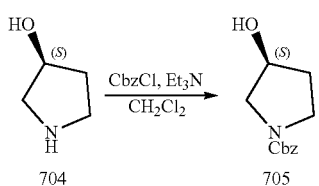

Synthesis of benzyl (S)-3-hydroxypyrrolidine-1-carboxylate (705)

To a stirring solution of (S)-pyrrolidin-3-ol 704 (1.5 g, 17.22 mmol) in $CH_2Cl_2$ (50 mL) under inert atmosphere were added triethylamine (7.4 mL, 51.72 mmol), benzyl chloroformate (50% in toluene, 7.05 mL, 20.66 mmol) at 0° C.; warmed to RT and stirred for 16 h. The reaction was monitored by TLC; after completion, the reaction mixture was poured into ice-cold water and extracted with $CH_2Cl_2$ (2×60 mL). The combined organic extracts were washed dried over sodium sulfate, filtered and concentrated in vacuo to obtain the crude. The crude was purified through column chromatography using 50% EtOAc/hexanes to afford compound 705 (2 g, 53%) as pale yellow liquid. TLC: 60% EtOAc/hexanes ($R_f$: 0.5); $^1$H NMR (DMSO-$d_6$, 500 MHz): δ 7.38-7.32 (m, 4H), 7.32-7.27 (m, 1H), 5.05 (s, 2H), 4.91 (br s, 1H), 4.26-4.24 (m, 1H), 3.42-3.27 (m, 3H), 3.24-3.13 (m, 1H), 1.91-1.81 (m, 1H), 1.78-1.70 (m, 1H); LC-MS: 98.78%; 222.0 ($M^+$+1); (column; Ascentis Express C18, (50×3.0 mm, 2.7 μm); RT 1.85 min. 0.025% Aq. TFA+5% ACN: ACN+5% 0.025% Aq. TFA, 1.2 mL/min).

Synthesis of benzyl (R)-3-(4-(5-(((tert-butoxycarbonyl) amino) methyl) thiazol-2-yl) phenoxy) pyrrolidine-1-carboxylate (706)

To a stirring solution of tert-butyl ((2-(4-hydroxyphenyl) thiazol-5-yl) methyl) carbamate 356 (700 mg, 2.28 mmol) in diethyl ether (30 mL) under argon atmosphere were added benzyl (S)-3-hydroxypyrrolidine-1-carboxylate 705 (758 mg, 3.42 mmol), triphenylphosphine (1.19 g, 4.54 mmol), DIAD (0.906 mL, 4.57 mmol) at 0° C.; warmed to RT and stirred for 24 h. The reaction was monitored by TLC; after completion, the reaction mixture was poured into ice-cold water and extracted with EtOAc (2×75 mL). The combined organic extracts were washed dried over sodium sulfate, filtered and concentrated in vacuo to obtain the crude. The crude was purified through column chromatography using 50% EtOAc/hexanes to afford compound 706 (1.6 g, crude) as an off-white solid. TLC: 50% EtOAc/hexanes ($R_f$: 0.5); LC-MS: 33.04%; 510.1 ($M^+$+1); (column; Ascentis Express C18, (50×3.0 mm, 2.7 μm); RT 2.85 min. 0.025% Aq. TFA+5% ACN: ACN+5% 0.025% Aq. TFA, 1.2 mL/min). LC-MS shows 65.46%, TPPO as major impurity at RT 2.25.

Synthesis of benzyl (R)-3-(4-(5-(aminomethyl) thiazol-2-yl) phenoxy) pyrrolidine-1-carboxylate hydrochloride (707)

To a stirring solution of benzyl (R)-3-(4-(5-(((tert-butoxycarbonyl) amino) methyl) thiazol-2-yl) phenoxy) pyrrolidine-1-carboxylate 706 (1.6 g, crude) in $CH_2Cl_2$ (30 mL) was added 4 N HCl in 1, 4-dioxane (3 mL) under argon atmosphere at 0° C.; warmed to RT and stirred for 2 h. The reaction was monitored by TLC; after completion of the reaction, the volatiles were removed in vacuo. The crude washed with diethyl ether (10 mL) and dried in vacuo to afford compound 707 (550 mg; HCl salt) as an off-white solid. TLC: 50% EtOAc/hexanes ($R_f$: 0.1); 41 NMR (DMSO-$d_6$, 500 MHz): δ 8.54 (br s, 1H), 7.91 (s, 1H), 7.86 (d, J=8.7 Hz, 1H), 7.40-7.32 (m, 1H), 7.09 (d, J=8.7 Hz, 1H), 5.23-4.97 (m, 1H), 4.32 (q, J=5.6 Hz, 1H), 3.80-3.31 (m, 1H), 2.29-2.05 (m, 1H); LC-MS: 99.37%; 432.0 ($M^+$+Na); (column; Ascentis Express C18, (50×3.0 mm, 2.7 μm); RT 1.93 min. 0.025% Aq. TFA+5% ACN: ACN+5% 0.025% Aq. TFA, 1.2 mL/min).

Synthesis of benzyl (R)-3-(4-(5-((5, 5-dioxido-11-oxo-10, 11-dihydrodibenzo [b, f] [1, 4] thiazepine-8-carboxamido) methyl) thiazol-2-yl) phenoxy) pyrrolidine-1-carboxylate (708)

To a stirring solution of 92 (200 mg, 0.66 mmol) in DMF (15 mL) under inert atmosphere were added EDCI.HCl (190 mg, 0.99 mmol), HOBt (135 mg, 0.99 mmol), benzyl (R)-3-(4-(5-(aminomethyl) thiazol-2-yl) phenoxy) pyrrolidine-1-carboxylate hydrochloride 707 (299 mg, 0.66 mmol) and diisopropylethylamine (0.63 mL, 3.30 mmol) at 0° C.; warmed to RT and stirred for 16 h. The reaction was monitored by TLC; after completion of the reaction, the reaction mixture was poured into ice-cold water (50 mL) and extracted with EtOAc (2×60 mL). The combined organic extracts were dried over sodium sulfate, filtered and concentrated in vacuo to obtain the crude. The crude was purified through silica gel (100-200 mesh) column chromatography using 5% MeOH/$CH_2Cl_2$ to afford compound 708 (300 mg, 67%) as an off-white solid. TLC: 4% MeOH/$CH_2Cl_2$ ($R_f$: 0.4); $^1$H-NMR (DMSO-$d_6$, 500 MHz): δ 11.51 (s, 1H), 9.45 (t, J=5.8 Hz, 1H), 8.06 (d, J=8.1 Hz, 1H), 8.01-7.96 (m, 2H), 7.90 (td, J=7.5, 1.2 Hz, 1H), 7.87-7.79 (m, 5H), 7.73 (s, 1H), 7.42-7.26 (m, 5H), 7.04 (d, J=8.7 Hz, 2H), 5.15-5.01 (m, 3H), 4.66 (br d, J=5.8 Hz, 2H), 3.71-3.60 (m, 1H), 3.58-3.39 (m, 3H), 2.27-2.04 (m, 2H); LC-MS: 91.64%; 695.1 ($M^+$+1); (column; Ascentis Express C18, (50×3.0 mm, 2.7 μm); RT 2.61 min. 0.025% Aq. TFA+5% ACN: ACN+5% 0.025% Aq. TFA, 1.2 mL/min).

Synthesis of (R)-11-oxo-N-((2-(4-(pyrrolidin-3-yloxy) phenyl) thiazol-5-yl) methyl)-10, 11-dihydrodibenzo [b, f] [1, 4] thiazepine-8-carboxamide 5, 5-dioxide hydrochloride (11103)

To a stirring solution of benzyl (R)-3-(4-(5-((5, 5-dioxido-11-oxo-10, 11-dihydrodibenzo [b, f] [1, 4] thiazepine-8-carboxamido) methyl) thiazol-2-yl) phenoxy) pyrrolidine-1-carboxylate 708 (100 mg, 0.14 mmol) in t-butanol (10 mL) under inert atmosphere was added 10% Pd/C (50% wet, 200 mg), ammonium formate (180 mg, 2.88 mmol) at RT; heated to 80° C. and stirred for 16 h. The reaction was monitored by TLC; after completion of the reaction, the volatiles were concentrated in vacuo to obtain the crude. The crude was purified through silica gel (100-200 mesh) column chromatography using 12% MeOH/$CH_2Cl_2$ to afford crude amine (30 mg).

To the above crude amine (30 mg) in $CH_2Cl_2$ (5 mL) under inert atmosphere was added 4 N HCl in 1, 4-dioxane (3 mL) at 0° C. and stirred for 30 min. The reaction was monitored by TLC; after completion of the reaction, the volatiles were removed in vacuo. The crude washed with triturated with EtOAc (5 mL) and dried in vacuo to afford 11103 (22 mg, 68.9%) as an off-white solid. TLC: 10% MeOH/$CH_2Cl_2$ ($R_f$: 0.2); $^1$H NMR (DMSO-$d_6$, 400 MHz): δ 11.53 (s, 1H), 9.50 (t, J=5.8 Hz, 1H), 9.41-9.24 (m, 2H), 8.06 (d, J=8.3 Hz, 1H), 7.98 (td, J=7.3, 1.5 Hz, 2H), 7.93-7.81 (m, 6H), 7.74 (s, 1H), 7.06 (d, J=8.9 Hz, 2H), 5.21 (t, J=4.4 Hz, 1H), 4.66 (d, J=5.6 Hz, 2H), 3.40-3.22 (m, 4H), 2.29-2.09 (m, 2H); LC-MS: 92.21%; 561.1 ($M^+$+1); (column; Ascentis Express C18, (50×3.0 mm, 2.7 μm); RT 1.81 min. 0.025% Aq. TFA+5% ACN: ACN+5% 0.025% Aq TFA, 1.2 mL/min); HPLC (purity): 97.17%; (column; X-select CSH C-18 (150×4.66 mm, 3.5 μm); RT 5.28 min. ACN+5% 0.05% TFA (Aq): 0.05% TFA (Aq)+5% ACN; 1.0 mL/min, Diluent: ACN:water)

Synthesis of 11028 & 11134
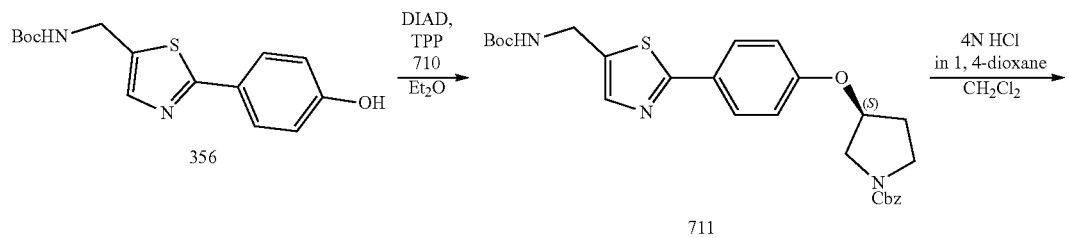
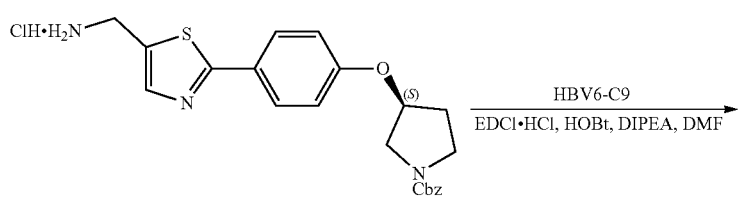
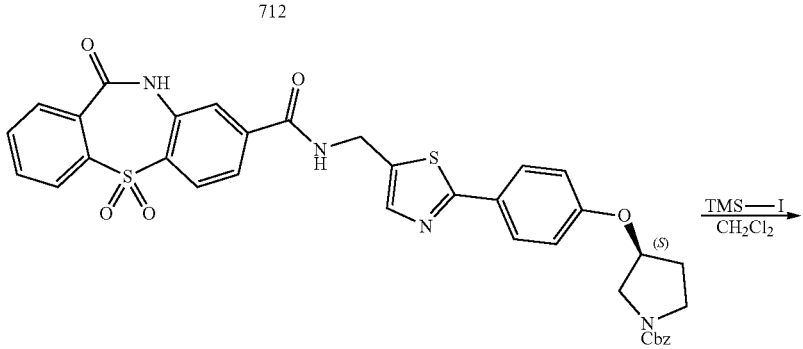
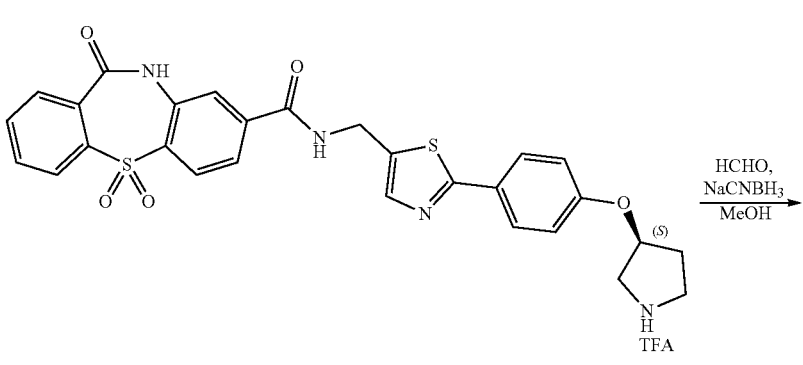
11028
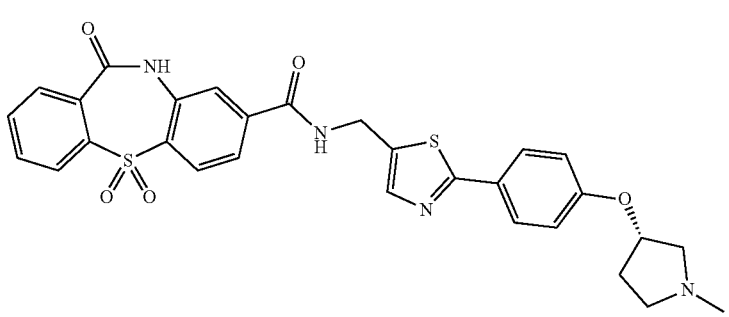
11134

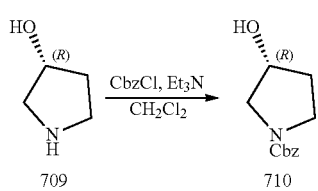

Synthesis of benzyl (R)-3-hydroxypyrrolidine-1-carboxylate (710)

To a stirring solution of (R)-pyrrolidin-3-ol 709 (1.5 g, 17.24 mmol) in CH$_2$Cl$_2$ (50 mL) under inert atmosphere were added triethylamine (7.4 mL, 51.72 mmol), benzyl chloroformate (50% in toluene, 7.05 mL, 20.66 mmol) at 0° C.; warmed to RT and stirred for 16 h. The reaction was monitored by TLC; after completion, the reaction mixture was poured into ice-cold water and extracted with CH$_2$Cl$_2$ (2×60 mL). The combined organic extracts were dried over sodium sulfate, filtered and concentrated in vacuo to obtain the crude. The crude was purified through column chromatography using 50% EtOAc/hexanes to afford compound 710 (1.5 g, 39%) as pale yellow liquid. TLC: 60% EtOAc/hexanes (R$_f$: 0.5); $^1$H NMR (DMSO-d$_6$, 500 MHz): δ 7.40-7.34 (m, 4H), 7.33-7.28 (m, 1H), 5.06 (s, 2H), 4.93 (br s, 1H), 4.26-4.24 (m, 1H), 3.42-3.30 (m, 3H), 3.23-3.17 (m, 1H), 1.93-1.82 (m, 1H), 1.80-1.71 (m, 1H); LC-MS: 99.47%; 222.0 (M$^+$+1); (column; Ascentis Express C18, (50×3.0 mm, 2.7 μm); RT 1.86 min. 0.025% Aq.TFA+5% ACN: ACN+5% 0.025% Aq. TFA, 1.2 mL/min).

Synthesis of benzyl (S)-3-(4-(5-(((tert-butoxycarbonyl) amino) methyl) thiazol-2-yl) phenoxy) pyrrolidine-1-carboxylate (711)

To a stirring solution of tert-butyl ((2-(4-hydroxyphenyl) thiazol-5-yl) methyl) carbamate 356 (700 mg, 2.28 mmol) in diethyl ether (30 mL) under argon atmosphere were added benzyl (R)-3-hydroxypyrrolidine-1-carboxylate 710 (758 mg, 3.43 mmol), triphenylphosphine (1.19 g, 4.57 mmol), DIAD (0.906 mL, 4.57 mmol) at 0° C.; warmed to RT and stirred for 48 h. The reaction was monitored by TLC; after completion, the reaction mixture was poured into ice-cold water and extracted with EtOAc (2×75 mL). The combined organic extracts were washed dried over sodium sulfate, filtered and concentrated in vacuo to obtain the crude. The crude was purified through column chromatography using 50% EtOAc/hexanes to afford compound 711 (1.6 g, crude) as an off-white solid. TLC: 50% EtOAc/hexanes (R$_f$: 0.4); LC-MS: 42.16%; 510.1 (M$^+$+1); (column; Ascentis Express C18, (50×3.0 mm, 2.7 μm); RT 2.86 min. 0.025% Aq. TFA+5% ACN: ACN+5% 0.025% Aq. TFA, 1.2 mL/min). LC-MS shows 53.36% TPPO as major impurity at RT 2.25.

Synthesis of benzyl (S)-3-(4-(5-(aminomethyl) thiazol-2-yl) phenoxy) pyrrolidine-1-carboxylate hydrochloride (712)

To a stirring solution of benzyl (S)-3-(4-(5-(((tert-butoxycarbonyl) amino) methyl) thiazol-2-yl) phenoxy) pyrrolidine-1-carboxylate 711 (1.6 g, crude) in CH$_2$Cl$_2$ (30 mL) was added 4 N HCl in 1, 4-dioxane (3 mL) under argon atmosphere at 0° C.; warmed to RT and stirred for 2 h. The reaction was monitored by TLC; after completion of the reaction, the volatiles were removed in vacuo. The crude washed with diethyl ether (10 mL) and EtOAc (2×5 mL) and dried in vacuo to afford compound 712 (510 mg; HCl salt) as an off-white solid. TLC: 50% EtOAc/hexanes (R$_f$: 0.1); 41 NMR (DMSO-d$_6$, 400 MHz): δ 8.50 (br s, 3H), 7.91 (s, 1H), 7.86 (d, J=8.7 Hz, 2H), 7.43-7.25 (m, 5H), 7.09 (d, J=8.9 Hz, 2H), 5.17-4.93 (m, 3H), 4.32 (q, J=5.5 Hz, 2H), 3.74-3.61 (m, 1H), 3.60-3.36 (m, 3H), 2.29-2.05 (m, 2H); LC-MS: 93.90%; 432.0 (M$^+$+Na); (column; Ascentis Express C18, (50×3.0 mm, 2.7 μm); RT 1.94 min. 0.025% Aq. TFA+5% ACN: ACN+5% 0.025% Aq. TFA, 1.2 mL/min).

Synthesis of benzyl (S)-3-(4-(5-((5,5-dioxido-11-oxo-10, 11-dihydrodibenzo [b, f] [1, 4] thiazepine-8-carboxamido) methyl) thiazol-2-yl) phenoxy) pyrrolidine-1-carboxylate (713)

To a stirring solution of 92 (200 mg, 0.66 mmol) in DMF (15 mL) under inert atmosphere were added EDCI.HCl (190 mg, 0.99 mmol), HOBt (135 mg, 0.99 mmol), benzyl (S)-3-(4-(5-(aminomethyl) thiazol-2-yl) phenoxy) pyrrolidine-1-carboxylate hydrochloride 712 (294 mg, 0.66 mmol) and diisopropylethylamine (0.63 mL, 3.30 mmol) at 0° C.; warmed to RT and stirred for 16 h. The reaction was monitored by TLC; after completion, the reaction mixture was poured into ice-cold water (50 mL) and extracted with EtOAc (2×30 mL). The combined organic extracts were dried over sodium sulfate, filtered and concentrated in vacuo to obtain the crude. The crude was purified through silica gel (100-200 mesh) column chromatography using 4% MeOH/CH$_2$Cl$_2$ to afford compound 713 (220 mg, 49%) as an off-white solid. TLC: 4% MeOH/CH$_2$Cl$_2$ (R$_f$: 0.4); LC-MS: 82.34%; 695.2 (M$^+$+1); (column; Ascentis Express C18, (50×3.0 mm, 2.7 μm); RT 2.56 min. 0.025% Aq. TFA+5% ACN: ACN+5% 0.025% Aq. TFA, 1.2 mL/min).

Synthesis of (S)-11-oxo-N-((2-(4-(pyrrolidin-3-yloxy) phenyl) thiazol-5-yl) methyl)-10, 11-dihydrodibenzo [b, f] [1, 4] thiazepine-8-carboxamide 5, 5-dioxide TFA salt (11028)

To a stirring solution of benzyl (S)-3-(4-(5-((5,5-dioxido-11-oxo-10, 11-dihydrodibenzo [b, f] [1, 4] thiazepine-8-carboxamido) methyl) thiazol-2-yl) phenoxy) pyrrolidine-1-carboxylate 713 (100 mg, 0.14 mmol) in CH$_2$Cl$_2$ (5 mL) under inert atmosphere was added trimethylsilyl iodide (0.02 mL, 0.014 mmol) at 0° C.; warmed to RT and stirred for 30 min. The reaction was monitored by TLC; after completion of the reaction, the volatiles were concentrated in vacuo to obtain the crude. The crude was purified through column chromatography using 10% MeOH/CH$_2$Cl$_2$ followed by preparative HPLC purification to afford 11028 (38 mg, 47%) as an off-white solid. TLC: 10% MeOH/CH$_2$Cl$_2$ (R$_f$: 0.2); $^1$H NMR (DMSO-d$_6$, 400 MHz): δ 11.52 (s, 1H), 9.46 (t, J=5.8 Hz, 1H), 9.06 (br s, 1H), 8.90 (br s, 1H), 8.06 (d, J=8.3 Hz, 1H), 8.00-7.96 (m, 2H), 7.93-7.80 (m, 6H), 7.74 (s, 1H), 7.06 (d, J=8.9 Hz, 2H), 5.21 (t, J=4.7 Hz, 1H), 4.67 (d, J=5.6 Hz, 2H), 3.51-3.43 (m, 2H), 3.39-3.26 (m, 2H), 2.27-2.21 (m, 1H), 2.18-2.10 (m, 1H); LC-MS: 98.35%; 561.1 (M⁺+1); (column; Ascentis Express C18, (50×3.0 mm, 2.7 µm); RT 1.83 min. 0.025% Aq. TFA+5% ACN: ACN+5% 0.025% Aq. TFA, 1.2 mL/min). HPLC (purity): 99.08%; (column; X-select CSH-C18 (150×4.6 mm, 3.5 µm); RT 5.73 min. 0.05% TFA (Aq)+5% ACN: ACN+5% 0.05% TFA (Aq): 1.0 mL/min, Diluent: ACN: water: DMSO).

Synthesis of (S)—N-((2-(4-((1-methylpyrrolidin-3-yl) oxy) phenyl)thiazol-5-yl) methyl)-11-oxo-10, 11-dihydrodibenzo [b, f] [1, 4] thiazepine-8-carboxamide 5,5-dioxide (11134)

To a stirring solution of 11028 (100 mg, 0.17 mmol) in MeOH (10 mL) under inert atmosphere were added paraformaldehyde (55 mg, 0.89 mmol) and sodium cyanoborohydride (26 mg, 0.89 mmol) at 0° C.; warmed to RT and stirred for 16 h. The reaction was monitored by TLC; after completion of the reaction, the reaction mixture was diluted with water (50 mL) and extracted with 10% MeOH/CH₂Cl₂ (2×30 mL). The combined organic extracts were dried over sodium sulfate, filtered and concentrated in vacuo to obtain the crude. The crude was purified through silica gel (100-200 mesh) column chromatography using 8% MeOH/CH₂Cl₂ to afford 11134 (35 mg, 34%) as an off-white solid. TLC: 10% MeOH/CH₂Cl₂ (R$_f$: 0.4); 41 NMR (DMSO-d₆, 400 MHz): δ 11.53 (s, 1H), 9.48 (t, J=5.8 Hz, 1H), 8.05 (d, J=8.2 Hz, 1H), 8.01-7.95 (m, 2H), 7.93-7.80 (m, 6H), 7.73 (s, 1H), 7.01 (d, J=8.9 Hz, 2H), 5.11-5.05 (m, 1H), 4.66 (d, J=5.5 Hz, 2H), 3.17-3.10 (m, 2H), 2.96-2.86 (m, 1H), 2.60 (s, 3H), 2.57-2.54 (m, 1H), 2.44-2.37 (m, 1H), 2.02-1.93 (m, 1H); LC-MS: 98.35%; 593.1 (M⁺+1); (Column; X-select CSH C-18 (150×4.6 mm, 3.5 µm); RT 1.89 min. 0.025% Aq. TFA+5% ACN: ACN+5% 0.025% Aq. TFA, 1.0 mL/min); HPLC (purity): 97.97%; (column; X-select CSH C-18 (150× 4.6 mm, 3.5 µm); RT 6.45 min. 0.05% TFA (Aq)+5% ACN: ACN+5% 0.5% TFA (Aq); 1.0 mL/min, Diluent: ACN: water).

Synthesis of 11026

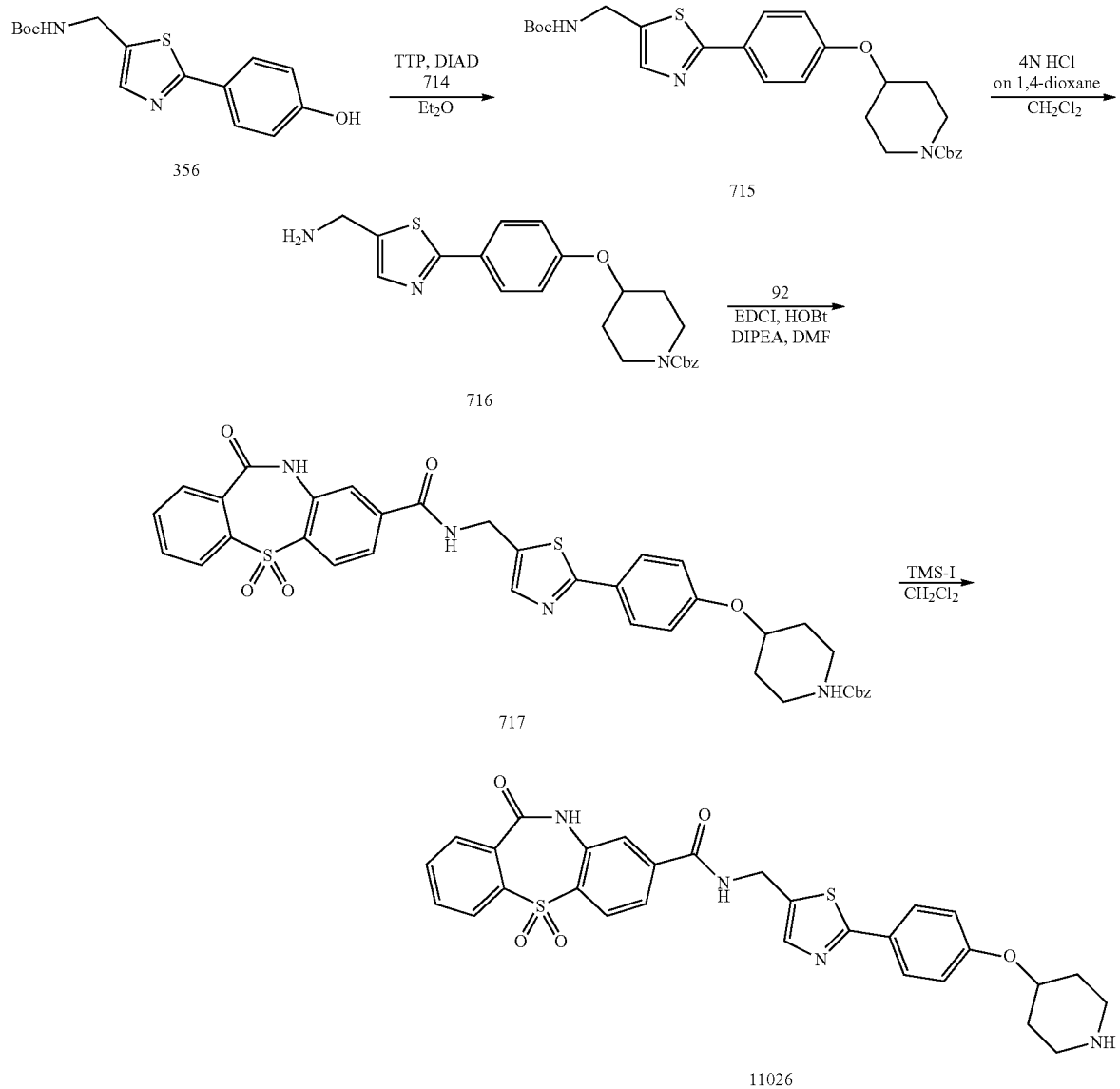

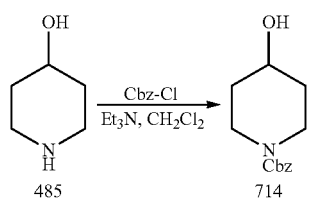

Synthesis of benzyl 4-hydroxypiperidine-1-carboxylate (714)

To a stirring solution of piperidin-4-ol 485 (1 g, 9.90 mmol) in $CH_2Cl_2$ (10 mL) under argon atmosphere were added triethylamine (2.08 mL, 14.85 mmol), Cbz-Cl (50% in toluene) (3.4 mL, 11.88 mmol) at 0° C.; warmed to RT and stirred for 16 h. The reaction was monitored by TLC; after completion of the reaction, the reaction mixture was diluted with water (40 mL) and extracted with $CH_2Cl_2$ (2×50 mL). The combined organic extracts were washed with water (50 mL) and brine (50 mL); dried over sodium sulfate, filtered and concentrated in vacuo to obtain the crude. The crude was purified through silica gel column chromatography using 50% EtOAc/hexanes to afford compound 714 (1.3 g, 56%) as colorless liquid. TLC: 70% EtOAc/hexanes ($R_f$: 0.3); $^1H$ NMR (500 MHz, DMSO-$d_6$): δ 7.41-7.28 (m, 5H), 5.06 (s, 2H), 4.71 (d, J=4.1 Hz, 1H), 3.76-3.61 (m, 3H), 3.08-3.04 (m, 2H), 1.75-1.67 (m, 2H), 1.34-1.23 (m, 2H); LC-MS: 98.38%; 236.0 ($M^+$+1); (column; Ascentis Express C-18, (50×3.0 mm, 2.7 μm); RT 1.96 min. 0.025% Aq. TFA+5% ACN: ACN+5% 0.025% Aq. TFA, 1.2 mL/min);

Synthesis of benzyl 4-(4-(5-(((tert-butoxycarbonyl) amino) methyl) thiazol-2-yl) phenoxy) piperidine-1-carboxylate (715)

To a stirring solution of tert-butyl ((2-(4-hydroxyphenyl) thiazol-5-yl) methyl) carbamate (356) (1 g, 3.26 mmol) in diethyl ether (30 mL) under argon atmosphere were added triphenylphosphine (2.56 g, 9.80 mmol), DIAD (1.98 g, 9.80 mmol) and benzyl 4-hydroxypiperidine-1-carboxylate 714 (921 mg, 3.92 mmol) at 0° C.; warmed to RT and stirred for 48 h. The reaction was monitored by LCMS; after completion of the reaction, the volatiles were removed in vacuo to obtain the crude. The crude was purified through silica gel column chromatography using 20-30% EtOAc/hexanes to afford compound 715 (2.2 g, impure) as pale yellow liquid. This material was taken to next step without further purification. TLC: 50% EtOAc/hexanes ($R_f$: 0.5); LC-MS: 19.62%; 524.1 ($M^+$+1); (column; Ascentis Express C-18 (50×3.0 mm, 2.7 μm); RT 3.00 min. 0.025% Aq. TFA+5% ACN: ACN+5% 0.025% Aq TFA, 1.2 mL/min).

Synthesis of benzyl 4-(4-(5-(aminomethyl) thiazol-2-yl) phenoxy) piperidine-1-carboxylate (716)

To a stirring solution of compound 715 (2.2 g, crude. 4.20 mmol) in $CH_2Cl_2$ (10 mL) was added 4 N HCl in 1, 4-dioxane (5 mL) under argon atmosphere at 0° C.; warmed to RT and stirred for 2 h. The reaction was monitored by TLC; after completion of the reaction, the volatiles were removed in vacuo. The crude washed with diethyl ether (5 mL) and EtOAc (5 mL) and dried in vacuo to afford compound 716 (420 mg, HCl salt) as white solid. TLC: 50% EtOAc/hexanes ($R_f$: 0.1); $^1H$ NMR (500 MHz, DMSO-$d_6$): δ 8.44 (br s, 3H), 7.88 (s, 1H), 7.83 (d, J=8.7 Hz, 2H), 7.39-7.29 (m, 5H), 7.09 (d, J=8.7 Hz, 2H), 5.08 (s, 2H), 4.72-4.64 (m, 1H), 4.33-4.27 (m, 2H), 3.77-3.69 (m, 2H), 3.34-3.24 (m, 2H), 1.99-1.92 (m, 2H), 1.63-1.53 (m, 2H); LC-MS: 75.11%; 424 ($M^+$+1); (column; Ascentis Express C-18 (50×3.0 mm, 2.7 μm); RT 2.04 min. 0.025% Aq. TFA+5% ACN: ACN+5% 0.025% Aq TFA, 1.2 mL/min).

Synthesis of benzyl 4-(4-(5-((5, 5-dioxido-11-oxo-10, 11-dihydrodibenzo [b, f] [1, 4] thiazepine-8-carboxamido) methyl) thiazol-2-yl) phenoxy)piperidine-1-carboxylate (717)

To a stirring solution of 92 (200 mg, 0.66 mmol) in DMF (6 mL) under inert atmosphere were added EDCI.HCl (189 mg, 0.99 mmol), HOBt (135 mg, 0.99 mmol), diisopropyl ethyl amine (0.60 mL, 3.30 mmol) and compound 716 (333 mg, 0.72 mmol) at 0° C.; warmed to RT and stirred for 16 h. The reaction was monitored by TLC; after completion of the reaction, the reaction mixture was diluted with water (20 mL) and extracted with EtOAc (2×30 mL). The combined organic extracts were washed with water (30 mL) and brine (30 mL); dried over sodium sulfate, filtered and concentrated in vacuo to obtain the crude. The crude was purified through silica gel column chromatography using 2% MeOH/$CH_2Cl_2$ to afford compound 717 (160 mg, 34%) as white solid. TLC: 10% MeOH/$CH_2Cl_2$ ($R_f$: 0.6); $^1H$ NMR (500 MHz, DMSO-$d_6$): δ 11.51 (br s, 1H), 9.44 (t, J=5.5 Hz, 1H), 8.06 (d, J=8.1 Hz, 1H), 8.01-7.95 (m, 2H), 7.93-7.78 (m, 6H), 7.72 (s, 1H), 7.40-7.30 (m, 5H), 7.06 (d, J=8.7 Hz, 2H), 5.09 (s, 2H), 4.69-4.64 (m, 3H), 3.75-3.69 (m, 2H), 1.98-1.89 (m, 2H), 1.63-1.52 (m, 2H), 1.31-1.15 (m, 2H); LC-MS: 96.50%; 709.2 ($M^+$+1) (column; Ascentis Express C-18 (50×3.0 mm, 2.7 μm); RT 2.61 min. 0.025% Aq. TFA+5% ACN: ACN+5% 0.025% Aq TFA, 1.2 mL/min).

Synthesis of 11-oxo-N-((2-(4-(piperidin-4-yloxy) phenyl) thiazol-5-yl) methyl)-10, 11-dihydrodibenzo [b, f] [1, 4] thiazepine-8-carboxamide 5,5-dioxide (11026)

To a stirring solution of compound 717 (140 mg, 0.19 mmol) in $CH_2Cl_2$ (5 mL) was added trimethylsilyl iodide (0.02 mL, 0.19 mmol) under inert atmosphere at 0° C.; and stirred for 30 min. The reaction was monitored by TLC; after completion of the reaction, the volatiles were removed in vacuo. The residue was diluted with water and basified to pH~8 using saturated $NaHCO_3$ solution. The obtained solid was filtered and dried in vacuo to obtain the crude. The crude was purified through silica gel column chromatography using 10% MeOH/$CH_2Cl_2$ and 0.05 mL aqueous ammonia to afford compound 11026 (25 mg, 22%) as white solid. TLC: 10% MeOH/$CH_2Cl_2$ ($R_f$: 0.1); $^1H$ NMR (400 MHz, DMSO-$d_6$): δ 9.45 (t, J=5.8 Hz, 1H), 8.05 (d, J=8.2 Hz, 1H), 7.98 (td, J=7.6, 1.1 Hz, 2H), 7.92-7.84 (m, 3H), 7.84-7.76 (m, 3H), 7.72 (s, 1H), 7.03 (d, J=8.8 Hz, 2H), 4.66 (d, J=5.6

Hz, 2H), 4.53-4.47 (m, 1H), 3.02-2.96 (m, 2H), 2.69-2.60 (m, 2H), 2.00-1.90 (m, 2H), 1.56-1.45 (m, 2H); LC-MS: 97.84%; 589.1 (M++1); (column; Ascentis Express C-18, (50×3.0 mm, 2.7 μm); RT 1.85 min. 0.025% Aq. TFA+5% ACN: ACN+5% 0.025% Aq. TFA, 1.2 mL/min); HPLC (purity): 94.94%; (column; X select CSH C-18 (150×4.6 mm, 3.5 μm); RT 5.74 min. 0.05% TFA+5% ACN: ACN+ 5% 0.05% TFA; 1.0 mL/min, Diluent: ACN:water: DMSO.
Synthesis of 1996
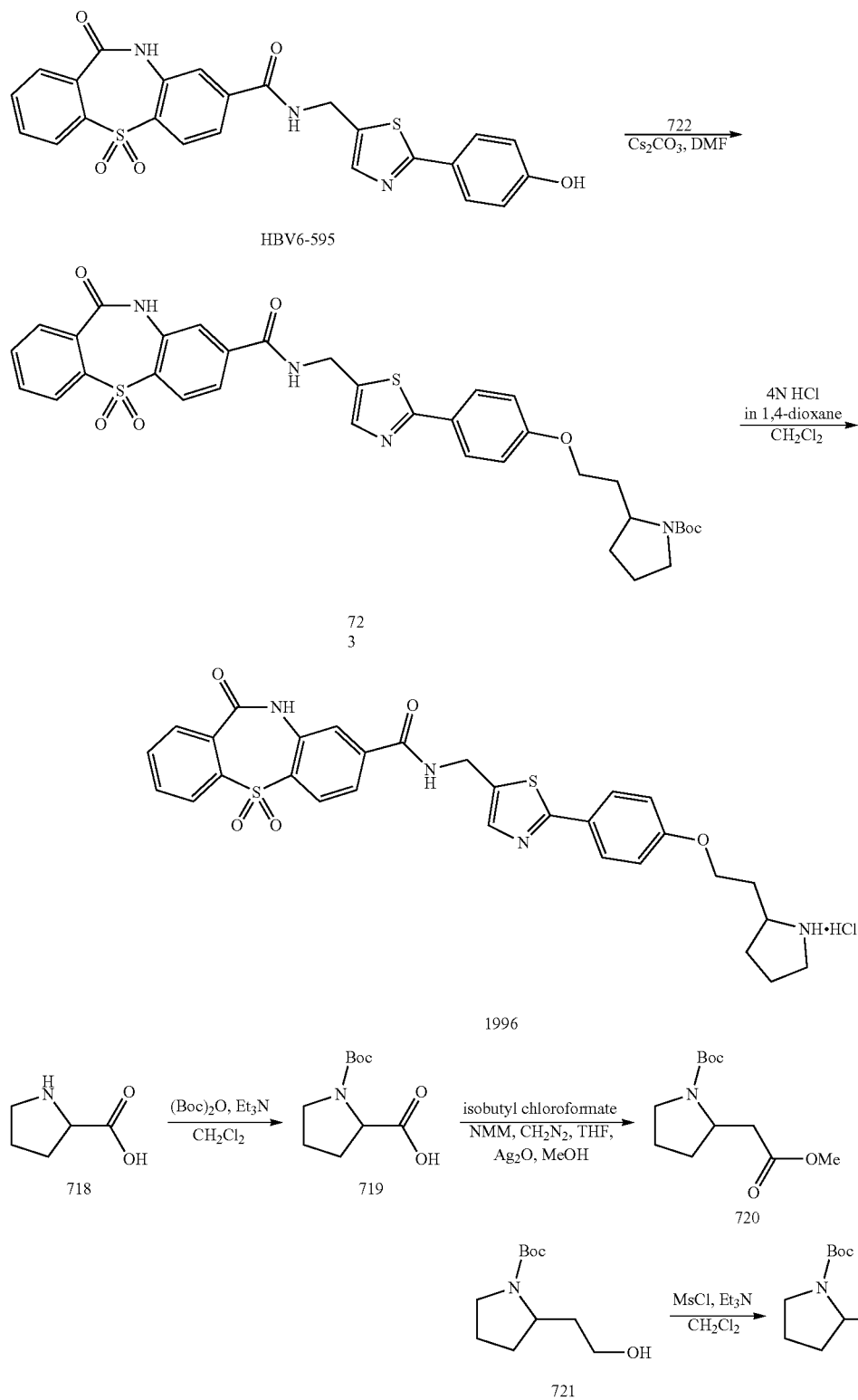

Synthesis of (tert-butoxycarbonyl) proline (719)

To a stirring solution of proline 718 (10 g, 86.96 mmol) in CH$_2$Cl$_2$ (100 mL) were added triethyl amine (15.75 mL, 113.04 mmol) and di-t-butyl dicarbonate (29.93 mL, 130.43 mmol) in CH$_2$Cl$_2$ (50 mL) at 0° C. under inert atmosphere. The reaction mixture was gradually warmed to RT and stirred for 4 h. The reaction was monitored by TLC; after completion of the reaction, the reaction mixture was quenched with saturated citric acid solution (100 mL). The organic layer was separated, washed with water (100 mL) and concentrated in vacuo to afford compound 719 (13 g) as colorless liquid. This crude material was taken to next step without further purification. TLC: 10% MeOH/CH$_2$Cl$_2$ (R$_f$: 0.4); $^1$H NMR (500 MHz, DMSO-d$_6$): δ 12.47 (br s, 1H), 4.08-4.00 (m, 1H), 3.36-3.21 (m, 2H), 2.22-2.07 (m, 1H), 1.87-1.73 (m, 3H), 1.45 (s, 9H).

Synthesis of tert-butyl 2-(2-methoxy-2-oxoethyl) pyrrolidine-1-carboxylate (720)

To a stirring solution of compound 719 (5 g, crude) in THF (100 mL) were added 4-Methylmorpholine (3.06 mL, 27.91 mmol) followed by isobutyl chloroformate (4.56 mL, 34.88 mmol) at −30° C. under inert atmosphere. The reaction mixture was allowed to stir at −30° C. for 1 h. Then freshly prepared CH$_2$N$_2$ solution (~75 mL) was added at −30° C. The reaction mixture was gradually warmed to RT and stirred for 16 h. The reaction was monitored by TLC; after completion of the reaction, the excess of CH$_2$N$_2$ was quenched with acetic acid (2 mL) and the volatiles were concentrated in vacuo. The residue was diluted with water (100 mL) and extracted with EtOAc (2×100 mL). The combined organic extracts were dried over sodium sulfate, filtered and concentrated in vacuo to obtain the crude. The crude was dissolved in methanol (75 mL) and Ag$_2$O (6.45 g, 27.91 mmol) was added in portion wise at 0° C. The reaction mixture was stirred at RT for 2 h. Then CH$_2$Cl$_2$ (30 mL) was added and filtered through a pad of celite. The filtrate was concentrated in vacuo and purified through flash column chromatography using 5% EtOAc/hexanes to afford compound 720 (2 g, 37%) as colorless oily liquid. TLC: 10% EtOAc/hexanes (R$_f$: 0.2); $^1$H NMR (400 MHz, CDCl$_3$): δ 4.25-4.03 (m, 1H), 3.67 (s, 3H), 3.43-3.30 (m, 2H), 2.98-2.75 (m, 1H), 2.31 (dd, J=15.1, 9.7 Hz, 1H), 2.13-1.98 (m, 1H), 1.89-1.71 (m, 3H), 1.46 (s, 9H).

Synthesis of tert-butyl 2-(2-hydroxyethyl) pyrrolidine-1-carboxylate (721)

To a stirring solution of compound 720 (200 mg, 0.82 mmol) in THF (50 mL) was added lithium aluminium hydride (38 mg, 0.99 mmol) at 0° C. under inert atmosphere. The reaction mixture was gradually warmed to RT and stirred for 3 h. The reaction was monitored by TLC; after completion of the reaction, the reaction mixture was cooled to 0° C., quenched with 10% aqueous sodium hydroxide (2 mL) and stirred for 20 min, filtered through a pad of celite. The celite pad was eluted with EtOAc (30 mL). The filtrate was dried over sodium sulfate, filtered and concentrated in vacuo to afford compound 721 (180 mg, 97%) as colorless oily liquid. TLC: 20% EtOAc/hexanes (R$_f$: 0.1); $^1$H NMR (500 MHz, DMSO-d$_6$): δ 4.36 (t, J=4.9 Hz, 1H), 3.75-3.71 (m, 1H), 3.43-3.39 (m, 2H), 3.26-3.15 (m, 2H), 1.91-1.63 (m, 6H), 1.39 (s, 9H); LC-MS (Agilent 6310 Ion trap): 89.07%; 216.2 (M$^+$+1); (column; Kinetex EVO C-18 (50× 3.0 mm, 2.6 um); RT 2.95 min. 2.5 mM Aq. NH$_4$OAc: ACN, 0.8 mL/min).

Synthesis of tert-butyl 2-(2-((methylsulfonyl) oxy) ethyl) pyrrolidine-1-carboxylate (722)

To a stirring solution of compound 721 (150 mg, 0.7 mmol) in CH$_2$Cl$_2$ (10 mL) were added triethylamine (0.29 mL, 2.09 mmol) followed by methanesulfonyl chloride (0.11 mL, 1.39 mmol) drop wise over a period of 10 min. at 0° C. under inert atmosphere and allowed to stir at the same temperature for 3 h. The reaction was monitored by TLC; after completion of the reaction, the reaction mixture was diluted with ice cold water (20 mL) and extracted with CH$_2$Cl$_2$ (2×30 mL). The combined organic extracts were dried over sodium sulfate, filtered and concentrated in vacuo to afford compound 722 (120 mg) colorless oily liquid. This crude material was taken to next step without further purification. TLC: 40% EtOAc/hexanes (R$_f$: 0.3).

Synthesis of tert-butyl 2-(2-(4-(5-((5, 5-dioxido-11-oxo-10, 11-dihydrodibenzo [b, f] [1, 4] thiazepine-8-carboxamido) methyl) thiazol-2-yl) phenoxy) ethyl) pyrrolidine-1-carboxylate (723)

To a stirring solution of N-((2-(4-hydroxyphenyl) thiazol-5-yl) methyl)-11-oxo-10, 11-dihydrodibenzo [b, f] [1, 4] thiazepine-8-carboxamide 5, 5-dioxide 595 (500 mg, 1.02 mmol) in DMF (5 mL) were added compound 722 (900 mg, crude) and cesium carbonate (1 g, 3.05 mmol) at 0° C. under inert atmosphere. The reaction mixture was heated to 70° C. and stirred for 18 h. The reaction was monitored by TLC; after completion of the reaction, the reaction mixture was diluted with water (50 mL) and extracted with EtOAc (2×60 mL). The combined organic extracts were dried over sodium sulfate, filtered and concentrated in vacuo to obtain the crude. The crude was purified through flash column chromatography using 2-4% MeOH/CH$_2$Cl$_2$ to afford compound 723 (90 mg, 13%) as an off white solid. TLC: 5% MeOH/CH$_2$Cl$_2$ (R$_f$: 0.4); $^1$H NMR (500 MHz, DMSO-d$_6$): δ 11.51 (s, 1H), 9.44 (t, J=5.5 Hz, 1H), 8.06 (d, J=8.1 Hz, 1H), 8.01-7.96 (m, 2H), 7.90 (t, J=7.0 Hz, 1H), 7.88-7.78 (m, 5H), 7.72 (s, 1H), 6.99 (d, J=8.7 Hz, 2H), 4.66 (d, J=5.8 Hz, 2H), 4.09-4.00 (m, 2H), 3.91-3.84 (m, 1H), 3.26-3.22 (m, 2H), 2.17-2.05 (m, 2H), 1.95-1.80 (m, 2H), 1.80-1.71 (m, 2H), 1.35 (s, 9H); LC-MS: 93.56%; 589.2 (M$^+$-Boc+1); (column; Kinetex EVO C-18 (50×3.0 mm, 2.6 um); RT 3.47 min. 2.5 mM NH$_4$OOCH in water+5% ACN: ACN+5% 2.5 mM NH$_4$OOCH in water, 0.8 mL/min).

Synthesis of 11-oxo-N-((2-(4-(2-(pyrrolidin-2-yl) ethoxy) phenyl) thiazol-5-yl) methyl)-10, 11-dihydrodibenzo [b, f] [1, 4] thiazepine-8-carboxamide 5, 5-dioxide hydrochloride (1996)

To a stirring solution of compound 723 (80 mg, 0.12 mmol) in CH$_2$Cl$_2$ (5 mL) was added 4 N HCl in 1, 4-dioxane (0.2 mL) at 0° C. under inert atmosphere. The reaction mixture was gradually warmed to RT and stirred for 2 h. The reaction was monitored by TLC; after completion of the reaction, the volatiles were removed in vacuo to obtain the crude. The crude was washed with CH$_2$Cl$_2$ (15 mL), n-hexane (15 mL) and dried in vacuo to afford 1996 (50 mg, 73%, HCl salt) as an off white solid. TLC: 5% MeOH/CH$_2$Cl$_2$ (R$_f$: 0.1); $^1$H NMR (400 MHz, DMSO-d$_6$): δ 11.53 (s, 1H), 9.48 (t, J=5.8 Hz, 1H), 9.04 (br s, 1H), 8.59 (br s, 1H), 8.06 (d, J=8.3 Hz, 1H), 8.01-7.95 (m, 2H), 7.90 (td, J=7.5, 1.6 Hz, 1H), 7.87-7.80 (m, 5H), 7.73 (s, 1H), 7.04 (d, J=8.9 Hz, 2H), 4.66 (d, J=5.6 Hz, 2H), 4.19-4.08 (m, 2H), 3.64-3.56 (m, 1H), 3.26-3.08 (m, 2H), 2.22-2.06 (m, 3H), 1.98-1.82 (m, 2H), 1.67-1.57 (m, 1H); LC-MS: 99.79%; 589.1 (M$^+$+1); (column; Ascentis Express C18, (50×3.0 mm, 2.7 μm); RT 1.84 min. 0.025% Aq. TFA+5% ACN: ACN+5% 0.025% Aq. TFA, 1.2 mL/min); HPLC (purity): 96.60%; (column; X-Select CSH-C-18 (150×4.6 mm, 3.5 μm); RT 5.68 min. 0.05% TFA+5% ACN: ACN+5% 0.05% TFA; 1.0 mL/min, Diluent: ACN:H$_2$O:DMSO).
Synthesis of 11107 and 11107-A
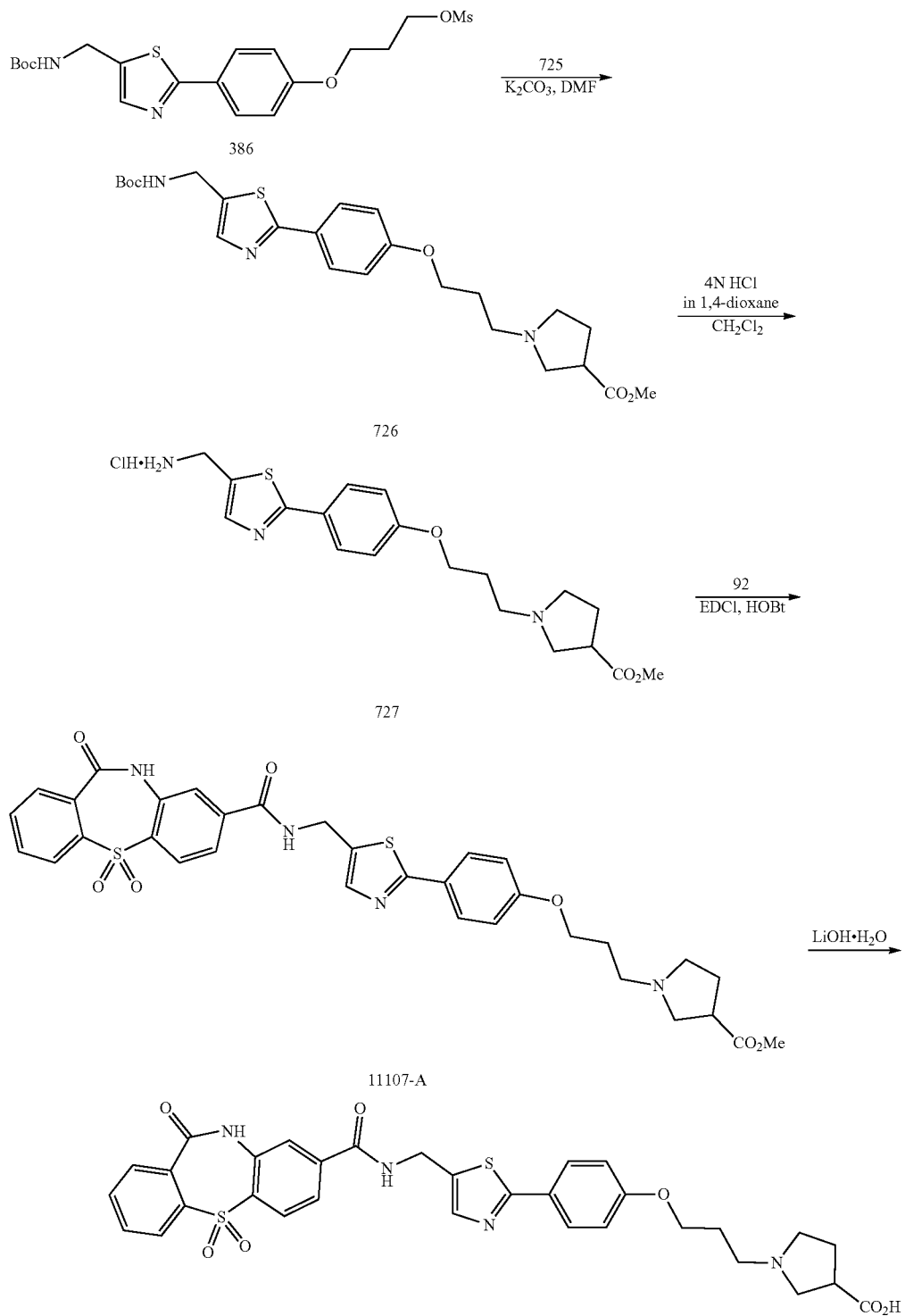

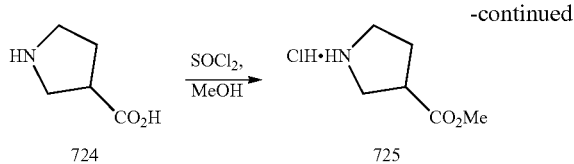

Synthesis of methyl pyrrolidine-3-carboxylate hydrochloride (725)

To a stirring solution of pyrrolidine-3-carboxylic acid 724 (4 g, 34.78 mmol) in methanol (60 mL) under inert atmosphere was added thionyl chloride (3.8 mL, 52.17 mmol) drop wise at 0° C. The reaction mixture was heated to reflux temperature and stirred for 4 h. The reaction was monitored by TLC; after completion of the reaction, the volatiles were removed in vacuo to afford compound 725 (4 g, HCl salt) as colorless syrup. This crude material was taken to next step without further purification. TLC: 10% MeOH/CH$_2$Cl$_2$ (R$_f$: 0.3); $^1$H NMR (400 MHz, DMSO-d$_6$): δ=9.72-9.52 (m, 2H), 3.65 (s, 3H), 3.39-3.33 (m, 1H), 3.31-3.23 (m, 2H), 3.20-3.16 (m, 1H), 3.14-3.11 (m, 1H), 2.24-2.11 (m, 1H), 2.08-1.95 (m, 1H).

Synthesis of methyl 1-(3-(4-(5-(((tert-butoxycarbonyl) amino) methyl) thiazol-2-yl) phenoxy) propyl) pyrrolidine-3-carboxylate (726)

To a stirring solution of 3-(4-(5-(((tert-butoxycarbonyl) amino) methyl) thiazol-2-yl) phenoxy) propyl methanesulfonate 386 (3 g, crude) in DMF (25 mL) under inert atmosphere were added compound 725 (1.67 g, crude), potassium carbonate (2.8 g, 20.31 mmol) at RT; heated to 80° C. and stirred for 16 h. The reaction was monitored by TLC; after completion of the reaction, the reaction mixture was diluted with water (100 mL) and extracted with EtOAC (2×100 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 726 (1.1 g, 34%) as colorless viscous syrup. TLC: 5% MeOH/CH$_2$Cl$_2$ (R$_f$ 0.5); $^1$H NMR (500 MHz, DMSO-d$_6$): δ 7.81 (d, J=8.7 Hz, 2H), 7.60 (s, 1H), 7.53 (br s, 1H), 7.02 (d, J=8.7 Hz, 2H), 4.31 (d, J=5.8 Hz, 2H), 4.06 (t, J=6.4 Hz, 2H), 3.61 (s, 3H), 3.05-3.02 (m, 1H), 2.82-2.69 (m, 2H), 2.57-2.54 (m, 3H), 2.07-1.84 (m, 5H), 1.40 (s, 9H); LC-MS: 78.25%; 476.2 (M$^+$+1); (column; Kinetex EVO C-18 (50× 3.0 mm, 2.6 um); RT 2.69 min. 2.5 mM NH$_4$OOCH in water+5% ACN: ACN+5% 2.5 mM NH$_4$OOCH in water, 0.8 mL/min).

Synthesis of methyl 1-(3-(4-(5-(aminomethyl) thiazol-2-yl) phenoxy) propyl) pyrrolidine-3-carboxylate hydrochloride (727)

To a stirring solution of compound 726 (1.1 g, 2.31 mmol) in CH$_2$Cl$_2$ (2.5 mL) under inert atmosphere was added 4 N HCl in 1, 4-dioxane (8 mL) drop wise at 0° C.; warmed to RT and stirred for 3 h. The reaction was monitored by TLC; after completion of the reaction, the volatiles were removed in vacuo to obtain the crude. The crude was washed with EtOAc (2×5 mL), diethylether (2×5 mL) and dried in vacuo to afford compound 727 (700 mg, HCl salt) as an off white solid. TLC: 10% MeOH/CH$_2$Cl$_2$ (R$_f$ 0.1); LC-MS: 67.23%; 376.3 (M$^+$+1); (column; Cortecs C18 (50×3.0 mm, 2.7 μm); RT 3.04 min. 2.5 mM Aq. NH$_4$HCO$_3$: ACN, 0.8 mL/min).

Synthesis of methyl 1-(3-(4-(5-((5, 5-dioxido-11-oxo-10, 11-dihydrodibenzo [b, f] [1, 4] thiazepine-8-carboxamido) methyl) thiazol-2-yl) phenoxy) propyl) pyrrolidine-3-carboxylate (11107-A)

To a stirring solution of 11-oxo-10, 11-dihydrodibenzo [b, f] [1, 4] thiazepine-8-carboxylic acid 5, 5-dioxide 92 (200 mg, 0.66 mmol) in DMF (20 mL) were added compound 727 (325 mg, 0.79 mmol), EDCI.HCl (190 mg, 0.99 mmol), HOBt (136 mg, 0.99 mmol) followed by diisopropylethylamine (0.34 mL, 1.98 mmol) at 0° C. under inert atmosphere. The reaction mixture was gradually warmed to RT and stirred for 16 h. The reaction was monitored by TLC; after completion of the reaction, the reaction mixture was diluted with water (30 mL) and extracted with EtOAc (2×50 mL). The combined organic extracts were dried over sodium sulfate, filtered and concentrated in vacuo to obtain the crude. The crude was purified through column chromatography using 5% MeOH/CH$_2$Cl$_2$ to afford 11107-A (180 mg, 41%) as an off white solid. TLC: 10% MeOH/CH$_2$Cl$_2$ (R$_f$: 0.7); $^1$H NMR (400 MHz, DMSO-d$_6$): δ 11.52 (s, 1H), 9.45 (t, J=5.7 Hz, 1H), 8.06 (d, J=8.3 Hz, 1H), 8.00-7.95 (m, 2H), 7.93-7.84 (m, 3H), 7.83-7.77 (m, 3H), 7.72 (s, 1H), 7.01 (d, J=8.9 Hz, 2H), 4.66 (d, J=5.5 Hz, 2H), 4.06 (t, J=6.3 Hz, 2H), 3.61 (s, 3H), 3.11-3.01 (m, 1H), 2.92-2.71 (m, 2H), 2.63-2.55 (m, 2H), 2.45-2.39 (m, 2H), 2.17-1.84 (m, 4H); LC-MS: 97.88%; 661.1 (M$^+$+1); (column; Ascentis Express C18, (50×3.0 mm, 2.7 μm); RT 1.89 min. 0.025% Aq. TFA+5% ACN: ACN+5% 0.025% Aq. TFA, 1.2 mL/min).

Synthesis of 1-(3-(4-(5-((5, 5-dioxido-11-oxo-10, 11-dihydrodibenzo [b, f] [1, 4] thiazepine-8-carboxamido) methyl) thiazol-2-yl) phenoxy) propyl) pyrrolidine-3-carboxylic acid (11107)

To a stirring solution of methyl 1-(3-(4-(5-((5, 5-dioxido-11-oxo-10, 11-dihydrodibenzo [b, f] [1, 4] thiazepine-8-carboxamido) methyl) thiazol-2-yl) phenoxy) propyl) pyrrolidine-3-carboxylate 11107-A (90 mg, 0.13 mmol) in a mixture of THF:MeOH:H$_2$O (2:1:1, 8 mL) was added lithium hydroxide monohydrate (17 mg, 0.41 mmol) at 0° C. The reaction mixture was gradually warmed to RT and stirred for 2 h. The reaction was monitored by TLC; after completion of the reaction, the volatiles were removed in vacuo. The residue was acidified with 2 N HCl to pH~5 and extracted with EtOAc (2×30 mL). The combined organic extracts were dried over sodium sulfate, filtered and concentrated in vacuo to obtain the crude. The crude was triturated with diethylether (2×5 mL) and dried in vacuo to afford 11107 (30 mg, 34%) as an off white solid. TLC: 10% MeOH/CH$_2$Cl$_2$ (R$_f$: 0.1); $^1$H NMR (400 MHz, DMSO-d$_6$): δ 11.53 (br s, 1H), 9.50 (t, J=5.8 Hz, 1H), 8.05 (d, J=8.3 Hz, 1H), 8.01-7.95 (m, 2H), 7.92-7.78 (m, 6H), 7.72 (s, 1H), 7.01 (d, J=8.9 Hz, 2H), 4.66 (d, J=5.6 Hz, 2H), 4.07 (t, J=6.3 Hz, 2H), 3.02-2.96 (m, 2H), 2.85-2.78 (m, 1H), 2.77-2.63

(m, 4H), 2.03-1.92 (m, 4H); LC-MS: 96.27%; 647.1 (M⁺+ 1); (column; Ascentis Express C18, (50×3.0 mm, 2.7 μm); RT 1.84 min. 0.025% Aq. TFA+5% ACN: ACN+5% 0.025% Aq. TFA, 1.2 mL/min); HPLC (purity): 94.30%; (column; X-Select CSH-C-18 (150×4.6 mm, 3.5 μm); RT 5.63 min. 0.05% TFA+5% ACN: ACN+5% 0.05% TFA; 1.0 mL/min, Diluent: ACN:H₂O:DMSO).

Synthesis of 1988

Synthesis of tert-butyl ((2-(4-(3-(2, 2, 2-trifluoroacetamido) propoxy) phenyl) thiazol-5-yl) methyl) carbamate (728)

To a stirring solution of tert-butyl ((2-(4-(3-amino-propoxy) phenyl) thiazol-5-yl) methyl) carbamate 404 (250 mg, 0.68 mmol) in CH₂Cl₂ (10 mL) under inert atmosphere was added triethylamine (0.29 mL, 2.06 mmol), followed by addition of trifluoroacetic anhydride (0.11 mL, 0.82 mmol) for 5 min at 0° C.; warmed to RT and stirred for 3 h. The

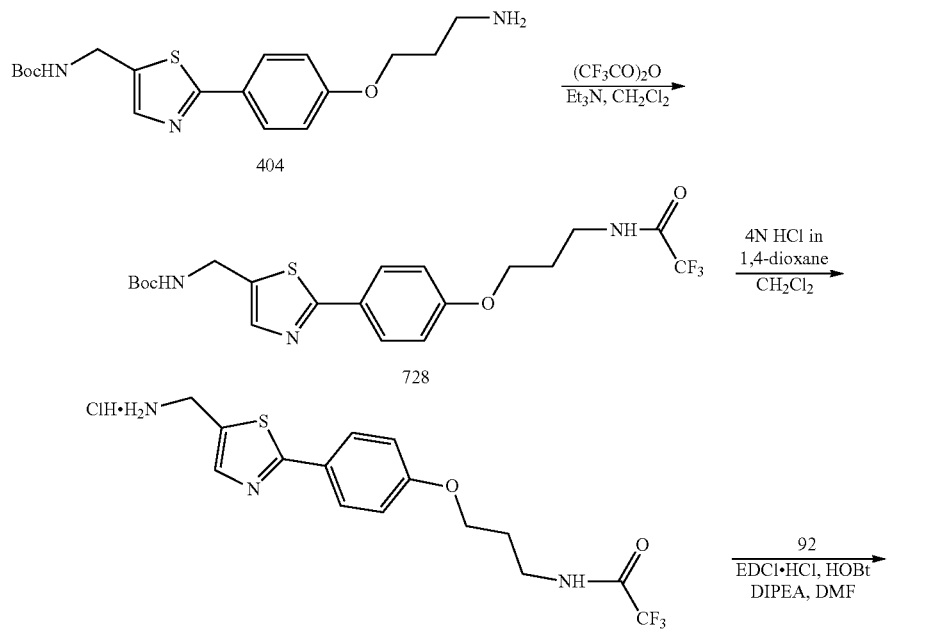

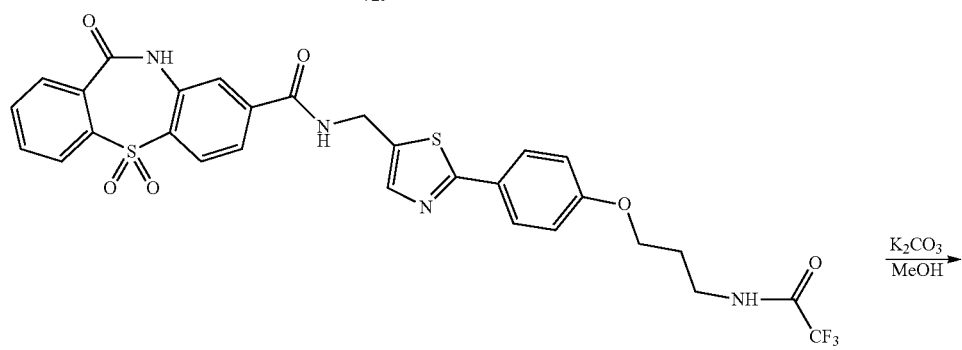

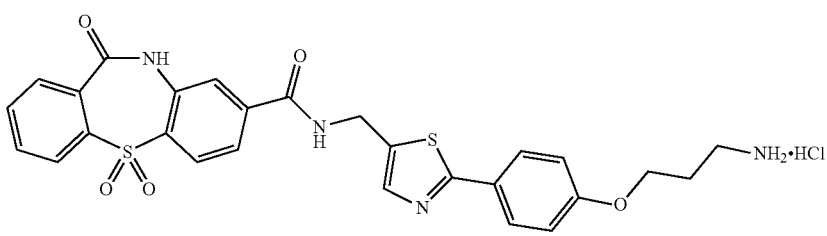

reaction was monitored by TLC; after completion of the reaction, the reaction mixture was diluted with 10% H$_2$O/MeOH (10 mL) and the volatiles were removed in vacuo to obtain the crude. The crude was triturated with diethylether (2×10 mL) and dried in vacuo to afford compound 728 (230 mg, 73%) as an off-white solid. TLC: 10% MeOH/CH$_2$Cl$_2$ (R$_f$: 0.8); $^1$H NMR (DMSO-d$_6$, 500 MHz): δ 9.50 (t, J=5.2 Hz, 1H), 7.82 (d, J=8.7 Hz, 2H), 7.61 (s, 1H), 7.53 (t, J=5.5 Hz, 1H), 7.02 (d, J=8.7 Hz, 2H), 4.31 (d, J=5.8 Hz, 2H), 4.06 (t, J=6.1 Hz, 2H), 3.37 (q, J=6.4 Hz, 2H), 1.96 (p, J=6.5 Hz, 2H), 1.40 (s, 9H); LC-MS: 97.62%; 460.1 (M$^+$+1); (column; Ascentis Express C18, (50×3.0 mm, 2.7 μm); RT 2.64 min. 0.025% Aq. TFA+5% ACN: ACN+5% 0.025% Aq. TFA, 1.2 mL/min).

Synthesis of N-(3-(4-(5-(aminomethyl) thiazol-2-yl) phenoxy) propyl)-2, 2, 2-trifluoroacetamide hydrochloride (729)

To a stirring solution of compound 728 (230 mg, 0.50 mmol) in CH$_2$Cl$_2$ (10 mL) under inert atmosphere was added 4 N HCl in 1, 4-dioxane (1 mL) at 0° C.; warmed to RT and stirred for 3 h. The reaction was monitored by TLC; after completion of the reaction, the volatiles were removed in vacuo to obtain the crude, which was triturated with EtOAc (2×10 mL), and dried in vacuo to afford compound 729 (180 mg, HCl salt) as an off-white solid. TLC: 10% MeOH/CH$_2$Cl$_2$ (R$_f$: 0.2); $^1$H-NMR (DMSO-d$_6$, 500 MHz): δ 9.53 (t, J=5.8 Hz, 1H), 8.54 (br s, 3H), 7.90 (s, 1H), 7.86 (d, J=8.7 Hz, 2H), 7.05 (d, J=8.7 Hz, 2H), 4.31 (q, J=5.6 Hz, 2H), 4.07 (t, J=6.1 Hz, 2H), 3.42-3.33 (m, 2H), 1.97 (p, J=6.5 Hz, 2H);

Synthesis of 11-oxo-N-((2-(4-(3-(2, 2, 2-trifluoroacetamido) propoxy) phenyl) thiazol-5-yl) methyl)-10, 11-dihydrodibenzo [b, f] [1, 4] thiazepine-8-carboxamide 5, 5-dioxide (730)

To a stirring solution of 92 (150 mg, 0.49 mmol) in DMF (10 mL) under inert atmosphere were added EDCI.HCl (142 mg, 0.74 mmol), HOBt (100 mg, 0.74 mmol), diisopropylethylamine (0.72 mL, 2.47 mmol) and compound 729 (195 mg, 0.54 mmol) at 0° C.; warmed to RT and stirred for 16 h. The reaction was monitored by TLC; after completion of the reaction, the reaction mixture was diluted with water (100 mL) and extracted with EtOAc (2×75 mL). The combined organic extracts were dried over sodium sulfate, filtered and concentrated in vacuo to obtain the crude. The crude was purified through silica gel column chromatography using 5% MeOH/CH$_2$Cl$_2$ to afford compound 730 (180 mg, 57%) as an off-white solid. TLC: 10% MeOH/CH$_2$Cl$_2$ (R$_f$: 0.8); $^1$H-NMR (DMSO-d$_6$, 400 MHz): 11.51 (br s, 1H), 9.68-9.29 (m, 2H), 8.05 (d, J=8.3 Hz, 1H), 8.00-7.95 (m, 2H), 7.93-7.78 (m, 6H), 7.72 (s, 1H), 7.01 (d, J=8.9 Hz, 2H), 4.66 (d, J=5.4 Hz, 2H), 4.05 (t, J=6.0 Hz, 2H), 3.40-3.33 (m, 2H), 1.95 (p, J=6.4 Hz, 2H); LC-MS: 94.34%; 654.1 (M$^+$+1) (column; Ascentis Express C18, (50×3.0 mm, 2.7 μm); RT 2.46 min. 0.025% Aq. TFA+5% ACN: ACN+5% 0.025% Aq. TFA, 1.2 mL/min).

Synthesis of N-((2-(4-(3-aminopropoxy) phenyl) thiazol-5-yl) methyl)-11-oxo-10, 11-dihydrodibenzo [b, f] [1, 4] thiazepine-8-carboxamide 5, 5-dioxide hydrochloride (1988)

To a stirring solution of compound 730 (140 mg, 0.21 mmol) in MeOH (10 mL) under inert atmosphere was added potassium carbonate (90 mg, 0.65 mmol) at RT; heated to 80° C. and stirred for 4 h. The reaction was monitored by TLC; after completion of the reaction, the volatiles were removed in vacuo to obtain the crude. The crude was purified through silica gel column chromatography using 10% MeOH/CH$_2$Cl$_2$ (aqueous ammonia) to afford crude amine (200 mg).

To the above crude amine (200 mg) in CH$_2$Cl$_2$ (10 mL) under inert atmosphere was added 4 N HCl in 1, 4-dioxane (4 mL) at 0° C. and stirred for 30 min. The reaction was monitored by TLC; after completion of the reaction, the volatiles were concentrated in vacuo to afford 1988 (85 mg, 63%) as white solid. TLC: 10% MeOH/CH$_2$Cl$_2$ (R$_f$: 0.2); $^1$H-NMR (DMSO-d$_6$, 400 MHz): δ 11.54 (s, 1H), 9.54 (t, J=5.8 Hz, 1H), 8.14-8.07 (m, 2H), 8.05 (d, J=8.2 Hz, 2H), 7.98 (td, J=7.5, 1.1 Hz, 2H), 7.93-7.80 (m, 6H), 7.72 (s, 1H), 7.03 (d, J=8.9 Hz, 2H), 4.66 (d, J=5.5 Hz, 2H), 4.12 (t, J=6.1 Hz, 2H), 3.00-2.88 (m, 2H), 2.05 (p, J=6.7 Hz, 2H); LC-MS: 96.04%; 549.1 (M$^+$+1); (column; Ascentis Express C18, (50×3.0 mm, 2.7 μm); RT 1.80 min. 0.025% Aq. TFA+5% ACN: ACN+5% 0.025% Aq. TFA, 1.2 mL/min); HPLC (purity): 95.01%; (column; X select CSH C-18 (150×4.6 mm, 3.5 μm); RT 5.85 min. 0.05% TFA+5% ACN: ACN+5% 0.05% TFA; 1.0 mL/min, Diluent: DMSO:ACN:water).

Synthesis of 1989

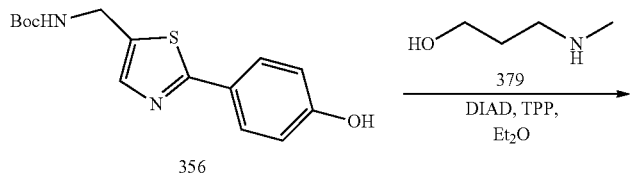

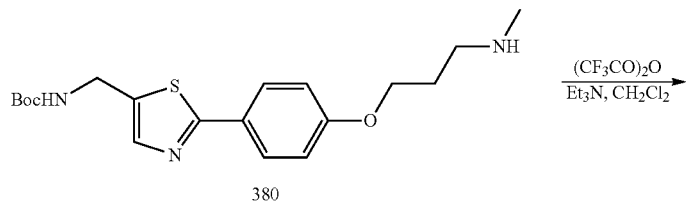

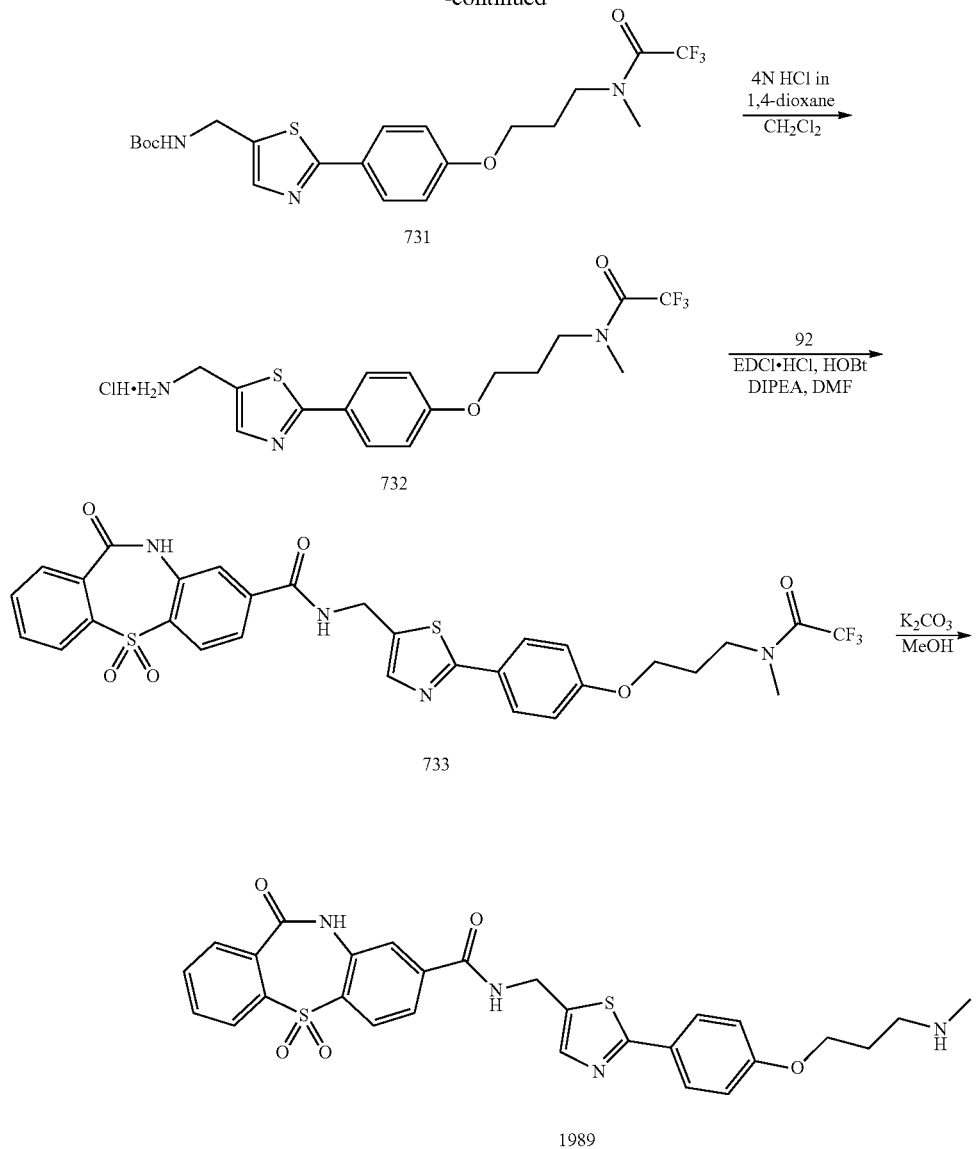

Synthesis of tert-butyl ((2-(4-(3-(2, 2, 2-trifluoro-N-methylacetamido) propoxy) phenyl) thiazol-5-yl) methyl) carbamate (731)

To a stirring solution of compound 380 (250 mg, 0.66 mmol) in CH$_2$Cl$_2$ (10 mL) under inert atmosphere were added triethylamine (0.14 mL, 0.99 mmol), followed by dropwise addition of trifluoroacetic anhydride (0.14 mL, 0.99 mmol) for 5 min at 0° C.; warmed to RT and stirred for 4 h. The reaction was monitored by TLC; after completion of the reaction, the reaction mixture was diluted with water (50 mL) and extracted with EtOAc (2×75 mL). The combined organic extracts were dried over sodium sulfate, filtered and concentrated in vacuo to obtain the crude. The crude was purified through silicagel column chromatography using 2% MeOH/CH$_2$Cl$_2$ to afford compound 731 (150 mg, 47%) as thick syrup. TLC: 5% MeOH/CH$_2$Cl$_2$ (R$_f$: 0.8); LC-MS: 81.19%; 474.1 (M$^+$+1); (column; Ascentis Express C18, (50×3.0 mm, 2.7 pin); RT 2.72 min. 0.025% Aq. TFA+5% ACN: ACN+5% 0.025% Aq. TFA, 1.2 mL/min).

Synthesis of N-(3-(4-(5-(aminomethyl) thiazol-2-yl) phenoxy) propyl)-2, 2, 2-trifluoro-N-methylacetamide hydrochloride (732)

To a stirring solution of compound 731 (150 mg, 0.31 mmol) in CH$_2$Cl$_2$ (10 mL) under inert atmosphere was added 4 N HCl in 1, 4-dioxane (2 mL) at 0° C.; warmed to RT and stirred for 3 h. The reaction was monitored by TLC; after completion of the reaction, the volatiles were removed in vacuo to obtain the crude, which was triturated with EtOAc (2×5 mL), diethyl ether (5 mL) and dried in vacuo to afford compound 732 (100 mg, 77%; HCl salt) as an off-white solid. TLC: 5% MeOH/CH$_2$Cl$_2$ (R$_f$: 0.1); $^1$H-NMR (DMSO-d$_6$, 400 MHz): δ 8.55 (br s, 3H), 8.37 (s, 1H), 8.10 (s, 1H), 7.51 (d, 1H), 4.40 (q, J=5.6 Hz, 2H); LC-MS: 88.64%; 374.0 (M$^+$+1); (column; Ascentis Express C18, (50×3.0 mm, 2.7 μm); RT 2.72 min. 0.025% Aq. TFA+5% ACN: ACN+5% 0.025% Aq. TFA, 1.2 mL/min).

Synthesis of 11-oxo-N-((2-(4-(3-(2, 2, 2-trifluoro-N-methylacetamido) propoxy) phenyl) thiazol-5-yl) methyl)-10, 11-dihydrodibenzo [b, f] [1, 4] thiazepine-8-carboxamide 5, 5-dioxide (733)

To a stirring solution of 92 (70 mg, 0.23 mmol) in DMF (8 mL) under inert atmosphere were added EDCI.HCl (66 mg, 0.34 mmol), HOBt (47 mg, 0.34 mmol), diisopropylethylamine (0.12 mL, 0.69 mmol) and compound 732 (103 mg, 0.25 mmol) at 0° C.; warmed to RT and stirred for 16 h. The reaction was monitored by TLC; after completion of the reaction, the reaction mixture was diluted with water (50 mL) and extracted with EtOAc (2×50 mL). The combined organic extracts were dried over sodium sulfate, filtered and concentrated in vacuo to obtain the crude. The crude was purified through silicagel column chromatography using 5% MeOH/CH$_2$Cl$_2$ to afford compound 733 (50 mg, 32%) as an off-white solid. TLC: 10% MeOH/CH$_2$Cl$_2$ (R$_f$: 0.5); $^1$H-NMR (DMSO-d$_6$, 400 MHz): δ 11.49 (br s, 1H), 9.42 (t, J=5.7 Hz, 1H), 8.03 (d, J=8.2 Hz, 1H), 7.98-7.92 (m, 2H), 7.90-7.76 (m, 6H), 7.70 (s, 1H), 6.98 (d, J=9.0 Hz, 2H), 4.64 (d, J=5.6 Hz, 2H), 4.11-3.96 (m, 2H), 3.64-3.51 (m, 2H), 2.97 (s, 3H), 2.08-1.94 (m, 2H); LC-MS: 95.56%; 659.1 (M$^+$+1); (column; Ascentis Express C18, (50×3.0 mm, 2.7 μm); RT 2.48 min. 0.025% Aq. TFA+5% ACN: ACN+5% 0.025% Aq. TFA, 1.2 mL/min).

Synthesis of N-((2-(4-(3-(methylamino) propoxy) phenyl) thiazol-5-yl) methyl)-11-oxo-10, 11-dihydrodibenzo [b, f] [1, 4] thiazepine-8-carboxamide 5, 5-dioxide (1989)

To a stirring solution of compound 733 (50 mg, 0.07 mmol) in MeOH (5 mL) under inert atmosphere was added potassium carbonate (52 mg, 0.37 mmol) in a sealed tube at RT; heated to 70° C. and stirred for 3 h. The reaction was monitored by TLC; after completion of the reaction, the volatiles were removed in vacuo to obtain the crude. The crude was purified through silica gel column chromatography using aqueous ammonia: MeOH:CH$_2$Cl$_2$ (1:1:8) to afford 1989 (25 mg, 59%) as an off-white solid. TLC: 5% MeOH/CH$_2$Cl$_2$ (R$_f$: 0.2 $^1$H NMR (DMSO-d$_6$, 400 MHz): δ 9.45 (t, J=5.8 Hz, 1H), 8.05 (d, J=8.2 Hz, 1H), 8.00-7.95 (m, 2H), 7.90 (td, J=7.5, 1.4 Hz, 1H), 7.87-7.85 (m, 2H), 7.83-7.77 (m, 3H), 7.72 (s, 1H), 7.01 (d, J=8.9 Hz, 2H), 4.66 (d, J=5.6 Hz, 2H), 4.07 (t, J=6.4 Hz, 2H), 2.66 (t, J=6.9 Hz, 2H), 2.32 (s, 3H), 1.92-1.83 (m, 2H); LC-MS: 98.03%; 563.1 (M$^+$+1); (column; Ascentis Express C18, (50×3.0 mm, 2.7 μm); RT 1.81 min. 0.025% Aq. TFA+5% ACN: ACN+5% 0.025% Aq. TFA, 1.2 mL/min); HPLC (purity): 97.45%; (column; X select CSH C-18 (150×4.6 mm, 3.5 μm); RT 6.00 min. 0.05% TFA+5% ACN: ACN+5% 0.05% TFA; 1.0 mL/min, Diluent: DMSO:ACN:water).

Synthesis of 1990

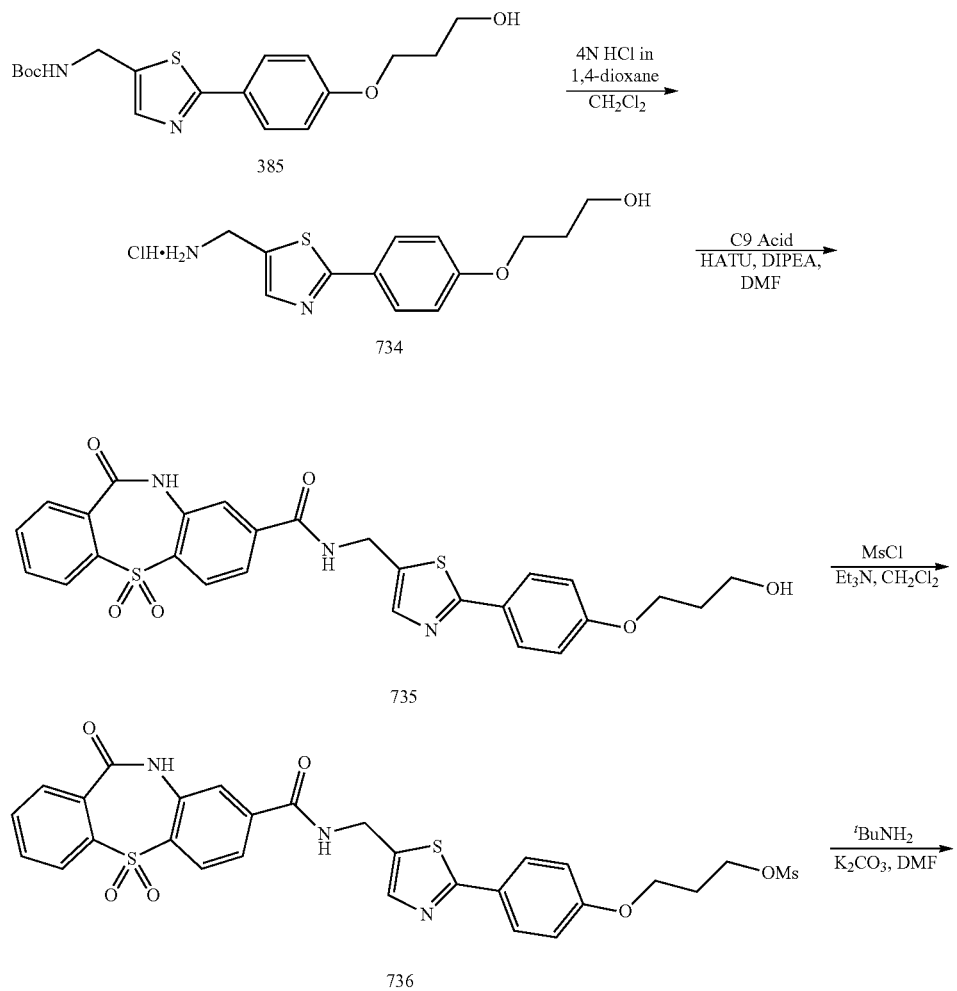

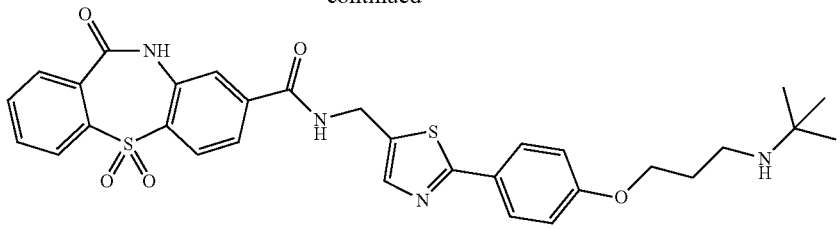

1990

Synthesis of 3-(4-(5-(aminomethyl) thiazol-2-yl) phenoxy) propan-1-ol hydrochloride (734)

To a stirring solution of tert-butyl ((2-(4-(3-hydroxypropoxy) phenyl) thiazol-5-yl) methyl) carbamate 385 (1.2 g, 3.29 mmol) in $CH_2Cl_2$ (20 mL) under inert atmosphere was added 4 N HCl in 1, 4-dioxane (4 mL) at 0° C.; warmed to RT and stirred for 3 h. The reaction was monitored by TLC; after completion of the reaction, the volatiles were removed in vacuo. The crude triturated with diethyl ether (10 mL) and dried in vacuo to afford compound 734 (1.2 g; HCl salt) as an off-white solid. TLC: 5% EtOAc/hexanes ($R_f$: 0.1); LC-MS: 97.67%; 264.9 ($M^+$+1); (column; Ascentis Express C18, (50×3.0 mm, 2.7 μm); RT 1.35 min. 0.025% Aq. TFA+5% ACN: ACN+5% 0.025% Aq. TFA, 1.2 mL/min).

Synthesis of N-((2-(4-(3-hydroxypropoxy) phenyl) thiazol-5-yl) methyl)-11-oxo-10, 11-dihydrodibenzo [b, f] [1, 4] thiazepine-8-carboxamide 5, 5-dioxide (735)

To a stirring solution of 92 (1 g, 3.30 mmol) in DMF (25 mL) under inert atmosphere were added HATU (1.87 g, 4.95 mmol), diisopropylethylamine (2.4 mL, 13.20 mmol) and 3-(4-(5-(aminomethyl) thiazol-2-yl) phenoxy) propan-1-ol hydrochloride 734 (1.09 g, 3.62 mmol) at 0° C. warmed to RT and stirred for 16 h. The reaction was monitored by TLC; after completion of the reaction, the diluted with water (10 mL) and extracted with EtOAc (2×75 mL). The combined organic extracts were dried over sodium sulfate, filtered and concentrated in vacuo to obtain the crude. The crude was purified through silica gel column chromatography using 3% MeOH/$CH_2Cl_2$ to afford compound 735 (1 g, 56%) as an off-white solid. TLC: 5% MeOH/$CH_2Cl_2$ ($R_f$: 0.1); $^1$H-NMR (DMSO-$d_6$, 400 MHz): δ 11.51 (s, 1H), 9.44 (t, J=5.8 Hz, 1H), 8.06 (d, J=8.3 Hz, 1H), 8.01-7.95 (m, 2H), 7.93-7.84 (m, 3H), 7.84-7.78 (m, 3H), 7.72 (s, 1H), 7.01 (d, J=8.9 Hz, 2H), 4.66 (d, J=5.6 Hz, 2H), 4.55 (t, J=5.1 Hz, 1H), 4.08 (t, J=6.4 Hz, 2H), 3.61-3.50 (m, 2H), 1.87 (p, J=6.3 Hz, 2H);

Synthesis of 3-(4-(5-((5, 5-dioxido-11-oxo-10, 11-dihydrodibenzo [b, f] [1, 4] thiazepine-8-carboxamido) methyl) thiazol-2-yl) phenoxy) propyl methanesulfonate (736)

To a stirring solution of compound 735 (1.0 g, 1.82 mmol) in $CH_2Cl_2$ (20 mL) under inert atmosphere were added triethylamine (0.5 mL, 3.62 mmol), methanesulfonyl chloride (0.15 mL, 1.82 mmol) at 0° C.; warmed to RT and stirred for 24 h. The reaction was monitored by TLC; after completion of the reaction, the reaction mixture was diluted with $CH_2Cl_2$ (100 mL), washed with water (2×50 mL) The organic extract was dried over sodium sulfate, filtered and concentrated in vacuo to obtain the crude. The crude was triturated with n-pentane (10 mL) and dried in vacuo to afford compound 736 (1 g, crude, mixture of mono and dimesylated compounds) as colorless sticky solid. TLC: 5% MeOH/$CH_2Cl_2$ ($R_f$: 0.4); LC-MS: 41.67%; 628.0 ($M^+$+1) (monomesylated compound), 39.31%; 706.0 ($M^+$+1) (dimesylated compound); (column; Ascentis Express C-18, (50×3.0 mm, 2.7 μm); RT 2.28 min (monomesylated compound), 2.44 min (dimesylated compound); 0.025% Aq. TFA+5% ACN: ACN+5% 0.025% Aq. TFA, 1.2 mL/min).

Synthesis of N-((2-(4-(3-(tert-butylamino) propoxy) phenyl) thiazol-5-yl) methyl)-11-oxo-10, 11-dihydrodibenzo [b, f] [1, 4] thiazepine-8-carboxamide 5, 5-dioxide (1990)

To a stirring solution of compound 736 (500 mg, crude) in MeOH (10 mL) under inert atmosphere were added potassium carbonate (330 mg, 2.39 mmol), 2-methylpropan-2-amine (0.42 mL, 3.98 mmol) in a sealed tube at RT; heated to 80° C. and stirred for 16 h. The reaction was monitored by TLC; after completion of the reaction, the reaction mixture was diluted with water (50 mL) and extracted with 10% MeOH/$CH_2Cl_2$ (2×75 mL). The combined organic extract was dried over sodium sulfate, filtered and concentrated in vacuo to obtain the crude the volatiles were removed in vacuo to obtain the crude. The crude was purified through basic alumina column chromatography using 10% MeOH/$CH_2Cl_2$ to afford 1990 (50 mg, 9%, over 2 steps) as an off-white solid. TLC: 5% MeOH/$CH_2Cl_2$ ($R_f$: 0.1, eluted twice); $^1$H NMR (DMSO-$d_6$, 400 MHz): δ 9.47 (t, J=5.6 Hz, 1H), 8.36-8.29 (m, 1H), 8.05 (d, J=8.2 Hz, 1H), 8.00-7.95 (m, 2H), 7.93-7.77 (m, 6H), 7.72 (s, 1H), 7.02 (br d, J=8.7 Hz, 2H), 4.66 (br d, J=5.3 Hz, 2H), 4.11 (t, J=6.0 Hz, 3H), 2.81 (t, J=7.0 Hz, 2H), 2.00-1.88 (m, 2H), 1.14 (s, 9H); LC-MS: 90.26%; 605.1 ($M^+$+1); (column; Ascentis Express C18, (50×3.0 mm, 2.7 μm); RT 1.93 min. 0.025% Aq. TFA+5% ACN: ACN+5% 0.025% Aq. TFA, 1.2 mL/min); HPLC (purity): 91.83%; (column; X select CSH C-18 (150×4.6 mm, 3.5 μm); RT 6.37 min. 0.05% TFA+5% ACN: ACN+5% 0.05% TFA; 1.0 mL/min, Diluent: ACN: water).

Synthesis of 11108

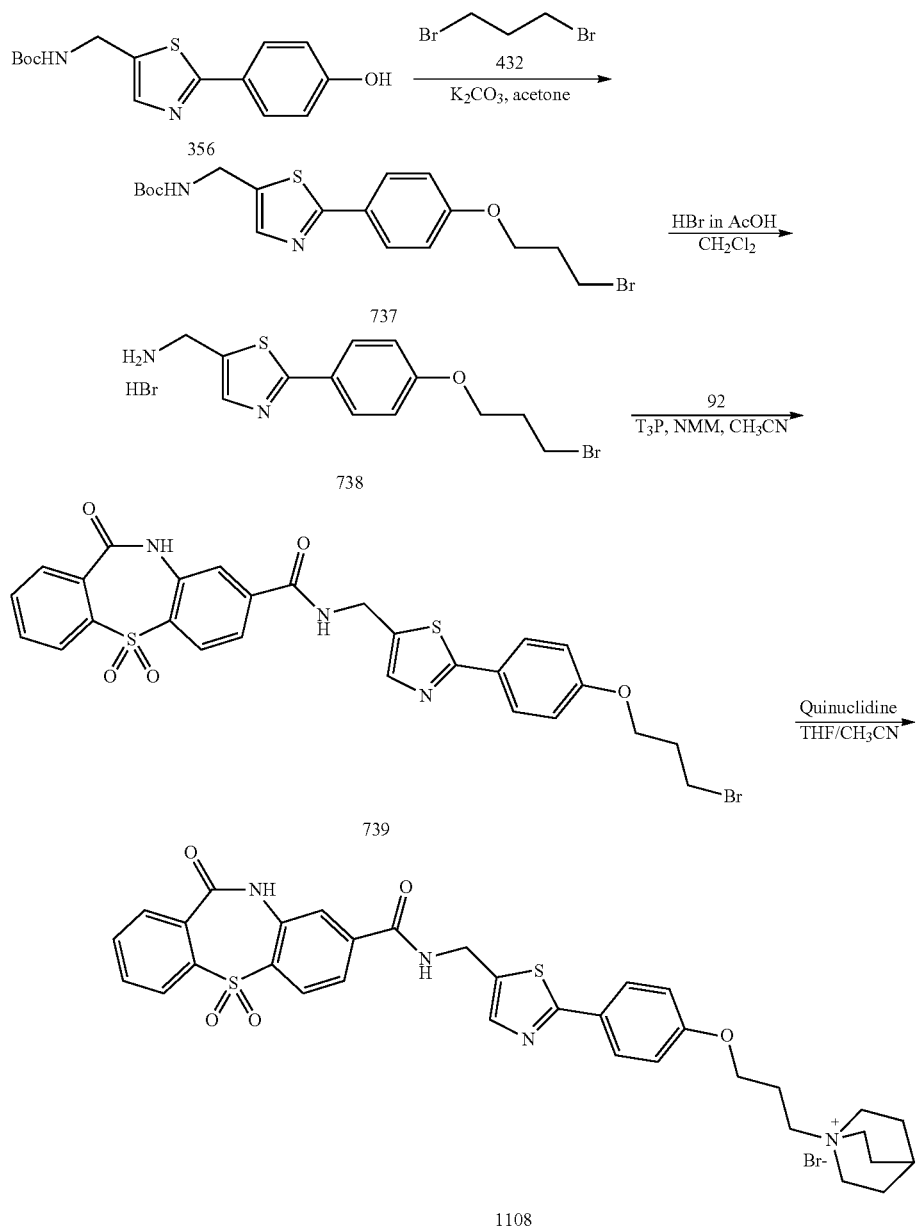

Synthesis of tert-butyl ((2-(4-(3-bromopropoxy) phenyl) thiazol-5-yl) methyl) carbamate (737)

To a stirring solution of tert-butyl ((2-(4-hydroxyphenyl) thiazol-5-yl) methyl) carbamate 356 (1 g, 3.27 mmol) in acetone (50 mL) were added 1,3-dibromopropane 432 (1.7 mL, 16.35 mmol) and potassium carbonate (2.3 g, 16.35 mmol) at RT under inert atmosphere. The reaction mixture was heated to reflux temperature and stirred for 16 h. The reaction was monitored by TLC; after completion of the reaction, the volatiles were removed in vacuo. The residue was diluted with EtOAc (60 mL), washed with water (40 mL) followed by brine (20 mL). The organic layer was separated, dried over sodium sulfate, filtered and concentrated in vacuo to obtain the crude. The crude was purified through column chromatography using 1% MeOH/CH$_2$Cl$_2$ to afford compound 737 (1.1 g, 79%) as an off white solid. TLC: 5% MeOH/CH$_2$Cl$_2$ (R$_f$: 0.8); $^1$H NMR (400 MHz, DMSO-d$_6$): δ 7.82 (d, J=8.8 Hz, 2H), 7.61 (s, 1H), 7.53 (t, J=5.8 Hz, 1H), 7.05 (d, J=8.9 Hz, 2H), 4.31 (d, J=6.0 Hz, 2H), 4.14 (t, J=6.0 Hz, 2H), 3.68 (t, J=6.6 Hz, 2H), 2.30-2.24 (m, 2H), 1.40 (s, 9H).

Synthesis of (2-(4-(3-bromopropoxy) phenyl) thiazol-5-yl) methanamine hydrobromide (738)

To a stirring solution of compound 737 (200 mg, 0.47 mmol) in CH$_2$Cl$_2$ (5 mL) was added hydrobromic acid in acetic acid (0.6 mL, 2.34 mmol) at 0° C. under inert atmosphere. The reaction mixture was gradually warmed to RT and stirred for 4 h. The reaction was monitored by TLC; after completion of the reaction, the volatiles were removed in vacuo to obtain the crude. The crude was triturated with diethylether (2×10 mL) and dried in vacuo to afford compound 738 (200 mg, HBr salt) as an off white solid. TLC: 40% EtOAc/hexanes (R$_f$: 0.1); $^1$H NMR (400 MHz, DMSO-d$_6$): δ 8.26 (br s, 3H), 7.90-7.83 (m, 3H), 7.09 (d, J=8.9 Hz, 2H), 4.35 (q, J=5.6 Hz, 2H), 4.16 (t, J=6.0 Hz, 2H), 3.68 (t, J=6.5 Hz, 2H), 2.31-2.24 (m, 2H).

Synthesis of N-((2-(4-(3-bromopropoxy) phenyl) thiazol-5-yl) methyl)-11-oxo-10,11-dihydrodibenzo [b, f] [1, 4] thiazepine-8-carboxamide 5, 5-dioxide (739)

To a stirring solution of 11-oxo-10, 11-dihydrodibenzo [b, f] [1, 4] thiazepine-8-carboxylic acid 5, 5-dioxide 92 (200 mg, 0.66 mmol) in acetonitrile (10 mL) were added compound 738 (216 mg, 0.66 mmol), Propylphosphonic anhydride (0.98 mL, 3.3 mmol) and N-Methylmorpholine (0.37 mL, 3.3 mmol) at 0° C. under inert atmosphere. The reaction mixture was gradually warmed to RT and stirred for 16 h. The reaction was monitored by TLC; after completion of the reaction, the volatiles were removed in vacuo. The residue was diluted with EtOAc (40 mL), washed with water (20 mL) followed by brine (20 mL). The organic layer was separated, dried over sodium sulfate, filtered and concentrated in vacuo to obtain the crude. The crude was triturated with diethylether (2×10 mL) and dried in vacuo to afford compound 739 (181 mg, 45%) as an off white solid. TLC: 5% MeOH/CH$_2$Cl$_2$ (R$_f$: 0.4); $^1$H NMR (500 MHz, DMSO-d$_6$): δ 11.52 (s, 1H), 9.45 (t, J=5.5 Hz, 1H), 8.06 (d, J=8.1 Hz, 1H), 8.01-7.96 (m, 2H), 7.92-7.79 (m, 6H), 7.73 (s, 1H), 7.04 (d, J=8.7 Hz, 2H), 4.66 (d, J=5.8 Hz, 2H), 4.14 (t, J=5.8 Hz, 2H), 3.67 (t, J=6.4 Hz, 2H), 2.29-2.24 (m, 2H).

Synthesis of 1-(3-(4-(5-((5, 5-dioxido-11-oxo-10, 11-dihydrodibenzo [b, f] [1, 4] thiazepine-8-carboxamido) methyl) thiazol-2-yl) phenoxy) propyl) quinuclidin-1-ium bromide (11108)

To a stirring solution of compound 739 (50 mg, 0.08 mmol) in a mixture of THF/acetonitrile (1:1, 10 mL) was added Quinuclidine (9.5 mg, 0.08 mmol) at RT under inert atmosphere. The reaction mixture was heated to reflux temperature and stirred for 16 h. The reaction was monitored by TLC; after completion of the reaction, the volatiles were removed in vacuo to obtain the crude. The crude was triturated with diethylether (2×10 mL), CH$_3$CN/MeOH (10%, 5 mL) and dried in vacuo. The obtained solid was dissolved in CH$_3$CN/MeOH/H$_2$O (1:1:1, 3 mL) and lyophilized for 16 h to afford 11108 (30 mg, 57%) as an off white solid. TLC: 10% MeOH/CH$_2$Cl$_2$ (R$_f$: 0.1); $^1$H NMR (400 MHz, DMSO-d$_6$): δ 11.55 (br s, 1H), 9.46 (t, J=5.0 Hz, 1H), 8.03 (d, J=8.3 Hz, 1H), 7.99-7.94 (m, 2H), 7.89 (td, J=7.4, 1.2 Hz, 1H), 7.86-7.80 (m, 4H), 7.79-7.71 (m, 2H), 7.03 (d, J=8.8 Hz, 2H), 4.66 (d, J=5.5 Hz, 2H), 4.10 (t, J=5.8 Hz, 2H), 3.46-3.38 (m, 6H), 3.27-3.23 (m, 2H), 2.22-2.12 (m, 2H), 2.10-2.05 (m, 1H), 1.90-1.82 (m, 6H); LC-MS: 92.59%; 643.2 (M$^+$+1); (column; Ascentis Express C18, (50×3.0 mm, 2.7 μm); RT 1.90 min. 0.025% Aq. TFA+5% ACN: ACN+5% 0.025% Aq. TFA, 1.2 mL/min); HPLC (purity): 90.14%; (column; X-Select CSH-C-18 (150×4.6 mm, 3.5 μm); RT 6.31 min. 0.05% TFA+5% ACN: ACN+5% 0.05% TFA; 1.0 mL/min, Diluent: ACN:H$_2$O).

Synthesis of 11108-B

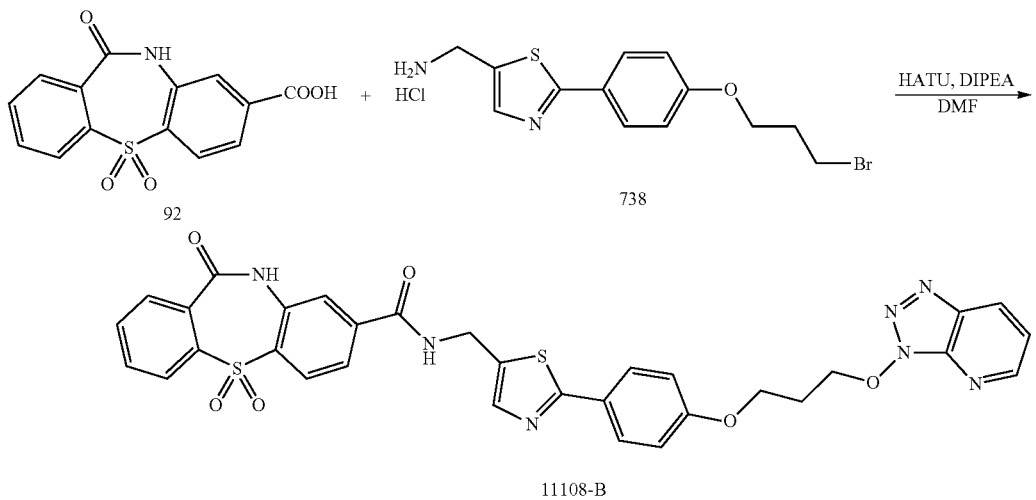

11108-B

Synthesis of N-((2-(4-(3-43H-[1,2,3]triazolo[4,5-b] pyridin-3-yl)oxy)propoxy) phenyl)thiazol-5-yl) methyl)-11-oxo-10,11-dihydrodibenzo[b,f] [1,4] thiazepine-8-carboxamide 5,5-dioxide (11108-B)

To a stirring solution of 11-oxo-10, 11-dihydrodibenzo [b, f] [1, 4] thiazepine-8-carboxylic acid 5, 5-dioxide 92 (200 mg, 0.66 mmol) in DMF (2 mL) were added HATU (376 mg, 0.99 mmol), diisopropylethylamine (0.36 mL, 1.98 mmol) and compound 738 (215 mg, 0.66 mmol) at 0° C. under inert atmosphere. The reaction mixture was gradually warmed to RT and stirred for 16 h. The reaction was monitored by TLC; after completion of the reaction, the reaction mixture was diluted with water (5 mL) and extracted with EtOAc (2×5 mL). The combined organic extracts were dried over sodium sulfate, filtered and concentrated in vacuo to obtain the crude. The crude was purified through silicagel column chromatography using 4% MeOH/CH$_2$Cl$_2$ to afford 11108-B (50 mg, 12%) as an off white solid. TLC: 10% MeOH/ CH$_2$Cl$_2$ (R$_f$: 0.4); $^1$H NMR (DMSO-d$_6$, 400 MHz): δ 11.52 (br s, 1H), 9.45 (t, J=5.6 Hz, 1H), 8.80 (dd, J=1.4, 4.4 Hz, 1H), 8.62 (dd, J=1.3, 8.4 Hz, 1H), 8.05 (d, J=8.2 Hz, 1H), 7.98 (dt, J=7.6, 1.1 Hz, 2H), 7.93-7.79 (m, 6H), 7.73 (s, 1H), 7.58 (dd, J=4.4, 8.4 Hz, 1H), 7.05 (d, J=8.8 Hz, 2H), 4.80 (t, J=6.3 Hz, 2H), 4.66 (br d, J=5.5 Hz, 2H), 4.32 (t, J=6.2 Hz, 2H), 2.26 (p, J=6.3 Hz, 2H); LC-MS: 94.98%; 668.1 (M$^+$+1); (column; Ascentis Express C18, (50×3.0 mm, 2.7 μm); RT 2.37 min. 0.025% Aq. TFA+5% ACN: ACN+5% 0.025% Aq. TFA, 1.2 mL/min); HPLC (purity): 94.02%; (column; X-select CSH-C18 (150×4.6 mm, 3.5 μm); RT 10.06 min. 5 mM Aq. NH$_4$HCO$_3$: ACN; 1.0 mL/min, Diluent: DMSO: ACN:water).

Synthesis of N-((2-(4-(3-chloro-2-hydroxypropoxy) phenyl) thiazol-5-yl) methyl)-11-oxo-10, 11-dihydrodibenzo [b, f] [1, 4] thiazepine-8-carboxamide 5, 5-dioxide (743): A common Intermediate solid. TLC: 5% MeOH/CH$_2$Cl$_2$ (R$_f$: 0.8); $^1$H-NMR (DMSO-d$_6$, 400 MHz): δ 7.82 (d, J=8.7 Hz, 2H), 7.61 (s, 1H), 7.53 (d, J=5.0 Hz, 1H), 7.06 (d, J=8.9 Hz, 2H), 4.40 (dd, J=11.4, 2.7 Hz, 1H), 4.31 (br d, J=5.6 Hz, 2H), 3.90 (dd, J=11.4, 6.6 Hz, 1H), 3.38-3.33 (m, 1H), 2.87-2.84 (m, 1H), 2.73 (dd, J=5.0, 2.6 Hz, 1H), 1.40 (s, 9H); LC-MS: 83.49%; 363.0 (M$^+$+1); (column; Ascentis Express C18, (50×3.0 mm, 2.7 μm); RT 2.42 min. 0.025% Aq. TFA+5% ACN: ACN+5% 0.025% Aq. TFA, 1.2 mL/min).

Synthesis of 1-(4-(5-(aminomethyl) thiazol-2-yl) phenoxy)-3-chloropropan-2-ol hydrochloride (742)

To a stirring solution of compound 741 (1.9 g, 5.24 mmol) in CH$_2$Cl$_2$ (20 mL) was added 4 N HCl in 1, 4-dioxane (15 mL) under inert atmosphere at 0° C.; warmed to RT and stirred for 4 h. The reaction was monitored by TLC; after

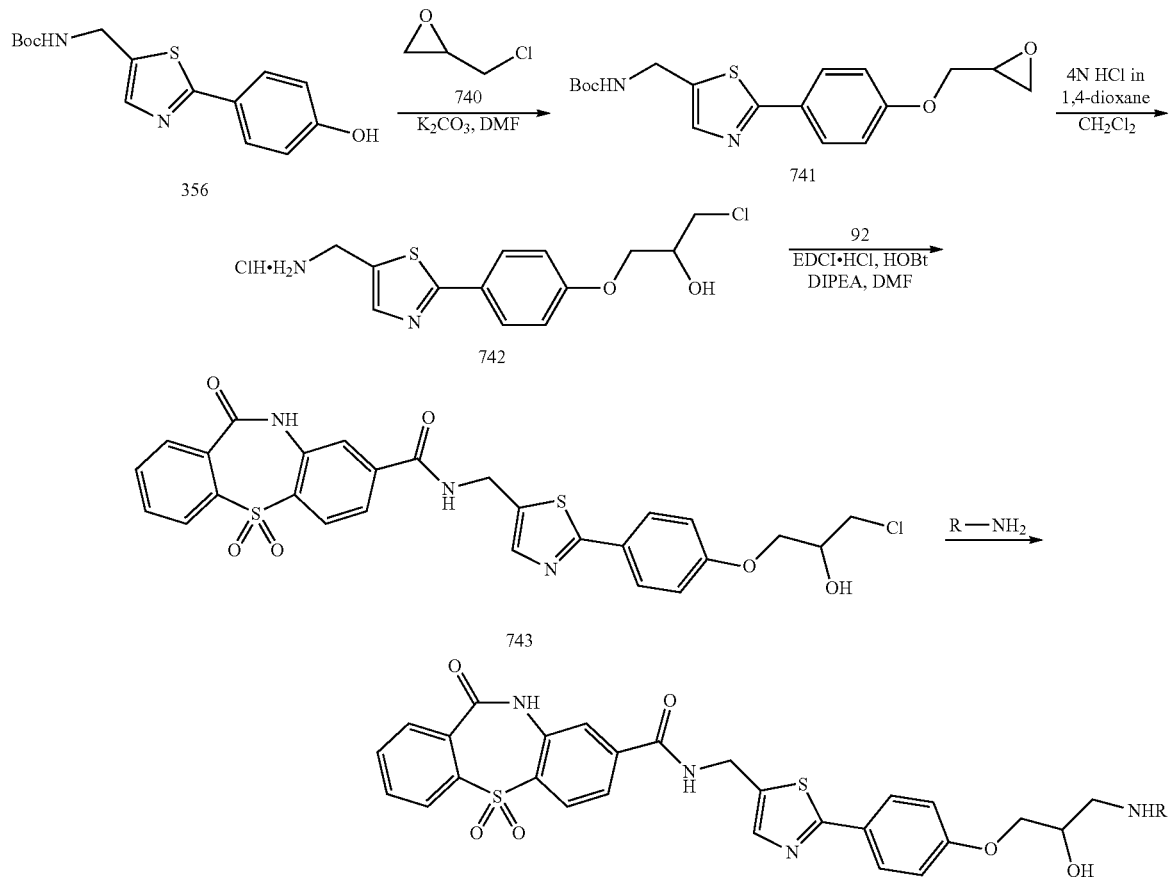

Synthesis of tert-butyl ((2-(4-(oxiran-2-ylmethoxy) phenyl) thiazol-5-yl) methyl) carbamate (741)

To a stirring solution of tert-butyl ((2-(4-hydroxyphenyl) thiazol-5-yl) methyl) carbamate 356 (2.5 g, 8.16 mmol) in DMF (50 mL) under inert atmosphere were added epichlorohydrin 740 (1.89 g, 20.42 mmol) and potassium carbonate (2.8 g, 20.42 mmol) at RT; heated to 70-80° C. and stirred for 3 h. The reaction was monitored by TLC; after completion of the reaction, the reaction mixture was poured into ice-cold water (100 mL) and the precipitated solid was filtered and titurated with 15% EtOAc/hexanes and dried in vacuo to afford compound 741 (1.9 g, 64%) as an off-white completion of the reaction, the volatiles were removed in vacuo. The crude washed with 50% EtOAc/hexanes (5 mL) and dried in vacuo to afford compound 742 (1.5 g, 86%; HCl salt) as white solid. TLC: 5% MeOH/CH$_2$Cl$_2$ (R$_f$: 0.1); $^1$H-NMR (DMSO-d$_6$, 400 MHz): δ 8.67 (br s, 3H), 7.92 (s, 1H), 7.86 (d, J=9.0 Hz, 2H), 7.09 (br d, J=9.0 Hz, 2H), 4.30 (q, J=5.2 Hz, 2H), 4.06 (s, 2H), 3.79-3.66 (m, 3H), 3.56 (s, 2H); LC-MS: 90.32%; 298.9 (M$^+$+1); (column; Ascentis Express C18, (50×3.0 mm, 2.7 μm); RT 1.50 min. 0.025% Aq. TFA+5% ACN: ACN+5% 0.025% Aq. TFA, 1.2 mL/min).

Synthesis of N-((2-(4-(3-chloro-2-hydroxypropoxy) phenyl) thiazol-5-yl) methyl)-11-oxo-10, 11-dihydrodibenzo [b, f] [1, 4] thiazepine-8-carboxamide 5, 5-dioxide (743)

To a stirring solution of compound 742 (1.2 g, 3.96 mmol) and 92 (1.0 g, 3.30 mmol) in DMF (40 mL) under inert atmosphere were added HOBt (801 mg, 5.94 mmol), EDCI.HCl (945 mg, 5.95 mmol), diisopropyl ethyl amine (2.1 mL, 11.88 mmol) at 0° C.; warmed to RT and stirred for 16 h. The reaction was monitored by TLC; after completion of the reaction, the reaction mixture was poured into ice-cold water (30 mL) and extracted with 10% MeOH/CH$_2$Cl$_2$ (2×250 mL). The combined organic extracts were dried over sodium sulfate, filtered and concentrated in vacuo to obtain the crude. The crude was purified through silicagel column chromatography using 4% MeOH/CH$_2$Cl$_2$ to afford compound 743 (1.1 g, 48%) as white solid. TLC: 7% MeOH/CH$_2$Cl$_2$ (R$_f$: 0.8); $^1$H NMR (DMSO-d$_6$, 500 MHz): δ 11.51 (s, 1H), 9.45 (br t, J=5.8 Hz, 1H), 8.06 (d, J=8.7 Hz, 1H), 7.98 (t, J=8.4 Hz, 2H), 7.90 (td, J=7.5, 1.2 Hz, 1H), 7.87-7.79 (m, 5H), 7.73 (s, 1H), 7.04 (d, J=8.7 Hz, 2H), 5.58 (d, J=4.6 Hz, 1H), 4.66 (br d, J=5.8 Hz, 2H), 4.07-4.01 (m, 3H), 3.79-3.64 (m, 2H); LC-MS: 89.09%; 584.0 (M++1); (column; Ascentis Express C18, (50×3.0 mm, 2.7 µm); RT 2.22 min. 0.025% Aq. TFA+5% ACN: ACN+5% 0.025% Aq. TFA, 1.2 mL/min).

Preparation

Compound 743 was synthesized as mentioned above and converted to final products as HCl salt/TFA salt/free amine using commercially available amines employing typical procedures L and the results are captured in the Table 4:

Typical Procedure L:

To a stirring solution of compound 743 (250 mg, 0.42 mmol) in EtOH (10 mL) in a sealed tube was added 33% ethanolic ammonia (10 mL) at 0° C.; heated to 50° C. and stirred for 3 h. The reaction was monitored by TLC; after completion of the reaction, the volatiles were removed in vacuo and the residue washed with 20% EtOAc/hexanes and dried in vacuo to obtain the crude which was purified by preparative HPLC purification/triturated to afford the desired product.

Commercial Amines Used for the Preparation

| | |
|---|---|
| CH$_3$NH$_2$ | 240 |
| HN(CH$_3$)$_2$ (HN with two methyl) | 243 |
| HN with diethyl | 387 |
| HN-isopropyl | 412 |
| H$_2$N-tBu | 469 |

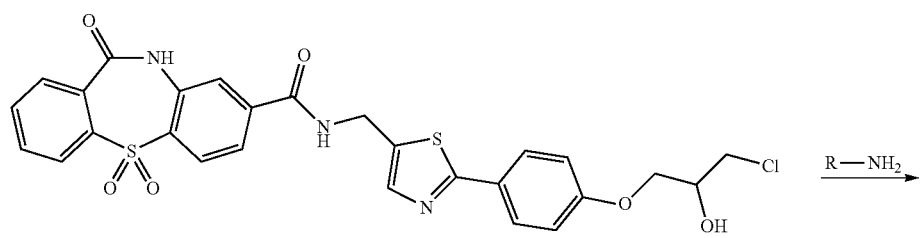

743

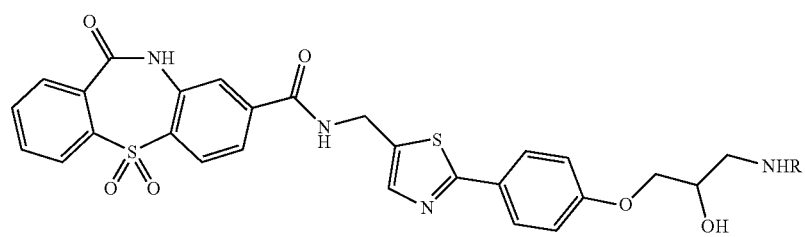

Targets

TABLE 4

Synthesis from compound 743 using various amines

| Example | Structure | Procedure, Intermediate, amine | Rx. Yield (%) | Mass Spec. Found | Mass Spec. Calculated | $^1$H-NMR |
|---|---|---|---|---|---|---|
| 11084 | 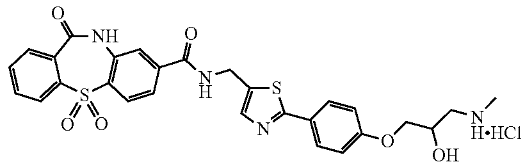 | L, 743, 240 | 38 | 579.0 (M$^+$ + 1) | 614.11 for C$_{28}$H$_{27}$ClN$_4$O$_6$S$_2$ | $^1$H-NMR (DMSO-d$_6$, 400 MHz): δ 11.52 (s, 1H), 9.46 (t, J = 5.7 Hz, 1H), 8.49-8.42 (m, 1H), 8.06 (d, J = 8.2 Hz, 1H), 8.01-7.95 (m, 2H), 7.93-7.80 (m, 6H), 7.73 (s, 1H), 7.04 (d, J = 8.9 Hz, 2H), 5.99-5.82 (m, 1H), 4.66 (br d, J = 5.6 Hz, 2H), 4.17-4.10 (m, 1H), 4.02 (br d, J = 5.0 Hz, 3H), 3.19-3.10 (m, 1H), 3.06-2.96 (m, 1H), 2.61 (t, J = 5.4 Hz, 3H); |
| 11085 | 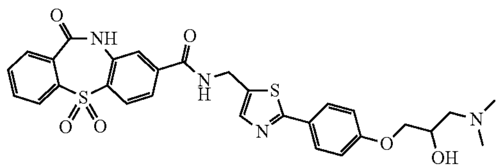 [SMILES: CN(C)CC(O)COc1ccc(-c2ncc(CNC(=O)c3ccc4c(c3)NC(=O)c3ccccc3S4(=O)=O)s2)cc1] | L$^a$, 743, 243 | 25 | 593.1 (M$^+$ + 1) | 592.15 for C$_{29}$H$_{28}$N$_4$O$_6$S$_2$ | $^1$H-NMR (DMSO-d$_6$, 400 MHz): δ 11.48 (m, 1H), 9.46 (t, J = 5.4 Hz, 1H), 8.06 (br d, J = 8.2 Hz, 1H), 7.98 (t, J = 7.8 Hz, 2H), 7.93-7.77 (m, 6H), 7.72 (s, 1H), 7.02 (br d, J = 8.4 Hz, 2H), 4.87 (br s, 1H), 4.66 (br d, J = 4.7 Hz, 2H), 4.02 (br d, J = 6.1 Hz, 1H), 3.94-3.86 (m, 2H), 2.42-37 (m, 1H), 2.31-2.25 (m, 1H), 2.18 (s, 6H); |
| 11086 | 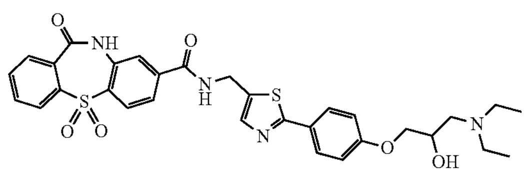 [SMILES: CCN(CC)CC(O)COc1ccc(-c2ncc(CNC(=O)c3ccc4c(c3)NC(=O)c3ccccc3S4(=O)=O)s2)cc1] | L$^b$, 743, 387 | 41 | 621.1 (M+ + 1) | 620.18 for C$_{31}$H$_{32}$N$_4$O$_6$S$_2$ | $^1$H-NMR (DMSO-d$_6$, 400 MHz): δ 11.50 (br s, 1H), 9.44 (t, J = 5.7 Hz, 1H), 8.05 (d, J = 8.2 Hz, 1H), 7.98 (dd, J = 7.5, 1.2 Hz, 2H), 7.93-7.77 (m, 6H), 7.72 (s, 1H), 7.02 (d, J = 8.9 Hz, 2H), 4.83-4.75 (m, 1H), 4.66 (br d, J = 5.5 Hz, 2H), 4.05 (dd, J = 9.8, 3.2 Hz, 1H), 3.94-3.89 (m, 1H), 3.89-3.82 (m, 1H), 2.57-2.44 (m, 3H), 2.44-2.41 (m, 2H), 2.39-2.36 (m, 1H), 0.94 (t, J = 7.1 Hz, 6H); |
| 11087 | 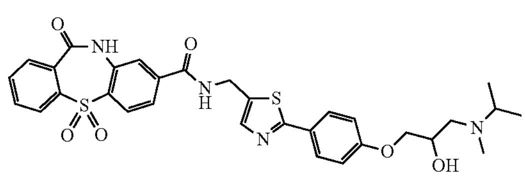 [SMILES: CC(C)N(C)CC(O)COc1ccc(-c2ncc(CNC(=O)c3ccc4c(c3)NC(=O)c3ccccc3S4(=O)=O)s2)cc1] | L$^c$, 743, 412 | 31 | 621.1 (M$^+$ + 1) | 620.18 for C$_{31}$H$_{32}$N$_4$O$_6$S$_2$ | $^1$H-NMR (DMSO-d$_6$, 400 MHz): δ 11.51 (br s, 1H), 9.44 (t, J = 5.8 Hz, 1H), 8.05 (d, J = 8.1 Hz, 1H), 8.01-7.95 (m, 2H), 7.92-7.84 (m, 3H), 7.82-7.79 (m, 3H), 7.72 (s, 1H), 7.02 (d, J = 9.3 Hz, 2H), 4.75 (br s, 1H), 4.66 (br d, J = 5.2 Hz, 2H), 4.04 (dd, J = 9.9, 2.9 Hz, |

TABLE 4-continued

Synthesis from compound 743 using various amines

| Example | Structure | Procedure, Intermediate, amine | Rx. Yield (%) | Mass Spec. Found | Mass Spec. Calculated | $^1$H-NMR |
|---|---|---|---|---|---|---|
| | | | | | | 1H), 3.96-3.82 (m, 2H), 2.75 (td, J = 13.2, 6.4 Hz, 1H), 2.34 (br d, J = 5.8 Hz, 1H), 2.31 (br d, J = 5.8 Hz, 1H), 2.18 (s, 3H), 0.92 (dd, J = 6.4, 2.9 Hz, 6H); |
| 11088 | 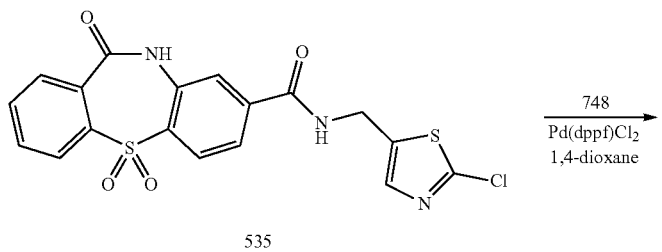 | $L^b$, 743, 469 | 25 | 621.1 (M$^+$ + 1) | 734.17 for $C_{33}H_{33}F_3N_6O_8S_2$ | $^1$H-NMR (DMSO-d$_6$, 400 MHz): δ 11.53 (s, 1H), 9.47 (t, J = 5.8 Hz, 1H), 8.41-8.23 (m, 2H), 8.06 (d, J = 8.2 Hz, 1H), 8.01-7.96 (m, 2H), 7.93-7.80 (m, 6H), 7.73 (s, 1H), 7.06 (d, J = 9.0 Hz, 2H), 5.91 (d, J = 4.7 Hz, 1H), 4.66 (br d, J = 5.6 Hz, 2H), 4.16-4.09 (m, 1H), 4.08-4.05 (m, 2H), 3.22-3.06 (m, 1H), 3.01-2.89 (m, 1H), 1.29 (s, 9H); |

$L^a$: Dimethyl amine (2 M sol. In THF, 4 mL), 80° C., 24 h.
$L^b$: compd: 743 (100 mg), Diethyl amine (37 mg, 3 equiv), EtOH (5 mL), 80° C., 24 h.
$L^c$: compd: 743 (200 mg), N-methylpropan-2-amine (75 mg, 3 equiv), EtOH (10 mL), 80° C., 48 h in sealed tube Synthesis of 11011

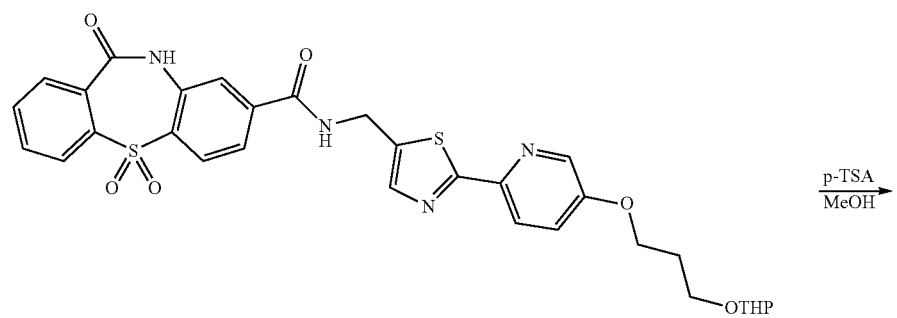

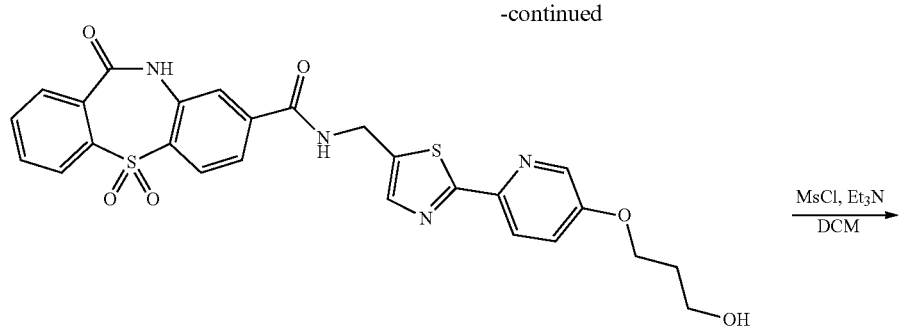

750

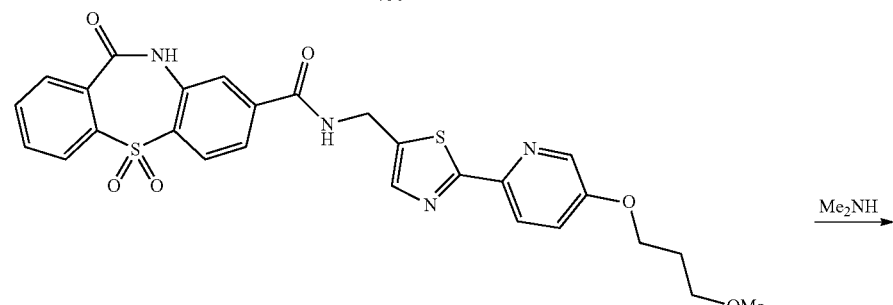

751

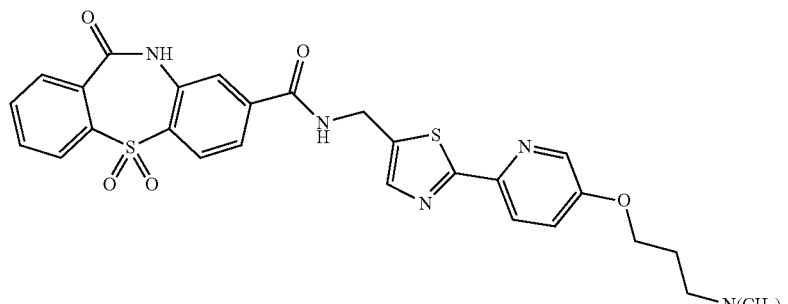

11011

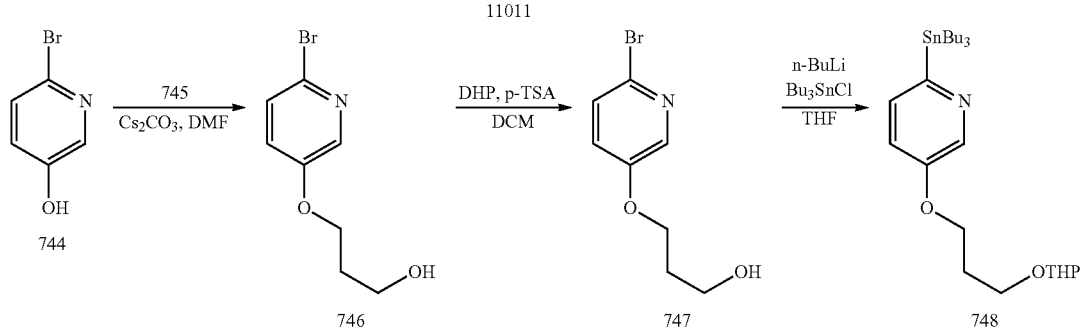

Synthesis of 3-((6-bromopyridin-3-yl) oxy) propan-1-ol (746)

To a stirring solution of 6-bromopyridin-3-ol (744) 1 g, 5.74 mmol) in DMF (10 mL) under inert atmosphere was added $Cs_2CO_3$ (5.5 g, 17.22 mmol) at RT and stirred for 5 min. Then 3-bromo-1-propanol 745 (0.86 g, 6.32 mmol) was added and continued stirring at RT for 16 h. The reaction was monitored by TLC; after completion of the reaction, the reaction mixture was diluted with water (20 mL) and extracted with EtOAc (2×20 mL). The organic extract was dried over sodium sulfate, filtered and concentrated in vacuo to obtain the crude. The crude was purified through silica gel column chromatography using 40% EtOAc/hexanes to afford compound 746 (700 mg, 53%) as colorless syrup. TLC: 50% EtOAc/hexanes ($R_f$: 0.2); $^1$H NMR (DMSO-$d_6$, 400 MHz): δ 8.11 (d, J=3.2 Hz, 1H), 7.53 (d, J=8.4 Hz, 1H), 7.38 (dd, J=8.8, 3.1 Hz, 1H), 4.56 (t, J=5.2 Hz, 1H), 4.11 (t, J=6.4 Hz, 3H), 3.57-3.52 (m, 2H), 1.86 (p, J=6.3 Hz, 2H); LC-MS: 56.62%; 231.8 (M$^+$+1); (column; Ascentis Express C18, (50×3.0 mm, 2.7 μm); RT 1.73 min. 0.025% Aq. TFA+5% ACN: ACN+5% 0.025% Aq. TFA, 1.2 mL/min).

Synthesis of 2-bromo-5-(3-((tetrahydro-2H-pyran-2-yl) oxy) propoxy) pyridine (747)

To a stirring solution of compound 746 (700 mg, 3.03 mmol) in DCM (10 mL) under inert atmosphere were added dihydropyran (305 mg, 3.63 mmol) and p-toluene sulfonic acid (5 mg) at 0-5° C.; stirred at RT for 16 h. The reaction was monitored by TLC and LC-MS; after completion volatiles were evaporated in vacuo to obtain the crude. The crude was purified through silica gel column chromatography using 30% EtOAc/hexanes to afford compound 747 (700 mg, 73%) as colorless syrup. TLC: 30% EtOAc/hexanes ($R_f$: 0.5); $^1H$ NMR (DMSO-$d_6$, 400 MHz): δ 8.12 (d, J=2.9 Hz, 1H), 7.53 (d, J=8.7 Hz, 1H), 7.40 (dd, J=8.7, 3.2 Hz, 1H), 4.59-4.53 (m, 1H), 4.12 (t, J=6.3 Hz, 2H), 3.81-3.65 (m, 2H), 3.48 (td, J=9.9, 6.3 Hz, 1H), 3.44-3.38 (m, 1H), 1.97 (p, J=6.3 Hz, 2H), 1.78-1.65 (m, 1H), 1.65-1.56 (m, 1H), 1.53-1.34 (m, 4H);

Synthesis of 5-(3-((tetrahydro-2H-pyran-2-yl) oxy) propoxy)-2-tributyl stannyl) pyridine (748)

To a stirring solution of compound 747 (1 g, 3.17 mmol) in dry THF (20 mL) under inert atmosphere was added n-BuLi (1.9 mL, 3.17 mmol) at −78° C. and stirred for 30 min. Then tributyltin chloride (3 g, 9.52 mmol) was added at −78° C. and continued stirring for 1 h. The reaction was monitored by TLC; after completion of the reaction, the reaction mixture was quenched with ammonium chloride solution (30 mL) and extracted with EtOAc (2×30 mL). The organic extract was dried over sodium sulfate, filtered and concentrated in vacuo to afford compound 748 (1.8 g, crude) as colorless syrup. TLC: 30% EtOAc/hexanes ($R_f$: 0.7); LC-MS: 39.52%; 528.1 (M$^+$+1); (column; Ascentis Express C18, (50×3.0 mm, 2.7 μm); RT 2.60 min. 0.025% Aq. TFA+5% ACN: ACN+5% 0.025% Aq. TFA, 1.2 mL/min.

Synthesis of 11-oxo-N-((2-(5-(3-((tetrahydro-2H-pyran-2-yl) oxy) propoxy) pyridin-2-yl) thiazol-5-yl) methyl)-10, 11-dihydrodibenzo [b, f] [1, 4] thiazepine-8-carboxamide 5, 5-dioxide (749)

To a stirring solution of N-((2-chlorothiazol-5-yl) methyl)-11-oxo-10, 11-dihydrodibenzo [b, f] [1, 4] thiazepine-8-carboxamide 5, 5-dioxide (535) (500 mg, 1.16 mmol) in 1, 4-dioxane (25 mL) under inert atmosphere were added compound 748 (1.8 g, 3.48 mmol) and Pd(dppf)Cl$_2$ (85 mg, 0.116 mmol) at RT and purged under argon atmosphere 30 min; heated to 110° C. and stirred for 16 h. The reaction was monitored by TLC; after completion the volatiles were removed in vacuo to obtain the crude. The crude was purified through combiflash column chromatography using 30% EtOAc/hexanes to afford compound 749 (75 mg, 10%) as an off-white solid. TLC: 30% MeOH/CH$_2$Cl$_2$ ($R_f$: 0.4); $^1H$ NMR (DMSO-$d_6$, 400 MHz): LC-MS: 94.65%; 635.1 (M$^+$+1); (column; Ascentis Express C18, (50×3.0 mm, 2.7 μm); RT 2.51 min. 0.025% Aq. TFA+5% ACN: ACN+5% 0.025% Aq. TFA, 1.2 mL/min).

Synthesis of N-((2-(5-(3-hydroxypropoxy) pyridin-2-yl) thiazol-5-yl) methyl)-11-oxo-10, 11-dihydrodibenzo [b, f] [1, 4] thiazepine-8-carboxamide 5, 5-dioxide (750)

To to a stirring solution of compound 749 (30 mg, 0.047 mmol) in MeOH (5 mL) under argon atmosphere was added p-Toluenesulfonic acid (4 mg, 0.023 mmol) at RT and stirred for 3 h. The reaction was monitored by TLC; after completion of the reaction, the reaction mixture was diluted with water (1 mL) and pH was neutralized with aqueous saturated Na$_2$CO$_3$ solution and extracted with 5% MeOH/EtOAc (2×1 mL). The combined organic extracts were dried over sodium sulfate and concentrated vacuo to afford compound 750 (20 mg, 76%) as an off-white solid. TLC: 10% MeOH/EtOAc ($R_f$: 0.5); $^1H$ NMR (DMSO-$d_6$, 400 MHz): δ 11.54 (br s, 1H), 9.52-9.44 (m, 1H), 8.31 (d, J=3.1 Hz, 1H), 8.09-7.97 (m, 3H), 7.95-7.77 (m, 4H), 7.54 (dd, J=8.7, 2.9 Hz, 1H), 7.49 (d, J=8.2 Hz, 2H), 7.18-7.07 (m, 2H), 4.69 (d, J=5.5 Hz, 1H), 4.63-4.59 (m, 1H), 4.24-4.14 (m, 2H), 3.60-3.56 (m, 1H), 1.94-1.86 (m, 2H);

Synthesis of 3-((6-(5-((5, 5-dioxido-11-oxo-10, 11-dihydrodibenzo [b, f] [1,4] thiazepine-8-carboxamido) methyl) thiazol-2-yl) pyridin-3-yl) oxy) propyl methane sulfonate (751)

To a stirring solution of compound 750 (220 mg, 0.40 mmol) in CH$_2$Cl$_2$ (10 mL) under inert atmosphere were added triethylamine (0.11 mL, 0.80 mmol) and methanesulfonyl chloride (0.04 mL, 0.60 mmol) at 0-5° C.; warmed to RT and stirred for 16 h. The reaction was monitored by TLC; after completion of the reaction, the reaction mixture was diluted with CH$_2$Cl$_2$ (5 mL) and washed with water (2×5 mL). The organic extract was dried over sodium sulfate, filtered and concentrated in vacuo to afford compound 751 (200 mg, crude) as an off-white solid. TLC: 5% MeOH/CH$_2$Cl$_2$ ($R_f$: 0.3); LC-MS: 27.24%; 629.0 (M$^+$+1); (column; Ascentis Express C18, (50×3.0 mm, 2.7 μm); RT 2.21 min. 0.025% Aq. TFA+5% ACN: ACN+5% 0.025% Aq. TFA, 1.2 mL/min).

Synthesis of N-((2-(5-(3-(dimethylamino) propoxy) pyridin-2-yl) thiazol-5-yl) methyl)-11-oxo-10, 11-dihydrodibenzo [b, f] [1, 4] thiazepine-8-carboxamide 5, 5-dioxide (11011)

To a stirring solution of compound 751 (200 mg, 0.31 mmol) under argon atmosphere was added dimethyl amine (7 mL) in a sealed tube. The reaction mixture was heated to 60° C. and stirred for 16 h. The reaction was monitored by TLC; after completion the reaction the volatiles were removed in vacuo to obtain the crude. The crude was purified through basic alumina column chromatography using 2% MeOH/CH$_2$Cl$_2$ to afford 1 1011 (20 mg, 11%) as an off-white solid. TLC: 10% MeOH/CH$_2$Cl$_2$ ($R_f$: 0.1); $^1H$ NMR (DMSO-$d_6$, 400 MHz): δ 11.49 (br s, 1H), 9.45 (t, J=5.7 Hz, 1H), 8.28 (d, J=2.6 Hz, 1H), 8.06 (d, J=8.2 Hz, 1H), 8.03-7.95 (m, 3H), 7.93-7.85 (m, 3H), 7.84-7.79 (m, 1H), 7.77 (s, 1H), 7.51 (dd, J=8.8, 2.9 Hz, 1H), 4.67 (d, J=5.6 Hz, 2H), 4.13 (t, J=6.4 Hz, 2H), 2.40 (t, J=7.1 Hz, 2H), 2.17 (s, 6H), 1.92-1.85 (m, 2H); LC-MS: 98.18%; 578.1 (M$^+$+1); (column; Ascentis Express C18, (50×3.0 mm, 2.7 μm); RT 1.78 min. 0.025% Aq. TFA+5% ACN: ACN+5% 0.025% Aq. TFA, 1.2 mL/min); HPLC (purity): 96.44%; (column; X select CSH C-18 (150×4.6 mm, 3.5 μm); RT 5.39 min. 0.05% TFA+5% ACN: ACN+5% 0.05% TFA; 1.0 mL/min, Diluent: ACN:Water).

Synthesis of 11006, 11007, 11007-A & 11067
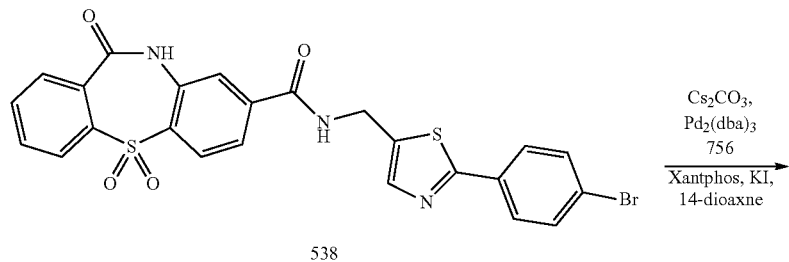
538
Cs$_2$CO$_3$,
Pd$_2$(dba)$_3$
756
Xantphos, KI,
14-dioaxne
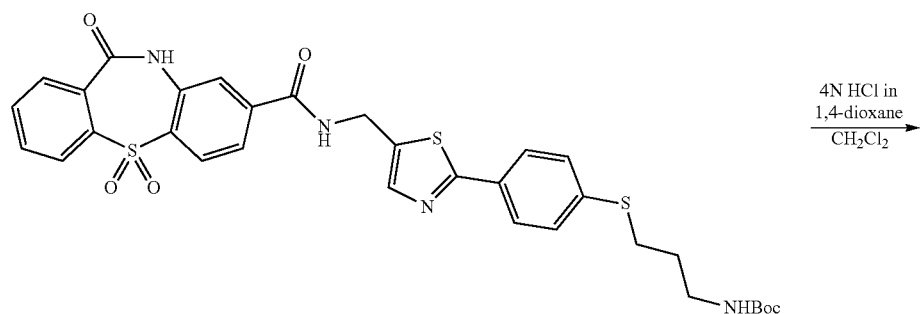
11007-A
4N HCl in
1,4-dioxane
CH$_2$Cl$_2$
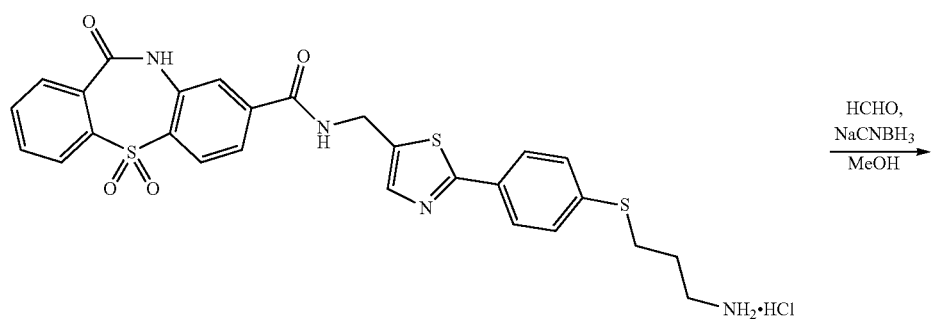
11007
HCHO,
NaCNBH$_3$
MeOH
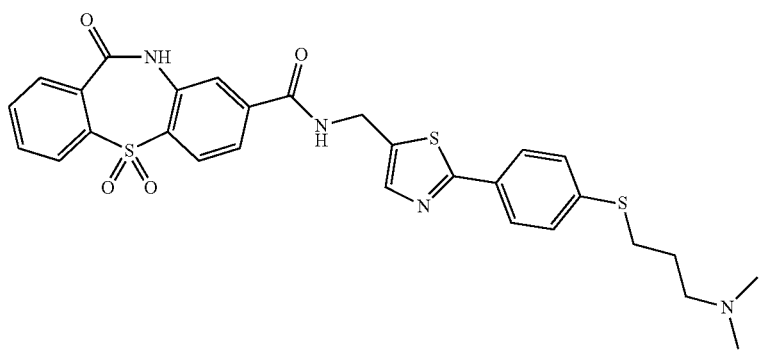
11006

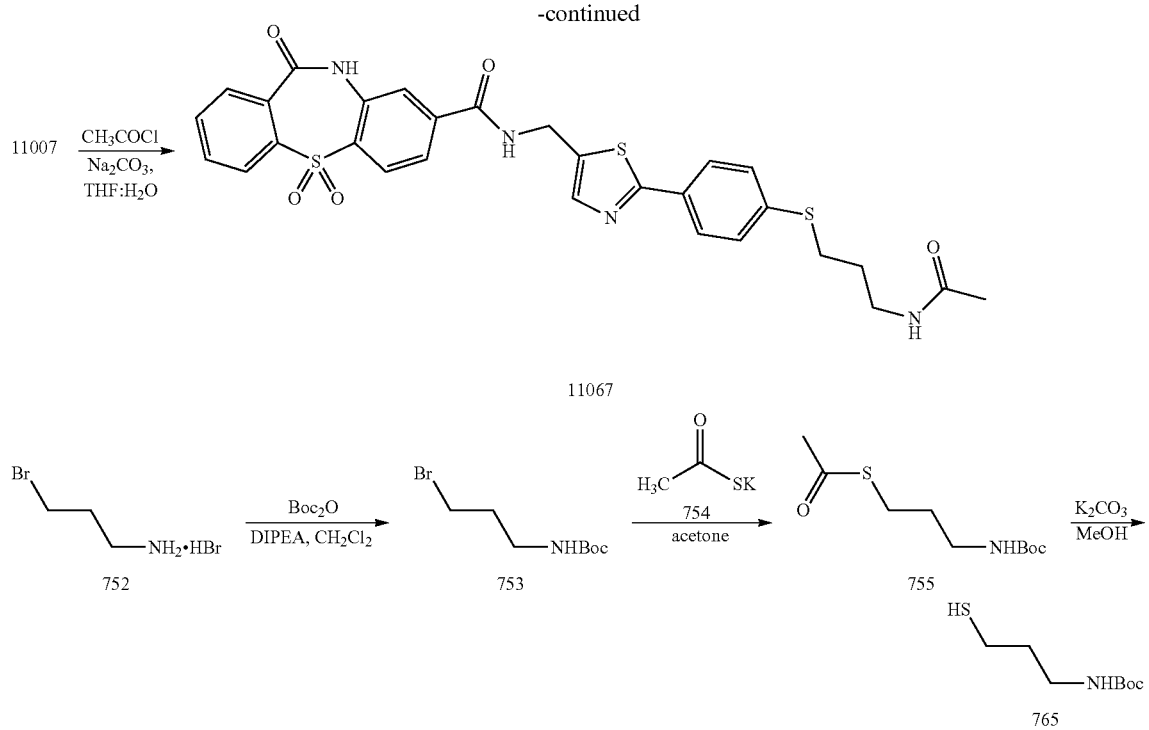

Synthesis of tert-butyl (3-bromopropyl) carbamate (753)

To a stirring solution of 3-bromopropan-1-amine hydrobromide 752 (20 g, 91.35 mmol) in CH$_2$Cl$_2$ (200 mL) under inert atmosphere were added Boc-anhydride (39.80 g, 182.15 mmol), diisopropylethylamine (75 mL, 135.05 mmol) at 0° C.; warmed to RT and stirred for 16 h. The reaction was monitored by TLC; after completion of the reaction, the reaction mixture was diluted with water (500 mL) and extracted with CH$_2$Cl$_2$ (2×500 mL). The combined organic extracts were dried over sodium sulfate, filtered and concentrated in vacuo to obtain the crude. The crude was purified through silica gel flash column chromatography using 5-20% EtOAc/hexanes to afford compound 753 (15 g, 68%) as colorless liquid. TLC: 30% EtOAc/hexanes (R$_f$: 0.8); $^1$H NMR (DMSO-d$_6$, 400 MHz): δ 6.88 (br s, 1H), 3.50 (t, J=6.6 Hz, 2H), 3.09-2.98 (m, 2H), 1.91 (p, J=6.7 Hz, 2H), 1.38 (s, 9H); LC-MS (Agilent 6310 Ion Trap): 91.42%; 138.4 (M$^+$+1) (Des Boc) (Column; Kinetex EVO C-18 (50×3.0 mm, 2.6 um); RT 3.78 min. 2.5 mM Aq. NH$_4$OAc: ACN, 0.8 mL/min).

Synthesis of S-(3-((tert-butoxycarbonyl) amino) propyl) ethanethioate (755)

To a stirring solution of compound 753 (15 g, 63.29 mmol) in acetone (250 mL) under inert atmosphere was added potassium thioacetate 754 (7.2 g, 63.29 mmol) at RT and stirred for 3 h. The reaction was monitored by TLC; after completion of the reaction, the reaction mixture was diluted with water (250 mL) and extracted with EtOAc (2×250 mL). The combined organic extracts were dried over sodium sulfate, filtered and concentrated in vacuo to afford compound 755 (10 g, crude) as colorless syrup. TLC: 30% EtOAc/hexanes (R$_f$: 0.2); $^1$H NMR (400 MHz, DMSO-d$_6$): δ 6.82 (br s, 1H), 2.94 (q, J=6.6 Hz, 2H), 2.80 (t, J=7.2 Hz, 2H), 2.31 (s, 3H), 1.60 (p, J=7.1 Hz, 2H), 1.37 (s, 9H);

Synthesis of tert-butyl (3-mercaptopropyl) carbamate (756)

To a stirring solution of compound 755 (10 g, crude) in MeOH (100 mL) under inert atmosphere was added potassium carbonate (17.76 g, 128.57 mmol) portionwise for 15 min at 0° C.; warmed to RT and stirred for 2 h. The reaction was monitored by TLC; after completion of the reaction, the reaction mixture was diluted with filtered through celite. The filtrate was concentrated in vacuo to afford crude compound 756 (7 g) as pale brown syrup. The crude was carried forward for next step without further purification. TLC: 30% EtOAc/hexanes (R$_f$: 0.7);

Synthesis of tert-butyl (3-((4-(5-((5, 5-dioxido-11-oxo-10, 11-dihydrodibenzo [b, f] [1, 4] thiazepine-8-carboxamido) methyl) thiazol-2-yl) phenyl) thio) propyl) carbamate (11007-A)

To a stirring solution of compound 538 (4 g, 7.21 mmol) in 1, 4-dioxane (40 mL) were added tert-butyl (3-mercaptopropyl) carbamate 756 (4.14 g, 21.64 mmol) cesium carbonate (7.05 g, 21.66 mmol) and potassium iodide (1.19 g, 7.22 mmol) at RT and purged under argon atmosphere for 15 min. To this were added Pd$_2$(dba)$_3$ (661 mg, 0.72 mmol), Xantphos (292 mg, 0.50 mmol) purged under argon atmosphere for 5 min; heated to 110° C. and stirred for 16 h. The reaction was monitored by TLC; after completion of the reaction, the reaction mixture was filtered through celite. The filtrate was concentrated in vacuo to obtain the crude. The crude was purified through silicagel flash column chromatography using 1-5% MeOH/CH$_2$Cl$_2$. The obtained compound was triturated with 5% MeOH/CH$_2$Cl$_2$ (2 mL), n-pentane (5 mL) and further purified by preparative HPLC purification to afford 11007-A (130 mg, 3%) as white solid. TLC: 10% MeOH/CH$_2$Cl$_2$ (R$_f$: 0.4). $^1$H-NMR (DMSO-d$_6$, 400 MHz): δ 11.50 (br s, 1H), 9.46 (t, J=5.7 Hz, 1H), 8.06 (d, J=8.2 Hz, 1H), 7.98 (dd, J=7.8, 1.2 Hz, 2H), 7.90 (td, J=7.5, 1.4 Hz, 1H), 7.87-7.84 (m, 2H), 7.84-7.77 (m, 4H), 7.36 (d, J=8.5 Hz, 2H), 6.89 (t, J=4.7 Hz, 1H), 4.68 (d, J=5.5 Hz, 2H), 3.07-2.96 (m, 4H), 1.70 (p, J=6.9 Hz, 2H), 1.36 (s, 9H); LC-MS: 95.07%; 663.1 (M$^+$+1); (column; Kinetex EVO C-18 (50×3.0 mm, 2.6 um); RT 3.28 min. 2.5 mM Aq. NH$_4$OOCH+5% ACN: ACN+5% 2.5 mM Aq.NH$_4$OOCH, 0.8 mL/min); HPLC (purity): 95.22%; (column; X-select CSH-C18 (150×4.6 mm, 3.5 μm); RT 10.62 min. 0.05% TFA+5% ACN:ACN: +5% 0.05% ACN; 1.0 mL/min, Diluent: DMSO:ACN:water).

Synthesis of N-((2-(4-((3-aminopropyl) thio) phenyl) thiazol-5-yl) methyl)-11-oxo-10, 11-dihydrodibenzo [b, f] [1, 4] thiazepine-8-carboxamide 5, 5-dioxide hydrochloride (11007)

To a stirring solution of 11007-A (200 mg, 0.30 mmol) in CH$_2$Cl$_2$ (20 mL) under inert atmosphere was added 4 N HCl in 1, 4-dioxane (2 mL) at 0° C.; warmed to RT and stirred for 4 h. The reaction was monitored by TLC; after completion of the reaction, the volatiles were removed in vacuo to afford 11007 (160 mg, 88%; HCl salt) as an off-white solid. TLC: 10% MeOH/CH$_2$Cl$_2$ (R$_f$: 0.1); $^1$H-NMR (DMSO-d$_6$, 400 MHz): δ 11.53 (s, 1H), 9.50 (t, J=5.7 Hz, 1H), 8.06 (d, J=8.2 Hz, 1H), 7.98 (dd, J=7.6, 1.1 Hz, 2H), 7.94-7.74 (m, 10H), 7.45-7.38 (m, 2H), 4.68 (d, J=5.6 Hz, 2H), 3.12 (t, J=7.2 Hz, 2H), 2.97-2.83 (m, 2H), 1.88 (p, J=7.3 Hz, 2H); LC-MS: 95.89%; 566.0 (M$^+$+1); (column; Ascentis Express C18, (50×3.0 mm, 2.7 μm); RT 1.88 min. 0.025% Aq. TFA+5% ACN: ACN+5% 0.025% Aq. TFA, 1.2 mL/min); HPLC (purity): 96.17%; (column; X-select CSH C-18 (150× 4.6 mm, 3.5 μm); RT 5.95 min. 0.05% TFA (Aq)+5% ACN: ACN+5% 0.5% TFA (Aq); 1.0 mL/min, Diluent: ACN: water).

Synthesis of N-((2-(4-((3-(dimethylamino) propyl) thio) phenyl)thiazol-5-yl) methyl)-11-oxo-10, 11-dihydrodibenzo [b, f] [1, 4] thiazepine-8-carboxamide 5, 5-dioxide (11006)

To a stirring solution of 11007 (130 mg, 0.21 mmol) in MeOH (10 mL) under inert atmosphere were added paraformaldehyde (32 mg, 1.08 mmol) and sodium cyanoborohydride (68 mg, 1.08 mmol) at 0° C.; warmed to RT and stirred for 16 h. The reaction was monitored by TLC; after completion of the reaction, the reaction mixture was diluted with water (50 mL) and extracted with 10% MeOH/CH$_2$Cl$_2$ (2×50 mL). The combined organic extracts were dried over sodium sulfate, filtered and concentrated in vacuo to obtain the crude. The crude was purified through silica gel column chromatography using 1-4% MeOH/CH$_2$Cl$_2$. The compound obtained was titurated with 5% MeOH/CH$_2$Cl$_2$ (5 mL) to afford 11006 (20 mg, 15%) as an off-white solid. TLC: 10% MeOH/CH$_2$Cl$_2$ (R$_f$: 0.4); $^1$H-NMR (DMSO-d$_6$, 400 MHz): δ 11.51 (br s, 1H), 9.46 (t, J=5.4 Hz, 1H), 8.06 (d, J=8.2 Hz, 1H), 8.01-7.95 (m, 2H), 7.93-7.84 (m, 3H), 7.84-7.77 (m, 4H), 7.38 (d, J=8.5 Hz, 2H), 4.68 (d, J=5.3 Hz, 2H), 3.03 (t, J=7.2 Hz, 2H), 2.38 (t, J=6.3 Hz, 2H), 2.16 (s, 6H), 1.73 (p, J=6.9 Hz, 2H); LC-MS: 98.35%; 593.1 (M$^+$+ 1); (Column; X-select CSH C-18 (150×4.6 mm, 3.5 μm); RT 1.89 min. 0.025% Aq. TFA+5% ACN: ACN+5% 0.025% Aq. TFA, 1.0 mL/min); HPLC (purity): 97.97%; (column; X-select CSH C-18 (150×4.6 mm, 3.5 μm); RT 6.45 min. 0.05% TFA (Aq)+5% ACN: ACN+5% 0.5% TFA (Aq); 1.0 mL/min, Diluent: ACN:water).

Synthesis of N-((2-(4-((3-acetamidopropyl) thio) phenyl) thiazol-5-yl) methyl)-11-oxo-10, 11-dihydrodibenzo [b, f] [1, 4] thiazepine-8-carboxamide 5, 5-dioxide (11067)

To a stirring solution of 11007 (35 mg, 0.058 mmol) in THF:H$_2$O (4:2, 2 mL) were added sodium carbonate (30 mg, 0.29 mmol), acetyl chloride (0.012 mL, 0.17 mmol) at 0° C.; warmed to RT and stirred for 2 h. The reaction was monitored by TLC; after completion of the reaction, the reaction mixture was diluted with water (50 mL) and extracted with EtOAc (2×100 mL). The combined organic extracts were dried over sodium sulfate, filtered and concentrated in vacuo to obtain the crude. The crude was purified through silica gel column chromatography using 3% MeOH/CH$_2$Cl$_2$ to afford 11067 (15 mg, 43%) as white solid. TLC: 5% MeOH/ CH$_2$Cl$_2$ (R$_f$: 0.6); $^1$H-NMR (DMSO-d$_6$, 400 MHz): δ 11.51 (br s, 1H), 9.46 (t, J=5.6 Hz, 1H), 8.06 (d, J=8.2 Hz, 1H), 7.98 (td J=7.5, 1.1 Hz, 2H), 7.93-7.85 (m, 4H), 7.84-7.77 (m, 4H), 7.37 (d, J=8.5 Hz, 2H), 4.68 (d, J=5.5 Hz, 2H), 3.19-3.10 (m, 2H), 3.02 (t, J=7.2 Hz, 2H), 1.79 (s, 3H), 1.71 (p, J=6.9 Hz, 2H); LC-MS: 97.37%; 607.1 (M$^+$+1); (column; Ascentis Express C-18, (50×3.0 mm, 2.7 μm); RT 2.14 min. 0.025% Aq. TFA+5% ACN: ACN+5% 0.025% Aq. TFA, 1.2 mL/min); HPLC (purity): 98.83%; (column; X-select CSH C-18 (150×4.6 mm, 3.5 μm); RT 8.14 min. 0.05% TFA (Aq)+5% ACN: ACN+5% 0.5% TFA (Aq); 1.0 mL/min, Diluent: ACN:water).

Synthesis of 11063

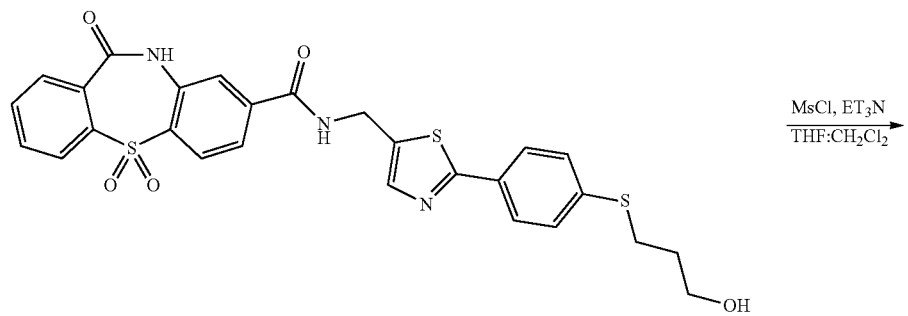

11063-A

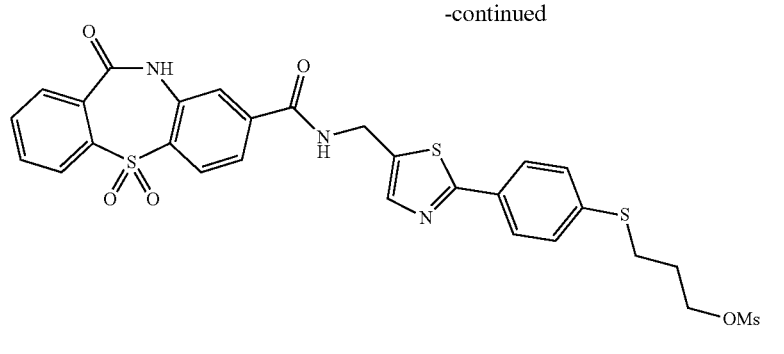 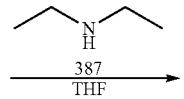

757

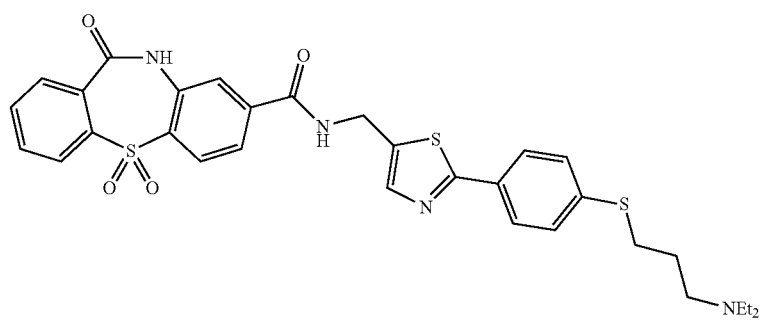

11063

Synthesis of 3-((4-(5-((5, 5-dioxido-11-oxo-10, 11-dihydrodibenzo [b, f] [1, 4] thiazepine-8-carboxamido) methyl) thiazol-2-yl) phenyl) thio) propyl methanesulfonate (757)

To a stirring solution of 1 1063-A (500 mg, 0.88 mmol) in THF: $CH_2Cl_2$ (1:1, 20 mL) under inert atmosphere were added triethylamine (1.2 mL, 8.84 mmol), methanesulfonyl chloride (0.36 mL, 4.40 mmol) at 0° C.; warmed to RT and stirred for 16 h. The reaction was in monitored by TLC; after completion of the reaction, the reaction mixture was diluted with $CH_2Cl_2$ (100 mL) and washed with 10% sodium bicarbonate solution (50 mL). The organic extract was dried over sodium sulfate, filtered and concentrated in vacuo to afford mixture of mono and di-compound 757 (1.4 g) as brown thick syrup. TLC: 5% MeOH/$CH_2Cl_2$ ($R_f$: 0.7, 0.8); LC-MS: 39.97%; 644.0 ($M^+$+1) (monomesylated mass), 42.82%; 722.0 ($M^+$+1) (dimesylated mass); (column; Ascentis Express C-18, (50×3.0 mm, 2.7 μm); RT: 2.49, 0.58 min. 0.025% Aq. TFA+5% ACN: ACN+5% 0.025% Aq. TFA, 1.2 mL/min);

Synthesis of N-((2-(4-((3-(diethylamino) propyl) thio) phenyl) thiazol-5-yl) methyl)-11-oxo-10, 11-dihydrodibenzo [b, f] [1, 4] thiazepine-8-carboxamide 5, 5-dioxide (11063)

To a stirring solution of 3-((4-(5-((5, 5-dioxido-11-oxo-10, 11-dihydrodibenzo [b, f] [1, 4] thiazepine-8-carboxamido) methyl) thiazol-2-yl) phenyl) thio) propyl methanesulfonate 1 (120 mg, mixture of compounds) in THF (1 mL) in a sealed tube was added diethylamine 387 (1 mL, 8 vol) at RT and heated to 75° C. and stirred for 16 h. The reaction was monitored by TLC; after completion the volatiles were removed in vacuo to obtain the crude. The crude was purified through silica gel (100-200 mesh) column chromatography using 4-5% MeOH/$CH_2Cl_2$ to afford 11063 (15 mg, 13%) as an off-white solid. TLC: 10% MeOH/$CH_2Cl_2$ ($R_f$. 0.4); $^1$H-NMR (DMSO-$d_6$, 400 MHz): δ 11.51 (br s, 1H), 9.46 (t, J=5.6 Hz, 1H), 8.06 (d, J=8.2 Hz, 1H), 8.01-7.95 (m, 2H), 7.93-7.74 (m, 7H), 7.37 (d, J=8.4 Hz, 2H), 4.68 (d, J=5.4 Hz, 2H), 3.04 (t, J=7.0 Hz, 2H), 2.52-2.40 (m, 6H), 1.70 (quin, J=7.0 Hz, 2H), 0.94 (t, J=7.1 Hz, 6H); LC-MS: 97.40%; 621.1 ($M^+$+1); (column; Ascentis Express C18, (50×3.0 mm, 2.7 μm); RT 2.80 min. 0.025% Aq. TFA+5% ACN: ACN+5% 0.025% Aq. TFA, 1.2 mL/min). HPLC (purity): 98.67%; (column; X select CSH C-18 (150×4.6 mm, 3.5 μm); RT 6.14 min. 0.05% TFA+5% ACN: ACN+5% 0.05% TFA; 1.0 mL/min, Diluent: water: DMSO:ACN).

Synthesis of 11064

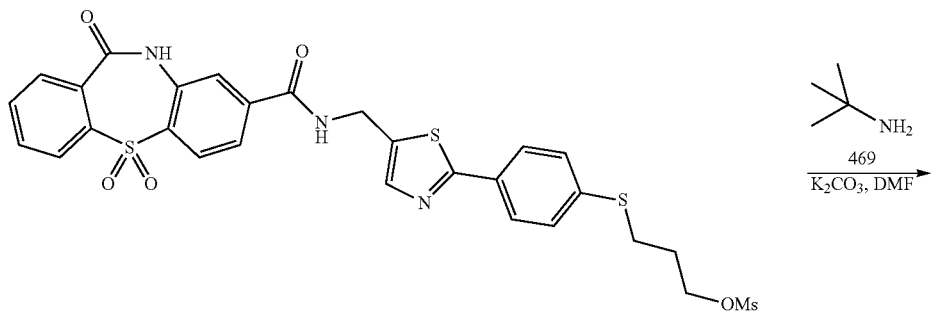

757

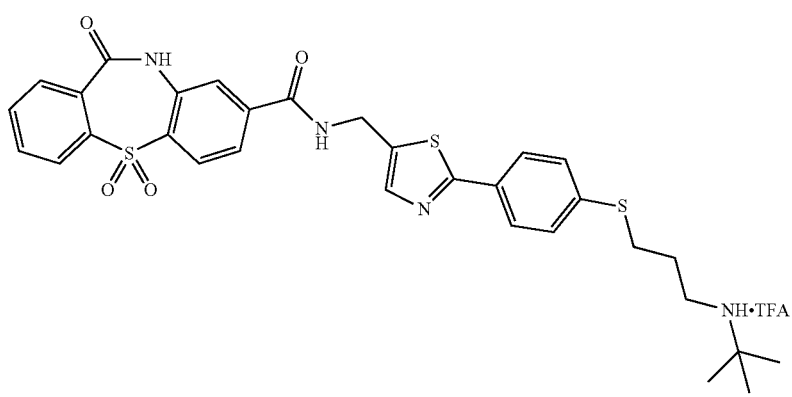

11064

Synthesis of N-((2-(4-((3-(tert-butylamino) propyl) thio) phenyl) thiazol-5-yl) methyl)-11-oxo-10, 11-dihydrodibenzo [b, f] [1, 4] thiazepine-8-carboxamide 5, 5-dioxide TFA Salt (11064)

To a stirring solution of compound 757 (300 mg, mixture) in DMF (8 mL) under inert atmosphere was added potassium carbonate (128 mg, 0.93 mmol), 2-methylpropan-2-amine 469 (0.46 mL, 4.65 mmol) in a sealed tube at RT; heated to 80° C. and stirred for 16 h. The reaction was monitored by TLC; after completion of the reaction, the reaction mixture was diluted with water (100 mL) and extracted with EtOAc (2×50 mL). The combined organic extracts were dried over sodium sulfate and concentrated in vacuo to obtain the crude. The crude was purified through silica gel column chromatography using 2-5% MeOH/ $CH_2Cl_2$ and further purified by preparative HPLC purification to afford 11064 (25 mg, 9%) as an off-white solid. TLC: 5% MeOH/$CH_2Cl_2$ ($R_f$: 0.3); $^1$H-NMR (DMSO-$d_6$, 400 MHz): δ 11.52 (s, 1H), 9.47 (t, J=5.8 Hz, 1H), 8.29-8.16 (m, 2H), 8.05 (d, J=8.3 Hz, 1H), 8.00-7.94 (m, 2H), 7.89 (td, J=7.5, 1.6 Hz, 1H), 7.87-7.77 (m, 5H), 7.42 (d, J=8.7 Hz, 2H), 4.67 (d, J=5.4 Hz, 2H), 3.13 (t, J=7.2 Hz, 2H), 3.04-2.94 (m, 2H), 1.91-1.83 (m, 2H), 1.24 (s, 9H); LC-MS: 98.77%; 621.1 (M$^+$+1); (column; Ascentis Express C18, (50×3.0 mm, 2.7 μm); RT 1.97 min. 0.025% Aq.TFA+5% ACN: ACN+5% 0.025% Aq. TFA, 1.2 mL/min); HPLC (purity): 99.27%; (column; X select CSH C-18 (150×4.6 mm, 3.5 μm); RT 6.29 min. 0.05% TFA+5% ACN: ACN+5% 0.05% TFA; 1.0 mL/min, Diluent: ACN: DMSO).

Synthesis of 11065

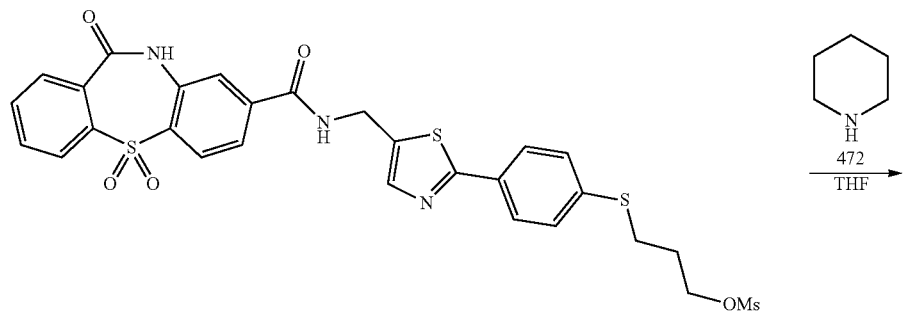

757

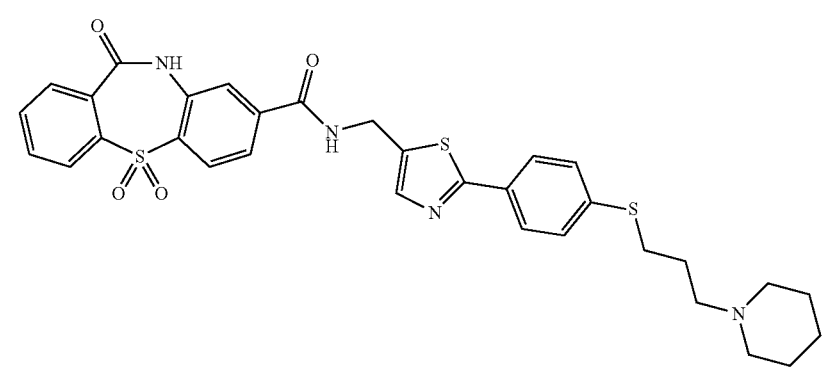

11065

Synthesis of 11-oxo-N-((2-(4-((3-(piperidin-1-yl) propyl) thio) phenyl) thiazol-5-yl) methyl)-10, 11-dihydrodibenzo [b, f] [1, 4] thiazepine-8-carboxamide 5, 5-dioxide (11065)

To a stirring solution of 3-((4-(5-((5, 5-dioxido-11-oxo-10, 11-dihydrodibenzo [b, f] [1, 4] thiazepine-8-carboxamido) methyl) thiazol-2-yl) phenyl) thio) propyl methanesulfonate 757 (300 mg, mixture of compounds) in THF (5 mL) in a sealed tube was added piperidine 472 (2 mL, 6.6 vol) at RT and heated to 70° C. and stirred for 16 h. The reaction was monitored by TLC; after completion the volatiles were removed in vacuo to obtain the crude. The crude was either purified through basic alumina column chromatography using 1-2% MeOH/CH$_2$Cl$_2$ to obtain the crude. The crude was diluted with EtOAc (50 mL), washed with water (50 mL). The organic extract was dried over sodium sulfate, filtered and concentrated in vacuo and triturated with EtOAc (5 mL) to afford 11065 (20 mg, 7%) as an off-white solid. TLC: 5% MeOH/CH$_2$Cl$_2$ (R$_f$: 0.4); $^1$H-NMR (DMSO-d$_6$, 400 MHz): δ 11.51 (br s, 1H), 9.46 (t, J=5.6 Hz, 1H), 8.06 (d, J=8.3 Hz, 1H), 7.98 (td, J=1.3, 7.5, 1.3 Hz, 2H), 7.90 (td, J=7.4, 1.4 Hz, 1H), 7.87-7.76 (m, 6H), 7.38 (d, J=8.5 Hz, 2H), 4.68 (d, J=5.6 Hz, 2H), 3.03 (t, J=7.2 Hz, 2H), 2.42-2.21 (m, 6H), 1.81-1.69 (m, 2H), 1.77-1.72 (m, 2H), 1.52-1.44 (m, 4H), 1.42-1.29 (m, 2H); LC-MS: 98.99%; 633.1 (M$^+$+1); (column; Ascentis Express C18, (50×3.0 mm, 2.7 μm); RT 1.98 min. 0.025% Aq. TFA+5% ACN: ACN+5% 0.025% Aq. TFA, 1.2 mL/min). HPLC (purity): 96.51%; (column; X select CSH C-18 (150×4.6 mm, 3.5 μm); RT 6.17 min. 0.05% TFA+5% ACN: ACN+5% 0.05% TFA; 1.0 mL/min, Diluent: water:DMSO:ACN).

Synthesis of 11066

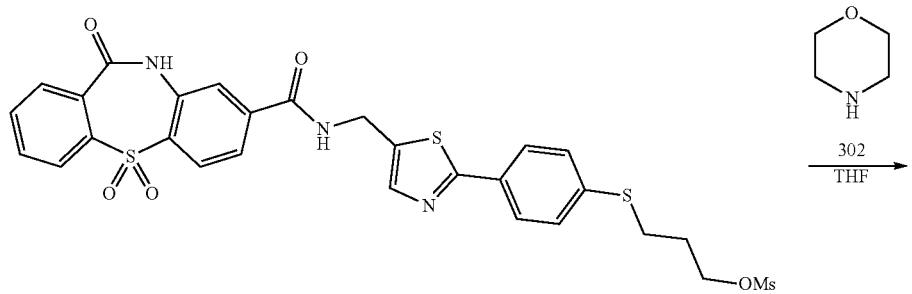

757

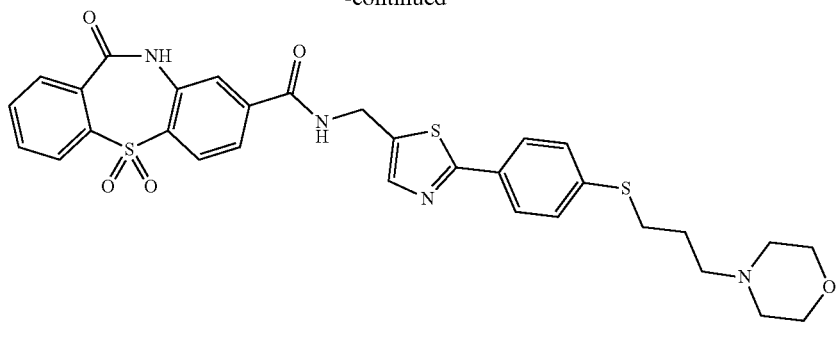

11066

Synthesis of N-((2-(4-((3-morpholinopropyl) thio) phenyl) thiazol-5-yl) methyl)-11-oxo-10, 11-dihydrodibenzo [b, f] [1, 4] thiazepine-8-carboxamide 5, 5-dioxide (11066)

To a stirring solution of 3-((4-(5-(((5, 5-dioxido-11-oxo-10, 11-dihydrodibenzo [b, f] [1, 4] thiazepine-8-carboxamido) methyl) thiazol-2-yl) thio) propyl methanesulfonate 757 (300 mg, mixture of compounds) in THF (5 mL) in a sealed tube was added morpholine (2 mL, 6.6 vol) at RT and heated to 70° C. and stirred for 16 h. The reaction was monitored by TLC; after completion the volatiles were removed in vacuo to obtain the crude. The crude was purified through basic alumina column chromatography using 1-2% MeOH/CH$_2$Cl$_2$ to obtain the crude. The crude was diluted with water (10 mL), washed with water (50 mL). The organic extract was dried over sodium sulfate and stirred for 16 h. The obtained solid was filtered, washed with n-pentane (5 mL) and dried in vacuo to afford 11066 (72 mg, 24%) as an off-white solid. TLC: 5% MeOH/CH$_2$Cl$_2$ (R$_f$: 0.3); $^1$H-NMR (DMSO-d$_6$, 400 MHz): δ 11.52 (s, 1H), 9.46 (t, J=5.7 Hz, 1H), 8.06 (d, J=8.3 Hz, 1H), 7.98 (td, J=7.5, 1.1 Hz, 2H), 7.93-7.84 (m, 3H), 7.84-7.76 (m, 4H), 7.38 (d, J=8.4 Hz, 2H), 4.68 (d, J=5.5 Hz, 2H), 3.55 (t, J=4.6 Hz, 4H), 3.05 (t, J=7.2 Hz, 2H), 2.32 (d, J=4.0 Hz, 5H), 1.75 (p, J=7.0 Hz, 2H); LC-MS: 99.08%; 635.1 (M$^+$+1); (column; Ascentis Express C18, (50×3.0 mm, 2.7 μm); RT 1.91 min. 0.025% Aq. TFA+5% ACN: ACN+5% 0.025% Aq. TFA, 1.2 mL/min). HPLC (purity): 99.03%; (column; X select CSH C-18 (150×4.6 mm, 3.5 μm); RT 5.91 min. 0.05% TFA+5% ACN: ACN+5% 0.05% TFA; 1.0 mL/min, Diluent: ACN: water).

Synthesis of 11032, 11063-A, 11063-B

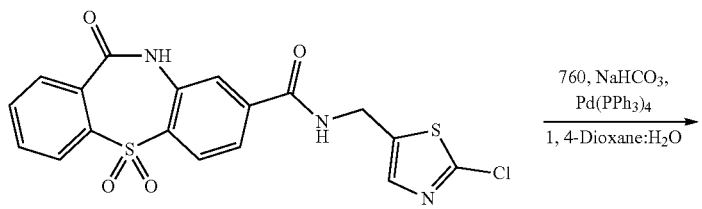

535

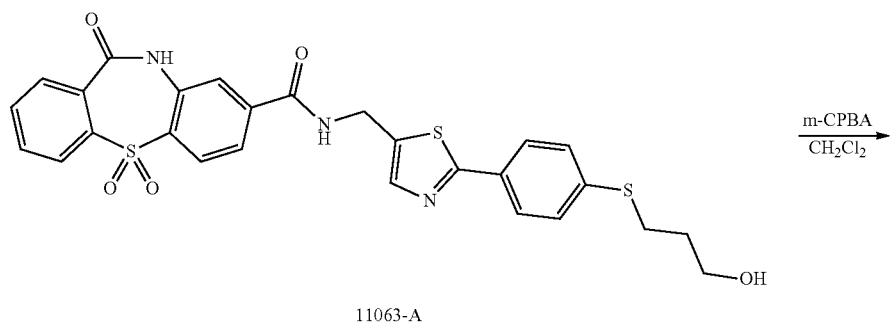

11063-A

-continued
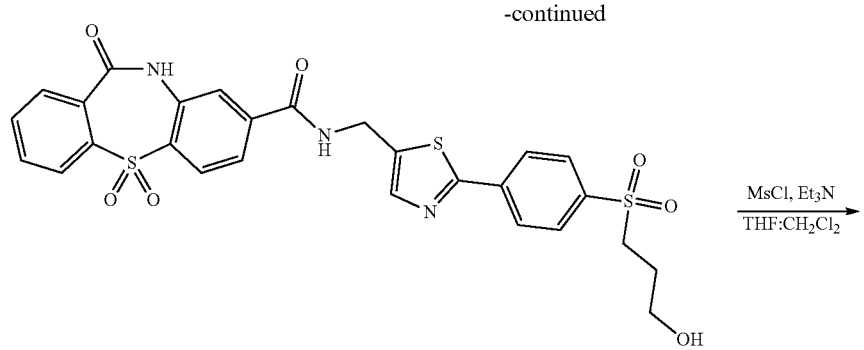
11063-B
MsCl, Et₃N
─────────→
THF:CH₂Cl₂
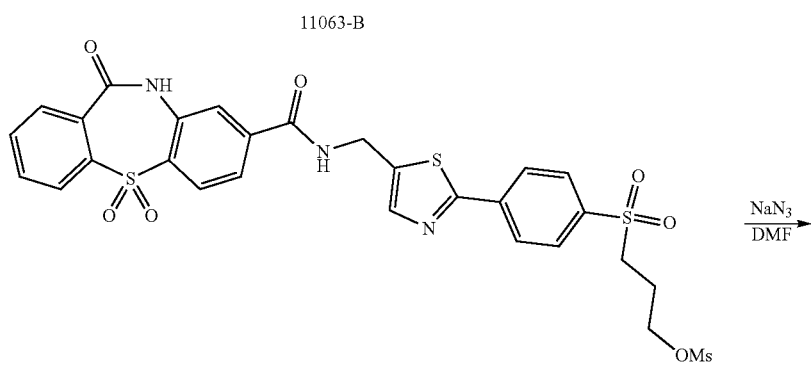
761
NaN₃
─────→
DMF
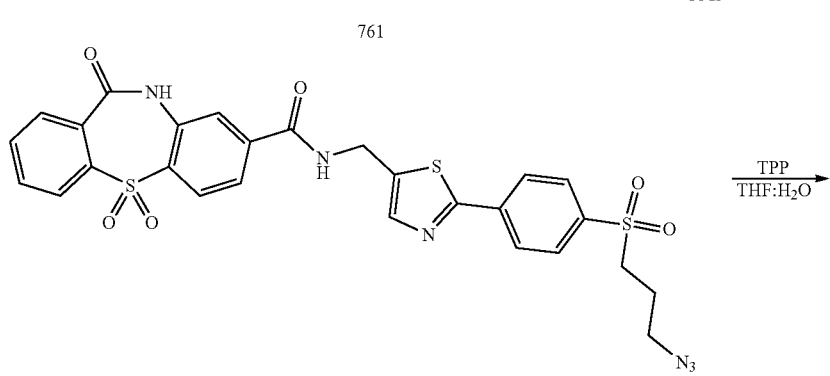
762
TPP
─────→
THF:H₂O
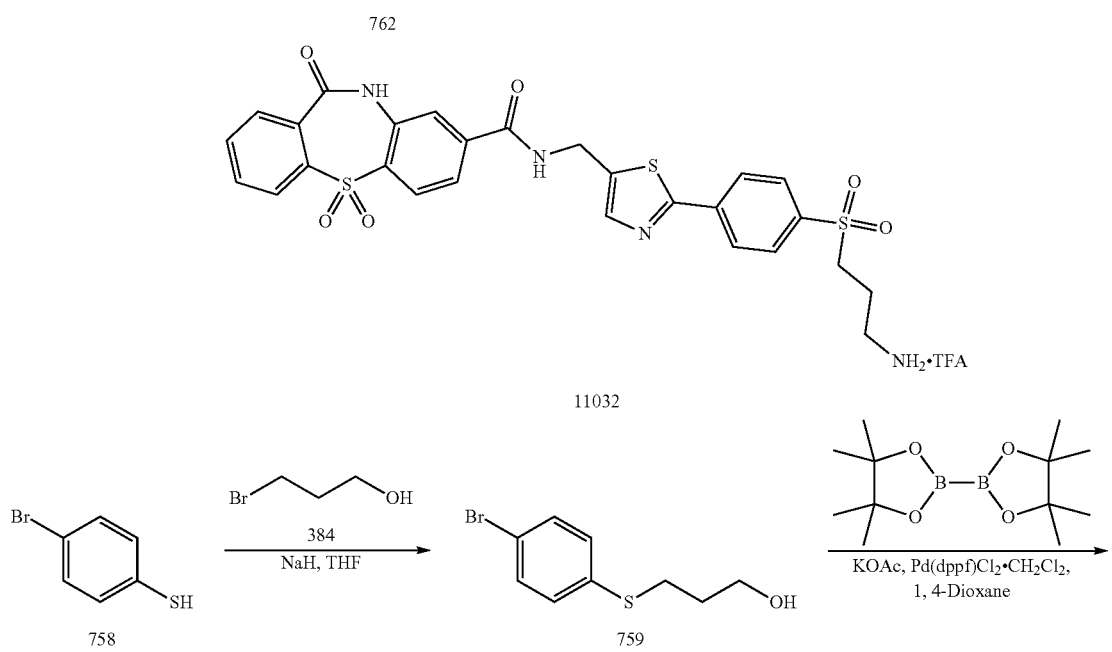
11032

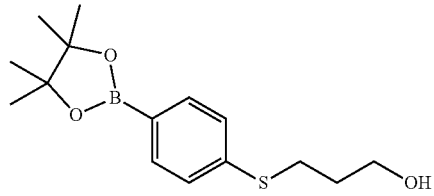

760

Synthesis of 3-((4-bromophenyl) thio) propan-1-ol (759)

To a stirring solution of 4-bromobenzenethiol 758 (5 g, 26.45 mmol) in THF (100 mL) under argon atmosphere was added sodium hydride (60%, 1.9 g, 79.16 mmol) portion wise for 10 min at 0° C.; warmed to RT and stirred for 1 h. To this was added 3-bromopropan-1-ol 384 (4.3 g, 31.74 mmol) at 0° C.; warmed to RT and stirred for 16 h. The reaction was monitored by TLC; after completion of the reaction, the reaction mixture was quenched with ice-cold water (50 mL) and extracted with EtOAc (2×150 mL), washed with water (100 mL), brine (100 mL). The organic extract was dried over sodium sulfate, filtered and concentrated in vacuo to obtain the crude. The crude was purified through silica gel column chromatography using 20% EtOAc/hexanes to afford compound 759 (4.5 g, 69%) as colorless thick syrup. TLC: 30% EtOAc/hexanes ($R_f$: 0.4); $^1$H-NMR (DMSO-$d_6$, 400 MHz): δ 7.48 (d, J=8.1 Hz, 2H), 7.26 (d, J=8.7 Hz, 2H), 4.55 (t, J=5.2 Hz, 1H), 3.51-3.45 (m, 2H), 3.00 (t, J=7.2 Hz, 2H), 1.70 (p, J=6.7 Hz, 2H);

Synthesis of 3-((4-(4, 4, 5, 5-tetramethyl-1, 3, 2-dioxaborolan-2-yl) phenyl) thio) propan-1-ol (760) (SAP-MA1623-71)

To a stirring solution of compound 759 (3 g, 12.14 mmol) in 1, 4-dioxane (90 mL) under inert atmosphere were added bispinacolato diboron (4.17 g, 16.51 mmol), potassium acetate (3.6 g, 36.43 mmol) at RT and purged under argon atmosphere for 15 min; to this was added Pd(dppf)Cl$_2$.CH$_2$Cl$_2$ (991 mg, 1.21 mmol) and purged under argon atmosphere for 5 min, heated to 100° C. and stirred for 16 h. The reaction was monitored by TLC; after completion of the reaction, the volatiles were concentrated in vacuo to obtain the crude. The crude was purified through silica gel column chromatography using 10-30% EtOAc/hexanes to afford compound 760 (4.7 g, 43%) as colorless syrup. TLC: 30% EtOAc/hexanes ($R_f$: 0.3); $^1$H-NMR (DMSO-$d_6$, 400 MHz): δ 7.56 (d, J=8.3 Hz, 2H), 7.27 (d, J=8.3 Hz, 2H), 4.55 (t, J=5.2 Hz, 1H), 3.51-3.45 (m, 2H), 3.01 (t, J=7.3 Hz, 2H), 1.78-1.61 (m, 2H), 1.27 (s, 12H);

Synthesis of N-((2-(4-((3-hydroxypropyl) thio) phenyl) thiazol-5-yl) methyl)-11-oxo-10, 11-dihydrodibenzo [b, f] [1, 4] thiazepine-8-carboxamide 5, 5-dioxide (11063-A)

To a stirring solution of N-((2-chlorothiazol-5-yl) methyl)-11-oxo-10, 11-dihydrodibenzo [b, f] [1, 4] thiazepine-8-carboxamide 5, 5-dioxide 535 (2.5 g, 5.77 mmol) in 1, 4-dioxane: H$_2$O (2:1, 113 mL) were added 2 3-((4-(4, 4, 5, 5-tetramethyl-1, 3, 2-dioxaborolan-2-yl) phenyl) thio) propan-1-ol 760 (3.4 g, 11.54 mmol), sodium bicarbonate (1.94 g, 23.09 mmol) and purged under argon atmosphere for 30 min. To this was added Pd(PPh$_3$)$_4$ (560 mg, 0.48 mmol) and purged under argon atmosphere for 5 min at RT; heated to 90° C. and stirred for 16 h. The reaction was monitored by TLC and LC-MS; after completion the reaction, the reaction mixture was diluted with water (100 mL) and extracted with EtOAc (2×100 mL). The combined organic extracts were dried over sodium sulfate, filtered and concentrated in vacuo to obtain the crude. The crude was purified through silica gel column chromatography using 1-6% MeOH/CH$_2$Cl$_2$, triturated with 5% MeOH/CH$_2$Cl$_2$ (10 mL), n-pentane (20 mL) and dried in vacuo to afford 11063-A (3 g, 43%) as an off-white solid. TLC: 5% MeOH/CH$_2$Cl$_2$ ($R_f$: 0.4); $^1$H NMR (DMSO-$d_6$, 400 MHz): δ 11.51 (s, 1H), 9.46 (t, J=5.8 Hz, 1H), 8.06 (d, J=8.3 Hz, 1H), 8.02-7.95 (m, 2H), 7.92-7.85 (m, 3H), 7.84-7.76 (m, 4H), 7.37 (d, J=8.7 Hz, 2H), 4.68 (d, J=5.6 Hz, 2H), 4.57 (t, J=5.2 Hz, 1H), 3.54-3.47 (m, 2H), 3.09-3.02 (m, 2H), 1.78-1.70 (m, 2H); LC-MS: 94.81%; 566.1 (M$^+$+1); (column; Ascentis Express C18, (50×3.0 mm, 2.7 μm); RT 2.30 min. 0.025% Aq. TFA+5% ACN: ACN+5% 0.025% Aq. TFA, 1.2 mL/min); HPLC (purity): 98.73%; (column; X-Select CSH-C-18 (150×4.6 mm, 3.5 μm); RT 8.25 min. 0.05% TFA (Aq)+5% ACN: ACN+5% 0.05% TFA (Aq); 1.0 mL/min, Diluent: ACN: DMSO).

Synthesis of N-((2-(4-((3-hydroxypropyl) sulfonyl) phenyl) thiazol-5-yl) methyl)-11-oxo-10, 11-dihydrodibenzo [b, f] [1, 4] thiazepine-8-carboxamide 5, 5-dioxide (11063-B)

To a stirring solution of 11063-A (200 mg, 0.35 mmol) in CH$_2$Cl$_2$ (10 mL) under argon atmosphere was added m-chloro perbenzoic acid (73 mg, 0.42 mmol) at 0° C.; warmed to RT and stirred for 30 min. The reaction was monitored by TLC; after completion of the reaction, the reaction mixture was diluted with water (100 mL), aqueous ammonia (20 mL) and extracted with 10% MeOH/CH$_2$Cl$_2$ (2×100 mL). The combined organic extracts were dried over sodium sulfate, filtered and concentrated in vacuo to obtain the crude. The crude was purified through silica gel column chromatography using 1-5% MeOH/CH$_2$Cl$_2$, triturated with 10% MeOH/CH$_2$Cl$_2$ and dried in vacuo to afford 11063-B (60 mg, 28%) as an off-white solid. TLC: 10% MeOH/CH$_2$Cl$_2$ ($R_f$: 0.4); $^1$H NMR (DMSO-$d_6$, 400 MHz): δ 11.65 (br s, 1H), 9.62 (t, J=5.7 Hz, 1H), 8.24 (d, J=8.7 Hz, 2H), 8.16 (d, J=8.3 Hz, 1H), 8.11-8.04 (m, 4H), 8.03-7.90 (m, 5H), 4.82 (d, J=5.5 Hz, 2H), 4.71 (t, J=5.3 Hz, 1H), 3.50 (q, J=6.1 Hz, 2H), 3.46-3.42 (m, 2H), 1.83-1.73 (m, 2H); LC-MS: 98.25%; 596.1 (M−1)$^+$; (column; Kinetex EVO C-18 (50×3.0 mm, 2.6 um); RT 2.28 min. 2.5 mM Aq. NH$_4$OOCH+5% ACN: ACN+5% 2.5 mM Aq.NH$_4$OOCH, 0.8 mL/min); HPLC (purity): 98.97%; (column; X-Select CSH-C-18 (150×4.6 mm, 3.5 μm); RT 8.25 min. 0.05% TFA (Aq)+5% ACN: ACN+5% 0.05% TFA (Aq); 1.0 mL/min, Diluent: ACN:H$_2$O:DMSO).

Synthesis of 3-((4-(5-((5, 5-dioxido-11-oxo-10, 11-dihydrodibenzo [b, f] [1, 4] thiazepine-8-carboxamido) methyl) thiazol-2-yl) phenyl) sulfonyl) propyl methanesulfonate (761)

To a stirring solution of N-((2-(4-((3-hydroxypropyl) sulfonyl) phenyl) thiazol-5-yl) methyl)-11-oxo-10, 11-dihydrodibenzo [b, f] [1, 4] thiazepine-8-carboxamide 5, 5-dioxide 11063-B (350 mg, 0.58 mmol) in THF: $CH_2Cl_2$ (1:1, 16 mL) under inert atmosphere were added triethylamine (6 mL, 41.58 mmol), methanesulfonyl chloride (1.2 mL, 14.73 mmol) at 0° C.; warmed to RT and stirred for 16 h. The reaction was monitored by TLC; after completion of the reaction, the reaction mixture was diluted with $CH_2Cl_2$ (100 mL) and washed with water (75 mL). The organic extract was dried over sodium sulfate, filtered and concentrated in vacuo to afford crude compound 761 (450 mg) as colorless liquid. The crude was carried forward for next step without further purification. TLC: 30% EtOAc/hexanes ($R_f$: 0.8);

Synthesis of N-((2-(4-((3-azidopropyl) sulfonyl) phenyl) thiazol-5-yl) methyl)-11-oxo-10, 11-dihydrodibenzo [b, f] [1, 4] thiazepine-8-carboxamide 5, 5-dioxide (762)

To a stirring solution of compound 761 (450 mg, crude) in DMF (5 mL) under inert atmosphere was added sodium azide (129 mg, 1.99 mmol) at RT and stirred for 16 h. The reaction was monitored by TLC; after completion of the reaction, the reaction mixture was diluted with EtOAc (100 mL) washed with water (100 mL), brine (50 mL). The organic extract was dried over sodium sulphate, filtered and concentrated in vacuo to afford crude compound 762 (320 mg) as colorless sticky solid. The crude was carried forward for next step without further purification TLC: 20% EtOAc/ hexanes ($R_f$: 0.4);

Synthesis of N-((2-(4-((3-aminopropyl) sulfonyl) phenyl) thiazol-5-yl) methyl)-11-oxo-10, 11-dihydrodibenzo [b, f] [1, 4] thiazepine-8-carboxamide 5, 5-dioxide TFA salt (11032)

To a stirring solution of compound 762 (320 mg, crude) in THF:$H_2O$ (4:1, 10 mL) was added triphenyl phosphine (134 mg, 0.51 mmol) at RT and stirred for 16 h. The reaction was monitored by TLC; after completion of the reaction; the volatiles were removed in vacuo to obtain the crude amine (250 mg crude). The crude was purified by preparative HPLC purification to afford 11032 (15 mg, 4.6%) as an off-white solid. TLC: 5% MeOH/$CH_2Cl_2$ ($R_f$: 0.3); $^1$H NMR (DMSO-$d_6$, 400 MHz): δ 11.53 (s, 1H), 9.53 (t, J=5.8 Hz, 1H), 8.17 (d, J=8.7 Hz, 2H), 8.06 (d, J=8.3 Hz, 1H), 8.00-7.89 (m, 6H), 7.88-7.79 (m, 3H), 7.63 (br s, 3H), 4.72 (d, J=5.5 Hz, 2H), 3.50-3.44 (m, 2H), 2.91-2.83 (m, 2H), 1.87-1.80 (m, 2H); LC-MS: 99.29%; 597.1 (M$^+$+1); (column; Ascentis Express C18, (50×3.0 mm, 2.7 µm); RT 1.79 min. 0.025% Aq. TFA+5% ACN: ACN+5% 0.025% Aq. TFA, 1.2 mL/min). HPLC (purity): 98.76%; (column; X select CSH C-18 (150×4.6 mm, 3.5 µm); RT 5.50 min. 0.05% TFA+5% ACN: ACN+5% 0.05% TFA; 1.0 mL/min, Diluent: DMSO:ACN:water).

Synthesis of 11033

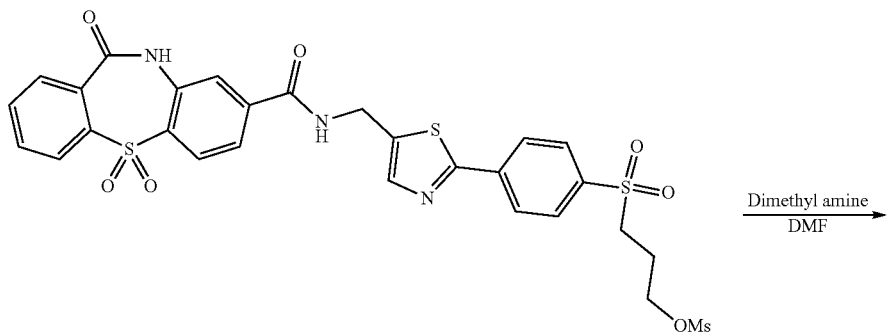

761

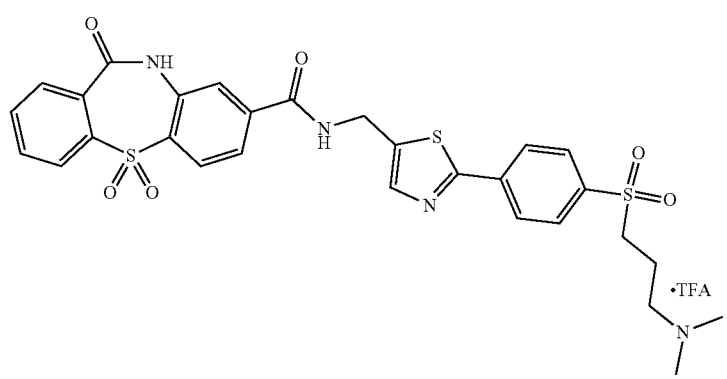

11033

Synthesis of N-((2-(4-((3-(dimethylamino) propyl) sulfonyl) phenyl) thiazol-5-yl) methyl)-11-oxo-10, 11-dihydrodibenzo [b, f] [1, 4] thiazepine-8-carboxamide 5, 5-dioxide TFA Salt (11033)

To a stirring solution of 3-((4-(5-((5, 5-dioxido-11-oxo-10, 11-dihydrodibenzo [b, f] [1, 4] thiazepine-8-carboxamido) methyl) thiazol-2-yl) phenyl) sulfonyl) propyl methanesulfonate 761 (250 mg, 0.37 mmol) in DMF (1 mL) in a sealed tube was added 2 M dimethylamine in THF (20 mL, 31.11 mmol) at RT and heated to 70° C. and stirred for 16 h. The reaction was monitored by TLC; after completion the volatiles were removed in vacuo to obtain the crude. The crude was either purified through silica gel column chromatography using 5-10% MeOH/CH$_2$Cl$_2$ and further purified by preparative HPLC purification. The compound obtained was lyophilized for 16 h to afford 11033 (20 mg, 9%) as an off-white solid. TLC: 5% MeOH/CH$_2$Cl$_2$ (R$_f$: 0.3); $^1$H NMR (DMSO-d$_6$, 400 MHz): δ 11.53 (s, 1H), 9.53 (t, J=5.8 Hz, 1H), 9.29 (br s, 1H), 8.17 (d, J=8.5 Hz, 2H), 8.06 (d, J=8.3 Hz, 1H), 8.01-7.94 (m, 4H), 7.93-7.80 (m, 5H), 4.72 (d, J=5.6 Hz, 2H), 3.47-3.42 (m, 2H), 3.11 (t, J=6.8 Hz, 2H), 2.74 (s, 6H), 1.99-1.89 (m, 2H); LC-MS: 97.65%; 624.1 (M$^+$+1); (column; Ascentis Express C18, (50×3.0 mm, 2.7 μm); RT 1.79 min. 0.025% Aq. TFA+5% ACN: ACN+5% 0.025% Aq. TFA, 1.2 mL/min). HPLC (purity): 99.70%; (column; X select CSH C-18 (150×4.6 mm, 3.5 μm); RT 5.59 min. 0.05% TFA+5% ACN: ACN+5% 0.05% TFA; 1.0 mL/min, Diluent: DMSO:ACN:water)

Synthesis of 1654

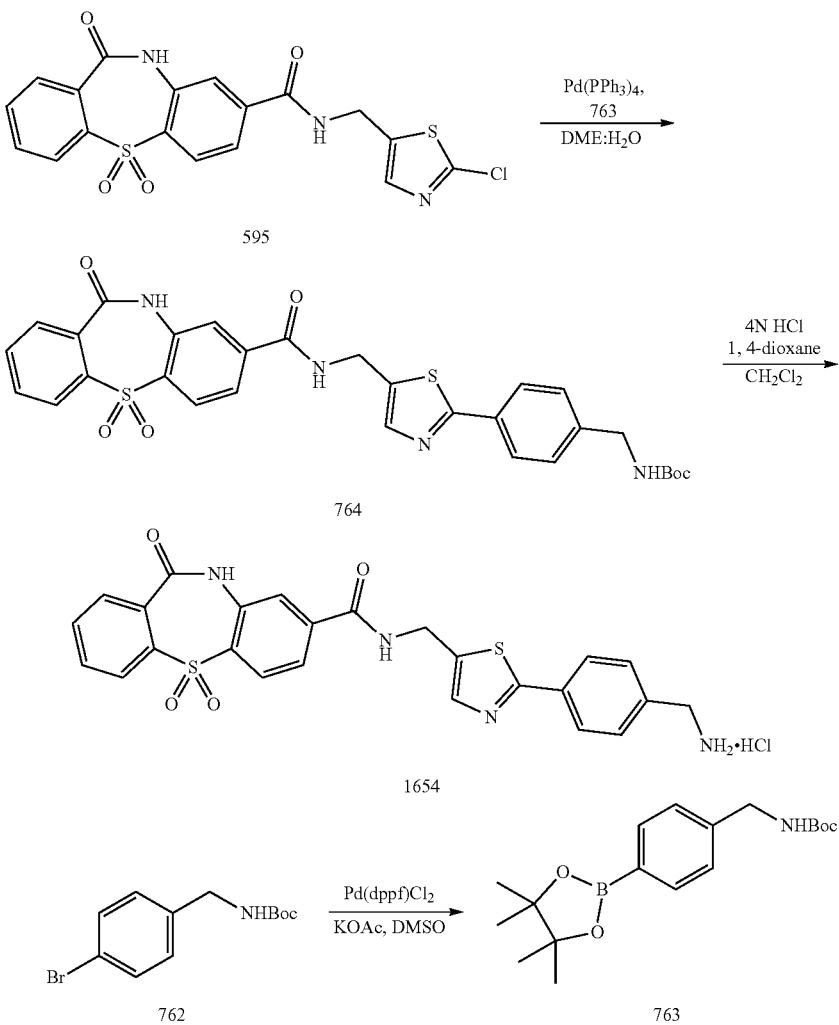

Synthesis of tert-butyl (4-(4, 4, 5, 5-tetramethyl-1, 3, 2-dioxaborolan-2-yl) benzyl) carbamate (763)

To a stirring solution of tert-butyl (4-bromobenzyl) carbamate 762 (1 g, 3.49 mmol) in DMSO (20 mL) under inert atmosphere were added bispinacolato diboron (1.06 g, 4.19 mmol), potassium acetate (1.02 g, 10.48 mmol) at RT and stirred under argon atmosphere for 30 min, added Pd(dppf)$_2$Cl$_2$ (255 mg, 0.35 mmol) and heated to 90-100° C. and stirred for 16 h. The reaction was monitored by TLC; after completion of the reaction, the reaction mixture was diluted with water (100 mL) extracted with EtOAc (2×100 mL). The combined organic extracts were dried over sodium sulphate, filtered and concentrated in vacuo obtain the crude. The crude was purified through silica gel column chromatography using 10% EtOAc/hexanes to afford compound 763

(500 mg, 43%). TLC: 20% EtOAc/hexanes ($R_f$ 0.8); $^1$H NMR (DMSO-$d_6$, 400 MHz): δ 7.62 (d, J=7.8 Hz, 2H), 7.38 (t, J=5.5 Hz, 1H), 7.24 (d, J=7.9 Hz, 2H), 4.13 (d, J=6.2 Hz, 2H), 1.39 (s, 9H), 1.28 (s, 12H).

Synthesis of tert-butyl (4-(5-((5, 5-dioxido-11-oxo-10, 11-dihydrodibenzo [b, f] [1, 4] thiazepine-8-carboxamido) methyl) thiazol-2-yl) benzyl) carbamate (764)

To a stirring solution of compound 763 (150 mg, 0.34 mmol) in 1, 2 dimethoxy ethane: $H_2O$ (4:1, 5 mL) were added (4-hydroxyphenyl) boronic acid 762 (230 mg, 0.69 mmol), sodium carbonate (128 mg, 1.21 mmol) and purged under argon atmosphere for 30 min. To this was added Pd(PPh$_3$)$_4$ (40 mg, 0.034 mmol) at RT; heated to 100° C. and stirred for 16 h. The reaction was monitored by TLC; after completion the reaction mixture was diluted with water (100 mL) and extracted with 10% MeOH/$CH_2Cl_2$ (2×100 mL). The combined organic extracts were dried over sodium sulfate, filtered and concentrated in vacuo to obtain the crude. The crude was purified through silica gel column chromatography using 3% MeOH/$CH_2Cl_2$ to afford compound 764 (70 mg, 33%) as white solid. TLC: 5% MeOH/$CH_2Cl_2$ ($R_f$: 0.3); $^1$H-NMR (DMSO-$d_6$, 400 MHz): δ 11.52 (s, 1H), 9.47 (t, J=5.7 Hz, 1H), 8.06 (d, J=8.3 Hz, 1H), 7.98 (dd, J=7.5, 1.5 Hz, 2H), 7.90 (td, J=7.5, 1.5 Hz, 1H), 7.87-7.80 (m, 5H), 7.78 (s, 1H), 7.43 (t, J=5.7 Hz, 1H), 7.32 (d, J=8.3 Hz, 2H), 4.68 (d, J=5.5 Hz, 2H), 4.15 (d, J=6.1 Hz, 2H), 1.39 (s, 9H).

Synthesis of N-((2-(4-(aminomethyl) phenyl) thiazol-5-yl) methyl)-11-oxo-10, 11-dihydrodibenzo [b, f] [1, 4] thiazepine-8-carboxamide 5, 5-dioxide hydrochloride (1654)

To a stirring solution of compound 764 (65 mg, 0.10 mmol) in $CH_2Cl_2$ (2 mL) under inert atmosphere was added 4 N HCl in 1, 4-dioxane (1 mL) at 0° C.; warmed to RT and stirred for 3 h. The reaction was monitored by TLC; after completion of the reaction, the volatiles were removed in vacuo to obtain the crude. The crude was washed with EtOAc (2×5 mL) and dried in vacuo to afford 1654 (40 mg, 69%) as an off-white solid. TLC: 10% MeOH/$CH_2Cl_2$ ($R_f$: 0.2); $^1$H-NMR (DMSO-$d_6$, 500 MHz): δ 11.54 (s, 1H), 9.53 (t, J=5.8 Hz, 1H), 8.31 (br s, 3H), 8.06 (d, J=8.1 Hz, 1H), 8.01-7.88 (m, 5H), 7.87-7.82 (m, 4H) 7.57 (d, J=8.1 Hz, 2H), 4.69 (d, J=5.5 Hz, 2H), 4.07 (q, J=5.8 Hz, 2H); LC-MS: 96.02%; 505.0 ($M^+$+1); (column; Ascentis Express C18, (50×3.0 mm, 2.7 μm); RT 1.78 min. 0.025% Aq. TFA+5% ACN: ACN+5% 0.025% Aq. TFA, 1.2 mL/min); HPLC (purity): 96.27%; (column; X-select CSH C-18 (150×4.6 mm, 3.5 μm); RT 5.43 min. ACN+5% 0.05% TFA (Aq): 0.05% TFA (Aq)+5% ACN; 1.0 mL/min, Diluent: ACN: water).

Synthesis of 1839

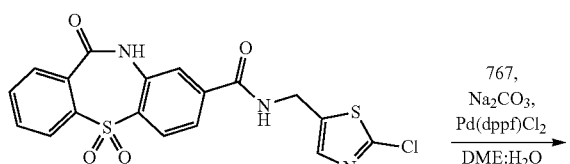

Synthesis of (2-bromophenethoxy) (tert-butyl) dimethylsilane (766)

To a stirring solution of 2-(2-bromophenyl) ethan-1-ol 765 (2 g, 9.95 mmol) in $CH_2Cl_2$ (50 mL) under inert atmosphere was added imidazole (1.35 g, 19.85 mmol) at 0° C. and stirred for 10 min, followed by addition of TBDMS-Cl (1.79 g, 11.93 mmol) at 0° C.; warmed to RT and stirred for 16 h. The reaction was monitored by TLC; after completion of the reaction, the reaction mixture was diluted with water (50 mL) and extracted with $CH_2Cl_2$ (3×50 mL). The combined organic extracts were dried over sodium sulfate, filtered and concentrated in vacuo to obtain the crude. The crude was purified through silica gel column chromatography using 2-5% EtOAc/hexanes to afford compound 766 (3

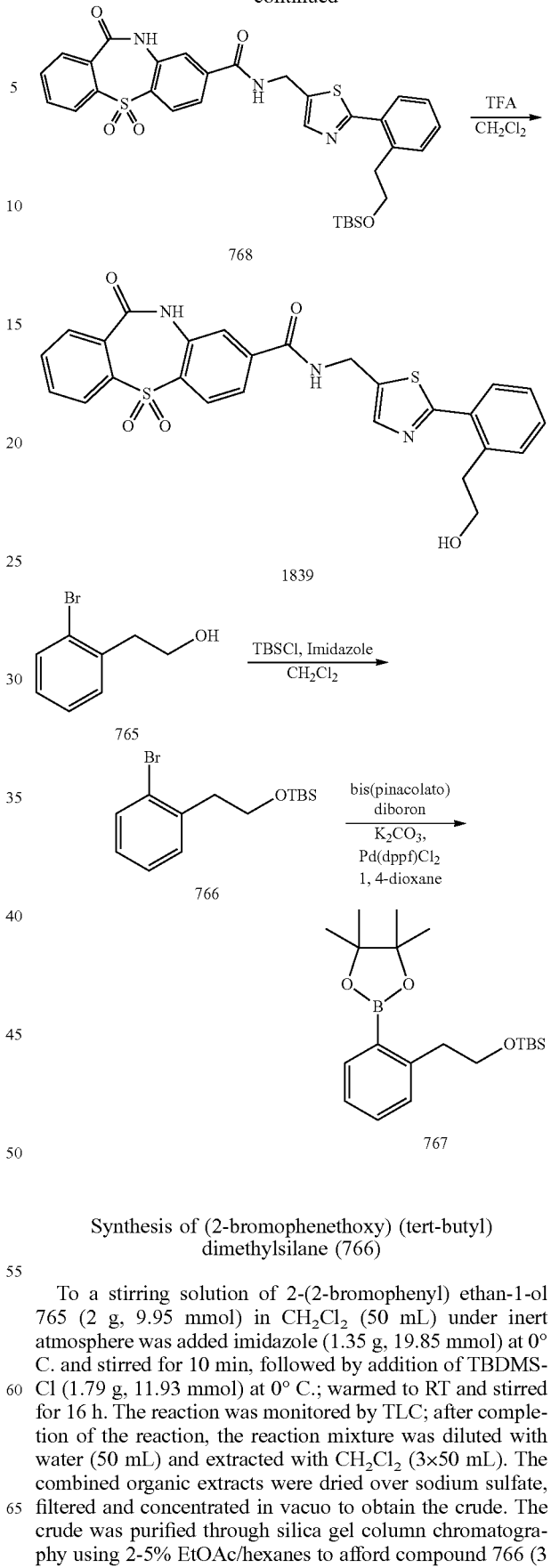

g, 96%) as colorless liquid. TLC: 10% EtOAc/hexanes ($R_f$: 0.8); $^1$H-NMR (DMSO-$d_6$, 500 MHz): δ 7.57 (d, J=8.1 Hz, 1H), 7.36-7.28 (m, 2H), 7.16 (t, J=7.5 Hz, 1H), 3.78 (t, J=6.8 Hz, 2H), 2.90 (t, J=6.7 Hz, 2H), 0.82 (s, 9H), 0.06 (s, 6H).

Synthesis of tert-butyldimethyl(2-(4, 4, 5, 5-tetramethyl-1, 3, 2-dioxaborolan-2-yl) phenethoxy) silane (767)

To a stirring solution of compound 766 (1 g, 3.18 mmol) in 1, 4-dioxane (30 mL) under argon atmosphere were added bispinacolato diboron (1.20 g, 4.74 mmol), potassium carbonate (1.31 g, 9.49 mmol) at RT and purged argon atmosphere for 5 min, added Pd(dppf)Cl$_2$ (232 mg, 0.31 mmol) and heated to reflux and stirred for 16 h. The reaction was monitored by TLC; after completion of the reaction, the reaction mixture was filtered through celite. The filtrate was concentrated in vacuo to obtain the crude. The crude was purified through silica gel flash column chromatography using 5-20% EtOAc/hexanes to afford compound 767 (300 mg, 26%) as pale yellow liquid. TLC: 2% EtOAc/hexanes ($R_f$: 0.5); LC-MS: 93.59%; 363.2 (M$^+$+1); (column; X-select CSH C-18 (50×3.0 mm, 2.5 μm); RT 5.19 min. 2.5 mM NH$_4$OOCH (Aq)+5% ACN: ACN+5% 2.5 mM NH$_4$OOCH (Aq); 0.8 mL/min).

Synthesis of N-((2-(2-(2-((tert-butyldimethylsilyl) oxy) ethyl) phenyl) thiazol-5-yl) methyl)-11-oxo-10, 11-dihydrodibenzo [b, f] [1, 4] thiazepine-8-carboxamide 5, 5-dioxide (768)

To a stirring solution of N-((2-chlorothiazol-5-yl) methyl)-11-oxo-10, 11-dihydrodibenzo [b, f] [1, 4] thiazepine-8-carboxamide 5, 5-dioxide 535 (200 mg, 0.46 mmol) in 1, 2-dimethoxy ethane: H$_2$O (3:1, 26 mL) under inert atmosphere were added compound 767 (334 mg, 0.92 mmol), sodium carbonate (147 mg, 1.38 mmol) in a sealed tube at RT and purged under argon atmosphere for 15 min, added Pd(dppf)Cl$_2$ (33.76 mg, 0.046 mmol) and purged under argon atmosphere for 10 min and heated to 100° C. and stirred for 16 h. The reaction was monitored by TLC; after completion of the reaction, the reaction mixture was filtered through celite and the filtrate was concentrated in vacuo to obtain the crude. The crude was purified through silica gel flash column chromatography using 2% MeOH/ CH$_2$Cl$_2$ to afford compound 768 (150 mg, crude) as pale yellow liquid. TLC: % MeOH/CH$_2$Cl$_2$ ($R_f$: 0.4);

Synthesis of N-((2-(2-(2-hydroxyethyl) phenyl) thiazol-5-yl) methyl)-11-oxo-10, 11-dihydrodibenzo [b, f] [1, 4] thiazepine-8-carboxamide 5, 5-dioxide (1839)

To a stirring solution of compound 768 (150 mg, 0.23 mmol) in CH$_2$Cl$_2$ (5 mL) under inert atmosphere was added trifluoroacetic acid (0.3 mL) at 0° C.; warmed to RT and stirred for 4 h. The reaction was monitored by TLC; after completion of the reaction, the reaction mixture was diluted with washed with water (75 mL) and extracted with 5% MeOH/CH$_2$Cl$_2$ (3×50 mL), The combined organic extracts were dried over sodium sulfate, filtered and concentrated in vacuo to obtain the crude. The crude was purified by preparative HPLC purification to afford 1839 (80 mg, 33% over 2 steps) as an off-white solid. TLC: 5% MeOH/CH$_2$Cl$_2$ ($R_f$: 0.3); $^1$H-NMR (DMSO-$d_6$, 400 MHz): δ 11.51 (s, 1H), 9.48 (t, J=5.6 Hz, 1H), 8.06 (d, J=8.3 Hz, 1H), 7.98 (td, J=7.7, 1.1 Hz, 2H), 7.93-7.80 (m, 5H), 7.53 (d, J=7.5 Hz, 1H), 7.44-7.36 (m, 2H), 7.34-7.26 (m, 1H), 4.71 (d, J=5.6 Hz, 2H), 4.65-4.56 (m, 1H), 3.56 (t, J=7.0 Hz, 2H), 3.04 (t, J=7.0 Hz, 2H); LC-MS: 95.17%; 520.1 (M$^+$+1); (column; Ascentis Express C18, (50×3.0 mm, 2.7 μm); RT 2.14 min. 0.025% Aq. TFA+5% ACN: ACN+5% 0.025% Aq. TFA, 1.2 mL/min); HPLC (purity): 95.97%; (column; X-select CSH C-18 (150×4.6 mm, 3.5 μm); RT 7.82 min. 0.05% TFA (Aq)+5% ACN: ACN+5% 0.05% TFA (Aq): 1.0 mL/min, Diluent: DMSO:ACN:water).

Synthesis of 1842

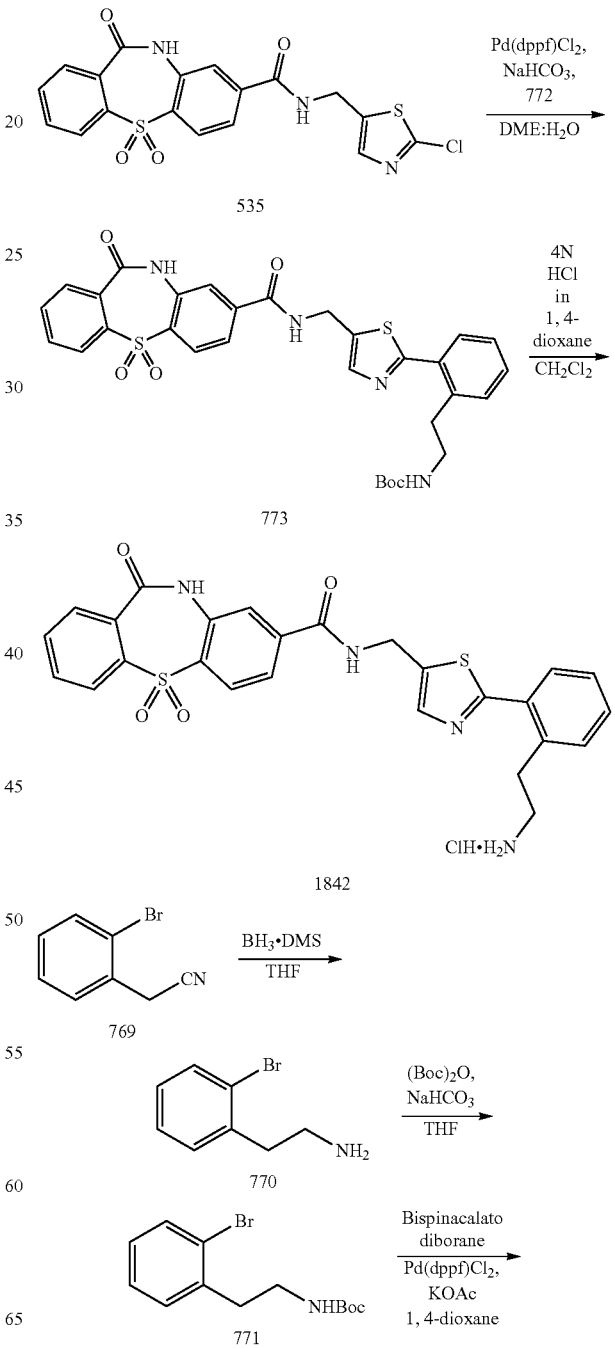

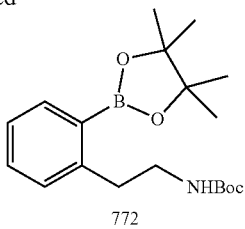

772

Synthesis of 2-(2-bromophenyl) ethan-1-amine (770)

To a stirring solution of 2-(2-bromophenyl) acetonitrile 769 (1 g, 5.10 mmol) in THF (25 mL) under inert atmosphere was added borane dimethyl sulfide complex (3.06 mL, 15.30 mmol, 5.0 M) dropwise for 5 min at RT and heated to 80° C. and stirred for 16 h. The reaction was monitored by TLC; after completion of the reaction, the reaction mixture was quenched with MeOH (5 mL). To this was added 2 N HCl (20 mL) and refluxed for 1 h. The reaction mixture was basified using 10% aqueous NaHCO$_3$ solution (50 mL) and extracted with EtOAc (2×100 mL). The combined organic extracts were dried over sodium sulfate, filtered and concentrated in vacuo to afford compound 770 (750 mg, crude) as colorless oil. The crude was carried forward for next step without further purification. TLC: 5% MeOH/CH$_2$Cl$_2$ (R$_f$: 0.1);

Synthesis of tert-butyl (2-bromophenethyl) carbamate (771)

To a stirring solution of compound 770 (750 mg, 3.75 mmol) in THF:H$_2$O (4:1. 10 mL) were added NaHCO$_3$ (788 mg, 9.37 mmol) and Boc-anhydride (1.63 g, 7.50 mmol) at RT and stirred for 5 h. The reaction was monitored by TLC; after completion of the reaction, the reaction mixture was diluted with water (30 mL) and extracted with EtOAc (2×100 mL). The crude was purified through silica gel column chromatography using 10% EtOAc/hexanes to afford compound 771 (600 mg, 53%) as thick syrup. TLC: 30% EtOAc/hexanes (R$_f$: 0.8). $^1$H-NMR (DMSO-d$_6$, 500 MHz): δ 7.57 (d, J=8.1 Hz, 1H), 7.35-7.26 (m, 2H), 7.19-7.12 (m, 1H), 6.91 (t, J=5.5 Hz, 1H), 3.16 (q, J=6.7 Hz, 2H), 2.82 (t, J=7.2 Hz, 2H), 1.36 (s, 9H).

Synthesis of tert-butyl (2-(4, 4, 5, 5-tetramethyl-1, 3, 2-dioxaborolan-2-yl) phenethyl) carbamate (772)

To a stirring solution of compound 771 (600 mg, 2.00 mmol) in 1, 4-dioxane (20 mL) under inert atmosphere were added bispinacolato diboron (556 mg, 2.20 mmol), potassium acetate (686 mg, 7.00 mmol) RT and purged argon atmosphere for 30 min, added Pd(dppf)Cl$_2$ (146 mg, 0.20 mmol) and heated to 100° C. and stirred for 6 h. The reaction was monitored by TLC; after completion of the reaction, the reaction mixture was filtered through celite, washed with EtOAc (2×50 mL). The filtrate was concentrated in vacuo to afford compound 772 (600 mg). TLC: 10% EtOAc/hexanes (R$_f$: 0.8); LC-MS: 66.71%; 248.1 (M$^+$+1) (Des Boc); (column; Ascentis Express C18, (50×3.0 mm, 2.7 μm); RT 3.17 min. 0.025% Aq. TFA+5% ACN: ACN+5% 0.025% Aq. TFA, 1.2 mL/min).

Synthesis of tert-butyl (2-(5-((5, 5-dioxido-11-oxo-10, 11-dihydrodibenzo [b, f] [1, 4] thiazepine-8-carboxamido) methyl) thiazol-2-yl) phenethyl) carbamate (773)

To a stirring solution of N-((2-chlorothiazol-5-yl) methyl)-11-oxo-10, 11-dihydrodibenzo [b, f] [1, 4] thiazepine-8-carboxamide 5, 5-dioxide 535 (150 mg, 0.34 mmol) in 1, 2-dimethoxy ethane:H$_2$O (4:1, 10 mL) under inert atmosphere were added compound 772 (300 mg, 0.86 mmol), sodium carbonate (128 mg, 1.21 mmol) at RT and purged under argon atmosphere for 30 min; added Pd(dppf)Cl$_2$ (25 mg, 0.034 mmol) and heated to 110° C. and stirred for 16 h. The reaction was monitored by TLC; after completion of the reaction, the reaction mixture the volatiles were removed in vacuo to obtain the crude. The crude was purified through silica gel column chromatography using 2% MeOH/CH$_2$Cl$_2$ to afford compound 773 (60 mg, 28%) as brown syrup. TLC: 2% MeOH/CH$_2$Cl$_2$ (R$_f$: 0.4); $^1$H-NMR (DMSO-d$_6$, 500 MHz): δ 11.52 (s, 1H), 9.48 (t, J=5.8 Hz, 1H), 8.06 (d, J=8.1 Hz, 1H), 8.00-7.96 (m, 2H), 7.93-7.80 (m, 5H), 7.55 (d, J=7.2 Hz, 1H), 7.41-7.37 (m, 1H), 7.35-7.28 (m, 2H), 6.83 (t, J=4.6 Hz, 1H), 4.71 (d, J=5.8 Hz, 2H), 3.14 (q, J=6.3 Hz, 2H), 3.03-2.97 (m, 2H), 1.30 (s, 9H); LC-MS: 97.49%; 619.1 (M$^+$+1); (column; Ascentis Express C18, (50×3.0 mm, 2.7 μm); RT 2.55 min. 0.025% Aq. TFA+5% ACN: ACN+5% 0.025% Aq. TFA, 1.2 mL/min).

Synthesis of N-((2-(2-(2-aminoethyl) phenyl) thiazol-5-yl) methyl)-11-oxo-10, 11-dihydrodibenzo [b, f] [1, 4] thiazepine-8-carboxamide 5, 5-dioxide hydrochloride (1842)

To a stirring solution of compound 773 (60 mg, 0.097 mmol) in CH$_2$Cl$_2$ (5 mL) was added 4 N HCl in 1, 4-dioxane (1 mL) under argon atmosphere at 0° C.; warmed to RT and stirred for 2 h. The reaction was monitored by TLC; after completion of the reaction, the volatiles were removed in vacuo. The crude washed with EtOAc (5 mL) and dried in vacuo to afford compound 1842 (35 mg, 65%; HCl salt) as white solid. TLC: 5% MeOH/CH$_2$Cl$_2$ (R$_f$: 0.1); $^1$H-NMR (DMSO-d$_6$, 400 MHz): δ 11.54 (s, 1H), 9.56 (t, J=5.8 Hz, 1H), 8.07 (d, J=8.2 Hz, 1H), 7.98 (td, J=7.4, 1.3 Hz, 2H), 7.94-7.82 (m, 8H), 7.61 (dd, J=7.6, 0.9 Hz, 1H), 7.50-7.35 (m, 3H), 4.72 (d, J=5.6 Hz, 2H), 3.21-3.13 (m, 2H), 3.12-3.02 (m, 2H); LC-MS: 99.26%; 519.1 (M$^+$+1); (column; Ascentis Express C18, (50×3.0 mm, 2.7 μm); RT 1.85 min. 0.025% Aq. TFA+5% ACN: ACN+5% 0.025% Aq. TFA, 1.2 mL/min). HPLC (purity): 98.26%; (column; X-select CSH-C18 (150×4.6 mm, 3.5 μm); RT 6.21 min. 0.05% TFA (Aq)+5% ACN: ACN+5% 0.05% TFA (Aq); 1.0 mL/min, Diluent: DMSO:ACN:water).

Synthesis of 1841

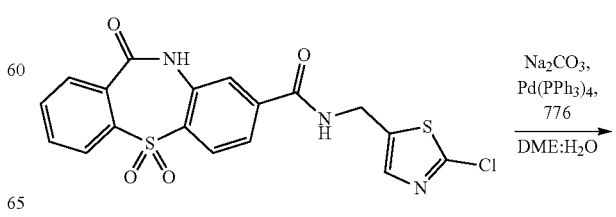

535

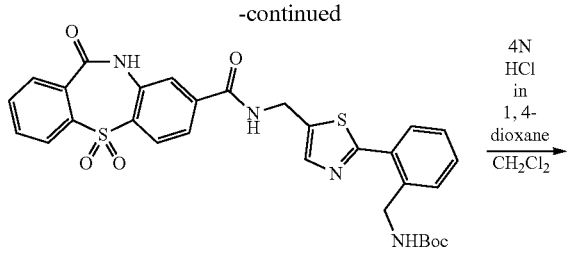

777

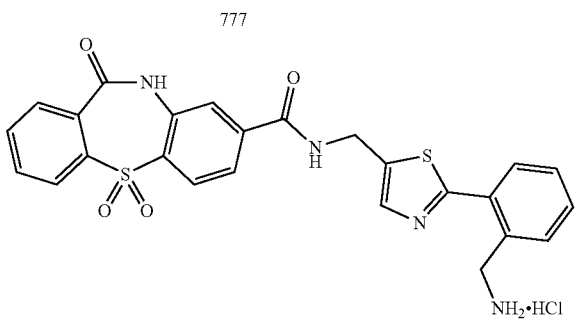

1841

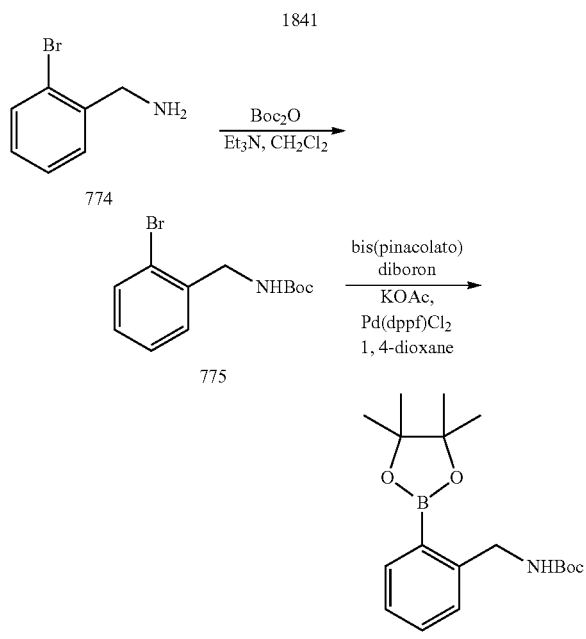

Synthesis of tert-butyl (2-bromobenzyl) carbamate (775)

To a stirring solution of (2-bromophenyl) methanamine 774 (2 g, 10.75 mmol) in CH$_2$Cl$_2$ (20 mL) under inert atmosphere were added triethylamine (2.29 mL, 16.13 mmol) and Boc-anhydride (2.81 g, 12.89 mmol) at RT and stirred for 16 h. The reaction was monitored by TLC; after completion of the reaction, the reaction mixture was diluted with water (50 mL) and extracted with CH$_2$Cl$_2$ (2×100 mL). The crude was purified through silica gel flash column chromatography using 5% EtOAc/hexanes to afford compound 775 (2.8 g, 91%) as an off-white solid. TLC: 20% EtOAc/hexanes (R$_f$: 0.8). $^1$H NMR (400 MHz, DMSO-d$_6$): δ 7.58 (dd, J=1.0, 7.9 Hz, 1H), 7.43 (br t, J=5.6 Hz, 1H), 7.41-7.35 (m, 1H), 7.28 (br d, J=7.4 Hz, 1H), 7.20 (td, J=7.6, 1.8 Hz, 1H), 4.16 (d, J=6.1 Hz, 2H), 1.41 (s, 9H);

Synthesis of tert-butyl (2-(4, 4, 5, 5-tetramethyl-1, 3, 2-dioxaborolan-2-yl) benzyl) carbamate (776)

To a stirring solution of compound 775 (1 g, 3.49 mmol) in 1, 4-dioxane (20 mL) under argon atmosphere were added bispinacolato diboron (1.06 g, 4.18 mmol), potassium acetate (1.03 g, 10.51 mmol) at RT and purged argon atmosphere for 15 min, added Pd(dppf)Cl$_2$ (256 mg, 0.35 mmol) and heated to 100° C. and stirred for 16 h. The reaction was monitored by TLC; after completion of the reaction, the reaction mixture was filtered through celite. The filtrate was concentrated in vacuo to obtain the crude. The crude was purified through silica gel flash column chromatography using 2-10% EtOAc/hexanes to afford compound 776 (700 mg, 56%) as pale yellow liquid. TLC: 2% EtOAc/hexanes (R$_f$: 0.5); $^1$H NMR (400 MHz, DMSO-d$_6$): δ 7.65 (dd, J=7.3, 1.1 Hz, 1H), 7.44 (dt, J=7.5, 1.1 Hz, 1H), 7.27-7.19 (m, 3H), 7.14 (br t, J=6.0 Hz, 1H), 4.38 (br d, J=6.1 Hz, 2H), 1.40 (s, 9H), 1.31 (s, 12H); LC-MS: 74.04%; 332.3 (M$^+$+1); column; Ascentis Express C18, (50×3.0 mm, 2.7 μm); RT 3.09 min. 0.025% Aq. TFA+5% ACN: ACN+5% 0.025% Aq. TFA, 1.2 mL/min);

Synthesis of tert-butyl (2-(5-((5, 5-dioxido-11-oxo-10, 11-dihydrodibenzo [b, f] [1, 4] thiazepine-8-carboxamido) methyl) thiazol-2-yl) benzyl) carbamate (777)

To a stirring solution of N-((2-chlorothiazol-5-yl) methyl)-11-oxo-10, 11-dihydrodibenzo [b, f] [1, 4] thiazepine-8-carboxamide 5, 5-dioxide 535 (200 mg, 0.46 mmol) in 1, 2-dimethoxy ethane:H$_2$O (4:1, 25 mL) under inert atmosphere were added compound 776 (200 mg, 0.55 mmol), sodium carbonate (147 mg, 1.38 mmol) in a sealed tube at RT and purged under argon atmosphere for 15 min, added Pd(PPh$_3$)$_4$ (53.30 mg, 0.046 mmol) and purged under argon atmosphere for 10 min and heated to 120° C. and stirred for 6 h. The reaction was monitored by TLC; after completion of the reaction, the reaction mixture was filtered through celite and the filtrate was concentrated in vacuo to obtain the crude. The crude was purified through silica gel flash column chromatography using 2-5% MeOH/CH$_2$Cl$_2$ to afford compound 777 (150 mg, 54%) as an off-white solid. TLC: 5% MeOH/CH$_2$Cl$_2$ (R$_f$: 0.2); LC-MS: 93.68%; 605.1 (M$^+$+1); (column; Ascentis Express C18, (50×3.0 mm, 2.7 μm); RT 2.57 min. 0.025% Aq. TFA+5% ACN: ACN+5% 0.025% Aq. TFA, 1.2 mL/min).

Synthesis of N-((2-(2-(aminomethyl) phenyl) thiazol-5-yl) methyl)-11-oxo-10, 11-dihydrodibenzo [b, f] [1, 4] thiazepine-8-carboxamide 5, 5-dioxide hydrochlorde (1841)

To a stirring solution of compound 777 (150 mg, 0.24 mmol) in CH$_2$Cl$_2$ (10 mL) under inert atmosphere was added 4 N HCl in 1, 4-dioxane (1 mL) at 0° C.; warmed to RT and stirred for 3 h. The reaction was monitored by TLC; after completion of the reaction, the volatiles were removed in vacuo to obtain the crude. The crude was triturated with diethyl ether (50 mL) and dried in vacuo to afford 1841 (65 g, 48%) as white solid. TLC: 5% EtOAc/hexanes (R$_f$: 0.2); $^1$H NMR (DMSO-d$_6$, 400 MHz): δ 11.48 (br s, 1H), 9.56 (t, J=5.7 Hz, 1H), 8.33 (br s, 2H), 8.08 (d, J=8.3 Hz, 1H), 8.02-7.96 (m, 2H), 7.94-7.78 (m, 6H), 7.64-7.59 (m, 1H), 7.58-7.52 (m, 2H), 4.73 (d, J=5.5 Hz, 2H), 4.25 (s, 2H); LC-MS: 99.47%; 505.1 (M$^+$+1); (column; Ascentis Express C18, (50×3.0 mm, 2.7 μm); RT 1.84 min. 0.025% Aq. TFA+5% ACN: ACN+5% 0.025% Aq. TFA, 1.2 mL/min). HPLC (purity): 99.71%; (column; X-select CSH-C18 (150× 4.6 mm, 3.5 μm); RT 6.10 min. 0.05% TFA (Aq)+5% ACN: ACN+5% 0.05% TFA (Aq); 1.0 mL/min, Diluent: DMSO: ACN:water).

Synthesis of 11002-A, 11002 & 11004
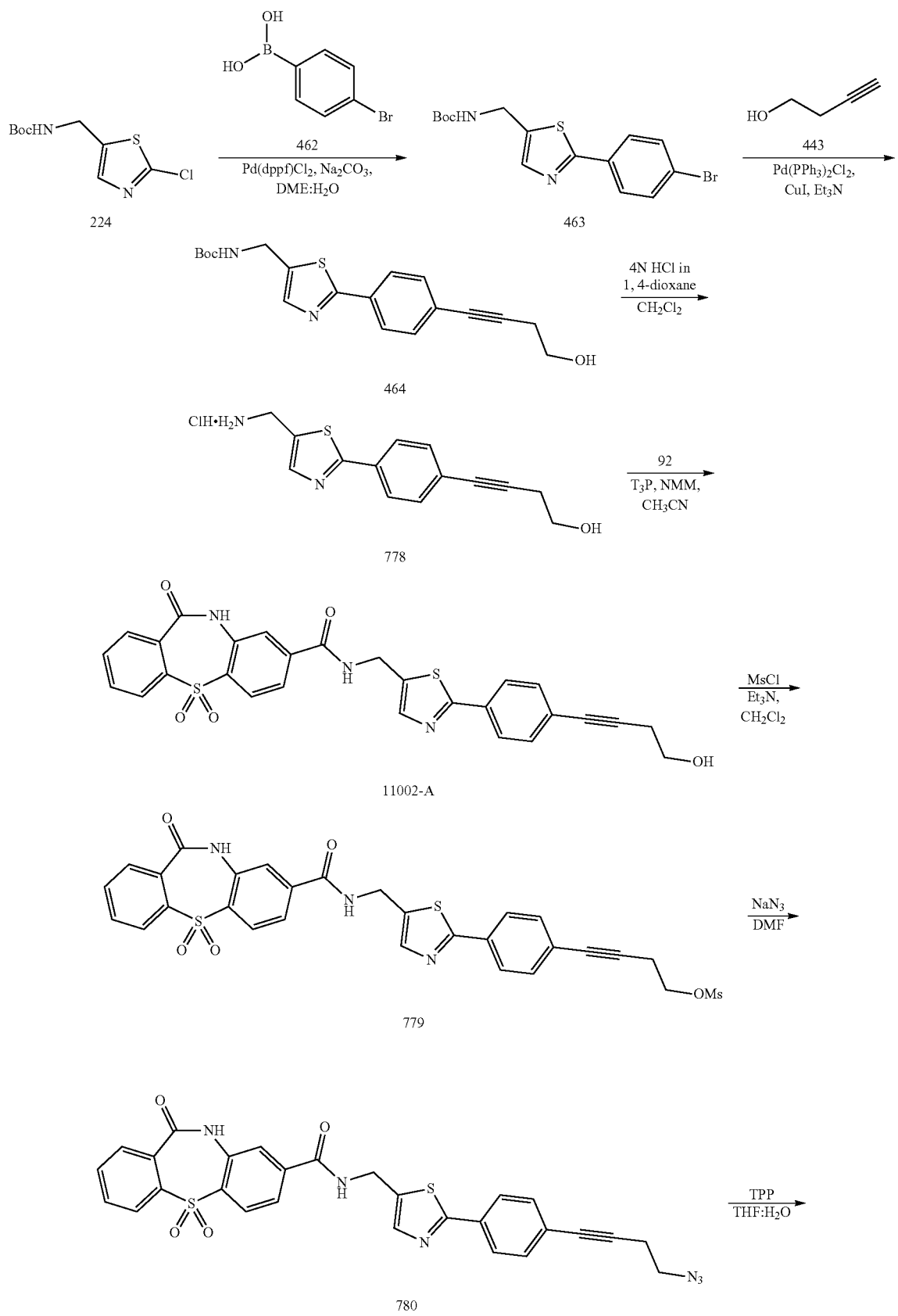

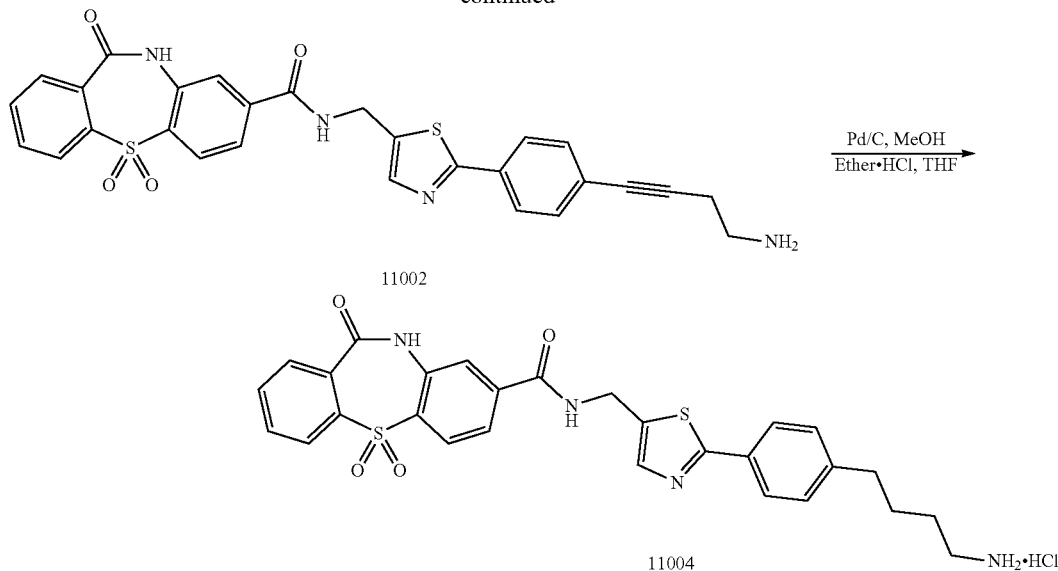

Synthesis of 4-(4-(5-(aminomethyl) thiazol-2-yl) phenyl) but-3-yn-1-ol hydrochloride (778)

To a stirring solution of compound 464 (310 mg, 0.86 mmol) in CH$_2$Cl$_2$ (10 mL) was added 4 N HCl in 1, 4-dioxane (5 mL) under inert atmosphere at 0° C.; warmed to RT and stirred for 3 h. The reaction was monitored by TLC; after completion of the reaction, the volatiles were removed in vacuo. The crude was triturated with EtOAc (5 mL), diethylether (5 mL) and dried in vacuo to afford compound 778 (280 mg, quantitative; HCl salt) as an off-white solid. TLC: 5% MeOH/CH$_2$Cl$_2$ (R$_f$: 0.1); LC-MS: 94.71%; 258.9 (M$^+$+1); (column; Kinetex EVO C-18 (50× 3.0 mm, 2.6 um); RT 1.48 min. 2.5 mM Aq. NH$_4$OOCH+5% ACN: ACN+5% 2.5 mM Aq.NH$_4$OOCH, 0.8 mL/min).

Synthesis of N-((2-(4-(4-hydroxybut-1-yn-1-yl) phenyl) thiazol-5-yl) methyl)-11-oxo-10, 11-dihydrodibenzo [b, f] [1, 4] thiazepine-8-carboxamide 5, 5-dioxide (11002-A)

To a stirring solution of compound 92 (150 mg, 0.49 mmol) in CH$_3$CN (20 mL) under argon atmosphere was added, 1-propylphosphonic acid cyclic anhydride (50% solution in EtOAc, 0.89 mL, 1.48 mmol), 4-(4-(5-(aminomethyl) thiazol-2-yl) phenyl) but-3-yn-1-ol hydrochloride (160 mg, 0.54 mmol) at 0° C.; warmed to RT and stirred for 24 h. The reaction was monitored by TLC; after completion of the reaction, the volatiles were concentrated in vacuo. The residue was diluted with water (50 mL) and extracted with EtOAc (2×50 mL). The combined organic extracts were dried over sodium sulfate and concentrated in vacuo. The crude purified through silica gel column chromatography to afford 11002-A (130 mg, 48%) as an off-white solid. TLC: 5% MeOH/CH$_2$Cl$_2$ (R$_f$: 0.5); $^1$H NMR (400 MHz, DMSO-d$_6$): δ 11.47 (brs, 1H), 9.48 (t, J=5.7 Hz, 1H), 8.06 (d, J=8.3 Hz, 1H), 7.98 (dd, J=7.5, 1.4 Hz, 2H), 7.90 (td, J=7.5, 1.5 Hz, 1H), 7.87-7.79 (m, 6H), 7.47 (d, J=8.5 Hz, 2H), 4.90 (t, J=5.6 Hz, 1H), 4.69 (br d, J=5.6 Hz, 2H), 3.64-3.54 (m, 2H), 2.57 (t, J=6.8 Hz, 2H); LC-MS: 99.59%; 544.0 (M$^+$+1) (column; Ascentis Express C18, (50×3.0 mm, 2.7 µm); RT 2.17 min. 0.025% Aq. TFA+5% ACN: ACN+5% 0.025% Aq. TFA, 1.2 mL/min); HPLC (purity): 98.71%; (column; X-select CSH C-18 (150×4.6 mm, 3.5 µm); RT 8.43 min. 0.05% TFA (Aq)+5% ACN: ACN+5% 0.05% TFA (Aq); 1.0 mL/min, Diluent: DMSO:ACN:water).

Synthesis of 4-(4-(5-((5, 5-dioxido-11-oxo-10, 11-dihydrodibenzo [b, f] [1, 4] thiazepine-8-carboxamido) methyl) thiazol-2-yl) phenyl) but-3-yn-1-yl methanesulfonate (779)

To a stirring solution of 1 1002-A (650 mg, 1.19 mmol) in CH$_2$Cl$_2$ (50 mL) under inert atmosphere were added triethyl amine (0.2 mL, 2.39 mmol), methanesulfonyl chloride (0.11 mL, 1.43 mmol) at 0° C.; warmed to RT and stirred for 6 h. The reaction was monitored by TLC; after completion of the reaction, the reaction mixture was quenched with ice-cold water (50 mL) and extracted with CH$_2$Cl$_2$ (2×75 mL). The combined organic extracts were dried over sodium sulfate, filtered and concentrated in vacuo to afford crude compound 779 (800 mg) as colorless thick syrup. TLC: 5% MeOH/CH$_2$Cl$_2$ (R$_f$: 0.8); LC-MS: 52.47%; 622.0 (M$^+$+1); 28.75%; 700.0 (M$^+$+1) (Dimesylated compound); (column; Ascentis Express C-18, (50×3.0 mm, 2.7 µm); RT 2.38 min, 2.53 min. 0.025% Aq. TFA+5% ACN: ACN+5% 0.025% Aq. TFA, 1.2 mL/min);

Synthesis of N-((2-(4-(4-azidobut-1-yn-1-yl) phenyl) thiazol-5-yl) methyl)-11-oxo-10, 11-dihydrodibenzo [b, 0.1] [1, 4] thiazepine-8-carboxamide 5, 5-dioxide (780)

To a stirring solution of compound 779 (800 mg, 1.27 mmol) in DMF (10 mL) under inert atmosphere was added sodium azide (100 mg, 1.54 mmol) at RT and stirred for 16 h. The reaction was monitored by TLC; after completion of the reaction, the reaction mixture was diluted with water (50 mL) and extracted with EtOAc (2×50 mL). The combined organic extracts were dried over sodium sulphate, filtered and concentrated in vacuo to obtain the crude. The crude was purified through silica gel column chromatography using 5% MeOH/CH$_2$Cl$_2$ to afford compound 780 (400 mg) as an off-white solid. TLC: 5% MeOH/CH$_2$Cl$_2$ (R$_f$: 0.6); $^1$H NMR (400 MHz, DMSO-$d_6$): 11.51 (s, 1H), 9.48 (t, J=5.5 Hz, 1H), 8.06 (d, J=8.1 Hz, 1H), 8.01-7.96 (m, 2H), 7.94-7.78 (m, 7H), 7.48 (d, J=8.1 Hz, 2H), 4.69 (br d, J=5.8 Hz, 2H), 3.53 (t, J=6.4 Hz, 2H), 2.77 (t, J=6.4 Hz, 2H);

Synthesis of N-((2-(4-(4-aminobut-1-yn-1-yl) phenyl) thiazol-5-yl) methyl)-11-oxo-10, 11-dihydrodibenzo [b, f] [1, 4] thiazepine-8-carboxamide 5, 5-dioxide (11002)

To a stirring solution of compound 780 (430 mg, 0.75 mmol) in THF:$H_2O$ (4:1, 45 mL) was added triphenyl phosphine (238 mg, 0.90 mmol) at 0° C.; warmed to RT and stirred for 16 h. The reaction was monitored by TLC and LC-MS; after completion of the reaction; the reaction mixture was quenched with water (50 mL) and extracted with 10% MeOH/$CH_2Cl_2$ (2×50 mL). The combined organic extracts were dried over sodium sulphate, filtered and concentrated in vacuo to obtain the crude. The crude was purified through basic alumina column chromatography using $NH_4OH$: MeOH: 11002 (80 mg, 19%) as an off-white solid. TLC: 10% MeOH/$CH_2Cl_2$ ($R_f$: 0.1); $^1$H NMR (400 MHz, DMSO-$d_6$): δ 9.48 (t, J=5.7 Hz, 1H), 8.05 (d, J=8.2 Hz, 1H), 7.98 (td, J=7.3, 0.9 Hz, 2H), 7.94-7.75 (m, 7H), 7.48 (d, J=8.4 Hz, 2H), 5.47-5.04 (m, 2H), 4.69 (d, J=5.5 Hz, 2H), 2.75 (t, J=6.8 Hz, 2H) 2.61-2.50 (m, 1H), 2.49-2.41 (m, 1H); LC-MS: 96.45%; 543.0 (M$^+$+1); (column; Ascentis Express C18, (50×3.0 mm, 2.7 μm); RT 1.85 min. 0.025% Aq. TFA+5% ACN: ACN+5% 0.025% Aq. TFA, 1.2 mL/min); HPLC (purity): 97.99%; (column; X-select CSH C-18 (150×4.6 mm, 3.5 μm); RT 6.10 min. 0.05% TFA (Aq)+5% ACN: ACN+5% 0.05% TFA (Aq); 1.0 mL/min, Diluent: DMSO:ACN:water).

Synthesis of N-((2-(4-(4-aminobutyl) phenyl) thiazol-5-yl) methyl)-11-oxo-10, 11-dihydrodibenzo [b, f] [1, 4] thiazepine-8-carboxamide 5, 5-dioxide hydrochloride salt (11004)

To a stirring solution of 11002 (200 mg, 0.35 mmol) in MeOH (15 mL) under inert atmosphere was added 10% Pd/C (150 mg) at RT and stirred under hydrogen atmosphere (balloon pressure) at RT for 16 h. The reaction was monitored by TLC; after completion of the reaction, the reaction mixture was filtered through celite and eluted with 20% MeOH/$CH_2Cl_2$ (250 mL). The filtrate was concentrated in vacuo to obtain the crude. The crude was purified through basic alumina column chromatography using $NH_4OH$:MeOH:$CH_2Cl_2$ (1:1:8) to afford amine (25 mg, crude)

The above crude amine (25 mg, crude) was dissolved in THF (10 mL) under inert atmosphere was added $Et_2O$.HCl (5 mL) at 0° C.; warmed to RT and stirred for 2 h. The volatiles were removed in vacuo and the obtained crude was triturated with EtOAc (5 mL), diethylether (5 mL) and dried in vacuo to afford 11004 (80 mg, 10% over 3 steps) as an off-white solid. TLC: 10% MeOH/$CH_2Cl_2$ ($R_f$: 0.4); $^1$H NMR (400 MHz, DMSO-$d_6$): δ 11.51 (br s, 1H), 9.47 (t, J=5.7 Hz, 1H), 8.06 (d, J=8.2 Hz, 1H), 8.01-7.95 (m, 2H), 7.90 (td, J=7.5, 1.5 Hz, 1H), 7.87-7.81 (m, 6H), 7.46 (d, J=8.4 Hz, 2H), 4.69 (d, J=5.5 Hz, 2H), 2.64-2.49 (m, 4H), 2.22 (s, 6H); LC-MS: 95.39%; 547.1 (M$^+$+1); (column; Ascentis Express C18, (50×3.0 mm, 2.7 μm); RT 1.87 min. 0.025% Aq. TFA+5% ACN: ACN+5% 0.025% Aq. TFA, 1.2 mL/min); HPLC (purity): 95.30%; (column; X-select CSH C-18 (150×4.6 mm, 3.5 μm); RT 8.39 min. 0.05% TFA+5% ACN: ACN+5% 0.05% TFA; 1.0 mL/min, Diluent: DMSO: ACN).

Synthesis of 11003 & 11005

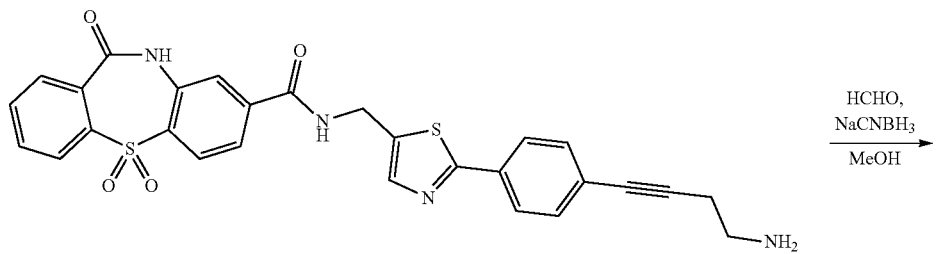

11002

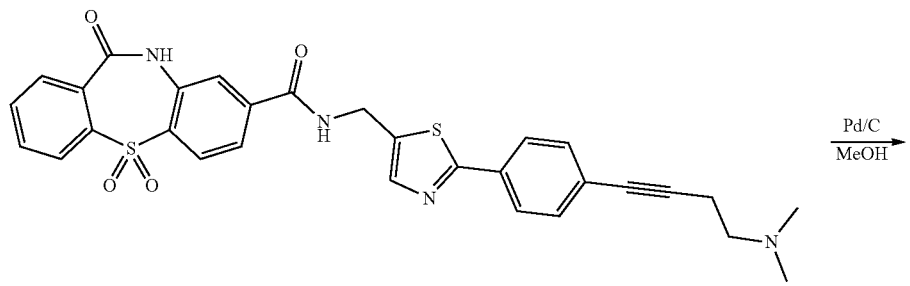

11003

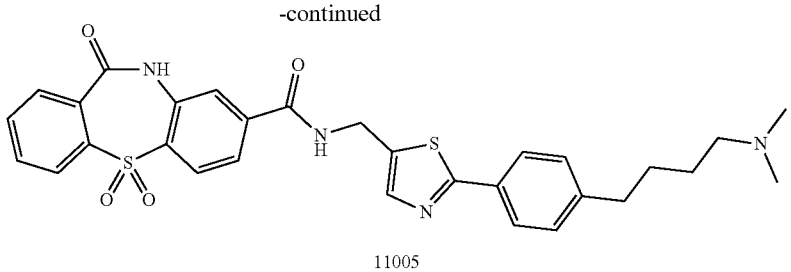

11005

Synthesis of N-((2-(4-(4-(dimethylamino) but-1-yn-1-yl) phenyl) thiazol-5-yl) methyl)-11-oxo-10, 11-dihydrodibenzo [b, f] [1, 4] thiazepine-8-carboxamide 5, 5-dioxide (11003)

To a stirring solution of 11002 (220 mg, 0.40 mmol) in MeOH (15 mL) under inert atmosphere were added paraformaldehyde (60 mg, 2.02 mmol) and sodium cyanoborohydride (127 mg, 2.02 mmol) at RT and stirred for 16 h. The reaction was monitored by TLC; after completion of the reaction, the reaction mixture was diluted with water (10 mL) and extracted with 10% MeOH/$CH_2Cl_2$ (2×100 mL). The combined organic extracts were dried over sodium sulfate, filtered and concentrated in vacuo to obtain the crude. The crude was purified through basic alumina column chromatography using $NH_4OH$: MeOH:$CH_2Cl_2$ (1:1:8) to afford 11003 (140 mg, 60%) as an off-white solid. TLC: 10% MeOH/$CH_2Cl_2$ ($R_f$: 0.4); 41 NMR (400 MHz, DMSO-$d_6$): δ 11.50 (s, 1H), 9.47 (t, J=5.6 Hz, 1H), 8.03 (d, J=8.4 Hz, 1H), 7.95 (t, J=7.4 Hz, 2H), 7.91-7.82 (m, 3H), 7.82-7.73 (m, 4H), 7.72-7.64 (m, 2H), 7.29 (d, J=7.9 Hz, 2H), 4.65 (d, J=5.3 Hz, 2H), 2.81-2.71 (m, 2H), 2.67-2.56 (m, 2H), 1.67-1.44 (m, 4H); LC-MS: 96.66%; 571.1 ($M^+$+1); (Column; X-select CSH C-18 (150×4.6 mm, 2.7 μm); RT 1.86 min. 0.025% Aq. TFA+5% ACN: ACN+5% 0.025% Aq. TFA, 1.0 mL/min); HPLC (purity): 98.60%; (column; X-select CSH C-18 (150×4.6 mm, 3.5 μm); RT 6.47 min. 0.05% TFA+5% ACN: ACN+5% 0.05% TFA; 1.0 mL/min, Diluent: DMSO:ACN).

Synthesis of N-((2-(4-(4-(dimethylamino) butyl) phenyl) thiazol-5-yl) methyl)-11-oxo-10, 11-dihydrodibenzo [b, f] [1, 4] thiazepine-8-carboxamide 5, 5-dioxide (11005)

To a stirring solution of 11003 (140 mg, 0.24 mmol) in MeOH (15 mL) under inert atmosphere was added 10% Pd/C (50 mg) at RT and stirred under hydrogen atmosphere (balloon pressure) at RT for 16 h. The reaction was monitored by TLC; after completion of the reaction, the reaction mixture was filtered through celite and eluted with 20% MeOH/$CH_2Cl_2$ (200 mL). The filtrate was concentrated in vacuo to obtain the crude. The crude was purified through basic alumina column chromatography using 10% MeOH/$CH_2Cl_2$ to afford 11005 (15 mg, 10%). TLC: 10% MeOH/$CH_2Cl_2$ ($R_f$: 0.2); $^1$H NMR (400 MHz, DMSO-$d_6$): δ 1150 (br s, 1H), 9.46 (br t, J=5.5 Hz, 1H), 8.06 (d, J=8.2 Hz, 1H), 8.01-7.95 (m, 2H), 7.93-7.87 (m, 1H), 7.87-7.76 (m, 6H), 7.29 (d, J=8.1 Hz, 2H), 4.68 (br d, J=5.3 Hz, 2H), 2.61 (t, J=7.6 Hz, 2H), 2.20 (t, J=7.2 Hz, 2H), 2.09 (s, 5H), 1.65-1.51 (m, 2H), 1.44-1.36 (m, 2H); LC-MS: 95.02%; 575.1 ($M^+$+1); (Column; X-select CSH C-18 (150×4.6 mm, 2.7 μm); RT 1.89 min. 0.025% Aq. TFA+5% ACN: ACN+5% 0.025% Aq. TFA, 1.0 mL/min); HPLC (purity): 97.71%; (column; X-select CSH C-18 (150×4.6 mm, 3.5 μm); RT 9.02 min. 5 mM $NH_4OAc$: ACN; 1.0 mL/min, Diluent: DMSO:ACN:water).

Synthesis of 11061

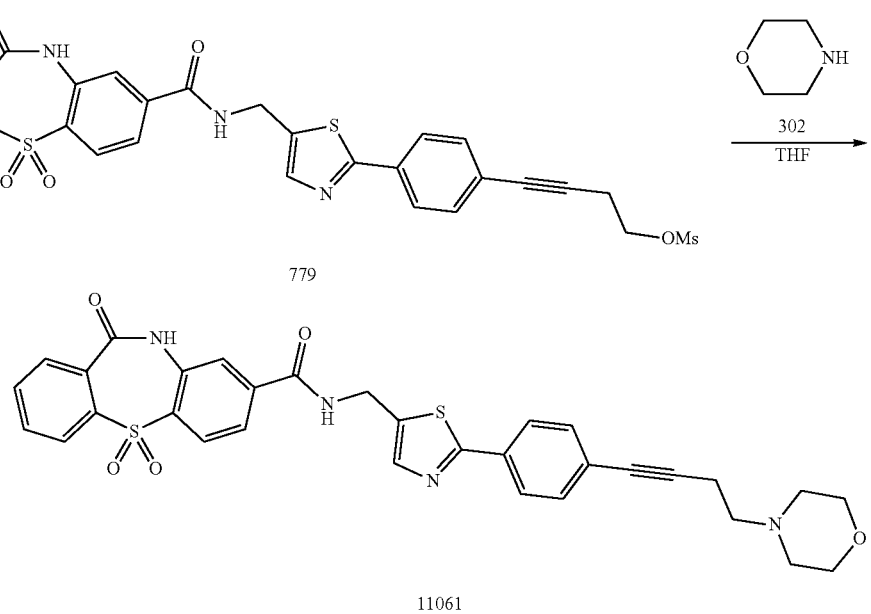

779

11061

Synthesis of N-((2-(4-(4-morpholinobut-1-yn-1-yl) phenyl) thiazol-5-yl) methyl)-11-oxo-10, 11-dihydrodibenzo [b, f] [1, 4] thiazepine-8-carboxamide 5, 5-dioxide (11061)

To a stirring solution of 4-(4-(5-((5, 5-dioxido-11-oxo-10, 11-dihydrodibenzo [b, f] [1, 4] thiazepine-8-carboxamido) methyl) thiazol-2-yl) phenyl) but-3-yn-1-yl methanesulfonate 779 (330 mg, crude) in THF (15 mL) was added morpholine 302 (0.23 mL, 2.65 mmol) in a sealed tube at RT under inert atmosphere. The reaction mixture was heated to 70° C. and stirred for 16 h. The reaction was monitored by TLC and LCMS; after completion of the reaction, the reaction mixture was diluted with water (50 mL) and extracted with EtOAc (2×50 mL). The combined organic extracts were dried over sodium sulfate, filtered and concentrated in vacuo to obtain the crude. The crude was purified through silica gel column chromatography using 1-5% MeOH/CH$_2$Cl$_2$ followed by trituration with acetonitrile (2×2 mL) to afford 11061 (30 mg, 9%) as an off-white solid. TLC: 10% MeOH/CH$_2$Cl$_2$ (R$_f$: 0.4); $^1$H NMR (400 MHz, DMSO-d$_6$): δ 11.49 (br s, 1H), 9.48 (t, J=5.6 Hz, 1H), 8.06 (d, J=8.3 Hz, 1H), 8.01-7.96 (m, 2H), 7.93-7.79 (m, 7H), 7.46 (d, J=8.4 Hz, 2H), 4.69 (d, J=5.5 Hz, 2H), 3.61-3.55 (m, 4H), 2.64-2.55 (m, 4H), 2.45-2.39 (m, 4H); LC-MS: 93.38%; 613.1 (M$^+$+1); (column; Ascentis Express C18, (50×3.0 mm, 2.7 μm); RT 1.87 min. 0.025% Aq. TFA+5% ACN: ACN+5% 0.025% Aq. TFA, 1.2 mL/min); HPLC (purity): 93.71%; (column; X-Select CSH-C-18 (150×4.6 mm, 3.5 μm); RT 5.87 min. 0.05% TFA+5% ACN: ACN+5% 0.05% TFA; 1.0 mL/min, Diluent: ACN:H$_2$O: DMSO).

Synthesis of 1835

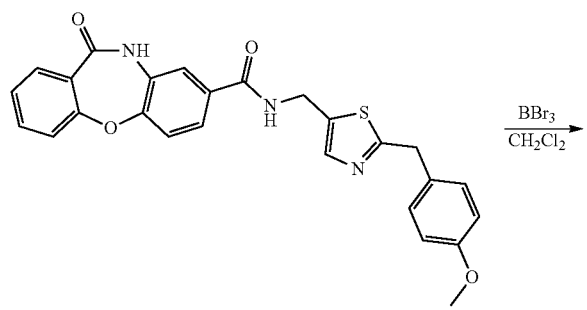

1835-A

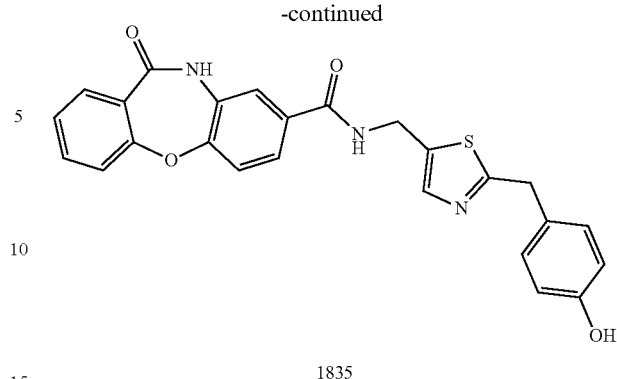

1835

Synthesis of N-((2-(4-hydroxybenzyl) thiazol-5-yl) methyl)-11-oxo-10, 11-dihydrodibenzo [b, f] [1, 4] oxazepine-8-carboxamide (1835)

To a stirring solution of N-((2-(4-methoxybenzyl) thiazol-5-yl) methyl)-11-oxo-10, 11-dihydrodibenzo [b, f] [1, 4] oxazepine-8-carboxamide (1835-A) (150 mg, 0.31 mmol) in CH$_2$Cl$_2$ (10 mL) under inert atmosphere was added BBr$_3$ (0.06 mL, 0.63 mmol) at 0° C.; warmed to RT and stirred for 24 h. The reaction was monitored by TLC; after completion of the reaction, the reaction mixture was quenched with ice-cold water (10 mL) and the obtained solid was filtered, washed with 10% NaHCO$_3$ solution (100 mL). The obtained solid was dried in vacuo to obtain the crude which was titurated with EtOAc (10 mL) and dried in vacuo to afford 1835 (130 mg, 90%) as an off-white solid. TLC: 10% EtOAc/hexanes (R$_f$: 0.4); $^1$H NMR (DMSO-d$_6$, 400 MHz): δ 10.59 (s, 1H), 9.12-9.06 (m, 1H), 7.78 (dd, J=7.8, 1.6 Hz, 1H), 7.65-7.62 (m, 2H), 7.61-7.56 (m, 1H), 7.53 (s, 1H), 7.41-7.31 (m, 3H), 7.08 (d, J=8.5 Hz, 2H), 6.69 (d, J=8.4 Hz, 2H), 4.53 (d, J=5.9 Hz, 2H), 4.10 (s, 2H); LC-MS: 94.88%; 458.1 (M+1)$^+$; (column; Kinetex EVO C-18 (50×3.0 mm, 2.6 um); RT 2.38 min. 2.5 mM Aq. NH$_4$OOCH+5% ACN: ACN+5% 2.5 mM Aq.NH$_4$OOCH, 0.8 mL/min); HPLC (purity): 97.47%; (column; X-select CSH C-18 (150×4.6 mm, 3.5 μm); RT 7.77 min. 0.05% TFA+5% ACN: ACN+5% 0.05% TFA; 1.0 mL/min, Diluent: DMSO:ACN:water).

Synthesis of 1736

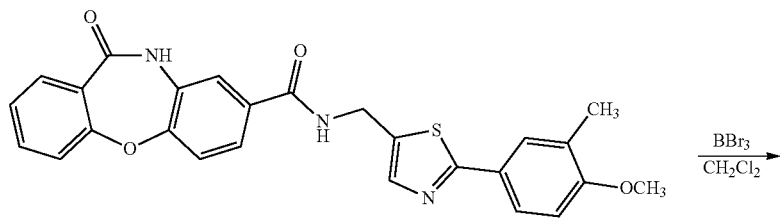

736-A

-continued

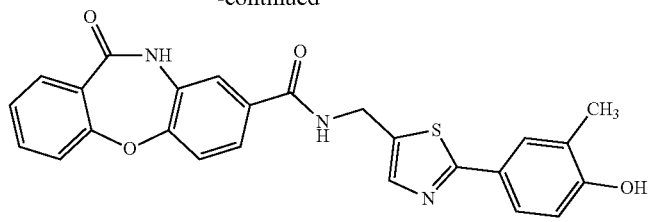

736

Synthesis of N-((2-(4-hydroxy-3-methylphenyl)thiazol-5-yl)methyl)-11-oxo-10,11-dihydrodibenzo[b,f][1,4]oxazepine-8-carboxamide (1736)

To a stirring solution of 1736-A (120 mg, 0.25 mmol) in CH$_2$Cl$_2$ (10 mL) was added BBr$_3$ (0.048 mL, 0.50 mmol) at 0° C.; warmed to RT and stirred for 16 h. The reaction was monitored by TLC; after completion of the reaction, the reaction mixture was quenched with ice-cold water (10 mL). The precipitated solid was filtered, washed with 10% NaHCO$_3$ solution (20 mL), water (10 mL), n-pentane (10 mL) and dried in vacuo to afford compound 1736 (110 mg, 95%) as an off-white solid. TLC: 5% MeOH/CH$_2$Cl$_2$ (R$_f$: 0.2); $^1$H-NMR (DMSO-d$_6$, 500 MHz): δ 10.64 (s, 1H), 9.84 (s, 1H), 9.17 (t, J=5.2 Hz, 1H), 7.78 (d, J=6.9 Hz, 1H), 7.72-7.58 (m, 5H), 7.53 (d, J=8.2 Hz, 1H), 7.42 (d, J=8.3 Hz, 1H), 7.38-7.31 (m, 2H), 6.83 (d, J=8.3 Hz, 1H), 4.62 (d, J=5.1 Hz, 2H), 2.15 (s, 3H); LC-MS: 95.08%; 457.9 (M$^+$+1); (column; Ascentis Express C18, (50×3.0 mm, 2.7 μm); RT 2.19 min. 0.025% Aq. TFA+5% ACN: ACN+5% 0.025% Aq. TFA, 1.2 mL/min); HPLC (purity): 97.99%; (column; Zorbax SB C-18 (150×4.6 mm, 3.5 μm); RT 7.56 min. ACN+5% 0.05% TFA (Aq): 0.05% TFA (Aq)+5% ACN; 1.0 mL/min, Diluent: DMSO:ACN:water).

Synthesis of N-((2-(4-hydroxy-3,5-dimethylphenyl)thiazol-5-yl)methyl)-11-oxo-10,11-dihydrodibenzo[b,f][1,4]oxazepine-8-carboxamide (1738)

To a stirring solution of 1738-A (120 mg, 0.24 mmol) in CH$_2$Cl$_2$ (15 mL) was added BBr$_3$ (62 mg, 0.24 mmol) at 0° C.; warmed to RT and stirred for 16 h. The reaction was monitored by TLC; after completion of the reaction, the reaction mixture was cooled to 0° C., quenched with ice-cold water (5 mL) and the precipitated solid was filtered washed with 10% aqueous sodium carbonate solution and in vacuo to obtain the crude. The crude was titurated with MeOH (2 mL) and dried in vacuo to afford 1738 (100 mg, 86%) as an of-white solid. TLC: 5% MeOH/CH$_2$Cl$_2$ (R$_f$: 0.1); $^1$H NMR (DMSO-d$_6$, 400 MHz): δ 10.64 (s, 1H), 9.18 (t, J=5.8 Hz, 1H), 8.74 (br s, 1H), 7.78 (dd, J=7.7, 1.7 Hz, 1H), 7.69 (d, J=2.0 Hz, 1H), 7.66-7.60 (m, 3H), 7.45 (s, 2H), 7.42 (d, J=8.4 Hz, 1H), 7.38-7.31 (m, 2H), 4.62 (d, J=5.6 Hz, 2H), 2.19 (s, 6H); LC-MS: 96.50%; 472.0 (M$^+$+1); (column; Ascentis Express C18, (50×3.0 mm, 2.7 μm); RT 2.23 min. 0.025% Aq. TFA+5% ACN: ACN+5% 0.025% Aq. TFA, 1.2 mL/min); HPLC (purity): 98.22%; (column; X-select CSH C-18 (150×4.6 mm, 3.5 μm); RT 8.70 min. ACN+5% 0.05% TFA (Aq): 0.05% TFA (Aq)+5% ACN; 1.0 mL/min, Diluent: DMSO:ACN:water).

Synthesis of 1738

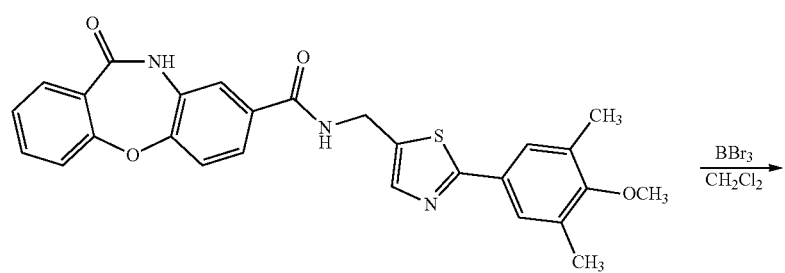

1738-A

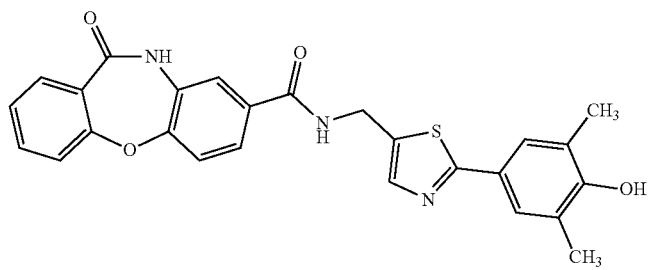

1738

Synthesis of 1709

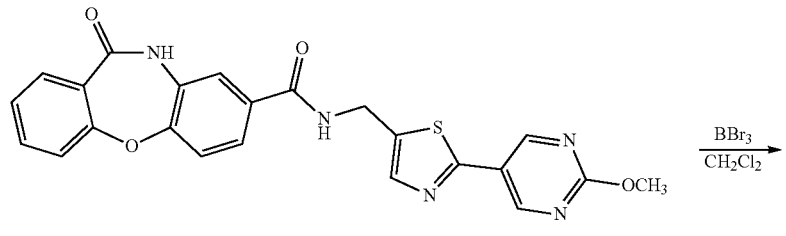

Synthesis of N-((2-(2-hydroxypyrimidin-5-yl) thiazol-5-yl) methyl)-11-oxo-10, 11-dihydrodibenzo [b, f] [1, 4] oxazepine-8-carboxamide (1709)

To a stirring solution of N-((2-(2-methoxypyrimidin-5-yl) thiazol-5-yl) methyl)-11-oxo-10, 11-dihydrodibenzo [b, 1] [1, 4] oxazepine-8-carboxamide 1709-A (50 mg, 0.10 mmol) in CH$_2$Cl$_2$ (15 mL) was added BBr$_3$ (0.10 mL, 1.08 mmol) at 0° C.; warmed to RT and stirred for 24 h. The reaction was monitored by TLC; after completion of the reaction, the reaction mixture was cooled to 0° C., quenched with ice-cold water (10 mL) and stirred for 15 min. The obtained solid was filtered, washed to with saturated sodium carbonate solution (5 mL) and water (10 mL) and dried in vacuo to obtain the crude. The crude was titurated with MeOH (2 mL), diethyl ether (2 mL) and pentane (5 mL) and dried in vacuo to afford 1709 (35 mg, 72%) as an off-white solid. TLC: 10% MeOH/CH$_2$Cl$_2$ (R$_f$: 0.3); $^1$H NMR (DMSO-d$_6$, 400 MHz): δ 12.42 (s, 1H), 10.65 (s, 1H), 9.22 (t, J=5.7 Hz, 1H), 8.70 (s, 2H), 7.78 (dd, J=7.7, 1.6 Hz, 1H), 7.72-7.68 (m, 2H), 7.66-7.59 (m, 2H), 7.42 (d, J=8.4 Hz, 1H), 7.39-7.31 (m, 2H), 4.63 (d, J=5.6 Hz, 2H); LC-MS: 97.71%; 445.9 (M$^+$+1); (column; Ascentis Express C18, (50×3.0 mm, 2.7 μm); RT 1.84 min. 0.025% Aq. TFA+5% ACN: ACN+5% 0.025% Aq. TFA, 1.2 mL/min); HPLC (purity): 94.09%; (column; X-select CSH C-18 (150×4.6 mm, 3.5 μm); RT 5.87 min. ACN+5% 0.05% TFA (Aq): 0.05% TFA (Aq)+5% ACN; 1.0 mL/min, Diluent: ACN:water).

Synthesis of 1615

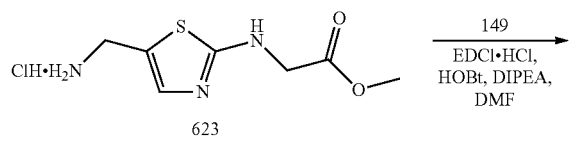

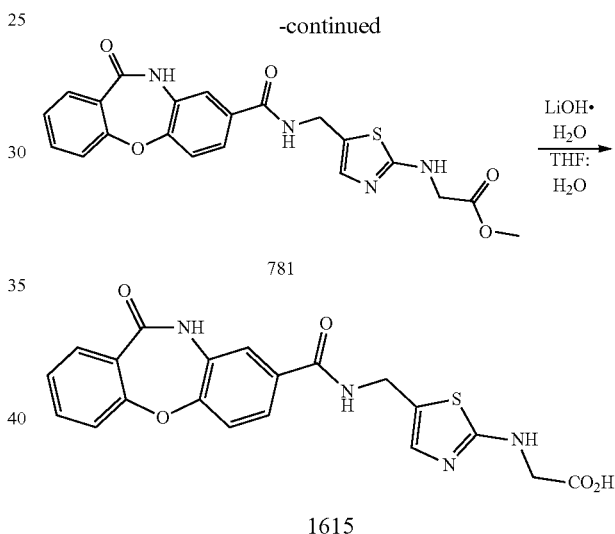

Synthesis of methyl (5-((11-oxo-10, 11-dihydrodibenzo [b, f] [1, 4] oxazepine-8-carboxamido) methyl) thiazol-2-yl) glycinate (781)

To a stirring solution of compound 149 (150 mg, 0.58 mmol) in DMF (5 mL) under inert atmosphere were added methyl (5-(aminomethyl) thiazol-2-yl) glycinate hydrochloride 623 (139 mg, 0.58 mmol), EDCI.HCl (212 mg, 1.17 mmol), HOBt (158 mg, 1.17 mmol) and diisopropylethylamine (0.5 mL, 2.94 mmol) at 0° C.; warmed to RT and stirred for 16 h. The reaction was monitored by TLC; after completion of the reaction, the reaction mixture was diluted with water (50 mL) and the precipitated solid was filtered and dried in vacuo to obtain the crude. The crude was purified through silicagel column chromatography using 5-10% MeOH/CH$_2$Cl$_2$ to afford compound 781 (72 mg, 27%) as an off-white solid. TLC: 10% MeOH/CH$_2$Cl$_2$ (R$_f$: 0.4); $^1$H-NMR (DMSO-d$_6$ 500 MHz): δ 10.61 (s, 1H), 8.97 (t, J=5.5 Hz, 1H), 7.85-7.76 (m, 1H), 7.70-7.57 (m, 3H), 7.49-7.25 (m, 4H), 6.86 (s, 1H), 4.38 (d, J=5.5 Hz, 2H), 3.99 (d, J=6.1 Hz, 2H), 3.62 (s, 3H).

Synthesis of (5-((11-oxo-10, 11-dihydrodibenzo [b, f] [1, 4] oxazepine-8-carboxamido) methyl) thiazol-2-yl) glycine (1615)

To a stirring solution of compound 781 (70 mg, 0.16 mmol) in THF:H₂O (1:1, 10 mL) was added lithium hydroxide monohydrate (38.4 mg, 0.80 mmol) at RT and stirred for 4 h. The reaction was monitored by TLC; after completion of the reaction, the reaction mixture was diluted with water (30 mL), washed with EtOAc (2×25 mL). The pH of the aqueous layer was acidified with 4 N HCl to ~2. The precipitated solid was filtered and triturated with CH₃CN (2 mL), MeOH:CH₃CN (1:1, 1 mL), MeOH (1 mL) and dried in vacuo to afford 1615 (30 mg, 44%) as an off-white solid. TLC: 10% MeOH/CH₂Cl₂ (R$_f$: 0.2); ¹H-NMR (DMSO-d₆, 400 MHz): δ 10.60 (s, 1H), 8.95 (t, J=5.2 Hz, 1H), 7.77 (dd, J=7.6, 1.4 Hz, 1H), 7.68-7.55 (m, 3H), 7.51 (br s, 1H), 7.43-7.28 (m, 3H), 6.85 (s, 1H), 4.36 (d, J=5.6 Hz, 2H), 3.77 (d, J=4.8 Hz, 2H); LC-MS: 93.23%; 424.9 (M⁺+1); (column; Ascentis Express C18, (50×3.0 mm, 2.7 μm); RT 1.86 min. 0.025% Aq. TFA+5% ACN: ACN+5% 0.025% Aq. TFA, 1.2 mL/min); HPLC (purity): 93.86%; (column; X-select CSH C-18 (150×4.6 mm, 3.5 μm); RT 5.54 min. 0.05% TFA (Aq):ACN; 1.0 mL/min).

Synthesis of 1616

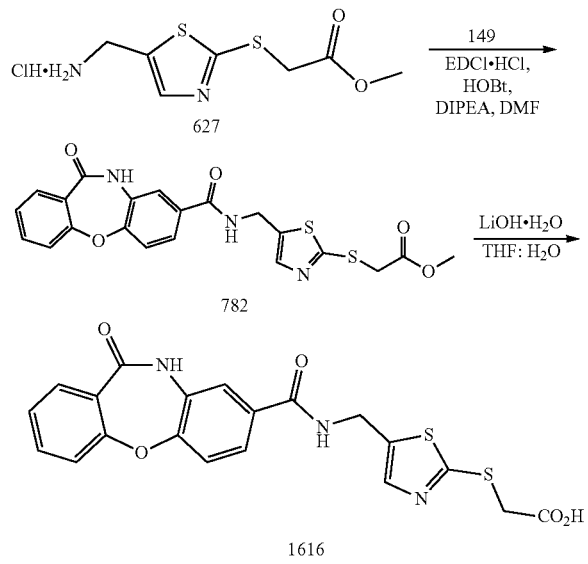

Synthesis of methyl 2-((5-((11-oxo-10, 11-dihydrodibenzo [b, f] [1, 4]oxazepine-8-carboxamido) methyl) thiazol-2-yl) thio) acetate (782)

To a stirring solution of compound 149 (150 mg, 0.59 mmol) in DMF (5 mL) under inert atmosphere were added EDCI.HCl (224 mg, 1.18 mmol), HOBt (158 mg, 1.18 mmol) and diisopropylethylamine (0.30 mL, 1.81 mmol) and methyl 2-((5-(aminomethyl) thiazol-2-yl) thio) acetate hydrochloride 627 (139 mg, 0.65 mmol) at 0° C.; warmed to RT and stirred for 16 h. The reaction was monitored by TLC; after completion of the reaction, the reaction mixture was diluted with water (50 mL); the obtained solid was filtered, triturated with CH₃CN (2 mL), diethyl ether (5 mL) and dried in vacuo to afford compound 782 (180 mg, 67%) as an off-white solid. TLC: 10% MeOH/CH₂Cl₂ (R$_f$: 0.5); ¹H-NMR (DMSO-d₆ 500 MHz): δ 10.60 (s, 1H), 9.13 (t, J=5.6 Hz, 1H), 7.76 (d, J=6.7 Hz, 1H), 7.67-7.54 (m, 4H), 7.40 (d, J=8.4 Hz, 1H), 7.37-7.29 (m, 2H), 4.52 (d, J=5.5 Hz, 2H), 4.10 (s, 2H), 3.62 (s, 3H).

Synthesis of 2-((5-((11-oxo-10, 11-dihydrodibenzo [b, f] [1, 4] oxazepine-8-carboxamido) methyl) thiazol-2-yl) thio) acetic acid (1616)

To a stirring solution of compound 782 (150 mg, 0.33 mmol) in THF:H₂O (5:1, 6 mL) was added lithium hydroxide monohydrate (31.6 mg, 0.66 mmol) at RT and stirred for 3 h. The reaction was monitored by TLC; after completion of the reaction, the reaction mixture was diluted with water (50 mL), washed with EtOAc (2×50 mL). The pH of the aqueous layer was acidified with 4 N HCl to ~2. The precipitated solid was filtered washed with CH₃CN (5 mL) and dried in vacuo to afford 1616 (90 mg, 62%) as an off-white solid. TLC: 10% MeOH/CH₂Cl₂ (R$_f$: 0.2); ¹H-NMR (DMSO-d₆, 500 MHz): δ 12.98 (br s, 1H), 10.62 (s, 1H), 9.15 (t, J=5.6 Hz, 1H), 7.78 (dd, J=7.7, 1.3 Hz, 1H), 7.69-7.58 (m, 3H), 7.56 (s, 1H), 7.42 (d, J=8.4 Hz, 1H), 7.38-7.31 (m, 2H), 4.54 (d, J=5.5 Hz, 2H), 4.00 (s, 2H); LC-MS: 98.46%; 440.2 (M−1)⁺; (column; X-select C18, (50×3.0 mm, 2.5 μm); RT 2.64 min. 5 mM Aq. NH₄OAc+ ACN; 0.8 mL/min); HPLC (purity): 96.34%; (column; Zorbax SB C-18 (150×4.6 mm, 3.5μ); RT 7.27 min. ACN: 0.05% TFA (Aq); 1.0 mL/min; Diluent: ACN:water).

Synthesis of 1691

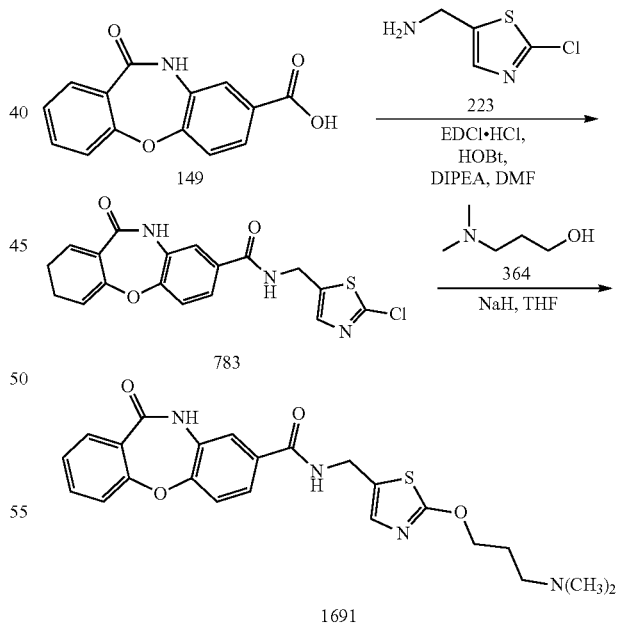

Synthesis of N-((2-chlorothiazol-5-yl) methyl)-11-oxo-10, 11-dihydrodibenzo [b, f] [1, 4] oxazepine-8-carboxamide (783)

To a stirring solution of compound 149 (500 mg, 1.96 mmol) in DMF (10 mL) under inert atmosphere were added compound 223 (398 mg, 2.15 mmol), EDCI.HCl (561 mg, 2.94 mmol), HOBt (397 mg, 2.94 mmol) and diisopropylethylamine (1.75 mL, 9.80 mmol) at 0° C.; warmed to RT and stirred for 16 h. The reaction was monitored by TLC; after completion of the reaction, the reaction mixture was diluted with ice cold-water (50 mL), extracted with EtOAc (2×100 mL). The combined organic extracts were dried over sodium sulfate, filtered and concentrated in vacuo to obtain the crude. The crude was purified through silicagel column chromatography using 8% MeOH/to $CH_2Cl_2$ to afford compound 783 (390 mg, 52%) as an off-white solid. TLC: 10% MeOH/$CH_2Cl_2$ ($R_f$: 0.4); $^1$H-NMR (DMSO-$d_6$ 500 MHz): δ 10.63 (s, 1H), 9.23 (t, J=5.6 Hz, 1H), 7.78 (dd, J=7.7, 1.6 Hz, 1H), 7.68 (s, 1H), 7.65-7.58 (m, 3H), 7.43 (d, J=8.4 Hz, 1H), 7.39-7.31 (m, 2H), 4.56 (d, J=5.8 Hz, 2H).

Synthesis of N-((2-(3-(dimethylamino) propoxy) thiazol-5-yl) methyl)-11-oxo-10, 11-dihydrodibenzo [b, f] [1, 4] oxazepine-8-carboxamide (1691)

To a stirring solution of 3-(dimethylamino) propan-1-ol 364 (0.11 mL, 0.97 mmol) in THF (15 mL) under argon atmosphere was added sodium hydride (60%, 39 mg, 1.62 mmol) at 0° C. and stirred for 15 min. To this was added compound 783 (125 mg, 0.32 mmol) at 0° C.; heated to 60° C. and stirred for 16 h. The reaction was monitored by TLC; after completion of the reaction, the reaction mixture was quenched with water (5 mL) and the extracted with EtOAc (2×50 mL). The combined organic extracts were dried over sodium sulfate, filtered and concentrated in vacuo to obtain the crude. The crude compound was purified through silicagel column chromatography using 5% MeOH/$CH_2Cl_2$ to afford 1691 (15 mg, 10%) as an off-white solid. TLC: 10% MeOH/$CH_2Cl_2$ ($R_f$: 0.4); $^1$H-NMR (DMSO-$d_6$, 400 MHz): δ 10.62 (br s, 1H), 9.07 (t, J=5.3 Hz, 1H), 7.78 (dd, J=7.8, 1.6 Hz, 1H), 7.68-7.56 (m, 3H), 7.41 (d, J=8.4 Hz, 1H), 7.38-7.31 (m, 2H), 7.05 (s, 1H), 4.44 (d, J=5.6 Hz, 2H), 4.32 (t, J=6.5 Hz, 2H), 2.28 (t, J=7.0 Hz, 2H), 2.11 (s, 6H), 1.88-1.79 (m, 2H); LC-MS: 95.08%; 453.1 (M$^+$+1); (column; Ascentis Express C18, (50×3.0 mm, 2.7 μm); RT 1.73 min. 0.025% Aq. TFA+5% ACN: ACN+5% 0.025% Aq. TFA, 1.2 mL/min); HPLC (purity): 93.73%; (column; Zorbax SB C-18 (150×4.6 mm, 3.5 μm); RT 5.64 min. ACN: 0.05% TFA (Aq); 1.0 mL/min).

Synthesis of 1687

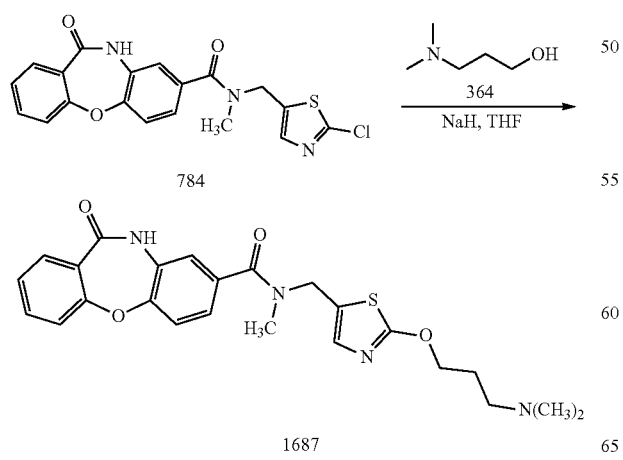

Synthesis of N-((2-(3-(dimethylamino) propoxy) thiazol-5-yl) methyl)-N-methyl-11-oxo-10, 11-dihydrodibenzo [b, f] [1, 4] oxazepine-8-carboxamide (1687)

To a stirring solution of 3-(dimethylamino) propan-1-ol 364 (0.14 mL, 1.12 mmol) in THF (10 mL) under argon atmosphere was added sodium hydride (60%, 41 mg, 1.69 mmol) portion wise at 0° C. and stirred for 10 min. To this was added compound 784 (150 mg, 0.37 mmol) at 0° C.; heated to 60° C. and stirred for 4 h. The reaction was monitored by TLC; after completion of the reaction, the reaction mixture was quenched with water (0.5 mL) and the volatiles were removed in vacuo to obtain the crude. The crude compound was purified through basic alumina column chromatography using 2% MeOH/$CH_2Cl_2$ to afford 1687 (75 mg, 43%) as an off-white solid. TLC: 10% MeOH/$CH_2Cl_2$ ($R_f$: 0.4); $^1$H-NMR (DMSO-$d_6$, 400 MHz): δ 10.56 (br s, 1H), 7.79 (dd, J=7.8, 1.6 Hz, 1H), 7.64-7.60 (m, 1H), 7.42-7.31 (m, 3H), 7.23-7.17 (m, 3H), 4.59 (br s, 2H), 4.35 (t, J=6.5 Hz, 2H), 2.85 (s, 3H), 2.30 (t, J=7.1 Hz, 2H), 2.12 (s, 6H), 1.88-1.81 (m, 2H); LC-MS: 97.53%; 467.1 (M$^+$+1); (column; Ascentis Express C18, (50×3.0 mm, 2.7 μm); RT 1.75 min. 0.025% Aq. TFA+5% ACN: ACN+5% 0.025% Aq. TFA, 1.2 mL/min); HPLC (purity): 96.51%; (column; X-select CSH C-18 (150×4.6 mm, 3.5 μm); RT 5.80 min. 0.05% TFA (Aq): ACN; 1.0 mL/min).

Synthesis of 1614

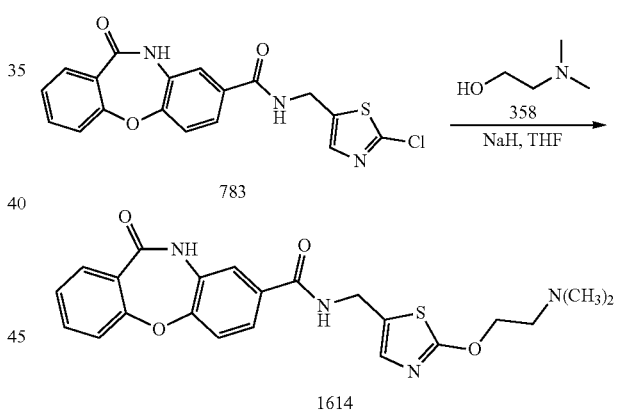

Synthesis of N-((2-(2-(dimethylamino) ethoxy) thiazol-5-yl) methyl)-11-oxo-10, 11-dihydrodibenzo [b, f] [1, 4] oxazepine-8-carboxamide (1614)

To a stirring solution of 2-(dimethylamino) ethan-1-ol 358 (70 mg, 0.77 mmol) in THF (10 mL) under argon atmosphere was added sodium hydride (60%, 28 mg, 1.16 mmol) at 0° C. and stirred for 10 min. To this was added N-((2-chlorothiazol-5-yl) methyl)-11-oxo-10, 11-dihydrodibenzo [b, f] [1, 4] oxazepine-8-carboxamide 783 (150 mg, 0.38 mmol) at 0° C.; heated to reflux and stirred for 16 h. The reaction was monitored by TLC; after completion of the reaction, the reaction mixture was quenched with ice-cold water (5 mL) and the extracted with EtOAc (2×50 mL). The combined organic extracts were dried over sodium sulfate, filtered and concentrated in vacuo to obtain the crude. The crude compound was purified through silicagel column chromatography using 10% MeOH/CH$_2$Cl$_2$ and further purified by preparative HPLC purification to afford 1614 (35 mg, 20%) as an off-white solid. TLC: 10% MeOH/CH$_2$Cl$_2$ (R$_f$: 0.4); $^1$H-NMR (DMSO-d$_6$, 500 MHz): δ 10.64 (s, 1H), 9.12 (t, J=5.6 Hz, 1H), 7.78 (dd, J=7.7. 1.6 Hz, 1H), 7.69 (s, 1H), 7.65-7.58 (m, 2H), 7.41 (d, J=8.4 Hz, 1H), 7.38-7.31 (m, 2H), 7.05 (s, 1H), 4.44 (d, J=5.5 Hz, 2H), 4.37 (t, J=5.6 Hz, 2H), 2.59 (t, J=5.5 Hz, 2H), 2.16 (s, 6H); LC-MS: 99.24%; 439.0 (M$^+$+1); (column; Ascentis Express C18, (50×3.0 mm, 2.7 μm); RT 1.95 min. 0.025% Aq. TFA+5% ACN: ACN+5% 0.025% Aq. TFA, 1.2 mL/min); HPLC (purity): 98.60%; (column; Zorbax SB C-18 (150×4.6 mm, 3.5 μm); RT 5.65 min. 0.05% TFA (Aq): ACN; 1.0 mL/min).

Synthesis of 1686

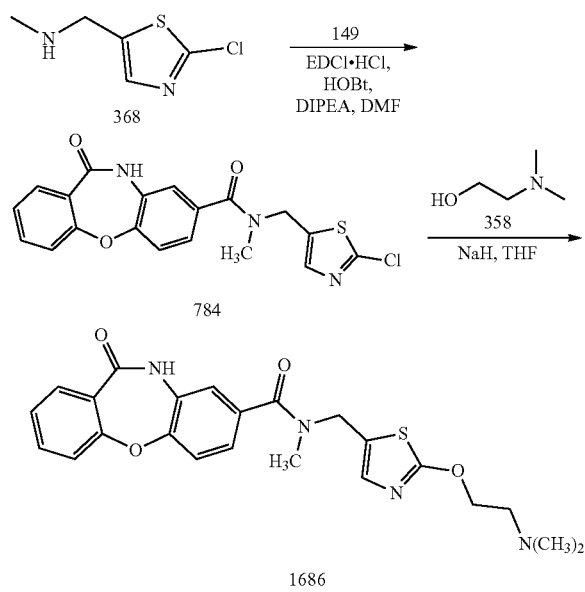

Synthesis of N-((2-chlorothiazol-5-yl) methyl)-N-methyl-11-oxo-10, 11-dihydrodibenzo [b, f] [1, 4] oxazepine-8-carboxamide (784)

To a stirring solution of compound 149 (400 mg, 1.57 mmol) in DMF (5 mL) under argon atmosphere were added EDCI.HCl (570 mg, 3.15 mmol), HOBt (425 mg, 3.15 mmol) at 0° C. RT and stirred for 10 min. To this were added compound 368 (280 mg, 1.73 mmol) and diisopropylethylamine (0.8 mL, 4.72 mmol) at RT and stirred for 16 h. The reaction was monitored by TLC; after completion of the reaction, the reaction mixture was diluted with ice-cold water (50 mL) and the obtained solid was filtered, triturated with CH$_3$CN: diethyl ether (1:4, 10 mL) and dried in vacuo to afford compound 784 (520 mg, 89%) as an off-white solid. TLC: 10% MeOH/CH$_2$Cl$_2$ (R$_f$: 0.3); $^1$H-NMR (DMSO-d$_6$, 500 MHz): δ 10.56 (br s, 1H), 7.79 (dd, J=7.7, 1.0 Hz, 1H), 7.71 (br s, 1H), 7.66-7.61 (m, 1H), 7.42-7.31 (m, 3H), 7.27-7.20 (m, 2H), 4.70 (br s, 2H), 2.89 (s, 3H).

Synthesis of N-((2-(2-(dimethylamino) ethoxy) thiazol-5-yl) methyl)-N-methyl-11-oxo-10, 11-dihydrodibenzo [b, f] [1, 4] oxazepine-8-carboxamide (1686)

To a stirring solution of 2-(dimethylamino) ethan-1-ol 358 (0.12 mL, 1.12 mmol) in THF (10 mL) under argon atmosphere was added sodium hydride (60%, 41 mg, 1.69 mmol) portion wise at 0° C. and stirred for 10 min. To this was added compound 784 (150 mg, 0.37 mmol) at 0° C.; heated to 60° C. and stirred for 4 h. The reaction was monitored by TLC; after completion of the reaction, the reaction mixture was quenched with water (0.5 mL) and the volatiles were removed in vacuo to obtain the crude. The crude compound was purified through basic alumina column chromatography using 2% MeOH/CH$_2$Cl$_2$ to afford 1686 (85 mg, 50%) as an off-white solid. TLC: 10% MeOH/CH$_2$Cl$_2$ (R$_f$: 0.4); $^1$H-NMR (DMSO-d$_6$, 500 MHz): δ 10.56 (br s, 1H), 7.79 (dd, J=7.8, 1.6 Hz, 1H), 7.66-7.60 (m, 1H), 7.42-7.31 (m, 3H), 7.24-7.16 (m, 3H), 4.59 (br s, 2H), 4.40 (t, J=5.6 Hz, 2H), 2.85 (s, 3H), 2.62 (t, J=5.6 Hz, 2H), 2.19 (s, 6H); LC-MS: 98.25%; 453.1 (M$^+$+1); (column; Ascentis Express C18, (50×3.0 mm, 2.7 μm); RT 1.72 min. 0.025% Aq. TFA+5% ACN: ACN+5% 0.025% Aq. TFA, 1.2 mL/min); HPLC (purity): 97.15%; (column; X-select CSH C-18 (150× 4.6 mm, 3.5 μm); RT 5.67 min. 0.05% TFA (Aq): ACN; 1.0 mL/min).

Synthesis of 1613-A

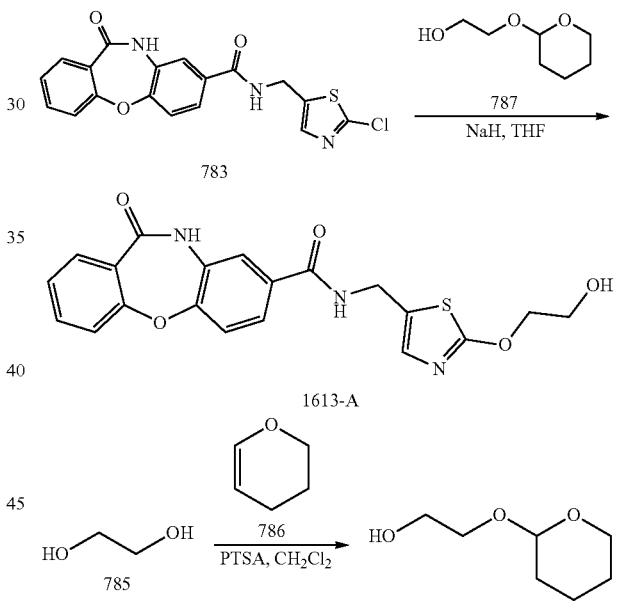

Synthesis of 2-((tetrahydro-2H-pyran-2-yl) oxy) ethan-1-ol (787)

To a stirring solution of ethane-1, 2-diol 785 (20 g, 322.5 mmol) in CH$_2$Cl$_2$ (250 mL) under inert atmosphere was added p-toluene sulfonic acid (3 g, 0.16 mmol) and 3, 4-dihydro-2H-pyran 786 (13.5 g, 0.16 mmol) at 0° C.; warmed to RT and stirred for 16 h. The reaction was monitored by TLC; after completion of the reaction, the diluted with CH$_2$Cl$_2$ (200 mL) and washed with water (100 mL). The organic extracts were dried over sodium sulfate, filtered and concentrated in vacuo to obtain the crude. The crude was purified through silica gel column chromatography using 30% EtOAc/hexanes to afford compound 787 (6 g, 13%) as colorless thick syrup. TLC: 50% EtOAc/hexanes (R$_f$: 0.4); $^1$H-NMR (CDCl$_3$, 400 MHz): δ 4.74-4.53 (m, 1H), 3.98-3.61 (m, 5H), 3.59-3.48 (m, 1H), 1.91-1.68 (m, 2H), 1.66-1.48 (m, 5H).

Synthesis of 11-oxo-N-((2-(2-((tetrahydro-2H-pyran-2-yl) oxy) ethoxy) thiazol-5-yl) methyl)-10, 11-dihydrodibenzo [b, f] [1, 4] oxazepine-8-carboxamide (1613-A)

To a stirring solution of compound 787 (19 mg, 0.12 mmol) in THF (4 mL) under argon atmosphere was added sodium hydride (60%, 4.5 mg, 0.18 mmol) at 0° C. and stirred for 30 min. To this was added N-((2-chlorothiazol-5-yl) methyl)-11-oxo-10, 11-dihydrodibenzo [b, f] [1, 4] oxazepine-8-carboxamide 783 (25 mg, 0.06 mmol) at 0° C.; heated to 60° C. and stirred for 16 h. The reaction was monitored by TLC; after completion of the reaction, the reaction mixture was quenched with saturated citric acid solution (1 mL) and the extracted with EtOAc (2×25 mL). The combined organic extracts were dried over sodium sulfate, filtered and concentrated in vacuo. The crude compound was diluted with 10% MeOH/CH$_2$Cl$_2$ (20 mL), saturated citric acid solution (3 mL) and the organic extract was dried over sodium sulfate, filtered and concentrated in vacuo to obtain the crude; which was triturated CH$_3$OH (2×2 mL) and dried in vacuo to afford 1613-A (12 mg, 45%) as an off-white solid. TLC: 5% MeOH/CH$_2$Cl$_2$ (R$_f$ 0.4); $^1$H-NMR (DMSO-d$_6$, 400 MHz): δ 10.62 (s, 1H), 9.09 (t, J=5.7 Hz, 1H), 7.78 (dd, J=7.7, 1.7 Hz, 1H), 7.68-7.57 (m, 3H), 7.41 (d, J=8.5 Hz, 1H), 7.38-7.31 (m, 2H), 7.05 (s, 1H), 4.91 (t, J=5.5 Hz, 1H), 4.44 (d, J=5.5 Hz, 2H), 4.30 (t, J=5.2 Hz, 2H), 3.68 (q, J=5.2 Hz, 2H); LC-MS: 96.28%; 412.0 (M$^+$+1); (column; X-Select CSH C-18, (50×3.0 mm, 2.5 μm); RT 2.46 min. 2.5 mM Aq. NH$_4$OOCH+5% ACN: ACN+5% 2.5 mM Aq. NH$_4$OOCH, 1.2 mL/min); HPLC (purity): 96.02%; (column; X-select CSH C-18 (150×4.6 mm, 3.5 μm); RT 8.39 min. 0.05% TFA (Aq): ACN; 1.0 mL/min).

Synthesis of 1705 and 1706

Synthesis of N-((2-(6-methoxypyridin-3-yl) thiazol-5-yl) methyl)-11-oxo-10, 11-dihydrodibenzo [b, f] [1, 4] oxazepine-8-carboxamide (1705)

To a stirring solution of N-((2-chlorothiazol-5-yl) methyl)-11-oxo-10, 11-dihydrodibenzo [b, f] [1, 4] oxazepine-8-carboxamide 783 (300 mg, 0.77 mmol) in 1, 2 dimethoxy ethane: H$_2$O (4:1, 10 mL) were added (6-methoxypyridin-3-yl) boronic acid 582 (143 mg, 0.93 mmol), sodium carbonate (244 mg, 2.31 mmol) in a sealed tube and purged under argon atmosphere for 15 min. To this was added Pd(PPh$_3$)$_4$ (88 mg, 0.07 mmol) at RT; heated to 110° C. and stirred for 16 h. The reaction was monitored by TLC; after completion the reaction mixture was diluted with water (50 mL) and extracted with CH$_2$Cl$_2$ (2×30 mL). The combined organic extracts were dried over sodium sulfate, filtered and concentrated in vacuo to obtain the crude. The crude was purified through silica gel column chromatography using 2-8% MeOH/CH$_2$Cl$_2$ to afford 1705 (160 mg, 45%) as an off-white solid. TLC: 5% MeOH/CH$_2$Cl$_2$ (R$_f$: 0.4); $^1$H-NMR (DMSO-d$_6$, 500 MHz): δ 10.65 (s, 1H), 9.23 (t, J=5.8 Hz, 1H), 8.68 (d, J=2.0 Hz, 1H), 8.16 (dd, J=8.7, 2.5 Hz, 1H), 7.80-7.76 (m, 2H), 7.70 (d, J=2.0 Hz, 1H), 7.66-7.60 (m, 2H), 7.43 (d, J=8.4 Hz, 1H), 7.39-7.29 (m, 2H), 6.92 (d, J=8.7 Hz, 1H), 4.66 (d, J=5.6 Hz, 2H), 3.90 (s, 3H); LC-MS: 98.15%; 459.0 (M$^+$+1); (column; Ascentis Express C18, (50×3.0 mm, 2.7 μm); RT 2.26 min. 0.025% Aq.TFA+5% ACN: ACN+5% 0.025% Aq. TFA, 1.2 mL/min); HPLC (purity): 99.44%; (column; X-select CSH C-18 (150×4.6 mm, 3.5 μm); RT 8.52 min. ACN+5% 0.05% TFA (Aq): 0.05% TFA (Aq)+5% ACN; 1.0 mL/min, Diluent: ACN: water).

Synthesis of N-((2-(6-hydroxypyridin-3-yl) thiazol-5-yl) methyl)-11-oxo-10, 11-dihydrodibenzo [b, f] [1, 4] oxazepine-8-carboxamide (1706)

To a stirring solution of 1705 (100 mg, 0.21 mmol) in DMF (5 mL) under inert atmosphere were added lithium chloride (46 mg, 1.08 mmol) p-toluenesulfonic acid (215 mg, 1.08 mmol) at RT in a sealed tube; heated to 120° C. and stirred for 16 h. The reaction was monitored by TLC and LC-MS; after completion the reaction mixture was diluted with water (50 mL) and the precipitate was filtered. The solid was suspended in EtOAc (10 mL), stirred for 5 h, filtered and dried in vacuo to afford 1706 (40 mg, 42%) as an off-white solid. TLC: 5% MeOH/CH$_2$Cl$_2$ (R$_f$: 0.4); $^1$H-NMR (DMSO-d$_6$, 500 MHz): δ 11.72 (br s, 1H), 10.62 (br s, 1H), 9.18 (t, J=5.2 Hz, 1H), 7.92 (br s, 1H), 7.88 (d, J=9.5 Hz, 1H), 7.77 (d, J=7.5 Hz, 1H), 7.67 (d, J=8.1 Hz, 2H), 7.64-7.59 (m, 2H), 7.41 (d, J=8.4 Hz, 1H), 7.37-7.30 (m, 2H), 6.41 (d, J=9.5 Hz, 1H), 4.60 (d, J=5.2 Hz, 2H); LC-MS: 94.14%; 445.0 (M$^+$+1); (column; Ascentis Express C18, (50×3.0 mm, 2.7 μm); RT 1.90 min. 0.025% Aq. TFA+5% ACN: ACN+5% 0.025% Aq. TFA, 1.2 mL/min); HPLC (purity): 93.67%; (column; X-select CSH C-18 (150× 4.6 mm, 3.5 μm); RT 6.06 min. ACN+5% 0.05% TFA (Aq): 0.05% TFA (Aq)+5% ACN; 1.0 mL/min, Diluent: DMSO: ACN:water).

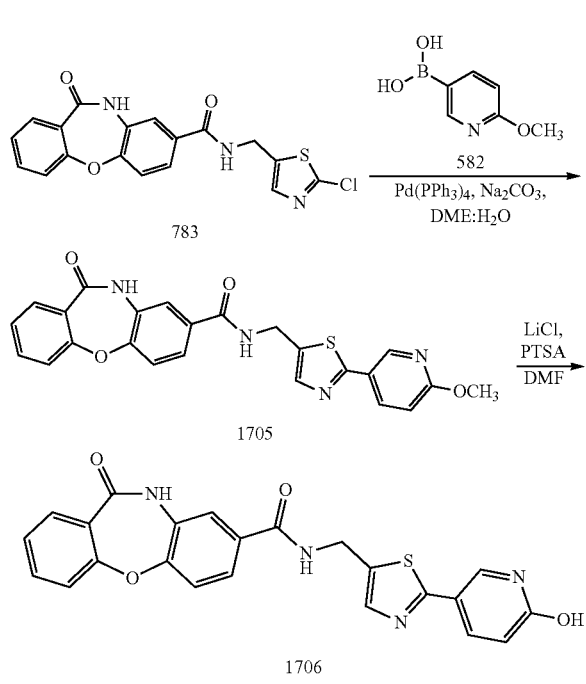

Synthesis of 1707

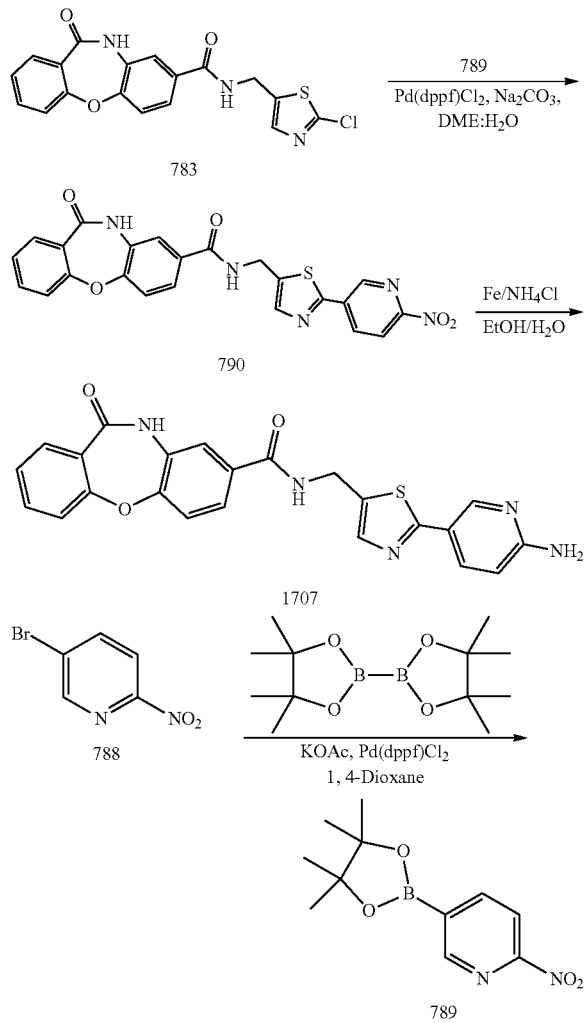

carboxamide 783 (300 mg, 0.77 mmol) in 1, 2-dimethoxy ethane: H₂O (4:1, 20 mL) under inert atmosphere were added 2-nitro-5-(4, 4, 5, 5-tetramethyl-1, 3, 2-dioxaborolan-2-yl) pyridine 789 (600 mg, crude) and sodium carbonate (248 mg, 2.33 mmol) at RT and purged under argon atmosphere for 15 min. To this was added Pd(dppf)Cl₂ (57 mg, 0.07 mmol) and heated to 100° C. and stirred for 16 h. The reaction was monitored by TLC; after completion of the reaction, the volatiles were removed in vacuo to obtain the crude. The crude was purified through silica gel column chromatography using 4% MeOH/CH₂Cl₂ to afford compound 790 (200 mg, 54%) as an off-white solid. TLC: 5% MeOH/CH₂Cl₂ (R$_f$: 0.3). LC-MS: 47.25%; 474.0 (M⁺+1); (column; Ascentis Express C18, (50×3.0 mm, 2.7 μm); RT 2.249 min. 0.025% Aq.TFA+5% ACN: ACN+5% 0.025% Aq TFA, 1.2 mL/min).

Synthesis of N-((2-(6-aminopyridin-3-yl) thiazol-5-yl) methyl)-11-oxo-10, 11-dihydrodibenzo [b, f] [1, 4] oxazepine-8-carboxamide (1707)

To a stirring solution of compound 790 (100 mg, 0.21 mmol) in EtOH: H₂O (1:1, 10 mL) under inert atmosphere were added iron powder (118 mg, 2.11 mmol), ammonium chloride (113 mg, 2.11 mmol) at RT; heated to 90° C. for 2 h. The reaction was monitored by TLC; after completion of the reaction, the reaction mixture was filtered through celite and washed with 5% MeOH/CH₂Cl₂ (30 mL). The filtrate was concentrated in vacuo to obtain the crude. The crude was purified through silicagel column chromatography using 5% MeOH/CH₂Cl₂, triturated with EtOAc (10 mL), MeOH (10 mL) and dried in vacuo to afford 1707 (20 mg, 21%) as an off-white solid. TLC: 5% MeOH/CH₂Cl₂ (R$_f$: 0.2); ¹H NMR (DMSO-d₆, 400 MHz): δ 10.63 (s, 1H), 9.17 (t, J=5.8 Hz, 1H), 8.42 (d, J=2.0 Hz, 1H), 7.85-7.76 (m, 2H), 7.71-7.59 (m, 4H), 7.42 (d, J=8.3 Hz, 1H), 7.39-7.30 (m, 2H), 6.53-6.47 (m, 3H), 4.61 (d, J=5.5 Hz, 2H); LC-MS: 98.86%; 444.0 (M⁺+1); (column; Ascentis Express C18, (50×3.0 mm, 2.7 μm); RT 1.76 min. 0.025% Aq.TFA+5% ACN: ACN+5% 0.025% Aq TFA, 1.2 mL/min). HPLC (purity): 96.35%; (column; X-select CSH C-18 (150×4.6 mm, 3.5 μm); RT 5.61 min. 5% ACN+5% 0.05% TFA (Aq): ACN+5% 0.05% TFA; 1.0 mL/min, Diluent: ACN:water).

Synthesis of 2-nitro-5-(4, 4, 5, 5-tetramethyl-1, 3, 2-dioxaborolan-2-yl) pyridine (789)

To a stirring solution of 5-bromo-2-nitropyridine 788 (1 g, 4.95 mmol) in 1, 4-dioxane (20 mL) under inert atmosphere were added bispinacolato diboron (1.9 g, 7.42 mmol), potassium acetate (1.45 g, 14.85 mmol) at RT and purged under argon atmosphere for 15 min; to this was added Pd(dppf)Cl₂ (362 mg, 0.49 mmol) and purged under argon atmosphere for 5 min, heated to 100° C. and stirred for 4 h. The reaction was monitored by TLC; after completion of the reaction, the volatiles were concentrated in vacuo to obtain the crude. The crude was triturated with diethylether (20 mL) and dried in vacuo to afford compound 789 (980 mg, crude) as an brown sticky solid. TLC: 20% MeOH/CH₂Cl₂ (R$_f$: 0.2);

Synthesis of N-((2-(6-nitropyridin-3-yl) thiazol-5-yl) methyl)-11-oxo-10, 11-dihydrodibenzo [b, f] [1, 4] oxazepine-8-carboxamide (790)

To a stirring solution N-((2-chlorothiazol-5-yl) methyl)-11-oxo-10, 11-dihydrodibenzo [b, f] [1, 4] oxazepine-8-

Synthesis of 1770, 1770-A

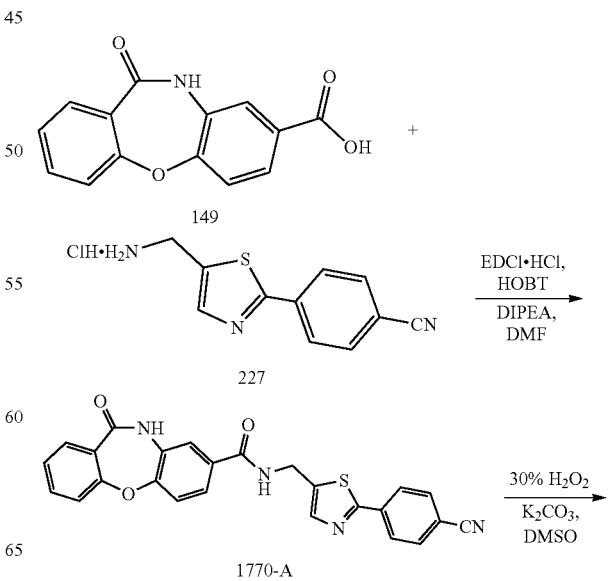

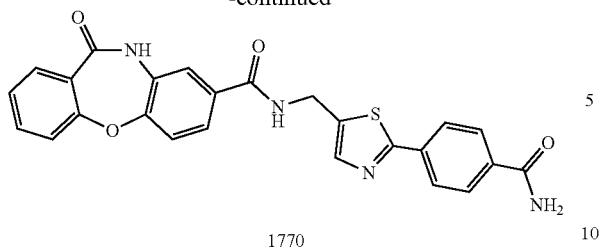

1770

Synthesis of N-((2-(4-cyanophenyl) thiazol-5-yl) methyl)-11-oxo-10, 11-dihydrodibenzo [b, f] [1, 4] oxazepine-8-carboxamide (1770-A)

To a stirring solution of 149 (150 mg, 0.58 mmol) in DMF (7.5 mL) under inert atmosphere were added EDCI.HCl (168 mg, 0.88 mmol), HOBt (119 mg, 0.88 mmol), 4-(5-(aminomethyl) thiazol-2-yl) benzonitrile hydrochloride 227 (148 mg, 0.58 mmol) and diisopropylethylamine (0.32 mL, 1.76 mmol) at 0° C.; warmed to RT and stirred for 16 h. The reaction was monitored by TLC; after completion of the reaction, the reaction mixture was diluted with water (50 mL) and extracted with 10% MeOH/CH$_2$Cl$_2$ (2×100 mL). The combined organic extracts were dried over sodium sulfate, filtered and concentrated in vacuo to obtain the crude. The crude was purified through silicagel column chromatography using 5% MeOH/CH$_2$Cl$_2$ to afford 1770-A (120 mg, 45%) as white solid. TLC: 5% MeOH/CH$_2$Cl$_2$ (R$_f$: 0.5); $^1$H NMR (DMSO-d$_6$, 400 MHz): δ 10.65 (s, 1H), 9.27 (t, J=5.6 Hz, 1H), 8.07 (d, J=8.5 Hz, 2H), 7.97-7.88 (m, 3H), 7.78 (dd, J=7.7, 1.6 Hz, 1H), 7.70 (s, 1H), 7.66-7.60 (m, 2H), 7.43 (d, J=8.4 Hz, 1H), 7.39-7.31 (m, 2H), 4.69 (d, J=5.6 Hz, 2H); LC-MS: 99.16%; 453.2 (M$^+$+1); (column; Ascentis Express C18, (50×3.0 mm, 2.7 μm); RT 2.35 min. 0.025% Aq. TFA+5% ACN: ACN+5% 0.025% Aq. TFA, 1.2 mL/min). HPLC (purity): 98.94%; (column; X-Select CSH C-18 (150×4.6 mm, 3.5 μm); RT 8.92 min. ACN+5% 0.05% TFA (Aq): 0.05% TFA (Aq): 5% ACN; 1.0 mL/min, Diluent: ACN:water).

Synthesis of N-((2-(4-carbamoylphenyl) thiazol-5-yl) methyl)-11-oxo-10, 11-dihydrodibenzo [b, f] [1, 4] oxazepine-8-carboxamide (1770)

To a stirring solution of 1770-A (80 mg, 0.17 mmol) in DMSO (3 mL) under inert atmosphere were added potassium carbonate (122 mg, 0.88 mmol), 30% hydrogen peroxide (0.16 mL, 1.41 mmol) at 0° C.; warmed to RT and stirred for 2 h. The reaction was monitored by TLC; after completion of the reaction, the reaction mixture was diluted with ice-cold water and the precipitated solid was filtered, washed with MeOH: EtOAc (1:1, 20 mL). The obtained solid was suspended in 50% n-pentane/diethylether (10 mL) and stirred for 16 h, the solvent was decanted and the solid was dried in vacuo to afford 1770 (25 mg, 30%) as white solid. TLC: 5% MeOH/CH$_2$Cl$_2$ (R$_f$: 0.3); $^1$H NMR (DMSO-d$_6$, 500 MHz): δ 10.62 (br s, 1H), 9.29 (br s, 1H), 8.06 (br s, 1H), 7.96-7.94 (m, 4H), 7.84 (s, 1H), 7.74 (dd, J=7.7, 1.5 Hz, 1H), 7.69 (s, 1H), 7.62-7.54 (m, 2H), 7.44 (br s, 1H), 7.37 (d, J=8.3 Hz, 1H), 7.34-7.27 (m, 2H), 4.67 (s, 2H); LC-MS: 99.24%; 471.0 (M$^+$+1); (column; Ascentis Express C18, (50×3.0 mm, 2.7 μm); RT 1.96 min. 0.025% Aq. TFA+5% ACN: ACN+5% 0.025% Aq. TFA, 1.2 mL/min); HPLC (purity): 99.45%; (column; X-select CSH C-18 (150× 4.6 mm, 3.5 μm); RT 6.96 min. ACN+5% 0.05% TFA (Aq): 0.05% TFA (Aq)+5% ACN; 1.0 mL/min, Diluent: DMSO: ACN:water).

Synthesis of 1612-A & 1612

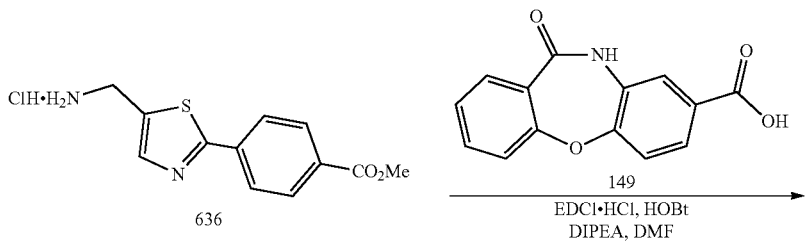

636     149

EDCl•HCl, HOBt
DIPEA, DMF

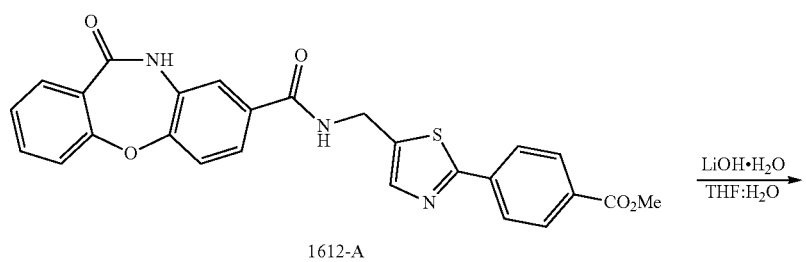

1612-A

LiOH•H$_2$O
THF:H$_2$O

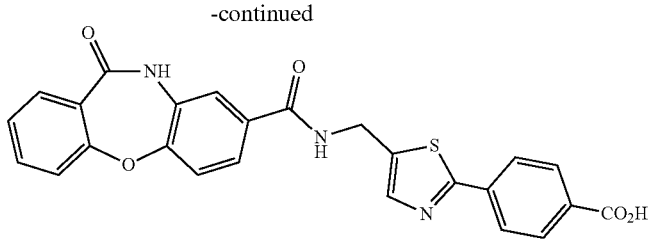

1612

Synthesis of methyl 4-(5-((11-oxo-10, 11-dihydrodibenzo [b, f] [1, 4] oxazepine-8-carboxamido) methyl) thiazol-2-yl) benzoate (1612-A)

To a stirring solution of compound 149 (150 mg, 0.58 mmol) in DMF (6 mL) under inert atmosphere were added EDCI.HCl (167 mg, 0.88 mmol), HOBt (119 mg, 0.88 mmol), methyl 4-(5-(aminomethyl) thiazol-2-yl) benzoate hydrochloride 636 (183 mg, 0.64 mmol) and diisopropylethylamine (0.50 mL, 2.94 mmol) at 0° C.; warmed to RT and stirred for 16 h. The reaction was monitored by TLC; after completion of the reaction, the reaction mixture was poured into ice-cold water (50 mL) and stirred for 10 min. The precipitated solid was filtered and dried in vacuo to obtain the crude. The crude was purified through silica gel column chromatography using 2% MeOH/CH$_2$Cl$_2$ to afford compound 1612-A (160 mg, 56%) as an off-white solid. TLC: 10% MeOH/CH$_2$Cl$_2$ (R$_f$. 0.5); $^1$H NMR (DMSO-d$_6$, 500 MHz): δ 10.64 (s, 1H), 9.25 (t, J=5.6 Hz, 1H), 8.04 (s, 4H), 7.88 (s, 1H), 7.78 (dd, J=7.8, 1.4 Hz, 1H), 7.70 (s, 1H), 7.66-7.61 (m, 2H), 7.43 (d, J=8.4 Hz, 1H), 7.39-7.31 (m, 2H), 4.69 (d, J=5.8 Hz, 2H), 3.87 (s, 3H); LC-MS: 97.06%; 485.9 (M$^+$+1); (column; Ascentis Express C18, (50×3.0 mm, 2.7 μm); RT 2.45 min. 0.025% Aq. TFA+5% ACN: ACN+5% 0.025% Aq. TFA, 1.2 mL/min); HPLC (purity): 97.26%; (column; X-select CSH C-18 (150×4.6 mm, 3.5 μm); RT 9.55 min. ACN+0.5% TFA (Aq): 0.5% TFA (Aq)+ACN; 1.0 mL/min, Diluent: ACN:water).

Synthesis of 4-(5-((11-oxo-10, 11-dihydrodibenzo [b, f] [1, 4] oxazepine-8-carboxamido) methyl) thiazol-2-yl) benzoic acid (1612)

To a stirring solution of 1612-A (60 mg, 0.12 mmol) in THF:H$_2$O (4:1, 5 mL) was added lithium hydroxide monohydrate (11 mg, 0.24 mmol) at RT and stirred for 16 h. The reaction was monitored by TLC; after completion of the reaction, the reaction mixture was diluted with ice-cold water (10 mL) and the pH was adjusted to with 2 N HCl to ~4. The precipitated solid was filtered washed with water (20 mL) diethyl ether (5 mL), n-pentane (10 mL) and dried in vacuo to afford 1612 (50 mg, 86%) as an off-white solid. TLC: 10% MeOH/CH$_2$Cl$_2$ (R$_f$; 0.2); $^1$H NMR (DMSO-d$_6$, 400 MHz): δ 13.12 (br s, 1H), 10.64 (s, 1H), 9.26 (t, J=5.7 Hz, 1H), 8.02-7.99 (m, 4H), 7.87 (s, 1H), 7.78 (dd, J=7.7, 1.7 Hz, 1H), 7.70 (s, 1H), 7.66-7.60 (m, 2H), 7.43 (d, J=8.4 Hz, 1H), 7.39-7.31 (m, 2H), 4.68 (d, J=5.5 Hz, 2H); LC-MS: 96.31%; 472.0 (M$^+$+1); (column; Ascentis Express C18, (50×3.0 mm, 2.7 μm); RT 2.21 min. 0.025% Aq. TFA+5% ACN: ACN+5% 0.025% Aq. TFA, 1.2 mL/min); HPLC (purity): 96.41%; (column; Zorbax SB C-18 (150×4.6 mm, 3.5 μm); RT 6.86 min. ACN+5% 0.5% TFA (Aq): 0.5% TFA (Aq)+5% ACN; 1.0 mL/min, Diluent: ACN:water).

Synthesis of 1620

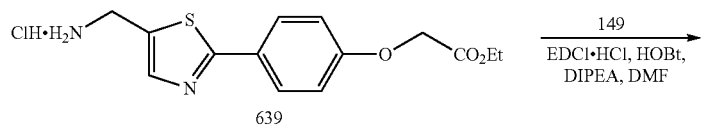

639

$\xrightarrow{\text{149}}$ EDCl·HCl, HOBt, DIPEA, DMF

791

$\xrightarrow{\text{LiOH·H}_2\text{O}}$ THF/H$_2$O

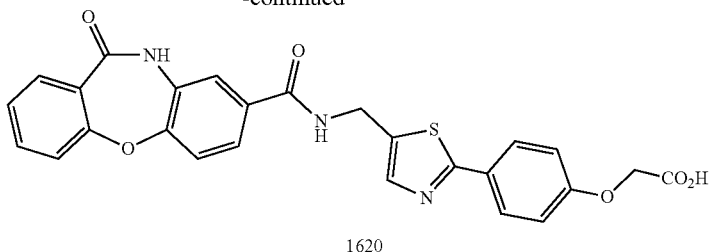

1620

Synthesis of ethyl 2-(4-(5-((11-oxo-10, 11-dihydrodibenzo[b,f][1,4]oxazepine-8-carboxamido)methyl)thiazol-2-yl)phenoxy)acetate (791)

To a stirring solution of compound 149 (75 mg, 0.29 mmol) in DMF (5 mL) under inert atmosphere were added ethyl 2-(4-(5-(aminomethyl) thiazol-2-yl) phenoxy) acetate hydrochloride 639 (96 mg, 0.29 mmol), EDCI.HCl (84 mg, 0.44 mmol), HOBt (60 mg, 0.44 mmol), and diisopropylethylamine (0.27 mL, 1.47 mmol) at 0° C.; warmed to RT and stirred for 16 h. The reaction was monitored by TLC; after completion of the reaction, the reaction mixture was poured into ice-cold water (50 mL) and extracted with EtOAc (2×150 mL). The combined organic extracts were dried over sodium sulfate, filtered and concentrated in vacuo to obtain the crude. The crude was purified through silica gel column chromatography using 3% MeOH/CH$_2$Cl$_2$ to afford compound 791 (60 mg, 39%) as white solid. TLC: 5% MeOH/CH$_2$Cl$_2$ (R$_f$: 0.6); $^1$H NMR (DMSO-d$_6$, 500 MHz): δ 10.63 (s, 1H), 9.19 (t, J=5.8 Hz, 1H), 7.81 (d, J=9.0 Hz, 2H), 7.78 (dd, J=7.8, 1.4 Hz, 1H), 7.73-7.69 (m, 2H), 7.65-7.61 (m, 2H), 7.42 (d, J=8.4 Hz, 1H), 7.36 (d, J=8.1 Hz, 1H), 7.35-7.31 (m, 1H), 7.01 (d, J=9.0 Hz, 2H), 4.84 (s, 2H), 4.64 (d, J=5.5 Hz, 2H), 4.17 (q, J=7.2 Hz, 2H), 1.21 (t, J=7.1 Hz, 3H).

Synthesis of 2-(4-(5-((11-oxo-10, 11-dihydrodibenzo [b, f] [1, 4] oxazepine-8-carboxamido) methyl) thiazol-2-yl) phenoxy) acetic acid (1620)

To a stirring solution of compound 791 (60 mg, 0.11 mmol) in THF:H$_2$O (4:1, 6 mL) was added lithium hydroxide monohydrate (24 mg, 0.56 mmol) at RT and stirred for 2 h. The reaction was monitored by TLC; after completion of the reaction, the volatiles were removed in vacuo. The residue was diluted water (50 mL) and the pH was acidified with 2 N HCl to ~6. The precipitated solid was filtered and dried in vacuo to afford 1620 (50 mg, 88%) as white solid. TLC: 10% MeOH/CH$_2$Cl$_2$ (R$_f$: 0.2); $^1$H-NMR (DMSO-d$_6$, 500 MHz): δ 13.05 (br s, 1H), 10.63 (s, 1H), 9.20 (t, J=5.8 Hz, 1H), 7.81 (d, J=9.0 Hz, 2H), 7.78 (dd, J=7.8, 1.7 Hz, 1H), 7.72-7.69 (m, 2H), 7.65-7.61 (m, 2H), 7.42 (d, J=8.4 Hz, 1H), 7.36 (d, J=8.1 Hz, 1H), 7.35-7.31 (m, 1H), 7.00 (d, J=9.0 Hz, 2H), 4.74 (s, 2H), 4.64 (d, J=5.5 Hz, 2H); LC-MS: 98.03%; 501.9 (M$^+$+1); (column; Ascentis Express C18, (50×3.0 mm, 2.7 μm); RT 2.11 min. 0.025% Aq. TFA+5% ACN: ACN+5% 0.025% Aq. TFA, 1.2 mL/min); HPLC (purity): 99.39%; (column; Zorbax SB C-18 (150×4.6 mm, 3.5 μm); RT 7.71 min; ACN+0.5% TFA (Aq): 0.5% TFA (Aq): 5% ACN; 1.0 mL/min, Diluent: ACN:water).

Synthesis of 11161

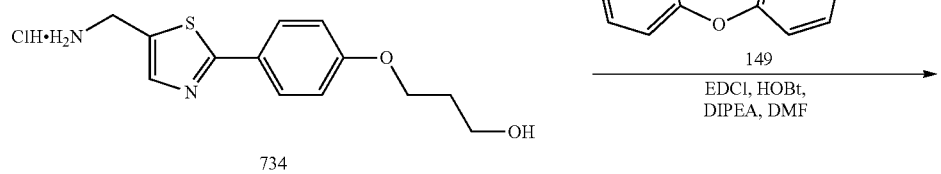

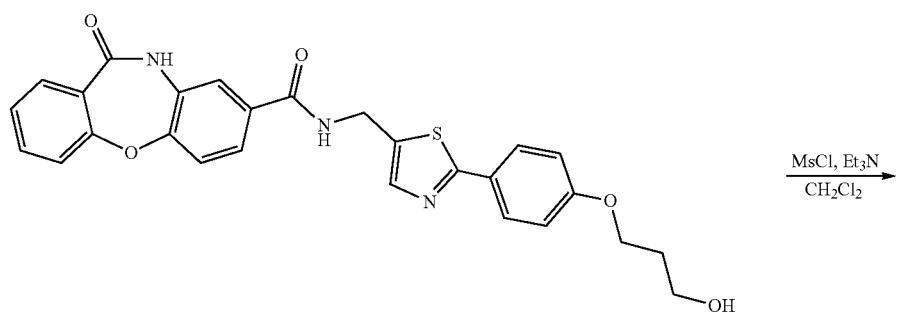

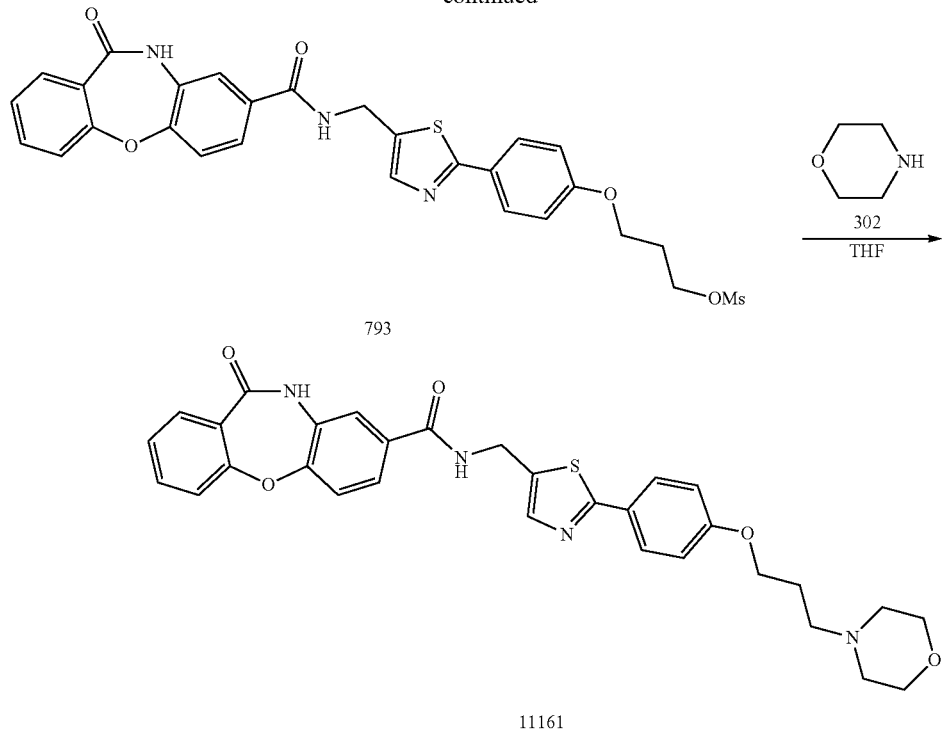

Synthesis of N-((2-(4-(3-hydroxypropoxy) phenyl) thiazol-5-yl) methyl)-11-oxo-10, 11-dihydrodibenzo [b, f] [1, 4] oxazepine-8-carboxamide (792)

To a stirring solution of 11-oxo-10, 11-dihydrodibenzo [b, f] [1, 4] oxazepine-8-carboxylic acid 149 (1 g, 3.94 mmol) in DMF (30 mL) were added 3-(4-(5-(aminomethyl) thiazol-2-yl) phenoxy) propan-1-ol hydrochloride 734 (1.3 g, 4.33 mmol), EDCI.HCl (1.13 g, 5.9 mmol), HOBt (797 mg, 5.9 mmol) followed by diisopropylethylamine (3.43 mL, 19.68 mmol) at 0° C. under inert atmosphere. The reaction mixture was gradually warmed to RT and stirred for 16 h. The reaction was monitored by TLC and LCMS; after completion of the reaction, the reaction mixture was diluted with ice cold water (100 mL) and extracted with EtOAc (2×100 mL). The combined organic extracts were dried over sodium sulfate, filtered and concentrated in vacuo to obtain the crude. The crude was purified through column chromatography using 1-5% MeOH/CH$_2$Cl$_2$ followed by triturations with 5% MeOH/CH$_2$Cl$_2$ (2×5 mL) to afford compound 792 (800 mg, 41%) as an off white solid. TLC: 10% MeOH/CH$_2$Cl$_2$ (R$_f$: 0.5); $^1$H NMR (400 MHz, DMSO-d$_6$): δ 10.64 (s, 1H), 9.20 (t, J=5.8 Hz, 1H), 7.83-7.76 (m, 3H), 7.72-7.68 (m, 2H), 7.66-7.60 (m, 2H), 7.43 (d, J=8.4 Hz, 1H), 7.38-7.31 (m, 2H), 7.01 (d, J=8.9 Hz, 2H), 4.63 (d, J=5.6 Hz, 2H), 4.56 (t, J=5.1 Hz, 1H), 4.08 (t, J=6.3 Hz, 2H), 3.55 (q, J=6.0 Hz, 2H), 1.91-1.82 (m, 2H); LC-MS: 95.30%; 502.2 (M$^+$+1); (column; Kinetex EVO C-18 (50×3.0 mm, 2.6 um); RT 2.49 min. 2.5 mM NH$_4$OOCH in water+5% ACN: ACN+5% 2.5 mM NH$_4$OOCH in water, 0.8 mL/min).

Synthesis of 3-(4-(5-((11-oxo-10, 11-dihydrodibenzo [b, f] [1, 4] oxazepine-8-carboxamido) methyl) thiazol-2-yl) phenoxy) propyl methanesulfonate (793)

To a stirring solution of compound 792 (200 mg, 0.4 mmol) in CH$_2$Cl$_2$ (10 mL) were added triethylamine (0.33 mL, 2.39 mmol) followed by methanesulfonyl chloride (0.1 mL, 1.2 mmol) at 0° C. under inert atmosphere. The reaction mixture was gradually warmed to RT and stirred for 4 h. The reaction was monitored by TLC; after completion of the reaction, the reaction mixture was quenched with saturated sodium bicarbonate solution (50 mL) and extracted with CH$_2$Cl$_2$ (2×50 mL). The combined organic extracts were dried over sodium sulfate, filtered and concentrated in vacuo to afford compound 793 (250 mg) as pale brown viscous syrup. This crude material was taken to next step without further purification. TLC: 10% MeOH/CH$_2$Cl$_2$ (R$_f$: 0.6); LC-MS: 46.00%; 580.1 (M$^+$+1); (column; Kinetex EVO C-18 (50×3.0 mm, 2.6 um); RT 2.85 min. 2.5 mM NH$_4$OOCH in water+5% ACN: ACN+5% 2.5 mM NH$_4$OOCH in water, 0.8 mL/min).

Synthesis of N-((2-(4-(3-morpholinopropoxy) phenyl) thiazol-5-yl) methyl)-11-oxo-10, 11-dihydrodibenzo [b, f] [1, 4] oxazepine-8-carboxamide (11161)

To a stirring solution of compound 793 (180 mg, crude) in THF (5 mL) was added morpholine (0.11 mL, 1.29 mmol) in a sealed tube at RT under inert atmosphere. The reaction mixture was heated to 70° C. and stirred for 16 h. The reaction was monitored by TLC and LCMS; after completion of the reaction, the reaction mixture was diluted with water (100 mL) and extracted with EtOAc (2×100 mL). The combined organic extracts were dried over sodium sulfate, filtered and concentrated in vacuo to obtain the crude. The crude was purified through silica gel column chromatography using 2-10% MeOH/CH$_2$Cl$_2$ followed by trituration with 10% MeOH/CH$_2$Cl$_2$ (2×2 mL) to afford 11161 (80 mg, 32%) as an off-white solid. TLC: 10% MeOH/CH$_2$Cl$_2$ (R$_f$: 0.4); $^1$H NMR (400 MHz, DMSO-d$_6$): δ 10.64 (s, 1H), 9.19 (t, J=5.8 Hz, 1H), 7.82-7.76 (m, 3H), 7.72-7.69 (m, 2H), 7.66-7.61 (m, 2H), 7.42 (d, J=8.4 Hz, 1H), 7.39-7.31 (m, 2H), 7.01 (d, J=8.9 Hz, 2H), 4.63 (d, J=5.6 Hz, 2H), 4.06 (t, J=6.4 Hz, 2H), 3.56 (t, J=4.6 Hz, 4H), 2.44-2.33 (m, 6H), 1.91-1.85 (m, 2H); LC-MS: 92.40%; 571.2 (M$^+$+1); (column; Ascentis Express C18, (50×3.0 mm, 2.7 μm); RT 1.85 min. 0.025% Aq. TFA+5% ACN: ACN+5% 0.025% Aq. TFA, 1.2 mL/min); HPLC (purity): 94.04%; (column; X-Select CSH-C-18 (150×4.6 mm, 3.5 μm); RT 5.75 min. 0.05% TFA+5% ACN: ACN+5% 0.05% TFA; 1.0 mL/min, Diluent: ACN:H$_2$O:DMSO).

Synthesis of 11160

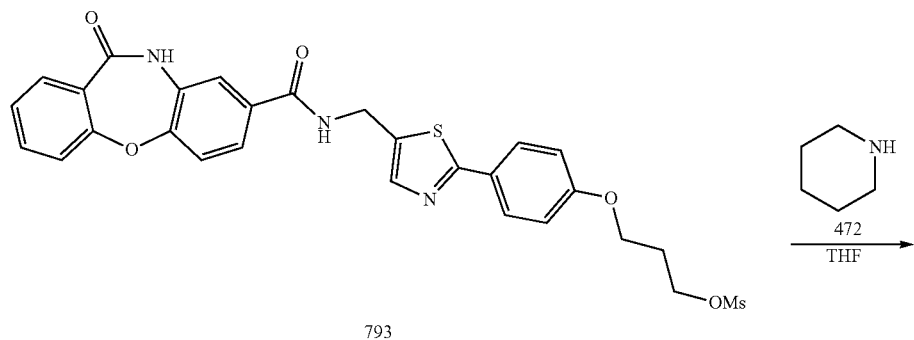

793 reaction mixture was heated to 70° C. and stirred for 16 h. The reaction was monitored by TLC; after completion of the reaction mixture was diluted with water (50 mL), and extracted with EtOAc (2×50 mL). The combined organic extracts were dried over sodium sulfate, filtered and concentrated in vacuo to obtain the crude. The crude was purified through silica gel column chromatography using 1-6% MeOH/CH$_2$Cl$_2$ which was further triturated with 10% MeOH/CH$_2$Cl$_2$ (2×5 mL) to afford 11160 (90 mg, 36%) as an off-white solid. TLC: 10% MeOH/CH$_2$Cl$_2$ (R$_f$: 0.3); $^1$H NMR (400 MHz, DMSO-d$_6$): δ 10.65 (s, 1H), 9.22 (t, J=5.7 Hz, 1H), 7.85-7.74 (m, 3H), 7.71-7.68 (m, 2H), 7.66-7.60

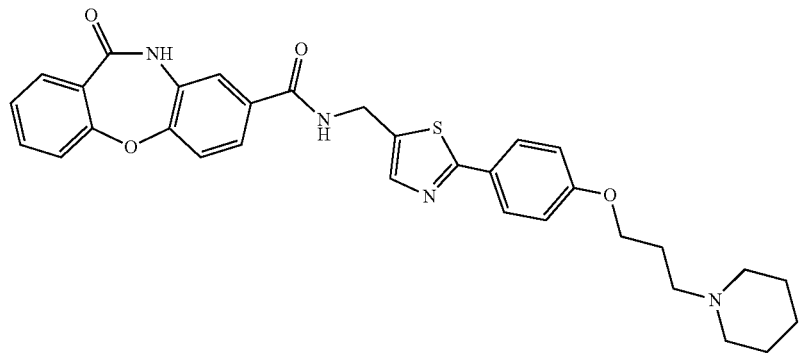

11160

Synthesis of 11-oxo-N-((2-(4-(3-(piperidin-1-yl) propoxy) phenyl) thiazol-5-yl) methyl)-10, 11-dihydrodibenzo [b, f] [1, 4] oxazepine-8-carboxamide (11160)

To a stirring solution of 3-(4-(5-((11-oxo-10, 11-dihydrodibenzo [b, 1] [1, 4] oxazepine-8-carboxamido) methyl) thiazol-2-yl) phenoxy) propyl methanesulfonate 793 (250 mg, 0.43 mmol) in THF (5 mL) was added piperidine 472 (0.21 mL, 2.15 mmol) at RT under inert atmosphere. The (m, 2H), 7.42 (d, J=8.4 Hz, 1H), 7.38-7.28 (m, 2H), 7.02 (d, J=8.9 Hz, 2H), 4.63 (d, J=5.5 Hz, 2H), 4.08 (t, J=6.1 Hz, 2H), 2.92-2.62 (m, 4H), 2.46-2.35 (m, 2H), 2.03-2.01 (m, 2H), 1.61-1.63 (m, 4H), 1.46-1.44 (m, 2H); LC-MS: 99.16%; 569.3 (M$^+$+1); (column; Ascentis Express C-18, (50×3.0 mm, 2.7 μm); RT 1.87 min. 0.025% Aq. TFA+5% ACN: ACN+5% 0.025% Aq. TFA, 1.2 mL/min); HPLC (purity): 99.01%; (column; X-Select CSH-C-18 (150×4.6 mm, 3.5 μm); RT 6.03 min. 0.05% TFA+5% ACN: ACN+5% 0.05% TFA; 1.0 mL/min, Diluent: DMSO:ACN).

Synthesis of 11162

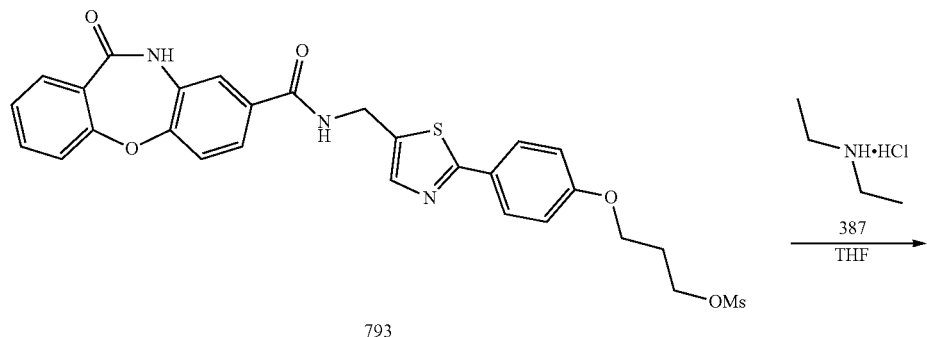

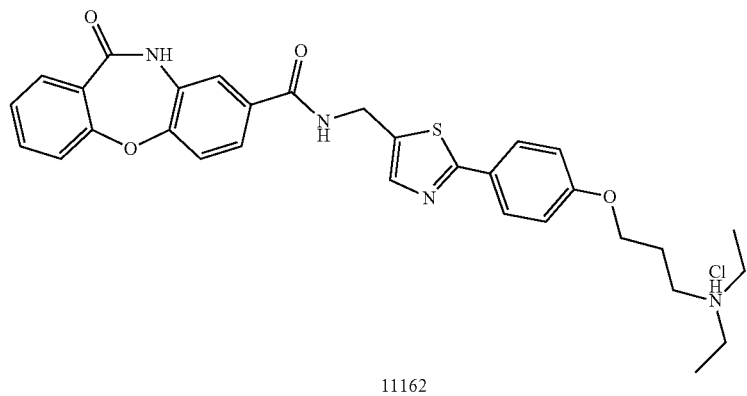

Synthesis of N-((2-(4-(3-(diethylamino) propoxy) phenyl) thiazol-5-yl) methyl)-11-oxo-10, 11-dihydrodibenzo [b, f] [1, 4] oxazepine-8-carboxamide hydrochloride (11162)

To a stirring solution of 3-(4-(5-((11-oxo-10, 11-dihydrodibenzo [b, f] [1, 4] oxazepine-8-carboxamido) methyl) thiazol-2-yl) phenoxy) propyl methanesulfonate 793 (200 mg, 0.34 mmol) in THF (10 mL) was added diethylamine hydrochloride 387 (1 mL, 1.04 mmol) at RT under inert atmosphere. The reaction mixture was heated to 80° C. and stirred for 16 h in a sealed tube. The reaction was monitored by TLC; after completion of the reaction, the volatiles were removed in vacuo to obtain the crude. The crude was purified through silica gel column chromatography using 5% MeOH/CH$_2$Cl$_2$ to afford 11162 (80 mg, 41%) as an off white solid. TLC: 5% MeOH/CH$_2$Cl$_2$ (R$_f$: 0.2); $^1$H NMR (400 MHz, DMSO-d$_6$): δ 10.65 (s, 1H), 9.86 (br s, 1H), 9.23 (t, J=5.8 Hz, 1H), 7.82 (d, J=8.8 Hz, 2H), 7.78 (dd, J=7.7, 1.6 Hz, 1H), 7.71-7.69 (m, 2H), 7.64-7.61 (m, 2H), 7.43 (d, J=8.4 Hz, 1H), 7.38-7.29 (m, 2H), 7.03 (d, J=8.9 Hz, 2H), 4.63 (d, J=5.6 Hz, 2H), 4.12 (t, J=6.0 Hz, 2H), 3.20-3.11 (m, 6H), 2.12 (br s, 2H), 1.21 (br s, 6H); LC-MS: 95.66%; 557.1 (M$^+$+1); (column; Ascentis Express C-18, (50×3.0 mm, 2.7 μm); RT 1.97 min. 0.025% Aq. TFA+5% ACN: ACN+5% 0.025% Aq. TFA, 1.2 mL/min); HPLC (purity): 97.95%; (column; X-Select CSH-C-18 (150×4.6 mm, 3.5 μm); RT 5.94 min. 0.05% TFA+5% ACN: ACN+5% 0.05% TFA; 1.0 mL/min, Diluent: H$_2$O: ACN).

Synthesis of 1712

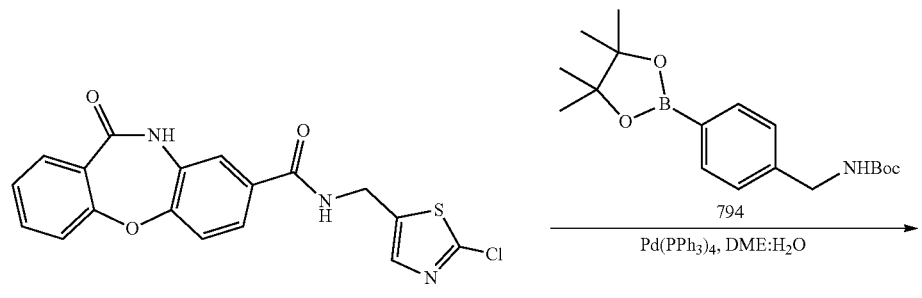

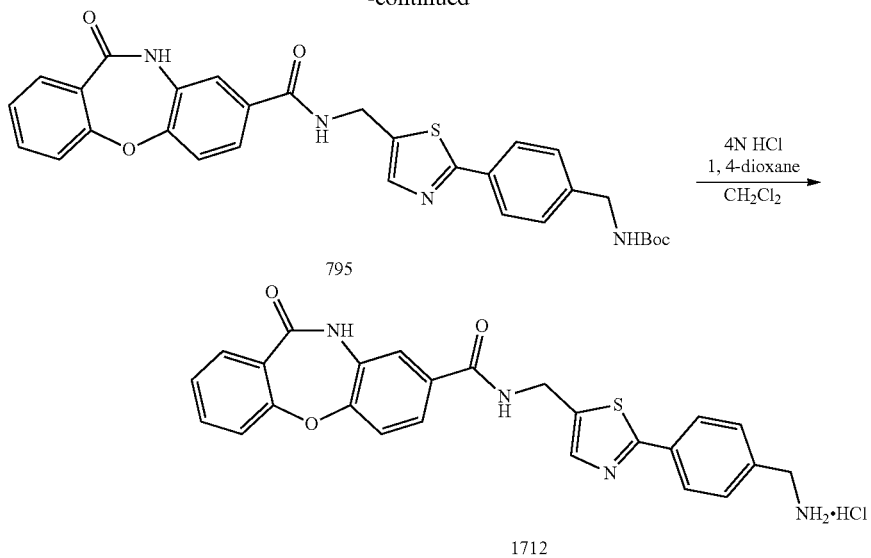

Synthesis of tert-butyl (4-(5-((11-oxo-10, 11-dihydrodibenzo [b, f] [1, 4] oxazepine-8-carboxamido) methyl) thiazol-2-yl) benzyl) carbamate (795)

To a stirring solution of N-((2-chlorothiazol-5-yl) methyl)-11-oxo-10, 11-dihydrodibenzo [b, 1] [1, 4] oxazepine-8-carboxamide 783 (150 mg, 0.38 mmol) in 1, 2 dimethoxy ethane: H₂O (4:1, 6 mL) were added tert-butyl (4-(4, 4, 5, 5-tetramethyl-1, 3, 2-dioxaborolan-2-yl) benzyl) carbamate 794 (259 mg, 0.77 mmol), sodium carbonate (144 mg, 1.36 mmol) and purged under argon atmosphere for 15 min. To this was added Pd(PPh₃)₄ (45 mg, 0.039 mmol) at RT; heated to 100° C. and stirred for 16 h. The reaction was monitored by TLC; after completion the reaction mixture was diluted with water (100 mL) and extracted with 10% MeOH/CH₂Cl₂ (2×100 mL). The combined organic extracts were dried over sodium sulfate, filtered and concentrated in vacuo to obtain the crude. The crude was purified through silica gel column chromatography using 4% MeOH/CH₂Cl₂ to afford compound 795 (150 mg, 69%) as white solid. TLC: 5% MeOH/CH₂Cl₂ (R$_f$: 0.4); ¹H-NMR (DMSO-d₆, 400 MHz): δ 10.77 (s, 1H), 9.35 (t, J=5.6 Hz, 1H), 7.97 (d, J=8.1 Hz, 2H), 7.94-7.89 (m, 2H), 7.84 (s, 1H), 7.80-7.74 (m, 2H), 7.59-7.54 (m, 2H), 7.52-7.43 (m, 4H), 4.79 (d, J=5.5 Hz, 2H), 4.29 (d, J=5.8 Hz, 2H), 1.53 (s, 9H); LC-MS: 94.24%; 557.1 (M⁺+1); (column; X Select CSH C-18, (50×3.0 mm, 2.5 μm); RT 3.19 min. 2.5 mM Aq. NH4OOCH+5% ACN: ACN+5% 2.5 mM Aq.NH4OOCH, 0.8 mL/min).

Synthesis of N-((2-(4-(aminomethyl) phenyl) thiazol-5-yl) methyl)-11-oxo-10, 11-dihydrodibenzo [b, f] [1, 4] oxazepine-8-carboxamide hydrochloride (1712)

To a stirring solution of compound 795 (150 mg, 0.26 mmol) in CH₂Cl₂ (3 mL) under inert atmosphere was added 4 N HCl in 1, 4-dioxane (1.5 mL) at 0° C.; warmed to RT and stirred for 2 h. The reaction was monitored by TLC; after completion of the reaction, the volatiles were removed in vacuo to obtain the crude. The crude was washed with CH₂Cl₂ (2×5 mL) and dried in vacuo to afford 1712 (95 mg, 72%) as white solid. TLC: 10% MeOH/CH₂Cl₂ (R$_f$: 0.2); ¹H-NMR (DMSO-d₆, 400 MHz): δ 10.67 (s, 1H), 9.30 (t, J=5.8 Hz, 1H), 8.40 (br s, 3H), 7.93 (d, J=8.4 Hz, 2H), 7.81 (s, 1H), 7.78 (dd, J=7.7, 1.7 Hz, 1H), 7.71 (s, 1H), 7.67-7.60 (m, 2H), 7.57 (d, J=8.4 Hz, 2H), 7.43 (d, J=8.3 Hz, 1H), 7.38-7.30 (m, 2H), 4.66 (d, J=5.6 Hz, 2H), 4.06 (q, J=5.7 Hz, 2H); LC-MS: 99.11%; 457.0 (M⁺+1). (column; Ascentis Express C18, (50×3.0 mm, 2.7 μm); RT 1.79 min. 0.025% Aq. TFA+5% ACN: ACN+5% 0.025% Aq. TFA, 1.2 mL/min). HPLC (purity): 98.28%; (column; Zorbax SB C-18 (150×4.6 mm, 3.5 μm); RT 5.61 min. ACN+5% 0.05% TFA (Aq): 0.05% TFA (Aq)+5% ACN; 1.0 mL/min, Diluent: ACN:water).

Example 2: Assay Measuring Activity of Compounds on Viral Production in and on Viability of AD38 Cells AD38 cells grown in a 175 cm flask with "Growth Medium" (DMEM/F12 (1:1) (cat #SH30023.01, Hyclone, 1× Pen/step (cat #: 30-002-CL, Mediatech, Inc), 10% FBS (cat #: 101, Tissue Culture Biologics), 250 μg/mL G418 (cat #: 30-234-CR, Mediatech, Inc), 1 μg/mL Tetracycline (cat #: T3325, Teknova)) were detached with 0.25% trypsin. Tetracycline-free "treatment medium" (15 mL DMEM/F12 (1:1) (cat #SH30023.01, Hyclone, 1x Pen/step (cat #: 30-002-CL, Mediatech, Inc), with 2% FBS, Tet-system approved (cat #: 631106, Clontech) were then added to mix and spun at 1300 rpm for 5 min. Pelleted cells were then re-suspended/washed with 50 mL of 1×PBS 2 times and 10 mL Treatment Medium one time. AD38 cells were then re-suspended with 10 mL of Treatment Medium and counted. Wells of a collagen coated 96-well NUNC microtiter plate were seeded at 50,000/well in 180 μL of Treatment Medium, and 20 μL of in treatment media with either 10% DMSO (Control) or a 10× solution of compound in 10% DMSO was added. Plates were incubated for 6 days at 37° C.

Viral load production was assayed by quantitative PCR of the core sequence. Briefly, 5 μL of clarified supernatant was added to a PCR reaction mixture that contained forward primers HBV-f 5'-CTGTGCCTTGGGTGGCTTT-3', Reverse primers HBV-r 5'-AAGGAAAGAAGTCAG- AAGGCAAAA-3' and Fluorescent TaqMan™ Probes HBV-probe 5'-FAM/AGCTCCAAA/ZEN/TTCTT-TATAAGGGTCGATGTCCATG/3IABkFQ-3' in Quanta Biosciences PerfeCTa® qPCR Toughmix®, and was subsequently on an Applied Biosystems VIIA7 in a final volume of 20 µL. The PCR mixture was incubated at 45° C. for 5 minutes, then 95° C. for 10 min, followed by 40 cycles of 10 seconds at 95° C. and 20 seconds at 60° C. Viral load was quantitated against known standards by using ViiA™ 7 Software. Viral load in the supernatant from wells with treated cells were compared against viral load in supernatant from DMSO control wells (≥3 per plate).

At the end of compound treatment period cell viability was assessed using a Promega CellTiter-Glo protocol. All supernatant was removed the previously treated 96-well microtiter plate, and 50 µL Tetracycline-free treatment medium (DMEM/F12 (1:1), 1x Pen/step (cat #: 30-002-CL, Mediatech, Inc), with 2% FBS, Tet-system approved (cat #: 631106, Clontech), and 1% DMSO was added back to each well. Another 50 µL of CellTiter-Glo reagent solution (Promega, G7573) was then added at room temperature and the contents mixed for 2 minutes on an orbital shaker to induce cell lysis. This was followed by incubation at room temperature for 10 minutes to stabilize the luminescent signal. The luminescence was recorded for 0.2 seconds per well on a Tecan multimode platereader (Infinite M1000 pro). The luminescent signal from each well was normalized against that of untreated (DMSO) control wells. All results were reported percent viability (with controls being 100%).

TABLE 5

Compounds and Biological activity

| Example | AD38 Viral Load (%) (VL with cmpd/VL in DMSO control) at 10 µM | AD38 Viability Normalized Result (cmpd/DMSO %) at 10 µM |
| --- | --- | --- |
| 1425 | 0.6 | 100 |
| 1432 | 21.8 | 101 |
| 1473 | 26.5 | 79 |
| 1496 | 9.6 | 57 |
| 1424 | 0.5 | 97 |
| 1431 | 5.5 | 103 |
| 1421 | 1.3 | 104 |
| 1525 | 0.2 | 104 |
| 1528 | 0.8 | 76 |
| 1526 | 0.8 | 94 |
| 1535 | 0.8 | 84 |
| 1546 | 2.2 | 97 |
| 1541 | 3.7 | 98 |
| 1544 | 2.6 | 88 |
| 1551 | 0.4 | 99 |
| 1557 | 0.6 | 98 |
| 1558 | 0.5 | 106 |
| 1548 | 0.4 | 97 |
| 1552 | 0.4 | 102 |
| 1559 | 0.7 | 87 |
| 1529 | 2.0 | 97 |
| 1553 | 0.5 | 107 |
| 1562 | 0.9 | 97 |
| 1549 | 106.2 | 105 |
| 1556 | 1.6 | 105 |
| 1594 | 0.9 | 105 |
| 1592 | 1.3 | 99 |
| 1561 | 10.3 | 96 |
| 1566 | 0.6 | 95 |
| 1555 | 1.0 | 89 |
| 1595 | 0.3 | 109 |
| 1550 | 4.0 | 96 |
| 1584 | 1.4 | 101 |
| 1585 | 64.1 | 96 |
| 1589 | 80.0 | 98 |
| 1581 | 34.4 | 93 |

TABLE 5-continued

Compounds and Biological activity

| Example | AD38 Viral Load (%) (VL with cmpd/VL in DMSO control) at 10 µM | AD38 Viability Normalized Result (cmpd/DMSO %) at 10 µM |
| --- | --- | --- |
| 1587 | 2.8 | 99 |
| 1590 | 6.2 | 95 |
| 1596 | 3.8 | 25 |
| 1598 | 1.4 | 97 |
| 1606 | 3.0 | 91 |
| 1611 | 1.4 | 100 |
| 1618 | 1.9 | 100 |
| 1586 | 27.9 | 83 |
| 1599-A | 50.9 | 98 |
| 1604 | 0.9 | 82 |
| 1605 | 0.7 | 96 |
| 1607 | 52.8 | 98 |
| 1612-A | 12.4 | 101 |
| 1617 | 2.2 | 101 |
| 1619 | 1.3 | 95 |
| 1620 | 41.9 | 103 |
| 1583 | 1.0 | 0 |
| 1599 | 5.9 | 61 |
| 1603 | 32.8 | 108 |
| 1608 | 12.4 | 98 |
| 1612 | 6.9 | 105 |
| 1616 | 105.0 | 103 |
| 1621 | 25.9 | 81 |
| 1624 | 0.8 | 98 |
| 1602 | 59.8 | 97 |
| 1614 | 8.5 | 98 |
| 1615 | 54.9 | 103 |
| 1626 | 2.7 | 99 |
| 1629 | 3.2 | 107 |
| 1580 | 104.3 | 102 |
| 1625 | 51.9 | 96 |
| 1648 | 9.9 | 95 |
| 1661 | 45.2 | 90 |
| 1627 | 6.0 | 63 |
| 1628 | 21.8 | 95 |
| 1636 | 76.9 | 95 |
| 1650 | 58.8 | 82 |
| 1679 | 1.1 | 94 |
| 1698 | 2.7 | 91 |
| 1613-A | 11.5 | 95 |
| 1637 | 2.3 | 101 |
| 1686 | 58.4 | 102 |
| 1687 | 49.2 | 102 |
| 1691 | 77.1 | 89 |
| 1645 | 6.7 | 101 |
| 1645-B | 77.8 | 100 |
| 1654 | 0.5 | 94 |
| 1660 | 86.8 | 102 |
| 1668 | 23.4 | 106 |
| 1694 | 61.1 | 91 |
| 1704 | 47.6 | 96 |
| 1732 | 18.8 | 100 |
| 1734 | 10.6 | 96 |
| 1645-A | 0.3 | 98 |
| 1654-A | 2.6 | 68 |
| 1680 | 15.0 | 94 |
| 1696 | 0.8 | 109 |
| 1664 | 0.6 | 99 |
| 1665 | 2.7 | 90 |
| 1673 | 3.2 | 105 |
| 1697 | 5.5 | 90 |
| 1703 | 3.1 | 93 |
| 1705 | 3.7 | 93 |
| 1712-1 | 5.2 | 97 |
| 1749 | 54.3 | 109 |
| 1752 | 29.8 | 98 |
| 1764 | 1.1 | 107 |
| 1770-A | 29.8 | 100 |
| 1666 | 0.9 | 98 |
| 1670 | 0.9 | 102 |
| 1746 | 5.6 | 92 |
| 1747 | 3.0 | 95 |
| 1750 | 1.1 | 107 |
| 1753 | 2.4 | 97 |

TABLE 5-continued

Compounds and Biological activity

| Example | AD38 Viral Load (%) (VL with cmpd/VL in DMSO control) at 10 μM | AD38 Viability Normalized Result (cmpd/DMSO %) at 10 μM |
|---|---|---|
| 1758 | 3.8 | 15 |
| 1760 | 6.4 | 94 |
| 1761 | 10.7 | 97 |
| 1766 | 1.3 | 98 |
| 1770 | 32.5 | 77 |
| 1675 | 2.3 | 115 |
| 1677-A | 2.3 | 103 |
| 1695 | 22.9 | 102 |
| 1701 | 2.1 | 94 |
| 1702 | 5.3 | 102 |
| 1735 | 3.1 | 92 |
| 1736-A | 14.1 | 97 |
| 1738-A | 1.8 | 104 |
| 1751 | 2.8 | 18 |
| 1754 | 1.6 | 93 |
| 1755 | 0.4 | 93 |
| 1667 | 0.5 | 93 |
| 1710 | 39.9 | 96 |
| 1711 | 6.5 | 96 |
| 1714-A | 49.2 | 106 |
| 1736 | 6.8 | 94 |
| 1737 | 7.2 | 112 |
| 1738 | 2.9 | 93 |
| 1763 | 12.9 | 93 |
| 1769 | 43.3 | 101 |
| 1772 | 7.1 | 109 |
| 1653 | 65.4 | 108 |
| 1671-A | 0.7 | 111 |
| 1767 | 0.5 | 94 |
| 1669 | 13.1 | 104 |
| 1671 | 18.2 | 100 |
| 1677-B | 2.4 | 89 |
| 1700 | 9.2 | 105 |
| 1706 | 57.5 | 103 |
| 1708 | 0.8 | 90 |
| 1709-A | 29.5 | 106 |
| 1672 | 0.6 | 101 |
| 1674 | 0.3 | 121 |
| 1709 | 51.1 | 94 |
| 1768 | 0.4 | 94 |
| 1806-A | 0.3 | 66 |
| 1707 | 10.7 | 88 |
| 1804-A | 6.6 | 90 |
| 1805 | 0.6 | 97 |
| 1806 | 0.8 | 105 |
| 1804 | 0.5 | 103 |
| 1815 | 0.2 | 88 |
| 1814 | 0.9 | 92 |
| 1817 | 0.3 | 97 |
| 1826 | 11.8 | 91 |
| 1838 | 1.4 | 113 |
| 1819 | 0.5 | 118 |
| 1820 | 3.2 | 105 |
| 1831 | 3.8 | 112 |
| 1832 | 14.1 | 98 |
| 1911 | 0.4 | 111 |
| 1855 | 2.5 | 102 |
| 1905 | 0.3 | 109 |
| 1910 | 19.0 | 94 |
| 1913 | 68.1 | 111 |
| 1915 | 15.7 | 100 |
| 1842 | 46.5 | 109 |
| 1857 | 1.5 | 107 |
| 1861 | 5.9 | 94 |
| 1862 | 19.9 | 107 |
| 1863 | 9.4 | 106 |
| 1917 | 1.1 | 108 |
| 1839 | 6.6 | 96 |
| 1840 | 3.2 | 107 |
| 1856 | 1.3 | 96 |
| 1860 | 7.5 | 98 |
| 1866 | 2.9 | 98 |
| 1877 | 0.2 | 96 |
| 1878 | 1.0 | 103 |
| 1914 | 120.4 | 77 |
| 1821 | 0.5 | 102 |
| 1833 | 67.4 | 102 |
| 1858 | 0.7 | 103 |
| 1859 | 2.7 | 89 |
| 1864 | 3.0 | 93 |
| 1904 | 0.5 | 89 |
| 1816 | 0.2 | 82 |
| 1835-A | 0.3 | 89 |
| 1865 | 1.0 | 94 |
| 1921 | 1.2 | 101 |
| 1935 | 0.7 | 112 |
| 1893 | 2.0 | 91 |
| 1907 | 0.5 | 85 |
| 1879-A | 2.5 | 121 |
| 1942 | 3.0 | 106 |
| 1823-A | 5.8 | 92 |
| 1835 | 12.3 | 94 |
| 1841 | 9.1 | 104 |
| 1879 | 7.2 | 104 |
| 1908 | 7.0 | 94 |
| 1916 | 15.5 | 103 |
| 1932 | 2.2 | 101 |
| 1974 | 15.3 | 103 |
| 1823 | 5.2 | 96 |
| 1920 | 48.8 | 85 |
| 1922 | 60.3 | 39 |
| 1930 | 23.8 | 91 |
| 1934 | 40.0 | 69 |
| 1936 | 13.5 | 94 |
| 1941 | 5.2 | 84 |
| 1975 | 1.0 | 63 |
| 1885-A | 4.5 | 107 |
| 1909 | 1.3 | 95 |
| 1929 | 1.2 | 93 |
| 1931 | 8.5 | 97 |
| 1822 | 1.5 | 89 |
| 1951 | 1.8 | 101 |
| 1958 | 1.5 | 91 |
| 1971 | 7.0 | 87 |
| 1943 | 1.9 | 98 |
| 1944 | 2.5 | 93 |
| 1947 | 2.3 | 101 |
| 1949 | 2.9 | 99 |
| 1954 | 0.5 | 106 |
| 1957 | 1.5 | 94 |
| 1960 | 0.8 | 106 |
| 1880 | 6.7 | 104 |
| 1880-A | 0.7 | 124 |
| 1886 | 1.5 | 106 |
| 1927 | 4.7 | 92 |
| 1959 | 5.0 | 92 |
| 1970 | 1.5 | 121 |
| 1993 | 0.5 | 96 |
| 1906 | 7.8 | 89 |
| 1992 | 5.0 | 89 |
| 11002-A | 1.0 | 106 |
| 11016-A | 6.7 | 103 |
| 11017-A | 8.8 | 102 |
| 1952 | 0.8 | 106 |
| 1953 | 0.4 | 118 |
| 1956 | 2.3 | 88 |
| 11016 | 38.8 | 106 |
| 11017 | 21.0 | 86 |
| 11019 | 14.3 | 93 |
| 11019-A | 1.0 | 95 |
| 1901-A | 3.0 | 118 |
| 1901-B | 69.4 | 108 |
| 1973 | 33.7 | 100 |
| 11004 | 5.5 | 94 |
| 11018 | 3.9 | 98 |
| 11018-A | 0.6 | 104 |
| 11041 | 47.4 | 94 |
| 11042 | 0.8 | 109 |

TABLE 5-continued

Compounds and Biological activity

| Example | AD38 Viral Load (%) (VL with cmpd/VL in DMSO control) at 10 μM | AD38 Viability Normalized Result (cmpd/DMSO %) at 10 μM |
|---|---|---|
| 1972 | 23.5 | 100 |
| 1981 | 0.2 | 105 |
| 11001 | 1.7 | 77 |
| 11002 | 0.9 | 90 |
| 11003 | 0.3 | 97 |
| 11007-A | 0.9 | 75 |
| 11043 | 12.0 | 100 |
| 11044 | 5.1 | 124 |
| 1881 | 0.8 | 108 |
| 11006 | 1.3 | 97 |
| 11007 | 2.0 | 101 |
| C38-02 | 0.5 | 94 |
| 11074 | 0.6 | 103 |
| 1995 | 16.3 | 103 |
| 11005 | 1.9 | 102 |
| 11032-A | 12.9 | 110 |
| 11038 | 2.0 | 99 |
| 11067 | 2.5 | 99 |
| 11073 | 2.2 | 94 |
| 11078 | 45.7 | 96 |
| 1889 | 4.6 | 98 |
| 1995-A | 2.4 | 107 |
| 11039 | 1.9 | 92 |
| 11040 | 1.9 | 104 |
| 11053 | 3.6 | 104 |
| 11079 | 3.3 | 102 |
| 11082 | 1.2 | 95 |
| 11083 | 0.8 | 62 |
| 1882 | 1.0 | 103 |
| 1990 | 4.1 | 98 |
| 11054 | 14.1 | 102 |
| 11055 | 4.0 | 94 |
| 11056 | 0.8 | 96 |
| 1988 | 1.3 | 103 |
| 1991 | 2.0 | 98 |
| 11048 | 1.2 | 103 |
| 11051 | 1.2 | 103 |
| 11057 | 1.0 | 101 |
| 11077 | 0.9 | 90 |
| 1989 | 2.5 | 90 |
| 1994 | 0.9 | 92 |
| 11046 | 0.9 | 100 |
| 11047 | 1.4 | 96 |
| 11050 | 0.7 | 96 |
| 11080 | 1.4 | 84 |
| 11084 | 9.7 | 91 |
| 11086 | 4.7 | 88 |
| 1998 | 3.7 | 99 |
| 11011 | 5.3 | 98 |
| 11045 | 0.6 | 94 |
| 11085 | 3.4 | 88 |
| 11087 | 7.1 | 103 |
| 11088 | 17.9 | 100 |
| 11093 | 4.6 | 102 |
| 11094 | 0.6 | 94 |
| 11102 | 0.5 | 93 |
| 11104-A | 0.9 | 74 |
| C20-01 | 1.5 | 98 |
| C20-02 | 0.5 | 95 |
| C38-01 | 1.3 | 99 |
| 1888 | 1.2 | 100 |
| 11028 | 5.2 | 92 |
| 11029 | 5.3 | 105 |
| 11063 | 1.2 | 102 |
| 11063-A | 0.4 | 104 |
| 11091 | 1.3 | 89 |
| 11103 | 2.5 | 102 |
| 11104 | 9.4 | 97 |
| 11116 | 0.9 | 97 |
| 11131 | 2.0 | 88 |
| 1997 | 9.7 | 104 |
| 11026 | 5.5 | 100 |
| 11049 | 0.8 | 89 |
| 11063-B | 5.4 | 95 |
| 11065 | 1.2 | 66 |
| 11066 | 0.4 | 104 |
| 11092 | 0.5 | 101 |
| 11099 | 3.9 | 90 |
| 11101 | 1.9 | 85 |
| 11118 | 1.9 | 95 |
| 11134 | 1.4 | 90 |
| 11135 | 1.8 | 91 |
| 11106 | 3.3 | 97 |
| 11106-A | 3.6 | 90 |
| 11137 | 3.6 | 96 |
| 11148 | 0.3 | 98 |
| 11149 | 0.2 | 100 |
| 11032 | 51.7 | 103 |
| 11033 | 17.1 | 95 |
| 11064 | 4.1 | 85 |
| 11100 | 6.8 | 102 |
| 11150 | 0.4 | 100 |
| 11152 | 1.6 | 96 |
| C51-01 | 0.4 | 99 |
| C51-02 | 0.2 | 98 |
| 11105 | 1.6 | 95 |
| 11107-A | 7.7 | 100 |
| 11112 | 4.0 | 100 |
| 11117-A | 0.3 | 110 |
| 11142 | 0.8 | 87 |
| 11158 | 6.4 | 100 |
| 11160 | 17.7 | 104 |
| 11162 | 8.7 | 104 |
| 11182 | 0.7 | 104 |
| 1996 | 17.4 | 100 |
| 11061 | 0.9 | 95 |
| 11107 | 6.4 | 96 |
| 11108 | 11.2 | 95 |
| 11108-B | 0.8 | 101 |
| 11113 | 4.9 | 92 |
| 11138 | 1.0 | 96 |
| 11139 | 5.5 | 104 |
| 11140 | 5.5 | 99 |
| 11161 | 1.7 | 104 |
| C44-01 | 2.6 | 97 |

INCORPORATION BY REFERENCE

All publications and patents mentioned herein, including those items listed below, are hereby incorporated by reference in their entirety for all purposes as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approxi-

What is claimed is:

1. A compound represented by:

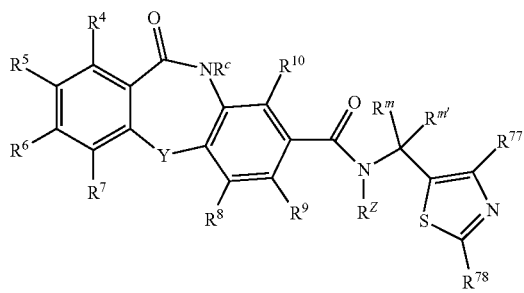

wherein

Y is O;

$R^Z$ is selected from the group consisting of H, methyl, ethyl, propyl, phenyl and benzyl;

$R^{m'}$ and $R^m$ are each independently selected from the group consisting of H, $C_{1-6}$alkyl (optionally substituted by one, two or three substituents each independently selected from halogen and hydroxyl), and $C_{2-6}$alkenyl (optionally substituted by one, two or three substituents each independently selected from halogen and hydroxyl);

$R^c$ is selected from the group consisting of H, $C_{1-6}$alkyl and $C_{2-6}$alkenyl;

$R^{77}$ is selected from the group consisting of H, halogen, cyano, and $C_{1-6}$alkyl;

$R^{78}$ is phenyl (optionally substituted with one, two, three or four substituents each independently selected from the group consisting of $R^{73}$);

$X^2$ is selected from the group consisting of $S(O)_w$ (wherein w is 0, 1, or 2), O, —C(O)— and NR', $R^{79}$ is selected from the group consisting of H, hydroxyl, halogen, $C_{1-6}$alkyl, —C(O)—O—$C_{1-6}$alkyl, heterocycle (optionally substituted by one or more substituents selected from the group consisting of halogen, NR'R', —C(O)—O—$C_{1-6}$alkyl, carboxy and $C_{1-6}$alkyl), —C(O)—NR'R", —C(=NH)—NR'R", heteroaryl, phenyl (optionally substituted by one or more substituents selected from the group consisting of halogen, NR'R', —C(O)—O—$C_{1-6}$alkyl, carboxy, $C_{1-6}$alkoxy, and $C_{1-6}$alkyl), $C_{2-6}$alkenyl, $C_{2-6}$alkynyl, $C_{1-6}$alkoxy, carboxy, NR'R", —C(O)—$C_{1-6}$alkyl, $C_{3-6}$cycloalkyl, —NR'—C(O)— $C_{1-6}$alkyl, NR'—C (O)— O—$C_{1-6}$alkyl, —S(O)$_w$—$C_{1-6}$alkyl (where w is 0, 1 or 2), —S(O)$_w$—NR'R" (where w is 0, 1 or 2), and —NR'—S(O)$_w$— $C_{1-6}$alkyl (where w is 0, 1 or 2));

$R^{73}$ is selected from the group consisting of H, halogen, hydroxyl, nitro, cyano, carboxy, oxo, $C_{1-6}$alkyl, —C(O)—O—$C_{1-6}$alkyl, heterocycle (optionally substituted by one or more substituents selected from the group consisting of halogen, hydroxyl, oxo, NR'R', —C(O)—O—$C_{1-6}$alkyl, carboxy and $C_{1-6}$alkyl), —C(O)—NR'—$C_{1-6}$alkyl, —C(=NH)—NR'R", heteroaryl, phenyl, $C_{2-6}$alkenyl, $C_{2-6}$alkynyl, $C_{1-6}$alkoxy, carboxy, oxo, NR'R", —C(O)—$C_{1-6}$alkyl, —$C_{3-6}$cycloalkyl, NR'—C(O)—C$_{1-6}$alkyl, NR'—C(O)—O—C$_{1-6}$alkyl, —S(O)$_w$—C$_{1-6}$alkyl (where w is 0, 1 or 2), —S(O)$_w$—NR'R" (where w is 1, 2 or 3), —NR'—S(O)$_w$—C$_{1-6}$alkyl (where w is 0, 1 or 2), C(O)—NR'—C$_{1-6}$alkyl, C(O)—C$_{1-3}$alkylene-NR'— C(O)—O—C$_{1-6}$alkyl, X$^2$— R$^{79}$; and X$^2$—C$_{1-6}$alkylene-R$^{79}$;

R' is selected, independently for each occurrence, from H, methyl, ethyl, cyclopropyl, cyclobutyl, and propyl;

R" is selected, independently for each occurrence, from H, methyl, ethyl, propyl, (optionally substituted by hydroxyl), butyl (optionally substituted by hydroxyl), —C(O)-methyl and —C(O)-ethyl, or R' and R" taken together with the nitrogen to which they are attached may form a 4-7 membered heterocycle optionally substituted by one, two or more substituents selected from the group consisting of halogen, hydroxyl, NH$_2$, —C(O)—O—C$_{1-3}$alkyl, —C(O)—C$_{1-3}$alkyl, carboxy, oxo, and C$_{1-3}$alkyl;

each of moieties R$^4$, R$^5$, R$^6$, R$^7$, R$^8$, R$^9$, and R$^{10}$ is independently selected for each occurrence from the group consisting of hydrogen, C$_{1-6}$alkyl, C$_{1-6}$alkoxy, C$_{2-6}$alkynyl, C$_{2-6}$alkenyl, halogen, hydroxyl, nitro, cyano, and NR'R";

wherein for each occurrence, C$_{1-6}$alkyl, C$_{2-6}$alkenyl or C$_{2-6}$alkynyl may be optionally substituted with one, two, three or more substituents selected from the group consisting of halogen, hydroxyl, nitro, cyano, carboxy, C$_{3-6}$cycloalkyl, C$_{2-4}$alkenyl, C$_{2-4}$alkynyl, C$_{1-3}$alkoxy, NR'R", —NR'—S(O)$_w$— C$_{1-2}$alkyl (where w is 0, 1 or 2), NR'—C(O)—C$_{1-3}$alkyl, NR'—C(O)— O—C$_{1-3}$alkyl, and S(O)$_w$—NR'R"(where w is 0, 1 or 2); C$_{1-6}$alkoxy may be optionally substituted with one, two, three or more substituents selected from the group consisting of halogen, hydroxyl, nitro, cyano, carboxy, C$_{1-3}$alkyl, NR'R", —NR'—S(O)$_w$— C$_{1-2}$alkyl (where w is 0, 1 or 2), and S(O)$_w$—NR'R" (where w is 0, 1 or 2); C$_{1-6}$alkylene may be optionally substituted by a substituent selected from the group consisting of C$_{3-6}$cycloalkyl, hydroxyl, cyano, and halogen;

and pharmaceutically acceptable salts and N-oxides thereof.

2. The compound of claim 1, wherein R$^{77}$ is selected from the group consisting of H, CH$_3$ and CF$_3$.

3. The compound of claim 1, wherein R$^7$ is H or halogen.

4. The compound of claim 1, wherein R$^{10}$ is H, halogen or methyl.

5. The compound of claim 1, wherein R$^{m'}$ and R$^m$ are each H.

6. The compound of claim 1, wherein R$^Z$ is H.

7. The compound of claim 1, wherein each of R$^4$, R$^5$, R$^6$, R$^7$, R$^8$, R$^9$, and R$^{10}$ is H.

8. The compound of claim 1, wherein R$^{77}$ is H.

9. A pharmaceutically acceptable composition comprising a compound of claim 1, and a pharmaceutically acceptable excipient.

10. A method of treating a hepatitis B infection in a patient in need thereof, comprising administering an effective amount of a compound of claim 1.

11. A method of treating a hepatitis B infection in a patient in need thereof, comprising administering a first compound selected from a compound of claim 1, and optionally administering one or more additional compounds.

12. A method of treating a hepatitis B infection in a patient in need thereof, comprising administering an amount of a compound of claim 1, and administering another HBV capsid assembly promoter.

* * * * *

UNITED STATES PATENT AND TRADEMARK OFFICE
CERTIFICATE OF CORRECTION

PATENT NO. : 10,968,211 B2
APPLICATION NO. : 16/426727
DATED : April 6, 2021
INVENTOR(S) : William Turner, Jr. et al.

Page 1 of 1

It is certified that error appears in the above-identified patent and that said Letters Patent is hereby corrected as shown below:

In the Claims

In Claim 1, Column 680, delete Lines 1-2, and please insert --R77 is selected from the group consisting of H, halogen, cyano, and C1-6alkyl;--

Signed and Sealed this
Twenty-sixth Day of April, 2022

Katherine Kelly Vidal
*Director of the United States Patent and Trademark Office*